(12) United States Patent
John et al.

(10) Patent No.: US 7,727,997 B2
(45) Date of Patent: Jun. 1, 2010

(54) N,N'-SUBSTITUTED-1,3-DIAMINO-2-HYDROXYPROPANE DERIVATIVES

(75) Inventors: Varghese John, San Francisco, CA (US); Michel Maillard, Redwood Shores, CA (US); Barbara Jagodzinska, Redwood City, CA (US); James Beck, Kalamazoo, MI (US); Andrea Gailunas, Burlingame, CA (US); John Freskos, Clayton, MO (US); John Mickelson, Dexter, MI (US); Lakshman Samala, Plainsboro, NJ (US); Jennifer Sealey, Burlingame, CA (US); Ruth Tenbrink, Labadie, MO (US); Larry Fang, Foster City, CA (US); Roy Hom, San Francisco, CA (US)

(73) Assignee: Elan Pharmaceuticals, Inc., So. San Francisco, CA (US)

( * ) Notice: Subject to any disclaimer, the term of this patent is extended or adjusted under 35 U.S.C. 154(b) by 609 days.

(21) Appl. No.: 11/636,903

(22) Filed: Dec. 11, 2006

(65) Prior Publication Data

US 2007/0213316 A1 Sep. 13, 2007

Related U.S. Application Data

(62) Division of application No. 10/291,318, filed on Nov. 8, 2002, now Pat. No. 7,176,242.

(60) Provisional application No. 60/345,635, filed on Jan. 3, 2002, provisional application No. 60/344,086, filed on Dec. 28, 2001, provisional application No. 60/337,122, filed on Nov. 8, 2001.

(51) Int. Cl.
A61K 31/133 (2006.01)
C07D 217/00 (2006.01)
(52) U.S. Cl. .................................. 514/277; 546/268.1
(58) Field of Classification Search ............... 548/125; 546/268.1; 544/63; 514/222.2, 277, 359
See application file for complete search history.

(56) References Cited

U.S. PATENT DOCUMENTS

| | | | |
|---|---|---|---|
| 4,351,842 A | 9/1982 | Coles | |
| 4,522,811 A | 6/1985 | Eppstein et al. | |
| 5,145,684 A | 9/1992 | Liversidge et al. | |
| 5,387,742 A | 2/1995 | Cordell | |
| 5,559,256 A * | 9/1996 | Gordon et al. | 552/303 |
| 5,593,846 A | 1/1997 | Schenk et al. | |
| 5,604,102 A | 2/1997 | McConlogue et al. | |
| 5,612,486 A | 3/1997 | McConlogue et al. | |
| 5,720,936 A | 2/1998 | Wadsworth et al. | |
| 5,721,130 A | 2/1998 | Seubert et al. | |
| 5,744,346 A | 4/1998 | Chrysler et al. | |
| 5,766,846 A | 6/1998 | Schlossmacher et al. | |
| 5,811,633 A | 9/1998 | Wadsworth et al. | |
| 5,850,003 A | 12/1998 | McConlogue et al. | |
| 5,877,015 A | 3/1999 | Hardy et al. | |
| 5,877,399 A | 3/1999 | Hsiao et al. | |
| 5,912,410 A | 6/1999 | Cordell | |
| 5,942,400 A | 8/1999 | Anderson et al. | |
| 6,045,829 A | 4/2000 | Liversidge et al. | |

FOREIGN PATENT DOCUMENTS

| | | |
|---|---|---|
| EP | 0 652 009 | 5/1995 |
| WO | 98/22597 | 5/1998 |
| WO | 98/33795 | 8/1998 |
| WO | 00/03819 | 1/2000 |
| WO | 00/17369 | 3/2000 |
| WO | 00/47618 | 8/2000 |
| WO | 01/23533 | 2/2001 |
| WO | 01/64001 | 4/2001 |
| WO | 01/10387 | 8/2001 |
| WO | 02/02505 | 1/2002 |
| WO | 02/02512 | 1/2002 |
| WO | 02/02518 | 1/2002 |
| WO | 02/02520 | 1/2002 |
| WO | 02/14264 | 2/2002 |

OTHER PUBLICATIONS

B. Gisin, "Aminodiacylhydrazin-Umlagerung," Helv. Chim. Acta, vol. 53, 1030-1043 (1970).

Bennett, Frank, "The Synthesis of Novel HIV-Protease Inhibitors via Silica Gel Assisted Addition of Amines to Epoxides," Synlett, 703-704 (1993).

Burness et al., "β-Keto Acetals. I. Synthesis of Pyrazoles and Pyrimidines and the Steric Inhibition of Resonance in 5-Alkyl-1-p-nitrophenylpyrazoles," J. Org. Chem., 21, 97-101 (1956).

Calderwood et al., "Organocerium reactions of benzamides and thiobenzamides: A direct synthesis of tertiary carbinamines," Tet. Lett., 38:1241-1244 (1997).

(Continued)

*Primary Examiner*—Kamal A Saeed
*Assistant Examiner*—Janet L Coppins
(74) *Attorney, Agent, or Firm*—McDonnell Boehnen Hulbert & Berghoff LLP

(57) ABSTRACT

Disclosed are compounds of the formula

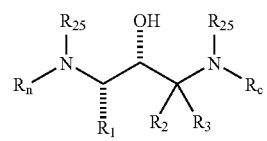

wherein the variables $R_N$, $R_C$, $R_1$, $R_{25}$, $R_2$, and $R_3$ are as defined herein. These compounds have activity as inhibitors of beta-secretase and are therefore useful in treating a variety of disorders such as Alzheimer's Disease.

27 Claims, No Drawings

OTHER PUBLICATIONS

Hyafil et al., "In Vitro and in Vivo Reversal of Multidrug Resistance by GF120918, an Acridonecarboxamide Derivative," Cancer Research, 53, 4595-4602 (1993).

Dantzig et al., "Reversal of P-Glycoprotein-mediated Multidrug Resistance by a Potent Cyclopropyldibenzosuberane Modulator," Cancer Research, 56:4171-4179 (1996).

Miyaura et al., "Palladium-Catalyzed Cross-Coupling Reactions of Organoboron Compounds," Chem. Rev., 95:2457-2483 (1995).

Ciganek, Engelbert, "Tertiary Carbinamines by Addition of Organocerium Reagents to Nitriles," J. Org. Chem., 57:4521-4527 (1992).

Citron et al., "Mutation of the β-amyloid precursor protein in familial Alzheimer's disease increases β-protein production," Nature, 360:672-674 (1992).

Witherspoon et al., "Flow cytometric assay of modulation of P-glycoprotein function in whole blood by the multidrug resistance inhibitor GG918," Clin. Cancer Res., 2:7-12 (1996).

Daves et al., "Pyrimidines. XIII. 2- and 6-Substituted 4-Pyrimidinecarboxylic Acids (1a)," Midwest Research Institute, J. Heterocycl. Chem., 1:130-133 (Jul. 1964).

Emilien, Prospects for Pharmacological Intervention in Alzheimer Disease, Arch. Neurol. 57:454-459 (2000) [name spelled incorrectly in parent IDS].

Organic Syntheses, Collective vol. 2, Edited by A.H. Blatt, John Wiley & Sons, 313-315 (1961).

Felman et al., "Synthesis and antiulcer activity of novel 5-(2-ethenyl substituted)-3(2H)-furanones," J. Med. Chem., 35:1183-1190 (1992).

Bold et al., "New Aza-Dipeptide Analogues as Potent and Orally Absorbed HIV-1 Protease Inhibitors: Candidates for Clinical Development," J. Medicinal Chemistry, 41:3387-3401 (1998).

Games et al., "Alzheimer-type neuropathology in transgenic mice overexpressing V717F -amyloid precursor protein," Nature, 373:523-527 (1995) [name spelled incorrectly in parent IDS].

Hardy et al., "Framing β-amyloid," Nature Genet., 1:233-234 (1992).

Plouvier et al., "Synthesis of Two New Thiazole-containing Oligopeptides as Potential DNA Minor Groove Binding Analogs of Netropsin," Heterocycles, 32(4):693-701 (1991).

Hussain et al., "Identification of a Novel Aspartic Protease (Asp 2) as β-Secretase," Mol. Cell. Neurosci., 14:419-427 (1999).

Gould, Philip, "Salt selection for basic drugs," International Journal of Pharmaceutics, 33:201-217 (1986).

Deno et al., "Protonated cyclopropane intermediates in the reactions of cyclopropanecarboxylic acids," J. Am. Chem. Soc., 92:3700-3703 (1970).

Tang et al., "Models for metal binding sites in zinc enzymes. Syntheses of tris[4(5)-imidazolyl]carbinol (4-TIC), tris(2-imidazolyl)carbinol (2-TIC), and related ligands, and studies on metal complex binding constants and spectra," J. Am. Chem. Soc., 100:3918-3922 (1978).

Diercks et al., "Tris(benzocyclobutadieno)benzene, the triangular [4]phenylene with a completely bond-fixed cyclohexatriene ring: cobalt-catalyzed synthesis from hexaethynylbenzene and thermal ring opening to 1,2:5,6:9,10-tribenzo-3,4,7,8,11,12-hexadehydro[12]annulene," J. Am. Chem. Soc., 3150-3152 (1986).

Snyder et al., "Organoboron Compounds, and the Study of Reaction Mechanisms. Primary Aliphatic Boronic Acids," J. Am. Chem. Soc., 60:105-111 (1938).

Schapira et al., "3-Oxo-1,2-benzoisothiazoline-2-acetic Acid 1,1-Dioxide Derivatives. I. Reaction of Esters with Alkoxides," J. Heterocyclic Chem., 17:1281-1288 (1980).

Grunewald et al., "Examination of the Role of the Acidic Hydrogen in Imparting Selectivity of 7-(Aminosulfonyl)-1,2,3,4-tetrahydroisoquinoline (SK&F 29661) Toward Inhibition of Phenylethanolamine N-Methyltransferase vs the 2-Adrenoceptor," J. Med. Chem., 40:3997-4005 (1997).

Martin et al., "Cyclopropane-Derived Peptidomimetics. Design, Synthesis, Evaluation, and Structure of Novel HIV-1 Protease Inhibitors," J. Med. Chem., 41:1581-1597 (1998).

Alterman et al., "Design and Synthesis of New Potent C2-Symmetric HIV-1 Protease Inhibitors. Use of L-Mannaric Acid as a Peptidomimetic Scaffold," J. Med. Chem., 41:3782-3792 (1998).

Cushman et al., "Synthesis of Analogs of 2-Methoxyestradiol with Enhanced Inhibitory Effects on Tubulin Polymerization and Cancer Cell Growth," J. Med. Chem., 40:2323-2334 (1997).

Amblard et al., "Synthesis and Characterization of Bradykinin B2 Receptor Agonists Containing Constrained Dipeptide Mimics," J. Med. Chem., 42:4193-4201 (1999).

Getman et al., "Discovery of a novel class of potent HIV-1 protease inhibitors containing the (R)-(hydroxyethyl)urea isostere," J. Med. Chem., 36:288-291 (1992).

Vazquez et al., "Inhibitors of HIV-1 Protease Containing the Novel and Potent (R)-(Hydroxyethyl)sulfonamide Isostere," J. Med. Chem., 38:581-584 (1994).

Minutolo et al., "Salicylaldoxime Moiety as a Phenolic "A-Ring" Substitute in Estrogen Receptor Ligands," J. Med. Chem., 4288-4291 (2000).

Martin et al., "Cyclopropane-Derived Peptidomimetics. Design, Synthesis, and Evaluation of Novel Enkephalin Analogues," J. Org. Chem., 65:1305-1318 (2000).

Berge et al., "Pharmaceutical Salts," J. Pharm. Sci., 66(1):1-19 (1977).

Kang et al., "The precursor of Alzheimer's disease amyloid A4 protein resembles a cell-surface receptor," Nature, 325:733-736 (1987).

Kitaguchi et al., "Novel precursor of Alzheimer's disease amyloid protein shows protease inhibitory activity," Nature, 331:530-532 (1988) [year is incorrect in parent IDS].

Klumpp et al., "Lithiation of cyclopropylcarbinols," J. Am. Chem. Soc., 101:7065-7066 (1979).

Kosugi et al., "(α-Ethoxyvinyl)tributyltin; An Efficient Reagent for the Nucleophilic Acetylation of Organic Halides via Palladium Catalysis," Bull. Chem. Soc. Jpn., 60:767-768 (1987).

Fedorynski et al., "Synthesis of 1-Arylcyclopropanecarbonitriles Under Phase-Transfer Catalytic Conditions," Organic Preparations and Procedures Int., 27(3):355-359 (1995).

Lin et al., "Human aspartic protease memapsin 2 cleaves the -secretase site of -amyloid precursor protein," PNAS USA, 97:1456-1460 (2000).

Luo et al., "Mice deficient in BACE1, the Alzheimer's β-secretase, have normal phenotype and abolished β-amyloid generation," Nature Neuroscience, 4:231-232 (2001).

Nakata et al., "Regioselective oxidation of β-hydroxyazo compounds to β-hydroxyazoxy compounds and its application to syntheses of maniwamycins A and B," Tetrahedron Letters, 6095-6098 (1993) [name misspelled on parent IDS].

Ottoni et al., "Acylation of Indole under Friedel—Crafts Conditions—An Improved Method to Obtain 3-Acylindoles Regioselectively," Org. Lett., 1005 (2001).

Mashraqui et al., "Cyclophanes. 14. Synthesis, structure assignment, and conformational properties of [2.2](2,5)oxazolo- and thiazolophanes," J. Am. Chem. Soc., 104:4461-4465 (1982).

Meyers et al., "Hydrogenation of Aromatic Nuclei: 1-DECALOL," Organic Syntheses, vol. 51, p. 103 (1971).

Organic Syntheses, "Cyclobutylamine," Collective vol. 5, John Wiley & Sons, 273-276 (1973).

Okauchi et al., "A General Method for Acylation of Indoles at the 3-Position with Acyl Chlorides in the Presence of Dialkylaluminum Chloride," Org. Lett., 2(10):1485-1487 (2000).

Dunn et al., "A Simple 'One-Pot' Conversion of Carboxylic Acids into Nitriles," Org. Prep. Proceed. Intern., 396-399 (1982).

Heck, Richard, Palladium Reagents in Organic Synthesis, 342-365 (1985).

Pirttilä et al., "Longitudinal study of cerebrospinal fluid amyloid proteins and apolipoprotein E in patients with probable Alzheimer's disease," Neuroscience Letters, 249(1):21-24 (1998).

Barton, J.W., "Protection of N-H Bonds and NR," Protective Groups in Organic Chemistry, Plenum Press, New York, NY, Chapt. 2, p. 43-93 (1973).

R.C. Larock in Comprehensive Organic Transformations, VCH Publishers, p. 313 (1989).

R.C. Larock in Comprehensive Organic Transformations, VCH Publishers, 981, 979 and 972 (1989).

Rosenberg et al., "Potent, low molecular weight renin inhibitors containing a C-terminal heterocycle: hydrogen bonding at the active site," J. Medicincal Chemistry, 33:1582-1590 (1990).

Zhao et al., "Hydrazide-Containing Inhibitors of HIV-1 Integrase," J. Medicinal Chemistry, 40:937-941 (1997) [name incorrect on parent IDS].

Sinha et al., Nature, 40:537-540 (1999).

Kiselyov et al., "Acylation of activated aromatic substrates under mild conditions with (RCO)2O/Me2S/BF3," Tet. Lett., 36(23):4005-4008 (1995).

Jin et al., "Palladium-catalyzed cyanation reactions of aryl chlorides," Tet. Lett., 41(18):3271-3273 (2000).

Arrowsmith et al., "Amino-alcohol dipeptide analogues: A simple synthesis of a versatile isostere for the development of proteinase inhibitors," Tetrahedron Letters, 28:5569-5572 (1987).

Shibata et al., "An expeditious synthesis of (2R,3S)-3-tert-butoxycarbonylamino-1-isobutylamino-4-phenyl-2-butanol, a key building block of HIV protease inhibitors," Tetrahedron Letters, 38:619-620 (1997).

Gao et al., "Asymmetric hetero Diels-Alder reaction catalyzed by stable and easily prepared CAB catalysts," Tetrahedron, 50:979-988 (1994).

Thurkauf et al., "Synthesis and anticonvulsant activity of 1-phenylcyclohexylamine analogs," J. Med. Chem., 33:1452-1458 (1990).

Vassar et al., "β-Secretase Cleavage of Alzheimer's Amyloid Precursor Protein by the Transmembrane Aspartic Protease BACE," Science, 286:735-741 (1999).

Wilk, Bogdan K., "A Convenient Preparation of Alkyl Nitriles by the Mitsunobu Procedure," Synth. Commun., 23(17):2481-2484 (1993).

Yan et al., "Membrane-anchored aspartyl protease with Alzheimer's disease -secretase activity," Nature, 402:533-537 (1999).

Chevallier et al., "Cathepsin D displays in vitro β-secretase-like specificity," Brain Research, 750:11-19 (1997).

CAPLUS abstract of 1960:38832, Sicher, J. et al., "Amino acids and peptides. XXVIII," Collection of Czechoslovak Chemical Communications, 24:3719-3729 (1959).

CAPLUS abstract of 1999:684298, Lubisch, W. et al., "New substituted benzamides: preparation and application," DE patent 19817461 A1 (1999).

* cited by examiner

SEQUENCE LISTING

<160> NUMBER OF SEQ ID NOS: 9

<210> SEQ ID NO 1
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal Biotin
<220> FEATURE:
<221> NAME/KEY: MISC_FEATURE
<222> LOCATION: (10)..(10)
<223> OTHER INFORMATION: covalent attachment of oregon green

<400> SEQUENCE: 1

```
Ser Glu Val Asn Leu Asp Ala Glu Phe Arg Lys Lys
1               5                   10
```

<210> SEQ ID NO 2
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Terminal Biotin
<220> FEATURE:
<221> NAME/KEY: MISC_FEATURE
<222> LOCATION: (10)..(10)
<223> OTHER INFORMATION: covalent attachment of oregon green

<400> SEQUENCE: 2

```
Ser Glu Val Lys Met Asp Ala Glu Phe Arg Lys Lys
1               5                   10
```

<210> SEQ ID NO 3
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal Biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

```
Gly Leu Asn Ile Lys Thr Glu Glu Ile Ser Glu Ile Ser Tyr Glu Val
1               5                   10                  15

Glu Phe Arg Cys Lys Lys
            20
```

<210> SEQ ID NO 4
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal Biotin
<220> FEATURE:
<221> NAME/KEY: MISC_FEATURE
<222> LOCATION: (30)..(30)
<223> OTHER INFORMATION: covalent attachment of oregon green

<400> SEQUENCE: 4

```
Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Lys Lys
                20                  25                  30
```

<210> SEQ ID NO 5
<211> LENGTH: 32
<212> TYPE: PRT
<213> ORGANISM: Artificial
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: N-terminal Biotin
<220> FEATURE:
<221> NAME/KEY: MISC_FEATURE
<222> LOCATION: (7)..(7)
<223> OTHER INFORMATION: Oxidized Cysteine
<220> FEATURE:
<221> NAME/KEY: MISC_FEATURE
<222> LOCATION: (19)..(19)
<223> OTHER INFORMATION: Oxidized Cysteine
<220> FEATURE:
<221> NAME/KEY: MISC_FEATURE
<222> LOCATION: (30)..(30)
<223> OTHER INFORMATION: covalently attached oregon green

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Lys Lys
            20                  25                  30

<210> SEQ ID NO 6
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal Biotin

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal Biotin

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial
<220> FEATURE:
<223> OTHER INFORMATION: Synthetic

<400> SEQUENCE: 8

Ser Glu Val Asn Leu Asp Ala Glu Phe
1               5
```

```
<210> SEQ ID NO 9
<211> LENGTH: 30
<212> TYPE: PRT
<213> ORGANISM: Artificial
<220> FEATURE:
<223> OTHER INFORMATION: Synthetic

<400> SEQUENCE: 9

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30
```

US 7,727,997 B2

N,N'-SUBSTITUTED-1,3-DIAMINO-2-HYDROXYPROPANE DERIVATIVES

This application is a Divisional of U.S. patent application Ser. No. 10/291,318 filed Nov. 8, 2002 now U.S. Pat. No. 7,176,242, which claims priority of invention under 35 U.S.C. §119(e) from U.S. provisional application Nos. 60/345,635, 60/344,086, and 60/337,122, filed Jan. 3, 2002, Dec. 28, 2001, and Nov. 8, 2001, respectively, the disclosures of which are incorporated herein by reference.

BACKGROUND OF THE INVENTION

1. Field of the Invention

The invention is directed to compounds useful in treatment of Alzheimer's disease and similar diseases.

2. Description of the Related Art

Alzheimer's disease (AD) is a progressive degenerative disease of the brain primarily associated with aging. Clinicalation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurogenerative disorders. Beta-amyloid is a defining feature of AD, now believed to be a causative precursor or factor in the development of the disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39-42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide.

An aspartyl protease has been identified as the enzyme responsible for processing of APP at the beta-secretase cleavage site. The beta-secretase enzyme has been disclosed using varied nomenclature, including BACE, Asp, and Memapsin.

Several lines of evidence indicate that progressive cerebral deposition of beta-amyloid peptide (A beta) plays a seminal role in the pathogenesis of AD and can precede cognitive symptoms by years or decades. Release of A beta from neuronal cells grown in culture and the presence of A beta in cerebrospinal fluid (CSF) of both normal individuals and AD patients has been demonstrated.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD.

BACE1 knockout mice fail to produce A beta, and a normal phenotype. When crossed with transgenic mice that overexpress APP, the progeny show reduced amounts of A beta in brain extracts as compared with control animals (Luo et. al., 2001 Nature Neuroscience 4:231-232). This evidence further supports the proposal that inhibition of beta-secretase activity and reduction of A beta in the brain provides a therapeutic method for the treatment of AD and other beta amyloid disorders.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF INVENTION

In a broad aspect, the invention provides compounds of formula X:

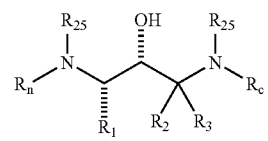

and the pharmaceutically acceptable salts thereof wherein
$R_1$ is —$(CH_2)_{1\text{-}2}$—$S(O)_{0\text{-}2}$—$(C_1$-$C_6$ alkyl), or
  $C_1$-$C_{10}$ alkyl optionally substituted with 1, 2, or 3 groups independently selected from halogen, —OH, =O, —SH, —C≡N, —$CF_3$, —$C_1$-$C_3$ alkoxy, amino, mono- or dialkylamino, —N(R)C(O)R'—, —OC(=O)-amino and —OC(=O)-mono- or dialkylamino, or
  $C_2$-$C_6$ alkenyl or $C_2$-$C_6$ alkynyl, each of which is optionally substituted with 1, 2, or 3 groups independently selected from halogen, —OH, —SH, —C≡N, —$CF_3$, $C_1$-$C_3$ alkoxy, amino, and mono- or dialkylamino, or
  aryl, heteroaryl, heterocyclyl, —$C_1$-$C_6$ alkyl-aryl, —$C_1$-$C_6$ alkyl-heteroaryl, or —$C_1$-$C_6$ alkyl-heterocyclyl, where the ring portions of each are optionally substituted with 1, 2, 3, or 4 groups independently selected from halogen, —OH, —SH, —C≡N, —$NR_{105}R'_{105}$, —$CO_2R$, —N(R)COR', or —N(R)$SO_2R'$, —C(=O)—($C_1$-$C_4$)alkyl, —$SO_2$-amino, —$SO_2$-mono or dialkylamino, —C(=O)-amino, —C(=O)-mono or dialkylamino, —$SO_2$—($C_1$-$C_4$)alkyl, or $C_1$-$C_6$ alkoxy optionally substituted with 1, 2, or 3 groups which are independently selected from halogen, or $C_3$-$C_7$ cycloalkyl optionally substituted with 1, 2, or 3 groups independently selected from halogen, —OH, —SH, —C≡N, —$CF_3$, $C_1$-$C_3$ alkoxy, amino, —$C_1$-$C_6$ alkyl and mono- or dialkylamino, or $C_1$-$C_{10}$ alkyl optionally substituted with 1, 2, or 3 groups independently selected from halogen, —OH, —SH, —C≡N, —$CF_3$, —$C_1$-$C_3$ alkoxy, amino, mono- or dialkylamino and —$C_1$-$C_3$ alkyl, or $C_2$-$C_{10}$ alkenyl or $C_2$-$C_{10}$ alkynyl each of which is optionally substituted with 1, 2, or 3 groups independently selected from halogen, —OH, —SH, —C≡N, —$CF_3$, $C_1$-$C_3$ alkoxy, amino, $C_1$-$C_6$ alkyl and mono- or dialkylamino; and the heterocyclyl group is optionally further substituted with oxo;

where R and R' independently are hydrogen, $C_1$-$C_{10}$ alkyl, $C_1$-$C_{10}$ alkylaryl or $C_1$-$C_{10}$ alkylheteroaryl;

$R_2$ is hydrogen, $C_1$-$C_6$ alkyl optionally substituted with one, two or three substituents independently selected from the group consisting of $C_1$-$C_3$ alkyl, halogen hydroxy, —SH, cyano, —$CF_3$, $C_1$-$C_3$ alkoxy, amino, mono($C_1$-$C_6$)alkylamino, or di($C_1$-$C_6$)alkylamino;

$R_3$ is selected from the group consisting of hydrogen, $C_1$-$C_6$ alkyl optionally substituted with one, two or three substituents independently selected from the group consisting of $C_1$-$C_3$ alkyl, halogen hydroxy, —SH, cyano, —$CF_3$, $C_1$-$C_3$ alkoxy, amino, mono($C_1$-$C_6$)alkylamino, or di($C_1$-$C_6$) alkylamino:

or $R_2$ and $R_3$ are taken together with the carbon to which they are attached to form a 3 or 4-membered carbocyclic ring;

each $R_{25}$ is independently selected from the group consisting of hydrogen or $C_1$-$C_6$ alkyl;

$R_C$ is hydrogen, —$(CR_{245}R_{250})_{0-4}$-aryl, —$(CR_{245}R_{250})_{0-4}$-heteroaryl, —$(CR_{245}R_{250})_{0-4}$-heterocyclyl, —$(CR_{245}R_{250})_{0-4}$-aryl-heteroaryl, —$(CR_{245}R_{250})_{0-4}$-aryl-heterocyclyl, —$(CR_{245}R_{250})_{0-4}$-aryl-aryl, —$(CR_{245}R_{250})_{0-4}$-heteroaryl-aryl, —$(CR_{245}R_{250})_{0-4}$-heteroaryl-heterocyclyl, —$(CR_{245}R_{250})_{0-4}$-heteroaryl-heteroaryl, —$(CR_{245}R_{250})_{0-4}$-heterocyclyl-heteroaryl, —$(CR_{245}R_{250})_{0-4}$-heterocyclyl-heterocyclyl, —$(CR_{245}R_{250})_{0-4}$-heterocyclyl-aryl, —$[C(R_{255})(R_{260})]_{1-3}$—CO—N—$(R_{255})_2$, —CH(aryl)$_2$, —CH(heteroaryl)$_2$, —CH(heterocyclyl)$_2$, —CH(aryl)(heteroaryl), —$(CH_2)_{0-1}$—CH($(CH_2)_{0-6}$—OH)—$(CH_2)_{0-1}$-aryl, —$(CH_2)_{0-1}$—CH($(CH_2)_{0-6}$—OH—$(CH_2)_{0-1}$-heteroaryl, —CH(-aryl or -heteroaryl)-CO—O($C_1$-$C_4$ alkyl), —CH(—$CH_2$—OH)—CH(OH)-phenyl-$NO_2$, ($C_1$-$C_6$ alkyl)-O—($C_1$-$C_6$ alkyl)—OH; —$CH_2$—NH—$CH_2$—CH(—O—$CH_2$—$CH_3$)$_2$, —$(CH_2)_{0-6}$—C(=$NR_{235}$)(N$R_{235}R_{240}$), or $C_1$-$C_{10}$ alkyl optionally substituted with 1, 2, or 3 groups independently selected from the group consisting of $R_{205}$, —OC=ON$R_{235}R_{240}$, —S(=O)$_{0-2}$($C_1$-$C_6$ alkyl), —SH, —$NR_{235}$C=ON$R_{235}R_{240}$, —C=ON$R_{235}R_{240}$, and —S(=O)$_2$N$R_{235}R_{240}$, or —$(CH_2)_{0-3}$—($C_3$-$C_8$) cycloalkyl wherein the cycloalkyl is optionally substituted with 1, 2, or 3 groups independently selected from the group consisting of $R_{205}$, —$CO_2H$, and —$CO_2$—($C_1$-$C_4$ alkyl), or cyclopentyl, cyclohexyl, or cycloheptyl ring fused to aryl, heteroaryl, or heterocyclyl wherein one, two or three carbons of the cyclopentyl, cyclohexyl, or cycloheptyl is optionally replaced with a heteroatom independently selected from NH, N$R_{215}$, O, or S(=O)$_{0-2}$, and wherein the cyclopentyl, cyclohexyl, or cycloheptyl group can be optionally substituted with one or two groups that are independently $R_{205}$, =O, —CO—N$R_{235}R_{240}$, or —$SO_2$—($C_1$-$C_4$ alkyl), or $C_2$-$C_{10}$ alkenyl or $C_2$-$C_{10}$ alkynyl, each of which is optionally substituted with 1, 2, or 3 $R_{205}$ groups, wherein each aryl and heteroaryl is optionally substituted with 1, 2, or 3 $R_{200}$, and wherein each heterocyclyl is optionally substituted with 1, 2, 3, or 4 $R_{210}$;

$R_{200}$ at each occurrence is independently selected from —OH, —$NO_2$, halogen, —$CO_2H$, C≡N, —$(CH_2)_{0-4}$—CO—N$R_{220}R_{225}$, —$(CH_2)_{0-4}$—CO—($C_1$-$C_{12}$ alkyl), —$(CH_2)_{0-4}$—CO—($C_2$-$C_{12}$ alkenyl), —$(CH_2)_{0-4}$—CO—($C_2$-$C_{12}$ alkynyl), —$(CH_2)_{0-4}$—CO—($C_3$-$C_7$ cycloalkyl), —$(CH_2)_{0-4}$—CO-aryl, —$(CH_2)_{0-4}$—CO-heteroaryl, —$(CH_2)_{0-4}$—CO-heterocyclyl, —$(CH_2)_{0-4}$—CO—O—$R_{215}$, —$(CH_2)_{0-4}$—$SO_2$—N$R_{220}R_{225}$, —$(CH_2)_{0-4}$—SO—($C_1$-$C_8$ alkyl), —$(CH_2)_{0-4}$—$SO_2$—($C_1$-$C_{12}$ alkyl), —$(CH_2)_{0-4}$—$SO_2$—($C_3$-$C_7$ cycloalkyl), —$(CH_2)_{0-4}$—N(H or $R_{215}$)—CO—O—$R_{215}$, —$(CH_2)_{0-4}$—N(H or $R_{215}$)—CO—N($R_{215}$)$_2$, —$(CH_2)_{0-4}$—N—CS—N($R_{215}$)$_2$, —$(CH_2)_{0-4}$—N(—H or $R_{215}$)—CO—$R_{220}$, —$(CH_2)_{0-4}$—N$R_{220}R_{225}$, —$(CH_2)_{0-4}$—O—CO—($C_1$-$C_6$ alkyl), —$(CH_2)_{0-4}$—O—P(O)—(O$R_{240}$)$_2$, —$(CH_2)_{0-4}$—O—CO—N($R_{215}$)$_2$, —$(CH_2)_{0-4}$—O—CS—N($R_{215}$)$_2$, —$(CH_2)_{0-4}$—O—($R_{215}$), —$(CH_2)_{0-4}$—O—($R_{215}$)—COOH, —$(CH_2)_{0-4}$—S—($R_{215}$), —$(CH_2)_{0-4}$—O—($C_1$-$C_6$ alkyl optionally substituted with 1, 2, 3, or 5 —F), $C_3$-$C_7$ cycloalkyl, —$(CH_2)_{0-4}$—N(H or $R_{215}$)—$SO_2$—$R_{220}$, —$(CH_2)_{0-4}$—$C_3$-$C_7$ cycloalkyl, or $C_1$-$C_{10}$ alkyl optionally substituted with 1, 2, or 3 $R_{205}$ groups, or $C_2$-$C_{10}$ alkenyl or $C_2$-$C_{10}$ alkynyl, each of which is optionally substituted with 1 or 2 $R_{205}$ groups, wherein the aryl and heteroaryl groups at each occurrence are optionally substituted with 1, 2, or 3 groups that are independently $R_{205}$, $R_{210}$, or $C_1$-$C_6$ alkyl substituted with 1, 2, or 3 groups that are independently $R_{205}$ or $R_{210}$, and wherein the heterocyclyl group at each occurrence is optionally substituted with 1, 2, or 3 groups that are independently $R_{210}$;

$R_{205}$ at each occurrence is independently selected from $C_1$-$C_6$ alkyl, halogen, —OH, —O-phenyl, —SH, —C≡N, —$CF_3$, $C_1$-$C_6$ alkoxy, $NH_2$, NH($C_1$-$C_6$ alkyl) or N—($C_1$-$C_6$ alkyl)($C_1$-$C_6$ alkyl);

$R_{210}$ at each occurrence is independently selected from halogen, $C_1$-$C_6$ alkoxy, $C_1$-$C_6$ haloalkoxy, —N$R_{220}R_{225}$, OH, C≡N, —CO—($C_1$-$C_4$ alkyl), —$SO_2$—N$R_{235}R_{240}$, —CO—N$R_{235}R_{240}$, —$SO_2$—($C_1$-$C_4$ alkyl), =O, or $C_1$-$C_6$ alkyl, $C_2$-$C_6$ alkenyl, $C_2$-$C_6$ alkynyl or $C_3$-$C_7$ cycloalkyl, each of which is optionally substituted with 1, 2, or 3 $R_{205}$ groups;

$R_{215}$ at each occurrence is independently selected from $C_1$-$C_6$ alkyl, —$(CH_2)_{0-2}$-(aryl), $C_2$-$C_6$ alkenyl, $C_2$-$C_6$ alkynyl, $C_3$-$C_7$ cycloalkyl, and —$(CH_2)_{0-2}$-(heteroaryl), —$(CH_2)_{0-2}$-(heterocyclyl), wherein the aryl group at each occurrence is optionally substituted with 1, 2, or 3 groups that are independently $R_{205}$ or $R_{210}$, and wherein the heterocyclyl and heteroaryl groups at each occurrence are optionally substituted with 1, 2, or 3 $R_{210}$;

$R_{220}$ and $R_{225}$ at each occurrence are independently selected from —H, —$C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, —$C_1$-$C_6$ alkyl chain with one double bond and one triple bond, -aryl, -heteroaryl, and -heterocyclyl, or —$C_1$-$C_{10}$ alkyl optionally substituted with —OH, —$NH_2$ or halogen, wherein
  the aryl, heterocyclyl and heteroaryl groups at each occurrence are optionally substituted with 1, 2, or 3 $R_{270}$ groups $R_{235}$ and $R_{240}$ at each occurrence are independently H, or $C_1$-$C_6$ alkyl;

$R_{245}$ and $R_{250}$ at each occurrence are independently selected from —H, $C_1$-$C_4$ alkyl, $C_1$-$C_4$ alkylaryl, $C_1$-$C_4$ alkylheteroaryl, $C_1$-$C_4$ hydroxyalkyl, $C_1$-$C_4$ alkoxy, $C_1$-$C_4$ haloalkoxy, —$(CH_2)_{0-4}$—$C_3$-$C_7$ cycloalkyl, $C_2$-$C_6$ alkenyl, $C_2$-$C_6$ alkynyl, and phenyl; or $R_{245}$ and $R_{250}$ are taken together with the carbon to which they are attached to form a carbocycle of 3, 4, 5, 6, or 7 carbon atoms, where one carbon atom is optionally replaced by a heteroatom selected from —O—, —S—, —$SO_2$—, and —$NR_{220}$—;

$R_{255}$ and $R_{260}$ at each occurrence are independently selected from —H, —$(CH_2)_{1-2}$—$S(O)_{0-2}$—$(C_1$-$C_6$ alkyl), —$(C_1$-$C_4$ alkyl)-aryl, —$(C_1$-$C_4$ alkyl)-heteroaryl, —$(C_1$-$C_4$ alkyl)-heterocyclyl, -aryl, -heteroaryl, -heterocyclyl, —$(CH_2)_{0-4}$-$R_{265}$—$(CH_2)_{0-4}$-aryl, —$(CH_2)_{1-4}$—$R_{265}$—$(CH_2)_{0-4}$-heteroaryl, —$(CH_2)_{1-4}$—$R_{265}$—$(CH_2)_{0-4}$-heterocyclyl, or
  $C_1$-$C_6$ alkyl, $C_2$-$C_6$ alkenyl, $C_2$-$C_6$ alkynyl or —$(CH_2)_{0-4}$—$C_3$-$C_7$ cycloalkyl, each of which is optionally substituted with 1, 2, or 3 $R_{205}$ groups, wherein
  each aryl or phenyl is optionally substituted with 1, 2, or 3 groups that are independently $R_{205}$, $R_{210}$, or
    $C_1$-$C_6$ alkyl substituted with 1, 2, or 3 groups that are independently $R_{205}$ or $R_{210}$, and wherein
  each heterocyclyl is optionally substituted with 1, 2, 3, or 4 $R_{210}$;

$R_{265}$ at each occurrence is independently —O—, —S— or —N($C_1$-$C_6$ alkyl)-;

$R_{270}$ at each occurrence is independently $R_{205}$, halogen $C_1$-$C_6$ alkoxy, $C_1$-$C_6$ haloalkoxy, $NR_{235}R_{240}$, —OH, —C≡N, —CO—($C_1$-$C_4$ alkyl), —$SO_2$—$NR_{235}R_{240}$, —CO—$NR_{235}R_{240}$, —$SO_2$—($C_1$-$C_4$ alkyl), =O, or
  $C_1$-$C_6$ alkyl, $C_2$-$C_6$ alkenyl, $C_2$-$C_6$ alkynyl or —$(CH_2)_{0-4}$—$C_3$-$C_7$ cycloalkyl, each of which is optionally substituted with 1, 2, or 3 $R_{205}$ groups;

$R_N$ is $R'_{100}$, —$SO_2R'_{100}$, —$(CRR')_{1-6}R'_{100}$, —C(=O)—$(CRR')_{0-6}R_{100}$, —C(=O)—$(CRR')_{1-6}$—O—$R'_{100}$, —C(=O)—$(CRR')_{1-6}$—S—$R'_{100}$, —C(=O)—$(CRR')_{1-6}$—C(=O)—$R_{100}$, —C(=O)—$(CRR')_{1-6}$—$SO_2$—$R_{100}$ or —C(=O)—$(CRR')_{1-6}$—$NR_{100}$—$R'_{100}$;

$R_{100}$ and $R'_{100}$ independently re aryl, heteroaryl, -aryl-W-aryl, -aryl-W-heteroaryl, -aryl-W-heterocyclyl, -heteroaryl-W-aryl, -heteroaryl-W-heteroaryl, -heteroaryl-W-heterocyclyl, -heterocyclyl-W-aryl, -heterocyclyl-W-heteroaryl, -heterocyclyl-W-heterocyclyl, —CH[$(CH_2)_{0-2}$—O—$R_{150}$]—$(CH_2)_{0-2}$-aryl, —CH[$(CH_2)_{0-2}$—O—$R_{150}$]—$(CH_2)_{0-2}$-heterocyclyl or —CH [$(CH_2)_{0-2}$—O—$R_{150}$]—$(CH_2)_{0-2}$-heteroaryl, where the ring portions of each are optionally substituted with 1, 2, or 3 groups independently selected from
  —OR, —$NO_2$, halogen, —C≡N, —$OCF_3$, —$CF_3$, —$(CH_2)_{0-4}$—O—P(=O)(OR)(OR'), —$(CH_2)_{0-4}$—CO—$NR_{105}R'_{105}$, —$(CH_2)_{0-4}$—O—$(CH_2)_{0-4}$—$CONR_{102}R_{102}'$, —$(CH_2)_{0-4}$—CO—($C_1$-$C_{12}$ alkyl), —$(CH_2)_{0-4}$—CO—($C_2$-$C_{12}$ alkenyl), —$(CH_2)_{0-4}$—CO—($C_2$-$C_{12}$ alkynyl), —$(CH_2)_{0-4}$—CO—$(CH_2)_{0-4}$—($C_3$-$C_7$ cycloalkyl), —$(CH_2)_{0-4}$-$R_{110}$, —$(CH_2)_{0-4}$-$R_{120}$, —$(CH_2)_{0-4}$-$R_{130}$, —$(CH_2)_{0-4}$—CO—$R_{110}$, —$(CH_2)_{0-4}$—CO—$R_{120}$, —$(CH_2)_{0-4}$—CO—$R_{130}$, —$(CH_2)_{0-4}$—CO—$R_{140}$, —$(CH_2)_{0-4}$—CO—O—$R_{150}$, —$(CH_2)_{0-4}$—$SO_2$—$NR_{105}R'_{105}$, —$(CH_2)_{0-4}$—SO—($C_1$-$C_8$ alkyl), —$(CH_2)_{0-4}$—$SO_2$—($C_1$-$C_{12}$ alkyl), —$(CH_2)_{0-4}$—$SO_2$—$(CH_2)_{0-4}$—($C_3$-$C_7$ cycloalkyl), —$(CH_2)_{0-4}$—N($R_{150}$)—CO—O—$R_{150}$, —$(CH_2)_{0-4}$—N($R_{150}$)—CO—N($R_{150}$))$_2$, —$(CH_2)_{0-4}$—N($R_{150}$)—CS—N($R_{150}$)$_2$, —$(CH_2)_{0-4}$—N($R_{150}$)—CO—$R_{105}$, —$(CH_2)_{0-4}$—$NR_{105}R'_{105}$, —$(CH_2)_{0-4}$-$R_{140}$, —$(CH_2)_{0-4}$—O—CO—($C_1$-$C_6$ alkyl), —$(CH_2)_{0-4}$—O—P(O)—(O—$R_{110}$)$_2$, —$(CH_2)_{0-4}$—O—CO—N($R_{150}$)$_2$, —$(CH_2)_{0-4}$—O—CS—N($R_{150}$)$_2$, —$(CH_2)_{0-4}$—O—($R_{150}$), —$(CH_2)_{0-4}$—O—$R_{150}'$—COOH, —$(CH_2)_{0-4}$—S—($R_{150}$), —$(CH_2)_{0-4}$—N($R_{150}$)—$SO_2$—$R_{105}$, —$(CH_2)_{0-4}$—$C_3$-$C_7$ cycloalkyl, ($C_2$-$C_{10}$)alkenyl, or ($C_2$-$C_{10}$)alkynyl, or $R_{100}$ is $C_1$-$C_{10}$ alkyl optionally substituted with 1, 2, or 3 $R_{115}$ groups, or $R_{100}$ is —($C_1$-$C_6$ alkyl)-O—$C_1$-$C_6$ alkyl) or —($C_1$-$C_6$ alkyl)-S—($C_1$-$C_6$ alkyl), each of which is optionally substituted with 1, 2, or 3 $R_{115}$ groups, or $R_{100}$ is $C_3$-$C_8$ cycloalkyl optionally substituted with 1, 2, or 3 $R_{115}$ groups;

W is —$(CH_2)_{0-4}$—, —O—, —$S(O)_{0-2}$—, —N($R_{135}$)—, —CR(OH)— or —C(O)—;

$R_{102}$ and $R_{102}'$ independently are hydrogen, or
  $C_1$-$C_{10}$ alkyl optionally substituted with 1, 2, or 3 groups that are independently halogen, aryl or —$R_{110}$;

$R_{105}$ and $R'_{105}$ independently re —H, —$R_{110}$, —$R_{120}$, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), $C_2$-$C_6$ alkenyl, $C_2$-$C_6$ alkynyl, or $C_1$-$C_6$ alkyl chain with one double bond and one triple bond, or
  $C_1$-$C_6$ alkyl optionally substituted with —OH or —$NH_2$; or,
  $C_1$-$C_6$ alkyl optionally substituted with 1, 2, or 3 groups independently selected from halogen, or $R_{105}$ and $R'_{105}$ together with the atom to which they are attached form a 3 to 7 membered carbocyclic ring, where one member is optionally a heteroatom selected from —O—, —$S(O)_{0-2}$—, —N($R_{135}$)—, the ring being optionally substituted with 1, 2 or three $R_{140}$ groups;

$R_{115}$ at each occurrence is independently halogen, —OH, —$CO_2R_{102}$, —$C_1$-$C_6$ thioalkoxy, —$CO_2$-phenyl, —$NR_{105}R'_{135}$, —$SO_2$—($C_1$-$C_8$ alkyl), —C(=O)$R_{180}$, $R_{180}$, —$CONR_{105}R'_{105}$, —$SO_2NR_{105}R'_{105}$, —NH—CO—($C_1$-$C_6$ alkyl), —NH—C(=O)—OH, —NH—C(=O)—OR, —NH—C(=O)—O-phenyl, —O—C(=O)—($C_1$-$C_6$ alkyl), —O—C(=O)-amino, —O—C(=O)-mono- or dialkylamino, —O—C(=O)-phenyl, —O—($C_1$-$C_6$ alkyl)-$CO_2H$, —NH—$SO_2$—($C_1$-$C_6$ alkyl), $C_1$-$C_6$ alkoxy or $C_1$-$C_6$ haloalkoxy;

$R_{135}$ is $C_1$-$C_6$ alkyl, $C_2$-$C_6$ alkenyl, $C_2$-$C_6$ alkynyl, $C_3$-$C_7$ cycloalkyl, —$(CH_2)_{0-2}$-(aryl), —$(CH_2)_{0-2}$-(heteroaryl), or —$(CH_2)_{0-2}$-(heterocyclyl);

$R_{140}$ is heterocyclyl optionally substituted with 1, 2, 3, or 4 groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, and =O;

$R_{150}$ is hydrogen, $C_3$-$C_7$ cycloalkyl, —($C_1$-$C_2$ alkyl)-($C_3$-$C_7$ cycloalkyl), $C_2$-$C_6$ alkenyl, $C_2$-$C_6$ alkynyl, $C_1$-$C_6$ alkyl with one double bond and one triple bond, —$R_{110}$, —$R_{120}$, or
  $C_1$-$C_6$ alkyl optionally substituted with 1, 2, 3, or 4 groups independently selected from —OH, —$NH_2$, $C_1$-$C_3$ alkoxy, $R_{110}$, and halogen;

$R_{150}'$ is $C_3$-$C_7$ cycloalkyl, —($C_1$-$C_3$ alkyl)-($C_3$-$C_7$ cycloalkyl), $C_2$-$C_6$ alkenyl, $C_2$-$C_6$ alkynyl, $C_1$-$C_6$ alkyl with one double bond and one triple bond, —$R_{110}$, —$R_{120}$, or $C_1$-$C_6$ alkyl optionally substituted with 1, 2, 3, or 4 groups independently selected from —OH, —$NH_2$, $C_1$-$C_3$ alkoxy, $R_{110}$, and halogen;

$R_{180}$ is selected from morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl, each of which is optionally substituted with 1, 2, 3, or 4 groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, and =O;

$R_{110}$ is aryl optionally substituted with 1 or 2 $R_{125}$ groups;

$R_{125}$ at each occurrence is independently halogen, amino, mono- or dialkylamino, —OH, —C≡N, —$SO_2$—$NH_2$, —$SO_2$—NH—$C_1$-$C_6$ alkyl, —$SO_2$—N($C_1$-$C_6$ alkyl)$_2$, —$SO_2$—($C_1$-$C_4$ alkyl), —CO—$NH_2$, —CO—NH—$C_1$-$C_6$ alkyl, or —CO—N($C_1$-$C_6$ alkyl)$_2$, or $C_1$-$C_6$ alkyl, $C_2$-$C_6$ alkenyl or $C_2$-$C_6$ alkynyl, each of which is optionally substituted with 1, 2, or 3 groups that are independently selected from $C_1$-$C_3$ alkyl, halogen, —OH, —SH, —C≡N, —$CF_3$, $C_1$-$C_3$ alkoxy, amino, and mono- and dialkylamino, or $C_1$-$C_6$ alkoxy optionally substituted with one, two or three of halogen;

$R_{120}$ is heteroaryl, which is optionally substituted with 1 or 2 $R_{125}$ groups; and $R_{130}$ is heterocyclyl optionally substituted with 1 or 2 $R_{125}$ groups.

In another broad aspect, the invention provides compounds of Formula X where $R_1$ is:

(I) $C_1$-$C_6$ alkyl, optionally substituted with one, two or three substituents selected from the group consisting of $C_1$-$C_3$ alkyl, $C_1$-$C_7$ alkyl (optionally substituted with $C_1$-$C_3$ alkyl and $C_1$-$C_3$ alkoxy), —F, —Cl, —Br, —I, —OH, —SH, —C≡N, —$CF_3$, $C_1$-$C_3$ alkoxy, —$NR_{1-a}R_{1-b}$, and —OC=O—$NR_{1-a}R_{1-b}$, where $R_{1-a}$ and $R_{1-b}$ are independently at each occurrence —H or $C_1$-$C_6$ alkyl, (II) —$CH_2$—S(O)$_{0-2}$—($C_1$-$C_6$ alkyl), (III) —$CH_2$—$CH_2$—S(O)$_{0-2}$—($C_3$-$C_6$ alkyl), (IV) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (V) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (VI) —($CH_2$)$_{n1}$—($R_{1-aryl}$) where $n_1$ is zero or one and where $R_{1-aryl}$ is phenyl, naphthyl, indanyl, indenyl, dihydronaphthyl, or tetralinyl each of which is optionally substituted with one, two, three, four, or five of the following substituents on the aryl ring:

(A) $C_1$-$C_6$ alkyl optionally substituted with one, two or three substituents selected from the group consisting of $C_1$-$C_3$ alkyl, —F, —Cl, —Br, —I, —OH, —SH, —$NR_{1-a}R_{1-b}$, —C≡N, —$CF_3$, and $C_1$-$C_3$ alkoxy, (B) $C_2$-$C_6$ alkenyl optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$, (C) $C_2$-$C_6$ optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$, (D) —F, Cl, —Br and —I, (E) —$C_1$-$C_6$ haloalkoxy (F) —$C_1$-$C_6$ alkoxy (G) —$NR_{N-2}R_{N-3}$, (H) —OH, (I) —C≡N, (J) $C_3$-$C_7$ cycloalkyl, optionally substituted with one, two or three substituents independently selected from the group consisting of —F, —Cl, —OH, —SH, —C≡N, —$CF_3$, $C_1$-$C_3$ alkoxy, and —$NR_{1-a}R_{1-b}$, (K) —CO—($C_1$-$C_4$ alkyl), (L) —$SO_2$—$NR_{1-a}R_{1-b}$, (M) —CO—$NR_{1-a}R_{1-b}$, (N) —$SO_2$—($C_1$-$C_4$ alkyl), (VII) —($CH_2$)$_{n1}$—($R_{1-heteroaryl}$) where $R_{1-heteroaryl}$ is selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyridinyl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{1-heteroaryl}$ group is bonded to —($CH_2$)$_{n1}$— by any ring atom of the parent $R_{N-heteroaryl}$ group substituted by hydrogen such that the new bond to the $R_{1-heteroaryl}$ group replaces the hydrogen atom and its bond, where heteroaryl is optionally substituted with one, two, three, four, or five of:

(1) $C_1$-$C_6$ alkyl optionally substituted with one, two or three substituents selected from the group consisting of $C_1$-$C_3$ alkyl, —F, —Cl, —Br, —I, —OH, —SH, —$NR_{1-a}R_{1-b}$, —C≡N, —$CF_3$, and $C_1$-$C_3$ alkoxy, (2) $C_2$-$C_6$ alkenyl with one or two double bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$,
(3) C$_2$-C$_6$ alkynyl with one or two triple bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$,
(4) —F, —Cl, —Br and —I,
(5) —C$_1$-C$_6$ haloalkoxy,
(6) —C$_1$-C$_6$ alkoxy
(7) —NR$_{N-2}$R$_{N-3}$,
(8) —OH,
(9) —C≡N,
(10) C$_3$-C$_7$ cycloalkyl, optionally substituted with one, two or three substituents independently selected from the group consisting of —F, —Cl, —OH, —SH, —C≡N, —CF$_3$, C$_1$-C$_3$ alkoxy, and —NR$_{1-a}$R$_{1-b}$,
(11) —CO—(C$_1$-C$_4$ alkyl),
(12) —SO$_2$—NR$_{1-a}$R$_{1-b}$,
(13) —CO—NR$_{1-a}$R$_{1-b}$,
(14) —SO$_2$—(C$_1$-C$_4$ alkyl), with the proviso that when n$_1$ is zero R$_{1-heteroaryl}$ is not bonded to the carbon chain by nitrogen,
(VIII) —(CH$_2$)$_{n1}$—(R$_{1-heterocycle}$) where n$_1$ is as defined above and R$_{1-heterocycle}$ is selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, homothiomorpholinyl S-oxide, dithianyl, pyranyl, dihydrofuranyl, pyrrolidinonyl, imidazolidinonyl, imidazolidinondionyl, wherein each of the above is optionally fused to a benzene, pyridine, or pyrimidine ring, and
where the R$_{1-heterocycle}$ group is bonded by any atom of the parent R$_{1-heterocycle}$ group substituted by hydrogen such that the new bond to the R$_{1-heterocycle}$ group replaces the hydrogen atom and its bond, where heterocycle is optionally substituted with one, two, three or four:
(1) C$_1$-C$_6$ alkyl optionally substituted with one, two or three substituents independently selected from the group consisting of C$_1$-C$_3$ alkyl, —F, —Cl, —Br, —I, —OH, —SH, —NR$_{1-a}$R$_{1-b}$, —C≡N, —CF$_3$, and C$_1$-C$_3$ alkoxy,
(2) C$_2$-C$_6$ alkenyl optionally substituted with one, two or three substituents selected from the group consisting of —F, —Cl, —OH, —SH, —C≡N, —CF$_3$, C$_1$-C$_3$ alkoxy, —NR$_{1-a}$R$_{1-b}$,
(3) C$_2$-C$_6$ alkynyl optionally substituted with one, two or three substituents independently selected from the group consisting of —F, —Cl, —OH, —SH, —C≡N, —CF$_3$, C$_1$-C$_3$ alkoxy, and —NR$_{1-a}$R$_{1-b}$,
(4) —F, —Cl, —Br and —I,
(5) C$_1$-C$_6$ alkoxy,
(6) —C$_1$-C$_6$ haloalkoxy,
(7) —NR$_{N-2}$R$_{N-3}$,
(8) —OH,
(9) —C≡N,
(10) C$_3$-C$_7$ cycloalkyl, optionally substituted with one, two or three substituents independently selected from the group consisting of —F, —Cl, —OH, —SH —C≡N, —CF$_3$, C$_1$-C$_3$ alkoxy, and —NR$_{1-a}$R$_{1-b}$,
(11) —CO—(C$_1$-C$_4$ alkyl),
(12) —SO$_2$—NR$_{1-a}$R$_{1-b}$,
(13) CO—NR$_{1-a}$R$_{1-b}$,
(14) —SO$_2$—(C$_1$-C$_4$ alkyl),
(15) =O, with the proviso that when n$_1$ is zero R$_{1-heterocycle}$ is not bonded to the carbon chain by nitrogen; where R$_2$ is selected from the group consisting of:
(I) —H,
(II) C$_1$-C$_6$ alkyl, optionally substituted with one, two or three substituents independently selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$,
(III) —(CH$_2$)$_{0-4}$—R$_{30}$ where R$_{30}$ is R$_{1-aryl}$, R$_{1-heteroaryl}$, or R$_{1-heterocycle}$
(IV) C$_2$-C$_6$ alkenyl with one or two double bonds, optionally substituted with one, two or three substituents independently selected from the group consisting of —F, —Cl, —OH, —SH, —C≡N, —CF$_3$, C$_1$-C$_3$ alkoxy, and —NR$_{1-a}$R$_{1-b}$,
(V) C$_2$-C$_6$ alkynyl optionally substituted with one, two or three substituents independently selected from the group consisting of —F, —Cl, —OH, —SH, —C≡N, —CF$_3$, C$_1$-C$_3$ alkoxy, and —NR$_{1-a}$R$_{1-b}$,
(VI) —(CH$_2$)$_{0-4}$—C$_3$-C$_7$ cycloalkyl, optionally substituted with one, two or three substituents independently selected from the group consisting of —F, —Cl, —OH, —SH, —C≡N, —CF$_3$, C$_1$-C$_3$ alkoxy, and —NR$_{1-a}$R$_{1-b}$,
where R$_3$ is selected from the group consisting of:
(I) —H,
(II) C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$,
(III) —(CH$_2$)$_{0-4}$—R$_{30}$,
(IV) C$_2$-C$_6$ alkenyl,
(V) C$_2$-C$_6$ alkynyl,
(VI) —(CH$_2$)$_{0-4}$—C$_3$-C$_7$ cycloalkyl, optionally substituted with one, two or three substituents independently selected from the group consisting of —F, —Cl, —OH, —SH, —C≡N, —CF$_3$, C$_1$-C$_3$ alkoxy, and —NR$_{1-a}$R$_{1-b}$,
or R$_2$ and R$_3$ are taken together with the carbon to which they are attached to form a carbocycle of three, four, five, six, and seven carbon atoms, optionally where one carbon atom is replaced by a heteroatom selected from the group consisting of —O—, —S—, —SO$_2$—, —NR$_{N-2}$—;
R$_N$ is:
(I) R$_{N-1}$—X$_N$— where X$_N$ is selected from the group consisting of:
(A) —CO—,
(B) —SO$_2$—,
(C) —(CR'R'')$_{1-6}$ wherein
R' and R'' at each occurrence are the same or different and are —H or C$_1$-C$_4$ alkyl,
(D) —CO—(CR'R'')$_{1-6}$—X$_{N-1}$ wherein X$_{N-1}$ is selected from the group consisting of —O—, —S— and —NR'—,
(E) a single bond, and
(F) —CO—(CR'R'')$_{1-6}$—
where R$_{N-1}$ is selected from the group consisting of:
(A) R$_{N-aryl}$ wherein R$_{N-aryl}$ at each occurrence is independently phenyl; naphthyl; tetralinyl; indanyl; indenyl; dihydronaphthyl; or 6,7,8,9-tetrahydro-5H-benzo[a]cycloheptenyl; each of which is optionally substituted with 1, 2, or 3 groups that at each occurrence are independently:
(1) C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$, wherein R$_{1-a}$ and R$_{1-b}$ at each occurrence are independently H or C$_1$-C$_6$ alkyl,
(2) —OH,
(3) —NO$_2$,
(4) —F, —Cl, —Br, —I,
(5) —CO$_2$H,
(6) —C≡N,
(7) —(CH$_2$)$_{0-4}$—CO—NR$_{N-2}$R$_{N-3}$ wherein at each occurrence R$_{N-2}$ and R$_{N-3}$ are the same or different and are selected from the group consisting of:
   (a) —H,
   (b) —C$_1$-C$_8$ alkyl optionally substituted with one substituent selected from the group consisting of:
      (i) —OH,
      (ii) —NH$_2$,
      (iii) phenyl,
   (c) —C$_1$-C$_8$ alkyl optionally substituted with 1, 2, or 3 groups that are independently —F, —Cl, —Br, or —I,
   (d) —C$_3$-C$_8$ cycloalkyl,
   (e) —(C$_1$-C$_2$ alkyl)-(C$_3$-C$_8$ cycloalkyl),
   (f) —(C$_1$-C$_6$ alkyl)-O—(C$_1$-C$_3$ alkyl),
   (g) —C$_2$-C$_6$ alkenyl,
   (h) —C$_2$-C$_6$ alkynyl,
   (i) —C$_1$-C$_6$ alkyl chain with one double bond and one triple bond,
   (j) —R$_{1-aryl}$,
   (k) —R$_{1-heteroaryl}$,
   (l) —R$_{1-heterocycle}$, or
   (m) R$_{N-2}$, R$_{N-3}$ and the nitrogen to which they are attached form a 5, 6, or 7 membered heterocycloalkyl or heteroaryl group, wherein said heterocycloalkyl or heteroaryl group is optionally fused to a benzene, pyridine, or pyrimidine ring, and said groups are unsubstituted or substituted with 1, 2, 3, 4, or 5 groups that at each occurrence are independently C$_1$-C$_6$ alkyl, C$_1$-C$_6$ alkoxy, halogen, halo C$_1$-C$_6$ alkyl, halo C$_1$-C$_6$ alkoxy, —CN, —NO$_2$, —NH$_2$, NH(C$_1$-C$_6$ alkyl), N(C$_1$-C$_6$ alkyl)(C$_1$-C$_6$ alkyl), —OH, —C(O)NH$_2$, —C(O)NH(C$_1$-C$_6$ alkyl), —C(O)N(C$_1$-C$_6$ alkyl)(C$_1$-C$_6$ alkyl), C$_1$-C$_6$ alkoxy C$_1$-C$_6$ alkyl, C$_1$-C$_6$ thioalkoxy, and C$_1$-C$_6$ thioalkoxy C$_1$-C$_6$ alkyl;
(B) —R$_{N-heteroaryl}$ where R$_{N-heteroaryl}$ is selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzisothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyridinyl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, imidazopyrazolyl, quinazolinonyl, pyrazopyridyl, benzooxadiazolyl, dihydropyrimidinonyl, and dihydrobenzfuranonyl, where each of the above is optionally fused to a benzene, pyridine, or pyrimidine ring, where the R$_{N-heteroaryl}$ group is bonded by any atom of the parent R$_{N-heteroaryl}$ group substituted by hydrogen such that the new bond to the R$_{N-heteroaryl}$ group replaces the hydrogen atom and its bond, where heteroaryl is optionally substituted with one, two, three, or four of:
(1) C$_1$-C$_6$ alkyl, optionally substituted with one, two or three substituents independently selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$,
(2) —OH,
(3) —NO$_2$,
(4) —F, —Cl, —Br, —I,
(5) —CO$_2$H,
(6) —C≡N,
(7) —(CH$_2$)$_{0-4}$—CO—NR$_{N-2}$R$_{N-3}$,
(8) —(CH$_2$)$_{0-4}$—CO—(C$_1$-C$_{12}$ alkyl),
(9) —(CH$_2$)$_{0-4}$—CO—(C$_2$-C$_{12}$ alkenyl),
(10) —(CH$_2$)$_{0-4}$—CO—(C$_2$-C$_{12}$ alkynyl),
(11) —(CH$_2$)$_{0-4}$—CO—(C$_3$-C$_8$ cycloalkyl),
(12) —(CH$_2$)$_{0-4}$—CO—R$_{1-aryl}$,
(13) —(CH$_2$)$_{0-4}$—CO—R$_{1-heteroaryl}$,
(14) —(CH$_2$)$_{0-4}$—CO-R$_{1-heterocycle}$,
(15) —(CH$_2$)$_{0-4}$—CO—R$_{N-4}$,
(16) —(CH$_2$)$_{0-4}$—CO$_2$—R$_{N-5}$,
(17) —(CH$_2$)$_{0-4}$—SO$_2$—NR$_{N-2}$R$_{N-3}$,
(18) —(CH$_2$)$_{0-4}$—SO-(aryl C$_1$-C$_8$ alkyl),
(19) —(CH$_2$)$_{0-4}$—SO$_2$—(C$_1$-C$_{12}$ alkyl),
(20) —(CH$_2$)$_{0-4}$—SO$_2$—(C$_3$-C$_8$ cycloalkyl),
(21) —(CH$_2$)$_{0-4}$—N(H or R$_{N-5}$)—CO—O—R$_{N-5}$,
(22) —(CH$_2$)$_{0-4}$—N(H or R$_{N-5}$)—CO—N(R$_{N-5}$)$_2$,
(23) —(CH$_2$)$_{0-4}$—N—CS—N(R$_{N-5}$)$_2$,
(24) —(CH$_2$)$_{0-4}$—N(—H or R$_{N-5}$)—CO—R$_{N-2}$,
(25) —(CH$_2$)$_{0-4}$—NR$_{N-2}$R$_{N-3}$,
(26) —(CH$_2$)$_{0-4}$—R$_{N-4}$,
(27) —(CH$_2$)$_{0-4}$—O—CO—(C$_1$-C$_6$ alkyl),
(28) —(CH$_2$)$_{0-4}$—O—P(O)—(OR$_{100}$)$_2$,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$),
(32) —(CH$_2$)$_{0-4}$—O—(R$_{N-5}$)—COOH,
(33) —(CH$_2$)$_{0-4}$—S—(R$_{N-5}$),
(34) —(CH$_2$)$_{0-4}$—O—(C$_1$-C$_6$ alkyl optionally substituted with one, two, three, four, or five of —F),
(35) C$_3$-C$_8$ cycloalkyl,
(36) C$_2$-C$_6$ alkenyl optionally substituted with C$_1$-C$_3$ alkyl, —F, —Cl, —Br, —I, —OH, —SH, —C≡N, —CF$_3$, C$_1$-C$_3$ alkoxy, or —NR$_{1-a}$R$_{1-b}$,
(37) C$_2$-C$_6$ alkynyl optionally substituted with C$_1$-C$_3$ alkyl, —F, —Cl, —Br, —I, —OH, —SH, —C≡N, —CF$_3$, C$_1$-C$_3$ alkoxy, or —NR$_{1-a}$R$_{1-b}$,

(38) —$(CH_2)_{0-4}$—N(—H or $R_{N-5}$)—$SO_2$—$R_{N-2}$,
(39) —$(CH_2)_{1-4}$—$C_3$-$C_8$ cycloalkyl,
(C) $R_{N-aryl}$-W—$R_{N-aryl}$,
(D) $R_{N-aryl}$-W—$R_{N-heteroaryl}$,
(E) $R_{N-aryl}$-W—$R_{1-heterocycle}$,
(F) $R_{N-heteroaryl}$-W—$R_{N-aryl}$,
(G) $R_{N-heteroaryl}$-W—$R_{N-heteroaryl}$,
(H) $R_{N-heteroaryl}$-W—$R_{1-heterocycle}$,
(I) $R_{N-heterocycle}$-W—$R_{N-aryl}$,
(J) $R_{N-heterocycle}$-W—$R_{N-heteroaryl}$,
(K) $R_{N-heterocycle}$-W—$R_{1-heterocycle}$,
where W is
 (1) —$(CH_2)_{1-4}$—,
 (2) —O—,
 (3) —$S(O)_{0-2}$—,
 (4) —$N(R_{N-5})$—,
 (5) —CO—; or
 (6) a bond;
(II) —CO—($C_1$-$C_{10}$ alkyl) wherein the alkyl is optionally substituted with one two or three substituents independently selected from the group consisting of:
 (A) —OH,
 (B) —$C_1$-$C_6$ alkoxy,
 (C) —$C_1$-$C_6$ thioalkoxy,
 (D) —$CO_2$—$R_{N-8}$ where $R_{N-8}$ at each occurrence is independently —H, $C_1$-$C_6$ alkyl or -phenyl which is optionally substituted with 1 or 2 groups that are independently halogen, $C_1$-$C_4$ alkoxy, $C_1$-$C_4$ alkyl or —$C(O)NH_2$,
 (E) —CO—$NR_{N-2}R_{N-3}$,
 (F) —CO—$R_{N-4}$,
 (G) —$SO_2$—($C_1$-$C_8$ alkyl),
 (H) —$SO_2$—$NR_{N-2}R_{N-3}$,
 (I) —NH—CO—($C_1$-$C_6$ alkyl),
 (J) —NH—CO—O—$R_{N-8}$,
 (K) —$NR_{N-2}R_{N-3}$,
 (L) —$R_{N-4}$,
 (M) —O—CO—($C_1$-$C_6$ alkyl),
 (N) —O—CO—$NR_{N-8}R_{N-8}$,
 (O) —O—($C_1$-$C_5$ alkyl)—COOH,
 (P) —O—($C_1$-$C_6$ alkyl optionally substituted with one, two, or three groups that are independently —F, —Cl, —Br, or —I),
 (Q) —NH—$SO_2$—($C_1$-$C_6$ alkyl),
 (R) halogen,
 (S) —N(H or $R_{N-5}$)—$SO_2$-$R_{N-2}$,
 (T) —N(H or $R_{N-5}$)—CO—($R_{N-2}$), and
 (U) —$SO_2$—$R_{N-2}$,
 (V) $R_{N-aryl}$;
(III) —CO—($C_1$-$C_6$ alkyl)-O—($C_1$-$C_6$ alkyl) wherein each alkyl is unsubstituted or independently substituted with one, two, or three substituents selected from the group consisting of:
 (A) —OH,
 (B) —$C_1$-$C_6$ alkoxy,
 (C) —$C_1$-$C_6$ thioalkoxy,
 (D) —CO—O—$R_{N-8}$,
 (E) —CO—$NR_{N-2}R_{N-3}$,
 (F) —CO—$R_{N-4}$,
 (G) —$SO_2$—($C_1$-$C_8$ alkyl),
 (H) —$SO_2$—$NR_{N-2}R_{N-3}$,
 (I) —NH—CO—($C_1$-$C_6$ alkyl),
 (J) —NH—CO—O—$R_{N-8}$,
 (K) —$NR_{N-2}R_{N-3}$,
 (L) —$R_{N-4}$,
 (M) —O—CO—($C_1$-$C_6$ alkyl),
 (N) —O—CO—$NR_{N-8}R_{N-8}$,
 (O) —O—($C_1$-$C_5$ alkyl)—$CO_2H$,
 (P) —O—($C_1$-$C_6$ alkyl optionally substituted with one, two, or three groups that are independently —F, —Cl, —Br, or —I),
 (Q) —NH—$SO_2$—($C_1$-$C_6$ alkyl),
 (R) halogen,
 (S) —N(H or $R_{N-5}$)—$SO_2$—$R_{N-2}$,
 (T) —N(H or $R_{N-5}$)—CO—($R_{N-2}$),
 (U) —$SO_2$—$R_{N-2}$, and
 (V) $R_{N-aryl}$;
(IV) —CO—($C_1$-$C_6$ alkyl)-S—($C_1$-$C_6$ alkyl) wherein each alkyl is unsubstituted or substituted with one, two, or three of substituents independently selected from the group consisting of:
 (A) —OH,
 (B) —$C_1$-$C_6$ alkoxy,
 (C) —$C_1$-$C_6$ thioalkoxy,
 (D) —CO—O—$R_{N-8}$,
 (E) —CO—$NR_{N-2}R_{N-3}$,
 (F) —CO—$R_{N-4}$,
 (G) —$SO_2$—($C_1$-$C_8$ alkyl),
 (H) —$SO_2$—$NR_{N-2}R_{N-3}$,
 (I) —NH—CO—($C_1$-$C_6$ alkyl)
 (J) —NH—CO—O—$R_{N-8}$,
 (K) —$NR_{N-2}R_{N-3}$,
 (L) —$R_{N-4}$,
 (M) —O—CO—($C_1$-$C_6$ alkyl),
 (N) —O—CO—$NR_{N-8}R_{N-8}$,
 (O) —O—($C_1$-$C_5$ alkyl)—COOH,
 (P) —O—($C_1$-$C_6$ alkyl optionally substituted with one, two, or three groups that are independently —F, —Cl, —Br, or —I),
 (Q) —NH—$SO_2$—($C_1$-$C_6$ alkyl),
 (R) halogen,
 (S) —N(H or $R_{N-5}$)—$SO_2$—$R_{N-2}$,
 (T) —N(H or $R_{N-5}$)—CO—($R_{N-2}$),
 (U) —$SO_2$—$R_{N-2}$, and
 (V) $R_{N-aryl}$;
(V) —CO—CH(—$(CH_2)_{0-2}$—O—$R_{N-10}$)—$(CH_2)_{0-2}$—($R_{N-aryl}$ or $R_{N-heteroaryl}$)) wherein
$R_{N-10}$ is selected from the group consisting of:
 (1) —H,
 (2) $C_1$-$C_6$ alkyl,
 (3) $C_3$-$C_8$ cycloalkyl,
 (4) $C_2$-$C_6$ alkenyl,
 (5) $C_2$-$C_6$ alkynyl,
 (6) $R_{1-aryl}$,
 (7) $R_{N-heteroaryl}$,
 (8) $R_{N-heterocycle}$,
(VI) —CO—($C_3$-$C_8$ cycloalkyl) where the cycloalkyl group is optionally substituted with one or two substituents independently selected from the group consisting of:
 (A) —$(CH_2)_{0-4}$—OH,
 (B) —$(CH_2)_{0-4}$—$C_1$-$C_6$ alkoxy,
 (C) —$(CH_2)_{0-4}$—$C_1$-$C_6$ thioalkoxy,
 (D) —$(CH_2)_{0-4}$—CO—O—$R_{N-8}$,
 (E) —$(CH_2)_{0-4}$—CO—$NR_{N-2}R_{N-3}$,
 (F) —$(CH_2)_{0-4}$—CO—$R_{N-4}$,
 (G) —$(CH_2)_{0-4}$—$SO_2$—($C_1$-$C_8$ alkyl),
 (H) —$(CH_2)_{0-4}$—$SO_2$—$NR_{N-2}R_{N-3}$,
 (I) —$(CH_2)_{0-4}$—NH—CO—($C_1$-$C_6$ alkyl),
 (J) —NH—CO—O—$R_{N-8}$,
 (K) —$(CH_2)_{0-4}$—$NR_{N-2}R_{N-3}$,
 (L) —$(CH_2)_{0-4}$—$R_{N-4}$,
 (M) —O—CO—($C_1$-$C_6$ alkyl),
 (N) —O—CO—$NR_{N-8}R_{N-8}$,
 (O) —O—($C_1$-$C_6$ alkyl)—$CO_2H$, (P) —O—($C_1$-$C_6$ alkyl optionally substituted with one, two, or three groups that are independently selected from —F, —Cl, —Br, and —I),
(Q) —NH—$SO_2$—($C_1$-$C_6$ alkyl),
(R) halogen,
(S) —N(H or $R_{N-5}$)—$SO_2$—$R_{N-2}$,
(T) —N(H or $R_{N-5}$)—CO—($R_{N-2}$),
(U) —$SO_2$—$R_{N-2}$, and
(V) $R_{N-aryl}$;

where $R_C$ is:
(I) —$C_1$-$C_{10}$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1-a}R_{1-b}$, —OC=O $NR_{1-a}R_{1-b}$, —S(=O)$_{0-2}R_{1-a}$, —$NR_{1-a}$C=O $NR_{1-a}R_{1-b}$, —C=O $NR_{1-a}R_{1-b}$, and —S(=O)$_2NR_{1-a}R_{1-b}$, (II) —(CH$_2$)$_{0-3}$—($C_3$-$C_8$)cycloalkyl where cycloalkyl can be optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$CO_2$H, —$CO_2$—($C_1$-$C_4$ alkyl), and —$NR_{1-a}R_{1-b}$, (III) —($CR_{C-x}R_{C-y}$)$_{0-4}$-$R_{C-aryl}$ at each occurrence is independently phenyl; naphthyl; tetralinyl; indanyl; indenyl; dihydronaphthyl; or 6,7,8,9-tetrahydro-5H-benzo[a]cycloheptenyl; each of which is optionally substituted with 1, 2, or 3 groups that at each occurrence are independently:
(1) $C_1$-$C_6$ alkyl, optionally substituted with one, two or three substituents selected from the group consisting of $C_1$-$C_3$ alkyl, —F, —Cl, —Br, —I,
—OH, —SH, —C≡N, —$CF_3$, $C_1$-$C_3$ alkoxy, and —$NR_{1-a}R_{1-b}$,
(2) —OH,
(3) —$NO_2$,
(4) —F, —Cl, —Br, —I,
(5) —$CO_2$H,
(6) —C≡N, and
(7) —(CH$_2$)$_{0-4}$—CO—$NR_{N-2}R_{N-3}$;
where $R_{C-x}$ and $R_{C-y}$ are independently
—H,
$C_1$-$C_4$ alkyl optionally substituted with one or two —OH,
$C_1$-$C_4$ alkoxy optionally substituted with 1, 2, or 3 —F,
—(CH$_2$)$_{0-4}$—$C_3$-$C_8$ cycloalkyl,
$C_2$-$C_6$ alkenyl,
$C_2$-$C_6$ alkynyl, and
phenyl,
or $R_{C-x}$ and $R_{C-y}$ are taken together with the carbon to which they are attached to form a carbocycle of three, four, five, six and seven carbon atoms, optionally where one carbon atom is replaced by a heteroatom selected from the group consisting of —O—, —S—, —$SO_2$—, —$NR_{N-2}$— and $R_{C-aryl}$ is defined as is defined above;

(IV) —($CR_{C-x}R_{C-y}$)$_{0-4}$—$R_{C-heteroaryl}$ where $R_{C-heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzoisothiazolyl, benzimidazolyl, benzofuranyl, furanyl, thienyl, pyrrolyl, oxadiazolyl, thiadiazolyl, triazolyl, tetrazolyl, oxazolopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, imidazopyrazolyl, quinazolinonyl, pyrazopyridyl, benzooxadiazolyl, dihydropyrimidinonyl, dihydrobenzofuranonyl, pyridinyl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{C-heteroaryl}$ group is bonded by any atom of the parent $R_{C-heteroaryl}$ group substituted by hydrogen such that the new bond to the $R_{C-heteroaryl}$ group replaces the hydrogen atom and its bond, where heteroaryl is optionally substituted 1, 2, 3, or 4 groups that are independently:
(1) $C_1$-$C_6$ alkyl, optionally substituted with 1, 2, or 3 groups independently selected from the group consisting of $C_1$-$C_3$ alkyl, —F, —Cl, —Br, —I, —OH, —SH, —C≡N, —$CF_3$, $C_1$-$C_3$ alkoxy, and —$NR_{1-a}R_{1-b}$,
(2) —OH,
(3) —$NO_2$,
(4) —F, —Cl, —Br, —I,
(5) —CO—OH,
(6) —C≡N,
(7) —(CH$_2$)$_{0-4}$—CO—$NR_{N-2}R_{N-3}$,
(8) —(CH$_2$)$_{0-4}$—CO—($C_1$-$C_{12}$ alkyl),
(9) —(CH$_2$)$_{0-4}$—CO—($C_2$-$C_{12}$ alkenyl),
(10) —(CH$_2$)$_{0-4}$—CO—($C_2$-$C_{12}$ alkynyl),
(11) —(CH$_2$)$_{0-4}$—CO—($C_3$-$C_7$ cycloalkyl),
(12) —(CH$_2$)$_{0-4}$CO—$R_{1-aryl}$,
(13) —(CH$_2$)$_{0-4}$—CO—$R_{1-heteroaryl}$,
(14) —(CH$_2$)$_{0-4}$—CO—$R_{1-heterocycle}$,
(15) —(CH$_2$)$_{0-4}$—CO—$R_{N-4}$,
(16) —(CH$_2$)$_{0-4}$—CO—O—$R_{N-5}$,
(17) —(CH$_2$)$_{0-4}$—$SO_2$—$NR_{N-2}R_{N-3}$,
(18) —(CH$_2$)$_{0-4}$—SO—($C_1$-$C_8$ alkyl),
(19) —(CH$_2$)$_{0-4}$—$SO_2$—($C_1$-$C_{12}$ alkyl),
(20) —(CH$_2$)$_{0-4}$—$SO_2$—($C_3$-$C_7$ cycloalkyl),
(21) —(CH$_2$)$_{0-4}$—N(H or $R_{N-5}$)—CO—O—$R_{N-5}$,
(22) —(CH$_2$)$_{0-4}$—N(H or $R_{N-5}$)—CO—N($R_{N-5}$)$_2$,
(23) —(CH$_2$)$_{0-4}$—N—CS—N($R_{N-5}$)$_2$,
(24) —(CH$_2$)$_{0-4}$—N(—H or $R_{N-5}$)—CO—$R_{N-2}$,
(25) —(CH$_2$)$_{0-4}$—$NR_{N-2}R_{N-3}$,
(26) —(CH$_2$)$_{0-4}$—$R_{N-4}$,
(27) —(CH$_2$)$_{0-4}$—O—CO—($C_1$-$C_6$ alkyl),
(28) —(CH$_2$)$_{0-4}$—O—P(O)—(O$R_{100}$)$_2$,
(29) —(CH$_2$)$_{0-4}$—O—CO—N($R_{N-5}$)$_2$,
(30) —(CH$_2$)$_{0-4}$—O—CS—N($R_{N-5}$)$_2$,
(31) —(CH$_2$)$_{0-4}$—O—($R_{N-5}$),
(32) —(CH$_2$)$_{0-4}$—O—($R_{N-5}$)—COOH,
(33) —(CH$_2$)$_{0-4}$—S—($R_{N-5}$),
(34) —(CH$_2$)$_{0-4}$—O—($C_1$-$C_6$ alkyl optionally substituted with one, two, three, four, or five of —F),
(35) $C_3$-$C_8$ cycloalkyl,
(36) $C_2$-$C_6$ alkenyl optionally substituted with $C_1$-$C_3$ alkyl, —F, —Cl, —Br, —I, —OH, —SH, —C≡N, —$CF_3$, $C_1$-$C_3$ alkoxy, or —$NR_{1-a}R_{1-b}$,

(37) $C_2$-$C_6$ alkynyl optionally substituted with $C_1$-$C_3$ alkyl, —F, —Cl, —Br, —I, —OH, —SH, —C≡N, —CF$_3$, $C_1$-$C_3$ alkoxy, or —NR$_{1-a}$R$_{1-b}$,

(38) —(CH$_2$)$_{0-4}$—N(—H or R$_{N-5}$)—SO$_2$-R$_{N-2}$, and

(39) —(CH$_2$)$_{1-4}$—(C$_3$-C$_8$ cycloalkyl), (V) —(CR$_{C-x}$R$_{C-y}$)$_{0-4}$—R$_{C-aryl}$—R$_{C-aryl}$, (VI) —(CR$_{C-x}$R$_{C-y}$)$_{0-4}$—R$_{C-aryl}$—R$_{C-heteroaryl}$, (VII) —(CR$_{C-x}$R$_{C-y}$)$_{0-4}$—R$_{C-heteroaryl}$—R$_{C-aryl}$, (VIII) —(CR$_{C-x}$R$_{C-y}$)$_{0-4}$—R$_{C-heteroaryl}$—R$_{C-heteroaryl}$, (IX) —(CR$_{C-x}$R$_{C-y}$)$_{0-4}$—R$_{C-aryl}$—R$_{C-heterocycle}$, wherein R$_{C-heterocycle}$ is selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, homothiomorpholinyl S-oxide, dithianyl, pyranyl, dihydrofuranyl, pyrrolidinonyl, imidazolidinonyl, imidazolidinondionyl, wherein each of the above is optionally fused to a benzene, pyridine, or pyrimidine ring, and where the R$_{1-heterocycle}$ group is bonded by any atom of the parent R$_{1-heterocycle}$ group substituted by hydrogen such that the new bond to the R$_{1-heterocycle}$ group replaces the hydrogen atom and its bond, where heterocycle is optionally substituted with one, two, three or four:

(1) $C_1$-$C_6$ alkyl optionally substituted with one, two or three substituents independently selected from the group consisting of $C_1$-$C_3$ alkyl, —F, —Cl, —Br, —I, —OH, —SH, —NR$_{1-a}$R$_{1-b}$, —C≡N, —CF$_3$, and $C_1$-$C_3$ alkoxy, (2) $C_2$-$C_6$ alkenyl optionally substituted with one, two or three substituents selected from the group consisting of —F, —Cl, —OH, —SH, —C≡N, —CF$_3$, $C_1$-$C_3$ alkoxy, —NR$_{1-a}$R$_{1-b}$, (3) $C_2$-$C_6$ alkynyl optionally substituted with one, two or three substituents independently selected from the group consisting of —F, —Cl, —OH, —SH, —C≡N, —CF$_3$, $C_1$-$C_3$ alkoxy, and —NR$_{1-a}$R$_{1-b}$, (4) —F, —Cl, —Br and —I, (5) $C_1$-$C_6$ alkoxy, (6) —$C_1$-$C_6$ haloalkoxy, (7) —NR$_{N-2}$R$_{N-3}$, (8) —OH, (9) —C≡N,

(10) $C_3$-$C_7$ cycloalkyl, optionally substituted with one, two or three substituents independently selected from the group consisting of —F, —Cl, —OH, —SH —C≡N, —CF$_3$, $C_1$-$C_3$ alkoxy, and —NR$_{1-a}$R$_{1-b}$,

(11) —CO—(C$_1$-C$_4$ alkyl),

(12) —SO$_2$—NR$_{1-a}$R$_{1-b}$,

(13) —CO—NR$_{1-a}$R$_{1-b}$,

(14) —SO$_2$—(C$_1$-C$_4$ alkyl),

(15) =O, with the proviso that when n$_1$ is zero R$_{1-heterocycle}$ is not bonded to the carbon chain by nitrogen;

(X) —(CR$_{C-x}$R$_{C-y}$)$_{0-4}$—R$_{C-heteroaryl}$—R$_{C-heterocycle}$, (XI) —(CR$_{C-x}$R$_{C-y}$)$_{0-4}$—R$_{C-heterocycle}$—R$_{C-aryl}$, (XII) —(CR$_{C-x}$R$_{C-y}$)$_{0-4}$—R$_{C-heterocycle}$—C-heteroaryl, (XIII) —(CR$_{C-x}$R$_{C-y}$)$_{0-4}$—R$_{C-heterocycle}$—R$_{C-heterocycle}$, (XIV) —(CR$_{C-x}$R$_{C-y}$)$_{0-4}$—R$_{C-heterocycle}$, (XV) —[C(R$_{C-1}$)(R$_{C-2}$)]$_{1-3}$—CO—N—(R$_{C-3}$)$_2$ where R$_{C-1}$ and R$_{C-2}$ are the same or different and are selected from the group consisting of:

(A) —H, (B) —C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_1$, (C) C$_2$-C$_6$ alkenyl optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$, (D) C$_2$-C$_6$ alkynyl optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$, (E) —(CH$_2$)$_{1-2}$—S(O)$_{0-2}$—(C$_1$-C$_6$ alkyl), (F) —(CH$_2$)$_{0-4}$—C$_3$-C$_8$ cycloalkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$ (G) —(C$_1$-C$_4$ alkyl)-R$_{C-aryl}$, (H) —(C$_1$-C$_4$ alkyl)-R$_{C-heteroaryl}$, (I) —(C$_1$-C$_4$ alkyl)-R$_{C-heterocycle}$, (J) —R$_{C-heteroaryl}$, (K) —R$_{C-heterocycle}$, (M) —(CH$_2$)$_{1-4}$—R$_{C-4}$—(CH$_2$)$_{0-4}$—R$_{C-aryl}$ where R$_{C-4}$ is —O—, —S— or —NR$_{C-5}$— where R$_{C-5}$ is C$_1$-C$_6$ alkyl, (N) —(CH$_2$)$_{1-4}$—R$_{C-4}$—(CH$_2$)$_{0-4}$—R$_{C-heteroaryl}$, (O) —R$_{C-aryl}$, and where R$_{C-3}$ at each occurrence is the same or different and is:

(A) —H, (B) —C$_3$-C$_6$ alkyl optionally substituted with one, two or three substituents independently selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$, (C) C$_2$-C$_6$ alkenyl with one or two double bonds, optionally substituted with one, two or three substituents independently selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$, (D) C$_2$-C$_6$ alkynyl optionally substituted with one, two or three substituents independently selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$, (E) —(CH$_2$)$_{0-4}$—C$_3$-C$_8$ cycloalkyl, optionally substituted with one, two or three substituents independently selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$, (F) —R$_{C-aryl}$, (G) —R$_{C-heteroaryl}$, (H) —R$_{C-heterocycle}$, (I) —(C$_1$-C$_4$ alkyl)-R$_{C-aryl}$, J) —(C$_1$-C$_4$ alkyl)-R$_{C-heteroaryl}$, (K) —(C$_1$-C$_4$ alkyl)-R$_{C-heterocycle}$, (XVI) —CH(R$_{C-aryl}$)$_2$, (XVII) —CH(R$_{C-heteroaryl}$)$_2$, (XVIII) —CH(R$_{C-aryl}$)(R$_{C-heteroaryl}$), (XIX) -cyclopentyl, -cyclohexyl, or -cycloheptyl ring fused to R$_{C-aryl}$ or R$_{C-heteroaryl}$ or R$_{C-heterocycle}$, where one carbon of cyclopentyl, cyclohexyl, or -cycloheptyl is optionally replaced with NH, $NR_{N-5}$, O, $S(=O)_{0-2}$, and where cyclopentyl, cyclohexyl, or -cycloheptyl can be optionally substituted with one or two —$C_1$-$C_3$ alkyl, —F, —OH, —SH, —C≡N, —$CF_3$, $C_1$-$C_6$ alkoxy, =O, and —$NR_{1-a}R_{1-b}$, (XX) $C_2$-$C_{10}$ alkenyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$, (XXI) $C_2$-$C_{10}$ alkynyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$, (XXI) —$(CH_2)_{0-1}$—$CHR_{C-6}$—$(CH_2)_{0-1}$—$R_{C-aryl}$ where $R_{C-6}$ is —$(CH_2)_{0-6}$—OH, (XXII) —$(CH_2)_{0-1}$—$CHR_{C-6}$—$(CH_2)_{0-1}$—$R_{C-heteroaryl}$, (XXIII) —CH(—$R_{C-aryl}$ or $R_{C-heteroaryl}$)—$CO_2(C_1$-$C_4$ alkyl), (XXIV) —CH(—$CH_2$—OH)—CH(—OH)—$NO_2$, (XXV) ($C_1$-$C_6$ alkyl)—O—($C_1$-$C_6$ alkyl)-OH, (XXVII) —$CH_2$—NH—$CH_2$—CH(—O—$CH_2$—$CH_3$)$_2$, (XXVIII) —H, (XXIX) —$(CH_2)_{0-6}$—C(=$NR_{1-a}$)($NR_{1-a}R_{1-b}$);

$R_{25}$ at each occurrence is independently selected from the group consisting of hydrogen, $C_1$-$C_6$ alkyl, $C_1$-$C_6$ alkoxy, $C_1$-$C_6$ alkoxy $C_1$-$C_6$ alkyl, hydroxy $C_1$-$C_6$ alkyl, halo $C_1$-$C_6$ alkyl, $C_1$-$C_6$ alkanoyl, each of which is unsubstituted or substituted with 1, 2, 3, or 4 groups independently selected from halogen, alkyl, hydroxy, alkoxy, and $NH_2$, and —$R_{26}$-$R_{27}$, wherein $R_{26}$ is selected from the group consisting of —C(O)—, —O—, —S—, —SO—, —$SO_2$—, —$CO_2$—, —C(O)NH—, and —C(O)N($C_1$-$C_6$ alkyl)-;

$R_{27}$ is selected from the group consisting of alkyl, alkoxy, phenyl, pyridyl, and cyclopropyl, and pharmaceutically acceptable salts thereof.

Disclosed is a method of treating a patient who has, or in preventing a patient from getting, a disease or condition selected from the group consisting of Alzheimer's disease, for helping-prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which comprises administration of a therapeutically effective amount of a compound of the invention or a pharmaceutically acceptable salt thereof.

Also disclosed are methods for inhibiting beta-secretase activity, for inhibiting cleavage of amyloid precursor protein (APP), in a reaction mixture, at a site between Met596 and Asp597, numbered for the APP-695 amino acid isotype; or at a corresponding site of an isotype or mutant thereof, for inhibiting production of amyloid beta peptide (A beta) in a cell, for inhibiting the production of beta-amyloid plaque in an animal, and for treating or preventing a disease characterized by beta-amyloid deposits in the brain which comprise administration of a therapeutically effective amount of a compound of the invention or a pharmaceutically acceptable salt thereof.

The invention also discloses pharmaceutical compositions comprising compounds of the invention.

The invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity. The inhibitory activities of the compounds of the invention are readily demonstrated, for example, using one or more of the assays described herein or known in the art.

DETAILED DESCRIPTION OF THE INVENTION

In a specific aspect within Formula X, the invention provides compounds of formula Z1:

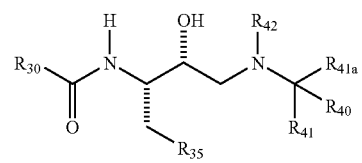

or a pharmaceutically acceptable salt thereof, wherein $R_{30}$ is selected from the group consisting of phenyl, pyrazolopyrimidinyl, oxa-aza-benzoazulenyl, isoxazolyl, triazolopyridinyl, pyrrolidinonyl, tetrahydrothia-aza-fluorenyl, pyridyl, piperidinyl, dihydrocyclopentaquinolinyl, furyl, naphthothienyl, phthalazinonyl, thiadiazolyl, thienopyrimidinonyl, oxa-diaza-cyclopentanaphthalenyl, dihydrobenzodioxepinyl, chromanonyl, chromenonyl, oxazolidinyl, benzophenone, pyrazinyl mono N-oxide, benzofuranyl, pyrazolyl, -isoxazolyl-phenyl, phenyl-triazolyl, benzimidazolyl, indolyl, phenyl-pyrrolyl, chromanyl, isoquinolinyl, -thienyl-thienyl, benzothienyl, -phenyl-thiadiazolyl, chromanonyl, quinolinyl, -pyrrolyl-C(O)-phenyl, -phenyl-O-phenyl, -phenyl-oxazolyl, -pyrrolidinonyl-phenyl, -phenyl-pyrimidinyl, -phenyl-oxadiazolyl, bicyclo[2.2.1]heptenyl, cyclopentyl, thieno[2,3-b]thiophene, cyclohexyl, -phenyl-imidazolyl, benzoxazole; dihydro-1H-indolyl; 2,3-dihydro-benzo[b]thiophene 1,1-dioxide; benzo[b]thiophene 1,1-dioxide; 2,3-dihydro-benzo[d]isothiazole 1,1-dioxide; -phenyl-thiazolyl; -phenyl-pyrazolyl, -phenyl-C(O)-piperidyl, -phenyl-C(O)-pyrrolidinyl, -phenyl-isoxazolyl, isoindolyl, purinyl, oxaxolyl, thiazolyl, pyridazinonyl, thiazolyl, pyranyl, dihydropyranopyridinyl, diazepanyl, cyclopropyl, dihydronaphthoisoxazolyl, benzoindazole, dihydrocyclopentachromenonyl, imidazopyrazolyl, tetrahydrocyclopentachromenonyl, dihydroquinolinonyl, pyridyl N-oxide, isochromanyl, quinazolinonyl, pyrazolopyridinyl, dihydrobenzothiophene dioxide, dihydrofurobenzoisoxazolyl, dihydropyrimidine dionyl, thienopyrazolyl, oxazolyl, tetrahydrocyclopentapyrazolyl, dihydronaphthalenonyl, dihydrobenzofuranonyl, dihydrocyclopentathienyl, tetrahydrocyclopentapyrazolyl, tetrahydropyrazoloazepinyl, indazolyl, tetrahydrocycloheptaisoxazolyl, tetrahydroindolonyl, pyrrolidinyl, thienopyridinyl, dioxodihydrobenzoisothiazolonyl, triazolopyrimidinyl, thienyl, dihydrothienopyrimidinonyl, and benzooxadiazolyl, wherein each of the above is unsubstituted or substituted with 1, 2, 3, 4, or 5 groups that are independently selected from the group consisting of $C_1$-$C_{10}$ alkyl optionally substituted with 1 phenyl or 1 CN; OH, hydroxy $C_1$-$C_{10}$ alkyl optionally substituted with phenyl or ($C_1$-$C_4$ alkyl)phenyl, $C_1$-$C_6$ alkoxy optionally substituted with 1 or 2 groups that are independently hydroxy or phenyl; haloalkyl, haloalkoxy, $(CH_2)_{0-4}C(O)NR_{31}R_{32}$, —$NR_{31}$—$SO_2$—($C_1$-$C_6$ alkyl) wherein the alkyl group is optionally substituted with 1, 2, or 3 groups that are independently halogen or $R_{33}$, —$SO_2$—$NH(C_1$-$C_6$ alkyl) wherein the alkyl group is optionally substituted with 1 or 2 groups that are independently halogen, OH, alkoxy, or $R_{33}$; —($C_1$-$C_6$ alkyl)—$SO_2$—($C_1$-$C_6$ alkyl) wherein the alkyl group is optionally substituted with 1 or 2 groups that are independently halogen, OH, $C_1$-$C_4$ alkoxy, or $R_{33}$; —$SO_2$—($C_1$-$C_6$ alkyl) wherein the alkyl group is optionally substituted with 1 or 2 groups that are independently OH or $C_1$-$C_4$ alkoxy, —$SO_2$—$N(C_1$-$C_6$ alkyl)($C_1$-$C_6$ alkyl) wherein each alkyl group is optionally substituted with 1 or 2 groups that are independently halogen, OH or $R_{33}$; —$SO_2$—$NH(C_1$-$C_6$ alkyl)-phenyl wherein the phenyl is optionally substituted with 1 or 2 groups that are independently $C_1$-$C_4$ alkoxy or halogen, —O—($C_1$-$C_6$ alkyl)-phenyl, —($C_1$-$C_6$ alkyl)-O-phenyl, —($C_1$-$C_6$ alkyl)-O—($C_1$-$C_6$ alkyl)-phenyl, triazolidine-3,5-dione, halogen, —NHC(O)NH$_2$, —NHC(O)NH($C_1$-$C_6$ alkyl), —NHC(O)N($C_1$-$C_6$ alkyl)($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —N($C_1$-$C_6$ alkyl)C(O)N($C_1$-$C_6$ alkyl)($C_1$-$C_6$ alkyl), —($C_1$-$C_6$ alkyl) thienyl, —($C_1$-$C_6$ alkyl) furanyl, —S—($C_1$-$C_6$ alkyl) phenyl, —$SO_2NR_{31}R_{32}$, —C(O)—$NR_{31}R_{32}$, —$NR_{31}R_{32}$, dithiane, —NHC(S)NH$_2$, —NHC(S)NH($C_1$-$C_6$ alkyl), —NHC(S)N($C_1$-$C_6$ alkyl)($C_1$-$C_6$ alkyl), —$CO_2$($C_1$-$C_6$ alkyl), tetrahydropyran, phenyl optionally substituted with 1 or 2 groups that are independently F, Cl or Br; pyridine, —$C_2$-$C_4$ alkynyl-phenyl, —O—$C_3$-$C_8$ cycloalkyl, —O—($C_1$-$C_6$ alkyl)-$R_{33}$; pyrrole optionally substituted with one or two methyl groups; 2,3-dihydro-benzofuran; benzo[1,2,5]oxadiazole, —C(O)—($C_1$-$C_{10}$ alkyl) wherein the alkyl group is optionally substituted with NH$_2$, N($C_1$-$C_6$ alkyl), or N($C_1$-$C_6$ alkyl)($C_1$-$C_6$ alkyl); —C(O)NH-phenyl, —C(O)N($C_1$-$C_6$ alkyl)-phenyl, 4,4-dimethyl-4,5-dihydro-oxazole, —($C_1$-$C_6$ alkyl)-S-pyridine, —($C_1$-$C_6$ alkyl)-$SO_2$-pyridine, —($C_1$-$C_6$ thioalkoxy)-pyridine, thiazole optionally substituted with 1 or 2 methyl groups, pyrazole, S—($C_1$-$C_6$ alkyl), indole, ($C_1$-$C_6$ thioalkoxy)-($C_1$-$C_6$ alkyl), $C_2$-$C_8$ alkynyl, —$CO_2$—($C_1$-$C_6$ alkyl), $C_1$-$C_{10}$ alkanoyl; —$(CH_2)_{0-4}$—$SO_2$—($C_1$-$C_{10}$ alkyl) wherein the alkyl group is optionally substituted with OH;

wherein $R_{31}$, and $R_{32}$ at each occurrence are independently selected from the group consisting of hydrogen, $C_1$-$C_8$ alkyl, $C_2$-$C_8$ alkenyl, hydroxy $C_1$-$C_6$ alkyl, $C_1$-$C_6$ haloalkyl, $C_1$-$C_6$ alkoxy $C_1$-$C_6$ alkyl, —$(CH_2)_{0-4}$—$SO_2$—($C_1$-$C_6$ alkyl) wherein the alkyl is optionally substituted with 1, 2, 3 or 4 independently selected halogen atoms; —$(CH_2)_{0-4}$—$SO_2$-imidazolyl, —($C_1$-$C_6$ alkyl)-C(O)NH$_2$, —($C_1$-$C_6$ alkyl)-C(O)NH($C_1$-$C_6$ alkyl), —($C_1$-$C_6$ alkyl)-C(O)N($C_1$-$C_6$ alkyl)($C_1$-$C_6$ alkyl), —($C_1$-$C_6$ alkyl)-NH$_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), —($C_1$-$C_6$ alkyl)phenyl, —($C_1$-$C_6$ alkyl)pyridyl, —C(O) furanyl, ($C_1$-$C_6$ alkyl)-tetrahydrofuran, cyclopropyl, cyclobutyl, cyclopentyl, cyclohexyl, —$CO_2$—($C_1$-$C_6$ alkyl), —($C_1$-$C_6$ alkyl)-furanyl, —$(CH_2)_{0-4}$—$SO_2$-thienyl, wherein the phenyl and pyridyl groups are unsubstituted or substituted with 1, 2, 3, 4, or 5 groups that are independently $C_1$-$C_4$ alkyl, hydroxy, $C_1$-$C_4$ alkoxy, halogen, or $R_{31}$, $R_{32}$ and the nitrogen to which they are attached form a 5, 6, or 7 membered heterocycloalkyl or a 6 membered heteroaryl ring, each of which is optionally fused to a benzene, pyridine or pyrimidine ring and each of which is optionally substituted with $C_1$-$C_6$ alkoxy, hydroxy, hydroxy $C_1$-$C_6$ alkyl, $C_1$-$C_4$ alkoxy $C_1$-$C_6$ alkyl, —C(O)NH$_2$, —C(O)NH—($C_1$-$C_6$ alkyl)-phenyl;

$R_{33}$ at each occurrence is independently, H, NH$_2$, NH($C_1$-$C_6$ alkyl), N($C_1$-$C_6$ alkyl)($C_1$-$C_6$ alkyl), N($C_1$-$C_6$ alkyl) (phenyl), N($C_1$-$C_6$ alkyl)(benzyl);

$R_{35}$ is phenyl, $C_3$-$C_8$ cycloalkyl, —S-phenyl, benzodioxole, thienyl, $C_1$-$C_6$ alkyl, furanyl, imidazolyl, each of which is unsubstituted or substituted with 1, 2, 3, 4, or 5 groups that are independently $C_1$-$C_4$ alkyl, $C_1$-$C_4$ alkoxy, OH, hydroxy $C_1$-$C_6$ alkyl, halogen, halo $C_1$-$C_6$ alkyl, halo $C_1$-$C_6$ alkoxy, —O—($C_1$-$C_6$ alkyl)-phenyl, —$CO_2$—($C_1$-$C_6$ alkyl), —($C_1$-$C_4$ alkyl)-($C_5$-$C_6$ cycloalkyl), or $(CH_2)_{0-4}$CN;

$R_{40}$ is phenyl, -phenyl-pyridyl, biphenyl, -phenyl-benzothienyl, -phenyl-thienyl, -phenyl-furanyl, -phenyl-pyrimidinyl, -phenyl-isoxazolyl, —C(O)-pyridyl, —($C_1$-$C_4$ alkyl)-O—C(O)NH-phenyl wherein the phenyl is optionally substituted with 1, 2, or 3 halogen atoms; —($C_1$-$C_4$ alkyl)-O—C(O)N($C_1$-$C_6$ alkyl)-phenyl, —($C_1$-$C_6$ alkyl)-phenyl, —($C_1$-$C_4$ alkyl)—$SO_2NH_2$, —($C_1$-$C_4$ alkyl)-$SO_2NH(C_1$-$C_6$ alkyl), —($C_1$-$C_4$ alkyl)-$SO_2N(C_1$-$C_6$ alkyl)($C_1$-$C_6$ alkyl), —$SO_2NH_2$, —$SO_2NH(C_1$-$C_6$ alkyl), —$SO_2N(C_1$-$C_6$ alkyl)($C_1$-$C_6$ alkyl), CN, —$(CH_2)_{0-4}$-($C_3$-$C_8$ cycloalkyl), —($C_1$-$C_4$ alkyl)-C(O)O—($C_1$-$C_4$ alkyl), —($C_1$-$C_4$ alkyl)-$R_{33}$, $C_1$-$C_{10}$ alkyl, $C_2$-$C_8$ alkenyl, —($C_1$-$C_4$ alkyl)-NHC(O)—($C_1$-$C_4$ alkyl), —$(CH_2)_{0-4}$—C(O)NH$_2$, —$(CH_2)_{0-4}$—C(O)NH($C_1$-$C_6$ alkyl), —$(CH_2)_{0-4}$—C(O)N($C_1$-$C_6$ alkyl)($C_1$-$C_6$ alkyl), naphthyl, tetrahydronapthyl, dihydronaphthyl, —$(CH_2)_{0-4}$-imidazolyl, —$(CH_2)_{0-4}$-pyrrolidinyl, oxazolidinone 3,4-dihydro-benzo[e][1,2]oxathiine 2,2-dioxide, pyrimidinyl, 3,4-dihydro-2H-benzo[e][1,2]thiazine 1,1-dioxide, pyridyl, or pyrimidyl, alkoxyalkyl, -phenyl-benzothienyl, -phenyl-cyclohexyl, -phenyl-cyclopentyl, -phenyl-($C_1$-$C_6$ alkyl)-cyclopentyl, -phenyl-($C_1$-$C_6$ alkyl)-cyclohexyl, -phenyl-oxazolyl, furanyl, tetrahydrofuranyl, wherein each of the above is unsubstituted or substituted with 1, 2, 3, 4, or 5 groups that are independently halogen, $C_1$-$C_8$ alkyl optionally substituted with 1 or two groups that are independently CN or OH; $C_1$-$C_6$ alkoxy, halo($C_1$-$C_8$ alkyl), halo($C_1$-$C_4$ alkoxy), —O—($C_1$-$C_4$ alkyl)-phenyl wherein the phenyl is optionally substituted with 1 or 2 halogens, CN, —CHO, $C_1$-$C_4$ thioalkoxy, —NHSO$_2$—($C_1$-$C_6$ alkyl), —N($C_1$-$C_4$ alkyl)SO$_2$—($C_1$-$C_4$ alkyl) wherein the alkyl groups are optionally substituted with 1, 2, or 3 halogens; OH; —SO$_2$$R_{33}$; $R_{33}$; $C_2$-$C_8$ alkynyl; $C_2$-$C_8$ alkenyl; thioalkoxyalkyl; —SO$_2$—($C_1$-$C_{10}$ alkyl); —N$R_{31}$$R_{32}$; —C(O)—N$R_{31}$$R_{32}$; —OC(O)$R_{33}$; $C_1$-$C_8$ alkanoyl; —($C_1$-$C_6$ alkyl)-C(O)—($C_1$-$C_6$ alkoxy);

$R_{41a}$ and $R_{41}$ are independently H, cyclohexyl, phenyl, or $C_1$-$C_6$ alkyl optionally substituted with 1 or 2 groups that are phenyl, hydroxy, $C_1$-$C_4$ thioalkoxy, $C_1$-$C_4$ thioalkoxy $C_1$-$C_6$ alkyl; or —$C_1$-$C_6$ alkyl-SO$_2$—$C_1$-$C_6$ alkyl;

$R_{40}$, $R_{41}$, and the atom to which they are attached form a $C_3$-$C_8$ cycloalkyl ring which is optionally substituted with $C_1$-$C_4$ alkyl, $C_1$-$C_4$ alkoxy, halogen, —CO$_2$NH$_2$, —CO$_2$NH($C_1$-$C_6$ alkyl), —CO$_2$N($C_1$-$C_6$ alkyl)($C_3$-$C_6$ alkyl), thiazolyl optionally substituted with $C_1$-$C_6$ alkyl, isoxazolyl optionally substituted with $C_1$-$C_6$ alkyl, or phenyl which is optionally substituted with 1, 2, or 3 groups that are independently halogen or $C_1$-$C_6$ alkyl; and $R_{42}$ is H, $C_1$-$C_6$ alkyl optionally substituted with OH; benzyl; —NHC(O)—($C_1$-$C_6$ alkyl); —NHC(O)-phenyl wherein the phenyl is optionally substituted with 1 or 2 alkyl groups.

Preferred compounds of formula Z1 include the compounds of formula Z2:

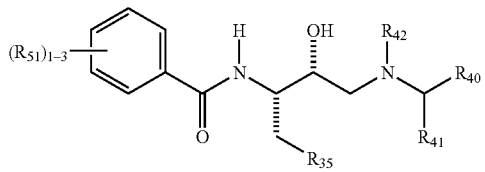

Z2 or a pharmaceutically acceptable salt thereof, wherein $R_{51}$ at each occurrence is independently $C_1$-$C_6$ alkyl, $C_1$-$C_6$ alkoxy, —NHSO$_2$—($C_1$-$C_4$ alkyl) wherein the alkyl group is optionally substituted with 1, 2, or 3 halogens, —SO$_2$—NH—($C_1$-$C_6$ alkyl)-NH$_2$, —SO$_2$—NH—($C_1$-$C_6$ alkyl)-NH($C_1$-$C_4$ alkyl), —SO$_2$—NH—($C_1$-$C_6$ alkyl)-N($C_1$-$C_4$ alkyl)($C_1$-$C_4$ alkyl), [1,2,4]triazolidine-3,5-dione, —NHC(O)NH$_2$, —NHC(O)NH($C_1$-$C_6$ alkyl), —NHC(O)N($C_1$-$C_6$ alkyl)($C_1$-$C_6$ alkyl), —N($C_1$-$C_6$ alkyl)C(O)NH$_2$, —N($C_1$-$C_6$ alkyl)C(O)NH($C_1$-$C_6$ alkyl), —N($C_1$-$C_6$ alkyl)C(O)N($C_1$-$C_6$ alkyl)($C_1$-$C_6$ alkyl), halogen, —CF$_3$, OH, —SO$_2$N$R_{31}$$R_{32}$, —C(O)N$R_{31}$$R_{32}$, —N$R_{31}$$R_{32}$, hydroxy $C_1$-$C_{10}$ alkyl optionally substituted with phenyl or ($C_1$-$C_4$ alkyl)phenyl, —O—($C_1$-$C_4$ alkyl)-phenyl, —NHC(S)NH$_2$, —NHC(S)NH($C_1$-$C_6$ alkyl), —NHC(S)N($C_1$-$C_6$ alkyl)($C_1$-$C_6$ alkyl), ($C_1$-$C_4$ alkyl)-O-phenyl, —C(O)—($C_1$-$C_6$ alkyl) wherein the alkyl group is optionally substituted with NH$_2$, N($C_1$-$C_6$ alkyl), or N($C_1$-$C_6$ alkyl)($C_1$-$C_6$ alkyl); —O—$C_3$-$C_6$ cycloalkyl, oxazole optionally substituted with 1, or 2 groups that are independently $C_1$-$C_4$ alkyl or phenyl, hydroxy $C_1$-$C_4$ alkoxy, aminoalkoxy, NH($C_1$-$C_6$alkyl)-alkoxy, N($C_1$-$C_6$alkyl)($C_1$-$C_6$alkyl)-alkoxy, wherein $R_{31}$ and $R_{32}$ at each occurrence are independently selected from the group consisting of hydrogen, $C_1$-$C_6$ alkyl, hydroxy $C_1$-$C_6$ alkyl, $C_1$-$C_6$ haloalkyl, —($C_1$-$C_6$ alkyl)-C(O)NH$_2$, —($C_1$-$C_6$ alkyl)-C(O)NH($C_1$-$C_6$ alkyl), —($C_1$-$C_6$ alkyl)-C(O)N($C_1$-$C_6$ alkyl)(CO$_1$-$C_6$ alkyl), —($C_1$-$C_6$ alkyl)-NH$_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), —($C_1$-$C_6$ alkyl)phenyl, —($C_1$-$C_6$ alkyl)pyridyl, —C(O) furanyl, ($C_1$-$C_6$ alkyl)-tetrahydrofuran, wherein the phenyl and pyridyl groups are unsubstituted or substituted with 1, 2, 3, 4, or 5 groups that are independently $C_1$-$C_4$ alkyl, hydroxy, $C_1$-$C_4$ alkoxy, halogen, or wherein at each occurrence $R_{31}$, $R_{32}$ and the nitrogen to which they are attached independently form a pyrrolidinyl, piperazinyl, piperidinyl, azepanyl, pyridinyl, or pyrimidinyl ring, each of which is optionally fused to a benzene, pyridine or pyrimidine ring and each of which is optionally substituted with $C_1$-$C_6$ alkoxy, $C_1$-$C_6$ alkyl, hydroxy, hydroxy $C_1$-$C_6$ alkyl, $C_1$-$C_4$ alkoxy $C_1$-$C_6$ alkyl, —C(O)NH$_2$, or —C(O)NH—($C_1$-$C_6$ alkyl)-phenyl.

Preferred compounds of Z2 are those wherein $R_{41}$ and $R_{42}$ are both hydrogen.

Other preferred compounds of Z2 are those wherein $R_{35}$ is phenyl, cyclohexyl, —S-phenyl, benzodioxole, thienyl, $C_3$-$C_6$ alkyl, furanyl, each of which is unsubstituted or substituted with 1, 2, 3, 4, or 5 groups that are independently $C_1$-$C_4$ alkyl, $C_1$-$C_4$ alkoxy, OH, hydroxy $C_1$-$C_6$ alkyl, halogen, halo $C_1$-$C_6$ alkyl, halo $C_1$-$C_6$ alkoxy, —O—($C_1$-$C_6$ alkyl)-phenyl, —CO$_2$—($C_1$-$C_6$ alkyl), —($C_1$-$C_4$ alkyl)-($C_5$-$C_6$ cycloalkyl).

Other preferred compounds of Z1 are those wherein $R_{35}$ is phenyl, cyclohexyl, —S-phenyl, benzodioxole, thienyl, $C_3$-$C_6$ alkyl, furanyl, each of which is unsubstituted or substituted with 1, 2, 3, 4, or 5 groups that are independently $C_1$-$C_4$ alkyl, $C_1$-$C_4$ alkoxy, OH, hydroxy $C_1$-$C_6$ alkyl, halogen, halo $C_1$-$C_6$ alkyl, halo $C_1$-$C_6$ alkoxy, —O—($C_1$-$C_6$ alkyl)-phenyl, —CO$_2$—($C_1$-$C_6$ alkyl), —($C_1$-$C_4$ alkyl)-($C_5$-$C_6$ cycloalkyl);

$R_{40}$ is phenyl, -phenyl-pyridine, biphenyl, -phenyl-benzothienyl, -phenyl-thienyl, -phenyl-furanyl, -phenyl-pyrimidinyl, -phenyl-isooxazolyl, —C(O)-pyridyl, —($C_1$-$C_4$ alkyl)-O—C(O)NH-phenyl, —($C_1$-$C_4$ alkyl)-O—C(O)N($C_1$-$C_6$ alkyl)-phenyl, —($C_1$-$C_4$ alkyl)-phenyl, —($C_1$-$C_4$ alkyl)-SO$_2$NH$_2$, —($C_1$-$C_4$ alkyl)-SO$_2$NH($C_1$-$C_6$ alkyl), —($C_1$-$C_4$ alkyl)-SO$_2$N($C_1$-$C_6$ alkyl)($C_1$-$C_6$ alkyl), CN, —(CH$_2$)$_{0-4}$—($C_3$-$C_8$ cycloalkyl), —($C_1$-$C_4$ alkyl)-C(O)O—($C_1$-$C_4$ alkyl), —($C_1$-$C_4$ alkyl)-$R_{33}$, $C_1$-$C_8$ alkyl, —($C_1$-$C_4$ alkyl)-NHC(O)—($C_1$-$C_4$ alkyl), —(CH$_2$)$_{0-4}$—C(O)NH$_2$, —(CH$_2$)$_{0-4}$—C(O)NH($C_1$-$C_6$ alkyl), —(CH$_2$)$_{0-4}$—C(O)N($C_1$-$C_6$ alkyl)($C_1$-$C_6$ alkyl), tetrahydronapthyl, dihydronaphthyl, wherein each of the above is unsubstituted or substituted with 1, 2, 3, 4, or 5 groups that are independently halogen, $C_1$-$C_4$ alkyl, $C_1$-$C_4$ alkoxy, halo ($C_1$-$C_4$ alkyl), —O—($C_1$-$C_4$ alkyl)-phenyl wherein the phenyl is optionally substituted with 1 or 2 halogens, —CHO, $C_1$-$C_4$ thioalkoxy, —NHSO$_2$—($C_1$-$C_4$ alkyl), —N($C_1$-$C_4$ alkyl)SO$_2$—($C_1$-$C_4$ alkyl) wherein the alkyl groups are optionally substituted with 1, 2, or 3 halogens; OH, SO$_2$$R_{33}$, $R_{33}$;

$R_{41}$ is H, cyclohexyl, phenyl, or $C_1$-$C_6$ alkyl optionally substituted with 1 or 2 groups that are phenyl, hydroxy, or $C_1$-$C_4$ thioalkoxy; and $R_{42}$ is hydrogen or —CH$_2$CN.

More preferred compounds of Z2 include those wherein $R_{35}$ is phenyl, $C_3$-$C_8$ cycloalkyl, —S-phenyl, benzodioxole, thienyl, $C_3$-$C_6$ alkyl, furanyl, each of which is unsubstituted or substituted with 1, 2, 3, 4, or 5 groups that are independently $C_1$-$C_4$-alkyl, $C_1$-$C_4$ alkoxy, OH, hydroxy $C_1$-$C_6$ alkyl, halogen, CF$_3$, OCF$_3$, —Obenzyl, —CO$_2$—($C_1$-$C_6$ alkyl), —($C_1$-$C_4$ alkyl)-($C_5$-$C_6$ cycloalkyl);

$R_{40}$ is phenyl, -phenyl-pyridine, biphenyl, -phenyl-benzothienyl, -phenyl-thienyl, -phenyl-furanyl, -phenyl-pyrimidinyl, -phenyl-isoxazolyl, —C(O)-pyridyl, —($C_1$-$C_4$ alkyl)-O—C(O)NH-phenyl, —($C_1$-$C_4$ alkyl)-O—C(O)N($C_1$-$C_6$ alkyl)-phenyl, —($C_1$-$C_4$ alkyl)-phenyl, —($C_1$-$C_4$ alkyl) —$SO_2NH_2$, —($C_1$-$C_4$ alkyl)-$SO_2NH$($C_1$-$C_6$ alkyl), —($C_1$-$C_4$ alkyl)-$SO_2N$($C_1$-$C_6$ alkyl)($C_1$-$C_6$ alkyl), CN, —($C_1$-$C_4$alkyl)-($C_3$-$C_6$cycloalkyl), —($C_1$-$C_4$alkyl)-C(O)O—($C_1$-$C_4$ alkyl), —($C_1$-$C_4$ alkyl)-$R_{33}$, $C_1$-$C_8$ alkyl, —($C_1$-$C_4$ alkyl)-NHC(O)—($C_1$-$C_4$ alkyl), —C(O)$NH_2$, wherein each of the above rings is unsubstituted or substituted with 1, 2, or 3 groups that are independently halogen, $C_1$-$C_4$ alkyl, $C_1$-$C_4$ alkoxy, $CF_3$, —O—($C_1$-$C_4$ alkyl)-phenyl wherein the phenyl is optionally substituted with 1 or 2 halogens, —CHO, —$NHSO_2$—($C_1$-$C_4$ alkyl), —N($C_1$-$C_4$ alkyl)$SO_2$—($C_1$-$C_4$ alkyl) wherein the alkyl is optionally substituted with 1, 2, or 3 halogens, $R_{41}$ is H, cyclohexyl, phenyl, or $C_1$-$C_6$ alkyl optionally substituted with 1 or 2 groups that are phenyl, hydroxy, or $C_1$-$C_4$ thioalkoxy; and $R_{42}$ is hydrogen or —$CH_2CN$;

$R_{51}$ at each occurrence is independently $C_1$-$C_6$ alkyl, $C_1$-$C_6$ alkoxy, —$NHSO_2$—($C_1$-$C_4$ alkyl) wherein the alkyl group is optionally substituted with 1, 2, or 3 halogens, —$SO_2$—NH—($C_1$-$C_6$ alkyl)-$NH_2$, —$SO_2$—NH—($C_1$-$C_6$ alkyl)-NH($C_1$-$C_4$ alkyl), —$SO_2$—NH—($C_1$-$C_6$ alkyl)-N($C_1$-$C_4$ alkyl)($C_1$-$C_4$ alkyl), [1,2,4]triazolidine-3,5-dione, —NHC(O)$NH_2$, —NHC(O)NH($C_1$-$C_6$ alkyl), —NHC(O)N($C_1$-$C_6$ alkyl)($C_1$-$C_6$ alkyl), —N($C_1$-$C_6$ alkyl)C(O)$NH_2$, —N($C_1$-$C_6$alkyl)C(O)NH($C_1$-$C_6$alkyl), —N($C_1$-$C_6$alkyl)C(O)N($C_1$-$C_6$ alkyl)($C_1$-$C_6$ alkyl), halogen, —$CF_3$, OH, —$SO_2NR_{31}R_{32}$, —C(O)$NR_{31}R_{32}$, —$NR_{31}R_{32}$, hydroxy $C_1$-$C_{10}$ alkyl optionally substituted with phenyl or 2-methylphenyl, —O—($C_1$-$C_4$ alkyl)-phenyl, —NHC(S)$NH_2$, —NHC(S)NH($C_1$-$C_6$ alkyl), —NHC(S)N($C_1$-$C_6$ alkyl)($C_1$-$C_6$ alkyl), ($C_1$-$C_4$ alkyl)-O-phenyl, —C(O)—($C_1$-$C_6$ alkyl) wherein the alkyl group is optionally substituted with $NH_2$, N($C_1$-$C_6$ alkyl), or N($C_1$-$C_6$ alkyl)($C_1$-$C_6$ alkyl); —O—$C_3$-$C_6$ cycloalkyl, oxazole optionally substituted with 1, or 2 groups that are independently $C_1$-$C_4$ alkyl or phenyl, hydroxy $C_1$-$C_4$ alkoxy, aminoalkoxy, NH($C_1$-$C_6$alkyl)-alkoxy, N($C_1$-$C_6$alkyl)($C_1$-$C_6$alkyl)-alkoxy, wherein $R_{31}$ and $R_{32}$ at each occurrence are independently selected from the group consisting of hydrogen, $C_1$-$C_6$ alkyl, hydroxy $C_1$-$C_6$ alkyl, —($C_1$-$C_6$ alkyl)-C(O)N($C_1$-$C_6$ alkyl)($C_1$-$C_6$ alkyl), —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), —($C_1$-$C_6$ alkyl)phenyl, —($C_1$-$C_6$ alkyl)pyridyl, —C(O)furanyl, ($C_1$-$C_6$ alkyl)-tetrahydrofuran, wherein the phenyl group is unsubstituted or substituted with 1, 2, or 3 groups that are independently $C_1$-$C_4$ alkoxy, or halogen, wherein at each occurrence $R_{31}$, $R_{32}$ and the nitrogen to which they are attached independently form a pyrrolidinyl, piperazinyl, piperidinyl, or azepanyl, each of which is optionally fused to a benzene, pyridine or pyrimidine ring and each of which is optionally substituted with hydroxy, $C_1$-$C_6$ alkyl, hydroxy $C_1$-$C_6$ alkyl, $C_1$-$C_4$ alkoxy $C_1$-$C_6$ alkyl, —C(O)$NH_2$, or —C(O)NH-benzyl.

Even more preferred compounds of Z2 are those wherein $R_{35}$ is phenyl; halophenyl, dihalophenyl; trihalophenyl; tetrahalophenyl; pentahalophenyl; halo, benzyloxyphenyl; halo, alkylphenyl; benzyloxyphenyl; cyclohexyl; ($C_1$-$C_4$ alkoxy)carbonylphenyl; ($C_1$-$C_4$ alkoxy)phenyl; —S-phenyl, or benzodioxole;

$R_{41}$ is H, cyclohexyl, phenyl, or $C_1$-$C_6$ alkyl optionally substituted with 1 or 2 groups that are phenyl, hydroxy, or $C_1$-$C_4$ thioalkoxy; and $R_{42}$ is hydrogen or —$CH_2CN$.

Other preferred compounds of Z2 are those wherein $R_{35}$ is 3,5-dihalophenyl;

$R_{40}$ is phenyl, -phenyl-pyridine, biphenyl, -phenyl-benzothienyl, -phenyl-thienyl, -phenyl-furanyl, -phenyl-pyrimidinyl, -phenyl-isoxazolyl, —($C_1$-$C_4$ alkyl)-O—C(O)NH-phenyl, —($C_1$-$C_4$ alkyl)-O—C(O)N($C_1$-$C_6$ alkyl)-phenyl, —($C_1$-$C_4$ alkyl)-$SO_2NH_2$, CN, —($C_1$-$C_4$ alkyl)-($C_3$-$C_6$ cycloalkyl), —($C_1$-$C_4$ alkyl)-C(O)O—($C_1$-$C_4$ alkyl), —($C_1$-$C_4$ alkyl)-$R_{33}$, or $C_1$-$C_8$ alkyl, wherein each of the above is unsubstituted or substituted with 1, 2, or 3 groups that are independently halogen, $C_1$-$C_4$ alkyl, $C_1$-$C_4$ alkoxy, $CF_3$, —O—($C_1$-$C_4$ alkyl)-phenyl wherein the phenyl is optionally substituted with 1 or 2 halogens, —CHO, or —$NHSO_2$—($C_1$-$C_4$ alkyl).

Even more preferred compounds of Z2 are those wherein $R_{35}$ is 3,5-difluorophenyl; 3,5-dichlorophenyl; or 3-chloro,5-fluorophenyl; and $R_{40}$ is phenyl which is unsubstituted or substituted with 1, 2, or 3 groups that are independently fluoro, chloro, bromo, iodo, methyl, ethyl, methoxy, ethoxy, $CF_3$, or —Obenzyl wherein the phenyl is optionally substituted with 1 or 2 groups that are independently halogen, or —$NHSO_2CH_3$.

Even more preferred compounds of Z2 are those wherein $R_{51}$ at each occurrence is independently $C_1$-$C_6$ alkyl, —$C_1$-$C_6$ alkoxy, —$NHSO_2CH_3$, —$SO_2$—NH-(ethyl)-NH($CH_3$), [1,2,4]triazolidine-3,5-dione, —NHC(O)$NH_2$, —$CF_3$, OH, —$SO_2NR_{31}R_{32}$, —C(O)$NR_{31}R_{32}$, hydroxyoctyl, —CH(OH)-2-methylphenyl, —Obenzyl, or —NHC(S)NH($CH_3$);

wherein $R_{31}$ and $R_{32}$ at each occurrence are independently selected from the group consisting of hydrogen, $C_1$-$C_6$ alkyl, hydroxy $C_1$-$C_6$ alkyl, —($CH_2$)C(O)N($CH_3$)$_2$, —$CH_2CH_2N$($CH_3$)$_2$, benzyl, phenethyl, —$CH_2CH_2$pyridyl, —C(O)furanyl, or at each occurrence $R_{31}$, $R_{32}$ and the nitrogen to which they are attached independently form a pyrrolidinyl, piperazinyl, piperidinyl, or azepanyl, each of which is optionally substituted with hydroxymethyl, hydroxyethyl, methoxymethyl, or —C(O)$NH_2$.

Even more preferred compounds of Z2 are those wherein $R_{40}$ is 3-ethylphenyl or 3-methoxyphenyl; and $R_{42}$ is hydrogen.

Preferred compounds of Z2 include those wherein $R_{51}$ at each occurrence is independently $C_1$-$C_6$ alkyl, $C_1$-$C_6$ alkoxy, —C(O)$NR_{31}R_{32}$, —C(O)$CH_2NH_2$, cyclopentyloxy, —NHC(O)NH(ethyl), oxazole optionally substituted with 1 or 2 groups that are independently $C_1$-$C_4$ alkyl or phenyl, hydroxyethoxy, diethylaminoethoxy, wherein $R_{31}$ and $R_{32}$ at each occurrence are independently selected from the group consisting of hydrogen, $C_1$-$C_6$ alkyl, hydroxy $C_1$-$C_6$ alkyl, —$CH_2$-tetrahydrofuran.

Other preferred compounds of Z2 include those wherein $R_{35}$ is cyclohexyl.

More preferred compounds include those wherein $R_{40}$ is phenyl, or $C_1$-$C_8$ alkyl, wherein each is unsubstituted or substituted with 1, 2, 3, 4, or 5 groups that are independently halogen, $C_1$-$C_4$ alkyl, $C_1$-$C_4$ alkoxy, halo($C_1$-$C_4$ alkyl); and $R_{42}$ and $R_4$, are both hydrogen.

More preferred compounds include those wherein $R_{40}$ is phenyl, 3-methoxyphenyl, 4-methoxyphenyl, 3-ethoxyphenyl, 4-ethoxyphenyl, 3-trifluoromethylphenyl, 4-trifluoromethylphenyl, 2-methylphenyl, 3-methylphenyl, 2-ethylphenyl, 3-ethylphenyl, or $C_3$-$C_6$ alkyl; and $R_{51}$ at each occurrence is independently $C_1$-$C_6$ alkyl, $C_1$-$C_6$ alkoxy, or halogen, wherein $R_{31}$ and $R_{32}$ at each occurrence are independently selected from the group consisting of hydrogen, $C_1$-$C_6$ alkyl, hydroxy $C_1$-$C_6$ alkyl, and —($C_1$-$C_6$ alkyl)phenyl wherein the phenyl group is unsubstituted or substituted with 1, 2, or 3 groups that are independently $C_1$-$C_4$ alkoxy, or halogen, wherein at each occurrence $R_{31}$, $R_{32}$ and the nitrogen to which they are attached independently form a pyrrolidinyl, piperazinyl, piperidinyl, or azepanyl, each of which is optionally fused to a benzene, pyridine or pyrimidine ring and each of which is optionally substituted with hydroxy, hydroxy $C_1$-$C_6$ alkyl, $C_1$-$C_4$ alkoxy $C_1$-$C_6$ alkyl, —C(O)NH$_2$, or —C(O)NH-benzyl.

More preferred compounds include those wherein $R_{35}$ is 3-halo, 5-benzyloxyphenyl; 3-benzyloxyphenyl; or 4-benzyloxyphenyl;

$R_{41}$ is H, cyclohexyl, phenyl, or $C_1$-$C_6$ alkyl optionally substituted with 1 or 2 groups that are phenyl, hydroxy, or $C_1$-$C_4$ thioalkoxy; and $R_{42}$ is hydrogen or —CH$_2$CN.

More preferred compounds include those wherein $R_{40}$ is phenyl, -phenyl-pyridine, biphenyl, —($C_1$-$C_4$ alkyl)-O—C(O)NH-phenyl, —($C_1$-$C_4$ alkyl)-O—C(O)N($C_1$-$C_6$ alkyl)-phenyl, —($C_1$-$C_4$ alkyl)-SO$_2$NH$_2$, —($C_1$-$C_4$ alkyl)-($C_3$-$C_6$ cycloalkyl), —($C_1$-$C_4$ alkyl)-C(O)O—($C_1$-$C_4$ alkyl), —($C_1$-$C_4$ alkyl)-$R_{33}$, or $C_1$-$C_8$ alkyl, wherein each of the above is unsubstituted or substituted with 1, 2, or 3 groups that are independently halogen, $C_1$-$C_4$ alkyl, $C_1$-$C_4$ alkoxy, CF$_3$, —Obenzyl wherein the phenyl is optionally substituted with 1 or 2 halogens, —CHO, or —NHSO$_2$—($C_1$-$C_4$ alkyl).

More preferred compounds include those wherein $R_{40}$ is phenyl or $C_1$-$C_8$ alkyl, wherein each of the above is unsubstituted or substituted with 1, 2, or 3 groups that are independently halogen, $C_1$-$C_4$ alkyl, $C_1$-$C_4$ alkoxy, CF$_3$, —Obenzyl wherein the phenyl is optionally substituted with 1 or 2 halogens, —CHO, or —NHSO$_2$—($C_1$-$C_4$ alkyl); and $R_{41}$ is hydrogen or $C_1$-$C_6$ alkyl optionally substituted with 1 or 2 groups that are phenyl, hydroxy, or $C_1$-$C_4$ thioalkoxy;

$R_{42}$ is hydrogen; and $R_{51}$ at each occurrence is independently $C_1$-$C_6$ alkyl, $C_1$-$C_6$ alkoxy, —NHSO$_2$—($C_1$-$C_4$ alkyl) wherein the alkyl group is optionally substituted with 1, 2, or 3 halogens, —SO$_2$—NH—($C_1$-$C_6$ alkyl)-NH$_2$, —SO$_2$—NH—($C_1$-$C_6$ alkyl)-NH($C_1$-$C_4$ alkyl), —SO$_2$—NH—($C_1$-$C_6$ alkyl)-N($C_1$-$C_4$ alkyl)($C_1$-$C_4$ alkyl), —NHC(O)NH$_2$, —NHC(O)NH($C_3$-$C_6$ alkyl), —NHC(O)N($C_1$-$C_6$ alkyl)($C_1$-$C_6$ alkyl), —N($C_1$-$C_6$ alkyl)C(O)NH$_2$, —N($C_1$-$C_6$ alkyl)C(O)NH ($C_1$-$C_6$ alkyl), —N($C_1$-$C_6$ alkyl)C(O)N($C_1$-$C_6$ alkyl)($C_1$-$C_6$ alkyl), halogen, —CF$_3$, OH, —SO$_2$NR$_{31}$R$_{32}$, —C(O)NR$_{31}$R$_{32}$, —NR$_{31}$R$_{32}$, hydroxy $C_1$-$C_{10}$ alkyl, —Obenzyl, —NHC(S)NH$_2$, —NHC(S)NH($C_1$-$C_6$ alkyl), —NHC(S)N($C_1$-$C_6$ alkyl)($C_1$-$C_6$ alkyl), ($C_1$-$C_4$ alkyl)-O-phenyl, —C(O)—($C_1$-$C_6$ alkyl), —O-cyclopentyl, —O-cyclohexyl, hydroxy $C_1$-$C_4$ alkoxy, aminoalkoxy, NH($C_1$-$C_6$alkyl)-alkoxy, N($C_1$-$C_6$alkyl)($C_1$-$C_6$alkyl)-alkoxy, wherein $R_{31}$ and $R_{32}$ at each occurrence are independently selected from the group consisting of hydrogen, $C_1$-$C_6$ alkyl, hydroxy $C_1$-$C_6$ alkyl, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), and benzyl wherein the phenyl group is unsubstituted or substituted with 1, or 2 groups that are independently $C_1$-$C_4$ alkoxy, or halogen, wherein at each occurrence $R_{31}$, $R_{32}$ and the nitrogen to which they are attached independently form a pyrrolidinyl, piperazinyl, or piperidinyl, each of which is optionally substituted with hydroxy, hydroxy $C_1$-$C_6$ alkyl, $C_1$-$C_4$ alkoxy $C_1$-$C_6$ alkyl, —C(O)NH$_2$, or —C(O)NH-benzyl.

More preferred compounds include those wherein $R_{40}$ is phenyl or $C_1$-$C_8$ alkyl, wherein each of the above is unsubstituted or substituted with 1, 2, or 3 groups that are independently halogen, $C_1$-$C_4$ alkyl, $C_1$-$C_4$ alkoxy, or CF$_3$; and $R_{51}$ at each occurrence is independently $C_1$-$C_6$ alkyl, $C_1$-$C_6$ alkoxy, —NHSO$_2$CH$_3$, —NHSO$_2$CF$_3$, halogen, —CF$_3$, OH, —SO$_2$NR$_{31}$R$_{32}$, —C(O)NR$_{31}$R$_{32}$, —NR$_{31}$R$_{32}$, hydroxy $C_1$-$C_{10}$ alkyl, hydroxy $C_1$-$C_4$ alkoxy, aminoalkoxy, NH($C_1$-$C_6$alkyl)-alkoxy, N($C_1$-$C_6$alkyl)($C_1$-$C_6$alkyl)-alkoxy, wherein $R_{31}$ and $R_{32}$ at each occurrence are independently selected from the group consisting of hydrogen, $C_1$-$C_6$ alkyl, hydroxy $C_1$-$C_6$ alkyl, and benzyl wherein the phenyl group is unsubstituted or substituted with 1 or 2 groups that are independently methoxy, ethoxy, or halogen, or wherein at each occurrence $R_{31}$, $R_{32}$ and the nitrogen to which they are attached independently form a pyrrolidinyl, piperazinyl, or piperidinyl ring each of which is optionally substituted with hydroxy, hydroxy $C_1$-$C_6$ alkyl, $C_1$-$C_4$ alkoxy $C_1$-$C_6$ alkyl, or —C(O)NH$_2$.

More preferred compounds include those wherein $R_{35}$ is 3-fluoro, 5-benzyloxyphenyl or 3-chloro, 5-benzyloxyphenyl.

More preferred compounds include those wherein $R_{35}$ is —S-phenyl, benzo[1,3]dioxole, furanyl, or thienyl;

$R_{41}$ is H, cyclohexyl, phenyl, or $C_1$-$C_6$ alkyl optionally substituted with 1 or 2 groups that are phenyl, hydroxy, or $C_1$-$C_4$ thioalkoxy; and $R_{42}$ is hydrogen or —CH$_2$CN.

More preferred compounds include those wherein $R_{40}$ is phenyl, -phenyl-pyridine, biphenyl, -phenyl-pyrimidinyl, —($C_1$-$C_4$ alkyl)-O—C(O)NH-phenyl, —($C_1$-$C_4$ alkyl)-O—C(O)N($C_1$-$C_6$ alkyl)-phenyl, —($C_1$-$C_4$ alkyl)-SO$_2$NH$_2$, —($C_1$-$C_4$ alkyl)—($C_3$-$C_6$ cycloalkyl), —($C_1$-$C_4$ alkyl)-C(O)O—($C_1$-$C_4$ alkyl), —($C_1$-$C_4$ alkyl)-$R_{33}$, or $C_3$-$C_8$ alkyl, wherein each of the above is unsubstituted or substituted with 1, 2, or 3 groups that are independently halogen, $C_1$-$C_4$ alkyl, $C_1$-$C_4$ alkoxy, CF$_3$, —Obenzyl wherein the phenyl is optionally substituted with 1 or 2 halogens, —CHO, or —NHSO$_2$—($C_1$-$C_4$ alkyl), —NHSO$_2$CF$_3$.

Still more preferred compounds include those wherein $R_{40}$ is phenyl or $C_1$-$C_8$ alkyl, wherein each of the above is unsubstituted or substituted with 1, 2, or 3 groups that are independently halogen, $C_1$-$C_4$ alkyl, $C_1$-$C_4$ alkoxy, CF$_3$, —Obenzyl wherein the phenyl is optionally substituted with 1 or 2 halogens, —CHO, or —NHSO$_2$—($C_1$-$C_4$ alkyl); and $R_{41}$ is hydrogen or $C_1$-$C_6$ alkyl optionally substituted with 1 or 2 groups that are phenyl, hydroxy, or $C_1$-$C_4$ thioalkoxy; and;

$R_{42}$ is hydrogen; and $R_{51}$ at each occurrence is independently $C_1$-$C_6$ alkyl, $C_1$-$C_6$ alkoxy, —NHSO$_2$—($C_1$-$C_4$ alkyl) wherein the alkyl group is optionally substituted with 1, 2, or 3 halogens, —SO$_2$—NH—($C_1$-$C_6$ alkyl)-NH$_2$, —SO$_2$—NH—($C_1$-$C_6$ alkyl)-

NH($C_1$-$C_4$ alkyl), —$SO_2$—NH—($C_1$-$C_6$ alkyl)-N($C_1$-$C_4$ alkyl)($C_1$-$C_4$ alkyl), —NHC(O)$NH_2$, —NHC(O)NH($C_1$-$C_6$ alkyl), —NHC(O)N($C_1$-$C_6$ alkyl)($C_1$-$C_6$ alkyl), —N($C_1$-$C_6$ alkyl)C(O)$NH_2$, —N($C_1$-$C_6$ alkyl)C(O)NH ($C_1$-$C_6$ alkyl), —N($C_1$-$C_6$ alkyl)C(O)N($C_1$-$C_6$ alkyl)($C_1$-$C_6$ alkyl), halogen, —$CF_3$, OH, —$SO_2NR_{31}R_{32}$, —C(O) $NR_{31}R_{32}$, —$NR_{31}R_{32}$, hydroxy $C_1$-$C_{10}$ alkyl, —Obenzyl, —NHC(S)$NH_2$, —NHC(S)NH($C_1$-$C_6$ alkyl), —NHC(S) N($C_1$-$C_6$ alkyl)($C_1$-$C_6$ alkyl), ($C_1$-$C_4$ alkyl)-O-phenyl, —C(O)—($C_1$-$C_6$ alkyl), —O-cyclopentyl, —O-cyclohexyl, hydroxy $C_1$-$C_4$ alkoxy, aminoalkoxy, NH($C_1$-$C_6$ alkyl)-alkoxy, N($C_1$-$C_6$ alkyl)($C_1$-$C_6$ alkyl)-alkoxy, wherein $R_{31}$ and $R_{32}$ at each occurrence are independently selected from the group consisting of hydrogen, $C_1$-$C_6$ alkyl, hydroxy $C_1$-$C_6$ alkyl, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), and benzyl wherein the phenyl group is unsubstituted or substituted with 1, or 2 groups that are independently $C_1$-$C_4$ alkoxy, or halogen, wherein at each occurrence $R_{31}$, $R_{32}$ and the nitrogen to which they are attached independently form a pyrrolidinyl, piperazinyl, or piperidinyl, each of which is optionally substituted with hydroxy, hydroxy $C_1$-$C_6$ alkyl, $C_1$-$C_4$ alkoxy $C_1$-$C_6$ alkyl, —C(O)$NH_2$, or —C(O)NH-benzyl.

Still more preferred compounds include those wherein $R_{40}$ is phenyl or $C_1$-$C_8$ alkyl, wherein each of the above is unsubstituted or substituted with 1, 2, or 3 groups that are independently halogen, $C_1$-$C_4$ alkyl, $C_1$-$C_4$ alkoxy, or $CF_3$; and $R_{51}$ at each occurrence is independently $C_1$-$C_6$ alkyl, $C_1$-$C_6$ alkoxy, —$NHSO_2CH_3$, —$NHSO_2CF_3$, halogen, —$CF_3$, OH, —$SO_2NR_{31}R_{32}$, —C(O)$NR_{31}R_{32}$, —$NR_{31}R_{32}$, hydroxy $C_1$-$C_{10}$ alkyl, hydroxy $C_1$-$C_4$ alkoxy, aminoalkoxy, NH($C_1$-$C_6$alkyl)-alkoxy, N($C_1$-$C_6$alkyl)($C_1$-$C_6$alkyl)-alkoxy, wherein $R_{31}$ and $R_{32}$ at each occurrence are independently selected from the group consisting of hydrogen, $C_1$-$C_6$ alkyl, hydroxy $C_1$-$C_6$ alkyl, and benzyl wherein the phenyl group is unsubstituted or substituted with 1 or 2 groups that are independently methoxy, ethoxy, or halogen, or wherein at each occurrence $R_{31}$, $R_{32}$ and the nitrogen to which they are attached independently form a pyrrolidinyl, piperazinyl, or piperidinyl ring each of which is optionally substituted with hydroxy, hydroxy $C_1$-$C_6$ alkyl, $C_1$-$C_4$ alkoxy $C_1$-$C_6$ alkyl, or —C(O)$NH_2$.

Particularly preferred compounds of Formula X are those where $R_1$ is 3,5-difluorophenyl.

In another specific aspect within Formula X, the invention provides compounds of formula Z3

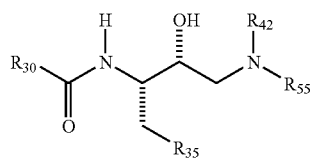

Z3 or a pharmaceutically acceptable salt thereof, wherein $R_{30}$ is selected from the group consisting of phenyl, pyrazolopyrimidinyl, oxa-aza-benzoazulenyl, isoxazolyl, triazolopyridinyl, pyrrolidinonyl, tetrahydrothia-aza-fluorenyl, pyridyl, piperidinyl, dihydrocyclopentaquinolinyl, furyl, naphthothienyl, phthalazinonyl, thiadiazolyl, thienopyrimidinonyl, oxa-diaza-cyclopentanaphthalenyl, dihydrobenzodioxepinyl, chromanonyl, chromenonyl, oxazolidinyl, purinyl, oxaxolyl, thiazolyl, pyridazinonyl, thiazolyl, pyranyl, dihydropyranopyridinyl, diazepanyl, cyclopropyl, dihydronaphthoisoxazolyl, benzoindazole, dihydrocyclopentachromenonyl, imidazopyrazolyl, tetrahydrocyclopentachromenonyl, dihydroquinolinonyl, pyridyl, isochromanyl, quinazolinonyl, pyrazolopyridinyl, dihydrobenzothiophene dioxide, dihydrofurobenzoisoxazolyl, dihydropyrimidine dionyl, thienopyrazolyl, oxazolyl, tetrahydrocyclopentapyrazolyl, dihydronaphthalenonyl, dihydrobenzofuranonyl, dihydrocyclopentathienyl, tetrahydrocyclopentapyrazolyl, tetrahydropyrazoloazepinyl, indazolyl, tetrahydrocycloheptaisoxazolyl, tetrahydroindolonyl, pyrrolidinyl, thienopyridinyl, dioxodihydrobenzoisothiazolonyl, triazolopyrimidinyl, thienyl, dihydrothienopyrimidinonyl, and benzooxadiazolyl, wherein each of the above is unsubstituted or substituted with 1, 2, 3, 4, or 5 groups that are independently selected from the group consisting of $C_1$-$C_{10}$ alkyl optionally substituted with phenyl, hydroxy, hydroxy $C_1$-$C_{10}$ alkyl optionally substituted with phenyl or ($C_1$-$C_4$ alkyl)phenyl, $C_1$-$C_6$ alkoxy optionally substituted with 1 or 2 hydroxy groups, —C(O)$NR_{31}R_{32}$, —$NR_{31}$—$SO_2$—($C_1$-$C_6$ alkyl) wherein the alkyl group is optionally substituted with 1, 2, or 3 $R_{33}$ groups, —$SO_2$—NH($C_1$-$C_6$ alkyl) wherein the alkyl group is optionally substituted with 1 or 2 $R_{33}$ groups, —$SO_2$—N($C_1$-$C_6$ alkyl)($C_1$-$C_6$ alkyl) wherein each alkyl group is optionally substituted with 1 or 2 $R_{33}$ groups, —$SO_2$—NH($C_1$-$C_6$ alkyl)-phenyl wherein the phenyl is optionally substituted with 1 or 2 groups that are independently $C_1$-$C_4$ alkoxy or halogen, —O—($C_1$-$C_6$ alkyl)-phenyl, —($C_1$-$C_6$ alkyl)-O-phenyl, —($C_1$-$C_6$ alkyl)-O—($C_1$-$C_6$ alkyl)-phenyl, triazolidine-3,5-dione, halogen, —NHC(O)$NH_2$, —N($C_1$-$C_6$ alkyl)C(O)$NH_2$, —N($C_1$-$C_6$ alkyl)C(O)NH($C_1$-$C_6$ alkyl), —N($C_1$-$C_6$ alkyl)C(O)N($C_1$-$C_6$ alkyl)($C_1$-$C_6$ alkyl), —($C_1$-$C_6$ alkyl)thienyl, —($C_1$-$C_6$ alkyl) furanyl, —S—($C_1$-$C_6$ alkyl)phenyl, —$SO_2NR_{31}R_{32}$, —C(O)—$NR_{31}R_{32}$, —$NR_{31}R_{32}$, dithiane, —NHC(S)$NH_2$, —NHC(S)NH($C_3$-$C_6$ alkyl), —NHC(S)N($C_1$-$C_6$ alkyl)($C_1$-$C_6$ alkyl), —$CO_2$($C_1$-$C_6$ alkyl), tetrahydropyran, phenyl optionally substituted with 1 or 2 groups that are independently F, Cl or Br, pyridine, —$C_2$-$C_4$ alkynyl-phenyl, —O—$C_3$-$C_6$ cycloalkyl, —O—($C_1$-$C_6$ alkyl)-$R_{33}$, benzo[1,2,5]oxadiazole, —C(O)—($C_1$-$C_6$ alkyl) wherein the alkyl group is optionally substituted with $NH_2$, N($C_1$-$C_6$ alkyl), or N($C_1$-$C_6$ alkyl)($C_1$-$C_6$ alkyl); —C(O)NH-phenyl, —C(O)N($C_1$-$C_6$ alkyl)-phenyl, 4,4-Dimethyl-4,5-dihydro-oxazole, —($C_1$-$C_6$ alkyl) —S-pyridine, —($C_1$-$C_6$ alkyl) —$SO_2$-pyridine, —($C_1$-$C_6$ thioalkoxy) -pyridine, wherein $R_{31}$ and $R_{32}$ at each occurrence are independently selected from the group consisting of hydrogen, $C_1$-$C_6$ alkyl, hydroxy $C_1$-$C_6$ alkyl, $C_1$-$C_6$ haloalkyl, —($C_1$-$C_6$ alkyl)-C(O)$NH_2$, —($C_1$-$C_6$ alkyl)-C(O)NH($C_1$-$C_6$ alkyl), —($C_1$-$C_6$ alkyl)-C(O)N($C_1$-$C_6$ alkyl)($C_1$-$C_6$ alkyl), —($C_1$-$C_6$ alkyl)-$NH_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), —($C_1$-$C_6$ alkyl)phenyl, —($C_1$-$C_6$ alkyl)pyridyl, —C(O) furanyl, ($C_1$-$C_6$ alkyl) -tetrahydrofuran, wherein the phenyl and pyridyl groups are unsubstituted or substituted with 1, 2, 3, 4, or 5 groups that are independently $C_1$-$C_4$ alkyl, hydroxy, $C_1$-$C_4$ alkoxy, halogen, or $R_{31}$, $R_{32}$ and the nitrogen to which they are attached form a 5, 6, or 7 membered heterocycloalkyl or a 6 membered heteroaryl ring, each of which is optionally fused to a benzene, pyridine or pyrimidine ring and each of which is optionally substituted with $C_1$-$C_6$ alkoxy, hydroxy, hydroxy $C_1$-$C_6$ alkyl, $C_1$-$C_4$ alkoxy $C_1$-$C_6$ alkyl, —C(O)NH$_2$, —C(O)NH—($C_1$-$C_6$ alkyl)-phenyl, $R_{33}$ at each occurrence is independently, H, NH$_2$, NH($C_1$-$C_6$ alkyl), N($C_1$-$C_6$ alkyl)($C_1$-$C_6$ alkyl), N($C_1$-$C_6$ alkyl)(phenyl);

$R_{35}$ is phenyl, $C_3$-$C_8$ cycloalkyl, —S-phenyl, benzodioxole, thienyl, $C_1$-$C_6$ alkyl, furanyl, each of which is unsubstituted or substituted with 1, 2, 3, 4, or 5 groups that are independently $C_1$-$C_4$ alkyl, $C_1$-$C_4$ alkoxy, OH, hydroxy $C_1$-$C_6$ alkyl, halogen, halo $C_1$-$C_6$ alkyl, halo $C_1$-$C_6$ alkoxy, —O—($C_1$-$C_6$ alkyl)-phenyl, —CO$_2$—($C_1$-$C_6$ alkyl), —($C_1$-$C_4$ alkyl)-($C_1$-$C_6$ cycloalkyl);

$R_{42}$ is H, $C_1$-$C_6$ alkyl, benzyl, —NHC(O)—($C_1$-$C_6$ alkyl), or —NHC(O)-phenyl wherein the phenyl is optionally substituted with 1 or 2 alkyl groups, $R_{55}$ is cyclohexyl; cyclopentyl; azepanone; phenyl; piperidinyl; —SO$_2$-phenyl; pyrrolidinyl; or 4,5,6,7-tetrahydrothiazolo[5,4-c]pyridine; wherein each is optionally substituted with —C(O)NH$_2$; —C(O)NH($C_1$-$C_6$ alkyl); —C(O)N($C_1$-$C_6$ alkyl)($C_1$-$C_6$ alkyl); $C_1$-$C_6$ alkoxycarbonyl; —O—($C_1$-$C_6$ alkyl)-C(O)NR$_{31}$R$_{32}$; —($C_1$-$C_6$ alkyl)-phenyl; 4,5-dihydro-2H-pyridazin-3-one; $C_5$-$C_6$ cycloalkyl which is optionally substituted with one CN group, phenyloxy wherein the phenyl group is optionally substituted with —NHC(O)$C_1$-$C_6$ alkyl, —N($C_1$-$C_6$ alkyl)-C(O)$C_1$-$C_6$ alkyl, wherein $R_{31}$, $R_{32}$ and the nitrogen to which they are attached form a pyrrolidine, piperidine, piperazine, morpholine, or thiamorpholine ring, wherein each ring is unsubstituted or substituted with 1, 2, or 3 groups that are independently OH, $C_1$-$C_6$ alkyl, $C_1$-$C_6$ alkoxy, —($C_1$-$C_6$ alkyl)-imidazole wherein the imidazole is optionally substituted with 1 or 2 $C_1$-$C_4$ alkyl groups, or hydroxy ($C_1$-$C_6$ alkyl) wherein the alkyl group is optionally substituted with 1 phenyl ring, or $R_{42}$, $R_{55}$ and the nitrogen to which they are attached form a tetrahydroisoquinolinyl, dihydroisoquinolinyl, or isoquinolinyl group which is optionally substituted by 1, 2, 3, or 4 groups that are independently halogen, $C_1$-$C_4$ alkyl, $C_1$-$C_4$ alkoxy, CN, OH, and phenyl, wherein the phenyl is optionally substituted with halogen, hydroxyl, $C_1$-$C_4$ alkoxy, and $C_1$-$C_4$ alkyl.

More preferred compounds of Z3 include those wherein $R_{30}$ is selected from the group consisting of phenyl, pyrrolidinonyl, pyridyl, piperidinyl, furyl, cyclopropyl, and thienyl, wherein each of the above is unsubstituted or substituted with 1, 2, 3, 4, or 5 groups that are independently selected from the group consisting of $C_1$-$C_{10}$ alkyl, hydroxy, hydroxy $C_1$-$C_{10}$ alkyl $C_1$-$C_6$ alkoxy, —NR$_{31}$—SO$_2$—($C_1$-$C_6$ alkyl), —SO$_2$—NH($C_1$-$C_6$ alkyl), —SO$_2$—N($C_1$-$C_6$ alkyl)($C_1$-$C_6$ alkyl), halogen, —NHC(O)NH$_2$, —N($C_1$-$C_6$ alkyl)C(O)NH$_2$, —N($C_1$-$C_6$ alkyl)C(O)NH($C_1$-$C_6$ alkyl), —N($C_1$-$C_6$ alkyl)C(O)N($C_1$-$C_6$ alkyl)($C_1$-$C_6$ alkyl), —SO$_2$NR$_{31}$R$_{32}$, —C(O)—NR$_{31}$R$_{32}$, —NR$_{31}$R$_{32}$, —C$_2$-$C_4$ alkynyl-phenyl, —O—$C_3$-$C_6$ cycloalkyl, —O—($C_1$-$C_6$ alkyl)-R$_{33}$, benzo[1,2,5]oxadiazole, —C(O)—($C_1$-$C_6$ alkyl);

wherein $R_{31}$ and $R_{32}$ at each occurrence are independently selected from the group consisting of hydrogen, $C_1$-$C_6$ alkyl, hydroxy $C_1$-$C_6$ alkyl, $C_1$-$C_6$ haloalkyl, —($C_1$-$C_6$ alkyl)-C(O)NH$_2$, —($C_1$-$C_6$ alkyl)-C(O)NH($C_1$-$C_6$ alkyl), —($C_1$-$C_6$ alkyl)-C(O)N($C_1$-$C_6$ alkyl)($C_1$-$C_6$ alkyl), —($C_1$-$C_6$ alkyl)-NH$_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), benzyl, and —C(O)furanyl, wherein the phenyl and pyridyl groups are unsubstituted or substituted with 1, 2, or 3, groups that are independently $C_1$-$C_4$ alkyl, hydroxy, $C_1$-$C_4$ alkoxy, or halogen, or $R_{31}$, $R_{32}$ and the nitrogen to which they are attached form a 5, 6, or 7 membered heterocycloalkyl or a 6 membered heteroaryl ring, each of which is optionally substituted with $C_1$-$C_6$ alkoxy, hydroxy, hydroxy $C_1$-$C_6$ alkyl, $C_1$-$C_4$ alkoxy $C_1$-$C_6$ alkyl, or —C(O)NH$_2$;

$R_{35}$ is phenyl, $C_3$-$C_6$ cycloalkyl, or —S-phenyl, each of which is unsubstituted or substituted with 1, 2, or 3 groups that are independently $C_1$-$C_4$ alkyl, $C_1$-$C_4$ alkoxy, CF$_3$, OCF$_3$, halogen, —Obenzyl, —CO$_2$—($C_1$-$C_6$ alkyl), —($C_1$-$C_4$ alkyl)-($C_5$-$C_6$ cycloalkyl);

$R_{42}$ is H, $C_1$-$C_6$ alkyl, benzyl, —NHC(O)—($C_1$-$C_6$ alkyl), or —NHC(O)-phenyl wherein the phenyl is optionally substituted with 1 or 2 alkyl groups, $R_{55}$ is cyclohexyl; azepanone; phenyl; piperidinyl; —SO$_2$-phenyl; pyrrolidinyl; or 4,5,6,7-tetrahydro-thiazolo[5,4-c]pyridine; wherein each is optionally substituted with —C(O)NH$_2$; $C_1$-$C_6$ alkoxycarbonyl; —O—($C_1$-$C_6$ alkyl)-C(O)NR$_{31}$R$_{32}$; —($C_1$-$C_6$ alkyl)-phenyl; 4,5-dihydro-2H-pyridazin-3-one; cyclopentyl which is optionally substituted with one CN group, phenyloxy wherein the phenyl group is optionally substituted with —NHC(O)$C_1$-$C_6$ alkyl, wherein $R_{31}$, $R_{32}$ and the nitrogen to which they are attached form a pyrrolidine, piperidine, piperazine, or morpholine ring, wherein each ring is unsubstituted or substituted with 1, 2, or 3 groups that are independently OH, —($C_1$-$C_6$ alkyl)-imidazole wherein the imidazole is optionally substituted with 1 or 2 $C_1$-$C_4$ alkyl groups, or hydroxy ($C_1$-$C_6$ alkyl) wherein the alkyl group is optionally substituted with 1 phenyl ring, or $R_{42}$, $R_{55}$ and the nitrogen to which they are attached form a tetrahydroisoquinolinyl, group which is optionally substituted by 1, 2, 3, or 4 groups that are independently halogen, $C_1$-$C_4$ alkyl, $C_1$-$C_4$ alkoxy, CN, OH, and phenyl, wherein the phenyl is optionally substituted with halogen, hydroxyl, $C_1$-$C_4$ alkoxy, and $C_1$-$C_4$ alkyl.

Even more preferred compounds of Z3 include those wherein $R_{30}$ is selected from the group consisting of phenyl, pyridyl, or piperidinyl wherein each of the above is unsubstituted or substituted with 1, 2, 3, 4, or 5 groups that are independently selected from the group consisting of $C_1$-$C_{10}$ alkyl, hydroxy, hydroxy $C_1$-$C_{10}$ alkyl $C_1$-$C_6$ alkoxy, halogen, —SO$_2$NR$_{31}$R$_{32}$, —C(O)—NR$_{31}$R$_{32}$, —NR$_{31}$R$_{32}$, —O—$C_3$-$C_6$ cycloalkyl, —C(O)—($C_1$-$C_6$ alkyl);

wherein $R_{31}$ and $R_{32}$ at each occurrence are independently selected from the group consisting of hydrogen, $C_1$-$C_6$ alkyl, hydroxy $C_1$-$C_6$ alkyl, —($C_1$-$C_6$ alkyl)-NH$_2$, —(C$_1$-C$_6$ alkyl) —NH(C$_1$-C$_6$ alkyl), —(C$_1$-C$_6$ alkyl)-N(C$_1$-C$_6$ alkyl)(C$_1$-C$_6$ alkyl), benzyl, and —C(O)furanyl, wherein
the phenyl group is unsubstituted or substituted with 1, 2, or 3, groups that are independently C$_1$-C$_4$ alkyl, hydroxy, C$_1$-C$_4$ alkoxy, or halogen, or
R$_{31}$, R$_{32}$ and the nitrogen to which they are attached form a pyrrolidinyl, piperidinyl, morpholinyl, pyridinyl, or pyrimidinyl ring, each of which is optionally substituted with C$_1$-C$_6$ alkoxy, hydroxy, hydroxy C$_1$-C$_6$ alkyl, C$_1$-C$_4$ alkoxy C$_1$-C$_6$ alkyl, or —C(O)NH$_2$;
R$_{35}$ is phenyl, cyclohexyl, cyclopentyl, or —S-phenyl, each of which is unsubstituted or substituted with 1, 2, or 3 groups that are independently C$_1$-C$_4$ alkyl, C$_1$-C$_4$ alkoxy, CF$_3$, OCF$_3$, halogen, —Obenzyl, —CO$_2$—(C$_1$-C$_6$ alkyl), —(C$_1$-C$_4$ alkyl)-(C$_5$-C$_6$ cycloalkyl).

In a specific aspect, the invention provides compounds of formula X100:

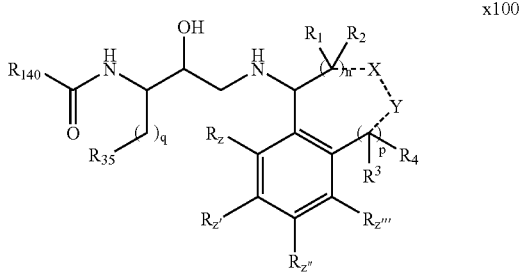

x100 and the pharmaceutically acceptable salts thereof, wherein
n, p, and q are independently 0, 1 or 2;
a dashed line res a single or double bond;
R$_1$, R$_2$, R$_3$, and R$_4$ are independently selected from hydrogen, halogen, C$_1$-C$_6$ alkyl, hydroxy, C$_1$-C$_6$ alkoxy, halo(C$_1$-C$_6$) alkyl, hydroxy(C$_1$-C$_6$)alkyl, halo(C$_1$-C$_6$)alkoxy, thio(C$_1$-C$_6$)alkyl, (C$_1$-C$_6$)alkoxy(C$_1$-C$_6$)alkyl, amino(C$_1$-C$_6$)alkyl, mono(C$_1$-C$_6$)alkylamino(C$_1$-C$_6$)alkyl, di(C$_1$-C$_6$)alkylamino(C$_1$-C$_6$)alkyl,
—(CH$_2$)$_{0-4}$-aryl or —(CH$_2$)$_{0-4}$-heteroaryl,
C$_2$-C$_6$ alkenyl or C$_2$-C$_6$ alkynyl, each of which is optionally substituted with one, two or three substituents independently selected from the group consisting of halogen, hydroxy, —SH, cyano, —CF$_3$, C$_1$-C$_3$ alkoxy, amino, mono (C$_1$-C$_6$)alkylamino, and di(C$_1$-C$_6$)alkylamino,
—(CH$_2$)$_{0-4}$—C$_3$-C$_7$ cycloalkyl, where the cycloalkyl is optionally substituted with one, two or three substituents independently selected from the group consisting of halogen, hydroxy, —SH, cyano, —CF$_3$, C$_1$-C$_3$ alkoxy, amino, mono(C$_1$-C$_6$)alkylamino, and di(C$_1$-C$_6$)alkylamino;
R$_z$, R$_z$', R$_z$", and R$_z$"' independently re
C$_1$-C$_6$ alkyl, optionally substituted with one, two or three substituents independently selected from C$_1$-C$_3$ alkyl, halogen, —OH, —SH, —C≡N, —CF$_3$, C$_1$-C$_6$ alkoxy, amino, mono(C$_3$-C$_6$)alkylamino, and di(C$_1$-C$_6$)alkylamino,
hydroxy, nitro, halogen, —CO$_2$H, cyano,
—(CH$_2$)$_{0-4}$—CO—NR$_{142}$R$_{144}$ where R$_{142}$ and R$_{144}$ independently re hydrogen, C$_1$-C$_6$ alkyl, hydroxyl(C$_1$-C$_6$) alkyl, amino(C$_1$-C$_6$)alkyl, haloalkyl, C$_3$-C$_7$ cycloalkyl, —(C$_1$-C$_2$ alkyl)-(C$_3$-C$_7$ cycloalkyl), —(C$_1$-C$_6$ alkyl)-O—(C$_1$-C$_3$ alkyl), —C$_2$-C$_6$ alkenyl with one or two double bonds, —C$_2$-C$_6$ alkynyl with one or two triple bonds, —C$_1$-C$_6$ alkyl chain with one double bond and one triple bond, —R$_{1\text{-}aryl}$ where R$_{1\text{-}aryl}$ is as defined above, or —R$_{1\text{-}heteroaryl}$ where R$_{1\text{-}heteroaryl}$,
—(CH$_2$)$_{0-4}$—CO—(C$_1$-C$_{12}$ alkyl), —(CH$_2$)$_{0-4}$—CO—(C$_2$-C$_{12}$ alkenyl), CH$_2$)$_{0-4}$—CO—(C$_2$-C$_{12}$)alkynyl, —(CH$_2$)$_{0-4}$—CO—(C$_3$-C$_7$ cycloalkyl), —(CH$_2$)$_{0-4}$—CO—R$_{1\text{-}aryl}$ where R$_{1\text{-}aryl}$, is as defined above, —(CH$_2$)$_{0-4}$—CO—R$_{1\text{-}heteroaryl}$ where R$_{1\text{-}heteroaryl}$ is as defined above, —(CH$_2$)$_{0-4}$—CO—R$_{1\text{-}heterocycle}$, —(CH$_2$)$_{0-4}$—CO—R$_{146}$ where R$_{146}$ is heterocycloalkyl, where the heterocycloalkyl is optionally substituted with 1-4 of C$_1$-C$_6$ alkyl,
—(CH$_2$)$_{0-4}$—CO—O—R$_{148}$ where R$_{148}$ is selected from the group consisting of: C$_1$-C$_6$ alkyl, —(CH$_2$)$_{0-2}$—(R$_{1\text{-}aryl}$), C$_2$-C$_6$ alkenyl, C$_2$-C$_6$ alkynyl, C$_3$-C$_7$ cycloalkyl, and —(CH$_2$)$_{0-2}$—(R$_{1\text{-}heteroaryl}$),
—(CH$_2$)$_{0-4}$—SO$_2$—NR$_{142}$R$_{144}$, —(CH$_2$)$_{0-4}$—SO—(C$_1$-C$_8$ alkyl), —(CH$_2$)$_{0-4}$—SO$_2$—(C$_1$-C$_{12}$ alkyl), —(CH$_2$)$_{0-4}$—SO$_2$—(C$_3$-C$_7$ cycloalkyl), —(CH$_2$)$_{0-4}$—N(H or R$_{148}$)—CO—O—R$_{148}$, —(CH$_2$)$_{0-4}$—N(H or R$_{148}$)—CO—N(R$_{148}$)$_2$, —(CH$_2$)$_{0-4}$—N—CS—N(R$_{148}$)$_2$, —(CH$_2$)$_{0-4}$—N(—H or R$_{148}$)—CO—R$_{142}$, —(CH$_2$)$_{0-4}$—NR$_{142}$R$_{144}$, —(CH$_2$)$_{0-4}$—R$_{146}$ where R$_{N\text{-}4}$ is as defined above,
—(CH$_2$)$_{0-4}$—O—CO—(C$_1$-C$_6$ alkyl), —(CH$_2$)$_{0-4}$—O—P(O)—(OR$_{150}$)$_2$ where each R$_{150}$ is independently hydrogen or C$_1$-C$_4$ alkyl, —(CH$_2$)$_{0-4}$—O—CO—N(R$_{148}$)$_2$, —(CH$_2$)$_{0-4}$—O—CS—N(R$_{148}$)$_2$, —(CH$_2$)$_{0-4}$—O—(R$_{148}$)$_2$, —(CH$_2$)$_{0-4}$—O—(R$_{148}$)$_2$—CO$_2$H, —(CH$_2$)$_{0-4}$—S—(R$_{148}$)$_2$, —(CH$_2$)$_{0-4}$-O-halo(C$_1$-C$_6$)alkyl, —(CH$_2$)$_{0-4}$—O—(C$_1$-C$_6$)alkyl, C$_3$-C$_7$ cycloalkyl,
C$_2$-C$_6$ alkenyl or C$_2$-C$_6$ alkynyl, each of which is optionally substituted with C$_1$-C$_3$ alkyl, halogen, hydroxy, —SH, cyano, —CF$_3$, C$_1$-C$_3$ alkoxy, amino, mono(C$_1$-C$_6$)alkylamino, and di(C$_1$-C$_6$)alkylamino,
—(CH$_2$)$_{0-4}$—N(—H or R$_{148}$)—SO$_2$—R$_{142}$, or —(CH$_2$)$_{0-4}$—C$_3$-C$_7$ cycloalkyl;
R$_{35}$ is phenyl, cyclohexyl, —S-phenyl, benzodioxole, thienyl, C$_3$-C$_6$ alkyl, furanyl, each of which is unsubstituted or substituted with 1, 2, 3, 4, or 5 groups that are independently C$_1$-C$_4$ alkyl, C$_1$-C$_4$ alkoxy, OH, hydroxy C$_1$-C$_6$ alkyl, halogen, halo C$_1$-C$_6$ alkyl, halo C$_1$-C$_6$ alkoxy, —O—(C$_1$-C$_6$ alkyl)-phenyl, —CO$_2$—(C$_1$-C$_6$ alkyl), or —(C$_1$-C$_4$ alkyl)-(C$_5$-C$_6$ cycloalkyl);
X and Y are independently selected from O, NR$_5$, C(O), CR$_1$R$_2$, SO$_2$, and S,
where R$_5$ is hydrogen, C$_1$-C$_6$ alkyl, SO$_2$R$_5$', C(O)R$_5$' where R$_5$' is hydrogen, halogen, C$_1$-C$_6$ alkyl, hydroxy, C$_1$-C$_6$ alkoxy, halo(C$_1$-C$_6$)alkyl, halo(C$_1$-C$_6$)alkoxy, thio(C$_1$-C$_6$)alkyl, (C$_1$-C$_6$)alkoxy(C$_1$-C$_6$)alkyl, amino(C$_1$-C$_6$) alkyl, mono(C$_1$-C$_6$)alkylamino(C$_1$-C$_6$)alkyl, di(C$_1$-C$_6$) alkylamino (C$_1$-C$_6$)alkyl,
—(CH$_2$)$_{0-4}$-aryl or —(CH$_2$)$_{0-4}$-heteroaryl,
C$_2$-C$_6$ alkenyl or C$_2$-C$_6$ alkynyl, each of which is optionally substituted with one, two or three substituents independently selected from the group consisting of halogen, hydroxy, —SH, cyano, —CF$_3$, C$_1$-C$_3$ alkoxy, amino, mono (C$_1$-Cr)alkylamino, and di(C$_1$-C$_6$)alkylamino,
—(CH$_2$)$_{0-4}$—C$_3$-C$_7$ cycloalkyl, where the cycloalkyl is optionally substituted with one, two or three substituents independently selected from the group consisting of halogen, hydroxy, —SH, cyano, —CF$_3$, C$_1$-C$_3$ alkoxy, amino, mono(C$_1$-C$_6$)alkylamino, and di(C$_1$-C$_6$)alkylamino;
R$_{140}$ res phenyl or naphthyl, each of which is optionally substituted with 1-5 groups independently selected from $C_1$-$C_6$ alkyl, optionally substituted with one, two or three substituents selected from the group consisting of $C_1$-$C_3$ alkyl, -halogen, hydroxy, —SH, cyano, —$CF_3$, $C_1$-$C_3$ alkoxy, amino, mono($C_1$-$C_6$)alkylamino, and di($C_1$-$C_6$)alkylamino, hydroxy, nitro, halogen, —$CO_2H$, cyano, —$(CH_2)_{0-4}$—CO—$NR_{142}R_{144}$ where $R_{142}$ and $R_{144}$ independently re hydrogen, $C_1$-$C_6$ alkyl, hydroxyl($C_1$-$C_6$) alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl with one or two double bonds, —$C_2$-$C_6$ alkynyl with one or two triple bonds, —$C_1$-$C_6$ alkyl chain with one double bond and one triple bond, —$R_{1-aryl}$ where $R_{1-aryl}$, is as defined above, or —$R_{1-heteroaryl}$ where $R_{1-heteroaryl}$, —$(CH_2)_{0-4}$—CO—($C_1$-$C_{12}$ alkyl), —$(CH_2)_{0-4}$—CO—($C_2$-$C_{12}$ alkenyl), $CH_2)_{0-4}$—CO—($C_2$-$C_{12}$)alkynyl, —$(CH_2)_{0-4}$—CO—($C_3$-$C_7$ cycloalkyl), —$(CH_2)_{0-4}$—CO—$R_{1-aryl}$ where $R_{1-aryl}$ is as defined above, —$(CH_2)_{0-4}$—CO—$R_{1-heteroaryl}$ where $R_{1-heteroaryl}$ is as defined above, —$(CH_2)_{0-4}$—CO—$R_{1-heterocycle}$, —$(CH_2)_{0-4}$—CO—$R_{146}$ where $R_{146}$ is heterocycloalkyl, where the heterocycloalkyl is optionally substituted with 1-4 of $C_1$-$C_6$ alkyl, —$(CH_2)_{0-4}$—CO—O—$R_{148}$ where $R_{148}$ is selected from the group consisting of: $C_1$-$C_6$ alkyl, —$(CH_2)_{0-2}$—($R_{1-aryl}$), $C_2$-$C_6$ alkenyl, $C_2$-$C_6$ alkynyl, $C_3$-$C_7$ cycloalkyl, and —$(CH_2)_{0-2}$—($R_{1-heteroaryl}$), —$(CH_2)_{0-4}$—$SO_2$—$NR_{142}R_{144}$, —$(CH_2)_{0-4}$—SO—($C_1$-$C_8$ alkyl), —$(CH_2)_{0-4}$—$SO_2$—($C_1$-$C_{12}$ alkyl), —$(CH_2)_{0-4}$—$SO_2$—($C_3$-$C_7$ cycloalkyl), —$(CH_2)_{0-4}$—N(H or $R_{148}$)—CO—O—$R_{148}$, —$(CH_2)_{0-4}$—N(H or $R_{148}$)—CO—N($R_{148}$)$_2$, —$(CH_2)_{0-4}$—N—CS—N($R_{148}$)$_2$, —$(CH_2)_{0-4}$—N(—H or $R_{148}$)—CO—$R_{142}$, —$(CH_2)_{0-4}$—$NR_{142}R_{144}$, —$(CH_2)_{0-4}$—$R_{146}$ where $R_{N-4}$ is as defined above, —$(CH_2)_{0-4}$—O—CO—($C_1$-$C_6$ alkyl), —$(CH_2)_{0-4}$—O—P(O)—$(OR_{150})_2$ where each $R_{150}$ is independently hydrogen or $C_1$-$C_4$ alkyl, —$(CH_2)_{0-4}$—O—CO—N($R_{148}$)$_2$, —$(CH_2)_{0-4}$—O—CS—N($R_{148}$)$_2$—$(CH_2)_{0-4}$—O—($R_{148}$)$_2$, —$(CH_2)_{0-4}$—O—($R_{148}$)$_2$—$CO_2H$, —$(CH_2)_{0-4}$—S—($R_{148}$)$_2$, —$(CH_2)_{0-4}$—O-halo($C_1$-$C_6$) alkyl, —$(CH_2)_{0-4}$—O—($C_1$-$C_6$)alkyl, $C_3$-$C_7$ cycloalkyl, $C_2$-$C_6$ alkenyl or $C_2$-$C_6$ alkynyl, each of which is optionally substituted with $C_1$-$C_3$ alkyl, halogen, hydroxy, —SH, cyano, —$CF_3$, $C_1$-$C_3$ alkoxy, amino, mono($C_1$-$C_6$)alkylamino, and di($C_1$-$C_6$)alkylamino, and —$(CH_2)_{0-4}$—N(—H or $R_{148}$)—$SO_2$—$R_{142}$, or —$(CH_2)_{0-4}$—$C_3$-$C_7$ cycloalkyl.

In a more preferred embodiment q is 1.

In a more preferred embodiment, two or three of $R_z$, $R_z'$, $R_z''$, and $R_z'''$ is hydrogen, and the other one or two of $R_z$, $R_z'$, $R_z''$, and $R_z'''$ is hydroxy, nitro, halogen, —$CO_2H$, cyano, or $C_1$-$C_6$ alkyl, where the alkyl is optionally substituted with one, two or three substituents independently selected from $C_1$-$C_3$ alkyl, halogen, —OH, —SH, —C≡N, —$CF_3$, $C_1$-$C_6$ alkoxy, amino, mono ($C_1$-$C_6$)alkylamino, and di($C_1$-$C_6$)alkylamino.

Preferred compounds of formula X100 include those where three of $R_z$, $R_z'$, $R_z''$, and $R_z'''$ are hydrogen and the other is ($C_1$-$C_6$)alkyl, halogen, or ($C_1$-$C_6$)alkoxy.

Other preferred compounds of formula X100 include those where wherein $R_{140}$ is phenyl substituted with 1, 2, or 3 groups independently selected from $C_1$-$C_6$ alkyl, optionally substituted with one, two or three groups independently selected from $C_1$-$C_3$ alkyl, -halogen, hydroxy, —SH, cyano, —$CF_3$, $C_1$-$C_3$ alkoxy, amino, mono($C_1$-$C_6$)alkylamino, and di($C_1$-$C_6$)alkylamino, hydroxy, nitro, halogen, —$CO_2H$, cyano, —$(CH_2)_{0-4}$—CO—$NR_{142}R_{144}$ where $R_{142}$ and $R_{144}$ independently re hydrogen, $C_1$-$C_6$ alkyl, hydroxy($C_1$-$C_6$) alkyl, amino($C_1$-$C_6$)alkyl, and $C_3$-$C_7$ cycloalkyl.

Still other preferred compounds of formula X100 include those where $R_{140}$ is phenyl substituted with one of hydroxy, nitro, halogen, —$CO_2H$, cyano, or $C_1$-$C_6$ alkyl where the alkyl is optionally substituted with one, two or three groups independently selected from $C_1$-$C_3$ alkyl, -halogen, hydroxy, —SH, cyano, —$CF_3$, $C_1$-$C_3$ alkoxy, amino, mono($C_1$-$C_6$)alkylamino, and di($C_1$-$C_6$)alkylamino; and one of —$(CH_2)_{0-4}$—CO—$NR_{142}R_{144}$.

Other preferred compounds of formula X100 are those where $R_{140}$ is phenyl substituted with one of —C(O)$NR_{142}R_{144}$ and $R_{142}$ and $R_{144}$ are independently hydrogen or $C_1$-$C_6$ alkyl.

More preferred compounds of formula X100 include those where $R_{142}$ and $R_{144}$ are the same and are propyl.

Other specific compounds of formula X100 include those where $R_{35}$ is phenyl substituted with 1-5 halogen, or substituted with 1, 2, or 3 groups independently selected from ($C_1$-$C_6$)alkyl, hydroxy, halogen, ($C_1$-$C_6$)alkoxy, amino, mono($C_1$-$C_6$)alkylamino, and di($C_1$-$C_6$)alkylamino.

Preferred compounds of formula X100 include those where $R_{35}$ is phenyl substituted with 2 halogens.

Still other preferred compounds of formula $X_{100}$ are those where $R_{35}$ is 3,5-difluorophenyl.

Other specific compounds of formula X100 include those where $R_{140}$ is phenyl substituted with one of hydroxy, nitro, halogen, —$CO_2H$, cyano, or $C_1$-$C_6$ alkyl where the alkyl is optionally substituted with one, two or three groups independently selected from $C_1$-$C_3$ alkyl, -halogen, hydroxy, —SH, cyano, —$CF_3$, $C_1$-$C_3$ alkoxy, amino, mono($C_1$-$C_6$)alkylamino, and di($C_1$-$C_6$)alkylamino; and one of —$(CH_2)_{0-4}$—CO—$NR_{142}R_{144}$.

Preferred specific compounds of formula $X_{100}$ are those where $R_{140}$ is phenyl substituted with one of —C(O)$NR_{142}R_{144}$ and $R_{142}$ and $R_{144}$ are independently hydrogen or $C_1$-$C_6$ alkyl.

Other preferred specific compounds of formula X100 are those where $R_{142}$ and $R_{144}$ are the same and are propyl.

Preferred compounds of formula X100 are those where n is 1 and p is 0.

Still other preferred compounds of formula X100 are those where the dashed lines all re single bonds.

In other preferred compounds of formula X100, $R_1$ is hydrogen and X is $SO_2$.

In other preferred compounds of Z100, Y is methylene.

More preferred compounds of X100 are those where Z' is 2-propyl.

Other more preferred compounds of X100 are those where Y is methylene and $R_2$ is hydrogen, hydroxy($C_1$-$C_3$)alkyl, or ($C_1$-$C_3$)alkyl.

A preferred $R_2$ group is methyl.

In another specific aspect of formula X100, $R_1$ is hydrogen; X is $SO_2$ and Y is $NR_5$, or X is $NR_5$ and Y is $SO_2$, where each $R_5$ is hydrogen, ($C_1$-$C_6$)alkyl, or hydroxy($C_1$-$C_6$)alkyl.

In a preferred aspect of X100, $R_1$ is hydrogen;

X is C(O) and Y is $NR_5$, or X is $NR_5$ and Y is C(O), where each $R_5$ is hydrogen, ($C_1$-$C_6$)alkyl, or hydroxy($C_1$-$C_6$)alkyl.

Preferred compounds of formula X100 include those of formula X101

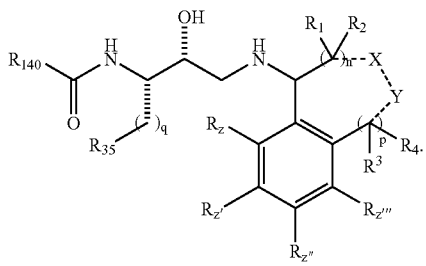

Other preferred compounds of formula X100 include those of formula X102

Preferred compounds of formula X100 include those of formula X103

Other preferred compounds of formula X100 include those of formula X104

Preferred compounds of formula X103 include those wherein $R_2$ is $(C_1-C_3)$alkyl.

Other preferred compounds of formula X103 include those wherein $R_2$ is methyl.

Still other preferred compounds of formula X103 include those wherein $R_2$ is hydroxy$(C_1-C_3)$alkyl.

Preferred compounds of formula X104 include those wherein $R_2$ is $(C_1-C_3)$alkyl.

Other preferred compounds of formula X104 include those wherein $R_2$ is methyl.

Still other preferred compounds of formula X104 include those wherein $R_2$ is hydroxy$(C_1-C_3)$alkyl.

In a specific aspect, the invention provides compounds of the formula Z4:

wherein
$R_{100}$ is H, $C_1-C_8$ alkoxycarbonyl, phenyl $C_1-C_6$ alkyl, or phenyl $C_1-C_6$ alkoxycarbonyl;
$R_{110}$ is phenyl $C_3-C_6$ alkyl, thienyl, —S-phenyl, furanyl, or benzodioxolyl, wherein each is optionally substituted with 1, 2, 3, 4, or 5 groups that are independently halogen, $C_1-C_4$ alkyl, $C_1-C_4$ alkoxy, or phenyl $C_1-C_6$ alkoxy; and
$R_{120}$ is H, phenyl $C_1-C_6$ alkyl, $C_3-C_8$ cycloalkyl optionally substituted with $C_1-C_6$ alky or phenyl, $C_3-C_8$ cycloalkyl $C_1-C_4$ alkyl, or $C_1-C_6$ alkyl optionally substituted with —C(O)NR$_{121}$R$_{122}$, wherein each of the above is optionally substituted with 1, 2, or 3 groups that are independently $C_1-C_6$ alkyl, $C_2-C_6$ alkenyl, $C_2-C_6$ alkynyl, halogen, or $C_1-C_6$ alkoxy; wherein
$R_{121}$ and $R_{122}$ are independently H, or $C_1-C_6$ alkyl.

More preferred compound of Z4 include those wherein $R_{100}$ is tertiary butoxy carbonyl.

More preferred compound of Z4 include those wherein $R_{110}$ is phenyl $C_1-C_6$ alkyl optionally substituted with 1, 2, 3, 4, or 5 groups that are independently halogen, $C_1-C_4$ alkyl, $C_1-C_4$ alkoxy, or phenyl $C_1-C_6$ alkoxy.

More preferred compound of Z4 include those wherein $R_{110}$ is monohalophenyl, dihalophenyl, or trihalophenyl.

More preferred compound of Z4 include those wherein $R_{110}$ is thienyl, or —S-phenyl each of which is optionally substituted with 1, 2, 3, 4, or 5 groups that are independently halogen, $C_1-C_4$ alkyl, $C_1-C_4$ alkoxy, benzyloxy.

More preferred compound of Z4 include those wherein $R_{110}$ is furanyl, or benzodioxolyl each of which is optionally substituted with 1, 2, 3, 4, or 5 groups that are independently halogen, $C_1-C_4$ alkyl, $C_1-C_4$ alkoxy, benzyloxy.

More preferred compound of Z4 include those wherein $R_{120}$ is benzyl optionally substituted with 1, 2, or 3 groups that are independently $C_1-C_6$ alkyl, $C_2-C_6$ alkenyl, $C_2-C_6$ alkynyl, halogen, or $C_1-C_6$ alkoxy.

More preferred compound of Z4 include those wherein $R_{120}$ is cyclopropyl optionally substituted with $C_1-C_6$ alky or phenyl; or cyclopropyl $C_1-C_4$ alkyl, wherein each of the above is optionally substituted with 1, 2, or 3 groups that are independently $C_1-C_6$ alkyl, $C_2-C_6$ alkenyl, $C_2-C_6$ alkynyl, halogen, or $C_1-C_6$ alkoxy.

Even more preferred compound of Z4 include those wherein
$R_{110}$ is phenyl $C_1-C_6$ alkyl optionally substituted with 1, 2, 3, 4, or 5 groups that are independently halogen, $C_1-C_4$ alkyl, $C_1-C_4$ alkoxy, or phenyl $C_1-C_6$ alkoxy; and
$R_{120}$ is H or benzyl optionally substituted with 1, 2, or 3 groups that are independently $C_1-C_6$ alkyl, $C_2-C_6$ alkenyl, $C_2-C_6$ alkynyl, halogen, or $C_1-C_6$ alkoxy.

Other even more preferred compound of Z4 include those wherein $R_{110}$ is phenyl $C_1$-$C_6$ alkyl optionally substituted with 1, 2, 3, 4, or 5 groups that are independently halogen, $C_1$-$C_4$ alkyl, $C_1$-$C_4$ alkoxy, or phenyl $C_1$-$C_6$ alkoxy; and $R_{120}$ is cyclopropyl optionally substituted with $C_1$-$C_6$ alky or phenyl; or cyclopropyl $C_1$-$C_4$ alkyl, wherein each of the above is optionally substituted with 1, 2, or 3 groups that are independently $C_1$-$C_6$ alkyl, $C_2$-$C_6$ alkenyl, $C_2$-$C_6$ alkynyl, halogen, or $C_1$-$C_6$ alkoxy.

Other even more preferred compound of Z4 include those wherein $R_{110}$ is thienyl, or —S-phenyl each of which is optionally substituted with 1, 2, 3, 4, or 5 groups that are independently halogen, $C_1$-$C_4$ alkyl, $C_1$-$C_4$ alkoxy, benzyloxy; and $R_{120}$ is H or benzyl optionally substituted with 1, 2, or 3 groups that are independently $C_1$-$C_6$ alkyl, $C_2$-$C_6$ alkenyl, $C_2$-$C_6$ alkynyl, halogen, or $C_1$-$C_6$ alkoxy.

Other even more preferred compound of Z4 include those wherein $R_{110}$ is thienyl, or —S-phenyl each of which is optionally substituted with 1, 2, 3, 4, or 5 groups that are independently halogen, $C_1$-$C_4$ alkyl, $C_1$-$C_4$ alkoxy, benzyloxy; and $R_{120}$ is cyclopropyl optionally substituted with $C_1$-$C_6$ alky or phenyl; or cyclopropyl $C_1$-$C_4$ alkyl, wherein each of the above is optionally substituted with 1, 2, or 3 groups that are independently $C_1$-$C_6$ alkyl, $C_2$-$C_6$ alkenyl, $C_2$-$C_6$ alkynyl, halogen, or $C_1$-$C_6$ alkoxy.

Other even more preferred compound of Z4 include those wherein $R_{110}$ is furanyl, or benzodioxolyl each of which is optionally substituted with 1, 2, 3, 4, or 5 groups that are independently halogen, $C_1$-$C_4$ alkyl, $C_1$-$C_4$ alkoxy, or benzyloxy.

$R_{120}$ is H or benzyl optionally substituted with 1, 2, or 3 groups that are independently $C_1$-$C_6$ alkyl, $C_2$-$C_6$ alkenyl, $C_2$-$C_6$ alkynyl, halogen, or $C_1$-$C_6$ alkoxy.

Even more preferred compound of Z4 include those wherein $R_{110}$ is furanyl, or benzodioxolyl each of which is optionally substituted with 1, 2, 3, 4, or 5 groups that are independently halogen, $C_1$-$C_4$ alkyl, $C_1$-$C_4$ alkoxy, or benzyloxy;

$R_{120}$ is cyclopropyl optionally substituted with $C_1$-$C_6$ alky or phenyl; or cyclopropyl $C_1$-$C_4$ alkyl, wherein each of the above is optionally substituted with 1, 2, or 3 groups that are independently $C_1$-$C_6$ alkyl, $C_2$-$C_6$ alkenyl, $C_2$-$C_6$ alkynyl, halogen, or $C_1$-$C_6$ alkoxy.

Other even more preferred compounds of the instant invention are those wherein $R_{51}$ at each occurrence is independently H, —$SO_2NH$-propyl-OH, —$SO_2NH$-ethyl—OH, —$SO_2NH$-ethyl—$OCH_3$, —$SO_2NH$—$CH(CH_3)_2$—$CH_2OH$, —$SO_2NH$—($CH_2CH(OH)CH_3$), —$SO_2NH$-ethyl-$NH(CH_3)$, —$SO_2NH$($CH_2CH_2OH)_2$, —$SO_2NHCH(CH_3)CH_2OH$, —$SO_2N$($CH_3)_2$, —$SO_2NH(CH_2CH(OH)CH_3)$, —$SO_2$-pyrrolidine, —$SO_2$-(2,6-dimethylpiperidine), —$SO_2$-(2-propylpiperidine), —$SO_2$-(hydroxypropyl), —C(O)-(2-methoxymethylpyrrolidine), —C(O)-(2-methylpyrrolidine), —C(O)-(2,6-dimethylpyrrolidine), —C(O)-(2-hydroxymethylpyrrolidine), —C(O)N(methyl)(ethyl), —C(O)N(methyl)(propyl), —C(O)N(methyl)(butyl), —C(O)N(propyl)(butyl), —C(O)N(allyl)(cyclopentyl), —C(O)N(allyl)(cyclohexyl), —C(O)N(methyl)(methyl), —C(O)N(ethyl)(ethyl), —C(O)N(butyl)(butyl), —C(O)N(isopropyl)(isopropyl), —C(O)N(propyl)(propyl), —C(O)N(methyl)(cyclohexyl), —C(O)N(ethyl)(cyclohexyl), —C(O)NH(cyclobutyl), —C(O)NH(cyclopentyl), —C(O)N($CH_3$)(cyclopentyl), —C(O)NH(2-methylcyclohexyl), —C(O)NH(pentyl), —C(O)N(pentyl)(pentyl), —C(O)NH(isopentyl), —C(O)NH(ethoxyethyl), —C(O)N($CH_3$)(methoxyethyl), —C(O)N(propyl)(methoxyethyl), —C(O)N(methoxyethyl)(methoxyethyl), —C(O)N(ethoxyethyl)(ethoxyethyl), —C(O)N(ethyl)(methoxyethyl), —C(O)N(propyl)(hydroxyethyl), —C(O)N(hydroxyethyl)(ethyl), ethynyl, methyl, bromo, —N($CH_3$)$SO_2$($CH_3$), —N($CH_3$)$SO_2$-thienyl, —N(hydroxypropyl)$SO_2CH_3$, —$CH_2$)—$SO_2$—($CH_3$), or —C(O)—$CH(CH_3)CH_2CH_2CH_3$.

Still more preferred are compounds wherein there are two $R_{51}$ groups.

Yet even more preferred are compounds wherein the $R_{51}$ groups are at the 3 and 5 positions of the phenyl group.

More preferred compounds of the instant invention are those wherein $R_{51}$ at each occurrence is independently selected from the group consisting of $C_1$-$C_4$ alkyl, —C(O)N($C_1$-$C_6$ alkyl)($C_1$-$C_6$ alkyl), —C(O)$NH_2$, —C(O)N($C_2$-$C_6$ alkenyl)($C_3$-$C_8$ cycloalkyl), —C(O)NH($C_3$-$C_8$ cycloalkyl), —C(O)NH($C_1$-$C_6$ alkyl), C(O)-(pyrrolidine) optionally substituted with 1 or two groups that are independently alkoxyalkyl or hydroxy, halogen, —C(O)N($C_1$-$C_6$ hydroxyalkyl)($C_1$-$C_6$ alkyl), —C(O)NH(alkoxyalkyl), —C(O)N(alkoxyalkyl)(alkoxyalkyl), —C(O)N($C_1$-$C_6$ alkyl)(alkoxyalkyl), —C(O)N($C_1$-$C_6$ hydroxyalkyl)(alkyl), —$NHSO_2CF_3$, —N($C_1$-$C_6$ alkyl)-$SO_2$-thienyl, —N($C_1$-$C_6$ hydroxyalkyl)$SO_2$—($C_1$-$C_6$ alkyl), —NHC(O)$C_1$-$C_4$ alkyl, oxazolyl optionally substituted with 1 or 2 methyl groups, thiazolyl optionally substituted with 1 or 2 methyl groups, pyrazolyl optionally substituted with 1 or 2 methyl groups, imidazolyl optionally substituted with 1 or 2 methyl groups, isoxazolyl optionally substituted with 1 or 2 methyl groups, pyrimidinyl optionally substituted with 1 or 2 methyl or halogen groups, —$NHSO_2CH_3$, —$NHSO_2$-imidazolyl wherein the imidazole ring is optionally substituted with 1 or 2 methyl groups, —N($C_1$-$C_6$ alkyl)$SO_2$($C_1$-$C_6$ alkyl), —$SO_2NH$—$C_1$-$C_6$ hydroxyalkyl, —$SO_2NH$—$C_1$-$C_6$ alkyl-NH($C_1$-$C_4$ alkyl), —$SO_2$-piperazinyl optionally substituted with 1 or 2 methyl groups, —$SO_2$-pyrrolidine optionally substituted with 1 or 2 methyl groups, —$SO_2$-piperidine optionally substituted with 1 or 2 $C_1$-$C_4$ alkyl groups, —$SO_2N$($C_1$-$C_4$ hydroxyalkyl)($C_1$-$C_4$ hydroxyalkyl), —$SO_2NH_2$, —$SO_2N$($C_1$-$C_6$ alkyl)($C_1$-$C_6$ alkyl), $C_2$-$C_6$ alkynyl, —$SO_2$—($C_1$-$C_6$ hydroxyalkyl), —$SO_2NH$($C_1$-$C_6$ hydroxyalkyl), —$SO_2N$($C_1$-$C_6$ alkyl)($C_1$-$C_6$ hydroxyalkyl), —($C_1$-$C_4$ alkyl)-$SO_2$—($C_1$-$C_4$ alkyl), or —C(O)—($C_1$-$C_{10}$ alkyl).

Even more preferred compounds of the instant invention are those wherein $R_{51}$ at each occurrence is independently selected from the group consisting of —$SO_2NH$-propyl-OH, —$SO_2NH$-ethyl-OH, —$SO_2NH$-ethyl-$OCH_3$, —$SO_2NH$—$CH(CH_3)_2$—$CH_2OH$, —$SO_2NH$—($CH_2CH(OH)CH_3$), —$SO_2NH$-ethyl-$NH(CH_3)$, —$SO_2NH$ (—$CH_2CH_2OH)_2$, —$SO_2NHCH(CH_3)CH_2OH$, —$SO_2N(CH_3)_2$, —$SO_2NH$($CH_2CH(OH)CH_3$), —$SO_2$-pyrrolidine, —$SO_2$-(2,6-dimethylpiperidine), —$SO_2$-(2-propylpiperidine), —$SO_2$-(hydroxypropyl), —C(O)-(2-methoxymethylpyrrolidine), —C(O)-(2-methylpyrrolidine), —C(O)-(2,6-dimethylpyrrolidine), —C(O)-(2-hydroxymethylpyrrolidine), —C(O)N(methyl)(ethyl), —C(O)N(methyl)(propyl), —C(O)N(methyl)(butyl), —C(O)N(propyl)(butyl), —C(O)N(allyl)(cyclopentyl), —C(O)N(allyl)(cyclohexyl), —C(O)N(methyl)(methyl), —C(O)N(ethyl)(ethyl), —C(O)N(butyl)(butyl), —C(O)N(isopropyl)(isopropyl), —C(O)N(propyl)(propyl), —C(O)N(methyl)(cyclohexyl), —C(O)N(ethyl)(cyclohexyl), —C(O)NH(cyclobutyl), —C(O)NH(cyclopentyl), —C(O)N($CH_3$)(cyclopentyl), —C(O)NH(2-methylcyclohexyl), —C(O)NH(pentyl), —C(O)N(pentyl)(pentyl), —C(O)NH(isopentyl), —C(O)NH(ethoxyethyl), —C(O)N(methoxyethyl)(methoxyethyl), —C(O)N($CH_3$)(methoxyethyl), —C(O)N(propyl)(methoxyethyl), —C(O)N(ethoxyethyl)(ethoxyethyl), —C(O)N(ethyl)(methoxyethyl), —C(O)N(propyl)(hydroxyethyl), —C(O)N(hydroxyethyl)(ethyl), ethynyl, methyl, bromo, —N($CH_3$)$SO_2$($CH_3$), —N($CH_3$)$SO_2$-thienyl, —N(hydroxypropyl)$SO_2CH_3$, —($CH_2$)—$SO_2$—($CH_3$), or —C(O)—CH($CH_3$)$CH_2CH_2CH_3$.

More preferred compounds of the instant invention are those wherein $R_{30}$ is pyridyl which is unsubstituted or substituted with 1 or 2 groups that are independently selected from the group consisting of $C_1$-$C_4$ alkyl, —C(O)N($C_1$-$C_6$ alkyl)($C_1$-$C_6$ alkyl), —C(O)$NH_2$, —C(O)N($C_2$-$C_6$ alkenyl)($C_3$-$C_8$ cycloalkyl), —C(O)NH($C_3$-$C_8$ cycloalkyl), —C(O)NH($C_1$-$C_6$ alkyl), C(O)-(pyrrolidine) optionally substituted with 1 or two groups that are independently alkoxyalkyl or hydroxy, halogen, —C(O)N($C_1$-$C_6$ hydroxyalkyl)($C_1$-$C_6$ alkyl), —C(O)NH(alkoxyalkyl), —C(O)N(alkoxyalkyl)(alkoxyalkyl), —C(O)N($C_1$-$C_6$ alkyl)(alkoxyalkyl), —C(O)N($C_1$-$C_6$ hydroxyalkyl)(alkyl), —$NHSO_2CF_3$, —N($C_1$-$C_6$ alkyl)-$SO_2$-thienyl, —N($C_1$-$C_6$ hydroxyalkyl)$SO_2$—($C_1$-$C_6$ alkyl), —NHC(O)$C_1$-$C_4$ alkyl, oxazolyl optionally substituted with 1 or 2 methyl groups, thiazolyl optionally substituted with 1 or 2 methyl groups, pyrazolyl optionally substituted with 1 or 2 methyl groups, imidazolyl optionally substituted with 1 or 2 methyl groups, isoxazolyl optionally substituted with 1 or 2 methyl groups, pyrimidinyl optionally substituted with 1 or 2 methyl or halogen groups, —$NHSO_2CH_3$, —$NHSO_2$-imidazolyl wherein the imidazole ring is optionally substituted with 1 or 2 methyl groups, —N($C_1$-$C_6$ alkyl)$SO_2$($C_1$-$C_6$ alkyl), —$SO_2$NH—$C_1$-$C_6$ hydroxyalkyl, —$SO_2$NH—$C_1$-$C_6$ alkyl-NH($C_1$-$C_4$ alkyl), —$SO_2$-piperazinyl optionally substituted with 1 or 2 methyl groups, —$SO_2$-pyrrolidine optionally substituted with 1 or 2 methyl groups, —$SO_2$-piperidine optionally substituted with 1 or 2 $C_1$-$C_4$ alkyl groups, —$SO_2$N($C_1$-$C_4$ hydroxyalkyl)($C_1$-$C_4$ hydroxyalkyl), —$SO_2NH_2$, —$SO_2$N($C_1$-$C_6$ alkyl)($C_1$-$C_6$ alkyl), $C_2$-$C_6$ alkynyl, —$SO_2$—($C_1$-$C_6$ hydroxyalkyl), —$SO_2$NH($C_1$-$C_6$ hydroxyalkyl), —$SO_2$N($C_1$-$C_6$ alkyl)($C_1$-$C_6$ hydroxyalkyl), —($C_1$-$C_4$ alkyl)—$SO_2$—($C_1$-$C_4$ alkyl), or —C(O)—($C_1$-$C_{10}$ alkyl).

Even more preferred compounds of the instant invention are those wherein $R_{30}$ is pyridyl which is unsubstituted or substituted with at least one group that is —$SO_2$NH-propyl-OH, —$SO_2$NH-ethyl-OH, —$SO_2$NH-ethyl-$OCH_3$, —$SO_2$NH—CH($CH_3$)$_2$—$CH_2$OH, —$SO_2$NH—($CH_2$CH(OH)$CH_3$), —$SO_2$NH-ethyl-NH($CH_3$), —$SO_2$NH(—$CH_2CH_2$OH)$_2$, —$SO_2$NHCH($CH_3$)$CH_2$OH, —$SO_2$N($CH_3$)$_2$, —$SO_2$NH($CH_2$CH(OH)$CH_3$), —$SO_2$-pyrrolidine, —$SO_2$-(2,6-dimethylpiperidine), —$SO_2$-(2-propylpiperidine), —$SO_2$-(hydroxypropyl), —C(O)-(2-methoxymethylpyrrolidine), —C(O)-(2-methylpyrrolidine), —C(O)-(2,6-dimethylpyrrolidine), —C(O)-(2-hydroxymethylpyrrolidine), —C(O)N(methyl)(ethyl), —C(O)N(methyl)(propyl), —C(O)N(methyl)(butyl), —C(O)N(propyl)(butyl), —C(O)N(allyl)(cyclopentyl), —C(O)N(allyl)(cyclohexyl), —C(O)N(methyl)(methyl), —C(O)N(ethyl)(ethyl), —C(O)N(butyl)(butyl), —C(O)N(isopropyl)(isopropyl), —C(O)N(propyl)(propyl), —C(O)N(methyl)(cyclohexyl), —C(O)N(ethyl)(cyclohexyl), —C(O)NH(cyclobutyl), —C(O)NH(cyclopentyl), —C(O)N($CH_3$)(cyclopentyl), —C(O)NH(2-methylcyclohexyl), —C(O)NH(pentyl), —C(O)N(pentyl)(pentyl), —C(O)NH(isopentyl), —C(O)NH(ethoxyethyl), —C(O)N($CH_3$)(methoxyethyl), —C(O)N(propyl)(methoxyethyl), —C(O)N(methoxyethyl)(methoxyethyl), —C(O)N(ethoxyethyl)(ethoxyethyl), —C(O)N(ethyl)(methoxyethyl), —C(O)N(propyl)(hydroxyethyl), —C(O)N(hydroxyethyl)(ethyl), ethynyl, methyl, bromo, —N($CH_3$)$SO_2$($CH_3$), —N($CH_3$)$SO_2$-thienyl, —N(hydroxypropyl)$SO_2CH_3$, —($CH_2$)—$SO_2$—($CH_3$), or —C(O)—CH($CH_3$)$CH_2CH_2CH_3$.

Other preferred compounds of the formula X are those of formula Z5

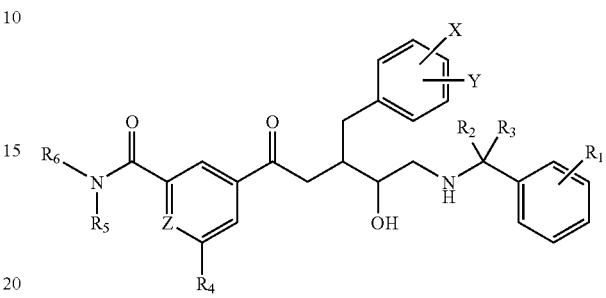

Z5 or a pharmaceutically acceptable salt thereof, wherein $R_1$ is $C_1$-$C_4$ alkyl, $C_2$-$C_4$ alkynyl, or $CF_3$;

$R_2$ and $R_3$ are both hydrogen; or $R_2$ and $R_3$ and the carbon to which they are attached form a cyclopropyl ring;

$R_4$ is oxazolyl optionally substituted with methyl, thiazolyl, $C_2$-$C_4$ alkynyl, or $C_1$-$C_4$ alkyl;

$R_5$ is $C_1$-$C_4$ alkyl;

$R_6$ is $C_1$-$C_4$ alkyl;

X and Y are independently halogen;

Z is CH or N.

Preferred compounds within Formula Z5 are those where Z is CH. Within this group, more preferred are those wherein $R_2$ and $R_3$ are both H.

Other preferred compounds of the invention are those of formula Z6

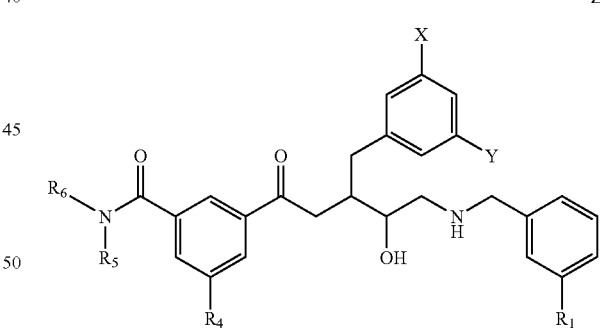

Z6

Preferred compounds of Formula Z6 include those where $R_1$ is ethyl, ethynyl or $CF_3$; and $R_4$ is 2-oxazolyl optionally substituted with methyl, 2-thiazolyl, ethynyl, or methyl, hereinafter compounds of Z6-1. Preferred compounds of Z6-1 are those where $R_5$ is propyl; and $R_6$ is propyl. More preferably, $R_1$ is ethyl; $R_4$ is 2-oxazolyl optionally substituted with methyl; and X and Y are both F.

Other preferred compounds of Z6-1 are those where $R_1$ is ethyl, or $CF_3$; and $R_4$ is 2-thiazolyl. More preferably, $R_5$ is propyl; and $R_6$ is propyl; or $R_5$ is methyl; and $R_6$ is propyl or butyl; and X and Y are both F. Still more preferable are compounds where $R_1$ is ethyl. Particularly preferred compounds are those where $R_1$ is $CF_3$; $R_5$ is propyl; and $R_6$ is propyl.

Other preferred compounds of Z6-1 are those where $R_1$ is ethynyl; and $R_4$ is ethynyl, methyl, or 2-oxazolyl. More preferably, $R_5$ is propyl; and $R_6$ is propyl; and X and Y are both F. Even more preferred are compounds where $R_4$ is ethynyl or methyl.

Other preferred compounds of the invention are those of formula Z7

Z7

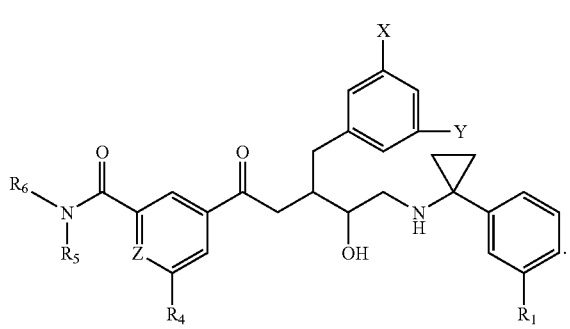

Preferred compounds of Z7 are those where $R_1$ is ethyl or ethynyl; $R_4$ is methyl or 2-oxazolyl, hereinafter compounds of formula Z7-1.

Preferred compounds of Z7-1 include those where $R_5$ and $R_6$ are both propyl; and X and Y are both F. More preferably, Z is N; and $R_4$ is methyl. Even more preferred are compounds of Z7-1 where Z is CH; and $R_4$ is methyl or 2-oxazolyl.

Other preferred compounds of the invention are those of formula Z8

Z8

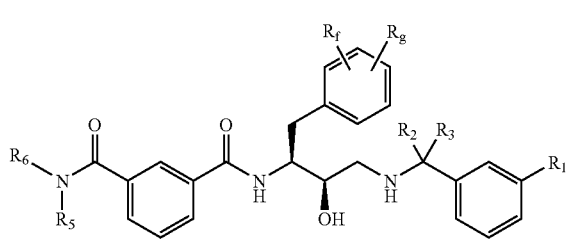

or a pharmaceutically acceptable salt thereof, wherein
$R_1$ is $C_2$-$C_3$ alkyl;
$R_2$ and $R_3$ are both hydrogen; or
$R_f$ and $R_g$ are independently halogen;
$R_5$ is $C_1$-$C_2$ alkyl sulfonyl;
$R_6$ is hydroxy($C_1$-$C_4$)alkyl, preferably hydroxyethyl or ($C_1$-$C_4$)alkoxy($C_1$-$C_4$)alkyl, preferably methoxyethyl.

Yet other preferred compounds of the invention are those of formula Z9

Z9

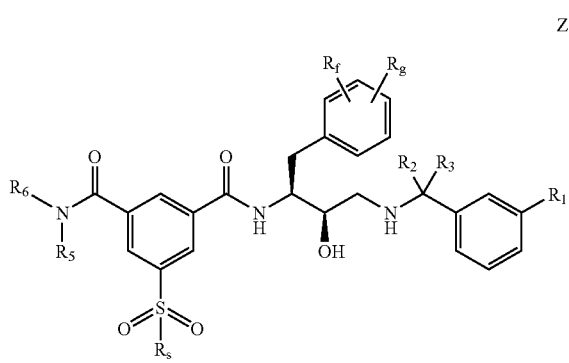

or a pharmaceutically acceptable salt thereof, wherein
$R_1$ is $C_2$-$C_3$ alkyl;
$R_2$ and $R_3$ are both hydrogen; or
$R_f$ and $R_g$ are independently halogen;
$R_5$ and $R_6$ are independently $C_3$-$C_4$ alkyl; or
$R_5$ is H and $R_6$ is $C_3$ alkyl; or
$R_5$, $R_6$, and the nitrogen to which they are attached form a pyrrolidinyl ring optionally substituted with methoxymethyl; and
$R_s$ is $C_1$-$C_2$ alkyl, hydroxy($C_2$-$C_4$)alkyl, N-[hydroxy($C_2$-$C_4$)alkyl]-N—($C_1$-$C_2$)alkylamino, N-methyl-N—($C_4$(t-butyl) alkyl)amino, —NH($C_1$-$C_4$ hydroxyalkyl), —N($C_1$-$C_3$ hydroxyalkyl)($C_1$-$C_3$ hydroxyalkyl), —N($C_1$-$C_2$ alkyl)($C_1$-$C_2$ alkyl), pyrrolidin-1-yl optionally substituted with hydroxymethyl or methoxymethyl, $C_1$-$C_2$ alkoxy $C_2$-$C_3$ alkyl, 1-piperazinyl, —$NH_2$, —NH($C_2$-$C_3$ alkyl-NH($C_1$-$C_2$ alkyl)), or $C_1$-$C_4$ alkylamino.

Preferred compounds of formula Z9 include those where $R_s$ is N-[hydroxy($C_4$-alkyl]-N-methylamino, —N($C_1$-$C_3$ hydroxyalkyl)($C_1$-$C_3$ hydroxyalkyl), or —NH($C_1$-$C_4$ hydroxyalkyl), hereinafter compounds of Z9-1.

Preferred compounds of formula Z9-1 include those where the hydroxyalkyl is 2-hydroxy-1,1-dimethylethyl; 2-hydroxyethyl; 3-hydroxypropyl; 1(R)-2-hydroxy-1-methylethyl; 1(S)-2-hydroxy-1-methylethyl; 1(S)-2-hydroxy-1-methylethyl; 2(R)-2-hydroxypropyl; or 2(S)-2-hydroxypropyl.

Preferred compound of formula Z9 include those wherein $R_s$ is 3-hydroxypropyl, 4-hydroxybutyl.

Other preferred compound of formula Z9 include those wherein $R_s$ is 2(R)-2-methoxymethylpyrrolidin-1-yl, 2(R)-2-hydroxymethylpyrrolidin-1-yl, 2(S)-2-hydroxymethylpyrrolidin-1-yl, pyrrolidin-1-yl or 1-piperazinyl, hereinafter Z9-1A. More preferably, $R_s$ is 2(R)-2-methoxymethylpyrrolidin-1-yl, 2(R)-2-hydroxymethylpyrrolidin-1-yl, or 2(S)-2-hydroxymethylpyrrolidin-1-yl.

Still other preferred compound of formula Z9 include those wherein $R_5$, $R_6$, and the nitrogen to which they are attached form a 2(S)-2-methoxymethyl)pyrrolidin-1-yl, hereinafter compounds of Z9-2.

Preferred compound of formula z9-2 include those wherein $R_s$ is —NH(tert-butyl), —N($CH_3$)($CH_2CH_3$), —N($CH_3$)$_2$, or 2(S)-2-methoxymethylpyrrolidin-1-yl, hereinafter Z9-3.

Preferred compounds of formula Z9 include those where $R_s$ is N-[hydroxy($C_4$ alkyl)]-N-methylamino. Particularly preferred are those where Rs is N-(hydroxy-t-butyl)-N-methylamino. By "hydroxy-t-butyl" is meant a 1-Hydroxy-1-methyl-ethyl group.

Other preferred compounds include those of Z9, Z9-1, Z9-1A, Z9-2, and Z9-3, wherein $R_1$ is ethyl or isopropyl. More preferably, $R_1$ is ethyl.

Other preferred compounds of the invention are those of formula Z10

Z10

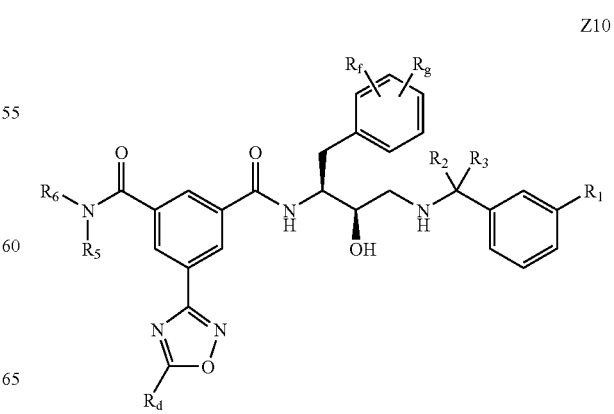

or a pharmaceutically acceptable salt thereof, wherein
$R_1$ is $C_2$-$C_3$ alkyl;
$R_2$ and $R_3$ are both hydrogen; or
$R_f$ and $R_g$ are independently halogen;
$R_5$ and $R_6$ are independently $C_1$-$C_4$ alkyl; and
$R_d$ is $C_1$-$C_2$ alkyl (preferably methyl), N-hydroxy($C_2$-$C_3$) alkyl-N—($C_1$-$C_2$)alkylamino, or $C_1$-$C_2$ alkylamino.

Other preferred compounds of the invention are those of formula Z11

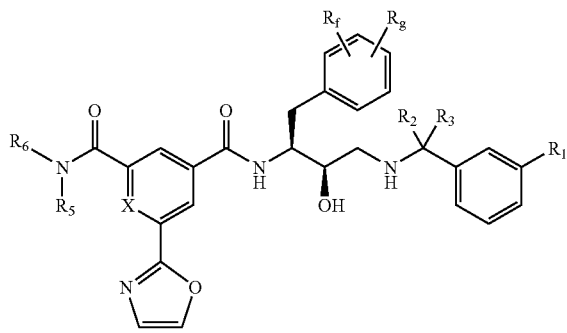

Z11 or a pharmaceutically acceptable salt thereof, wherein
X is nitrogen or CH;
$R_1$ is $C_2$-$C_3$ alkyl, amino, mono($C_1$-$C_3$)alkylamino, di($C_1$-$C_3$) alkylamino, amino($C_1$-$C_3$)alkyl, mono($C_1$-$C_3$)alkylamino ($C_1$-$C_2$)alkyl, or di($C_1$-$C_3$)alkylamino($C_1$-$C_2$)alkyl;
$R_2$ and $R_3$ are both hydrogen; or
$R_f$ and $R_g$ are both hydrogen or independently halogen;
$R_5$ and $R_6$ are independently methyl or $C_2$-$C_3$-$C_4$ alkyl, where at least one of $R_5$ and $R_6$ is not methyl.

Preferred compounds of Z11 include those where at least one of $R_5$ and $R_6$ is $C_3$ alkyl, hereinafter compounds of Z1-1. Even more preferred compounds of Z11 are those where each of $R_5$ and $R_6$ is propyl.

Preferred compounds of Z11 and Z11-1 are those where X is CH. More preferably, $R_1$ is di($C_1$-$C_2$)alkylamino. Even more preferred are those where at least one of $R_5$ and $R_6$ is propyl.

Other preferred compounds of Z11-1 are those where X is nitrogen. More preferably, both of $R_5$ and $R_6$ are not methyl. Other more preferred compounds of Z11-1 are those where $R_1$ is di($C_1$-$C_2$)alkylamino($C_1$-$C_2$)alkyl. More preferably, the di($C_1$-$C_2$)alkylamino($C_1$-$C_2$)alkyl group is N,N-dimethyl-($C_1$-$C_2$)alkyl.

Other preferred compounds of the invention are those of formula Z12

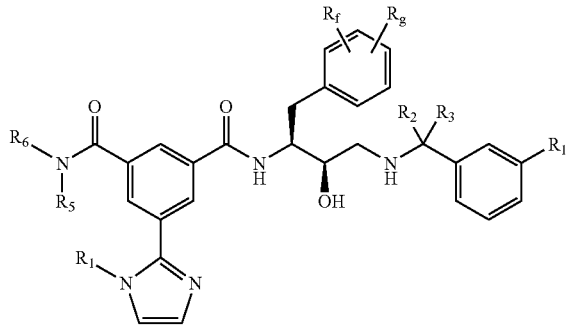

Z12 or a pharmaceutically acceptable salt thereof, wherein
$R_1$ is $C_2$-$C_3$ alkyl,;
$R_2$ and $R_3$ are both hydrogen; or
$R_2$, $R_3$, and the carbon to which they are attached form a cyclopropyl ring;
$R_f$ and $R_g$ are independently halogen;
$R_5$ and $R_6$ are independently $C_3$-$C_4$ alkyl (more preferably, at least one of $R_5$ and $R_6$ is propyl); and
$R_j$ is hydrogen or $C_1$-$C_2$ alkoxymethyl.

Other preferred compounds of the invention are those of formula Z13

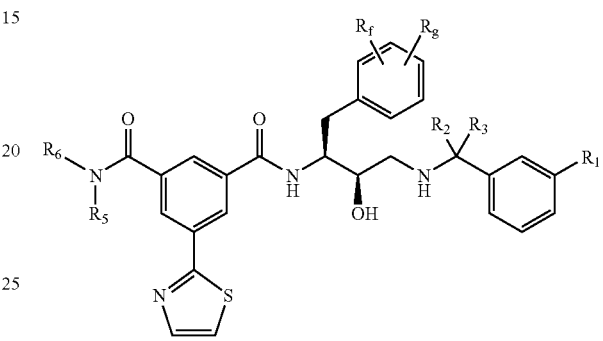

Z13 or a pharmaceutically acceptable salt thereof, wherein
$R_1$ is $C_2$-$C_4$ alkynyl, $C_2$-$C_4$ alkyl preferably ethyl, isopropyl, or trifluoromethyl;
$R_2$ and $R_3$ are both hydrogen; or
$R_2$ and $R_3$ together form a 3-membered ring with the carbon atom to which they are attached;
$R_f$ and $R_g$ are independently halogen; and
$R_5$ and $R_6$ are independently $C_3$-$C_4$ alkyl; or
one of $R_5$ and $R_6$ is methyl or ethyl and the other is $C_3$ or $C_{4,5}$(butyl)alkyl.

Preferred compounds of formula Z13 include those where $R_1$ is ethyl, n-propyl, isopropyl, or trifluoromethyl, more preferably ethyl or isopropyl. Even more preferred are compounds where $R_5$ and $R_6$ are independently propyl or butyl. Still more preferred are compounds where both of $R_2$ and $R_3$ are hydrogen. Particularly preferred are those wherein $R_f$ and $R_g$ are both chloro or fluoro.

Other preferred compounds of Z13 are those where $R_1$ is ethyl or trifluoromethyl, hereinafter compounds of Z13-1. Among these, compounds where $R_5$ is methyl, ethyl or propyl and $R_6$ is $C_3$-$C_4$ alkyl are more preferred. Even more preferred are those where $R_6$ is propyl or butyl. Particularly preferred are those where $R_6$ is butyl and $R_5$ is methyl.

Other preferred compounds of Formula Z13 are those where $R_5$ is methyl, hereinafter compounds of Z13-2. Preferred compounds of Z13-2 include those where $R_f$ and $R_g$ are both chloro or fluoro. More preferably, both of $R_2$ and $R_3$ are hydrogen.

Other preferred compounds of Formula Z13 are those wherein both of $R_2$ and $R_3$ are hydrogen; and
$R_1$ is $C_2$-$C_3$ alkynyl.

Still other preferred compounds of Formula Z13 are those wherein $R_5$ and $R_6$ are independently propyl or butyl, hereinafter Z13-3. More preferably, in compounds of Formula Z13-3, both of $R_2$ and $R_3$ are hydrogen. Still more preferably, $R_f$ and $R_g$ are both chloro or fluoro. Even more preferably, $R_2$ and $R_3$ together form a 3-membered ring with the carbon atom to which they are attached.

Other preferred compounds of the invention are those of formula Z14

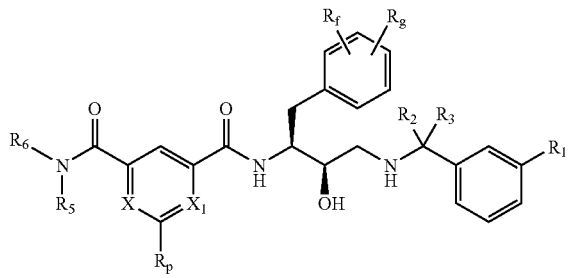

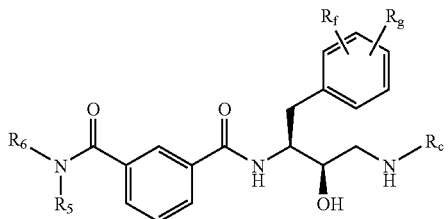

or a pharmaceutically acceptable salt thereof, wherein one of X or $X_1$ is nitrogen or $N^+$—$O^-$ while the other is CH;
$R_1$ is $C_2$-$C_4$ alkynyl, cyano, or $C_1$-$C_3$ alkyl;
$R_2$ and $R_3$ are both hydrogen; or
$R_2$ and $R_3$ together form a 3-membered ring with the carbon atom to which they are attached;
$R_f$ and $R_g$ are independently halogen;
$R_p$ is hydrogen, $C_1$-$C_2$ alkyl, or oxazolyl; and
$R_5$ and $R_6$ are independently $C_3$-$C_4$ alkyl.

Preferred compounds of formula Z14 include those where X is nitrogen; $R_1$ is $C_1$-$C_2$ alkyl; $R_2$ and $R_3$ are hydrogen; and $R_p$ is hydrogen, $C_1$-$C_2$ alkyl, or oxazol-2-yl.

Other preferred compounds of Z14 are those where X is nitrogen; $R_1$ is $C_2$-$C_3$ alkynyl; $R_2$ and $R_3$ together form a 3-membered ring with the carbon atom to which they are attached; and $R_p$ is $C_1$-$C_2$ alkyl. Even more preferred are compounds where X is nitrogen; and $R_1$ is $C_2$ alkynyl.

Other preferred compounds of Z14 are those where X is nitrogen; $R_1$ is $C_1$-$C_2$ alkyl, preferably ethyl; $R_2$ and $R_3$ are hydrogen; and $R_1$ is hydrogen, $C_1$-$C_2$ alkyl, or oxazol-2-yl.

Still other preferred compounds of Z14 are those where X is nitrogen; $R_1$ is $C_1$-$C_2$ alkyl; $R_2$ and $R_3$ are hydrogen; and $R_p$ is hydrogen, $C_1$-$C_2$ alkyl, oxazol-2-yl, or cyano. More preferably, $R_p$ is cyano, methyl or oxazol-2-yl. Even more preferably, $R_p$ is methyl. Equally preferably, $R_p$ is oxazol-2-yl. Equally preferably, $R_p$ is cyano.

Yet other preferred compounds of Z14 are those wherein X is nitrogen; $R_1$ is $C_2$-$C_3$ alkyl; $R_2$ and $R_3$ together form a 3-membered ring with the carbon atom to which they are attached; and $R_p$ is $C_1$-$C_2$ alkyl.

Preferred compounds of Z14 include those where $R_f$ and $R_g$ are both chloro or fluoro. Still other preferred compounds of Z14 are those where $R_5$ and $R_6$ are independently propyl or butyl.

Yet still other compounds of Z14 include those wherein $R_f$ and $R_g$ are both chloro or fluoro, and $R_5$ and $R_6$ are independently propyl or butyl.

Still other compounds of formula Z14 include those wherein X is CH and X' is N. More preferably, Rp is cyano, methyl or oxazol-2-yl. More preferably, $R_f$ and $R_g$ are both chloro or fluoro, and $R_5$ and $R_6$ are independently propyl or butyl. Equally preferably, compounds of Z14 include those wherein $R_2$ and $R_3$ together form a 3-membered ring with the carbon atom to which they are attached.

Still other preferred compounds of the invention are those of formula Z15 or a pharmaceutically acceptable salt thereof, wherein
$R_C$ is a group of the formula

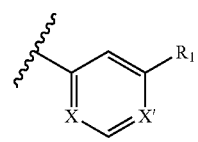

where one of X and X' is nitrogen and the other is CH and $R_1$ is $C_2$-$C_4$ alkyl or —($C_1$-$C_2$ alkyl)-N($C_1$-$C_2$ alkyl)($C_1$-$C_2$ alkyl);
$R_f$ and $R_g$ are independently halogen;
$R_p$ is $C_1$-$C_2$ alkyl; and
$R_5$ and $R_6$ are independently hydrogen or $C_3$-$C_4$ (sec butyl) alkyl.

Preferred compounds of Z15 include those where X is nitrogen; X' is CH; and $R_5$ and $R_6$ are independently propyl or butyl.

Other preferred compounds of Z15 are those where X is CH; X' is nitrogen; and $R_5$ and $R_6$ are independently propyl or butyl. More preferably, $R_1$ is —$CH_2N(CH_3)CH_3$, or ethyl. Still more preferably $R_1$ is —$CH_2N(CH_3)CH_3$.

Particularly preferred compounds of Z15 include those where one of $R_5$ and $R_6$ is hydrogen and the other is $C_4$ butyl, more preferably sec-butyl.

Other preferred compounds of the invention are those of formula Z16

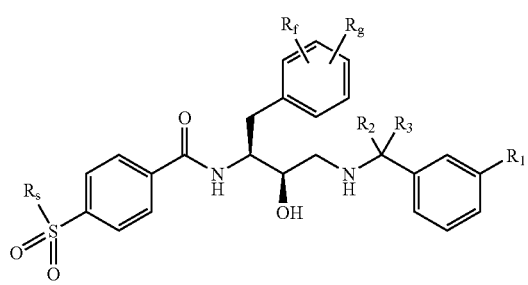

or a pharmaceutically acceptable salt thereof, wherein
$R_s$ is methylamino, ethylamino, $C_3$ alkylamino, di($C_3$-alkyl) amino, or a group of the formula

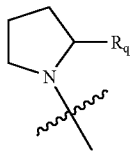

where $R_q$ is $C_1$-$C_2$ alkoxy($C_1$-$C_2$)alkyl;
$R_1$ is $C_2$-$C_3$ alkyl;
$R_2$ and $R_3$ are both hydrogen; and
$R_f$ and $R_g$ are independently halogen.

Other preferred compounds of the invention are those of formula Z17

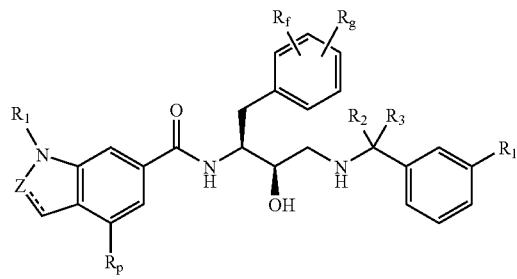

Z17 or a pharmaceutically acceptable salt thereof, wherein
Z is $CH_2$ when the dashed line represents a single bond or CH or a nitrogen atom when the dashed line represents a double bond;
$R_1$ is $C_2$-$C_3$ alkyl,;
$R_2$ and $R_3$ are both hydrogen; or
$R_2$, $R_3$ and the carbon to which they are attached form a cyclopropyl ring;
$R_f$ and $R_g$ are independently halogen;
$R_p$ is hydrogen, cyano, $C_1$-$C_3$ alkyl, amino, N—($C_1$-$C_3$ alkylsulfonyl)-N—(($C_1$-$C_3$)alkyl)amino (good when Z=CH), 2-oxazolyl, or 1-pyrrolyl optionally substituted in the 2 and 5 positions with $C_1$-$C_2$ alkyl; and
$R_j$ is $C_1$-$C_5$ alkyl.

Preferred compounds of formula Z17 include those where Rp is —N($CH_3$)$SO_2$($C_1$-$C_2$ alkyl); and $R_1$ is ethyl.

Other preferred compounds of formula Z17 include those where Z is $CH_2$, hereinafter compounds of Z17-1. Preferred compounds of Z17-1 include those where $R_p$ is N—($C_1$-$C_3$ alkylsulfonyl)-N—(($C_1$-$C_3$)alkyl)amino.

Other preferred compounds of Z17 are those where $R_j$ is methyl.

Still other preferred compounds of Z17-1 are those where $R_p$ is N-(methylsulfonyl)-N—(($C_1$-$C_2$)alkyl)amino; and $R_j$ is $C_3$-$C_4$ alkyl, preferably butyl, hereinafter Z17-2.

Preferred compounds of Z17-2 include those wherein $R_p$ is —N($CH_3$)$SO_2$($C_1$-$C_2$ alkyl); and $R_1$ is ethyl.

Other preferred compounds of Z17 are those where $R_p$ is 2-oxazolyl. In these compounds, Z is preferably $CH_2$ or CH. More preferably, Z is CH.

Other preferred compounds of Z17 are those where $R_p$ is cyano; Z is $CH_2$ or CH; and $R_j$ is $C_3$-$C_4$ alkyl. Preferably, Z is CH and $R_j$ is butyl.

Still other preferred compounds of Z17, Z17-1, and Z17-2 are those wherein at least one of $R_f$ and $R_g$ is fluorine. More preferably, both are fluorine.

Still other preferred compounds of Z17, Z17-1, and Z17-2 are those wherein R2, R3, and the carbon to which they are attached form a cyclopropyl ring.

Other preferred compounds of the invention are those of formula Z18

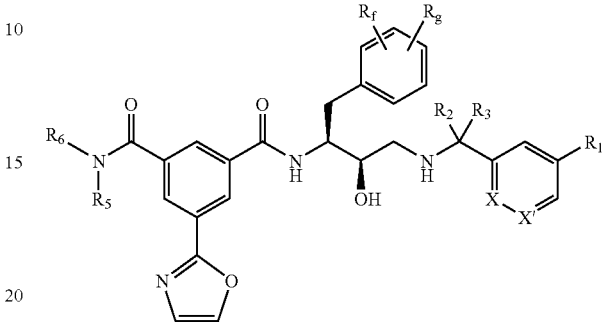

Z18 or a pharmaceutically acceptable salt thereof, wherein both of X and X' are CH, or one of X and X' is nitrogen and the other is CH;
$R_1$ is $C_2$-$C_3$ alkynyl, $C_{1,2}$-$C_3$ alkyl, amino, mono($C_1$-$C_3$)alkylamino, or di($C_1$-$C_3$)alkylamino, aminoalkyl, mono($C_1$-$C_3$)alkylamino($C_3$-$C_2$)alkyl, di($C_1$-$C_3$)alkylamino($C_1$-$C_2$)alkyl, $CF_3$, $C_1$-$C_2$ alkoxy, halogen, —$NHSO_2$($C_1$-$C_2$ alkyl);
$R_2$ and $R_3$ are both hydrogen; or
$R_2$ and $R_3$ together form a 3-membered ring with the carbon atom to which they are attached;
$R_f$ and $R_g$ are both hydrogen or independently halogen;
$R_5$ and $R_6$ are independently $C_{1,2,3}$-$C_4$ alkyl; or
one of $R_5$ and $R_6$ is methyl or ethyl and the other is $C_3$ or $C_4$ alkyl, preferably butyl.

Preferred compounds of Formula Z18 include those where $R_1$ is bromo or chloro.

Other preferred compounds of Z18 include those of Z18-1, i.e., compounds of formula Z18 where $R_1$ is $C_2$-$C_3$ alkyl.

Other preferred compounds of Z18 include those of Z18-2, i.e., compounds of formula Z18 where $R_1$ is di($C_1$-$C_3$)alkylamino and both of $R_f$ and $R_g$ are chloro or fluoro.

Still other preferred compounds of Z18 include those of Z18-3, i.e., compounds of formula Z18 where $R_1$ is di($C_1$-$C_3$) alkylamino($C_1$-$C_2$)alkyl, and both of $R_f$ and $R_g$ are chloro or fluoro.

More preferred compounds of formula Z18 include those where X is nitrogen; $R_f$ and $R_g$ are both fluoro; $R_1$ is $C_1$-$C_3$ alkyl; and $R_2$ and $R_3$ together form a 3-membered ring with the carbon atom to which they are attached.

Preferred compounds of Z18-1 include those where both X and X' are CH; and $R_f$ and $R_g$ are both chloro or fluoro, hereinafter compounds of formula Z18-1-A. More preferred compounds of Z18-1 and Z18-1-A are those where one of $R_5$ and $R_6$ is methyl or ethyl and the other is $C_3$ or $C_4$ alkyl, preferably butyl.

Still other more preferred compounds of Z18-1 include compounds of formula Z18-1-B, i.e., compounds of Z18-1 where $R_5$ and $R_6$ are independently $C_2$-$C_4$ alkyl. Preferred compounds of Z18-1-B include those where $R_5$ is $C_2$-$C_4$ alkyl and $R_6$ is ethyl.

Other preferred compounds of Z18-1-A are those where one of $R_5$ and $R_6$ is methyl or ethyl and the other is $C_3$ or $C_4$ alkyl, preferably butyl. More preferably, one of $R_5$ and $R_6$ is methyl. Yet other preferred compounds of Z18-1-A are those where $R_5$ and $R_6$ are independently propyl or butyl.

Other preferred compounds of formula Z18 are compounds of formula Z18-4, i.e., compounds of formula Z18 where $R_1$ is $C_2$ alkynyl. Preferred compounds of Z18-4 include those where both X and X' are CH; and $R_f$ and $R_g$ are both chloro or fluoro.

Other preferred compounds of Z18-4 include those wherein X is nitrogen and X' is $CH_3$.

Other preferred compounds of Z18-1-A are those where $R_5$ and $R_6$ are independently propyl or butyl.

Still other preferred compounds of Z18 include those compounds wherein $R_1$ is $CF_3$, or $-NHSO_2CH_3$; $R_2$ and $R_3$ are both H; and $R_5$ and $R_6$ are independently $C_3$ or $C_4$ alkyl, hereinafter Z18-5.

Yet still other preferred compounds of Z18 include those wherein X is CH and X' is nitrogen, hereinafter Z18-6.

Preferred compounds of any of the embodiments of Z18, Z18-1-A, -1-B, Z18-2, Z18-3, Z18-4, Z18-5, Z18-6 are those where $R_2$ and $R_3$ together form a 3-membered ring with the carbon atom to which they are attached, hereinafter Z18-7.

More preferred compounds of Z18-7 include those wherein at least one of $R_f$ and $R_g$ is fluoro. More preferably, both $R_f$ and $R_g$ are fluoro.

Other preferred compounds of the invention are those of formula Z19

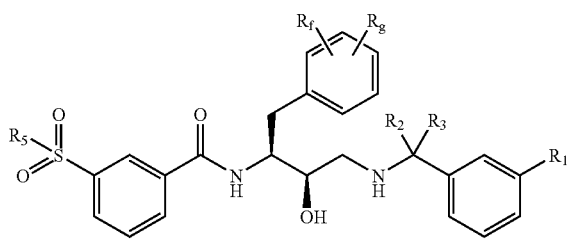

Z19 or a pharmaceutically acceptable salt thereof, wherein
$R_1$ is $C_2$-$C_3$ alkyl, or $C_1$-$C_2$ alkoxy;
$R_2$ and $R_3$ are both hydrogen;
$R_f$ and $R_g$ are independently halogen;
$R_s$ is $C_3$-$C_9$ alkyl (preferably $C_3$-$C_4$ alkyl), thiazolinyl or thiazolidinyl.

Preferred compounds of formula Z19 include those where $R_S$ is 2-thiazolidinyl or 2-thiazolinyl and $R_1$ is $C_2$-$C_3$ alkyl.

Other preferred compounds of Z19 are those where $R_S$ is methyl, propyl or, more preferably, t-butyl. Still more preferably at least one of Rf and Rg is fluoro. Even more preferably, $R_1$ is also $C_2$-$C_3$ alkyl.

Other preferred compounds of formula Z19 include those wherein Rs is $C_8$ alkyl. More preferably, the $C_8$ alkyl is $-CH_2CH(n-propyl)(n-propyl)$. Even more preferably $R_1$ is also $C_1$-$C_2$ alkoxy. Even more preferably, $R_1$ is methoxy.

Other preferred compounds of the invention are those of formula Z20

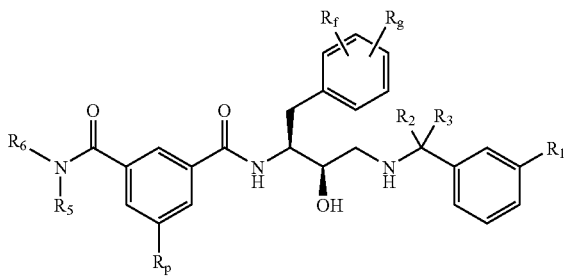

Z20 or a pharmaceutically acceptable salt thereof, wherein
$R_1$ is $C_2$-$C_3$ alkyl, $CF_3$, or $-NH(C_3$-$C_6$ cycloalkyl);
$R_2$ and $R_3$ are both hydrogen; or
$R_2$ and $R_3$ together with the carbon atom to which they are attached form a 3-membered ring;
$R_p$ is pyridyl, piperazinyl, amino, amino($C_1$-$C_{5(3)}$)alkyl, mono($C_1$-$C_2$)alkylamino ($C_1$-$C_5$)alkyl, di($C_1$-$C_2$)alkylamino ($C_1$-$C_{(4)5}$)alkyl, mono($C_1$-$C_3$)alkylamino, di($C_1$-$C_3$)alkylamino, amino($C_3$-$C_4$)alkynyl, mono($C_1$-$C_2$)alkylamino ($C_3$-$C_4$)alkynyl, di($C_1$-$C_2$)alkylamino($C_3$-$C_5$) alkynyl, $-N(C_1$-$C_2$ alkyl)-$SO_2(C_1$-$C_2$ alkyl), $-NH-SO_2(C_1$-$C_2$ alkyl), $-N(C_1$-$C_2$ alkyl)-$SO_2$-thienyl, $-N(C_1$-$C_2$ alkyl)-$SO_2(C_1$-$C_2$ haloalkyl), di($C_1$-$C_2$)alkylamino($C_3$-$C_4$)alkynyl, pyrimidinyl, pyrazolyl, imidazolyl, or $C_2$-$C_4$ alkynyl;
$R_f$ and $R_g$ are independently halogen;
$R_5$ and $R_6$ are independently $C_3$-$C_4$ alkyl.

Preferred compounds of Formula Z20 include those of formula Z20-1, i.e., compounds of Z20 where $R_5$ and $R_6$ are both $C_3$ alkyl.

Other preferred compounds of Formula Z20 include those of formula Z20-2, i.e., compounds of Z20 where $R_2$ and $R_3$ are hydrogen.

Still other preferred compounds of Z20 are compounds of formula Z20-3, i.e., compounds of Z20 where $R_2$ and $R_3$ together form a 3-membered ring with the carbon atom to which they are attached.

Preferred compounds of Z20-1, -2, and -3 are those where $R_p$ is 4-pyridyl, 2-pyrimidinyl, 4-pyrazolyl, or 4-imidazolyl, more preferably $R_p$ is 4-pyridyl, hereinafter Z20-3A. Other preferred compounds of formulas Z20-1, -2, and -3 are those where $R_p$ is diethylamino or dimethylamino, hereinafter Z20-3B. Still other preferred compounds of formulas Z20-1, -2, and -3 are those $R_p$ is amino or $C_1$-$C_6$ alkylamino, hereinafter Z20-3C. Yet other preferred compounds of Z20-1, -2, and -3 are those where $R_p$ is 1-piperazinyl, hereinafter Z20-3D. Still other preferred compounds of Z20-1, -2, and -3 include compounds where $R_p$ is amino($C_2$-$C_4$)alkyl where the amino is optionally mono substituted with $C_1$-$C_2$ alkyl, hereinafter Z20-3E; or where $R_p$ is $-N(CH_3)-SO_2CH_3$, $-NH-SO_2CH_3$, $-N(CH_3)-SO_2$-thien-2-yl, or $-N(CH_3)-SO_2CF_3$, hereinafter Z20-3F.

Other preferred compounds of Z20 are those where $R_p$ is di($C_1$-$C_2$)alkylamino($C_3$-$C_5$)alkyl, more preferably, N,N-dimethylamino($C_3$-$C_5$)alkyl, hereinafter Z20-3G.

Particularly preferred compounds of Z20-1,-2, and -3 are those where $R_p$ is 3-(mono($C_1$-$C_2$)alkylamino)propyn-1-yl, hereinafter Z20-3H. Other particularly preferred compounds of Z20 are those where $R_p$ is 3-(mono($C_1$-$C_2$)alkylamino) propyn-1-yl, 3-(di($C_1$-$C_2$)alkylamino)propyn-1-yl, or 4-(di($C_1$-$C_2$)alkylamino)propyn-1-yl, hereinafter Z20-3I.

Other preferred compounds of Z20, Z20-1, -2, and -3 are those where $R_p$ is di($C_1$-$C_2$)alkylamino($C_3$-$C_5$)alkyl; and $R_5$ and $R_6$ are both $C_3$ alkyl, hereinafter Z20-3J.

Still other preferred compounds of Z20, Z20-1, -2,-3, are those where $R_p$ is $C_2$-$C_3$ alkynyl, hereinafter Z20-4. More preferably, $R_p$ is $C_2$ alkynyl.

Also preferred are compounds of formulas Z20, Z20-1, -2, -3, -3A to -3J and Z20-4 when $R_1$ is —NH($C_3$-$C_6$ cycloalkyl) preferably —NHcyclopropyl. More preferably, at least one of $R_f$ and $R_g$ is fluoro. Even more preferably, both are fluoro.

Also preferred are compounds of formulas Z20, Z20-1, -2, -3, -3A to -3J and Z20-4 when $R_1$ is $CF_3$. More preferably, at least one of $R_f$ and $R_g$ is fluoro. Even more preferably, both are fluoro.

Other preferred compounds of Z20, Z20-1, -2, -3, -3A to -3J and -4 include those wherein $R_1$ is ethyl or isopropyl. Preferably $R_1$ is isopropyl. More preferably $R_1$ is ethyl. More preferably, at least one of $R_f$ and $R_g$ is fluoro. Even more preferably, both are fluoro. Still more preferably, $R_f$ and $R_g$ are attached to the 3 and 5 positions of the phenyl ring (with position 1 being the point of attachment to the $CH_2$ group.)

Other preferred compounds of the invention are those of formula Z21

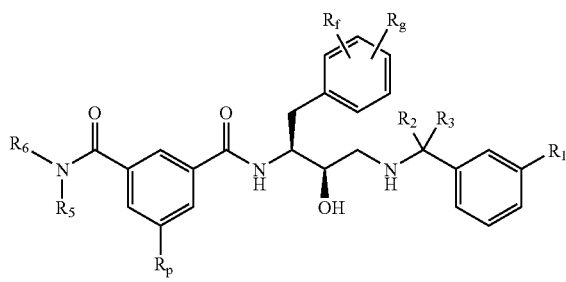

Z21 or a pharmaceutically acceptable salt thereof, wherein
$R_1$ is $C_2$-$C_3$ alkynyl;
$R_2$ and $R_3$ are both hydrogen;
$R_p$ is $C_1$-$C_3$ alkyl;
$R_f$ and $R_g$ are independently halogen;
$R_5$ and $R_6$ are independently $C_3$-$C_4$ alkyl; or
one of $R_5$ and $R_6$ is methyl and the other is $C_3$ or $C_4$ alkyl.

Preferred compounds of formula Z21 include those where one of $R_5$ and $R_6$ is methyl and the other is butyl, herein after Z21-1.

Other preferred compounds of formula Z21 and Z21-1 include those where $R_p$ is methyl.

Other preferred compounds of the invention are those of formula Z22

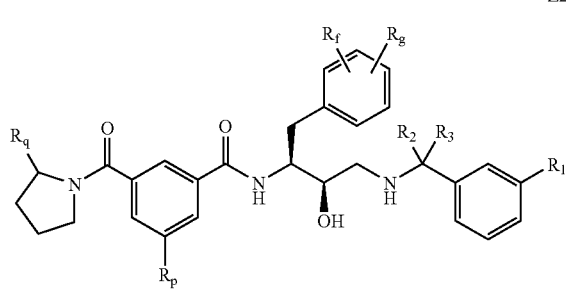

Z22 or a pharmaceutically acceptable salt thereof, wherein
$R_1$ is $C_1$-$C_2$ alkyl, $C_2$-$C_4$ alkynyl or $C_3$ (isopropyl)-$C_4$ alkyl;
$R_2$ and $R_3$ are both hydrogen; or
$R_2$ and $R_3$ together form a 3-membered ring with the carbon atom to which they are attached;
$R_f$ and $R_g$ are independently halogen;
$R_p$ is $C_1$-$C_3$ alkyl or a group of the formula:
$R_sSO_2$— where $R_s$ is
$R_{51}R_{61}N$— and $R_{51}$ and $R_{61}$ independently represent hydrogen or $C_1$-$C_4$ alkyl groups; or
a group of the formula:

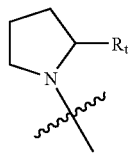

where $R_t$ is $C_1$-$C_2$ alkoxy($C_1$-$C_2$)alkyl; and
$R_q$ is $C_1$-$C_3$ alkoxy($C_1$-$C_2$)alkyl, $C_1$-$C_4$ alkyl, —C(O)$NH_2$, or H.

Preferred compounds of formula Z22 include those where $R_1$ is $C_2$ alkynyl; $R_2$ and $R_3$ together form a 3-membered ring with the carbon atom to which they are attached; and $R_p$ is $R_sSO_2$— where $R_s$ is

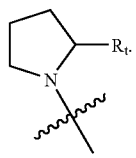

Other preferred compounds of formula Z22 include those where $R_1$ is $C_1$-$C_2$ alkyl; $R_2$ and $R_3$ are hydrogen; and $R_p$ is $R_sSO_2$— where $R_s$ is $C_3$-$C_4$ amino, preferably propyl, more preferably t-butylamino.

Still other preferred compounds of formula Z22 include those where $R_1$ is $C_1$-$C_2$ alkyl; $R_2$ and $R_3$ are hydrogen; $R_p$ is $C_1$-$C_2$ alkyl; and $R_q$ is $C_3$-$C_4$ alkyl, preferably propyl or butyl.

Yet other preferred compounds of formula Z22 include those where $R_1$ is $C_1$-$C_2$ alkyl; $R_2$ and $R_3$ are hydrogen; $R_p$ is $C_1$-$C_2$ alkyl; and $R_q$ is propoxy($C_1$-$C_2$)alkyl.

Other preferred compounds of formula Z22 include those where $R_1$ is $C_1$-$C_2$ alkyl; $R_2$ and $R_3$ are hydrogen; $R_p$ is $C_1$-$C_2$ alkyl; and $R_q$ is methoxy($C_1$-$C_2$)alkyl.

Other preferred compounds of formula Z22 include those where $R_1$ is $C_1$-$C_2$ alkyl; $R_2$ and $R_3$ together form a 3-membered ring with the carbon atom to which they are attached; $R_p$ is $C_1$-$C_2$ alkyl; and $R_q$ is $C_1$-$C_2$ alkyl.

Other preferred compounds of formula Z22 include those where $R_1$ is $C_1$-$C_2$ alkyl; $R_2$ and $R_3$ are hydrogen; $R_p$ is $C_1$-$C_2$ alkyl; and $R_q$ is $C_1$-$C_2$ alkyl.

Particularly preferred are compounds of Z22 where $R_1$ is isopropyl.

Other preferred compounds of Z22 include those wherein $R_q$ is (R)-methoxymethyl, methyl, propyl, (S)-propyl, (R)-propyl, butyl, (R)-butyl, (S)-butyl, (R)-2-methoxymethyl, or (R)-2-methoxyethyl.

Other preferred compounds of the invention are those of formula Z23

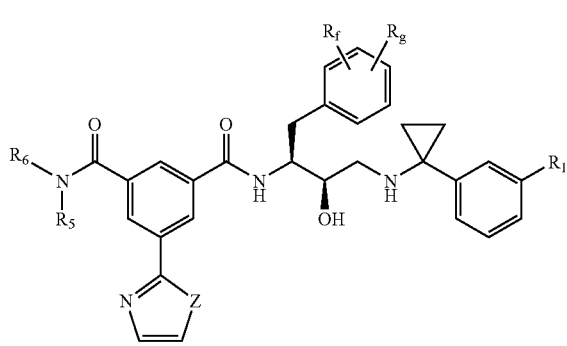

Z23 or a pharmaceutically acceptable salt thereof, wherein
Z is oxygen, nitrogen, or sulfur;
$R_1$ is chloro, bromo, hydrogen or $C_1$-$C_2$ alkyl;
$R_f$ and $R_g$ are independently halogen; and
$R_5$ and $R_6$ are independently $C_3$-$C_4$ alkyl; or one of $R_5$ and $R_6$ is methyl and the other is $C_3$ or $C_4$ alkyl.

Preferred compounds of Formula Z23 include those where Z is nitrogen; and $R_1$ is $C_1$-$C_3$ alkyl.

Preferred compounds of formula Z23 are those where $R_1$ is bromo, and Z is oxygen, hereinafter Z23-1. Other preferred compounds of formula Z23 are those wherein Z is nitrogen, hereinafter Z23-2. Still other preferred compounds of formula Z23 are those wherein Z is sulfur, hereinafter compounds of formula Z23-3.

Particularly preferred compounds of Z23, Z23-1, Z23-2, and Z23-3 are those where one of $R_5$ and $R_6$ is methyl and the other is butyl. Equally preferred are those where at least one of $R_5$ and $R_6$ is propyl. Still more preferably, $R_1$ is $C_1$-$C_3$ alkyl. Even more preferably, $R_1$ is $C_2$-$C_3$ alkyl. $R_1$ can also be ethyl.

Other preferred compounds of the invention are those of formula Z24

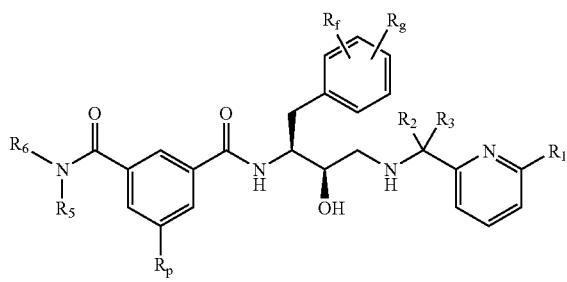

Z24 or a pharmaceutically acceptable salt thereof, wherein
$R_1$ is $C_1$-$C_2$-$C_3$ alkyl,;
$R_2$ and $R_3$ are both hydrogen; or
$R_p$ is $C_1$-$C_2$ alkyl;
$R_f$ and $R_g$ are both hydrogen or independently halogen; and
$R_5$ and $R_6$ are independently $C_3$-$C_4$ alkyl.

Preferred compounds of formula Z24 include those where $R_1$ is ethyl. More preferably, Rp is also methyl. Still more preferably, $R_f$ and $R_g$ are both halogen.

Other preferred compounds of the invention are those of formula Z25

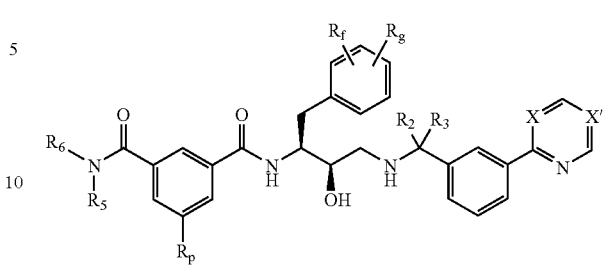

Z25 or a pharmaceutically acceptable salt thereof, wherein one of X and X' is nitrogen and the other is CH or $CR_1$;
$R_1$ is $C_1$-$C_2$-$C_3$ alkyl
$R_2$ and $R_3$ are both hydrogen; or
$R_2$, $R_3$, and the carbon to which they are attached form a cyclopropyl ring;
$R_p$ is $C_1$-$C_2$ alkyl;
$R_f$ and $R_g$ are independently halogen; and
$R_5$ and $R_6$ are independently $C_3$-$C_4$ alkyl.

Preferred compounds of Z25 include compounds where X is CH and X' is nitrogen. Particularly preferred compounds of formula Z25 include those where $R_1$ is ethyl. Even more preferred is when $R_2$ and $R_3$ are both hydrogen.

Other preferred compounds of the invention are those of formula Z26

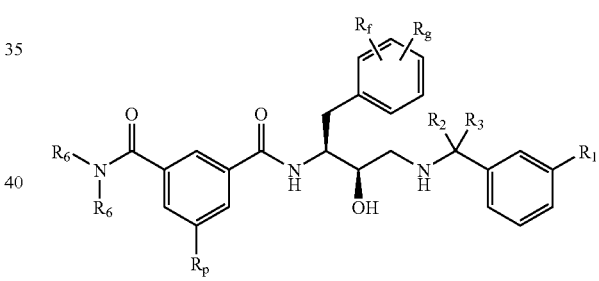

Z26 or a pharmaceutically acceptable salt thereof, wherein $R_1$ is a group of the formula:

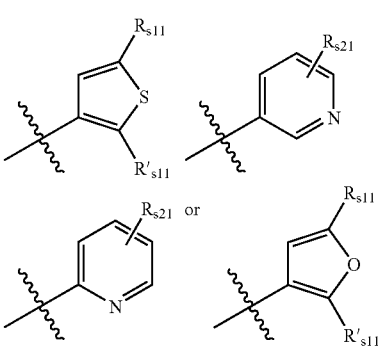

where
one of $R_{s11}$ and $R'_{s11}$ is hydrogen and the other is $C_1$-$C_3$ acyl, $C_1$-$C_2$ alkyl or CHO; or one of $R_{s11}$ and $R'_{s11}$ is methyl and the other is CHO or methyl,
each $R_{s21}$ is $C_1$-$C_3$ alkoxy, halogen, H, $C_1$-$C_2$-alkyl or cyano; or
$R_1$ is cyclopentyl, cyclohexyl, oxazolyl, isoxazolyl optionally substituted with one or two $C_1$-$C_2$ alkyl groups, phenyl, thien-2-yl optionally substituted with CHO, unsubstituted thien-3-yl;
$R_2$ and $R_3$ are both hydrogen;
$R_p$ is $C_1$-$C_2$ alkyl;
$R_f$ and $R_g$ are independently halogen; and
$R_5$ and $R_6$ are independently $C_3$-$C_4$ alkyl.

Preferred compounds of formula Z26 include compounds of Z26 where $R_1$ is 6-($C_1$-$C_2$)alkoxypyridin-2-yl.

Other preferred compounds of formula Z26 include compounds of Z26 where $R_1$ is 2-formylthien-3-yl.

Still other preferred compounds of formula Z26 include compounds of Z26 where $R_1$ is 5-formylthien-3-yl.

Other preferred compounds of formula Z26 include compounds where $R_{s21}$ is cyano.

Yet other preferred compounds of formula Z26 include compounds of Z26 where $R_1$ is 5-cyanopyrid-3-yl.

Other preferred compounds of formula Z26 are those of formula Z26-1, i.e., compounds of Z26 where $R_1$ is 6-halopyrid-3-yl. Particularly preferred compounds of Z26-1 are those where halogen in $R_1$ is fluoro or chloro.

Still other preferred compounds of formula Z26 are those wherein $R_1$ is a thienyl group optionally substituted with $R_s11$, or $R'_s11$, cyclopentyl, cyclohexyl, oxazolyl, isoxazolyl optionally substituted with one or two $C_1$-$C_2$ alkyl groups, phenyl, or thien-2-yl optionally substituted with CHO. More preferably, the unsubstituted thienyl group is a thien-3-yl or a thien-2-yl.

Other preferred compounds of the invention are those of formula Z27

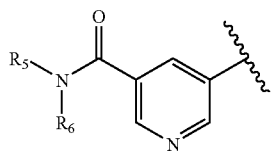

or a pharmaceutically acceptable salt thereof, wherein Z is

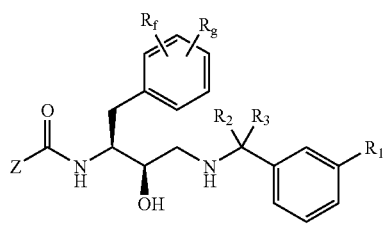

pyridyl or the pyridyl N-oxide
wherein the pyridyl or the pyridyl N-oxide is substituted with C(O)NR$_5$R$_6$, wherein
$R_5$ and $R_6$ are independently $C_3$-$C_4$ alkyl; or
$R_5$ is methyl or ethyl and $R_6$ is $C_3$ alkyl;
$R_1$ is $C_1$-$C_3$ alkyl or halogen;
$R_2$ and $R_3$ are both hydrogen;

$R_s$ is $C_1$-$C_3$ alkylsulfonyl, $C_1$-$C_3$ alkylsulfonyl($C_1$-$C_3$)alkyl, —NHSO$_2$($C_1$-$C_2$ alkyl), or —N($C_1$-$C_2$ alkyl)SO$_2$($C_1$-$C_2$ alkyl); and
$R_f$ and $R_g$ are independently halogen.

Preferably $R_1$ in compounds of formula Z27 is ethyl. More preferably, Z is

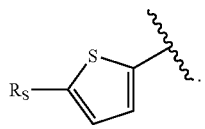

Equally preferably, $R_s$ is $C_1$-$C_3$ alkylsulfonyl, $C_1$-$C_3$ alkylsulfonyl($C_1$-$C_3$)alkyl, —NHSO$_2$CH$_3$, or —NCH$_3$SO$_2$CH$_3$.

Other preferred compounds include those wherein Z is pyridyl substituted with C(O)NR$_5$R$_6$, wherein $R_5$ and $R_6$ are independently $C_3$-$C_4$ alkyl; or $R_5$ is methyl or ethyl and $R_6$ is $C_3$ alkyl. More preferably, $R_5$ and $R_6$ are propyl. Still more preferably, Z is

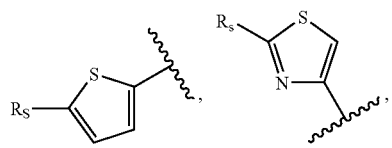

or the N-oxide thereof.

Other preferred compounds of the invention are those of formula Z28

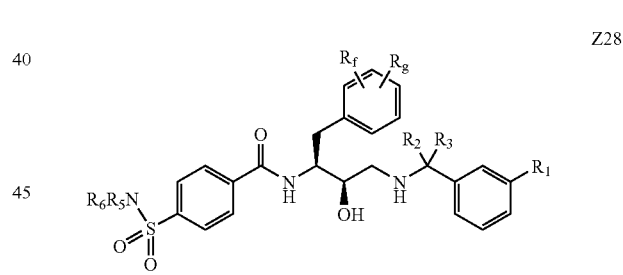

or a pharmaceutically acceptable salt thereof, wherein
$R_1$ is $C_2$-$C_3$ alkyl;
$R_2$ and $R_3$ are both hydrogen;
$R_5$ and $R_6$ independently represent (a) $C_1$-$C_3$ alkyl optionally substituted with phenyl and (b) phenyl optionally substituted with halogen; and
$R_f$ and $R_g$ are independently halogen.

Preferred compounds of formula Z28 include those where $R_5$ is methyl optionally substituted with phenyl and $R_6$ is phenyl.

Other preferred compounds of formula Z28 include those where $R_5$ is $C_1$-$C_2$ alkyl and $R_6$ is 4-halophenyl, preferably 4-chlorophenyl.

Other preferred compounds of the invention are those of formula Z29

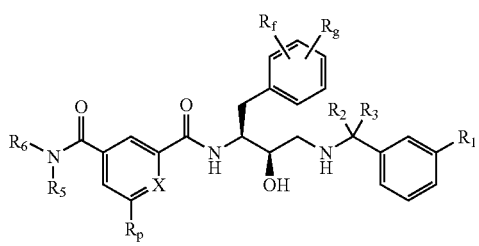

or a pharmaceutically acceptable salt thereof, wherein
X is nitrogen or $N^+$—$O^-$;
$R_1$ is $C_2$-$C_4$ alkynyl or $C_1$-$C_3$ alkyl;
$R_2$ and $R_3$ are both hydrogen; or
$R_2$ and $R_3$ together form a 3-membered ring with the carbon atom to which they are attached;
$R_f$ and $R_g$ are independently halogen;
$R_p$ is hydrogen or $C_1$-$C_2$ alkyl; and
$R_5$ and $R_6$ are independently $C_3$-$C_4$ alkyl.

Preferred compounds of formula Z29 include those where $R_1$ is ethyl. More preferred compounds of formula Z29 include those where X is nitrogen; $R_p$ is $C_1$-$C_2$ alkyl (preferably methyl); and $R_1$ is ethyl.

Other preferred compounds of the invention are those of formula Z30

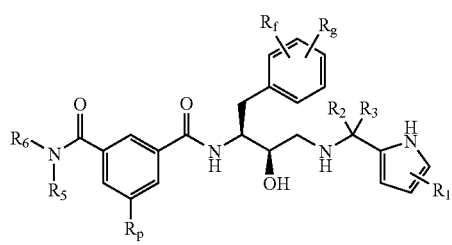

or a pharmaceutically acceptable salt thereof, wherein
$R_1$ is hydrogen or $C_1$-$C_3$ alkyl;
$R_2$ and $R_3$ are both hydrogen;
$R_p$ is $C_1$-$C_2$ alkyl;
$R_f$ and $R_g$ are independently halogen; and
$R_5$ and $R_6$ are independently $C_3$-$C_4$ alkyl.

Another preferred group of compounds of the invention is represented by formula Z31

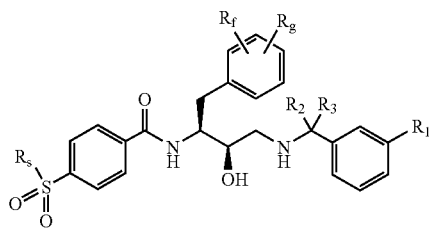

or a pharmaceutically acceptable salt thereof, wherein
$R_s$ is $NR_{s31}R_{s41}$ where
$R_{s31}$ is $C_1$-$C_2$ alkyl; and
$R_{s41}$ is $C_1$-$C_6$ alkyl, allyl, cyano($C_1$-$C_3$)alkyl, ($C_4$-$C_7$) cycloalkyl, pyridyl ($C_1$-$C_3$)alkyl, phenyl, phenyl ($C_1$-$C_3$)alkyl, amino($C_1$-$C_3$)alkyl, mono($C_1$-$C_3$)alkylamino ($C_1$-$C_2$)alkyl, or di($C_1$-$C_3$)alkylamino ($C_1$-$C_2$)alkyl; or
$R_s$ is $CH_3$, —$N(C_1$-$C_2$ alkyl)phenyl, or —$N(C_2$-$C_3$ alkyl)($C_3$-$C_4$ alkyl);
$R_1$ is $C_2$-$C_3$ alkyl;
$R_2$ and $R_3$ are both hydrogen; and
$R_f$ and $R_g$ are independently halogen.

Preferred compounds of formula Z31 include those where $R_{s41}$ is pyridylethyl or phenylethyl.

Other preferred compounds of Z31 are those where $R_{s41}$ is diethylamino($C_1$-$C_2$)alkyl, more preferably diethylaminomethyl.

Still other preferred compounds of Z31 are those where $R_{s41}$ is $C_{3-5}$ alkyl.

Particularly preferred compounds of formula Z31 include those where $R_s$ is (2-cyanoethyl)(methyl)amino.

Other particularly preferred compounds of formula Z31 include those where $R_s$ is (cyclohexyl)(methyl)amino.

In a preferred aspect of formula Z31, $R_{s41}$ is $C_1$-$C_6$ alkyl, allyl, cyano($C_1$-$C_3$)alkyl, ($C_4$-$C_7$)cycloalkyl, pyridyl($C_1$-$C_3$) alkyl, phenyl, or phenyl($C_1$-$C_3$)alkyl.

In another preferred aspect of Z31, $R_{s41}$ is phenyl or cyclohexyl.

In yet another preferred aspect of Z31, $R_s$ is —$N(CH_3)$phenyl, or —$N$(ethyl)($C_3$-$C_4$ alkyl).

Other preferred compounds of the invention are those of formula Z32

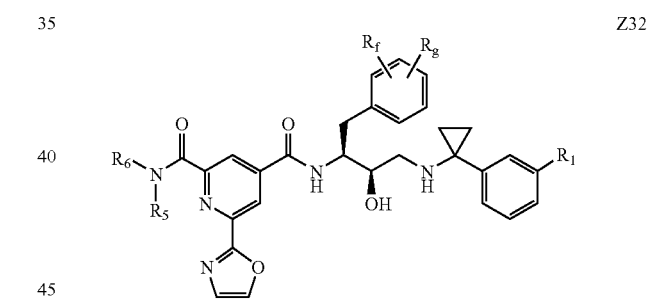

or a pharmaceutically acceptable salt thereof, wherein
$R_1$ is $C_2$-$C_3$ alkynyl or $C_1$-$C_3$ alkyl;
$R_f$ and $R_g$ are independently halogen;
$R_5$ and $R_6$ are independently $C_1$-$C_4$ alkyl.

Preferred compounds of formula Z33 include those where $R_5$ and $R_6$ are $C_3$ alkyl.

Other preferred compounds of formula Z33 include those where $R_5$ is methyl and $R_6$ is $C_3$ alkyl.

Particularly compounds of formula Z33 include those where $R_1$ is ethyl.

Other particularly preferred compounds of formula Z33 include those where $R_5$ and $R_6$ are both propyl or $R_5$ is methyl and $R_6$ is propyl, hereinafter Z33-1.

Still other preferred compounds of formula Z33 and Z33-1 include those wherein $R_1$ is $C_2$-$C_3$ alkynyl (preferably $C_2$ alkynyl).

Other preferred compounds of the invention are those of formula Z33

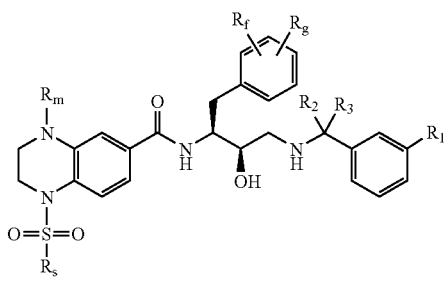

or a pharmaceutically acceptable salt thereof, wherein
$R_s$ is $C_1$-$C_4$ alkyl;
$R_m$ is $C_1$-$C_4$ alkyl;
$R_1$ is $C_2$-$C_3$ alkyl;
$R_2$ and $R_3$ are both hydrogen; and
$R_f$ and $R_g$ are independently halogen.

Other preferred compounds of the invention are those of formula Z34

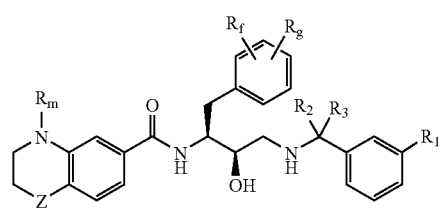

or a pharmaceutically acceptable salt thereof, wherein
$R_m$ is $C_1$-$C_4$ alkyl;
$R_1$ is $C_2$-$C_3$ alkyl;
$R_2$ and $R_3$ are both hydrogen; and
$R_f$ and $R_g$ are independently halogen;
Z is S, S(O), S(O)$_2$, or O.

Preferred compounds of formula Z34 include those where Z is S or S(O). More preferably, $R_1$ is $C_2$ alkyl.

Other preferred compounds of the invention are those of formula Z35

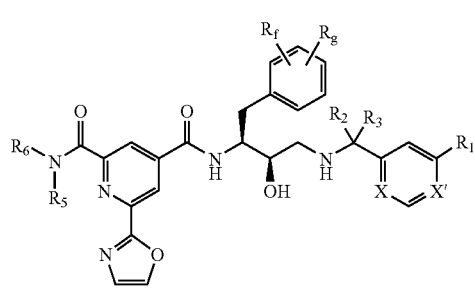

or a pharmaceutically acceptable salt thereof, wherein
one of X and X' is CH and the other is N;
$R_1$ is $C_2$-$C_4$ alkynyl; amino($C_1$-$C_3$)alkyl, mono($C_1$-$C_3$)alkylamino($C_1$-$C_2$)alkyl, or di($C_1$-$C_3$)alkylamino($C_1$-$C_2$)alkyl;
$R_2$ and $R_3$ are both hydrogen; or
$R_2$ and $R_3$ together form a 3-membered ring with the carbon atom to which they are attached;

$R_f$ and $R_g$ are independently, halogen;
$R_5$ and $R_6$ are independently $C_1$-$C_3$-$C_4$ alkyl.

Preferred compounds of formula Z35 include those where $R_2$ and $R_3$ together form a 3-membered ring with the carbon atom to which they are attached; X is N; and X' is CH, hereinafter Z35-1.

Other preferred compounds of formula Z35 include those of formula Z35-1, i.e., compounds of Z35 where $R_2$ and $R_3$ are hydrogen; X' is N; and X is CH, hereinafter Z35-2.

More preferred compounds of Z35, Z35-1, and Z35-2 include those where $R_1$ is $C_2$ alkynyl. More preferably, $R_1$ is also di($C_1$-$C_3$)alkylamino($C_1$-$C_3$)alkyl. Even more preferably, $R_1$ is dimethylamino($C_1$-$C_2$)alkyl.

Other preferred compounds of the invention are those of formula Z36

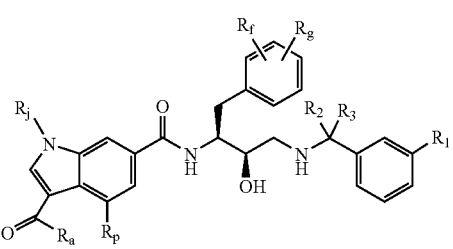

or a pharmaceutically acceptable salt thereof, wherein
$R_1$ is $C_2$-$C_3$ alkyl,;
$R_2$ and $R_3$ are both hydrogen;
$R_f$ and $R_g$ are independently halogen;
$R_p$ is hydrogen, cyano, $C_1$-$C_3$ alkyl, amino, N—($C_1$-$C_3$ alkylsulfonyl)-N—(($C_1$-$C_3$)alkyl)amino, 2-oxazolyl, or 1-pyrrolyl optionally substituted in the 2 and 5 positions with $C_1$-$C_2$ alkyl;
$R_a$ is $C_1$-$C_3$ alkyl, H or trifluoromethyl; and
$R_j$ is $C_1$-$C_5$ alkyl.

Preferred compounds of Z36 include those where $R_j$ is methyl or ethyl and $R_p$ is hydrogen, methyl, or ethyl.

Other preferred compounds of Z36 include those where $R_j$ is methyl and $R_p$ is hydrogen.

Other preferred compounds of the invention are those of formula Z37

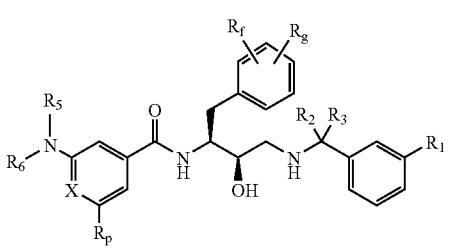

or a pharmaceutically acceptable salt thereof, wherein
X is nitrogen or N$^+$—O$^-$;
$R_1$ is $C_2$-$C_4$ alkynyl, cyano, $C_1$-$C_3$ alkyl, or CF$_3$;
$R_2$ and $R_3$ are both hydrogen; or
$R_2$ and $R_3$ together form a 3-membered ring with the carbon atom to which they are attached;
$R_f$ and $R_g$ are independently halogen;
$R_p$ is hydrogen, cyano or $C_1$-$C_2$ alkyl; and
$R_5$ and $R_6$ are independently $C_1$-$C_4$ alkyl.

Preferred compounds of formula Z37 include those of formula Z37-1, i.e., compounds of Z37 where X is N. Preferred compounds of Z37-1 include those where $R_p$ is cyano. More preferred compounds of Z37-1 are those where $R_5$ is methyl and $R_6$ is $C_2$-$C_4$ alkyl. Particularly preferred compounds of Z37-1 are those where $R_6$ is propyl.

Other preferred compounds of formula Z37 include those wherein $R_1$ is $C_2$-$C_3$ alkyl; $R_p$ is methyl or ethyl; and $R_5$ and $R_6$ are independently $C_3$-$C_4$ alkyl. More preferably, $R_2$ and $R_3$ are also hydrogen.

Other preferred compounds of Z37 include those wherein $R_1$ is $C_2$-$C_3$ alkynyl, or $C_2$ alkyl; and $R_p$ is methyl.

Still other preferred compounds of Z37 include those wherein $R_1$ is $CF_3$. More preferably, Rp is also methyl. Even more preferably X is CH.

Other preferred compounds of the invention are those of formula Z38

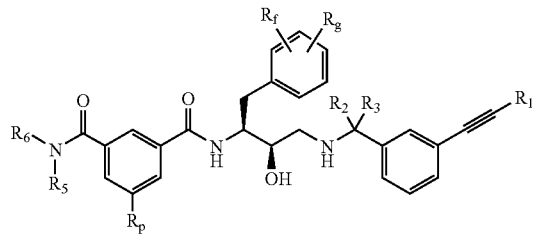

Z38 or a pharmaceutically acceptable salt thereof, wherein
$R_1$ is hydrogen, methyl, or —$CH_2OH$;
$R_2$ and $R_3$ are both hydrogen; or
$R_2$ and $R_3$ together with the carbon atom to which they are attached form a 3-membered ring;
$R_p$ is $C_2$-$C_3$ alkynyl or $C_1$-$C_3$ alkyl;
$R_f$ and $R_g$ are independently halogen;
$R_5$ and $R_6$ are independently $C_3$-$C_4$ alkyl, or
$R_5$ is methyl and $R_6$ is $C_3$-$C_4$ alkyl.

In preferred compounds of Formula Z38 include those wherein $R_p$ is methyl, hereinafter Z38-1.

Other preferred compounds of Formula Z38 include those wherein $R_p$ is $C_2$ alkynyl, hereinafter Z38-2.

Other preferred compounds of Z38, Z38-1, and Z38-2 include those wherein $R_1$ is hydrogen and $R_2$ and $R_3$ are both hydrogen, hereinafter Z38-3. Preferred compounds of Z38-3 include those wherein $R_5$ and $R_6$ are both $C_3$-$C_4$ alkyl. Even more preferably, both are $C_3$ alkyl.

Still other preferred compounds of Z38, Z38-1, and Z38-2 include those wherein $R_1$ is hydrogen and $R_2$ and $R_3$ form a 3-membered ring, hereinafter Z38-4.

Other preferred compounds of Z38, Z38-1, and Z38-2 include those wherein $R_1$ is —$CH_2OH$. Preferably, $R_2$ and $R_3$ are also hydrogen, hereinafter Z38-4A.

Even more preferred compounds of Z38 are those where $R_1$ is hydrogen and $R_2$ and $R_3$ together with the carbon atom to which they are attached form a 3-membered ring, hereinafter Z38-5.

Preferred compounds of formula Z38-5 include those wherein $R_p$ is $C_2$-$C_3$ alkynyl (preferably $C_2$ alkynyl) or methyl. More preferably, at least one of $R_5$ and $R_6$ is $C_3$ alkyl. Still more preferably, $R_5$ is methyl or propyl and $R_6$ is propyl, hereinafter Z38-5A.

Still other preferred Z38, Z38-1, Z38-2, Z38-3, Z38-4, Z38-4A, Z38-5 and Z38-5A include compounds are those where $R_f$ and $R_g$ are both chloro or fluoro. Particularly preferred among Z38 compounds are those where $R_f$ and $R_g$ are both fluoro and are in the 3 and 5 positions with respect to the point of attachment of the phenyl group.

Other preferred compounds of the invention are those of formula Z39

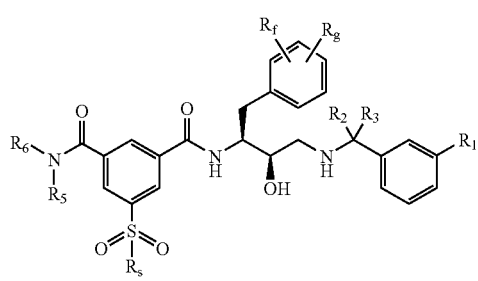

Z39 wherein
$R_1$ is $C_2$-$C_3$ alkyl;
$R_2$ and $R_3$ are both methyl or
$R_2$, $R_3$, and the carbon to which they are attached form a cyclopropyl ring;
$R_f$ and $R_g$ are independently halogen;
$R_5$ and $R_6$ are independently $C_3$-$C_4$ alkyl; and
$R_s$ is —$NH(C_1$-$C_4$ hydroxyalkyl).

Preferred compounds of Z39 include those wherein the hydroxyalkyl group is 2-hydroxy-1,1,dimethylethyl. More preferably, $R_1$ is also ethyl.

Preferably $R_2$ and $R_3$ are both methyl. Equally preferably, $R_2$, $R_3$, and the carbon to which they are attached form a cyclopropyl ring.

Other preferred compounds of the invention are those of formula Z40

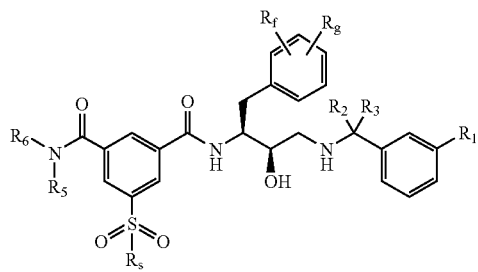

Z40 wherein
$R_1$ is $C_2$-$C_3$ alkynyl;
$R_2$ and $R_3$ are both hydrogen; or
$R_f$ and $R_g$ are independently halogen;
$R_5$ and $R_6$ are independently $C_3$-$C_4$ alkyl; and
$R_s$ is —$NH(C_2$-$C_4$ hydroxyalkyl).

Preferred compounds of Z40 include those wherein the hydroxyalkyl group is 2-hydroxy-1,1,dimethylethyl; or 2-hydroxyethyl.

Other preferred compounds of the invention are those of formula Z41

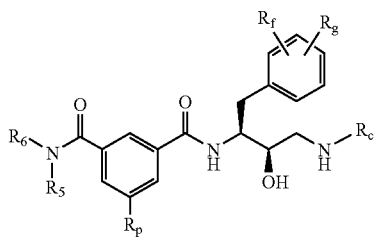

Z41 wherein,
$R_c$ is $C_4$-$C_5$ alkyl; cyclopropyl; tetrahydronaphthylenyl; —CH($C_2$ alkyl-S—($C_1$-$C_2$)alkyl)C(O)NH($C_4$ alkyl); —CH($C_2$ alkyl-$SO_2$—($C_1$-$C_2$)alkyl)C(O)NH($C_4$ alkyl); pyrimidyl optionally substituted with $C_3$-$C_4$ alkyl; thiochroman1,1-dioxide; —$CH_2$-thiazolyl optionally substituted with $C_3$-$C_4$ alkyl, or —$CH_2$-isoxazolyl optionally substituted with $C_1$-$C_5$ alkyl;
$R_f$ and $R_g$ are independently halogen;
$R_p$ is —$NHSO_2CF_3$, —$SO_2NH(C_3$-$C_4$ hydroxyalkyl), —$NHSO_2CH_3$, oxazol-2-yl, or $C_2$-$C_4$ alkynyl; and
$R_5$ and $R_6$ are independently $C_3$-$C_4$ alkyl.

Preferred compounds of Z41 include those wherein $R_c$ is $C_4$-$C_5$ alkyl (preferably isobutyl or isopentyl); cyclopropyl; tetrahydronaphthylenyl; —CH($C_2$ alkyl-S—($C_1$-$C_2$)alkyl)C(O)NH($C_4$ alkyl); —CH($C_2$ alkyl-$SO_2$—($C_1$-$C_2$)alkyl)C(O)NH($C_4$ alkyl); pyrimidyl optionally substituted with $C_3$-$C_4$ alkyl; thiochroman1,1-dioxide; —$CH_2$-thiazolyl optionally substituted with $C_3$-$C_4$ alkyl, hereinafter Z41-1.

More Preferred compounds of Z41-1 include those wherein $R_c$ is isobutyl; 1,2,3,4-tetrahydronaphthylen-1-yl, —CH($CH_2CH_2$—S—$CH_3$)C(O)NH($C_1$-$C_5$ alkyl) where the alkyl group is preferably isobutyl, or 2-tert butylpyrimidin-4-yl, hereinafter Z41-2.

Other preferred compounds of Z41 include those wherein $R_p$ is —$SO_2NH$(2-hydroxy-1,1-dimethylethyl), hereinafter Z41-3.

Other preferred compounds of Z41, Z41-1, Z41-2, and Z41-3 include those wherein $R_5$ and $R_6$ are both $C_3$ alkyl.

Other preferred compounds of Z41 include those wherein $R_p$ is oxazol-2-yl; and $R_c$ is —$CH_2$-(2-isobutylthiazol-5-yl).

Still other preferred compounds of Z41 include those wherein $R_p$ is $C_2$-$C_3$ alkynyl (preferably $C_2$ alkynyl) and $R_c$ is —$CH_2$-(2-isobutylthiazol-5-yl).

Yet other preferred compounds of formula Z41 include those wherein $R_p$ is —$CH_2$-isoxazolyl optionally substituted with $C_1$-$C_5$ alkyl. More preferably, $R_p$ is —$CH_2$-isoxazol-5-yl. Even more preferably, it is —$CH_2$-(3-isobutylisoxazol-5-yl). Even more preferably $R_p$ is also $C_2$-$C_3$ alkynyl. Still more preferably $R_5$ and $R_6$ are both $C_3$ alkyl.

Other preferred compounds of the invention are those of formula Z42

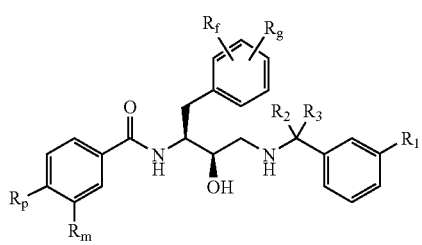

Z42 wherein
$R_1$ is $C_2$-$C_3$ alkyl, or halogen;
$R_2$ and $R_3$ are both hydrogen; or
$R_2$, $R_3$, and the carbon to which they are attached form a cyclopropyl ring;
$R_f$ and $R_g$ are independently halogen; and
$R_m$ is —NH—$SO_2CF_3$, oxazol-2-yl, —N($CH_3$)$SO_2CH_3$, —N($C_3$-$C_4$ hydroxyalkyl)$SO_2$($C_1$-$C_2$ alkyl), and $R_p$ is H; or
$R_m$ is H and $R_p$ is —NH—$SO_2CF_3$, —$CH_2SO_2$($C_1$-$C_2$ alkyl) where the alkyl group is preferably methyl; or
$R_m$ is —C(O)pyrrolidinyl and $R_p$ is OH.

Preferred compounds of formula Z42 include those wherein $R_m$ is H and $R_p$ is —NH—$SO_2CF_3$, —$CH_2SO_2$($C_1$-$C_2$ alkyl), hereinafter Z42-1. Also preferred are compounds of Z42 wherein $R_m$ is —NH—$SO_2CF_3$, oxazol-2-yl, —N($CH_3$)$SO_2CH_3$, —N($C_3$-$C_4$ hydroxyalkyl))$SO_2$($C_1$-$C_2$ alkyl), and $R_p$ is H, hereinafter Z42-2.

Preferred compounds of Z42, Z42-1, and Z42-2 include those wherein R1 is ethyl, bromo, or iodo. More preferred is when $R_2$ and $R_3$ are also both hydrogen;

Other preferred compounds of the invention are those of formula Z43

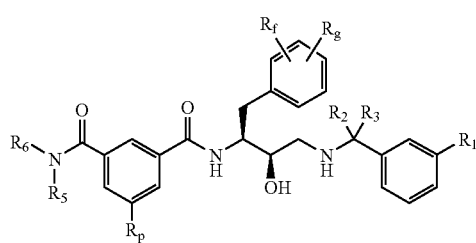

Z43 wherein
$R_1$ is $C_2$-$C_5$ alkyl, $C_3$-$C_6$ cyanoalkyl, $C_3$-$C_6$ alkenyl, —$NHSO_2$($C_1$-$C_2$ alkyl), $C_4$-$C_5$ haloalkyl, —$C_3$ alkyl-$CO_2$—($C_1$-$C_2$ alkyl), CN, —N($C_1$-$C_2$ alkyl)$SO_2$($C_1$-$C_2$ alkyl), —$SO_2$($C_1$-$C_2$ alkyl), —S(O)($C_1$-$C_6$ alkyl), —NH—($C_3$-$C_6$ cycloalkyl), or —OC(O)N($C_1$-$C_2$ alkyl)($C_1$-$C_2$ alkyl),
$R_2$ and $R_3$ are both hydrogen;
$R_f$ and $R_g$ are independently halogen;
$R_p$ is $C_1$-$C_2$ alkyl;
$R_5$ and $R_6$ are independently $C_3$-$C_5$ alkyl, $C_1$-$C_2$ alkoxy $C_1$-$C_3$ alkyl, or $C_3$-$C_5$ alkenyl (preferably $C_3$ alkenyl) or
$R_5$ is H and $R_6$ is $C_4$-$C_6$ alkyl or ($C_1$-$C_2$ alkoxy)-($C_2$-$C_3$ alkyl),;
$R_5$ is ethyl and $R_6$ is $C_2$-$C_3$ hydroxyalkyl or —($C_1$-$C_2$ alkyl)-N($C_1$-$C_2$ alkyl)($C_1$-$C_2$ alkyl); or
$R_5$ is $CH_3$ and $R_6$ is $C_4$-$C_5$ alkyl, cyclohexyl, —($C_1$-$C_2$ alkyl)-phenyl, —($C_1$-$C_2$ alkyl)-pyridyl, or —$CH_2$-furyl; or
$R_5$ is methyl or ethyl and $R_6$ is ($C_1$-$C_2$ alkoxy)-($C_2$-$C_3$ alkyl) or —$CH_2$—($C_3$-$C_6$ cycloalkyl), or
$R_5$, $R_6$, and the nitrogen to which they are attached form a piperidinyl ring optionally substituted with $C_3$-$C_4$ alkyl or OH, azepanyl, pyrrolidine-2-carboxylic acid amide, 3-hydroxypiperidin-1-yl.

Preferred compounds of formula Z43 include those wherein $R_1$ is $C_2$-$C_4$ alkyl, hereinafter Z43-1. Preferably, $R_1$ is ethyl, isopropyl, isobutyl, sec-butyl, or isopentyl. More preferably ethyl or isopropyl. Still more preferably ethyl.

Other preferred compounds of formula Z43 and Z43-1 include those wherein $R_5$ and $R_6$ are simultaneously ethoxyethyl (hereinafter Z43-1A), $R_5$ is propyl and $R_6$ is butyl (hereinafter Z43-1B), $R_5$ is ethyl and $R_6$ is butyl (hereinafter Z43-1C), $R_5$ is methyl or ethyl and $R_6$ is —$CH_2$-(cyclopropyl), isobutyl, or $C_2$-$C_4$ alkynyl(hereinafter Z43-1D), or $R_5$ is ethyl and $R_6$ is propyl (hereinafter Z43-1E), or $R_5$ is hydrogen and $R_6$ is sec-butyl (hereinafter Z43-1F).

Even more preferred compounds of Z43, Z43-1, Z43-1A, Z43-1B, Z43-1C, Z43-1D, Z43-1E and Z431F are those wherein $R_p$ is methyl or $C_2$ alkynyl.

Other preferred compounds of formula Z43 include those wherein $R_5$, $R_6$, and the nitrogen to which they are attached form a 2-propyl piperidin-1-yl ring.

Still other preferred compounds of formula Z43 include those wherein $R_1$ is cyclopentyl, cyclohexyl, propenyl, allyl, or —($C_3$-$C_6$ alkyl)-CN, 4-chlorobutyl, 3-pyridyl, methyl 2-methylpropanoate, hex-5-enyl, CN, —N($CH_3$)$SO_2CH_3$, —$SO_2CH_2CH_3$, 3-methylpyrid-2-yl, oxazol-2-yl, 3,5-dimethylisoxazol-4-yl, 3-methylthien-2-yl, 2-pyridyl, 4-carbaldehydefuran-5-yl, and 2-carbaldehydethien-5-yl, 2-carbaldehyde-3-methylthien-5-yl, 2-methoxypyridin-4-yl, —NH-cyclopropyl, —NHSO$_2$CH$_3$; and $R_p$ is methyl, hereinafter Z43-2. Preferred compounds of formula Z43-2 include those wherein $R_5$ and $R_6$ are also both $C_3$ alkyl. Also preferred is when $R_5$ is ethyl and $R_6$ is butyl.

Preferred compounds of Z43, Z43-1, and Z43-2 include those wherein $R_1$ is $C_2$-$C_3$ alkynyl (preferably $C_2$ alkynyl), hereinafter Z43-3.

Preferred compounds of Z43, Z43-1, Z43-2, and Z43-3 include those wherein $R_5$ and $R_6$ are independently $C_3$-$C_5$ alkyl, $C_1$-$C_2$ alkoxy $C_1$-$C_3$ alkyl. Other preferred compounds of Z43, Z43-1, Z43-2, and Z43-3 include those wherein $R_5$ is H and $R_6$ is $C_{4,5}$-$C_6$ alkyl or ($C_1$-$C_2$ alkoxy)-($C_2$-$C_3$ alkyl). Still other preferred compounds of Z43, Z43-1, Z43-2, and Z43-3 include those wherein $R_5$ is ethyl and $R_6$ is $C_2$-$C_3$ hydroxyalkyl or —($C_1$-$C_2$ alkyl)-N($C_1$-$C_2$ alkyl)($C_1$-$C_2$ alkyl). More preferably, the —($C_1$-$C_2$ alkyl)-N($C_1$-$C_2$ alkyl)($C_1$-$C_2$ alkyl) is —($C_1$-$C_2$ alkyl)-N($CH_3$)$_2$.

Yet still other preferred compounds of Z43, Z43-1, Z43-2, and Z43-3 include those wherein $R_5$ is $CH_3$ and $R_6$ is $C_4$-$C_5$ alkyl, cyclohexyl, —($C_1$-$C_2$ alkyl)-phenyl, —($C_1$-$C_2$ alkyl)-pyridyl, or —$CH_2$-furyl. Preferably, $R_5$ is $CH_3$ and $R_6$ is $C_4$-$C_5$ alkyl, hereinafter Z43-4. Still yet other preferred compounds of Z43, Z43-1, Z43-2, and Z43-3 include those wherein $R_5$ is methyl or ethyl and $R_6$ is ($C_1$-$C_2$ alkoxy)-($C_2$-$C_3$ alkyl).

Other preferred compounds of Z43, Z43-1, Z43-2, and Z43-3 include those wherein $R_5$, $R_6$, and the nitrogen to which they are attached form a piperidinyl ring optionally substituted with $C_3$-$C_4$ alkyl or OH, azepanyl, pyrrolidine-2-carboxylic acid amide, or 3-hydroxypiperidin-1-yl.

Further preferred compounds Z43, Z43-1, Z43-2, Z43-3, and Z43-4 include those wherein $R_p$ is methyl.

Other preferred compounds of the invention are those of formula Z44

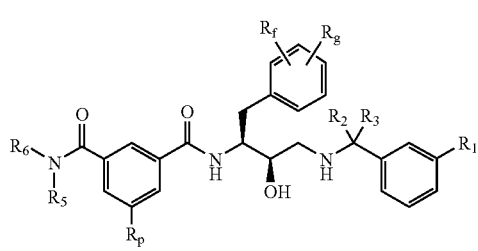

Z44 wherein $R_1$ is $C_2$-$C_3$ alkyl; halogen, —NH($C_3$-$C_6$ cycloalkyl) preferably the cycloalkyl group is a cyclopropyl group, $R_f$ and $R_g$ are independently halogen;

$R_p$ is $C_1$-$C_2$ alkyl, oxazolyl, thiazolyl, or $C_2$-$C_3$ alkynyl;

$R_2$, $R_3$, and the carbon to which they are attached form a cyclopropyl ring; or $R_2$ and $R_3$ are both methyl;

$R_5$ and $R_6$ are independently $C_3$-$C_4$ alkyl; or $R_5$ is methyl and $R_6$ is $C_3$-$C_5$ alkyl.

Preferred compounds of formula Z44 include those wherein $R_2$ and $R_3$ are both methyl; and $R_5$ and $R_6$ are independently $C_3$-$C_4$ alkyl, hereinafter Z44-1.

Preferred compounds of formula Z44 and Z44-1 include those wherein $R_p$ is oxazol-2-yl or thiazol-2-yl.

Preferred compounds of formula Z44 include those wherein $R_p$ is $C_2$-$C_3$ alkynyl; and $R_5$ and $R_6$ are independently $C_3$-$C_4$ alkyl.

Also preferred are compounds wherein R1 is bromo, chloro, or iodo or —NH(cyclopropyl).

Other preferred compounds of the invention are those of formula Z45

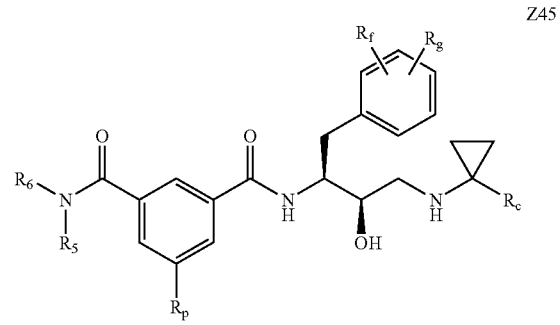

Z45 wherein $R_c$ is isoxazolyl optionally substituted with $C_3$-$C_5$ alkyl, thiazolyl optionally substituted with $C_3$-$C_4$ alkyl, or —$C_1$-$C_3$ alkyl-C(O)NH($C_1$-$C_3$ alkyl);

$R_f$ and $R_g$ are independently halogen;

$R_p$ is $C_1$-$C_2$ alkyl, oxazolyl, thiazolyl, or $C_2$-$C_4$ alkynyl;

$R_5$ and $R_6$ are independently $C_3$-$C_4$ alkyl.

Preferred compounds of formula Z45 include those wherein $R_p$ is oxazol-2-yl or thiazol-2-yl, hereinafter Z45-1. More preferred compounds of Z45-1 include those wherein $R_c$ is 3-isobutylisoxazol-5-yl or N-isobutyl-2-methylpropion-2-yl amide; and $R_f$ and $R_g$ are independently Cl or F.

Other preferred compounds of formula Z45 include those wherein $R_c$ is 2-isobutylthiazol-2-yl; and $R_f$ and $R_g$ are independently Cl or F.

Still other preferred compounds of formula Z45 include those wherein $R_c$ is 3-isobutylisoxazol-5-yl or N-isobutyl-2-methylpropion-2-yl amide; $R_f$ and R are independently Cl or F; and $R_p$ is $C_2$-$C_3$ alkynyl.

Other preferred compounds of the invention are those of formula Z46

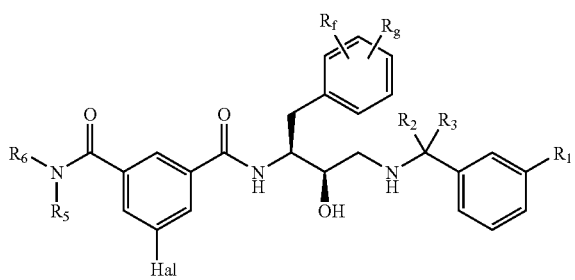

Z46 wherein
Hal is a halogen;
$R_1$ is $C_1$-$C_2$ alkyl, or halogen;
$R_2$ and $R_3$ are both hydrogen;
$R_f$ and $R_g$ are independently halogen;
$R_z$ is $C_1$-$C_2$ alkyl;
$R_5$ and $R_6$ are independently $C_3$-$C_4$ alkyl.

Preferred compounds of formula Z45 include those wherein Hal is bromo or chloro. More preferably, $R_1$ is also methyl, ethyl, bromo or iodo. More preferably $R_1$ is methyl or ethyl. Even more preferably, it is ethyl.

Other preferred compounds of the invention are those of formula Z47

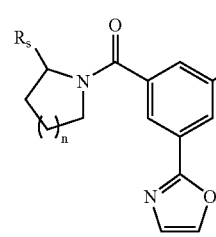

Z47 n is 0, 1 or 2;
$R_1$ is $C_1$-$C_2$ alkyl;
$R_2$ and $R_3$ are both hydrogen;
$R_f$ and $R_g$ are independently halogen;
$R_s$ is ($C_1$-$C_2$ alkoxy)-($C_1$-$C_2$ alkyl).

Preferred compounds of Z47 include those wherein $R_s$ is methoxymethyl. Preferably n is 1.

Other preferred compounds of the invention are those of formula Z48

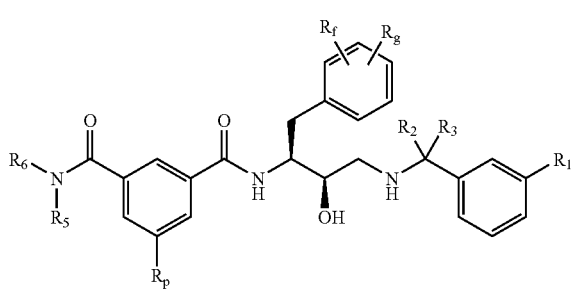

Z48 wherein
$R_1$ is $C_1$-$C_2$ alkyl;
$R_2$ and $R_3$ are both hydrogen;
$R_f$ and $R_g$ are independently halogen;
$R_p$ is isoxazole optionally substituted with $C_1$-$C_2$ alkyl;
$R_5$ and $R_6$ are independently $C_3$-$C_4$ alkyl.

Preferred compounds of formula Z48 include those wherein $R_p$ is 3-methylisoxazol-4-yl, 5-oxazolyl, 3-oxazolyl, 3-methyloxazol-2-yl, 3-ethyloxazol-2-yl.

Preferred compounds of $Z_1$-$Z_{48}$ include those wherein at least one of $R_f$ and $R_g$ is fluoro. More preferably, both are fluoro. Even more preferably, $R_f$ and $R_g$ are in the 3 and 5 positions with respect to the point of attachment of the phenyl group.

In another aspect, the invention includes compounds of the formula Z49:

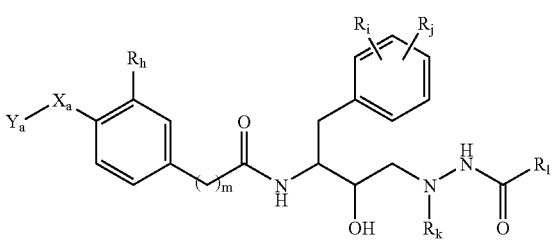

Z49 wherein Ya is

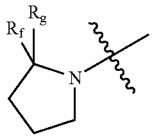

or —N(CH$_2$CH$_2$CH$_3$)$_2$;
$R_f$ and $R_g$ are both hydrogen or taken together with the carbon to which they are attached form a carbonyl;
$X_a$ is a covalent bond or a carbonyl;
$R_h$ is hydrogen or hydroxy;
$R_i$ and $R_j$ are independently hydrogen or a halogen selected from Br, F, Cl or I;
$R_k$ is —$C_{1-6}$ alkyl;
$R_l$ is —$C_{1-6}$ alkyl or phenyl optionally substituted with $C_1$-$C_6$ alkyl, $C_1$-$C_6$ alkoxy, halogen, hydroxy, amino, mono($C_1$-$C_6$)alkylamino, di($C_1$-$C_6$)alkylamino, trifluoromethyl; and
m is 0 or 1.

In this embodiment, $R_f$ and $R_g$ preferably are taken together with the carbon to which they are attached to form a carbonyl, $X_a$ is preferably a covalent bond, $R_h$ is preferably hydrogen, m is preferably 1, and $R_i$ and $R_j$ are preferably hydrogen. More preferably, $R_k$ is ethyl and $R_e$ is a meta-substituted ethyl phenyl group, —CH$_2$CH$_2$CH(CH$_3$)$_2$, methyl or phenyl. $R_1$ is preferably phenyl.

In another preferred aspect of Z49, $R_f$ and $R_g$ are hydrogen, $X_a$ is a carbonyl, $R_h$ is hydroxyl, $R_i$ and $R_j$ are hydrogen and $R_k$ is ethyl. In another aspect, and in accordance with these preferred groups, $R_e$ is preferably a meta-substituted ethyl phenyl group, —CH$_2$CH$_2$CH(CH$_3$)$_2$, or a methyl group.

In accordance with this embodiment, $R_a$ is preferably methyl and $R_d$ is preferably ethyl, X is preferably O, and $R_b$ and $R_c$ are preferably hydrogen. In another aspect, and in accordance with these preferred groups, $R_e$ is preferably a meta-substituted ethyl phenyl group, —CH$_2$CH$_2$CH(CH$_3$)$_2$, methyl or phenyl. Alternatively, and in accordance with this embodiment, X is preferably S, $R_b$ and $R_c$ are hydrogen, and $R_e$ is a meta-substituted ethyl phenyl group or a methyl group. $R_e$ is preferably phenyl.

In another aspect, the invention provides compounds of the formula Z50:

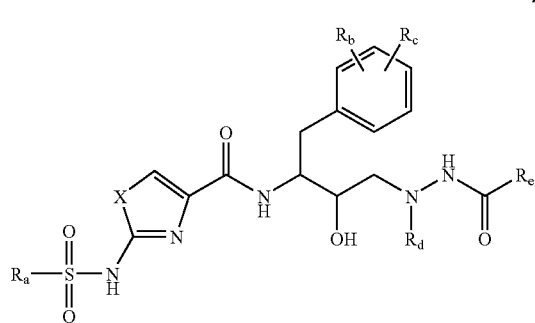

Z50 wherein
$R_a$ and $R_d$ are $C_{1-6}$ alkyl;
X is O or S;
$R_b$ and $R_c$ are independently hydrogen or a halogen selected from Br, F, Cl or I; and
$R_e$ is —$C_{1-6}$ alkyl or phenyl optionally substituted with $C_1$-$C_6$ alkyl, $C_1$-$C_6$ alkoxy, halogen, hydroxy, amino, mono($C_1$-$C_6$)alkylamino, di($C_1$-$C_6$)alkylamino, trifluoromethyl.

In another aspect, the invention provides compounds of formula Z51:

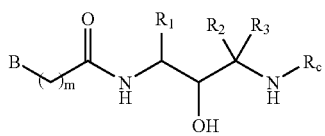

Z51 and pharmaceutically acceptable salts thereof wherein
m is 0-5;
B is aryl or heteroaryl optionally substituted with one or two groups independently selected from $R_6$, $R'_6$, $R''_6$ and $R'''_6$, or
B is cycloalkyl or heterocycloalkyl optionally substituted with one, two, three, four, five, six, seven or eight groups independently selected from $R_{6a}$, $R_{6b}$, $R'_{6a}$, $R'_{6b}$, $R''_{6a}$, $R''_{6b}$, $R'''_{6a}$ and $R'''_{6b}$;
$C_1$-$C_8$ alkyl, $C_2$-$C_7$ alkenyl or $C_2$-$C_7$ alkynyl, each of which is optionally substituted with one, two or three groups selected from —NRR', —SR, —CN, —OCF$_3$, —CF$_3$, —CONRR', —CO$_2$R, —SO$_2$NRR', —O—P(=O)(OR)(OR'), —N(R)—C(=O)(R'), —N(R)(SO$_2$R'), —SO$_2$R, —C(=O)R, —NO$_2$, halogen, —(CH$_2$)$_{0-4}$-aryl, and —(CH$_2$)$_{0-4}$-heteroaryl, or
R and R' independently are —H, —(C$_1$-C$_{10}$)alkyl, —(CH$_2$)$_{0-4}$—R$_{aryl}$, —(CH$_2$)$_{0-4}$—R$_{heteroaryl}$, —(CH$_2$)$_{0-4}$—R$_{heterocyclyl}$, or
$C_2$-$C_7$ alkenyl or $C_2$-$C_7$ alkynyl, each of which is optionally substituted with one, two or three substituents selected from the group consisting of halogen, —OH, —SH, —C≡N, —CF$_3$, $C_1$-$C_3$ alkoxy, amino, mono- or dialkylamino, and $C_1$-$C_6$ alkyl, or —(CH$_2$)$_{0-4}$—$C_3$-$C_7$ cycloalkyl optionally substituted with one, two or three substituents selected from the group consisting of halogen, —OH, —SH, —C≡N, —CF$_3$, $C_1$-$C_3$ alkoxy, amino, mono- or dialkylamino, and $C_1$-$C_6$ alkyl;
benzyl where the phenyl ring is optionally substituted with 1-3 groups independently selected from halogen, —OH, —SH, —C≡N, mono or dialkylamino, $C_1$-$C_6$ alkoxy, or trifluoromethyl;

$R_6$, $R'_6$, $R''_6$, $R'''_6$, $R_{6a}$, $R_{6b}$, $R'_{6a}$, $R'_{6b}$, $R''_{6a}$, $R''_{6b}$, $R'''_{6a}$ and $R'''_{6b}$ independently are —OR, —NO$_2$, halogen, —CO$_2$R, —C≡N, —NRR', —SR, —SO$_2$R, —C(=O)R, —OCF$_3$, —CF$_3$, —CONRR', —SO$_2$NRR', —O—P(=O)(OR)(OR'), —N(R)(COR'), —N(R)(SO$_2$R'), —(CH$_2$)$_{0-4}$—CO—NR$_7$R'$_7$, —(CH$_2$)$_{0-4}$—O—(CH$_2$)$_{0-4}$—CONRR', —(CH$_2$)$_{0-4}$—CO—(C$_1$-C$_{12}$ alkyl), —(CH$_2$)$_{0-4}$—CO—(C$_2$-C$_{12}$ alkenyl), —(CH$_2$)$_{0-4}$—CO—(C$_2$-C$_{12}$ alkynyl), —(CH$_2$)$_{0-4}$—CO—(C$_3$-C$_7$ cycloalkyl), —(CH$_2$)$_{0-4}$—R$_{aryl}$, —(CH$_2$)$_{0-4}$—R$_{heteroaryl}$, —(CH$_2$)$_{0-4}$—R$_{heterocyclyl}$, —(CH$_2$)$_{0-4}$—CO—R$_{aryl}$, —(CH$_2$)$_{0-4}$—CO—R$_{heteroaryl}$, —(CH$_2$)$_{0-4}$CO—R$_{heterocyclyl}$, —(CH$_2$)$_{0-4}$—CO—R$_{10}$, —(CH$_2$)$_{0-4}$—CO—O—R$_{11}$, —(CH$_2$)$_{0-4}$—SO$_2$—NR$_7$R'$_7$, —(CH$_2$)$_{0-4}$—SO—(C$_1$-C$_8$ alkyl), —(CH$_2$)$_{0-4}$—SO$_2$—(C$_1$-C$_{12}$ alkyl), —(CH$_2$)$_{0-4}$—SO$_2$—(C$_3$-C$_7$ cycloalkyl), —(CH$_2$)$_{0-4}$—N(H or R$_{11}$)—CO—O—R$_{11}$, —(CH$_2$)$_{0-4}$—N(H or R$_{11}$)—CO—N(R$_{11}$)$_2$, —(CH$_2$)$_{0-4}$—N(H or R$_{11}$)—CS—N(R$_{11}$)$_2$, —(CH$_2$)$_{0-4}$—N(—H or R$_{11}$)—CO—R$_7$, —(CH$_2$)$_{0-4}$—NR$_7$R'$_7$, —(CH$_2$)$_{0-4}$—R$_{10}$, —(CH$_2$)$_{0-4}$—O—CO—(C$_1$-C$_6$ alkyl), —(CH$_2$)$_{0-4}$—O—P(O)—(O—R$_{aryl}$)$_2$, —(CH$_2$)$_{0-4}$—O—CO—N(R$_{11}$)$_2$, —(CH$_2$)$_{0-4}$—O—CS—N(R$_{11}$)$_2$, —(CH$_2$)$_{0-4}$—O—(R$_{11}$), —(CH$_2$)$_{0-4}$—O—(R$_{11}$)—COOH, —(CH$_2$)$_{0-4}$—S—(R$_{11}$), $C_3$-$C_7$ cycloalkyl, —(CH$_2$)$_{0-4}$—N(—H or R$_{11}$)—SO$_2$—R$_7$, or —(CH$_2$)$_{0-4}$—$C_3$-$C_7$ cycloalkyl, or $C_1$-$C_8$ alkyl optionally substituted with one, two or three groups independently selected from $C_1$-$C_6$ alkyl, —F, —Cl, —Br, —I, —OR, —NO$_2$, —F, —Cl, —Br, —I, —CO$_2$R, —C≡N, —NRR', —SR, —SO$_2$R, —C(=O)R, —OCF$_3$, —CF$_3$, —CONRR', —SO$_2$NRR', —O—P(=O)(OR)(OR'), —N(R)(COR'), —N(R)(SO$_2$R'), —(CH$_2$)$_{0-4}$—CO—NR$_7$R'$_7$, —(CH$_2$)$_{0-4}$—CO—(C$_1$-C$_{12}$ alkyl), —(CH$_2$)$_{0-4}$—CO—(C$_2$-C$_{12}$ alkenyl), —(CH$_2$)$_{0-4}$—CO—(C$_2$-C$_{12}$ alkynyl), —(CH$_2$)$_{0-4}$—CO—(C$_3$-C$_7$ cycloalkyl), —(CH$_2$)$_{0-4}$—R$_{aryl}$, —(CH$_2$)$_{0-4}$—R$_{heteroaryl}$, —(CH$_2$)$_{0-4}$—R$_{heterocyclyl}$, —(CH$_2$)$_{0-4}$—CO—R$_{aryl}$, —(CH$_2$)$_{0-4}$—CO—R$_{heteroaryl}$, —(CH$_2$)$_{0-4}$—CO—R$_{heterocyclyl}$, —(CH$_2$)$_{0-4}$—CO—R$_{10}$, —(CH$_2$)$_{0-4}$—CO—O—R$_{11}$, —(CH$_2$)$_{0-4}$—SO$_2$—NR$_7$R'$_7$, —(CH$_2$)$_{0-4}$—SO—(C$_1$-C$_8$ alkyl), —(CH$_2$)$_{0-4}$—SO$_2$—(C$_1$-C$_{12}$ alkyl), —(CH$_2$)$_{0-4}$—SO$_2$—(C$_3$-C$_7$ cycloalkyl), —(CH$_2$)$_{0-4}$—N(H or R$_{11}$)—CO—O—R$_{11}$, —(CH$_2$)$_{0-4}$—N(H or R$_{11}$)—CO—N(R$_{11}$)$_2$, —(CH$_2$)$_{0-4}$—N(H or R$_{11}$)—CS—N(R$_{11}$)$_2$, —(CH$_2$)$_{0-4}$—N(—H or R$_{11}$)—CO—R$_7$, —(CH$_2$)$_{0-4}$—NR$_7$R'$_7$, —(CH$_2$)$_{0-4}$—R$_{10}$, —(CH$_2$)$_{0-4}$—O—CO—(C$_1$-C$_6$ alkyl), —(CH$_2$)$_{0-4}$—O—P(O)—(O—R$_{aryl}$)$_2$, —(CH$_2$)$_{0-4}$—O—CO—N(R$_{11}$)$_2$, —(CH$_2$)$_{0-4}$—O—CS—N(R$_{11}$)$_2$, —(CH$_2$)$_{0-4}$—O—(R$_{11}$), —(CH$_2$)$_{0-4}$—O—(R$_{11}$)—COOH, —(CH$_2$)$_{0-4}$—S—(R$_{11}$), $C_3$-$C_7$ cycloalkyl, —(CH$_2$)$_{0-4}$—N(—H or R$_{11}$)—SO$_2$—R$_7$, or —(CH$_2$)$_{0-4}$—$C_3$-$C_7$ cycloalkyl, or $C_2$-$C_7$ alkenyl or $C_2$-$C_7$ alkynyl, each of which is optionally substituted with one, two or three groups independently selected from halogen or —OH, or $C_2$-$C_7$ alkenyl or $C_2$-$C_7$ alkynyl, each of which is optionally substituted with one, two or three groups independently selected from halogen, $C_1$-$C_3$ alkyl, —OH, —SH, —C≡N, —CF$_3$, $C_1$-$C_3$ alkoxy, amino, and mono- or dialkylamino, or —(CH$_2$)$_{0-4}$—O—($C_1$-$C_6$ alkyl), where the alkyl portion is optionally substituted with one, two, three, four, or five of halogen, or any two of $R_{6a}$, $R_{6b}$, $R'_{6a}$, $R'_{6b}$, $R''_{6a}$, $R''_{6b}$, $R'''_{6a}$ and $R'''_{6b}$ together are oxo;

$R_7$ and $R'_7$ are the same or different and represent —H, —$C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, —$C_1$-$C_6$ alkyl chain with one double bond and one triple bond, or —$C_1$-$C_6$ alkyl optionally substituted with —OH or —NH$_2$; or;

—$C_1$-$C_6$ alkyl optionally substituted with one, two or three groups independently selected from halogen; or heterocyclyl optionally substituted with halogen, amino, mono- or dialkylamino, —OH, —C≡N, —SO$_2$—NH$_2$, —SO$_2$—NH—$C_1$-$C_6$ alkyl, —SO$_2$—N($C_1$-$C_6$ alkyl)$_2$, —SO$_2$—($C_1$-$C_4$ alkyl), —CO—NH$_2$, —CO—NH—$C_1$-$C_6$ alkyl, oxo and —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_1$-$C_6$ alkoxy optionally substituted with one, two or three of halogen;

aryl or heteroaryl, each of which is optionally substituted with halogen, amino, mono- or dialkylamino, —OH, —C≡N, —SO$_2$—NH$_2$, —SO$_2$—NH—$C_1$-$C_6$ alkyl, —SO$_2$—N($C_1$-$C_6$ alkyl)$_2$, —SO$_2$—($C_1$-$C_4$ alkyl), —CO—NH$_2$, —CO—NH—$C_1$-$C_6$ alkyl, and —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_1$-$C_6$ alkoxy optionally substituted with one, two or three of halogen;

$R_{10}$ is heterocyclyl optionally substituted with one, two, three or four groups independently selected from $C_1$-$C_6$ alkyl;

$R_{11}$ is $C_1$-$C_6$ alkyl, $C_2$-$C_6$ alkenyl, $C_2$-$C_6$ alkynyl, $C_3$-$C_7$ cycloalkyl, —(CH$_2$)$_{0-2}$—$R_{aryl}$, or —(CH$_2$)$_{0-2}$—$R_{heteroaryl}$;

$R_{aryl}$ is aryl optionally substituted with halogen, amino, mono- or dialkylamino, —OH, —C≡N, —SO$_2$—NH$_2$, —SO$_2$—NH—$C_1$-$C_6$ alkyl, —SO$_2$—N($C_1$-$C_6$ alkyl)$_2$, —SO$_2$—($C_1$-$C_4$ alkyl), —CO—NH$_2$, —CO—NH—$C_1$-$C_6$ alkyl, or —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_1$-$C_6$ alkoxy optionally substituted with one, two or three of halogen;

$R_{heteroaryl}$ is heteroaryl, each of which is optionally substituted with halogen, amino, mono- or dialkylamino, —OH, —C≡N, —SO$_2$—NH$_2$, —SO$_2$—NH—$C_1$-$C_6$ alkyl, —SO$_2$—N($C_1$-$C_6$ alkyl)$_2$, —SO$_2$—($C_1$-$C_4$ alkyl), —CO—NH$_2$, —CO—NH—$C_1$-$C_6$ alkyl, or —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_1$-$C_6$ alkoxy optionally substituted with one, two or three of halogen;

$R_{heterocyclyl}$ is heterocyclyl optionally substituted with halogen, amino, mono- or dialkylamino, —OH, —C≡N, —SO$_2$—NH$_2$, —SO$_2$—NH—$C_1$-$C_6$ alkyl, —SO$_2$—N($C_1$-$C_6$ alkyl)$_2$, —SO$_2$—($C_1$-$C_4$ alkyl), —CO—NH$_2$, —CO—NH—$C_1$-$C_6$ alkyl, =O or —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —CF$_3$, $C_1$-$C_3$ alkoxy, amino, and mono- or dialkylamino; or $C_1$-$C_6$ alkoxy optionally substituted with one, two or three of halogen;

$R_2$ and $R_3$ are independently hydrogen or $C_1$-$C_6$ alkyl; or $R_2$ and $R_3$ taken together with the carbon atom to which they are attached form a 3 or 4-membered ring;

$R_c$ is hydrogen or phenyl optionally substituted with $C_1$-$C_3$ alkyl, $C_2$-$C_4$ alkynyl, trifluoromethyl, or $C_1$-$C_2$ alkoxy.

In another aspect, the invention provides compounds of formula Z52:

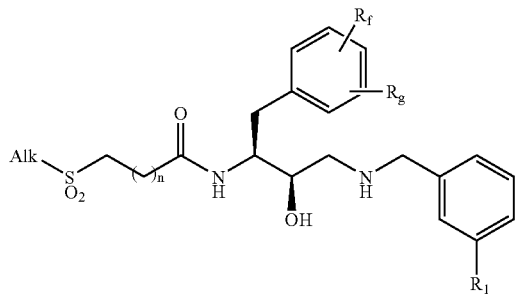

Z52 or pharmaceutically acceptable salts thereof, wherein n is 0, 1, 2, or 3 (preferably 1);

$R_1$ is $C_1$-$C_3$ alkoxy (preferably methoxy), halogen (preferably iodo), $C_1$-$C_3$ alkyl (preferably ethyl or isopropyl), or $C_2$-$C_3$ alkynyl (preferably $C_2$ alkynyl);

R$_f$ and R$_g$ are independently halogen, or both are hydrogen; and

Alk is C$_1$-C$_6$ alkyl (preferably methyl, ethyl, isobutyl or isopentyl).

Preferred examples of Z52 include those wherein n is 1 and R$_1$ is methoxy, C$_2$ alkynyl or ethyl. More preferably, R1 is methoxy.

The compounds of the invention inhibit beta-secretase and are therefore useful in treating and preventing Alzheimer's disease. The compounds of the invention are made by methods well known to those skilled in the art from starting compounds known to those skilled in the art. The process chemistry is well known to those skilled in the art. The most general process to prepare compounds of the invention is set forth in CHART A. Typically, amino acid (I) is protected at the amino group, yielding protected amino acid (II). Compound (II) is converted to an ester intermediate, and the intermediate is reacted with a carbon nucleofile yielding compound (III). The ketone moiety in compound (III) is reduced to yield alcohol (IV), which forms epoxide(V). The addition of amine R$_c$—NH$_2$ (VI) opens the epoxide, forming the protected alcohol (VII). The amine protecting group is removed, and the deprotected amine (VIII) is reacted with an amide forming agent of the formula (R$_{N\text{-}1}$—X$_N$)$_2$O or R$_{N\text{-}1}$—X$_N$—X$_2$ or R$_{N\text{-}1}$—X$_N$—OH (IX) to produce a target compound of formula (X).

The backbone of the compounds of the invention is a hydroxyethylamine moiety, —NH—CH(R)—CH(OH)—. It can be readily prepared by methods disclosed in the literature and known to those skilled in the art. For example, *J. Med. Chem.*, 36, 288-291 (1992), *Tetrahedron Letters*, 28, 5569-5572 (1987), *J. Med. Chem.*, 38, 581-584 (1994) and *Tetrahedron Letters*, 38, 619-620 (1997) all disclose processes to prepare hydroxyethylamine type compounds.

CHART A sets forth a general method used in the invention to prepare the appropriately substituted amines (X). The compounds of the invention are prepared by starting with the corresponding amino acid (I). The amino acids (I) are well known to those skilled in the art or can be readily prepared from known compounds by methods well known to those skilled in the art. The substituted amines (X) of the invention have at least two enantiomeric centers which give four enantiomers. The first of these enantiomeric centers derives from the amino acid starting material (I). It is preferred to commercially obtain or produce the desired enantiomer (S) rather than produce an enantiomerically impure mixture and then have to separate out the desired enantiomer (S). It is preferred to start the process with enantiomerically pure (S)-amino acid (I) of the same configuration as that of the substituted amine (X) product.

The first step of the process is to protect the free amino group of the (S)-amino acid (I) with an amino protecting group to produce the (S)-protected amino acid (II) by methods well known to those skilled in the art. Amino protecting groups are well known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. The function of the amino protecting group is to protect the free amino functionality (—NH$_2$) during subsequent reactions on the (S)-amino acid (I) which would not proceed well, either because the amino group would react and be functionalized in a way that is inconsistent with its need to be free for subsequent reactions, or the free amino group would interfere in the reaction. When the amino protecting group is no longer needed, it is removed by methods well known to those skilled in the art. By definition the amino protecting group must be readily removable as is known to those skilled in the art by methods well known to those skilled in the art. Suitable amino PROTECTING GROUP is selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl and 1-piperidyloxycarbonyl, 9-fluorenylmethyl carbonate, —CH—CH═CH$_2$ and phenyl-C(═N—)—H. It is preferred that the protecting group be t-butoxycarbonyl (BOC) and benzyloxycarbonyl (CBZ), it is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry," John Wiley and Sons, 1991 for guidance.

The (S)-protected compound (II) is transformed to a (S)-protected compound of formula (III) by first converting the (S)-protected amino acid (II) to a corresponding alkyl ester according to methods well established in the art, for example by reaction with a diazocompound. The ester intermediate is then reacted with a carbanionic nucleofile of those known to those skilled in the art, for example an organometallic compound obtained by reacting a compound of formula X$_1$—C(R$_2$)(R$_3$)—X$_1$ with a strong metal base, wherein wherein the reaction yields a halogen-metal exchange, and wherein —X$_1$ is a halogen selected from the group consisting of chlorine, bromine or iodine. The addition of this carbanionic nucleophile to the ester intermediate yields the (S)-protected compound (III). Suitable bases include, but are not limited to the alkyllithiums including, for example, sec-butyllithium, n-butyllithium, and t-butyllithium. Said reactions are preferably conducted at low temperature, for example −78 degrees C. Suitable reaction conditions include running the reaction in the presence of inert solvents or mixtures thereof, for example but not only ether, tetrahydrofuran or a mixture thereof. Wherein R$_2$ and R$_3$ are both hydrogen, then examples of X$_1$—C(R$_2$)(R$_3$)—X$_1$ include dibromomethane, diiodomethane, chloroiodomethane, bromoiodomethane and bromochloromethane. One skilled in the art knows the preferred conditions required to conduct this reaction. Furthermore, if R$_2$ and/or R$_3$ are not —H, then by the addition of —C(R$_2$)(R$_3$)—X$_1$ to esters of the (S)-protected amino acid (II) to produce the (S)-protected compound (III), an additional chiral center will be incorporated into the product, provided that R$_2$ and R$_3$ are not the same.

The (S)-protected compound (III) is then reduced by methods known to those skilled in the art for the reduction of ketones to the corresponding alcohol (IV). The reactants and reaction conditions for reducing the (S)-protected compound (III) to the corresponding alcohol (IV) include, for example, sodium borohydride, lithium borohydride, borane, diisobutylaluminum hydride, and lithium aluminium hydride. Sodium borohydride is the preferred reducing agent. The reduction is carried out for a period of time between 1 hour and 3 days at temperatures ranging from about −78 degrees C. to the reflux temperature of the reaction mixture. It is preferred to conduct the reduction between about −78 degrees C. and about 0 degrees C. A borane complex may be used, for example, borane-methyl sulfide complex, borane-piperidine complex, or borane-tetrahydrofuran complex. The preferred combination of reducing agents and reaction conditions needed are known to those skilled in the art, see for example, Larock, R. C. in Comprehensive Organic Transformations, VCH Publishers, 1989. The reduction of the (S)-protected compound (III) to the corresponding alcohol (IV) produces the second chiral center (third chiral center if $R_2$ and $R_3$ are not the same). The reduction of the (S)-protected compound (III) produces a mixture of enantiomers at the second center, (S, R/S)-alcohol (IV). This enantiomeric mixture is then separated by means known to those skilled in the art such as selective low-temperature recrystallization or chromatographic separation, for example by HPLC, employing commercially available chiral stationary phases. The enantiomer that is used in the remainder of the process of CHART A is the (S,S)-alcohol (IV) since this enantiomer is a precursor to the desired biologically active anti-Alzheimer (S,R)-substituted amine (X).

(S,S)-alcohol (IV) reacts intramolecularly to yield the corresponding epoxide (V) by means known to those skilled in the art. The stereochemistry of the (carbon bound to the —OH moiety in compound (IV) is maintained in the epoxide (V). Preferred reaction conditions include contacting compound (IV) with a base, for example, but not limited to, sodium hydroxide, potassium hydroxide, or lithium hydroxide. Reaction conditions include the presence of a $C_1$-$C_6$ alcohol solvent; ethanol is preferred. A common co-solvent, for example ethyl acetate, may also be employed. The reactions is preferably conducted at temperatures ranging from about −45 degrees C. to the reflux temperature of the reaction mixture; preferred temperature ranges are between about −20 degrees C. and about 20-25 degrees C.

The epoxide (V) is then reacted with the appropriately substituted C-terminal amine, $R_c$—$NH_2$ (VI) in reaction conditions known to those skilled in the art, leading to the opening the epoxide to yield the enantiomerically pure (S,R)-protected alcohol (VII). The substituted C-terminal amines, $R_c$—$NH_2$ (VI) of this invention are commercially available or are known to those skilled in the art and can be readily prepared from known compounds. Further, it is preferred that when $R_c$ is phenyl, it is substituted in the 3-position or 3,5-positions.

Suitable reaction conditions for opening the epoxide (V) include running the reaction in an organic, preferably inert w. $C_1$-$C_6$ alcohol solvents are preferred and isopropyl alcohol most preferred. The reaction can be run at temperatures ranging from about 20-25 degrees C. up to the reflux temperature of the reaction mixture and preferably at a temperature between about 50 degrees C. and the reflux temperature of the reaction mixture. When the substituted C-terminal amine (VI) is a 1-amino-3,5-cis-dimethyl cyclohexyldicarboxylate it is preferably prepared as follows. To dimethyl-5-aminoisophthalate in acetic acid and methanol, is added rhodium in alumina in a high-pressure bottle. The bottle is saturated with hydrogen at 55 psi and shaken for one week of time. The mixture is then filtered through a layer of diatomaceous earth and rinsed with methanol three times, the solvents are removed under reduced pressure (with heat) to give a concentrate. The concentrate is triturated with ether and filtered again to give the desired C-terminal amine (VI). When the substituted C-terminal amine (VI) is 1-amino-3,5-cis-dimethoxy cyclohexane it is prepared by following the general procedure above and making non-critical variations but starting with 3,5-dimethoxyaniline. When the substituted C-terminal amine (VI) is an aminomethyl group where the substituent on the methyl group is an aryl group, for example $NH_2$—$CH_2$—$R_{C\text{-}aryl}$, and $NH_2$—$CH_2$—$R_{C\text{-}aryl}$ is not commercially available it is preferably prepared as follows. A suitable starting material is the (appropriately substituted) aralkyl compound. The first step is bromination of the alkyl substitutent via methods known to those skilled in the art, see for example R. C. Larock in Comprehensive Organic Transformations, VCH Publishers, 1989, p. 313. Next the alkyl halide is reacted with azide to produce the aryl-(alkyl)-azide. Last the azide is reduced to the corresponding amine by hydrogen/catalyst to give the C-terminal amine (VI) of formula $NH_2$—$CH_2$—$R_{C\text{-}aryl}$. The suitably functionalized C-terminal amines (VI) may readily be prepared by one skilled in the art via known methods in the literature, making non-significant modifications. Select literature references include 1) Calderwood, et al., *Tet. Lett.,* 1997, 38, 1241, 2) Ciganek, *J. Org. Chem.,* 1992, 57, 4521, 3) Thurkauf, et al., *J. Med. Chem.,* 1990, 33, 1452, 4) Werner, et al., *Org. Syn., Coll.* Vol. 5, 273, 5) *J. Med. Chem.,* 1999, 42, 4193, 6) *Chem. Rev.* 1995, 95, 2457, 7) *J. Am. Chem. Soc.,* 1986, 3150, 8) Felman et al., *J. Med. Chem.,* 1992, 35, 1183, 9) *J. Am. Chem . Soc.* 1970, 92, 3700, 10) *J. Med. Chem.,* 1997, 40, 2323.

CHART B discloses an alternative process for the synthesis of the enantiomerically pure (S,R)-protected alcohol (VII) from the (S)-protected compound (III). In this process, (S)-protected compound (III) is reacted with the appropriately substituted C-terminal amine $R_c$—$NH_2$ (VI) in the preferred reaction conditions described above to yield (S)-protected ketone (XI) which is reduced in the preferred conditions described above to yield (S,R)-protected alcohol (VII).

CHART C discloses another alternative process for the synthesis of enantiomerically pure (S,R)-protected alcohol (VII) from the epoxide (V). Epoxide (V) is reacted with azide, yielding the enantiomerically pure (S,R)-protected azide (XII) in reaction conditions known to those skilled in the art, for example, J. March, Advanced Organic Chemistry, $3^{rd}$ Edition, John Wiley & Sons Publishers, 1985, p. 380. (S,R)-protected azide (XII) is reduced to protected amine (XIII) by methods known to those skilled in the art for the reduction of an azide group in the presence of a t-butoxycarbonyl N-protecting group, for example catalytic hydrogenation. Alternative reducing conditions which may be used to avoid N-deprotection with protecting groups other than t-butoxycarbonyl are known to those skilled in the art, see for example, R. C. Larock in Comprehensive Organic Transformations, VCH Publishers, 1989, p. 409.

The (S,R)-protected compound (XIII)) is deprotected to yield (S,R)-amine (VII) by methods known to those skilled in the art for removal of amine protecting group. Suitable reaction conditions for the removal of an amine protecting group depend on the type of protecting group. For example, it is preferable to remove the preferred protecting group, BOC, by contacting (S,R)-protected alcohol (VII) with a mixture of and acid and an organic solvent, e.g. a trifluoroacetic acid/dichloromethane mixture, yielding the protonated salt of (S,R)-amine (VII). Optionally, (S,R)-amine (VII) can be purified by methods known to those skilled in the art, for example recrystallization. The free-base (S,R)-amine (VII) can be obtained by means known to those skilled in the art, such as for example, preparing the free base amine by contacting the salt with mild basic conditions. Additional BOC deprotection conditions and deprotection conditions for other protecting groups can be found in T. W. Green and P. G. M. Wuts in "Protective Groups in Organic Chemistry," John Wiley and Sons, 1991, p. 309. Typical chemically suitable salts include trifluoroacetate, chloride, sulfate, phosphate; preferred is trifluoroacetate and chloride.

(S,R)-amine (VIII) is reacted with an appropriately substituted acylating reagent (IX) such as an anhydride, acyl halide, or acid of the formula $(R_{N-1}-X_N)_2O$ or $R_{N-1}-X_N-X_2$ or $R_{N-1}-X_N-OH$ (IX) in reaction conditions known to those skilled in the art to produce (S,R)-substituted amine (X). Reaction conditions known to those skilled in the art can be found, for example, in R. C. Larock in Comprehensive Organic Transformations, VCH Publishers, 1989, p. 981, 979, and 972. $R_N$ is preferably selected from the group consisting of:

$R_{N-1}-X_N-$ wherein $X_N$ is —CO—, $R_{N-1}$ is $R_{N-aryl}$ or $R_{N-heteroaryl}$ wherein $R_{N-aryl}$ is phenyl where the substitution on phenyl is 1,3-, and wherein $R_{N-aryl}$ or $R_{N-heteroaryl}$ are substituted with one —CO—$NR_{N-2}R_{N-3}$, $R_{N-1}-X_N-$ wherein $X_N$ is —CO—, $R_{N-1}$ is $R_{N-aryl}$ or $R_{N-heteroaryl}$ wherein $R_{N-aryl}$ is phenyl substituted with one $C_1$ alkyl wherein the substitution on the phenyl is 1,3,5-, and wherein $R_{N-aryl}$ or $R_{N-heteroaryl}$ are substituted with one —CO—$NR_{N-2}R_{N-3}$, $R_{N-1}-X_N-$ wherein $X_N$ is —CO—, and $R_{N-1}$ is $R_{N-heteroaryl}$ wherein $R_{N-heteroaryl}$ is substituted with one —CO—$NR_{N-2}R_{N-3}$. $R_{N-2}$ and $R_{N-3}$ are preferably the same and are $C_3$ alkyl, $R_{N-1}-X_N-$ wherein $X_N$ is —CO—, and $R_{N-1}$ is $R_{N-aryl}$ wherein $R_{N-aryl}$ is phenyl substituted with one —CO—$NR_{N-2}R_{N-3}$ wherein the substitution on phenyl is 1,3-, $R_{N-1}-X_N-$ wherein $X_N$ is —CO—, and $R_{N-1}$ is $R_{N-aryl}$ wherein $R_{N-aryl}$, is phenyl substituted with one $C_1$ alkyl and with one —CO—$NR_{N-2}R_{N-3}$ wherein the substitution on the phenyl is 1,3,5-. $X_N$ is preferably (A) —CO— and (B) —$SO_2$—; more preferably $X_N$ is —CO—. $X_2$ is selected from the group consisting of —Cl, —Br; more preferably, $X_2$ is —Cl.

Acylating reagents, $(R_{N-1}-X_N)_2O$ or $R_{N-1}-X_N-X_2$ or $R_{N-1}-X_N-OH$ (IX) are known to those skilled in the art and are commercially available or can be readily prepared from known starting materials by methods disclosed in the literature. Isophthalic acid derivatives (IX) of the formula $R_{N-2}R_{N-3}N$—CO-phenyl-CO— or methylisophthalic acid derivatives (IX) of the formula $R_{N-2}R_{N-3}N$—CO—$(CH_3-)$phenyl—CO— where the substitution is 5-methyl-1,3-isophthalic acid are the preferred acylating reagents. The most preferred 5-methyl-1,3-isophthalic acid derivative is 3-[(N,N-dipropylamino)carbonyl]-5-methylbenzoic acid (IX). These compounds are preferably synthesized according to the following method. An ester, preferably the monomethyl ester of isophthalic acid or methyl 5-methyl-1,3-isophthalate is dissolved in an orgonanic solvent or a mixture of solvents, preferably a THF/DMF mixture. 1,1'-Carbonyldiimidazole is added at a temperature of about 20-25 degrees C. A preferred amine (H—$NR_{N-2}R_{N-3}$) is added. Following from about 1 hr to about 24 hrs of stirring at a temperature from about 20 degrees C. to the reflux temperature of the reaction mixture, the reaction mixture is partitioned between saturated aqueous ammonium chloride and a water immiscible organic solvent, for example ethyl acetate. The aqueous layer is separated and extracted twice more with the organic solvent. The organic extracts are combined and washed with a saturated aqueous solutions of bicarbonate and saline and dried over anhydrous sodium sulfate or magnesium sulfate. Filtration of the drying agent and removal of solvents by reduced pressure yields the methyl ester of the desired $R_{N-2}R_{N-3}N$—CO-phenyl-CO—O—$CH_3$ or a methylisophthalic acid acylating agent (IX) $R_{N-2}R_{N-3}N$—CO—$(CH_3-)$phenyl-CO—O—$CH_3$. Purification of the (methyl) ester can be carried out for example via chromatography on silica gel eluting with a mixture of ethyl acetate and hexanes as mobile phase. The isophthalate ester or methylisophthalate ester of the mono-alkyl or di-alkyl amide is contacted with an aqueous alkaline solution, for example lithium hydroxide in a minimum amount of THF/methanol/water and stirred 3-24 hours at 20 degrees C. to the reflux temperature of the reaction mixture. The solvents are then removed under reduced pressure and the products partitioned between water and a water immiscible solvent, for example ethyl acetate. If the formation of an emulsion hinders the separation of the two phases, a small amount of saline is added to aid the separation. The aqueous phase is extracted once more with a water immiscible solvent, for example ethyl acetate. The aqueous phase is then acidified via the addition of an acid, preferably hydrochloric acid, to pH≦3. The resulting mixture is extracted three times with a water immiscible solvent, for example ethyl acetate. The combined organic extracts are dried over anhydrous sodium or magnesium sulfate. The drying agent is removed by filtration and the organic solvent is removed under reduced pressure to yield the product. The mono- or di-alkyl amide isophthalate/methylisophthalate is reacted with (S,R)-amine (VIII) to produce the (S,R)-substituted amine (X).

If $R_{N-2}$ and $R_{N-3}$ are both —H, the following method is preferred. An ester, preferably the methyl ester of isophthalate or methyl 5-methyl-1,3-isophthalate is dissolved in an organic solvent or a mixture of organic solvents, preferably a THF/DMF mixture. CDI is added at about 20-25 degrees C. After five to thirty minutes, ammonia gas is bubbled into the mixture for 1 hr. The mixture is cooled to about 0 degrees C. for the duration of the ammonia bubbling. The reaction mixture is left stirring under a balloon of ammonia overnight at about 20-25 degrees C., and partitioned between saturated aqueous ammonium chloride and a water immiscible solvent, for example ethyl acetate. The phases are separated and the aqueous phase is twice extracted with ethyl acetate. The organic extracts are washed with saturated aqueous solutions of bicarbonate and saline and dried over anhydrous sodium or magnesium sulfate. Filtration of the drying agent and removal of solvents under reduced pressure yields the ester of the desired isophthalic acid or the isophthalic acid derivative acylating reagent (IX). Purification of the (methyl) ester can be carried by example via chromatography on silica gel with an isopropanol/chloroform eluting mixture. The isophthalate ester or methylisophthalate ester of the primary amide is contacted with an aqueous alkaline solution such as lithium hydroxide in THF/methanol/water and stirred overnight at about 20-25 degrees C. after which time the solvents are removed under reduced pressure and the solids are partitioned between water and a water immiscible solvent, for example ethyl acetate. If the formation of an emulsions hinders separation of the two phases, a small amount of saline solution is added to improve separation. The aqueous phase is separated and extracted with a water immiscible solvent, for example ethyl acetate. The aqueous phase is then acidified with acid, preferably hydrochloric acid, to pH≦3. The resulting mixture is extracted with ethyl acetate. The combined organic extracts are dried over anhydrous sodium or magnesium sulfate. The drying agent is removed by filtration and the organic solvent removed under reduced pressure to yield the product. The amide isophthalic acid derivative is reacted with (VIII) to produce (X).

When it is preferred that the amine moiety be part of cyclic group, for example morpholinyl, piperazinyl, piperidinyl and pyrrolidinyl, etc the following method is preferably used. An ester, preferably the methyl ester of isophthalic acid or methyl 5-methyl-1,3-isophthalate is dissolved in an anhydrous solvent, for example methylene chloride, and a small quantity of a dipolar aprotic solvent, for example DMF is added. The mixture is cooled to about 0 degrees C. and oxalyl chloride is added. The mixture is stirred at about 0 degrees C. for about 30 minutes to about two hours after which the solvents are removed under reduced pressure. The crude acid chloride solid is left under vacuum overnight, and dissolved in dry methylene and cooled to about 0 degrees C. prior to the addition of a cyclic amine and a tertiary amine base, for example N-methyl piperidine. The reaction mixture is stirred at about 0 degrees C. for about 1 to about 6 hrs before the solvents are removed under reduced pressure. The residue is diluted with water and a water immiscible solvent, for example ethyl acetate, for example, and the phases are separated. The aqueous phase is extracted with a water immiscible solvent, for example ethyl acetate, and the combined organic extracts are washed with saturated aqueous bicarbonate and dried over anhydrous sodium or magnesium sulfate. Filtration of the drying agent and removal of solvents under reduced pressure yields the product cyclic amide. The cyclic amide is contacted with an aqueous alkaline solution, for example lithium hydroxide in THP/methanol/water and stirred overnight at about 20-25 degrees C., after which time the solvents are removed under reduced pressure and the residue is partitioned between water and a water immiscible solvent, for example ethyl acetate. The aqueous phase is extracted with ethyl acetate. Removal of water from the aqueous phase under reduced pressure yields the target cyclic amide product (IX).

When the $R_{N-1}$ moiety in the target product is a carbocycle, for example but not limited to, cyclohexane, with the starting reagent may be a suitably functionalized dimethyl isophthalate and the method one of those taught in the literature (Meyers, A. I., Org. Syn., 1971, 51, 103) one may reduce the six-membered ring with reducing agents such as rhodium (5%) on alumina in the presence of acetic acid and methanol under a hydrogen atmosphere to afford the corresponding dimethyl cyclohexane dicarboxylate.

CHART D sets forth an alternative process for production of the (S,R)-substituted amine (X) from the (S,R)-protected azide (XII), which is produced from the corresponding epoxide (V) in CHART C. The amino protecting group is removed to produce the corresponding unprotected azide (XIV) by methods previously described in CHART A for the conversion of (S,R)-protected alcohol (VII) to the corresponding (S,R)-amine (VIII). The (S,R)-unprotected azide (XIV) is then acylated on nitrogen to produce the corresponding (S,R)-azide (XV). Next, the azide functionality is reduced as previously discussed for the conversion of the (S,R)-protected azide (XII) to the corresponding (S,R)-protected amine (XIII) to give the (S,R)-free amiine (XVI). Last, the (S,R)-free amine (XVI) is transformed to the corresponding (S,R)-substituted amine (X) by nitrogen alkylation with a compound of the formula $R_c$—$X_3$ to give the corresponding (S,R)-substituted amine (X). $X_3$ is an appropriate leaving group, such as but not limited to, —Cl, —Br, —I, —O-mesylate, —O-tosylate, O-triflate, etc. $X_3$ may also be an aldehyde; the corresponding coupling with (XVI) via the well known reductive amination procedure gives the (S,R)-substituted amine (X).

Carbocylic amide forming agents (IX) are also provided for by the invention. For example, the carbocyclic amide forming agents of the formula R'—CH—C(R")(R''')—CH—$X_N$—OH (IX) are readily prepared from known starting materials by methods disclosed in the literature and known to those skilled in the art, for example, J. Med. Chem. 1998, 41, 1581, J. Org. Chem. 2000, 65, 1305. It is also understood that instead of the carboxylic acid, one may readily employ an acyl halide, where the halide is preferably chloride, or a suitable group to produce a mixed anhydride; these methods are taught by CHART A. For additional guidance on the formation of carbocyles and preferably cyclopropanes, one may consult M. P. Doyle; M. A. McKervery; T. Ye in Modern Catalytic Methods for Organic Synthesis with Diazo Compounds From Cyclopropanes to Ylides, Wiley-Interscience, 1998, pp. 163-279.

CHARTs E, F, G, and H disclose various methods to produce the $R_N$ portion of the substituted amine (X) where the phenyl ring of the $R_N$ 1,3-disubstituted moiety, —CO-phenyl-CO—, is further substituted in the 5-position with various groups such as amides, nitriles, halides, and amines. These compounds are prepared by methods known to those skilled in the art. The process chemistry of each reaction is known to those skilled in the art. The novelty here is represented by the order of each process step and/or the specific reactants used. One skilled in the art knowing the desired product would know at least one method to prepare the desired product by using known starting materials. Hence, the following discussion is not necessary but is set forth to further aid those interested in preparing the compounds of the invention.

CHART E discloses alternate processes for the transformation of the aniline (XVII) or acid ester (XVIII) to the corresponding acid (IX-XXIII). One process begins with the commercially available aniline (XVII). The aniline (XVII) is treated with a diazotizing reagent such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the halo acid ester (XIX).

Alternatively, the acid ester (XVIII) is treated with N-halosuccinimide and trifluoromethanesulfonic acid to give the halo acid ester (XIX). The halo acid ester (XIX) is then converted to the ester amide (XXI) using a primary or secondary amine of the formula H—$NG_1G_2$ where $G_1$ and $G_2$ are the same or different or can be cyclized. $G_1$ and $G_2$ become part of the substituted amine (X) and are included in the definition of $R_N$. $R_N$ includes $R_{N-1}X_N$— where the linker, —$X_N$—, includes —CO— and $R_{N-1}$ includes $R_{N-aryl}$. $R_{N-aryl}$ is defined to include phenyl (-phenyl) optionally substituted with one or two amides:

—CO—$NR_{N-2}R_{N-3}$ and
—CO—$R_{N-4}$.

Alternatively, the halo acid ester (XIX) is converted to the acid chloride halo ester (XX) by methods known to those skilled in the art. One of skill in the art will appreciate that other acid halides may also be used. The dihalo ester (XX) is treated with a primary or secondary amine of the formula H—$NG_1G_2$ to give the ester amide (XXI). The ester amide (XXI) is then reacted with an AMINE in a carbon monoxide atmosphere in the presence of a palladium catalyst using methods such as those reviewed by Heck, (Palladium Reagents in Organic Synthesis, 1985 pp. 342-365). to give the diamide (XXII). Hydrolysis of the ester portion of the diamide (XXII) using methods well known to those skilled in the art gives the diamide acid (XXIII).

In CHART F, an alternate route to intermediate diamide (XXII) is shown starting from commercially available phenol (XXIV). The phenol (XXIV) is treated with a trifluoromethanesulfonating reagent such as trifluoromethanesulfonic anhydride to give triflate (XXV). The triflate (XXV) is reacted under the conditions of palladium catalysis in the presence of carbon monoxide and an amine of the formula H—NR$_{Nalpha}$R$_{Nbeta}$ (AMINE) as for the conversion of the ester amide (XXI) to the corresponding diamide (XXII) in CHART E to give the diester (XXVI). The diester (XXVI) is hydrolyzed using methods known to those skilled in the art to give the monoacid (XXVII). The monoacid (XXVII) is then converted to the diamide (XXII) using conditions such as for the conversion of the halo acid ester (XIX) to the ester amide (XXI) in CHART E.

CHART G discloses another route to prepare the ester amide (XXI). The reaction starts with commercially available nitro compound (XXVIII) which is condensed with an (AMINE) using coupling methods known to those skilled in the art to give the nitro amide (XXX). The nitro amide (XXX) can also be prepared by first treating the nitro compound (XXVIII) with reagents such as thionyl chloride, or DMF and oxalyl chloride, or other methods known to those skilled in the art to give the acyl chloride (XXIX), which upon treatment with the (AMINE) gives the nitro amide (XXX). Reduction of the nitro amide (XXX) using methods known to those skilled in the art (see, for example, Smith and March, Advanced Organic Chemistry, 5$^{th}$ ed.) gives amide aniline (XXXI). The amide aniline (XXXI) is then treated with diazotizing reagents such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the ester amide (XXI).

CHART H discloses a process to prepare the diamide acid (IX-XXIII) from the ester amide (XXI), where one of the amides is unsubstituted and is —CO—NH$_2$. This process starts from either the ester or the acid, for example the ester amide (XXI) is treated with copper (I) cyanide (CuCN) in N-methylpyrrolidinone or DMF, preferably N-methylpyrrolidinone, to give the nitrite (XXXII). The nitrite (XXXII) is converted to the primary amide (XXXIII) using urea-hydrogen peroxide complex (see *Synth. Commun.* (1993) 3149) or the methods of *Synth. Commun.* (1990) 1445, *Synth. Commun.* (1997) 3119, *J. Org. Chem.* (1992) 2521, *Tet. Lett.* (1996) 6555, *Ind. J. Chem.*, Sect. B, (1999) 974, *Tet. Lett.* (1995) 3469, *Tet. Lett.* (1998) 3005, or others. When the ester amide (XXI) is in the form of an ester, an additional hydrolysis step using lithium hydroxide, sodium hydroxide, potassium hydroxide, barium hydroxide, or other hydrolysis methods known to those skilled in the art is used to convert the diamide ester (XXXIII) to the diamide acid (IX-XXIII).

CHART I discloses an alternate synthetic route from the protected alcohol (VII) to the substituted amine (X) which uses a diprotected intermediate (XXXIV) wherein the nitrogen atom attached to the R$_c$ substituent is protected. Using the process of CHART I, the mono protected alcohol (VII) is reacted with a new protecting group to form the orthogonally protected (XXXIV). This is a common strategy employed in traditional peptide chemistry by those skilled in the art, see M. Bodansky, Principles of Peptide Chemistry. When the mono protected alcohol (VII) is protected with CBZ one skilled in the art could react it with either (BOC)$_2$O in methylene chloride or similar organic solvent or FMOC-Cl in methylene chloride or similar organic solvent to prepare orthogonally protected (XXXIV). Then the CBZ group is removed by hydrogenation in the presence of a catalytic amount of palladium on carbon in an alcoholic solvent, such as methanol, or ethyl acetate, or with catalytic palladium on carbon in alcoholic solvents in the presence of ammonium formate as is known to those skilled in the art. This gives the R$_c$—N protected (XXXV). Similarly, when the mono protected alcohol (VII) is protected as a BOC it can be reacted with CBZ-Cl under Schotten-Bauman conditions or CBZ-OSu in THF to prepare the reversed (XXXIV). Then the BOC group can be cleaved with hydrochloric acid (4 N) in methanol, ethanol or dioxane or with trifluoroacetic acid in methylene chloride or by other methods such as those described in The Peptides, Analysis, Synthesis, Biology, Vol. 3, Ed. E. Gross and J. Meienhofer (1981) to liberate the CBZ R$_c$—N protected (XXXV). This functional group manipulation gives various permutations in the sequence (VII) to (XXXIV) to (XXXV) as is apparent to one skilled in the art. When the appropriately R$_c$—N protected compound (XXXV) is reacted with the amide forming agent (IX), in acid form, under standard peptide coupling conditions, for example, EDC/HOBt in methylene chloride or DMF or a previously activated acid, (R$_{N-}$)$_2$O gives the corresponding R$_N$-substituted R$_c$—N protected (XXXVI). Simple de-protection of the R$_N$-substituted R$_c$—N protected (XXXVI) then gives the desired substituted amine (X). Thus when the R$_N$-substituted R$_c$—N protected (XXXVI) is protected with BOC, treatment with hydrochloric acid (4N) in dioxane or the other reagents discussed above gives the substituted amine (X). When the R$_N$-substituted R$_c$—N protected (XXXVI) is protected with CBZ, treatment with hydrogen from 10-50 psi in alcoholic solvents, such as methanol with a catalytic amount of palladium on carbon will give, after work-up, the desired substituted amine (X). Similarly when the R$_N$-substituted R$_c$—N protected (XXXVI) is protected with FMOC, treatment with a secondary amine, preferably either piperidine (10%) or diethylamine (10%) in an inert solvent such as, for example, methylene chloride will give after work up the desired substituted amine (X).

CHART J discloses a process to prepare compounds where the phenyl ring of the R$_N$ substituent of —CO-phenyl-CO— is substituted with a sulfonamide group in the 5-position. The process starts with the halo amide ester (XXI, CHART E) which is reacted with sodium nitrite, sulfur dioxide, copper chloride (II) and acetic acid by the method disclosed in *J. Med. Chem.*, 42, 3797 (1999) to prepare the sulfonyl chloride (XXXVII). The sulfonyl chloride (XXXVII) is then reacted with AMINE, as defined above, by methods known to those skilled in the art to produce the corresponding sulfonamide (XXXVIII). Last the sulfonamide (XXXVIII) is transformed to the corresponding sulfonamide acid (XXXIX) by methods known to those skilled in the art such as using lithium hydroxide, sodium hydroxide, potassium hydroxide, barium hydroxide, or other hydrolysis methods known to those skilled in the art.

CHART K discloses how to prepare the R$_N$ substituents where R$_N$ is R$_{N-1}$—X$_N$—, where X$_N$ is —CO— and R$_{N-1}$ is R$_{N-aryl}$ where R$_{N-aryl}$ is phenyl substituted with one alkyl group and one —CO—NR$_{N-2}$R$_{N-3}$ or —CO—R$_{N-4}$. See the discussion above for CHART E regarding the amine, H—NR$_{Nalpha}$R$_{Nbeta}$ (AMINE), used to form the amide R$_N$ substituents. The process starts with the halo amide ester (XXI)

which is then reacted with an alkyl boronic acid having the desired alkyl group in the presence of a palladium catalyst such as Pd(PPh$_3$)Cl$_2$ using the general method described in *J. Med. Chem.*, 4288 (2000). The alkyl boronic acids are commercially available or can be prepared by the process described in *J. Am. Chem. Soc.*, 60, 105 (1938). It is preferred that R$_{N-b}$ is bromo. This step produces the alkyl ester (XL) which is then hydrolyzed by means known to those skilled in the art to produce the desired alkyl acid (XLI).

CHART L discloses a process to prepare the amide forming agent (IX-XLVII) where the R$_N$ substituent is R$_{N-1}$—X$_N$—, where the linker, —X$_N$— is —CO—, where R$_{N-1}$ is R$_{N-aryl}$ and where R$_{N-aryl}$ is phenyl (-phenyl) substituted with groups:

C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, —NR$_{1-a}$R$_{1-b}$ where R$_{1-a}$ and R$_{1-b}$ are as defined above, and —N(—H and C$_1$-C$_3$ alkyl)-CO—R$_{N-5}$. This specific amide forming agent, (IX-XLVII) is prepared by starting with the phenyl nitro compound (XLII) which is reduced to the corresponding phenyl nitro hydroxy compound (XLIII) using borane-methyl sulfide or borane in THF. The phenyl nitro hydroxy compound (XLIII) is reduced to the corresponding phenyl amino hydroxy compound (XLIV) using hydrogen and palladium catalyst as is known to those skilled in the art. The phenyl amino hydroxy compound (XLIV) is reacted with an aldehyde in the presence of a reducing agent such as sodium cyanoborohydride or sodium triacetoxyborohydride to give the phenyl substituted amino hydroxy compound (XLV). The phenyl substituted amino hydroxy compound (XLV) is acylated with an acid chloride or acid anhydride by methods known to those skilled in the art to give the phenyl disubstituted amino hydroxy compound (XLVI). The phenryl disubstituted amino hydroxy compound (XLVI) is hydrolyzed using an alkali hydroxide, followed by acidification, to give the amide forming agent (IX-XLVII). The amide forming agent (XLVII) is then coupled with amine (VIII) using methods known to those skilled in the art and methods previously discussed, such as with diethyl cyanophosphonate, to give the substituted amine (X). Further treatment of the substituted amine (X) with diethyl cyanophosphonate gives the substituted amine where the hydroxyalkyl substituent on the phenyl ring has a phosphate substituent.

CHART M discloses a process to prepare amide forming gents (IX-L) where the R$_N$ substituent is R$_{N-1}$—X$_N$—, where the linker, —X$_N$— is —CO—, where R$_{N-1}$ is R$_{N-aryl}$ and where R$_{N-aryl}$ is phenyl (-phenyl) substituted with two groups. The first substituent at what is usually identified as position "5-" can be either:
—R$_{N-aryl}$ or
—R$_{N-heteroaryl}$. The second substituent at what is usually identified as position "3-" can be either:
—CO—NR$_{N-2}$R$_{N-3}$ or
—CO—R$_{N-4}$. R$_{Nalpha}$ and R$_{Nbeta}$ include both the non-cyclic amides, —CO—NR$_{N-2}$R$_{N-3}$ and the cyclic amides—CO—R$_{N-4}$ where R$_{N-2}$, R$_{N-3}$ and R$_{N-4}$ are as defined in the claims. The process starts with the trisubstituted phenyl compound (XLVIII) where R$_{N-d}$ is —Cl, —Br, —I or —O-triflate. Treatment with an aryl or heteroaryl boronic acid or heteroaryl or aryl boronic acid ester such as (aryl or heteroaryl)-B(OH)$_2$ or (aryl or heteroaryl)-B(OR$^a$)(OR$^b$) (where R$_a$ and R$_b$ are lower alkyl, ie. C$_1$-C$_6$, or taken together, R$_a$ and R$_b$ are lower alkylene, ie. C$_2$-C$_{12}$) in the presence of a metal catalyst with or without a base in an inert solvent yields (XLIX). Metal catalysts in these transformations include, but are not limited to, salts or phosphine complexes of Cu, Pd, or Ni (eg. Cu(OAc)$_2$, PdCl$_2$(PPh$_3$)$_2$, NiCl$_2$(PPh$_3$)$_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to, acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described in *Tetrahedron*, 50, 979-988 (1994). Intermediate (XLIX) is then hydrolyzed using alkali metal hydroxide, for example lithium, sodium or potassium hydroxide, followed by acidification, to give aryl or heteroaryl coupled acids (IX-L). Alternatively, as described in *Tetrahedron*, 50, 979-988 (1994), one may convert the R$_{N-d}$ to the corresponding boronic acid or boronic acid ester (OH)$_2$B— or (OR$^a$)(OR$^b$)B— and obtain the same products set forth above by treating with a suitable aryl or heteroaryl halide or triflate.

CHART N discloses a process to prepare amide forming agents (IX-LII) where the R$_N$ substituent is R$_{N-1}$—X$_N$— where the linker, —X$_N$— is —CO—, where R$_{N-1}$ is R$_{N-aryl}$ and where R$_{N-aryl}$ is phenyl (-phenyl) substituted with two groups. The first substituent at what is usually identified as position "5-" is —C≡C—R. The second substituent at what is usually identified as position "3-" can be either —CO—NR$_{N-2}$R$_{N-3}$ or —CO—R$_{N-4}$. The halo ester (XXI) is treated with a mixture of PdCl$_2$(Pphenyl$_3$)$_2$ and trimethylsilyl acetylene, using methods known to those skilled in the art, to give acetylene ester (LI). Acetylene ester (LI) is then hydrolyzed using alkali metal hydroxide, followed by acidification, to give acetylene acid (IX-LII).

CHARTs O and O' disclose processes to prepare amide forming agents (IX-LX) and (IX-LXIII) with an extended methylene group where the R$_N$ substituent is R$_{N-1}$—X$_N$— where the linker, —X$_N$— is —CO—, where R$_{N-1}$ is R$_{N-aryl}$ and where R$_{N-aryl}$ is phenyl (-phenyl) substituted with two groups. The substituent at what is usually identified as position "3-" can be either —CO—NR$_{N-2}$R$_{N-3}$ or —CO—R$_{N-4}$. In the process of CHART O, the substituent at the 5-position is —CH$_2$CO—NH$_2$ and in the process of CHART O', the substituent at the 5-position is —CH$_2$C≡N. The starting diester acid (LIII) is reduced with borane in solvents such as THF to give the corresponding diester alcohol (LIV). The diester alcohol (LIV) is converted to the corresponding diester bromo compound (LV) using a brominating agent such as PBr$_3$, CBr$_4$, or other halogenating agent such as are known to those skilled in the art. The bromine of the diester bromo compound (LV) is then displaced with cyanide to give the corresponding nitrile (LVI). In CHART O', the nitrile (LVI) is then hydrolyzed to the corresponding cyano ester (LXI). The cyano ester (LXI) is then coupled with H—$NR_{N\alpha}R_{N\beta}$ (AMINE), as previously described using methods known to those skilled in the art to give the corresponding cyano amide (LXII). The cyano amide (LXII) is then hydrolyzed to the corresponding cyano acid (IX-LXIII) which is in turn coupled with amine (VIII) to give the substituted amine (X). When the substituent on the extended methyl group is —CO—$NH_2$, the process of CHART O is used. There the nitrile (LVI) is converted to the corresponding diester amine (LVII) by methods known to those skilled in the art. The next steps are the same as for CHART O' where the diester amide (LVII) is hydrolyzed to the corresponding ester amine (LVIII) which is then converted to the corresponding diamide ester (LIX) which is hydrolyzed to the corresponding diamide acid (IX-LX). The diamide acid (IX-XL) is then coupled with the appropriate amine (VIII) to produce the desired substituted amide (X).

CHART P discloses a process to prepare amide forming agents (IX-LXVII) with an extended hydroxymethylene group where the $R_N$ substituent is $R_{N-1}$—$X_N$— where the linker, —$X_N$— is —CO—, where the $R_{N-1}$ is $R_{N-aryl}$, where $R_{N-aryl}$ is phenyl (-phenyl) substituted with two groups. The substituent at what is usually identified as position "3-" can be either —CO—$NR_{N-2}R_{N-3}$ or —CO—$R_{N-4}$. The process begins with a halo amide (LXIV), preferably iodo, which is converted to the corresponding aldehyde (LXV) and then to the corresponding alcohol (LXVI) by the method described in *Synth. Commun.* 28, 4270 (1998), optionally with variations known to those skilled in the art. Hydrolysis of the alcohol (LXVI) using alkali hydroxides, followed by acidification, gives the desired hydroxy acid (IX-LXVII). The hydroxy acid (IX-LXVII) is then coupled with the appropriate amine (VIII) to give the desired substituted amine (X).

CHART Q discloses a process to prepare amide forming agents (IX-LXXII) with an alkyl group or a halogen atom or an amino group at the 5-position where the $R_N$ substituent is $R_{N-1}$—$X_N$— where the linker, —$X_N$— is —CO—, where the $R_{N-1}$ is $R_{N-aryl}$, where $R_{N-aryl}$ is phenyl (-phenyl) substituted with two groups. The substituent at what is usually identified as position "3-" can be either —CO—$NR_{N-2}R_{N-3}$ or —CO—$R_{N-4}$. The process begins with an appropriately 5-substituted diacid (LXVIII) which is esterified by methods known to those skilled in the art to give the corresponding diester (LXIX). The diester (LXIX) is then hydrolyzed using alkali hydroxides, followed by acidification, to give the corresponding monoacid (LXX). Alternatively, the monoacid (LXX) can be produced directly from the diacid (LXVIII) by known methods. The monoacid (LXX) is then coupled with H—$NR_{Nalpha}R_{Nbeta}$ (AMINE) to give the corresponding amide ester (LXXI). The amide ester (LXXI) is then hydrolyzed using alkali hydroxides, followed by acidification, to give the corresponding acid amide (IX-LXXII).

CHART R discloses a general process to prepare the amide forming agents (IX-LXXVII) which, for example, have an alkyl group at what is known as the 5-position and a ketone at the 3-position. These acids (IX- LXXVII) are formed by starting with the acid (LXXIII) which is converted to the corresponding acid halide (LXXIV) using methods known to those skilled in the art. The acid halide (LXXIV) is preferably the acid chloride. The acid halide (LXXIV) in the presence of copper (I) bromide and tetrahydrofuran and at temperatures ranging from −78 degrees C. to 0 degrees C. is treated with a Grignard reagent (aryl-Mg—X, or alkyl-Mg—X, where X is —Cl or —Br) to give the ketone esters (LXXVI and LXXVI'). Many Grignard reagents are available for purchase; others are prepared by methods known to those skilled in the art. An alternative method for preparing the ketone esters (LXXVI, LXXVI') is to prepare the Weinreb amide (LXXV), either from the acid (LXXIII) directly or by way of acid halide (LXXIV) followed by treatment with N,O-dimethylhydroxylamine to give Weinreb amide (LXXV) and then treating the Weinreb amide (LXXV) with a Grignard reagent, by methods known to those skilled in the art. The ketone esters (LXXVI, LXXVI') are then hydrolyzed using alkali hydroxides, followed by acidification, to give the ketone acids (LXXVII, LXXVII').

CHART S discloses various methods to modify the $R_N$ portion of the substituted amine (X) where the phenyl ring of the $R_N$ moiety is further substituted in the 3-position with various groups such as aryl and heteroaryl. These compounds are prepared by methods known to those skilled in the art. The process chemistry of each reaction is known to those skilled in the art. What is novel here is the order of each process step and/or the specific reactants used. One skilled in the art knowing the desired product would know at least one method to prepare the desired product by using known starting materials. Hence, the following discussion is not necessary but is set forth to further aid those interested in preparing the compounds of the invention.

CHART S sets forth a general method used in the invention to prepare the substituted amines (X) where $R_N$=$R_{N-aryl}$—$R_N$-aryl-$X_N$ or $R_{N-heteroaryl}$—$R_{N-aryl}$—$X_N$. Treatment of the (S,R)-amine (VIII) with amide forming agents (IX) according to the methods set forth above where for CHART S, $R_{N-1}$ is Br—$R_{N-aryl}$ generates the corresponding (S,R)-substituted amine (X) where $R_N$ is Br—$N_{R-aryl}$—$X_N$. Further treatment with an aryl boronic acid or aryl boronic acid ester such as (aryl or heteroaryl)-B(OH)$_2$ or (aryl or heteroaryl)-B(OR$^a$)(OR$^b$) (where $R_a$ and $R_b$ are lower alkyl, ie. $C_1$-$C_6$, or taken together, $R_a$ and $R_b$ are lower alkylene, ie. $C_2$-$C_{12}$) in the presence of a metal catalyst with or without a base in an inert solvent yields the (S,R)-substituted amine (X) where $R_N$ is $N_{R-aryl}$—$N_{R-aryl}$—$X_N$ or $R_{N-heteroaryl}$—$R_{N-aryl}$—$X_N$. Metal catalysts in these transformations include, but are not limited to, salts or phosphine complexes of Cu, Pd, or Ni (eg. Cu(OAc)$_2$, PdCl$_2$(PPh$_3$)$_2$, NiCl$_2$(PPh$_3$)$_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis (trimethylsilyl)amide), trialkyl amines (preferably diisopropylethylamine or triethylamine) or aromatic amines (preferably pyridine). Inert solvents may include, but are not limited to, acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloaalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described in *Tetrahedron*, 50, 979-988 (1994).

Where the above chemistry is incompatible with other functionality in the (S,R)-substituted amine (X) where $R_N$ is Br—$N_{R\text{-}aryl}$—$X_N$, then one skilled in the art will readily understand that an alternative sequence of coupling steps is required. For example, treatment of an appropriately substituted amide forming agent (IX) $R_{N\text{-}1}$—$X_N$—OH where $R_{N\text{-}1}$ is Br—$R_{N\text{-}aryl}$ with a boronic acid or boronic acid ester under the conditions described above will afford the appropriately substituted amide forming agent (IX) where $R_{N\text{-}1}$ is $N_{R\text{-}aryl}$—$N_{R\text{-}aryl}$ or $R_{N\text{-}heteroaryl}$—$R_{N\text{-}aryl}$. When the amide forming agent (IX) where $R_{N\text{-}1}$ is $N_{R\text{-}aryl}$—$N_{R\text{-}aryl}$ or $R_{N\text{-}heteroaryl}$—$R_{N\text{-}aryl}$ is treated with the (S,R)-amine (VIII), one then obtains the same substituted amines (X) set forth in CHART S.

The above examples for CHART S are not meant to limit the scope of the chemistry. In addition to bromine, a suitable group may include iodine or triflate. Alternatively, as described in *Tetrahedron*, 50, 979-988 (1994), one may convert the Br—$R_{N\text{-}aryl}$ to the corresponding boronic acid or boronic acid ester $(OH)_2B$—$R_{N\text{-}aryl}$ or $(OR^a)(OR^b)B$—$R_{N\text{-}aryl}$ and obtain the same products set forth above by treating with a suitable aryl or heteroaryl halide or triflate. Additionally, each —$R_{N\text{-}aryl}$ and —$R_{N\text{-}heteroaryl}$ are interchangeable at each occurrence in the chemistry described above.

CHART T discloses a process to prepare amide forming agents (IX-LXXIX) where the $R_N$ substituent is $R_{N\text{-}1}$—$X_N$—, where the linker, —$X_N$— is —CO—, where $R_{N\text{-}1}$ is $R_{N\text{-}aryl}$ and where $R_{N\text{-}aryl}$ is phenyl substituted with —CO—$NR_{Nalpha}R_{Nbeta}$ (AMINE) and with an amide of the formulas:

—$(CH_2)_{0\text{-}4}$—N(—H and $R_{N\text{-}5}$)—CO—$R_{N\text{-}2}$

—$(CH_2)_{0\text{-}4}$—N(—H or $R_{N\text{-}5}$)—$SO_2$—$R_{N\text{-}2}$.

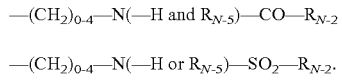

The process begins with the amide aniline (XXXI) which is reacted with the corresponding acid halide or sulfonyl halide, or acid anhydride or sulfonyl anhydride to produce the corresponding amide ester (LXXVIII). Suitable solvents include THF or dichloromethane at temperatures ranging from −78 degrees to 100 degrees C. The amide ester (LXXVIII) is then hydrolyzed to the corresponding amide acid (IX-LXXIX) by methods known to those skilled in the art. When the amide forming agent (IX-LXXIX) is reacted with the appropriate amine (VIII), the desired compound (X) is obtained.

CHART U discloses a general method for preparing various C-terminal amines (VI) as reed by the preparation of C-terminal amine (LXXXIV). Methods to prepare amines of this type are well understood using methods known to those skilled in the art, or one may consult the references: 1) *JACS*, 1970, 92, 3700, and 2) U.S. Pat. No. 4,351,842.

CHART V further discloses general methods for preparing various C-terminal amines (VI) as reed by the preparation of C-terminal amines (LXXXIX). Multiple examples of the heterocyclic carboxylic acids or acid chlorides are commercially available. Optionally, the carboxylic acid (LXXXV) may be converted to the acid chloride (LXXXVI) with reagents such as, but not limited to, thionyl chloride. Displacement with ammonia generates the common intermediate amides (LXXXVII) which are readily reduced to amines (VI-LXXXIX) using a variety of methods detailed previously. Alternatively, other heteroaryls are commercially available as the methyl halide (LXXXVIII) which are treated with ammonia to yield the title C-terminal amines (VI-LXXXVIII).

CHART W discloses general methods for preparing thiazolyl containing C-terminal amines as reed by the preparation of C-terminal amines (LXXXXI). The synthesis of the thiazoles is outlined in CHART W; these procedures are amply taught in the literature and are modified from the procedures outlined in: Mashraqui, S H; Keehn, P M. *J. Am. Chem. Soc.* 1982, 104, 4461-4465. The synthesis of substituted 5-aminomethylthiazoles (XCI) was achieved from 5-hydroxymethylthiazole (XC) by the procedure described in: Alterman et al. *J. Med. Chem.* 1998, 41, 3782-3792. All other thiazole analogs were transformed to the hydroxymethyl derivative using CHART W, and converted to the aminomethyl derivative by the Alterman procedure without notable changes.

CHART X discloses general methods for preparing isoxazolyl containing C-terminal amines as reed by the preparation of C-terminal amines (XCII). The synthesis of isoxazole derivatives was modified from the procedure in: Felman, S W et al. *J. Med. Chem.* 1992, 35, 1183-1190 and is readily understood by those skilled in the art making non-notable changes to achieve the title compounds. The substituted hydroxylamine precursors were synthesized using the procedure taught by Bousquet, E W. *Org. Synth. Coll.* Vol II, 313-315. Commercially available propargylamine may be protected using any number of methods known in the art (see: Greene, T W; Wuts, P G M. *Protective Groups in Organic Synthesis*, 3$^{rd}$ Ed. New York: John Wiley, 1999. Chapter 7.), preferred is a BOC protecting group. Substituted propargyl amines may be obtained by a number of methods commonly known in the art.

CHART Y discloses a general route to prepare hydroxyethylamines where one carbon atom of the peptide backbone, along with $R_2$ and $R_3$ form a ring. It is understood that the invention also allows for a heteroatom to be incorporated into the ring. In summary, the synthesis of compounds where $R_2$ and $R_3$ may form a ring proceeds from a suitably protected amino acid aldehyde and cycloalkyllithium species, both of which are commercially available or where known procedures for making such compounds are known in the art. The general procedure involved is also precedent in the literature, for example, see Klumpp, et al., *J. Am. Chem. Soc.*, 1979, 101, 7065, and it is intended that making non-critical variations, one may obtain the title compounds provided for by CHART Y. Treatment of a suitably protected amino acid aldehyde and cycloalkyllithium species affords alcohol (XCIII). These reactions are carried out in an inert solvent such as, for example, tetrahydrofuran or diethyl ether. Optimally the reactions are conducted at low temperatures, for example below 0 degrees C. Carbonylation via the Klumpp procedure yields the acid (XCIV) which when exposed to Curtius, or related procedures well known to those skilled in the art, generates the primary amine (XCV). The primary amines (XCV) may be capped C-terminally via the conditions set forth in CHART C & D followed by nitrogen deprotection and capping N-terminally via the conditions set forth in CHART A.

The compounds of the invention may contain geometric or optical isomers as well as tautomers. Thus, the invention includes all tautomers and pure geometric isomers, such as the E and Z geometric isomers, as well as mixtures thereof. Furthermore, the invention includes pure enantiomers and diasteriomers as well as mixtures thereof, including racemic mixtures. The individual geometric isomers, enantiomers, or diasteriomers may be prepared or isolated by methods known in the art.

Compounds of the invention with the stereochemistry designated in formula X may be included in mixtures, including racemic mixtures, with other enantiomers, diasteriomers, geometric isomers or tautomers. Compounds of the invention with the stereochemistry designated in formula X are typically in these mixtures in excess of 50 percent. Preferably, compounds of the invention with the stereochemistry designated in formula X are in these mixtures in excess of 80 percent. Most preferably, compounds of the invention with the stereochemistry designated in formula X are in these mixtures in excess of 90 percent.

The compounds of the invention are typically amines and as such form salts when reacted with acids. Pharmaceutically acceptable salts are preferred over the corresponding (S,R)-substituted amines (X) and and the substituted amines with $R_N$ cyclized (X') since they produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.,* 33, 201-217 (1986) and *J. Pharm. Sci.,* 66(1), 1, (1977).

The invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Methods of the Invention

The compounds of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. The compounds and compositions of the invention are particularly useful for treating or preventing Alzheimer's disease. The compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In addition, the compounds of the invention can also be used with inhibitors of P-glycoproten (P-gp). The use of P-gp inhibitors is known to those skilled in the art. See for example, *Cancer Research,* 53, 4595-4602 (1993), *Clin. Cancer Res.,* 2, 7-12 (1996), *Cancer Research,* 56, 4171-4179 (1996), International Publications WO99/64001 and WO01/10387. The important thing is that the blood level of the P-gp inhibitor be such that it exerts its effect in inhibiting P-gp from decreasing brain blood levels of the compounds of the invention. To that end the P-gp inhibitor and the compounds of the invention can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102, 918 and other steroids. It is to be understood that additional agents will be found that do the same function and are also considered to be useful.

The P-gp inhibitors can be administered orally, parenterally, (IV, IM, IM-depo, SQ, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered IV, IM, depo-IM, SQ or depo-SQ.

The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

There is nothing novel about the route of administration nor the dosage forms for administering the P-gp inhibitors. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the invention administered, the particular condition being treated, the severity of the condition being treated, the age, weight, general physical condition of the particular patient, other medication the individual may be taking as is well known to those skilled in the art.

Dosage Forms and Amounts

The compounds of the invention can be administered orally, parenternally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenternal administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenternally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenternal dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, Frontotemporal dementias with parkinsonism (FTDP) and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, *Arch. Neurol.* 57:454), and other neurotropic agents of the future.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Reactive assay systems are described, for example, in U.S. Pat. Nos. 5,942,400, 5,744,346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et. al., 1999, Mol. Cell. Neurosci. 14:419-427; Vassar et. al., 1999, Science 286:735-741; Yan et. al., 1999, Nature 402: 533-537; Sinha et. al., 1999, Nature 40:537-540; and Lin et. al., 2000, PNAS USA 97:1456-1460). Synthetic forms of the enzyme have also been described (WO98/22597 and WO00/17369). Beta-secretase can be extracted and purified from human brain tissue and can be produced in cells, for example mammalian cells expressing recombinant enzyme.

Useful inhibitory compounds are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal" isotype described by Kang et. al., 1987, Nature 325:733-6, the 770 amino acid isotype described by Kitaguchi et. al., 1981, Nature 331:530-532, and variants such as the Swedish Mutation (KM670-1NL) (APP-SW), the London Mutation (V7176F), and others. See, for example, U.S. Pat. No. 5,766,846 and also Hardy, 1992, Nature Genet. 1:233-234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et. al., 1999, Neuro. Lett. 249:21-4, and in U.S. Pat. No. 5,612,486. Useful antibodies to detect A beta include, for example, the monoclonal antibody 6E10 (Senetek, St. Louis, Mo.) that specifically recognizes an epitope on amino acids 1-16 of the A beta peptide; antibodies 162 and 164 (New York State Institute for Basic Research, Staten Island, N.Y.) that are specific for human A beta 1-40 and 1-42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4-7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze beta-secretase activity and /or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015, and 5,811,633, and in Ganes et. al., 1995, Nature 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

DEFINITIONS

By "alkyl" and "$C_1$-$C_6$ alkyl" in the invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxy" in the invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the invention is meant fluorine, bromine, chlorine, and iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl or di($C_1$-$C_6$)alkylamino($C_1$-$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, —COOH, —C(=O)O($C_1$-$C_6$ alkyl), —C(=O)NH$_2$, —C(=O)N(mono- or di-$C_1$-$C_6$ alkyl), —S($C_1$-$C_6$ alkyl), —SO$_2$($C_1$-$C_6$ alkyl), —O—C(=O)($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—SO$_2$—($C_1$-$C_6$ alkyl), —N($C_1$-$C_6$ alkyl)-SO$_2$—($C_1$-$C_6$ alkyl), —NH—C(=O)NH$_2$, —NH—C(=O)N(mono- or di-$C_1$-$C_6$ alkyl), —NH($C_1$-$C_6$ alkyl)-C(=O)—NH$_2$ or —NH($C_1$-$C_6$ alkyl)-C(=O)—N-(mono- or di-$C_1$-$C_6$ alkyl).

By "heteroaryl" is meant one or more aromatic ring systems of 5-, 6-, or 7-membered rings which includes fused ring systems of 9-11 atoms containing at least one and up to four heteroatoms selected from nitrogen, oxygen, or sulfur.

Preferred heteroaryl groups of the invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl or di($C_1$-$C_6$)alkylamino ($C_1$-$C_6$)alkyl, —COOH, —C(=O)O($C_1$-$C_6$ alkyl), —C(=O)NH$_2$, —C(=O)N(mono- or di-$C_1$-$C_6$ alkyl), —S($C_1$-$C_6$ alkyl), —SO$_2$($C_1$-$C_6$ alkyl), —O—C(=O)($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—SO$_2$—($C_1$-$C_6$ alkyl), —N($C_1$-$C_6$ alkyl)-SO$_2$—($C_1$-$C_6$ alkyl), —NH—C(=O)NH$_2$, —NH—C(=O)N(mono- or di-$C_1$-$C_6$ alkyl), —NH($C_1$-$C_6$ alkyl)-C(=O)—NH$_2$ or —NH($C_1$-$C_6$ alkyl)-C(=O)—N-(mono- or di-$C_1$-$C_6$ alkyl).

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. Heterocycles may be fused to aryl rings. Examples include tetrahydroisoquinoline and indoline. The heterocycle groups herein are unsubstituted or, as specified, substituted in one or more substitutable positions with various groups. For example, such heterocycle groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl or =O.

All temperatures are in degrees Celsius.

TLC refers to thin-layer chromatography.

psi refers to pounds/in$^2$.

HPLC refers to high pressure liquid chromatography.

THF refers to tetrahydrofuran.

DMF refers to dimethylformamide.

EDC refers to ethyl-1-(3-dimethylaminopropyl)carbodiimide or 1-(3-dimethylaminopropyl)-3-ethylcarbodiimide hydrochloride.

HOBt refers to 1-hydroxy benzotriazole hydrate.

NMM refers to N-methylmorpholine.

NBS refers to N-bromosuccinimide.

TEA refers to triethylamine.

BOC refers to 1,1-dimethylethoxy carbonyl or t-butoxycarbonyl, —CO—O—C(CH$_3$)$_3$.

CBZ refers to benzyloxycarbonyl, —CO—O—CH$_2$-phenyl.

FMOC refers to 9-fluorenylmethyl carbonate.

TFA refers to trifluoracetic acid.

CDI refers to 1,1'-carbonyldiimidazole.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, hemical shifts are reported in ppm ($\delta$) downfield from TMS.

NMR refers to nuclear (proton) magnetic resonance spectroscopy, chemical shifts are reported in ppm ($\delta$) downfield from TMS.

IR refers to infrared spectroscopy.

MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.

HRMS refers to high resolution mass spectrometry.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

BOP refers to benzotriazol-1-yloxy-tris(dimethylamino)phosphonium hexafluorophosphate.

TBDMSCl refers to t-butyldimethylsilyl chloride.

TBDMSOTf refers to t-butyldimethylsilyl trifluosulfonic acid ester.

Trisomy 21 refers to Down's Syndrome.

The following terms are used (in EXAMPLEs 321 and above) for the amide forming agent (IX):

"PHTH" refers to $(CH_3—CH_2—CH_2—)_2N—CO$-phenyl-CO—OH where the attachment to the -phenyl- ring is 1,3-;

"5-Me-PHTH" refers to $(CH_3—CH_2—CH_2—)_2N—CO—(CH_3-)$phenyl-CO—OH where the attachment to the -phenyl- ring is 1,3- for the carbonyl groups and 5- for the methyl group;

"3,5-pyridinyl" refers to $(CH_3—CH_2—CH_2—)_2N—CO$-(pyridinyl)-CO—OH where the attachment to the -pyridinyl- ring is 3,5- for the carbonyl groups;

"—$SO_2$—" refers to $(CH_3—CH_2—CH_2—)_2CH—SO_2$-phenyl-CO—OH where the attachment to the -phenyl- ring is 1,3-;

"5-OMe-PHTH" refers to $(CH_3—CH_2—CH_2—)_2N—CO—(CH_3—O-)$phenyl —CO—OH where the attachment to the -phenyl- ring is 1,3- for the carbonyl groups and 5- for the methoxy group;

"5-Cl-PHTH" refers to $(CH_3—CH_2—CH_2—)_2N—CO—(Cl-)$phenyl-CO—OH where the attachment to the -phenyl- ring is 1,3- for the carbonyl groups and 5- for the chlorine atom;

"5—F-PHTH" refers to $(CH_3—CH_2—CH_2—)_2N—CO—(F-)$phenyl-CO—OH where the attachment to the -phenyl- ring is 1,3- for the carbonyl groups and 5- for the fluorine atom;

"thienyl" refers to $(CH_3—CH_2—CH_2—)_2N—CO$-thienyl—CO—OH where the attachment to the thiophene ring is -2,5;

"2,4-pyridinyl" refers to $(CH_3—CH_2—CH_2—)_2N—CO$-(pyridinyl)-CO—OH where the attachment to the -pyridinyl- ring is 2,4- for the carbonyl groups;

"4,6-pyrimidinyl" refers to $(CH_3—CH_2—CH_2—)_2N—CO$-(pyrimidinyl-)phenyl-CO—OH where the attachment to the -pyrimidiny-1 ring is 4,6- for the carbonyl groups;

"morpholinyl" refers to morpholinyl—CO-phenyl-CO—OH where the attachment to the -phenyl- ring is 1,3 for the carbonyl groups.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

The invention provides compounds, compositions, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

EXAMPLES

The following examples describe how to prepare the various compounds and/or perform the various processes of the invention and are to be construed as merely illustrative, and not limitations of the preceding disclosure. Those skilled in the art will promptly recognize appropriate variations from the procedures both as to reactants and as to reaction conditions and techniques.

Preparation 1 3-Amino-5-(methoxycarbonyl)benzoic acid (XVII)

A suspension of mono-methyl 5-nitro-isophthalate (22.5 g, 100 mmol) and palladium on carbon (5%, 2.00 g) in methanol (100 mL) is shaken in a hydrogenation apparatus under hydrogen (50 psi) for 3 hours. The mixture is then filtered through diatomaceous earth and concentrated to give the title compound, NMR (300 MHz, CDCl$_3$) delta 7.67, 7.41, 7.40 and 3.83; MS (ESI−) for C$_9$H$_9$NO$_4$ m/z (M−H)$^−$=194.

Preparation 2 3-Bromo-5-(methoxycarbonyl)benzoic acid (XIX)

A mixture of copper (II) bromide. (1.85 g, 8.30 mmol), n-butyl nitrite (1.07 g, 10.4 mmol), and acetonitrile (30 mL) is stirred in a round bottomed flask in a water bath to which a few chunks of ice has been added. 3-Amino-5-(methoxycarbonyl)benzoic acid (XVII, PREPARATION 1, 1.35 g, 6.92 mmol) is added as a slurry in warm acetonitrile (70 mL) over 15 min and the mixture is stirred at 20-25 degrees C. for an additional 2 hour, at which time the mixture is partitioned between dichloromethane and hydrochloric acid (3N). The organic phase is separated and dried over sodium sulfate and concentrated to dryness. Chromatography (silica gel, 125 mL; methanol/dichloromethane, 15/85) and concentration of the appropriate fractions gives a solid which is crystallized from methanol to give the title compound in two crops, NMR (DMSO-$d_6$) delta 3.90, 8.26 and 8.65.

Preparation 3 Methyl
3-bromo-5-[(dipropylamino)carbonyl]benzoate
(XXI)

Carbonyl diimidazole (3.0 g, 18 mmol) is added to a solution of 3-bromo-5-(methoxycarbonyl)benzoic acid (XIX, PREPARATION 2, 3.9 g, 15 mmol) in THF (30 mL). The mixture is stirred for 0.5 hours. Dipropylamine (AMINE, 4.2 mL, 30 mmol) is added to the mixture, which is then stirred for 24 hours. The solvent is then removed under reduced pressure and the mixture is partitioned between ethyl acetate and water. The organic phase is then washed with saline, dried over anhydrous magnesium sulfate, filtered, and concentrated. Column chromatography (silica gel; ethyl acetate/hexanes, 15/85) gives the title compound, IR (diffuse reflectance) 2968, 2958, 1714, 1637, 1479, 1440, 1422, 1321, 1310, 1288, 1273, 1252, 889, 772 and 718 $cm^{-1}$; NMR (300 MHz, $CDCl_3$) δ 8.21, 7.96, 7.70, 3.95, 3.46, 3.15, 1.69, 1.57, 1.00 and 0.78; MS (ESI+) for $C_{15}H_{20}BrNO_3$ m/z $(M+H)^+$=344.1.

Preparation 4
3-Bromo-5-[(dipropylamino)carbonyl]benzoic acid

To a solution of methyl 3-bromo-5-[(dipropylamino)carbonyl]benzoate (XXI, PREPARATION 3, 1.4 g, 4.1 mmol) in THF/water/methanol (4/2/2, 8 mL) is added to lithium hydroxide monohydrate (0.17 g, 4.05 mmol). The mixture is stirred at 20 degrees-25 degrees C. for 1 hour and then solvent is removed under reduced pressure. The residue is dissolved in water (50 mL) and hydrochloric acid (1 N) is added to adjust the pH to about 3. The aqueous mixture is extracted with ethyl acetate and the organic phase is separated and dried over magnesium sulfate to give the title compound. Analytical calculated for $C_{14}H_{18}BrNO_3$: C, 51.23; H, 5.53; N, 4.27; Br, 24.35. Found: C, 51.37; H, 5.56; N, 4.28.

Preparation 5 Methyl 3-(aminocarbonyl)-5-[(dipropylamino)carbonyl]-benzoate (XXII)

To a mixture of methyl 3-bromo-5-[(dipropylamino)carbonyl]benzoate (XXI, PREPARATION 3, 0.5 g, 1.47 mmol) in dry N-methyl pyrrolidinone under a carbon monoxide atmosphere is added palladium (II) acetate (0.017 g, 0.074 mmol), 1,3-bis(diphenylphosphino)propane (0.045 g, 0.11 mmol), hexamethyldisilazane (1.0 mL, 4.7 mmol), and diisopropylethylamine (0.38 g, 2.94 mmol). The mixture is heated at 100 degrees C. for 24 hours. The mixture is cooled to 20-25 degrees C. and partitioned between water and ethyl acetate. The layers are separated and the aqueous phase is back-washed with ethyl acetate. The organic phases are combined and washed three times with saline, dried over anhydrous magnesium sulfate, filtered and concentrated. Column chromatography (silica gel, 75 mL; methanol/methylene chloride, 2.5/97.5) gives the title compound, NMR ($CDCl_3$) delta 0.77, 1.02, 1.57, 1.71, 3.17, 3.49, 3.98, 5.78, 6.34, 8.07, 8.20 and 8.48.

Preparation 6 3-(Aminocarbonyl)-5-[(dipropylamino)carbonyl]benzoic acid (XXIII)

To a mixture of methyl 3-(aminocarbonyl)-5-[(dipropylamino)carbonyl]benzoate (XXII, PREPARATION 5, 0.197 g, 0.64 mmol) in methanol (5.0 mL) is added sodium hydroxide (1N, 3.0 mL). The mixture is stirred at 20-25 degrees C. for 24 hours. The mixture is acidified to about pH 5 with hydrochloric acid (10%). Water (50 mL) is added and the mixture is washed twice with ethyl acetate (2×50 mL). The organic extracts are combined and dried over anhydrous magnesium sulfate and concentrated to give the title compound, NMR (DMSO-$d_6$) delta 0.66, 0.930, 1.48, 1.62, 3.12, 3.35, 7.54, 7.98, 8.22 and 8.51.

Preparation 7
3-Cyano-5-[(dipropylamino)carbonyl]benzoic acid
(IX/XXXII)

A mixture of 3-bromo-5-[(dipropylamino)carbonyl]benzoic acid (PREPARATION 4, 0.596 g, 1.82 mmol) and copper nitrile (0.325 g, 3.63 mmol) in N-methylpyrrolidinone (1.5 mL) is stirred at 175 degrees C. for 2.5 hour, at which time the mixture is cooled and partitioned between ethyl acetate and hydrochloric acid (3N). The organic layer is washed twice more with hydrochloric acid (3N) and then twice more with saline which had been acidified with a small amount of hydrochloric acid (3N). The organic layer is dried over magnesium sulfate and concentrated under high vacuum to give the title compound, NMR ($CDCl_3$) delta 0.80, 1.02, 1.60, 1.73, 3.17, 3.51, 7.90, 8.31 and 8.41; an aliquot is crystallized from ethyl ether/dichloromethane/hexane-IR (diffuse reflectance) 3017, 2970, 2937, 2898, 2877, 2473, 2432, 2350, 2318, 2236, 1721, 1608, 1588, 1206 and 1196 $cm^{-1}$.

Preparation 8 3-(Aminocarbonyl)-5-[(dipropylamino)carbonyl]benzoic acid (XXXIII)

A mixture of 3-cyano-5-[(dipropylamino)carbonyl]benzoic acid (IX/XXXII, PREPARATION 7, 0.602 g, 2.19 mmol), potassium carbonate (0.212 g, 1.53 mmol), and acetone (2.5 mL) is stirred at 20-25 degrees C. Water (2.5 mL) and urea-hydrogen peroxide adduct (0.825 g, 8.78 mmol) are added and the mixture is stirred for 15 hours at 20-25 degrees C., at which time additional urea-hydrogen peroxide adduct (0.204 g) is added; after stirring for another 3 hours, an additional 0.205 g of urea-hydrogen peroxide is added. After a total of 39 hours has elapsed, the acetone is removed under reduced pressure and the residue is acidified with hydrochloric acid (3N) to pH=2-4. The mixture is extracted with dichloromethane, the organic layer is separated and washed with hydrochloric acid (0.5 N), and the organic phase is dried with anhydrous magnesium sulfate to a solid. The solid is crystallized from dichloromethane/hexane/methanol to give the title compound, MS (ESI+) for $C_{15}H_{20}N_2O_4$ m/z $(M+H)^+$=293.2.

Preparation 9 Methyl
3-[(dipropylamino)carbonyl]-5-nitrobenzoate (XXX)

Carbonyl diimidazole (3.90 g, 24.0 mmol) is added to a mixture of mono-methyl 5-nitro-isophthalate (XXVIII, 4.50 g, 20.0 mmol) in dry THF (50 mL). The mixture is stirred for 0.5 hours. Dipropylamine (3.28 mL, 24.0 mmol) is added slowly to the mixture. The reaction mixture is then stirred for 4 hours. The solvent is removed under reduced pressure and the mixture is partitioned between ethyl acetate and water. The organic phase is separated and washed with saline, dried over anhydrous sodium sulfate, filtered, and concentrated. Column chromatography (silica gel; ethyl acetate/hexanes, 15/85) gives the title compound, NMR (300 MHz, $CDCl_3$) delta 8.88, 8.41, 8.35, 4.00, 3.48, 3.15, 1.72, 1.57, 1.00 and 0.77; MS (ESI+) for $C_{15}H_{20}N_2O_5$ m/z $(M+H)^+$=309.2.

Preparation 10 Methyl 3-amino-5-[(dipropylamino)carbonyl]benzoate (XXXI)

A suspension of methyl 3-[(dipropylamino)carbonyl]-5-nitrobenzoate (XXX, PREPARATION 9, 6.00g, 20.0 mmol) and palladium on carbon (5%, 0.600 g) in methanol (40 mL) is shaken in a hydrogenation apparatus under hydrogen (45 psi) for 3 hours. The mixture is then filtered through diatomaceous earth and concentrated to give the title compound, NMR (300 MHz, CDCl$_3$) delta 7.27, 6.77, 4.10, 3.82, 3.38, 3.10, 1.62, 1.46, 0.91 and 0.68.

Preparation 11 Methyl 3-(chlorosulfonyl)-5-[(dipropylamino)carbonyl]-benzoate (XXXVII)

Methyl 3-amino-5-[(dipropylamino)carbonyl]benzoate (XXXI, PREPARATION 10, 1.11 g, 4 mmol) is added to a mixture of water (5 mL) and concentrated hydrochloric acid (1 mL). Sodium nitrite (0.276 g, 4 mmol) is added to the mixture slowly at 0 degrees C. The mixture is then added to an acetic acid solution (5 mL) of CuCl$_2$.2H$_2$O saturated with sulfur dioxide. The mixture is stirred for 0.5 hours and poured into ice water. The mixture is extracted with ethyl acetate. The organic phase is separated and washed with saturated sodium bicarbonate, water, and saline and dried over anhydrous sodium sulfate, filtered, and concentrated to give the title compound, NMR (300 MHz, CDCl$_3$) delta 8.69, 8.38, 8.20, 4.01, 3.49, 3.14, 1.72, 159, 1.01 and 0.79; MS (ESI+) for C$_{15}$H$_{20}$ClNO$_5$S m/z (M+H)$^+$=362.2

Preparation 12 Methyl 3-(aminosulfonyl)-5-[(dipropylamino)carbonyl]-benzoate (XXXVIII)

To a solution of methyl 3-(chlorosulfonyl)-5-[(dipropylamino)carbonyl]benzoate (XXXVII, PREPARATION 11, 0.100 g, 0.300 mmol) in dry THF (3 mL) is added ammonia (7 N solution in methanol, 0.214 mL, 1.50 mmol). The mixture is stirred for 18 hours and solvent is then removed. The residue is partitioned between ethyl acetate and water. The organic phase is separate and washed with saline, dried over anhydrous sodium sulfate, filtered, and concentrated to give the title compound, NMR (300 MHz, CDCl$_3$) delta 8.45, 8.07, 8.01, 6.05, 3.93, 3.44, 3.09, 1.67, 1.52, 0.96 and 0.73; MS (ESI+) for C$_{12}$H$_{22}$N$_2$O$_5$S m/z (M+H)$^+$=343.3.

Preparation 13 3-(Aminosulfonyl)-5-[(dipropylamino)carbonyl]benzoic acid (XXXVIII)

Lithium hydroxide monohydrate (0.011 g, 0.263 mmol) is added to a solution of methyl 3-(aminosulfonyl)-5-[(dipropylamino)carbonyl]benzoate (XXXVIII, PREPARATION 12, 0.090 g, 0.263 mmol) in a mixture of THF/methanol/water (2/1/1, 2 mL). The mixture is stirred at 20-25 degrees C. for 3 hours. The mixture is then diluted with water and hydrochloric acid (1 N) is added to bring the pH to less than 3. The aqueous solution is extracted with ethyl acetate. The organic phase is separated and washed with saline, dried over anhydrous sodium sulfate, filtered and concentrated to give the title compound. $^1$H NMR (300 MHz, CDCl$_3$) delta 10.36 (s, 1 H), 8.39 (s, 1 H), 8.09 (s, 2 H), 6.06 (s, 2 H), 3.48 (t, J=7 Hz, 2 H), 3.15 (t, J=7 Hz, 2 H), 1.71 (m, 2 H), 1.55 (m, 2 H), 0.97 (t, J=7 Hz, 3 H), 0.74 (t, J=7 Hz, 3 H). MS (ESI+) for C$_{11}$H$_{20}$N$_2$O$_5$S m/z 329.2 (M+H)$^+$.

Preparation 14 Methyl 3-[(dipropylamino)carbonyl]-5-(1-pyrrolidinylsulfonyl)-benzoate (XXXVIII)

Following the general procedure of PREPARATION 12 and making non-critical variations but using pyrrolidine (0.347 mL, 4.16 mmol), the title compound is obtained, MS (ESI+) for C$_{19}$H$_{28}$N$_2$O$_5$S m/z (M+H)$^+$=397.1.

Preparation 15 3-[(Dipropylamino)carbonyl]-5-(1-pyrrolidinylsulfonyl)benzoic acid (XXXIX)

Following the general procedure of PREPARATION 13 and making non-critical variations, the title compound is obtained, MS (ESI+) for C$_{18}$H$_{26}$N$_2$O$_5$S m/z (M+H)$^+$=383.3.

Preparation 16 Methyl 3-[(dipropylamino)carbonyl]-5-[(methylamino)-sulfonyl]benzoate (XXXVIII)

Following the general procedure of PREPARATION 12 and making non-critical variations but using methyl amine (2 N solution in THF, 0.692 mL, 1.38 mmol), the title compound is obtained, MS (ESI+) for C$_{16}$H$_{24}$N$_2$O$_5$S m/z (M+H)$^+$=357.1.

Preparation 17 3-[(Dipropylamino)carbonyl]-5-[(methylamino)-sulfonyl]benzoic acid (XXXIX)

Following the general procedure of PREPARATION 13 and making non-critical variations, the title compound is obtained, MS (ESI+) for C$_{15}$H$_{22}$N$_2$O$_5$S m/z (M+H)$^+$=343.1.

Preparation 18 Methyl 3-t(dimethylamino)sulfonyl)-5-[(dipropylamino)-carbonyl]benzoate (XXXVIII)

Following the general procedure of PREPARATION 12 and making non-critical variations but using dimethylamine (2 N solution in THF, 0.692 mL, 1.38 mmol), the title compound is obtained, MS (ESI+) for C$_{17}$H$_{26}$N$_2$O$_5$S m/z (M+H)$^+$=371.1.

Preparation 19 3-[(Dimethylamino)sulfonyl]-5-[(dipropylamino)carbonyl]-benzoic acid (XXXIX)

Following the general procedure of PREPARATION 13 and making non-critical variations, the title compound is obtained, MS (ESI+) for C$_{16}$H$_{24}$N$_2$O$_5$S m/z (M+H)$^+$=357.1.

Preparation 20 Methyl 3-[(dipropylamino)carbonyl]-5-ethylbenzoate (IX)

Ethylboronic acid (0.800 g, 10.8 mmol), dichlorobis(triphenylphosphine)-palladium(II) (0.252 g, 0.360 mmol), potassium carbonate (2.50 g, 18.0 mmol) and lithium chloride (0.151 g, 3.60 mmol) are added to a mixture of methyl 3-bromo-5-[(dipropylamino)carbonyl]benzoate (1.23 g, 3.60 mmol) in dry DMF (20 mL). The mixture is heated at 100 degrees C. for 18 hours. The mixture is then partitioned between ethyl acetate and water. The phases are separated and the ethyl acetate phase is washed with saline, dried over sodium sulfate and concentrated. The concentrate is column chromatographed (silica gel; ethyl acetate/hexanes, 15/85) to give the title compound, MS (ESI+) for C$_{17}$H$_{25}$NO$_3$ m/z (M+H)$^+$=292.2.

Preparation 21 3-[(Dipropylamino)carbonyl]-5-ethylbenzoic acid (IX)

Lithium hydroxide monohydrate (0.0680 g, 1.6 mmol) is added to a mixture of methyl 3-[(dipropylamino)carbonyl]-

5-ethylbenzoate (PREPARATION 20, 0.450 g, 1.6 mmol) in a mixture of THF/methanol/water (2/1/1, 8 mL). The mixture is stirred at 20-25 degrees C. for 3 hours. The mixture is then diluted with water (20 mL) and hydrochloric acid (1 N) is added to bring the pH to less than 3. The aqueous mixture is extracted with ethyl acetate. The organic phase is separated and washed with saline, dried over anhydrous magnesium sulfate, filtered and concentrated to give the title compound, MS (ESI+) for $C_{16}H_{23}NO_3$ m/z $(M+H)^+$=278.2.

Example 1 tert-Butyl (1S)-3-bromo-1-(3,5-difluorobenzyl)-2-oxopropylcarbamate (III)

N-methyl-morpholine (5.83 Ml, 53 mmole, 1.05 eq.) is added to (2S)-2-[(tert-butoxycarbonyl)amino]-3-(3,5-difluorophenyl)propanoic acid (II, 15 g, 50 mmole) in THF (100 mL) and the reaction is cooled to −78 degrees C. Isobutyl chloroformate (6.87 mL, 53 mmole, 1.05 eq.) is added rapidly. The cold bath is then removed and the mixture stirred for 1 hour. The reaction is monitored by TLC to insure completion of the reaction and the mixture is then filtered and washed with dry THF (50 ml) and kept cold in the filtered flask at −20 degrees C.

In an ice-salt bath is placed a 500 ml graduate cylinder containing ether (200 mL) and aqueous potassium hydroxide (40%, 60 ml). 1-Methyl-3-nitro-1-nitrosoguanidine (5.6 g, 106 mmole, 2.1 eq.) is added slowly with stirring and temperature kept below 0 degrees C. The mixture turned yellow and the bubbling lasted for 10 minutes. The stirring is stopped and without mixing the layers, the top diazomethane ethereal layer is transferred with non-ground tip pipette into the stirred mixed anhydride mixture at −20 degrees C. The reaction is monitored by TLC (ethyl acetate/hexane, 50/50; $R_f$=0.69). After 1 hour nitrogen is then bubbled into the mixture. The solvent is removed under reduced pressure (with heat) and the mixture is partitioned between ether and water. The phases are separated, the organic phase is washed with bicarbonate, saline, dried over anhydrous sodium sulfate and solvent removed under reduced pressure (with heat). The residue is dissolved in ether (100 mL) and hydrobromic acid (48%, 15 mL, 135 mmole, 2.7 eq,) is added at −20 degrees C., the cold bath is removed and the mixture is stirred for another 0.5 hours. The reaction is monitored by TLC (ethyl acetate/hexane, 50/50; $R_f$=0.88). The mixture is partitioned between ether and water, washed with bicarbonate, saline, dried over anhydrous sodium sulfate and the solvent removed. The residue is recrystallized from ethanol to give the title compound, TLC (ethyl acetate/hexane, 50/50) $R_f$=0.88; MS $(MH^+)$=379.3.

Example 2 tert-Butyl (1S,2S)-3-bromo-1-(3,5-difluorobenzyl)-2-hydroxypropylcarbamate (IV)

Sodium borohydride (1.32 g, 34.9 mmole, 1.1 eq.) is added to tert-Butyl (1S)-3-bromo-1-(3,5-difluorobenzyl)-2-oxopropylcarbamate (III, EXAMPLE 1, 12 g, 31.75 mmole) dissolved in absolute alcohol (500 mL) at −78 degrees C. The reaction mixture is stirred for 0.5 hour and monitored by TLC (ethyl acetate/hexane, 20/80; $R_f$=0.2). The mixture is quenched with water (10 mL) and the solvent removed under reduced pressure with heat (not exceeding 30 degrees C.) to dryness. The solid is partitioned between dichloromethane and water, washed with saline, dried over anhydrous sodium sulfate. The solvent is removed under reduced pressure to give the title compound, TLC (ethyl acetate/hexane, 20/80) $R_f$=0.2; MS $(MH^+)$=381.2.

Example 3 tert-Butyl (1S)-2-(3,5-difluorophenyl)-1-[(2S)-oxiranyl]ethylcarbamate (V)

tert-Butyl (1S,2S)-3-bromo-1-(3,5-difluorobenzyl)-2-hydroxypropylcarbamate (IV, EXAMPLE 2) is dissolved in absolute alcohol (150 mL) and ethyl acetate (100 mL) and potassium hydroxide (2.3 g, 34.9 mmole, 1.1 eq.) in ethyl alcohol (85%, 5 mL) is added at −20 degrees C. The cold bath is then removed and the mixture stirred for 0.5 hour. The reaction is monitored by TLC (ethyl acetate/hexane, 20/80). When the reaction is complete; it is diluted with dichloromethane and extracted, washed with water, saline, dried over anhydrous sodium sulfate and the solvent removed under reduced pressure. The crude material is purified by flash chromatography on silica gel to give the title compound, TLC (ethyl acetate/hexane, 20/80) $R_f$=0.3; MS $(MH^+)$=300.4.

Example 4 tert-Butyl (1S,2R)-1-(3,5-difluorobenzyl)-2-hydroxy-3-[(3-methoxybenzyl)amino]propylcarbamate (VII)

tert-Butyl (1S)-2-(3,5-difluorophenyl)-1-[(2S)-oxiranyl]ethylcarbamate (V, EXAMPLE 3, 245 mg, 0.82 mmol) is suspended in isopropyl alcohol (6 mL) and 3-methoxybenzylamine (160 microL, 1.22 mmol) is added with stirring at 20-25 degrees C. This mixture is heated to gentle reflux (bath temp 85 degrees C.) under nitrogen for 2 hours, whereupon the resulting mixture is concentrated under reduced pressure to give the title compound. The title compound is purified by flash chromatography (2-5% methanol/methylene chloride; gradient elution) to give purified title compound.

Example 5

(2R,3S)-3-amino-4-(3,5-difluorophenyl)-1-[(3-methoxybenzyl)amino]-2-butanol trifluoroacetate (VIII)

tert-Butyl (1S,2R)-1-(3,5-difluorobenzyl)-2-hydroxy-3-[(3-methoxybenzyl)amino]propylcarbamate (VII, EXAMPLE 4, 258 mg, 0.59 mmol) is dissolved in methylene chloride (1 mL) at 20-25 degrees C., and trifluoroacetic acid (1 mL) is added with stirring under nitrogen. The reaction mixture is stirred at 20-25 degrees C. for 1 hour, whereupon the reaction mixture is concentrated under reduced pressure to give the title compound. The title compound is used in the next reaction without further purification.

Example 6

$N^1$-{(1S,2R)-1-(3,5-difluorobenzyl)-2-hydroxy-3-[(3-methoxybenzyl)amino]propyl}-5-methyl-$N^3$,$N^3$-dipropylisophthalamide (X)

(2R,3S)-3-amino-4-(3,5-difluorophenyl)-1-[(3-methoxybenzyl)amino]-2-butanol trifluoroacetate salt (VIII, EXAMPLE 5) is dissolved in anhydrous DMF (3 mL) and cooled to 0 degrees C. Triethylamine (500 microliter, 3.6 mmol) and 5-methyl-N,N-dipropylisophthalamic acid (156 mg, 0.59 mmol) are added with stirring. The mixture is warmed to 20-25 degrees C. briefly to allow for complete dissolution of the carboxylic acid, before recooling to 0 degrees C. 1-Hydroxybenzotriazole (157 mg, 1.2 mmol) is added with stirring, followed by 1-(3-dimethylaminopropyl)-3-ethylcarbodiimide hydrochloride (229 mg, 1.2 mmol). The resulting mixture is stirred at 0 degrees C. for 5 minutes, then warmed to 20-25 degrees C. for 15 hours. The reaction mixture is then quenched with aqueous citric acid (10%), and the mixture extracted three times with ethyl acetate. The combined organic extracts are washed with saturated sodium bicarbonate, saline, dried over sodium sulfate, filtered and concentrated under reduced pressure to give the title compound in crude form. This material is purified by flash chromatography (2-10% methanol/methylene chloride gradient elution) to give purified title compound, MS (ES) $MH^+$=582.3.

Examples 7-9

Following the general procedure of Example 1 and making non critical variations but starting with the protecting group of Column A and using the acid of Column B, the protected compound (III) of Column C is obtained:

| EXAMPLE | Column A | Column B | Column C |
|---|---|---|---|
| 7 | BOC | Hydrochloric | tert-butyl (1S)-3-chloro-1-(3,5-difluorobenzyl)-2-oxopropylcarbamate |
| 8 | CBZ | Hydrobromic | benzyl (1S)-3-bromo-1-(3,5-difluorobenzyl)-2-oxopropylcarbamate |
| 9 | CBZ | Hydrochloric | benzyl (1S)-3-chloro-1-(3,5-difluorobenzyl)-2-oxopropylcarbamate |

Examples 10-12

Following the general procedure of EXAMPLE 2 and making non critical variations but starting with the protected compound (III)-of Column A, the alcohol (IV) of Column B is obtained:

| EXAMPLE | Column A | Column B |
|---|---|---|
| 10 | 7 | Tert-butyl (1S,2S)-3-chloro-1-(3,5-difluorobenzyl)-2-hydroxypropylcarbamate |
| 11 | 8 | Benzyl (1S,2S)-3-bromo-1-(3,5-difluorobenzyl)-2-hydroxypropylcarbamate |
| 12 | 9 | Benzyl (1S,2S)-3-chloro-1-(3,5-difluorobenzyl)-2-hydroxypropylcarbamate |

Example 13

Benzyl (1S)-2-(3,5-difluorophenyl)-1-[(2S)-oxiranyl]ethylcarbamate (V)

Following the general procedure of Example 3 and making non critical variations but starting with the alcohol (IV) of Example 12, the title compound is obtained.

Examples 14-107

Following the general procedure of EXAMPLE 4 and making non-critical variations but reacting tert-butyl (1S,2S)-1-(2-oxiranyl)-2-phenylethylcarbamate (V, commercially available) with the C-terminal amine (VI) of Column A, the protected alcohol (VII) of Column B is obtained.

| Example No. | Column A<br>C-terminal amine (VI) | Column B<br>Protected alcohol (VII) |
|---|---|---|
| 14 | $H_2N$—$CH_2CH_3$ | tert-butyl (1S,2R)-1-benzyl-3-(ethylamino)-2-hydroxypropylcarbamate |
| 15 | $H_2N$—$CH_2$-phenyl | tert-butyl (1S,2R)-1-benzyl-3-(benzylamino)-2-hydroxypropylcarbamate |
| 16 | $H_2N$—$CH(CH_3)_2$ | tert-butyl (1S,2R)-1-benzyl-3-(isopropylamino)-2-hydroxypropylcarbamate |
| 17 | $H_2N$—$CH_2$-phenyl-4-$CH_3$ | tert-butyl (1S,2R)-1-benzyl-2-hydroxy-3-[(4-methylbenzyl)amino]propylcarbamate |
| 18 | $H_2N$—$(CH_2)_2$-phenyl-4-$OCH_3$ | tert-butyl (1S,2R)-1-benzyl-2-hydroxy-3-{[2-(4-methoxyphenyl)ethyl]amino}propylcarbamate |
| 19 | $H_2N$—$CH_2$-phenyl-3-$OCH_3$ | tert-butyl (1S,2R)-1-benzyl-2-hydroxy-3-[(3-methoxybenzyl)amino]propylcarbamate |
| 20 | $H_2N$—$CH$(-phenyl)-$CO$—$OC_2H_5$ | ethyl ({(2R,3S)-3-[(tert-butoxycarbonyl)amino]-2-hydroxy-4-phenylbutyl}amino)(phenyl) acetate |
| 21 | $H_2N$—$(CH_2)_2$-phenyl | tert-butyl (1S,2R)-1-benzyl-2-hydroxy-3-[(2-phenylethyl)amino]propylcarbamate |
| 22 | $H_2N$—$CH$(—$CH_2OH$)—$CH(OH)$-phenyl-4-$NO_2$ | tert-butyl (1S,2R)-1-benzyl-2-hydroxy-3-{[(1S)-2-hydroxy-1-(hydroxymethyl)-2-(4-nitrophenyl)ethyl]amino}propylcarbamate |

-continued

| Example No. | Column A<br>C-terminal amine<br>(VI) | Column B<br>Protected alcohol (VII) |
|---|---|---|
| 23 | $H_2N-CH_2$-phenyl-2-Cl | tert-butyl (1S,2R)-1-benzyl-3-[(2-chlorobenzyl)amino]-2-hydroxypropylcarbamate |
| 24 | $H_2N-CH_2$-phenyl-4-Cl | tert-butyl (1S,2R)-1-benzyl-3-[(4-chlorobenzyl)amino]-2-hydroxypropylcarbamate |
| 25 | $H_2N-(CH_2)_2-O-(CH_2)_2-OH$ | tert-butyl (1S,2R)-1-benzyl-2-hydroxy-3-{[2-(2-hydroxyethoxy)ethyl]amino}propylcarbamate |
| 26 | $H_2N$-1-indanyl | tert-butyl (1S,2R)-1-benzyl-3-(2,3-dihydro-1H-inden-1-ylamino)-2-hydroxypropylcarbamate |
| 27 | $H_2N-CH_2-CH(OH)-CH_3$ | tert-butyl (1S,2R)-1-benzyl-2-hydroxy-3-[(2-hydroxypropyl)amino]propylcarbamate |
| 28 | $H_2N-CH2$-tetrahydrofuranyl | tert-butyl (1S,2R)-1-benzyl-2-hydroxy-3-[(tetrahydro-2-furanylmethyl)amino]propylcarbamate |
| 29 | $H_2N-CH_2-CH(-OCH_2CH_3)$ | tert-butyl (1S,2R)-1-benzyl-3-[(2,2-diethoxyethyl)amino]-2-hydroxypropylcarbamate |
| 30 | $H_2N-(CH_2)_4-CH_3$ | tert-butyl (1S,2R)-1-benzyl-2-hydroxy-3-(pentylamino)propylcarbamate |
| 31 | $H_2N$-cyclohexyl | tert-butyl (1S,2R)-1-benzyl-3-(cyclohexylamino)-2-hydroxypropylcarbamate |
| 32 | $H_2N-CH_2$-pyridin-2-yl | tert-butyl (1S,2R)-1-benzyl-2-hydroxy-3-[(2-pyridinylmethyl)amino]propylcarbamate |
| 33 | $H_2N-CH_2$-phenyl-2-$NH_2$ | tert-butyl (1S,2R)-3-[(2-aminobenzyl)amino]-1-benzyl-2-hydroxypropylcarbamate |
| 34 | $H_2N-CH_2$-pyridin-3-yl | tert-butyl (1S,2R)-1-benzyl-2-hydroxy-3-[(3-pyridinylmethyl)amino]propylcarbamate |
| 35 | $H_2N-(CH_2)_2$-pyrrolidin-1-yl | tert-butyl (1S,2R)-1-benzyl-2-hydroxy-3-{[2-(1-pyrrolidinyl)ethyl]amino}propylcarbamate |
| 36 | $H_2N-CH_2-CH(OH)$-phenyl | tert-butyl (1S,2R)-1-benzyl-2-hydroxy-3-[(2-hydroxy-2-phenylethyl)amino]propylcarbamate |
| 37 | $H_2N-(CH_2)_3-O-(CH_2)_3-CH_3$ | tert-butyl (1S,2R)-1-benzyl-3-[(3-butoxypropyl)amino]-2-hydroxypropylcarbamate |
| 38 | $H_2N-(CH_2)_3-O-CH(CH_3)_2$ | tert-butyl (1S,2R)-1-benzyl-2-hydroxy-3-[(3-isopropoxypropyl)amino]propylcarbamate |
| 39 | $H_2N-(CH_2)_2-CH(CH_3)_2$ | tert-butyl (1S,2R)-1-benzyl-2-hydroxy-3-(isopentylamino)propylcarbamate |
| 40 | $H_2N-(CH_2)_3$-phenyl | tert-butyl (1S,2R)-1-benzyl-2-hydroxy-3-[(3-phenylpropyl)amino]propylcarbamate |
| 41 | $H_2N-(CH_2)_2-OCH_3$ | tert-butyl (1S,2R)-1-benzyl-2-hydroxy-3-[(2-methoxyethyl)amino]propylcarbamate |
| 42 | $H_2N-(CH_2)_2-O$-phenyl | tert-butyl (1S,2R)-1-benzyl-2-hydroxy-3-[(2-phenoxyethyl)amino]propylcarbamate |
| 43 | $H_2N-(CH_2)_2-O-(CH_2)_2-CH_3$ | tert-butyl (1S,2R)-1-benzyl-2-hydroxy-3-[(2-propoxyethyl)amino]propylcarbamate |
| 44 | $H_2N-(CH_2)_2-C(CH_3)_3$ | tert-butyl (1S,2R)-1-benzyl-3-[(3,3-dimethylbutyl)amino]-2-hydroxypropylcarbamate |
| 45 | $H_2N-(CH_2)_4$-phenyl | tert-butyl (1S,2R)-1-benzyl-2-hydroxy-3-[(4-phenylbutyl)amino]propylcarbamate |
| 46 | $H_2N-CH_2$-phenyl-3-I | tert-butyl (1S,2R)-1-benzyl-2-hydroxy-3-[(3-iodobenzyl)amino]propylcarbamate |
| 47 | $H_2N-CH_2$-phenyl-4-$NO_2$ | tert-butyl (1S,2R)-1-benzyl-2-hydroxy-3-[(4-nitrobenzyl)amino]propylcarbamate |

-continued

| Example No. | Column A<br>C-terminal amine (VI) | Column B<br>Protected alcohol (VII) |
|---|---|---|
| 48 | $H_2N-CH_2$-phenyl-3-Cl | tert-butyl (1S,2R)-1-benzyl-3-[(3-chlorobenzyl)amino]-2-hydroxypropylcarbamate |
| 49 | $H_2N-(CH_2)_2$-phenyl-4-Cl | tert-butyl (1S,2R)-1-benzyl-3-{[2-(4-chlorophenyl)ethyl]amino}-2-hydroxypropylcarbamate |
| 50 | $H_2N-(CH_2)_2$-pyridin-2-yl | tert-butyl (1S,2R)-1-benzyl-2-hydroxy-3-{[2-(2-pyridinyl)ethyl]amino}propylcarbamate |
| 51 | $H_2N-CH_2$-pyridin-4-yl | tert-butyl (1S,2R)-1-benzyl-2-hydroxy-3-[(4-pyridinylmethyl)amino]propylcarbamate |
| 52 | $H_2N-(CH_2)_2-$(N-methylpyrrolidin-2-yl) | tert-butyl (1S,2R)-1-benzyl-2-hydroxy-3-{[2-(1-methyl-2-pyrrolidinyl)ethyl]amino}propylcarbamate |
| 53 | $H_2N-CH_2$-phenyl-2,3-dimethyl | tert-butyl (1S,2R)-1-benzyl-3-[(2,3-dimethylbenzyl)amino]-2-hydroxypropylcarbamate |
| 54 | $H_2N-CH_2$-phenyl-2-$OCF_3$ | tert-butyl (1S,2R)-1-benzyl-2-hydroxy-3-{[2-(trifluoromethoxy)benzyl]amino}propylcarbamate |
| 55 | $H_2N-CH_2$-phenyl-2-Cl-6-O-phenyl | tert-butyl (1S,2R)-1-benzyl-3-[(2-chloro-6-phenoxybenzyl)amino]-2-hydroxypropylcarbamate |
| 56 | $H_2N-CH_2$-phenyl-4-$CF_3$ | tert-butyl (1S,2R)-1-benzyl-2-hydroxy-3-{[4-(trifluoromethyl)benzyl]amino}propylcarbamate |
| 57 | $H_2N-CH_2$-phenyl-2,3-dichloro | tert-butyl (1S,2R)-1-benzyl-3-[(2,3-dichlorobenzyl)amino]-2-hydroxypropylcarbamate |
| 58 | $H_2N-CH_2$-phenyl-3,5-dichloro | tert-butyl (1S,2R)-1-benzyl-3-[(3,5-dichlorobenzyl)amino]-2-hydroxypropylcarbamate |
| 59 | $H_2N-CH_2$-phenyl-3,5-difluoro | tert-butyl (1S,2R)-1-benzyl-3-[(3,5-difluorobenzyl)amino]-2-hydroxypropylcarbamate |
| 60 | $H_2N-CH_2$-phenyl-4-$OCF_3$ | tert-butyl (1S,2R)-1-benzyl-2-hydroxy-3-{[4-(trifluoromethoxy)benzyl]amino}propylcarbamate |
| 61 | $H_2N-(CH_2)_2$-phenyl-4-$SO_2-NH_2$ | tert-butyl (1S,2R)-3-{[4-(aminosulfonyl)benzyl]amino}-1-benzyl-2-hydroxypropylcarbamate |
| 62 | $H_2N-CH_2$-phenyl-4-$OCH_3$ | tert-butyl (1S,2R)-1-benzyl-2-hydroxy-3-[(4-methoxybenzyl)amino]propylcarbamate |
| 63 | $H_2N-CH_2$-phenyl-4-$CH_3$ | tert-butyl (1S,2R)-1-benzyl-2-hydroxy-3-[(4-methylbenzyl)amino]propylcarbamate |
| 64 | $H_2N-CH_2$-Ph-(3,4,5-trimethoxy) | tert-butyl (1S,2R)-1-benzyl-2-hydroxy-3-[(3,4,5-trimethoxybenzyl)amino]propylcarbamate |
| 65 | $H_2N-CH_2$-phenyl-3-$OCF_3$ | tert-butyl (1S,2R)-1-benzyl-2-hydroxy-3-{[3-(trifluoromethoxy)benzyl]amino}propylcarbamate |
| 66 | $H_2N-CH_2$-phenyl-3,5-dimethoxy | tert-butyl (1S,2R)-1-benzyl-3-[(3,5-dimethoxybenzyl)amino]-2-hydroxypropylcarbamate |
| 67 | $H_2N-CH_2$-phenyl-2,4-dimethoxy | tert-butyl (1S,2R)-1-benzyl-3-[(2,4-dimethoxybenzyl)amino]-2-hydroxypropylcarbamate |
| 68 | $H_2N-CH_2$-phenyl-phenyl | tert-butyl (1S,2R)-1-benzyl-3-[([1,1'-biphenyl]-3-ylmethyl)amino]-2-hydroxypropylcarbamate |
| 69 | $H_2N-CH_2$-phenyl-3,4-dichloro | tert-butyl (1S,2R)-1-benzyl-3-[(3,4-dichlorobenzyl)amino]-2-hydroxypropylcarbamate |
| 70 | $H_2N-CH_2$-phenyl-4-F | tert-butyl (1S,2R)-1-benzyl-3-[(4-fluorobenzyl)amino]-2-hydroxypropylcarbamate |
| 71 | $H_2N-CH_2$-phenyl-3-$CF_3$ | tert-butyl (1S,2R)-1-benzyl-2-hydroxy-3-{[3-(trifluoromethyl)benzyl]amino}propylcarbamate |

-continued

| Example No. | Column A C-terminal amine (VI) | Column B Protected alcohol (VII) |
|---|---|---|
| 72 | H$_2$N—CH$_2$-phenyl-2-CH$_3$ | tert-butyl (1S,2R)-1-benzyl-2-hydroxy-3-[(2-methylbenzyl)amino]propylcarbamate |
| 73 | H$_2$N—CH((R)—CH$_3$)-phenyl | tert-butyl (1S,2R)-1-benzyl-2-hydroxy-3-{[(1R)-1-phenylethyl]amino}propylcarbamate |
| 74 | H$_2$N—CH((S)—CH$_3$)-phenyl | tert-butyl (1S,2R)-1-benzyl-2-hydroxy-3-{[(1S)-1-phenylethyl]amino}propylcarbamate |
| 75 | H$_2$N—CH$_2$-phenyl-3,5-(bis)trifluoromethyl | tert-butyl (1S,2R)-1-benzyl-3-{[3,5-bis(trifluoromethyl)benzyl]amino}-2-hydroxypropylcarbamate |
| 76 | H$_2$N—CH$_2$-phenyl-2-CF$_3$ | tert-butyl (1S,2R)-1-benzyl-2-hydroxy-3-{[2-(trifluoromethyl)benzyl]amino}propylcarbamate |
| 77 | H$_2$N—CH((S)—CH$_3$)-(naphth-1-yl) | tert-butyl (1S,2R)-1-benzyl-2-hydroxy-3-{[(1S)-1-(1-naphthyl)ethyl]amino}propyl carbamate |
| 78 | —NH$_2$—CH((R)—CH$_3$)-(naphth-1-yl) | tert-butyl (1S,2R)-1-benzyl-2-hydroxy-3-{[(1R)-1-(1-naphthyl)ethyl]amino}propylcarbamate |
| 79 | H$_2$N—CH$_2$-phenyl-3-OCH$_3$-4-OH | tert-butyl (1S,2R)-1-benzyl-2-hydroxy-3-[(4-hydroxy-3-methoxybenzyl)amino]propylcarbamate |
| 80 | H$_2$N—CH$_2$-phenyl-3,4-dihydroxy | tert-butyl (1S,2R)-1-benzyl-3-[(3,4-dihydroxybenzyl)amino]-2-hydroxypropylcarbamate |
| 81 | H$_2$N—(CH$_2$)$_3$—OCH$_3$ | tert-butyl (1S,2R)-1-benzyl-2-hydroxy-3-[(3-methoxypropyl)amino]propylcarbamate |
| 82 | H$_2$N—CH((S)—CH$_3$)—CH$_2$—OH | tert-butyl (1S,2R)-1-benzyl-2-hydroxy-3-{[(1S)-2-hydroxy-1-methylethyl]amino}propyl carbamate |
| 83 | H$_2$N—CH((R)—CH$_3$)—CH$_2$—OH | tert-butyl (1S,2R)-1-benzyl-2-hydroxy-3-{[(1R)-2-hydroxy-1-methylethyl]amino}propyl carbamate |
| 84 | H$_2$N—CH$_2$—C≡CH | tert-butyl (1S,2R)-1-benzyl-2-hydroxy-3-(2-propynylamino)propylcarbamate |
| 85 | H$_2$N—(CH$_2$)$_2$-phenyl-2-F | tert-butyl (1S,2R)-1-benzyl-3-{[2-(2-fluorophenyl)ethyl] amino}-2-hydroxypropylcarbamate |
| 86 | H$_2$N—(CH$_2$)$_2$-phenyl-3-F | tert-butyl (1S,2R)-1-benzyl-3-{[2-(3-fluorophenyl)ethyl] amino}-2-hydroxypropyl carbamate |
| 87 | H$_2$N—(CH$_2$)$_2$-phenyl-4-F | tert-butyl (1S,2R)-1-benzyl-3-{[2-(4-fluorophenyl)ethyl] amino}-2-hydroxypropyl carbamate |
| 88 | H$_2$N—(CH$_2$)$_2$-phenyl-4-Br | tert-butyl (1S,2R)-1-benzyl-3-{[2-(4-bromophenyl)ethyl] amino}-2-hydroxypropyl carbamate |
| 89 | H$_2$N—(CH$_2$)$_2$-phenyl-3-OCH$_3$ | tert-butyl (1S,2R)-1-benzyl-2-hydroxy-3-{[2-(3-methoxyphenyl)ethyl]amino}propylcarbamate |
| 90 | H$_2$N—(CH$_2$)$_2$-phenyl-2,4-dichloro | tert-butyl (1S,2R)-1-benzyl-3-{[2-(2,4-dichlorophenyl)ethyl]amino}-2-hydroxypropylcarbamate |
| 91 | H$_2$N—(CH$_2$)$_2$-phenyl-3-Cl | tert-butyl (1S,2R)-1-benzyl-3-{[2-(3-chlorophenyl)ethyl]amino}-2-hydroxypropylcarbamate |
| 92 | H$_2$N—(CH$_2$)$_2$-phenyl-2,5-dimethoxy | tert-butyl (1S,2R)-1-benzyl-3-{[2-(2,5-dimethoxyphenyl)ethyl]amino}-2-hydroxypropylcarbamate |
| 93 | H$_2$N—(CH$_2$)$_2$-phenyl-4-CH$_3$ | tert-butyl (1S,2R)-1-benzyl-2-hydroxy-3-{[2-(4-methylphenyl)ethyl]amino}propylcarbamate |
| 94 | H$_2$N—CH(—(R)CH$_2$—OH)—CH$_2$-phenyl | tert-butyl (1S,2R)-1-benzyl-3-{[(1R)-1-benzyl-2-hydroxyethyl]amino}-2-hydroxypropylcarbamate |

-continued

| Example No. | Column A C-terminal amine (VI) | Column B Protected alcohol (VII) |
|---|---|---|
| 95 | H$_2$N—(CH$_2$)$_3$-(1-morpholinyl) | tert-butyl (1S,2R)-1-benzyl-2-hydroxy-3-{[3-(4-morpholinyl)propyl]amino}propylcarbamate |
| 96 | H$_2$N—CH$_2$—C(CH$_3$)$_2$ | tert-butyl (1S,2R)-1-benzyl-3-[(3,3-dimethylbutyl)amino]-2-hydroxypropylcarbamate |
| 97 | H$_2$N—(CH$_2$)$_2$-(1-morpholinyl) | tert-butyl (1S,2R)-1-benzyl-2-hydroxy-3-{[2-(4-morpholinyl)ethyl]amino}propylcarbamate |
| 98 | H$_2$N—CH(OH)—CH$_2$—CH$_3$ | tert-butyl (1S,2R)-1-benzyl-2-hydroxy-3-[(1-hydroxypropyl)amino]propylcarbamate |
| 99 | H$_2$N—(CH$_2$)$_2$-(thien-2-yl) | tert-butyl (1S,2R)-1-benzyl-2-hydroxy-3-[(2-thienylmethyl)amino]propylcarbamate |
| 100 | H$_2$N—(CH$_2$)$_4$—OH | tert-butyl (1S,2R)-1-benzyl-2-hydroxy-3-[(4-hydroxybutyl)amino]propylcarbamate |
| 101 | H$_2$N—CH(—(S)CH$_2$—OH)-phenyl | tert-butyl (1S,2R)-1-benzyl-2-hydroxy-3-{[(1S)-2-hydroxy-1-phenylethyl]amino} propylcarbamate |
| 102 | H$_2$N—CH$_2$-phenyl-2,4-dichloro | tert-butyl (1S,2R)-1-benzyl-3-[(2,4-dichlorobenzyl)amino]-2-hydroxypropylcarbamate |
| 103 | H$_2$N—CH(—(R)CH$_2$—OH)-phenyl | tert-butyl (1S,2R)-1-benzyl-2-hydroxy-3-{[(1R)-2-hydroxy-1-phenylethyl]amino} propylcarbamate |
| 104 | H$_2$N—CH$_2$-phenyl-4-C(CH$_3$)$_3$ | tert-butyl (1S,2R)-1-benzyl-3-[(4-tert-butylbenzyl)amino]-2-hydroxypropylcarbamate |
| 105 | H$_2$N—CH(CH$_3$)-phenyl | tert-butyl (1S,2R)-1-benzyl-2-hydroxy-3-[(1-phenylethyl)amino]propylcarbamate |
| 106 | H$_2$N—(1R,2S)-2-hydroxyinden-1-yl | tert-butyl (1S,2R)-1-benzyl-2-hydroxy-3-{[(1R,2S)-2-hydroxy-2,3-dihydro-1H-inden-1-yl]amino}propylcarbamate |
| 107 | H$_2$N—CH$_2$-phenyl-3,4-dimethyl | tert-butyl (1S,2R)-1-benzyl-3-[(3,4-dimethylbenzyl)amino]-2-hydroxypropylcarbamate |

Examples 108-164

Following the general procedure of Example 4 and making non-critical variations but reacting tert-butyl (1S)-2-(3,5-difluorophenyl)-1-[(2S)-oxiranyl]ethylcarbamate (V, EXAMPLE 3) with the C-terminal amine (VI) of Column A, the protected alcohol (VII) of Column B is obtained.

| EXA | Column A C-terminal amine (VI) | Column B Protected alcohol (VII) |
|---|---|---|
| 108 | H$_2$N—(CH$_2$)$_6$—CO—O—CH$_3$ | methyl 7-{[(2R,3S)-3-[(tert-butoxycarbonyl)amino]-4-(3,5-difluorophenyl)-2-hydroxybutyl]amino}heptanoate |
| 109 | H$_2$N—CH(—CH$_3$)—CO—NH—CH$_2$—CH(CH$_3$)$_2$ r/s | tert-butyl (1S,2R)-1-(3,5-difluorobenzyl)-2-hydroxy-3-{[2-(isobutylamino)-1-methyl-2-oxoethyl]amino}propylcarbamate |
| 110 | H$_2$N—CH((S)—CH$_3$)—CO—NH—CH$_2$—CH(CH$_3$)$_2$ | tert-butyl (1S,2R)-1-(3,5-difluorobenzyl)-2-hydroxy-3-{[(1S)-2-(isobutylamino)-1-methyl-2-oxoethyl]amino}propylcarbamate |
| 111 | H$_2$N—C(—CH$_3$)$_2$—CO—NH—CH$_2$—CH(CH$_3$)$_2$ | tert-butyl (1S,2R)-1-(3,5-difluorobenzyl)-2-hydroxy-3-{[2-(isobutylamino)-1,1-dimethyl-2-oxoethyl]amino}propylcarbamate |
| 112 | H$_2$N—CH$_2$—CO—NH—CH$_2$—CH(CH$_3$)$_2$ | tert-butyl (1S,2R)-1-(3,5-difluorobenzyl)-2-hydroxy-3-{[2- |

-continued

| EXA | Column A<br>C-terminal amine<br>(VI) | Column B<br>Protected alcohol (VII) |
|---|---|---|
| 113 | H$_2$N—CH((S)—CH$_2$CH$_3$)—CO—NH—CH$_2$—CH(CH$_3$)$_2$ | tert-butyl (1S,2R)-1-(3,5-difluorobenzyl)-2-hydroxy-3-({(1S)-1-[(isobutylamino)carbonyl]propyl}amino)propylcarbamate |
| 114 | H$_2$N—CH((R)—CH$_2$CH$_3$)—CO—NH—CH$_2$—CH(CH$_3$)$_2$ | tert-butyl (1S,2R)-1-(3,5-difluorobenzyl)-2-hydroxy-3-({(1R)-1-[(isobutylamino)carbonyl]propyl}amino)propylcarbamate |
| 115 | H$_2$N—CH$_2$-phenyl | tert-butyl (1S,2R)-3-(benzylamino)-1-(3,5-difluorobenzyl)-2-hydroxypropylcarbamate |
| 116 | H$_2$N—CH$_2$—CH$_3$ | tert-butyl (1S,2R)-1-(3,5-difluorobenzyl)-3-(ethylamino)-2-ydroxypropylcarbamate |
| 117 | H$_2$N—CH$_2$—CH(CH$_3$)$_2$ | tert-butyl (1S,2R)-1-(3,5-difluorobenzyl)-2-hydroxy-3-(isobutylamino)propylcarbamate |
| 118 | H$_2$N—CH$_2$—CH(CH$_3$)—CONH—CH$_2$—CH(CH$_3$)$_2$ | tert-butyl (1S,2R)-1-(3,5-difluorobenzyl)-2-hydroxy-3-{[3-(isobutylamino)-2-methyl-3-oxopropyl]amino}propylcarbamate |
| 119 | H$_2$N—CH$_2$-phenyl-4-N(CH$_3$)$_2$ | tert-butyl (1S,2R)-1-(3,5-difluorobenzyl)-3-{[4-(dimethylamino)benzyl]amino}-2-hydroxypropylcarbamate |
| 120 | H$_2$N—CH((S)—CH$_2$-phenyl)-CO—NH—CH$_2$—CH(CH$_3$)$_2$ | tert-butyl (1S,2R)-3-{[(1S)-1-(3,5-difluorobenzyl)-2-(isobutylamino)-2-oxoethyl]amino}-1-(3,5-difluorobenzyl)-2-hydroxypropylcarbamate |
| 121 | H$_2$N—CH((S)—CH(CH$_3$)$_2$)—CO—NH—CH$_2$—CH(CH$_3$)$_2$ | tert-butyl (1S,2R)-1-(3,5-difluorobenzyl)-2-hydroxy-3-({(1S)-1-[(isobutylamino)carbonyl]-3-methylbutyl}amino)propylcarbamate |
| 122 | H$_2$N—CH$_2$—CH$_2$N(CH$_3$)$_2$ | tert-butyl (1S,2R)-1-(3,5-difluorobenzyl)-3-{[2-(dimethylamino)ethyl]amino}-2-hydroxypropylcarbamate |
| 123 | H$_2$N—CH$_2$-(pyridin-3-yl) | tert-butyl (1S,2R)-1-(3,5-difluorobenzyl)-2-hydroxy-3-[(3-pyridinylmethyl)amino]propylcarbamate |
| 124 | H$_2$N—CH((S)—CH$_2$—O—CH$_2$-phenyl)-CO—NH—CH$_2$—CH(CH$_3$)$_2$ | tert-butyl (1S,2R)-3-{[(1S)-1-[(benzyloxy)methyl]-2-(isobutylamino)-2-oxoethyl]amino}-1-(3,5-difluorobenzyl)-2-hydroxypropylcarbamate |
| 125 | H$_2$N—C(—CH$_3$)$_2$-phenyl | tert-butyl (1S,2R)-1-(3,5-difluorobenzyl)-2-hydroxy-3-[(1-methyl-1-phenylethyl)amino]propylcarbamate |
| 126 | H$_2$N—CH((R)—CH(CH$_3$)$_2$)—CO—NH—CH$_2$—CH(CH$_3$)$_2$ | tert-butyl (1S,2R)-1-(3,5-difluorobenzyl)-2-hydroxy-3-({(1R)-1-[(isobutylamino)carbonyl]-3-methylbutyl}amino)propylcarbamate |
| 127 | H$_2$N—CH((S)—CH$_2$—CH$_2$—CH$_3$)-CO—NH—CH$_2$—CH(CH$_3$)$_2$ | tert-butyl (1S,2R)-1-(3,5-difluorobenzyl)-2-hydroxy-3-({(1S)-1-[(isobutylamino)carbonyl]butyl}amino)propylcarbamate |
| 128 | H$_2$N—CH((S)—CH$_2$—OH)—CO—NH—CH$_2$—CH(CH$_3$)$_2$ | tert-butyl (1S,2R)-1-(3,5-difluorobenzyl)-2-hydroxy-3-{[(1S)-1-(hydroxymethyl)-2-(isobutylamino)-2-oxoethyl]amino}propylcarbamate |

-continued

| EXA | Column A<br>C-terminal amine<br>(VI) | Column B<br>Protected alcohol (VII) |
|---|---|---|
| 129 | H₂N—CH₂—CH₂-phenyl | tert-butyl (1S,2R)-1-(3,5-difluorobenzyl)-2-hydroxy-3-[(2-phenylethyl)amino]propylcarbatmate |
| 130 | H₂N—CH((S)—CH₃)—CO—NH—CH₂-phenyl | tert-butyl (1S,2R)-3-{[2-(benzylamino)-1-methyl-2-oxoethyl]amino}-1-(3,5-difluorobenzyl)-2-hydroxypropylcarbamate |
| 131 | H₂N—CH((S)—CH₂—CH₃)-phenyl | tert-butyl (1S,2R)-1-(3,5-difluorobenzyl)-3-{[(1S)-2-(benzylamino)-1-methyl-2-oxoethyl]amino}-2-hydroxypropylcarbamate |
| 132 | H₂N—CH₂-phenyl-3-OCH₃ | tert-butyl (1S,2R)-1-(3,5-difluorobenzyl)-2-hydroxy-3-[(3-methoxybenzyl)amino]propylcarbamate |
| 133 | H₂N—CH((S)-phenyl)CO—NHCH₂CH(CH₃)₂ | tert-butyl (1S,2R)-1-(3,5-difluorobenzyl)-2-hydroxy-3-{[(1S)-2-(isobutylamino)-2-oxo-1-phenylethyl]amino}propylcarbamate |
| 134 | H₂N—CH₂—CH₂—CH(CH₃)₂ | tert-butyl (1S,2R)-1-(3,5-difluorobenzyl)-2-hydroxy-3-(isopentylamino)propylcarbamate |
| 135 | H₂N-cyclohexyl | tert-butyl (1S,2R)-1-(3,5-difluorobenzyl)-3-(cyclohexylamino)-2-hydroxypropylcarbamate |
| 136 | H₂N—(CH₂)₃—CH₃ | tert-butyl (1S,2R)-1-(3,5-difluorobenzyl)-3-(butylamino)-2-hydroxypropylcarbamate |
| 137 | H₂N—(CH₂)₃—O—CH₃ | tert-butyl (1S,2R)-1-(3,5-difluorobenzyl)-2-hydroxy-3-[(3-methoxypropyl)amino]propylcarbamate |
| 138 | H₂N—CH₂—CH(OH)-phenyl | tert-butyl (1S,2R)-1-(3,5-difluorobenzyl)-2-hydroxy-3-[(2-hydroxy-2-phenylethyl)amino]propylcarbamate |
| 139 | H₂N-cyclohexyl-3,5-dimethoxy | tert-butyl (1S,2R)-1-(3,5-difluorobenzyl)-3-{[(3R,5S)-3,5-dimethoxycyclohexyl]amino}-2-hydroxypropylcarbamate |
| 140 | H₂N-cyclohexyl-3,5-di-(—CO—OCH₃) | dimethyl (1R,3S)-5-({(2R,3S)-3-[(tert-butoxycarbonyl)amino]-2-hydroxy-4-phenylbutyl}amino)-1,3-cyclohexanedicarboxylate |
| 141 | H₂N-cyclohexyl-3,5-di-(—COOH) | (1R,3S)-5-({(2R,3S)-3-[(tert-butoxycarbonyl)amino]-2-hydroxy-4-phenylbutyl}amino)-1,3-cyclohexanedicarboxylic acid |
| 142 | H₂N—CH((R)—CH₂—CH₃)-phenyl | tert-butyl (1S,2R)-1-(3,5-difluorobenzyl)-2-hydroxy-3-{[(1R)-1-phenylpropyl]amino}propylcarbamate |
| 143 | H₂N—CH₂-phenyl-3-Cl | tert-butyl (1S,2R)-1-(3,5-difluorobenzyl)-3-[(3-chlorobenzyl)amino]-2-hydroxypropylcarbamate |
| 144 | H₂N—CH₂-phenyl-3-OCH₃ | tert-butyl (1S,2R)-1-(3,5-difluorobenzyl)-2-hydroxy-3-[(3-methoxybenzyl)amino]propylcarbamate |
| 145 | H₂N—CH₂-phenyl-phenyl | tert-butyl (1S,2R)-1-(3,5-difluorobenzyl)-3-[([1,1'-biphenyl]-3-ylmethyl)amino]-2-hydroxypropylcarbamate |
| 146 | H₂N—CH₂-phenyl-3-I | tert-butyl (1S,2R)-1-(3,5-difluorobenzyl)-2-hydroxy-3-[(3-iodobenzyl)amino]propylcarbamate |
| 147 | H₂N—CH₂-phenyl-3-CH₃ | tert-butyl (1S,2R)-1-(3,5-difluorobenzyl)-2-hydroxy-3-[(3-methylbenzyl)amino]propylcarbamate |
| 148 | H₂N—CH₂—CH(—CH₃)-phenyl | tert-butyl (1S,2R)-1-(3,5-difluorobenzyl)-2-hydroxy-3-[(2-phenylpropyl)amino]propylcarbamate |

-continued

| EXA | Column A<br>C-terminal amine<br>(VI) | Column B<br>Protected alcohol (VII) |
|---|---|---|
| 149 | $H_2N$—$CH_2$-(thiazol-5-yl) | tert-butyl (1S,2R)-1-(3,5-difluorobenzyl)-2-hydroxy-3-[(1,3-thiazol-5-ylmethyl)amino]propylcarbamate |
| 150 | $H_2N$—$CH_2$-(thien-2-yl) | tert-butyl (1S,2R)-1-(3,5-difluorobenzyl)-2-hydroxy-3-[(2-thienylmethyl)amino]propylcarbamate |
| 151 | $H_2N$-4-methoxytetralin-1-yl | tert-butyl (1S,2R)-1-(3,5-difluorobenzyl)-2-hydroxy-3-[(5-methoxy-1,2,3,4-tetrahydro-1-naphthalenyl)amino]propylcarbamate |
| 152 | $H_2N$—$CH_2$-pyrazin-2-yl | tert-butyl (1S,2R)-1-(3,5-difluorobenzyl)-2-hydroxy-3-[(2-pyrazinylmethyl)amino]propylcarbamate |
| 153 | $H_2N$—$CH_2$-phenyl-3,5-difluoro | tert-butyl (1S,2R)-1-(3,5-difluorobenzyl)-3-[(3,5-difluorobenzyl)amino]-2-hydroxypropylcarbamate |
| 154 | $H_2N$—$CH_2$-phenyl-3,4-methylenedioxy | tert-butyl (1S,2R)-3-[(1,3-benzodioxol-5-ylmethyl)amino]-1-(3,5-difluorobenzyl)-2-hydroxypropylcarbamate |
| 155 | $H_2N$—$CH_2$-phenyl-3,5-dimethoxy | tert-butyl (1S,2R)-1-(3,5-difluorobenzyl)-3-[(3,5-dimethoxybenzyl)amino]-2-hydroxypropylcarbamate |
| 156 | $H_2N$—$CH_2$-phenyl-3-$CF_3$ | tert-butyl (1S,2R)-1-(3,5-difluorobenzyl)-2-hydroxy-3-{[3-(trifluoromethyl)benzyl]amino}propylcarbamate |
| 157 | $H_2N$—$CH_2$-(furan-2-yl) | tert-butyl (1S,2R)-1-(3,5-difluorobenzyl)-3-[(2-furylmethyl)amino]-2-hydroxypropylcarbamate |
| 158 | $H_2N$-(7-methoxytetralin-1-yl) | tert-butyl (1S,2R)-1-(3,5-difluorobenzyl)-2-hydroxy-3-[(7-methoxy-1,2,3,4-tetrahydro-1-naphthalenyl)amino]propylcarbamate |
| 159 | $H_2N$—$CH_2$-phenyl-3-O—$CF_3$ | tert-butyl (1S,2R)-1-(3,5-difluorobenzyl)-2-hydroxy-3-{[3-(trifluoromethoxy)benzyl]amino}propylcarbamate |
| 160 | $H_2N$—$CH_2$-phenyl-3-F | tert-butyl (1S,2R)-1-(3,5-difluorobenzyl)-3-[(3-fluorobenzyl)amino]-2-hydroxypropylcarbamate |
| 161 | $H_2N$—$CH_2$-phenyl-3-O—$CH(CH_3)_2$ | tert-butyl (1S,2R)-1-(3,5-difluorobenzyl)-2-hydroxy-3-[(3-isopropoxybenzyl)amino]propylcarbamate |
| 162 | $H_2N$—$CH_2$-phenyl-3-Br | tert-butyl (1S,2R)-1-(3,5-difluorobenzyl)-3-[(3-bromobenzyl)amino]-2-hydroxypropylcarbamate |
| 163 | $H_2N$—$CH_2$-(5-methylfuran-2-yl) | tert-butyl (1S,2R)-1-(3,5 difluorobenzyl)-2-hydroxy-3-{[(5-methyl-2-furyl)methyl]amino}propylcarbamate |
| 164 | $H_2N$-(5-methoxytetralin-1-yl) | tert-butyl (1S,2R)-1-(3,5-difluorobenzyl)-2-hydroxy-3-[(5-methoxy-1,2,3,4-tetrahydro-1-naphthalenyl)amino]propylcarbamate |

Example 165 tert-Butyl-(1S,2R)-3-azido-1-(3,5-difluorobenzyl)-2-hydroxypropylcarbamate (XII)

Sodium azide (0.22 g, 4 mmole) and ammonium chloride (2 eq) are added to tert-butyl (1S)-2-(3,5-difluorophenyl)-1-[(2S)-oxiranyl]ethylcarbamate (V, EXAMPLE 3, 0.6 g, 2 mmole). The reaction is heated to 75-80 degrees C. and stirred for 16 hours. The reaction is monitored by TLC to insure completion. The solvent is removed under reduced pressure. The concentrate is partitioned between ethyl acetate and water, the phases are separated and the organic phase is washed with bicarbonate and saline, dried over anhydrous sodium sulfate and concentrated to give the title compound, TLC (ethyl acetate/hexane) $R_f$=0.45; MS ($MH^+$)=343.

Example 166

(2R,3S)-3-amino-1-azido-4-(3,5-difluorophenyl)-2-butanol (XIV)

tert-Butyl-(1S,2R)-3-azido-1-(3,5-difluorobenzyl)-2-hydroxypropylcarbamate (XII, EXAMPLE 165, 0.48 g, 1.41 mmole) is dissolved in dichloromethane (20 ml) to which trifluoroacetic acid (5 ml) is added. The reaction is stirred at 20-25 degrees C. for 16 hours and the solvent is removed under reduced pressure with heat. Ethyl acetate is added twice and evaporated twice to give the title compound as the trifluoroacetic acid salt which is used in the next reaction without further purification; MS (MH$^+$)=242.

Example 167

$N^1$-[(1S,2R)-3-azido-1-(3,5-difluorobenzyl)-2-hydroxypropyl]5-methyl-$N^3$,$N^3$-dipropylisophthalamide 0(XV)

To (2R,3S)-3-amino-1-azido-4-(3,5-difluorophenyl)-2-buta (XIV, EXAMPLE 166, 0.34 g, 1.4 mmole) in dichloromethane (20 ml) is added N,N-dipropylamidoisophthalic acid (IX, 0.53 g, 2 mmole), t-butyl alcohol (0.27 g, 2 mmole) and triethylamine (0.84 ml, 6 mmole) and ethyl-1-(3-dimethylaminopropyl)carbodiimide (0.58 g, 3 mmole). The mixture is stirred at 20-25 degrees C. for 16 hours. The reaction is monitored by TLC (methanol/dichloromethane, 20/80+ethyl acetate/hexane, 50/50; R$_f$=0.76). When the reaction is complete as measured by TLC, the reaction mixture is partitioned between dichloromethane and water, washed with hydrochloric acid (0.5 N), bicarbonate, saline, dried over anhydrous sodium sulfate and the solvent is removed under reduced pressure with heat to produce a concentrate. The concentrate is column chouromatographed on silica gel to give the title compound; MS (MH$^+$)=488.

Example 168

$N^1$-[(1S,2R)-3-amino-1-(3,5-difluorobenzyl)-2-hydroxypropyl]-5-methyl-$N^3$,$N^3$-dipropylisophthalamide acetic acid salt (XVI)

$N^1$-[(1S,2R)-3-azido-1-(3,5-difluorobenzyl)-2-hydroxypropyl]5-methyl-$N^3$,$N^3$-dipropylisophthalamide (XV, EXAMPLE 167, 0.3 g, 0.62 mmole) in ethyl acetate (20 ml) and acetic acid (5 ml) is placed in a Parr pressure bottle. Palladium on carbon (10%, 5 g) is added and the mixture shaken under hydrogen at 50 psi for 2 hours. The mixture is filtered through a diatomaceous earth and the filtrate is concentrated to give the title compound; MS (MH$^+$)=462.

Example 169

$N^1$-{(1S,2R)-1-(3,5-difluorobenzyl)-3-[(2-furylmethyl)amino]-2-hydroxypropyl}-5-methyl-$N^3$,$N^3$-dipropylisophthalamide (X)

$N^1$-[(1S,2R)-3-amino-1-(3,5-difluorobenzyl)-2-hydroxypropyl]-5-methyl-$N^3$,$N^3$-dipropylisophthalamide acetic acid salt (XVI, EXAMPLE 168, 76 mg, 0.146 mmol) is dissolved in absolute ethanol (2 mL). 3-Furaldehyde (20 microL, 0.231 mmol) and triethylamine (30 microL, 0.215 mmol) are added via syringe, with stirring at 20-25 degrees C. After 10 minutes, palladium on carbon 122 mg, 5 weight %) is added and the mixture placed under a hydrogen atmosphere (50 psi) and shaken for 20 minutes. The resulting mixture is then filtered through diatomaceous earth, with ethanol washings. The filtrate is purified by flash chromatography (2-10% methanol/methylene chloride) to give purified title compound, MS (MH$^+$)=542.2.

Example 169a tert-butyl (1S,2R)-1-(3,5-difluorobenzyl)-3-{[(1S)-2-(ethylamino)-1-methyl-2-oxoethyl]amino}-2-hydroxypropylcarbamate (VII)

Following the general procedure of EXAMPLEs 4 and 14-164 and making non-critical variations and reacting tert-butyl (1S)-2-(3,5-difluorophenyl)-1-[(2S)-oxiranyl]ethylcarbamate (V, EXAMPLE 3) with (2S)-2-amino-N-ethylpropanamide (VI), the title compound is obtained.

Examples 170-320

Following the general procedure of Example 5 and making non-critical variations but starting with the protected alcohol (VII) of Column A, the amine (VIII) of Column B is obtained.

Column A lists the Protected Alcohols (VII) by reference to a specific Example number above.

| EXA | A | Column B<br>Amine (VIII) |
|---|---|---|
| 170 | 14 | (2R,3S)-3-amino-1-(ethylamino)-4-phenyl-2-butanol |
| 171 | 15 | (2R,3S)-3-amino-1-(benzylamino)-4-phenyl-2-butanol |
| 172 | 16 | (2R,3S)-3-amino-1-(isopropylamino)-4-phenyl-2-butanol |
| 173 | 17 | (2R,3S)-3-amino-1-[(4-methylbenzyl)amino]-4-phenyl-2-butanol |
| 174 | 18 | (2R,3S)-3-amino-1-{[2-(4-methoxyphenyl)ethyl]amino}-4-phenyl-2-butanol |
| 175 | 19 | (2R,3S)-3-amino-1-[(3-methoxybenzyl)amino]-4-phenyl-2-butanol |
| 176 | 20 | ethyl {[(2R,3S)-3-amino-2-hydroxy-4-phenylbutyl]amino}(phenyl)acetate |
| 177 | 21 | (2R,3S)-3-amino-4-phenyl-1-[(2-phenylethyl)amino]-2-butanol |
| 178 | 22 | (2S)-2-{[(2R,3S)-3-amino-2-hydroxy-4-phenylbutyl]amino}-1-(4-nitrophenyl)-1,3-propanediol |
| 179 | 23 | (2R,3S)-3-amino-1-[(2-chlorobenzyl)amino]-4-phenyl-2-butanol |
| 180 | 24 | (2R,3S)-3-amino-1-[(4-chlorobenzyl)amino]-4-phenyl-2-butanol |
| 181 | 25 | (2R,3S)-3-amino-1-{[2-(2-hydroxyethoxy)ethyl]amino}-4-phenyl-2-butanol |
| 182 | 26 | (2R,3S)-3-amino-1-(2,3-dihydro-1H-inden-1-ylamino)-4-phenyl-2-butanol |
| 183 | 27 | (2R,3S)-3-amino-1-[(2-hydroxypropyl)amino]-4-phenyl-2-butanol |
| 184 | 28 | (2R,3S)-3-amino-4-phenyl-1-[(tetrahydro-2-furanylmethyl)amino]-2-butanol |
| 185 | 29 | (2R,3S)-3-amino-1-[(2,2-diethoxyethyl)amino]-4-phenyl-2-butanol |
| 186 | 30 | (2R,3S)-3-amino-1-(butylamino)-4-phenyl-2-butanol |
| 187 | 31 | (2R,3S)-3-amino-1-(cyclohexylamino)-4-phenyl-2-butanol |
| 188 | 32 | (2R,3S)-3-amino-4-phenyl-1-[(2-pyridinylmethyl)amino]-2-butanol |
| 189 | 33 | (2R,3S)-3-amino-1-[(2-aminobenzyl)amino]-4-phenyl-2-butanol |
| 190 | 34 | (2R,3S)-3-amino-4-phenyl-1-[(3-pyridinylmethyl)amino]-2-butanol |
| 191 | 35 | (2R,3S)-3-amino-4-phenyl-1-{[2-(1-pyrrolidinyl)ethyl]amino}-2-butanol |
| 192 | 36 | (2R,3S)-3-amino-1-[(2-hydroxy-2-phenylethyl)amino]-4-phenyl-2-butanol |

-continued

| EXA | A | Column B<br>Amine (VIII) |
|---|---|---|
| 193 | 37 | (2R,3S)-3-amino-1-[(3-butoxypropyl)amino]-4-phenyl-2-butanol |
| 194 | 38 | (2R,3S)-3-amino-1-[(3-isopropoxypropyl)amino]-4-phenyl-2-butanol |
| 195 | 39 | (2R,3S)-3-amino-1-(isopentylamino)-4-phenyl-2-butanol |
| 196 | 40 | (2R,3S)-3-amino-4-phenyl-1-[(3-phenylpropyl)amino]-2-butanol |
| 197 | 41 | (2R,3S)-3-amino-1-[(2-methoxyethyl)amino]-4-phenyl-2-butanol |
| 198 | 42 | (2R,3S)-3-amino-1-[(2-phenoxyethyl)amino]-4-phenyl-2-butanol |
| 199 | 43 | (2R,3S)-3-amino-4-phenyl-1-[(2-propoxyethyl)amino]-2-butanol |
| 200 | 44 | (2R,3S)-3-amino-1-[(3,3-dimethylbutyl)amino]-4-phenyl-2-butanol |
| 201 | 45 | (2R,3S)-3-amino-4-phenyl-1-[(4-phenylbutyl)amino]-2-butanol |
| 202 | 46 | (2R,3S)-3-amino-1-[(3-iodobenzyl)amino]-4-phenyl-2-butanol |
| 203 | 47 | (2R,3S)-3-amino-1-[(4-nitrobenzyl)amino]-4-phenyl-2-butanol |
| 204 | 48 | (2R,3S)-3-amino-1-[(3-chlorobenzyl)amino]-4-phenyl-2-butanol |
| 205 | 49 | (2R,3S)-3-amino-1-{[2-(4-chlorophenyl)ethyl]amino}-4-phenyl-2-butanol |
| 206 | 50 | (2R,3S)-3-amino-4-phenyl-1-{[2-(2-pyridinyl)ethyl]amino}-2-butanol |
| 207 | 51 | (2R,3S)-3-amino-4-phenyl-1-[(4-pyidinylmethyl)amino]-2-butanol |
| 208 | 52 | (2R,3S)-3-amino-1-{[2-(1-methyl-2-pyrrolidinyl)ethyl]amino}-4-phenyl-2-butanol |
| 209 | 53 | (2R,3S)-3-amino-1-[(2,3-dimethylbenzyl)amino]-4-phenyl-2-butanol |
| 210 | 54 | (2R,3S)-3-amino-4-phenyl-1-{[2-(trifluoromethoxy)benzyl]amino}-2-butanol |
| 211 | 55 | (2R,3S)-3-amino-1-[(2-chloro-6-phenoxybenzyl)amino]-4-phenyl-2-butanol |
| 212 | 56 | (2R,3S)-3-amino-4-phenyl-1-{[4-(trifluoromethyl)benzyl]amino}-2-butanol |
| 213 | 57 | (2R,3S)-3-amino-1-[(2,3-dichlorobenzyl)amino]-4-phenyl-2-butanol |
| 214 | 58 | (2R,3S)-3-amino-1-[(3,5-dichlorobenzyl)amino]-4-phenyl-2-butanol |
| 215 | 59 | (2R,3S)-3-amino-1-[(3,5-difluorobenzyl)amino]-4-phenyl-2-butanol |
| 216 | 60 | (2R,3S)-3-amino-4-phenyl-1-{[4-(trifluoromethoxy)benzyl]amino}-2-butanol |
| 217 | 61 | 4-({[(2R,3S)-3-amino-2-hydroxy-4-phenyl butyl]amino}methyl)benzenesulfonamide |
| 218 | 62 | (2R,3S)-3-amino-1-[(4-methoxybenzyl)amino]-4-phenyl-2-butanol |
| 219 | 63 | (2R,3S)-3-amino-1-[(4-methylbenzyl)amino]-4-phenyl-2-butanol |
| 220 | 64 | (2R,3S)-3-amino-4-phenyl-1-[(3,4,5-trimethoxybenzyl)amino]-2-butanol |
| 221 | 65 | (2R,3S)-3-amino-4-phenyl-1-{[3-(trifluoromethoxy)benzyl]amino}-2-butanol |
| 222 | 66 | (2R,3S)-3-amino-1-[(3,5-dimethoxybenzyl)amino]-4-phenyl-2-butanol |
| 223 | 67 | (2R,3S)-3-amino-1-[(2,4-dimethoxybenzyl)amino]-4-phenyl-2-butanol |
| 224 | 68 | (2R,3S)-3-amino-1-[([1,1'-biphenyl]-3-ylmethyl)amino]-4-phenyl-2-butanol |
| 225 | 69 | (2R,3S)-3-amino-1-[(3,4-dichlorobenzyl)amino]-4-phenyl-2-butanol |
| 226 | 70 | (2R,3S)-3-amino-1-[(2-fluorobenzyl)amino]-4-phenyl-2-butanol |
| 227 | 71 | (2R,3S)-3-amino-4-phenyl-1-{[3-(trifluoromethyl)benzyl]amino}-2-butanol |
| 228 | 72 | (2R,3S)-3-amino-1-[(2-methylbenzyl)amino]-4-phenyl-2-butanol |
| 229 | 73 | (2R,3S)-3-amino-4-phenyl-1-{[(1R)-1-phenylethyl]amino}-2-butanol |
| 230 | 74 | (2R,3S)-3-amino-4-phenyl-1-{[(1S)-1-phenylethyl]amino}-2-butanol |
| 231 | 75 | (2R,3S)-3-amino-1-{[3,5-bis(trifluoromethyl)benzyl]amino}-4-phenyl-2-butanol |
| 232 | 76 | (2R,3S)-3-amino-4-phenyl-1-{[2-(trifluoromethyl)benzyl]amino}-2-butanol |
| 233 | 77 | (2R,3S)-3-amino-1-{[(1S)-1-(1-naphthyl)ethyl]amino}-4-phenyl-2-butanol |
| 234 | 78 | (2R,3S)-3-amino-1-{[(1R)-1-(1-naphthyl)ethyl]amino}-4-phenyl-2-butanol |
| 235 | 79 | 4-({[(2R,3S)-3-amino-2-hydroxy-4-phenylbutyl]amino}methyl)-2-methoxyphenol |
| 236 | 80 | 4-({[(2R,3S)-3-amino-2-hydroxy-4-phenylbutyl]amino}methyl)-1,2-benzenediol |
| 237 | 81 | (2R,3S)-3-amino-1-[(3-methoxypropyl)amino]-4-phenyl-2-butanol |
| 238 | 82 | (2R,3S)-3-amino-1-{[(1S)-2-hydroxy-1-methylethyl]amino}-4-phenyl-2-butanol |
| 239 | 83 | (2R,3S)-3-amino-1-{[(1R)-2-hydroxy-1-methylethyl]amino}-4-phenyl-2-butanol |
| 240 | 84 | (2R,3S)-3-amino-4-phenyl-1-(2-propynylamino)-2-butanol |
| 241 | 85 | (2R,3S)-3-amino-1-{[2-(2-fluorophenyl)ethyl]amino}-4-phenyl-2-butanol |
| 242 | 86 | (2R,3S)-3-amino-1-{[2-(3-fluorophenyl)ethyl]amino}-4-phenyl-2-butanol |
| 243 | 87 | (2R,3S)-3-amino-1-{[2-(4-fluorophenyl)ethyl]amino}-4-phenyl-2-butanol |
| 244 | 88 | (2R,3S)-3-amino-1-{[2-(4-bromophenyl)ethyl]amino}-4-phenyl-2-butanol |
| 245 | 89 | (2R,3S)-3-amino-1-{[2-(3-methoxyphenyl)ethyl]amino}-4-phenyl-2-butanol |
| 246 | 90 | (2R,3S)-3-amino-1-{[2-(2,4-dichlorophenyl)ethyl]amino}-4-phenyl-2-butanol |
| 247 | 91 | (2R,3S)-3-amino-1-{[2-(3-chlorophenyl)ethyl]amino}-4-phenyl-2-butanol |
| 248 | 92 | (2R,3S)-3-amino-1-{[2-(2,5-dimethoxyphenyl)ethyl]amino}-4-phenyl-2-butanol |
| 249 | 93 | (2R,3S)-3-amino-1-{[2-(4-methylphenyl)ethyl]amino}-4-phenyl-2-butanol |
| 250 | 94 | (2R,3S)-3-amino-1-{[(1R)-1-benzyl-2-hydroxyethyl]amino}-4-phenyl-2-butanol |
| 251 | 95 | (2R,3S)-3-amino-1-{[3-(4-morpholinyl)propyl]amino}-4-phenyl-2-butanol |
| 252 | 96 | (2R,3S)-3-amino-1-(isobutylamino)-4-phenyl-2-butanol |
| 253 | 97 | (2R,3S)-3-amino-1-{[2-(4-morpholinyl)ethyl]amino}-4-phenyl-2-butanol |
| 254 | 98 | (2R,3S)-3-amino-4-phenyl-1-[(2-hydroxybutyl)amino]-2-butanol |
| 255 | 99 | (2R,3S)-3-amino-4-phenyl-1-{[2-(2-thienyl)ethyl]amino}-2-butanol |
| 256 | 100 | 4-{[(2R,3S)-3-amino-2-hydroxy-4-phenylbutyl]amino}-1-butanol |
| 257 | 101 | (2R,3S)-3-amino-1-{[(1S)-2-hydroxy-1-phenylethyl]amino}-4-phenyl-2-butanol |
| 258 | 102 | (2R,3S)-3-amino-1-[(2,4-dichlorobenzyl)amino]-4-phenyl-2-butanol |
| 259 | 103 | (2R,3S)-3-amino-1-{[(1R)-2-hydroxy-1-phenylethyl]amino}-4-phenyl-2-butanol |
| 260 | 104 | (2R,3S)-3-amino-1-[(4-tert-butylbenzyl)amino]-4-phenyl-2-butanol |
| 261 | 105 | (2R,3S)-3-amino-4-phenyl-1-[(1-phenylethyl)amino]-2-butanol |
| 262 | 106 | (1R,2S)-1-{[(2R,3S)-3-amino-2-hydroxy-4-phenylbutyl]amino}-2,3-dihydro-1H-inden-2-ol |
| 263 | 107 | (2R,3S)-3-amino-1-[(3,4-dimethylbenzyl)amino]-4-phenyl-2-butanol |
| 264 | 108 | methyl 7-{[(2R,3S)-3-amino-4-(3,5-difluorophenyl)-2-hydroxybutyl]amino}heptanoate |
| 265 | 109 | 2-{[(2R,3S)-3-amino-4-(3,5-difluorophenyl)-2-hydroxybutyl]amino}-N-isobutylpropanamide |
| 266 | 110 | (2S)-2-{[(2R,3S)-3-amino-4-(3,5-difluorophenyl)-2-hydroxybutyl]amino}-N-isobutylpropanamide |
| 267 | 111 | 2-{[(2R,3S)-3-amino-4-(3,5-difluorophenyl)-2-hydroxybutyl]amino}-N-isobutyl-2-methylpropanamide |

-continued

| EXA | A | Column B Amine (VIII) |
|---|---|---|
| 268 | 112 | 2-{[(2R,3S)-3-amino-4-(3,5-difluorophenyl)-2-hydroxybutyl]amino}-N-isobutylacetamide |
| 269 | 113 | (2S)-2-{[(2R,3S)-3-amino-4-(3,5-difluorophenyl)-2-hydroxybutyl]amino}-N-isobutylbutanamide |
| 270 | 114 | (2R)-2-{[(2R,3S)-3-amino-4-(3,5-difluorophenyl)-2-hydroxybutyl]amino}-N-isobutylbutanamide |
| 271 | 115 | (2R,3S)-3-amino-1-(benzylamino)-4-(3,5-difluorophenyl)-2-butanol |
| 272 | 116 | (2R,3S)-3-amino-4-(3,5-difluorophenyl)-1-(ethylamino)-2-butanol |
| 273 | 117 | (2R,3S)-3-amino-4-(3,5-difluorophenyl)-1-(isobutylamino)-2-butanol |
| 274 | 118 | 3-{[(2R,3S)-3-amino-4-(3,5-difluorophenyl)-2-hydroxybutyl]amino}-N-isobutyl-2-methylpropanamide |
| 275 | 119 | (2R,3S)-3-amino-4-(3,5-difluorophenyl)-1-{[4-(dimethylamino)benzyl]amino}-2-butanol |
| 276 | 120 | (2S)-2-{[(2R,3S)-3-amino-4-(3,5-difluorophenyl)-2-hydroxybutyl]amino}-N-isobutyl-3-phenylpropanamide |
| 277 | 121 | (2S)-2-{[(2R,3S)-3-amino-4-(3,5-difluorophenyl)-2-hydroxybutyl]amino}-N-isobutyl-3-methylbutanamide |
| 278 | 122 | (2R,3S)-3-amino-4-(3,5-difluorophenyl)-1-{[2-(dimethylamino)ethyl]amino}-2-butanol |
| 279 | 123 | (2R,3S)-3-amino-4-(3,5-difluorophenyl)-1-[(3-pyridinylmethyl)amino]-2-butanol |
| 280 | 124 | (2S)-2-{[(2R,3S)-3-amino-4-(3,5-difluorophenyl)-2-hydroxybutyl]amino}-3-(benzyloxy)-N-isobutylpropanamide |
| 281 | 125 | (2R,3S)-3-amino-4-(3,5-difluorophenyl)-1-[(1-methyl-1-phenylethyl)amino]-2-butanol |
| 282 | 126 | (2R)-2-{[(2R,3S)-3-amino-4-(3,5-difluorophenyl)-2-hydroxybutyl]amino}-N-isobutyl-3-methylbutanamide |
| 283 | 127 | (2S)-2-{[(2R,3S)-3-amino-4-(3,5-difluorophenyl)-2-hydroxybutyl]amino}-N-isobutylpentanamide |
| 284 | 128 | (2S)-2-{[(2R,3S)-3-amino-4-(3,5-difluorophenyl)-2-hydroxybutyl]amino}-3-hydroxy-N-isobutylpropanamide |
| 285 | 129 | (2R,3S)-3-amino-4-(3,5-difluorophenyl)-1-[(2-phenylethyl)amino]-2-butanol |
| 286 | 130 | (2S)-2-{[(2R,3S)-3-amino-4-(3,5-difluorophenyl)-2-hydroxybutyl]amino}-N-benzylpropanamide |
| 287 | 131 | (2R,3S)-3-amino-4-(3,5-difluorophenyl)-1-{[(1S)-1-phenylpropyl]amino}-2-butanol |
| 287a | 169a | (2S)-2-{[(2R,3S)-3-amino-4-(3,5-difluorophenyl)-2-hydroxybutyl]amino}-N-ethylpropanamide |
| 288 | 132 | (2R,3S)-3-amino-4-(3,5-difluorophenyl)-1-[(3-methoxybenzyl)amino]-2-butanol |
| 289 | 133 | (2S)-2-{[(2R,3S)-3-amino-4-(3,5-difluorophenyl)-2-hydroxybutyl]amino}-N-isobutyl-2-phenylethanamide |
| 290 | 134 | (2R,3S)-3-amino-4-(3,5-difluorophenyl)-1-(isopentylamino)-2-butanol |
| 291 | 135 | (2R,3S)-3-amino-1-(cyclohexylamino)-4-(3,5-difluorophenyl)-2-butanol |
| 292 | 136 | (2R,3S)-3-amino-1-(butylamino)-4-(3,5-difluorophenyl)-2-butanol |
| 293 | 137 | (2R,3S)-3-amino-4-(3,5-difluorophenyl)-1-[(3-methoxypropyl)amino]-2-butanol |
| 294 | 138 | (2R,3S)-3-amino-4-(3,5-difluorophenyl)-1-[(2-hydroxy-2-phenylethyl)amino]-2-butanol |
| 295 | 139 | (2R,3S)-3-amino-4-(3,5-difluorophenyl)-1-{[(3R,5S)-3,5-dimethoxycyclohexyl]amino}-2-butanol |
| 296 | 140 | dimethyl (1R,3S)-5-{[(2R,3S)-3-amino-4-(3,5-difluorophenyl)-2-hydroxybutyl]amino}-1,3-cyclohexanedicarboxylate |
| 297 | 141 | (1R,3S)-5-{[(2R,3S)-3-amino-4-(3,5-difluorophenyl)-2-hydroxybutyl]amino}-1,3-cyclohexanedicarboxylic acid |
| 298 | 142 | (2R,3S)-3-amino-4-(3,5-difluorophenyl)-1-{[(1R)-1-phenylpropyl]amino}-2-butanol |
| 299 | 143 | (2R,3S)-3-amino-1-[(3-chlorobenzyl)amino]-4-(3,5-difluorophenyl)-2-butanol |
| 300 | 144 | (2R,3S)-3-amino-4-(3,5-difluorophenyl)-1-[(3-methoxybenzyl)amino]-2-butanol |
| 301 | 145 | (2R,3S)-3-amino-1-[([1,1'-biphenyl]-3-ylmethyl)amino]-4-(3,5-difluorophenyl)-2-butanol |
| 302 | 146 | (2R,3S)-3-amino-4-(3,5-difluorophenyl)-1-[(3-iodobenzyl)amino]-2-butanol |
| 303 | 147 | (2R,3S)-3-amino-4-(3,5-difluorophenyl)-1-[(3-methylbenzyl)amino]-2-butanol |
| 304 | 148 | (2R,3S)-3-amino-4-(3,5-difluorophenyl)-1-[(2-phenylpropyl)amino]-2-butanol |
| 305 | 149 | (2R,3S)-3-amino-4-(3,5-difluorophenyl)-1-[(1,3-thiazol-5-ylmethyl)amino]-2-butanol |
| 306 | 150 | (2R,3S)-3-amino-4-(3,5-difluorophenyl)-1-[(2-thienylmethyl)amino]-2-butanol |
| 307 | 151 | (2R,3S)-3-amino-4-(3,5-difluorophenyl)-1-[(5-methoxy-1,2,3,4-tetrahydro-1-naphthalenyl)amino]-2-butanol |
| 308 | 152 | (2R,3S)-3-amino-4-(3,5-difluorophenyl)-1-[(2-pyrazinylmethyl)amino]-2-butanol |
| 309 | 153 | (2R,3S)-3-amino-1-[(3,5-difluorobenzyl)amino]-4-(3,5-difluorophenyl)-2-butanol |
| 310 | 154 | (2R,3S)-3-amino-1-[(1,3-benzodioxol-5-ylmethyl)amino]-4-(3,5-difluorophenyl)-2-butanol |
| 311 | 155 | (2R,3S)-3-amino-4-(3,5-difluorophenyl)-1-[(3,5-dimethoxybenzyl)amino]-2-butanol |
| 312 | 156 | (2R,3S)-3-amino-4-(3,5-difluorophenyl)-1-{[3-(trifluoromethyl)benzyl]amino}-2-butanol |
| 313 | 157 | (2R,3S)-3-amino-4-(3,5-difluorophenyl)-1-[(2-furylmethyl)amino]-2-butanol |
| 314 | 158 | (2R,3S)-3-amino-4-(3,5-difluorophenyl)-1-[(7-methoxy-1,2,3,4-tetrahydro-1-naphthalenyl)amino]-2-butanol |
| 315 | 159 | (2R,3S)-3-amino-4-(3,5-difluorophenyl)-1-{[3-(trifluoromethoxy)benzyl]amino}-2-butanol |
| 316 | 160 | (2R,3S)-3-amino-4-(3,5-difluorophenyl)-1-[(3-fluorobenzyl)amino]-2-butanol |
| 317 | 161 | (2R,3S)-3-amino-4-(3,5-difluorophenyl)-1-[(3-isopropoxybenzyl)amino]-2-butanol |
| 318 | 162 | (2R,3S)-3-amino-1-[(3-bromobenzyl)amino]-4-(3,5-difluorophenyl)-2-butanol |
| 319 | 163 | (2R,3S)-3-amino-4-(3,5-difluorophenyl)-1-[(5-methyl-2-furylmethyl)amino]-2-butanol |
| 320 | 164 | (2R,3S)-3-amino-4-(3,5-difluorophenyl)-1-[(5-methoxy-1,2,3,4-tetrahydro-1-naphthalenyl)amino]-2-butanol |

The following compounds can be prepared using essentially the general procedures outlined and examples described above and elsewhere in this document.

| EXA | |
|---|---|
| 321 | $N^1$-[(1S,2R)-1-benzyl-3-(ethylamino)-2-hydroxypropyl]-$N^3$,$N^3$-dipropylisophthalamide |
| 322 | $N^1$-[(1S,2R)-1-benzyl-3-(benzylamino)-2-hydroxypropyl]-$N^3$,$N^3$-dipropylisophthalamide |
| 323 | $N^1$-[(1S,2R)-1-benzyl-2-hydroxy-3-(isopropylamino)propyl]-$N^3$,$N^3$-dipropylisophthalamide |
| 324 | $N^1$-[(1S,2R)-1-benzyl-2-hydroxy-3-(4-toluidino)propyl]-$N^3$,$N^3$-dipropylisophthalamide |

| EXA | |
|---|---|
| 325 | N$^1$-((1S,2R)-1-benzyl-2-hydroxy-3-{[2-(4-methoxyphenyl)ethyl]amino} propyl)-N$^3$,N$^3$-ipropylisophthalamide |
| 326 | N$^1$-{(1S,2R)-1-benzyl-2-hydroxy-3-[(3-methoxybenzyl)amino]propyl}-N$^3$,N$^3$-dipropylisophthalamide |
| 327 | ethyl {[(3S)-3-({3-[(dipropylamino) carbonyl] benzoyl}amino)-2-hydroxy-4-phenylbutyl]amino}(phenyl)acetate |
| 329 | N$^1$-((1S)-1-benzyl-2-hydroxy-3-{[(1S)-2-hydroxy-1-(hydroxymethyl)-2-(4-nitrophenyl)ethyl]amino}propyl)-N$^3$,N$^3$-dipropylisophthalamide |
| 330 | N$^1$-{(1S,2R)-1-benzyl-3-[(2-chlorobenzyl)amino]-2-hydroxypropyl}-N$^3$,N$^3$-dipropylisophthalamide |
| 331 | N$^1$-{(1S,2R)-1-benzyl-3-[(4-chlorobenzyl)amino]-2-hydroxypropyl}-N$^3$,N$^3$-dipropylisophthalamide |
| 332 | N$^1$-((1S,2R)-1-benzyl-2-hydroxy-3-{[2-(2-hydroxyethoxy) ethyl]amino}propyl)-N$^3$,N$^3$-dipropylisophthalamide |
| 333 | N$^1$-[(1S,2R)-1-benzyl-3-(2,3-dihydro-1H-inden-1-ylamino)-2-hydroxypropyl]-N$^3$,N$^3$-dipropylisophthalamide |
| 334 | N$^1$-{(1S,2R)-1-benzyl-2-hydroxy-3-[(2-hydroxypropyl)amino]propyl}-N$^3$,N$^3$-dipropylisophthalamide |
| 335 | N$^1$-{(1S,2R)-1-benzyl-2-hydroxy-3-[(tetrahydro-2-furanylmethyl)amino]propyl}-N$^3$,N$^3$-dipropylisophthalamide |
| 336 | N$^1$-{(1S,2R)-1-benzyl-3-[(2,2-diethoxyethyl)amino]-2-hydroxypropyl}-N$^3$,N$^3$-dipropylisophthalamide |
| 337 | N$^1$-[(1S,2R)-1-benzyl-3-(butylamino)-2-hydroxypropyl]-N$^3$,N$^3$-dipropylisophthalamide |
| 338 | N$^1$-[(1S,2R)-1-benzyl-3-(cyclohexylamino)-2-hydroxypropyl]-N$^3$,N$^3$-dipropylisophthalamide |
| 339 | N$^1$-{(1S,2R)-1-benzyl-2-hydroxy-3-[(2-pyridinylmethyl)amino]propyl}-N$^3$,N$^3$-dipropylisophthalamide |
| 340 | N$^1$-{(1S,2R)-3-[(2-aminobenzyl)amino]-1-benzyl-2-hydroxypropyl}-N$^3$,N$^3$-dipropylisophthalamide |
| 341 | N$^1$-{(1S,2R)-1-benzyl-2-hydroxy-3-[(3-pyridinylmethyl)amino]propyl}-N$^3$,N$^3$-dipropylisophthalamide |
| 342 | N$^1$-((1S,2R)-1-benzyl-2-hydroxy-3-{[2-(1-pyrrolidinyl)ethyl] amino} propyl)-N$^3$,N$^3$-dipropylisophthalamide |
| 343 | N$^1$-{(1S,2R)-1-benzyl-2-hydroxy-3-[(2-hydroxy-2-phenylethyl)amino]propyl}-N$^3$,N$^3$-dipropylisophthalamide |
| 344 | N$^1$-{(1S,2R)-1-benzyl-3-[(3-butoxypropyl)amino]-2-hydroxypropyl}-N$^3$,N$^3$-dipropylisophthalamide |
| 345 | N$^1$-{(1S,2R)-1-benzyl-2-hydroxy-3-[(3-isopropoxypropyl)amino]propyl}-N$^3$,N$^3$-dipropylisophthalamide |
| 346 | N$^1$-[(1S,2R)-1-benzyl-2-hydroxy-3-(isopentylamino)propyl]-N$^3$,N$^3$-dipropylisophthalamide |
| 347 | N$^1$-{(1S,2R)-1-benzyl-2-hydroxy-3-[(3-phenylpropyl)amino]propyl}-N$^3$,N$^3$-dipropylisophthalamide |
| 348 | N$^1$-{(1S,2R)-1-benzyl-2-hydroxy-3-[(2-methoxyethyl)amino]propyl}-N$^3$,N$^3$-dipropylisophthalamide |
| 349 | N$^1$-{(1S,2R)-1-benzyl-2-hydroxy-3-[(2-phenoxyethyl)amino]propyl}-N$^3$,N$^3$-dipropylisophthalamide |
| 350 | N$^1$-{(1S,2R)-1-benzyl-2-hydroxy-3-[(2-phenoxyethyl)amino]propyl}-N$^3$,N$^3$-dipropylisophthalamide |
| 351 | N$^1$-{(1S,2R)-1-benzyl-3-[(3,3-dimethylbutyl)amino]-2-hydroxypropyl}-N$^3$,N$^3$-dipropylisophthalamide |
| 352 | N$^1$-{(1S,2R)-1-benzyl-2-hydroxy-3-[(4-phenylbutyl)amino]propyl}-N$^3$,N$^3$-dipropylisophthalamide |
| 353 | N$^1$-{(1S,2R)-1-benzyl-2-hydroxy-3-[(3-iodobenzyl)amino]propyl}-N$^3$,N$^3$-dipropylisophthalamide |
| 354 | N$^1$-{(1S)-1-benzyl-2-hydroxy-3-[(4-nitrobenzyl)amino]propyl}-N$^3$,N$^3$-dipropylisophthalamide |
| 355 | N$^1$-{(1S,2R)-1-benzyl-3-[(3-chlorobenzyl)amino]-2-hydroxypropyl}-N$^3$,N$^3$-dipropylisophthalamide |
| 356 | N$^1$-((1S,2R)-1-benzyl-3-{[2-(4-chlorophenyl)ethyl]amino}-2-hydroxypropyl)-N$^3$,N$^3$-dipropylisophthalamide |
| 357 | N$^1$-((1S,2R)-1-benzyl-2-hydroxy-3-{[2-(2-pyridinyl)ethyl]amino}propyl)-N$^3$,N$^3$-dipropylisophthalamide |
| 358 | N$^1$-{(1S,2R)-1-benzyl-2-hydroxy-3-[(4-pyridinylmethyl)amino]propyl}-N$^3$,N$^3$-dipropylisophthalamide |
| 359 | N$^1$-((1S,2R)-1-benzyl-2-hydroxy-3-{[2-(1-methyl-2-pyrrolidinyl)ethyl]amino}propyl)-N$^3$,N$^3$-dipropylisophthalamide |
| 360 | N$^1$-{(1S,2R)-1-benzyl-3-[(2,3-dimethylbenzyl)amino]-2-hydroxypropyl}-N$^3$,N$^3$-dipropylisophthalamide |
| 361 | N$^1$-((1S,2R)-1-benzyl-2-hydroxy-3-{[2-(trifluoromethoxy) benzyl]amino}propyl)-N$^3$,N$^3$-dipropylisophthalamide |
| 362 | N$^1$-{(1S,2R)-1-benzyl-3-[(2-chloro-6-phenoxybenzyl)amino]-2-hydroxypropyl}-N$^3$,N$^3$-dipropylisophthalamide |

| EXA | |
|---|---|
| 363 | N$^1$-((1S,2R)-1-benzyl-2-hydroxy-3-{[4-(trifluoromethyl)benzyl]amino}propyl)-N$^3$,N$^3$-dipropylisophthalamide |
| 364 | N$^1$-{(1S,2R)-1-benzyl-3-[(2,3-dichlorobenzyl)amino]-2-hydroxypropyl}-N$^3$,N$^3$-dipropylisophthalamide |
| 365 | N$^1$-{(1S,2R)-1-benzyl-3-[(3,5-dichlorobenzyl)amino]-2-hydroxypropyl}-N$^3$,N$^3$-dipropylisophthalamide |
| 366 | N$^1$-{(1S,2R)-1-benzyl-3-[(3,5-difluorobenzyl)amino]-2-hydroxypropyl}-N$^3$,N$^3$-dipropylisophthalamide |
| 367 | N$^1$-((1S,2R)-1-benzyl-2-hydroxy-3-{[4-(trifluoromethoxy)benzyl]amino}propyl)-N$^3$,N$^3$-dipropylisophthalamide |
| 368 | N$^1$-[(1S,2R)-3-({2-[4-(aminosulfonyl)phenyl]ethyl}amino)-1-benzyl-2-hydroxypropyl]-N$^3$,N$^3$-dipropylisophthalamide |
| 369 | N$^1$-{(1S,2R)-1-benzyl-2-hydroxy-3-[(4-methoxybenzyl)amino]propyl}-N$^3$,N$^3$-dipropylisophthalamide |
| 370 | N$^1$-{(1S,2R)-1-benzyl-2-hydroxy-3-[(4-methylbenzyl)amino]propyl}-N$^3$,N$^3$-dipropylisophthalamide |
| 371 | N$^1$-{(1S,2R)-1-benzyl-2-hydroxy-3-[(3,4,5-trimethoxybenzyl)amino]propyl}-N$^3$,N$^3$-dipropylisophthalamide |
| 372 | N$^1$-((1S,2R)-1-benzyl-2-hydroxy-3-{[3-(trifluoromethoxy)benzyl]amino} propyl)-N$^3$,N$^3$-dipropylisophthalamide |
| 373 | N$^1$-{(1S,2R)-1-benzyl-3-[(3,5-dimethoxybenzyl)amino]-2-hydroxypropyl}-N$^3$,N$^3$-dipropylisophthalamide |
| 374 | N$^1$-{(1S,2R)-1-benzyl-3-[(2,4-dimethoxybenzyl)amino]-2-hydroxypropyl}-N$^3$,N$^3$-dipropylisophthalamide |
| 375 | N$^1$-{(1S,2R)-1-benzyl-3-[([1,1'-biphenyl]-3-ylmethyl)amino]-2-hydroxypropyl}-N$^3$,N$^3$-dipropylisophthalamide |
| 376 | N$^1$-{(1S,2R)-1-benzyl-3-[(3,4-dichlorobenzyl)amino]-2-hydroxypropyl}-N$^3$,N$^3$-dipropylisophthalamide |
| 377 | N$^1$-{(1S,2R)-1-benzyl-3-[(2-fluorobenzyl)amino]-2-hydroxypropyl}-N$^3$,N$^3$-dipropylisophthalamide |
| 378 | N$^1$-((1S,2R)-1-benzyl-2-hydroxy-3-{[3-(trifluoromethyl)benzyl]amino} propyl)-N$^3$,N$^3$-dipropylisophthalamide |
| 379 | N$^1$-{(1S,2R)-1-benzyl-2-hydroxy-3-[(2-methylbenzyl)amino]propyl}-N$^3$,N$^3$-dipropylisophthalamide |
| 380 | N$^1$-((1S,2R)-1-benzyl-2-hydroxy-3-{[(1R)-1-phenylethyl]amino}propyl)-N$^3$,N$^3$-dipropylisophthalamide |
| 381 | N$^1$-((1S,2R)-1-benzyl-2-hydroxy-3-{[(1S)-1-phenylethyl]amino}propyl)-N$^3$,N$^3$-dipropylisophthalamide |
| 382 | N$^1$-((1S,2R)-1-benzyl-3-{[3,5-bis(trifluoromethyl)benzyl]amino}-2-hydroxypropyl)-N$^3$,N$^3$-dipropylisophthalamide |
| 383 | N$^1$-((1S,2R)-1-benzyl-2-hydroxy-3-{[2-(trifluoromethyl)benzyl]amino} propyl)-N$^3$,N$^3$-dipropylisophthalamide |
| 384 | N$^1$-((1S,2R)-1-benzyl-2-hydroxy-3-{[(1S)-1-(1-naphthyl)ethyl]amino}propyl)-N$^3$,N$^3$-dipropylisophthalamide |
| 385 | N$^1$-((1S,2R)-1-benzyl-2-hydroxy-3-{[(1R)-1-(1-naphthyl)ethyl]amino}propyl)-N$^3$,N$^3$-dipropylisophthalamide |
| 386 | N$^1$-{(1S,2R)-1-benzyl-2-hydroxy-3-[(4-hydroxy-3-methoxybenzyl)amino]propyl}-N$^3$,N$^3$-dipropylisophthalamide |
| 387 | N$^1$-{(1S,2R)-1-benzyl-3-[(3,4-dihydroxybenzyl)amino]-2-hydroxypropyl}-N$^3$,N$^3$-dipropylisophthalamide |
| 388 | N$^1$-{(1S)-1-benzyl-2-hydroxy-3-[(3-methoxypropyl)amino]propyl}-N$^3$,N$^3$-dipropylisophthalamide |
| 389 | N$^1$-((1S,2R)-1-benzyl-2-hydroxy-3-{[(1S)-2-hydroxy-1-methylethyl]amino}propyl)-N$^3$,N$^3$-dipropylisophthalamide |
| 390 | N$^1$-((1S,2R)-1-benzyl-2-hydroxy-3-{[(1R)-2-hydroxy-1-methylethyl]amino}propyl)-N$^3$,N$^3$-dipropylisophthalamide |
| 391 | N$^1$-[(1S,2R)-1-benzyl-2-hydroxy-3-(2-propynylamino)propyl]-N$^3$,N$^3$-dipropylisophthalamide |
| 392 | N$^1$-((1S,2R)-1-benzyl-3-{[2-(2-fluorophenyl)ethyl]amino}-2-hydroxypropyl)-N$^3$,N$^3$-dipropylisophthalamide |
| 393 | N$^1$-((1S,2R)-1-benzyl-3-{[2-(3-fluorophenyl)ethyl]amino}-2-hydroxypropyl)-N$^3$,N$^3$-dipropylisophthalamide |
| 394 | N$^1$-((1S,2R)-1-benzyl-3-{[2-(4-fluorophenyl)ethyl]amino}-2-hydroxypropyl)-N$^3$,N$^3$-dipropylisophthalamide |
| 395 | N$^1$-((1S,2R)-1-benzyl-3-{[2-(4-bromophenyl)ethyl]amino}-2-hydroxypropyl)-N$^3$,N$^3$-dipropylisophthalamide |
| 396 | N$^1$-((1S)-1-benzyl-2-hydroxy-3-{[2-(3-methoxyphenyl)ethyl]amino}propyl)-N$^3$,N$^3$-dipropylisophthalamide |
| 397 | N$^1$-((1S,2R)-1-benzyl-3-{[2-(2,4-dichlorophenyl)ethyl]amino}-2-hydroxypropyl)-N$^3$,N$^3$-dipropylisophthalamide |
| 398 | N$^1$-((1S,2R)-1-benzyl-3-{[2-(3-chlorophenyl)ethyl]amino}-2-hydroxypropyl)-N$^3$,N$^3$-dipropylisophthalamide |

| EXA | |
|---|---|
| 399 | N$^1$-((1S)-1-benzyl-3-{[2-(2,5-dimethoxyphenyl)ethyl]amino}-2-hydroxypropyl)-N$^3$,N$^3$-dipropylisophthalamide |
| 400 | N$^1$-((1S,2R)-1-benzyl-2-hydroxy-3-{[2-(4-methylphenyl)ethyl]amino}propyl)-N$^3$,N$^3$-dipropylisophthalamide |
| 401 | N$^1$-((1S,2R)-1-benzyl-3-{[(1R)-1-benzyl-2-hydroxyethyl]amino}-2-hydroxypropyl)-N$^3$,N$^3$-dipropylisophthalamide |
| 402 | N$^1$-((1S,2R)-1-benzyl-2-hydroxy-3-{[3-(4-morpholinyl)propyl]amino}propyl)-N$^3$,N$^3$-dipropylisophthalamide |
| 403 | N$^1$-[(1S,2R)-1-benzyl-2-hydroxy-3-(isobutylamino)propyl]-N$^3$,N$^3$-dipropylisophthalamide |
| 404 | N$^1$-((1S,2R)-1-benzyl-2-hydroxy-3-{[2-(4-morpholinyl)ethyl]amino}propyl)-N$^3$,N$^3$-dipropylisophthalamide |
| 405 | N$^1$-{(1S,2R)-1-benzyl-2-hydroxy-3-[(2-hydroxybutyl)amino]propyl}-N$^3$,N$^3$-dipropylisophthalamide |
| 406 | N$^1$-((1S,2R)-1-benzyl-2-hydroxy-3-{[2-(2-thienyl)ethyl]amino}propyl)-N$^3$,N$^3$-dipropylisophthalamide |
| 407 | N$^1$-{(1S,2R)-1-benzyl-2-hydroxy-3-[(4-hydroxybutyl)amino]propyl}-N$^3$,N$^3$-dipropylisophthalamide |
| 408 | N$^1$-((1S,2R)-1-benzyl-2-hydroxy-3-{[(1S)-2-hydroxy-1-phenylethyl]amino}propyl)-N$^3$,N$^3$-dipropylisophthalamide |
| 409 | N$^1$-{(1S,2R)-1-benzyl-3-[(2,4-dichlorobenzyl)amino]-2-hydroxypropyl}-N$^3$,N$^3$-dipropylisophthalamide |
| 410 | N$^1$-((1S,2R)-1-benzyl-2-hydroxy-3-{[(1R)-2-hydroxy-1-phenylethyl]amino}propyl)-N$^3$,N$^3$-dipropylisophthalamide |
| 411 | N$^1$-{(1S,2R)-1-benzyl-3-[(4-tert-butylbenzyl)amino]-2-hydroxypropyl}-N$^3$,N$^3$-dipropylisophthalamide |
| 412 | N$^1$-{(1S,2R)-1-benzyl-2-hydroxy-3-[(1-phenylethyl)amino]propyl}-N$^3$,N$^3$-dipropylisophthalamide |
| 413 | N$^1$-((1S,2R)-1-benzyl-2-hydroxy-3-{[(1R,2S)-2-hydroxy-2,3-dihydro-1H-inden-1-yl]amino}propyl)-N$^3$,N$^3$-dipropylisophthalamide |
| 414 | N$^1$-{(1S,2R)-1-benzyl-3-[(3,4-dimethylbenzyl)amino]-2-hydroxypropyl}-N$^3$,N$^3$-dipropylisophthalamide |
| 416 | N$^1$-((1S,2R)-1-(3,5-difluorobenzyl)-2-hydroxy-3-{[2-(isobutylamino)-1-methyl-2-oxoethyl]amino}propyl)-N$^3$,N$^3$-dipropylisophthalamide |
| 417 | N$^1$-((1S,2R)-1-(3,5-difluorobenzyl)-2-hydroxy-3-{[(1S)-2-(isobutylamino)-1-methyl-2-oxoethyl]amino}propyl)-N$^3$,N$^3$-dipropylisophthalamide |
| 418 | N$^1$-((1S,2R)-1-(3,5-difluorobenzyl)-2-hydroxy-3-{[(1S)-2-(isobutylamino)-1-methyl-2-oxoethyl]amino}propyl)-N$^5$,N$^5$-dipropyl-3,5-pyridinedicarboxamide |
| 419 | N$^1$-((1S,2R)-1-(3,5-difluorobenzyl)-2-hydroxy-3-{[2-(isobutylamino)-1,1-dimethyl-2-oxoethyl]amino}propyl)-5-methyl-N$^3$,N$^3$-dipropylisophthalamide |
| 420 | N$^1$-((1S,2R)-1-(3,5-difluorobenzyl)-2-hydroxy-3-{[2-(isobutylamino)-2-oxoethyl]amino}propyl)-5-methyl-N$^3$,N$^3$-dipropylisophthalamide |
| 421 | N$^1$-[(1S,2R)-1-(3,5-difluorobenzyl)-2-hydroxy-3-({(1S)-1-[(isobutylamino)carbonyl]propyl}amino)propyl]-5-methyl-N$^3$,N$^3$-dipropylisophthalamide |
| 422 | N$^1$-[(1S,2R)-1-(3,5-difluorobenzyl)-2-hydroxy-3-({(1R)-1-[(isobutylamino)carbonyl]propyl}amino)propyl]-5-methyl-N$^3$,N$^3$-dipropylisophthalamide |
| 423 | N$^1$-[(1S,2R)-3-(benzylamino)-1-(3,5-difluorobenzyl)-2-hydroxypropyl]-5-methyl-N$^3$,N$^3$-dipropylisophthalamide |
| 424 | N$^1$-[(1S,2R)-1-(3,5-difluorobenzyl)-3-(ethylamino)-2-hydroxypropyl]-5-methyl-N$^3$,N$^3$-dipropylisophthalamide |
| 425 | N$^1$-[(1S,2R)-1-(3,5-difluorobenzyl)-2-hydroxy-3-(isobutylamino)propyl]-5-methyl-N$^3$,N$^3$-dipropylisophthalamide |
| 426 | N$^1$-((1S,2R)-1-(3,5-difluorobenzyl)-2-hydroxy-3-{[3-(isobutylamino)-2-methyl-3-oxopropyl]amino}propyl)-5-methyl-N$^3$,N$^3$-dipropylisophthalamide |
| 427 | N$^1$-((1S,2R)-1-(3,5-difluorobenzyl)-3-{[4-(dimethylamino)benzyl]amino}-2-hydroxypropyl)-5-methyl-N$^3$,N$^3$-dipropylisophthalamide |
| 428 | N$^1$-[(1S,2R)-3-{[(1S)-1-benzyl-2-(isobutylamino)-2-oxoethyl]amino}-1-(3,5-difluorobenzyl)-2-hydroxypropyl]-5-methyl-N$^3$,N$^3$-dipropylisophthalamide |
| 429 | N$^1$-[(1S,2R)-1-(3,5-difluorobenzyl)-2-hydroxy-3-({(1S)-1-[(isobutylamino)carbonyl]-2-methylpropyl}amino)propyl]-5-methyl-N$^3$,N$^3$-dipropylisophthalamide |
| 430 | N$^1$-((1S,2R)-1-(3,5-difluorobenzyl)-3-{[2-(dimethylamino)ethyl]amino}-2-hydroxypropyl)-5-methyl-N$^3$,N$^3$-dipropylisophthalamide |
| 431 | N$^1$-{(1S,2R)-1-(3,5-difluorobenzyl)-2-hydroxy-3-[(3-pyridinylmethyl)amino]propyl}-5-methyl-N$^3$,N$^3$-dipropylisophthalamide |

| EXA | |
|---|---|
| 432 | N$^1$-[(1S,2R)-3-{[(1S)-1-[(benzyloxy)methyl]-2-(isobutylamino)-2-oxoethyl]amino}-1-(3,5-difluorobenzyl)-2-hydroxypropyl]-5-methyl-N$^3$,N$^3$-dipropylisophthalamide |
| 433 | N$^1$-{(1S,2R)-1-(3,5-difluorobenzyl)-2-hydroxy-3-[(1-methyl-1-phenylethyl)amino]propyl}-5-methyl-N$^3$,N$^3$-dipropylisophthalamide |
| 434 | N$^1$-[(1S,2R)-1-(3,5-difluorobenzyl)-2-hydroxy-3-({(1R)-1-[(isobutylamino)carbonyl]-2-methylpropyl}amino)propyl]-5-methyl-N$^3$,N$^3$-dipropylisophthalamide |
| 435 | N$^1$-[(1S,2R)-1-(3,5-difluorobenzyl)-2-hydroxy-3-({(1S)-1-[(isobutylamino)carbonyl]butyl}amino)propyl]-5-methyl-N$^3$,N$^3$-dipropylisophthalamide |
| 436 | N$^1$-((1S,2R)-1-(3,5-difluorobenzyl)-2-hydroxy-3-{[(1S)-1-(hydroxymethyl)-2-(isobutylamino)-2-oxoethyl]amino}propyl)-5-methyl-N$^3$,N$^3$-dipropylisophthalamide |
| 437 | N$^1$-{(1S,2R)-1-(3,5-difluorobenzyl)-2-hydroxy-3-[(2-phenylethyl)amino]propyl}-5-methyl-N$^3$,N$^3$-dipropylisophthalamide |
| 438 | N$^1$-[(1S,2R)-3-{[(1S)-2-(benzylamino)-1-methyl-2-oxoethyl]amino}-1-(3,5-difluorobenzyl)-2-hydroxypropyl]-5-methyl-N$^3$,N$^3$-dipropylisophthalamide |
| 439 | N$^1$-((1S,2R)-1-(3,5-difluorobenzyl)-2-hydroxy-3-{[(1S)-1-phenylpropyl]amino}propyl)-5-methyl-N$^3$,N$^3$-dipropylisophthalamide |
| 440 | N$^1$-((1S,2R)-1-(3,5-difluorobenzyl)-3-{[(1S)-2-(ethylamino)-1-methyl-2-oxoethyl]amino}-2-hydroxypropyl)-5-methyl-N$^3$,N$^3$-dipropylisophthalamide |
| 441 | N$^1$-((1S,2R)-1-(3,5-difluorobenzyl)-2-hydroxy-3-{[(1S)-2-(isobutylamino)-2-oxo-1-phenylethyl]amino}propyl)-5-methyl-N$^3$,N$^3$-dipropylisophthalamide |
| 442 | N$^1$-[(1S,2R)-1-(3,5-difluorobenzyl)-2-hydroxy-3-(isopentylamino)propyl]-5-methyl-N$^3$,N$^3$-dipropylisophthalamide |
| 443 | N$^1$-[(1S,2R)-3-(cyclohexylamino)-1-(3,5-difluorobenzyl)-2-hydroxypropyl]-5-methyl-N$^3$,N$^3$-dipropylisophthalamide |
| 444 | N$^1$-[(1S,2R)-3-(butylamino)-1-(3,5-difluorobenzyl)-2-hydroxypropyl]-5-methyl-N$^3$,N$^3$-dipropylisophthalamide |
| 445 | N$^1$-{(1S,2R)-1-(3,5-difluorobenzyl)-2-hydroxy-3-[(3-methoxypropyl)amino]propyl}-5-methyl-N$^3$,N$^3$-dipropylisophthalamide |
| 446 | N$^1$-{(1S,2R)-1-(3,5-difluorobenzyl)-2-hydroxy-3-[(2-hydroxy-2-phenylethyl)amino]propyl}-5-methyl-N$^3$,N$^3$-dipropylisophthalamide |
| 447 | N$^1$-((1S,2R)-1-(3,5-difluorobenzyl)-3-{[(3R,5S)-3,5-dimethoxycyclohexyl]amino}-2-hydroxypropyl)-5-methyl-N$^3$,N$^3$-dipropylisophthalamide |
| 448 | dimethyl (1R,3S)-5-{[(2R,3S)-4-(3,5-difluorophenyl)-3-({3-[(dipropylamino)carbonyl]-5-methylbenzoyl}amino)-2-hydroxybutyl]amino}-1,3-cyclohexanedicarboxylate |
| 449 | (1R,3S)-5-{[(2R,3S)-4-(3,5-difluorophenyl)-3-({3-[(dipropylamino)carbonyl]-5-methylbenzoyl}amino)-2-hydroxybutyl]amino}-1,3-cyclohexanedicarboxylic acid |
| 450 | N$^1$-((1S,2R)-1-(3,5-difluorobenzyl)-2-hydroxy-3-{[(1R)-1-phenylpropyl]amino}propyl)-5-methyl-N$^3$,N$^3$-dipropylisophthalamide |
| 451 | N$^1$-[(1S,2R)-3-[(3-chlorobenzyl)amino]-1-(3,5-difluorobenzyl)-2-hydroxypropyl]-5-methyl-N$^3$,N$^3$-dipropylisophthalamide |
| 452 | N$^1$-{(1S,2R)-1-(3,5-difluorobenzyl)-2-hydroxy-3-[(3-methoxybenzyl)amino]propyl}-3-[(2-propylpentyl)sulfonyl]benzamide |
| 453 | N$^1$-[(1S,2R)-3-[([1,1'-biphenyl]-3-ylmethyl)amino]-1-(3,5-difluorobenzyl)-2-hydroxypropyl]-5-methyl-N$^3$,N$^3$-dipropylisophthalamide |
| 454 | N$^1$-{(1S,2R)-1-(3,5-difluorobenzyl)-2-hydroxy-3-[(3-iodobenzyl)amino]propyl}-5-methyl-N$^3$,N$^3$-dipropylisophthalamide |
| 455 | N$^1$-{(1S,2R)-1-(3,5-difluorobenzyl)-2-hydroxy-3-[(3-methylbenzyl)amino]propyl}-5-methyl-N$^3$,N$^3$-dipropylisophthalamide |
| 456 | N$^1$-{(1S,2R)-1-(3,5-difluorobenzyl)-2-hydroxy-3-[(2-phenylpropyl)amino]propyl}-5-methyl-N$^3$,N$^3$-dipropylisophthalamide |
| 457 | N$^1$-{(1S,2R)-1-(3,5-difluorobenzyl)-2-hydroxy-3-[(1,3-thiazol-5-ylmethyl)amino]propyl}-5-methyl-N$^3$,N$^3$-dipropylisophthalamide |
| 458 | N$^1$-{(1S,2R)-1-(3,5-difluorobenzyl)-2-hydroxy-3-[(2-thienylmethyl)amino]propyl}-5-methyl-N$^3$,N$^3$-dipropylisophthalamide |
| 459 | N$^1$-{(1S,2R)-1-(3,5-difluorobenzyl)-2-hydroxy-3-[(5-methoxy-1,2,3,4-tetrahydro-1-naphthalenyl)amino]propyl}-5-methyl-N$^3$,N$^3$-dipropylisophthalamide |
| 460 | N$^1$-{(1S,2R)-1-(3,5-difluorobenzyl)-2-hydroxy-3-[(2-pyrazinylmethyl)amino]propyl}-5-methyl-N$^3$,N$^3$-dipropylisophthalamide |
| 461 | N$^1$-{(1S,2R)-1-(3,5-difluorobenzyl)-3-[(3,5-difluorobenzyl)amino]-2-hydroxypropyl}-5-methyl-N$^3$,N$^3$-dipropylisophthalamide |
| 462 | N$^1$-{(1S,2R)-3-[(1,3-benzodioxol-5-ylmethyl)amino]-1-benzyl-2-hydroxypropyl}-N$^3$,N$^3$-dipropylisophthalamide |

| EXA | |
|---|---|
| 463 | $N^1$-{(1S,2R)-1-(3,5-difluorobenzyl)-3-[(3,5-dimethoxybenzyl)amino]-2-hydroxypropyl}-5-methyl-$N^3$,$N^3$-dipropylisophthalamide |
| 464 | $N^1$-((1S,2R)-1-(3,5-difluorobenzyl)-2-hydroxy-3-{[3-(trifluoromethyl)benzyl]amino}propyl)-5-methyl-$N^3$,$N^3$-dipropylisophthalamide |
| 466 | Racemic $N^1$-{(1S,2R)-1-(3,5-difluorobenzyl)-2-hydroxy-3-[(7-methoxy-1,2,3,4-tetrahydro-1-naphthalenyl)amino]propyl}-5-methyl-$N^3$,$N^3$-dipropylisophthalamide |
| 467 | $N^1$-((1S,2R)-1-(3,5-difluorobenzyl)-2-hydroxy-3-{[3-(trifluoromethoxy)benzyl]amino}propyl)-5-methyl-$N^3$,$N^3$-dipropylisophthalamide |
| 468 | $N^1$-{(1S,2R)-1-(3,5-difluorobenzyl)-3-[(3-fluorobenzyl)amino]-2-hydroxypropyl}-5-methyl-$N^3$,$N^3$-dipropylisophthalamide |
| 469 | $N^1$-{(1S,2R)-1-(3,5-difluorobenzyl)-2-hydroxy-3-[(3-isopropoxybenzyl)amino]propyl}-5-methyl-$N^3$,$N^3$-dipropylisophthalamide |
| 470 | $N^1$-[(1S,2R)-3-[(3-bromobenzyl)amino]-1-(3,5-difluorobenzyl)-2-hydroxypropyl]-5-methyl-$N^3$,$N^3$-dipropylisophthalamide |
| 471 | $N^1$-((1S,2R)-1-(3,5-difluorobenzyl)-2-hydroxy-3-{[(5-methyl-2-furyl)methyl]amino}propyl)-5-methyl-$N^3$,$N^3$-dipropylisophthalamide |
| 472 | $N^1$-{(1S,2R)-1-(3,5-difluorobenzyl)-2-hydroxy-3-[(5-methoxy-1,2,3,4-tetrahydro-1-naphthalenyl)amino]propyl}-5-methyl-$N^3$,$N^3$-dipropylisophthalamide "isomer A" |
| 473 | $N^1$-{(1S,2R)-1-(3,5-difluorobenzyl)-2-hydroxy-3-[(5-methoxy-1,2,3,4-tetrahydro-1-naphthalenyl)amino]propyl}-5-methyl-$N^3$,$N^3$-dipropylisophthalamide "isomer B" |
| 475 | $N^1$-[(1S,2R)-3-(benzylamino)-1-(3,5-difluorobenzyl)-2-hydroxypropyl]-5-methoxy-$N^3$,$N^3$-dipropylisophthalamide |
| 476 | $N^1$-[(1S,2R)-3-(benzylamino)-1-(3,5-difluorobenzyl)-2-hydroxypropyl]-$N^3$,$N^3$-dipropylisophthalamide |
| 477 | $N^1$-[(1S,2R)-3-(benzylamino)-1-(3,5-difluorobenzyl)-2-hydroxypropyl]-5-chloro-$N^3$,$N^3$-dipropylisophthalamide |
| 478 | $N^3$-[(1S,2R)-3-(benzylamino)-1-(3,5-difluorobenzyl)-2-hydroxypropyl]-$N^5$,$N^5$-dipropyl-3,5-pyridinedicarboxamide |
| 479 | $N^1$-[(1S,2R)-3-(benzylamino)-1-(3,5-difluorobenzyl)-2-hydroxypropyl]-5-fluoro-$N^3$,$N^3$-dipropylisophthalamide |
| 480 | $N^2$-[(1S,2R)-3-(benzylamino)-1-(3,5-difluorobenzyl)-2-hydroxypropyl]-$N^5$,$N^5$-dipropyl-2,5-thiophenedicarboxamide |
| 481 | $N^4$-[(1S,2R)-3-(benzylamino)-1-(3,5-difluorobenzyl)-2-hydroxypropyl]-$N^2$,$N^2$-dipropyl-2,4-pyridinedicarboxamide |
| 482 | $N^4$-[(1S,2R)-3-(benzylamino)-1-(3,5-difluorobenzyl)-2-hydroxypropyl]-$N^6$,$N^6$dipropyl-4,6-pyrimidinedicarboxamide |
| 483 | N-[(1S,2R)-3-(benzylamino)-1-(3,5-difluorobenzyl)-2-hydroxypropyl]-3-(4-morpholinylcarbonyl)benzamide |
| 484 | $N^1$-{(1S,2R)-1-benzyl-2-hydroxy-3-[(3-methylbenzyl)amino]propyl}-$N^3$,$N^3$-dipropylisophthalamide |
| 485 | $N^1$-{(1S,2R)-1-(3,5-difluorobenzyl)-2-hydroxy-3-[(3-methoxybenzyl)amino]propyl}-$N^5$,$N^5$-dipropylpentanediamide |
| 486 | $N^1$-[(1S,2R)-3-{[(1R)-1-[(benzyloxy)methyl]-2-(isobutylamino)-2-oxoethyl]amino}-1-(3,5-difluorobenzyl)-2-hydroxypropyl]-5-methyl-$N^3$,$N^3$-dipropylisophthalamide |
| 487 | $N^1$-((1S,2R)-1-(3,5-difluorobenzyl)-2-hydroxy-3-{[(1R)-1-(hydroxymethyl)-2-(isobutylamino)-2-oxoethyl]amino}propyl)-5-methyl-$N^3$,$N^3$-dipropylisophthalamide |
| 488 | $N^1$-[(1S,2R)-1-benzyl-2-hydroxy-3-(pentylamino)propyl]-$N^3$,$N^3$-dipropylisophthalamide |
| 489 | $N^1$-[(1S)-3-({2-[4-(aminosulfonyl)phenyl]ethyl}amino)-1-benzyl-2-hydroxypropyl]-$N^3$,$N^3$-dipropylisophthalamide |
| 491 | $N^3$-{(1S,2R)-1-(3,5-difluorobenzyl)-2-hydroxy-3-[(1,3-thiazol-5-ylmethyl)amino]propyl}-$N^5$,$N^5$-dipropyl-3,5-pyridinedicarboxamide |
| 492 | 3-Benzoyl-N-{(1S,2R)-1-(3,5-difluorobenzyl)-2-hydroxy-3-[(3-methoxybenzyl)amino]propyl}benzamide |
| 493 | N-{(1S,2R)-1-(3,5-difluorobenzyl)-2-hydroxy-3-[(3-methoxybenzyl)amino]propyl}[1,1'-biphenyl]-3-carboxamide |
| 494 | $N^1$-{(1S,2R)-1-benzyl-2-hydroxy-3-[(3-methylbenzyl)amino]propyl}-$N^3$,$N^3$-dipropylisophthalamide |
| 495 | $N^1$-[(1S,2R)-3-(benzylamino)-1-(3,5-difluorobenzyl)-2-hydroxypropyl]-$N^3$-(2-methoxyethyl)-$N^3$-propylisophthalamide |
| 496 | N-{(1S,2R)-1-(3,5-difluorobenzyl)-2-hydroxy-3-[(3-methoxybenzyl)amino]propyl}-3-ethoxybenzamide |
| 497 | N-{(1S,2R)-1-(3,5-difluorobenzyl)-2-hydroxy-3-[(3-methoxybenzyl)amino]propyl}-2-naphthamide |
| 498 | $N^1$-{(1S,2R)-1-(3,5-difluorobenzyl)-2-hydroxy-3-[(1R)-1,2,3,4-tetrahydro-1-naphthalenylamino]propyl}-5-methyl-$N^3$,$N^3$-dipropylisophthalamide |

-continued

| EXA | |
|---|---|
| 499 | $N^1$-[(1R)-3-{[3,5-bis(trifluoromethyl)benzyl]amino}-1-(3,5-difluorobenzyl)-2-hydroxypropyl]-5-methyl-$N^3,N^3$-dipropylisophthalamide |
| 500 | $N^1$-((1S,2R)-1-benzyl-3-{[2-fluoro-5-(trifluoromethyl)benzyl]amino}-2-hydroxypropyl)-$N^3,N^3$-dipropylisophthalamide |
| 501 | $N^1$-{(1S,2R)-1-benzyl-3-[(2,3-difluorobenzyl)amino]-2-hydroxypropyl}-$N^3,N^3$-dipropylisophthalamide |
| 502 | $N^1$-((1S,2R)-1-benzyl-3-{[3-fluoro-4-(trifluoromethyl)benzyl]amino}-$N^3,N^3$-dipropylisophthalamide |
| 503 | $N^1$-{(1S,2R)-1-benzyl-3-[(2,5-difluorobenzyl)amino]-2-hydroxypropyl}-$N^3,N^3$-dipropylisophthalamide |
| 504 | $N^1$-((1S,2R)-1-benzyl-3-{[3-fluoro-5-(trifluoromethyl)benzyl]amino}-2-hydroxypropyl)-$N^3,N^3$-dipropylisophthalamide |
| 505 | $N^1$-{(1S,2R)-1-benzyl-3-[(3,4-difluorobenzyl)amino]-2-hydroxypropyl}-$N^3,N^3$-dipropylisophthalamide |
| 506 | $N^1$-((1S,2R)-1-benzyl-3-{[4-fluoro-3-(trifluoromethyl)benzyl]amino}-2-hydroxypropyl)-$N^3,N^3$-dipropylisophthalamide |
| 507 | $N^1$-((1S,2R)-1-benzyl-3-{[2-chloro-5-(trifluoromethyl)benzyl]amino}-2-hydroxypropyl)-$N^3,N^3$-dipropylisophthalamide |
| 508 | $N^1$-((1S,2R)-1-benzyl-3-{[4-chloro-3-(trifluoromethyl)benzyl]amino}-2-hydroxypropyl)-$N^3,N^3$-dipropylisophthalamide |
| 509 | $N^1$-[(1S,2R)-1-benzyl-3-(2,3-dihydro-1H-inden-2-ylamino)-2-hydroxypropyl]-$N^3,N^3$-dipropylisophthalamide |
| 510 | $N^1$-{(1S)-1-benzyl-2-hydroxy-3-[(3-nitrobenzyl)amino]propyl}-$N^3,N^3$-dipropylisophthalamide |
| 511 | $N^1$-((1S,2R)-1-benzyl-3-{[3-(difluoromethoxy)benzyl]amino}-2-hydroxypropyl)-$N^3,N^3$-dipropylisophthalamide |
| 512 | $N^1$-{(1S,2R)-1-benzyl-3-[(3-ethoxybenzyl)amino]-2-hydroxypropyl}-$N^3,N^3$-dipropylisophthalamide |
| 513 | $N^1$-((1S,2R)-1-benzyl-2-hydroxy-3-{[(5-methyl-2-pyrazinyl)methyl]amino}propyl)-$N^3,N^3$-dipropylisophthalamide |
| 514 | $N^1$-{(1S,2R)-1-benzyl-3-[(3-bromo-4-fluorobenzyl)amino]-2-hydroxypropyl}-$N^3,N^3$-dipropylisophthalamide |
| 515 | $N^1$-{(1S,2R)-1-(3,5-difluorobenzyl)-3-[(3,5-dimethylbenzyl)amino]-2-hydroxypropyl}-5-methyl-$N^3,N^3$-dipropylisophthalamide |
| 516 | $N^1$-{(1S,2R)-1-(3,5-difluorobenzyl)-3-[(3-ethoxybenzyl)amino]-2-hydroxypropyl}-5-methyl-$N^3,N^3$-dipropylisophthalamide |
| 517 | $N^1$-{(1S,2R)-1-(3,5-difluorobenzyl)-2-hydroxy-3-[(2-phenoxyethyl)amino]propyl}-5-methyl-$N^3,N^3$-dipropylisophthalamide |
| 518 | $N^1$-{(1S,2R)-1-(3,5-difluorobenzyl)-2-hydroxy-3-[(3-isobutoxybenzyl)amino]propyl}-5-methyl-$N^3,N^3$-dipropylisophthalamide |
| 519 | $N^1$-((1S,2R)-1-(3,5-difluorobenzyl)-2-hydroxy-3-{[(4-methyl-1,3-thiazol-2-yl)methyl]amino}propyl)-5-methyl-$N^3,N^3$-dipropylisophthalamide |
| 520 | $N^1$-[(1S,2R)-3-(benzylamino)-1-(3,5-difluorobenzyl)-2-hydroxypropyl]-$N^3$-methyl-$N^3$-propylisophalamide |
| 521 | $N^2$-[(1S,2R)-3-(benzylamino)-1-(3,5-difluorobenzyl)-2-hydroxypropyl]-$N^5,N^5$-dipropyl-2,5-furandicarboxamide |
| 522 | $N^3$-((1S,2R)-1-(3,5-difluorobenzyl)-2-hydroxy-3-{[3-(trifluoromethyl)benzyl]amino}propyl)-$N^5,N^5$-dipropyl-3,5-pyridinedicarboxamide |
| 523 | $N^3$-{(1S,2R)-1-(3,5-difluorobenzyl)-2-hydroxy-3-[(1-methyl-1-phenylethyl)amino]propyl}-$N^5,N^5$-dipropyl-3,5-pyridinedicarboxamide |
| 524 | $N^1$-[(1S,2R)-3-amino-1-(3,5-difluorobenzyl)-2-hydroxypropyl]-5-methyl-$N^3,N^3$-dipropylisophthalamide |
| 525 | $N^1$-{(1S,2R)-1-(3,5-difluorobenzyl)-3-[(1,2-diphenylethyl)amino]-2-hydroxypropyl}-5-methyl-$N^3,N^3$-dipropylisophthalamide |
| 526 | $N^1$-{(1S,2R)-1-(3,5-difluorobenzyl)-2-hydroxy-3-[(7-methoxy-1,2,3,4-tetrahydro-1-naphthalenyl)amino]propyl}-5-methyl-$N^3,N^3$-dipropylisophthalamide, isomer A |
| 527 | $N^1$-{(1S,2R)-1-(3,5-difluorobenzyl)-2-hydroxy-3-[(7-methoxy-1,2,3,4-tetrahydro-1-naphthalenyl)amino]propyl}-5-methyl-$N^3,N^3$-dipropylisophthalamide, isomer B |
| 528 | Benzyl-(1S,2R)-3-azido-1-(3,5-difluorobenzyl)-2-hydroxypropylcarbamate |
| 529 | N-{(1S,2R)-1-benzyl-2-hydroxy-3-[(3-methoxybenzyl)amino]propyl}-3-(dimethylamino)benzamide |

| EXA | |
|---|---|
| 530 | N-[(1S,2R)-1-benzyl-2-hydroxy-3-[(3-methoxybenzyl)amino]propyl]-2-methyl-1H-benzimidazole-5-carboxamide |
| 531 | 3-(aminosulfonyl)-N-{(1S)-1-benzyl-2-hydroxy-3-[(3-methoxybenzyl)amino]propyl}-4-chlorobenzamide |
| 532 | N-{(1S,2R)-1-benzyl-2-hydroxy-3-[(3-methoxybenzyl)amino]propyl}-3-cyanobenzamide |
| 533 | N-{(1S,2R)-1-benzyl-2-hydroxy-3-[(3-methoxybenzyl)amino]propyl}-4-chloro-3-nitrobenzamide |
| 534 | Methyl 3-[({(1S,2R)-1-benzyl-2-hydroxy-3-[(3-methoxybenzyl)amino]propyl}amino)carbonyl]-5-nitrobenzoate |
| 535 | tert-butyl 3-[({(1S,2R)-1-benzyl-2-hydroxy-3-[(3-methoxybenzyl)amino]propyl}amino)carbonyl]-phenylcarbamate |
| 536 | N-[(1S,2R)-1-benzyl-2-hydroxy-3-[(3-methoxybenzyl)amino]propyl]-9,10-dioxo-9,10-dihydro-2-anthourancenylcarboxamide |
| 537 | N-[(1S,2R)-1-benzyl-2-hydroxy-3-[(3-methoxybenzyl)amino]propyl]-1H-1,2,3-benzotriazole-6-carboxamide |
| 538 | N-{(1S,2R)-1-benzyl-2-hydroxy-3-[(3-methoxybenzyl)amino]propyl}-4-(3-methyl-5-oxo-4,5-dihydro-1H-pyrazol-1-yl)benzamide |
| 539 | N-{(1S,2R)-1-benzyl-2-hydroxy-3-[(3-methoxybenzyl)amino]propyl}-1H-indole-5-carboxamide |
| 540 | N-{(1S,2R)-1-benzyl-2-hydroxy-3-[(3-methoxybenzyl)amino]propyl}-3-fluoro-5-(trifluoromethyl)benzamide |
| 541 | N-{(1S,2R)-1-benzyl-2-hydroxy-3-[(3-methoxybenzyl)amino]propyl}-3-(trifluoromethyl)benzamide |
| 542 | N-{(1S,2R)-1-benzyl-2-hydroxy-3-[(3-methoxybenzyl)amino]propyl}-4-(butylamino)benzamide |
| 543 | N-{(1S,2R)-1-benzyl-2-hydroxy-3-[(3-methoxybenzyl)amino]propyl}-3-(trifluoromethoxy)benzamide |
| 544 | N-{(1S,2R)-1-benzyl-2-hydroxy-3-[(3-methoxybenzyl)amino]propyl}-3,5-dimethoxybenzamide |
| 545 | N-{(1S,2R)-1-benzyl-2-hydroxy-3-[(3-methoxybenzyl)amino]propyl}-3,5-dimethylbenzamide |
| 546 | N-{(1S,2R)-1-benzyl-2-hydroxy-3-[(3-methoxybenzyl)amino]propyl}-3,5-difluorobenzamide |
| 547 | N-{(1S,2R)-1-benzyl-2-hydroxy-3-[(3-methoxybenzyl)amino]propyl}-3,5-dichlorobenzamide |
| 548 | N-{(1S,2R)-1-benzyl-2-hydroxy-3-[(3-methoxybenzyl)amino]propyl}-4-(benzyloxy)benzamide |
| 549 | N-{(1S,2R)-1-benzyl-2-hydroxy-3-[(3-methoxybenzyl)amino]propyl}-1,3-benzodioxole-5-carboxamide |
| 550 | 3-(acetylamino)-N-{(1S,2R)-1-benzyl-2-hydroxy-3-[(3-methoxybenzyl)amino]propyl}benzamide |
| 551 | 4-(acetylamino)-N-{(1S,2R)-1-benzyl-2-hydroxy-3-[(3-methoxybenzyl)amino]propyl}benzamide |
| 552 | $N^1$-((1S,2R)-1-(3,5-difluorobenzyl)-3-{[(3,5-dimethyl-4-isoxazolyl)methyl]amino}-2-hydroxypropyl)-5-methyl-$N^3,N^3$-dipropylisophthalamide |
| 553 | $N^1$-{(1S,2R)-1-(3,5-difluorobenzyl)-2-hydroxy-3-[(3-phenylpropyl)amino]propyl}-5-methyl-$N^3,N^3$-dipropylisophthalamide |
| 554 | $N^1$-{(1S,2R)-1-(3,5-difluorobenzyl)-3-[(3-furylmethyl)amino]-2-hydroxypropyl}-5-methyl-$N^3,N^3$-dipropylisophthalamide |
| 555 | $N^1$-{(1S,2R)-1-(3,5-difluorobenzyl)-2-hydroxy-3-[(tetrahydro-3-furanylmethyl)amino]propyl}-5-methyl-$N^3,N^3$-dipropylisophthalamide |
| 556 | $N^1$-{(1S,2R)-1-(3,5-difluorobenzyl)-2-hydroxy-3-[(3-propoxybenzyl)amino]propyl}-5-methyl-$N^3,N^3$-dipropylisophthalamide |
| 557 | $N^1$-{(1S,2R)-1-(3,5-difluorobenzyl)-2-hydroxy-3-[(2-pyridinylmethyl)amino]propyl}-5-methyl-$N^3,N^3$-dipropylisophthalamide |
| 558 | $N^1$-[(1S,2R)-3-(benzylamino)-1-(3,5-difluorobenzyl)-2-hydroxypropyl]-5-hydroxy-$N^3,N^3$-dipropylisophthalamide |
| 559 | $N^1$-((1S,2R)-1-(3,5-difluorobenzyl)-2-hydroxy-3-{[1-methyl-1-(3-methylphenyl)ethyl]amino}propyl)-5-methyl-$N^3,N^3$-dipropylisophthalamide |
| 560 | $N^1$-{(1S,2R)-1-(3,5-difluorobenzyl)-2-hydroxy-3-[(1S)-1,2,3,4-tetrahydro-1-naphthalenylamino]propyl}-5-methyl-$N^3,N^3$-dipropylisophthalamide |
| 561 | $N^1$-{(1S,2R)-1-(3,5-difluorobenzyl)-3-[(2,5-dimethylbenzyl)amino]-2-hydroxypropyl}-5-methyl-$N^3,N^3$-dipropylisophthalamide |
| 562 | $N^1$-[(1S,2R)-3-{[2-chloro-5-(trifluoromethyl)benzyl]amino}-1-(3,5-difluorobenzyl)-2-hydroxypropyl]-5-methyl-$N^3,N^3$-dipropylisophthalamide |
| 563 | $N^1$-{(1S,2R)-1-(3,5-difluorobenzyl)-2-hydroxy-3-[(2-hydroxy-5-methylbenzyl)amino]propyl}-5-methyl-$N^3,N^3$-dipropylisophthalamide |
| 564 | $N^1$-((1S,2R)-1-(3,5-difluorobenzyl)-2-hydroxy-3-{[(1S,2R)-2-hydroxy-2,3-dihydro-1H-inden-1-yl]amino}propyl)-5-methyl-$N^3,N^3$-dipropylisophthalamide |

| EXA | |
|---|---|
| 565 | N¹-{(1S,2R)-1-(3,5-difluorobenzyl)-3-[(1R)-2,3-dihydro-1H-inden-1-ylamino]-2-hydroxypropyl}-5-methyl-N³,N³-dipropylisophthalamide |
| 566 | 5-chloro-N¹-{(1S,2R)-1-(3,5-difluorobenzyl)-2-hydroxy-3-[(1-methyl-1-phenylethyl)amino]propyl}-N³,N³-dipropylisophthalamide |
| 567 | N¹-[(1S,2R)-3-[(1-benzofuran-2-ylmethyl)amino]-1-(3,5-difluorobenzyl)-2-hydroxypropyl]-5-methyl-N³,N³-dipropylisophthalamide |
| 568 | N¹-[(1S,2R)-3-{[(1R)-1-(3-bromophenyl)ethyl]amino}-1-(3,5-difluorobenzyl)-2-hydroxypropyl]-5-methyl-N³,N³-dipropylisophthalamide |
| 569 | N¹-{(1S,2R)-1-(4-fluorobenzyl)-2-hydroxy-3-[(3-iodobenzyl)amino]propyl}-5-methyl-N³,N³-dipropylisophthalamide |
| 570 | N-{(1S,2R)-1-benzyl-2-hydroxy-3-[(3-methoxybenzyl)amino]propyl}-3-[butyl(butyryl)amino]-5-methylbenzamide |
| 571 | N¹-{1-benzyl-2-hydroxy-3-[(3-methoxybenzyl)amino]propyl}-4-methyl-N³,N³-dipropylisophthalamide |
| 572 | N³-{1-benzyl-2-hydroxy-3-[(3-methoxybenzyl)amino]propyl}-4-methyl-N¹,N¹-dipropylisophthalamide |
| 573 | N¹-{(1S,2R)-1-(3,5-difluorobenzyl)-2-hydroxy-3-[(3-methoxybenzyl)amino]propyl}-4-methyl-N³,N³-dipropylisophthalamide |
| 574 | N-{(1S,2R)-1-benzyl-2-hydroxy-3-[(3-methoxybenzyl)amino]propyl}-1-butyl-1H-indole-6-carboxamide |
| 575 | N¹-[(1S,2R)-3-anilino-1-(3,5-difluorobenzyl)-2-hydroxypropyl]-5-methyl-N³,N³-dipropylisophthalamide |
| 576 | 5-bromo-N¹-[(1S,2R)-3-[(3-bromobenzyl)amino]-1-(3,5-difluorobenzyl)-2-hydroxypropyl]-N³,N³-dipropylisophthalamide |
| 577 | N-{(1S,2R)-1-(3,5-difluorobenzyl)-2-hydroxy-3-[(3-iodobenzyl)amino]propyl}-4-methylpentanamide |
| 578 | N-{(1S,2R)-1-(3,5-difluorobenzyl)-2-hydroxy-3-[(3-iodobenzyl)amino]propyl}-3-methylpentanamide |
| 579 | N¹-{(1S,2R)-1-(3,5-difluorobenzyl)-2-hydroxy-3-[(3-hydroxybenzyl)amino]propyl}-5-methyl-N³,N³-dipropylisophthalamide |
| 580 | tert-butyl (1S)-1-(3,5-difluorobenzyl)-3-[(3-methoxybenzyl)amino]-2-oxopropylcarbamate |
| 581 | tert-butyl (1S,2R)-3-amino-1-(3,5-difluorobenzyl)-2-hydroxypropylcarbamate |
| 582 | Benzyl (1S,2R)-1-benzyl-2-hydroxy-3-[(3-methoxybenzyl)amino]propylcarbamate |
| 583 | Benzyl (1S,2R)-1-benzyl-2-hydroxy-3-(tert-butylcarbamoyl)-3-[(3-methoxybenzyl)amino]propyl-carbamate |
| 584 | tert-Butyl (2R,3S)-3-amino-2-hydroxy-4-phenylbutyl(3-methoxybenzyl)carbamate |
| 585 | tert-butyl (2R,3S)-3-({3-cyano-5-[(dipropylamino)carbonyl]benzoyl}amino)-2-hydroxy-4-phenylbutyl(3-methoxybenzyl)carbamate |
| 586 | N¹-{(1S,2R)-1-benzyl-2-hydroxy-3-[(3-methoxybenzyl)amino]propyl}-5-cyano-N³,N³-dipropylisophthalamide hydrochloride |

Example 587

N¹-{(1S,2R)-1-Benzyl-2-hydroxy-3-[(3-methoxybenzyl)amino]propyl}-N³,N³-dipropyl-1,3,5-benzenetricarboxamide To a mixture of 3-(aminocarbonyl)-5-[(dipropylamino)carbonyl]benzoic acid (IX, PREPARATION 6, 0.18 g, 0.616 mmol) in dry DMF (16 mL) is added EDC (0.182 g, 0.9 mmol), HOBT (0.127 g, 0.9 mmol), triethylamine (0.062 g, 0.616 mol), and (2R,3S)-3-amino-1-[(3-methoxybenzyl)amino]-4-phenyl-2-butanol (VIII, EXAMPLE 175, 0.185 g, 0.616 mmol). The mixture is stirred at 20-25 degrees C. for 3 days. The mixture is partitioned between water and ethyl acetate. The phases are separated and the organic phase is washed three times with water. The organic phase is dried over anhydrous magnesium sulfate, filtered and concentrated. Column chromatography (silica gel, 75 mL; methanol/methylene chloride, 10/90) gives the title compound, IR (diffuse reflectance) 3306, 3301, 3270, 2962, 1676, 1667, 1663, 1645, 1638, 1627, 1615, 1550, 1537, 1450 and 1439 cm⁻¹; NMR (CDCl₃) δ 0.645, 0.968, 1.20, 1.43, 1.67, 2.8, 2.97, 3.38, 3.47, 3.73, 3.87, 4.31, 6.78, 6.91, 7.23, 7.72, 7.87, 8.22 and 8.43.

Example 588

1-tert-butyl (1S,2R)-1-(3,5-difluorobenzyl)-2-hydroxy-3-[(3-iodobenzyl)amino]propylcarbamate (VII)

tert-Butyl (1S)-2-(3,5-difluorophenyl)-1-[(2S)-oxiranyl]ethylcarbamate (V, EXAMPLE 3, 1.75 g, 5.8 mmole) is mixed with isopropanol (30 ml). The reaction flask is charged with 3-iodobenzylamine (VI). The reaction mixture is heated to reflux for 45 minutes, HPLC analysis indicates complete disappearance of the epoxide (V). The reaction mixture is concentrated under reduced pressure and the residue is partitioned between ethyl acetate (150 ml) and aqueous hydrochloric acid (3%, 35 ml). The organic phase is separated and washed with aqueous hydrochloric acid (3%, 20 ml), bicarbonate, saline and dried over sodium sulfate. Concentration under reduced pressure gives the title compound, M+H=535.

Example 589

1-9H-fluoren-9-ylmethyl(2R,3S)-3-(3-t-butyloxycarbonyl)amino-4-(3,5-difluorophenyl)-2-hydroxybutyl (3'-iodobenzyl)carbamate hydrochloride (XXXIV)

1-tert-butyl (1S,2R)-1-(3,5-difluorobenzyl)-2-hydroxy-3-[(3-iodobenzyl)amino]propylcarbamate (VII, EXAMPLE 588, 2.5 g, 4.7 mmole) and triethylamine (0.72 ml, 5.1 mmole) in THF (10 ml) are mixed. The reaction is cooled to 0 degrees and treated with FMOC-Cl (1.2 g, 4.7 mmole) in THF (2 ml) via addition funnel. After 15 minutes HPLC indicates complete disappearance of starting material. The reaction is diluted with ethyl acetate and washed with aqueous potassium bisulfate, saturated aqueous bicarbonate, saline and dried over sodium sulfate. Concentration under reduced pressure gives crude product which is purified by flash chromatography, eluting with ethyl acetate/hexane (20/80) followed by ethyl acetate to give the title compound, M+H=757.

Example 590

1-9H-fluoren-9-ylmethyl(2R,3S)-3-amino-4-(3,5-difluorophenyl)-2-hydroxybutyl(3-iodobenzyl)carbamate hydrochloride (XXXV)

1-9H-fluoren-9-ylmethyl(2R,3S)-3-(3-t-butyloxycarbonyl)amino-4-(3,5-difluorophenyl)-2-hydroxybutyl(3'-iodobenzyl)carbamate hydrochloride (XXXIV, EXAMPLE 589, 2.9 g) in hydrochloric acid/dioxane (4N, 10 ml). The mixture is stirred 1 hour then slowly poured into rapidly stirring ether (200 ml). The product is filtered and dried to give the title compound, M+H=657.

Example 591

1-9H-fluoren-9-ylmethyl(2R,3S)-4-(3,5-difluorophenyl)-2-hydroxy-3-{[5-oxo-5-(1-piperidinyl)pentanoyl]amino}butyl(3-iodobenzyl)carbamate (XXXVI)

HOBt (81 mg, 0.6 mmole) and EDC (105 mg, 0.55 mmole) are added to 1-carboxy-5-piperdinylglutaramide (IX, 100 mg, 0.5 mmole) in DMF (2 ml). The acid is activated 60 minutes then treated with 1-9H-fluoren-9-ylmethyl(2R,3S)-3-amino-4-(3,5-difluorophenyl)-2-hydroxybutyl(3-iodobenzyl)carbamate hydrochloride (XXXV, EXAMPLE 590, 300 mg, 0.43 mmole) and NMM (0.19 ml, 1.72 mmole). The reaction is stirred 3 hours then concentrated under reduced pressure. The residue is partitioned between ethyl acetate and saturated aqueous bicarbonate. The organic phases are washed with aqueous potassium bisulfate, saline, dried over sodium sulfate and finally concentrated under reduced pressure to give crude product. Purification via flash chromatography with ethyl acetate/hexane (50/50) then methanol/ethyl acetate (10/90) gives the title compound, M+H=838.

Example 592

1- N-{(1S,2R)-1-(3,5-difluorobenzyl)-2-hydroxy-3-[(3-iodobenzyl)amino]propyl}-5-oxo-5-(1-piperidinyl)pentanamide trifluroacetate 1-N-{(1S,2R)-1-(3,5-difluorobenzyl)-2-hydroxy-3-[(3-iodobenzyl)amino]propyl}-5-oxo-5-(1-piperidinyl)pentanamide trifluroacetate (XXXVI, EXAMPLE 591, 240 mg, 0.29 mmole is dissolved in diethylamine (10%, 9 ml) in methylene chloride. The reaction is stirred at 20-25 degrees overnight. The next morning the reaction is concentrated under reduced pressure and the residue is redissolved in methylene chloride and purified by preparative reverse phase HPLC. The appropriate fractions are pooled and concentrated under reduced pressure and partitioned between ethyl acetate and saline. The organic phase is separated and dried over sodium sulfate and concentrated to give the title compound, M+H=614.

Example 593

5-(Aminosulfonyl)-$N^1$-{(1S,2R)-1-benzyl-2-hydroxy-3-[(3-methoxybenzyl)amino]propyl}-$N^3$,N-dipropylisophthalamide O-(7-Azabenzotriazol-1-yl)-N,N,N',N'-tetramethyluronium hexafluorophosphate (HATU, 0.0928 g, 0.244 mmol) is added to a mixture of, 3-(aminosulfonyl)-5-[(dipropylamino)-carbonyl]benzoic acid (XXXIX, PREPARATION 13, 0.0800 g, 0.244 mmol) and (2R,3S)-3-amino-1-[(3-methoxybenzyl)-amino]-4-phenyl-2-butanol (VIII, EXAMPLE 175, 0.0732 g, 0.244 mmol) in dry DMF (3 mL). The mixture is stirred for 18 hours at 20-25 degrees, and then partitioned between ethyl acetate and water. The organic phase is separated and washed with saline, dried over anhydrous sodium sulfate, filtered and concentrated. The concentrate is column chouromatographed (silica gel; methanol/dichloromethane, 5/95) to give the title compound, MS (ESI+) for $C_{32}H_{42}N_4O_6S$ m/z $(M+H)^+$=611.5; HRMS (FAB) calculated for $C_{32}H_{42}N_4O_6S+H_1$=611.2903, found=611.2904.

The following compounds can be prepared using essentially the general procedures outlined and examples described above and elsewhere in this document.

| EXA | |
|---|---|
| 594 | $N^1$-{(1S,2R)-1-benzyl-2-hydroxy-3-[(3-methoxybenzyl)amino]propyl}-$N^3$,$N^3$-dipropyl-5-(1-pyrrolidinylsulfonyl)isophthalamide |
| 595 | $N^1$-{(1S,2R)-1-benzyl-2-hydroxy-3-[(3-methoxybenzyl)amino]propyl}-5-[(methylamino)sulfonyl]-$N^3$,$N^3$-dipropylisophthalamide |
| 596 | $N^1$-{(1S,2R)-1-benzyl-2-hydroxy-3-[(3-methoxybenzyl)amino]propyl}-5-[(dimethylamino)sulfonyl]-$N^3$,$N^3$-dipropylisophthalamide |
| 597 | N-{(1S,2R)-1-benzyl-2-hydroxy-3-[(3-methoxybenzyl)amino]propyl}-2-methyl-3-(methylsulfonyl) propanamide hydrochloride |
| 598 | N-{(1S,2R)-1-benzyl-2-hydroxy-3-[(3-methoxybenzyl) amino]propyl}-3-(methylsulfonyl)propanamide hydrochloride |
| 599 | 2-amino-N-{(1S,2R)-1-benzyl-2-hydroxy-3-[(3-methoxybenzyl)amino]propyl}-1,3-thiazole-4-carboxamide dihydrochloride |

-continued

| EXA | |
|---|---|
| 600 | N-{(1S,2R)-1-benzyl-2-hydroxy-3-[(3-methoxybenzyl)amino]propyl}-5-(methylsulfonyl)pentanamide hydrochloride |
| 601 | $N^1$-{(1S,2R)-1-benzyl-2-hydroxy-3-[(3-methoxybenzyl) amino]propyl}-$N^4$-phenylsuccinamide hydrochloride |
| 602 | (3R)-$N^4$-{(1S,2R)-1-benzyl-2-hydroxy-3-[(3-methoxybenzyl)amino]propyl}-2,2,3-trimethylbutanediamide hydrochloride |
| 603 | N-{(1S,2R)-1-benzyl-2-hydroxy-3-[(3-methoxybenzyl)amino]propyl}-3-[(dipropylamino)sulfonyl]-propanamide hydrochloride |
| 604 | $N^1$-{(1S,2R)-1-benzyl-2-hydroxy-3-[(3-methoxybenzyl) amino]propyl}-$N^5$,$N^5$-dipropylpentanediamide hydrochloride |
| 605 | N-{(1S,2R)-1-benzyl-2-hydroxy-3-[(3-methoxybenzyl) amino]propyl}-4-oxo-4-(1-piperidinyl)butanamide hydrochloride |
| 606 | $N^1$-{(1S,2R)-1-benzyl-2-hydroxy-3-[(3-methoxybenzyl) amino]propyl}-$N^4$,$N^4$-dipropylsuccinamide hydrochloride |
| 607 | N-{(1S,2R)-1-benzyl-2-hydroxy-3-[(3-methoxybenzyl) amino]propyl}-5-oxo-5-(1-piperidinyl)pentanamide hydrochloride |
| 608 | $N^1$-{(1S,2R)-1-benzyl-2-hydroxy-3-[(3-methoxybenzyl) amino]propyl}-$N^5$-phenylpentanediamide hydrochloride |
| 609 | N-{(1S,2R)-1-benzyl-2-hydroxy-3-[(3-methoxybenzyl) amino]propyl}-3,3-dimethyl-4-oxo-4-(1-piperidinyl) butanamide hydrochloride |
| 610 | N-{(1S,2R)-1-benzyl-2-hydroxy-3-[(3-methoxybenzyl) amino]propyl}-4-(isopentylsulfonyl) butanamide hydrochloride |
| 611 | $N^1$-{(1S,2R)-1-benzyl-2-hydroxy-3-[(3-methoxybenzyl) amino]propyl}-2,2-dimethyl-$N^4$,$N^4$-dipropylsuccinamide hydrochloride |
| 612 | N-{(1S,2R)-1-benzyl-2-hydroxy-3-[(3-methoxybenzyl) amino]propyl}-4-[(dipropylamino)sulfonyl] butanamide hydrochloride |
| 613 | N-{(1S,2R)-1-benzyl-2-hydroxy-3-[(3-methoxybenzyl) amino]propyl}-4-[(methylanilino)sulfonyl]butanamide hydrochloride |
| 614 | N-{(1S,2R)-1-benzyl-2-hydroxy-3-[(3-methoxybenzyl) amino]propyl}-3-[(methylanilino)sulfonyl]propanamide |
| 615 | N-{(1S,2R)-1-benzyl-2-hydroxy-3-[(3-methoxybenzyl) amino]propyl} acetamide hydrochloride |
| 616 | N-{(1S,2R)-1-benzyl-2-hydroxy-3-[(3-methoxybenzyl) amino]propyl}-3-(isopentylsulfonyl) propanamide hydrochloride |
| 617 | N-{(1S,2R)-1-(3,5-difluorobenzyl)-2-hydroxy-3-[(3-iodobenzyl)amino]propyl}-5-oxo-5-(1-piperidinyl) pentanamide trifluoroacetate |
| 618 | N-{(1S,2R)-1-benzyl-2-hydroxy-3-[(3-iodobenzyl) amino]propyl}-5-oxo-5-(1-piperidinyl)pentanamide trifluoroacetate |
| 619 | N-{(1S,2R)-1-(3,5-difluorobenzyl)-2-hydroxy-3-[(3-iodobenzyl)amino]propyl}-3-[(dipropylamino)sulfonyl] propanamide |

Example 620

$N^1$-{(1S,2R)-1-Benzyl-2-hydroxy-3-[(3-methoxybenzyl)amino]propyl}-5-ethyl-$N^3$,$N^3$-dipropylisophthalamide Diethyl cyanophosphonate (0.132 mL, 0.870 mmol) is added to a mixture of 3-[(dipropylamino)carbonyl]-5-ethyl-benzoic acid (IX, PREPARATION 21, 0.200 g, 0.720 mmol), (2R,3S)-3-amino-1-[(3-methoxybenzyl)amino]-4-phenyl-2-butanol (VIII, EXAMPLE 175, 0.216 mg, 0.720 mmol), and triethylamine (0.121 mL, 0.870 mmol) in dichloromethane (3 mL). The mixture was stirred for 1 hour at 20-25 degrees C. Dichloromethane is then removed under reduced pressure. The residue is partitioned between ethyl acetate and water. The organic phase is separated and is washed with saline, dried over anhydrous sodium sulfate, filtered and concentrated. The concentrate is column chouromatographed (silica gel; methanol/dichloromethane, 5/95) to give the title compound, MS (ESI+) for $C_{34}H_{45}N_3O_4$ m/z (M+H)$^+$=560.4; HOURMS (FAB) calculated for $C_{34}H_{45}N_3O_4$+H=560.3488, found=560.3487.

The following compounds can be prepared using essentially the general procedures outlined and examples described above and elsewhere in this document.

| EXAMPLE | | M + H = |
|---|---|---|
| 621 | $N^1$-{(1S,2R)-1-Benzyl-2-hydroxy-3-[(3-methoxybenzyl)amino]propyl}-5-isobutyl-$N^3$,$N^3$-dipropylisophthalamide | |
| 622 | $N^1$-{(1S,2R)-1-Benzyl-2-hydroxy-3-[(3-methoxybenzyl)amino]propyl}-5-tert-butyl-$N^3$,$N^3$-dipropylisophthalamide | |
| 623 | EXAMPLE 623 $N^1$-{(1S,2R)-1-benzyl-2-hydroxy-3-[(3-methoxybenzyl)amino]propyl}-5-cyano-$N^3$-propylisophthalamide | |
| 624 | $N^1$-{(1S,2R)-1-(3,5-difluorobenzyl)-2-hydroxy-3-[(3-methoxybenzyl)amino]propyl}-$N^3$,$N^3$-dipropyl-1,3,5-benzenetricarboxamide | 611.0 |
| 625 | $N^1$-{(1S,2R)-1-benzyl-2-hydroxy-3-[(3-methoxybenzyl)amino]propyl}-$N^3$,$N^3$-dimethyl-$N^5$,$N^5$-dipropyl-1,3,5-benzenetricarboxamide | 603.0 |
| 626 | $N^1$-[(1S,2R)-3-amino-1-benzyl-2-hydroxypropyl]-$N^3$,$N^3$-dipropyl-1,3,5-benzenetricarboxamide | 455.1 |
| 627 | $N^1$-[(1S,2R)-1-benzyl-2-hydroxy-3-(isopentylamino)propyl]-$N^3$,$N^3$-dipropyl-1,3,5-benzenetricarboxamide | 525.6 |

| EXAMPLE | | M + H = |
|---|---|---|
| 628 | N¹-{(1S,2R)-1-benzyl-2-hydroxy-3-[(3-methoxybenzyl)amino]propyl}-N³-propyl-1,3,5-benzenetricarboxamide | 533.1 |

Example 629

N-{(1S,2R)-1-Benzyl-2-hydroxy-3-[(3-methoxybenzyl)amino]propyl}-3-[butyryl(propyl)amino]-5-methylbenzamide Following the procedure of Example 570 and making non-critical variations, diethyl cyanophosphonate (0.0760 mL, 0.550 mmol) is added to a mixture of 3-[butyryl(propyl)amino]-5-methylbenzoic acid (IX, 0.120 g, 0.460 mmol), (2R,3S)-3-amino-1-[(3-methoxybenzyl)amino]-4-phenyl-2-butanol (VIII, 0.137 g, 0.460 mmol), and triethylamine (0.0760 mL, 0.550 mmol) in dichloromethane (5 mL). The mixture is stirred for 1 hour at 20-25 degrees C. Dichloromethane is then removed under reduced pressure. The residue is partitioned between ethyl acetate and water. The organic is separated, is washed with saline, dried over anhydrous sodium sulfate, filtered and concentrated. The concentrate is column chromatographed (silica gel; methanol/dichloromethane, 5/95) to give the title compound, NMR (400 MHz, CDCl$_3$) δ 7.09, 4.15, 3.80, 3.79, 3.60, 3.02, 2.84, 2.36, 1.94, 1.56, 1.49, 0.87 and 0.81;. MS (ESI+) for C$_{33}$H$_{43}$N$_3$O$_4$ m/z (M+H)$^+$=546.3; HRMS (FAB) calculated for C$_{33}$H$_{43}$N$_3$O$_4$+H=546.3331, found=546.3331.

Example 630

N-{(1S,2R)-1-benzyl-2-hydroxy-3-[(3-methoxybenzyl)amino]propyl}-1-propyl-1H-indole-6-carboxamide

Example 631

N-{(1S,2R)-1-(3,5-difluorobenzyl)-2-hydroxy-3-[(3-methoxybenzyl)amino]propyl}-1-propyl-1H-indole-6-carboxamide

| EXA | | MH⁺ |
|---|---|---|
| 633 | N¹-{(1S,2R)-1-(3,5-difluorobenzyl)-3-[(3,4-dimethylbenzyl)amino]-2-hydroxypropyl}-5-methyl-N³,N³-dipropylisophthalamide | 580 |
| 634 | N¹-[(1S,2R)-3-[(3-aminobenzyl)amino]-1-(3,5-difluorobenzyl)-2-hydroxypropyl]-5-methyl-N³,N³-dipropylisophthalamide | 567 |
| 635 | N-{(1S,2R)-1-(3,5-difluorobenzyl)-2-hydroxy-3-[(3-iodobenzyl)amino]propyl}octanamide | 559 |
| 636 | N³-[(1S,2R)-1-(3,5-difluorobenzyl)-2-hydroxy-3-({1-methyl-1-[3-(trifluoromethyl)phenyl]ethyl}amino)propyl]-N⁵,N⁵-dipropyl-3,5-pyridinedicarboxamide | 635 |
| 637 | N¹-[(1S,2R)-1-(3,5-difluorobenzyl)-2-hydroxy-3-({1-methyl-1-[3-(trifluoromethyl)phenyl]ethyl}amino)propyl]-5-methyl-N³,N³-dipropylisophthalamide | 648 |
| 638 | N¹-((1S,2R)-1-(3,5-difluorobenzyl)-2-hydroxy-3-{[(1R,2S)-2-hydroxy-2,3-dihydro-1H-inden-1-yl]amino}propyl)-5-methyl-N³,N³-dipropylisophthalamide | 594 |
| 639 | N¹-{(1S,2R)-1-(3,5-difluorobenzyl)-3-[(1R)-2,3-dihydro-1H-inden-1-ylamino]-2-hydroxypropyl}-5-methyl-N³,N³-dipropylisophthalamide | 578 |
| 640 | N-{(1S,2R)-1-(3,5-difluorobenzyl)-2-hydroxy-3-[(3-iodobenzyl)amino]propyl}-3-methylbenzamide | 551 |
| 641 | N¹-[(1S,2R)-1-(3,5-difluorobenzyl)-2-hydroxy-3-(1H-isoindol-3-ylamino)propyl]-5-methyl-N³,N³-dipropylisophthalamide | 577 |
| 642 | N¹-((1S,2R)-1-(3,5-difluorobenzyl)-2-hydroxy-3-{[(1R,2S,5R)-2-isopropyl-5-methylcyclohexyl]amino}propyl)-5-methyl-N³,N³-dipropylisophthalamide | 600 |
| 643 | N¹,N¹-diallyl-5-chloro-N³-{(1S,2R)-1-(3,5-difluorobenzyl)-2-hydroxy-3-[(1-methyl-1-phenylethyl)amino]propyl}isophthalamide | 597 |
| 644 | 5-chloro-N¹-{(1S,2R)-1-(3,5-difluorobenzyl)-2-hydroxy-3-[(1-methyl-1-phenylethyl)amino]propyl}-N³,N³-bis(2-methoxyethyl)isophthalamide | 633 |
| 645 | N³-{(1S,2R)-1-(3,5-difluorobenzyl)-2-hydroxy-3-[(1-phenylcyclopentyl)amino]propyl}-N⁵,N⁵-dipropyl-3,5-pyridinedicarboxamide | 593 |
| 646 | N¹-{(1S,2R)-1-(3,5-difluorobenzyl)-3-[(3-ethylbenzyl)amino]-2-hydroxypropyl}-5-methyl-N³,N³-dipropylisophthalamide | 580 |
| 647 | N¹-((1S,2R)-1-(3,5-difluorobenzyl)-3-{[3-(dimethylamino)benzyl]amino}-2-hydroxypropyl)-5-methyl-N³,N³-dipropylisophthalamide | 595 |
| 648 | N¹-((1S,2R)-1-(3,5-difluorobenzyl)-3-{[(4,5-dimethyl-2-furyl)methyl]amino}-2-hydroxypropyl)-5-methyl-N³,N³-dipropylisophthalamide | 570 |
| 649 | N¹-{(1S,2R)-1-(3,5-difluorobenzyl)-2-hydroxy-3-[(1-phenylcyclopentyl)amino]propyl}-5-methyl-N³,N³-dipropylisophthalamide | 606 |
| 650 | N¹-[(1S,2R)-3-(cyclopropylamino)-1-(3,5-difluorobenzyl)-2-hydroxypropyl]-5-methyl-N³,N³-dipropylisophthalamide | 502 |
| 651 | N¹-{(1S,2R)-3-[(cyclopropylmethyl)amino]-1-(3,5-difluorobenzyl)-2-hydroxypropyl}-5-methyl-N³,N³-dipropylisophthalamide | 516 |
| 652 | N¹-{(1S,2R)-1-(3,5-difluorobenzyl)-2-hydroxy-3-[(3-iodobenzyl)amino]propyl}-N⁵,N⁵-dipropylpentanediamide | 630 |
| 653 | N³-{(1S,2R)-1-(3,5-difluorobenzyl)-3-[(2-furylmethyl)amino]-2-hydroxypropyl}-N⁵,N⁵-dipropyl-3,5-pyridinedicarboxamide | 529 |
| 654 | N¹-{(1S,2R)-1-(3,5-difluorobenzyl)-2-hydroxy-3-[(tetrahydro-2-furanylmethyl)amino]propyl}-5-methyl-N³,N³-dipropylisophthalamide | 546 |
| 655 | N³-{(1S,2R)-1-(3,5-difluorobenzyl)-2-hydroxy-3-[(1-phenylcyclopropyl)amino]propyl}-N⁵,N⁵-dipropyl-3,5-pyridinedicarboxamide | 565 |
| 656 | N¹-{(1S,2R)-1-(3,5-difluorobenzyl)-2-hydroxy-3-[(2-oxo-3-azepanyl)amino]propyl}-5-methyl-N³,N³-dipropylisophthalamide | 573 |
| 657 | N¹-((1S,2R)-1-(3,5-difluorobenzyl)-2-hydroxy-3-{[(3-methyl-2-furyl)methyl]amino}propyl)-5-methyl-N³,N³-dipropylisophthalamide | 556 |
| 658 | N¹-((1S,2R)-1-(3,5-difluorobenzyl)-2-hydroxy-3-{[(2S)-tetrahydro-2-furanylmethyl]amino}propyl)-5-methyl-N³,N³-dipropylisophthalamide | 546 |
| 659 | 5-chloro-N¹-{(1S,2R)-1-(3,5-difluorobenzyl)-2-hydroxy-3-[(1-methyl-1-phenylethyl)amino]propyl}-N³,N³-di(2-propynyl)isophthalamide | 593 |
| 660 | N¹-{(1S,2R)-1-(3,5-difluorobenzyl)-2-hydroxy-3-[(3-isopropenylbenzyl)amino]propyl}-5-methyl-N³,N³-dipropylisophthalamide | 592 |
| 661 | N¹-{(1S,2R)-1-(3,5-difluorobenzyl)-2-hydroxy-3-[(2-propoxyethyl)amino]propyl}-5-methyl-N³,N³-dipropylisophthalamide | 548 |
| 662 | N¹-[(1S,2R)-1-(3,5-difluorobenzyl)-3-(hexylamino)-2-hydroxypropyl]-5-methyl-N³,N³-dipropylisophthalamide | 546 |
| 663 | N-{(1S,2R)-1-(3,5-difluorobenzyl)-2-hydroxy-3-[(3-iodobenzyl)amino]propyl}-4-(3-methyl-5-oxo-4,5-dihydro-1H-pyrazol-1-yl)benzamide | 633 |
| 664 | methyl 4-({[(2R,3S)-4-(3,5-difluorophenyl)-3-({3-[(dipropylamino)carbonyl]-5-methylbenzoyl}amino)-2-hydroxybutyl]amino}methyl)benzoate | 610 |

-continued

| EXA | | MH+ |
|---|---|---|
| 665 | N$^1$-{(1S,2R)-1-(3,5-difluorobenzyl)-2-hydroxy-3-[(2-methoxyethyl)amino]propyl}-5-methyl-N$^3$,N$^3$-dipropylisophthalamide | 520 |
| 666 | N$^1$-{(1S,2R)-1-(3,5-difluorobenzyl)-2-hydroxy-3-[(5-isoxazolylmethyl)amino]propyl}-5-methyl-N$^3$,N$^3$-dipropylisophthalamide | 543 |
| 667 | (1R,2R)-N$^1$-{(1S,2R)-1-(3,5-difluorobenzyl)-2-hydroxy-3-[(3-iodobenzyl)amino]propyl}-N$^2$,N$^2$-dipropyl-1,2-cyclopropanedicarboxamide | 628 |
| 668 | N$^3$-((1S,2R)-1-(3,5-difluorobenzyl)-2-hydroxy-3-{[(2S)-tetrahydro-2-furanylmethyl]amino}propyl)-N$^5$,N$^5$-dipropyl-3,5-pyridinedicarboxamide | 533 |
| 669 | N$^1$-{(1S,2R)-1-(3,5-difluorobenzyl)-2-hydroxy-3-[(2-methoxybenzyl)amino]propyl}-5-methyl-N$^3$,N$^3$-dipropylisophthalamide | 582 |
| 670 | N$^1$-{(1S,2R)-1-(3,5-difluorobenzyl)-2-hydroxy-3-[(3-isopropylbenzyl)amino]propyl}-5-methyl-N$^3$,N$^3$-dipropylisophthalamide | 594 |
| 671 | 4-(butyrylamino)-N-{(1S,2R)-1-(3,5-difluorobenzyl)-2-hydroxy-3-[(3-iodobenzyl)amino]propyl}benzamide | 622 |
| 672 | N$^1$-[(1S,2R)-3-[(3-amino-3-oxopropyl)amino]-1-(3,5-difluorobenzyl)-2-hydroxypropyl]-5-methyl-N$^3$,N$^3$-dipropylisophthalamide | 533 |
| 673 | N$^3$-[(1S,2R)-3-(benzylamino)-1-(3,5-difluorobenzyl)-2-hydroxypropyl]-N$^5$,N$^5$-dipropyl-3,5-pyridinedicarboxamide 1-oxide | 555 |
| 674 | N$^1$-{(1S,2R)-1-(3,5-difluorobenzyl)-2-hydroxy-3-[(3-iodobenzyl)amino]propyl}-5-ethynyl-N$^3$,N$^3$-dipropylisophthalamide | 688 |
| 675 | N$^1$-{(1S,2R)-1-(3,5-difluorobenzyl)-2-hydroxy-3-[(7-oxabicyclo[2.2.1]hept-2-ylmethyl)amino]propyl}-5-methyl-N$^3$,N$^3$-dipropylisophthalamide | 572 |
| 676 | N$^1$-{(1S,2R)-1-(3,5-difluorobenzyl)-3-[(3-ethynylbenzyl)amino]-2-hydroxypropyl}-5-methyl-N$^3$,N$^3$-dipropylisophthalamide | 576 |
| 677 | N$^1$-((1S,2R)-1-(3,5-difluorobenzyl)-2-hydroxy-3-{[(2-methyl-1,3-thiazol-5-yl)methyl]amino}propyl)-5-methyl-N$^3$,N$^3$-dipropylisophthalamide | 573 |
| 678 | N$^1$-((1S,2R)-1-(3,5-difluorobenzyl)-3-{[(2-ethyl-1,3-thiazol-5-yl)methyl]amino}-2-hydroxypropyl)-5-methyl-N$^3$,N$^3$-dipropylisophthalamide | 587 |
| 679 | N$^1$-((1S,2R)-1-(3,5-difluorobenzyl)-2-hydroxy-3-{[(3R)-2-oxoazepanyl]amino}propyl)-5-methyl-N$^3$,N$^3$-dipropylisophthalamide | 573 |
| 680 | N$^1$-[(1S,2R)-3-(cyclobutylamino)-1-(3,5-difluorobenzyl)-2-hydroxypropyl]-5-methyl-N$^3$,N$^3$-dipropylisophthalamide | 516 |
| 681 | N$^1$-[(1S,2R)-3-(butylamino)-1-(3,5-difluorobenzyl)-2-hydroxypropyl]-5-ethynyl-N$^3$,N$^3$-dipropylisophthalamide | 528 |
| 682 | N$^1$-{(1S,2R)-1-(3,5-difluorobenzyl)-3-[(3-ethylbenzyl)amino]-2-hydroxypropyl}-5-ethynyl-N$^3$,N$^3$-dipropylisophthalamide | 590 |
| 683 | N$^1$-[(1S,2R)-1-(3,5-difluorobenzyl)-3-(5-hexynylamino)-2-hydroxypropyl]-5-methyl-N$^3$,N$^3$-dipropylisophthalamide | 542 |
| 684 | N$^3$-((1S,2R)-1-(3,5-difluorobenzyl)-2-hydroxy-3-{[(5-methyl-2-furyl)methyl]amino}propyl)-N$^5$,N$^5$-dipropyl-3,5-pyridinedicarboxamide | 543 |
| 685 | N$^1$-{(1S,2R)-1-(3,5-difluorobenzyl)-2-hydroxy-3-[(1-methyl-1-phenylethyl)amino]propyl}-N$^5$,N$^5$-dipropylpentanediamide | 532 |
| 686 | N$^1$-((1S,2R)-1-(3,5-difluorobenzyl)-3-{[1-(2-furyl)-1-methylethyl]amino}-2-hydroxypropyl)-5-methyl-N$^3$,N$^3$-dipropylisophthalamide | 570 |
| 687 | N$^1$-((1S,2R)-1-(3,5-difluorobenzyl)-2-hydroxy-3-{[(3-isobutyl-5-isoxazolyl)methyl]amino}propyl)-5-methyl-N$^3$,N$^3$-dipropylisophthalamide | 599 |
| 688 | N$^1$-((1S,2R)-1-(3,5-difluorobenzyl)-2-hydroxy-3-{[(2-isobutyl-1,3-thiazol-5-yl)methyl]amino}propyl)-5-methyl-N$^3$,N$^3$-dipropylisophthalamide | 615 |
| 689 | N-{(1S,2R)-1-(3,5-difluorobenzyl)-3-[(3-ethylbenzyl)amino]-2-hydroxypropyl}-3-[(dipropylamino)sulfonyl]propanamide | 554 |
| 690 | N$^1$-{(1S,2R)-1-benzyl-2-hydroxy-3-[(2-phenylethyl)amino]propyl}-N$^3$,N$^3$-dipropylisophthalamide | 516 |
| 691 | N$^1$-((1S,2R)-1-benzyl-3-{[2-(2-chlorophenyl)ethyl]amino}-2-hydroxypropyl)-N$^3$,N$^3$-dipropylisophthalamide | 551 |
| 692 | N$^1$-((1S,2R)-1-benzyl-2-hydroxy-3-{[3-(2-oxo-1-pyrrolidinyl)propyl]amino}propyl)-N$^3$,N$^3$-dipropylisophthalamide | 537 |
| 693 | N$^1$-{(1S,2R)-1-benzyl-3-[(cyclohexylmethyl)amino]-2-hydroxypropyl}-N$^3$,N$^3$-dipropylisophthalamide | 508 |
| 694 | N$^1$-[(1S,2R)-1-benzyl-3-(cyclopropylamino)-2-hydroxypropyl]-N$^3$,N$^3$-dipropylisophthalamide | 452 |
| 695 | N$^1$-{(1S,2R)-1-benzyl-2-hydroxy-3-[(2-oxo-3-azepanyl)amino]propyl}-N$^3$,N$^3$-dipropylisophthalamide | 523 |
| 696 | N-[(1S,2R)-3-(benzylamino)-1-(3,5-difluorobenzyl)-2-hydroxypropyl]-3-(butylsulfonyl)benzamide | 531 |
| 697 | N$^1$-{(1S,2R)-1-benzyl-3-({2-[(2-ethylhexyl)oxy]ethyl}amino)-2-hydroxypropyl}-N$^3$,N$^3$-dipropylisophthalamide | 568 |
| 698 | N$^1$-((1S,2R)-3-benzyl-2-hydroxy-3-{[(1S,2R)-2-hydroxy-2,3-dihydro-1H-inden-1-yl]amino}propyl)-N$^3$,N$^3$-dipropylisophthalamide | 544 |
| 699 | N$^1$-((1S,2R)-1-benzyl-2-hydroxy-3-{[1-(4-hydroxyphenyl)ethyl]amino}propyl)-N$^3$,N$^3$-dipropylisophthalamide | 532 |
| 700 | N$^1$-{(1S,2R)-1-benzyl-3-(cycloheptylamino)-2-hydroxypropyl}-N$^3$,N$^3$-dipropylisophthalamide | 508 |
| 701 | N$^1$-{(1S,2R)-1-benzyl-3-[([1,1'-biphenyl]-2-ylmethyl)amino]-2-hydroxypropyl}-N$^3$,N$^3$-dipropylisophthalamide | 578 |
| 702 | N$^1$-{(1S,2R)-1-benzyl-3-[(2-fluorobenzyl)amino]-2-hydroxypropyl}-N$^3$,N$^3$-dipropylisophthalamide | 520 |
| 703 | N-{(1S,2R)-1-(3,5-difluorobenzyl)-2-hydroxy-3-[(3-methoxybenzyl)amino]propyl}-3-(dimethylamino)benzamide | 484 |
| 704 | N-{(1S,2R)-1-(3,5-difluorobenzyl)-2-hydroxy-3-[(3-methoxybenzyl)amino]propyl}-1-naphthamide | 491 |
| 705 | N$^1$-[(1S,2R)-1-benzyl-3-({2-[({5-[(dimethylamino)methyl]-2-furyl}methyl)sulfanyl]ethyl}amino)-2-hydroxypropyl]-N$^3$,N$^3$-dipropylisophthalamide | 609 |
| 706 | N$^1$-[(1S,2R)-1-benzyl-3-({2-[(2-chloro-6-fluorobenzyl)sulfanyl]ethyl}amino)-2-hydroxypropyl]-N$^3$,N$^3$-dipropylisophthalamide | 615 |
| 707 | N$^1$-[(1S,2R)-3-[([1,1'-biphenyl]-4-ylmethyl)amino]-1-(3,5-difluorobenzyl)-2-hydroxypropyl]-5-methyl-N$^3$,N$^3$-dipropylisophthalamide | 628 |
| 708 | N$^1$-((1S,2R)-1-(3,5-difluorobenzyl)-2-hydroxy-3-(1-naphthylamino)propyl)-5-methyl-N$^3$,N$^3$-dipropylisophthalamide | 588 |
| 709 | N$^1$-{(1S,2R)-1-(3,5-difluorobenzyl)-2-hydroxy-3-[(1H-imidazol-5-ylmethyl)amino]propyl}-5-methyl-N$^3$,N$^3$-dipropylisophthalamide | 542 |
| 710 | N$^1$-((1S,2R)-1-(3,5-difluorobenzyl)-2-hydroxy-3-{[(2-phenyl-1H-imidazol-5-yl)methyl]amino}propyl)-5-methyl-N$^3$,N$^3$-dipropylisophthalamide | 618 |
| 711 | N$^1$-((1S,2R)-1-(3,5-difluorobenzyl)-2-hydroxy-3-{[(1-methyl-1H-imidazol-2-yl)methyl]amino}propyl)-5-methyl-N$^3$,N$^3$-dipropylisophthalamide | 556 |
| 712 | N$^1$-[(1S,2R)-3-{[(2-butyl-4-chloro-1H-imidazol-5-yl)methyl]amino}-1-(3,5-difluorobenzyl)-2-hydroxypropyl]-5-methyl-N$^3$,N$^3$-dipropylisophthalamide | 633 |
| 713 | N$^1$-((1S,2R)-3-{[(6-chloroimidazo[2,1-b][1,3]thiazol-5-yl)methyl]amino}-1-(3,5-difluorobenzyl)-2-hydroxypropyl]-N$^3$,N$^3$-dipropylisophthalamide | 633 |
| 714 | N$^1$-((1S,2R)-1-(3,5-difluorobenzyl)-2-hydroxy-3-{[(1-methyl-1H-benzimidazol-2-yl)methyl]amino}propyl)-5-methyl-N$^3$,N$^3$-dipropylisophthalamide | 606 |
| 715 | N$^1$-((1S,2R)-1-(3,5-difluorobenzyl)-2-hydroxy-3-{[(2-hydroxy-1-naphthyl)methyl]amino}propyl)-5-methyl-N$^3$,N$^3$-dipropylisophthalamide | 618 |
| 716 | N$^1$-((1S,2R)-1-(3,5-difluorobenzyl)-2-hydroxy-3-{[(4-oxo-4H-chouromen-3-yl)methyl]amino}propyl)-5-methyl-N$^3$,N$^3$-dipropylisophthalamide | 620 |
| 717 | N$^1$-((1S,2R)-1-(3,5-difluorobenzyl)-3-{[(1,5-dimethyl-3-oxo-2-phenyl-2,3-dihydro-1H-pyrazol-4-yl)methyl]amino}-2-hydroxypropyl)-5-methyl-N$^3$,N$^3$-dipropylisophthalamide | 662 |
| 718 | N$^1$-[(1S,2R)-3-({[5-cyano-6-(methylsulfanyl)-2-pyridinyl]methyl}amino)-1-(3,5-difluorobenzyl)-2-hydroxypropyl]-5-methyl-N$^3$,N$^3$-dipropylisophthalamide | 624 |

-continued

| EXA | | MH+ |
|---|---|---|
| 719 | [5-({[(2R,3S)-4-(3,5-difluorophenyl)-3-({3-[(dipropylamino)carbonyl]-5-methylbenzoyl}amino)-2-hydroxybutyl]amino}methyl)-2-furyl]methyl acetate | 614 |
| 720 | $N^1$-[(1S,2R)-3-[(1-benzofuran-3-ylmethyl)amino]-1-(3,5-difluorobenzyl)-2-hydroxypropyl]-5-methyl-$N^3,N^3$-dipropylisophthalamide | 592 |
| 721 | methyl 4-({[(2R,3S)-4-(3,5-difluorophenyl)-3-({3-[(dipropylamino)carbonyl]-5-methylbenzoyl}amino)-2-hydroxybutyl]amino}methyl)-1-methyl-1H-pyrrole-2-carboxylate | 613 |
| 722 | $N^1$-[(1S,2R)-1-(3,5-difluorobenzyl)-2-hydroxy-3-({[1-(phenylsulfonyl)-1H-pyrrol-2-yl]methyl}amino)propyl]-5-methyl-$N^3,N^3$-dipropylisophthalamide | 681 |
| 723 | $N^1$-((1S,2R)-1-(3,5-difluorobenzyl)-2-hydroxy-3-{[(1-methyl-1H-pyrrol-2-yl)methyl]amino}propyl)-5-methyl-$N^3,N^3$-dipropylisophthalamide | 555 |
| 724 | $N^1$-[(1S,2R)-3-{[(4-chloro-1-methyl-1H-pyrazol-3-yl)methyl]amino}-1-(3,5-difluorobenzyl)-2-hydroxypropyl]-5-methyl-$N^3,N^3$-dipropylisophthalamide | 591 |
| 725 | $N^1$-((1S,2R)-1-(3,5-difluorobenzyl)-2-hydroxy-3-{[(3,5-dimethyl-1-phenyl-1H-pyrazol-4-yl)methyl]amino}-2-hydroxypropyl)-5-methyl-$N^3,N^3$-dipropylisophthalamide | 646 |
| 726 | $N^1$-[(1S,2R)-3-{[(5-chloro-3-methyl-1-phenyl-1H-pyrazol-4-yl)methyl]amino}-1-(3,5-difluorobenzyl)-2-hydroxypropyl]-5-methyl-$N^3,N^3$-dipropylisophthalamide | 667 |
| 727 | $N^1$-((1S,2R)-1-(3,5-difluorobenzyl)-2-hydroxy-3-{[(3-phenyl-1H-pyrazol-4-yl)methyl]amino}propyl)-5-methyl-$N^3,N^3$-dipropylisophthalamide | 618 |
| 728 | $N^1$-[(1S,2R)-3-{[(5-chloro-2-thienyl)methyl]amino}-1-(3,5-difluorobenzyl)-2-hydroxypropyl]-5-methyl-$N^3,N^3$-dipropylisophthalamide | 593 |
| 729 | $N^1$-((1S,2R)-1-(3,5-difluorobenzyl)-2-hydroxy-3-{[(3-phenoxy-2-thienyl)methyl]amino}propyl)-5-methyl-$N^3,N^3$-dipropylisophthalamide | 650 |
| 730 | $N^1$-{(1S,2R)-1-(3,5-difluorobenzyl)-2-hydroxy-3-[(3-quinolinylmethyl)amino]propyl}-5-methyl-$N^3,N^3$-dipropylisophthalamide | 603 |
| 731 | $N^1$-{(1S,2R)-1-(3,5-difluorobenzyl)-2-hydroxy-3-[(2-quinolinylmethyl)amino]propyl}-5-methyl-$N^3,N^3$-dipropylisophthalamide | 603 |
| 732 | $N^1$-((1S,2R)-1-(3,5-difluorobenzyl)-2-hydroxy-3-{[(1-methyl-1H-indol-2-yl)methyl]amino}propyl)-5-methyl-$N^3,N^3$-dipropylisophthalamide | 605 |
| 733 | $N^1$-[(1S,2R)-3-{[(1-benzyl-1H-indol-3-yl)methyl]amino}-1-(3,5-difluorobenzyl)-2-hydroxypropyl]-5-methyl-$N^3,N^3$-dipropylisophthalamide | 681 |
| 734 | $N^1$-((1S,2R)-1-(3,5-difluorobenzyl)-2-hydroxy-3-{[(1-methyl-1H-indol-3-yl)methyl]amino}propyl)-5-methyl-$N^3,N^3$-dipropylisophthalamide | 605 |
| 735 | $N^1$-{(1S,2R)-1-(3,5-difluorobenzyl)-2-hydroxy-3-[({1-[(4-methylphenyl)sulfonyl]-1H-indol-3-yl}methyl)amino]propyl}-5-methyl-$N^3,N^3$-dipropylisophthalamide | 745 |
| 736 | $N^1$-[(1S,2R)-3-{[(2-butyl-1H-imidazol-5-yl)methyl]amino}-1-(3,5-difluorobenzyl)-2-hydroxypropyl]-5-methyl-$N^3,N^3$-dipropylisophthalamide | 598 |
| 737 | methyl 3-({[(2R,3S)-4-(3,5-difluorophenyl)-3-({3-[(dipropylamino)carbonyl]-5-methylbenzoyl}amino)-2-hydroxybutyl]amino}methyl)-1H-indole-6-carboxylate | 649 |
| 738 | 3-[({(1S,2R)-1-benzyl-2-hydroxy-3-[(3-methoxybenzyl)amino]propyl}amino)carbonyl]-5-[butyl(butyryl)amino]benzyl diethyl phosphate | |

Example 739

$N^1$-{(1S,2R)-1-benzyl-2-hydroxy-3-[(3-methoxybenzyl)amino]propyl}-5-(cyanomethyl)-$N^3,N^3$-dipropylisophthalamide Step 1. A mixture of diethyl 1,3,5-benzenetricarboxylate (5.2 g) and borane methylsulfide complex (6.1 g) is stirred in THF (150 mL) at 20-25 degrees C. overnight. The mixture is then treated with methanol, concentrated to dryness, and chouromatographed (silica gel) to give diethyl 5-(hydroxymethyl)isophthalate. Diethyl 5-(hydroxymethyl)isophthalate (3.4 g) is hydroyzed in ethanol and water with lithium hydroxide monohydrate (0.57 g) at 20-25 degrees C. for 3.5 hours at which time the solvents are removed under reduced pressure. Water (100 mL) is added and the mixture is acidified to pH=4 with concentrated hydrochloric acid. The mixture is extracted with ethyl acetate and dried over magnesium sulfate, filtered, and concentrated to give 3-(ethoxycarbonyl)-5-(hydroxymethyl)benzoic acid, high resolution MS MH+=225.0769. 3-(Ethoxycarbonyl)-5-(hydroxymethyl)benzoic acid (2.3 g), EDC (3.0 g), 1-HOBT (2.1 g), diisopropylethylamine (2.7 mL), dipropyl amine (2.8 mL), and DMF (50 mL) are stirred at 20-25 degrees C. overnight. The mixture is then partitioned between ethyl acetate, water, and saline. The organic phase is separated and dried over magnesium sulfate, filtered, and concentrated. Chromatography (silica gel) gives ethyl 3-[(dipropylamino)carbonyl]-5-(hydroxymethyl)benzoate, NMR (CDCl$_3$) δ 0.77, 1.0, 1.4, 1.6, 1.7, 3.2, 3.5, 4.4, 4.8, 7.6, 8.0 and 8.1.

Step 2. A mixture of ethyl 3-[(dipropylamino)carbonyl]-5-(hydroxymethyl)benzoate (1.5 g) and phosphorous tribromide (0.95 mL) is stirred in dichloromethane (10 mL) and heated at 50 degrees C. for 4 hours and then cooled and partitioned between dichloromethane and water. The organic phase is separated and washed with aqueous sodium bicarbonate and then dried over magnesium sulfate and taken to dryness to give ethyl 3-(bromomethyl)-5-[(dipropylamino)carbonyl]benzoate, high resolution MS MH+=370.1020. Ethyl 3-(bromomethyl)-5-[(dipropylamino)carbonyl]benzoate (1.4 g) and sodium cyanide (0.2 g) are stirred in dry DMSO (25 mL) at 20-25 degrees C. for 3.5 hours and the mixture is then partitioned between ethyl acetate, water and saline. The organic layer is separated and dried over magnesium sulfate and taken to dryness under reduced pressure to give ethyl 3-(cyanomethyl)-5-[(dipropylamino)carbonyl]benzoate. Ethyl 3-(cyanomethyl)-5-[(dipropylamino)carbonyl]benzoate (0.6 g) is hydrolyzed with lithium hydroxide monohydrate (0.1 g) in ethanol and water at 20-25 degrees C. overnight and then added to water (50 mL). The pH is adjusted to 4 using concentrated hydrochloric acid and the mixture is partitioned between ethyl acetate, water, and saline. The organic phase is separated and dried over magnesium sulfate and taken to dryness under reduced pressure to give 3-(cyanomethyl)-5-[(dipropylamino)carbonyl]benzoic acid, MS M+H=287.2.

Step 3. A mixture of 3-(cyanomethyl)-5-[(dipropylamino)carbonyl]benzoic acid (IX, 0.13 g), (2R,3S)-3-amino-1-[(3-methoxybenzyl)amino]-4-phenyl-2-butanol (VIII, 0.14 g), HATU (0.17 g), and dichloromethane (10 mL) is stirred at 40 degrees C. overnight. After cooling, the mixture is washed with water and the organic phase is separated and dried over magnesium sulfate and taken to dryness under reduced pressure. Chromatography (silica gel) gives the title compound, M+H=571.2

Example 740

$N^1$-{(1S,2R)-1-benzyl-2-hydroxy-3-[(3-methoxybenzyl)amino]propyl}-5-(hydroxymethyl)-$N^3,N^3$-dipropylisophthalamide Following the procedure of CHART P and Example 739 and making non-critical variations but using 3-[(dipropylamino)carbonyl]-5-(hydroxymethyl)benzoic acid (IX) and (2R,3S)-3-amino-1-[(3-methoxybenzyl)amino]-4-phenyl-2-butanol (VIII), the title compound is obtained, HRMS (FAB)=615.3571.

Example 741

N$^1$-{(1S,2R)-1-benzyl-2-hydroxy-3-[(3-methoxybenzyl)amino]propyl}-5-ethynyl-N$^3$,N$^3$-dipropylisophthalamide Step 1: A mixture of methyl 3-bromo-5-[(dipropylamino)carbonyl]benzoate (XXI, 200 mg, 0.58 mmol), PdCl$_2$(Ph$_3$P)$_2$ (16 mg, 0.03 mol %) and copper (I) iodide (6 mg, 0.05 mol %) in triethylamine (1.2 mL) is heated to reflux. (Trimethylsilyl) acetylene (100 microliter, 0.7 mmol) is added, and the mixture stirred for 3 hours, cooled to 20-25 degrees, diluted with water (20 mL), and extracted with chloroform (3×15 mL). The combined organic extracts are washed with saline (20 mL), dried over sodium sulfate and concentrated under reduced pressure to give methyl 3-[(dipropylamino)carbonyl]-5-ethynylbenzoate (XXXII, 185.5 mg), NMR (300 MHz, CDCl$_3$): δ 7.95, 7.75, 7.43, 3.74, 3.25, 2.95, 1.49, 1.34, 0.79, 0.56 and 0.06.

Step 2: To a stirred mixture of the protected methyl 3-[(dipropylamino)carbonyl]-5-ethynylbenzoate (XXXII, Step 1, 185.3 mg, 0.49 mmol) in methanol (2.5 mL) is added a mixture of potassium hydroxide (2.9 mL of a 1 M mixture in water, 2.9 mmol). The reaction mixture is stirred for 4 hours diluted with chloroform (40 mL), the phases are separated and the organic phase is concentrated under reduced pressure to give 3-[(dipropylamino)carbonyl]-5-ethynylbenzoic acid, NMR (300 MHz, CDCl$_3$): δ 8.22, 8.05, 7.71, 3.48, 3.17, 3.16, 1.71, 1.55, 1.00 and 0.78.

Step 3: To a stirred mixture of 3-[(dipropylamino)carbonyl]-5-ethynylbenzoic acid (70 mg, 0.24 mmol) in DMF (2.5 mL) is added (2R,3S)-3-amino-1-[(3-methoxybenzyl)amino]-4-phenyl-2-butanol dihydrochloride (VIII, 81 mg, 0.24 mmol), HOBt (36 mg, 0.26 mmol) and diisopropylethylamine (170 microliter, 0.96 mmol). To this reaction mixture is added EDC (51mg, 0.26 mmol) and the reaction mixture is stirred overnight. The reaction mixture is diluted with ethyl acetate (30 mL), washed with water (3×50 mL), hydrochloric acid (1 N, 30 mL), saturated sodium bicarbonate (30 mL), saline (30 mL), dried over sodium sulfate and concentrated under reduced pressure. Purification by flash chromatography (silica, ethyl acetate to methanol/chloroform, 1/10) gives the title compound, IR (KBr): 3276, 2956, 2921, 1610, 1450 and 1264 cm$^{-1}$; ESI-MS (m/z) [M+H]$^+$=556.

Example 742

N$^1$-{(1S,2R)-1-benzyl-2-hydroxy-3-[(3-iodobenzyl)amino]propyl}-N$^3$,N$^3$-dipropyl-5-prop-1-ynylisophthalamide Following the general procedure of Example 741 and making non-critical variations but using propyne in place of (trimethylsilyl)acetylene and using (2R,3S)-3-amino-1-[(3-iodobenzyl)amino]-4-phenyl-2-butanol dihydrochloride (VIII) in place of (2R,3S)-3-amino-1-[(3-methoxybenzyl)amino]-4-phenyl-2-butanol dihydrochloride (VIII), the title compound is obtained, IR (ATR): 3305, 2930, 2872, 1613 and 1537 cm$^{-1}$; ESI-MS (m/z) [M+H]$^+$=666.

Example 743

N$^1$-((1S,2R)-1-benzyl-2-hydroxy-3-{[3-(trifluoromethyl)benzyl]amino}propyl)-5-ethynyl-N$^3$,N$^3$-dipropylisophthalamide Step 1: A mixture of tert-butyl (1S)-1-[(2S)-oxiranyl]-2-phenylethylcarbamate (V, 2.3 g, 8.7 mmol) and 3-(trifluoromethyl)benzylamine (VI, 1.9 mL, 13.1 mmol) in 2-propanol (70 mL) is heated at reflux for 4 hours. The reaction mixture is cooled to 20-25 degrees and concentrated under reduced pressure to give tert-butyl (1S,2R)-1-benzyl-2-hydroxy-3-{[3-(trifluoromethyl)benzyl]amino}propylcarbamate (VII, 3.1 g) as a solid, ESI-MS (m/z) [M+H]$^+$=439.

Step 2: A mixture of tert-butyl (1S,2R)-1-benzyl-2-hydroxy-3-{[3-(trifluoromethyl)benzyl]amino}propylcarbamate (VII, step 1, 2.5 g, 5.7 mmol) and hydrochloric acid (29 mL of a 4.0 M mixture in dioxane, 114 mmol) is stirred at 20-25 degrees. A precipitate forms and is collected by filtration, washed with ether, and dried under reduced pressure to give (2R,3S)-3-amino-4-phenyl-1-{[3-(trifluoromethyl)benzyl]amino}-2-butanol dihydrochloride (VIII, 2.13 g), ESI-MS (m/z) [M+]$^+$=339.

Step 3: A mixture of 3-[(dipropylamino)carbonyl]-5-ethynylbenzoic acid (IX, 231 mg, 0.8 mmol), (2R,3S)-3-amino-4-phenyl-1-{[3-(trifluoromethyl)benzyl]amino}-2-butanol dihydrochloride (VIII, Step 2, 493.5 mg, 1.2 mmol) HOBt (162 mg, 1.2 mmol), and diisopropylethylamine (832 Micro Liter, 4.8 mmol) is stirred in methylene chloride (4 mL) for 15 minutes EDC (206 mg, 1.2 mmol) is added and the reaction mixture is stirred overnight. The reaction mixture is diluted with water, and extracted with methylene chloride (3×25 mL). The organic phase is washed with hydrochloric acid (1N, 25 mL), saturated sodium bicarbonate (25 mL), saline dried over sodium sulfate and concentrated under reduced pressure. Purification by flash column chromatography (silica, 100% ethyl acetate to methanol/chloroform, 1/9) gives title compound, IR (ATR): 3302, 2963, 2932 and 1615 cm$^{-1}$; MS (m/z) [M+H]$^+$=549.

Example 744

N$^1$-{(1S,2R)-1-benzyl-2-hydroxy-3-[(3-iodobenzyl)amino]propyl}-5-ethynyl-N$^3$,N$^3$-dipropylisophthalamide Following the general procedure of Example 744 and making non-critical variations but using 3-iodobenzylamine hydrochloride salt (VI), the title compound is obtained, IR (ATR) 3295, 2960, 2927 and 1616 cm$^{-1}$, APCI-MS (m/z) [M+H]$^+$=652.

Example 745

N$^1$-{(1S,2R)-1-benzyl-3-[(3-fluorobenzyl)amino]-2-hydroxypropyl}-5-ethynyl-N$^3$,N$^3$-dipropylisophthalamide Following the general procedure of Example 744 and making non-critical variations but using 3-fluorobenzylamine (VI), the title compound is obtained, IR (ATR): 3217, 2961, 2918 and 1615 cm$^{-1}$; APCI-MS (m/z) [M+H]$^+$=544.

Example 746

N$^1$-{(1S,2R)-1-benzyl-2-hydroxy-3-[(3-methoxybenzyl)amino]propyl}-N$^3$,N$^3$-dipropyl-5-(8-quinolinyl)isophthalamide Step 1: A mixture of methyl-3-bromo-5-[(dipropylamino)carbonyl]benzoate (XLVIII, 200 mg, 0.58 mmol), 8-quinolineboronic acid (200.6 mg, 1.2 mmol), sodium carbonate (870 Micro Liter of a 2 M mixture in water, 1.74 mmol) in toluene (6 mL) is degassed under reduced pressure for 15 minutes and purged with argon. Palladium tetrakis(triphenylphosphine) (139 mg, 0.12 mmol) is added and the reaction mixture is degassed under reduced pressure for 15 minutes and purged with argon. The reaction mixture is heated at reflux overnight, cooled to 20-25 degrees C. and diluted with chloroform. The organic phase is separated and washed with water (3×50 mL), and saline, dried over sodium sulfate and concentrated under reduced pressure. Purification by flash column chromatography (silica, ethyl acetate/hexanes, 1.3/1) gives methyl 3-[(dipropylamino)carbonyl]-5-(8-quinolinyl) benzoate (XLIX, 176 mg), NMR (300 MHz, $CDCl_3$): delta 8.91, 8.42, 8.21, 8.09, 7.95, 7.86, 7.77, 7.64, 3.94, 3.49, 3.34, 1.64, 0.99 and 0.84.

Step 2: To a mixture of methyl 3-[(dipropylamino)carbonyl]-5-(8-quinolinyl)benzoate (XLIX, step 1, 175.5 mg, 0-45 mmol) in methanol (2 mL) is added lithium hydroxide (32.3 mg, 1.4 mmol) and water (500 microliter). After stirring overnight, the reaction mixture is partitioned between ethyl acetate (10 mL) and water (10 mL). The aqueous phase is separated and acidified with hydrochloric acid (1N), and extracted with chloroform (3×40 mL). The organic phase is washed with saline, dried (sodium sulfate) and concentrated under reduced pressure to give 3-[(dipropylamino)carbonyl]-5-(8-quinolinyl)benzoic acid (IX-L, 130 mg), NMR (300 MHz, $CD_3OD$) δ 8.84, 8.39, 8.35, 8.05, 7.96, 7.90, 7.87, 7.79, 7.68, 3.50, 3.37, 1.76-1.61, 0.99 and 0.84.

Step 3: A mixture of 3-[(dipropylamino)carbonyl]-5-(8-quinolinyl)benzoic acid (IX-L, Step 2, 130 mg, 0.35 mmol), (2R,3S)-3-amino-1-[(3-methoxybenzyl)amino]-4-phenyl-2-butanol dihydrochloride (VIII, 117 mg, 0.35 mmol), HOBt (70 mg, 0.52 mmol) and diisopropylethylamine (241 microliter, 1.4 mmol) in methylene chloride (2 mL) is stirred for 15 minutes EDC (89 mg, 0.52 mmol) is added and the reaction mixture is stirred overnight. The reaction mixture is diluted with water and extracted with methylene chloride (3×25 mL). The organic phase is washed with hydrochloric acid (1N, 25 mL), saturated sodium bicarbonate (25 mL), saline, dried (sodium sulfate), and concentrated under reduced pressure. Purification by flash column chromatography (silica; methanol/chloroform, 1/9) gives the title compound, IR (NaCl): 3301, 2916, 2365 and 1613 $cm^{-1}$; APCI-MS (m/z) $[M+H]^+$=659.

Example 747

$N^3$-{(1S,2R)-1-benzyl-2-hydroxy-3-[(3-methoxybenzyl)amino]propyl}-4'-methoxy-$N^5$,$N^5$-dipropyl[1,1'-biphenyl]-3,5-dicarboxamide hydrochloride Step 1: A mixture of 4-methoxyphenyl boronic acid (463 mg, 3.05 mmol), 3-bromo-5-[(dipropylamino)carbonyl]benzoic acid (XLVIII, 1 02 g, 3.05 mmol), and potassium phosphate (1.29 g, 6.10 mmol) in 1,2-dimethoxyethane (10 mL) and water (5 mL) is degassed with argon for 15 minutes Bis(triphenylphosphine)palladium (II) chloride (21 mg, 0.03 mmol) is added, the reaction mixture is degassed again with argon, and heated at 85 degrees C. overnight. The reaction mixture is cooled to 20-25 degrees C., and passed through a plug of diatomaceous earth.

The filtrate is acidified to pH=4 with hydrochloric acid (1N) and extracted with ethyl acetate. The organic phase is washed with water and saline and dried (magnesium sulfate). The product is purified by flash column chromatography (silica gel; ethyl acetate/acetic acid, 99/1) to give 5-[(dipropylamino)carbonyl]-4'-methoxy[1,1'-biphenyl]-3-carboxylic acid (IX-L, 667 mg), ESI-MS (m/z) $[M+H]^+$=356.

Step 2: A mixture of 5-[(dipropylamino)carbonyl]-4'-methoxy[1,1'-biphenyl]-3-carboxylic acid (IX-L, step 1, 316 mg, 0.89 mmol), (2R,3S)-3-amino-1-[(3-methoxybenzyl)amino]-4-phenyl-2-butanol dihydrochloride (VIII, 332 mg, 0.89 mmol), HOBt (181 mg, 1.34 mmol), and N-methylmorpholine (0.37 g, 3.56 mmol) in methylene chloride (8 mL) and dimethylformamide (2 mL) is stirred at 20-25 degrees for 15 minutes EDC (257 mg, 1.34 mmol) is added and the reaction mixture is stirred for 4.5 hours. The reaction mixture is partitioned between methylene chloride and water. The organic phase is washed with hydrochloric acid (1N), water, and saline, dried (magnesium sulfate), and concentrated. The concentrate is dissolved in a minimum of methanol, treated with hydrochloric acid (3 mL of a 1.0 M mixture in ether, 3 mmol), and stirred for 10 minutes. More ether is added to precipitate the rest of the product. The precipitate is collected by filtration and dried in the vacuum oven at 50 degrees C. to give the title compound, mp=205-209 degrees C.; IR (ATR): 2964 and 1649 $cm^{-1}$; APCI-MS (m/z) $[M+H]^+$=638.

Example 748

$N^3$-{(1S,2R)-1-(3,5-difluorobenzyl)-2-hydroxy-3-[(3-methoxybenzyl)amino]propyl}-$N^5$,$N^5$-dipropyl[1,1'-biphenyl]-3,5-dicarboxamide hydrochloride Step 1: A mixture of tert-butyl (1S)-2-(3,5-difluorophenyl)-1-[(2S)-oxiranyl]ethylcarbamate (V, 500 mg, 1.67 mmol) and 3-methoxybenzylamine (VI, 0.34g, 2.51 mmol) in 2-propanol (3 mL) is heated at reflux overnight, allowed to cool to 20-25 degrees C., and concentrated under reduced pressure. The residue is crystallized from ethyl acetate/hexanes and collected by filtration to afford tert-butyl (1S,2R)-1-(3,5-difluorobenzyl)-2-hydroxy-3-[(3-methoxybenzyl)amino]propylcarbamate (VII, 575 mg) as a solid: ESI-MS (m/z): 437 $[M+H]^+$.

Step 2: A mixture of tert-butyl (1S,2R)-1-(3,5-difluorobenzyl)-2-hydroxy-3-[(3-methoxybenzyl)amino]propylcarbamate (VII, Step 1, 535 mg, 1.23 mmol) in methanol (2 mL) is treated with hydrochloric acid (3.2 mL of a 1.0 M mixture in ether, 3.2 mmol), and stirred at 20-25 degrees C. for 30 minutes Ether is added until a precipitate formed. The precipitate is collected by filtration is (2R,3S)-3-amino-4-(3,5-difluorophenyl)-1-[(3-methoxybenzyl)amino]-2-butanol dihydrochloride (VIII).

Step 3: A mixture of 5-[(dipropylamino)carbonyl][1,1'-biphenyl]-3-carboxylic acid (IX, 188 mg, 0.56 mmol), (2R, 3S)-3-amino-4-(3,5-difluorophenyl)-1-[(3-methoxybenzyl)amino]-2-butanol dihydrochloride (VIII, Step 2, 230 mg, 0.56 mmol), HOBt (114 mg, 0.84 mmol), and N-methylmorpholine (0.23 g, 2.24 mmol) in methylene chloride (6 mL) and dimethylformamide (1 mL) is stirred at 20-25 degrees C. for 15 minutes EDC (161 mg, 0.84 mmol) is added and the reaction mixture is stirred at 20-25 degrees C. overnight. The reaction mixture is washed with water, 1 N hydrochloric acid, water, and saline, dried (sodium sulfate), and concentrated under reduced pressure to give the title compound, mp 230-233degrees C.; IR (ATR): 2965, 1651, 1596 and 1267 $cm^1$; ESI-MS (m/z) $[M+H]^+$=644.

Example 749

$N^3$-{(1S,2R)-1-benzyl-2-hydroxy-3-[(3-methoxybenzyl)amino]propyl}-$N^5$,$N^5$-dipropyl[1,1'-biphenyl]-3,5-dicarboxamide hydrochloride Following the general procedure of Example 748 and making non-critical variations but using (2R,3S)-3-amino-1-[(3-methoxybenzyl)amino]-4-phenyl-2-butanol dihydrochloride (VIII) in place of (2R,3S)-3-amino-4-(3,5-difluorophenyl)-1-[(3-methoxybenzyl)amino]-2-butanol dihydrochloride (VIII), the title compound is obtained, mp=214-219 degrees C.; IR (KBr): 3227, 2961, 1632 and 1605 cm$^{-1}$; ESI-MS (m/z) [M+H]$^+$=608.

Example 750

$N^3$-{(1S,2R)-1-benzyl-2-hydroxy-3-[(3-methoxybenzyl)amino]propyl}-4'-[(dimethylamino)sulfonyl]-$N^5$, $N^5$-dipropyl-1,1'-biphenyl-3,5-dicarboxamide Step 1: A flask is charged with 1,1'-bis(diphenylphosphino)ferrocene-dichloropalladium 1:1 complex (37 mg, 0.05 mmol), potassium acetate (492 mg, 4.5 mmol) and bis(pinacolato)diboron (408 mg, 1.6 mmol) and is degassed under reduced pressure for 15 min and purged with argon. To this mixture is added a mixture of methyl-3-bromo-5-[(dipropylamino)carbonyl]benzoate (XXI, 500 mg, 1.5 mmol) in anhydrous dimethyl sulfoxide (9 mL) and the reaction mixture is stirred at 80 degrees C. for 4 hours. The reaction mixture is cooled to 20-25 degrees C., diluted with toluene (50 mL), washed with water (3×150 mL), saline, dried (magnesium sulfate), and concentrated under reduced pressure to give methyl 3-[(dipropylamino)carbonyl]-5-(4,4,5,5-tetramethyl-1,3,2-dioxaborolan-2-yl)benzoate, ESI-MS (m/z) [M+H]$^+$=390.

Step 2: A mixture of methyl 3-[(dipropylamino)carbonyl]-5-(4,4,5,5-tetramethyl-1,3,2-dioxaborolan-2-yl)benzoate (Step 1, 534 mg, 1.4 mmol), 4-bromobenzenedimethyl-sulfonamide (363 mg, 1.4 mmol), and sodium carbonate (2 mL of a 2 M mixture in water, 4.1 mmol) in toluene (10 mL) is degassed under reduced pressure for 15 minutes and then purged with argon. Palladium tetrakis(triphenylphosphine) (40 mg, 0.025 mmol) is added and the reaction mixture is degassed under reduced pressure for 15 minutes and then purged with argon. The reaction mixture is heated at reflux for 4 hours, cooled to 20-25 degrees C., filtered through a plug of diatomaceous earth and sodium sulfate, and the filtrate is concentrated under reduced pressure. Purification by flash column chromatography (silica; ethyl acetate/hexanes, 1/1) gives methyl 4'-[(dimethylamino)sulfonyl]-5-[(dipropylamino)carbonyl][1,1'-biphenyl]-3-carboxylate (XXXVIII), ESI-MS (m/z) [M+H]$^+$=447.

Step 3: A mixture of methyl 4'-[(dimethylamino)sulfonyl]-5-[(dipropylamino)carbonyl][1,1'-biphenyl]-3-carboxylate (XXXVIII, step 2, 555 mg, 1.24 mmol) in methanol (6 mL) and sodium hydroxide (2 mL of a 6.0 M mixture in water, 12 mmol) is stirred at 20-25 degrees C. for 4 hours. The reaction mixture is partitioned between ethyl acetate (40 mL) and water (40 mL). The aqueous phase is acidified to pH=4 with hydrochloric acid (1N), extracted with ether (3×100 mL), and the combined organic phases are concentrated under reduced pressure to give methyl 4'-[(dimethylamino)sulfonyl]-5-[(dipropylamino)carbonyl][1,1'-biphenyl]-3-carboxylic acid (IX-XXXIX), NMR (300 MHz, CDCl$_3$): δ 8.37, 8.12, 7.89, 7.80, 3.51, 3.22, 2.76, 1.74, 1.59, 1.02 and 0.79.

Step 4: A mixture of the acid (IX-XXXIX, Step 3, 150 mg, 0.35 mmol), (2R,3S)-3-amino-1-[(3-methoxybenzyl)amino]-4-phenyl-2-butanol dihydrochloride (VIII, 129 mg, 0.35 mmol) HOBt (47 mg, 0.35 mmol), and N-methylmorpholine (122 □L, 1.1 mmol) is stirred in methylene chloride (4 mL) for 15 minutes EDC (107 mg, 0.62 mmol) is added and the reaction mixture is stirred overnight. The reaction mixture is diluted with water, and extracted with methylene chloride (3×25 mL). The organic phase is washed with hydrochloric acid (1N, 25 mL), saturated sodium bicarbonate (25 mL), saline, dried (sodium sulfate), and concentrated under reduced pressure. Purification by flash column chromatography (silica; 100% ethyl acetate to methanol/chloroform, 1/9) gives the title compound, IR (ATR): 2932, 2837 and 1593 cm$^{-1}$; APCI-MS (m/z) [M+H]$^+$=715.

Example 751

$N^3$-{(1S,2R)-1-benzyl-2-hydroxy-3-[(3-iodobenzyl)amino]propyl}-4'-[(dimethylamino)sulfonyl]-$N^5$,$N^5$-dipropyl-1,1'-biphenyl-3,5-dicarboxamide Following the general procedure of Example 750 and making non-critical variations but using 2R,3S)-3-amino-1-[(3-iodobenzyl)amino]-4-phenyl-2-butanol dihydrochloride (VIII), the title compound is obtained, IR (ATR): 3303, 2930, 2872 and 1614 cm$^{-1}$; APCI-MS (m/z) [M+H]$^+$=811.

Example 752

$N^1$-{(1S,2R)-1-benzyl-2-hydroxy-3-[(3-methoxybenzyl)amino]propyl}-$N^3$,$N^3$-dipropyl-5-(3-thienyl) isophthalamide hydrochloride Step 1: To an ice-cold mixture of methyl 3-amino-5-[(dipropylamino)carbonyl]benzoate (XLVIII, 1.0 g, 3.60 mmol) in aqueous hydrogen tetrafluoroborate (48% wt. in H$_2$O, 12.9 mmol) is added a cold mixture of aqueous sodium nitrite (0.25 g, 3.60 mmol) dropwise. The mixture is stirred for 10 min and then extracted with ethyl acetate. The organic phase is washed with water, dried over magnesium sulfate, filtered, and concentrated under reduced pressure to give a diazonium salt which is used without further purification, NMR (500 MHz, CD$_3$OD): δ 9.26, 8.86, 8.71, 4.03, 3.50, 3.22, 1.75, 1.60, 1.01 and 0.79.

Step 2: To a mixture of thiophene-3-boronic acid (1.0 g, 7.82 mmol) in methanol is added a concentrated aqueous mixture of potassium hydrogen difluoride (2.01 g, 25.8 mmol) dropwise. The reaction mixture is stirred for 10 minutes and concentrated under reduced pressure. The resulting solid is extracted with acetone and concentrated under reduced pressure gives crude material, which is recrystallized from acetone/ether to give potassium trifluoro(3-thienyl)borate salt, ESI-MS (m/z) [M+H]$^+$=151.

Step 3: A mixture of potassium trifluoro(3-thienyl)borate salt (step 2, 0.69 g, 1.82 mmol), diazonium salt from (XLVIII, step 1, 0.42 g, 2.19 mmol), and lead acetate (0.02 g, 0.09 mmol) in the dark is purged with argon for 15 minutes. Dioxane (8 mL) is added and the reaction mixture is degassed with argon and stirred at 20-25 degrees C. overnight. The reaction mixture is diluted with ether, washed with saline, dried over magnesium sulfate and concentrated under reduced pressure to give methyl 3-[(dipropylamino)carbonyl]-5-(3-thienyl)benzoate (XLIX) which is purified by flash chromatography (silica; ethyl acetate/hexanes, 1/1), ESI-MS (m/z) [M+H]$^+$=346.

Step 4: A mixture of methyl 3-[(dipropylamino)carbonyl]-5-(3-thienyl)benzoate (XLIX, step 3, 0.31 g, 0.88 mmol) in THF/methanol/sodium hydroxide (3/1/1, 5 mL) is stirred at 40 degrees C. for 2 hours. The reaction is cooled to 20-25 degrees C., diluted with water and extracted with ethyl acetate. The aqueous phase is acidified to pH=4 and extracted with ethyl acetate. The organic phase is washed with water and saline, dried over magnesium sulfate and concentrated under reduced pressure to give 3-[(dipropylamino)carbonyl]-5-(3-thienyl)benzoic acid (IX-L), ESI-MS (m/z) [M+H]$^+$=332.

Step 5: A mixture of 3-[(dipropylamino)carbonyl]-5-(3-thienyl)benzoic acid (IX-L, step 4, 0.26 g, 0.79 mmol), (2R,3S)-3-amino-1-[(3-methoxybenzyl)amino]-4-phenyl-2-butanol dihydrochloride (VIII, 0.26 g, 0.71 mmol), HOBt (0.16 g, 1.18 mmol), and triethylamine (0.44 mL, 3.15 mmol) in DMF (4 mL) is stirred at 20-25 degrees C. for 10 minutes EDC (0.23 g, 1.18 mmol) is added and the reaction mixture is stirred for 4 hours. The reaction mixture is diluted with water and extracted with ethyl acetate. The organic phase is washed with hydrochloric acid (1 N), water, and saline, dried over magnesium sulfate and concentrated under reduced pressure. Recrystallization (methylene chloride/hexanes, 1/1) gives the title compound, mp=199-201 degrees C.; IR (KBr): 3278, 2961, 2874 and 2837 $cm^{-1}$; ESI-MS (m/z) $[M+H]^+$=614.

Example 753

N-{(1R,2R)-1-(3,5-difluorobenzyl)-2-hydroxy-3-[(3-methoxybenzyl)amino]propyl}-3-methyl-5-pentanoylbenzamide Step 1: To an ice-cold, stirred mixture of oxalyl chloride (733 mg, 5.77 mmol) in methylene chloroide (5 mL) is added 3 drops of dimethylformamide. After 10 minutes 3-(methoxycarbonyl)-5-methylbenzoic acid (LXXIII, 560 mg, 2.89 mmol) is added. The reaction mixture is stirred for 1 hour and concentrated under reduced pressure to provide an acid chloride (LXXIV), which is used without further purification.

Step 2: To a −78 degrees C., stirred mixture of acid halide (LXXIV, step 1, 612 mg, 2.89 mmol) and copper (I) bromide (415 mg, 2.89 mmol) in tetrahydrofuran (5 mL) is added butyl magnesium chloride (1.44 mL of a 2.0 M mixture in tetrahydrofuran, 2.89 mmol). The reaction mixture is warmed to 20-25 degrees C., quenched by addition of saturated ammonium chloride, and diluted with ether. The organic phase is separated, washed with saline, dried (sodium sulfate), filtered, and concentrated under reduced pressure. Purification by flash column chromatography (silica; hexanes/ethyl acetate, 6.5/1) gives methyl 3-methyl-5-pentanoylbenzoate (LXXVI), NMR (300 MHz, $CD_3OD$): δ 8.43, 8.05, 3.96, 3.01, 1.77, 1.55 and 1.22.

Step 3: A mixture of methyl 3-methyl-5-pentanoylbenzoate (LXXVI, step 2. 133 mg, 0.605 mmol) in methanol (1 mL) is stirred with tetrahydrofuran/methanol/sodium hydroxide (2 N) (3/1/1, 3 mL) for 3 days. The reaction mixture is diluted with ethyl acetate and washed with water. The aqueous phase is separated and acidified with hydrochloric acid (1 N) and extracted with methylene chloride. The organic phase is dried (sodium sulfate), filtered, and concentrated under reduced pressure to give 3-methyl-5-pentanoylbenzoic acid (IX-LXXVII), NMR (300 MHz, $CD_3OD$): δ 8.44, 8.03, 3.10, 2.33, 1.78, 1.64 and 1.34.

Step 4: To a mixture of 3-methyl-5-pentanoylbenzoic acid (IX-LXXVII, 112 mg, 0.589 mmol), (2R,3S)-3-amino-4-(3,5-difluorophenyl)-1-[(3-methoxybenzyl)amino]-2-butanol dihydrochloride (VIII, 239 mg, 0.589 mmol), HOBt (80 mg, 0.589 mmol), and N-methylmorpholine (250 mg, 2.47 mmol) in methylene chloride (3 mL) is added EDC (203 mg, 1.06 mmol). The reaction mixture is stirred overnight and then partitioned between ethyl acetate and water. The organic phase is washed with hydrochloric acid (1 N), saturated sodium bicarbonate, saline, dried (sodium sulfate), filtered, and concentrated under reduced pressure. Purification by flash column chromatography (silica; methylene chloride/methanol, 12/1) gives the title compound, IR (ATR): 3297, 2957, 1687 and 1628 $cm^{-1}$; APCI-MS (m/z) $[M+H]^+$=539.

Example 754

$N^1$-(4-hydroxybutyl)-$N^3$-{(1S)-2-hydroxy-1-(4-hydroxybenzyl)-3-[(3-methoxybenzyl)amino]propyl}-5-methyl-$N^1$-propylisophthalamide Step 1: To a mixture of methyl(2S)-3-[4-(benzyloxy)phenyl]-2-(tert-butoxycarbonyl)aminopropanoate (1.79 g, 4.65 mmol) in a THF/methanol/water (1/2/1, 16 ml) is added lithium hydroxide (340 mg, 13.9 mmol) and the mixture stirred at 20-25 degrees C. for 12 hours. The mixture is quenched with citric acid (10%). The resulting mixture is extracted with ethyl acetate (3×15 ml). The combined organic extracts are washed three times with water, dried over sodium sulfate, filtered, and concentrated under reduced pressure to give (2S)-3-[4-(benzyloxy)phenyl]-2-[(tert-butoxycarbonyl)amino]propanoic acid which is carried on without purification. To a −78 degrees C., stirred mixture of (2S)-3-[4-(benzyloxy)phenyl]-2-[(tert-butoxycarbonyl)amino]propanoic acid (10.0 g, 27.0 mmol) in THF (200 mL) is added NMM (3.20 mL, 29.0 mmol) and isobutyl chloroformate (3.8 mL, 29.0 mmol). The cold bath is removed, the reaction mixture is stirred for 1 hour, and then filtered. The filtrate is kept cold and used in the next step. To an ice-cold, stirred mixture of ether (110 mL) and potassium hydroxide (40%, 35 mL) is slowly added 1-methyl-3-nitro-1-nitrosoguanidine (8.40 g, 57.0 mmol). The reaction mixture is stirred until gas evolution ends. The organic phase is separated and slowly added to an ice-cold, stirred mixture of the mixed anhydride filtrate from step 2. After the reaction mixture is stirred for 1 hour, nitrogen is bubbled into the mixture for 10 minutes The resulting mixture is concentrated under reduced pressure, diluted with ethyl acetate (200 mL), and washed with water (100 mL). The organic phase is washed with saturated sodium bicarbonate and saline, dried over sodium sulfate, filtered, and concentrated under reduced pressure to give the diazoketone, which is carried on without purification or characterization. To an ice-cold, stirred mixture of diazoketone in ether (100 mL) is added hydrobromous acid (48%, 4 mL, 73 mmol). The cold bath is removed, the reaction mixture stirred for 30 minutes, and partitioned between ether and water. The organic phase separated and washed with saturated sodium bicarbonate and saline, dried over sodium sulfate, filtered, and concentrated under reduced pressure to give tert-butyl (1S)-1-[4-(benzyloxy)benzyl]-3-bromo-2-oxopropylcarbamate (IV) which is used without further purification or characterization. To a −78 degrees C., stirred mixture of tert-butyl (1S)-1-[4-(benzyloxy)benzyl]-3-bromo-2-oxopropylcarbamate (IV) in a isopropanol/THF (2/1, 150 mL) is slowly added sodium borohydride (1.15 g, 30.0 mmol). The reaction mixture is stirred for 30 minutes followed by the addition of water (30 mL). The resulting mixture is warmed to 20-25 degrees C. and concentrated under reduced pressure in a water bath not exceeding 30 degrees C. The crude residue is dissolved in ethyl acetate and washed with water and saline. The organic phase is dried over magnesium sulfate, filtered and concentrated under reduced pressure to give the bromohydrin as a solid. To an ice-cold, stirred mixture of bromohydrin in ethanol (150 mL) and ethyl acetate (100 ml) is added a potassium hydroxyde (1 N) ethanol mixture (36 mL, 36 mmol). The cold bath is removed and the reaction mixture is stirred for 30 minutes. The resulting mixture is partitioned between ethyl acetate and water. The organic phase is separated and washed with saline, dried over magnesium sulfate, filtered, and concentrated under reduced pressure. Purification by flash chromatography (silica; hexanes/ethyl acetate, 5/1) gives tert-butyl (1S)-2-[4-(benzyloxy)phenyl]-1-[(2S)-oxiranyl]ethylcarbamate (V, as a 8/1 mixture of diastereomers), NMR (500 MHz, CDCl$_3$) δ 7.44-7.32, 7.14, 6.93, 5.07, 4.45, 3.61, 3.00-2.60 and 1.39.

Step 2: A mixture of 4-benzyloxybutyric acid (2.69 g, 13.8 mmol), propylamine (0.82 g, 13.8 mmol), HOBt (2.05 g, 15.2 mmol), N-methylmorpholine (1.68 g, 16.6 mmol) and EDC (2.91 g, 15.2 mmol) in DMF (6 mL) is stirred at 20-25 degrees C. for 18 hours. The mixture is diluted with ethyl acetate (40 mL) and washed with water (10 mL), hydrochloric acid (1 N, 10 mL), saturated sodium bicarbonate (10 mL), and saline (10 mL). The organic phase is separated, dried over magnesium sulfate, filtered, and concentrated under reduced pressure to provide 4-(benzyloxy)-N-propylbutanamide (2.59 g), APCI-MS (m/z) [M+H]$^+$=236.

Step 3: To an ice-cold, stirred mixture of 4-(benzyloxy)-N-propylbutanamide (2.59 g, 11.0 mmol) in THF (8 mL) is added lithium aluminum hydride (0.54 g, 14.3 mmol). The reaction mixture is heated to 40-50 degrees C. for 5 hours. The cooled reaction mixture is quenched with water (0.5 mL), sodium hydroxide (2 N, 1.0 mL), and saline (0.5 mL) then diluted with ether (30 mL). The precipitate that formed is filtered off, and the ether phase dried over magnesium sulfate, filtered, and concentrated under reduced pressure to give N-[4-(benzyloxy)butyl]-N-propylamine (2.41 g), APCI-MS (m/z): 222 [M+H]$^+$.

Step 4: A mixture of N-[4-(benzyloxy)butyl]-N-propylamine (2.31 g, 10.44 mmol), 3-(ethoxycarbonyl)-5-methylbenzoic acid (2.18 g, 10.44 mmol), HOBt (1.56 g, 11.49 mmol), N-methylmorpholine (1.37 mL, 12.52 mmol), and EDC (2.20 g, 11.49 mmol) in DMF (12 mL) is stirred at 20-25 degrees C. for 18 hours. The reaction mixture is diluted with ethyl acetate (80 mL) and washed with water (2×20 mL), hydrochloric acid (1 N, 20 mL), saturated sodium bicarbonate (20 mL) and saline (20 mL), dried over magnesium sulfate, filtered, and concentrated under reduced pressure. Purification by flash chromatography (silica; hexanes/ethyl acetate, 1/1) gives ethyl 3-{[[4-(benzyloxy)butyl](propyl)amino]carbonyl}-5-methylbenzoate (1.79 g), NMR, (500 MHz, DMSO-d$_6$): δ 7.80, 7.64, 7.40, 7.38-7.16, 4.50-4.43, 4.34-4.29, 3.53-3.30, 3.20-3.06, 2.41-2.36, 1.70-1.40, 1.36-1.29, 0.94-0.84 and 0.82-0.72; APCI-MS (m/z) [M+H]$^+$=412.

Step 5: To a mixture of ethyl 3-{[[4-(benzyloxy)butyl](propyl)-amino]carbonyl}-5-methylbenzoate (1.75 g, 4.25 mmol) in THF/ethanol/water (1/2/1, 30 mL) is added lithium hydroxide (0.31 g, 12.76 mmol). The reaction mixture is stirred for 2 h and then acidified to pH=3 with concentrated hydrochloric acid (0.5 mL). The reaction mixture is extracted with ethyl acetate (2×30 mL), dried over magnesium sulfate, filtered, and concentrated under reduced pressure to give 3-{[[4-(benzyloxy)butyl](propyl)-amino]carbonyl}-5-methylbenzoic acid (IX, 1.63 g), ESI-MS (m/z) [M+H]$^+$=384.

Step 6: A mixture of tert-butyl (1S)-2-[4-(benzyloxy)phenyl]-1-[(2S)-oxiranyl]ethylcarbamate (V, 1.58 g, 4.28 mmol) and 3-methoxybenzylamine (VI, 825 microliter, 6.42 mmol) in isopropanol (45 mL) is heated to 90 degrees C. for 4 hours. Upon cooling to 20-25 degrees C., the reaction mixture is concentrated under reduced pressure. Purification by flash chromatography (silica; methylene chloride/methanol/ammonium hydroxide 98/1/1 to 95/:4/1) gives tert-butyl (1S,2R)-1-[4-(benzyloxy)benzyl]-2-hydroxy-3-[(3-methoxybenzyl)amino]propylcarbamate (VII, 1.97 g), NMR (300 MHz, MeOH-d$_4$): δ 7.41-6.79; 5.05, 4.33-3.33, 3.74, 3.54, 3.03-2.46 and 1.29; ESI-MS (m/z) [M+H]$^+$=507.

Step 7: tert-Butyl (1S,2R)-1-[4-(benzyloxy)benzyl]-2-hydroxy-3-[(3-methoxybenzyl)amino]propylcarbamate (VII, step 6, 2.34 g, 4.62 mmol) in dioxane (10 mL) is treated with hydrochloric acid (12 mL of a 4.0 M mixture in dioxane, 48 mmol) for 2 hours. The precipitate that forms is collected by filtration, washed with ether, and dried under reduced pressure overnight to give (2R,3S)-3-amino-4-[4-(benzyloxy)phenyl]-1-[(3-methoxybenzyl)amino]-2-butanol hydrochloride (VIII), NMR (300 MHz, MeOH-d$_4$): δ 7.44-6.96, 5.05, 4.21, 3.83, 3.65) and 3.21-2.77; ESI-MS (m/z) [M+H]$^+$=407.

Step 8: To an ice-cold, stirred mixture of 3-{[[4-(benzyloxy)butyl](propyl)amino]carbonyl}-5-methylbenzoic acid (IX, 310 mg, 0.809 mmol), (2R,3S)-3-amino-4-[4-(benzyloxy)phenyl]-1-[(3-methoxybenzyl)amino]-2-butanol hydrochloride (VIII, 359 mg, 0.809 mmol), and bromotripyrrolidinophosphonium hexafluorophosphate (415 mg, 0.890 mmol) in methylene chloride (10 mL) is added diisopropylethylamine (285 microL, 1.62 mmol) dropwise. The resulting mixture is stirred at 0 degrees C. for 30 minutes and then warmed to 20-25 degrees C. After 4 hours, the reaction is concentrated under reduced pressure and is partitioned between ethyl acetate and water. The aqueous phase is separated and extracted with ethyl acetate (3×15 mL), the combined organic phases are dried over magnesium sulfate, and concentrated under reduced pressure. The concentrate is purified by flash chromatography (silica; methylene chloride/methanol/ammonium hydroxide 96/3/0.5) to give N$^1$-{(1S,2R)-1-[4-(benzyloxy)benzyl]-2-hydroxy-3-[(3-methoxybenzyl)amino]propyl}-N$^3$-[4-(benzyloxy)butyl]-5-methyl-N$^3$-propylisophthalamide NMR (300 MHz, Acetone-d$_6$): δ 7.99-6.74), 5.01 4.51-4.29, 4.36, 4.01, 3.80, 3.55-3.16, 2.98-2.82, 2.65-2.62, 2.36, 1.85-1.29, 1.01 and 0.68; ESI-MS (m/z) [M+H]$^+$=772.

Step 9. A mixture of N$^1$-{(1S,2R)-1-[4-(benzyloxy)benzyl]-2-hydroxy-3-[(3-methoxybenzyl)amino]propyl}-N$^3$-[4-(benzyloxy)butyl]-5-methyl-N$^3$-propylisophthalamide (X, 100 mg, 0.130 mmol) and palladium on carbon (10%, 100 mg) in absolute glacial acetic acid (5 mL) is shaken under an atmosphere of hydrogen at 35 psi for 5 hours. The resulting mixture is filtered through diatomaceous earth and washed with methanol. The combined filtrates are concentrated under reduced pressure. The concentrate is purified by flash column chromatography (silica; gradient of dichloromethane/methanol/ammonium hydroxide 97/3/0.05 to 93/7/0.05) to give the title compound: NMR (300 MHz, CD$_3$OD): δ 7.55-6.64, 4.19, 3.99-3.72, 3.63-3.36, 3.21-3.09, 2.79-2.69, 2.39, 1.90-1.40, 1.29 and 1.02-0.6; ESI-MS (m/z) [M+H]$^+$=592.

Example 755

N$^1$-{(1S,2R)-2-hydroxy-1-(4-hydroxybenzyl)-3-[(3-methoxybenzyl)amino]propyl}-N$^3$-(3-hydroxypropyl)-5-methyl-N$^3$-propylisophthalamide Example 756

N$^1$-{(1S,2R)-2-hydroxy-1-(4-hydroxybenzyl)-3-[(3-methoxybenzyl)amino]propyl}-5-methyl-N$^3$,N$^3$-dipropylisophthalamide Step 1. To a stirred mixture of 3-[(dipropylamino)-carbonyl]-5-methylbenzoic acid (IX, 150 mg, 0.570 mmol), (2R,3S)-3-amino-4-[4-(benzyloxy)phenyl]-1-[(3-methoxybenzyl)amino]-2-butanol hydrochloride (VIII, 274 mg, 0.571 mmol), N,N-diisopropylethylamine (400 microliter, 2.28 mmol), and HOBt (116 mg, 0.857 mmol) in dichloromethane (10 mL) is added EDC (165 mg, 0.857 mmol). The resulting mixture is stirred at 20-25 degrees C. for 16 hours. The reaction mixture is partitioned between dichloromethane and water. The aqueous phase is separated and extracted with dichloromethane (3×15 mL). The combined organic phases are washed with water, dried (magnesium sulfate), and concentrated under reduced pressure. Purification by flash column chromatography (silica; dichloromethane/methanol/ammonium hydroxide, 97/3/0.05) gives $N^1$-{(1S,2R)-1-[4-(benzyloxy)benzyl]-2-hydroxy-3-[(3-methoxybenzyl)amino]propyl}-5-methyl-$N^3$,$N^3$-dipropylisophthalamide, ESI-MS (m/z) [M+H]$^+$=652.

Step 2. A mixture of $N^1$-{(1S,2R)-1-[4-(benzyloxy)benzyl]-2-hydroxy-3-[(3-methoxybenzyl)amino]propyl}-5-methyl-$N^3$,$N^3$-dipropylisophthalamide (140 mg, 0.215 mmol) and palladium on carbon (10%, 140 mg) in absolute glacial acetic acid (5 mL) is shaken under an atmosphere of hydrogen at 35 psi for 5 hours The resulting mixture is filtered through diatomaceous earth and washed with methanol. The combined filtrates are concentrated under reduced pressure. The concentrate is purified by flash column chromatography (silica; methylene chloride/methanol/ammonium hydroxide gradient from 97/3/0.05 to 93/7/0.05) to give the title compound, IR (KBr) 2962, 2931, 1611, 1594 and 1263 cm$^{-1}$; ESI-MS (m/z) [M+H]$^+$=562.

Example 757

$N^1$-((1S,2R)-1-benzyl-3-{[3-(2,4-dimethylphenyl)propyl]amino}-2-hydroxypropyl)-5-methyl-$N^3$,$N^3$-dipropylisophthalamide Step 1: A stirred mixture of tert-butyl (1S)-1-[(2S)-oxiranyl]-2-phenylethylcarbamate (V, 247 mg, 0.939 mmol), sodium carbonate (299 mg, 2.82 mmol), and 3-(2,4-dimethylphenyl)propylamine (VI, 628 mg, 2.82 mmol) is heated at reflux overnight. The reaction mixture is cooled to 20-25 degrees C. and concentrated under reduced pressure. Purification by flash column chromatography (silica; methylene chloride/methanol/ammonium hydroxide, 98/2/1) gives tert-butyl (1S,2R)-1-benzyl-3-{[3-(2,4-dimethylphenyl)propyl]amino}-2-hydroxypropylcarbamate (VII), NMR (300 MHz, CD$_3$OD): δ 7.22-7.16, 3.81, 3.18, 2.77, 2.54, 2.15, 2.13, 1.89 and 1.23.

Step 2: To a stirred mixture of tert-butyl (1S,2R)-1-benzyl-3-{[3-(2,4-dimethylphenyl)propyl]amino}-2-hydroxypropylcarbamate (VII, 180 mg, 0.423 mmol) in dioxane (2 mL) is added hydrochloric acid (0.32 mL of a 4 N mixture in dioxane, 1.27 mmol). The reaction mixture is stirred overnight and concentrated under reduced pressure to give (2R, 3S)-3-amino-1-{[3-(2,4-dimethylphenyl)propyl]amino}-4-phenyl-2-butanol hydrochloride (VIII), NMR (300 MHz, CDCl$_3$): δ 7.14, 3.73, 2.70, 2.32 and 1.86.

Step 3: To a stirred mixture of (2R,3S)-3-amino-1-{[3-(2,4-dimethylphenyl)propyl]amino}-4-phenyl-2-butanol hydrochloride (VIII, 163 mg, 0.411 mmol), 3-[(dipropylamino)carbonyl]-5-methylbenzoic acid (IX, 108 mg, 0.411 mmol), HOBt (55 mg, 0.411 mmol), and N-methylmorpholine (133 mg, 1.32 mmol) in methylene chloride (5 mL) is added EDC (142 mg, 0.740 mmol). The reaction mixture is stirred overnight and then partitioned between ethyl acetate and water. The organic phase is washed with hydrochloric acid (1 N), saturated sodium bicarbonate, saline, dried (sodium sulfate), filtered, and concentrated under reduced pressure. Purification by flash column chromatography (silica; methylene chloride/methanol/ammonium hydroxide, 95/5/1) gives the title compound, IR (ATR): 3299, 2930 and 1614 cm$^{-1}$; APCI-MS (m/z) [M+H]$^+$=572.

Example 758

$N^1$-((1S,2R)-1-benzyl-2-hydroxy-3-{[3-(4-methylphenyl)propyl]amino}propyl)-5-methyl-$N^3$,$N^3$-dipropylisophthalamide hydrochloride Example 759

$N^1$-{(1S,2R)-1-benzyl-2-hydroxy-3-[(3-methoxybenzyl)amino]propyl}-5-methyl-$N^3$,$N^3$-dipropylisophthalamide Example 760

N-{(1S,2R)-1-benzyl-2-hydroxy-3-[(3-methoxybenzyl)amino]propyl}-1,3-dioxo-2-propyl-5-isoindolinecarboxamide Example 761

N-{(1R,2R)-1-benzyl-2-hydroxy-3-[(3-methoxybenzyl)amino]propyl}-3-bromo-5-methylbenzamide Example 762

3-bromo-N-{(1S,2R)-1-(3,5-difluorobenzyl)-2-hydroxy-3-[(3-methoxybenzyl)amino]propyl}-5-methylbenzamide Example 763

$N^1$-{(1S,2R)-1-benzyl-2-hydroxy-3-[(3-methoxybenzyl)amino]propyl}-4-methyl-$N^3$,$N^3$-dipropylisophthalamide Example 764

$N^1$-{(1S,2R)-1-(3,5-difluorobenzyl)-2-hydroxy-3-[(3-methoxybenzyl)amino]propyl}-4-methyl-$N^3$,$N^3$-dipropylisophthalamide Example 765

$N^3$-{(1S,2R)-1-benzyl-2-hydroxy-3-[(3-methoxybenzyl)amino]propyl}-4-methyl-$N^1$,$N^1$-dipropylisophthalamide 3-Bromo-4-methylbenzoic acid (10.94 g, 43.25 mmol), copper(I)cyanide (7.75 g, 86.5 mmol) and 1-methyl-2-pyrrolidinone (75 ml) are heated to 160 degrees C. overnight. The mixture is cooled and vacuum distilled to give a residue which is stirred in hydrochloric acid (6N, 60 ml) for 10 minutes. The resulting solid is collected by filtration, washed with water, ether, and dried. The solid is heated to 90 degrees C. in sodium hydroxide (2N, 250 ml) for 3 hours and the mixture is then cooled and stirred overnight at 20-25 degrees C. The reaction is acidified to about pH 3 with concentrated hydrochloric acid which gives a precipitate. The solids are collected by filtration and washed with water, then triturated in boiling water, filtered and dried in a vacuum oven at 60 degrees C. The solid is dissolved in methanol (75 ml) and concentrated hydrochloric acid (5 ml) is added and the mixture is refluxed overnight. The mixture then is cooled and concentrated under reduced pressure. Chromatography (silica gel; methanol/methylene chloride, 8/92) gives 5-(methoxycarbonyl)-2-methylbenzoic acid.

To 5-(methoxycarbonyl)-2-methylbenzoic acid (250 mg, 1.3 mmol) and triethylamine (0.72 ml, 5.2 mmol) in methylene chloride (14 ml) is added diethylcyanopyrocarbonate (90%, 0.24 ml, 1.4 mmol) with stirring. After 1 minute, (2R,3S)-3-amino-1-[(3-methoxybenzyl)amino]-4-phenyl-2-butanol dihydrochloride (VIII, 485 mg, 1.3 mmol) is added and the reaction is stirred overnight. The mixture is concentrated followed by chromatography (silica gel; methanol/methylene chloride 8/92) to afford 3-[({(1S,2R)-1-benzyl-2-hydroxy-3-[(3-methoxybenzyl)amino]propyl}amino)carbonyl]-4-methylbenzoate.

3-[({(1S,2R)-1-benzyl-2-hydroxy-3-[(3-methoxybenzyl)amino]propyl}amino)carbonyl]-4-methylbenzoate (200 mg, 0.42 mmol) is treated with lithium hydroxide (39 mg, 0.96 mmol) in tetrahydrofuran/methanol/water (2/1/1, 2 ml), and the mixture stirred overnight at 20-25 degrees C. The mixture is decanted and the supernatant concentrated to give 3-[({(1S,2R)-1-benzyl-2-hydroxy-3-[(3-methoxybenzyl)amino]propyl}amino)carbonyl]-4-methylbenzoic acid.

3-[({(1S,2R)-1-benzyl-2-hydroxy-3-[(3-methoxybenzyl)amino]propyl}amino)carbonyl]-4-methylbenzoic acid (124 mg, 0.27 mmol) is dissolved in triethylamine (0.07 ml, 0.54 mmol) and methylene chloride (3 ml) and treated with diethylcyanopyrocarbonate (90%, 0.06 ml, 0.32 mmol) with stirring for 2 minutes. Dipropylamine (0.04 ml, 0.32 mmol) is added and stirring continued overnight. The organic phase is diluted with methylene chloride and washed with saturated sodium bicarbonate (2×50 ml) and saline (50 ml) then dried over anhydrous sodium sulfate, filtered and concentrated. Chromatography (silica gel; methanol/methylene chloride, 8/92) gives the title compound, MS [M+H]$^+$=546.3.

Example 766

N-{(1S,2R)-1-benzyl-2-hydroxy-3-[(3-methoxybenzyl)amino]propyl}-3-(2-furyl)-5-methylbenzamide N-{(1R,2R)-1-benzyl-2-hydroxy-3-[(3-methoxybenzyl)amino]propyl}-3-bromo-5-methylbenzamide (X, EXAMPLE 761, 295 mg, 0.59 mmol), 2-furanylboronic acid (133 mg, 1.19 mmol) and sodium carbonate (366 mg, 2.95 mmol) are combined in dimethylformamide (5 ml) and sparged under a flow of nitrogen for 15 minutes. Tetrakis(triphenylphosphino)palladium (136 mg, 0.12 mmol) is added and the mixture heated to 100 degrees C. overnight. The mixture is cooled to 20-25 degrees C., diluted with chloroform (50 ml) and extracted with water (3×100 ml). The organic phase is separated and washed with saturated sodium bicarbonate (2×100 ml) and saline (100 ml), dried over anhydrous sodium sulfate, filtered, and concentrated under reduced pressure. The residue is chouromatographed (silica gel; methanol/methylene chloride, 8/92) to give the title compound, MS [M+H]$^+$=485.3.

Example 767

N-{(1S,2R)-1-benzyl-2-hydroxy-3-[(3-methoxybenzyl)amino]propyl}-3',5,5'-trimethyl-1,1'-biphenyl-3-carboxamide Example 768

3'-Acetyl-N-{(1S,2R)-1-benzyl-2-hydroxy-3-[(3-methoxybenzyl)amino]propyl}-5-methyl[1,1'-biphenyl]-3-carboxamide Example 769

N-{(1S,2R)-1-benzyl-2-hydroxy-3-[(3-methoxybenzyl)amino]propyl}-3'-methoxy-5-methyl[1,1'-biphenyl]-3-carboxamide Example 770

N-{(1S,2R)-1-benzyl-2-hydroxy-3-[(3-methoxybenzyl)amino]propyl}-5-methyl[1,1'-biphenyl]-3-carboxamide Example 771

3-Methyl-5-(3-thienyl)benzoic acid (IX)

Methyl 3-methyl-5-(3-thienyl)benzoate (257 mg, 1.1 mmol) is treated with lithium hydroxide (186 mg, 4.4 mmol) in tetrahydrofuran/methanol/water (8 ml, 2:1:1) and the mixture is stirred for 2 hours at 20-25 degrees C. The mixture is acidified and concentrated to give the title compound, MS [M+H]$^+$=217.0.

Example 772

N-{(1S,2R)-1-benzyl-2-hydroxy-3-[(3-methoxybenzyl)amino]propyl}-3-methyl-5-(3-thienyl)benzamide Example 773

N-{(1S,2R)-1-benzyl-2-hydroxy-3-[(3-methoxybenzyl)amino]propyl}-3-methyl-5-(2-thienyl)benzamide Example 774

N-{(1S,2R)-1-(3,5-difluorobenzyl)-2-hydroxy-3-[(3-methoxybenzyl)amino]propyl}-3-methyl-5-(3-thienyl)benzamide Example 775

N-{(1S,2R)-1-(3,5-difluorobenzyl)-2-hydroxy-3-[(3-iodobenzyl)amino]propyl}-3-methyl-5-(3-thienyl)benzamide Example 776

N-{(1S,2R)-1-benzyl-2-hydroxy-3-[(3-methoxybenzyl)amino]propyl}-4-methyl-3-(3-thienyl)benzamide Example 777

N$^1$-{(1S,2R)-1-Benzyl-2-hydroxy-3-[(3-methoxybenzyl)amino]propyl}-N$^3$,N$^3$,N$^5$,N$^5$-tetrapropylbenzene-1,3,5-tricarboxamide hydrochloride Example 778

N$^1$-{(1S,2R)-1-(3,5-Difluorobenzyl)-3-[(3-ethylbenzyl)amino]-2-hydroxypropyl}-N$^3$,N$^3$-dipropylbenzene-1,3,5-tricarboxamide

Example 779

Ethyl 3-[({(1S,2R)-1-benzyl-2-hydroxy-3-[(3-methoxybenzyl)amino]propyl}amino)carbonyl]-5-[(dipropylamino)carbonyl]benzoate hydrochloride

Example 780

$N^1$-{(1S,2R)-2-Hydroxy-1-(4-hydroxybenzyl)-3-[(3-methoxybenzyl)amino]propyl}-$N^3$,$N^3$-dipropylbenzene-1,3,5-tricarboxamide

Example 781

$N^1$-{(1S,2R)-1-Benzyl-2-hydroxy-3-[(3-methoxybenzyl)amino]propyl}-$N^3$,$N^3$-dipropyl-5-{[(trifluoromethyl)sulfonyl]amino}isophthalamide

Example 782

5-Amino-$N^1$-{(1S,2R)-1-benzyl-2-hydroxy-3-[(3-methoxybenzyl)amino]propyl}-$N^3$,$N^3$-dipropylisophthalamide

Example 783

$N^1$-{(1S,2R)-1-Benzyl-2-hydroxy-3-[(3-methoxybenzyl)amino]propyl}-$N^3$,$N^3$-dipropyl-5-[(trifluoroacetyl)amino]isophthalamide

Example 784

$N^1$-{(1S,2R)-1-Benzyl-2-hydroxy-3-[(3-methoxybenzyl)amino]propyl}-5-[(methylsulfonyl)amino]-$N^3$,$N^3$-dipropylisophthalamide hydrochloride

Example 785

$N^1$-{(1S,2R)-1-Benzyl-2-hydroxy-3-[(3-methoxybenzyl)amino]propyl}-$N^3$,$N^3$-dipropyl-5-[(thien-2-ylsulfonyl)amino]isophthalamide hydrochloride

Example 786

$N^1$-{(1S,2R)-1-Benzyl-2-hydroxy-3-[(3-methoxybenzyl)amino]propyl}-$N^3$,$N^3$-dipropyl-5-[(thien-2-ylcarbonyl)amino]isophthalamide

Example 787

$N^1$-{(1S,2R)-1-Benzyl-2-hydroxy-3-[(3-methoxybenzyl)amino]propyl}-5-(methacryloylamino)-$N^3$,$N^3$-dipropylisophthalamide

Example 788

$N^1$-{(1S,2R)-1-Benzyl-2-hydroxy-3-[(3-methoxybenzyl)amino]propyl}-5-[(2,2-dimethylpropanoyl)amino]-$N^3$,$N^3$-dipropylisophthalamide

Example 789

$N^1$-{(1S,2R)-1-Benzyl-2-hydroxy-3-[(3-methoxybenzyl)amino]propyl}-5-[(phenylsulfonyl)amino]-$N^3$,$N^3$-dipropylisophthalamide

Example 790

N-{(1S,2R)-1-benzyl-2-hydroxy-3-[(3-methoxybenzyl)amino]propyl}-5-(methylthio)pentanamide

Example 791 tert-butyl (2R,3S)-3-({3-[(dipropylamino)sulfonyl]propanoyl}amino)-2-hydroxy-4-phenylbutyl(3-methoxybenzyl)carbamate

Example 792

2-Butylcyclopropylamine hydrochloride (VI)

A solution of triethylphosphonoacetate (22.4 g, 0.1 mol) in 13 mL of diglyme is added to a mixture of 13 mL of diglyme and sodium hydride (60%, 5.7 g, 0.12 mol) in mineral oil. When hydrogen evolution ceased, 1,2-epoxyhexane (12 g, 0.12 mol) in diglyme (12 mL) is added. The mixture is stirred for 1 day at 25 degrees C. and 3 hours at 140 degrees C. A mixture of sodium hydroxide (15 g in 25 mL of water) is added in the cold. The mixture is refluxed 15 hours, diluted with cold water (100 mL), and washed with ether (3×50 mL). Acidification to pH=2 with sulfuric acid (25%), extraction with ether (5×25 mL), drying the ether over anhydrous sodium sulfate, filtration and concentration gives 2-butylcyclopropanecarboxylic acid. The acid (5.0 g, 0.035 mmol) in dichloromethane (15 mL) is heated with thionyl chloride (5.1 g, 3.1 mL) for 15 hours at 60 degrees C. The reaction mixture is distilled (76 degrees C.-80 degrees C.) to give the acid chloride which is dissolved in acetone (15 mL), cooled to −10 degrees C. and treated with sodium azide (2.2 g, 33.8 mmol) in water (5 mL). The reaction mixture is stirred at −10 degrees C. for another 1 hour and then poured onto ice/water, extracted with ether (3×10 mL), dried, and cautiously evaporated to dryness at 20-25 degrees C. under reduced pressure. The residue is dissolved in toluene (15 mL) and carefully warmed to 100 degrees C. while vigorously stirring for 1 hour. Concentrated hydrochloric acid (7 mL) is added and the reaction mixture is refluxed for 15 minutes. The acidic layer is evaporated to dryness to give the title compound, $MH^+$=114.2.

Example 793

2-Aminomethyl-3-methylfuran (VI)

3-Methylfuroic acid (4.0 g, 32 mmol) is dissolved in DMF (10 mL) at 20-25 degrees C., and 1,1-carbonyldiimidazole (5.7 g, 35 mmol) is added. After 15 minutes, ammonia is bubbled into the mixture for approximately 2 minutes. This mixture is stirred at 20-25 degrees C. for 2 hours then the mixture is concentrated under reduced pressure. The residue is partitioned between ethyl acetate and 10% aqueous citric acid. The layers are separated, and the aqueous layer extracted with additional ethyl acetate (2×). The combined organic phases are washed with saturated sodium bicarbonate, then saline and dried over magnesium sulfate, filtered and concentrated. Crystals formed upon standing, which are isolated by filtration and washing with a small amount of ethyl acetate/hexanes (80/20), MS(ESI): $MH^+$: 126.1. 3-Methylfuroic amide (317 mg, 2.5 mmol) is dissolved in dry THF (5 mL). Lithium aluminum hydride (230 mg, 6.0 mmol) is added in one portion, and the mixture heated to reflux overnight. The mixture is cooled to 0 degrees C., and quenched by addition of THF/water (50/50). The mixture is then diluted with THF, and filtered through diatomaceous earth. The filtrate is concentrated to give the title compound, MS(ESI): (M−H)+: 109.1.

Example 794

4-Aminomethyl-3,5-dimethylisoxazole (VI)

4-Chloromethyl-3,5-dimethylisoxazole (700 mg, 4.8 mmol) is suspended in concentrated aqueous ammonia at 20-25 degrees C., and vigorously stirred overnight. The reaction mixture is extracted with isopropyl alcohol/chloroform (10/90, 2×). The combined organic phases are concentrated under nitrogen flow. The residue is purified by flash chromatography methanol/methylene chloride (5-20%, 1% triethylamine) to give the title compound, MR (CDCl$_3$, 300 MHz) delta 3.62, 2.37, 2.29, and 1.44.

Example 795

5-Hydroxymethyl-2-(2-methylpropyl)thiazole (VI)

Isovalerothioamide is synthesized according to the procedure in *J. Med. Chem.* 41, 602-617 (1998). Isovaleramide (10 g, 9.9 mmol) is suspended in dry ether (400 mL), then phosphorous(V) sulfide (4.4 g, 0.99 mmol) is added in portions. This is vigorously stirred at 20-25 degrees C. for 2 hours, then filtered. The filtrate is concentrated under reduced pressure and the residue used without further purification: MS(ESI): MH+: 118.1.

Isovalerothioamide (6.0 g, 51 mmol) and ethyl formylchloroacetate (*Heterocycles* 32 (4), 693-701, (1991), 5.0 g, 33 mmol) are dissolved in dry DMF (20 mL), and heated to 95 degrees C. for 4 hours. The reaction is subsequently cooled to 0 degrees C., and cold water (50 mL) is added. The mixture is basified to pH=8 with solid sodium bicarbonate, then extracted with ether (3×35 mL). The combined organic extracts are washed with water, then saline and dried over magnesium sulfate, filtered, and concentrated. The residue is purified by flash chromatography (ethyl acetate/hexanes 4-10% elution) to give the desired product. NMR (CDCl$_3$, 300 MHz) δ 8.27, 4.45-4.30, 3.70-3.50, 3.00-2.80, 2.30-2.10, 1.40-1.20, and 1.10-0.90.

A solution of ethyl 2-(2-methylpropyl)thiazole-5-carboxylate (2.05 g, 9.6 mmol) in THF (10 mL) is added dropwise with stirring to a suspension of lithium aluminum hydride (730 mg, 19 mmol) in dry THF (50 mL) at 0 degrees C. Upon complete addition, the reaction mixture is allowed to stir at 20-25 degrees C. The reaction mixture is cooled to 0 degrees C., and water (0.75 mL), aqueous sodium hydroxide (15%, 0.75 mL), and water (2.25 mL) is added in succession. This mixture is stirred at 0 degrees C. for 1 hour, then filtered through diatomaceous earth, (THF and chloroform). The filtrate is concentrated to give 5-hydroxymethyl-2-(2-methylpropyl)thiazole, MS(ESI): MH+: 172.1.

Example 796

3-(2-Methylpropyl)-5-aminomethylisoxazole (VI)

Isovaleraldehyde (5.4 mL, 50 mmol) and hydroxylamine hydrochloride (3.5 g, 50.4 mmol) are vigorously stirred in water (6 mL). To this is added a solution of sodium carbonate (2.65 g, 25 mmol) in water (15 mL). This is vigorously stirred overnight. The mixture is extracted with ether. The organic layer is washed with water, then dried over sodium sulfate, filtered and concentrated. This is used in subsequent reactions without further purification: MS(ESI): MH+: 102.1.

Propargylamine (8.0 mL, 117 mmol) is dissolved in methylene chloride (60 mL), and di-tert-butyl dicarbonate (25 g, 114 mmol) is added. This is stirred overnight, and concentrated to provide the BOC-protected propargylamine, which is used without further purification: MS(ESI): MNa+: 178.0.

BOC-propargylamine (6.2 g, 39.7 mmol) and isovaleroxime (3.97 g, 39.3 mmol) is dissolved in methylene chloride (60 mL), and triethylamine (0.55 mL, 3.95 mmol) is added. This is cooled to 0 degrees C., and bleach (5% aqueous solution, 59.1 g) is added dropwise with vigorous stirring. After addition is complete, the mixture is allowed to warm to 20-25 degrees C. over 22 hours. The layers are separated, and the aqueous layer is extracted with methylene chloride (2×). The combined organic extracts are washed with saline, dried over magnesium sulfate, filtered and concentrated. The residue is purified by chromatography (silica gel, ethyl acetate/hexanes 5-10%) to give the BOC-protected title compound, MS(ESI): MH+: 255.3.

BOC-protected 3-(2-methylpropyl)-5-aminomethylisoxazole (2.4 g, 9.3 mmol) is dissolved in methylene chloride (10 mL) and treated with trifluoroacetic acid (10 mL) at 20-25 degrees C. This is stirred at −20-25 degrees C. for 70 minutes, then concentrated. The product is dissolved in methylene chloride, and washed with aqueous potassium carbonate (1 M) until basic (pH=11). The organic layer is isolated, dried over sodium sulfate, filtered and concentrated to give the title compound: MS(ESI): MH+: 155.2.

Example 797 tert-butyl (3R)-2-oxo-1-propylazepanylcarbamate (VI)

To N-t-Boc-D-Lys-OH (10 g, 41.4 mmole) in DMF (4 liters) is added benzotriazol-1yloxytripyrrolidino-phosphonium hexafluorophosphate (BOP, 18.3 g, 41.4 mmole) and sodium bicarbonate (17.4 g, 206.8 mmole); the reaction is stirred at 20-25 degrees C. for 12 hours. The reaction is then concentrated to 50 ml volume and diluted with ethyl acetate and washed with sodium bicarbonate 3×, water, 1 m potassium bisulfate and brine, dried and concentrated. Purification by chromatography on silica gel afforded 5.05 g of the tert-butyl (3R)-2-oxoazepanylcarbamate as a solid; the procedure employed is similar to that described in *J. Med. Chem.* 1999, 4193. M+H− (t-Boc) (m/e=129.2), M+Na (m/e=251.1).

To the above lactam (2 g, 8.77 mmole) in dry THF (20 ml) is added n-butyllithium/hexane (2.5 M, 5.3 ml, 13.2 mmole) at −78 degrees C., the reaction is stirred for 1 hour and 1-bromopropane (3.2 ml, 35.1 mmole) is added. The reaction is stirred for 1 hour and the cold bath removed and stirring continued for another 16 hours. Tetrabutylammonium iodide (0.49 g, 2.63 mmole) is added and the reaction stirred for another 16 hours. The reaction is partitioned between ethyl acetate/hydrochloric acid+ice+water, the mixture is washed with water and saline and concentrated. Purification by chromatography on silica gel afforded the title compound, MS (M+Na+) 293.3.

Example 798

N$^1$-{(1S,2R)-1-(3,5-difluorobenzyl)-3-[(3-ethynylbenzyl)amino]-2-hydroxypropyl}-5-methyl-N$^3$,N$^3$-dipropylisophthalamide Following the procedure described in *J. Am. Chem. Soc.* 1986, 3150, the trifluoroacetic acid salt of N$^1$-{(1S,2R)-1-(3, 5-difluorobenzyl)-2-hydroxy-3-[(3-iodobenzyl)amino]propyl}-5-methyl-N$^3$,N$^3$-dipropylisophthalamide (92.9 mg, 0.117 mmol) is dissolved in triethylamine (0.2 M, 0.6 mL)

before the addition of PdCl$_2$(PPh$_3$)$_2$ (3.3 mg, 0.005 mmol), and copper (I) iodide (1.1 mg, 0.006 mmol). The reaction is heated to reflux. While the reaction is refluxing, trimethylsilylacetylene (0.02 ml, 0.14 mmol) is added via syringe. The reaction is refluxed for 3 hour under N$_2$ (g), and the reaction cooled to 20-25 degrees C. before partitioning between aqueous sodium bicarbonate and ethyl acetate. The product is extracted with ethyl acetate (3×), washed with saline, dried over sodium sulfate$_4$, and filtered before the removal of solvent under reduced pressure.

The TMS protected acetylene (0.117 mmol) is dissolved in methanol (0.2 M, 0.5 mL) before the addition of potassium hydroxide (1M, 0.7 mL, 0.7 mmol). The reaction is stirred at 20-25 degrees C. for 6 hours, at which point the mixture is partitioned between sodium bicarbonate and ethyl acetate. The product is extracted with ethyl acetate (3×), washed with saline, dried over sodium sulfate, and filtered before the removal of solvent under reduced pressure. Column chromatography (silica gel; 1.5-2% isopropanol/chloroform under basic conditions; a few drops of ammonium hydroxide per 100 mL of elution solvent) gives the title compound, MS m/z (M+H)$^+$=576.3.

Example 799

1-phenylcyclopropylamine (VI)

Following the procedure described in N. W. Werner et. al., *J. Org. Syn. Coll.* Vol. 5, 273-276, sodium azide (0.915 g, 14.1 mmol) is slowly added to a solution of 1-phenyl-cyclopropanecarboxlic acid (1.0 g, 6.1 mmol) in concentrated sulfuric acid (5 ml) and dichloromethane (10 ml). The sodium sulfate precipitated out of solution. The reaction mixture is heated to 50 degrees C. for 17 hours and then cooled to 0 degrees C. The mixture is basified to pH=11 with sodium hydroxide (1N) and extracted with dichloromethane (2×). The organic layers are combined, dried over sodium sulfate, filtered and concentrated. The residue is purified by chromatography (silica gel; isopropyl alcohol/chloroform/ammonium hydroxide 4/95/1) to give the title compound, MS (ESI+) for C$_9$H$_{11}$N m/z (M+H)$^+$=134.

Example 800

7-methoxy-1,2,3,4-tetrahydro-1-naphthalenamine (VI)

7-Methoxy-1-tetralone (2.0 g, 11.3 mmol), hydroxylamine hydrochloride (1.56 g, 22.6 mmol) and sodium acetate (1.8 g, 22.6 mmol) are suspended in ethanol/water (3/1, 40 mL). The mixture is heated for 45 min. at 100 degrees C. The mixture is allowed to cool overnight and the precipitate obtained is filtered and washed with water to yield an intermediate oxime, MS (ES) (M+H): 192.1. The oxime is dissolved in glacial acetic acid (25 ml) and palladium/carbon (500 mg) is added and the mixture hydrogenated under 50 psi at 20-25 degrees C. overnight. The catalyst is filtered over diatomaceous earth and washed with methanol. The combined filtrates are concentrated. The concentrate is triturated with ether to give the title compound, MS (CI) (M+H)$^+$: 178.2.

The following compounds are prepared essentially according to the procedures set forth above and generally described in the Charts.

Example 801

3-Amino-N-{(1S,2R)-1-benzyl-2-hydroxy-3-[(3-methoxybenzyl)amino]propyl}-2-methylbutanamide dihydrochloride Example 802

N-{(1S,2R)-1-Benzyl-2-hydroxy-3-[(3-methoxybenzyl)amino]propyl}-2-ethylhexanamide hydrochloride Example 803

N-{(1S,2R)-1-benzyl-2-hydroxy-3-[(3-iodobenzyl)amino]propyl}-3-[(isobutylsulfonyl)amino]propanamide trifluoroacetate Example 804

N$^1$-{(1S,2R)-1-(3,5-difluorobenzyl)-2-hydroxy-3-[(3-iodobenzyl)amino]propyl}-N$^3$-(isobutylsulfonyl)-beta-alaninamide trifluoroacetate Example 805

5-bromo-N$^1$-{(1S,2R)-1-(3,5-difluorobenzyl)-2-hydroxy-3-[(3-iodobenzyl)amino]propyl}-N$^3$,N$^3$-dipropylisophthalamide hydrochloride Example 806

N$^1$-{(1S,2R)-1-(3,5-difluorobenzyl)-2-hydroxy-3-[(1-phenylcyclopropyl)amino]propyl}-5-methyl-N$^3$,N$^3$-dipropylisophthalamide Example 806-A 5-bromo-N$^1$-[(1S,2R)-3-[(3-bromobenzyl)amino]-1-(3,5-difluorobenzyl)-2-hydroxypropyl]-N$^3$,N$^3$-dipropylisophthalamide

| EXA | |
|---|---|
| 807 | N-{(1S,2R)-1-benzyl-2-hydroxy-3-[(3-methoxybenzyl)amino]propyl}-3-methyl-5-(2-propylpentanoyl)benzamide |
| 808 | N-{(1S,2R)-1-(3,5-difluorobenzyl)-3-[(3-ethylbenzyl)amino]-2-hydroxypropyl}-3-(2-ethylpentanoyl)-5-methylbenzamide |
| 809 | N-{(1S,2R)-1-benzyl-3-[(3-ethylbenzyl)amino]-2-hydroxypropyl}-3-methyl-5-(2-propylpentanoyl)benzamide |
| 810 | N-{(1S,2R)-1-benzyl-3-[(3-ethynylbenzyl)amino]-2-hydroxypropyl}-3-methyl-5-(2-propylpentanoyl)benzamide |
| 811 | N-{(1S,2R)-1-(3,5-difluorobenzyl)-3-[(3-ethylbenzyl)amino]-2-hydroxypropyl}-3-(2-ethylbutanoyl)-5-methylbenzamide |

-continued

| EXA | |
|---|---|
| 812 | N$^1$-{(1S,2R)-1-benzyl-3-[(3-ethylbenzyl)amino]-2-hydroxypropyl}-5-(2-propylpentanoyl)isophthalamide |
| 813 | N-{(1S,2R)-1-benzyl-3-[(3-ethylbenzyl)amino]-2-hydroxypropyl}-3-(2-ethylpentanoyl)-5-methylbenzamide |
| 814 | N$^1$-{(1S,2R)-1-(3,5-difluorobenzyl)-3-[(3-ethylbenzyl)amino]-2-hydroxypropyl}-5-(2-propylpentanoyl)isophthalamide |
| 815 | N$^1$-{(1S,2R)-1-(3,5-difluorobenzyl)-2-hydroxy-3-[(3-methoxybenzyl)amino]propyl}-5-(2-propylpentanoyl)isophthalamide |
| 816 | N-[(1S,2R)-3-[(3-ethylbenzyl)amino]-2-hydroxy-1-(4-hydroxybenzyl)propyl]-3-methyl-5-(2-propylpentanoyl)benzamide |
| 817 | N-{(1S,2R)-1-(3,5-difluorobenzyl)-2-hydroxy-3-[(3-methoxybenzyl)amino]propyl}-3-methyl-5-(2-propylpentanoyl)benzamide |
| 818 | N-{(1S,2R)-1-(3,5-difluorobenzyl)-3-[(3-ethylbenzyl)amino]-2-hydroxypropyl}-3-methyl-5-(2-propylpentanoyl)benzamide |
| 819 | N$^1$-((1S,2R)-1-(3,5-difluorobenzyl)-2-hydroxy-3-{[3-(3-pyridinyl)benzyl]amino}propyl)-5-methyl-N$^3$,N$^3$-dipropylisophthalamide |
| 820 | N$^1$-((1S,2R)-1-(3,5-difluorobenzyl)-2-hydroxy-3-{[3-(4-pyridinyl)benzyl]amino}propyl)-5-methyl-N$^3$,N$^3$-dipropylisophthalamide |
| 821 | N$^1$-{(1S,2R)-1-(3,5-difluorobenzyl)-2-hydroxy-3-[(3-methoxybenzyl)amino]propyl}-N$^3$,N$^3$-dipropyl-5-(1-propynyl)isophthalamide |
| 822 | N$^1$-{(1S,2R)-1-(3,5-difluorobenzyl)-3-[(3-ethylbenzyl)amino]-2-hydroxypropyl}-N$^3$,N$^3$-dipropyl-5-(1-propynyl)isophthalamide |
| 823 | N$^1$-{(1S,2R)-1-(3,5-difluorobenzyl)-3-[(3-ethylbenzyl)amino]-2-hydroxypropyl}-N$^3$,N$^3$-dipropyl-5-(2-propynyl)isophthalamide |
| 824 | N$^1$-{(1S,2R)-1-(3,5-difluorobenzyl)-2-hydroxy-3-[(3-methoxybenzyl)amino]propyl}-N$^3$,N$^3$-dipropyl-5-(2-propynyl)isophthalamide |
| 825 | N$^1$-{(1S,2R)-1-(cyclohexylmethyl)-2-hydroxy-3-[(3-methoxybenzyl)amino]propyl}-5-methyl-N$^3$,N$^3$-dipropylisophthalamide |
| 826 | N$^1$-[(1S,2R)-3-(benzylamino)-2-hydroxy-1-(3-thienylmethyl)propyl]-5-methyl-N$^3$,N$^3$-dipropylisophthalamide |
| 827 | N$^1$-[(1S,2R)-2-hydroxy-3-[(3-methoxybenzyl)amino]-1-(2-thienylmethyl)propyl]-5-methyl-N$^3$,N$^3$-dipropylisophthalamide |
| 828 | N$^1$-{(1S)-1-[(1R)-2-(benzylamino)-1-hydroxyethyl]-3-butynyl}-N$^3$,N$^3$-dipropyl-1,3,5-benzenetricarboxamide |
| 829 | N$^1$-[(1S,2R)-2-hydroxy-3-[(3-methoxybenzyl)amino]-1-(3-thienylmethyl)propyl]-5-methyl-N$^3$,N$^3$-dipropylisophthalamide |
| 830 | N$^1$-[(1S,2R)-3-(benzylamino)-2-hydroxy-1-(2-thienylmethyl)propyl]-5-methyl-N$^3$,N$^3$-dipropylisophthalamide |
| 831 | N$^1$-{(1S,2R)-1-(3-furylmethyl)-2-hydroxy-3-[(3-methoxybenzyl)amino]propyl}-5-methyl-N$^3$,N$^3$-dipropylisophthalamide |
| 832 | N$^1$-{(1S,2R)-3-(benzylamino)-1-[4-(benzyloxy)benzyl]-2-hydroxypropyl}-N$^3$,N$^3$-dipropyl-1,3,5-benzenetricarboxamide |
| 833 | N$^1$-{(1S,2R)-1-(2-furylmethyl)-2-hydroxy-3-[(3-methoxybenzyl)amino]propyl}-5-methyl-N$^3$,N$^3$-dipropylisophthalamide |
| 834 | N$^1$-[(1S,2R)-3-(benzylamino)-1-(cyclohexylmethyl)-2-hydroxypropyl]-5-methyl-N$^3$,N$^3$-dipropylisophthalamide |
| 835 | N$^1$-{(1S,2R)-2-hydroxy-1-(4-hydroxybenzyl)-3-[(3-methoxybenzyl)amino]propyl}-5-methyl-N$^3$,N$^3$-dipropylisophthalamide |
| 836 | N$^1$-[(1S,2R)-3-(benzylamino)-2-hydroxy-1-(1-naphthylmethyl)propyl]-N$^3$,N$^3$-dipropyl-1,3,5-benzenetricarboxamide |
| 837 | 2,3,5-trideoxy-3-({3-[(dipropylamino)carbonyl]-5-methylbenzoyl}amino)-5-[(3-methoxybenzyl)amino]-1-S-phenyl-1-thio-D-erythouro-pentitol |
| 838 | N$^1$-[(1S,2R)-3-(benzylamino)-1-(3-furylmethyl)-2-hydroxypropyl]-5-methyl-N$^3$,N$^3$-dipropylisophthalamide |
| 839 | N$^1$-((1S)-1-{(1R)-1-hydroxy-2-[(3-methoxybenzyl)amino]ethyl}-3-methylbutyl)-5-methyl-N$^3$,N$^3$-dipropylisophthalamide |
| 840 | N$^1$-[(1S,2R)-3-(benzylamino)-1-(4-fluorobenzyl)-2-hydroxypropyl]-N$^3$,N$^3$-dipropyl-1,3,5-benzenetricarboxamide |
| 841 | N$^1$-{(1S,2R)-1-(4-fluorobenzyl)-2-hydroxy-3-[(3-methoxybenzyl)amino]propyl}-5-methyl-N$^3$,N$^3$-dipropylisophthalamide |
| 842 | N$^1$-[(1S,2R)-3-(benzylamino)-1-(2-furylmethyl)-2-hydroxypropyl]-5-methyl-N$^3$,N$^3$-dipropylisophthalamide |
| 843 | N$^1$-[(1S,2R)-2-hydroxy-3-[(3-methoxybenzyl)amino]-1-(1-naphthylmethyl)propyl]-5-methyl-N$^3$,N$^3$-dipropylisophthalamide |

-continued

| EXA | |
|---|---|
| 844 | N$^1$-{(1S)-1-[(1R)-2-(benzylamino)-1-hydroxyethyl]-3-methylbutyl}-N$^3$,N$^3$-dipropyl-1,3,5-benzenetricarboxamide |
| 845 | N$^1$-{(1S,2R)-1-[4-(benzyloxy)benzyl]-2-hydroxy-3-[(3-methoxybenzyl)amino]propyl}-5-methyl-N$^3$,N$^3$-dipropylisophthalamide |
| 846 | N$^1$-[(1S,2R)-3-(benzylamino)-2-hydroxy-1-(4-hydroxybenzyl)propyl]-5-methyl-N$^3$,N$^3$-dipropylisophthalamide |
| 847 | N$^1$-((1S)-1-{(1R)-1-hydroxy-2-[(3-methoxybenzyl)amino]ethyl}-3-butynyl)-5-methyl-N$^3$,N$^3$-dipropylisophthalamide |
| 848 | N$^1$-((1S)-1-{(1R)-1-hydroxy-2-[(3-methoxybenzyl)amino]ethyl}-3-butynyl)-N$^3$,N$^3$-dipropyl-1,3,5-benzenetricarboxamide |
| 849 | 5-(benzylamino)-2,3,5-trideoxy-3-({3-[(dipropylamino)carbonyl]-5-methylbenzoyl}amino)-1-S-phenyl-1-thio-D-erythouro-pentitol |
| 850 | N$^1$-{(1S,2R)-1-[4-(benzyloxy)benzyl]-2-hydroxy-3-[(3-methoxybenzyl)amino]propyl}-N$^3$,N$^3$-dipropyl-1,3,5-benzenetricarboxamide |
| 851 | N$^1$-[(1S,2R)-3-(benzylamino)-2-hydroxy-1-(4-hydroxybenzyl)propyl]-N$^3$,N$^3$-dipropyl-1,3,5-benzenetricarboxamide |
| 852 | N$^1$-[(1S,2R)-2-hydroxy-3-[(3-methoxybenzyl)amino]-1-(1-naphthylmethyl)propyl]-N$^3$,N$^3$-dipropyl-1,3,5-benzenetricarboxamide |
| 853 | N$^1$-{(1S)-1-[(1R)-2-(benzylamino)-1-hydroxyethyl]-3-methylbutyl}-5-methyl-N$^3$,N$^3$-dipropylisophthalamide |
| 854 | N$^1$-{(1S,2R)-1-(4-fluorobenzyl)-2-hydroxy-3-[(3-methoxybenzyl)amino]propyl}-N$^3$,N$^3$-dipropyl-1,3,5-benzenetricarboxamide |
| 855 | N$^1$-[(1S,2R)-3-(benzylamino)-1-(3-furylmethyl)-2-hydroxypropyl]-N$^3$,N$^3$-dipropyl-1,3,5-benzenetricarboxamide |
| 856 | N$^1$-((1S)-1-{(1R)-1-hydroxy-2-[(3-methoxybenzyl)amino]ethyl}-3-methylbutyl)-N$^3$,N$^3$-dipropyl-1,3,5-benzenetricarboxamide |
| 857 | N$^1$-[(1S,2R)-3-(benzylamino)-1-(4-fluorobenzyl)-2-hydroxypropyl]-5-methyl-N$^3$,N$^3$-dipropylisophthalamide |
| 858 | N$^1$-[(1S,2R)-3-(benzylamino)-1-(2-furylmethyl)-2-hydroxypropyl]-N$^3$,N$^3$-dipropyl-1,3,5-benzenetricarboxamide |
| 859 | N$^1$-{(1S,2R)-2-hydroxy-1-(4-hydroxybenzyl)-3-[(3-methoxybenzyl)amino]propyl}-N$^3$,N$^3$-dipropyl-1,3,5-benzenetricarboxamide |
| 860 | N$^1$-[(1S,2R)-3-(benzylamino)-2-hydroxy-1-(1-naphthylmethyl)propyl]-5-methyl-N$^3$,N$^3$-dipropylisophthalamide |
| 861 | N$^1$-{(1S,2R)-1-(cyclohexylmethyl)-2-hydroxy-3-[(3-methoxybenzyl)amino]propyl}-N$^3$,N$^3$-dipropyl-1,3,5-benzentricarboxamide |
| 862 | N$^1$-[(1S,2R)-3-(benzylamino)-2-hydroxy-1-(2-thienylmethyl)propyl]-N$^3$,N$^3$-dipropyl-1,3,5-benzenetricarboxamide |
| 863 | N$^1$-{(1S,2R)-1-(3-furylmethyl)-2-hydroxy-3-[(3-methoxybenzyl)amino]propyl}-N$^3$,N$^3$-dipropyl-1,3,5-benzenetricarboxamide |
| 864 | N$^1$-{(1S,2R)-3-(benzylamino)-1-[4-(benzyloxy)benzyl]-2-hydroxypropyl}-5-methyl-N$^3$,N$^3$-dipropylisophthalamide |
| 865 | N$^1$-{(1S,2R)-1-(2-furylmethyl)-2-hydroxy-3-[(3-methoxybenzyl)amino]propyl}-N$^3$,N$^3$-dipropyl-1,3,5-benzenetricarboxamide |
| 866 | N$^1$-[(1S,2R)-3-(benzylamino)-2-hydroxy-1-(3-thienylmethyl)propyl]-N$^3$,N$^3$-dipropyl-1,3,5-benzenetricarboxamide |
| 867 | N$^1$-[(1S,2R)-2-hydroxy-3-[(3-methoxybenzyl)amino]-1-(2-thienylmethyl)propyl]-N$^3$,N$^3$-dipropyl-1,3,5-benzenetricarboxamide |
| 868 | N$^1$-{(1S)-1-[(1R)-2-(benzylamino)-1-hydroxyethyl]-3-butynyl}-5-methyl-N$^3$,N$^3$-dipropylisophthalamide |
| 869 | N$^1$-[(1S,2R)-2-hydroxy-3-[(3-methoxybenzyl)amino]-1-(3-thienylmethyl)propyl]-N$^3$,N$^3$-dipropyl-1,3,5-benzenetricarboxamide |
| 870 | N$^1$-{(1S,2R)-1-(cyclohexylmethyl)-2-hydroxy-3-[(3-methoxybenzyl)amino]propyl}-N$^3$,N$^3$-dipropyl-1,3,5-benzenetricarboxamide |
| 871 | N$^1$-[(1S,2R)-2-hydroxy-3-[(3-methoxybenzyl)amino]-1-(3-thienylmethyl)propyl]-N$^3$,N$^3$-dipropyl-1,3,5-benzenetricarboxamide |
| 872 | N$^1$-[(1S,2R)-2-hydroxy-3-[(3-methoxybenzyl)amino]-1-(2-thienylmethyl)propyl]-N$^3$,N$^3$-dipropyl-1,3,5-benzenetricarboxamide |

| EXA | |
|---|---|
| 873 | $N^1$-{(1S,2R)-1-(2-furylmethyl)-2-hydroxy-3-[(3-methoxybenzyl)amino]propyl}-$N^3$,$N^3$-dipropyl-1,3,5-benzenetricarboxamide |
| 874 | $N^1$-{(1S,2R)-1-(3-furylmethyl)-2-hydroxy-3-[(3-methoxybenzyl)amino]propyl}-$N^3$,$N^3$-dipropyl-1,3,5-benzenetricarboxamide |
| 875 | $N^1$-{(1S,2R)-2-hydroxy-1-(4-hydroxybenzyl)-3-[(3-methoxybenzyl)amino]propyl}-$N^3$,$N^3$-dipropyl-1,3,5-benzenetricarboxamide |
| 876 | $N^1$-((1S)-1-{(1R)-1-hydroxy-2-[(3-methoxybenzyl)amino]ethyl}-3-methylbutyl)-$N^3$,$N^3$-dipropyl-1,3,5-benzenetricarboxamide |
| 877 | $N^1$-{(1S,2R)-1-(4-fluorobenzyl)-2-hydroxy-3-[(3-methoxybenzyl)amino]propyl}-$N^3$,$N^3$-dipropyl-1,3,5-benzenetricarboxamide |
| 878 | $N^1$-[(1S,2R)-2-hydroxy-3-[(3-methoxybenzyl)amino]-1-(1-naphthylmethyl)propyl]-$N^3$,$N^3$-dipropyl-1,3,5-benzenetricarboxamide |
| 879 | $N^1$-{(1S,2R)-1-[4-(benzyloxy)benzyl]-2-hydroxy-3-[(3-methoxybenzyl)amino]propyl}-$N^3$,$N^3$-dipropyl-1,3,5-benzenetricarboxamide |
| 880 | $N^1$-{(1S,2R)-2-hydroxy-1-[3-(hydroxymethyl)benzyl]-3-[(3-methoxybenzyl)amino]propyl}-5-methyl-$N^3$,$N^3$-dipropylisophthalamide |
| 881 | $N^1$-{(1S,2R)-3-[(3-ethylbenzyl)amino]-2-hydroxy-1-[3-(hydroxymethyl)benzyl]propyl}-5-methyl-$N^3$,$N^3$-dipropylisophthalamide |
| 882 | $N^1$-{(1S,2R)-2-hydroxy-1-[3-(hydroxymethyl)benzyl]-3-[(3-iodobenzyl)amino]propyl}-5-methyl-$N^3$,$N^3$-dipropylisophthalamide |
| 883 | $N^1$-{(1S,2R)-2-hydroxy-1-[4-(hydroxymethyl)benzyl]-3-[(3-iodobenzyl)amino]propyl}-5-methyl-$N^3$,$N^3$-dipropylisophthalamide |
| 884 | $N^1$-{(1S,2R)-3-[(3-ethylbenzyl)amino]-2-hydroxy-1-[4-(hydroxymethyl)benzyl]propyl}-5-methyl-$N^3$,$N^3$-dipropylisophthalamide |
| 885 | $N^1$-{(1S,2R)-2-hydroxy-1-[4-(hydroxymethyl)benzyl]-3-[(3-methoxybenzyl)amino]propyl}-5-methyl-$N^3$,$N^3$-dipropylisophthalamide |
| 886 | $N^1$-{(1S,2R)-1-(3-fluoro-5-hydroxybenzyl)-2-hydroxy-3-[(3-methoxybenzyl)amino]propyl}-5-methyl-$N^3$,$N^3$-dipropylisophthalamide |
| 887 | $N^1$-[(1S,2R)-3-[(3-ethylbenzyl)amino]-1-(3-fluoro-5-hydroxybenzyl)-2-hydroxypropyl]-5-methyl-$N^3$,$N^3$-dipropylisophthalamide |
| 888 | $N^1$-{(1S,2R)-1-(3-fluoro-5-hydroybenzyl)-2-hydroxy-3-[(3-iodobenzyl)amino]propyl}-5-methyl-$N^3$,$N^3$-dipropylisophthalamide |
| 889 | $N^1$-{(1S,2R)-1-[3-(benzyloxy)-5-fluorobenzyl]-2-hydroxy-3-[(3-iodobenzyl)amino]propyl}-5-methyl-$N^3$,$N^3$-dipropylisophthalamide |
| 890 | $N^1$-{(1S,2R)-1-[3-(benzyloxy)-5-fluorobenzyl]-2-hydroxy-3-[(3-methoxybenzyl)amino]propyl}-5-methyl-$N^3$,$N^3$-dipropylisophthalamide |
| 891 | N-{(1S,2R)-1-[4-(benzyloxy)benzyl]-2-hydroxy-3-[(3-methoxybenzyl)amino]propyl}-3-[(dipropylamino)sulfonyl]propanamide |
| 892 | $N^1$-{(1S,2R)-1-[4-(benzyloxy)benzyl]-2-hydroxy-3-[(3-methoxybenzyl)amino]propyl}-$N^5$,$N^5$-dipropylpentanediamide |
| 893 | 3-[(dipropylamino)sulfonyl]-N-[(1S,2R)-2-hydroxy-3-[(3-methoxybenzyl)amino]-1-(1-naphthylmethyl)propyl]propanamide |
| 894 | $N^1$-[(1S,2R)-2-hydroxy-3-[(3-methoxybenzyl)amino]-1-(1-naphthylmethyl)propyl]-$N^5$,$N^5$-dipropylpentanediamide |
| 895 | 3-[(dipropylamino)sulfonyl]-N-{(1S,2R)-1-(4-fluorobenzyl)-2-hydroxy-3-[(3-methoxybenzyl)amino]propyl}propanamide |
| 896 | $N^1$-{(1S,2R)-1-(4-fluorobenzyl)-2-hydroxy-3-[(3-methoxybenzyl)amino]propyl}-$N^5$,$N^5$-dipropylpentanediamide |
| 897 | 3-[(dipropylamino)sulfonyl]-N-{(1S,2R)-2-hydroxy-1-(4-hydroxybenzyl)-3-[(3-methoxybenzyl)amino]propyl}propanamide |
| 898 | $N^1$-{(1S,2R)-2-hydroxy-1-(4-hydroxybenzyl)-3-[(3-methoxybenzyl)amino]propyl}-$N^5$,$N^5$-dipropylpentanediamide |
| 899 | 3-[(dipropylamino)sulfonyl]-N-{(1S,2R)-1-(3-furylmethyl)-2-hydroxy-3-[(3-methoxybenzyl)amino]propyl}propanamide |
| 900 | $N^1$-{(1S,2R)-1-(2-furylmethyl)-2-hydroxy-3-[(3-methoxybenzyl)amino]propyl}-$N^5$,$N^5$-dipropylpentanediamide |
| 901 | 3-[(dipropylamino)sulfonyl]-N-{(1S,2R)-1-(2-furylmethyl)-2-hydroxy-3-[(3-methoxybenzyl)amino]propyl}propanamide |

-continued

| EXA | |
|---|---|
| 902 | $N^1$-{(1S,2R)-1-(3-furylmethyl)-2-hydroxy-3-[(3-methoxybenzyl)amino]propyl}-$N^5,N^5$-dipropylpentanediamide |
| 903 | 3-[(dipropylamino)sulfonyl]-N-[(1S,2R)-2-hydroxy-3-[(3-methoxybenzyl)amino]-1-(2-thienylmethyl)propyl]propanamide |
| 904 | $N^1$-[(1S,2R)-2-hydroxy-3-[(3-methoxybenzyl)amino]-1-(3-thienylmethyl)propyl]-$N^5,N^5$-dipropylpentanediamide |
| 905 | 3-[(dipropylamino)sulfonyl]-N-[(1S,2R)-2-hydroxy-3-[(3-methoxybenzyl)amino]-1-(3-thienylmethyl)propyl]propanamide |
| 906 | $N^1$-[(1S,2R)-2-hydroxy-3-[(3-methoxybenzyl)amino]-1-(2-thienylmethyl)propyl]-$N^5,N^5$-dipropylpentanediamide |
| 907 | N-{(1S,2R)-1-(3,5-difluorobenzyl)-2-hydroxy-3-[(3-methoxybenzyl)amino]propyl}-3-{[(2R)-1-ethylpyrrolidinyl]carbonyl}-5-methylbenzamide |
| 908 | N-{(1S,2R)-1-(3,5-difluorobenzyl)-2-hydroxy-3-[(3-methoxybenzyl)amino]propyl}-3-{[(2S)-1-ethylpyrrolidinyl]carbonyl}-5-methylbenzamide |
| 909 | N-{(1S,2R)-1-(3,5-difluorobenzyl)-2-hydroxy-3-[(3-methoxybenzyl)amino]propyl}-3-[(1-ethyl-1H-imidazol-2-yl)carbonyl]-5-methylbenzamide |
| 910 | N-{(1S,2R)-1-(3,5-difluorobenzyl)-2-hydroxy-3-[(3-methoxybenzyl)amino]propyl}-3-[(1-ethyl-4-methyl-1H-imidazol-5-yl)carbonyl]-5-methylbenzamide |
| 911 | $N^1$-((1S,2R)-1-(3,5-difluorobenzyl)-2-hydroxy-2-{1-[(3-methoxybenzyl)amino]cyclopropyl}ethyl)-5-methyl-$N^3,N^3$-dipropylisophthalamide |
| 912 | $N^1$-((1S,2S)-1-(3,5-difluorobenzyl)-2-{1-[(3-ethylbenzyl)amino]cyclopropyl}-2-hydroxyethyl)-5-methyl-$N^3,N^3$-dipropylisophthalamide |
| 913 | (1R,2R,3R)-$N^1$-{(1S,2R)-1-(3,5-difluorobenzyl)-2-hydroxy-3-[(3-methoxybenzyl)amino]propyl}-$N^2,N^2$-dipropyl-1,2,3-cyclopropanetricarboxamide |
| 914 | (1R,2R,3R)-$N^1$-{(1S,2R)-1-(3,5-difluorobenzyl)-2-hydroxy-3-[(3-methoxybenzyl)amino]propyl}-3-phenyl-$N^2,N^2$-dipropyl-1,2-cyclopropanedicarboxamide |
| 915 | (1R,2R,3R)-$N^1$-{(1S,2R)-1-(3,5-difluorobenzyl)-2-hydroxy-3-[(3-methoxybenzyl)amino]propyl}-3-methyl-$N^2,N^2$-dipropyl-1,2-cyclopropanedicarboxamide |
| 916 | (1R,2R,3S)-$N^1$-{(1S,2R)-1-(3,5-difluorobenzyl)-2-hydroxy-3-[(3-methoxybenzyl)amino]propyl}-3-methyl-$N^2,N^2$-dipropyl-1,2-cyclopropanedicarboxamide |
| 917 | (1R,2R,3S)-$N^1$-{(1S,2R)-1-(3,5-difluorobenzyl)-2-hydroxy-3-[(3-methoxybenzyl)amino]propyl}-3-phenyl-$N^2,N^2$-dipropyl-1,2-cyclopropanedicarboxamide |
| 918 | (1R,2R,3S)-$N^1$-{(1S,2R)-1-(3,5-difluorobenzyl)-2-hydroxy-3-[(3-methoxybenzyl)amino]propyl}-$N^2,N^2$-dipropyl-1,2,3-cyclopropanetricarboxamide |
| 919 | (1R,2R,3S)-3-(2-amino-2-oxoethyl)-$N^1$-{(1S,2R)-1-(3,5-difluorobenzyl)-2-hydroxy-3-[(3-methoxybenzyl) amino] propyl}-$N^2,N^2$-dipropyl-1,2-cyclopropanedicarboxamide |
| 920 | (1R,2R,3R)-3-(2-amino-2-oxoethyl)-$N^1$-{(1S,2R)-1-(3,5-difluorobenzyl)-2-hydroxy-3-[(3-methoxybenzyl)amino]-propyl}-$N^2,N^2$-dipropyl-1,2-cyclopropanedicarboxamide |
| 921 | (1R,2R,3S)-N-{(1S,2R)-1-(3,5-difluorobenzyl)-2-hydroxy-3-[(3-methoxybenzyl)amino]propyl}-2-[2-(dipropylamino)-2-oxoethyl]-3-methylcyclopropanecarboxamide |
| 922 | (1R,2R,3R)-N-{(1S,2R)-1-(3,5-difluorobenzyl)-2-hydroxy-3-[(3-methoxybenzyl)amino]propyl}-2-[2-(dipropylamino)-2-oxoethyl]-3-methylcyclopropanecarboxamide |
| 923 | (1S,2R,3R)-N-{(1S,2R)-1-(3,5-difluorobenzyl)-2-hydroxy-3-[(3-methoxybenzyl)amino]propyl}-2-[2-(dipropylamino)-2-oxoethyl]-3-phenylcyclopropanecarboxamide |
| 924 | (1S,2R,3S)-N-{(1S,2R)-1-(3,5-difluorobenzyl)-2-hydroxy-3-[(3-methoxybenzyl)amino]propyl}-2-[2-(dipropylamino)-2-oxoethyl]-3-phenylcyclopropanecarboxamide |
| 925 | (1S,2R,3R)-$N^1$-{(1S,2R)-1-(3,5-difluorobenzyl)-2-hydroxy-3-[(3-methoxybenzyl)amino]propyl}-3-[2-(dipropylamino)-2-oxoethyl]-1,2-cyclopropanedicarboxamide |
| 926 | (1S,2R,3S)-$N^1$-{(1S,2R)-1-(3,5-difluorobenzyl)-2-hydroxy-3-[(3-methoxybenzyl)amino]propyl}-3-[2-(dipropylamino)-2-oxoethyl]-1,2-cyclopropanedicarboxamide |
| 927 | $N^1$-{(1S,2R)-1-(3,5-difluorobenzyl)-2-hydroxy-3-[(3-methoxybenzyl)amino]propyl}-$N^3,N^3$-dipropyl-5-{[(trifluoromethyl)sulfonyl]amino}isophthalamide |
| 928 | $N^1$-{(1S,2R)-1-(3,5-difluorobenzyl)-3-[(3-ethylbenzyl)amino]-2-hydroxypropyl}-$N^3,N^3$-dipropyl-5-{[(trifluoromethyl)sulfonyl]amino}isophthalamide |

| EXA | |
|---|---|
| 929 | N$^1$-{(1S,2R)-1-benzyl-3-[(3-ethylbenzyl)amino]-2-hydroxypropyl}-N$^3$,N$^3$-dipropyl-5-{[(trifluoromethyl)sulfonyl]amino}isophthalamide |
| 930 | N$^1$-{(1S,2R)-1-(3,5-difluorobenzyl)-3-[(3-ethylbenzyl)amino]-2-hydroxypropyl}-5-{methyl[(trifluoromethyl)sulfonyl]amino}-N$^3$,N$^3$-dipropylisophthalamide |
| 931 | N$^1$-{(1S,2R)-1-(3,5-difluorobenzyl)-2-hydroxy-3-[(3-methoxybenzyl)amino]propyl}-5-{methyl[(trifluoromethyl)sulfonyl]amino}-N$^3$,N$^3$-dipropylisophthalamide |
| 932 | N$^1$-{(1S,2R)-1-(3,5-difluorobenzyl)-2-hydroxy-3-[(3-methoxybenzyl)amino]propyl}-N$^3$,N$^3$-dipropyl-5-{propyl[(trifluoromethyl)sulfonyl]amino}isophthalamide |
| 933 | N$^1$-{(1S,2R)-1-(3,5-difluorobenzyl)-2-hydroxy-3-[(3-methoxybenzyl)amino]propyl}-5-[(methylsulfonyl)amino]-N$^3$,N$^3$-dipropylisophthalamide |
| 934 | N$^1$-{(1S,2R)-1-(3,5-difluorobenzyl)-2-hydroxy-3-[(3-methoxybenzyl)amino]propyl}-5-[(phenylsulfonyl)amino]-N$^3$,N$^3$-dipropylisophthalamide |
| 935 | N-{(1S,2R)-1-(3,5-difluorobenzyl)-2-hydroxy-3-[(3-isopropylbenzyl)amino]propyl}-3-[(dipropylamino)sulfonyl]propanamide |
| 936 | N-{(1S,2R)-1-(3,5-difluorobenzyl)-3-[(3-ethynylbenzyl)amino]-2-hydroxypropyl}-3-[(dipropylamino)sulfonyl]propanamide |
| 937 | N-((1S,2R)-1-(3,5-difluorobenzyl)-3-{[3-(dimethylamino)benzyl]amino}-2-hydroxypropyl)-3-[(dipropylamino)sulfonyl]propanamide |
| 938 | N-((1S,2R)-1-(3,5-difluorobenzyl)-3-{[(2-ethyl-1,3-thiazol-5-yl)methyl]amino}-2-hydroxypropyl)-3-[(dipropylamino)sulfonyl]propanamide |
| 939 | N-((1S,2R)-1-(3,5-difluorobenzyl)-2-hydroxy-3-{[(2-isobutyl-1,3-thiazol-5-yl)methyl]amino}propyl)-3-[(dipropylamino)sulfonyl]propanamide |
| 940 | N-((1S,2R)-1-(3,5-difluorobenzyl)-2-hydroxy-3-{[(3-isobutyl-5-isoxazolyl)methyl]amino}propyl)-3-[(dipropylamino)sulfonyl]propanamide |
| 941 | N-[(1S,2R)-3-[(3-cyclopropylbenzyl)amino]-1-(3,5-difluorobenzyl)-2-hydroxypropyl]-3-[(dipropylamino)sulfonyl]propanamide |
| 942 | N$^1$-[(1S,2R)-3-[(3-cyclopropylbenzyl)amino]-1-(3,5-difluorobenzyl)-2-hydroxypropyl]-5-methyl-N$^3$,N$^3$-dipropylisophthalamide |
| 943 | N$^1$-((1S,2R)-1-(3,5-difluorobenzyl)-2-hydroxy-3-{[3-(1,3-thiazol-2-yl)benzyl]amino}propyl)-5-methyl-N$^3$,N$^3$-dipropylisophthalamide |
| 944 | N$^1$-((1S,2R)-1-(3,5-difluorobenzyl)-2-hydroxy-3-{[3-(1,3-oxazol-2-yl)benzyl]amino}propyl)-5-methyl-N$^3$,N$^3$-dipropylisophthalamide |
| 945 | N$^1$-[(1S,2R)-3-[(3-acetylbenzyl)amino]-1-(3,5-difluorobenzyl)-2-hydroxypropyl]-5-methyl-N$^3$,N$^3$-dipropylisophthalamide |
| 946 | N$^1$-[(1S,2R)-3-[(3-acetylbenzyl)amino]-1-(3,5-difluorobenzyl)-2-hydroxypropyl]-N$^3$,N$^3$-dipropyl-1,3,5-benzenetricarboxamide |
| 947 | N$^1$-[(1S,2R)-3-[(3-acetylbenzyl)amino]-1-(3,5-difluorobenzyl)-2-hydroxypropyl]-5-(aminosulfonyl)-N$^3$,N$^3$-dipropylisophthalamide |
| 948 | N$^1$-[(1S,2R)-3-[(3-acetylbenzyl)amino]-1-(3,5-difluorobenzyl)-2-hydroxypropyl]-5-(methylsulfonyl)-N$^3$,N$^3$-dipropylisophthalamide |
| 949 | N$^1$-[(1S,2R)-3-{[3-(diethylamino)benzyl]amino}-1-(3,5-difluorobenzyl)-2-hydroxypropyl]-5-methyl-N$^3$,N$^3$-dipropylisophthalamide |
| 950 | N$^1$-((1S,2R)-1-(3,5-difluorobenzyl)-2-hydroxy-3-{[3-(4-morpholinyl)benzyl]amino}propyl)-5-methyl-N$^3$,N$^3$-dipropylisophthalamide |
| 951 | N$^1$-((1S,2R)-1-(3,5-difluorobenzyl)-2-hydroxy-3-{[3-(1-piperazinyl)benzyl]amino}propyl)-5-methyl-N$^3$,N$^3$-dipropylisophthalamide |
| 952 | N$^1$-[(1S,2R)-3-{[3-(aminosulfonyl)benzyl]amino}-1-(3,5-difluorobenzyl)-2-hydroxypropyl]-5-methyl-N$^3$,N$^3$-dipropylisophthalamide |
| 953 | N$^1$-[(1S,2R)-1-(3,5-difluorobenzyl)-3-({3-[(dimethylamino)sulfonyl]benzyl}amino)-2-hydroxypropyl]-5-methyl-N$^3$,N$^3$-dipropylisophthalamide |
| 954 | N$^1$-((1S,2R)-1-(3,5-difluorobenzyl)-2-hydroxy-3-{[3-(1-piperidinylsulfonyl)benzyl]amino}propyl)-5-methyl-N$^3$,N$^3$-dipropylisophthalamide |

| EXA | |
|---|---|
| 955 | $N^1$-((1S,2R)-1-(3,5-difluorobenzyl)-2-hydroxy-3-{[3-(methylsulfonyl)benzyl]amino}propyl)-5-methyl-$N^3,N^3$-dipropylisophthalamide |
| 956 | $N^1$-((1S,2R)-1-(3,5-difluorobenzyl)-2-hydroxy-3-{[3-(isopropylsulfonyl)benzyl]amino}propyl)-5-methyl-$N^3,N^3$-dipropylisophthalamide |
| 957 | $N^1$-[(1S,2R)-3-{[3-(aminocarbonyl)benzyl]amino}-1-(3,5-difluorobenzyl)-2-hydroxypropyl]-5-methyl-$N^3,N^3$-dipropylisophthalamide |
| 958 | $N^1$-[(1S,2R)-1-(3,5-difluorobenzyl)-3-({3-[(dimethylamino)carbonyl]benzyl}amino)-2-hydroxypropyl]-5-methyl-$N^3,N^3$-dipropylisophthalamide |
| 959 | $N^1$-[(1S,2R)-3-[(3-cyanobenzyl)amino]-1-(3,5-difluorobenzyl)-2-hydroxypropyl]-5-methyl-$N^3,N^3$-dipropylisophthalamide |
| 960 | 3-({[(2R,3S)-4-(3,5-difluorophenyl)-3-({3-[(dipropylamino)carbonyl]-5-methylbenzoyl}amino)-2-hydroxybutyl]amino}methyl)phenylcarbamate |
| 961 | 3-({[(2R,3S)-4-(3,5-difluorophenyl)-3-({3-[(dipropylamino)carbonyl]-5-methylbenzoyl}amino)-2-hydroxybutyl]amino}methyl)phenyl dimethylcarbamate |
| 962 | $N^1$-((1S,2R)-1-(3,5-difluorobenzyl)-2-hydroxy-3-{[3-(1-propynyl)benzyl]amino}propyl)-5-methyl-$N^3,N^3$-dipropylisophthalamide |
| 963 | $N^1$-((1S,2R)-1-(3,5-difluorobenzyl)-2-hydroxy-3-{[3-(3-methyl-1-butynyl)benzyl]amino}propyl)-5-methyl-$N^3,N^3$-dipropylisophthalamide |
| 964 | $N^1$-((1S,2R)-1-(3,5-difluorobenzyl)-2-hydroxy-3-{[3-(2-propynyl)benzyl]amino}propyl)-5-methyl-$N^3,N^3$-dipropylisophthalamide |
| 965 | $N^1$-((1S,2R)-1-(3,5-difluorobenzyl)-2-hydroxy-3-{[3-(5-isobutyl-1,3,4-oxadiazol-2-yl)methyl]amino}propyl)-5-methyl-$N^3,N^3$-dipropylisophthalamide |
| 966 | $N^1$-((1S,2R)-1-(3,5-difluorobenzyl)-3-{[3-(5-ethyl-1,3,4-oxadiazol-2-yl)methyl]amino}-2-hydroxypropyl)-5-methyl-$N^3,N^3$-dipropylisophthalamide |
| 967 | $N^1$-((1S,2R)-1-(3,5-difluorobenzyl)-3-{[3-(5-ethyl-1,3,4-thiadiazol-2-yl) methyl]amino}-2-hydroxypropyl)-5-methyl-$N^3,N^3$-dipropylisophthalamide |
| 968 | $N^1$-((1S,2R)-1-(3,5-difluorobenzyl)-2-hydroxy-3-{[3-(5-isobutyl-1,3,4-thiadiazol-2-yl) methyl]amino}propyl)-5-methyl-$N^3,N^3$-dipropylisophthalamide |
| 969 | $N^1$-((1S,2R)-1-(3,5-difluorobenzyl)-3-{[3-(3-ethyl-1,2,4-thiadiazol-5-yl) methyl]amino}-2-hydroxypropyl)-5-methyl-$N^3,N^3$-dipropylisophthalamide |
| 970 | $N^1$-((1S,2R)-1-(3,5-difluorobenzyl)-2-hydroxy-3-{[3-(3-isobutyl-1,2,4-thiadiazol-5-yl) methyl]amino}propyl)-5-methyl-$N^3,N^3$-dipropylisophthalamide |
| 971 | $N^1$-((1S,2R)-1-(3,5-difluorobenzyl)-2-hydroxy-3-{[3-(3-isobutyl-1,2,4-oxadiazol-5-yl) methyl]amino}propyl)-5-methyl-$N^3,N^3$-dipropylisophthalamide |
| 972 | $N^1$-((1S,2R)-1-(3,5-difluorobenzyl)-3-{[3-(3-ethyl-1,2,4-oxadiazol-5-yl) methyl]amino}-2-hydroxypropyl)-5-methyl-$N^3,N^3$-dipropylisophthalamide |
| 973 | $N^1$-((1S,2R)-1-(3,5-difluorobenzyl)-3-{[(2-ethyl-1,3-oxazol-5-yl)methyl]amino}-2-hydroxypropyl)-5-methyl-$N^3,N^3$-dipropylisophthalamide |
| 974 | $N^1$-((1S,2R)-1-(3,5-difluorobenzyl)-2-hydroxy-3-{[(2-isobutyl-1,3-oxazol-5-yl)methyl]amino}propyl)-5-methyl-$N^3,N^3$-dipropylisophthalamide |
| 975 | $N^1$-((1S,2R)-1-(3,5-difluorobenzyl)-2-hydroxy-3-{[(5-isobutyl-1,3,4-oxadiazol-2-yl)methyl]amino}propyl)-5-methyl-$N^3,N^3$-dipropylisophthalamide |
| 976 | $N^1$-((1S,2R)-1-(3,5-difluorobenzyl)-2-hydroxy-3-{[(5-isobutyl-1,3,4-thiadiazol-2-yl)methyl]amino}propyl)-5-methyl-$N^3,N^3$-dipropylisophthalamide |
| 977 | $N^1$-((1S,2R)-1-(3,5-difluorobenzyl)-3-{[(5-ethyl-1,3,4-thiadiazol-2-yl)methyl]amino}-2-hydroxypropyl)-5-methyl-$N^3,N^3$-dipropylisophthalamide |
| 978 | $N^1$-((1S,2R)-1-(3,5-difluorobenzyl)-3-{[(5-ethyl-1,3,4-oxadiazol-2-yl)methyl]amino}-2-hydroxypropyl)-5-methyl-$N^3,N^3$-dipropylisophthalamide |
| 979 | $N^1$-((1S,2R)-1-(3,5-difluorobenzyl)-3-{[(3-ethyl-1,2,4-oxadiazol-5-yl)methyl]amino}-2-hydroxypropyl)-5-methyl-$N^3,N^3$-dipropylisophthalamide |
| 980 | $N^1$-((1S,2R)-1-(3,5-difluorobenzyl)-3-{[(3-ethyl-1,2,4-thiadiazol-5-yl)methyl]amino}-2-hydroxypropyl)-5-methyl-$N^3,N^3$-dipropylisophthalamide |

| EXA | |
|---|---|
| 981 | N$^1$-((1S,2R)-1-(3,5-difluorobenzyl)-2-hydroxy-3-{[(3-isobutyl-1,2,4-thiadiazol-5-yl)methyl]amino}propyl)-5-methyl-N$^3$,N$^3$-dipropylisophthalamide |
| 982 | N$^1$-((1S,2R)-1-(3,5-difluorobenzyl)-2-hydroxy-3-{[(3-isobutyl-1,2,4-oxadiazol-5-yl)methyl]amino}propyl)-5-methyl-N$^3$,N$^3$-dipropylisophthalamide |
| 983 | N$^1$-((1S,2R)-1-(3,5-difluorobenzyl)-3-{[(2-ethyl-2H-tetraazol-5-yl)methyl]amino}-2-hydroxypropyl)-5-methyl-N$^3$,N$^3$-dipropylisophthalamide |
| 984 | N$^1$-((1S,2R)-1-(3,5-difluorobenzyl)-2-hydroxy-3-{[(2-isobutyl-2H-tetraazol-5-yl)-methyl]amino}propyl)-5-methyl-N$^3$,N$^3$-dipropylisophthalamide |
| 985 | N$^1$((1S,2R)-1-(3,5-difluorobenzyl)-3-{[(2-ethyl-4-pyrimidinyl)methyl]amino}-2-hydroxypropyl)-5-methyl-N$^3$,N$^3$-dipropylisophthalamide |
| 986 | N$^1$-((1S,2R)-1-(3,5-difluorobenzyl)-2-hydroxy-3-{[(2-isopropyl-4-pyrimidinyl)methyl]amino}propyl)-5-methyl-N$^3$,N$^3$-dipropylisophthalamide |
| 987 | N$^1$-((1S,2R)-1-(3,5-difluorobenzyl)-3-{[(2-ethynyl-4-pyrimidinyl)methyl]amino}-2-hydroxypropyl)-5-methyl-N$^3$,N$^3$-dipropylisophthalamide |
| 988 | N$^1$-((1S,2R)-1-(3,5-difluorobenzyl)-2-hydroxy-3-{[(6-isopropyl-4-pyrimidinyl)methyl]amino}propyl)-5-methyl-N$^3$,N$^3$-dipropylisophthalamide |
| 989 | N$^1$-[(1S,2R)-1-(3,5-difluorobenzyl)-3-({[6-(dimethylamino)-4-pyrimidinyl]methyl}amino)-2-hydroxypropyl]-5-methyl-N$^3$,N$^3$-dipropylisophthalamide |
| 990 | N$^1$-[(1S,2R)-1-(3,5-difluorobenzyl)-3-({[2-(dimethylamino)-4-pyrimidinyl]methyl}amino)-2-hydroxypropyl]-5-methyl-N$^3$,N$^3$-dipropylisophthalamide |
| 991 | N$^1$-[(1S,2R)-1-(3,5-difluorobenzyl)-3-({[(dimethylamino)-2-pyrimidinyl]methyl}amino)-2-hydroxypropyl]-5-methyl-N$^3$,N$^3$-dipropylisophthalamide |
| 992 | N$^1$-((1S,2R)-1-(3,5-difluorobenzyl)-2-hydroxy-3-{[(4-isopropyl-2-pyrimidinyl)methyl]amino}propyl)-5-methyl-N$^3$,N$^3$-dipropylisophthalamide |
| 993 | N$^1$-((1S,2R)-1-(3,5-difluorobenzyl)-3-{[(4-ethyl-2-pyrimidinyl)methyl]amino}-2-hydroxypropyl)-5-methyl-N$^3$,N$^3$-dipropylisophthalamide |
| 994 | N$^1$-((1S,2R)-1-(3,5-difluorobenzyl)-3-{[(5-ethyl-3-pyridazinyl)methyl]amino}-2-hydroxypropyl)-5-methyl-N$^3$,N$^3$-dipropylisophthalamide |
| 995 | N$^3$-((1S,2R)-1-(3,5-difluorobenzyl)-3-{[3-(dimethylamino)benzyl]amino}-2-hydroxypropyl)-N$^5$,N$^5$-dipropyl-3,5-pyridinedicarboxamide |
| 996 | N$^1$-((1S,2R)-1-(3,5-difluorobenzyl)-2-hydroxy-3-{[(5-isopropyl-3-pyridazinyl)methyl]amino}propyl)-5-methyl-N$^3$,N$^3$-dipropylisophthalamide |
| 997 | N$^3$-((1S,2R)-1-(3,5-difluorobenzyl)-2-hydroxy-3-{[3-(1-propynyl)benzyl]amino}propyl)-N$^5$,N$^5$-dipropyl-3,5-pyridinedicarboxamide |
| 998 | N$^1$-((1S,2R)-1-(3,5-difluorobenzyl)-2-hydroxy-3-{[(6-isopropyl-4-pyridazinyl)methyl]amino}propyl)-5-methyl-N$^3$,N$^3$-dipropylisophthalamide |
| 999 | N$^3$-{(1S,2R)-1-(3,5-difluorobenzyl)-3-[(3-ethynylbenzyl)amino]-2-hydroxypropyl}-N$^5$,N$^5$-dipropyl-3,5-pyridinedicarboxamide |
| 1000 | N$^1$-((1S,2R)-1-(3,5-difluorobenzyl)-3-{[(6-ethyl-4-pyridazinyl)methyl]amino}-2-hydroxypropyl)-5-methyl-N$^3$,N$^3$-dipropylisophthalamide |
| 1001 | N$^3$-{(1S,2R)-1-(3,5-difluorobenzyl)-2-hydroxy-3-[(3-isopropylbenzyl)amino]propyl}-N$^5$,N$^5$-dipropyl-3,5-pyridinedicarboxamide |
| 1002 | N$^1$-((1S,2R)-1-(3,5-difluorobenzyl)-3-{[(6-ethyl-2-pyrazinyl)methyl]amino}-2-hydroxypropyl)-5-methyl-N$^3$,N$^3$-dipropylisophthalamide |
| 1003 | N$^3$-{(1S,2R)-1-(3,5-difluorobenzyl)-3-[(3-ethylbenzyl)amino]-2-hydroxypropyl}-N$^5$,N$^5$-dipropyl-3,5-pyridinedicarboxamide |
| 1004 | N$^1$-((1S,2R)-1-(3,5-difluorobenzyl)-2-hydroxy-3-{[(6-isopropyl-2-pyrazinyl)methyl]amino}propyl)-5-methyl-N$^3$,N$^3$-dipropylisophthalamide |
| 1005 | N$^1$-[(1S,2R)-2-hydroxy-3-[(3-methoxybenzyl)amino]-1-(3,4,5-trifluorobenzyl)propyl]-5-methyl-N$^3$,N$^3$-dipropylisophthalamide |
| 1006 | N$^1$-((1S,2R)-2-hydroxy-1-(3,4,5-trifluorobenzyl)-3-{[3-(trifluoromethyl)benzyl]amino}propyl)-5-methyl-N$^3$,N$^3$-dipropylisophthalamide |

| EXA | |
|---|---|
| 1007 | $N^1$-((1S,2R)-2-hydroxy-1-(2,3,5,6-tetrafluorobenzyl)-3-{[3-(trifluoromethyl)benzyl]amino}propyl)-5-methyl-$N^3,N^3$-dipropylisophthalamide |
| 1008 | $N^1$-[(1S,2R)-2-hydroxy-3-[(3-methoxybenzyl)amino]-1-(2,3,5,6-tetrafluorobenzyl)propyl]-5-methyl-$N^3,N^3$-dipropylisophthalamide |
| 1009 | $N^1$-((1S,2R)-1-(3,5-difluorobenzyl)-2-hydroxy-3-{[(1R,2S)-2-hydroxy-6-methoxy-2,3-dihydro-1H-inden-1-yl]amino}propyl)-5-methyl-$N^3,N^3$-dipropylisophthalamide |
| 1010 | $N^1$-((1S,2R)-1-(3,5-difluorobenzyl)-2-hydroxy-3-{[(1R,2S)-2-hydroxy-6-methoxy-2,3-dihydro-1H-inden-1-yl]amino}propyl)-$N^3,N^3$-dipropyl-1,3,5-benzenetricarboxamide |
| 1011 | $N^1$-((1S,2R)-1-(3,5-difluorobenzyl)-3-{[(1R,2S)-6-ethyl-2-hydroxy-2,3-dihydro-1H-inden-1-yl]amino}-2-hydroxypropyl)-5-methyl-$N^3,N^3$-dipropylisophthalamide |
| 1012 | $N^1$-((1S,2R)-1-(3,5-difluorobenzyl)-3-{[(1R,2S)-6-ethyl-2-hydroxy-2,3-dihydro-1H-inden-1-yl]amino}-2-hydroxypropyl)-$N^3,N^3$-dipropyl-1,3,5-benzenetricarboxamide |
| 1013 | $N^1$-{(1S,2R)-2-hydroxy-1-(1H-indol-5-ylmethyl)-3-[(3-methoxybenzyl)amino]propyl}-5-methyl-$N^3,N^3$-dipropylisophthalamide |
| 1014 | $N^1$-[(1S,2R)-3-[(3-ethylbenzyl)amino]-2-hydroxy-1-(1H-indol-5-ylmethyl)propyl]-5-methyl-$N^3,N^3$-dipropylisophthalamide |
| 1015 | $N^1$-[(1S,2R)-2-hydroxy-3-[(3-methoxybenzyl)amino]-1-(3-methylbenzyl)propyl]-5-methyl-$N^3,N^3$-dipropylisophthalamide |
| 1016 | $N^1$-[(1S,2R)-2-hydroxy-3-[(3-methoxybenzyl)amino]-1-(3-methylbenzyl)propyl]-$N^3,N^3$-dipropyl-1,3,5-benzenetricarboxamide |
| 1017 | $N^1$-{(1S,2R)-2-hydroxy-3-[(3-methoxybenzyl)amino]-1-[3-(trifluoromethyl)benzyl]propyl}-5-methyl-$N^3,N^3$-dipropylisophthalamide |
| 1018 | $N^1$-{(1S,2R)-2-hydroxy-3-[(3-methoxybenzyl)amino]-1-[3-(trifluoromethyl)benzyl]propyl}-$N^3,N^3$-dipropyl-1,3,5-benzenetricarboxamide |
| 1019 | $N^1$-[(1S,2R)-2-hydroxy-3-[(3-methoxybenzyl)amino]-1-(2-pyridinylmethyl)propyl]-5-methyl-$N^3,N^3$-dipropylisophthalamide |
| 1020 | $N^1$-[(1S,2R)-2-hydroxy-3-[(3-methoxybenzyl)amino]-1-(2-pyridinylmethyl)propyl]-$N^3,N^3$-dipropyl-1,3,5-benzenetricarboxamide |
| 1021 | $N^1$-{(1S,2R)-1-[3-fluoro-5-(trifluoromethyl)benzyl]-2-hydroxy-3-[(3-methoxybenzyl)amino]propyl}-5-methyl-$N^3,N^3$-dipropylisophthalamide |
| 1022 | $N^1$-{(1S,2R)-1-[3-fluoro-5-(trifluoromethyl)benzyl]-2-hydroxy-3-[(3-methoxybenzyl)amino]propyl}-$N^3,N^3$-dipropyl-1,3,5-benzenetricarboxamide |
| 1023 | $N^1$-{(1S,2R)-2-hydroxy-3-[(3-methoxybenzyl)amino]-1-[3-(trifluoromethoxy)benzyl]propyl}-5-methyl-$N^3,N^3$-dipropylisophthalamide |
| 1024 | $N^1$-{(1S,2R)-2-hydroxy-3-[(3-methoxybenzyl)amino]-1-[3-(trifluoromethoxy)benzyl]propyl}-$N^3,N^3$-dipropyl-1,3,5-benzenetricarboxamide |
| 1025 | $N^1$-{(1S,2R)-2-hydroxy-1-(3-hydroxybenzyl)-3-[(3 methoxybenzyl)amino]propyl}-5-methyl-$N^3,N^3$-dipropylisophthalamide |
| 1026 | $N^1$-{(1S,2R)-2-hydroxy-1-(3-hydroxybenzyl)-3-[(3-methoxybenzyl)amino]propyl}-$N^3,N^3$-dipropyl-1,3,5-benzenetricarboxamide |
| 1027 | $N^1$-[(1S,2R)-2-hydroxy-3-[(3-methoxybenzyl)amino]-1-(4-methylbenzyl)propyl]-5-methyl-$N^3,N^3$-dipropylisophthalamide |
| 1028 | $N^1$-[(1S,2R)-2-hydroxy-3-[(3-methoxybenzyl)amino]-1-(4-methylbenzyl)propyl]-$N^3,N^3$-dipropyl-1,3,5-benzenetricarboxamide |
| 1029 | $N^1$-{(1S,2R)-1-(4-fluoro-3-methylbenzyl)-2-hydroxy-3-[(3-methoxybenzyl)amino]propyl}-5-methyl-$N^3,N^3$-dipropylisophthalamide |
| 1030 | $N^1$-{(1S,2R)-1-(4-fluoro-3-methylbenzyl)-2-hydroxy-3-[(3-methoxybenzyl)amino]propyl}-$N^3,N^3$-dipropyl-1,3,5-benzenetricarboxamide |
| 1031 | $N^1$-{(1S,2R)-1-(4-chlorobenzyl)-2-hydroxy-3-[(3-methoxybenzyl)amino]propyl}-5-methyl-$N^3,N^3$-dipropylisophthalamide |
| 1032 | $N^1$-{(1S,2R)-1-(4-chlorobenzyl)-2-hydroxy-3-[(3-methoxybenzyl)amino]propyl}-$N^3,N^3$-dipropyl-1,3,5-benzenetricarboxamide |
| 1033 | $N^1$-{(1S,2R)-2-hydroxy-1-(3-methoxybenzyl)-3-[(3-methoxybenzyl)amino]propyl}-5-methyl-$N^3,N^3$-dipropylisophthalamide |

-continued

| EXA | |
|---|---|
| 1034 | N$^1$-{(1S,2R)-2-hydroxy-1-(3-methoxybenzyl)-3-[(3-methoxybenzyl)amino]propyl}-N$^3$,N$^3$-dipropyl-1,3,5-benzenetricarboxamide |
| 1035 | N$^1$-{(1S,2R)-2-hydroxy-1-(4-methoxybenzyl)-3-[(3-methoxybenzyl)amino]propyl}-5-methyl-N$^3$,N$^3$-dipropylisophthalamide |
| 1036 | N$^1$-{(1S,2R)-2-hydroxy-1-(4-methoxybenzyl)-3-[(3-methoxybenzyl)amino]propyl}-N$^3$,N$^3$-dipropyl-1,3,5-benzenetricarboxamide |
| 1037 | N$^1$-{(1S,2R)-1-(3-chloro-5-fluorobenzyl)-2-hydroxy-3-[(3-methoxybenzyl)amino]propyl}-5-methyl-N$^3$,N$^3$-dipropylisophthalamide |
| 1038 | N$^1$-{(1S,2R)-1-(3-chloro-5-fluorobenzyl)-2-hydroxy-3-[(3-methoxybenzyl)amino]propyl}-N$^3$,N$^3$-dipropyl-1,3,5-benzenetricarboxamide |
| 1039 | N$^1$-{(1S,2R)-1-(4-chloro-3-fluorobenzyl)-2-hydroxy-3-[(3-methoxybenzyl)amino]propyl}-5-methyl-N$^3$,N$^3$-dipropylisophthalamide |
| 1040 | N$^1$-{(1S,2R)-1-(4-chloro-3-fluorobenzyl)-2-hydroxy-3-[(3-methoxybenzyl)amino]propyl}-N$^3$,N$^3$-dipropyl-1,3,5-benzenetricarboxamide |
| 1041 | N$^1$-{(1S,2R)-1-(3,5-dichlorobenzyl)-2-hydroxy-3-[(3-methoxybenzyl)amino]propyl}-5-methyl-N$^3$,N$^3$-dipropylisophthalamide |
| 1042 | N$^1$-{(1S,2R)-1-(3,5-dichlorobenzyl)-2-hydroxy-3-[(3-methoxybenzyl)amino]propyl}-N$^3$,N$^3$-dipropyl-1,3,5-benzenetricarboxamide |
| 1043 | N$^1$-{(1S,2R)-1-[4-(dimethylamino)benzyl]-2-hydroxy-3-[(3-methoxybenzyl)amino]propyl}-5-methyl-N$^3$,N$^3$-dipropylisophthalamide |
| 1044 | N$^1$-{(1S,2R)-1-[4-(dimethylamino)benzyl]-2-hydroxy-3-[(3-methoxybenzyl)amino]propyl}-N$^3$,N$^3$-dipropyl-1,3,5-benzenetricarboxamide |
| 1045 | N$^1$-{(1S,2R)-1-(3-chlorobenzyl)-2-hydroxy-3-[(3-methoxybenzyl)amino]propyl}-5-methyl-N$^3$,N$^3$-dipropylisophthalamide |
| 1046 | N$^1$-{(1S,2R)-1-(3-chlorobenzyl)-2-hydroxy-3-[(3-methoxybenzyl)amino]propyl}-5-methyl-N$^3$,N$^3$-dipropylisophthalamide |
| 1047 | N$^1$-{(1S,2R)-1-(3-fluorobenzyl)-2-hydroxy-3-[(3-methoxybenzyl)amino]propyl}-5-methyl-N$^3$,N$^3$-dipropylisophthalamide |
| 1048 | N$^1$-{(1S,2R)-1-(3-fluorobenzyl)-2-hydroxy-3-[(3-methoxybenzyl)amino]propyl}-N$^3$,N$^3$-dipropyl-1,3,5-benzenetricarboxamide |
| 1049 | N$^1$-{(1S,2R)-2-hydroxy-1-(4-isopropylbenzyl)-3-[(3-methoxybenzyl)amino]propyl}-5-methyl-N$^3$,N$^3$-dipropylisophthalamide |
| 1050 | N$^1$-{(1S,2R)-2-hydroxy-1-(4-isopropylbenzyl)-3-[(3-methoxybenzyl)amino]propyl}-N$^3$,N$^3$-dipropyl-1,3,5-benzenetricarboxamide |
| 1051 | N$^1$-{(1S,2R)-2-hydroxy-3-[(3-methoxybenzyl)amino]-1-[(6-methoxy-2-pyridinyl)methyl]propyl}-5-methyl-N$^3$,N$^3$-dipropylisophthalamide |
| 1052 | N$^1$-{(1S,2R)-2-hydroxy-3-[(3-methoxybenzyl)amino]-1-[(6-methoxy-2-pyridinyl)methyl]propyl}-N$^3$,N$^3$-dipropyl-1,3,5-benzenetricarboxamide |
| 1053 | N$^1$-{(1S,2R)-2-hydroxy-3-[(3-methoxybenzyl)amino]-1-[(5-methyl-2-pyridinyl)methyl]propyl}-5-methyl-N$^3$,N$^3$-dipropylisophthalamide |
| 1054 | N$^1$-{(1S,2R)-2-hydroxy-3-[(3-methoxybenzyl)amino]-1-[(5-methyl-2-pyridinyl)methyl]propyl}-N$^3$,N$^3$-dipropyl-1,3,5-benzenetricarboxamide |
| 1055 | N$^1$-{(1S,2R)-1-(3-fluoro-4-methylbenzyl)-2-hydroxy-3-[(3-methoxybenzyl)amino]propyl}-5-methyl-N$^3$,N$^3$-dipropylisophthalamide |
| 1056 | N$^1$-{(1S,2R)-1-(3-fluoro-4-methylbenzyl)-2-hydroxy-3-[(3-methoxybenzyl)amino]propyl}-N$^3$,N$^3$-dipropyl-1,3,5-benzenetricarboxamide |
| 1057 | N$^1$-{(1S,2R)-1-(3-fluoro-4-methoxybenzyl)-2-hydroxy-3-[(3-methoxybenzyl)amino]propyl}-5-methyl-N$^3$,N$^3$-dipropylisophthalamide |
| 1058 | N$^1$-{(1S,2R)-1-(3-fluoro-4-methoxybenzyl)-2-hydroxy-3-[(3-methoxybenzyl)amino]propyl}-N$^3$,N$^3$-dipropyl-1,3,5-benzenetricarboxamide |

| EXA | |
|---|---|
| 1059 | N$^1$-[(1S,2R)-2-hydroxy-3-[(3-methoxybenzyl)amino]-1-(2-methoxy-5-methylbenzyl)propyl]-5-methyl-N$^3$,N$^3$-dipropylisophthalamide |
| 1060 | N$^1$-[(1S,2R)-2-hydroxy-3-[(3-methoxybenzyl)amino]-1-(2-methoxy-5-methylbenzyl)propyl]-N$^3$,N$^3$-dipropyl-1,3,5-benzenetricarboxamide |
| 1061 | N$^1$-[(1S,2R)-2-hydroxy-3-[(3-methoxybenzyl)amino]-1-(1,3-thiazol-2-ylmethyl)propyl]-5-methyl-N$^3$,N$^3$-dipropylisophthalamide |
| 1062 | N$^1$-[(1S,2R)-2-hydroxy-3-[(3-methoxybenzyl)amino]-1-(1,3-thiazol-2-ylmethyl)propyl]-N$^3$,N$^3$-dipropyl-1,3,5-benzenetricarboxamide |
| 1063 | N$^1$-{(1S,2R)-1-[(5-chloro-2-thienyl)methyl]-2-hydroxy-3-[(3-methoxybenzyl)amino]propyl}-5-methyl-N$^3$,N$^3$-dipropylisophthalamide |
| 1064 | N$^1$-{(1S,2R)-1-[(5-chloro-2-thienyl)methyl]-2-hydroxy-3-[(3-methoxybenzyl)amino]propyl}-N$^3$,N$^3$-dipropyl-1,3,5-benzenetricarboxamide |
| 1,065 | N-{(1S,2R)-1-(3,5-difluorobenzyl)-3-[(3-ethylbenzyl)amino]-2-hydroxypropyl}-4-hydroxy-3-(1-pyrrolidinylcarbonyl)benzamide |
| 1,066 | N-{(1S,2R)-1-(3,5-difluorobenzyl)-3-[(3-ethylbenzyl)amino]-2-hydroxypropyl}-5-methyl-2-[(methylsulfonyl)amino]-1,3-thiazole-4-carboxamide |
| 1,067 | N-{(1S,2R)-1-(3,5-difluorobenzyl)-3-[(3-ethylbenzyl)amino]-2-hydroxypropyl}-2-[(methylsulfonyl)amino]-1,3-oxazole-4-carboxamide |
| 1,068 | N-{(1S,2R)-1-(3,5-difluorobenzyl)-3-[(3-ethylbenzyl)amino]-2-hydroxypropyl}-2-[(propylsulfonyl)amino]-1,3-thiazole-4-carboxamide |
| 1,069 | N-{(1S,2R)-1-(3,5-difluorobenzyl)-2-hydroxy-3-[(3-methoxybenzyl)amino]propyl}-4-hydroxy-3-(1-pyrrolidinylcarbonyl)benzamide |
| 1,070 | N-{(1S,2R)-1-(3,5-difluorobenzyl)-2-hydroxy-3-[(3-methoxybenzyl)amino]propyl}-2-[(propylsulfonyl)amino]-1,3-thiazole-4-carboxamide |
| 1,071 | N-{(1S,2R)-1-benzyl-3-[(3-ethylbenzyl)amino]-2-hydroxypropyl}-2-[(methylsulfonyl)amino]-1,3-oxazole-4-carboxamide |
| 1,072 | N-((1S,2R)-1-(3,5-difluorobenzyl)-3-{[1-(3-ethylphenyl)cyclopropyl]amino}-2-hydroxypropyl)-2-[(methylsulfonyl)amino]-1,3-oxazole-4-carboxamide |
| 1,073 | N-((1S,2R)-1-(3,5-difluorobenzyl)-3-{[1-(3-ethylphenyl)-1-methylethyl]amino}-2-hydroxypropyl)-4-hydroxy-3-(1-pyrrolidinylcarbonyl)benzamide |
| 1,074 | N-((1S,2R)-1-(3,5-difluorobenzyl)-3-{[1-(3-ethylphenyl)-1-methylethyl]amino}-2-hydroxypropyl)-2-[(methylsulfonyl)amino]-1,3-oxazole-4-carboxamide |
| 1,075 | N-{(1S,2R)-1-benzyl-2-hydroxy-3-[(3-methoxybenzyl)amino]propyl}-2-[(methylsulfonyl)amino]-1,3-oxazole-4-carboxamide |
| 1,076 | N-((1S,2R)-1-(3,5-difluorobenzyl)-3-{[1-(3-ethylphenyl)-1-methylethyl]amino}-2-hydroxypropyl)-5-methyl-2-[(methylsulfonyl)amino]-1,3-oxazole-4-carboxamide |
| 1,077 | N-((1S,2R)-1-(3,5-difluorobenzyl)-3-{[1-(3-ethylphenyl)cyclopropyl]amino}-2-hydroxypropyl)-4-hydroxy-3-(1-pyrrolidinylcarbonyl)benzamide |
| 1,078 | N-{(1S,2R)-1-(3,5-difluorobenzyl)-3-[(3-ethynylbenzyl)amino]-2-hydroxypropyl}-2-[(methylsulfonyl)amino]-1,3-oxazole-4-carboxamide |
| 1,079 | N-{(1S,2R)-1-(3,5-difluorobenzyl)-2-hydroxy-3-[(3-methoxybenzyl)amino]propyl}-2-[(methylsulfonyl)amino]-1,3-oxazole-4-carboxamide |
| 1,080 | N-{(1S,2R)-1-(3,5-difluorobenzyl)-3-[(3-ethynylbenzyl)amino]-2-hydroxypropyl}-5-methyl-2-[(methylsulfonyl)amino]-1,3-oxazole-4-carboxamide |
| 1,081 | N-{(1S,2R)-1-(3,5-difluorobenzyl)-2-hydroxy-3-[(3-methoxybenzyl)amino]propyl}-4-hydroxy-3-(1-piperidinylcarbonyl)benzamide |
| 1,082 | N-{(1S,2R)-1-(3,5-difluorobenzyl)-2-hydroxy-3-[(3-iodobenzyl)amino]propyl}-4-[(methylsulfonyl)amino]-1,3-oxazole-2-carboxamide |
| 1,083 | N-{(1S,2R)-1-benzyl-2-hydroxy-3-[(3-iodobenzyl)amino]propyl}-2-[(methylsulfonyl)amino]-1,3-oxazole-4-carboxamide |
| 1,084 | N-{(1S,2R)-1-(3,5-difluorobenzyl)-2-hydroxy-3-[(3-iodobenzyl)amino]propyl}-5-methyl-4-[(methylsulfonyl)amino]-1,3-oxazole-2-carboxamide |

| EXA | |
|---|---|
| 1,085 | N-{(1S,2R)-1-(3,5-difluorobenzyl)-3-[(3-ethylbenzyl)amino]-2-hydroxypropyl}-4-hydroxy-3-(1-piperidinylcarbonyl)benzamide |
| 1,086 | N-{(1S,2R)-1-(3,5-difluorobenzyl)-3-[(3-ethylbenzyl)amino]-2-hydroxypropyl}-4-[(methylsulfonyl)amino]-1,3-oxazole-2-carboxamide |
| 1,087 | N-{(1S,2R)-1-benzyl-2-hydroxy-3-[(3-iodobenzyl)amino]propyl}-5-methyl-2-[(methylsulfonyl)amino]-1,3-oxazole-4-carboxamide |
| 1,088 | N-{(1S,2R)-1-(3,5-difluorobenzyl)-3-[(3-ethylbenzyl)amino]-2-hydroxypropyl}-5-methyl-4-[(methylsulfonyl)amino]-1,3-oxazole-2-carboxamide |
| 1,089 | N-{(1S,2R)-1-(3,5-difluorobenzyl)-3-[(3-ethylbenzyl)amino]-2-hydroxypropyl}-4-hydroxy-3-(4-morpholinylcarbonyl)benzamide |
| 1,090 | N-{(1S,2R)-1-(3,5-difluorobenzyl)-3-[(3-ethylbenzyl)amino]-2-hydroxypropyl}-4-[(ethylsulfonyl)amino]-1,3-oxazole-2-carboxamide |
| 1,091 | N-{(1S,2R)-1-(3,5-difluorobenzyl)-2-hydroxy-3-[(3-iodobenzyl)amino]propyl}-5-methyl-2-[(methylsulfonyl)amino]-1,3-oxazole-4-carboxamide |
| 1,092 | N-{(1S,2R)-1-(3,5-difluorobenzyl)-2-hydroxy-3-[(3-iodobenzyl)amino]propyl}-4-[(ethylsulfonyl)amino]-1,3-oxazole-2-carboxamide |
| 1,093 | N-{(1S,2R)-1-(3,5-difluorobenzyl)-3-[(3-ethylbenzyl)amino]-2-hydroxypropyl}-4-hydroxy-3-(4-morpholinylcarbonyl)benzamide |
| 1,094 | N-{(1S,2R)-1-(3,5-difluorobenzyl)-2-hydroxy-3-[(3-iodobenzyl)amino]propyl}-4-[(propylsulfonyl)amino]-1,3-oxazole-2-carboxamide |
| 1,095 | N-{(1S,2R)-1-(3,5-difluorobenzyl)-2-hydroxy-3-[(3-methoxybenzyl)amino]propyl}-5-methyl-2-[(methylsulfonyl)amino]-1,3-oxazole-4-carboxamide |
| 1,096 | N-{(1S,2R)-1-(3,5-difluorobenzyl)-2-hydroxy-3-[(3-iodobenzyl)amino]propyl}-4-[(methylsulfonyl)amino]-1,3-thiazole-2-carboxamide |
| 1,097 | N-{(1S,2R)-1-(3,5-difluorobenzyl)-2-hydroxy-3-[(3-methoxybenzyl)amino]propyl}-4-hydroxy-3-(1-piperazinylcarbonyl)benzamide |
| 1,098 | N-{(1S,2R)-1-(3,5-difluorobenzyl)-3-[(3-ethylbenzyl)amino]-2-hydroxypropyl}-4-[(methylsulfonyl)amino]-1,3-thiazole-2-carboxamide |
| 1,099 | N-{(1S,2R)-1-(3,5-difluorobenzyl)-3-[(3-ethylbenzyl)amino]-2-hydroxypropyl}-5-methyl-2-[(methylsulfonyl)amino]-1,3-oxazole-4-carboxamide |
| 1,100 | N-{(1S,2R)-1-(3,5-difluorobenzyl)-3-[(3-ethylbenzyl)amino]-2-hydroxypropyl}-2-[(methylsulfonyl)amino]-1,3-oxazole-5-carboxamide |
| 1,101 | N-{(1S,2R)-1-(3,5-difluorobenzyl)-3-[(3-ethylbenzyl)amino]-2-hydroxypropyl}-4-hydroxy-3-(1-piperazinylcarbonyl)benzamide |
| 1,102 | N-{(1S,2R)-1-(3,5-difluorobenzyl)-3-[(3-ethylbenzyl)amino]-2-hydroxypropyl}-4-methyl-2-[(methylsulfonyl)amino]-1,3-oxazole-5-carboxamide |
| 1,103 | $N^4$-{(1S,2R)-1-(3,5-difluorobenzyl)-3-[(3-ethylbenzyl)amino]-2-hydroxypropyl}-2-[(methylsulfonyl)amino]1,3-oxazole-4,5-dicarboxamide |
| 1,104 | N-{(1S,2R)-1-(3,5-difluorobenzyl)-2-hydroxy-3-[(3-iodobenzyl)amino]propyl}-4-[(methylsulfonyl)amino]-1,3-oxazole-2-carboxamide |
| 1,105 | $N^1$-{(1S,2R)-1-(3,5-difluorobenzyl)-3-[(3-ethylbenzyl)amino]-2-hydroxypropyl}-4-hydroxy-$N^3$-methylisophthalamide |
| 1,106 | N-{(1S,2R)-1-(3,5-difluorobenzyl)-2-hydroxy-3-[(3-iodobenzyl)amino]propyl}-4-methyl-2-[(methylsulfonyl)amino]-1,3-oxazole-5-carboxamide |
| 1,107 | N-{(1S,2R)-1-(3,5-difluorobenzyl)-3-[(3-ethylbenzyl)amino]-2-hydroxypropyl}-2-[(ethylsulfonyl)amino]-1,3-oxazole-4-carboxamide |
| 1,108 | N-{(1S,2R)-1-(3,5-difluorobenzyl)-2-hydroxy-3-[(3-iodobenzyl)amino]propyl}-4-[(methylsulfonyl)amino]-1,3-oxazole-2-carboxamide |
| 1,109 | $N^1$-{(1S,2R)-1-(3,5-difluorobenzyl)-2-hydroxy-3-[(3-methoxybenzyl)amino]propyl}-4-hydroxy-$N^3$-methylisophthalamide |
| 1,110 | N-{(1S,2R)-1-(3,5-difluorobenzyl)-2-hydroxy-3-[(3-iodobenzyl)amino]propyl}-4-methyl-5-[(methylsulfonyl)amino]-1,3-oxazole-2-carboxamide |
| 1,111 | N-{(1S,2R)-1-(3,5-difluorobenzyl)-2-hydroxy-3-[(3-methoxybenzyl)amino]propyl}-2-[(ethylsulfonyl)amino]-1,3-oxazole-4-carboxamide |
| 1,112 | N-{(1S,2R)-1-(3,5-difluorobenzyl)-3-[(3-ethylbenzyl)amino]-2-hydroxypropyl}-4-methyl-5-[(methylsulfonyl)amino]-1,3-oxazole-2-carboxamide |

-continued

| EXA | |
|---|---|
| 1,113 | N¹-{(1S,2R)-1-(3,5-difluorobenzyl)-2-hydroxy-3-[(3-methoxybenzyl)amino]propyl}-N³-ethyl-4-hydroxyisophthalamide |
| 1,114 | N-{(1S,2R)-1-(3,5-difluorobenzyl)-3-[(3-ethylbenzyl)amino]-2-hydroxypropyl}-5-[(methylsulfonyl)amino]-1,3-oxazole-2-carboxamide |
| 1,115 | N-{(1S,2R)-1-(3,5-difluorobenzyl)-2-hydroxy-3-[(3-iodobenzyl)amino]propyl}-2-[(ethylsulfonyl)amino]-1,3-oxazole-4-carboxamide |
| 1,116 | N-{(1S,2R)-1-(3,5-difluorobenzyl)-3-[(3-ethylbenzyl)amino]-2-hydroxypropyl}-5-[(methylsulfonyl)amino]-3-isoxazolecarboxamide |
| 1,117 | N¹-{(1S,2R)-1-(3,5-difluorobenzyl)-3-[(3-ethylbenzyl)amino]-2-hydroxypropyl}-N³-ethyl-4-hydroxyisophthalamide |
| 1,118 | N-{(1S,2R)-1-(3,5-difluorobenzyl)-2-hydroxy-3-[(3-iodobenzyl)amino]propyl}-5-[(methylsulfonyl)amino]-3-isoxazolecarboxamide |
| 1,119 | N-{(1S,2R)-1-(3,5-difluorobenzyl)-2-hydroxy-3-[(3-iodobenzyl)amino]propyl}-2-[(propylsulfonyl)amino]-1,3-oxazole-4-carboxamide |
| 1,120 | N-{(1S,2R)-1-(3,5-difluorobenzyl)-2-hydroxy-3-[(3-iodobenzyl)amino]propyl}-3-[(methylsulfonyl)amino]-5-isoxazolecarboxamide |
| 1,121 | N¹-{(1S,2R)-1-(3,5-difluorobenzyl)-2-hydroxy-3-[(3-iodobenzyl)amino]propyl}-N³-ethyl-4-hydroxyisophthalamide |
| 1,122 | N-{(1S,2R)-1-(3,5-difluorobenzyl)-3-[(3-ethylbenzyl)amino]-2-hydroxypropyl}-3-[(methylsulfonyl)amino]-5-isoxazolecarboxamide |
| 1,123 | N-{(1S,2R)-1-(3,5-difluorobenzyl)-2-hydroxy-3-[(3-methoxybenzyl)amino]propyl}-2-[(propylsulfonyl)amino]-1,3-oxazole-4-carboxamide |
| 1,124 | N-{(1S,2R)-1-(3,5-difluorobenzyl)-2-hydroxy-3-[(3-iodobenzyl)amino]propyl}-5-(hydroxymethyl)-2-[(methylsulfonyl)amino]-1,3-oxazole-4-carboxamide |
| 1,125 | N³-(cyclopropylmethyl)-N¹-{(1S,2R)-1-(3,5-difluorobenzyl)-2-hydroxy-3-[(3-iodobenzyl)amino]propyl}-4-hydroxyisophthalamide |
| 1,126 | 5-cyclopropyl-N-{(1S,2R)-1-(3,5-difluorobenzyl)-2-hydroxy-3-[(3-iodobenzyl)amino]propyl}-2-[(methylsulfonyl)amino]-1,3-oxazole-4-carboxamide |
| 1,127 | N-{(1S,2R)-1-(3,5-difluorobenzyl)-3-[(3-ethylbenzyl)amino]-2-hydroxypropyl}-2-[(propylsulfonyl)amino]-1,3-oxazole-4-carboxamide |
| 1,128 | N-{(1S,2R)-1-(3,5-difluorobenzyl)-2-hydroxy-3-[(3-iodobenzyl)amino]propyl}-5-isopropyl-2-[(methylsulfonyl)amino]-1,3-oxazole-4-carboxamide |
| 1,129 | N³-(cyclopropylmethyl)-N¹-{(1S,2R)-1-(3,5-difluorobenzyl)-3-[(3-ethylbenzyl)amino]-2-hydroxypropyl}-4-hydroxyisophthalamide |
| 1,130 | N-[(1S,2R)-1-(3,5-difluorobenzyl)-2-hydroxy-3-(isopentylamino)propyl]-2-[(methylsulfonyl)amino]-1,3-oxazole-4-carboxamide |
| 1,131 | N-{(1S,2R)-1-(3,5-difluorobenzyl)-3-[(3-ethylbenzyl)amino]-2-hydroxypropyl}-5-methyl-2-[(propylsulfonyl)amino]-1,3-oxazole-4-carboxamide |
| 1,132 | N-[(1S,2R)-3-(cyclopropylamino)-1-(3,5-difluorobenzyl)-2-hydroxypropyl]-2-[(methylsulfonyl)amino]-1,3-oxazole-4-carboxamide |
| 1,133 | N-[(1S,2R)-3-[(3-ethylbenzyl)amino]-2-hydroxy-1-(4-hydroxybenzyl)propyl]-2-[(methylsulfonyl)amino]-1,3-oxazole-4-carboxamide |
| 1,134 | N¹-{(1S,2R)-1-(3,5-difluorobenzyl)-3-[(3-ethylbenzyl)amino]-2-hydroxypropyl}-4-hydroxy-N³-isobutylisophthalamide |
| 1,135 | 2-{[(cyclopropylmethyl)sulfonyl]amino}-N-{(1S,2R)-1-(3,5-difluorobenzyl)-3-[(3-ethylbenzyl)amino]-2-hydroxypropyl}-1,3-oxazole-4-carboxamide |
| 1,136 | N¹-{(1S,2R)-1-(3,5-difluorobenzyl)-3-[(3-ethylbenzyl)amino]-2-hydroxypropyl}-4-hydroxy-N³-isobutyl-N³-methylisophthalamide |
| 1,137 | N-{(1S,2R)-1-(3,5-difluorobenzyl)-3-[(3-ethylbenzyl)amino]-2-hydroxypropyl}-2-[(isobutylsulfonyl)amino]-1,3-oxazole-4-carboxamide |
| 1,138 | N3-(cyclopropylmethyl)-N¹-{(1S,2R)-1-(3,5-difluorobenzyl)-3-[(3-ethylbenzyl)amino]-2-hydroxypropyl}-4-hydroxy-N³-methylisophthalamide |
| 1,139 | N-{(1S,2R)-1-(3,5-difluorobenzyl)-2-hydroxy-3-[(3-methoxybenzyl)amino]propyl}-2-[(isobutylsulfonyl)amino]-1,3-oxazole-4-carboxamide |

-continued

| EXA | | |
|---|---|---|
| 1,140 | N$^1$-{(1S,2R)-1-(3,5-difluorobenzyl)-3-[(3-ethylbenzyl)amino]-2-hydroxypropyl}-4-hydroxy-N$^3$-methyl-N$^3$-propylisophthalamide | |
| 1,141 | N-{(1S,2R)-1-(3,5-difluorobenzyl)-2-hydroxy-3-[(3-iodobenzyl)amino]propyl}-2-[(isobutylsulfonyl)amino]-1,3-oxazole-4-carboxamide | |
| 1,142 | N$^1$-{(1S,2R)-1-(3,5-difluorobenzyl)-2-hydroxy-3-[(3-methoxybenzyl)amino]propyl}-4-hydroxy-N$^3$-methyl-N$^3$-propylisophthalamide | |
| 1,143 | N-{(1S,2R)-1-(3,5-difluorobenzyl)-2-hydroxy-3-[(3-iodobenzyl)amino]propyl}-2-[(phenylsulfonyl)amino]-1,3-oxazole-4-carboxamide | |
| 1,144 | N$^1$-{(1S,2R)-1-(3,5-difluorobenzyl)-2-hydroxy-3-[(3-methoxybenzyl)amino]propyl}-N3-ethyl-4-hydroxy-N$^3$-propylisophthalamide | |
| 1,145 | N-{(1S,2R)-1-(3,5-difluorobenzyl)-2-hydroxy-3-[(3-iodobenzyl)amino]propyl}-2-{[(4-methylphenyl)sulfonyl]amino}-1,3-oxazole-4-carboxamide | |
| 1,146 | N$^1$-{(1S,2R)-1-(3,5-difluorobenzyl)-3-[(3-ethylbenzyl)amino]-2-hydroxypropyl}-N3-ethyl-4-hydroxy-N$^3$-propylisophthalamide | |
| 1,147 | N-{(1S,2R)-1-(3,5-difluorobenzyl)-3-[(3-ethylbenzyl)amino]-2-hydroxypropyl}-2-{[(4-methylphenyl)sulfonyl]amino}-1,3-oxazole-4-carboxamide | |
| 1,148 | N-{(1S,2R)-1-(3,5-difluorobenzyl)-3-[(3-ethylbenzyl)amino]-2-hydroxypropyl}-2-[(phenylsulfonyl)amino]-1,3-oxazole-4-carboxamide | |
| 1,149 | N$^1$-{(1S,2R)-1-(3,5-difluorobenzyl)-3-[(3-ethylbenzyl)amino]-2-hydroxypropyl}-4-hydroxy-N$^3$,N$^3$-dipropylisophthalamide | |
| 1,150 | N-{(1S,2R)-1-(3,5-difluorobenzyl)-3-[(3-ethylbenzyl)amino]-2-hydroxypropyl}-2-[methyl(methylsulfonyl)amino]-1,3-oxazole-4-carboxamide | |
| 1,151 | N$^1$-{(1S,2R)-1-(3,5-difluorobenzyl)-2-hydroxy-3-[(3-methoxybenzyl)amino]propyl}-4-hydroxy-N$^3$,N$^3$-dipropylisophthalamide | |
| 1,152 | N-{(1S,2R)-1-(3,5-difluorobenzyl)-2-hydroxy-3-[(3-iodobenzyl)amino]propyl}-2-[methyl(methylsulfonyl)amino]-1,3-oxazole-4-carboxamide | |
| 1,153 | N$^1$-{(1S,2R)-1-(3,5-difluorobenzyl)-2-hydroxy-3-[(3-iodobenzyl)amino]propyl}-4-hydroxy-N$^3$,N$^3$-dipropylisophthalamide | |
| 1,154 | N-{(1S,2R)-1-(3,5-difluorobenzyl)-2-hydroxy-3-[(3-iodobenzyl)amino]propyl}-2-[(methylsulfonyl)amino]-1,3-thiazole-4-carboxamide | |
| 1,155 | N-{(1S,2R)-1-(3,5-difluorobenzyl)-3-[(3-ethylbenzyl)amino]-2-hydroxypropyl}-2-[(methylsulfonyl)amino]-1,3-thiazole-4-carboxamide | |
| | | MH+ |
| 1,156 | N-{(1S,2R)-1-benzyl-2-hydroxy-3-[(3-methoxybenzyl)amino]propyl}-3-methyl-5-[propionyl(propyl)amino]benzamide | |
| 1,157 | N-{(1S,2R)-1-benzyl-2-hydroxy-3-[(3-methoxybenzyl)amino]propyl}-1-butyl-1H-indole-5-carboxamide | 532.5 |
| 1,159 | N-{(1S,2R)-1-benzyl-2-hydroxy-3-[(3-methoxybenzyl)amino]propyl}-3-[butyl(propionyl)amino]-5-methylbenzamide | |
| 1,160 | N-{(1S,2R)-1-benzyl-2-hydroxy-3-[(3-methoxybenzyl)amino]propyl}-4-methyl-1-propyl-1H-indole-6-carboxamide | 546.3 |
| 1,161 | N-{(1S,2R)-1-benzyl-2-hydroxy-3-[(3-methoxybenzyl)amino]propyl}-1-(1-propylbutyl)-1H-indole-6-carboxamide | 500.3 |
| 1,162 | N$^1$-((1S,2R)-1-benzyl-2-hydroxy-3-{[(2-oxo-2,3-dihydro-1,3-benzoxazol-6-yl)methyl]amino}propyl)-5-methyl-N$^3$,N$^3$-dipropylisophthalamide | 542.2 |
| 1,163 | N$^1$-{(1S,2R)-1-(3,5-difluorobenzyl)-3-[(3-ethylbenzyl)amino]-2-hydroxypropyl}-N$^3$,N$^3$-dipropyl-5-{[(trifluoromethyl)sulfonyl]amino}isophthalamide | 573.3 |
| 1,164 | 3-[({(1S,2R)-1-benzyl-2-hydroxy-3-[(3-methoxybenzyl)amino]propyl}amino)carbonyl]-5-[(dipropylamino)carbonyl]benzoic acid | 713.0 |
| 1,165 | N$^1$-{(1S,2R)-1-(3,5-difluorobenzyl)-3-[(3-ethylbenzyl)amino]-2-hydroxypropyl}-N$^3$,N$^3$-dipropyl-5-prop-1-ynylisophthalamide | 576.1 |
| 1,166 | N-{(1S,2R)-1-benzyl-2-hydroxy-3-[(3-methoxybenzyl)amino]propyl}-2-(dipropylamino)isonicotinamide | 604.4 |

-continued

| EXA | | |
|---|---|---|
| 1,167 | N¹-{(1S,2R)-1-(3,5-difluorobenzyl)-3-[(3-ethylbenzyl)amino]-2-hydroxypropyl}-5-[(methylsulfonyl)amino]-N³,N³-dipropylisophthalamide | HRMS = 505.3176 |
| 1,168 | N¹-{(1S,2R)-1-(3,5-difluorobenzyl)-3-[(3-ethylbenzyl)amino]-2-hydroxypropyl}-5-[(ethylsulfonyl)amino]-N³,N³-dipropylisophthalamide | |
| 1,169 | N¹-{(1S,2R)-1-(3,5-difluorobenzyl)-3-[(3-ethylbenzyl)amino]-2-hydroxypropyl}-N³,N³-dipropyl-5-[(propylsulfonyl)amino]isophthalamide | |
| 1,170 | N¹-{(1S,2R)-1-(3,5-difluorobenzyl)-3-[(3-ethylbenzyl)amino]-2-hydroxypropyl}-5-[(isopropylsulfonyl)amino]-N³,N³-dipropylisophthalamide | |
| 1,171 | N¹-{(1S,2R)-1-(3,5-difluorobenzyl)-3-[(3-ethylbenzyl)amino]-2-hydroxypropyl}-5-[(isobutylsulfonyl)amino]-N³,N³-dipropylisophthalamide | |
| 1,172 | N¹-{(1S,2R)-1-(3,5-difluorobenzyl)-3-[(3-ethylbenzyl)amino]-2-hydroxypropyl}-N³,N³-dipropyl-5-[(thien-2-ylsulfonyl)amino]isophthalamide | |
| 1,173 | N¹-{(1S,2R)-1-(3,5-difluorobenzyl)-3-[(3-ethylbenzyl)amino]-2-hydroxypropyl}-5-[(2-furylsulfonyl)amino]-N³,N³-dipropylisophthalamide | |
| 1,174 | N¹-{(1S,2R)-1-(3,5-difluorobenzyl)-3-[(3-ethylbenzyl)amino]-2-hydroxypropyl}-N³,N³-dipropyl-5-[(1,3-thiazol-5-ylsulfonyl)amino]isophthalamide | |
| 1,175 | N¹-{(1S,2R)-1-(3,5-difluorobenzyl)-3-[(3-ethylbenzyl)amino]-2-hydroxypropyl}-5-[(1,3-oxazol-5-ylsulfonyl)amino]-N³,N³-dipropylisophthalamide | |
| 1,176 | N¹-{(1S,2R)-1-(3,5-difluorobenzyl)-3-[(3-ethylbenzyl)amino]-2-hydroxypropyl}-5-[(1,3-oxazol-4-ylsulfonyl)amino]-N³,N³-dipropylisophthalamide | |
| 1,177 | N¹-{(1S,2R)-1-(3,5-difluorobenzyl)-3-[(3-ethylbenzyl)amino]-2-hydroxypropyl}-N³,N³-dipropyl-5-[(1,3-thiazol-4-ylsulfonyl)amino]isophthalamide | |
| 1,178 | N¹-{(1S,2R)-1-(3,5-difluorobenzyl)-3-[(3-ethylbenzyl)amino]-2-hydroxypropyl}-5-{[(1-methyl-1H-imidazol-4-yl)sulfonyl]amino}-N³,N³-dipropylisophthalamide | |
| 1,179 | N¹-{(1S,2R)-1-(3,5-difluorobenzyl)-3-[(3-ethylbenzyl)amino]-2-hydroxypropyl}-5-[(phenylsulfonyl)amino]-N³,N³-dipropylisophthalamide | |
| 1,180 | 5-{[(5-cyanopyridin-2-yl)sulfonyl]amino}-N¹-{(1S,2R)-1-(3,5-difluorobenzyl)-3-[(3-ethylbenzyl)amino]-2-hydroxypropyl}-N³,N³-dipropylisophthalamide | |
| 1,181 | N¹-{(1S,2R)-1-(3,5-difluorobenzyl)-3-[(3-ethylbenzyl)amino]-2-hydroxypropyl}-N³,N³-dipropyl-5-({[5-(trifluoromethyl)pyridin-2-yl]sulfonyl}amino)isophthalamide | |
| 1,182 | N-{(1S,2R)-1-(3,5-difluorobenzyl)-3-[(3-ethylbenzyl)amino]-2-hydroxypropyl}-3-{[(1-methyl-1H-imidazol-4-yl)sulfonyl]amino}benzamide | |
| 1,183 | N-{(1S,2R)-1-(3,5-difluorobenzyl)-3-[(3-ethylbenzyl)amino]-2-hydroxypropyl}-3-({[5-(trifluoromethyl)pyridin-2-yl]sulfonyl}amino)benzamide | |
| 1,184 | 3-{[(5-cyanopyridin-2-yl)sulfonyl]amino}-N-{(1S,2R)-1-(3,5-difluorobenzyl)-3-[(3-ethylbenzyl)amino]-2-hydroxypropyl}benzamide | |
| 1,185 | N-{(1S,2R)-1-(3,5-difluorobenzyl)-3-[(3-ethylbenzyl)amino]-2-hydroxypropyl}-3-[(phenylsulfonyl)amino]benzamide | |
| 1,186 | N-{(1S,2R)-1-(3,5-difluorobenzyl)-3-[(3-ethylbenzyl)amino]-2-hydroxypropyl}-3-[(methylsulfonyl)amino]benzamide | |
| 1,187 | N-{(1S,2R)-1-(3,5-difluorobenzyl)-3-[(3-ethylbenzyl)amino]-2-hydroxypropyl}-3-[(ethylsulfonyl)amino]benzamide | |
| 1,188 | N-{(1S,2R)-1-(3,5-difluorobenzyl)-3-[(3-ethylbenzyl)amino]-2-hydroxypropyl}-3-[(propylsulfonyl)amino]benzamide | |
| 1,189 | N-{(1S,2R)-1-(3,5-difluorobenzyl)-3-[(3-ethylbenzyl)amino]-2-hydroxypropyl}-3-[(isobutylsulfonyl)amino]benzamide | |
| 1,190 | N-{(1S,2R)-1-(3,5-difluorobenzyl)-3-[(3-ethylbenzyl)amino]-2-hydroxypropyl}-3-[(isopropylsulfonyl)amino]benzamide | |

-continued

| EXA | | |
|---|---|---|
| 1,191 | N-{(1S,2R)-1-(3,5-difluorobenzyl)-3-[(3-ethylbenzyl)amino]-2-hydroxypropyl}-3-{[(1-ethylpropyl)sulfonyl]amino}benzamide | |
| 1,192 | 3-[(cyclohexylsulfonyl)amino]-N-{(1S,2R)-1-(3,5-difluorobenzyl)-3-[(3-ethylbenzyl)amino]-2-hydroxypropyl}benzamide | |
| 1,193 | N-{(1S,2R)-1-(3,5-difluorobenzyl)-3-[(3-ethylbenzyl)amino]-2-hydroxypropyl}-3-{[(1-propylbutyl)sulfonyl]amino}benzamide | |
| 1,194 | N-{(1S,2R)-1-(3,5-difluorobenzyl)-3-[(3-ethylbenzyl)amino]-2-hydroxypropyl}-3-[(thien-2-ylsulfonyl)amino]benzamide | |
| 1,195 | N-{(1S,2R)-1-(3,5-difluorobenzyl)-3-[(3-ethylbenzyl)amino]-2-hydroxypropyl}-3-[(2-furylsulfonyl)amino]benzamide | |
| 1,196 | N-{(1S,2R)-1-(3,5-difluorobenzyl)-3-[(3-ethylbenzyl)amino]-2-hydroxypropyl}-3-[(isoxazol-5-ylsulfonyl)amino]benzamide | |
| 1,197 | N-{(1S,2R)-1-(3,5-difluorobenzyl)-3-[(3-ethylbenzyl)amino]-2-hydroxypropyl}-3-[(isoxazol-3-ylsulfonyl)amino]benzamide | |
| 1,198 | N-{(1S,2R)-1-(3,5-difluorobenzyl)-3-[(3-ethylbenzyl)amino]-2-hydroxypropyl}-3-[(3-furylsulfonyl)amino]benzamide | |
| 1,199 | N-{(1S,2R)-1-(3,5-difluorobenzyl)-3-[(3-ethylbenzyl)amino]-2-hydroxypropyl}-3-[(thien-3-ylsulfonyl)amino]benzamide | |
| 1,200 | N-{(1S,2R)-1-(3,5-difluorobenzyl)-3-[(3-ethylbenzyl)amino]-2-hydroxypropyl}-3-[(1,3-thiazol-4-ylsulfonyl)amino]benzamide | |
| 1,201 | N-{(1S,2R)-1-(3,5-difluorobenzyl)-3-[(3-ethylbenzyl)amino]-2-hydroxypropyl}-3-[(1,3-thiazol-5-ylsulfonyl)amino]benzamide | |
| 1,202 | N-{(1S,2R)-1-(3,5-difluorobenzyl)-3-[(3-ethylbenzyl)amino]-2-hydroxypropyl}-3-[(1,3-thiazol-2-ylsulfonyl)amino]benzamide | |
| 1,203 | $N^1$-[(1S,2R)-1-(3,5-difluorobenzyl)-2-hydroxy-3-(isopentylamino)propyl]-$N^3$,$N^3$-dipropyl-5-{[(trifluoromethyl)sulfonyl]amino}isophthalamide | |
| 1,204 | $N^1$-[(1S,2R)-3-amino-1-(3,5-difluorobenzyl)-2-hydroxypropyl]-$N^3$,$N^3$-dipropyl-5-{[(trifluoromethyl)sulfonyl]amino}isophthalamide | |
| 1,205 | $N^1$-[(1S,2R)-3-amino-1-(3,5-difluorobenzyl)-2-hydroxypropyl]-5-[(methylsulfonyl)amino]-$N^3$,$N^3$-dipropylisophthalamide | |
| 1,206 | $N^1$-[(1S,2R)-1-(3,5-difluorobenzyl)-2-hydroxy-3-(isopentylamino)propyl]-5-[(methylsulfonyl)amino]-$N^3$,$N^3$-dipropylisophthalamide | |
| 1,207 | $N^1$-(tert-butyl)-$N^3$-{(1S,2R)-1-(3,5-difluorobenzyl)-3-[(3-ethylbenzyl)amino]-2-hydroxypropyl}isophthalamide | |
| 1,208 | $N^1$-(tert-butyl)-$N^3$-{(1S,2R)-1-(3,5-difluorobenzyl)-3-[(3-ethylbenzyl)amino]-2-hydroxypropyl}-5-methylisophthalamide | |
| 1,209 | 5-bromo-$N^1$-(tert-butyl)-$N^3$-{(1S,2R)-1-(3,5-difluorobenzyl)-3-[(3-ethylbenzyl)amino]-2-hydroxypropyl}isophthalamide | |
| 1,210 | 3-tert-butoxy-N-{(1S,2R)-1-(3,5-difluorobenzyl)-3-[(3-ethylbenzyl)amino]-2-hydroxypropyl}benzamide | |
| 1,211 | 3-tert-butoxy-N-{(1S,2R)-1-(3,5-difluorobenzyl)-3-[(3-ethylbenzyl)amino]-2-hydroxypropyl}-5-methylbenzamide | |
| 1,212 | N-{(1S,2R)-1-(3,5-difluorobenzyl)-3-[(3-ethylbenzyl)amino]-2-hydroxypropyl}-3-{[(trifluoromethyl)sulfonyl]amino}benzamide | |
| 1,213 | N-{(1S,2R)-1-(3,5-difluorobenzyl)-3-[(3-ethylbenzyl)amino]-2-hydroxypropyl}-3-(trifluoromethoxy)benzamide | |
| 1,214 | N-{(1S,2R)-1-(3,5-difluorobenzyl)-3-[(3-ethylbenzyl)amino]-2-hydroxypropyl}-3-methyl-5-(trifluoromethoxy)benzamide | |
| | | $[M + H]^+$ |
| 1,215 | N-{(1S,2R)-1-(3,5-difluorobenzyl)-2-hydroxy-3-[(3-iodobenzyl)amino]propyl}-2-hydroxy-2-(4-methylphenyl)acetamide | 581.4 |

-continued

| EXA | | |
|---|---|---|
| 1,216 | N1-{(1S,2R)-1-(3,5-difluorobenzyl)-2-hydroxy-3-[(3-iodobenzyl)amino]propyl}-4-hydroxy-N3-methylisophthalamide | 610.4 |
| 1,217 | N-{(1S,2R)-1-(3,5-difluorobenzyl)-2-hydroxy-3-[(3-iodobenzyl)amino]propyl}-2-hydroxy-2-(4-methoxy-3-nitrophenyl)acetamide | 642.4 |
| 1,218 | 5-(aminosulfonyl)-N-{(1S,2R)-1-(3,5-difluorobenzyl)-2-hydroxy-3-[(3-iodobenzyl)amino]propyl}-2-methoxybenzamide | 646.5 |
| 1,219 | N-{(1S,2R)-1-(3,5-difluorobenzyl)-2-hydroxy-3-[(3-iodobenzyl)amino]propyl}-4-hydroxy-3-(pyrrolidin-1-ylcarbonyl)benzamide | 650.5 |
| 1,220 | N-{(1S,2R)-1-(3,5-difluorobenzyl)-2-hydroxy-3-[(3-iodobenzyl)amino]propyl}-2-[(methylsulfonyl)amino]-1,3-oxazole-4-carboxamide | 621.4 |
| 1,221 | $N^1$-{(1S,2R)-1-(3,5-difluorobenzyl)-2-hydroxy-3-[(3-methoxybenzyl)amino]propyl}-5-(3,5-dimethylisoxazol-4-yl)-$N^3$,$N^3$-dipropylisophthalamide | 663.4 |
| 1,222 | $N^1$-{(1S,2R)-1-(3,5-difluorobenzyl)-2-hydroxy-3-[(3-methoxybenzyl)amino]propyl}-$N^3$,$N^3$-dipropyl-5-(1,3-thiazol-2-yl)isophthalamide | 651.4 |
| 1,223 | 3-(cyclohexylcarbonyl)-N-{(1S,2R)-1-(3,5-difluorobenzyl)-2-hydroxy-3-[(3-methoxybenzyl)amino]propyl}-5-methylbenzamide | 565.4 |
| 1,224 | $N^1$-{(1S,2R)-1-(3,5-difluorobenzyl)-2-hydroxy-3-[(3-methoxybenzyl)amino]propyl}-5-methyl-$N^3$-propylisophthalamide | 540.4 |
| 1,225 | 3-[cyclohexyl(hydroxy)methyl]-N-{(1S,2R)-1-(3,5-difluorobenzyl)-2-hydroxy-3-[(3-methoxybenzyl)amino]propyl}-5-methylbenzamide | 567.4 |
| 1,226 | $N^1$-{(1S,2R)-1-(3,5-difluorobenzyl)-3-[(3-ethylbenzyl)amino]-2-hydroxypropyl}-5-(4-methyl-1,3-oxazol-2-yl)-$N^3$,$N^3$-dipropylisophthalamide | 647.5 |
| 1,227 | $N^3$-{(1S,2R)-1-(3,5-difluorobenzyl)-3-[(3-ethylbenzyl)amino]-2-hydroxypropyl}-$N^5$,$N^5$-dipropylpyridine-3,5-dicarboxamide | 567 |
| 1,228 | $N^1$-((1S,2R)-1-(3,5-difluorobenzyl)-2-hydroxy-3-{[(3-isobutyl-1,2,4-oxadiazol-5-yl)methyl]amino}propyl)-5-methyl-$N^3$,$N^3$-dipropylisophthalamide | 600 |
| 1,229 | $N^3$-{(1S,2R)-1-(3,5-difluorobenzyl)-3-[(3-ethynylbenzyl)amino]-2-hydroxypropyl}-$N^5$,$N^5$-dipropylpyridine-3,5-dicarboxamide | 563 |
| 1,230 | $N^3$-{(1S,2R)-1-(3,5-difluorobenzyl)-2-hydroxy-3-[(3-isopropylbenzyl)amino]propyl}-$N^5$,$N^5$-dipropylpyridine-3,5-dicarboxamide | 581 |
| 1,231 | $N^1$-[(1S,2R)-3-[(1-acetylpiperidin-4-yl)amino]-1-(3,5-difluorobenzyl)-2-hydroxypropyl]-5-methyl-$N^3$,$N^3$-dipropylisophthalamide | 587 |
| 1,232 | $N^1$-{(1S,2R)-1-(3,5-difluorobenzyl)-2-hydroxy-3-[(3-pent-1-ynylbenzyl)amino]propyl}-5-methyl-$N^3$,$N^3$-dipropylisophthalamide | 618 |
| 1,233 | $N^1$-((1S,2R)-1-(3,5-difluorobenzyl)-2-hydroxy-3-{[3-(4-hydroxybut-1-ynyl)benzyl]amino}propyl)-5-methyl-$N^3$,$N^3$-dipropylisophthalamide | 620 |
| 1,234 | 1-{3-[({(1S,2R)-1-(3,5-difluorobenzyl)-3-[(3-ethylbenzyl)amino]-2-hydroxypropyl}amino)carbonyl]-5-methylbenzoyl}-L-prolinamide | 593 |
| 1,235 | $N^1$-{(1S,2R)-1-(3,5-difluorobenzyl)-3-[(3-ethylbenzyl)amino]-2-hydroxypropyl}-$N^3$-isopropyl-5-methylisophthalamide | 538 |
| 1,236 | $N^1$-{(1S,2R)-1-(3,5-difluorobenzyl)-3-[(3-ethylbenzyl)amino]-2-hydroxypropyl}-$N^3$-ethyl-$N^3$,5-dimethylisophthalamide | 538 |
| 1,237 | $N^1$-{(1S,2R)-1-(3,5-difluorobenzyl)-3-[(3-ethylbenzyl)amino]-2-hydroxypropyl}-$N^3$,5-dimethyl-$N^3$-prop-2-ynylisophthalamide | 548 |
| 1,238 | $N^1$-{(1S,2R)-1-(3,5-difluorobenzyl)-3-[(3-ethylbenzyl)amino]-2-hydroxypropyl}-$N^3$-isobutyl-5-methylisophthalamide | 552 |
| 1,239 | $N^1$-(sec-butyl)-$N^3$-{(1S,2R)-1-(3,5-difluorobenzyl)-3-[(3-ethylbenzyl)amino]-2-hydroxypropyl}-5-methylisophthalamide | 552 |

| EXA | | |
|---|---|---|
| 1,240 | $N^1$-butyl-$N^3$-{(1S,2R)-1-(3,5-difluorobenzyl)-3-[(3-ethylbenzyl)amino]-2-hydroxypropyl}-5-methylisophthalamide | 552 |
| 1,241 | $N^1$-{(1S,2R)-1-(3,5-difluorobenzyl)-3-[(3-ethylbenzyl)amino]-2-hydroxypropyl}-$N^3$,$N^3$-diethyl-5-methylisophthalamide | 552 |
| 1,242 | $N^1$-{(1S,2R)-1-(3,5-difluorobenzyl)-3-[(3-ethylbenzyl)amino]-2-hydroxypropyl}-$N^3$,5-dimethyl-$N^3$-propylisophthalamide | 552 |
| 1,243 | $N^1$-{(1S,2R)-1-(3,5-difluorobenzyl)-3-[(3-ethylbenzyl)amino]-2-hydroxypropyl}-$N^3$-isopropyl-$N^3$,5-dimethylisophthalamide | 552 |
| 1,244 | $N^1$-butyl-$N^3$-{(1S,2R)-1-(3,5-difluorobenzyl)-3-[(3-ethylbenzyl)amino]-2-hydroxypropyl}-$N^1$,5-dimethylisophthalamide | 566 |
| 1,245 | $N^1$-{(1S,2R)-1-(3,5-difluorobenzyl)-3-[(3-ethylbenzyl)amino]-2-hydroxypropyl}-$N^3$-isobutyl-$N^3$,5-dimethylisophthalamide | 566 |
| 1,246 | $N^1$-{(1S,2R)-1-(3,5-difluorobenzyl)-3-[(3-ethylbenzyl)amino]-2-hydroxypropyl}-$N^3$-ethyl-5-methyl-$N^3$-propylisophthalamide | 566 |
| 1,247 | $N^1$-{(1S,2R)-1-(3,5-difluorobenzyl)-3-[(3-ethylbenzyl)amino]-2-hydroxypropyl}-$N^3$-ethyl-$N^3$-isopropyl-5-methylisophthalamide | 566 |
| 1,248 | $N^1$,$N^1$-diallyl-$N^3$-{(1S,2R)-1-(3,5-difluorobenzyl)-3-[(3-ethylbenzyl)amino]-2-hydroxypropyl}-5-methylisophthalamide | 576 |
| 1,249 | 3-(azepan-1-ylcarbonyl)-N-{(1S,2R)-1-(3,5-difluorobenzyl)-3-[(3-ethylbenzyl)amino]-2-hydroxypropyl}-5-methylbenzamide | 578 |
| 1,250 | N-{(1S,2R)-1-(3,5-difluorobenzyl)-3-[(3-ethylbenzyl)amino]-2-hydroxypropyl}-3-[(4-hydroxypiperidin-1-yl)carbonyl]-5-methylbenzamide | 580 |
| 1,251 | N-{(1S,2R)-1-(3,5-difluorobenzyl)-3-[(3-ethylbenzyl)amino]-2-hydroxypropyl}-3-[(3-hydroxypiperidin-1-yl)carbonyl]-5-methylbenzamide | 580 |
| 1,252 | $N^1$-{(1S,2R)-1-(3,5-difluorobenzyl)-3-[(3-ethylbenzyl)amino]-2-hydroxypropyl}-$N^3$,$N^3$-diisopropyl-5-methylisophthalamide | 580 |
| 1,253 | $N^1$-butyl-$N^3$-{(1S,2R)-1-(3,5-difluorobenzyl)-3-[(3-ethylbenzyl)amino]-2-hydroxypropyl}-$N^1$-ethyl-5-methylisophthalamide | 580 |
| 1,254 | $N^1$-(cyclopropylmethyl)-$N^3$-{(1S,2R)-1-(3,5-difluorobenzyl)-3-[(3-ethylbenzyl)amino]-2-hydroxypropyl}-5-methyl-$N^1$-propylisophthalamide | 592 |
| 1,255 | 1-{3-[({(1S,2R)-1-(3,5-difluorobenzyl)-3-[(3-ethylbenzyl)amino]-2-hydroxypropyl}amino)carbonyl]-5-methylbenzoyl}-D-prolinamide | 593 |
| 1,256 | $N^1$-cyclohexyl-$N^3$-{(1S,2R)-1-(3,5-difluorobenzyl)-3-[(3-ethylbenzyl)amino]-2-hydroxypropyl}-$N^1$,5-dimethylisophthalamide | 592 |
| 1,257 | $N^1$-((1S,2R)-1-(3,5-difluorobenzyl)-2-hydroxy-3-{[1-(3-methylphenyl)cyclopropyl]amino}propyl)-5-methyl-$N^3$,$N^3$-dipropylisophthalamide | 592 |
| 1,258 | $N^3$-[(1S,2R)-1-(3,5-difluorobenzyl)-2-hydroxy-3-(1,2,3,4-tetrahydronaphthalen-1-ylamino)propyl]-$N^5$,$N^5$-diisopropylpyridine-3,5-dicarboxamide | 579 |
| 1,259 | N-{(1S,2R)-1-(3,5-difluorobenzyl)-3-[(3-ethylbenzyl)amino]-2-hydroxypropyl}-3-{[(trifluoromethyl)sulfonyl]amino}benzamide | 586.1 |

The compounds in the table immediately below were prepared essentially using the methods described above and illustrated below in the schemes.

Compounds in this application were named using Chemdraw Ultra version 6.0.2, which is available through Cambridgesoft.co, 100 Cambridge Park Drive, Cambridge, Mass. 02140, Namepro version 5.09, which is available from ACD labs, 90 Adelaide Street West, Toronto, Ontario, M5H, 3V9, Canada, or were derived from names generated using those programs.

1260

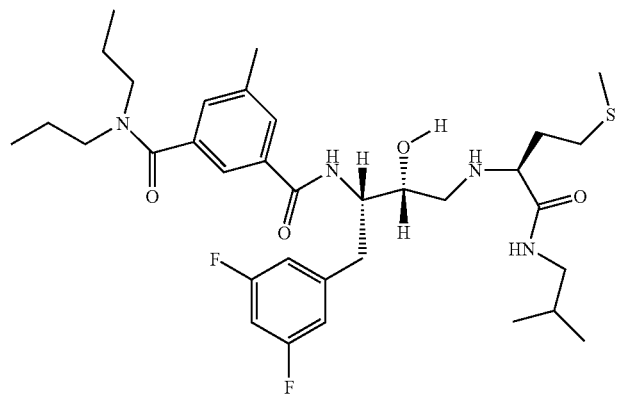

N-[1-(3,5-Difluoro-benzyl)-2-hydroxy-3-(1-isobutylcarbamoyl-3-methylsulfanyl-
propylamino)-propyl]-5-methyl-N',N'-dipropyl-isophthalamide

1261

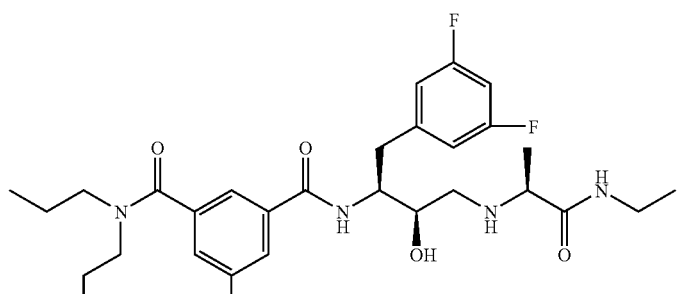

N-[1-(3,5-Difluoro-benzyl)-3-(1-ethylcarbamoyl-3-ethylamino)-2-
hydroxy-propyl]-5-methyl-N',N'-dipropyl-isophthalamide

1262

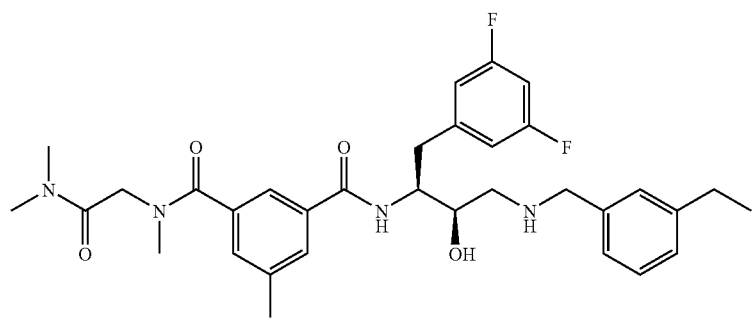

N-[1-(3,5-Difluoro-benzyl)-3-(3-ethyl-benzylamino)-2-hydroxy-
propyl]-N'-dimethylcarbamoylmethyl-5,N'-dimethyl-isophthalamide

1263

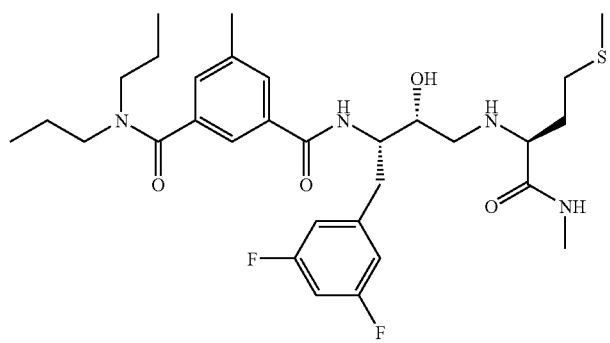

N-[1-(3,5-Difluoro-benzyl)-2-hydroxy-3-(1-methylcarbamoyl-3-methylsulfanyl-
propylamino)-propyl]-5-methyl-N',N'-dipropyl-isophthalamide

1264

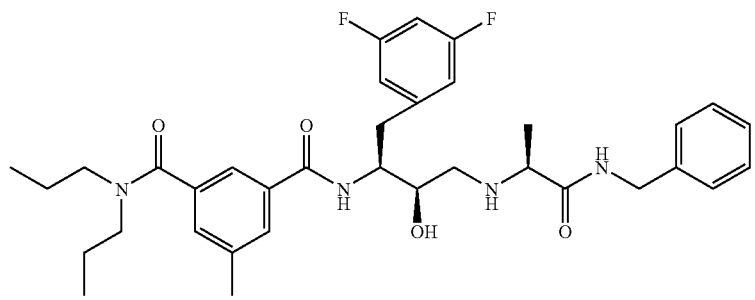

N-[3-(1-Benzylcarbamoyl-ethylamino)-1-(3,5-difluoro-benzyl)-2-hydroxy-
propyl]-5-methyl-N',N'-dipropyl-isophthalamide

1265

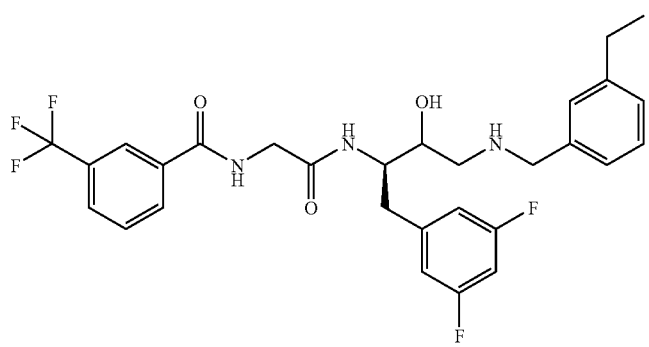

N-{[1-(3,5-Difluoro-benzyl)-3-(3-ethyl-benzylamino)-2-hydroxy-
propylcarbamoyl]-methyl}-3-trifluoromethyl-benzamide

1266

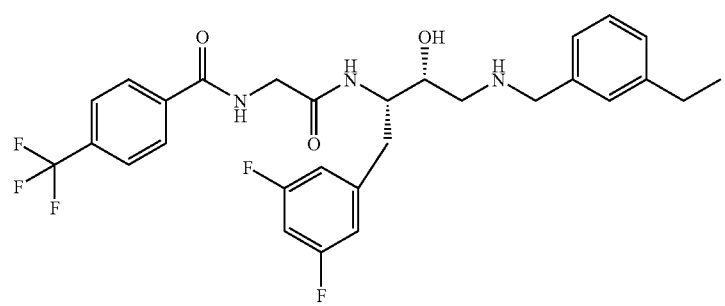

N-{[1-(3,5-Difluoro-benzyl)-3-(3-ethyl-benzylamino)-2-hydroxy-
propylcarbamoyl]-methyl}-4-trifluoromethyl-benzamide

1267

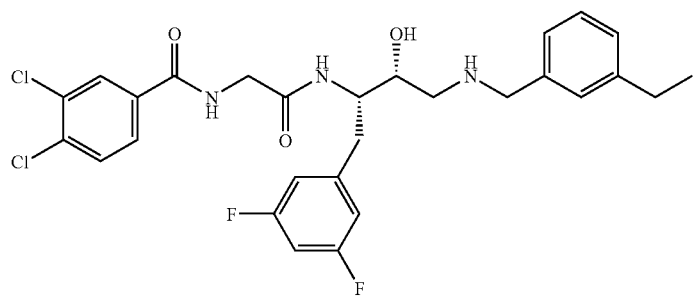

3,4-Dichloro-N-{[1-(3,5-difluoro-benzyl)-3-(3-ethyl-benzylamino)-2-
hydroxy-propylcarbamoyl]-methyl}-benzamide -continued

1268

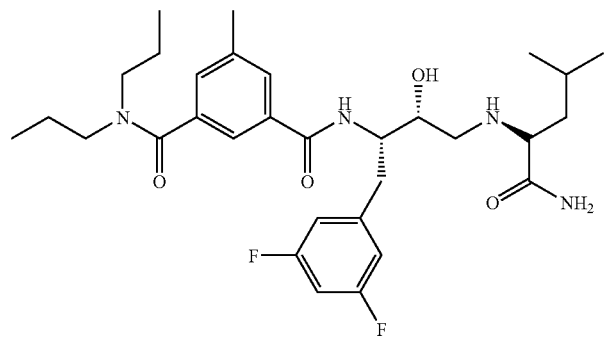

N-[3-(1-Carbamoyl-3-methyl-butylamino)-1-(3,5-difluoro-benzyl)-2-hydroxy-
propyl]-5-methyl-N',N'-dipropyl-isophthalamide

1269

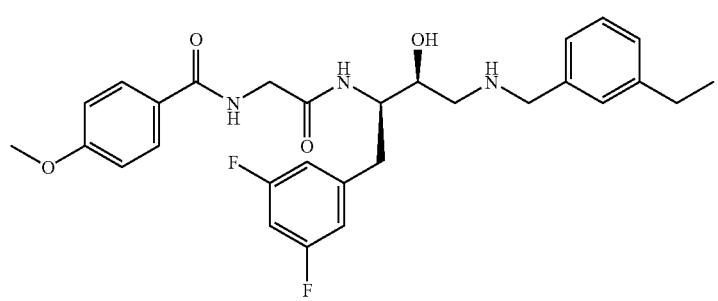

N-{[1-(3,5-Difluoro-benzyl)-3-(3-ethyl-benzylamino)-2-hydroxy-
propylcarbamoyl]-methyl}-4-methoxy-benzamide

1270

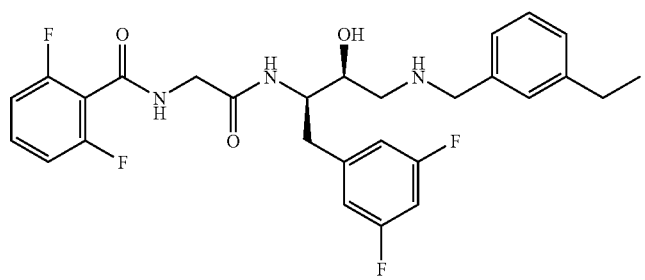

N-{[1-(3,5-Difluoro-benzyl)-3-(3-ethyl-benzylamino)-2-hydroxy-
propylcarbamoyl]-methyl}-2,6-difluoro-benzamide

1271

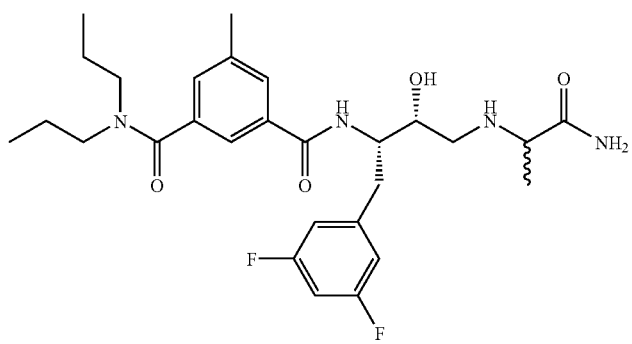

N-[3-(1-Carbamoyl-ethylamino)-1-(3,5-difluoro-benzyl)-2-hydroxy-
propyl]-5-methyl-N',N'-dipropyl-isophthalamide

1272

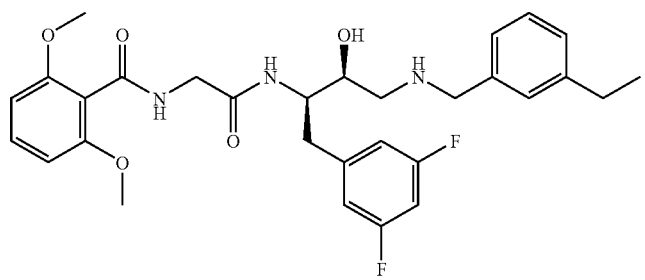

N-{[1-(3,5-Difluoro-benzyl)-3-(3-ethyl-benzylamino)-2-hydroxy-
propylcarbamoyl]-methyl}-2,6-dimethoxy-benzamide

1273

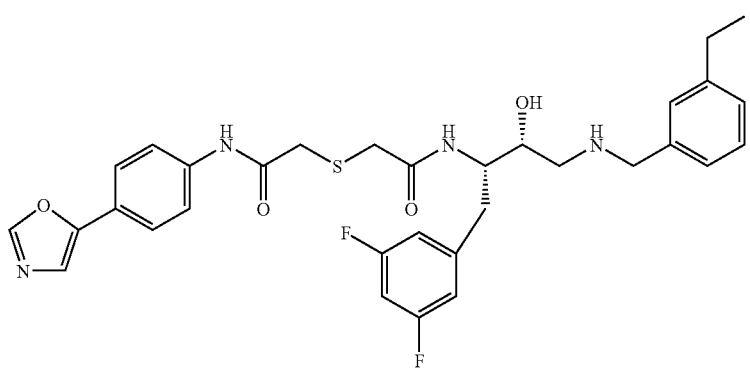

2-{[1-(3,5-Difluoro-benzyl)-3-(3-ethyl-benzylamino)-2-hydroxy-
propylcarbamoyl]-methylsulfanyl}-N-(4-oxazol-5-yl-phenyl)-acetamide

1274

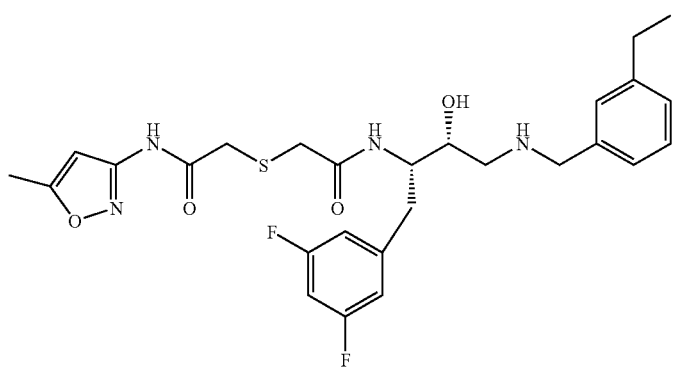

2-{[1-(3,5-Difluoro-benzyl)-3-(3-ethyl-benzylamino)-2-hydroxy-
propylcarbamoyl]-methylsulfanyl}-N-(5-methyl-isoxazol-3-yl)-acetamide

1275

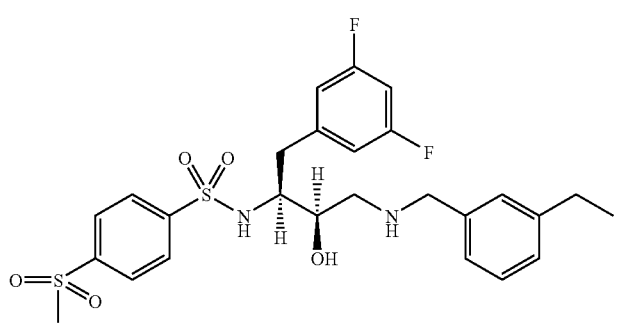

N-[1-(3,5-Difluoro-benzyl)-3-(3-ethyl-benzylamino)-2-hydroxy-
propyl]-4-methanesulfonyl-benzenesulfonamide

1276

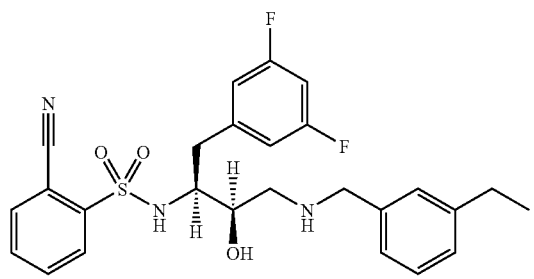

2-Cyano-N-[1-(3,5-difluoro-benzyl)-3-(3-ethyl-benzylamino)-2-hydroxy-propyl]-benzenesulfonamide

1277

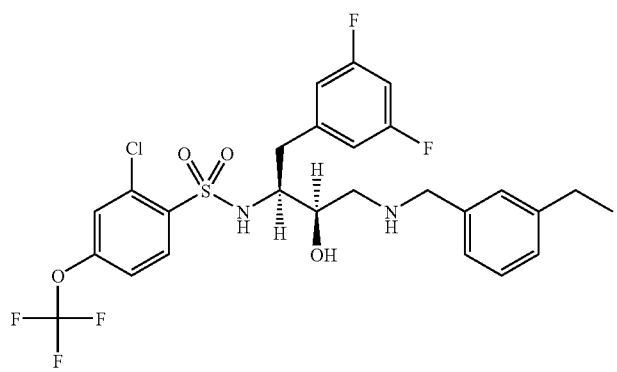

2-Chloro-N-[1-(3,5-difluoro-benzyl)-3-(3-ethyl-benzylamino)-2-hydroxy-propyl]-4-trifluoromethoxy-benzenesulfonamide

1278

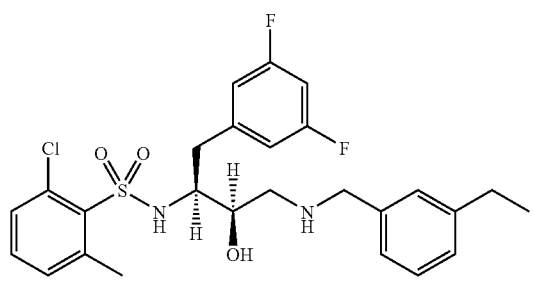

2-Chloro-N-[1-(3,5-difluoro-benzyl)-3-(3-ethyl-benzylamino)-2-hydroxy-propyl]-6-methyl-benzenesulfonamide

1279

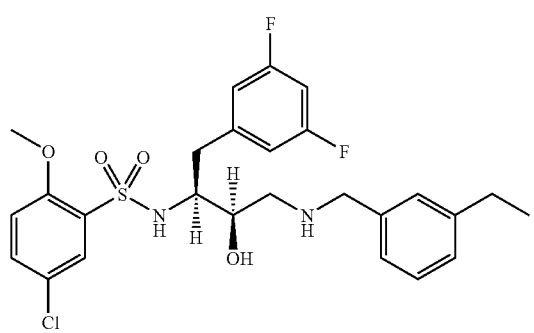

5-Chloro-N-[1-(3,5-difluoro-benzyl)-3-(3-ethyl-benzylamino)-2-hydroxy-propyl]-2-methoxy-benzenesulfonamide 1280
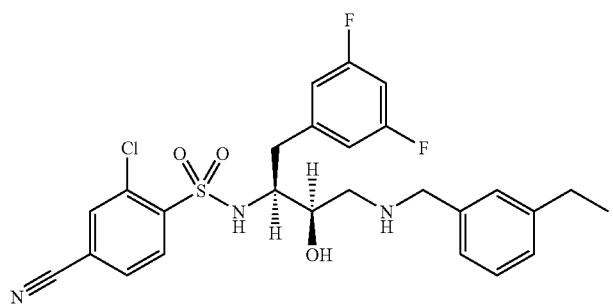
2-Chloro-4-cyano-N-[1-(3,5-difluoro-benzyl)-3-(3-ethyl-benzyl)-3-
(3-ethyl-benzylamino)-2-hydroxy-propyl]-benzenesulfonamide
1281
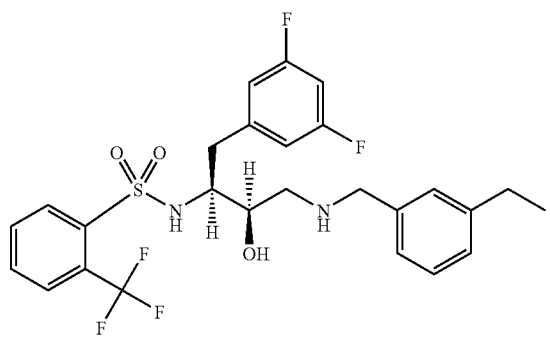
N-[1-(3,5-Difluoro-benzyl)-3-(3-ethyl-benzylamino)-2-hydroxy-
propyl]-2-trifluoromethyl-benzenesulfonamide
1282
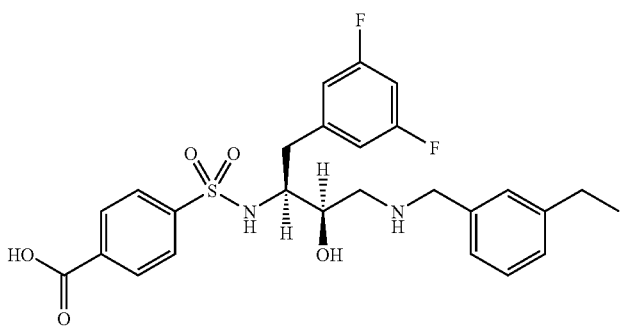
4-[1-(3,5-Difluoro-benzyl)-3-(3-ethyl-benzylamino)-2-
hydroxy-propylsulfamoyl]-benzoic acid
1283
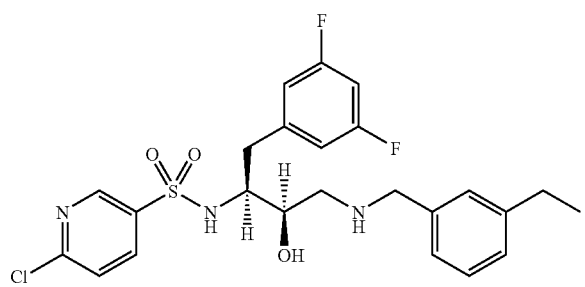
6-Chloro-pyridine-3-sulfonic acid [1-(3,5-difluoro-benzyl)-3-(3-ethyl-
benzylamino)-2-hydroxy-propyl]-amide

1284

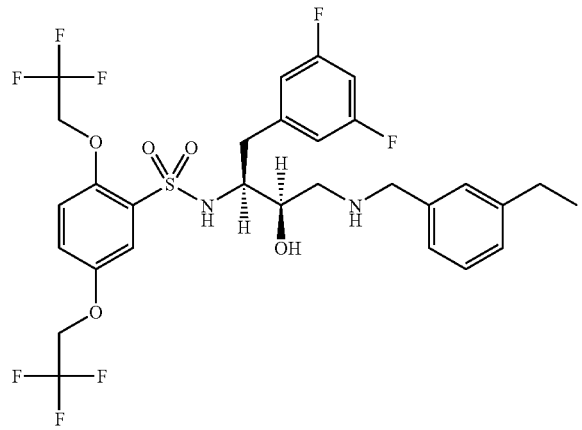

N-[1-(3,5-Difluoro-benzyl)-3-(3-ethyl-benzylamino)-2-hydroxy-
propyl]-2,5-bis-(2,2,2-trifluoro-ethoxy)-benzenesulfonamide

1285

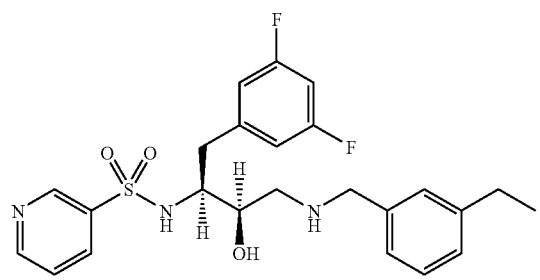

Pyridine-3-sulfonic acid [1-(3,5-difluoro-benzyl)-3-(3-ethyl-
benzylamino)-2-hydroxy-propyl]-amide

1286

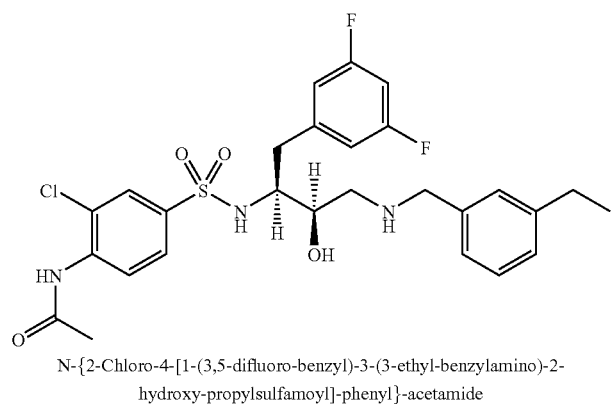

N-{2-Chloro-4-[1-(3,5-difluoro-benzyl)-3-(3-ethyl-benzylamino)-2-
hydroxy-propylsulfamoyl]-phenyl}-acetamide

1287

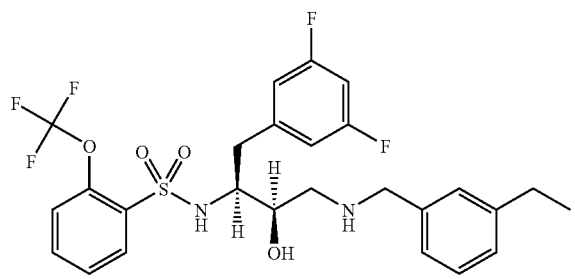

N-[1-(3,5-Difluoro-benzyl)-3-(3-ethyl-benzylamino)-2-hydroxy-
propyl]-2-trifluoromethoxy-benzenesulfonamide

1288

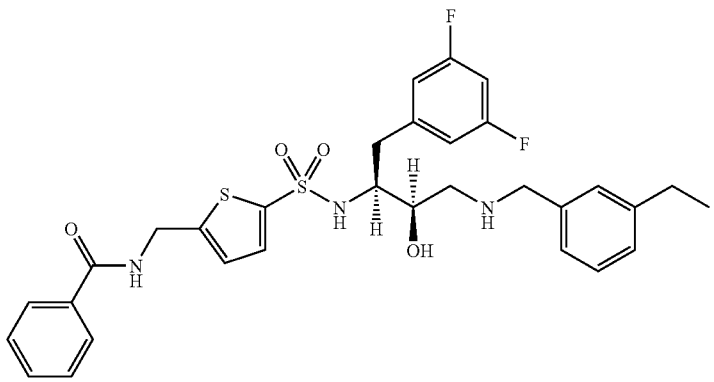

N-{5-[1-(3,5-Difluoro-benzyl)-3-(3-ethyl-benzylamino)-2-hydroxy-
propylsulfamoyl]-thiophen-2-ylmethyl}-benzamide

1289

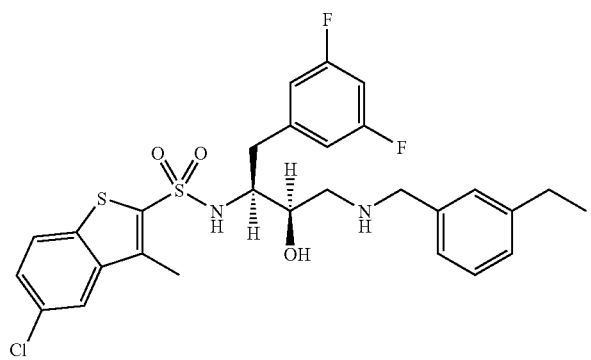

5-Chloro-3-methyl-benzo[b]thiophene-2-sulfonic acid [1-(3,5-difluoro-
benzyl)-3-(3-ethyl-benzylamino)-2-hydroxy-propyl]-amide

1290

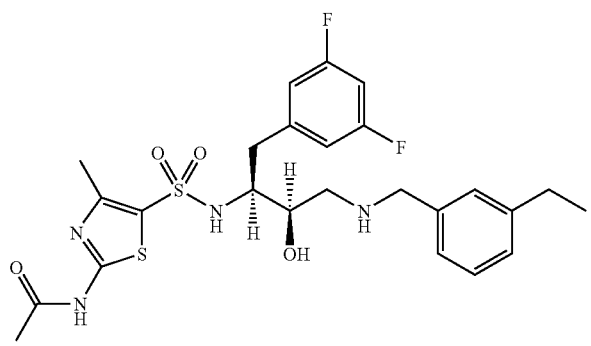

N-{5-[1-(3,5-Difluoro-benzyl)-3-(3-ethyl-benzylamino)-2-hydroxy-
propylsulfamoyl]-4-methyl-thiazol-2-yl}-acetamide

1291

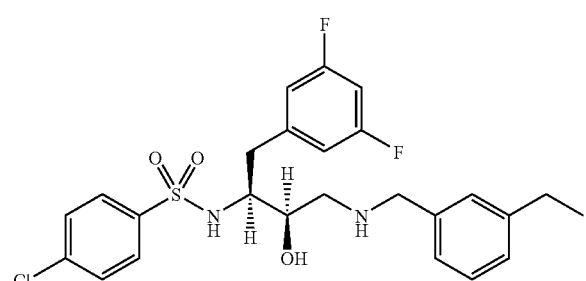

4-Chloro-N-[1-(3,5-difluoro-benzyl)-3-(3-ethyl-benzylamino)-2-
hydroxy-propyl]-benzenesulfonamide 1292
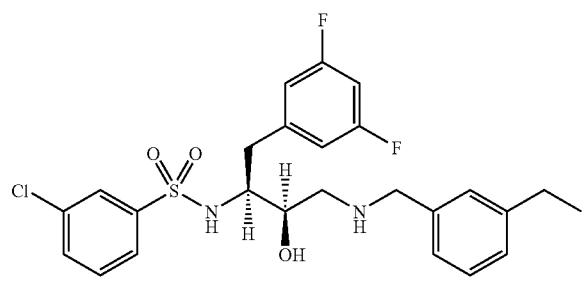
3-Chloro-N-[1-(3,5-difluoro-benzyl)-3-(3-ethyl-
benzylamino)-2-hydroxy-propyl]-benzenesulfonamide
1293
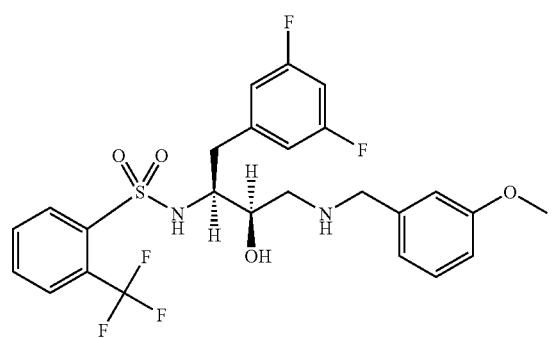
N-[1-(3,5-Difluoro-benzyl)-2-hydroxy-3-(3-methoxy-benzylamino)-
propyl]-2-trifluoromethyl-benzenesulfonamide
1294
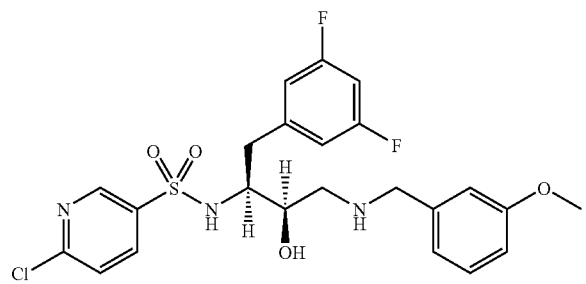
6-Chloro-pyridine-3-sulfonic acid [1-(3,5-difluoro-benzyl)-2-hydroxy-3-
(3-methoxy-benzylamino)-propyl]-amide
1295
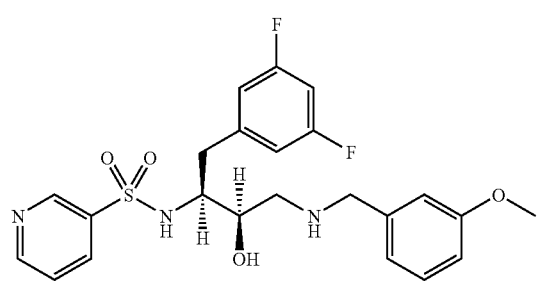
Pyridine-3-sulfonic acid [1-(3,5-difluoro-benzyl)-2-hydroxy-3-
(3-methoxy-benzylamino)-propyl]-amide

1296

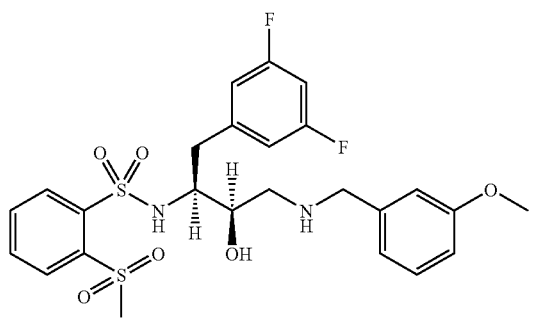

N-[1-(3,5-Difluoro-benzyl)-2-hydroxy-3-(3-methoxy-benzylamino)-
propyl]-2-methanesulfonyl-benzenesulfonamide

1297

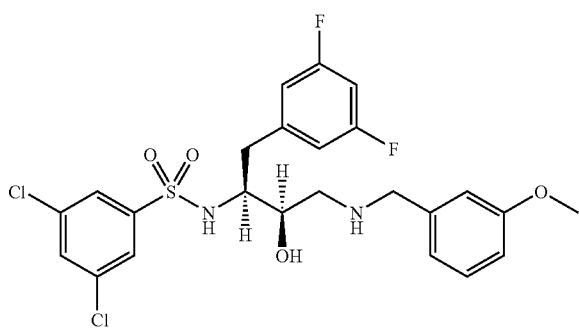

3,5-Dichloro-N-[1-(3,5-difluoro-benzyl)-2-hydroxy-3-(3-methoxy-
benzylamino)-propyl]-benzenesulfonamide

1298

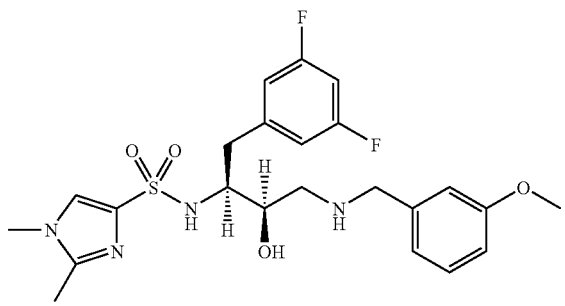

1,2-Dimethyl-1H-imidazole-4-sulfonic acid [1-(3,5-difluoro-
benzyl)-2-hydroxy-3-(3-methoxy-benzylamino)-propyl]-amide

1299

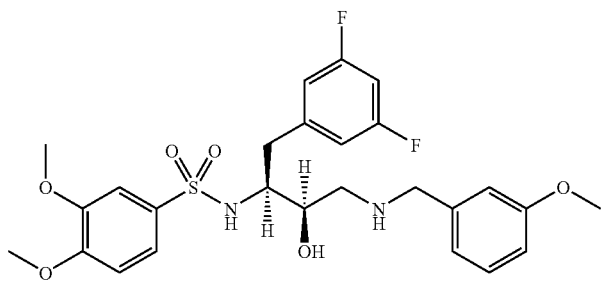

N-[1-(3,5-Difluoro-benzyl)-2-hydroxy-3-(3-methoxy-benzylamino)-
propyl]-3,4-dimethoxy-benzenesulfonamide

1300

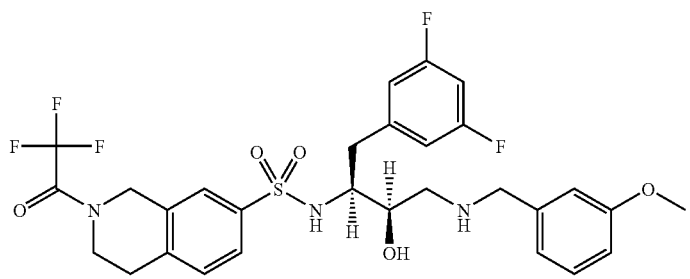

2-(2,2,2-Trifluoro-acetyl)-1,2,3,4-tetrahydro-isoquinoline-7-sulfonic acid
[1-(3,5-difluoro-benzyl)-2-hydroxy-3-(3-methoxy-benzylamino)-propyl]-amide

1301

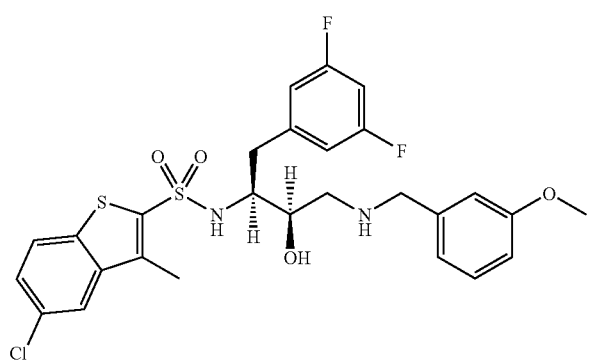

5-Chloro-3-methyl-benzo[b]thiophene-2-sulfonic acid [1-(3,5-difluoro-
benzyl)-2-hydroxy-3-(3-methoxy-benzylamino)-propyl]-amide

1302

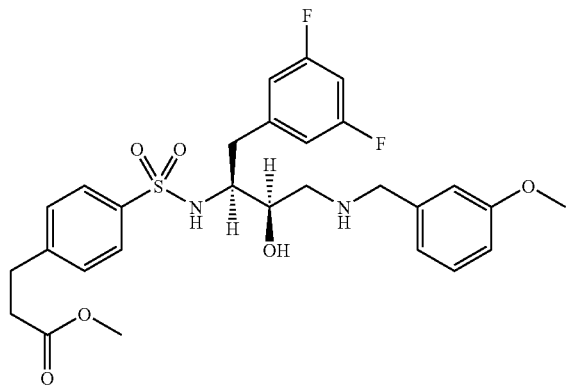

3-{4-[1-(3,5-Difluoro-benzyl)-2-hydroxy-3-(3-methoxy-benzylamino)-
propylsulfamoyl]-phenyl}-propionic acid methyl ester

1303

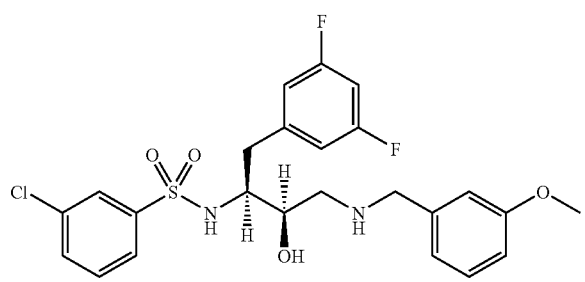

3-Chloro-N-[1-(3,5-difluoro-benzyl)-2-hydroxy-3-(3-methoxy-
benzylamino)-propyl]-benzenesulfonamide

1304

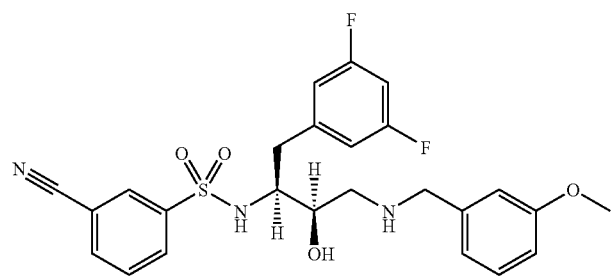

3-Cyano-N-[1-(3,5-difluoro-benzyl)-2-hydroxy-3-(3-methoxy-
benzylamino)-propyl]-benzenesulfonamide

1305

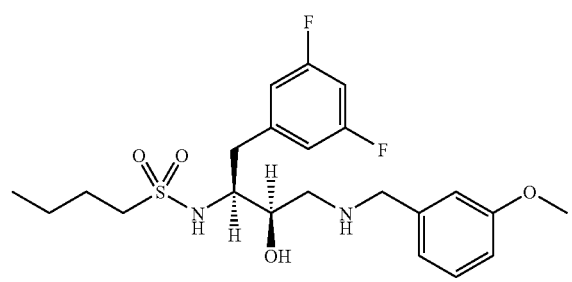

Butane-1-sulfonic acid [1-(3,5-difluoro-benzyl)-2-hydroxy-3-
(3-methoxy-benzylamino)-propyl]-amide

1306

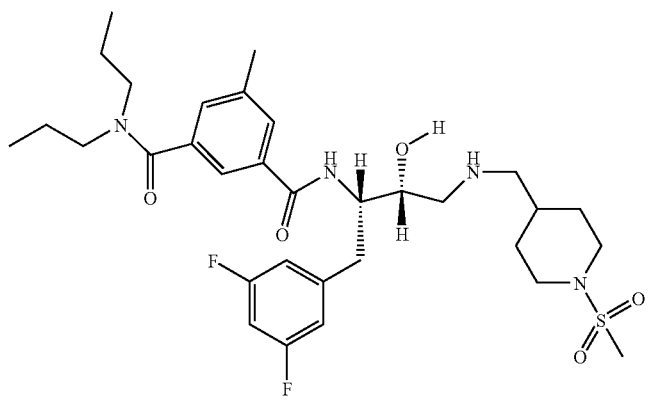

N-{1-(3,5-Difluoro-benzyl)-2-hydroxy-3-[(1-methanesulfonyl-piperidin-4-
ylmethyl)-amino]-propyl}-5-methyl-N',N'-dipropyl-isophthalamide

1307

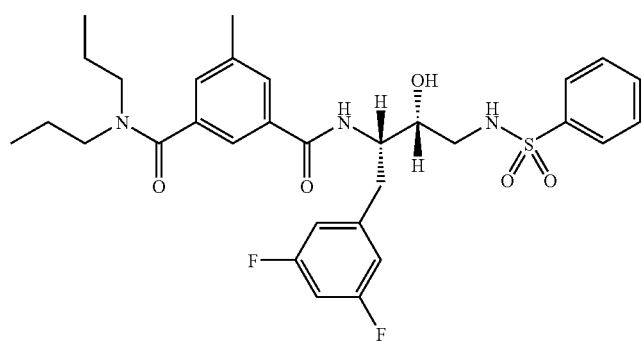

N-[3-Benzenesulfonylamino-1-(3,5-difluoro-benzyl)-2-hydroxy-
propyl]-5-methyl-N',N'-dipropyl-isophthalamide 1308
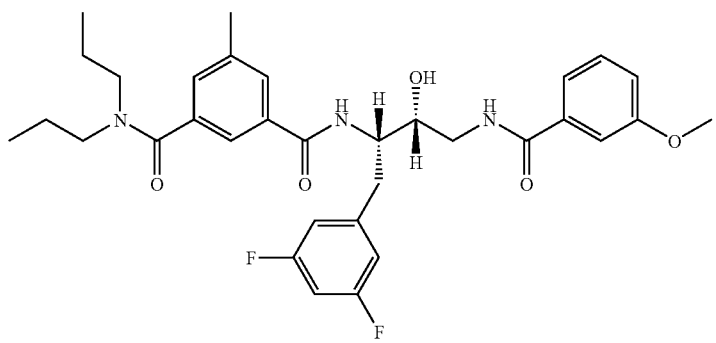
N-[1-(3,5-Difluoro-benzyl)-2-hydroxy-3-(3-methoxy-benzoylamino)-
propyl]-5-methyl-N',N'-dipropyl-isophthalamide
1309
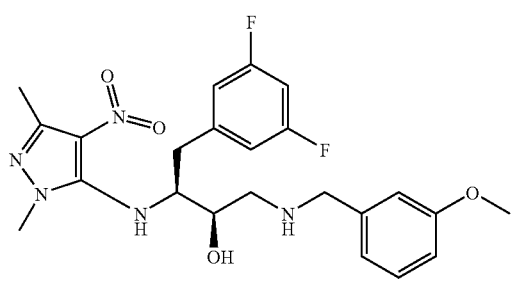
4-(3,5-Difluoro-phenyl)-3-(2,5-dimethyl-4-nitro-2H-pyrazol-
3-ylamino)-1-(3-methoxy-benzylamino)-butan-2-ol
1310
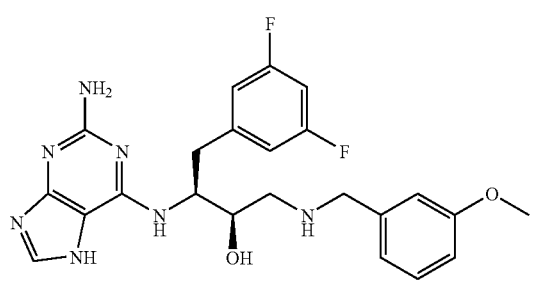
3-(2-Amino-7H-purin-6-ylamino)-4-(3,5-difluoro-phenyl)-
1-(3-methoxy-benzylamino)-butan-2-ol
1311
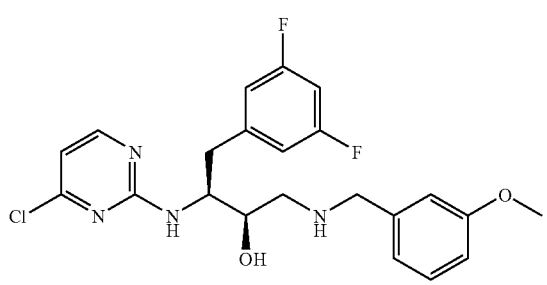
3-(4-Chloro-pyrimidin-2-ylamino)-4-(3,5-difluoro-
phenyl)-1-(3-methoxy-benzylamino)-butan-2-ol 1312
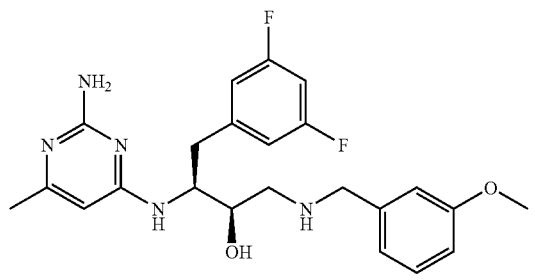
3-(2-Amino-6-methyl-pyrimidin-4-ylamino)-4-(3,5-difluoro-phenyl)-1-(3-methoxy-benzylamino)-butan-2-ol
1313
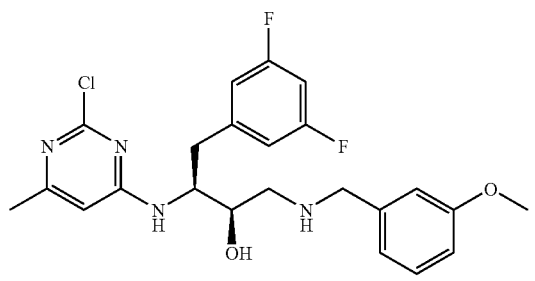
3-(2-Chloro-6-methyl-pyrimidin-4-ylamino)-4-(3,5-difluoro-phenyl)-1-(3-methoxy-benzylamino)-butan-2-ol
1314
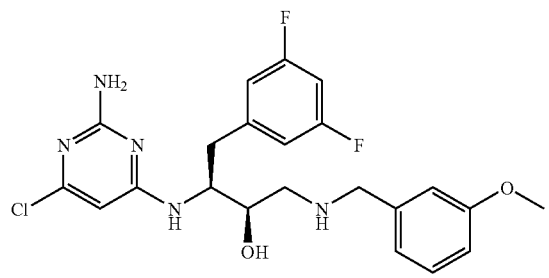
3-(2-Amino-6-chloro-pyrimidin-4-ylamino)-4-(3,5-difluoro-phenyl)-1-(3-methoxy-benzylamino)-butan-2-ol
1315
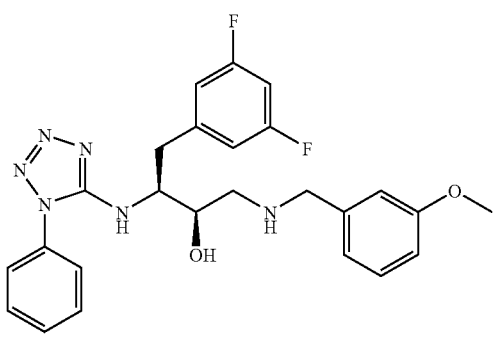
4-(3,5-Difluoro-phenyl)-1-(3-methoxy-benzylamino)-3-(1-phenyl-1H-tetrazol-5-ylamino)-butan-2-ol 1316
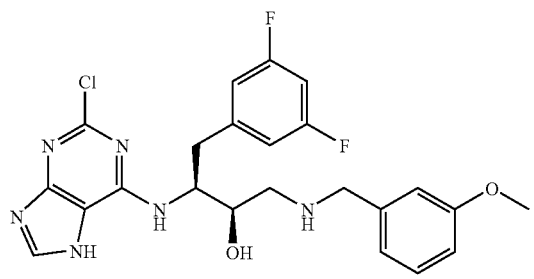
3-(2-Chloro-7H-purin-6-ylamino)-4-(3,5-difluoro-
phenyl)-1-(3-methoxy-benzylamino)-butan-2-ol
1317
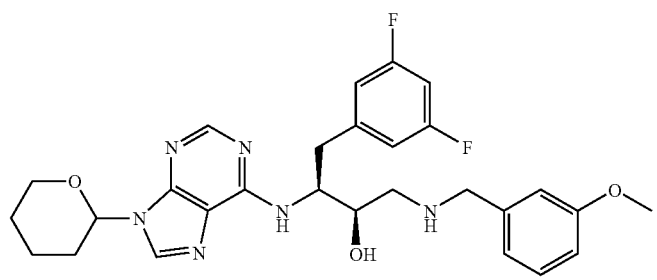
4-(3,5-Difluoro-phenyl)-1-(3-methoxy-benzylamino)-3-[9-
(tetrahydro-pyran-2-yl)-9H-purin-6-ylamino]-butan-2-ol
1318
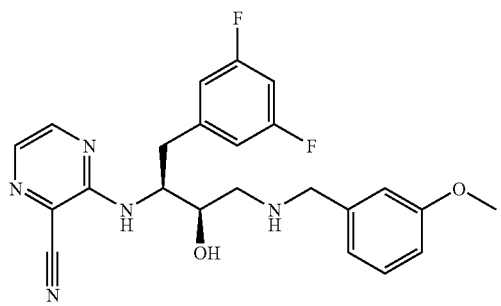
3-[1-(3,5-Difluoro-benzyl)-2-hydroxy-3-(3-methoxy-benzylamino)-
propylamino]-pyrazine-2-carbonitrile
1319
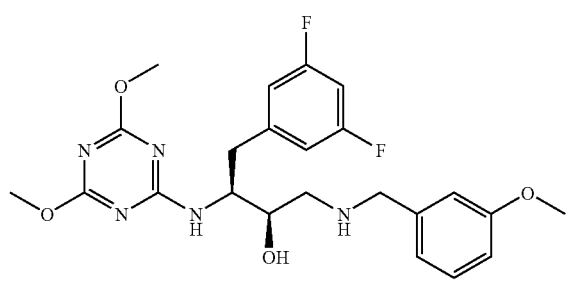
4-(3,5-Difluoro-phenyl)-3-(4,6-dimethoxy-[1,3,5]triazin-2-ylamino)-
1-(3-methoxy-benzylamino)-butan-2-ol 1320
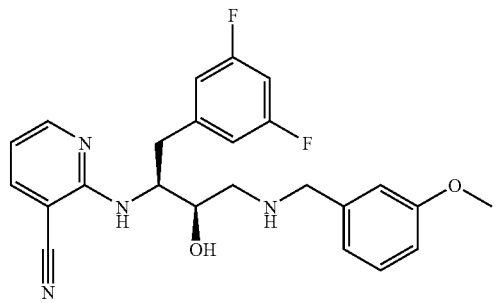
2-[1-(3,5-Difluoro-benzyl)-2-hydroxy-3-(3-methoxy-
benzylamino)-pyropylamino]-nicotinonitrile
1321
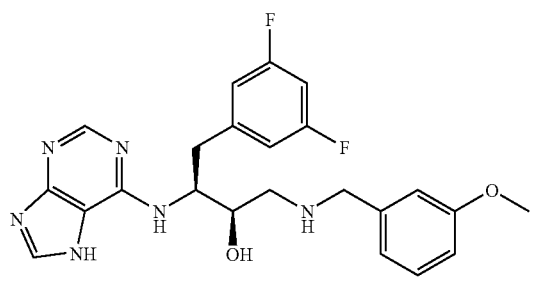
4-(3,5-Difluoro-phenyl)-1-(3-methoxy-benzylamino)-3-
(7H-purin-6-ylamino)-butan-2-ol
1322
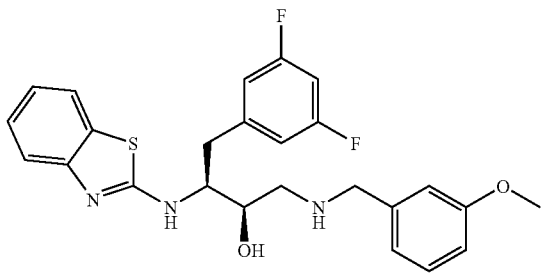
3-(Benzothiazol-2-ylamino)-4-(3,5-difluoro-
phenyl)-1-(3-methoxy-benzylamino)-butan-2-ol
1323
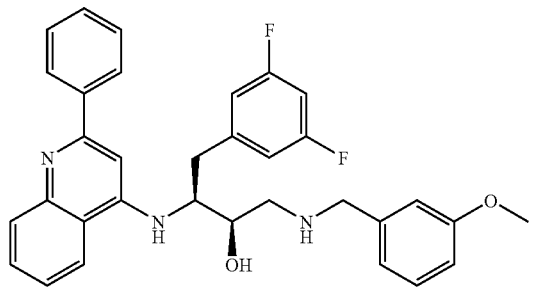
4-(3,5-Difluoro-phenyl)-1-(3-methoxy-benzylamino)-3-
(2-phenyl-quinolin-4-ylamino)-butan-2-ol 1324
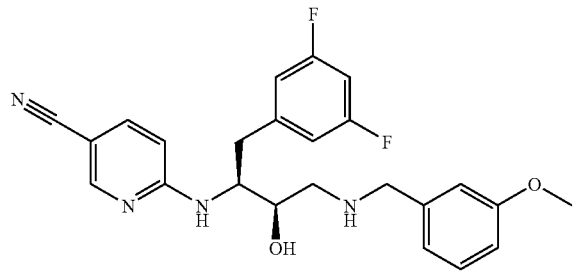
6-[1-(3,5-difluoro-benzyl)-2-hydroxy-3-(3-methoxy-benzylamino)-propylamino]-nicotinonitrile
1325
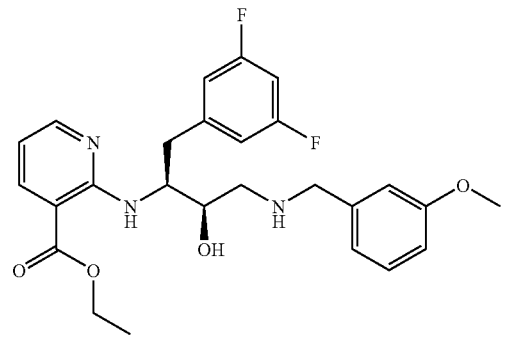
2-[1-(3,5-Difluoro-benzyl)-2-hydroxy-3-(3-methoxy-benzylamino)-propylamino]-nicotinic acid ethyl ester
1326
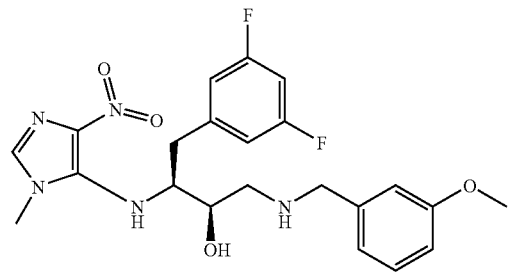
4-(3,5-Difluoro-phenyl)-1-(3-methoxy-benzylamino)-3-(3-methyl-5-nitro-3H-imidazol-4-ylamino)-butan-2-ol
1327
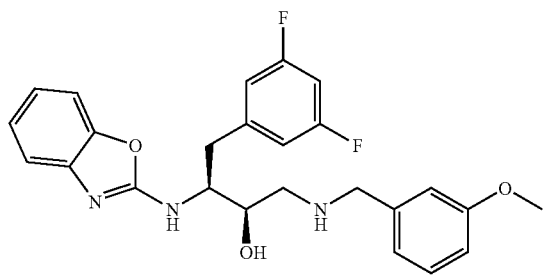
3-(Benzooxazol-2-ylamino)-4-(3,5-difluoro-phenyl)-1-(3-methoxy-benzylamino)-butan-2-ol -continued
1328
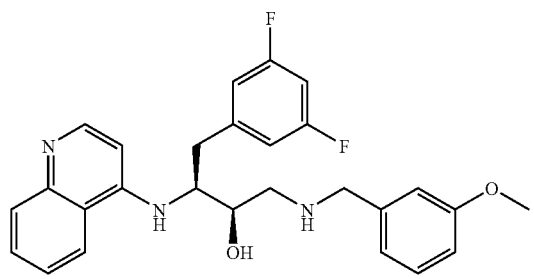
4-(3,5-Difluoro-phenyl)-1-(3-methoxy-benzylamino-3-
(quinolin-4-ylamino)-butan-2-ol
1329
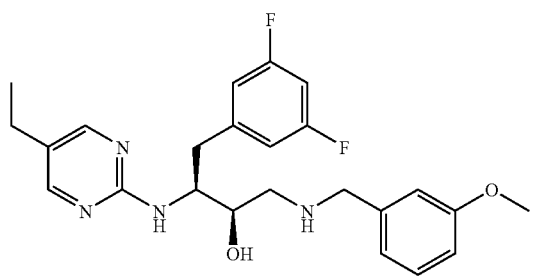
4-(3,5-Difluoro-phenyl)-3-(5-ethyl-pyrimidin-2-
ylamino)-1-(3-methoxy-benzylamino)-butan-2-ol
1330
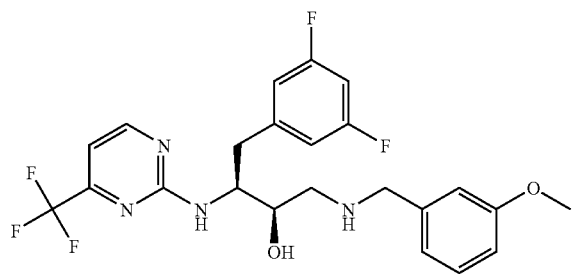
4-(3,5-Difluoro-phenyl)-1-(3-methoxy-benzylamino)-3-
(4-trifluoromethyl-pyrimidin-2-ylamino)-butan-2-ol
1331
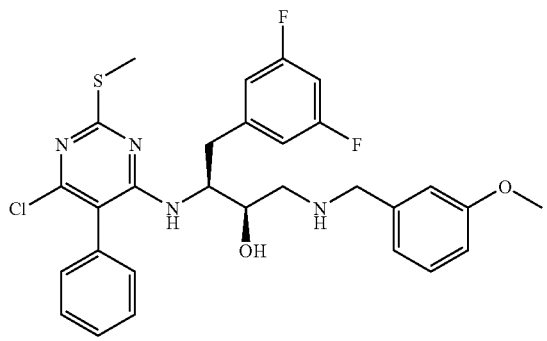
3-(6-Chloro-2-methylsulfanyl-5-phenyl-pyrimidin-4-
ylamino)-4-(3,5-difluoro-phenyl)-1-(3-methoxy-benzylamino)-butan-2-ol 1332
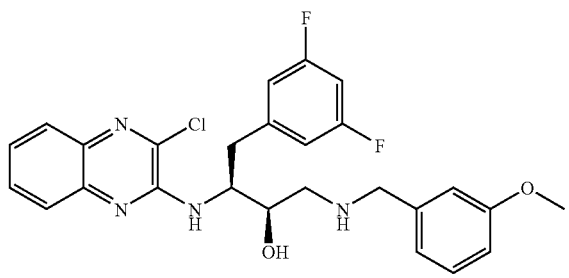
3-(3-Chloro-quinoxalin-2-ylamino)-4-(3,5-difluoro-
phenyl)-1-(3-methoxy-benzylamino)-butan-2-ol
1333
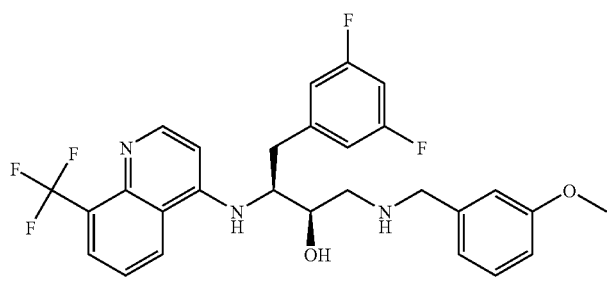
4-(3,5-Difluoro-phenyl)-1-(3-methoxy-benzylamino)-3-
(8-trifluoromethyl-quinolin-4-ylamino)-butan-2-ol
1334
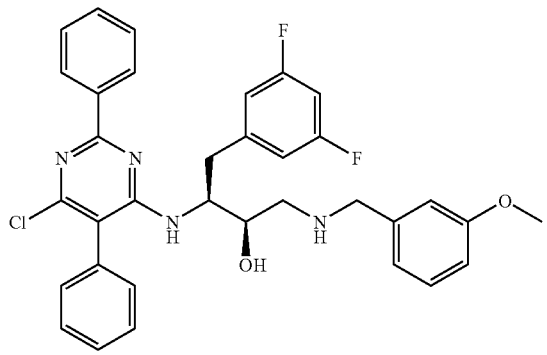
3-(6-Chloro-2,5-diphenyl-pyrimidin-4-ylamino)-4-(3,5-difluoro-phenyl)-1-
(3-methoxy-benzylamino)-butan-2-ol
1335
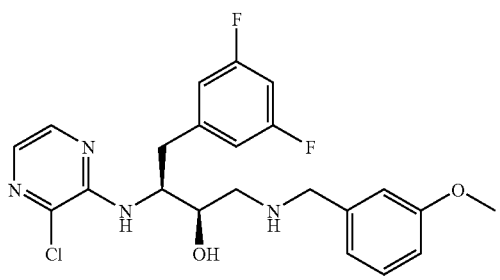
3-(3-Chloro-pyrazin-2-ylamino)-4-(3,5-difluoro-
phenyl)-1-(3-methoxy-benzylamino)-butan-2-ol 1336
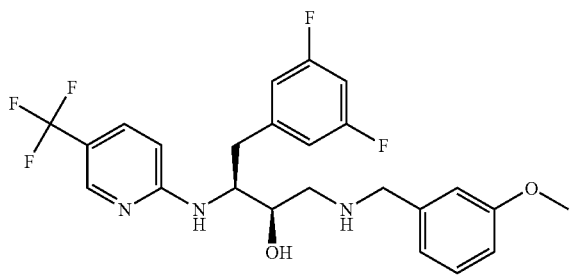
4-(3,5-Difluoro-phenyl)-1-(3-methoxy-benzylamino)-3-
(5-trifluoromethyl-pyridin-2-ylamino)-butan-2-ol
1337
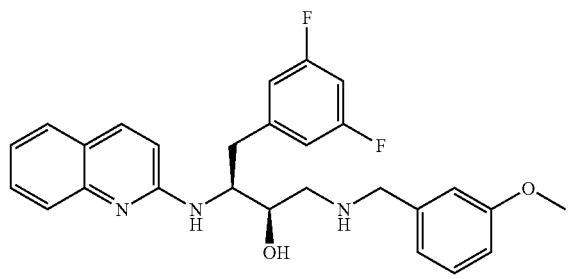
4-(3,5-Difluoro-phenyl)-1-(3-methoxy-
benzylamino)-3-(quinolin-2-ylamino)-butan-2-ol
1338
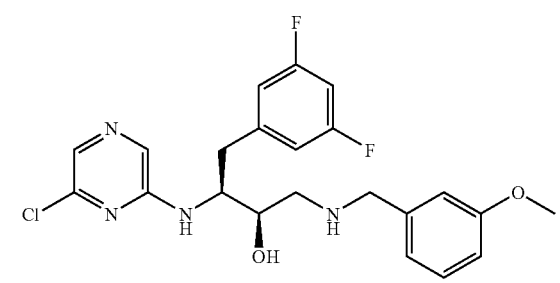
3-(6-Chloro-pyrazin-2-ylamino)-4-(3,5-difluoro-
phenyl)-1-(3-methoxy-benzylamino)-butan-2-ol
1339
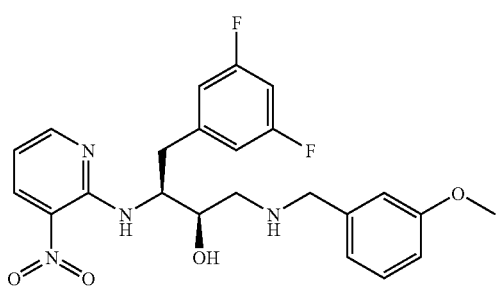
4-(3,5-Difluoro-phenyl)-1-(3-methoxy-benzylamino)-3-
(3-nitro-pyridin-2-ylamino)-butan-2-ol
1340
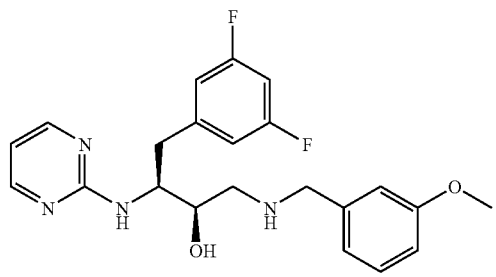
4-(3,5-Difluoro-phenyl)-1-(3-methoxy-
benzylamino)-3-(pyrimidin-2-ylamino)-butan-2-ol

1341

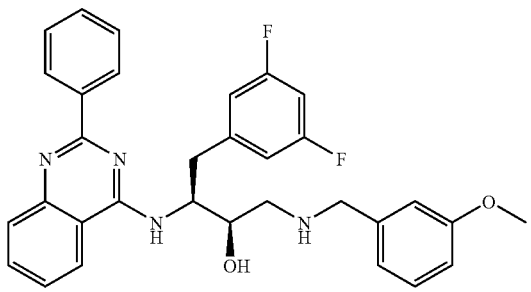

4-(3,5-Difluoro-phenyl)-1-(3-methoxy-benzylamino)-3-
(2-phenyl-quinazolin-4-ylamino)-butan-2-ol

1342

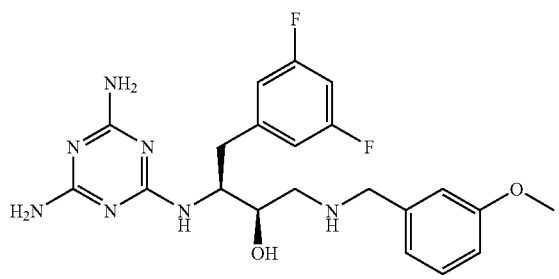

3-(4,5-Diamino-[1,3,5]triazin-2-ylamino)-4-(3,5-difluoro-
phenyl)-1-(3-methoxy-benzylamino)-butan-2-ol

1343

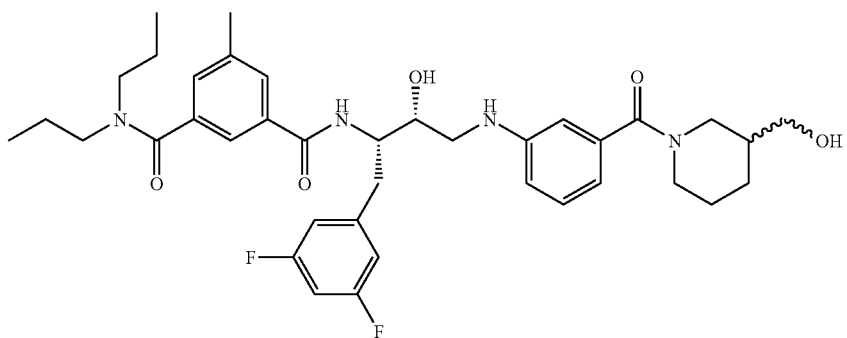

N-{1-(3,5-Difluoro-phenyl)-2-hydroxy-3-[3-(3-hydroxymethyl-piperidine-1-
carbonyl)-phenylamino]-propyl}-5-methyl-N',N'-dipropyl-isophthalamide

1344

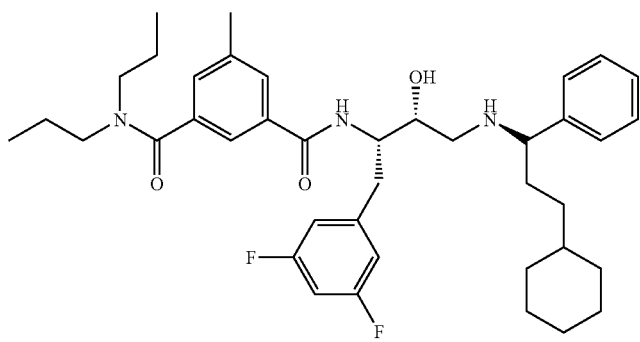

N-[3-(3-Cyclohexyl-1-phenyl-propylamino)-1-(3,5-difluoro-benzyl)-2-
hydroxy-propyl]-5-methyl-N',N'-dipropyl-isophthalamide

1345

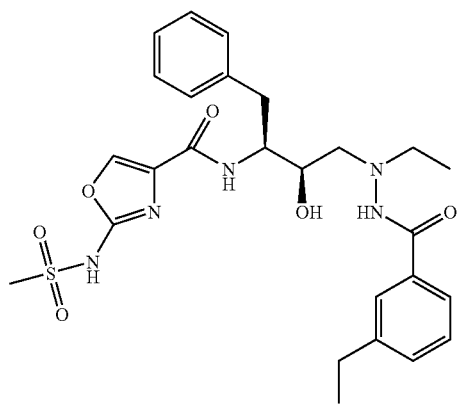

2-Methanesulfonylamino-oxazole-4-carboxylic acid
{1-benzyl-3-[N-ethyl-N'-(3-ethyl-benzoyl)-hydrazino]-2-hydroxy-propyl}-amide

1346

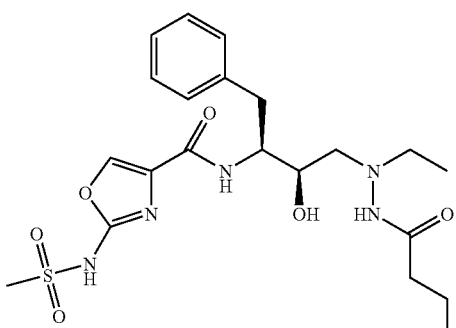

2-Methanesulfonylamino-oxazole-4-carboxlic acid {1-benzyl-3-[N-ethyl-N'-
(4-methyl-pentanoyl)-hydrazino]-2-hydroxy-propyl}-amide

1347

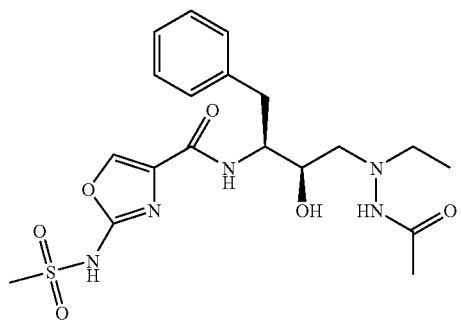

2-Methanesulfonylamino-oxazole-4-carboxylic acid
[3-(N'-acetyl-N-ethyl-hydrazino)-1-benzyl-2-hydroxy-propyl]-amide

1348

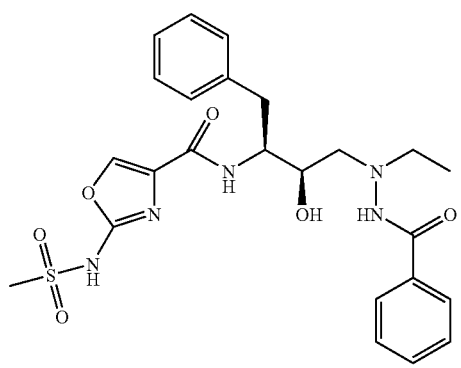

2-Methanesulfonylamino-oxazole-4-carboxylic acid
[3-(N'-benzoyl-N-ethyl-hydrazino)-1-benzyl-2-hydroxy-propyl]-amide 1349
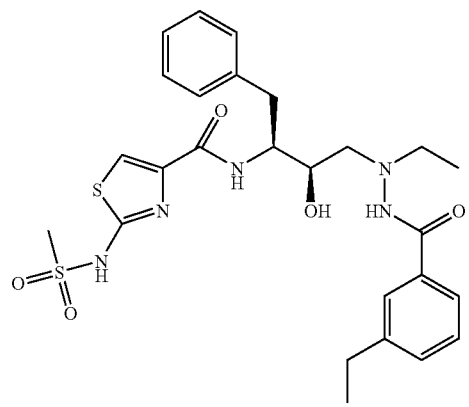
2-Methanesulfonylamino-thiazole-4-carboxylic acid
{1-benzyl-3-[N-ethyl-N'-(3-ethyl-benzoyl)-hydrazino]-2-hydroxy-propyl}-amide
1350
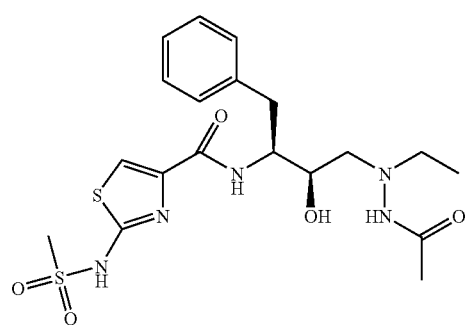
2-Methanesulfonylamino-thiazole-4-carboxylic acid
[3-(N'-acetyl-N-ethyl-hydrazino)-1-benzyl-2-hydroxy-propyl]-amide
1351
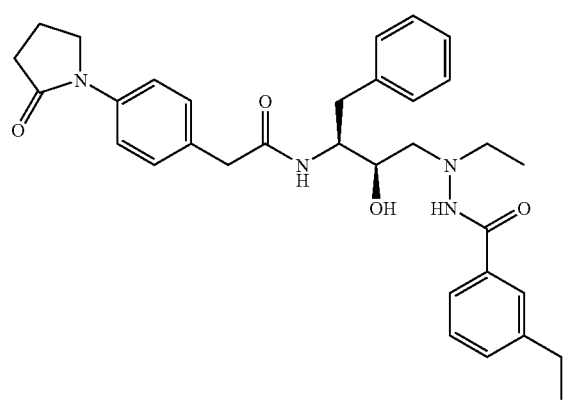
N-{1-Benzyl-3-[N-ethyl-N'-(3-ethyl-benzoyl)-hydrazino]-2-
hydroxy-propyl}-2-[4-(2-oxo-pyrrolidin-1-yl)-phenyl]-acetamide -continued

1352

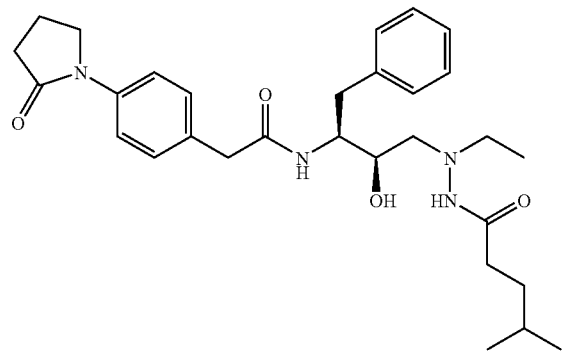

N-{1-Benzyl-3-[N-ethyl-N'-(4-methyl-pentanoyl)-hydrazino]-2-
hydroxy-propyl}-2-[4-(2-oxo-pyrrolidin-1-yl)-phenyl]-acetamide

1353

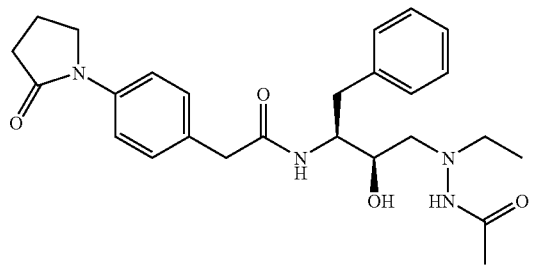

N-[3-(N'-Acetyl-N-ethyl-hydrazino)-1-benzyl-2-hydroxy-propyl]-2-
[4-(2-oxo-pyrrolidin-1-yl)-phenyl]-acetamide

1354

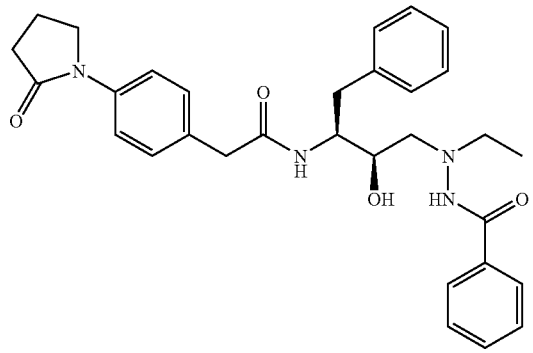

N-[3-(N'-Benzoyl-N-ethyl-hydrazino)-1-benzyl-2-hydroxy-propyl]-2-
[4-(2-oxo-pyrrolidin-1-yl)-phenyl]-acetamide

1355

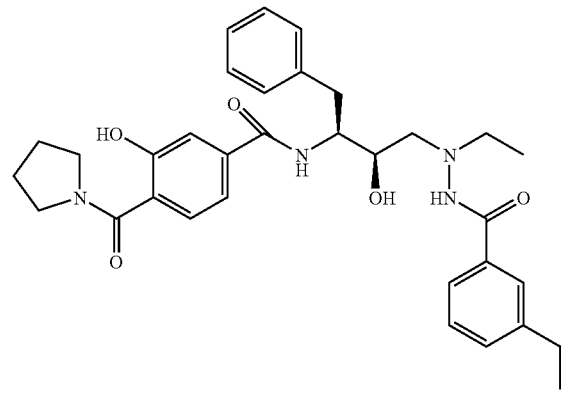

N-{1-Benzyl-3-[N-ethyl-N'-(3-ethyl-benzoyl)-hydrazino]-2-
hydroxy-propyl}-3-hydroxy-4-(pyrrolidine-1-carbonyl)-benzamide -continued

1356

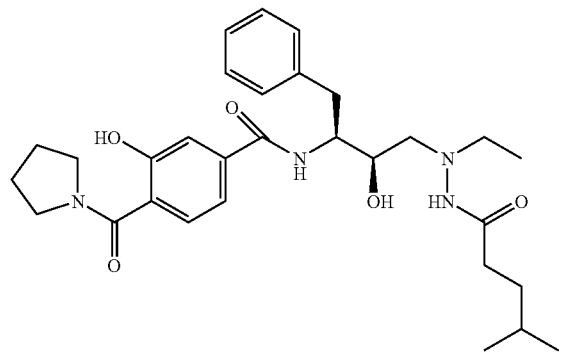

N-{1-Benzyl-3-[N-ethyl-N'-(4-methyl-pentanoyl)-hydrazino]-2-hydroxy-propyl}-3-hydroxy-4-(pyrrolidine-1-carbonyl)-benzamide

1341

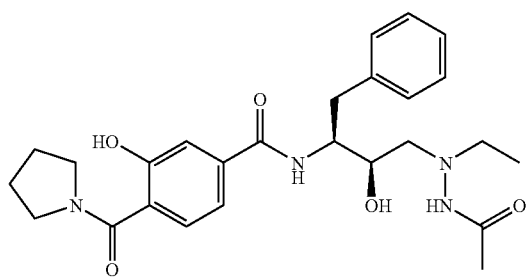

N-[3-(N'-Acetyl-N-ethyl-hydrazino)-1-benzyl-2-hydroxy-propyl]-3-hydroxy-4-(pyrrolidine-1-carbonyl)-benzamide

1342

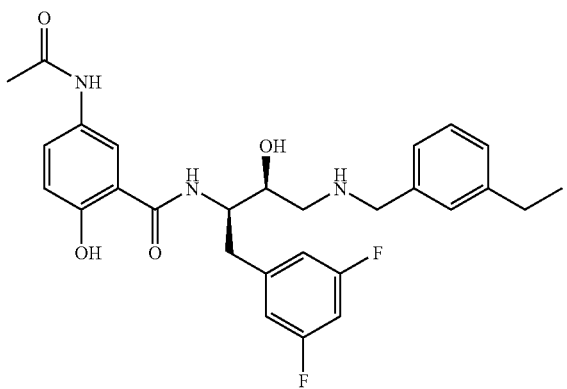

5-Acetylamino-N-[1-(3,5-difluoro-benzyl)-3-(3-ethyl-benzylamino)-2-hydroxy-propyl]-2-hydroxy-benzamide

1343

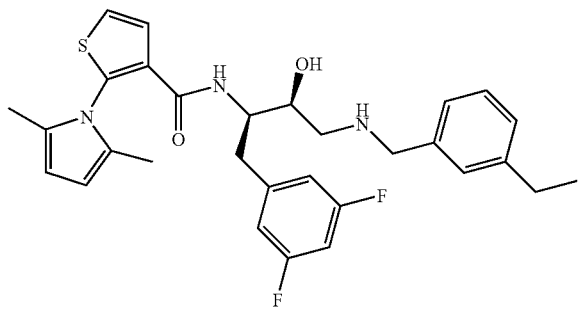

2-(2,5-Dimethyl-pyrrol-1-yl)-thiophene-3-carboxylic acid [1-(3,5-difluoro-benzyl)-3-(3-ethyl-benzylamino)-2-hydroxy-propyl]-amide -continued
1344
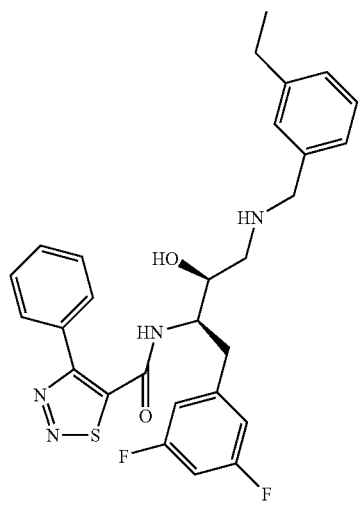
4-Phenyl-[1,2,3]thiadiazole-5-carboxylic acid
[1-(3,5-difluoro-benzyl)-3-(3-ethyl-benzylamino)-2-hydroxy-propyl]-amide
1345
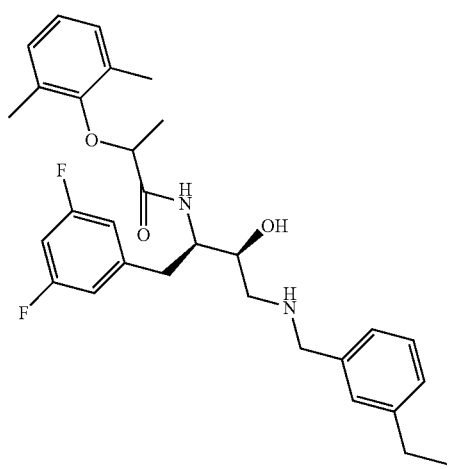
N-[1-(3,5-Difluoro-benzyl)-3-(3-ethyl-benzylamino)-2-
hydroxy-propyl]-2-(2,6-dimethyl-phenoxy)-propionamide
1346
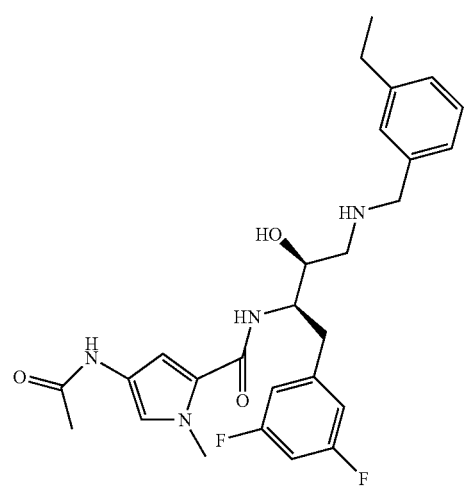
4-Acetylamino-1-methyl-1H-pyrrole-2-carboxylic acid
[1-(3,5-difluoro-benzyl)-3-(3-ethyl-benzylamino)-2-hydroxy-propyl]-amide -continued

1347

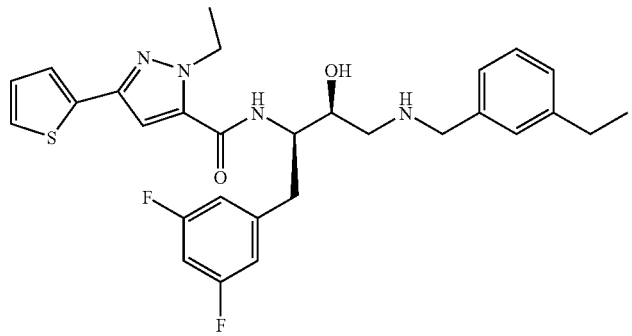

2-Ethyl-5-thiophen-2-yl-2H-pyrazole-3-carboxylic acid
[1-(3,5-difluoro-benzyl)-3-(3-ethyl-benzylamino)-2-hydroxy-propyl]-amide

1348

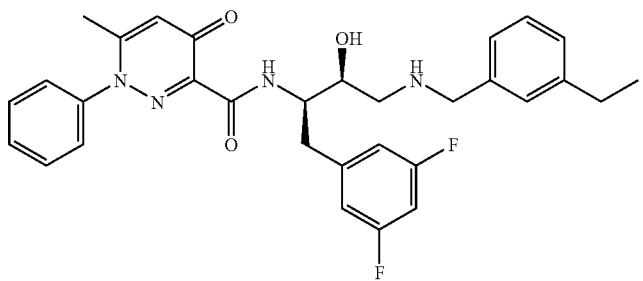

6-Methyl-4-oxo-1-phenyl-1,4-dihydro-pyridazine-3-carboxylic acid
[1-(3,5-difluoro-benzyl)-3-(3-ethyl-benzylamino)-2-hydroxy-propyl]-amide

1349

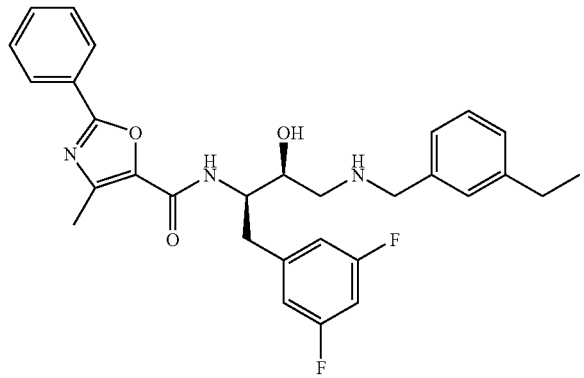

4-Methyl-2-phenyl-oxazole-5-carboxylic acid [1-(3,5-difluoro-
benzyl)-3-(3-ethyl-benzylamino)-2-hydroxy-propyl]-amide

1350

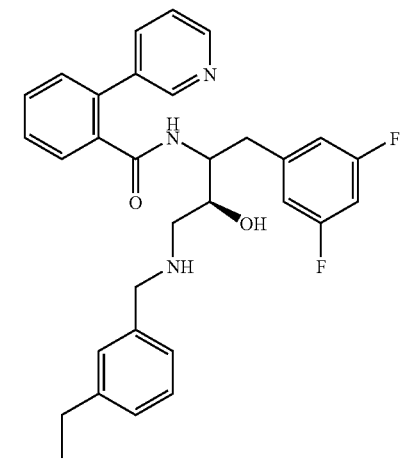

N-[1-(3,5-Difluoro-benzyl)-3-(3-ethyl-benzylamino)-2-
hydroxy-propyl]-2-pyridin-3-yl-benzamide 1351 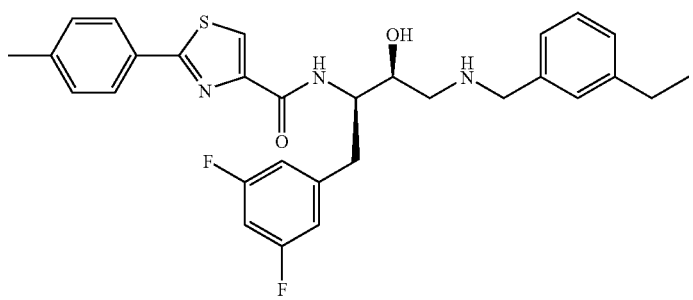
2-p-Tolyl-thiazole-4-carboxylic acid [1-(3,5-difluoro-benzyl)-3-
(3-ethyl-benzylamino)-2-hydroxy-propyl]amide 1352 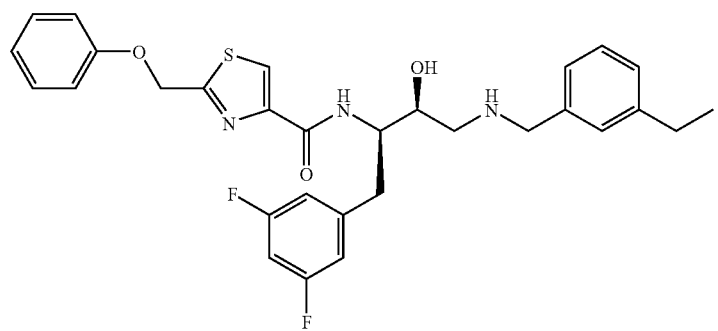
2-Phenoxymethyl-thiazole-4-carboxylic acid [1-(3,5-difluoro-benzyl)-3-
(3-ethyl-benzylamino)-2-hydroxy-propyl]-amide 1353 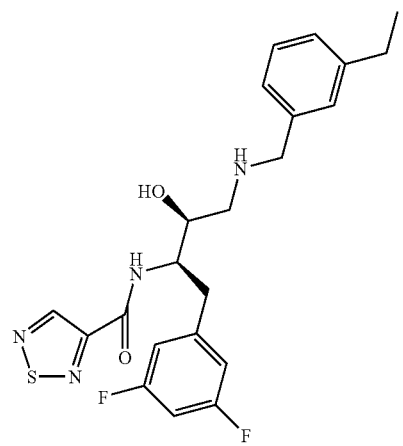
[1,2,5]Thiadiazole-3-carboxylic acid [1-(3,5-difluoro-benzyl)-3-
(3-ethyl-benzylamino)-2-hydroxy-propyl]-amide 1354 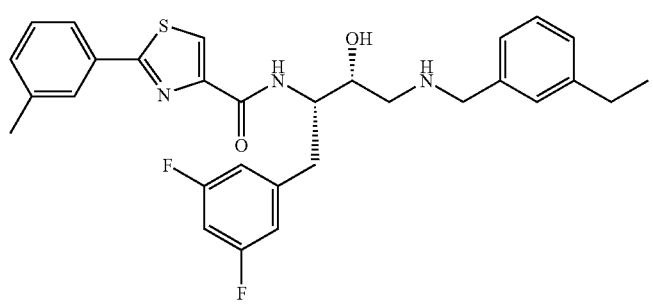
2-m-Tolyl-thiazole-4-carboxylic acid [1-(3,5-difluoro-benzyl)-3-
(3-ethyl-benzylamino)-2-hydroxy-propyl]-amide 1355
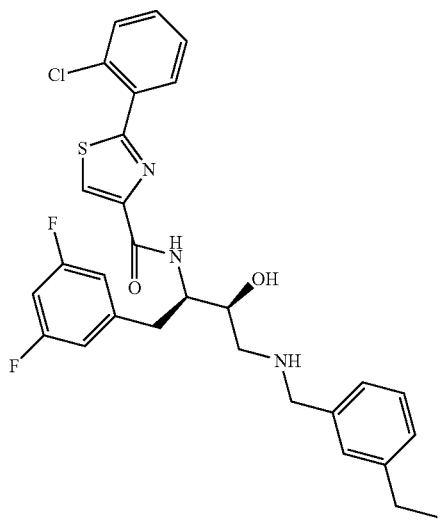
2-(2-Chloro-phenyl)-thiazole-4-carboxlic acid
[1-(3,5-difluoro-benzyl)-3-(3-ethyl-benzylamino)-2-hydroxy-propyl]-amide
1356
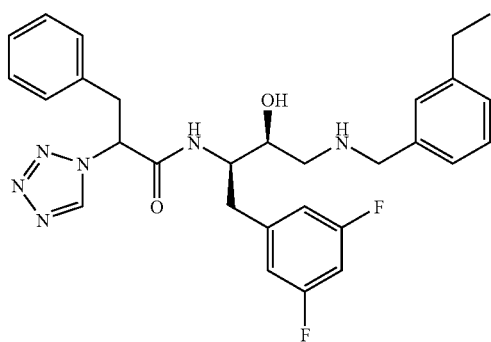
N-[1-(3,5-Difluoro-benzyl)-3-(3-ethyl-benzylamino)-2-hydroxy-
propyl]-3-phenyl-2-tetrazol-1-yl-proponamide
1357
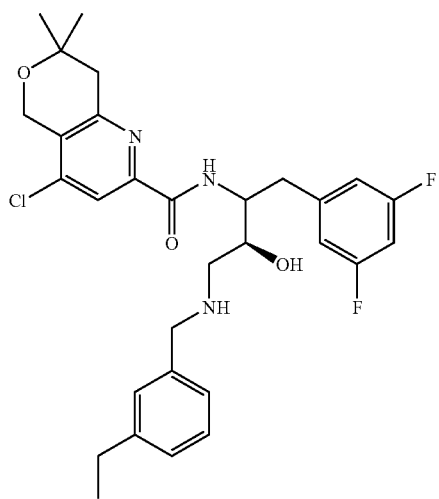
4-Chloro-7,7-dimethyl-7,8-dihydro-5H-pyrano[4,3-b]pyridine-2-carboxylic acid
[1-(3,5-difluoro-benzyl)-3-(3-ethyl-benzylamino)-2-hydroxy-propyl]-amide -continued
1358
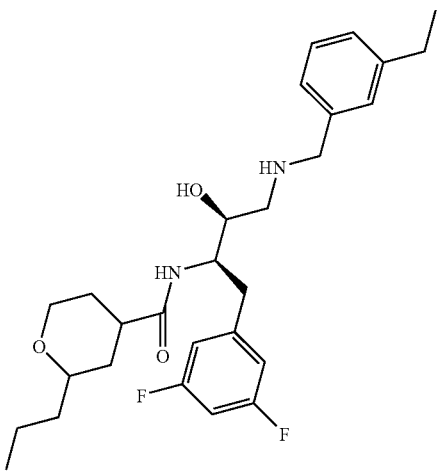
2-Propyl-tetrahydro-pyran-4-carboxylic acid [1-(3,5-difluoro-benzyl)-3-
(3-ethyl-benzylamino)-2-hydroxy-propyl]-amide
1359
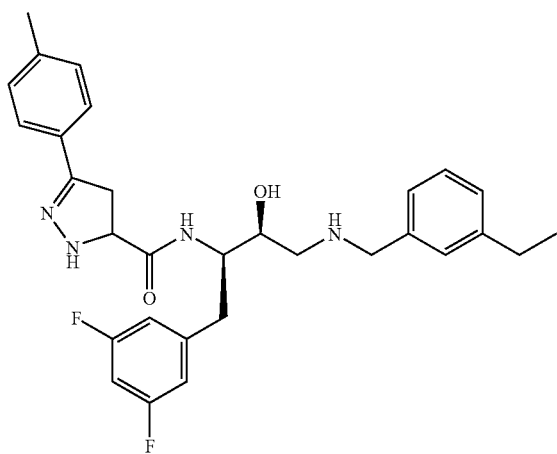
5-p-Tolyl-3,4-dihydro-2H-pyrazole-3-carboxylic acid [1-(3,5-difluoro-
benzyl)-3-(3-ethyl-benzylamino)-2-hydroxy-propyl]-amide
1360
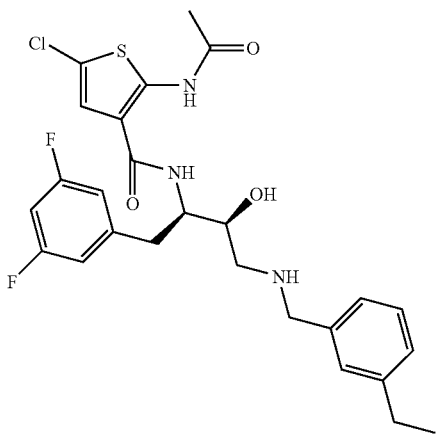
2-Acetylamino-5-chloro-thiophene-3-carboxylic acid [1-(3,5-
difluoro-benzyl)-3-(3-ethyl-benzylamino)-2-hydroxy-propyl]-amide 1361
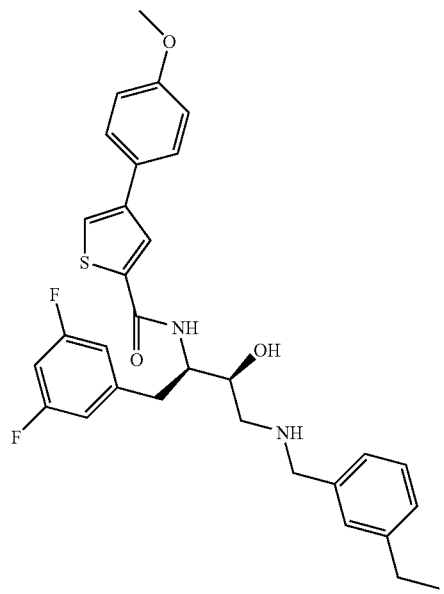
4-(4-Methoxy-phenyl)-thiophene-2-carboxylic acid
[1-(3,5-difluoro-benzyl)-3-(3-ethyl-benzylamino)-2-hydroxy-propyl]-amide
1362
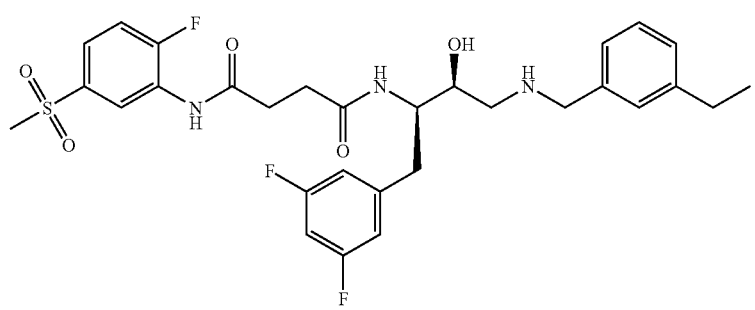
N-[1-(3,5-Difluoro-benzyl)-3-(3-ethyl-benzylamino)-2-
hydroxy-propyl]-N'-(2-fluoro-5-methanesulfonyl-phenyl)-succinamide
1363
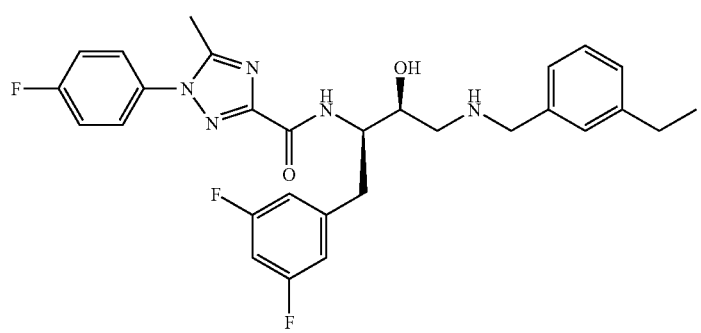
1-(4-Fluoro-phenyl)-5-methyl-1H-[1,2,4]triazole-3-carboxylic acid
[1-(3,5-difluoro-benzyl)-3-(3-ethyl-benzylamino)-2-hydroxy-propyl]-amide 1364
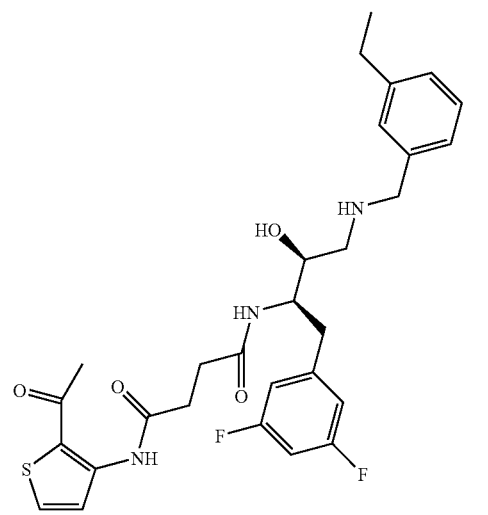
N-(2-Acetyl-thiophen-3-yl)-N'-[1-(3,5-difluoro-benzyl]-3-(3-ethyl-benzylamino)-2-hydroxy-propyl]-succinamide
1365
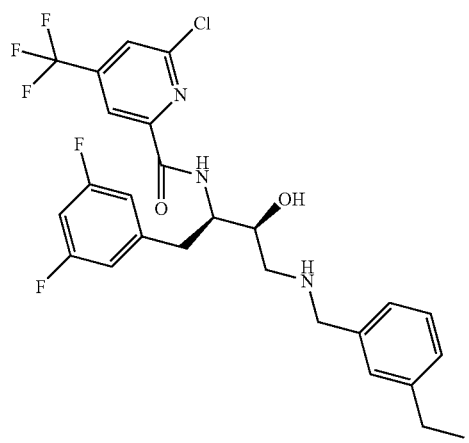
6-Chloro-4-trifluoromethyl-pyridine-2-carboxylic acid [1-(3,5-difluoro-benzyl)-3-(3-ethyl-benzylamino-2-hydroxy-propyl]-amide
1366
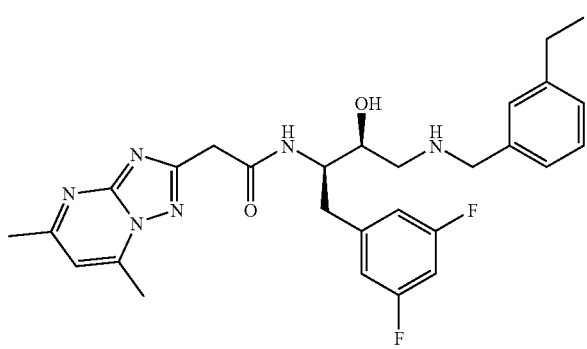
N-[1-(3,5-Difluoro-benzyl)-3-(3-ethyl-benzylamino)-2-hydroxy-propyl]-2-(5,7-dimethyl-[1,2,4]triazolo[1,5-a]pyrimidin-2-yl)-acetamide 1367
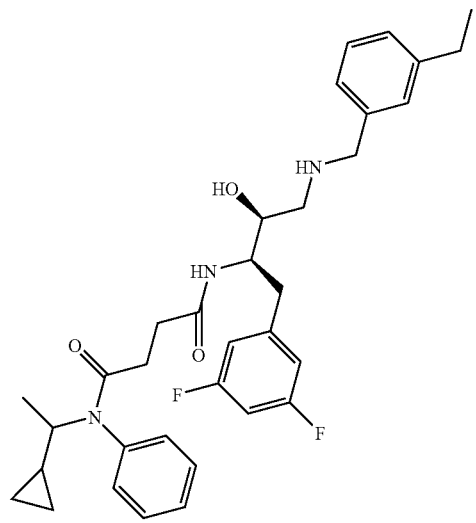
N-(1-cyclopropyl-ethyl)-N'-[1-(3,5-difluoro-benzyl)-3-(3-ethyl-benzylamino)-2-hydroxy-propyl]-N-phenyl-succinamide
1368
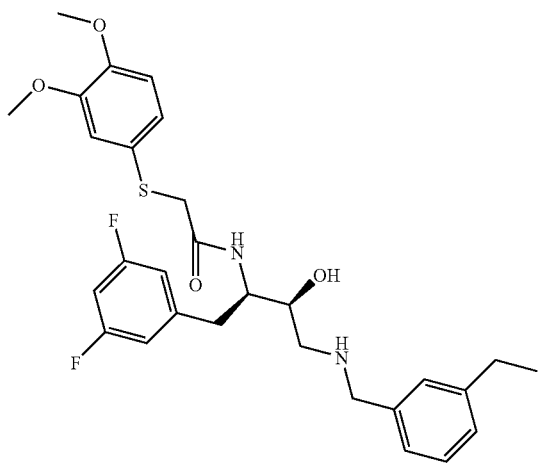
N-[1-(3,5-Difluoro-benzyl)-3-(3-ethyl-benzylamino)-2-hydroxy-propyl]-2-(3,4-dimethoxy-phenylsulfanyl)-acetamide
1369
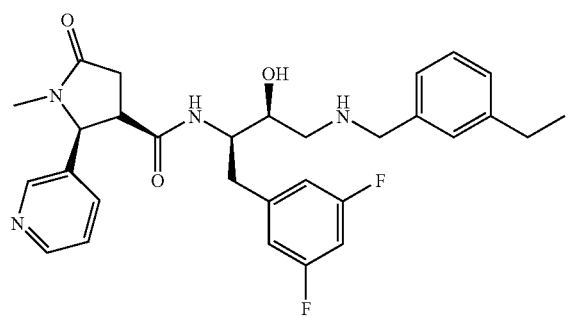
1-Methyl-5-oxo-2-pyridin-3-yl-pyrrolidine-3-carboxylic acid [1-(3,5-difluoro-benzyl)-3-(3-ethyl-benzylamino)-2-hydroxy-propyl]-amide -continued

1370

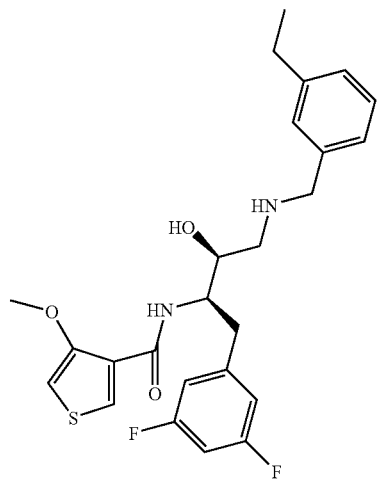

4-Methoxy-thiophene-3-carboxylic acid [1-(3,5-difluoro-benzyl)-3-(3-ethyl-benzylamino)-2-hydroxy-propyl]-amide

1371

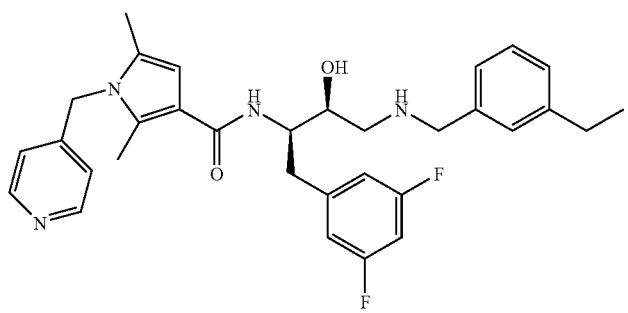

2,5-Dimethyl-1-pyridin-4-ylmethyl-1H-pyrrole-3-carboxylic acid [1-(3,5-difluoro-benzyl)-3-(3-ethyl-benzylamino)-2-hydroxy-propyl]-amide

1372

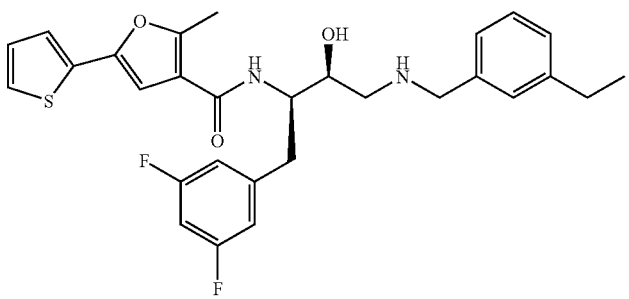

2-Methyl-5-thiophen-2-yl-furan-3-carboxylic acid [1-(3,5-difluoro-benzyl)-3-(3-ethyl-benzylamino)-2-hydroxy-propyl]-amide

1373

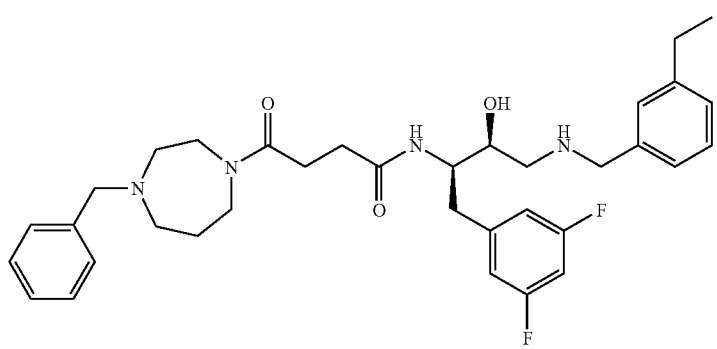

4-(4-Benzyl-[1,4]diazepan-1-yl)-N-[1-(3,5-difluoro-benzyl)-3-(3-ethyl-benzylamino)-2-hydroxy-propyl]-4-oxo-butyramide

1374

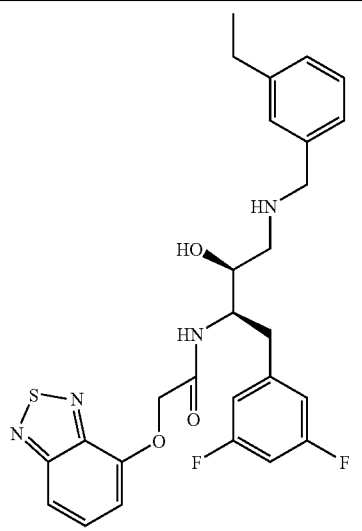

2-(Benzo[1,2,5]thiadiazol-4-yloxy)-N-[1-(3,5-difluoro-benzyl)-3-(3-ethyl-benzylamino)-2-hydroxy-propyl]-acetamide

1375

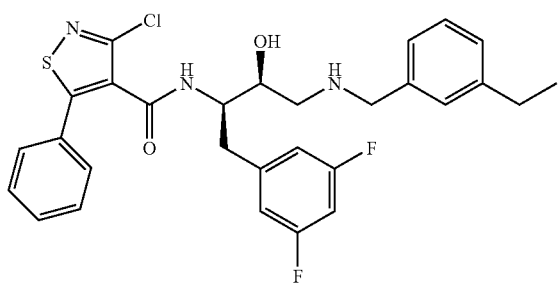

3-Chloro-5-phenyl-isothiazole-4-carboxylic acid [1-(3,5-difluoro-benzyl)-3-(3-ethyl-benzylamino)-2-hydroxy-propyl]-amide

1376

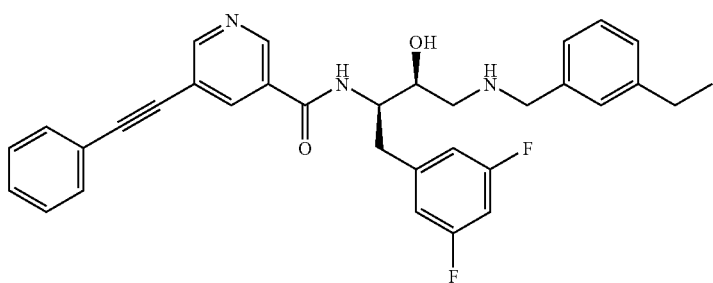

N-[1-(3,5-Difluoro-benzyl)-3-(3-ethyl-benzylamino)-2-hydroxy-propyl]-5-phenylethynyl-nicotinamide

1377

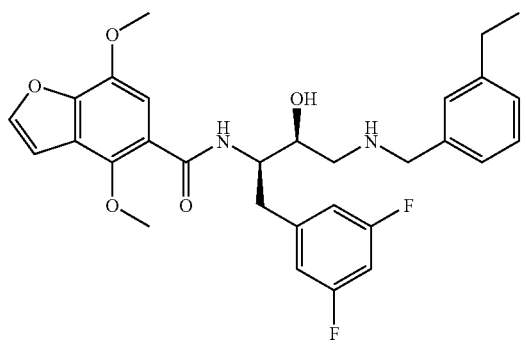

4,7-Dimethoxy-benzofuran-5-carboxylic acid [1-(3,5-difluoro-benzyl)-3-(3-ethyl-benzylamino)-2-hydroxy-propyl]-amide 1378
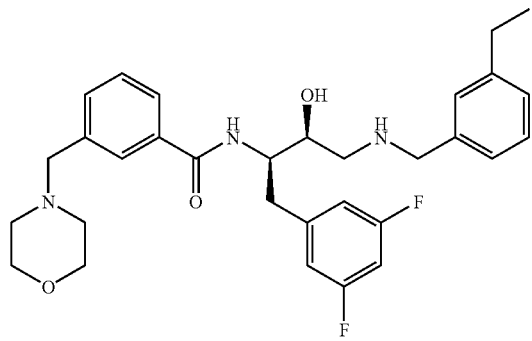
N-[1-(3,5-Difluoro-benzyl)-3-(3-ethyl-benzylamino)-2-
hydroxy-propyl]-3-morpholin-4-ylmethyl-benzamide
1379
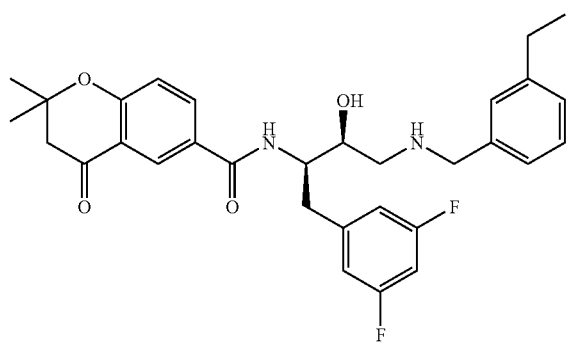
2,2-Dimethyl-4-oxo-chroman-6-carboxylic acid [1-(3,5-difluoro-benzyl)-3-
(3-ethyl-benzylamino)-2-hydroxy-propyl]-amide
1380
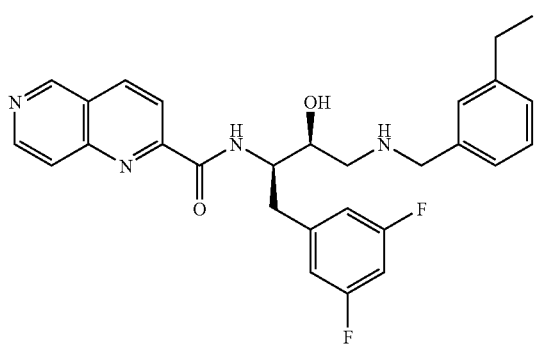
[1,6]Naphthyridine-2-carboxylic acid [1-(3,5-difluoro-benzyl)-3-
(3-ethyl-benzylamino)-2-hydroxy-propyl]-amide 1381
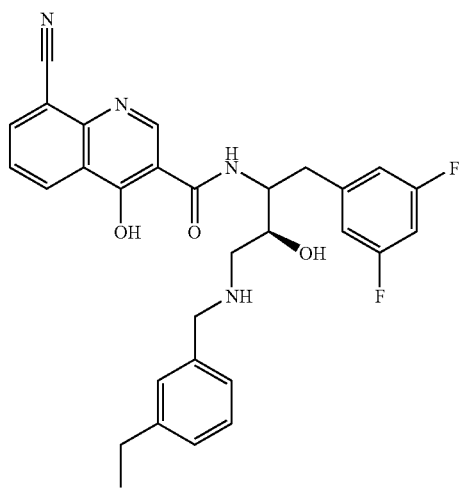
8-Cyano-4-hydroxy-quinoline-3-carboxylic acid [1-(3,5-difluoro-
benzyl)-3-(3-ethyl-benzylamino)-2-hydroxy-propyl]-amide
1382
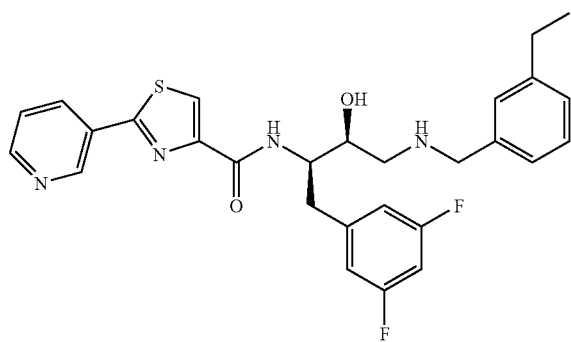
2-Pyridin-3-yl-thiazole-4-carboxylic acid [1-(3,5-difluoro-benzyl)-3-
(3-ethyl-benzylamino)-2-hydroxy-propyl]-amide
1383
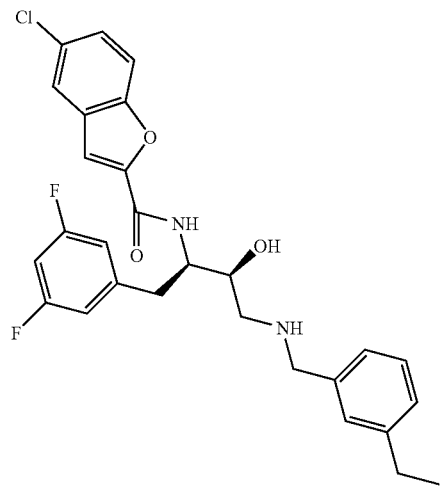
5-Chloro-benzofuran-2-carboxylic acid [1-(3,5-difluoro-benzyl)-3-
(3-ethyl-benzylamino)-2-hydroxy-propyl]-amide

| 1384 | 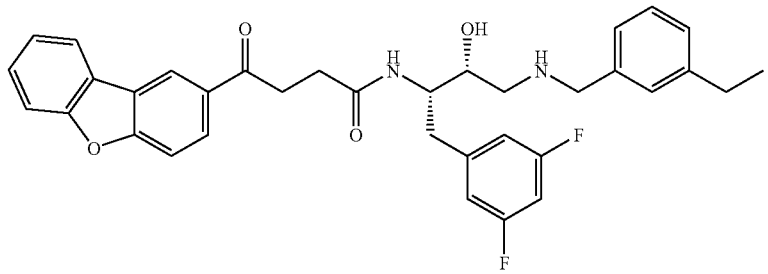
4-Dibenzofuran-2-yl-N-[1-(3,5-difluoro-benzyl)-3-(3-ethyl-benzylamino)-2-hydroxy-propyl]-4-oxo-butyramide |
| 1385 | 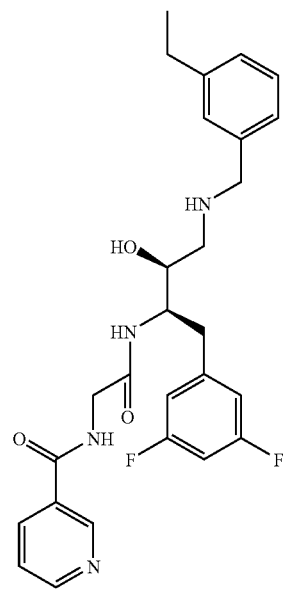
N-{[1-(3,5-Difluoro-benzyl)-3-(3-ethyl-benzylamino)-2-hydroxy-propylcarbamoyl]-methyl}-nicotinamide |
| 1386 | 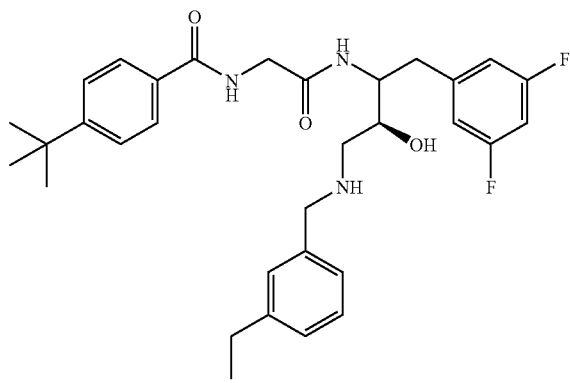
4-tert-Butyl-N-{[1-(3,5-difluoro-benzyl)-3-(3-ethyl-benzylamino)-2-hydroxy-propylcarbamoyl]-methyl}-benzamide |

1387
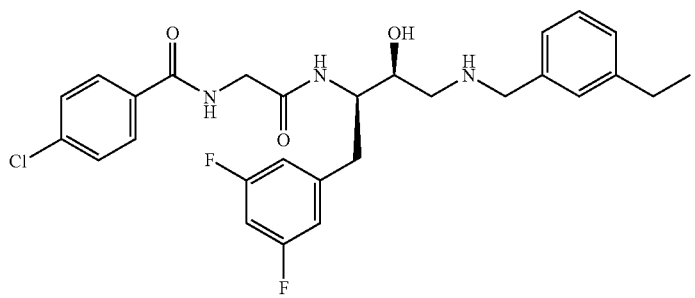
4-Chloro-N-{[1-(3,5-difluoro-benzyl)-3-(3-ethyl-benzylamino)-2-hydroxy-propylcarbamoyl]-methyl}-benzamide
1388
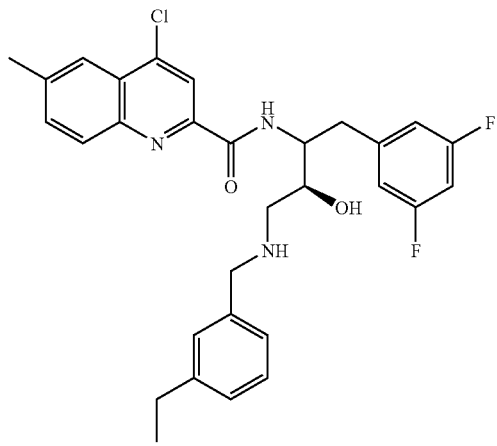
4-Chloro-6-methyl-quinoline-2-carboxylic acid [1-(3,5-difluoro-benzyl)-3-(3-ethyl-benzylamino)-2-hydroxy-propyl]-amide
1389
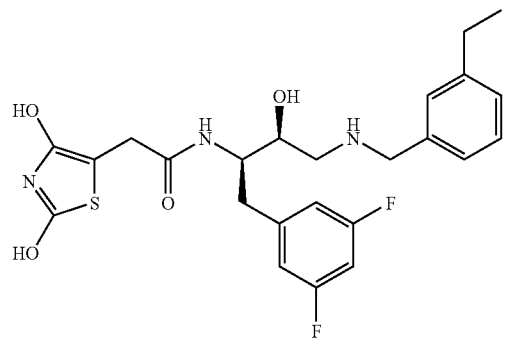
N-[1-(3,5-Difluoro-benzyl)-3-(3-ethyl-benzylamino)-2-hydroxy-propyl]-2-(2,4-dihydroxy-thiazol-5-yl)-acetamide -continued
1390
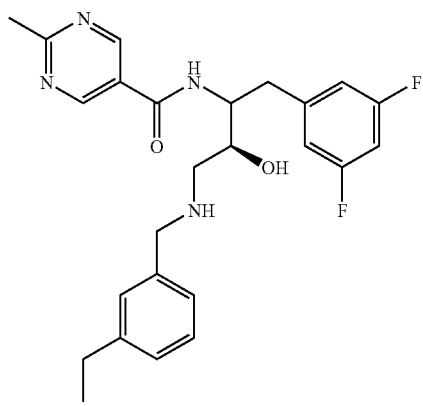
2-Methyl-pyrimidine-5-carboxylic acid [1-(3,5-difluoro-benzyl)-3-(3-ethyl-benzylamino)-2-hydroxy-propyl]-amide
1391
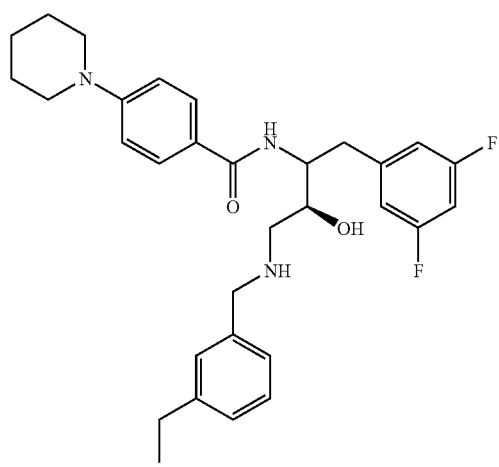
N-[1-(3,5-Difluoro-benzyl)-3-(3-ethyl-benzylamino)-2-hydroxy-propyl]-4-piperidin-1-yl-benzamide
1392
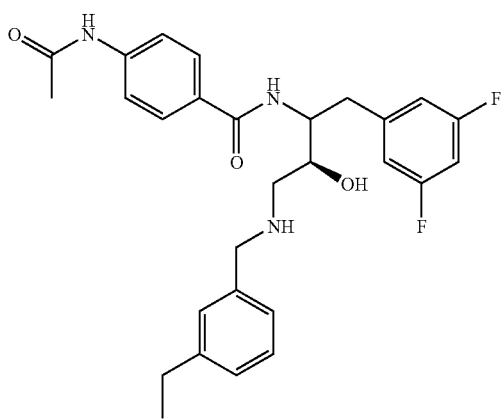
4-Acetylamino-N-[1-(3,5-difluoro-benzyl)-3-(3-ethyl-benzylamino)-2-hydroxy-propyl]-benzamide 1393
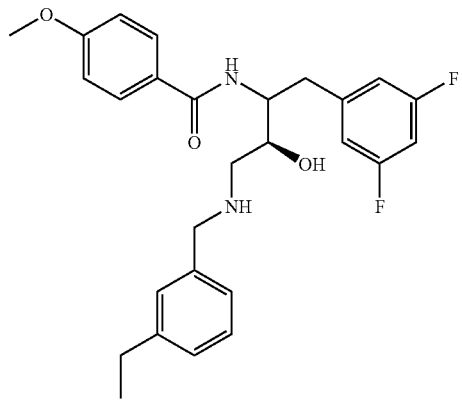
N-[1-(3,5-Difluoro-benzyl)-3-(3-ethyl-benzylamino)-
2-hydroxy-propyl]-4-methoxy-benzamide
1394
4-Methyl-oxazole-5-carboxylic acid [1-(3,5-difluoro-
benzyl)-3-(3-ethyl-benzylamino)-2-hydroxy-propyl]-amide
1395
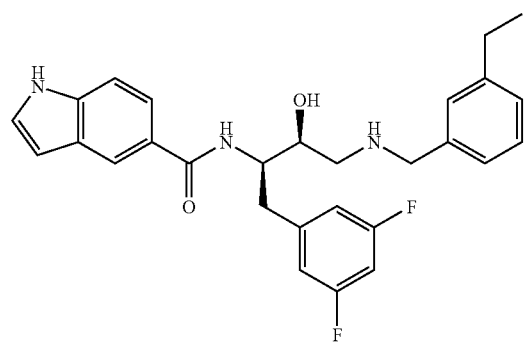
1H-Indole-5-carboxylic acid [1-(3,5-difluoro-benzyl)-3-
(3-ethyl-benzylamino)-2-hydroxy-propyl]-amide 1396
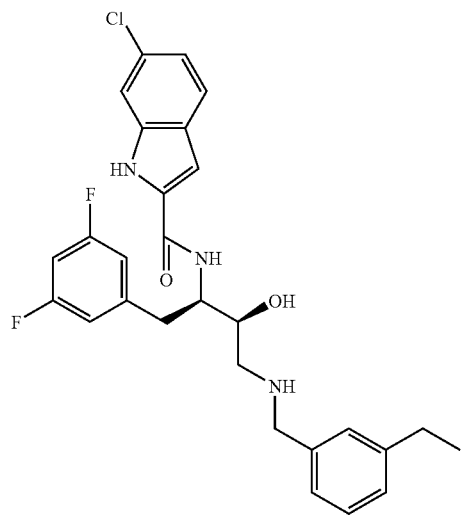
6-Chloro-1H-indole-2-carboxylic acid [1-(3,5-difluoro-benzyl)-3-(3-ethyl-benzylamino)-2-hydroxy-propyl]-amide
1397
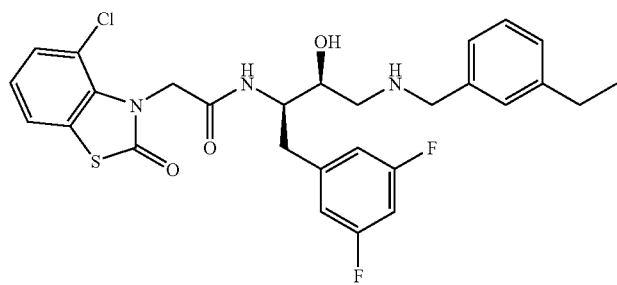
2-(4-Chloro-2-oxo-benzothiazol-3-yl)-N-[1-(3,5-difluoro-benzyl)-3-(3-ethyl-benzylamino)-2-hydroxy-propyl]-acetamide
1398
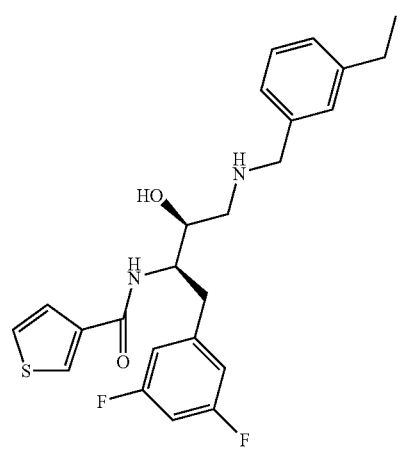
Thiophene-3-carboxylic acid [1-(3,5-difluoro-benzyl)-3-(3-ethyl-benzylamino)-2-hydroxy-propyl]-amide 1399
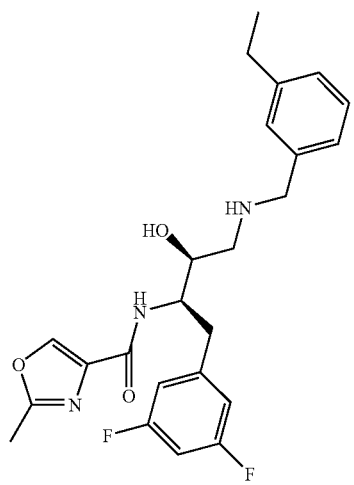
2-Methyl-oxazole-4-carboxylic acid [1-(3,5-difluoro-benzyl)-3-(3-ethyl-benzylamino)-2-hydroxy-propyl]-amide
1400
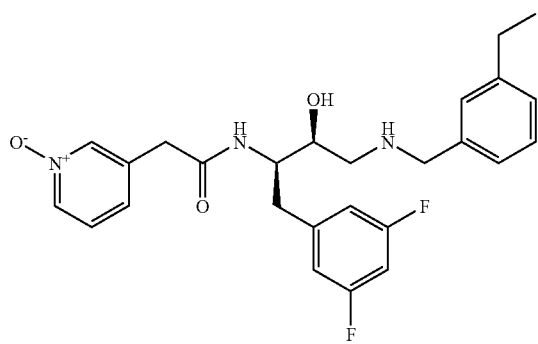
N-[1-(3,5-Difluoro-benzyl)-3-(3-ethyl-benzylamino)-2-hydroxy-propyl]-2-(1-oxy-pyridin-3-yl)-acetamide
1401
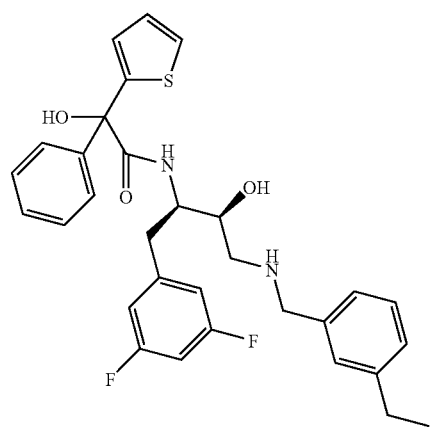
N-[1-(3,5-Difluoro-benzyl)-3-(3-ethyl-benzylamino)-2-hydroxy-2-phenyl-2-thiophen-2-yl-acetamide -continued
1402
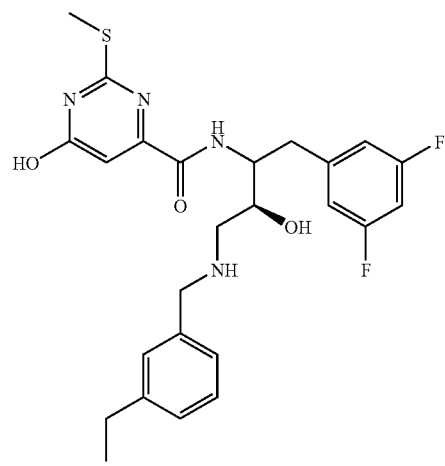
6-Hydroxy-2-methylsulfanyl-pyrimidine-4-carboxylic acid
[1-(3,5-difluoro-benzyl)-3-(3-ethyl-benzylamino)-2-hydroxy-propyl]-amide
1403
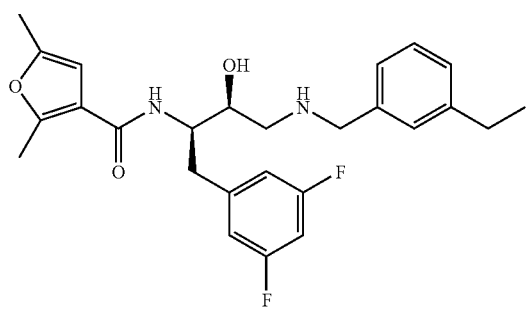
2,5-Dimethyl-furan-3-carboxylic acid [1-(3,5-difluoro-benzyl)-3-
(3-ethyl-benzylamino)-2-hydroxy-propyl]-amide
1404
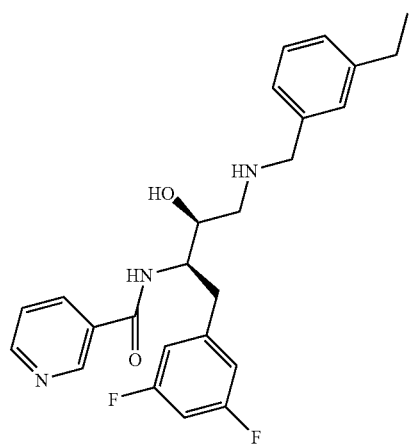
N-[1-(3,5-2-hydroxy-3-(3-ethyl-
benzylamino)-2-hydroxy-propyl]-nicotinamide -continued
1405
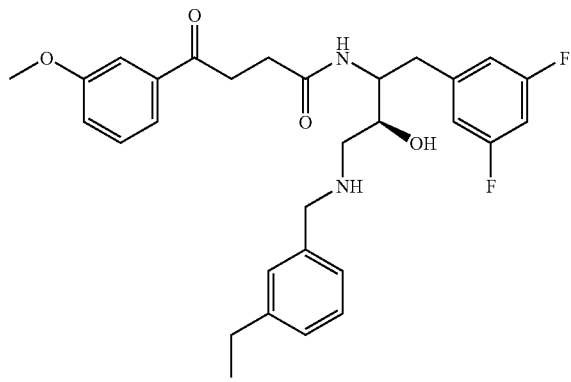
N-[1-(3,5-Difluoro-benzyl)-3-(3-ethyl-benzylamino)-2-hydroxy-propyl]-4-(3-methoxy-phenyl)-4-oxo-butyramide
1406
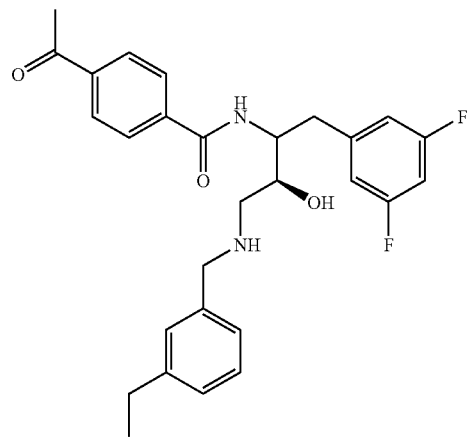
4-Acetyl-N-[1-(3,5-difluoro-benzyl)-3-(3-ethyl-benzylamino)-2-hydroxy-propyl]-benzamide
1407
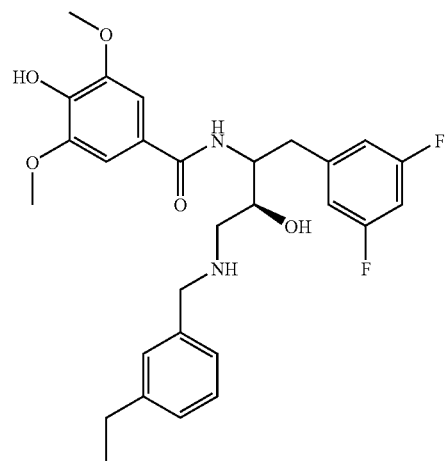
N-[1-(3,5-Difluoro-benzyl)-3-(3-ethyl-benzylamino)-2-hydroxy-propyl]-4-hydroxy-3,5-dimethoxy-benzamide 1408
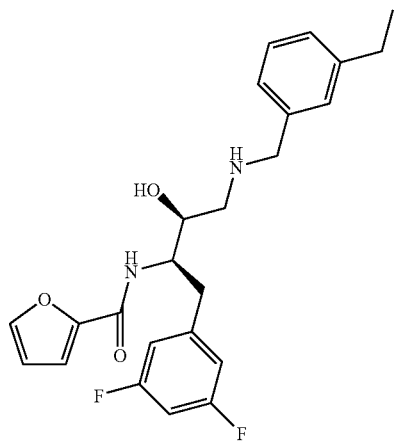
Furan-2-carboxylic acid [1-(3,5-difluoro-benzyl)-3-
(3-ethyl-benzylamino)-2-hydroxy-propyl]-amide
1409
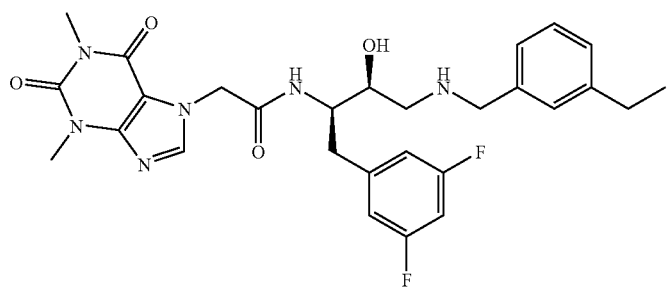
N-[1-(3,5-Difluoro-benzyl)-3-(3-ethyl-benzylamino)-2-hydroxy-propyl]-
2-(1,3-dimethyl-2,6-dioxo-1,2,3,6-tetrahydro-purin-7-yl)-acetamide
1410
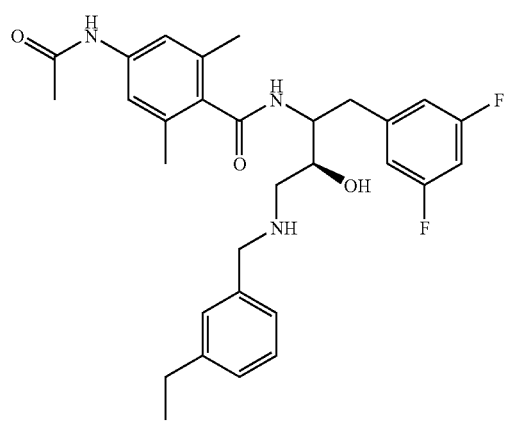
4-Acetylamino-N-[1-(3,5-difluoro-benzyl)-3-(3-ethyl-benzylamino)-2-
hydroxy-propyl]-2,6-dimethyl-benzamide 1411
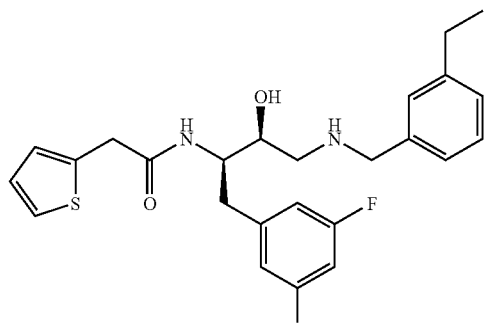
N-[1-(3,5-Difluoro-benzyl)-3-(3-ethyl-benzylamino)-2-
hydroxy-propyl]-2-thiophen-2-yl-acetamide
1412
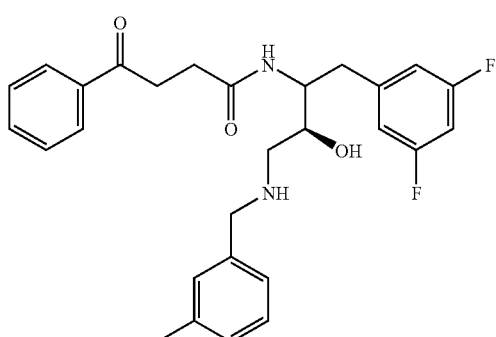
N-[1-(3,5-Difluoro-benzyl)-3-(3-ethyl-benzylamino)-2-
hydroxy-propyl]-4-oxo-4-phenyl-butyramide
1413
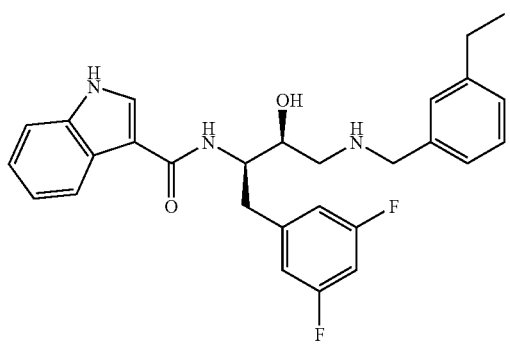
1H-Indole-3-carboxylic acid [1-(3,5-difluoro-benzyl)-3-
(3-ethyl-benzylamino)-2-hydroxy-propyl]-amide
1414
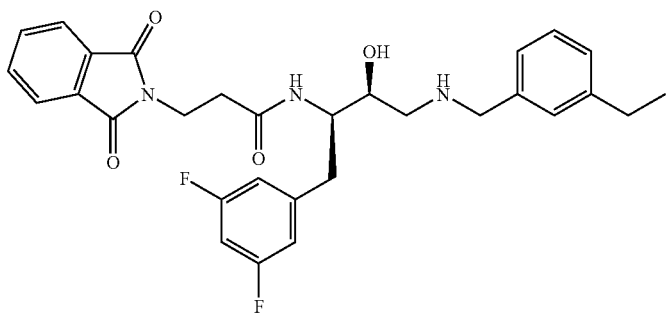
N-[1-(3,5-Difluoro-benzyl)-3-(3-ethyl-benzylamino)-2-
hydroxy-propyl]-3-(1,3-dioxo-1,3-dihydro-isoindol-2-yl)-propionamide 1415
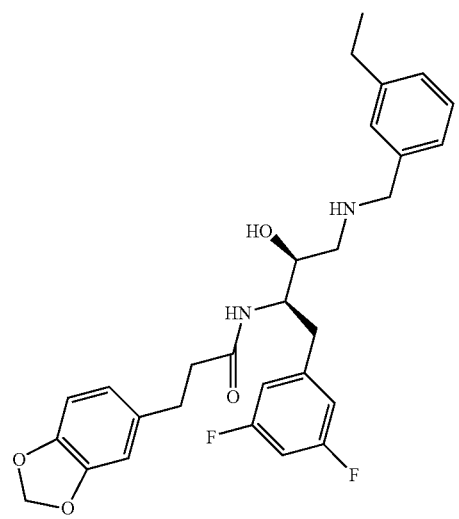
3-Benzo[1,3]dioxol-5-yl-N-[1-(3,5-difluoro-benzyl)-3-
(3-ethyl-benzylamino)-2-hydroxy-propyl]-propionamide
1416
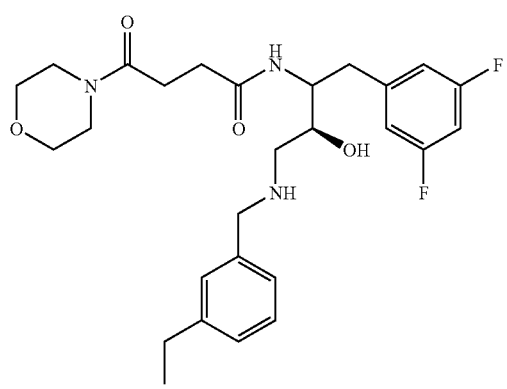
N-[1-(3,5-Difluoro-benzyl)-3-(3-ethyl-benzylamino)-2-hydroxy-
propyl]-4-morpholin-4-yl-4-oxo-butyramide
1417
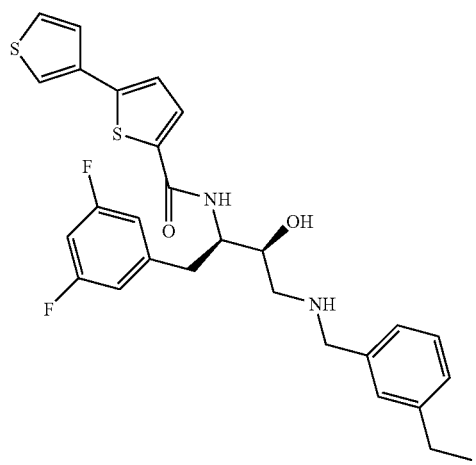
[2,3']Bithiophenyl-5-carboxylic acid [1-(3,5-difluoro-
benzyl)-3-(3-ethyl-benzylamino)-2-hydroxy-propyl]-amide -continued
1418
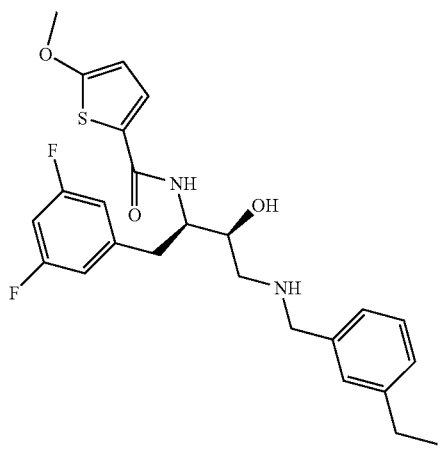
5-Methoxy-thiophene-2-carboxylic acid [1-(3,5-difluoro-
benzyl)-3-(3-ethyl-benzylamino)-2-hydroxy-propyl]-amide
1419
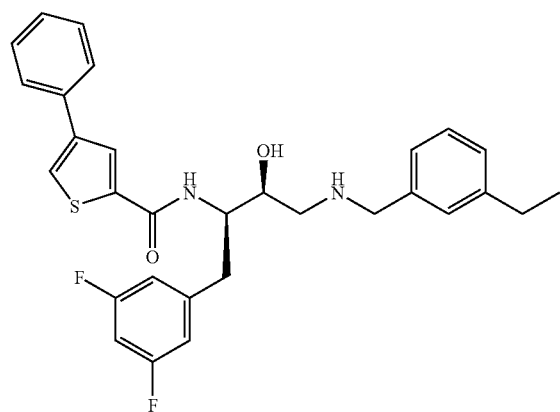
4-Phenyl-thiophene-2-carboxylic acid [1-(3,5-difluoro-benzyl)-3-
(3-ethyl-benzylamino)-2-hydroxy-propyl]-amide
1420
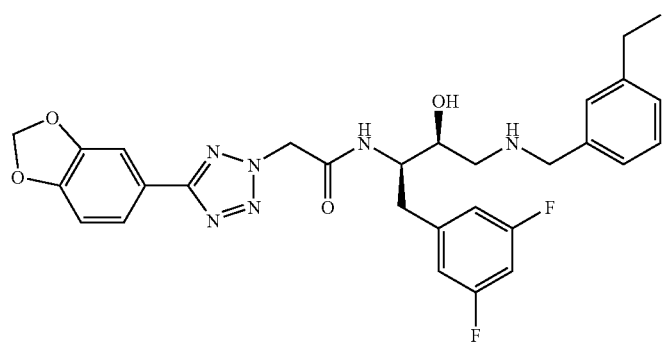
2-(5-Benzo[1,3]dioxol-5-yl-tetrazol-2-yl)-N-[1-(3,5-difluoro-
benzyl)-3-(3-ethyl-benzylamino)-2-hydroxy-propyl]-acetamide 1421
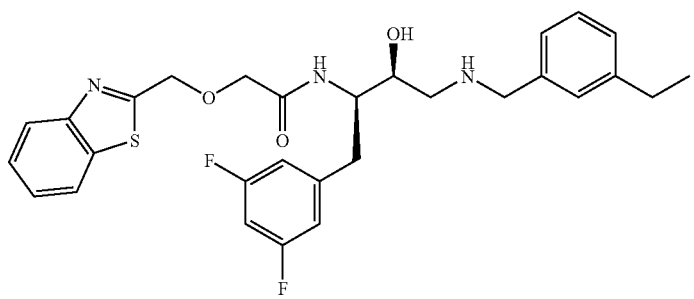
2-(Benzothiazol-2-ylmethoxy)-N-[1-(3,5-difluoro-benzyl)-3-
(3-ethyl-benzylamino)-2-hydroxy-propyl]-acetamide
1422
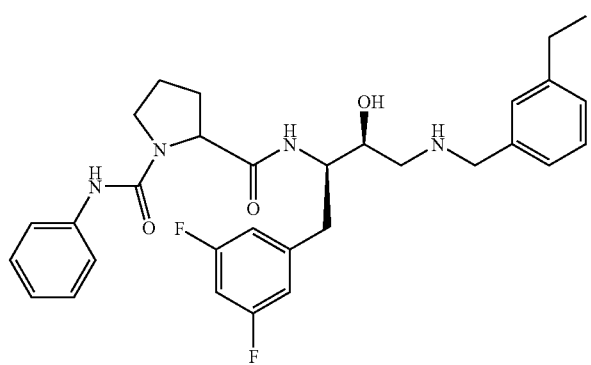
Pyrrolidine-1,2-dicarboxylic acid 1-{[1-(3,5-difluoro-
benzyl)-3-(3-ethyl-benzylamino)-2-hydroxy-propyl]-amide} 2-phenylamide
1423
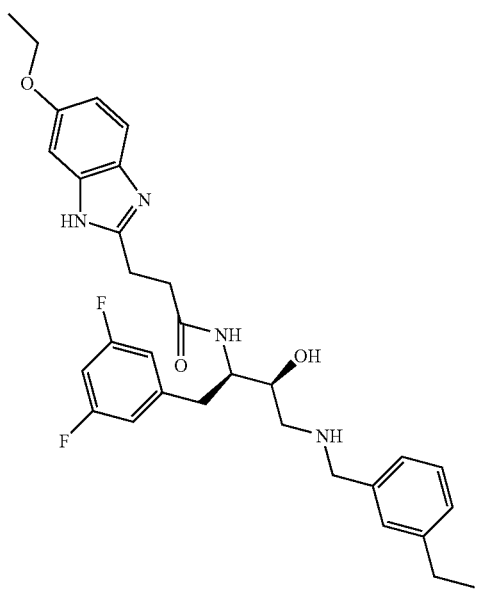
N-[1-(3,5-Difluoro-benzyl)-3-(3-ethyl-benzylamino)-2-hydroxy-
propyl]-3-(6-ethoxy-1H-benzoimidazol-2-yl)-propionamide -continued

1424

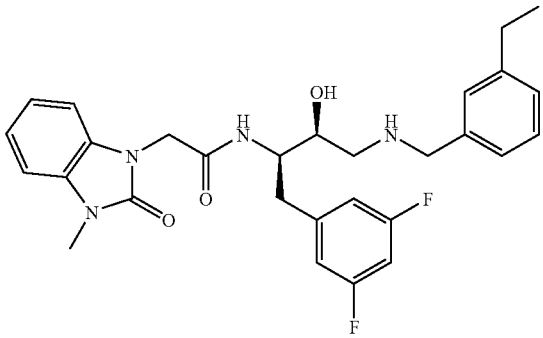

N-[1-(3,5-Difluoro-benzyl)-3-(3-ethyl-benzylamino)-2-hydroxy-propyl]-2-(3-methyl-2-oxo-2,3-dihydro-benzoimidazol-1-yl)-acetamide

1425

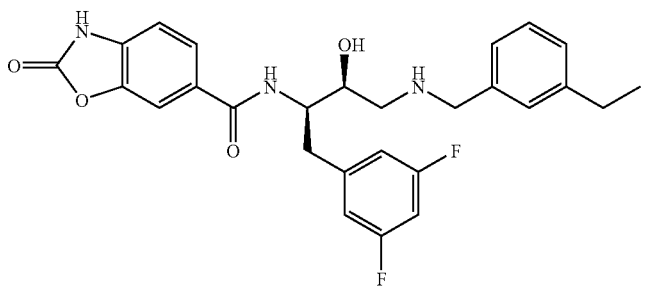

2-Oxo-2,3-dihydro-benzooxazole-6-carboxylic acid [1-(3,5-difluoro-benzyl)-3-(3-ethyl-benzylamino)-2-hydroxy-propyl]-amide

1426

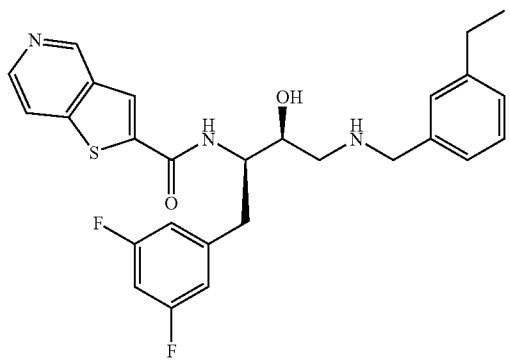

Thieno[3,2-c]pyridine-2-carboxylic acid [1-(3,5-difluoro-benzyl)-3-(3-ethyl-benzylamino)-2-hydroxy-propyl]-amide

1427

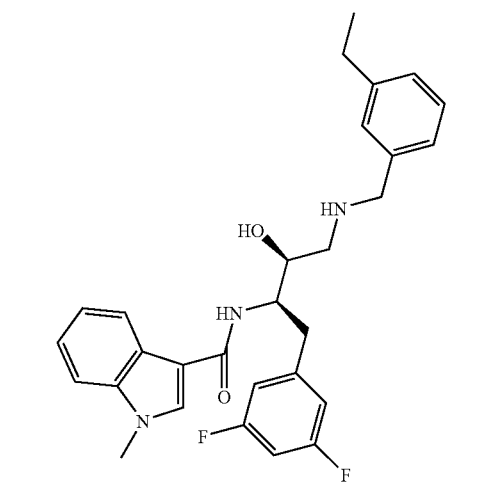

1-Methyl-1H-indole-3-carboxylic acid [1-(3,5-difluoro-benzyl)-3-(3-ethyl-benzylamino)-2-hydroxy-propyl]-amide -continued
1428
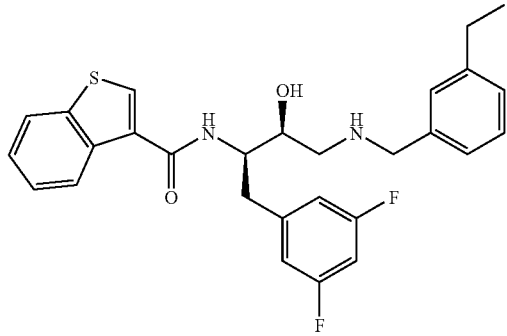
Benzo[b]thiophene-3-carboxylic acid [1-(3,5-difluoro-benzyl)-3-(3-ethyl-benzylamino)-2-hydroxy-propyl]-amide
1429
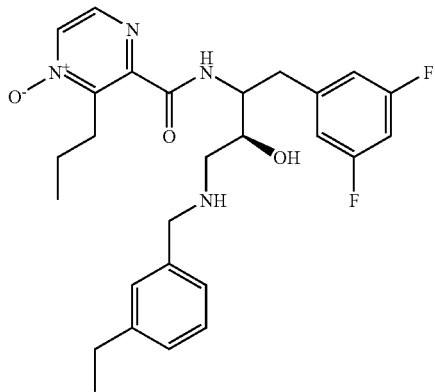
4-Oxy-3-propyl-pyrazine-2-carboxylic acid [1-(3,5-difluoro-benzyl)-3-(3-ethyl-benzylamino)-2-hydroxy-propyl]-amide
1430
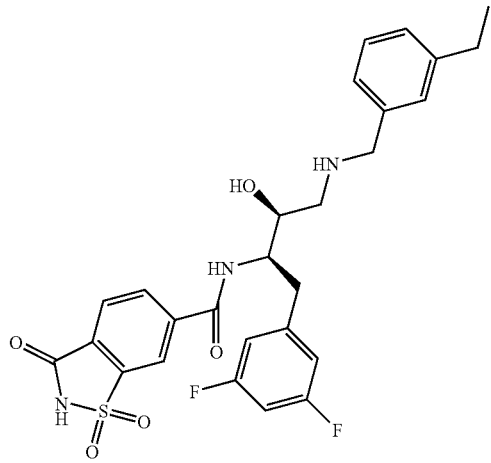
1,1,3-Trioxo-2,3-dihydro-1H-1l6-benzo[d]isothiazole-6-carboxylic acid [1-(3,5-difluoro-benzyl)-3-(3-ethyl-benzylamino)-2-hydroxy-propyl]-amide

1431

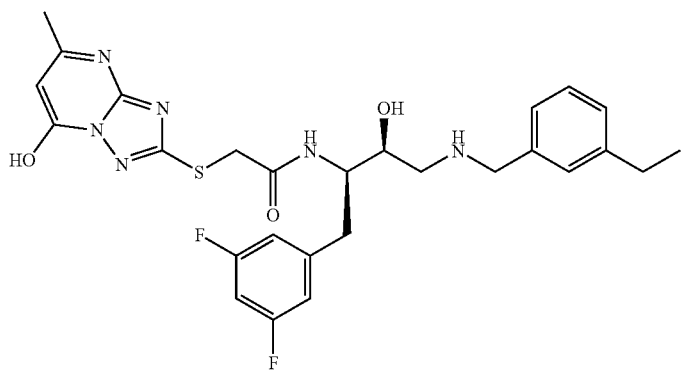

N-[1-(3,5-Difluoro-benzyl)-3-(3-ethyl-benzylamino)-2-hydroxy-propyl]-2-
(7-hydroxy-5-methyl-[1,2,4]triazolo[1,5-a]pyrimidin-2-ylsulfanyl)-acetamide

1432

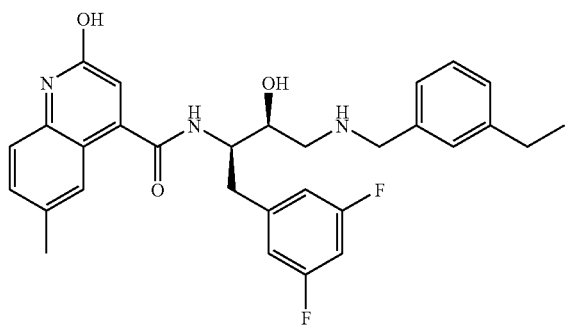

2-Hydroxy-6-methyl-quinoline-4-carboxylic acid [1-(3,5-difluoro-
benzyl)-3-(3-ethyl-benzylamino)-2-hydroxy-propyl]-amide

1433

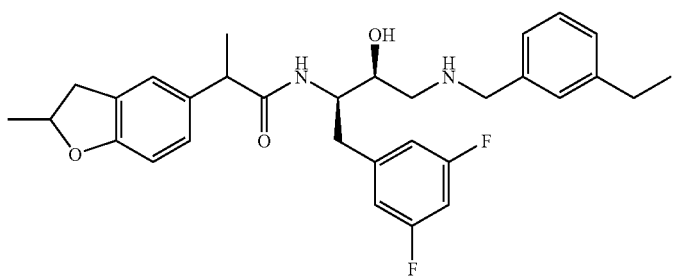

N-[1-(3,5-Difluoro-benzyl)-3-(3-ethyl-benzylamino)-2-hydroxy-propyl]-2-
(2-methyl-2,3-dihydro-benzofuran-5-yl)-propionamide

1434

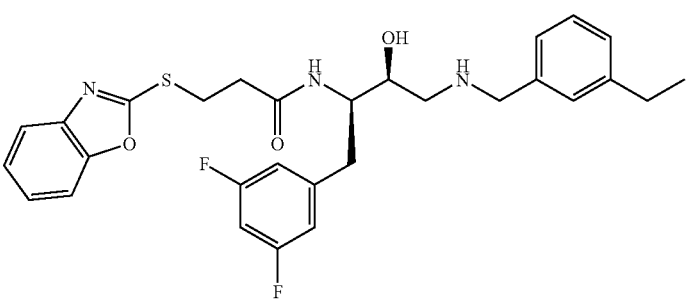

3-(Benzooxazol-2-ylsulfanyl)-N-[1-(3,5-difluoro-benzyl)-3-
(3-ethyl-benzylamino)-2-hydroxy-propyl]-propionamide -continued
1435
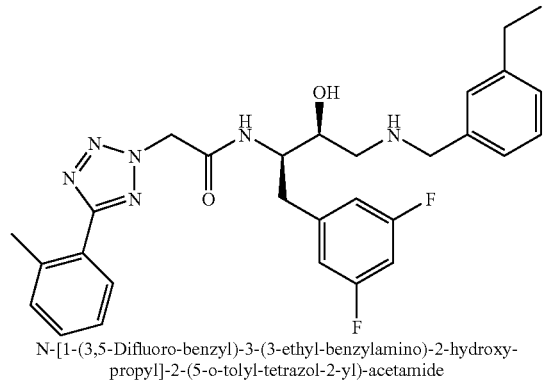
N-[1-(3,5-Difluoro-benzyl)-3-(3-ethyl-benzylamino)-2-hydroxy-propyl]-2-(5-o-tolyl-tetrazol-2-yl)-acetamide
1436
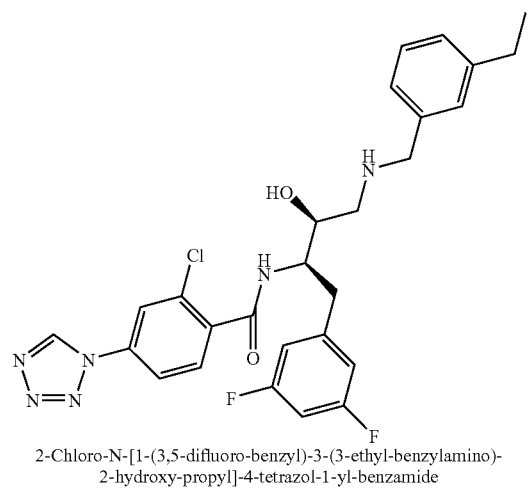
2-Chloro-N-[1-(3,5-difluoro-benzyl)-3-(3-ethyl-benzylamino)-2-hydroxy-propyl]-4-tetrazol-1-yl-benzamide
1437
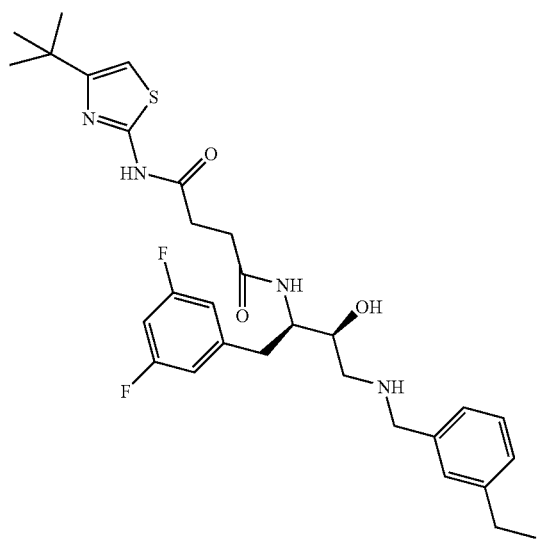
N-(4-tert-Butyl-thiazol-2-yl)-N'-[1-(3,5-difluoro-benzyl)-3-(3-ethyl-benzylamino)-2-hydroxy-propyl]-succinamide 1438
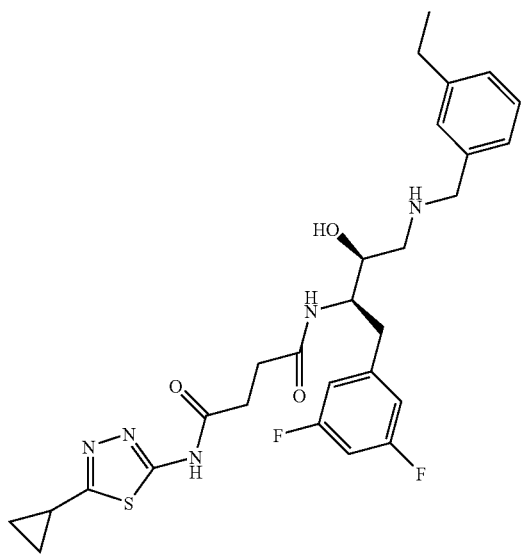
N-(5-Cyclopropyl-[1,3,4]thiadiazol-2-yl)-N'-[1-(3,5-difluoro-benzyl)-3-(3-ethyl-benzylamino)-2-hydroxy-propyl]-succinamide
1439
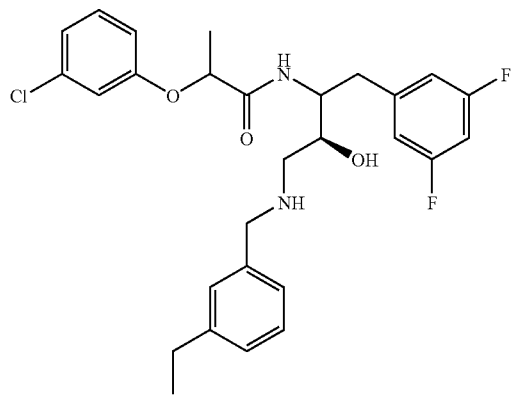
2-(3-Chloro-phenoxy)-N-[1-(3,5-difluoro-benzyl)-3-(3-ethyl-benzylamino)-2-hydroxy-propyl]-propionamide

1440

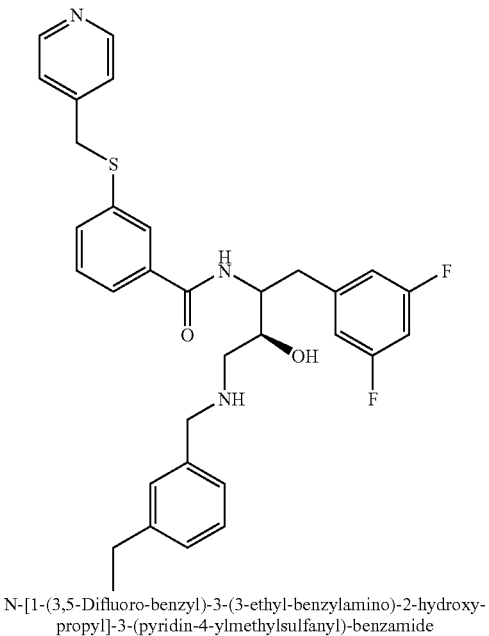

N-[1-(3,5-Difluoro-benzyl)-3-(3-ethyl-benzylamino)-2-hydroxy-propyl]-3-(pyridin-4-ylmethylsulfanyl)-benzamide The compounds in the table immediately below were prepared essentially using the methods described above and illustrated below in the schemes.

The following compounds were named using the Advanced Chemistry Development Inc. (ACD) nomenclature program, IUPAC Name Batch Version 4.5. The website for ACD is www.acdlabs.com.

| | Compound Name (IUPAC Name) |
|---|---|
| 1441 | $N^1$-{(1S,2R)-1-(3,5-difluorobenzyl)-3-[(3-ethylbenzyl)amino]-2-hydroxypropyl}-5-{[(2-hydroxyethyl)amino]sulfonyl}-$N^3,N^3$-dipropylisophthalamide |
| 1442 | $N^1$-((1S,2R)-1-(3,5-difluorobenzyl)-2-hydroxy-3-{[(2-isobutyl-1,3-thiazol-5-yl)methyl]amino}propyl)-5-ethynyl-$N^3,N^3$-dipropylisophthalamide |
| 1443 | $N^1$-{(1S,2R)-1-(3,5-difluorobenzyl)-2-hydroxy-3-[(3-isopropylbenzyl)amino]propyl}-5-ethynyl-$N^3,N^3$-dipropylisophthalamide |
| 1444 | $N^1$-{(1S,2R)-1-(3,5-difluorobenzyl)-2-hydroxy-3-[(3-isopropylbenzyl)amino]propyl}-5-(1,3-oxazol-2-yl)-$N^3,N^3$-dipropylisophthalamide |
| 1445 | $N^1$-{(1S,2R)-1-(3,5-difluorobenzyl)-3-[(3-ethylbenzyl)amino]-2-hydroxypropyl}-5-{[(2-hydroxy-1,1-dimethylethyl)amino]sulfonyl}-$N^3,N^3$-dipropylisophthalamide |
| 1446 | $N^1$-{(1S,2R)-1-(3,5-difluorobenzyl)-3-[(3-ethylbenzyl)amino]-2-hydroxypropyl}-5-(4-methyl-1,3-oxazol-2-yl)-$N^3,N^3$-dipropylisophthalamide |
| 1447 | $N^1$-((1S,2R)-1-(3,5-difluorobenzyl)-2-hydroxy-3-{[(2-isobutyl-1,3-thiazol-5-yl)methyl]amino}propyl)-5-(1,3-oxazol-2-yl)-$N^3,N^3$-dipropylisophthalamide |
| 1448 | $N^1$-{(1S,2R)-1-(3,5-difluorobenzyl)-3-[(3-ethylbenzyl)amino]-2-hydroxypropyl}-5-{[(3-hydroxypropyl)amino]sulfonyl}-$N^3,N^3$-dipropylisophthalamide |
| 1449 | $N^1$-{(1S,2R)-1-(3,5-difluorobenzyl)-2-hydroxy-3-[(3-propylbenzyl)amino]propyl}-5-methyl-$N^3,N^3$-dipropylisophthalamide |
| 1451 | $N^1$-{(1S,2R)-1-(3,5-difluorobenzyl)-3-[(3-ethynylbenzyl)amino]-2-hydroxypropyl}-5-ethynyl-$N^3,N^3$-dipropylisophthalamide |
| 1452 | $N^1$-((1S,2R)-1-(3,5-difluorobenzyl)-2-hydroxy-3-{[(3-isobutylisoxazol-5-yl)methyl]amino}propyl)-5-ethynyl-$N^3,N^3$-dipropylisophthalamide |
| 1453 | $N^1$-{(1S,2R)-1-(3,5-difluorobenzyl)-3-[(3-ethylbenzyl)amino]-2-hydroxypropyl}-5-[(dimethylamino)sulfonyl]-$N^3,N^3$-dipropylisophthalamide |
| 1454 | $N^1$-{(1S,2R)-1-(3,5-difluorobenzyl)-3-[(3-ethylbenzyl)amino]-2-hydroxypropyl}-5-(1,3-oxazol-2-yl)-$N^3,N^3$-dipropylisophthalamide hydrochloride |
| 1455 | $N^1$-((1S,2R)-1-(3,5-difluorobenzyl)-3-{[3-(5-formylthien-2-yl)benzyl]amino}-2-hydroxypropyl)-5-methyl-$N^3,N^3$-dipropylisophthalamide |
| 1456 | 5-bromo-$N^1$-{(1S,2R)-1-(3,5-difluorobenzyl)-2-hydroxy-3-[(3-iodobenzyl)amino]propyl}-$N^3,N^3$-dipropylisophthalamide |
| 1457 | $N^1$-{(1S,2R)-1-(3,5-difluorobenzyl)-3-[(3-ethylbenzyl)amino]-2-hydroxypropyl}-5-({[(1R)-2-hydroxy-1-methylethyl]amino}sulfonyl)-$N^3,N^3$-dipropylisophthalamide |
| 1458 | $N^1$-{(1S,2R)-1-(3,5-difluorobenzyl)-2-hydroxy-3-[(3-isobutylbenzyl)amino]propyl}-5-methyl-$N^3,N^3$-dipropylisophthalamide |
| 1459 | $N^1$-((1S,2R)-1-(3,5-difluorobenzyl)-2-hydroxy-3-{[3-(trifluoromethyl)benzyl]amino}propyl)-5-ethynyl-$N^3,N^3$-dipropylisophthalamide |
| 1460 | N-{(1S,2R)-1-(3,5-difluorobenzyl)-3-[(3-ethylbenzyl)amino]-2-hydroxypropyl}-3-{[(2R)-2-(methoxymethyl)pyrrolidin-1-yl]carbonyl}-5-methylbenzamide hydrochloride |

| | Compound Name (IUPAC Name) |
|---|---|
| 1461 | N$^1$-{(1S,2R)-1-(3,5-difluorobenzyl)-3-[(3-ethylbenzyl)amino]-2-hydroxypropyl}-5-({[(1S)-2-hydroxy-1-methylethyl]amino}sulfonyl)-N$^3$,N$^3$-dipropylisophthalamide |
| 1462 | N$^1$-butyl-N$^3$-{(1S,2R)-1-(3,5-difluorobenzyl)-3-[(3-ethylbenzyl)amino]-2-hydroxypropyl}-5-methyl-N$^1$-propylisophthalamide |
| 1463 | N$^1$,N$^1$-dibutyl-N$^3$-{(1S,2R)-1-(3,5-difluorobenzyl)-3-[(3-ethylbenzyl)amino]-2-hydroxypropyl}-5-methylisophthalamide |
| 1464 | N$^1$-((1S,2R)-1-(3,5-difluorobenzyl)-2-hydroxy-3-{[3-(3-hydroxyprop-1-ynyl)benzyl]amino}propyl)-5-methyl-N$^3$,N$^3$-dipropylisophthalamide |
| 1465 | N$^1$-{(1S,2R)-1-(3,5-difluorobenzyl)-3-[(3-ethylbenzyl)amino]-2-hydroxypropyl}-5-{[(2S)-2-(hydroxymethyl)pyrrolidin-1-yl]sulfonyl}-N$^3$,N$^3$-dipropylisophthalamide |
| 1467 | N$^1$-{(1S,2R)-1-(3,5-difluorobenzyl)-3-[(3-ethynylbenzyl)amino]-2-hydroxypropyl}-5-(1,3-oxazol-2-yl)-N$^3$,N$^3$-dipropylisophthalamide |
| 1469 | N$^1$-[(1S,2R)-3-{[3-(cyclopropylamino)benzyl]amino}-1-(3,5-difluorobenzyl)-2-hydroxypropyl]-5-ethynyl-N$^3$,N$^3$-dipropylisophthalamide |
| 1470 | N$^1$-{(1S,2R)-1-(3,5-difluorobenzyl)-2-hydroxy-3-[(3-thien-3-ylbenzyl)amino]propyl}-5-methyl-N$^3$,N$^3$-dipropylisophthalamide |
| 1471 | N$^1$-((1S,2R)-1-(3,5-difluorobenzyl)-2-hydroxy-3-{[3-(trifluoromethyl)benzyl]amino}propyl)-5-(1,3-oxazol-2-yl)-N$^3$,N$^3$-dipropylisophthalamide |
| 1472 | N$^1$-{(1S,2R)-1-(3,5-difluorobenzyl)-3-[(3-ethylbenzyl)amino]-2-hydroxypropyl}-5-(piperazin-1-ylsulfonyl)-N$^3$,N$^3$-dipropylisophthalamide |
| 1473 | N$^1$-((1S,2R)-1-(3,5-difluorobenzyl)-2-hydroxy-3-{[1-(3-iodophenyl)cyclopropyl]amino}propyl)-5-methyl-N$^3$,N$^3$-dipropylisophthalamide |
| 1474 | N$^1$-[(1S,2R)-3-[(3-sec-butylbenzyl)amino]-1-(3,5-difluorobenzyl)-2-hydroxypropyl]-5-methyl-N$^3$,N$^3$-dipropylisophthalamide |
| 1475 | N$^1$-{(1S,2R)-1-(3,5-difluorobenzyl)-3-[(3-ethylbenzyl)amino]-2-hydroxypropyl}-5-(3-methylisoxazol-4-yl)-N$^3$,N$^3$-dipropylisophthalamide hydrochloride |
| 1476 | N$^1$-((1S,2R)-1-(3,5-difluorobenzyl)-2-hydroxy-3-{[1-(3-isobutylisoxazol-5-yl)cyclopropyl]amino}propyl)-5-(1,3-oxazol-2-yl)-N$^3$,N$^3$-dipropylisophthalamide |
| 1477 | N$^1$-((1S,2R)-1-(3,5-difluorobenzyl)-3-{[1-(3-ethylphenyl)cyclopropyl]amino}-2-hydroxypropyl)-5-(1,3-oxazol-2-yl)-N$^3$,N$^3$-dipropylisophthalamide |
| 1478 | N$^4$-{(1S,2R)-1-(3,5-difluorobenzyl)-3-[(3-ethylbenzyl)amino]-2-hydroxypropyl}-6-methyl-N$^2$,N$^2$-dipropylpyridine-2,4-dicarboxamide |
| 1480 | N$^1$-{(1S,2R)-1-(3,5-difluorobenzyl)-2-hydroxy-3-[(3-methoxybenzyl)amino]propyl}-5-(1,3-oxazol-2-yl)-N$^3$,N$^3$-dipropylisophthalamide |
| 1481 | N$^1$-((1S,2R)-1-(3,5-difluorobenzyl)-3-{[1-(3-ethynylphenyl)cyclopropyl]amino}-2-hydroxypropyl)-5-(1,3-oxazol-2-yl)-N$^3$,N$^3$-dipropylisophthalamide |
| 1482 | 5-(aminosulfonyl)-N$^1$-{(1S,2R)-1-(3,5-difluorobenzyl)-3-[(3-ethylbenzyl)amino]-2-hydroxypropyl}-N$^3$,N$^3$-dipropylisophthalamide |
| 1483 | N$^1$-[(1S,2R)-1-(3,5-difluorobenzyl)-2-hydroxy-3-({3-[(1Z)-prop-1-enyl]benzyl}amino)propyl]-5-methyl-N$^3$,N$^3$-dipropylisophthalamide |
| 1484 | N$^1$-{(1S,2R)-1-(3,5-difluorobenzyl)-3-[(3-ethylbenzyl)amino]-2-hydroxypropyl}-N$^3$,N$^3$-dipropyl-5-(1H-pyrazol-4-yl)isophthalamide |
| 1485 | N$^1$-((1S,2R)-1-(3,5-difluorobenzyl)-3-{[1-(3-ethylphenyl)-1-methylethyl]amino}-2-hydroxypropyl)-5-ethynyl-N$^3$,N$^3$-dipropylisophthalamide |
| 1487 | N$^1$-[(1S,2R)-3-[(3-allylbenzyl)amino]-1-(3,5-difluorobenzyl)-2-hydroxypropyl]-5-methyl-N$^3$,N$^3$-dipropylisophthalamide |
| 1488 | N$^1$-((1S,2R)-1-(3,5-difluorobenzyl)-3-{[1-(3-ethylphenyl)cyclopropyl]amino}-2-hydroxypropyl)-5-methyl-N$^3$,N$^3$-dipropylisophthalamide |
| 1489 | N$^1$-((1S,2R)-1-(3,5-difluorobenzyl)-3-{[1-(3-ethylphenyl)-1-methylethyl]amino}-2-hydroxypropyl)-5-(1,3-oxazol-2-yl)-N$^3$,N$^3$-dipropylisophthalamide |
| 1490 | N$^1$-{(1S,2R)-1-(3,5-difluorobenzyl)-3-[(3-ethylbenzyl)amino]-2-hydroxypropyl}-N$^3$-ethyl-5-methyl-N$^3$-propylisophthalamide |
| 1491 | N$^1$-[(1S,2R)-3-{[3-(cyclopropylamino)benzyl]amino}-1-(3,5-difluorobenzyl)-2-hydroxypropyl]-5-methyl-N$^3$,N$^3$-dipropylisophthalamide |
| 1492 | N$^1$-((1S,2R)-1-(3,5-difluorobenzyl)-3-{[1-(3-ethynylphenyl)cyclopropyl]amino}-2-hydroxypropyl)-5-ethynyl-N$^3$,N$^3$-dipropylisophthalamide |
| 1493 | N$^1$-((1S,2R)-1-(3,5-difluorobenzyl)-2-hydroxy-3-{[1-(3-isobutylisoxazol-5-yl)cyclopropyl]amino}propyl)-5-methyl-N$^3$,N$^3$-dipropylisophthalamide |
| 1494 | N$^1$-((1S,2R)-1-(3,5-difluorobenzyl)-3-{[3-(5-formyl-4-methylthien-2-yl)benzyl]amino}-2-hydroxypropyl)-5-methyl-N$^3$,N$^3$-dipropylisophthalamide |
| 1496 | N$^1$-[(1S,2R)-1-(3,5-difluorobenzyl)-2-hydroxy-3-({3-[(methylsulfonyl)amino]benzyl}amino)propyl]-5-methyl-N$^3$,N$^3$-dipropylisophthalamide |
| 1498 | N$^1$-{(1S,2R)-1-(3,5-difluorobenzyl)-2-hydroxy-3-[(3-isopentylbenzyl)amino]propyl}-5-methyl-N$^3$,N$^3$-dipropylisophthalamide |
| 1500 | N$^1$-((1S,2R)-1-(3,5-difluorobenzyl)-3-{[1-(3-ethynylphenyl)cyclopropyl]amino}-2-hydroxypropyl)-5-methyl-N$^3$,N$^3$-dipropylisophthalamide |
| 1501 | N$^1$-{(1S,2R)-1-(3,5-difluorobenzyl)-3-[(3-ethylbenzyl)amino]-2-hydroxypropyl}-5-({[2-(methylamino)ethyl]amino}sulfonyl)-N$^3$,N$^3$-dipropylisophthalamide dihydrochloride |
| 1502 | N$^1$-((1S,2R)-1-(3,5-difluorobenzyl)-2-hydroxy-3-{[1-(3-isobutylisoxazol-5-yl)cyclopropyl]amino}propyl)-5-ethynyl-N$^3$,N$^3$-dipropylisophthalamide |
| 1504 | N$^1$-((1S,2R)-1-(3,5-difluorobenzyl)-2-hydroxy-3-{[1-(2-isobutyl-1,3-thiazol-5-yl)cyclopropyl]amino}propyl)-5-methyl-N$^3$,N$^3$-dipropylisophthalamide |
| 1505 | N$^1$-((1S,2R)-1-(3,5-difluorobenzyl)-3-{[1-(3-ethylphenyl)-1-methylethyl]amino}-2-hydroxypropyl)-5-methyl-N$^3$,N$^3$-dipropylisophthalamide |
| 1506 | N$^1$-{(1S,2R)-1-(3,5-difluorobenzyl)-3-[(3-ethylbenzyl)amino]-2-hydroxypropyl}-5-{[(2-hydroxyethyl)amino]sulfonyl}-N$^3$-propylisophthalamide |
| 1507 | N$^1$-{(1S,2R)-1-(3,5-difluorobenzyl)-3-[(3-ethylbenzyl)amino]-2-hydroxypropyl}-N$^3$,5-dimethyl-N$^3$-propylisophthalamide |
| 1508 | N$^1$-{(1S,2R)-1-(3,5-difluorobenzyl)-3-[(3-ethylbenzyl)amino]-2-hydroxypropyl}-N$^2$-(phenylsulfonyl)-3-[(1-propylbutyl)sulfonyl]alaninamide |
| 1509 | N$^1$-{(1S,2R)-1-(3,5-difluorobenzyl)-3-[(3-ethylbenzyl)amino]-2-hydroxypropyl}-N$^3$,N$^3$-diethyl-5-(1,3-oxazol-2-yl)isophthalamide |
| 1510 | N$^2$-[(benzylamino)carbonyl]-N$^1$-{(1S,2R)-1-(3,5-difluorobenzyl)-3-[(3-ethylbenzyl)amino]-2-hydroxypropyl}-3-[(1-propylbutyl)sulfonyl]alaninamide |
| 1511 | N$^1$-{(1S,2R)-1-(3,5-difluorobenzyl)-2-hydroxy-3-[(3-pyridin-3-ylbenzyl)amino]propyl}-5-methyl-N$^3$,N$^3$-dipropylisophthalamide |
| 1512 | N$^3$-{(1S,2R)-1-(3,5-difluorobenzyl)-3-[(3-ethylbenzyl)amino]-2-hydroxypropyl}-N$^5$,N$^5$-dipropylpyridine-3,5-dicarboxamide 1-oxide |
| 1513 | N$^1$-((1S,2R)-1-(3,5-difluorobenzyl)-3-{[3-(3-formyl-2-furyl)benzyl]amino}-2-hydroxypropyl)-5-methyl-N$^3$,N$^3$-dipropylisophthalamide |
| 1514 | N$^1$-{(1S,2R)-1-(3,5-difluorobenzyl)-3-[(3-ethylbenzyl)amino]-2-hydroxypropyl}-5-(1-methyl-1H-imidazol-2-yl)-N$^3$,N$^3$-dipropylisophthalamide |

| | Compound Name (IUPAC Name) |
|---|---|
| 1515 | N$^1$-{(1S,2R)-1-(3,5-difluorobenzyl)-3-[(3-ethylbenzyl)amino]-2-hydroxypropyl}-N$^3$,N$^3$-diethyl-5-methylisophthalamide |
| 1516 | N$^1$-((1S,2R)-1-(3,5-difluorobenzyl)-3-{[3-(ethylsulfinyl)benzyl]amino}-2-hydroxypropyl)-5-methyl-N$^3$,N$^3$-dipropylisophthalamide |
| 1517 | 3-{[butyl(ethyl)amino]sulfonyl}-N-{(1S,2R)-1-(3,5-difluorobenzyl)-3-[(3-ethylbenzyl)amino]-2-hydroxypropyl}propanamide |
| 1519 | N-{(1S,2R)-1-(3,5-difluorobenzyl)-3-[(3-ethylbenzyl)amino]-2-hydroxypropyl}-3-[(1-propylbutyl)sulfonyl]propanamide hydrochloride |
| 1520 | N$^1$-{(1S,2R)-1-(3,5-difluorobenzyl)-3-[(3-ethylbenzyl)amino]-2-hydroxypropyl}-N$^3$-isobutyl-N$^3$,5-dimethylisophthalamide |
| 1521 | N$^1$-{(1S,2R)-1-(3,5-difluorobenzyl)-2-hydroxy-3-[(3-pyridin-2-ylbenzyl)amino]propyl}-5-methyl-N$^3$,N$^3$-dipropylisophthalamide |
| 1523 | N$^1$-[(1S,2R)-1-(3,5-difluorobenzyl)-2-hydroxy-3-({3-[methyl(methylsulfonyl)amino]benzyl}amino)propyl]-5-methyl-N$^3$,N$^3$-dipropylisophthalamide |
| 1524 | N$^1$-{(1S,2R)-1-(3,5-difluorobenzyl)-3-[(3-ethylbenzyl)amino]-2-hydroxypropyl}-N$^2$-(3-phenylpropanoyl)-3-[(1-propylbutyl)sulfonyl]alaninamide trifluoroacetate |
| 1525 | N$^1$-((1S,2R)-1-(3,5-difluorobenzyl)-3-{[3-(ethylsulfonyl)benzyl]amino}-2-hydroxypropyl)-5-methyl-N$^3$,N$^3$-dipropylisophthalamide |
| 1526 | N$^2$-[(5-chlorothien-2-yl)sulfonyl]-N$^1$-{(1S,2R)-1-(3,5-difluorobenzyl)-3-[(3-ethylbenzyl)amino]-2-hydroxypropyl}-3-[(1-propylbutyl)sulfonyl]alaninamide |
| 1527 | N$^1$-[(1S,2R)-3-{[3-(5-acetylthien-2-yl)benzyl]amino}-1-(3,5-difluorobenzyl)-2-hydroxypropyl]-5-methyl-N$^3$,N$^3$-dipropylisophthalamide |
| 1529 | N-{(1S,2R)-1-(3,5-difluorobenzyl)-3-[(3-ethylbenzyl)amino]-2-hydroxypropyl}-3-(1,3-oxazol-2-yl)benzamide hydrochloride |
| 1530 | N$^1$-{(1S,2R)-1-(3,5-difluorobenzyl)-3-[(3-ethylbenzyl)amino]-2-hydroxypropyl}-5-dimethyl-N$^3$-(2-phenylethyl)isophthalamide |
| 1531 | N$^1$-((1S,2R)-1-(3,5-difluorobenzyl)-3-{[3-(3,5-dimethylisoxazol-4-yl)benzyl]amino}-2-hydroxypropyl)-5-methyl-N$^3$,N$^3$-dipropylisophthalamide |
| 1532 | N$^1$-{(1S,2R)-1-(3,5-difluorobenzyl)-3-[(3-ethylbenzyl)amino]-2-hydroxypropyl}-N$^3$,5-dimethyl-N$^3$-prop-2-ynylisophthalamide |
| 1533 | N$^1$-{(1S,2R)-1-(3,5-difluorobenzyl)-3-[(3-ethylbenzyl)amino]-2-hydroxypropyl}-N$^3$-ethyl-N$^3$,5-dimethylisophthalamide |
| 1535 | N$^1$-benzyl-N$^3$-{(1S,2R)-1-(3,5-difluorobenzyl)-3-[(3-ethylbenzyl)amino]-2-hydroxypropyl}-N$^1$,5-dimethylisophthalamide |
| 1536 | N$^1$-(sec-butyl)-N$^3$-{(1S,2R)-1-(3,5-difluorobenzyl)-3-[(3-ethylbenzyl)amino]-2-hydroxypropyl}-5-methyl-N$^1$-propylisophthalamide |
| 1537 | N$^1$-((1S,2R)-1-(3,5-difluorobenzyl)-2-hydroxy-3-{[3-(4-methylthien-2-yl)benzyl]amino}propyl)-5-methyl-N$^3$,N$^3$-dipropylisophthalamide |
| 1538 | methyl 3-({[(2R,3S)-4-(3,5-difluorophenyl)-3-({3-[(dipropylamino)carbonyl]-5-methylbenzoyl}amino)-2-hydroxybutyl]amino}methyl)phenyl(methyl)carbamate |
| 1539 | N$^1$-((1S,2R)-2-hydroxy-1-(2,3,5-trifluorobenzyl)-3-{[3-(trifluoromethyl)benzyl]amino}propyl)-5-methyl-N$^3$,N$^3$-dipropylisophthalamide |
| 1540 | N$^1$-{(1S,2R)-1-(3,5-difluorobenzyl)-3-[(3-ethylbenzyl)amino]-2-hydroxypropyl}-N$^3$,N$^3$-diisobutyl-5-methylisophthalmide |
| 1541 | N$^1$-{(1S,2R)-1-(3,5-difluorobenzyl)-3-[(3-ethylbenzyl)amino]-2-hydroxypropyl}-N$^3$,5-dimethyl-N$^3$-(2-pyridin-2-ylethyl)isophthalamide |
| 1542 | N$^1$-{(1S,2R)-1-(3-fluoro-5-hydroxybenzyl)-2-hydroxy-3-[(3-methoxybenzyl)amino]propyl}-5-methyl-N$^3$,N$^3$-dipropylisophthalamide hydrochloride |
| 1544 | N-{(1S,2R)-1-(3,5-difluorobenzyl)-2-hydroxy-3-[(3-iodobenzyl)amino]propyl}-4-hydroxy-3-(pyrrolidin-1-ylcarbonyl)benzamide |
| 1545 | 5-oxo-D-prolyl-N$^1$-{(1S,2R)-1-(3,5-difluorobenzyl)-3-[(3-ethylbenzyl)amino]-2-hydroxypropyl}-3-[(1-propylbutyl)sulfonyl]alaninamide hydrochloride |
| 1546 | N-{(1S,2R)-1-(3,5-difluorobenzyl)-3-[(3-ethylbenzyl)amino]-2-hydroxypropyl}-4-{[(trifluoromethyl)sulfonyl]amino}benzamide |
| 1547 | N$^1$-{(1S,2R)-1-(3,5-difluorobenzyl)-2-hydroxy-3-[(3-pyridin-4-ylbenzyl)amino]propyl}-5-methyl-N$^3$,N$^3$-dipropylisophthalamide |
| 1549 | N$^1$-{(1S,2R)-1-(3,5-difluorobenzyl)-2-hydroxy-3-[(6-methoxy-1,2,3,4-tetrahydronaphthalen-1-yl)amino]propyl}-5-methyl-N$^3$,N$^3$-dipropylisophthalamide |
| 1550 | N$^1$-{(1S,2R)-1-(3,5-difluorobenzyl)-3-[(3-ethylbenzyl)amino]-2-hydroxypropyl}-N$^2$-(phenylacetyl)-3-[(1-propylbutyl)sulfonyl]alaninamide |
| 1552 | methyl 3-({[(2R,3S)-4-(3,5-difluorophenyl)-3-({3-[(dipropylamino)carbonyl]-5-methylbenzoyl}amino)-2-hydroxybutyl]amino}methyl)phenylcarbamate |
| 1553 | 5-oxo-L-prolyl-N$^1$-{(1S,2R)-1-(3,5-difluorobenzyl)-3-[(3-ethylbenzyl)amino]-2-hydroxypropyl}-3-[(1-propylbutyl)sulfonyl]alaninamide hydrochloride |
| 1554 | N$^1$-{(1S,2R)-1-(3,5-difluorobenzyl)-3-[(3-ethylbenzyl)amino]-2-hydroxypropyl}-N$^3$-isobutyl-5-methylisophthalamide |
| 1555 | 4-({(1S,2R)-1-(3,5-difluorobenzyl)-3-[(3-ethylbenzyl)amino]-2-hydroxypropyl}amino)-4-oxo-3-{[(1-propylbutyl)sulfonyl]methyl}butanoic acid trifluoroacetate |
| 1556 | N-{(1S,2R)-1-(3,5-difluorobenzyl)-3-[(3-ethylbenzyl)amino]-2-hydroxpropyl}-3-[methyl(methylsulfonyl)amino]benzamide |
| 1557 | N$^1$-{(1S,2R)-1-(3,5-difluorobenzyl)-3-[(3-ethylbenzyl)amino]-2-hydroxypropyl}-N$^3$-ethyl-N$^3$-isopropyl-5-methylisophthalamide |
| 1558 | N$^1$-[(1S,2R)-2-hydroxy-3-[(3-methoxybenzyl)amino]-1-(thien-2-ylmethyl)propyl]-5-methyl-N$^3$,N$^3$-dipropylisophthalamide |
| 1559 | N-{(1S,2R)-1-(3,5-difluorobenzyl)-3-[(3-ethylbenzyl)amino]-2-hydroxypropyl}-3-{[(2-hydroxyethyl)(propyl)amino]sulfonyl}propanamide |
| 1560 | N$^1$-{(1S,2R)-1-(3,5-difluorobenzyl)-3-[(3-ethylbenzyl)amino]-2-hydroxypropyl}-N$^3$-isopropyl-N$^3$,5-dimethylisophthalamide |
| 1561 | N-{(1S,2R)-1-(3,5-difluorobenzyl)-3-[(3-ethylbenzyl)amino]-2-hydroxypropyl}-2-[(methylsulfonyl)amino]-1,3-thiazole-4-carboxamide |
| 1562 | N$^1$-allyl-N$^1$-cyclopentyl-N$^3$-{(1S,2R)-1-(3,5-difluorobenzyl)-3-[(3-ethylbenzyl)amino]-2-hydroxypropyl}-5-methylisophthalamide |
| 1563 | N-(3-({(1S,2R)-1-(3,5-difluorobenzyl)-3-[(3-ethylbenzyl)amino]-2-hydroxypropyl}amino)-3-oxo-2-{[(1-propylbutyl)sulfonyl]methyl}propyl)benzamide |
| 1564 | N-{(1S,2R)-1-(3,5-difluorobenzyl)-3-[(3-ethylbenzyl)amino]-2-hydroxypropyl}-3-(isopentylsulfonyl)propanamide |
| 1565 | N$^1$-((1S,2R)-1-(3,5-difluorobenzyl)-2-hydroxy-3-{[3-(5-methylthien-2-yl)benzyl]amino}propyl)-5-methyl-N$^3$,N$^3$-dipropylisophthalamide |
| 1567 | N$^1$-{(1S,2R)-1-(3,5-difluorobenzyl)-2-hydroxy-3-[(1-methylhexyl)amino]propyl}-5-methyl-N$^3$,N$^3$-dipropylisophthalamide |
| 1568 | N$^1$-[(1S,2R)-3-{[1-(aminocarbonyl)cyclohexyl]amino}-1-(3,5-difluorobenzyl)-2-hydroxypropyl]-5-methyl-N$^3$,N$^3$-dipropylisophthalamide |
| 1569 | N$^1$-{(1S,2R)-1-(3,5-difluorobenzyl)-3-[(2E)-hex-2-enylamino]-2-hydroxypropyl}-5-methyl-N$^3$,N$^3$-dipropylisophthalamide |

| | Compound Name (IUPAC Name) |
|---|---|
| 1571 | N-{(1S,2R)-1-(3,5-difluorobenzyl)-3-[(3-ethylbenzyl)amino]-2-hydroxypropyl}-3-hydroxyisoxazole-5-carboxamide |
| 1572 | $N^1$-[(1S,2R)-1-(3,5-difluorobenzyl)-3-({3-[(1E)-hex-1-enyl]benzyl}amino)2-hydroxypropyl]-5-methyl-$N^3$,$N^3$-dipropylisophthalamide |
| 1573 | $N^1$-{(1S,2R)-1-(3,5-difluorobenzyl)-3-[(3-ethylbenzyl)amino]-2-hydroxypropyl}-$N^3$-isopropyl-5-methylisophthalamide |
| 1574 | $N^1$-[(1S,2R)-2-hydroxy-3-[(3-methoxybenzyl)amino]-1-(thien-2-ylmethyl)propyl]-$N^3$,$N^3$-dipropylbenzene-1,3,5-tricarboxamide |
| 1575 | 2-[3-(2-amino-2-oxoethoxy)phenyl]-N-{(1S,2R)-1-(3,5-difluorobenzyl)-2-hydroxy-3-[(3-iodobenzyl)amino]propyl}acetamide |
| 1576 | $N^1$-{(1S,2R)-1-(3-bromobenzyl)-2-hydroxy-3-[(3-methoxybenzyl)amino]propyl}-5-methyl-$N^3$,$N^3$-dipropylisophthalamide |
| 1577 | $N^1$-{(1S,2R)-1-(3,5-difluorobenzyl)-3-[(2-ethylhexyl)amino]-2-hydroxypropyl}-5-methyl-$N^3$,$N^3$-dipropylisophthalamide |
| 1578 | $N^1$-((1S,2R)-1-(3,5-difluorobenzyl)-2-hydroxy-3-{[3-(6-methoxypyridin-3-yl)benzyl]amino}propyl)-5-methyl-$N^3$,$N^3$-dipropylisophthalamide |
| 1579 | $N^1$-((1S,2R)-1-(3,5-difluorobenzyl)-3-{[3-(2,4-dimethoxypyrimidine-5-yl)benzyl]amino}-2-hydroxypropyl)-5-methyl-$N^3$,$N^3$-dipropylisophthalamide |
| 1580 | N-{(1S,2R)-1-(3,5-difluorobenzyl)-3-[(3-ethylbenzyl)amino]-2-hydroxypropyl}-3-(2-ethylbutanoyl)benzamide |
| 1581 | N-{(1S,2R)-1-(3,5-difluorobenzyl)-3-[(3-ethylbenzyl)amino]-2-hydroxypropyl}-3-[(4-hydroxypiperidin-1-yl)carbonyl]-5-methylbenzamide |
| 1582 | $N^1$-{(1S,2R)-1-(3-bromobenzyl)-2-hydroxy-3-[(3-methoxybenzyl)amino]propyl}-$N^3$,$N^3$-dipropylbenzene-1,3,5-tricarboxamide |
| 1583 | 4'-[4-({(1S,2R)-1-(3,5-difluorobenzyl)-2-hydroxy-3-[(3-iodobenzyl)amino]propyl}amino)-4-oxobutanoyl]-1,1'-biphenyl-2-carboxamide |
| 1585 | N-{(1S,2R)-1-(3,5-difluorobenzyl)-3-[(3-ethylbenzyl)amino]-2-hydroxypropyl}-3-[(3-hydroxypiperidin-1-yl)carbonyl]-5-methylbenzamide |
| 1586 | $N^1$-{(1S,2R)-1-(3,5-difluorobenzyl)-2-hydroxy-3-[(3-hydroxy-1-phenylpropyl)amino]propyl}-5-methyl-$N^3$,$N^3$-dipropylisophthalamide |
| 1587 | $N^1$-{(1S,2R)-1-(3,5-difluorobenzyl)-3-[(3-ethylbenzyl)amino]-2-hydroxypropyl}-$N^3$-[2-(dimethylamino)ethyl]-$N^3$-ethyl-5-methylisophthalamide |
| 1588 | N-{(1S,2R)-1-(3,5-difluorobenzyl)-3-[(3-ethylbenzyl)amino]-2-hydroxypropyl}-4-methyl-4H,6H-pyrrolo[1,2-a][4,1]benzoxazepine-4-carboxamide |
| 1589 | 2-(5-acetylthien-2-yl)-N-{(1S,2R)-1-(3,5-difluorobenzyl)-3-[(3-ethylbenzyl)amino]-2-hydroxypropyl}acetamide |
| 1591 | $N^1$-{(1S,2R)-1-(3,5-difluorobenzyl)-3-[(3-ethylbenzyl)amino]-2-hydroxypropyl}-$N^3$,$N^3$-diisopropyl-5-methylisophthalamide |
| 1592 | N-{(1S,2R)-1-(3,5-difluorobenzyl)-3-[(3-ethylbenzyl)amino]-2-hydroxypropyl}-3-[(methylsulfonyl)amino]benzamide |
| 1594 | N-{(1S,2R)-1-(3,5-difluorobenzyl)-2-hydroxy-3-[(3-iodobenzyl)amino]propyl}-2-[4-(2-oxopyrrolidin-1-yl)phenyl]acetamide |
| 1595 | N-{(1S,2R)-1-(3-chloro-5-fluorobenzyl)-2-hydroxy-3-[(3-methoxybenzyl)amino]propyl}-3-[(dipropylamino)sulfonyl]propanamide |
| 1596 | $N^1$-[(1S,2R)-1-(3-chloro-5-fluorobenzyl)-2-hydroxy-3-(isopentylamino)propyl]-$N^3$,$N^3$-dipropylbenzene-1,3,5-tricarboxamide |
| 1597 | N-{(1S,2R)-1-(3,5-difluorobenzyl)-3-[(3-ethylbenzyl)amino]-2-hydroxypropyl}-3-{[(1-methyl-1H-imidazol-4-yl)sulfonyl]amino}benzamide trihydrochloride |
| 1598 | $N^1$-[(1S,2R)-1-(3,5-difluorobenzyl)-2-hydroxy-3-(pentylamino)propyl]-5-methyl-$N^3$,$N^3$-dipropylisophthalamide |
| 1599 | $N^1$-{(1S,2R)-1-(4-fluorobenzyl)-2-hydroxy-3-[(3-methoxybenzyl)amino]propyl}-$N^3$,$N^3$-dipropylbenzene-1,3,5-tricarboxamide |
| 1600 | $N^1$-[(1S,2R)-3-(benzylamino)-1-(3-chloro-5-fluorobenzyl)-2-hydroxypropyl]-5-methyl-$N^3$,$N^3$-dipropylisophthalamide |
| 1601 | $N^1$-cyclohexyl-$N^3$-{(1S,2R)-1-(3,5-difluorobenzyl)-3-[(3-ethylbenzyl)amino]-2-hydroxypropyl}-$N^1$-ethyl-5-methylisophthalamide |
| 1602 | 2-{[(2R,3S)-4-(3,5-difluorophenyl)-3-({3-[(dipropylamino)carbonyl]-5-methylbenzoyl}amino)-2-hydroxybutyl]amino}ethyl 2,4-difluorophenylcarbamate |
| 1603 | N-{(1S,2R)-1-(3,5-difluorobenzyl)-3-[(3-ethylbenzyl)amino]-2-hydroxypropyl}-3-{[(2S)-2-(methoxymethyl)pyrrolidin-1-yl]carbonyl}-5-methylbenzamide hydrochloride |
| 1605 | $N^1$-[(1S,2R)-1-(3-bromobenzyl)-2-hydroxy-3-(isopentylamino)propyl]-$N^3$,$N^3$-dipropylbenzene-1,3,5-tricarboxamide |
| 1606 | N-{(1S,2R)-1-(3,5-difluorobenzyl)-3-[(3-ethylbenzyl)amino]-2-hydroxypropyl}-2,8-dimethylquinoline-3-carboxamide |
| 1607 | $N^1$-{(1S,2R)-1-(3,5-difluorobenzyl)-2-hydroxy-3-[(6-hydroxyhexyl)amino]propyl}-5-methyl-$N^3$,$N^3$-dipropylisophthalamide |
| 1608 | $N^1$-((1S,2R)-1-(3,5-difluorobenzyl)-2-hydroxy-3-{[(2R)-2-hydroxypropyl]amino}propyl)-5-methyl-$N^3$,$N^3$-dipropylisophthalamide |
| 1609 | N-{(1S,2R)-1-benzyl-2-hydroxy-3-[(3-methoxybenzyl)amino]propyl}-3-[(1-propylbutyl)sulfonyl]propanamide |
| 1610 | N-{(1S,2R)-1-(3,5-difluorobenzyl)-3-[(3-ethylbenzyl)amino]-2-hydroxypropyl}-3-{[(2-hydroxy-1,1-dimethylethyl)amino]sulfonyl}benzamide |
| 1611 | $N^1$-{(1S,2R)-1-(3,5-difluorobenzyl)-2-hydroxy-3-[(4-phenylbutyl)amino]propyl}-5-methyl-$N^3$,$N^3$-dipropylisophthalamide |
| 1612 | N-{(1S,2R)-1-(3,5-difluorobenzyl)-3-[(3-iodobenzyl)amino]-2-hydroxypropyl}-7-(1H-imidazol-1-yl)-5,6-dihydronaphthalene-2-carboxamide |
| 1613 | 3-(acetylamino)-N-{(1S,2R)-1-(3,5-difluorobenzyl)-3-[(3-ethylbenzyl)amino]-2-hydroxypropyl}-4-methylbenzamide |
| 1614 | $N^1$-[(1S,2R)-3-{[2-(aminosulfonyl)ethyl]amino}-1-(3,5-difluorobenzyl)-2-hydroxypropyl]-5-methyl-$N^3$,$N^3$-dipropylisophthalamide |
| 1615 | $N^1$-((1S,2R)-1-(3,5-difluorobenzyl)-3-{[2-(ethylthio)ethyl]amino}-2-hydroxypropyl)-5-methyl-$N^3$,$N^3$-dipropylisophthalamide |
| 1617 | $N^1$-[(1S,2R)-3-[benzyl(cyanomethyl)amino]-1-(3,5-difluorobenzyl)-2-hydroxypropyl]-5-methyl-$N^3$,$N^3$-dipropylisophthalamide |
| 1618 | $N^1$-{(1S,2R)-1-(3,5-difluorobenzyl)-2-hydroxy-3-[(2-hydroxypropyl)amino]propyl}-5-methyl-$N^3$,$N^3$-dipropylisophthalamide |
| 1619 | $N^1$-[(1S,2R)-3-[(3-butoxypropyl)amino]-1-(3,5-difluorobenzyl)-2-hydroxypropyl]-5-methyl-$N^3$,$N^3$-dipropylisophthalamide |
| 1620 | N-{(1S,2R)-1-(3,5-difluorobenzyl)-3-[(3-ethylbenzyl)amino]-2-hydroxypropyl}-3-{[2-(2-hydroxyethyl)piperidin-1-yl]carbonyl}-5-methylbenzamide |
| 1621 | methyl N-[(2R,3S)-4-(3,5-difluorophenyl)-3-({3-[(dipropylamino)carbonyl]-5-methylbenzoyl}amino)-2-hydroxybutyl]-beta-alaninate |
| 1622 | N-{(1S,2R)-1-(3,5-difluorobenzyl)-3-[(3-ethylbenzyl)amino]-2-hydroxypropyl}-3-(1-hydroxy-2-propylpentyl)benzamide |
| 1623 | $N^1$-[(1S,2R)-3-(benzylamino)-1-(3-chloro-5-fluorobenzyl)-2-hydroxypropyl]-$N^3$,$N^3$-dipropylbenzene-1,3,5-tricarboxamide |

| | Compound Name (IUPAC Name) |
|---|---|
| 1624 | N-{(1S,2R)-1-(3,5-difluorobenzyl)-3-[(3-ethylbenzyl)amino]-2-hydroxypropyl}-4-[(methylsulfonyl)amino]butanamide |
| 1625 | $N^1$-[(1S,2R)-3-{[3-(1-benzothien-2-yl)benzyl]amino}-1-(3,5-difluorobenzyl)-2-hydroxypropyl]-5-methyl-$N^3,N^3$-dipropylisophthalamide |
| 1626 | 3-(benzyloxy)-N-{(1S,2R)-1-(3,5-difluorobenzyl)-3-[(3-ethylbenzyl)amino]-2-hydroxypropyl}isoxazole-5-carboxamide |
| 1627 | 2-{[(benzyloxy)carbonyl]amino}-7-[(cyclopropylmethyl)amino]-1,2,4,5,7-pentadeoxy-5-(3,5-difluorobenzyl)-1-[(1-propylbutyl)sulfonyl]-D-threo-hept-3-ulose trifluoroacetate |
| 1629 | N-{(1S,2R)-1-(3,5-difluorobenzyl)-3-[(3-ethylbenzyl)amino]-2-hydroxypropyl}-5-(1H-pyrazol-1-yl)pentanamide |
| 1630 | N-{(1S,2R)-1-(3,5-difluorobenzyl)-3-[(3-ethylbenzyl)amino]-2-hydroxypropyl}-1-(2-furylmethyl)-5-oxopyrrolidine-3-carboxamide |
| 1632 | $N^1$-{(1S,2R)-1-(3,5-difluorobenzyl)-2-hydroxy-3-[(5-hydroxypentyl)amino]propyl}-5-methyl-$N^3,N^3$-dipropylisophthalamide |
| 1633 | 3-[({(1S,2R)-1-(3,5-difluorobenzyl)-2-hydroxy-3-[(1-methyl-1-phenylethyl)amino]propyl}amino)sulfonyl]-N,N-dipropylbenzamide |
| 1634 | $N^1$-{(1S,2R)-1-(3,5-difluorobenzyl)-2-hydroxy-3-[(3-methoxybenzyl)amino]propyl}-$N^3,N^3$-dipropylpiperidine-1,3-dicarboxamide |
| 1635 | $N^1$-{(1S,2R)-1-(3,5-difluorobenzyl)-2-hydroxy-3-[(3-methoxybenzyl)amino]propyl}-$N^3,N^3$-diethylpiperidine-1,3-dicarboxamide |
| 1636 | 5-bromo-$N^1$-((1S,2R)-2-hydroxy-1-(pentafluorobenzyl)-3-{[3-(trifluoromethyl)benzyl]amino}propyl)-$N^3,N^3$-dipropylisophthalamide |
| 1637 | N-{(1S,2R)-1-(3,5-difluorobenzyl)-3-[(3-ethylbenzyl)amino]-2-hydroxypropyl}-4-[(methylsulfonyl)amino]benzamide |
| 1638 | N-{(1S,2R)-1-(3-bromobenzyl)-2-hydroxy-3-[(3-methoxybenzyl)amino]propyl}-3-[(dipropylamino)sulfonyl]propanamide |
| 1639 | 3-[(dipropylamino)sulfonyl]-N-[(1S,2R)-2-hydroxy-3-[(3-methoxybenzyl)amino]-1-(thien-2-ylmethyl)propyl]propanamide |
| 1640 | $N^1$-{(1S,2R)-1-(3,5-difluorobenzyl)-3-[(3-ethoxypropyl)amino]-2-hydroxypropyl}-5-methyl-$N^3,N^3$-dipropylisophthalamide |
| 1641 | $N^1$-[(1S,2R)-3-(benzylamino)-2-hydroxy-1-(thien-2-ylmethyl)propyl]-5-methyl-$N^3,N^3$-dipropylisophthalamide |
| 1642 | N-{(1S,2R)-1-(3,5-difluorobenzyl)-3-[(3-ethylbenzyl)amino]-2-hydroxypropyl}-2-hydroxy-4-(phenylsulfonyl)butanamide |
| 1643 | $N^1$-[(1S,2R)-1-(3,4-dichlorobenzyl)-2-hydroxy-3-(isopentylamino)propyl]-$N^3,N^3$-dipropylbenzene-1,3,5-tricarboxamide |
| 1645 | $N^1$-{(1S,2R)-1-(3,5-difluorobenzyl)-3-[(3,3-dimethylbutyl)amino]-2-hydroxypropyl}-5-methyl-$N^3,N^3$-dipropylisophthalamide |
| 1646 | $N^1$-[(1S,2R)-3-(benzylamino)-1-(3-bromobenzyl)-2-hydroxypropyl]-$N^3,N^3$-dipropylbenzene-1,3,5-tricarboxamide |
| 1647 | $N^1$-[(1S,2R)-1-(3-chloro-5-fluorobenzyl)-2-hydroxy-3-(isopentylamino)propyl]-5-methyl-$N^3,N^3$-dipropylisophthalamide |
| 1648 | $N^1$-[(1S,2R)-1-(3,5-difluorobenzyl)-3-[(1,3-diphenylpropyl)amino]-2-hydroxypropyl}-5-methyl-$N^3,N^3$-dipropylisophthalamide |
| 1649 | $N^1$-((1S,2R)-1-(3,5-difluorobenzyl)-2-hydroxy-3-{[(1S)-1-(hydroxymethyl)propyl]amino}propyl)-$N^3,N^3$-dipropylisophthalamide |
| 1650 | $N^1$-((1S,2R)-1-(3,5-difluorobenzyl)-2-hydroxy-3-{[(3S)-2-oxoazepan-3-yl]amino}propyl)-5-methyl-$N^3,N^3$-dipropylisophthalamide |
| 1651 | $N^1$-cyclohexyl-$N^5$-{(1S,2R)-1-(3,5-difluorobenzyl)-3-[(3-ethylbenzyl)amino]-2-hydroxypropyl}pentanediamide |
| 1652 | $N^1$-[(1S,2R)-2-hydroxy-3-[(3-methoxybenzyl)amino]-1-(3-methylbenzyl)propyl]-$N^3,N^3$-dipropylbenzene-1,3,5-tricarboxamide |
| 1653 | $N^1$-{(1S,2R)-1-(3,5-difluorobenzyl)-3-[(3-ethylbenzyl)amino]-2-hydroxypropyl}-$N^3$-[(2-propylpentyl)sulfonyl]-beta-alaninamide |
| 1654 | N-{(1S,2R)-1-(3,5-difluorobenzyl)-3-[(3-ethylbenzyl)amino]-2-hydroxypropyl}-3-(1,3-thiazol-2-yl)benzamide dihydrochloride |
| 1656 | $N^1$-[(1S,2R)-1-(3,5-difluorobenzyl)-2-hydroxy-3-({3-[methyl(phenyl)amino]propyl}amino)propyl]-5-methyl-$N^3,N^3$-dipropylisophthalamide |
| 1657 | $N^1$-[(1S,2R)-2-hydroxy-3-[(3-methoxybenzyl)amino]-1-(4-methylbenzyl)propyl]-$N^3,N^3$-dipropylbenzene-1,3,5-tricarboxamide |
| 1658 | N-{(1S,2R)-1-(3,5-difluorobenzyl)-3-[(3-ethylbenzyl)amino]-2-hydroxypropyl}-5-oxo-1-(thien-2-ylmethyl)pyrrolidine-3-carboxamide |
| 1659 | 4-[(butylthio)methyl]-N-{(1S,2R)-1-(3,5-difluorobenzyl)-3-[(3-ethylbenzyl)amino]-2-hydroxypropyl}-5-methyl-2-furamide |
| 1660 | N-{(1S,2R)-1-(3,5-difluorobenzyl)-3-[(3-ethylbenzyl)amino]-2-hydroxypropyl}-3-{[(2-hydroxyethyl)amino]sulfonyl}benzamide |
| 1661 | $N^1$-{(1S,2R)-1-(3,5-difluorobenzyl)-2-hydroxy-3-[(3-methylcyclohexyl)amino]propyl}-5-methyl-$N^3,N^3$-dipropylisophthalamide |
| 1662 | N-{(1S,2R)-1-(3,5-difluorobenzyl)-3-[(3-ethylbenzyl)amino]-2-hydroxypropyl}-4-(2-oxo-1,3-oxazolidin-3-yl)benzamide |
| 1663 | N-{(1S,2R)-1-(3,5-difluorobenzyl)-3-[(3-ethylbenzyl)amino]-2-hydroxypropyl}-4-(1H-pyrrol-1-yl)benzamide |
| 1665 | N-{(1S,2R)-1-(3,5-difluorobenzyl)-3-[(3-ethylbenzyl)amino]-2-hydroxypropyl}-1,3,4,5-tetrahydrothiopyrano[4,3-b]indole-8-carboxamide |
| 1666 | $N^1$-{(1S,2R)-1-(3,5-difluorobenzyl)-3-[(3-ethylbenzyl)amino]-2-hydroxypropyl}-$N^4$-[2-(trifluoromethyl)phenyl]succinamide |
| 1667 | $N^1$-[(1S,2R)-1-(3-bromobenzyl)-2-hydroxy-3-(isopentylamino)propyl]-5-methyl-$N^3,N^3$-dipropylisophthalamide |
| 1668 | N-{(1S,2R)-1-(3,5-difluorobenzyl)-3-[(3-ethylbenzyl)amino]-2-hydroxypropyl}-4,5-dimethyl-2-(1H-pyrrol-1-yl)thiophene-3-carboxamide |
| 1669 | $N^1$-{(1S,2R)-1-(3,5-difluorobenzyl)-3-[(2,3-dihydroxypropyl)amino]-2-hydroxypropyl}-5-methyl-$N^3,N^3$-dipropylisophthalamide |
| 1670 | $N^1$-((1S,2R)-1-(3,5-difluorobenzyl)-2-hydroxy-3-{[(2S)-2-hydroxypropyl]amino}propyl)-5-methyl-$N^3,N^3$-dipropylisophthalamide |
| 1671 | $N^1$-((1S,2R)-1-(3,5-difluorobenzyl)-2-hydroxy-3-{[(1R)-1-methylpropyl]amino}propyl)-5-methyl-$N^3,N^3$-dipropylisophthalamide |
| 1672 | 2-chloro-N-{(1S,2R)-1-(3,5-difluorobenzyl)-3-[(3-ethylbenzyl)amino]-2-hydroxypropyl}-4-(methylsulfonyl)benzamide |
| 1673 | $N^1$-{(1S,2R)-1-(3,5-difluorobenzyl)-2-hydroxy-3-[(2-hydroxyethyl)amino]propyl}-5-methyl-$N^3,N^3$-dipropylisophthalamide |
| 1674 | 3-[(dipropylamino)sulfonyl]-N-{(1S,2R)-2-hydroxy-1-(3-methoxybenzyl)-3-[(3-methoxybenzyl)amino]propyl}propanamide |
| 1675 | N-{(1S,2R)-1-(3,5-difluorobenzyl)-3-[(3-ethylbenzyl)amino]-2-hydroxypropyl}-3-{methyl[(trifluoromethyl)sulfonyl]amino}benzamide |
| 1676 | N-{(1S,2R)-1-(3,5-difluorobenzyl)-3-[(3-ethylbenzyl)amino]-2-hydroxypropyl}-3-hydroxy-6-(1-hydroxy-2,2-dimethylpropyl)pyridine-2-carboxamide |
| 1677 | $N^1$-[(1S,2R)-3-[(1,3-dicyclohexylpropyl)amino]-1-(3,5-difluorobenzyl)-2-hydroxypropyl]-5-methyl-$N^3,N^3$-dipropylisophthalamide |

| | Compound Name (IUPAC Name) |
|---|---|
| 1678 | N-{(1S,2R)-1-(3,5-difluorobenzyl)-3-[(3-ethylbenzyl)amino]-2-hydroxypropyl}-2,2'-bithiophene-5-carboxamide |
| 1679 | N-{(1S,2R)-1-(3,5-difluorobenzyl)-3-[(3-ethylbenzyl)amino]-2-hydroxypropyl}-4-(1H-imidazol-1-yl)butanamide |
| 1680 | $N^1$-{(1S,2R)-1-(3,5-difluorobenzyl)-3-[(3-ethylbenzyl)amino]-2-hydroxypropyl}-2,3-dihydroxy-$N^4$-(4-methoxyphenyl)succinamide |
| 1682 | $N^1$-{(1S,2R)-2-hydroxy-3-[(3-methoxybenzyl)amino]-1-[3-(trifluoromethyl)benzyl]propyl}-$N^3$,$N^3$-dipropylbenzene-1,3,5-tricarboxamide |
| 1683 | $N^1$-[(1S,2R)-3-(benzylamino)-2-hydroxy-1-(thien-2-ylmethyl)propyl]-$N^3$,$N^3$-dipropylbenzene-1,3,5-tricarboxamide |
| 1684 | $N^1$-[(1S,2R)-3-{[2-(aminocarbonyl)-1H-indol-6-yl]amino}-1-(3,5-difluorobenzyl)-2-hydroxypropyl]-5-methyl-$N^3$,$N^3$-dipropylisophthalamide |
| 1685 | $N^1$-[(1S,2R)-3-(benzylamino)-1-(3-bromobenzyl)-2-hydroxypropyl]-5-methyl-$N^3$,$N^3$-dipropylisophthalamide |
| 1686 | N-{(1S,2R)-1-(3,5-difluorobenzyl)-3-[(3-ethylbenzyl)amino]-2-hydroxypropyl}-2-(1-oxo-1,3-dihydro-2H-isoindol-2-yl)butanamide |
| 1687 | 3-chloro-N-{(1S,2R)-1-(3,5-difluorobenzyl)-3-[(3-ethylbenzyl)amino]-2-hydroxypropyl}-4-(methylsulfonyl)thiophene-2-carboxamide |
| 1688 | $N^1$-{(1S,2R)-1-(3,5-difluorobenzyl)-3-[(1-ethylpropyl)amino]-2-hydroxypropyl}-5-methyl-$N^3$,$N^3$-dipropylisophthalamide |
| 1689 | $N^1$-[(1S,2R)-1-(3,5-difluorobenzyl)-3-({[(5R)-3-ethyl-2-oxo-1,3-oxazolidin-5-yl]methyl}amino)-2-hydroxypropyl]-5-methyl-$N^3$,$N^3$-dipropylisophthalamide |
| 1690 | N-{(1S,2R)-1-(3,5-difluorobenzyl)-3-[(3-ethylbenzyl)amino]-2-hydroxypropyl}-5-methyl-7-(trifluoromethyl)pyrazolo[1,5-a]pyrimidine-2-carboxamide |
| 1691 | $N^1$-{(1S,2R)-1-benzyl-2-hydroxy-3-[(3-methoxybenzyl)amino]propyl}-$N^2$-[(methylthio)acetyl]-3-[(1-propylbutyl)sulfonyl]alaninamide hydrochloride |
| 1692 | $N^1$-{(1S,2R)-1-(3,5-difluorobenzyl)-3-[(2,3-dimethylcyclohexyl)amino]-2-hydroxypropyl}-5-methyl-$N^3$,$N^3$-dipropylisophthalamide |
| 1693 | N-{(1S,2R)-1-(3,5-difluorobenzyl)-3-[(3-ethylbenzyl)amino]-2-hydroxypropyl}-4,5-dimethoxy-1-benzothiophene-2-carboxamide |
| 1694 | $N^1$-[(1S,2R)-1-[3-fluoro-5-(trifluoromethyl)benzyl]-2-hydroxy-3-(isopentylamino)propyl]-$N^3$,$N^3$-dipropylbenzene-1,3,5-tricarboxamide |
| 1695 | $N^1$-[(1S,2R)-1-(3,5-difluorobenzyl)-3-({[(5S)-3-ethyl-2-oxo-1,3-oxazolidin-5-yl]methyl}amino)-2-hydroxypropyl]-5-methyl-$N^3$,$N^3$-dipropylisophthalamide |
| 1696 | $N^1$-{(1S,2R)-1-(1,3-benzodioxol-5-ylmethyl)-2-hydroxy-3-[(3-methoxybenzyl)amino]propyl}-$N^3$,$N^3$-dipropylbenzene-1,3,5-tricarboxamide |
| 1697 | N-{(1S,2R)-1-(3,5-difluorobenzyl)-3-[(3-ethylbenzyl)amino]-2-hydroxypropyl}-4-(3,5-dioxo-1,2,4-triazolidin-4-yl)benzamide |
| 1698 | N-{(1S,2R)-1-benzyl-2-hydroxy-3-[(3-methoxybenzyl)amino]propyl}-2-hydroxy-3-[(3-methoxyphenyl)sulfonyl]propanamide hydrochloride |
| 1699 | $N^1$-{(1S,2R)-1-(3,5-difluorobenzyl)-2-hydroxy-3-[(2-methylcyclohexyl)amino]propyl}-5-methyl-$N^3$,$N^3$-dipropylisophthalamide |
| 1700 | $N^1$-[(1S,2R)-3-[(2-{4-[(3-chlorobenzyl)oxy]phenyl}ethyl)amino]-1-(3,5-difluorobenzyl)-2-hydroxypropyl]-5-methyl-$N^3$,$N^3$-dipropylisophthalamide |
| 1701 | N-{(1S,2R)-1-(3,5-difluorobenzyl)-3-[(3-ethylbenzyl)amino]-2-hydroxypropyl}-2-hydroxy-4-oxo-4-thien-3-ylbutanamide |
| 1702 | $N^1$-{(1S,2R)-1-[3-(benzyloxy)-5-fluorobenzyl]-2-hydroxy-3-[(3-methoxybenzyl)amino]propyl}-$N^3$,$N^3$-dipropylbenzene-1,3,5-tricarboxamide |
| 1703 | N-{(1S,2R)-1-(3,5-difluorobenzyl)-3-[(3-ethylbenzyl)amino]-2-hydroxypropyl}-2-hydroxy-4-oxo-4-[3-(trifluoromethyl)phenyl]butanamide |
| 1704 | $N^1$-{(1S,2R)-2-hydroxy-3-(isopentylamino)-1-[3-(trifluoromethoxy)benzyl]propyl}-$N^3$,$N^3$-dipropylbenzene-1,3,5-tricarboxamide |
| 1705 | $N^1$-((1S,2R)-1-(3,5-difluorobenzyl)-2-hydroxy-3-{[1-(hydroxymethyl)-3-(methylthio)propyl]amino}propyl)-5-methyl-$N^3$,$N^3$-dipropylisophthalamide |
| 1706 | 2-(1H-1,2,3-benzotriazol-1-yl)-N-{(1S,2R)-1-(3,5-difluorobenzyl)-3-[(3-ethylbenzyl)amino]-2-hydroxypropyl}hexanamide |
| 1707 | $N^1$-[(1S,2R)-1-(3-fluoro-4-methylbenzyl)-2-hydroxy-3-(isopentylamino)propyl]-$N^3$,$N^3$-dipropylbenzene-1,3,5-tricarboxamide |
| 1708 | N-{(1S,2R)-1-(3,5-difluorobenzyl)-3-[(3-ethylbenzyl)amino]-2-hydroxypropyl}-3-(4,4-dimethyl-2,5-dioxoimidazolidin-1-yl)-2-{[(1-propylbutyl)sulfonyl]methyl}propanamide |
| 1709 | N-{(1S,2R)-1-(3,5-difluorobenzyl)-3-[(3-ethylbenzyl)amino]-2-hydroxypropyl}-4-{[(trifluoromethyl)sulfonyl]amino}butanamide |
| 1710 | N-{(1S,2R)-1-(3,5-difluorobenzyl)-3-[(3-ethylbenzyl)amino]-2-hydroxypropyl}-2-(5-methyl-1,3-dioxo-1,3-dihydro-2H-isoindol-2-yl)acetamide |
| 1712 | $N^1$-((1S,2R)-1-(3,5-difluorobenzyl)-2-hydroxy-3-{[1-(hydroxymethyl)propyl]amino}propyl)-5-methyl-$N^3$,$N^3$-dipropylisophthalamide |
| 1713 | $N^1$-[(1S,2R)-3-(benzylamino)-1-(3,5-dichlorobenzyl)-2-hydroxypropyl]-$N^3$,$N^3$-dipropylbenzene-1,3,5-tricarboxamide |
| 1714 | N-{(1S,2R)-1-benzyl-2-hydroxy-3-[(3-methoxybenzyl)amino]propyl}-3-{[(2-hydroxyethyl)(propyl)amino]sulfonyl}propanamide hydrochloride |
| 1715 | 5-(benzylthio)-N-{(1S,2R)-1-(3,5-difluorobenzyl)-3-[(3-ethylbenzyl)amino]-2-hydroxypropyl}nicotinamide |
| 1716 | N-{(1S,2R)-1-(3,5-difluorobenzyl)-3-[(3-ethylbenzyl)amino]-2-hydroxypropyl}-1H-pyrazole-5-carboxamide |
| 1717 | 6-chloro-N-{(1S,2R)-1-(3,5-difluorobenzyl)-3-[(3-ethylbenzyl)amino]-2-hydroxypropyl}-3-methyl-2-oxo-2,3-dihydro-1,3-benzoxazole-5-carboxamide |
| 1718 | N-{(1S,2R)-1-(3,5-difluorobenzyl)-3-[(3-ethylbenzyl)amino]-2-hydroxypropyl}-1H-benzimidazole-2-carboxamide |
| 1719 | $N^1$-{(1S,2R)-1-(cyclohexylmethyl)-2-hydroxy-3-[(3-methoxybenzyl)amino]propyl}-$N^3$,$N^3$-dipropylbenzene-1,3,5-tricarboxamide |
| 1720 | N-{(1S,2R)-1-(3,5-difluorobenzyl)-3-[(3-ethylbenzyl)amino]-2-hydroxypropyl}-6-hydroxy-4,7-dimethoxy-1-benzofuran-5-carboxamide |
| 1721 | $N^1$-{(1S,2R)-1-(3,5-difluorobenzyl)-2-hydroxy-3-[(4-methylcyclohexyl)amino]propyl}-5-methyl-$N^3$,$N^3$-dipropylisophthalamide |
| 1722 | N-{(1S,2R)-1-(3,5-difluorobenzyl)-3-[(3-ethylbenzyl)amino]-2-hydroxypropyl}[1,2,4]triazolo[4,3-a]pyridine-6-carboxamide |
| 1723 | N-{(1S,2R)-1-(3,5-difluorobenzyl)-3-[(3-ethylbenzyl)amino]-2-hydroxypropyl}-2-hydroxy-4-oxo-4-thien-2-ylbutanamide |
| 1724 | $N^1$-[(1S,2R)-3-(benzylamino)-1-(3,5-dichlorobenzyl)-2-hydroxypropyl]-5-methyl-$N^3$,$N^3$-dipropylisophthalamide |
| 1725 | N-{(1S,2R)-1-(3,5-difluorobenzyl)-3-[(3-ethylbenzyl)amino]-2-hydroxypropyl}-4-(2-hydroxy-5-methylphenyl)-4-oxobutanamide |
| 1726 | N-{(1S,2R)-1-(3,5-difluorobenzyl)-3-[(3-ethylbenzyl)amino]-2-hydroxypropyl}-3-phenoxybenzamide |

| | Compound Name (IUPAC Name) |
|---|---|
| 1727 | 4-[(aminocarbonyl)amino]-N-{(1S,2R)-1-(3,5-difluorobenzyl)-3-[(3-ethylbenzyl)amino]-2-hydroxypropyl}benzamide |
| 1728 | $N^1$-((1S,2R)-1-(3,5-difluorobenzyl)-2-hydroxy-3-{[(1S)-1-(hydroxymethyl)-3-(methylthio)propyl]amino}propyl)-5-methyl-$N^3$,$N^3$-dipropylisophthalamide |
| 1729 | N-{(1S,2R)-1-(3,5-difluorobenzyl)-3-[(3-ethylbenzyl)amino]-2-hydroxypropyl}-7-hydroxy-4-oxochromane-2-carboxamide |
| 1730 | $N^1$-((1S,2R)-1-(3,5-difluorobenzyl)-2-hydroxy-3-{[(1S)-1-(hydroxymethyl)-3-methylbutyl]amino}propyl)-5-methyl-$N^3$,$N^3$-dipropylisophthalamide |
| 1731 | $N^1$-((1S,2R)-1-(3,5-difluorobenzyl)-2-hydroxy-3-{[(1R)-1-(hydroxymethyl)propyl]amino}propyl)-$N^3$,$N^3$-dipropylisophthalamide |
| 1732 | $N^1$-{(1S,2R)-1-(3,5-difluorobenzyl)-2-hydroxy-3-[(1-methyl-3-phenylpropyl)amino]propyl}-5-methyl-$N^3$,$N^3$-dipropylisophthalamide |
| 1733 | N-{(1S,2R)-1-(3,5-difluorobenzyl)-3-[(3-ethylbenzyl)amino]-2-hydroxypropyl}-2-(2,3-dihydro-1-benzofuran-5-yl)-1,3-thiazole-4-carboxamide |
| 1734 | $N^1$-{(1S,2R)-1-[3-(benzyloxy)benzyl]-2-hydroxy-3-[(3-methoxybenzyl)amino]propyl}-5-methyl-$N^3$,$N^3$-dipropylisophthalamide |
| 1735 | N-{(1S,2R)-1-(4-chlorobenzyl)-2-hydroxy-3-[(3-methoxybenzyl)amino]propyl}-3-[(dipropylamino)sulfonyl]propanamide |
| 1736 | $N^1$-{(1S,2R)-1-(3,5-difluorobenzyl)-3-[(3-ethylbenzyl)amino]-2-hydroxypropyl}-$N^3$-pentylmalonamide |
| 1737 | N-{(1S,2R)-1-(3,5-difluorobenzyl)-3-[(3-ethylbenzyl)amino]-2-hydroxypropyl}-3-(trifluoromethoxy)benzamide |
| 1738 | 3-[(dipropylamino)sulfonyl]-N-{(1S,2R)-1-(3-fluoro-4-methylbenzyl)-2-hydroxy-3-[(3-methoxybenzyl)amino]propyl}propanamide |
| 1739 | N-[(1S,2R)-1-(3-chloro-5-fluorobenzyl)-2-hydroxy-3-(isopentylamino)propyl]-3-[(dipropylamino)sulfonyl]propanamide |
| 1740 | N-{(1S,2R)-1-(3,5-difluorobenzyl)-3-[(3-ethylbenzyl)amino]-2-hydroxypropyl}-3-(4,4-dimethyl-2,5-dioxoimidazolidin-1-yl)-2-{[(1-propylbutyl)sulfonyl]methyl}propanamide |
| 1741 | $N^1$-[4-(acetylamino)phenyl]-$N^4$-{(1S,2R)-1-(3,5-difluorobenzyl)-3-[(3-ethylbenzyl)amino]-2-hydroxypropyl}succinamide |
| 1742 | 3-(1-cyanoethyl)-N-{(1S,2R)-1-(3,5-difluorobenzyl)-3-[(3-ethylbenzyl)amino]-2-hydroxypropyl}benzamide |
| 1743 | $N^1$-{(1S,2R)-1-(3,5-difluorobenzyl)-3-[(3-ethylbenzyl)amino]-2-hydroxypropyl}-$N^4$-(5-phenyl-1,3,4-thiadiazol-2-yl)succinamide |
| 1744 | $N^1$-{(1S,2R)-3-(benzylamino)-2-hydroxy-1-[3-(trifluoromethoxy)benzyl]propyl}-$N^3$,$N^3$-dipropylbenzene-1,3,5-tricarboxamide |
| 1745 | $N^1$-{(1S,2R)-1-(3,5-difluorobenzyl)-2-hydroxy-3-{[2-(2-oxo-2-pyrrolidin-1-ylethoxy)phenyl]amino}propyl}-5-methyl-$N^3$,$N^3$-dipropylisophthalamide |
| 1746 | $N^1$-[(1S,2R)-1-(4-chlorobenzyl)-2-hydroxy-3-(isopentylamino)propyl]-$N^3$,$N^3$-dipropylbenzene-1,3,5-tricarboxamide |
| 1747 | N-{(1S,2R)-1-(3,5-difluorobenzyl)-3-[(3-ethylbenzyl)amino]-2-hydroxypropyl}-2-(1,1-dioxidotetrahydrothien-2-yl)acetamide |
| 1748 | $N^1$-[(1S,2R)-3-(benzylamino)-1-(4-chlorobenzyl)-2-hydroxypropyl]-5-methyl-$N^3$,$N^3$-dipropylisophthalamide |
| 1749 | N-{(1S,2R)-1-(3,5-difluorobenzyl)-3-[(3-ethylbenzyl)amino]-2-hydroxypropyl}-5-hex-1-ynylnicotinamide |
| 1750 | N-[(1S,2R)-1-(3-bromobenzyl)-2-hydroxy-3-(isopentylamino)propyl]-3-[(dipropylamino)sulfonyl]propanamide |
| 1751 | N-{(1S,2R)-1-(3,5-difluorobenzyl)-3-[(3-ethylbenzyl)amino]-2-hydroxypropyl}-3-methoxyisoxazole-5-carboxamide |
| 1752 | N-{(1S,2R)-1-(3,5-difluorobenzyl)-3-[(3-ethylbenzyl)amino]-2-hydroxypropyl}-2,3-dimethyl-1H-indole-7-carboxamide |
| 1753 | 4-(3-chlorophenyl)-N-{(1S,2R)-1-(3,5-difluorobenzyl)-3-[(3-ethylbenzyl)amino]-2-hydroxypropyl}-2-hydroxy-4-oxobutanamide |
| 1755 | N-{(1S,2R)-1-(3,5-difluorobenzyl)-3-[(3-ethylbenzyl)amino]-2-hydroxypropyl}-2-(1-methyl-1H-indol-3-yl)-2-oxoacetamide |
| 1756 | $N^1$-[(1S,2R)-1-(3-fluoro-4-methylbenzyl)-2-hydroxy-3-(isopentylamino)propyl]-5-methyl-$N^3$,$N^3$-dipropylisophthalamide |
| 1757 | 3-[(dipropylamino)sulfonyl]-N-[(1S,2R)-2-hydroxy-3-[(3-methoxybenzyl)amino]-1-(4-methylbenzyl)propyl]propanamide |
| 1758 | $N^1$-[(1S,2R)-3-(benzylamino)-1-(3-fluoro-4-methylbenzyl)-2-hydroxypropyl]-$N^3$,$N^3$-dipropylbenzene-1,3,5-tricarboxamide |
| 1759 | N-{(1S,2R)-1-(3,5-difluorobenzyl)-3-[(3-ethylbenzyl)amino]-2-hydroxypropyl}-2-[5-(4-methylphenyl)-2H-tetraazol-2-yl]acetamide |
| 1760 | N-{(1S,2R)-1-(3,5-dichlorobenzyl)-2-hydroxy-3-[(3-methoxybenzyl)amino]propyl}-3-[(dipropylamino)sulfonyl]propanamide |
| 1761 | $N^1$-[(1S,2R)-2-hydroxy-3-(isopentylamino)-1-(thien-2-ylmethyl)propyl]-$N^3$,$N^3$-dipropylbenzene-1,3,5-tricarboxamide |
| 1762 | N-{(1S,2R)-1-(3,5-difluorobenzyl)-3-[(3-ethylbenzyl)amino]-2-hydroxypropyl}-5-methyl-3-phenylisoxazole-4-carboxamide |
| 1764 | $N^1$-{(1S,2R)-1-(3,5-difluorobenzyl)-3-[(3-ethylbenzyl)amino]-2-hydroxypropyl}-$N^2$-[(methylsulfonyl)acetyl]-$N^2$-pentylglycinamide |
| 1765 | N-{(1S,2R)-1-(3,5-difluorobenzyl)-3-[(3-ethylbenzyl)amino]-2-hydroxypropyl}-4-(1H-indol-3-yl)-4-oxobutanamide |
| 1766 | $N^1$-(5-benzyl-1,3,4-thiadiazol-2-yl)-$N^4$-{(1S,2R)-1-(3,5-difluorobenzyl)-3-[(3-ethylbenzyl)amino]-2-hydroxypropyl}succinamide |
| 1767 | N-{(1S,2R)-1-(3,5-difluorobenzyl)-3-[(3-ethylbenzyl)amino]-2-hydroxypropyl}-4-(3-fluoro-4-methoxyphenyl)-4-oxobutanamide |
| 1768 | ethyl 4-{[(2R,3S)-4-(3,5-difluorophenyl)-3-({3-[(dipropylamino)carbonyl]-5-methylbenzoyl}amino)-2-hydroxybutyl]amino}piperidine-1-carboxylate |
| 1769 | N-{(1S,2R)-1-(3,5-difluorobenzyl)-3-[(3-ethylbenzyl)amino]-2-hydroxypropyl}-4-(2-fluorobenzoyl)-1H-pyrrole-2-carboxamide |
| 1770 | $N^1$-[(1S,2R)-3-(benzylamino)-1-(4-chlorobenzyl)-2-hydroxypropyl]-$N^3$,$N^3$-dipropylbenzene-1,3,5-tricarboxamide |
| 1772 | $N^1$-[(1S,2R)-2-hydroxy-1-(4-hydroxybenzyl)-3-(isopentylamino)propyl]-5-methyl-$N^3$,$N^3$-dipropylisophthalamide |
| 1773 | N-{(1S,2R)-1-(3,5-difluorobenzyl)-3-[(3-ethylbenzyl)amino]-2-hydroxypropyl}-2-(4-morpholin-4-ylphenyl)acetamide |
| 1774 | 3-[(dipropylamino)sulfonyl]-N-{(1S,2R)-2-hydroxy-3-[(3-methoxybenzyl)amino]-1-[3-(trifluoromethoxy)benzyl]propyl}propanamide |
| 1775 | $N^1$-benzyl-$N^1$-(1-cyclopropylethyl)-$N^4$-{(1S,2R)-1-(3,5-difluorobenzyl)-3-[(3-ethylbenzyl)amino]-2-hydroxypropyl}succinamide |
| 1776 | N-{(1S,2R)-1-(3,5-difluorobenzyl)-2-hydroxy-3-[(3-methoxybenzyl)amino]propyl}-3-(2,5-dimethylbenzoyl)-5-methylbenzamide |
| 1777 | $N^1$-{(1S,2R)-1-(3,5-difluorobenzyl)-3-[(3-ethylbenzyl)amino]-2-hydroxypropyl}-$N^4$-(2-methoxy-5-methylphenyl)succinamide |
| 1778 | N-{(1S,2R)-1-(3,5-difluorobenzyl)-3-[(3-ethylbenzyl)amino]-2-hydroxypropyl}-2-(3-hydroxyphenyl)acetamide |

| | Compound Name (IUPAC Name) |
|---|---|
| 1779 | N-{(1S,2R)-1-(3,5-difluorobenzyl)-2-hydroxy-3-[(3-methoxybenzyl)amino]propyl}-3-[hydroxy(2-methylphenyl)methyl]-5-methylbenzamide |
| 1780 | N-{(1S,2R)-1-(3,5-difluorobenzyl)-3-[(3-ethylbenzyl)amino]-2-hydroxypropyl}-5-(ethylthio)nicotinamide |
| 1781 | N-{(1S,2R)-1-(3,5-difluorobenzyl)-3-[(3-ethylbenzyl)amino]-2-hydroxypropyl}-4-[4-(2-furoyl)piperazin-1-yl]-4-oxobutanamide |
| 1782 | $N^1$-[(1S,2R)-3-(benzylamino)-1-(3-fluoro-4-methylbenzyl)-2-hydroxypropyl]-5-methyl-$N^3$,$N^3$-dipropylisophthalamide |
| 1783 | N-{(1S,2R)-1-(3,5-difluorobenzyl)-3-[(3-ethylbenzyl)amino]-2-hydroxypropyl}-3-oxoisoindoline-1-carboxamide |
| 1784 | N-{(1S,2R)-1-(3,5-difluorobenzyl)-3-[(3-ethylbenzyl)amino]-2-hydroxypropyl}-3-(ethylthio)benzamide |
| 1785 | N-{(1S,2R)-1-(3,5-difluorobenzyl)-3-[(3-ethylbenzyl)amino]-2-hydroxypropyl}thieno[2,3-b]quinoline-2-carboxamide |
| 1786 | N-{(1S,2R)-1-(3,5-difluorobenzyl)-3-[(3-ethylbenzyl)amino]-2-hydroxypropyl}-3-(4-methyl-1,3-oxazol-2-yl)benzamide |
| 1788 | N-{2-[({(1S,2R)-1-(3,5-difluorobenzyl)-3-[(3-ethylbenzyl)amino]-2-hydroxypropyl}amino)carbonyl]phenyl}-N-methyl-2-furamide |
| 1789 | N-{(1S,2R)-1-(3,5-difluorobenzyl)-3-[(3-ethylbenzyl)amino]-2-hydroxypropyl}-2-hydroxy-4-(3-methoxyphenyl)-4-oxobutanamide |
| 1790 | $N^1$-[(1S,2R)-3-(cycloheptylamino)-1-(3,5-difluorobenzyl)-2-hydroxypropyl]-5-methyl-$N^3$,$N^3$-dipropylisophthalamide |
| 1791 | $N^1$-[(1S,2R)-2-hydroxy-3-(isopentylamino)-1-(4-methylbenzyl)propyl]-$N^3$,$N^3$-dipropylbenzene-1,3,5-tricarboxamide |
| 1792 | 1 3-[(dipropylamino)sulfonyl]-N-{(1S,2R)-1-(3-fluoro-5-hydroxybenzyl)-2-hydroxy-3-[(3-methoxybenzyl)amino]propyl}propanamide |
| 1793 | 3-[(dipropylamino)sulfonyl]-N-{(1S,2R)-1-(3-fluoro-5-hydroxybenzyl)-2-hydroxy-3-[(3-methoxybenzyl)amino]propyl}propanamide hydrochloride |
| 1794 | N-{(1S,2R)-1-(3,5-difluorobenzyl)-3-[(3-ethylbenzyl)amino]-2-hydroxypropyl}-5-hydroxy-1H-indole-2-carboxamide |
| 1795 | N-{(1S,2R)-1-(3,5-difluorobenzyl)-3-[(3-ethylbenzyl)amino]-2-hydroxypropyl}-2,2-dimethylchromane-8-carboxamide |
| 1796 | 6-benzyl-N-{(1S,2R)-1-(3,5-difluorobenzyl)-3-[(3-ethylbenzyl)amino]-2-hydroxypropyl}pyrazine-2-carboxamide 4-oxide |
| 1797 | 2-{[({(1S,2R)-1-(3,5-difluorobenzyl)-2-hydroxy-3-[(3-methoxybenzyl)amino]propyl}amino)carbonyl]amino}-N,N-dipropylethanesulfonamide |
| 1798 | $N^1$-((1S,2R)-1-(3,5-difluorobenzyl)-2-hydroxy-3-{[(1R)-1-(hydroxymethyl)-2-methylpropyl]amino}propyl)-5-methyl-$N^3$,$N^3$-dipropylisophthalamide |
| 1799 | N-[(1S,2R)-3-(benzylamino)-1-(3-chloro-5-fluorobenzyl)-2-hydroxypropyl]-3-[(dipropylamino)sulfonyl]propanamide |
| 1800 | N-{(1S,2R)-1-(3,5-difluorobenzyl)-3-[(3-ethylbenzyl)amino]-2-hydroxypropyl}-4-(4-methoxyphenyl)-4-oxobutanamide |
| 1802 | N-{(1S,2R)-1-(3,5-difluorobenzyl)-3-[(3-ethylbenzyl)amino]-2-hydroxypropyl}-3-methyl-4-oxo-3,4-dihydrophthalazine-1-carboxamide |
| 1803 | N-{(1S,2R)-1-(3,5-difluorobenzyl)-3-[(3-ethylbenzyl)amino]-2-hydroxypropyl}-3,4-dihydro-2H-1,5-benzodioxepine-7-carboxamide |
| 1804 | N-{(1S,2R)-1-(3,5-difluorobenzyl)-3-[(3-ethylbenzyl)amino]-2-hydroxypropyl}-2-[4-(2,5-dioxopyrrolidin-1-yl)phenoxy]acetamide |
| 1806 | N-{(1S,2R)-1-(3,5-difluorobenzyl)-3-[(3-ethylbenzyl)amino]-2-hydroxypropyl}-5-methyl-4-oxo-3,4-dihydrothieno[2,3-d]pyrimidine-6-carboxamide |
| 1807 | $N^1$-[(1S,2R)-1-(1,3-benzodioxol-5-ylmethyl)-2-hydroxy-3-(isopentylamino)propyl]-$N^3$,$N^3$-dipropylbenzene-1,3,5-tricarboxamide |
| 1808 | $N^1$-{(1S,2R)-1-(3-chloro-5-fluorobenzyl)-2-hydroxy-3-[(3-methoxybenzyl)amino]propyl}-$N^5$,$N^5$-dipropylpentanediamide |
| 1809 | N-{(1S,2R)-1-(3,5-difluorobenzyl)-3-[(3-ethylbenzyl)amino]-2-hydroxypropyl}-6-fluoro-2-hydroxyquinoline-4-carboxamide |
| 1810 | N-{(1S,2R)-1-(3,5-difluorobenzyl)-3-[(3-ethylbenzyl)amino]-2-hydroxypropyl}-4-oxo-4-thien-2-ylbutanamide |
| 1811 | $N^3$-[({(1S,2R)-1-(3,5-difluorobenzyl)-2-hydroxy-3-[(3-methoxybenzyl)amino]propyl}amino)carbonyl]-$N^1$,$N^1$-dipropyl-beta-alaninamide |
| 1812 | $N^1$-{(1R,2R)-2-hydroxy-3-[(3-methoxybenzyl)amino]-1-[(phenylthio)methyl]propyl}-$N^3$,$N^3$-dipropylbenzene-1,3,5-tricarboxamide |
| 1814 | $N^1$-((1S,2R)-1-(3,5-difluorobenzyl)-2-hydroxy-3-{[(1R,2S)-1-(hydroxymethyl)-2-methylbutyl]amino}propyl)-5-methyl-$N^3$,$N^3$-dipropylisophthalamide |
| 1815 | N-{(1S,2R)-1-(3,5-difluorobenzyl)-3-[(3-ethylbenzyl)amino]-2-hydroxypropyl}-2-(phenoxymethyl)benzamide |
| 1816 | $N^1$-{(1S,2R)-1-(3,5-difluorobenzyl)-3-[(3-ethylbenzyl)amino]-2-hydroxypropyl}-$N^5$-(2,4-difluorophenyl)pentanediamide |
| 1817 | $N^1$-{(1S,2R)-1-(3,5-difluorobenzyl)-3-[(3-ethylbenzyl)amino]-2-hydroxypropyl}-$N^5$-(4,6-dimethylpyrimidin-2-yl)pentanediamide |
| 1818 | N-{(1S,2R)-1-(3,5-difluorobenzyl)-2-hydroxy-3-[(3-methoxybenzyl)amino]propyl}-3-(3-methoxybenzoyl)-5-methylbenzamide |
| 1819 | $N^1$-{(1R,2R)-1-[(benzyloxy)benzyl]-2-hydroxy-3-[(3-methoxybenzyl)amino]propyl}-$N^3$,$N^3$-dipropylbenzene-1,3,5-tricarboxamide |
| 1820 | 4-(3,4-dichlorophenyl)-N-{(1S,2R)-1-(3,5-difluorobenzyl)-3-[(3-ethylbenzyl)amino]-2-hydroxypropyl}-4-oxobutanamide |
| 1821 | methyl 4-{(2R,3R)-2-({3-[(dipropylamino)carbonyl]-5-methylbenzoyl}amino)-3-hydroxy-4-[(3-methoxybenzyl)amino]butyl}benzoate |
| 1822 | $N^1$-(4-acetylphenyl)-$N^5$-{(1S,2R)-1-(3,5-difluorobenzyl)-3-[(3-ethylbenzyl)amino]-2-hydroxypropyl}pentanediamide |
| 1824 | $N^1$-{(1R,2R)-2-hydroxy-3-[(3-methoxybenzyl)amino]-1-[(phenylthio)methyl]propyl}-5-methyl-$N^3$,$N^3$-dipropylisophthalamide |
| 1825 | 2-{[3-({(1S,2R)-1-(3,5-difluorobenzyl)-3-[(3-ethylbenzyl)amino]-2-hydroxypropyl}amino)-3-oxopropyl]thio}-N-methylbenzamide |
| 1826 | N-{(1S,2R)-1-benzyl-2-hydroxy-3-[(3-methoxybenzyl)amino]propyl}-3-[(1-propylbutyl)thio]propanamide |
| 1827 | $N^1$-{(1S,2R)-1-(3,5-difluorobenzyl)-3-[(3-ethylbenzyl)amino]-2-hydroxypropyl}-$N^4$-(4-ethoxyphenyl)succinamide |
| 1828 | $N^1$-[(1S,2R)-1-[3-(benzyloxy)-5-fluorobenzyl]-2-hydroxy-3-(isopentylamino)propyl]-$N^3$,$N^3$-dipropylbenzene-1,3,5-tricarboxamide |
| 1829 | 2-{[(2R,3S)-4-(3,5-difluorophenyl)-3-({3-[(dipropylamino)carbonyl]-5-methylbenzoyl}amino)-2-hydroxybutyl]amino}ethyl 3-methoxyphenylcarbamate |
| 1830 | 3-(benzyloxy)-N-{(1S,2R)-1-(3,5-difluorobenzyl)-3-[(3-ethylbenzyl)amino]-2-hydroxypropyl}benzamide |
| 1831 | $N^1$-((1S,2R)-1-(3,5-difluorobenzyl)-2-hydroxy-3-{[(1S)-2-hydroxy-1-methylethyl]amino}propyl)-5-methyl-$N^3$,$N^3$-dipropylisophthalamide |
| 1832 | $N^1$-((1S,2R)-2-hydroxy-1-(pentafluorobenzyl)-3-{[3-(trifluoromethyl)benzyl]amino}propyl)-5-methyl-$N^3$,$N^3$-dipropylisophthalamide |

-continued

| | Compound Name (IUPAC Name) |
|---|---|
| 1833 | N-{(1S,2R)-1-(3,5-difluorobenzyl)-3-[(3-ethylbenzyl)amino]-2-hydroxypropyl}-4-(4-hydroxyphenyl)-4-oxobutanamide |
| 1834 | 3-[(dipropylamino)sulfonyl]-N-{(1S,2R)-2-hydroxy-3-[(3-methoxybenzyl)amino]-1-[3-(trifluoromethyl)benzyl]propyl}propanamide |
| 1835 | N-{(1S,2R)-1-(3,5-difluorobenzyl)-3-[(3-ethylbenzyl)amino]-2-hydroxypropyl}-3-(piperidin-3-ylsulfonyl)benzamide |
| 1836 | 6-chloro-N-{(1S,2R)-1-(3,5-difluorobenzyl)-3-[(3-ethylbenzyl)amino]-2-hydroxypropyl}-4-hydroxyquinoline-2-carboxamide |
| 1837 | $N^1$-[(1S,2R)-2-hydroxy-3-[(3-methoxybenzyl)amino]-1-(thien-2-ylmethyl)propyl]-$N^5,N^5$-dipropylpentanediamide |
| 1838 | $N^1$-((1S)-1-{(1R)-1-hydroxy-2-[(3-methoxybenzyl)amino]ethyl}-3-methylbutyl)-5-methyl-$N^3,N^3$-dipropylisophthalamide |
| 1839 | N-{(1S,2R)-1-(3,5-difluorobenzyl)-3-[(3-ethylbenzyl)amino]-2-hydroxypropyl}-2-(6-oxo-3-phenylpyridazin-1(6H)-yl)acetamide |
| 1840 | N-{(1S,2R)-1-(3,5-difluorobenzyl)-3-[(3-ethylbenzyl)amino]-2-hydroxypropyl}-3-{4-[(methylsulfonyl)amino]phenyl}propanamide |
| 1842 | $N^1$-[(1S,2R)-3-(benzylamino)-2-hydroxy-1-(4-methylbenzyl)propyl]-5-methyl-$N^3,N^3$-dipropylisophthalamide |
| 1843 | 3-(2-chlorophenoxy)-N-{(1S,2R)-1-(3,5-difluorobenzyl)-2-hydroxy-3-[(3-iodobenzyl)amino]propyl}propanamide |
| 1844 | $N^1$-[(1S,2R)-1-(4-fluorobenzyl)-2-hydroxy-3-(isopentylamino)propyl]-$N^3,N^3$-dipropylbenzene-1,3,5-tricarboxamide |
| 1845 | Structure possibly contains peptides which are not supported in current version! |
| 1846 | 1N-{(1S,2R)-1-[3-(benzyloxy)-5-fluorobenzyl]-2-hydroxy-3-[(3-methoxybenzyl)amino]propyl}-3-[(dipropylamino)sulfonyl]propanamide hydrochloride |
| 1847 | N-{(1S,2R)-1-[3-(benzyloxy)-5-fluorobenzyl]-2-hydroxy-3-[(3-methoxybenzyl)amino]propyl}-3-[(dipropylamino)sulfonyl]propanamide hydrochloride |
| 1848 | N-{(1S,2R)-1-(3,5-difluorobenzyl)-3-[(3-ethylbenzyl)amino]-2-hydroxypropyl}-4-(4-methylphenyl)-4-oxobutanamide |
| 1849 | $N^1$-{(1S,2R)-1-(3,5-difluorobenzyl)-3-[(3-ethylbenzyl)amino]-2-hydroxypropyl}-$N^4$-[3-(trifluoromethyl)phenyl]succinamide |
| 1850 | $N^1$-{(1S,2R)-1-(1,3-benzodioxol-5-ylmethyl)-2-hydroxy-3-[(3-methoxybenzyl)amino]propyl}-5-methyl-$N^3,N^3$-dipropylisophthalamide |
| 1851 | N-{(1S,2R)-1-(3,5-difluorobenzyl)-3-[(3-ethylbenzyl)amino]-2-hydroxypropyl}-2-(5-pyridin-2-yl-2H-tetraazol-2-yl)acetamide |
| 1852 | Structure possibly contains peptides which are not supported in current version! |
| 1853 | 3-[(dipropylamino)sulfonyl]-N-[(1S,2R)-2-hydroxy-3-[(3-methoxybenzyl)amino]-1-(3-methylbenzyl)propyl]propanamide |
| 1854 | N-{(1S,2R)-1-(3,5-difluorobenzyl)-3-[(3-ethylbenzyl)amino]-2-hydroxypropyl}isoxazole-5-carboxamide |
| 1855 | N-{(1S,2R)-1-(3,5-difluorobenzyl)-3-[(3-ethylbenzyl)amino]-2-hydroxypropyl}-2-(3,5-dimethoxyphenoxy)acetamide |
| 1856 | N-{(1S,2R)-1-(3,5-difluorobenzyl)-3-[(3-ethylbenzyl)amino]-2-hydroxypropyl}-4-(2,5-dimethyl-1H-pyrrol-1-yl)-3-hydroxybenzamide |
| 1857 | $N^1$-{(1S,2R)-1-(3-bromobenzyl)-2-hydroxy-3-[(3-methoxybenzyl)amino]propyl}-$N^5,N^5$-dipropylpentanediamide |
| 1858 | $N^1$-[5-(cyclopentylmethyl)-1,3,4-thiadiazol-2-yl]-$N^4$-{(1S,2R)-1-(3,5-difluorobenzyl)-3-[(3-ethylbenzyl)amino]-2-hydroxypropyl}succinamide |
| 1859 | $N^1$-[(1S,2R)-3-(benzylamino)-2-hydroxy-1-[3-(trifluoromethyl)benzyl]propyl]-$N^3,N^3$-dipropylbenzene-1,3,5-tricarboxamide |
| 1860 | N-{(1S,2R)-1-(3,5-difluorobenzyl)-3-[(3-ethylbenzyl)amino]-2-hydroxypropyl}-2-(3-oxo-1,2-benzisothiazol-2(3H)-yl)acetamide |
| 1861 | $N^1$-((1S,2R)-1-(3,5-difluorobenzyl)-2-hydroxy-3-{[1-methyl-5-(pyrrolidin-1-ylcarbonyl)-1H-pyrrol-3-yl]amino}propyl)-5-methyl-$N^3,N^3$-dipropylisophthalamide |
| 1862 | N-{(1S,2R)-1-(3,5-difluorobenzyl)-3-[(3-ethylbenzyl)amino]-2-hydroxypropyl}-4-(3,4-difluorophenyl)-4-oxobutanamide |
| 1863 | N-{(1S,2R)-1-(3,5-difluorobenzyl)-3-[(3-ethylbenzyl)amino]-2-hydroxypropyl}-4-(2-naphthyl)-4-oxobutanamide |
| 1864 | N-{(1S,2R)-1-(3,5-difluorobenzyl)-3-[(3-ethylbenzyl)amino]-2-hydroxypropyl}-4,6-diethoxypyridine-2-carboxamide |
| 1865 | N-{(1S,2R)-1-(3,5-difluorobenzyl)-3-[(3-ethylbenzyl)amino]-2-hydroxypropyl}-4-(5-methyl-1H-pyrrol-2-yl)-4-oxobutanamide |
| 1866 | N-{(1S,2R)-1-(3,5-difluorobenzyl)-3-[(3-ethylbenzyl)amino]-2-hydroxypropyl}-3-({[2-(methylamino)ethyl]amino}sulfonyl)benzamide dihydrochloride |
| 1867 | N-{(1S,2R)-1-(3,5-difluorobenzyl)-2-hydroxy-3-[(3-methoxybenzyl)amino]propyl}-3-methyl-5-(4-methylbenzoyl)benzamide |
| 1868 | $N^1$-[(1S,2R)-1-(1,3-benzodioxol-5-ylmethyl)-3-(benzylamino)-2-hydroxypropyl]-5-methyl-$N^3,N^3$-dipropylisophthalamide |
| 1869 | N-{(1S,2R)-1-(3,5-difluorobenzyl)-3-[(3-ethylbenzyl)amino]-2-hydroxpropy)-3-(piperazin-1-ylsulfonyl)benzamide |
| 1870 | $N^1$-[(1S,2R)-3-({2-[4-(aminosulfonyl)phenyl]ethyl}amino)-1-(3,5-difluorobenzyl)-2-hydroxypropyl]-5-methyl-$N^3,N^3$-dipropylisophthalamide |
| 1871 | $N^1$-((1S,2R)-1-(3,5-difluorobenzyl)-2-hydroxy-3-{[2-hydroxy-1-(hydroxymethyl)ethyl]amino}propyl)-5-methyl-$N^3,N^3$-dipropylisophthalamide |
| 1872 | $N^1$-[(1S,2R)-1-(4-fluoro-3-methylbenzyl)-2-hydroxy-3-(isopentylamino)propyl]-$N^3,N^3$-dipropylbenzene-1,3,5-tricarboxamide |
| 1873 | N-{(1S,2R)-1-(3,5-difluorobenzyl)-3-[(3-ethylbenzyl)amino]-2-hydroxypropyl}-3-(3-oxo-2,1-benzisothiazol-1(3H)-yl)propanamide |
| 1874 | N-{(1S,2R)-1-(3,5-difluorobenzyl)-3-[(3-ethylbenzyl)amino]-2-hydroxypropyl}-2-(2,6-dihydroxypyrimidin-4-yl)acetamide |
| 1875 | $N^1$-{(1S,2R)-2-hydroxy-3-[(3-methoxybenzyl)amino]-1-[3-(trifluoromethyl)benzyl]propyl}-$N^5,N^5$-dipropylpentanediamide |
| 1876 | N-[(1S,2R)-3-(benzylamino)-2-hydroxy-1-(4-hydroxybenzyl)propyl]-3-[(dipropylamino)sulfonyl]propanamide |
| 1877 | N-{(1S,2R)-1-(3,5-difluorobenzyl)-3-[(3-ethylbenzyl)amino]-2-hydroxypropyl}-4-(3,4-difluorophenyl)-2-methyl-4-oxobutanamide |
| 1878 | $N^1$-{(1S,2R)-1-(3,5-difluorobenzyl)-3-[(3-ethylbenzyl)amino]-2-hydroxypropyl}-$N^5$-(2-pyridin-2-ylethyl)pentanediamide |
| 1879 | N-{(1S,2R)-1-(3,5-difluorobenzyl)-3-[(3-ethylbenzyl)amino]-2-hydroxypropyl}-2-[2-(4-fluorophenyl)-1,3-benzoxazol-5-yl]acetamide |
| 1880 | $N^2$-(anilinocarbonyl)-$N^1$-{(1S,2R)-1-(3,5-difluorobenzyl)-3-[(3-ethylbenzyl)amino]-2-hydroxypropyl}glycinamide |
| 1881 | N-{(1S,2R)-1-(3,5-difluorobenzyl)-3-[(3-ethylbenzyl)amino]-2-hydroxypropyl}-2-(1,3-dithian-2-yl)-3-furamide |
| 1882 | N-{(1S,2R)-1-(3,5-difluorobenzyl)-3-[(3-ethylbenzyl)amino]-2-hydroxypropyl}-2-[2-oxo-2-(propylamino)ethyl]benzamide |
| 1883 | N-[(1S,2R)-3-(benzylamino)-1-(3-bromobenzyl)-2-hydroxypropyl]-3-[(dipropylamino)sulfonyl]propanamide |

| | Compound Name (IUPAC Name) |
|---|---|
| 1884 | N-{(1S,2R)-1-(3,5-difluorobenzyl)-2-hydroxy-3-[(3-iodobenzyl)amino]propyl}-3-(2-fluorophenyl)propanamide |
| 1885 | N-{(1S,2R)-1-(3,5-difluorobenzyl)-3-[(3-ethylbenzyl)amino]-2-hydroxypropyl}-5-methylthiophene-2-carboxamide |
| 1886 | 2-[4-(benzyloxy)phenyl]-N-{(1S,2R)-1-(3,5-difluorobenzyl)-2-hydroxy-3-[(3-iodobenzyl)amino]propyl}acetamide |
| 1887 | N-{(1S,2R)-1-(3,5-difluorobenzyl)-3-[(3-ethylbenzyl)amino]-2-hydroxypropyl}-2-[(5,7-dimethyl[1,2,4]triazolo[4,3-a]pyrimidin-3-yl)thio]acetamide |
| 1888 | $N^1$-(1-acetyl-2,3-dihydro-1H-indol-7-yl)-$N^4$-{(1S,2R)-1-(3,5-difluorobenzyl)-3-[(3-ethylbenzyl)amino]-2-hydroxypropyl}succinamide |
| 1889 | $N^1$-(3-acetylphenyl)-$N^5$-{(1S,2R)-1-(3,5-difluorobenzyl)-3-[(3-ethylbenzyl)amino]-2-hydroxypropyl}pentanediamide |
| 1890 | 3-(4-chlorophenoxy)-N-{(1S,2R)-1-(3,5-difluorobenzyl)-3-[(3-ethylbenzyl)amino]-2-hydroxypropanamide |
| 1891 | $N^1$-[(1S,2R)-3-(benzylamino)-1-(3-fluoro-4-methoxybenzyl)-2-hydroxypropyl]-$N^3,N^3$-dipropylbenzene-1,3,5-tricarboxamide |
| 1892 | $N^1$-[(1S,2R)-3-(benzylamino)-2-hydroxy-1-(3-methylbenzyl)propyl]-$N^3,N^3$-dipropylbenzene-1,3,5-tricarboxamide |
| 1893 | N-{(1S,2R)-1-(3,5-difluorobenzyl)-3-[(3-ethylbenzyl)amino]-2-hydroxypropyl}-1H-indole-7-carboxamide |
| 1894 | $N^1$-[(1S,2R)-2-hydroxy-3-(isopentylamino)-1-(3-methylbenzyl)propyl]-$N^3,N^3$-dipropylbenzene-1,3,5-tricarboxamide |
| 1895 | N-{(1S,2R)-1-(3,5-difluorobenzyl)-3-[(3-ethylbenzyl)amino]-2-hydroxypropyl}-4-(1,2,3-thiadiazol-4-yl)benzamide |
| 1896 | N-{(1S,2R)-1-[3-(benzyloxy)-5-fluorobenzyl]-2-hydroxy-3-[(3-methoxybenzyl)amino]propyl}-3-[(dipropylamino)sulfonyl]propanamide |
| 1897 | N-{(1S,2R)-1-(3,5-difluorobenzyl)-3-[(3-ethylbenzyl)amino]-2-hydroxypropyl}-3-(4,4-dimethyl-2,5-dioxoimidazolidin-1-yl)-2-{[(1-propylbutyl)sulfonyl]methyl}propanamide |
| 1898 | $N^1$-[(1S,2R)-2-hydroxy-3-(isopentylamino)-1-(4-methylbenzyl)propyl]-5-methyl-$N^3,N^3$-dipropylisophthalamide |
| 1899 | $N^1$-{(1S,2R)-3-(benzylamino)-1-[3-fluoro-5-(trifluoromethyl)benzyl]-2-hydroxypropyl}-5-methyl-$N^3,N^3$-dipropylisophthalamide |
| 1900 | N-{(1S,2R)-1-(3,5-difluorobenzyl)-3-[(3-ethylbenzyl)amino]-2-hydroxypropyl}-2-[1-methyl-3-(methylthio)-1H-indol-2-yl]acetamide |
| 1901 | $N^1$-[(1S,2R)-1-(3,5-dichlorobenzyl)-2-hydroxy-3-(isopentylamino)propyl]-5-methyl-$N^3,N^3$-dipropylisophthalamide |
| 1902 | N-{(1S,2R)-1-(3,5-difluorobenzyl)-3-[(3-ethylbenzyl)amino]-2-hydroxypropyl}-4-(2-furyl)-4-oxobutanamide |
| 1903 | N-{(1S,2R)-1-(3,5-difluorobenzyl)-3-[(3-ethylbenzyl)amino]-2-hydroxypropyl}-3-(3-pyridin-2-yl-1,2,4-oxadiazol-5-yl)propanamide |
| 1904 | 2-[2-(acetylamino)-1,3-thiazol-4-yl]-N-{(1S,2R)-1-(3,5-difluorobenzyl)-3-[(3-ethylbenzyl)amino]-2-hydroxypropyl}acetamide |
| 1905 | N-{(1S,2R)-1-(3,5-difluorobenzyl)-3-[(3-ethylbenzyl)amino]-2-hydroxypropyl}-2-[(4-methyl-4H-1,2,4-triazol-3-yl)thio]-2-phenylacetamide |
| 1906 | $N^1$-[(1S,2R)-1-(4-chlorobenzyl)-2-hydroxy-3-(isopentylamino)propyl]-5-methyl-$N^3,N^3$-dipropylisophthalamide |
| 1907 | 4-(1,3-benzothiazol-2-yl)-N-{(1S,2R)-1-(3,5-difluorobenzyl)-3-[(3-ethylbenzyl)amino]-2-hydroxypropyl}butanamide |
| 1908 | $N^1$-(3-chloro-4-fluorophenyl)-$N^4$-{(1S,2R)-1-(3,5-difluorobenzyl)-3-[(3-ethylbenzyl)amino]-2-hydroxypropyl}succinamide |
| 1909 | $N^1$-[(1S,2R)-1-[3-(benzyloxy)-5-fluorobenzyl]-2-hydroxy-3-(isopentylamino)propyl]-5-methyl-$N^3,N^3$-dipropylisophthalamide |
| 1910 | N-{(1S,2R)-1-(3,5-difluorobenzyl)-3-[(3-ethylbenzyl)amino]-2-hydroxypropyl}-2-[(2-oxo-2,3-dihydroquinazolin-4-yl)thio]acetamide |
| 1911 | N-{(1S,2R)-1-(3,5-difluorobenzyl)-2-hydroxy-3-[(3-methoxybenzyl)amino]propyl}-3-methyl-5-(2-methylbenzoyl)benzamide |
| 1913 | $N^1$-[(1S,2R)-3-(benzylamino)-2-hydroxy-1-(4-methylbenzyl)propyl]-$N^3,N^3$-dipropylbenzene-1,3,5-tricarboxamide |
| 1914 | N-{(1S,2R)-1-(3,5-difluorobenzyl)-3-[(3-ethylbenzyl)amino]-2-hydroxypropyl}-4-propoxybenzamide |
| 1915 | N-{(1S,2R)-1-(3,5-difluorobenzyl)-3-[(3-ethylbenzyl)amino]-2-hydroxypropyl}-1-methyl-1H-indole-2-carboxamide |
| 1916 | 5-chloro-N-{(1S,2R)-1-(3,5-difluorobenzyl)-3-[(3-ethylbenzyl)amino]-2-hydroxypropyl}-2-(3-methyl-4H-1,2,4-triazol-4-yl)benzamide |
| 1917 | N-{(1S,2R)-1-(3,5-difluorobenzyl)-3-[(3-ethylbenzyl)amino]-2-hydroxypropyl}-4-(3,4-difluorophenyl)-2-methoxy-4-oxobutanamide |
| 1918 | N-{(1S,2R)-1-(3,5-difluorobenzyl)-3-[(3-ethylbenzyl)amino]-2-hydroxypropyl}-2-(3-thien-2-yl-1H-pyrazol-1-yl)acetamide |
| 1919 | $N^1$-{(1S,2R)-1-(3,5-difluorobenzyl)-3-[(3-ethylbenzyl)amino]-2-hydroxypropyl}-$N^5$-phenylpentanediamide |
| 1920 | N-{(1S,2R)-1-(3,5-difluorobenzyl)-3-[(3-ethylbenzyl)amino]-2-hydroxypropyl}-2-(2-thioxo-1,3-benzothiazol-3(2H)-yl)acetamide |
| 1923 | N-{(1S,2R)-1-(3,5-difluorobenzyl)-3-[(3-ethylbenzyl)amino]-2-hydroxypropyl}-2-(3-hydroxy-4-methylphenyl)acetamide |
| 1924 | $N^1$-[(1S,2R)-1-[3-fluoro-5-(trifluoromethyl)benzyl]-2-hydroxy-3-(isopentylamino)propyl]-5-methyl-$N^3,N^3$-dipropylisophthalamide |
| 1925 | N-{(1S,2R)-1-(3,5-difluorobenzyl)-3-[(3-ethylbenzyl)amino]-2-hydroxypropyl}-7-fluoro-4H-imidazo[5,1-c][1,4]benzoxazine-3-carboxamide |
| 1926 | N-{(1S,2R)-1-(3,5-difluorobenzyl)-3-[(3-ethylbenzyl)amino]-2-hydroxypropyl}-4-(3,4-dihydro-2H-1,5-benzodioxepin-7-yl)-4-oxobutanamide |
| 1927 | N-{(1S,2R)-1-(3,5-difluorobenzyl)-3-[(3-ethylbenzyl)amino]-2-hydroxypropyl}-1-benzofuran-3-carboxamide |
| 1928 | $N^1$-(3,4-dichlorophenyl)-$N^3$-{(1S,2R)-1-(3,5-difluorobenzyl)-3-[(3-ethylbenzyl)amino]-2-hydroxypropyl}malonamide |
| 1929 | $N^1$-{(1S,2R)-3-(benzylamino)-1-[3-fluoro-5-(trifluoromethyl)benzyl]-2-hydroxypropyl}-$N^3,N^3$-dipropylbenzene-1,3,5-tricarboxamide |
| 1930 | $N^1$-((1S,2R)-1-(3,5-difluorobenzyl)-2-hydroxy-3-{[(1R)-2-hydroxy-1-methylethyl]amino}propyl)-5-methyl-$N^3,N^3$-dipropylisophthalamide |
| 1931 | $N^1$-[(1S,2R)-3-(benzylamino)-2-hydroxy-1-(3-methylbenzyl)propyl]-5-methyl-$N^3,N^3$-dipropylisophthalamide |
| 1932 | $N^1$-{(1S,2R)-1-(3,5-difluorobenzyl)-3-[(3-ethylbenzyl)amino]-2-hydroxypropyl}-$N^5$-pyridin-3-ylpentanediamide |
| 1933 | N-{(1S,2R)-1-(3,5-difluorobenzyl)-3-[(3-ethylbenzyl)amino]-2-hydroxypropyl}-2-methyl-4-oxo-4H-chromene-6-carboxamide |
| 1934 | $N^1$-((1S,2R)-1-(3,5-difluorobenzyl)-2-hydroxy-3-{[3-(1H-imidazol-1-yl)propyl]amino}propyl)-5-methyl-$N^3,N^3$-dipropylisophthalamide |
| 1935 | 3-[(dipropylamino)sulfonyl]-N-{(1S,2R)-1-[3-fluoro-5-(trifluoromethyl)benzyl]-2-hydroxy-3-[(3-methoxybenzyl)amino]propyl}propanamide |
| 1936 | 3-[(dipropylamino)sulfonyl]-N-[(1S,2R)-2-hydroxy-1-(4-hydroxybenzyl)-3-(isopentylamino)propyl]propanamide |

| | Compound Name (IUPAC Name) |
|---|---|
| 1937 | N$^1$-[(1S,2R)-1-(1,3-benzodioxol-5-ylmethyl)-2-hydroxy-3-(isopentylamino)propyl]-5-methyl-N$^3$,N$^3$-dipropylisophthalamide |
| 1938 | 3-[(dipropylamino)sulfonyl]-N-[(1S,2R)-2-hydroxy-3-(isopentylamino)-1-(thien-2-ylmethyl)propyl]propanamide |
| 1939 | N-{(1S,2R)-1-(3,5-difluorobenzyl)-3-[(3-ethylbenzyl)amino]-2-hydroxypropyl}-4-[(2,2-dimethylpropanoyl)amino]-2-hydroxybenzamide |
| 1940 | N$^1$-[(1S,2R)-2-hydroxy-3-(isopentylamino)-1-(3-methoxybenzyl)propyl]-5-methyl-N$^3$,N$^3$-dipropylisophthalamide |
| 1941 | N-((1S,2R)-1-(4-fluorobenzyl)-2-hydroxy-3-{[3-(trifluoromethyl)benzyl]amino}propyl)-3-{[(3-methoxybenzyl)amino]sulfonyl}benzamide |
| 1943 | N-[6-({(1S,2R)-1-(3,5-difluorobenzyl)-3-[(3-ethylbenzyl)amino]-2-hydroxypropyl}amino)-6-oxohexyl]-2-furamide |
| 1944 | N-{(1S,2R)-1-(3,5-difluorobenzyl)-3-[(3-ethylbenzyl)amino]-2-hydroxypropyl}-2-[(1-phenyl-4,5-dihydro-1H-tetraazol-5-yl)thio]acetamide |
| 1945 | 4-acetyl-4-amino-N-{(1S,2R)-1-(3,5-difluorobenzyl)-3-[(3-ethylbenzyl)amino]-2-hydroxypropyl}cyclohexa-1,5-diene-1-sulfonamide |
| 1946 | N-((1S,2S)-1-benzyl-2-hydroxy-3-{[3-(trifluoromethyl)benzyl]amino}propyl)-3-{[(3-methoxybenzyl)amino]sulfonyl}benzamide |
| 1947 | N-{(1S,2R)-1-(3,5-difluorobenzyl)-3-[(3-ethylbenzyl)amino]-2-hydroxypropyl}-4-(3,4-dihydro-2H-chromen-6-yl)-4-oxobutanamide |
| 1948 | N$^1$-[(1S,2R)-2-hydroxy-3-(isopentylamino)-1-(3-methoxybenzyl)propyl]-N$^3$,N$^3$-dipropylbenzene-1,3,5-tricarboxamide |
| 1949 | N$^1$-{(1S,2R)-1-(3-fluoro-4-methylbenzyl)-2-hydroxy-3-[(3-methoxybenzyl)amino]propyl}-N$^5$,N$^5$-dipropylpentanediamide |
| 1950 | N-{(1S,2R)-1-(3,5-difluorobenzyl)-3-[(3-ethylbenzyl)amino]-2-hydroxypropyl}indolizine-2-carboxamide |
| 1951 | N$^1$-{(1S,2R)-3-(benzylamino)-2-hydroxy-1-[3-(trifluoromethoxy)benzyl]propyl}-5-methyl-N$^3$,N$^3$-dipropylisophthalamide |
| 1952 | N-{(1S,2R)-1-(3,5-difluorobenzyl)-3-[(3-ethylbenzyl)amino]-2-hydroxypropyl}nicotinamide 1-oxide |
| 1953 | N-[(1S,2R)-1-[3-(benzyloxy)-5-fluorobenzyl]-2-hydroxy-3-(isopentylamino)propyl]-3-[(dipropylamino)sulfonyl]propanamide |
| 1954 | 2-({(1S,2R)-1-(3,5-difluorobenzyl)-2-hydroxy-3-[(3-iodobenzyl)amino]propyl}amino)-2-oxoethyl carbamate |
| 1955 | N-{(1S,2R)-1-(3,5-difluorobenzyl)-3-[(3-ethylbenzyl)amino]-2-hydroxypropyl}-2,3-dihydro-1H-cyclopenta[b]quinoline-9-carboxamide |
| 1956 | N-{(1S,2R)-1-(3,5-difluorobenzyl)-3-[(3-ethylbenzyl)amino]-2-hydroxypropyl}-3-methyl-1H-pyrazole-5-carboxamide |
| 1957 | N-[5-({(1S,2R)-1-(3,5-difluorobenzyl)-3-[(3-ethylbenzyl)amino]-2-hydroxypropyl}amino)-5-oxopentyl]benzamide |
| 1958 | N-{(1S,2R)-1-(3,5-difluorobenzyl)-3-[(3-ethylbenzyl)amino]-2-hydroxypropyl}-4-[(methoxymethyl)thio]benzamide |
| 1959 | 3-(1,3-benzothiazol-2-yl)-N-{(1S,2R)-1-(3,5-difluorobenzyl)-3-[(3-ethylbenzyl)amino]-2-hydroxypropyl}-3-methoxypropanamide |
| 1960 | N-{(1S,2R)-1-(3,5-difluorobenzyl)-3-[(3-ethylbenzyl)amino]-2-hydroxypropyl}-3-{[(methylamino)carbonyl]amino}-3-thien-3-ylpropanamide |
| 1961 | N-{(1S,2R)-1-(3,5-difluorobenzyl)-3-[(3-ethylbenzyl)amino]-2-hydroxypropyl}-5-pyridin-2-ylthiophene-2-carboxamide |
| 1962 | N$^1$-{(1S,2R)-3-(benzylamino)-1-[3-(benzyloxy)-5-fluorobenzyl]-2-hydroxypropyl}-N$^3$,N$^3$-dipropylbenzene-1,3,5-tricarboxamide |
| 1963 | N-{(1S,2R)-1-(3,5-difluorobenzyl)-3-[(3-ethylbenzyl)amino]-2-hydroxypropyl}-2-(5,6-dimethyl-2,4-dioxo-1,2,3,4-tetrahydropyridin-3-yl)acetamide |
| 1964 | N$^1$-[(1S,2R)-1-(3-fluoro-4-methoxybenzyl)-2-hydroxy-3-(isopentylamino)propyl]-5-methyl-N$^3$,N$^3$-dipropylisophthalamide |
| 1965 | N-{(1S,2R)-1-(3,5-difluorobenzyl)-3-[(3-ethylbenzyl)amino]-2-hydroxypropyl}-2-isobutyl-1,3-dioxoisoindoline-5-carboxamide |
| 1967 | 5-(acetylamino)-N-{(1S,2R)-1-(3,5-difluorobenzyl)-3-[(3-ethylbenzyl)amino]-2-hydroxypropyl}-2-furamide |
| 1968 | N$^1$-{(1S,2R)-1-(3,5-difluorobenzyl)-3-[(3-ethylbenzyl)amino]-2-hydroxypropyl}-N$^2$-[(4-methoxyphenyl)acetyl]glycinamide |
| 1969 | N-{(1S,2R)-1-(3,5-difluorobenzyl)-3-[(3-ethylbenzyl)amino]-2-hydroxypropyl}isoquinoline-4-carboxamide |
| 1970 | N$^1$-[(1S,2R)-1-[3-(benzyloxy)benzyl]-2-hydroxy-3-(isopentylamino)propyl]-N$^3$,N$^3$-dipropylbenzene-1,3,5-tricarboxamide |
| 1971 | N-{(1S,2R)-1-(3,5-difluorobenzyl)-3-[(3-ethylbenzyl)amino]-2-hydroxypropyl}-2-(4-hydroxy-3-methoxyphenyl)acetamide |
| 1972 | N-{(1S,2R)-1-(3,5-difluorobenzyl)-3-[(3-ethylbenzyl)amino]-2-hydroxypropyl}-2-[(4-phenyl-4H-1,2,4-triazol-3-yl)thio]acetamide |
| 1973 | N-{(1S,2R)-1-(3,5-difluorobenzyl)-3-[(3-ethylbenzyl)amino]-2-hydroxypropyl}-2-(3,5-dimethoxyphenyl)acetamide |
| 1974 | N$^1$-[(1S,2R)-3-(benzylamino)-2-hydroxy-1-(3-methoxybenzyl)propyl]-5-methyl-N$^3$,N$^3$-dipropylisophthalamide |
| 1975 | N-{(1S,2R)-1-(3,5-difluorobenzyl)-3-[(3-ethylbenzyl)amino]-2-hydroxypropyl}-2-(2-ethyl-4H-[1,2,4]triazolo[1,5-a]benzimidazol-4-yl)acetamide |
| 1977 | 7-chloro-N-{(1S,2R)-1-(3,5-difluorobenzyl)-3-[(3-ethylbenzyl)amino]-2-hydroxypropyl}-1-benzofuran-2-carboxamide |
| 1978 | N-{(1S,2R)-1-(3,5-difluorobenzyl)-3-[(3-ethylbenzyl)amino]-2-hydroxypropyl}-2-(1,3-dioxo-1,3-dihydro-2H-isoindol-2-yl)propanamide |
| 1979 | N-{(1S,2R)-1-(3,5-difluorobenzyl)-3-[(3-ethylbenzyl)amino]-2-hydroxypropyl}-3-(2-oxo-2H-1,3-benzoxazin-3(4H)-yl)propanamide |
| 1980 | N-{(1S,2R)-1-(3,5-difluorobenzyl)-3-[(3-ethylbenzyl)amino]-2-hydroxypropyl}-2-(pyrimidin-2-ylthio)acetamide |
| 1981 | N$^1$-[3-(aminocarbonyl)-4,5,6,7-tetrahydro-1-benzothien-2-yl]-N$^4$-{(1S,2R)-1-(3,5-difluorobenzyl)-3-[(3-ethylbenzyl)amino]-2-hydroxypropyl}succinamide |
| 1982 | N-{(1S,2R)-1-(3,5-difluorobenzyl)-3-[(3-ethylbenzyl)amino]-2-hydroxypropyl}-2-[(5-phenyl-1,3,4-oxadiazol-2-yl)thio]acetamide |
| 1983 | N-{(1S,2R)-1-(3,5-difluorobenzyl)-3-[(3-ethylbenzyl)amino]-2-hydroxypropyl}quinoline-6-carboxamide |
| 1985 | N-{(1S,2R)-1-(3,5-difluorobenzyl)-3-[(3-ethylbenzyl)amino]-2-hydroxypropyl}-4-(2,3-dihydro-1,4-benzodioxin-6-yl)-4-oxobutanamide |
| 1986 | N-{(1S,2R)-1-(3,5-difluorobenzyl)-3-[(3-ethylbenzyl)amino]-2-hydroxypropyl}-3-(1H-indol-3-yl)-1H-pyrazole-5-carboxamide |
| 1987 | N-{(1S,2R)-1-(3,5-difluorobenzyl)-3-[(3-ethylbenzyl)amino]-2-hydroxypropyl}-2-hydroxy-4-{[(methylamino)carbonothioyl]amino}benzamide |
| 1988 | 6-chloro-N-{(1S,2R)-1-(3,5-difluorobenzyl)-3-[(3-ethylbenzyl)amino]-2-hydroxypropyl}nicotinamide |
| 1989 | N-{(1S,2R)-1-(3,5-difluorobenzyl)-3-[(3-ethylbenzyl)amino]-2-hydroxypropyl}-4-(3-hydroxyphenyl)-4-oxobutanamide |
| 1990 | N-{(1S,2R)-1-(3,5-difluorobenzyl)-3-[(3-ethylbenzyl)amino]-2-hydroxypropyl}-2-(phthalazin-1-ylthio)acetamide |

| | Compound Name (IUPAC Name) |
|---|---|
| 1991 | N-{(1S,2R)-1-(3,5-difluorobenzyl)-3-[(3-ethylbenzyl)amino]-2-hydroxypropyl}-2-[(1-oxidopyridin-2-yl)thio]acetamide |
| 1992 | 3-(acetylamino)-N-{(1S,2R)-1-(3,5-difluorobenzyl)-3-[(3-ethylbenzyl)amino]-2-hydroxypropyl}-5-fluoro-1H-indole-2-carboxamide |
| 1993 | N-((1S,2S)-1-benzyl-2-hydroxy-3-{[3-(trifluoromethyl)benzyl]amino}propyl)-3-{[(3-chlorobenzyl)amino]sulfonyl}benzamide |
| 1995 | $N^1$-[(1S,2R)-1-(1,3-benzodioxol-5-ylmethyl)-3-(benzylamino)-2-hydroxypropyl]-$N^3$,$N^3$-dipropylbenzene-1,3,5-tricarboxamide |
| 1996 | 4-(3,4-dichlorophenyl)-N-{(1S,2R)-1-(3,5-difluorobenzyl)-3-[(3-ethylbenzyl)amino]-2-hydroxypropyl}-2-hydroxy-3-methyl-4-oxobutanamide |
| 1997 | 3-[(dipropylamino)sulfonyl]-N-{(1S,2R)-2-hydroxy-3-(isopentylamino)-1-[3-(trifluoromethoxy)benzyl]propyl}propanamide |
| 1998 | $N^1$-{(1S,2R)-1-(3,5-difluorobenzyl)-3-[(3-ethylbenzyl)amino]-2-hydroxypropyl}-$N^4$-(5-methyl-1,3,4-thiadiazol-2-yl)succinamide |
| 1999 | N-{(1S,2R)-1-(3,5-difluorobenzyl)-3-[(3-ethylbenzyl)amino]-2-hydroxypropyl}-2-(2-ethyl-1H-benzimidazol-1-yl)acetamide |
| 2000 | N-{(1S,2R)-1-(1,3-benzodioxol-5-ylmethyl)-2-hydroxy-3-[(3-methoxybenzyl)amino]propyl}-3-[(dipropylamino)sulfonyl]propanamide |
| 2001 | N-{(1S,2R)-1-(3,5-difluorobenzyl)-3-[(3-ethylbenzyl)amino]-2-hydroxypropyl}-3-(2-oxo-1,3-benzoxazol-3(2H)-yl)propanamide |
| 2002 | N-[(1S,2R)-1-(3,5-dichlorobenzyl)-2-hydroxy-3-(isopentylamino)propyl]-3-[(dipropylamino)sulfonyl]propanamide |
| 2003 | $N^1$-{(1S,2R)-1-(3,5-difluorobenzyl)-3-[(3-ethylbenzyl)amino]-2-hydroxypropyl}-$N^4$-(6-methylpyridin-2-yl)succinamide |
| 2004 | ethyl (4R)-4-[({(1S,2R)-1-(3,5-difluorobenzyl)-3-[(3-ethylbenzyl)amino]-2-hydroxypropyl}amino)carbonyl]-1,3-oxazolidine-3-carboxylate |
| 2005 | N-{(1R,2R)-1-(3,5-difluorobenzyl)-2-hydroxy-3-[(3-methoxybenzyl)amino]propyl}-3-glycylbenzamide dihydrochloride |
| 2006 | N-{(1S,2R)-1-(3,5-difluorobenzyl)-3-[(3-ethylbenzyl)amino]-2-hydroxypropyl}-3-(1-methyl-1H-imidazol-2-yl)benzamide |
| 2007 | 4-(acetylamino)-N-{(1S,2R)-1-(3,5-difluorobenzyl)-3-[(3-ethylbenzyl)amino]-2-hydroxypropyl}butanamide trifluoroacetate |
| 2008 | $N^1$-{(1S,2R)-1-(3,5-difluorobenzyl)-3-[(3-ethylbenzyl)amino]-2-hydroxypropyl}-$N^2$-{[(3S)-tetrahydrofuran-3-yloxy]carbonyl}-D-leucinamide |
| 2009 | N-{(1S,2R)-1-(3,5-difluorobenzyl)-3-[(3-ethylbenzyl)amino]-2-hydroxypropyl}-3-(pyrrolidin-3-ylsulfonyl)benzamide |
| 2010 | N-{(1S,2R)-1-(3,5-difluorobenzyl)-2-hydroxy-3-[(3-methoxybenzyl)amino]propyl}-3-[(dipropylamino)methyl]benzamide dihydrochloride |
| 2011 | $N^1$-((1S,2R)-1-(3,5-difluorobenzyl)-2-hydroxy-3-{[(1R)-1-(hydroxymethyl)-3-methylbutyl]amino}propyl)-5-methyl-$N^3$,$N^3$-dipropylisophthalamide |
| 2012 | $N^1$-[(1S,2R)-3-[tert-butyl(cyclohexyl)amino]-1-(3,5-difluorobenzyl)-2-hydroxypropyl]-5-methyl-$N^3$,$N^3$-dipropylisophthalamide |
| 2013 | $N^1$-((1S,2R)-1-(3,5-difluorobenzyl)-2-hydroxy-3-{[(1S)-1-(hydroxymethyl)-2,2-dimethylpropyl]amino}propyl)-5-methyl-$N^3$,$N^3$-dipropylisophthalamide |
| 2014 | $N^1$-[(1S,2R)-1-(3,5-difluorobenzyl)-3-({[(2R)-1-ethylpyrrolidin-2-yl]methyl}amino)-2-hydroxypropyl]-5-methyl-$N^3$,$N^3$-dipropylisophthalamide |
| 2015 | $N^1$-((1S,2R)-1-(3,5-difluorobenzyl)-3-{[3-(dimethylamino)-2,2-dimethylpropyl]amino}-2-hydroxypropyl)-5-methyl-$N^3$,$N^3$-dipropylisophthalamide |
| 2016 | $N^1$-((1S,2R)-1-(3,5-difluorobenzyl)-3-{[2-(diisopropylamino)ethyl]amino}-2-hydroxypropyl)-5-methyl-$N^3$,$N^3$-dipropylisophthalamide |
| 2017 | $N^1$-((1S,2R)-1-(3,5-difluorobenzyl)-3-{[(1-ethylpyrrolidin-2-yl)methyl]amino}-2-hydroxypropyl)-5-methyl-$N^3$,$N^3$-dipropylisophthalamide |
| 2018 | $N^1$-[(1S,2R)-3-[(1-benzylpyrrolidin-3-yl)amino]-1-(3,5-difluorobenzyl)-2-hydroxypropyl]-5-methyl-$N^3$,$N^3$-dipropylisophthalamide |
| 2019 | $N^1$-{(1S,2R)-1-(3,5-difluorobenzyl)-2-hydroxy-3-[(3-pyrrolidin-1-ylpropyl)amino]propyl}-5-methyl-$N^3$,$N^3$-dipropylisophthalamide |
| 2020 | $N^1$-((1S,2R)-1-(3,5-difluorobenzyl)-3-{[3-(dimethylamino)propyl]amino}-2-hydroxypropyl)-5-methyl-$N^3$,$N^3$-dipropylisophthalamide |
| 2021 | $N^1$-[(1S,2R)-3-{[2-(acetylamino)ethyl]amino}-1-(3,5-difluorobenzyl)-2-hydroxypropyl]-5-methyl-$N^3$,$N^3$-dipropylisophthalamide |
| 2022 | $N^1$-((1S,2R)-1-(3,5-difluorobenzyl)-2-hydroxy-3-{[2-(6-oxo-1,4,5,6-tetrahydropyridazin-3-yl)phenyl]amino}propyl)-5-methyl-$N^3$,$N^3$-dipropylisophthalamide |
| 2023 | $N^1$-[(1S,2R)-3-[7-chloro-1-(2-hydroxy-3-methoxyphenyl)-3,4-dihydroisoquinolin-2(1H)-yl]-1-(3,5-difluorobenzyl)-2-hydroxypropyl]-5-methyl-$N^3$,$N^3$-dipropylisophthalamide |
| 2024 | $N^1$-[(1S,2R)-3-{[4-(1-cyanocyclopentyl)phenyl]amino}-1-(3,5-difluorobenzyl)-2-hydroxypropyl]-5-methyl-$N^3$,$N^3$-dipropylisophthalamide |
| 2025 | $N^1$-[(1S,2R)-3-({4-[4-(acetylamino)phenoxy]phenyl}amino)-1-(3,5-difluorobenzyl)-2-hydroxypropyl]-5-methyl-$N^3$,$N^3$-dipropylisophthalamide |
| 2026 | $N^1$-[(1S,2R)-3-[(4-benzoyl-2,3-dimethylphenyl)amino]-1-(3,5-difluorobenzyl)-2-hydroxypropyl]-5-methyl-$N^3$,$N^3$-dipropylisophthalamide |
| 2027 | $N^1$-[(1S,2R)-3-[(2-amino-2-oxo-1-phenylethyl)amino]-1-(3,5-difluorobenzyl)-2-hydroxypropyl]-5-methyl-$N^3$,$N^3$-dipropylisophthalamide |
| 2028 | $N^1$-((1S,2R)-1-(3,5-difluorobenzyl)-2-hydroxy-3-{4-[(1-methyl-1H-imidazol-2-yl)methyl]piperazin-1-yl}propyl)-5-methyl-$N^3$,$N^3$-dipropylisophthalamide |
| 2029 | $N^1$-((1S,2R)-1-[3,5-bis(trifluoromethyl)benzyl]-2-hydroxy-3-{[3-(trifluoromethyl)benzyl]amino}propyl)-5-methyl-$N^3$,$N^3$-dipropylisophthalamide |
| 2030 | (1S,2R)-$N^1$-[2-(tert-butylthio)ethyl]-$N^2$-{(1S,2R)-1-(3,5-difluorobenzyl)-3-[(3-ethylbenzyl)amino]-2-hydroxypropyl}cyclopropane-1,2-dicarboxamide |
| 2031 | N-{(1S,2R)-1-(3,5-difluorobenzyl)-3-[(3-ethylbenzyl)amino]-2-hydroxypropyl}-4,5-dihydronaphtho[2,1-d]isoxazole-3-carboxamide |
| 2032 | N-{(1S,2R)-1-(3,5-difluorobenzyl)-3-[(3-ethylbenzyl)amino]-2-hydroxypropyl}-1-methyl-1H-benzo[g]indazole-3-carboxamide |
| 2033 | N-{(1S,2R)-1-(3,5-difluorobenzyl)-3-[(3-ethylbenzyl)amino]-2-hydroxypropyl}-2-methyl-1,3-thiazole-4-carboxamide |
| 2034 | N-{(1S,2R)-1-(3,5-difluorobenzyl)-3-[(3-ethylbenzyl)amino]-2-hydroxypropyl}-4-methoxy-1H-pyrrole-3-carboxamide |
| 2035 | N-{(1S,2R)-1-(3,5-difluorobenzyl)-3-[(3-ethylbenzyl)amino]-2-hydroxypropyl}-9-oxo-1,2,3,9-tetrahydrocyclopenta[b]chromene-7-carboxamide |
| 2036 | N-{(1S,2R)-1-(3,5-difluorobenzyl)-3-[(3-ethylbenzyl)amino]-2-hydroxypropyl}-2-(2-oxo-2,3-dihydro-1H-benzimidazol-5-yl)acetamide |
| 2037 | N-{(1S,2R)-1-(3,5-difluorobenzyl)-3-[(3-ethylbenzyl)amino]-2-hydroxypropyl}-2-(2-oxo-2,3-dihydro-1,3-benzoxazol-5-yl)acetamide |
| 2038 | 2-[2-[(1,3-benzoxazol-2-yl)phenoxy]-N-{(1S,2R)-1-(3,5-difluorobenzyl)-3-[(3-ethylbenzyl)amino]-2-hydroxypropyl}acetamide |

| | Compound Name (IUPAC Name) |
|---|---|
| 2039 | 5-chloro-N-{(1S,2R)-1-(3,5-difluorobenzyl)-3-[(3-ethylbenzyl)amino]-2-hydroxypropyl}-2-morpholin-4-ylbenzamide |
| 2040 | 3-(3-chloroisoxazol-5-yl)-N-{(1S,2R)-1-(3,5-difluorobenzyl)-3-[(3-ethylbenzyl)amino]-2-hydroxypropyl}propanamide |
| 2041 | N-{(1S,2R)-1-(3,5-difluorobenzyl)-3-[(3-ethylbenzyl)amino]-2-hydroxypropyl}-4-(6-methoxy-1,1'-biphenyl-3-yl)-4-oxobutanamide |
| 2042 | 4-(1-benzofuran-2-yl)-N-{(1S,2R)-1-(3,5-difluorobenzyl)-3-[(3-ethylbenzyl)amino]-2-hydroxypropyl}-4-oxobutanamide |
| 2043 | N-{(1S,2R)-1-(3,5-difluorobenzyl)-3-[(3-ethylbenzyl)amino]-2-hydroxypropyl}-2-oxo-1,2,3,4-tetrahydroquinoline-3-carboxamide |
| 2044 | 2-(1-benzofuran-2-yl)-N-{(1S,2R)-1-(3,5-difluorobenzyl)-3-[(3-ethylbenzyl)amino]-2-hydroxypropyl}-2-methylpropanamide |
| 2045 | N-{(1S,2R)-1-(3,5-difluorobenzyl)-3-[(3-ethylbenzyl)amino]-2-hydroxypropyl}-6-methoxy-1-benzofuran-2-carboxamide |
| 2046 | N-{(1S,2R)-1-(3,5-difluorobenzyl)-3-[(3-ethylbenzyl)amino]-2-hydroxypropyl}-2-[4-(1H-pyrrol-1-yl)phenyl]propanamide |
| 2047 | N-{(1S,2R)-1-(3,5-difluorobenzyl)-3-[(3-ethylbenzyl)amino]-2-hydroxypropyl}-1H-imidazo[1,2-b]pyrazole-6-carboxamide |
| 2048 | N-{(1S,2R)-1-(3,5-difluorobenzyl)-3-[(3-ethylbenzyl)amino]-2-hydroxypropyl}-2-[(4-methyl-1,3-thiazol-2-yl)thio]acetamide |
| 2049 | N-{(1S,2R)-1-(3,5-difluorobenzyl)-3-[(3-ethylbenzyl)amino]-2-hydroxypropyl}-2-methoxy-4-(methylthio)benzamide |
| 2050 | N-{(1S,2R)-1-(3,5-difluorobenzyl)-3-[(3-ethylbenzyl)amino]-2-hydroxypropyl}-2-hydroxy-4-(propionylamino)benzamide |
| 2051 | N-{(1S,2R)-1-(3,5-difluorobenzyl)-3-[(3-ethylbenzyl)amino]-2-hydroxypropyl}-6-{[(4-methylphenyl)sulfonyl]amino}-4-oxohexanamide |
| 2052 | N-{(1S,2R)-1-(3,5-difluorobenzyl)-3-[(3-ethylbenzyl)amino]-2-hydroxypropyl}-1H-benzimidazole-5-carboxamide |
| 2053 | N-{(1S,2R)-1-(3,5-difluorobenzyl)-3-[(3-ethylbenzyl)amino]-2-hydroxypropyl}-2-methyl-2-(1-oxo-1,3-dihydro-2H-isoindol-2-yl)propanamide |
| 2054 | 7-(acetylamino)-N-{(1S,2R)-1-(3,5-difluorobenzyl)-3-[(3-ethylbenzyl)amino]-2-hydroxypropyl}-2-methylquinoline-5-carboxamide |
| 2054A | N$^3$-(tert-butoxycarbonyl)-N$^1$-{(1S,2R)-1-(3,5-difluorobenzyl)-3-[(3-ethylbenzyl)amino]-2-hydroxypropyl}-b-alaninamide |
| 2055 | N-{(1S,2R)-1-(3,5-difluorobenzyl)-3-[(3-ethylbenzyl)amino]-2-hydroxypropyl}-3-hydroxy-3-propylhexanamide |
| 2056 | N-{(1S,2R)-1-(3,5-difluorobenzyl)-3-[(3-ethylbenzyl)amino]-2-hydroxypropyl}-2-phenyl-2-(1H-pyrrol-1-yl)acetamide |
| 2057 | N-{(1S,2R)-1-(3,5-difluorobenzyl)-3-[(3-ethylbenzyl)amino]-2-hydroxypropyl}-1-methyl-5-phenyl-1H-pyrazole-3-carboxamide |
| 2058 | N-{(1S,2R)-1-(3,5-difluorobenzyl)-3-[(3-ethylbenzyl)amino]-2-hydroxypropyl}-2-(3-oxo-2,3-dihydro-1H-isoindol-1-yl)acetamide |
| 2059 | 4-[2-(acetylamino)-4,5-dimethylphenyl]-N-{(1S,2R)-1-(3,5-difluorobenzyl)-3-[(3-ethylbenzyl)amino]-2-hydroxypropyl}-4-oxobutanamide |
| 2060 | 6-chloro-N-{(1S,2R)-1-(3,5-difluorobenzyl)-3-[(3-ethylbenzyl)amino]-2-hydroxypropyl}pyrazine-2-carboxamide 4-oxide |
| 2061 | N-{(1S,2R)-1-(3,5-difluorobenzyl)-3-[(3-ethylbenzyl)amino]-2-hydroxypropyl}-6-methoxypyrazine-2-carboxamide 4-oxide |
| 2062 | 2-(1H,1'H-2,2'-biimidazol-1-yl)-N-{(1S,2R)-1-(3,5-difluorobenzyl)-3-[(3-ethylbenzyl)amino]-2-hydroxypropyl}acetamide |
| 2063 | 5-chloro-N-{(1S,2R)-1-(3,5-difluorobenzyl)-3-[(3-ethylbenzyl)amino]-2-hydroxypropyl}-2,3-dihydro-1-benzofuran-7-carboxamide |
| 2064 | N-{(1S,2R)-1-(3,5-difluorobenzyl)-3-[(3-ethylbenzyl)amino]-2-hydroxypropyl}-2-([1,2,4]triazolo[4,3-b]pyridazin-6-ylthio)acetamide |
| 2065 | N-{(1S,2R)-1-(3,5-difluorobenzyl)-3-[(3-ethylbenzyl)amino]-2-hydroxypropyl}-5-methyl-1-pyridin-4-yl-1H-1,2,3-triazole-4-carboxamide |
| 2066 | 2-butyl-N-{(1S,2R)-1-(3,5-difluorobenzyl)-3-[(3-ethylbenzyl)amino]-2-hydroxypropyl}-4-oxo-3,4-dihydroquinazoline-6-carboxamide |
| 2067 | N-{(1S,2R)-1-(3,5-difluorobenzyl)-3-[(3-ethylbenzyl)amino]-2-hydroxypropyl}-4-(7-methoxy-1-benzofuran-2-yl)-4-oxobutanamide |
| 2068 | N-{(1S,2R)-1-(3,5-difluorobenzyl)-3-[(3-ethylbenzyl)amino]-2-hydroxypropyl}-2-[(2-ethyl-1-oxo-2,3-dihydro-1H-isoindol-5-yl)oxy]propanamide |
| 2069 | N-{(1S,2R)-1-(3,5-difluorobenzyl)-3-[(3-ethylbenzyl)amino]-2-hydroxpropyl}pyrazine-2-carboxamide 4-oxide |
| 2070 | 7-chloro-N-{(1S,2R)-1-(3,5-difluorobenzyl)-3-[(3-ethylbenzyl)amino]-2-hydroxypropyl}quinoline-2-carboxamide |
| 2071 | 2-cyano-N-{(1S,2R)-1-(3,5-difluorobenzyl)-3-[(3-ethylbenzyl)amino]-2-hydroxypropyl}-3-(3,4-dimethoxyphenyl)-2-methylpropanamide |
| 2072 | N-{(1S,2R)-1-(3,5-difluorobenzyl)-3-[(3-ethylbenzyl)amino]-2-hydroxypropyl}-2-hydroxy-5-(propionylamino)benzamide |
| 2073 | N-{(1S,2R)-1-(3,5-difluorobenzyl)-3-[(3-ethylbenzyl)amino]-2-hydroxypropyl}-3-[2-oxo-5-(trifluoromethyl)pyridin-1(2H)-yl]propanamide |
| 2074 | 5-(4-chlorophenyl)-N-{(1S,2R)-1-(3,5-difluorobenzyl)-3-[(3-ethylbenzyl)amino]-2-hydroxypropyl}-2-furamide |
| 2075 | 4-cyano-N-{(1S,2R)-1-(3,5-difluorobenzyl)-3-[(3-ethylbenzyl)amino]-2-hydroxypropyl}-3-(1H-pyrrol-1-yl)thiophene-2-carboxamide |
| 2076 | N-{(1S,2R)-1-(3,5-difluorobenzyl)-3-[(3-ethylbenzyl)amino]-2-hydroxypropyl}-3,5-bis(methylthio)isothiazole-4-carboxamide |
| 2077 | 2-chloro-4-cyano-N-{(1S,2R)-1-(3,5-difluorobenzyl)-3-[(3-ethylbenzyl)amino]-2-hydroxypropyl}benzamide |
| 2078 | N-{(1S,2R)-1-(3,5-difluorobenzyl)-3-[(3-ethylbenzyl)amino]-2-hydroxypropyl}-3-[(methoxyacetyl)amino]-3-phenylpropanamide |
| 2079 | N-{(1S,2R)-1-(3,5-difluorobenzyl)-3-[(3-ethylbenzyl)amino]-2-hydroxypropyl}-3-fluoro-4-morpholin-4-ylbenzamide |
| 2080 | N-{(1S,2R)-1-(3,5-difluorobenzyl)-3-[(3-ethylbenzyl)amino]-2-hydroxypropyl}-4-(1-oxidothiomorpholin-4-yl)butanamide |
| 2081 | 4-chloro-N-{(1S,2R)-1-(3,5-difluorobenzyl)-3-[(3-ethylbenzyl)amino]-2-hydroxypropyl}-1,3-dimethyl-1H-pyrazolo[3,4-b]pyridine-5-carboxamide |
| 2082 | N-{2-[({(1S,2R)-1-(3,5-difluorobenzyl)-3-[(3-ethylbenzyl)amino]-2-hydroxypropyl}amino)carbonyl]phenyl}-5-methyl-2-furamide |
| 2083 | 1-(cyanomethyl)-N-{(1S,2R)-1-(3,5-difluorobenzyl)-3-[(3-ethylbenzyl)amino]-2-hydroxypropyl}-1H-pyrrole-2-carboxamide |
| 2084 | N$^1$-(2-chloropyridin-3-yl)-N$^4$-{(1S,2R)-1-(3,5-difluorobenzyl)-3-[(3-ethylbenzyl)amino]-2-hydroxypropyl}succinamide |
| 2085 | 3-(cyclopentyloxy)-N-{(1S,2R)-1-(3,5-difluorobenzyl)-3-[(3-ethylbenzyl)amino]-2-hydroxypropyl}-4-methoxybenzamide |
| 2086 | N-{(1S,2R)-1-(3,5-difluorobenzyl)-3-[(3-ethylbenzyl)amino]-2-hydroxypropyl}-2-(5-pyrrolidin-1-yl-2H-tetraazol-2-yl)acetamide |
| 2087 | N-{(1S,2R)-1-(3,5-difluorobenzyl)-3-[(3-ethylbenzyl)amino]-2-hydroxypropyl}-2,5-dimethyl-1-phenyl-1H-pyrrole-3-carboxamide |

| | Compound Name (IUPAC Name) |
|---|---|
| 2088 | 1-(4-acetylphenyl)-N-{(1S,2R)-1-(3,5-difluorobenzyl)-3-[(3-ethylbenzyl)amino]-2-hydroxypropyl}piperidine-4-carboxamide |
| 2089 | N-{(1S,2R)-1-(3,5-difluorobenzyl)-3-[(3-ethylbenzyl)amino]-2-hydroxypropyl}-2-methyl-2-(1H-1,2,4-triazol-1-yl)propanamide |
| 2090 | N-{(1S,2R)-1-(3,5-difluorobenzyl)-3-[(3-ethylbenzyl)amino]-2-hydroxypropyl}-5-(piperidin-1-ylmethyl)-2-furamide |
| 2091 | N-{(1S,2R)-1-(3,5-difluorobenzyl)-3-[(3-ethylbenzyl)amino]-2-hydroxypropyl}-2-methyl-2,3-dihydro-1-benzothiophene-2-carboxamide 1,1-dioxide |
| 2092 | 2-(2,1,3-benzoxadiazol-5-yl)-N-{(1S,2R)-1-(3,5-difluorobenzyl)-3-[(3-ethylbenzyl)amino]-2-hydroxypropyl}-1,3-thiazole-4-carboxamide |
| 2093 | N-{(1S,2R)-1-(3,5-difluorobenzyl)-3-[(3-ethylbenzyl)amino]-2-hydroxypropyl}-4,5-dihydrofuro[2,3-g][2,1]benzisoxazole-8-carboxamide |
| 2094 | N-{(1S,2R)-1-(3,5-difluorobenzyl)-3-[(3-ethylbenzyl)amino]-2-hydroxypropyl}-2-[(4-methyl-1,2,3-thiadiazol-5-yl)thio]acetamide |
| 2095 | N-{(1S,2R)-1-(3,5-difluorobenzyl)-3-[(3-ethylbenzyl)amino]-2-hydroxypropyl}-1-(2-furoyl)-4-hydroxyprolinamide |
| 2096 | N-{(1S,2R)-1-(3,5-difluorobenzyl)-3-[(3-ethylbenzyl)amino]-2-hydroxypropyl}-4-oxo-4,5,6,7-tetrahydro-1-benzofuran-3-carboxamide |
| 2097 | 4,5-dichloro-N-{(1S,2R)-1-(3,5-difluorobenzyl)-3-[(3-ethylbenzyl)amino]-2-hydroxypropyl}isothiazole-3-carboxamide |
| 2098 | $N^1$-{(1S,2R)-1-(3,5-difluorobenzyl)-3-[(3-ethylbenzyl)amino]-2-hydroxypropyl}-$N^5$-(1,3-thiazol-2-yl)pentanediamide |
| 2099 | N-acetyl-4-chloro-N-{(1S,2R)-1-(3,5-difluorobenzyl)-3-[(3-ethylbenzyl)amino]-2-hydroxypropyl}phenylalaninamide |
| 2100 | 8-chloro-N-{(1S,2R)-1-(3,5-difluorobenzyl)-3-[(3-ethylbenzyl)amino]-2-hydroxypropyl}-4-hydroxycinnoline-3-carboxamide |
| 2101 | N-{(1S,2R)-1-(3,5-difluorobenzyl)-3-[(3-ethylbenzyl)amino]-2-hydroxypropyl}-2,6-dioxohexahydropyrimidine-4-carboxamide |
| 2102 | N-{(1S,2R)-1-(3,5-difluorobenzyl)-3-[(3-ethylbenzyl)amino]-2-hydroxypropyl}-4-(5-methyl-4-phenyl-1,3-oxazol-2-yl)benzamide |
| 2103 | N-{(1S,2R)-1-(3,5-difluorobenzyl)-3-[(3-ethylbenzyl)amino]-2-hydroxypropyl}-2-phenylimidazo[1,2-a]pyridine-6-carboxamide |
| 2104 | N-{(1S,2R)-1-(3,5-difluorobenzyl)-3-[(3-ethylbenzyl)amino]-2-hydroxypropyl}-3-[3-(4-methoxyphenyl)-1,2,4-oxadiazol-5-yl]propanamide |
| 2105 | N-{(1S,2R)-1-(3,5-difluorobenzyl)-3-[(3-ethylbenzyl)amino]-2-hydroxypropyl}-2-(4-methyl-1,2,3-thiadiazol-5-yl)-1,3-thiazole-4-carboxamide |
| 2106 | N-{(1S,2R)-1-(3,5-difluorobenzyl)-3-[(3-ethylbenzyl)amino]-2-hydroxpropyl}-5-methyl-2-phenyl-2H-1,2,3-triazole-4-carboxamide |
| 2107 | N-{(1S,2R)-1-(3,5-difluorobenzyl)-3-[(3-ethylbenzyl)amino]-2-hydroxypropyl}-4-(3-pyridin-2-yl-1,2,4-oxadiazol-5-yl)butanamide |
| 2108 | N-{(1S,2R)-1-(3,5-difluorobenzyl)-3-[(3-ethylbenzyl)amino]-2-hydroxypropyl}-1,3-dimethyl-1H-thieno[2,3-c]pyrazole-5-carboxamide |
| 2109 | 4-(1,3-benzodioxol-5-yl)-N-{(1S,2R)-1-(3,5-difluorobenzyl)-3-[(3-ethylbenzyl)amino]-2-hydroxypropyl}butanamide |
| 2110 | N-{(1S,2R)-1-(3,5-difluorobenzyl)-3-[(3-ethylbenzyl)amino]-2-hydroxypropyl}-3-methyl-5-(4-methyl-1,2,3-thiadiazol-5-yl)isoxazole-4-carboxamide |
| 2111 | $N^1$-((1S,2R)-1-(3,5-difluorobenzyl)-3-{[2-(dimethylamino)-1-methylethyl]amino}-2-hydroxypropyl)-5-methyl-$N^3,N^3$-dipropylisophthalamide |
| 2112 | $N^1$-[(1S,2R)-1-(3,5-difluorobenzyl)-2-hydroxy-3-(2-methylmorpholin-4-yl)propyl]-5-methyl-$N^3,N^3$-dipropylisophthalamide |
| 2113 | $N^1$-((1S,2R)-1-(3,5-difluorobenzyl)-2-hydroxy-3-{2-[hydroxy(phenyl)methyl]-4-methylpiperazin-1-yl}propyl)-5-methyl-$N^3,N^3$-dipropylisophthalamide |
| 2114 | $N^1$-((1S,2R)-1-(3,5-difluorobenzyl)-2-hydroxy-3-{[(2R)-2-methylbutyl]amino}propyl)-5-methyl-$N^3,N^3$-dipropylisophthalamide |
| 2115 | $N^1$-[(1S,2R)-3-{[4-(diethylamino)-1-methylbutyl]amino}-1-(3,5-difluorobenzyl)-2-hydroxypropyl]-5-methyl-$N^3,N^3$-dipropylisophthalamide |
| 2116 | $N^1$-{(1S,2R)-1-(3,5-difluorobenzyl)-2-hydroxy-3-[(2-hydroxy-1,1-dimethylethyl)amino]propyl}-5-methyl-$N^3,N^3$-dipropylisophthalamide |
| 2117 | $N^1$-((1S,2R)-1-(3,5-difluorobenzyl)-2-hydroxy-3-{[3-(2-methylpiperidin-1-yl)propyl]amino}propyl)-5-methyl-$N^3,N^3$-dipropylisophthalamide |
| 2118 | $N^1$-((1S,2R)-1-(3,5-difluorobenzyl)-2-hydroxy-3-{[5-(trifluoromethyl)-1,3,4-thiadiazol-2-yl]amino}propyl)-5-methyl-$N^3,N^3$-dipropylisophthalamide |
| 2119 | $N^1$-{(1S,2R)-1-(3,5-difluorobenzyl)-2-hydroxy-3-[(3-methyl-4,5,6,7-tetrahydro-3H-3lambda4-[1,3]thiazolo[5,4-c]pyridin-2-yl)amino]propyl}-5-methyl-$N^3,N^3$-dipropylisophthalamide |
| 2120 | $N^1$-[(1S,2R)-3-[(3-ethylbenzyl)amino]-2-hydroxy-1-(1H-pyrazol-1-ylmethyl)propyl]-5-methyl-$N^3,N^3$-dipropylisophthalamide |
| 2121 | 3,5-bis(acetylamino)-N-{(1S,2R)-1-(3,5-difluorobenzyl)-3-[(3-ethylbenzyl)amino]-2-hydroxypropyl}benzamide |
| 2122 | $N^1$-[4-(aminosulfonyl)phenyl]-$N^4$-{(1S,2R)-1-(3,5-difluorobenzyl)-3-[(3-ethylbenzyl)amino]-2-hydroxypropyl}succinamide |
| 2123 | N-{(1S,2R)-1-(3,5-difluorobenzyl)-3-[(3-ethylbenzyl)amino]-2-hydroxypropyl}-4-[methyl(methylsulfonyl)amino]benzamide |
| 2124 | 1-acetyl-N-{(1S,2R)-1-(3,5-difluorobenzyl)-3-[(3-ethylbenzyl)amino]-2-hydroxypropyl}piperidine-4-carboxamide |
| 2125 | N-{(1S,2R)-1-(3,5-difluorobenzyl)-3-[(3-ethylbenzyl)amino]-2-hydroxypropyl}-3-(4-methoxyphenoxy)propanamide |
| 2126 | $N^1$-{(1S,2R)-1-(3,5-difluorobenzyl)-3-[(3-ethylbenzyl)amino]-2-hydroxypropyl}-$N^4$-methylsuccinamide |
| 2127 | $N^1$-{(1S,2R)-1-(3,5-difluorobenzyl)-3-[(3-ethylbenzyl)amino]-2-hydroxypropyl}-$N^4$-(2,6-dimethylphenyl)succinamide |
| 2128 | N-acetyl-N-{(1S,2R)-1-(3,5-difluorobenzyl)-3-[(3-ethylbenzyl)amino]-2-hydroxypropyl}-D-phenylalaninamide |
| 2129 | N-{(1S,2R)-1-(3,5-difluorobenzyl)-3-[(3-ethylbenzyl)amino]-2-hydroxypropyl}-2-[(4-methylphenyl)sulfonyl]acetamide |
| 2130 | N-{(1S,2R)-1-(3,5-difluorobenzyl)-3-[(3-ethylbenzyl)amino]-2-hydroxypropyl}-2-{[(ethylamino)carbonyl]amino}benzamide |
| 2131 | N-{(1S,2R)-1-(3,5-difluorobenzyl)-3-[(3-ethylbenzyl)amino]-2-hydroxypropyl}-1-phenyl-1,4,5,6-tetrahydrocyclopenta[c]pyrazole-3-carboxamide |
| 2132 | 4-(cyclopentyloxy)-N-{(1S,2R)-1-(3,5-difluorobenzyl)-3-[(3-ethylbenzyl)amino]-2-hydroxypropyl}benzamide |
| 2133 | $N^1$-{(1S,2R)-1-(3,5-difluorobenzyl)-3-[(3-ethylbenzyl)amino]-2-hydroxypropyl}-$N^4$-pyridin-3-ylsuccinamide |
| 2134 | $N^1$-{(1S,2R)-1-(3,5-difluorobenzyl)-3-[(3-ethylbenzyl)amino]-2-hydroxypropyl}-$N^4$-phenylsuccinamide |
| 2135 | N-{(1S,2R)-1-(3,5-difluorobenzyl)-3-[(3-ethylbenzyl)amino]-2-hydroxypropyl}-3,4-dihydroxybenzamide |
| 2136 | N-{(1S,2R)-1-(3,5-difluorobenzyl)-3-[(3-ethylbenzyl)amino]-2-hydroxypropyl}-5-(1H-1,2,4-triazol-1-yl)pentanamide |

| | Compound Name (IUPAC Name) |
|---|---|
| 2137 | N-{(1S,2R)-1-(3,5-difluorobenzyl)-3-[(3-ethylbenzyl)amino]-2-hydroxypropyl}-2-phenyl-1,3-oxazole-4-carboxamide |
| 2138 | N-{(1S,2R)-1-(3,5-difluorobenzyl)-3-[(3-ethylbenzyl)amino]-2-hydroxypropyl}-7-methoxy-4-oxo-1,2,3,4-tetrahydronaphthalene-2-carboxamide |
| 2139 | N-{(1S,2R)-1-(3,5-difluorobenzyl)-3-[(3-ethylbenzyl)amino]-2-hydroxypropyl}-4-{4-[(methylsulfonyl)amino]phenyl}-4-oxobutanamide |
| 2140 | N-{(1S,2R)-1-(3,5-difluorobenzyl)-3-[(3-ethylbenzyl)amino]-2-hydroxypropyl}-4-hydroxy-7-methoxy-1-benzofuran-5-carboxamide |
| 2141 | N-{(1S,2R)-1-(3,5-difluorobenzyl)-3-[(3-ethylbenzyl)amino]-2-hydroxypropyl}-4-hydroxy-7-methoxy-1-benzothiophene-5-carboxamide |
| 2142 | N-{(1S,2R)-1-(3,5-difluorobenzyl)-3-[(3-ethylbenzyl)amino]-2-hydroxypropyl}-3,6,6-trimethyl-4-oxo-4,5,6,7-tetrahydro-1-benzofuran-2-carboxamide |
| 2143 | N-{(1S,2R)-1-(3,5-difluorobenzyl)-3-[(3-ethylbenzyl)amino]-2-hydroxypropyl}-5,6-dihydro-4H-cyclopenta[b]thiophene-2-carboxamide |
| 2144 | N-{(1S,2R)-1-(3,5-difluorobenzyl)-3-[(3-ethylbenzyl)amino]-2-hydroxypropyl}-1,3-thiazole-4-carboxamide |
| 2145 | N-{(1S,2R)-1-(3,5-difluorobenzyl)-3-[(3-ethylbenzyl)amino]-2-hydroxypropyl}-2-(pyridin-2-yl-1,3-thiazol-4-yl)acetamide |
| 2146 | $N^1$-[5-(aminosulfonyl)-1,3,4-thiadiazol-2-yl]-$N^4$-{(1S,2R)-1-(3,5-difluorobenzyl)-3-[(3-ethylbenzyl)amino]-2-hydroxypropyl}succinamide |
| 2147 | N-{(1S,2R)-1-(3,5-difluorobenzyl)-3-[(3-ethylbenzyl)amino]-2-hydroxypropyl}-3-hydroxy-6-neopentylpyridine-2-carboxamide |
| 2148 | N-{(1S,2R)-1-(3,5-difluorobenzyl)-3-[(3-ethylbenzyl)amino]-2-hydroxypropyl}-1-(4-fluorophenyl)-1,4,5,6-tetrahydrocyclopenta[c]pyrazole-3-carboxamide |
| 2149 | N-{(1S,2R)-1-(3,5-difluorobenzyl)-3-[(3-ethylbenzyl)amino]-2-hydroxypropyl}-2-methyl-5,6,7,8-tetrahydro-4H-pyrazolo[1,5-a]azepine-3-carboxamide |
| 2150 | N-{(1S,2R)-1-(3,5-difluorobenzyl)-3-[(3-ethylbenzyl)amino]-2-hydroxypropyl}-2-methyl-3-furamide |
| 2151 | N-{(1S,2R)-1-(3,5-difluorobenzyl)-3-[(3-ethylbenzyl)amino]-2-hydroxypropyl}-3-furamide |
| 2152 | N-{(1S,2R)-1-(3,5-difluorobenzyl)-3-[(3-ethylbenzyl)amino]-2-hydroxypropyl}-4-(2-hydroxyethoxy)benzamide |
| 2153 | N-{(1S,2R)-1-(3,5-difluorobenzyl)-3-[(3-ethylbenzyl)amino]-2-hydroxypropyl}thiophene-2-carboxamide |
| 2154 | $N^1$-{(1S,2R)-1-(3,5-difluorobenzyl)-3-[(3-ethylbenzyl)amino]-2-hydroxypropyl}-$N^2$,$N^2$-dimethylphthalamide |
| 2155 | N-{(1S,2R)-1-(3,5-difluorobenzyl)-3-[(3-ethylbenzyl)amino]-2-hydroxypropyl}-5-methyl-2-phenyl-1,3-oxazole-4-carboxamide |
| 2156 | N-{(1S,2R)-1-(3,5-difluorobenzyl)-3-[(3-ethylbenzyl)amino]-2-hydroxypropyl}-4-(1,3-dioxo-1,3-dihydro-2H-isoindol-2-yl)-2-hydroxybutanamide |
| 2157 | 2-(2H-1,2,3-benzotriazol-2-yl)-N-{(1S,2R)-1-(3,5-difluorobenzyl)-3-[(3-ethylbenzyl)amino]-2-hydroxypropyl}butanamide |
| 2158 | N-{(1S,2R)-1-(3,5-difluorobenzyl)-3-[(3-ethylbenzyl)amino]-2-hydroxypropyl}-1H-indazole-3-carboxamide |
| 2159 | N-{(1S,2R)-1-(3,5-difluorobenzyl)-3-[(3-ethylbenzyl)amino]-2-hydroxypropyl}-3-hydroxyquinoxaline-2-carboxamide |
| 2160 | 2-(acetylamino)-N-{(1S,2R)-1-(3,5-difluorobenzyl)-3-[(3-ethylbenzyl)amino]-2-hydroxypropyl}-4,5-dimethylthiophene-3-carboxamide |
| 2161 | $N^1$-(2-cyanophenyl)-$N^4$-{(1S,2R)-1-(3,5-difluorobenzyl)-3-[(3-ethylbenzyl)amino]-2-hydroxypropyl}succinamide |
| 2162 | N-{(1S,2R)-1-(3,5-difluorobenzyl)-3-[(3-ethylbenzyl)amino]-2-hydroxypropyl}-1-ethyl-1H-indole-2-carboxamide |
| 2163 | N-{(1S,2R)-1-(3,5-difluorobenzyl)-3-[(3-ethylbenzyl)amino]-2-hydroxypropyl}-1-benzofuran-2-carboxamide |
| 2164 | 1-benzyl-N-{(1S,2R)-1-(3,5-difluorobenzyl)-3-[(3-ethylbenzyl)amino]-2-hydroxypropyl}-3,5-dimethyl-1H-pyrazole-4-carboxamide |
| 2165 | $N^1$-{(1S,2R)-1-(3,5-difluorobenzyl)-3-[(3-ethylbenzyl)amino]-2-hydroxypropyl}-$N^2$-[(4-methylphenyl)sulfonyl]glycinamide |
| 2166 | N-{(1S,2R)-1-(3,5-difluorobenzyl)-3-[(3-ethylbenzyl)amino]-2-hydroxypropyl}-4,8-dihydroxyquinoline-2-carboxamide |
| 2167 | N-{(1S,2R)-1-(3,5-difluorobenzyl)-3-[(3-ethylbenzyl)amino]-2-hydroxypropyl}-2-(1,1-dioxidotetrahydrothien-3-yl)acetamide |
| 2168 | methyl 5-[({(1S,2R)-1-(3,5-difluorobenzyl)-3-[(3-ethylbenzyl)amino]-2-hydroxypropyl}amino)carbonyl]-1H-benzimidazol-2-ylcarbamate |
| 2169 | N-{(1S,2R)-1-(3,5-difluorobenzyl)-3-[(3-ethylbenzyl)amino]-2-hydroxypropyl}-2-(2-methyl-1,3-benzoxazol-5-yl)acetamide |
| 2170 | N-{(1S,2R)-1-(3,5-difluorobenzyl)-3-[(3-ethylbenzyl)amino]-2-hydroxypropyl}-2-[ethyl(methyl)amino]-4-hydroxypyrimidine-5-carboxamide |
| 2171 | N-{(1S,2R)-1-(3,5-difluorobenzyl)-3-[(3-ethylbenzyl)amino]-2-hydroxypropyl}-2-(2-pyridin-4-yl-1,3-benzoxazol-5-yl)acetamide |
| 2172 | 4-[2-(diethylamino)ethoxy]-N-{(1S,2R)-1-(3,5-difluorobenzyl)-3-[(3-ethylbenzyl)amino]-2-hydroxypropyl}benzamide |
| 2173 | 3-(aminosulfonyl)-4-chloro-N-{(1S,2R)-1-(3,5-difluorobenzyl)-3-[(3-ethylbenzyl)amino]-2-hydroxypropyl}benzamide |
| 2174 | 2-(diethylamino)-N-{(1S,2R)-1-(3,5-difluorobenzyl)-3-[(3-ethylbenzyl)amino]-2-hydroxypropyl}-4-hydroxypyrimidine-5-carboxamide |
| 2175 | N-{(1S,2R)-1-(3,5-difluorobenzyl)-3-[(3-ethylbenzyl)amino]-2-hydroxypropyl}-5,6,7,8-tetrahydro-4H-cyclohepta[c]isoxazole-3-carboxamide |
| 2176 | $N^1$-{(1S,2R)-1-(3,5-difluorobenzyl)-3-[(3-ethylbenzyl)amino]-2-hydroxypropyl}-$N^4$,$N^4$-diphenylsuccinamide |
| 2177 | N-{(1S,2R)-1-(3,5-difluorobenzyl)-3-[(3-ethylbenzyl)amino]-2-hydroxypropyl}-6-hydroxy-4-methylpyridine-2-carboxamide |
| 2178 | N-{(1S,2R)-1-(3,5-difluorobenzyl)-3-[(3-ethylbenzyl)amino]-2-hydroxypropyl}-2-phenylimidazo[1,2-a]pyridine-7-carboxamide |
| 2179 | N-{(1S,2R)-1-(3,5-difluorobenzyl)-3-[(3-ethylbenzyl)amino]-2-hydroxypropyl}quinoline-4-carboxamide |
| 2180 | N-{(1S,2R)-1-(3,5-difluorobenzyl)-3-[(3-ethylbenzyl)amino]-2-hydroxypropyl}-2-(1,3-dimethyl-2,6-dioxo-1,2,3,6-tetrahydro-9H-purin-9-yl)acetamide |
| 2181 | N-{(1S,2R)-1-(3,5-difluorobenzyl)-3-[(3-ethylbenzyl)amino]-2-hydroxypropyl}-5-methoxy-1H-indole-2-carboxamide |
| 2182 | N-{(1S,2R)-1-(3,5-difluorobenzyl)-3-[(3-ethylbenzyl)amino]-2-hydroxypropyl}-4-(3,5-dimethyl-1H-pyrazol-1-yl)benzamide |
| 2183 | N-{(1S,2R)-1-(3,5-difluorobenzyl)-3-[(3-ethylbenzyl)amino]-2-hydroxypropyl}-5-methylisoxazole-3-carboxamide |
| 2184 | N-{(1S,2R)-1-(3,5-difluorobenzyl)-3-[(3-ethylbenzyl)amino]-2-hydroxypropyl}-3-methylisoxazole-5-carboxamide |
| 2185 | 2-(1-benzothien-4-yl)-N-{(1S,2R)-1-(3,5-difluorobenzyl)-3-[(3-ethylbenzyl)amino]-2-hydroxypropyl}acetamide |

| | Compound Name (IUPAC Name) |
|---|---|
| 2186 | N-{(1S,2R)-1-(3,5-difluorobenzyl)-3-[(3-ethylbenzyl)amino]-2-hydroxypropyl}-3-methyl-4-oxo-4,5,6,7-tetrahydro-1H-indole-2-carboxamide |
| 2187 | N-{(1S,2R)-1-(3,5-difluorobenzyl)-3-[(3-ethylbenzyl)amino]-2-hydroxypropyl}-1-benzothiophene-2-carboxamide |
| 2188 | N-{(1S,2R)-1-(3,5-difluorobenzyl)-3-[(3-ethylbenzyl)amino]-2-hydroxypropyl}-6-hydroxynicotinamide |
| 2189 | $N^1$-{(1S,2R)-1-(3,5-difluorobenzyl)-3-[(3-ethylbenzyl)amino]-2-hydroxypropyl}-$N^3$-[(4-methylphenyl)sulfonyl]-beta-alaninamide |
| 2190 | N-{(1S,2R)-1-(3,5-difluorobenzyl)-3-[(3-ethylbenzyl)amino]-2-hydroxypropyl}-2-hydroxyquinoline-4-carboxamide |
| 2191 | N-{(1S,2R)-1-(3,5-difluorobenzyl)-3-[(3-ethylbenzyl)amino]-2-hydroxypropyl}-2-(5-phenyl-1H-tetraazol-1-yl)acetamide |
| 2192 | 4-{[(cyclobutylcarbonyl)amino]methyl}-N-{(1S,2R)-1-(3,5-difluorobenzyl)-3-[(3-ethylbenzyl)amino]-2-hydroxypropyl}benzamide |
| 2193 | N-{(1S,2R)-1-(3,5-difluorobenzyl)-3-[(3-ethylbenzyl)amino]-2-hydroxypropyl}-4-(2-oxo-1,3-benzoxazol-3(2H)-yl)butanamide |
| 2194 | N-{(1S,2R)-1-(3,5-difluorobenzyl)-3-[(3-ethylbenzyl)amino]-2-hydroxypropyl}-2-(1,3-dioxooctahydro-2H-isoindol-2-yl)butanamide |
| 2195 | $N^1$-{(1S,2R)-1-(3,5-difluorobenzyl)-3-[(3-ethylbenzyl)amino]-2-hydroxypropyl}-$N^2$-(tetrahydrofuran-2-ylmethyl)phthalamide |
| 2196 | N-{(1S,2R)-1-(3,5-difluorobenzyl)-3-[(3-ethylbenzyl)amino]-2-hydroxypropyl}-4-(2,3-dihydro-1H-indol-1-yl)-4-oxobutanamide |
| 2197 | N-{(1S,2R)-1-(3,5-difluorobenzyl)-3-[(3-ethylbenzyl)amino]-2-hydroxypropyl}thieno[3,2-b]pyridine-6-carboxamide |
| 2198 | N-{(1S,2R)-1-(3,5-difluorobenzyl)-3-[(3-ethylbenzyl)amino]-2-hydroxypropyl}-2-[(6-methoxy-1H-benzimidazol-2-yl)thio]acetamide |
| 2199 | N-{(1S,2R)-1-(3,5-difluorobenzyl)-3-[(3-ethylbenzyl)amino]-2-hydroxypropyl}thieno[2,3-c]pyridine-2-carboxamide |
| 2200 | 2-(1H-benzimidazol-2-ylthio)-N-{(1S,2R)-1-(3,5-difluorobenzyl)-3-[(3-ethylbenzyl)amino]-2-hydroxypropyl}propanamide |
| 2201 | N-{(1S,2R)-1-(3,5-difluorobenzyl)-3-[(3-ethylbenzyl)amino]-2-hydroxypropyl}-3-[(2,4-difluorobenzyl)oxy]propanamide |
| 2202 | N-{(1S,2R)-1-(3,5-difluorobenzyl)-3-[(3-ethylbenzyl)amino]-2-hydroxypropyl}-5,6-dimethyl-4-oxo-3,4-dihydrothieno[2,3-d]pyrimidine-2-carboxamide |
| 2203 | N-{(1S,2R)-1-(3,5-difluorobenzyl)-3-[(3-ethylbenzyl)amino]-2-hydroxypropyl}-1-(2-fluorophenyl)-5-oxopyrrolidine-3-carboxamide |
| 2204 | N-{(1S,2R)-1-(3,5-difluorobenzyl)-3-[(3-ethylbenzyl)amino]-2-hydroxypropyl}-4-(5-methyl-1H-tetraazol-1-yl)benzamide |
| 2205 | N-{(1S,2R)-1-(3,5-difluorobenzyl)-3-[(3-ethylbenzyl)amino]-2-hydroxypropyl}-2-(4,4-dimethyl-4,5-dihydro-1,3-oxazol-2-yl)thiophene-3-carboxamide |
| 2206 | N-{(1S,2R)-1-(3,5-difluorobenzyl)-3-[(3-ethylbenzyl)amino]-2-hydroxypropyl}-5-(trifluoromethoxy)-1H-indole-2-carboxamide |
| 2207 | N-{(1S,2R)-1-(3,5-difluorobenzyl)-3-[(3-ethylbenzyl)amino]-2-hydroxypropyl}-1-phenyl-5-propyl-1H-pyrazole-4-carboxamide |
| 2208 | N-{(1S,2R)-1-(3,5-difluorobenzyl)-3-[(3-ethylbenzyl)amino]-2-hydroxypropyl}-5-[(pyridin-2-ylthio)methyl]-2-furamide |
| 2209 | 5-chloro-N-{(1S,2R)-1-(3,5-difluorobenzyl)-3-[(3-ethylbenzyl)amino]-2-hydroxypropyl}-2-morpholin-4-ylpyrimidine-4-carboxamide |
| 2210 | 5-chloro-N-{(1S,2R)-1-(3,5-difluorobenzyl)-3-[(3-ethylbenzyl)amino]-2-hydroxypropyl}-3-methyl-1-phenyl-1H-pyrazole-4-carboxamide |
| 2211 | N-{(1S,2R)-1-(3,5-difluorobenzyl)-3-[(3-ethylbenzyl)amino]-2-hydroxypropyl}-4-methyl-1,2,3-thiadiazole-5-carboxamide |
| 2212 | N-{(1S,2R)-1-(3,5-difluorobenzyl)-3-[(3-ethylbenzyl)amino]-2-hydroxypropyl}-2,1,3-benzoxadiazole-5-carboxamide |
| 2213 | N-{(1S,2R)-1-(3,5-difluorobenzyl)-3-[(3-ethylbenzyl)amino]-2-hydroxypropyl}-2-[(imidazo[1,2-a]pyridin-2-ylmethyl)thio]acetamide |
| 2214 | 2-(acetylamino)-N-{(1R,2R)-1-(3,5-difluorobenzyl)-2-hydroxy-3-[(3-iodobenzyl)amino]propyl}-1,3-oxazole-4-carboxamide |
| 2215 | N-{(1S,2R)-1-[3-(cyclohexylmethyl)benzyl]-2-hydroxy-3-[(3-methoxybenzyl)amino]propyl}acetamide |
| 2216 | 1 2-{[({(1S,2R)-1-benzyl-2-hydroxy-3-[(3-methoxybenzyl)amino]propyl}amino)carbonyl]amino}-N,N-dipropylethanesulfonamide hydrochloride |
| 2217 | 2-(3-azabicyclo[3.2.2]non-3-yl)-N-{(1S,2R)-1-(3,5-difluorobenzyl)-2-hydroxy-3-[(3-iodobenzyl)amino]propyl}acetamide |
| 2218 | 2-(4-benzoylphenoxy)-N-{(1S,2R)-1-(3,5-difluorobenzyl)-2-hydroxy-3-[(3-iodobenzyl)amino]propyl}propanamide |
| 2219 | N-{(1S,2R)-1-(3,5-difluorobenzyl)-2-hydroxy-3-[(3-iodobenzyl)amino]propyl}-4-(7-methoxy-2,3-dihydro-1-benzofuran-4-yl)-4-oxobutanamide |
| 2220 | N-{(1S,2R)-1-[3-(cyclohexylmethyl)benzyl]-2-hydroxy-3-[(3-methoxybenzyl)amino]propyl}-3-{[(trifluoromethyl)sulfonyl]amino}benzamide hydrochloride |
| 2221 | $N^1$-{(1S,2R)-1-[3-(cyclohexylmethyl)benzyl]-2-hydroxy-3-[(3-methoxybenzyl)amino]propyl}-5-methyl-$N^3,N^3$-dipropylisophthalamide hydrochloride |
| 2222 | 3-chloro-N-((1S,2R)-1-(4-fluorobenzyl)-2-hydroxy-3-{[3-(trifluoromethyl)benzyl]amino}propyl)benzamide |
| 2223 | 3-chloro-N-{(1S,2R)-1-(4-fluorobenzyl)-2-hydroxy-3-[(3-methoxybenzyl)amino]propyl}benzamide |
| 2224 | 3-chloro-N-((1S,2R)-1-(cyclohexylmethyl)-2-hydroxy-3-{[3-(trifluoromethyl)benzyl]amino}propyl)benzamide |
| 2225 | 3-chloro-N-{(1S,2R)-1-(cyclohexylmethyl)-2-hydroxy-3-[(3-methoxybenzyl)amino]propyl}benzamide |
| 2226 | N-((1S,2S)-1-benzyl-2-hydroxy-3-{[3-(trifluoromethyl)benzyl]amino}propyl)-3-chlorobenzamide |
| 2227 | N-{(1S,2S)-1-benzyl-2-hydroxy-3-[(3-methoxybenzyl)amino]propyl}-3-chlorobenzamide |
| 2228 | 3-{[(3-chlorobenzyl)amino]sulfonyl}-N-((1S,2R)-1-(4-fluorobenzyl)-2-hydroxy-3-{[3-(trifluoromethyl)benzyl]amino}propyl)benzamide |
| 2229 | 3-{[(3-chlorobenzyl)amino]sulfonyl}-N-{(1S,2R)-1-(4-fluorobenzyl)-2-hydroxy-3-[(3-methoxybenzyl)amino]propyl}benzamide |
| 2230 | 3-{[(3-chlorobenzyl)amino]sulfonyl}-N-((1S,2R)-1-(cyclohexylmethyl)-2-hydroxy-3-{[3-(trifluoromethyl)benzyl]amino}propyl)benzamide |
| 2231 | 3-{[(3-chlorobenzyl)amino]sulfonyl}-N-{(1S,2R)-1-(cyclohexylmethyl)-2-hydroxy-3-[(3-methoxybenzyl)amino]propyl}benzamide |
| 2232 | N-{(1S,2S)-1-benzyl-2-hydroxy-3-[(3-methoxybenzyl)amino]propyl}-3-{[(3-chlorobenzyl)amino]sulfonyl}benzamide |
| 2233 | N-{(1S,2R)-1-(4-fluorobenzyl)-2-hydroxy-3-[(3-methoxybenzyl)amino]propyl}-3-{[(3-methoxybenzyl)amino]sulfonyl}benzamide |
| 2234 | N-((1S,2R)-1-(cyclohexylmethyl)-2-hydroxy-3-{[3-(trifluoromethyl)benzyl]amino}propyl)-3-{[(3-methoxybenzyl)amino]sulfonyl}benzamide |
| 2235 | N-{(1S,2R)-1-(cyclohexylmethyl)-2-hydroxy-3-[(3-methoxybenzyl)amino]propyl}-3-{[(3-methoxybenzyl)amino]sulfonyl}benzamide |
| 2236 | N-{(1S,2S)-1-benzyl-2-hydroxy-3-[(3-methoxybenzyl)amino]propyl}-3-{[(3-methoxybenzyl)amino]sulfonyl}benzamide |

-continued

| | Compound Name (IUPAC Name) |
|---|---|
| 2237 | $N^1$-[(1R,2S)-2-hydroxy-3-[(3-methoxybenzyl)amino]-1-(4-methylbenzyl)propyl]-$N^3,N^3$-dipropylbenzene-1,3,5-tricarboxamide |
| 2238 | $N^1$-[(1R,2S)-2-hydroxy-3-(isopentylamino)-1-(4-methylbenzyl)propyl]-$N^3,N^3$-dipropylbenzene-1,3,5-tricarboxamide |
| 2239 | $N^1$-[(1R,2S)-2-hydroxy-3-[(3-methoxybenzyl)amino]-1-(4-methylbenzyl)propyl]-5-methyl-$N^3,N^3$-dipropylisophthalamide |
| 2240 | $N^1$-[(1R,2S)-2-hydroxy-3-(isopentylamino)-1-(4-methylbenzyl)propyl]-5-methyl-$N^3,N^3$-dipropylisophthalamide |
| 2241 | $N^1$-[(1R,2S)-2-hydroxy-3-[(3-methoxybenzyl)amino]-1-(4-methylbenzyl)propyl]-$N^5,N^5$-dipropylpentanediamide |
| 2242 | $N^1$-[(1R,2S)-2-hydroxy-3-(isopentylamino)-1-(4-methylbenzyl)propyl]-$N^5,N^5$-dipropylpentanediamide |
| 2243 | 3-[(dipropylamino)sulfonyl]-N-[(1R,2S)-2-hydroxy-3-[(3-methoxybenzyl)amino]-1-(4-methylbenzyl)propyl]propanamide |
| 2244 | 3-[(dipropylamino)sulfonyl]-N-[(1R,2S)-2-hydroxy-3-(isopentylamino)-1-(4-methylbenzyl)propyl]propanamide |
| 2245 | $N^1$-[(1S,2R)-2-hydroxy-3-[(3-methoxybenzyl)amino]-1-(4-methylbenzyl)propyl]-$N^5,N^5$-dipropylpentanediamide |
| 2246 | $N^1$-[(1S,2R)-3-(benzylamino)-2-hydroxy-1-(4-methylbenzyl)propyl]-$N^5,N^5$-dipropylpentanediamide |
| 2247 | $N^1$-[(1S,2R)-2-hydroxy-3-(isopentylamino)-1-(4-methylbenzyl)propyl]-$N^5,N^5$-dipropylpentanediamide |
| 2248 | N-[(1S,2R)-3-(benzylamino)-2-hydroxy-1-(4-methylbenzyl)propyl]-3-[(dipropylamino)sulfonyl]propanamide |
| 2249 | 3-[(dipropylamino)sulfonyl]-N-[(1S,2R)-2-hydroxy-3-(isopentylamino)-1-(4-methylbenzyl)propyl]propanamide |
| 2250 | N-{(1S,2R)-1-benzyl-2-hydroxy-3-[(3-methoxybenzyl)amino]propyl}-3-(4,5-dimethyl-2-furoyl)-5-methylbenzamide |
| 2251 | N-{(1S,2R)-1-benzyl-2-hydroxy-3-[(3-methoxybenzyl)amino]propyl}-2-hydroxy-3-(isopentylsulfonyl)propanamide hydrochloride |
| 2252 | N-{(1S,2R)-1-benzyl-2-hydroxy-3-[(3-methoxybenzyl)amino]propyl}-3-{[(2-methoxyethyl)(propyl)amino]sulfonyl}propanamide hydrochloride |
| 2253 | $N^1$-{(1R,2R)-3-(benzylamino)-2-hydroxy-1-[(phenylthio)methyl]propyl}-$N^3,N^3$-dipropylbenzene-1,3,5-tricarboxamide |
| 2254 | $N^1$-{(1R,2R)-2-hydroxy-3-(isopentylamino)-1-[(phenylthio)methyl]propyl}-$N^3,N^3$-dipropylbenzene-1,3,5-tricarboxamide |
| 2255 | $N^1$-{(1S,2R)-3-(benzylamino)-1-[4-(benzyloxy)benzyl]-2-hydroxypropyl}-$N^3,N^3$-dipropylbenzene-1,3,5-tricarboxamide |
| 2256 | $N^1$-[(1S,2R)-1-[4-(benzyloxy)benzyl]-2-hydroxy-3-(isopentylamino)propyl]-$N^3,N^3$-dipropylbenzene-1,3,5-tricarboxamide |
| 2257 | $N^1$-[(1S,2R)-2-hydroxy-3-[(3-methoxybenzyl)amino]-1-(1-naphthylmethyl)propyl]-$N^3,N^3$-dipropylbenzene-1,3,5-tricarboxamide |
| 2259 | $N^1$-[(1S,2R)-2-hydroxy-3-(isopentylamino)-1-(1-naphthylmethyl)propyl]-$N^3,N^3$-dipropylbenzene-1,3,5-tricarboxamide |
| 2260 | $N^1$-[(1S,2R)-1-(2-furylmethyl)-2-hydroxy-3-(isopentylamino)propyl]-$N^3,N^3$-dipropylbenzene-1,3,5-tricarboxamide |
| 2261 | $N^1$-{(1S,2R)-3-(benzylamino)-1-[3-(benzyloxy)benzyl]-2-hydroxypropyl}-$N^3,N^3$-dipropylbenzene-1,3,5-tricarboxamide |
| 2262 | $N^1$-[(1S,2R)-2-hydroxy-1-(4-hydroxybenzyl)-3-(isopentylamino)propyl]-$N^3,N^3$-dipropylbenzene-1,3,5-tricarboxamide |
| 2263 | $N^1$-((1S)-1-{(1R)-1-hydroxy-2-[(3-methoxybenzyl)amino]ethyl}but-3-ynyl)-$N^3,N^3$-dipropylbenzene-1,3,5-tricarboxamide |
| 2264 | $N^1$-{(1S)-1-[(1R)-2-(benzylamino)-1-hydroxyethyl]but-3-ynyl}-$N^3,N^3$-dipropylbenzene-1,3,5-tricarboxamide |
| 2265 | $N^1$-{(1S)-1-[(1R)-1-hydroxy-2-(isopentylamino)ethyl]but-3-ynyl}-$N^3,N^3$-dipropylbenzene-1,3,5-tricarboxamide |
| 2266 | $N^1$-[(1S,2R)-3-(benzylamino)-1-(cyclohexylmethyl)-2-hydroxypropyl]-$N^3,N^3$-dipropylbenzene-1,3,5-tricarboxamide |
| 2267 | $N^1$-[(1S,2R)-1-(cyclohexylmethyl)-2-hydroxy-3-(isopentylamino)propyl]-$N^3,N^3$-dipropylbenzene-1,3,5-tricarboxamide |
| 2268 | $N^1$-((1S)-1-{(1R)-1-hydroxy-2-[(3-methoxybenzyl)amino]ethyl}-3-methylbutyl)-$N^3,N^3$-dipropylbenzene-1,3,5-tricarboxamide |
| 2270 | $N^1$-{(1S)-1-[(1R)-1-hydroxy-2-(isopentylamino)ethyl]-3-methylbutyl}-$N^3,N^3$-dipropylbenzene-1,3,5-tricarboxamide |
| 2271 | $N^1$-{(1R,2R)-3-(benzylamino)-2-hydroxy-1-[(phenylthio)methyl]propyl}-5-methyl-$N^3,N^3$-dipropylisophthalamide |
| 2272 | $N^1$-{(1R,2R)-2-hydroxy-3-(isopentylamino)-1-[(phenylthio)methyl]propyl}-5-methyl-$N^3,N^3$-dipropylisophthalamide |
| 2273 | $N^1$-{(1S,2R)-3-(benzylamino)-1-[4-(benzyloxy)benzyl]-2-hydroxypropyl}-5-methyl-$N^3,N^3$-dipropylisophthalamide |
| 2274 | $N^1$-[(1S,2R)-1-[4-(benzyloxy)benzyl]-2-hydroxy-3-(isopentylamino)propyl]-5-methyl-$N^3,N^3$-dipropylisophthalamide |
| 2275 | $N^1$-[(1S,2R)-2-hydroxy-3-[(3-methoxybenzyl)amino]-1-(1-naphthylmethyl)propyl]-5-methyl-$N^3,N^3$-dipropylisophthalamide |
| 2277 | $N^1$-[(1S,2R)-2-hydroxy-3-(isopentylamino)-1-(1-naphthylmethyl)propyl]-5-methyl-$N^3,N^3$-dipropylisophthalamide |
| 2278 | $N^1$-[(1S,2R)-1-(2-furylmethyl)-2-hydroxy-3-(isopentylamino)propyl]-5-methyl-$N^3,N^3$-dipropylisophthalamide |
| 2279 | $N^1$-{(1S,2R)-3-(benzylamino)-1-[3-(benzyloxy)benzyl]-2-hydroxypropyl}-5-methyl-$N^3,N^3$-dipropylisophthalamide |
| 2280 | $N^1$-[(1S,2R)-1-[3-(benzyloxy)benzyl]-2-hydroxy-3-(isopentylamino)propyl]-5-methyl-$N^3,N^3$-dipropylisophthalamide |
| 2281 | $N^1$-[(1S,2R)-1-(4-fluorobenzyl)-2-hydroxy-3-(isopentylamino)propyl]-5-methyl-$N^3,N^3$-dipropylisophthalamide |
| 2282 | $N^1$-[(1S,2R)-2-hydroxy-3-(isopentylamino)-1-(thien-2-ylmethyl)propyl]-5-methyl-$N^3,N^3$-dipropylisophthalamide |
| 2283 | $N^1$-((1S)-1-{(1R)-1-hydroxy-2-[(3-methoxybenzyl)amino]ethyl}but-3-ynyl)-5-methyl-$N^3,N^3$-dipropylisophthalamide |
| 2284 | $N^1$-{(1S)-1-[(1R)-2-(benzylamino)-1-hydroxyethyl]but-3-ynyl}-5-methyl-$N^3,N^3$-dipropylisophthalamide |
| 2285 | $N^1$-{(1S)-1-[(1R)-1-hydroxy-2-(isopentylamino)ethyl]but-3-ynyl}-5-methyl-$N^3,N^3$-dipropylisophthalamide |
| 2286 | $N^1$-[(1S,2R)-1-(cyclohexylmethyl)-2-hydroxy-3-(isopentylamino)propyl]-5-methyl-$N^3,N^3$-dipropylisophthalamide |
| 2288 | $N^1$-{(1S)-1-[(1R)-1-hydroxy-2-(isopentylamino)ethyl]-3-methylbutyl}-5-methyl-$N^3,N^3$-dipropylisophthalamide |
| 2289 | $N^1$-{(1R,2R)-2-hydroxy-3-[(3-methoxybenzyl)amino]-1-[(phenylthio)methyl]propyl}-$N^5,N^5$-dipropylpentanediamide |
| 2290 | $N^1$-{(1R,2R)-3-(benzylamino)-2-hydroxy-1-[(phenylthio)methyl]propyl}-$N^5,N^5$-dipropylpentanediamide |
| 2291 | $N^1$-{(1R,2R)-2-hydroxy-3-(isopentylamino)-1-[(phenylthio)methyl]propyl}-$N^5,N^5$-dipropylpentanediamide |

| | Compound Name (IUPAC Name) |
|---|---|
| 2292 | $N^1$-{(1S,2R)-3-(benzylamino)-1-[4-(benzyloxy)benzyl]-2-hydroxypropyl}-$N^5,N^5$-dipropylpentanediamide |
| 2293 | $N^1$-[(1S,2R)-1-[4-(benzyloxy)benzyl]-2-hydroxy-3-(isopentylamino)propyl]-$N^5,N^5$-dipropylpentanediamide |
| 2295 | $N^1$-[(1S,2R)-3-(benzylamino)-2-hydroxy-1-(1-naphthylmethyl)propyl]-$N^5,N^5$-dipropylpentanediamide |
| 2296 | $N^1$-[(1S,2R)-2-hydroxy-3-(isopentylamino)-1-(1-naphthylmethyl)propyl]-$N^5,N^5$-dipropylpentanediamide |
| 2298 | $N^1$-[(1S,2R)-3-(benzylamino)-1-(2-furylmethyl)-2-hydroxypropyl]-$N^5,N^5$-dipropylpentanediamide |
| 2299 | $N^1$-[(1S,2R)-1-(2-furylmethyl)-2-hydroxy-3-(isopentylamino)propyl]-$N^5,N^5$-dipropylpentanediamide |
| 2300 | $N^1$-{(1S,2R)-1-[3-(benzyloxy)benzyl]-2-hydroxy-3-[(3-methoxybenzyl)amino]propyl}-$N^5,N^5$-dipropylpentanediamide |
| 2301 | $N^1$-{(1S,2R)-3-(benzylamino)-1-[3-(benzyloxy)benzyl]-2-hydroxypropyl}-$N^5,N^5$-dipropylpentanediamide |
| 2302 | $N^1$-[(1S,2R)-1-[3-(benzyloxy)benzyl]-2-hydroxy-3-(isopentylamino)propyl]-$N^5,N^5$-dipropylpentanediamide |
| 2304 | $N^1$-[(1S,2R)-3-(benzylamino)-1-(4-fluorobenzyl)-2-hydroxypropyl]-$N^5,N^5$-dipropylpentanediamide |
| 2305 | $N^1$-[(1S,2R)-1-(4-fluorobenzyl)-2-hydroxy-3-(isopentylamino)propyl]-$N^5,N^5$-dipropylpentanediamide |
| 2306 | $N^1$-[(1S,2R)-3-(benzylamino)-2-hydroxy-1-(thien-2-ylmethyl)propyl]-$N^5,N^5$-dipropylpentanediamide |
| 2307 | $N^1$-[(1S,2R)-2-hydroxy-3-(isopentylamino)-1-(thien-2-ylmethyl)propyl]-$N^5,N^5$-dipropylpentanediamide |
| 2308 | $N^1$-[(1S,2R)-3-(benzylamino)-2-hydroxy-1-(4-hydroxybenzyl)propyl]-$N^5,N^5$-dipropylpentanediamide |
| 2309 | $N^1$-[(1S,2R)-2-hydroxy-1-(4-hydroxybenzyl)-3-(isopentylamino)propyl]-$N^5,N^5$-dipropylpentanediamide |
| 2310 | $N^1$-((1S)-1-{(1R)-1-hydroxy-2-[(3-methoxybenzyl)amino]ethyl}but-3-ynyl)-$N^5,N^5$-dipropylpentanediamide |
| 2311 | $N^1$-{(1S)-1-[(1R)-2-(benzylamino)-1-hydroxyethyl]but-3-ynyl}-$N^5,N^5$-dipropylpentanediamide |
| 2312 | $N^1$-{(1S)-1-[(1R)-1-hydroxy-2-(isopentylamino)ethyl]but-3-ynyl}-$N^5,N^5$-dipropylpentanediamide |
| 2313 | $N^1$-{(1S,2R)-1-(cyclohexylmethyl)-2-hydroxy-3-[(3-methoxybenzyl)amino]propyl}-$N^5,N^5$-dipropylpentanediamide |
| 2314 | $N^1$-[(1S,2R)-3-(benzylamino)-1-(cyclohexylmethyl)-2-hydroxypropyl]-$N^5,N^5$-dipropylpentanediamide |
| 2315 | $N^1$-[(1S,2R)-1-(cyclohexylmethyl)-2-hydroxy-3-(isopentylamino)propyl]-$N^5,N^5$-dipropylpentanediamide |
| 2316 | $N^1$-((1S)-1-{(1R)-1-hydroxy-2-[(3-methoxybenzyl)amino]ethyl}-3-methylbutyl)-$N^5,N^5$-dipropylpentanediamide |
| 2317 | $N^1$-{(1S)-1-[(1R)-2-(benzylamino)-1-hydroxyethyl]-3-methylbutyl}-$N^5,N^5$-dipropylpentanediamide |
| 2318 | $N^1$-{(1S)-1-[(1R)-1-hydroxy-2-(isopentylamino)ethyl]-3-methylbutyl}-$N^5,N^5$-dipropylpentanediamide |
| 2319 | 3-[(dipropylamino)sulfonyl]-N-{(1R,2R)-2-hydroxy-3-[(3-methoxybenzyl)amino]-1-[(phenylthio)methyl]propyl}propanamide |
| 2320 | N-{(1R,2R)-3-(benzylamino)-2-hydroxy-1-[(phenylthio)methyl]propyl}-3-[(dipropylamino)sulfonyl]propanamide |
| 2321 | 3-[(dipropylamino)sulfonyl]-N-{(1R,2R)-2-hydroxy-3-1-[(phenylthio)methyl]propyl}propanamide |
| 2322 | N-{(1S,2R)-3-(benzylamino)-1-[4-(benzyloxy)benzyl]-2-hydroxypropyl}-3-[(dipropylamino)sulfonyl]propanamide |
| 2323 | N-[(1S,2R)-1-[4-(benzyloxy)benzyl]-2-hydroxy-3-(isopentylamino)propyl]-3-[(dipropylamino)sulfonyl]propanamide |
| 2324 | N-[(1S,2R)-3-(benzylamino)-2-hydroxy-1-(1-naphthylmethyl)propyl]-3-[(dipropylamino)sulfonyl]propanamide |
| 2325 | 3-[(dipropylamino)sulfonyl]-N-[(1S,2R)-2-hydroxy-3-(isopentylamino)-1-(1-naphthylmethyl)propyl]propanamide |
| 2326 | N-[(1S,2R)-3-(benzylamino)-1-(2-furylmethyl)-2-hydroxypropyl]-3-[(dipropylamino)sulfonyl]propanamide |
| 2327 | 3-[(dipropylamino)sulfonyl]-N-[(1S,2R)-1-(2-furylmethyl)-2-hydroxy-3-(isopentylamino)propyl]propanamide |
| 2328 | N-{(1S,2R)-1-[3-(benzyloxy)benzyl]-2-hydroxy-3-[(3-methoxybenzyl)amino]propyl}-3-[(dipropylamino)sulfonyl]propanamide |
| 2329 | N-{(1S,2R)-3-(benzylamino)-1-[3-(benzyloxy)benzyl]-2-hydroxypropyl}-3-[(dipropylamino)sulfonyl]propanamide |
| 2330 | N-[(1S,2R)-1-[3-(benzyloxy)benzyl]-2-hydroxy-3-(isopentylamino)propyl]-3-[(dipropylamino)sulfonyl]propanamide |
| 2331 | N-[(1S,2R)-3-(benzylamino)-1-(4-fluorobenzyl)-2-hydroxypropyl]-3-[(dipropylamino)sulfonyl]propanamide |
| 2332 | 3-[(dipropylamino)sulfonyl]-N-[(1S,2R)-1-(4-fluorobenzyl)-2-hydroxy-3-(isopentylamino)propyl]propanamide |
| 2333 | N-[(1S,2R)-3-(benzylamino)-2-hydroxy-1-(thien-2-ylmethyl)propyl]-3-[(dipropylamino)sulfonyl]propanamide |
| 2334 | 3-[(dipropylamino)sulfonyl]-N-((1S)-1-{(1R)-1-hydroxy-2-[(3-methoxybenzyl)amino]ethyl}but-3-ynyl)propanamide |
| 2335 | N'-[(1S,2R)-1-(3,5-difluorobenzyl)-2-hydroxy-3-({3-[(1Z)-prop-1-en-1-yl]benzyl}amino)propyl]-5-methyl-N,N-dipropylisophthalamide |
| 2335 | N-{(1S)-1-[(1R)-2-(benzylamino)-1-hydroxyethyl]but-3-ynyl}-3-[(dipropylamino)sulfonyl]propanamide |
| 2336 | 3-[(dipropylamino)sulfonyl]-N-{(1S)-1-[(1R)-1-hydroxy-2-(isopentylamino)ethyl]but-3-ynyl}propanamide |
| 2337 | N-{(1S,2R)-1-(cyclohexylmethyl)-2-hydroxy-3-[(3-methoxybenzyl)amino]propyl}-3-[(dipropylamino)sulfonyl]propanamide |
| 2338 | N-[(1S,2R)-3-(benzylamino)-1-(cyclohexylmethyl)-2-hydroxypropyl]-3-[(dipropylamino)sulfonyl]propanamide |
| 2339 | methyl [3-({[[(2R,3S)-4-(3,5-difluorophenyl)-3-({3-[(dipropylamino)carbonyl]-5-methylbenzoyl}amino)-2-hydroxybutyl]amino}methyl)phenyl]methylcarbamate |
| 2339 | N-[(1S,2R)-1-(cyclohexylmethyl)-2-hydroxy-3-(isopentylamino)propyl]-3-[(dipropylamino)sulfonyl]propanamide |
| 2340 | 3-[(dipropylamino)sulfonyl]-N-((1S)-1-{(1R)-1-hydroxy-2-[(3-methoxybenzyl)amino]ethyl}-3-methylbutyl)propanamide |
| 2341 | N-{(1S)-1-[(1R)-2-(benzylamino)-1-hydroxyethyl]-3-methylbutyl}-3-[(dipropylamino)sulfonyl]propanamide |
| 2342 | 3-[(dipropylamino)sulfonyl]-N-{(1S)-1-[(1R)-1-hydroxy-2-(isopentylamino)ethyl]-3-methylbutyl}propanamide |
| 2343 | $N^1$-[(1S,2R)-3-(benzylamino)-2-hydroxy-1-(3-methoxybenzyl)propyl]-$N^3,N^3$-dipropylbenzene-1,3,5-tricarboxamide |
| 2346 | $N^1$-[(1S,2R)-2-hydroxy-3-(isopentylamino)-1-(4-isopropylbenzyl)propyl]-$N^3,N^3$-dipropylbenzene-1,3,5-tricarboxamide |
| 2348 | $N^1$-[(1S,2R)-3-(benzylamino)-2-hydroxy-1-(4-methoxybenzyl)propyl]-$N^3,N^3$-dipropylbenzene-1,3,5-tricarboxamide |

| | Compound Name (IUPAC Name) |
|---|---|
| 2349 | $N^1$-[(1S,2R)-2-hydroxy-3-(isopentylamino)-1-(4-methoxybenzyl)propyl]-$N^3$,$N^3$-dipropylbenzene-1,3,5-tricarboxamide |
| 2350 | $N^1$-[(1S,2R)-3-(benzylamino)-1-(4-fluoro-3-methylbenzyl)-2-hydroxypropyl]-$N^3$,$N^3$-dipropylbenzene-1,3,5-tricarboxamide |
| 2351 | $N^1$-[(1S,2R)-1-(3-fluoro-4-methoxybenzyl)-2-hydroxy-3-(isopentylamino)propyl]-$N^3$,$N^3$-dipropylbenzene-1,3,5-tricarboxamide |
| 2352 | $N^1$-[(1S,2R)-3-(benzylamino)-2-hydroxy-1-(4-isopropylbenzyl)propyl]-5-methyl-$N^3$,$N^3$-dipropylisophthalamide |
| 2353 | $N^1$-[(1S,2R)-2-hydroxy-3-(isopentylamino)-1-(4-isopropylbenzyl)propyl]-5-methyl-$N^3$,$N^3$-dipropylisophthalamide |
| 2354 | $N^1$-{(1S,2R)-2-hydroxy-3-(isopentylamino)-1-[3-(trifluoromethoxy)benzyl]propyl}-5-methyl-$N^3$,$N^3$-dipropylisophthalamide |
| 2355 | $N^1$-[(1S,2R)-3-(benzylamino)-2-hydroxy-1-(4-methoxybenzyl)propyl]-5-methyl-$N^3$,$N^3$-dipropylisophthalamide |
| 2356 | $N^1$-[(1S,2R)-2-hydroxy-3-(isopentylamino)-1-(4-methoxybenzyl)propyl]-5-methyl-$N^3$,$N^3$-dipropylisophthalamide |
| 2357 | $N^1$-[(1S,2R)-3-(benzylamino)-1-(4-fluoro-3-methylbenzyl)-2-hydroxypropyl]-5-methyl-$N^3$,$N^3$-dipropylisophthalamide |
| 2358 | N'-((1S,2R)-1-(3,5-difluorobenzyl)-3-{[(4R)-2,2-dioxido-3,4-dihydro-1H-2,1-benzothiazin-4-yl]amino}-2-hydroxypropyl)-5-methyl-N,N-dipropylisophthalamide |
| 2359 | N'-((1S,2R)-1-(3,5-difluorobenzyl)-3-{[(4S)-2,2-dioxido-3,4-dihydro-1H-2,1-benzothiazin-4-yl]amino}-2-hydroxypropyl)-5-methyl-N,N-dipropylisophthalamide |
| 2358 | $N^1$-[(1S,2R)-1-(4-fluoro-3-methylbenzyl)-2-hydroxy-3-(isopentylamino)propyl]-5-methyl-$N^3$,$N^3$-dipropylisophthalamide |
| 2359 | $N^1$-{(1S,2R)-3-(benzylamino)-2-hydroxy-1-[3-(trifluoromethyl)benzyl]propyl}-5-methyl-$N^3$,$N^3$-dipropylisophthalamide |
| 2360 | $N^1$-[(1S,2R)-2-hydroxy-3-(isopentylamino)-1-(3-methylbenzyl)propyl]-5-methyl-$N^3$,$N^3$-dipropylisophthalamide |
| 2361 | $N^1$-{(1S,2R)-3-(benzylamino)-1-[3-(benzyloxy)-5-fluorobenzyl]-2-hydroxypropyl}-5-methyl-$N^3$,$N^3$-dipropylisophthalamide |
| 2362 | $N^1$-[(1S,2R)-3-(benzylamino)-1-(3-fluoro-4-methoxybenzyl)-2-hydroxypropyl]-5-methyl-$N^3$,$N^3$-dipropylisophthalamide |
| 2363 | $N^1$-{(1S,2R)-2-hydroxy-1-(3-methoxybenzyl)-3-[(3-methoxybenzyl)amino]propyl}-$N^5$,$N^5$-dipropylpentanediamide |
| 2364 | $N^1$-[(1S,2R)-3-(benzylamino)-2-hydroxy-1-(3-methoxybenzyl)propyl]-$N^5$,$N^5$-dipropylpentanediamide |
| 2365 | $N^1$-[(1S,2R)-2-hydroxy-3-(isopentylamino)-1-(3-methoxybenzyl)propyl]-$N^5$,$N^5$-dipropylpentanediamide |
| 2366 | $N^1$-[(1S,2R)-3-(benzylamino)-1-(3-chloro-5-fluorobenzyl)-2-hydroxypropyl]-$N^5$,$N^5$-dipropylpentanediamide |
| 2367 | $N^1$-[(1S,2R)-1-(3-chloro-5-fluorobenzyl)-2-hydroxy-3-(isopentylamino)propyl]-$N^5$,$N^5$-dipropylpentanediamide |
| 2368 | $N^1$-{(1S,2R)-1-(3,5-dichlorobenzyl)-2-hydroxy-3-[(3-methoxybenzyl)amino]propyl}-$N^5$,$N^5$-dipropylpentanediamide |
| 2369 | $N^1$-[(1S,2R)-3-(benzylamino)-1-(3,5-dichlorobenzyl)-2-hydroxypropyl]-$N^5$,$N^5$-dipropylpentanediamide |
| 2370 | $N^1$-[(1S,2R)-1-(3,5-dichlorobenzyl)-2-hydroxy-3-(isopentylamino)propyl]-$N^5$,$N^5$-dipropylpentanediamide |
| 2371 | $N^1$-{(1S,2R)-2-hydroxy-1-(4-isopropylbenzyl)-3-[(3-methoxybenzyl)amino]propyl}-$N^5$,$N^5$-dipropylpentanediamide |
| 2311 | $N^1$-[(1S,2R)-3-(benzylamino)-2-hydroxy-1-(4-isopropylbenzyl)propyl]-$N^5$,$N^5$-dipropylpentanediamide |
| 2312 | $N^1$-[(1S,2R)-2-hydroxy-3-(isopentylamino)-1-(4-isopropylbenzyl)propyl]-$N^5$,$N^5$-dipropylpentanediamide |
| 2313 | $N^1$-{(1S,2R)-1-[3-fluoro-5-(trifluoromethyl)benzyl]-2-hydroxy-3-[(3-methoxybenzyl)amino]propyl}-$N^5$,$N^5$-dipropylpentanediamide |
| 2314 | $N^1$-{(1S,2R)-3-(benzylamino)-1-[3-fluoro-5-(trifluoromethyl)benzyl]-2-hydroxypropyl}-$N^5$,$N^5$-dipropylpentanediamide |
| 2315 | $N^1$-[(1S,2R)-1-[3-fluoro-5-(trifluoromethyl)benzyl]-2-hydroxy-3-(isopentylamino)propyl]-$N^5$,$N^5$-dipropylpentanediamide |
| 2316 | $N^1$-{(1S,2R)-2-hydroxy-3-[(3-methoxybenzyl)amino]-1-[3-(trifluoromethoxy)benzyl]propyl}-$N^5$,$N^5$-dipropylpentanediamide |
| 2317 | $N^1$-{(1S,2R)-3-(benzylamino)-2-hydroxy-1-[3-(trifluoromethoxy)benzyl]propyl}-$N^5$,$N^5$-dipropylpentanediamide |
| 2318 | $N^1$-{(1S,2R)-2-hydroxy-3-(isopentylamino)-1-[3-(trifluoromethoxy)benzyl]propyl}-$N^5$,$N^5$-dipropylpentanediamide |
| 2319 | $N^1$-[(1S,2R)-3-(benzylamino)-1-(3-fluoro-4-methylbenzyl)-2-hydroxypropyl]-$N^5$,$N^5$-dipropylpentanediamide |
| 2320 | $N^1$-[(1S,2R)-1-(3-fluoro-4-methylbenzyl)-2-hydroxy-3-(isopentylamino)propyl]-$N^5$,$N^5$-dipropylpentanediamide |
| 2321 | $N^1$-{(1S,2R)-2-hydroxy-1-(4-methoxybenzyl)-3-[(3-methoxybenzyl)amino]propyl}-$N^5$,$N^5$-dipropylpentanediamide |
| 2322 | $N^1$-[(1S,2R)-3-(benzylamino)-2-hydroxy-1-(4-methoxybenzyl)propyl]-$N^5$,$N^5$-dipropylpentanediamide |
| 2323 | $N^1$-[(1S,2R)-2-hydroxy-3-(isopentylamino)-1-(4-methoxybenzyl)propyl]-$N^5$,$N^5$-dipropylpentanediamide |
| 2324 | $N^1$-{(1S,2R)-1-(4-chlorobenzyl)-2-hydroxy-3-[(3-methoxybenzyl)amino]propyl}-$N^5$,$N^5$-dipropylpentanediamide |
| 2325 | $N^1$-[(1S,2R)-3-(benzylamino)-1-(4-chlorobenzyl)-2-hydroxypropyl]-$N^5$,$N^5$-dipropylpentanediamide |
| 2326 | $N^1$-[(1S,2R)-1-(4-chlorobenzyl)-2-hydroxy-3-(isopentylamino)propyl]-$N^5$,$N^5$-dipropylpentanediamide |
| 2327 | $N^1$-{(1S,2R)-1-(1,3-benzodioxol-5-ylmethyl)-2-hydroxy-3-[(3-methoxybenzyl)amino]propyl}-$N^5$,$N^5$-dipropylpentanediamide |
| 2328 | $N^1$-[(1S,2R)-1-(1,3-benzodioxol-5-ylmethyl)-3-(benzylamino)-2-hydroxypropyl]-$N^5$,$N^5$-dipropylpentanediamide |
| 2329 | $N^1$-[(1S,2R)-1-(1,3-benzodioxol-5-ylmethyl)-2-hydroxy-3-(isopentylamino)propyl]-$N^5$,$N^5$-dipropylpentanediamide |
| 2330 | $N^1$-{(1S,2R)-1-(4-fluoro-3-methylbenzyl)-2-hydroxy-3-[(3-methoxybenzyl)amino]propyl}-$N^5$,$N^5$-dipropylpentanediamide |
| 2331 | $N^1$-[(1S,2R)-3-(benzylamino)-1-(4-fluoro-3-methylbenzyl)-2-hydroxypropyl]-$N^5$,$N^5$-dipropylpentanediamide |
| 2332 | $N^1$-[(1S,2R)-1-(4-fluoro-3-methylbenzyl)-2-hydroxy-3-(isopentylamino)propyl]-$N^5$,$N^5$-dipropylpentanediamide |

| | Compound Name (IUPAC Name) |
|---|---|
| 2333 | N¹-{(1S,2R)-3-(benzylamino)-2-hydroxy-1-[3-(trifluoromethyl)benzyl]propyl}-N⁵,N⁵-dipropylpentanediamide |
| 2335 | N¹-[(1S,2R)-2-hydroxy-3-[(3-methoxybenzyl)amino]-1-(3-methylbenzyl)propyl]-N⁵,N⁵-dipropylpentanediamide |
| 2336 | N¹-[(1S,2R)-3-(benzylamino)-2-hydroxy-1-(3-methylbenzyl)propyl]-N⁵,N⁵-dipropylpentanediamide |
| 2337 | N¹-[(1S,2R)-2-hydroxy-3-(isopentylamino)-1-(3-methylbenzyl)propyl]-N⁵,N⁵-dipropylpentanediamide |
| 2338 | N¹-{(1S,2R)-1-[3-(benzyloxy)-5-fluorobenzyl]-2-hydroxy-3-[(3-methoxybenzyl)amino]propyl}-N⁵,N⁵-dipropylpentanediamide |
| 2339 | N¹-{(1S,2R)-3-(benzylamino)-1-[3-(benzyloxy)-5-fluorobenzyl]-2-hydroxypropyl}-N⁵,N⁵-dipropylpentanediamide |
| 2340 | N¹-[(1S,2R)-1-[3-(benzyloxy)-5-fluorobenzyl]-2-hydroxy-3-(isopentylamino)propyl]-N⁵,N⁵-dipropylpentanediamide |
| 2341 | N¹-{(1S,2R)-1-(3-fluoro-4-methoxybenzyl)-2-hydroxy-3-[(3-methoxybenzyl)amino]propyl}-N⁵,N⁵-dipropylpentanediamide |
| 2342 | N¹-[(1S,2R)-3-(benzylamino)-1-(3-fluoro-4-methoxybenzyl)-2-hydroxypropyl]-N⁵,N⁵-dipropylpentanediamide |
| 2343 | N¹-[(1S,2R)-1-(3-fluoro-4-methoxybenzyl)-2-hydroxy-3-(isopentylamino)propyl]-N⁵,N⁵-dipropylpentanediamide |
| 2344 | N¹-[(1S,2R)-3-(benzylamino)-1-(3-bromobenzyl)-2-hydroxypropyl]-N⁵,N⁵-dipropylpentanediamide |
| 2345 | N¹-[(1S,2R)-1-(3-bromobenzyl)-2-hydroxy-3-(isopentylamino)propyl]-N⁵,N⁵-dipropylpentanediamide |
| 2346 | N-[(1S,2R)-3-(benzylamino)-2-hydroxy-1-(3-methoxybenzyl)propyl]-3-[(dipropylamino)sulfonyl]propanamide |
| 2347 | 3-[(dipropylamino)sulfonyl]-N-[(1S,2R)-2-hydroxy-3-(isopentylamino)-1-(3-methoxybenzyl)propyl]propanamide |
| 2348 | N-[(1S,2R)-3-(benzylamino)-1-(3,5-dichlorobenzyl)-2-hydroxypropyl]-3-[(dipropylamino)sulfonyl]propanamide |
| 2349 | 3-[(dipropylamino)sulfonyl]-N-{(1S,2R)-2-hydroxy-1-(4-isopropylbenzyl)-3-[(3-methoxybenzyl)amino]propyl}propanamide |
| 2350 | N-[(1S,2R)-3-(benzylamino)-2-hydroxy-1-(4-isopropylbenzyl)propyl]-3-[(dipropylamino)sulfonyl]propanamide |
| 2351 | 3-[(dipropylamino)sulfonyl]-N-[(1S,2R)-2-hydroxy-3-(isopentylamino)-1-(4-isopropylbenzyl)propyl]propanamide |
| 2352 | N-{(1S,2R)-3-(benzylamino)-1-[3-fluoro-5-(trifluoromethyl)benzyl]-2-hydroxypropyl}-3-[(dipropylamino)sulfonyl]propanamide |
| 2353 | 3-[(dipropylamino)sulfonyl]-N-[(1S,2R)-1-[3-fluoro-5-(trifluoromethyl)benzyl]-2-hydroxy-3-(isopentylamino)propyl]propanamide |
| 2354 | N-{(1S,2R)-3-(benzylamino)-2-hydroxy-1-[3-(trifluoromethoxy)benzyl]propyl}-3-[(dipropylamino)sulfonyl]propanamide |
| 2355 | N-[(1S,2R)-3-(benzylamino)-1-(3-fluoro-4-methylbenzyl)-2-hydroxypropyl]-3-[(dipropylamino)sulfonyl]propanamide |
| 2356 | 3-[(dipropylamino)sulfonyl]-N-[(1S,2R)-1-(3-fluoro-4-methylbenzyl)-2-hydroxy-3-(isopentylamino)propyl]propanamide |
| 2357 | 3-[(dipropylamino)sulfonyl]-N-{(1S,2R)-2-hydroxy-1-(4-methoxybenzyl)-3-[(3-methoxybenzyl)amino]propyl}propanamide |
| 2358 | N-[(1S,2R)-3-(benzylamino)-2-hydroxy-1-(4-methoxybenzyl)propyl]-3-[(dipropylamino)sulfonyl]propanamide |
| 2359 | 3-[(dipropylamino)sulfonyl]-N-[(1S,2R)-2-hydroxy-3-(isopentylamino)-1-(4-methoxybenzyl)propyl]propanamide |
| 2360 | N-[(1S,2R)-3-(benzylamino)-1-(4-chlorobenzyl)-2-hydroxypropyl]-3-[(dipropylamino)sulfonyl]propanamide |
| 2314 | N-[(1S,2R)-1-(4-chlorobenzyl)-2-hydroxy-3-(isopentylamino)propyl]-3-[(dipropylamino)sulfonyl]propanamide |
| 2315 | N-[(1S,2R)-1-(1,3-benzodioxol-5-ylmethyl)-3-(benzylamino)-2-hydroxypropyl]-3-[(dipropylamino)sulfonyl]propanamide |
| 2316 | N-[(1S,2R)-1-(1,3-benzodioxol-5-ylmethyl)-2-hydroxy-3-(isopentylamino)propyl]-3-[(dipropylamino)sulfonyl]propanamide |
| 2317 | 3-[(dipropylamino)sulfonyl]-N-{(1S,2R)-1-(4-fluoro-3-methylbenzyl)-2-hydroxy-3-[(3-methoxybenzyl)amino]propyl}propanamide |
| 2318 | N-[(1S,2R)-3-(benzylamino)-1-(4-fluoro-3-methylbenzyl)-2-hydroxypropyl]-3-[(dipropylamino)sulfonyl]propanamide |
| 2319 | 3-[(dipropylamino)sulfonyl]-N-[(1S,2R)-1-(4-fluoro-3-methylbenzyl)-2-hydroxy-3-(isopentylamino)propyl]propanamide |
| 2320 | N-{(1S,2R)-3-(benzylamino)-2-hydroxy-1-[3-(trifluoromethyl)benzyl]propyl}-3-[(dipropylamino)sulfonyl]propanamide |
| 2321 | 3-[(dipropylamino)sulfonyl]-N-{(1S,2R)-2-hydroxy-3-(isopentylamino)-1-[3-(trifluoromethyl)benzyl]propyl}propanamide |
| 2322 | N-[(1S,2R)-3-(benzylamino)-2-hydroxy-1-(3-methylbenzyl)propyl]-3-[(dipropylamino)sulfonyl]propanamide |
| 2323 | 3-[(dipropylamino)sulfonyl]-N-[(1S,2R)-2-hydroxy-3-(isopentylamino)-1-(3-methylbenzyl)propyl]propanamide |
| 2324 | N-{(1S,2R)-3-(benzylamino)-1-[3-(benzyloxy)-5-fluorobenzyl]-2-hydroxypropyl}-3-[(dipropylamino)sulfonyl]propanamide |
| 2325 | 3-[(dipropylamino)sulfonyl]-N-{(1S,2R)-1-(3-fluoro-4-methoxybenzyl)-2-hydroxy-3-[(3-methoxybenzyl)amino]propyl}propanamide |
| 2326 | N-[(1S,2R)-3-(benzylamino)-1-(3-fluoro-4-methoxybenzyl)-2-hydroxypropyl]-3-[(dipropylamino)sulfonyl]propanamide |
| 2327 | 3-[(dipropylamino)sulfonyl]-N-[(1S,2R)-1-(3-fluoro-4-methoxybenzyl)-2-hydroxy-3-(isopentylamino)propyl]propanamide |
| 2328 | N-{(1S,2R)-1-(3,5-difluorobenzyl)-3-[(3-ethylbenzyl)amino]-2-hydroxypropyl}-2-phenyl-2-(4H-1,2,4-triazol-3-ylthio)acetamide |
| 2329 | 1-acetyl-N-{(1S,2R)-1-(3,5-difluorobenzyl)-3-[(3-ethylbenzyl)amino]-2-hydroxypropyl}-2-phenylprolinamide |

A compound of the formula:

| Compound # | Compound Structure |
|---|---|
| 2330 | (structure shown) |

The compounds in the table immediately below were prepared essentially using the methods described above and illustrated below in the schemes.

The following compounds were named using the Advanced Chemistry Development Inc. (ACD) nomenclature program, IUPAC Name Batch Version 4.5. The website for ACD is www.acdlabs.com.

| | |
|---|---|
| 2332 | N'-((1S,2R)-1-(3,5-difluorobenzyl)-2-hydroxy-3-{[(3R,4S)-3-(hydroxymethyl)-6-isopropyl-2,2-dioxido-3,4-dihydro-1H-isothiochromen-4-yl]amino}propyl)-5-methyl-N,N-dipropylisophthalamide |
| 2333 | N'-((1S,2R)-1-(3,5-difluorobenzyl)-2-hydroxy-3-{[(3R,4S)-6-isopropyl-3-methyl-2,2-dioxido-3,4-dihydro-1H-isothiochromen-4-yl]amino}propyl)-5-methyl-N,N-dipropylisophthalamide |
| 2334 | N'-((1S,2R)-1-(3,5-difluorobenzyl)-2-hydroxy-3-{[(3R,4S)-6-isopropyl-2,2-dioxido-3-propyl-3,4-dihydro-1H-isothiochromen-4-yl]amino}propyl)-5-methyl-N,N-dipropylisophthalamide |
| 2336 | N'-((1S,2R)-1-(3,5-difluorobenzyl)-2-hydroxy-3-{[(3S,4R)-3-(hydroxymethyl)-6-isopropyl-2,2-dioxido-3,4-dihydro-1H-isothiochromen-4-yl]amino}propyl)-5-methyl-N,N-dipropylisophthalamide |
| 2337 | N'-((1S,2R)-1-(3,5-difluorobenzyl)-2-hydroxy-3-{[(3S,4R)-3-(2-hydroxyethyl)-6-isopropyl-2,2-dioxido-3,4-dihydro-1H-isothiochromen-4-yl]amino}propyl)-5-methyl-N,N-dipropylisophthalamide |
| 2339 | N'-((1S,2R)-1-(3,5-difluorobenzyl)-2-hydroxy-3-{[(3S,4S)-6-isopropyl-2,2-dioxido-3-propyl-3,4-dihydro-1H-isothiochromen-4-yl]amino}propyl)-5-methyl-N,N-dipropylisophthalamide |
| 2340 | N'-((1S,2R)-1-(3,5-difluorobenzyl)-2-hydroxy-3-{[(3S,4S)-6-isopropyl-3-methyl-2,2-dioxido-3,4-dihydro-1H-isothiochromen-4-yl]amino}propyl)-5-methyl-N,N-dipropylisophthalamide |
| 2341 | N'-((1S,2R)-1-(3,5-difluorobenzyl)-2-hydroxy-3-{[(4R)-6-isopropyl-2,2-dioxido-3,4-dihydro-1H-isothiochromen-4-yl]amino}propyl)-5-methyl-N,N-dipropylisophthalamide |

The compounds in the table immediately below were prepared essentially using the methods described above and illustrated below in the schemes.

The following compounds were named using the Advanced Chemistry Development Inc. (ACD) nomenclature program, IUPAC Name Batch Version 4.5. The website for ACD is www.acdlabs.com.

| | |
|---|---|
| 2342 | N-{(1S,2R)-1-(3,5-difluorobenzyl)-3-[(3-ethylbenzyl)amino]-2-hydroxypropyl}-3-[(3-methoxypropyl)(methylsulfonyl)amino]benzamide |
| 2343 | N-{(1S,2R)-1-(3,5-difluorobenzyl)-3-[(3-ethylbenzyl)amino]-2-hydroxypropyl}-4-[(3-methoxypropyl)(methylsulfonyl)amino]benzamide |
| 2344 | N-{(1S,2R)-1-(3,5-difluorobenzyl)-3-[(3-ethylbenzyl)amino]-2-hydroxypropyl}-4-[(2-methoxyethyl)(methylsulfonyl)amino]benzamide |
| 2345 | N-{(1S,2R)-1-(3,5-difluorobenzyl)-3-[(3-ethylbenzyl)amino]-2-hydroxypropyl}-6-[(2-methoxyethyl)(methylsulfonyl)amino]nicotinamide |
| 2346 | N-{(1S,2R)-1-(3,5-difluorobenzyl)-3-[(3-ethylbenzyl)amino]-2-hydroxypropyl}-6-[(3-hydroxypropyl)(methylsulfonyl)amino]nicotinamide |
| 2347 | N-{(1S,2R)-1-(3,5-difluorobenzyl)-3-[(3-ethylbenzyl)amino]-2-hydroxypropyl}-6-[(2-hydroxyethyl)(methylsulfonyl)amino]nicotinamide |
| 2348 | N-{(1S,2R)-1-(3,5-difluorobenzyl)-3-[(3-ethylbenzyl)amino]-2-hydroxypropyl}-6-[(2-methoxyethyl)(methylsulfonyl)amino]nicotinamide |
| 2349 | N-{(1S,2R)-1-(3,5-difluorobenzyl)-3-[(3-ethylbenzyl)amino]-2-hydroxypropyl}-2-[(2-methoxyethyl)(methylsulfonyl)amino]isonicotinamide |
| 2350 | N-{(1S,2R)-1-(3,5-difluorobenzyl)-3-[(3-ethylbenzyl)amino]-2-hydroxypropyl}-5-[(2-methoxyethyl)(methylsulfonyl)amino]nicotinamide |
| 2351 | N-{(1S,2R)-1-(3,5-difluorobenzyl)-3-[(3-ethylbenzyl)amino]-2-hydroxypropyl}-2-[(3-hydroxypropyl)(methylsulfonyl)amino]isonicotinamide |
| 2352 | N-{(1S,2R)-1-(3,5-difluorobenzyl)-3-[(3-ethylbenzyl)amino]-2-hydroxypropyl}-2-[(2-hydroxyethyl)(methylsulfonyl)amino]isonicotinamide |
| 2353 | N-{(1S,2R)-1-(3,5-difluorobenzyl)-3-[(3-ethylbenzyl)amino]-2-hydroxypropyl}-5-[(2-hydroxyethyl)(methylsulfonyl)amino]nicotinamide |
| 2354 | N-{(1S,2R)-1-(3,5-difluorobenzyl)-3-[(3-ethylbenzyl)amino]-2-hydroxypropyl}-5-[(3-hydroxypropyl)(methylsulfonyl)amino]nicotinamide |
| 2355 | N-{(1S,2R)-1-(3,5-difluorobenzyl)-3-[(3-ethylbenzyl)amino]-2-hydroxypropyl}-2-[(3-hydroxypropyl)(methylsulfonyl)amino]isonicotinamide |
| 2356 | N-{(1S,2R)-1-(3,5-difluorobenzyl)-3-[(3-ethylbenzyl)amino]-2-hydroxypropyl}-5-[(3-methoxypropyl)(methylsulfonyl)amino]nicotinamide |
| 2357 | N-{(1S,2R)-1-(3,5-difluorobenzyl)-3-[(3-ethylbenzyl)amino]-2-hydroxypropyl}-1-(methylsulfonyl)-1H-indole-5-carboxamide |
| 2358 | N-{(1S,2R)-1-(3,5-difluorobenzyl)-3-[(3-ethylbenzyl)amino]-2-hydroxypropyl}-1-(methylsulfonyl)indoline-5-carboxamide |
| 2359 | N-{(1S,2R)-1-(3,5-difluorobenzyl)-3-[(3-ethylbenzyl)amino]-2-hydroxypropyl}-1-(methylsulfonyl)indoline-4-carboxamide |
| 2360 | N-{(1S,2R)-1-(3,5-difluorobenzyl)-3-[(3-ethylbenzyl)amino]-2-hydroxypropyl}-1-(methylsulfonyl)indoline-6-carboxamide |
| 2361 | N-{(1S,2R)-1-(3,5-difluorobenzyl)-3-[(3-ethylbenzyl)amino]-2-hydroxypropyl}-1-(methylsulfonyl)-1H-indole-4-carboxamide |

| | Compound Name(s) |
|---|---|
| 2362 | N-{(1S,2R)-1-(3,5-difluorobenzyl)-3-[(3-ethylbenzyl)amino]-2-hydroxypropyl}-3-[1-methyl-1-(methylsulfonyl)ethyl]benzamide |
| 2363 | N-{(1S,2R)-1-(3,5-difluorobenzyl)-3-[(3-ethylbenzyl)amino]-2-hydroxypropyl}-4-[1-methyl-1-(methylsulfonyl)ethyl]benzamide |
| 2364 | N-{(1S,2R)-1-(3,5-difluorobenzyl)-3-[(3-ethylbenzyl)amino]-2-hydroxypropyl}-4-(ethylsulfonyl)benzamide |
| 2365 | N-{(1S,2R)-1-(3,5-difluorobenzyl)-3-[(3-ethylbenzyl)amino]-2-hydroxypropyl}-4-(propylsulfonyl)benzamide |
| 2366 | N-{(1S,2R)-1-(3,5-difluorobenzyl)-3-[(3-ethylbenzyl)amino]-2-hydroxypropyl}-4-(pentylsulfonyl)benzamide |
| 2367 | N-{(1S,2R)-1-(3,5-difluorobenzyl)-3-[(3-ethylbenzyl)amino]-2-hydroxypropyl}-4-[(2-hydroxyethyl)sulfonyl]benzamide |
| 2368 | N-{(1S,2R)-1-(3,5-difluorobenzyl)-3-[(3-ethylbenzyl)amino]-2-hydroxypropyl}-4-[(2-methoxyethyl)sulfonyl]benzamide |
| 2369 | N-{(1S,2R)-1-(3,5-difluorobenzyl)-3-[(3-ethylbenzyl)amino]-2-hydroxypropyl}-4-[(2-ethoxyethyl)sulfonyl]benzamide |
| 2370 | N-{(1S,2R)-1-(3,5-difluorobenzyl)-3-[(3-ethylbenzyl)amino]-2-hydroxypropyl}-4-[(3-hydroxypropyl)sulfonyl]benzamide |
| 2371 | N-{(1S,2R)-1-(3,5-difluorobenzyl)-3-[(3-ethylbenzyl)amino]-2-hydroxypropyl}-2,3-dihydro-1-benzothiophene-5-carboxamide; 1,1-dioxide |
| 2372 | N-{(1S,2R)-1-(3,5-difluorobenzyl)-3-[(3-ethylbenzyl)amino]-2-hydroxypropyl}-1-benzothiophene-5-carboxamide; 1,1-dioxide |
| 2374 | N-{(1S,2R)-1-(3,5-difluorobenzyl)-3-[(3-ethylbenzyl)amino]-2-hydroxypropyl}-2,3-dihydro-1-benzothiophene-6-carboxamide; 1,1-dioxide |
| 2375 | N-{(1S,2R)-1-(3,5-difluorobenzyl)-3-[(3-ethylbenzyl)amino]-2-hydroxypropyl}-1-benzothiophene-6-carboxamide; 1,1-dioxide |
| 2376 | N-{(1S,2R)-1-(3,5-difluorobenzyl)-3-[(3-ethylbenzyl)amino]-2-hydroxypropyl}-2-methyl-2,3-dihydro-1,2-benzisothiazole-6-carboxamide; 1,1-dioxide |
| 2377 | N-{(1S,2R)-1-(3,5-difluorobenzyl)-3-[(3-ethylbenzyl)amino]-2-hydroxypropyl}-2-methyl-2,3-dihydro-1,2-benzisothiazole-5-carboxamide; 1,1-dioxide |
| 2378 | N-{(1S,2R)-1-(3,5-difluorobenzyl)-3-[(3-ethylbenzyl)amino]-2-hydroxypropyl}-1-methyl-1,3-dihydro-2,1-benzisothiazole-6-carboxamide; 2,2-dioxide |
| 2343 | N-{(1S,2R)-1-(3,5-difluorobenzyl)-3-[(3-ethylbenzyl)amino]-2-hydroxypropyl}-1-methyl-1,3-dihydro-2,1-benzisothiazole-5-carboxamide; 2,2-dioxide |
| 2344 | N-{(1S,2R)-1-(3,5-difluorobenzyl)-3-[(3-ethylbenzyl)amino]-2-hydroxypropyl}-2,2-dimethylchromane-6-carboxamide |
| 2345 | N-{(1S,2R)-1-(3,5-difluorobenzyl)-3-[(3-ethylbenzyl)amino]-2-hydroxypropyl}-2,2-dimethylchromane-7-carboxamide |

The compounds in the table immediately below were prepared essentially using the methods described above and illustrated below in the schemes.

The following compounds were named using the Advanced Chemistry Development Inc. (ACD) nomenclature program, IUPAC Name Batch Version 4.5. The website for ACD is www.acdlabs.com.

| | Compound Name(s) |
|---|---|
| 2346 | benzyl (3R)-4-({(1S,2R)-1-benzyl-2-hydroxy-3-[(3-methoxybenzyl)amino]propyl}amino)-2,2,3-trimethyl-4-oxobutanoate |
| 2347 | N-{(1S,2R)-1-benzyl-2-hydroxy-3-[(3-methoxybenzyl)amino]propyl}-4-(phenylsulfonyl)butanamide |
| 2348 | (3S)-tetrahydrofuran-3-yl (1S,2R)-1-benzyl-2-hydroxy-3-[(3-methoxybenzyl)amino]propylcarbamate |
| 2349 | $N^1$-{(1S,2R)-1-benzyl-2-hydroxy-3-[(3-methoxybenzyl)amino]propyl}-$N^3$-(phenylsulfonyl)-beta-alaninamide |
| 2350 | $N^1$-{(1S,2R)-1-benzyl-2-hydroxy-3-[(3-methoxybenzyl)amino]propyl}-$N^3$-[(4-methylphenyl)sulfonyl]-beta-alaninamide |
| 2351 | $N^1$-{(1S,2R)-1-benzyl-2-hydroxy-3-[(3-methoxybenzyl)amino]propyl}-$N^3$-[(4-fluorophenyl)sulfonyl]-beta-alaninamide |
| 2352 | $N^1$-{(1S,2R)-1-benzyl-2-hydroxy-3-[(3-methoxybenzyl)amino]propyl}-$N^3$-[(4-methoxyphenyl)sulfonyl]-beta-alaninamide |
| 2353 | $N^1$-{(1S,2R)-1-benzyl-2-hydroxy-3-[(3-methoxybenzyl)amino]propyl}-$N^2$-[(4-methylphenyl)sulfonyl]glycinamide |
| 2354 | $N^1$-{(1S,2R)-1-benzyl-2-hydroxy-3-[(3-methoxybenzyl)amino]propyl}-$N^2$-[(4-fluorophenyl)sulfonyl]glycinamide |
| 2355 | $N^1$-{(1S,2R)-1-benzyl-2-hydroxy-3-[(3-methoxybenzyl)amino]propyl}-$N^2$-[(4-methoxyphenyl)sulfonyl]glycinamide |
| 2356 | N-{(1S,2R)-1-benzyl-2-hydroxy-3-[(3-methoxybenzyl)amino]propyl}-3-[(4-chlorophenyl)sulfonyl]propanamide |
| 2357 | $N^1$-{(1S,2R)-1-benzyl-2-hydroxy-3-[(3-methoxybenzyl)amino]propyl}-$N^2$-(benzylsulfonyl)glycinamide |
| 2358 | N-{(1S,2R)-1-benzyl-2-hydroxy-3-[(3-methoxybenzyl)amino]propyl}-3-[(4-fluorophenyl)sulfonyl]propanamide |
| 2359 | $N^1$-{(1S,2R)-1-benzyl-2-hydroxy-3-[(3-methoxybenzyl)amino]propyl}-$N^3$-[(4-chlorophenyl)sulfonyl]-beta-alaninamide |
| 2360 | $N^1$-{(1S,2R)-1-benzyl-2-hydroxy-3-[(3-methoxybenzyl)amino]propyl}-$N^3$-(benzylsulfonyl)-beta-alaninamide |
| 2361 | N-{(1S,2R)-1-benzyl-2-hydroxy-3-[(3-methoxybenzyl)amino]propyl}-3-[(4-methoxyphenyl)sulfonyl]propanamide |
| 2362 | N-{(1S,2R)-1-benzyl-2-hydroxy-3-[(3-methoxybenzyl)amino]propyl}-3-[(4-methylphenyl)sulfonyl]propanamide |
| 2363 | $N^1$-benzyl-$N^4$-{(1S,2R)-1-benzyl-2-hydroxy-3-[(3-methoxybenzyl)amino]propyl}-2,2-dimethylsuccinamide |
| 2364 | N-{(1S,2R)-1-benzyl-2-hydroxy-3-[(3-methoxybenzyl)amino]propyl}-3-(1,1-dioxido-3-oxo-1,2-benzisothiazol-2(3H)-yl)propanamide |
| 2365 | N-{(1S,2R)-1-benzyl-2-hydroxy-3-[(3-methoxybenzyl)amino]propyl}-3-(1,3-dioxo-1,3-dihydro-2H-isoindol-2-yl)propanamide |
| 2366 | (2R)-N-{(1S,2R)-1-benzyl-2-hydroxy-3-[(3-methoxybenzyl)amino]propyl}-2-methyl-3-(phenylsulfonyl)propanamide |
| 2367 | (2S)-N-{(1S,2R)-1-benzyl-2-hydroxy-3-[(3-methoxybenzyl)amino]propyl}-2-methyl-3-(phenylsulfonyl)propanamide |
| 2368 | $N^1$-benzyl-$N^5$-{(1S,2R)-1-benzyl-2-hydroxy-3-[(3-methoxybenzyl)amino]propyl}pentanediamide |
| 2369 | N-{(1S,2R)-1-benzyl-2-hydroxy-3-[(3-methoxybenzyl)amino]propyl}-2-[(phenylsulfonyl)methyl]acrylamide |
| 2370 | N-{(1S,2R)-1-benzyl-2-hydroxy-3-[(3-methoxybenzyl)amino]propyl}-2-[(isopentylsulfonyl)methyl]acrylamide |
| 2371 | $N^1$-{(1S,2R)-1-benzyl-2-hydroxy-3-[(3-methoxybenzyl)amino]propyl}-$N^3$-[(dipropylamino)carbonyl]-beta-alaninamide |

-continued

| | Compound Name(s) |
|---|---|
| 2372 | N¹-{(1S,2R)-1-benzyl-2-hydroxy-3-[(3-methoxybenzyl)amino]propyl}-N²-[(dipropylamino)carbonyl]glycinamide |
| 2373 | benzyl (4R)-4-{[(((1S,2R)-1-benzyl-3-{[3-(dimethylamino)-2,2-dimethylpropyl]amino}-2-hydroxypropyl)amino]carbonyl]-1,3-oxazolidine-3-carboxylate compound with methyl hydroperoxide (1:2) |
| 2374 | tert-butyl (2R,3S)-2-hydroxy-3-({2-hydroxy-3-[(3-methoxyphenyl)sulfonyl]propanoyl}amino)-4-phenylbutyl(3-methoxybenzyl)carbamate |
| 2383 | N¹-[(1S,2R)-1-[3-(benzyloxy)-5-fluorobenzyl]-2-hydroxy-3-(isopentylamino)propyl]-5-methyl-N³,N³-dipropylisophthalamide |
| 2386 | N¹-{(1S,2R)-1-[3-(benzyloxy)-5-fluorobenzyl]-2-hydroxy-3-(isopentylamino)propyl]-N³,N³-dipropylbenzene-1,3,5-tricarboxamide |
| 2405 | N¹-[(1S,2R)-1-(cyclohexylmethyl)-2-hydroxy-3-(isopentylamino)propyl]-5-methyl-N³,N³-dipropylisophthalamide |
| 2406 | N¹-[(1S,2R)-3-(benzylamino)-1-(cyclohexylmethyl)-2-hydroxypropyl]-5-methyl-N³,N³-dipropylisophthalamide |
| 2411 | N¹-[(1S,2R)-1-[4-(benzyloxy)benzyl]-2-hydroxy-3-(isopentylamino)propyl]-5-methyl-N³,N³-dipropylisophthalamide |
| 2413 | N¹-[(1S,2R)-1-(cyclohexylmethyl)-2-hydroxy-3-(isopentylamino)propyl]-N³,N³-dipropylbenzene-1,3,5-tricarboxamide |
| 2414 | N¹-[(1S,2R)-3-(benzylamino)-1-(cyclohexylmethyl)-2-hydroxypropyl]-N³,N³-dipropylbenzene-1,3,5-tricarboxamide |
| 2419 | N¹-[(1S,2R)-1-[4-(benzyloxy)benzyl]-2-hydroxy-3-(isopentylamino)propyl]-N³,N³-dipropylbenzene-1,3,5-tricarboxamide |
| 2421 | N-{(1S,2R)-1-(3,5-difluorobenzyl)-2-hydroxy-3-[(3-methoxybenzyl)amino]propyl}-3-[hydroxy(2-methylphenyl)methyl]-5-methylbenzamide |
| 2426 | N¹-[(1R,2S)-2-hydroxy-3-(isopentylamino)-1-(4-methylbenzyl)propyl]-5-methyl-N³,N³-dipropylisophthalamide |
| 2427 | N¹-[(1R,2S)-2-hydroxy-3-[(3-methoxybenzyl)amino]-1-(4-methylbenzyl)propyl]-5-methyl-N³,N³-dipropylisophthalamide |
| 2428 | N¹-[(1R,2S)-2-hydroxy-3-(isopentylamino)-1-(4-methylbenzyl)propyl]-N³,N³-dipropylbenzene-1,3,5-tricarboxamide |
| 2429 | N¹-[(1R,2S)-2-hydroxy-3-[(3-methoxybenzyl)amino]-1-(4-methylbenzyl)propyl]-N³,N³-dipropylbenzene-1,3,5-tricarboxamide |
| 2440 | N-{(1S,2R)-1-(3,5-difluorobenzyl)-3-[(3-ethylbenzyl)amino]-2-hydroxypropyl}-2-hydroxy-4-(phenylsulfonyl)butanamide |
| 2442 | benzyl (2R,3S)-4-(3,5-difluorophenyl)-3-[(3-(4,4-dimethyl-2,5-dioxoimidazolidin-1-yl)-2-{[(1-propylbutyl)sulfonyl]methyl}propanoyl]amino]-2-hydroxybutyl(3-ethylbenzyl)carbamate |
| 2445 | N-{(1S,2R)-1-(3,5-difluorobenzyl)-2-hydroxy-3-[(3-iodobenzyl)amino]propyl}-7-(1H-imidazol-1-yl)-5,6-dihydronaphthalene-2-carboxamide |
| 2446 | 2-{[({({(1S,2R)-1-benzyl-2-hydroxy-3-[(3-methoxybenzyl)amino]propyl}amino)carbonyl]amino}-N,N-dipropylethanesulfonamide hydrochloride |
| 2447 | benzyl (2R,3S)-4-(3,5-difluorophenyl)-2-hydroxy-3-({N-(3-phenylpropanoyl)-3-[(1-propylbutyl)sulfonyl]alanyl}amino)butyl(3-ethylbenzyl)carbamate |
| 2448 | N¹-[(1S,2R)-3-[[(benzyloxy)carbonyl](3-ethylbenzyl)amino]-1-(3,5-difluorobenzyl)-2-hydroxypropyl]-N²-{[(3S)-tetrahydrofuran-3-yloxy]carbonyl}-D-leucinamide |
| 2449 | N-{(1S,2R)-1-(3,5-difluorobenzyl)-3-[(3-ethylbenzyl)amino]-2-hydroxypropyl}-2-([1,3]oxazolo[4,5-b]pyridin-2-ylthio)acetamide |
| 2450 | N-{(1S,2R)-1-(3,5-difluorobenzyl)-3-[(3-ethylbenzyl)amino]-2-hydroxypropyl}-2-[(imidazo[1,2-a]pyridin-2-ylmethyl)thio]acetamide |
| 2451 | N-{(1S,2R)-1-(3,5-difluorobenzyl)-3-[(3-ethylbenzyl)amino]-2-hydroxypropyl}-2-[(5,7-dimethyl[1,2,4]triazolo[4,3-a]pyrimidin-3-yl)thio]acetamide |
| 2452 | N-{(1S,2R)-1-(3,5-difluorobenzyl)-3-[(3-ethylbenzyl)amino]-2-hydroxypropyl}-2,3-dihydro-1H-cyclopenta[b]quinoline-9-carboxamide |
| 2453 | N-{(1S,2R)-1-(3,5-difluorobenzyl)-3-[(3-ethylbenzyl)amino]-2-hydroxypropyl}-4-hydroxy-6-oxo-1-phenyl-1,6-dihydropyridazine-3-carboxamide |
| 2454 | 1817 or N-{(1S,2R)-1-(3,5-difluorobenzyl)-3-[(3-ethylbenzyl)amino]-2-hydroxypropyl}-1,3-dioxoisoindoline-5-carboxamide |
| 2455 | 1-benzyl-N-{(1S,2R)-1-(3,5-difluorobenzyl)-3-[(3-ethylbenzyl)amino]-2-hydroxypropyl}-1H-imidazole-2-carboxamide |
| 2456 | N-{(1S,2R)-1-(3,5-difluorobenzyl)-3-[(3-ethylbenzyl)amino]-2-hydroxypropyl}-2-(4,4-dimethyl-4,5-dihydro-1,3-oxazol-2-yl)thiophene-3-carboxamide |
| 2457 | N-{(1S,2R)-1-(3,5-difluorobenzyl)-3-[(3-ethylbenzyl)amino]-2-hydroxypropyl}-2-isobutyl-1,3-dioxoisoindoline-5-carboxamide |
| 2458 | N-{(1S,2R)-1-(3,5-difluorobenzyl)-3-[(3-ethylbenzyl)amino]-2-hydroxypropyl}-5-oxo-2-phenylpyrazolidine-3-carboxamide |
| 2459 | N-{(1S,2R)-1-(3,5-difluorobenzyl)-3-[(3-ethylbenzyl)amino]-2-hydroxypropyl}-5,6-dimethyl-4-oxo-3,4-dihydrothieno[2,3-d]pyrimidine-2-carboxamide |
| 2460 | N-{(1S,2R)-1-(3,5-difluorobenzyl)-3-[(3-ethylbenzyl)amino]-2-hydroxypropyl}-3-[(2,4-difluorobenzyl)oxy]propanamide |
| 2461 | N-{(1S,2R)-1-(3,5-difluorobenzyl)-3-[(3-ethylbenzyl)amino]-2-hydroxypropyl}thieno[2,3-c]pyridine-2-carboxamide |
| 2463 | N-{(1S,2R)-1-(3,5-difluorobenzyl)-3-[(3-ethylbenzyl)amino]-2-hydroxypropyl}-4-(2-methyl-1H-benzimidazol-1-yl)-4-oxobutanamide |
| 2464 | N-{(1S,2R)-1-(3,5-difluorobenzyl)-3-[(3-ethylbenzyl)amino]-2-hydroxypropyl}-3-(2,5-dioxopyrrolidin-1-yl)-4-methylbenzamide |
| 2465 | N-{(1S,2R)-1-(3,5-difluorobenzyl)-3-[(3-ethylbenzyl)amino]-2-hydroxypropyl}thieno[3,2-b]pyridine-6-carboxamide |
| 2466 | N-{(1S,2R)-1-(3,5-difluorobenzyl)-3-[(3-ethylbenzyl)amino]-2-hydroxypropyl}-4-(2,3-dihydro-1H-indol-1-yl)-4-oxobutanamide |
| 2468 | N-{(1S,2R)-1-(3,5-difluorobenzyl)-3-[(3-ethylbenzyl)amino]-2-hydroxypropyl}-2-(1,3-dioxooctahydro-2H-isoindol-2-yl)butanamide |
| 2469 | N¹-{(1S,2R)-1-(3,5-difluorobenzyl)-3-[(3-ethylbenzyl)amino]-2-hydroxypropyl}-N³-[(4-methylphenyl)sulfonyl]-beta-alaninamide |
| 2470 | N-{(1S,2R)-1-(3,5-difluorobenzyl)-3-[(3-ethylbenzyl)amino]-2-hydroxypropyl}-4-(1H-indol-3-yl)-4-oxobutanamide |
| 2471 | N²-(anilinocarbonothioyl)-N¹-{(1S,2R)-1-(3,5-difluorobenzyl)-3-[(3-ethylbenzyl)amino]-2-hydroxypropyl}glycinamide |
| 2472 | N-{(1S,2R)-1-(3,5-difluorobenzyl)-3-[(3-ethylbenzyl)amino]-2-hydroxpropyl}-3-methyl-4-oxo-4,5,6,7-tetrahydro-1H-indole-2-carboxamide |
| 2473 | N-{(1S,2R)-1-(3,5-difluorobenzyl)-3-[(3-ethylbenzyl)amino]-2-hydroxypropyl}-5,6,7,8-tetrahydro-4H-cyclohepta[c]isoxazole-3-carboxamide |
| 2475 | N¹-{(1S,2R)-1-(3,5-difluorobenzyl)-3-[(3-ethylbenzyl)amino]-2-hydroxypropyl}-N²-[(4-methylphenyl)sulfonyl]glycinamide |
| 2477 | N-{(1S,2R)-1-(3,5-difluorobenzyl)-3-[(3-ethylbenzyl)amino]-2-hydroxypropyl}-4-(3,5-dioxo-1,2,4-triazolidin-4-yl)benzamide |
| 2478 | N-{(1S,2R)-1-(3,5-difluorobenzyl)-3-[(3-ethylbenzyl)amino]-2-hydroxypropyl}-4-(2-hydroxyethoxy)benzamide |
| 2479 | N-{(1S,2R)-1-(3,5-difluorobenzyl)-3-[(3-ethylbenzyl)amino]-2-hydroxypropyl}-2-(1,3-dithian-2-yl)-3-furamide |

| | Compound Name(s) |
|---|---|
| 2481 | N-{(1S,2R)-1-(3,5-difluorobenzyl)-3-[(3-ethylbenzyl)amino]-2-hydroxypropyl}-2-methyl-5,6,7,8-tetrahydro-4H-pyrazolo[1,5-a]azepine-3-carboxamide |
| 2482 | N-{(1S,2R)-1-(3,5-difluorobenzyl)-3-[(3-ethylbenzyl)amino]-2-hydroxypropyl}-1-(4-fluorophenyl)-1,4,5,6-tetrahydrocyclopenta[c]pyrazole-3-carboxamide |
| 2484 | N-{(1S,2R)-1-(3,5-difluorobenzyl)-3-[(3-ethylbenzyl)amino]-2-hydroxypropyl}-5,6-dihydro-4H-cyclopenta[b]thiophene-2-carboxamide |
| 2485 | N-{(1S,2R)-1-(3,5-difluorobenzyl)-3-[(3-ethylbenzyl)amino]-2-hydroxypropyl}-3,6,6-trimethyl-4-oxo-4,5,6,7-tetrahydro-1-benzofuran-2-carboxamide |
| 2486 | N-{(1S,2R)-1-(3,5-difluorobenzyl)-3-[(3-ethylbenzyl)amino]-2-hydroxypropyl}-7-methoxy-4-oxo-1,2,3,4-tetrahydronaphthalene-2-carboxamide |
| 2487 | N-{(1S,2R)-1-(3,5-difluorobenzyl)-3-[(3-ethylbenzyl)amino]-2-hydroxypropyl}-2,3-dioxo-1,2,3,4-tetrahydroquinoxaline-6-carboxamide |
| 2488 | N-{(1S,2R)-1-(3,5-difluorobenzyl)-3-[(3-ethylbenzyl)amino]-2-hydroxypropyl}-4,5,6,7-tetrahydro-2H-indazole-3-carboxamide |
| 2489 | N-{(1S,2R)-1-(3,5-difluorobenzyl)-3-[(3-ethylbenzyl)amino]-2-hydroxypropyl}-5-methyl-4-oxo-3,4-dihydrothieno[2,3-d]pyrimidine-6-carboxamide |
| 2490 | N-{(1S,2R)-1-(3,5-difluorobenzyl)-3-[(3-ethylbenzyl)amino]-2-hydroxypropyl}-7-fluoro-4H-imidazo[5,1-c][1,4]benzoxazine-3-carboxamide |
| 2491 | N-{(1S,2R)-1-(3,5-difluorobenzyl)-3-[(3-ethylbenzyl)amino]-2-hydroxypropyl}-4-(3-fluoro-4-methoxyphenyl)-4-oxobutanamide |
| 2492 | methyl 4-({(1S,2R)-1-(3,5-difluorobenzyl)-3-[(3-ethylbenzyl)amino]-2-hydroxypropyl}amino)-4-oxobutyl-(dithiocarbamate) |
| 2493 | N-{(1S,2R)-1-(3,5-difluorobenzyl)-3-[(3-ethylbenzyl)amino]-2-hydroxypropyl}[1,2,4]triazolo[4,3-a]pyridine-6-carboxamide |
| 2494 | N-{(1S,2R)-1-(3,5-difluorobenzyl)-3-[(3-ethylbenzyl)amino]-2-hydroxypropyl}-1-phenyl-1,4,5,6-tetrahydrocyclopenta[c]pyrazole-3-carboxamide |
| 2495 | N-{(1S,2R)-1-(3,5-difluorobenzyl)-3-[(3-ethylbenzyl)amino]-2-hydroxypropyl}-2-[(4-methylphenyl)sulfonyl]acetamide |
| 2496 | 3-(2-chlorophenyl)-2-cyano-N-{(1S,2R)-1-(3,5-difluorobenzyl)-3-[(3-ethylbenzyl)amino]-2-hydroxypropyl}propanamide |
| 2498 | N-{(1S,2R)-1-(3,5-difluorobenzyl)-3-[(3-ethylbenzyl)amino]-2-hydroxypropyl}-4-(4-methylphenyl)-4-oxobutanamide |
| 2499 | N-{(1S,2R)-1-(3,5-difluorobenzyl)-3-[(3-ethylbenzyl)amino]-2-hydroxypropyl}-4-(2-hydroxy-5-methylphenyl)-4-oxobutanamide |
| 2500 | N-{(1S,2R)-1-(3,5-difluorobenzyl)-3-[(3-ethylbenzyl)amino]-2-hydroxypropyl}-3-(2,5-dioxo-2,5-dihydro-1H-pyrrol-1-yl)benzamide |
| 2501 | N-{(1S,2R)-1-(3,5-difluorobenzyl)-3-[(3-ethylbenzyl)amino]-2-hydroxypropyl}-4-oxo-4-thien-2-ylbutanamide or 2379 |
| 2502 | N-{(1S,2R)-1-(3,5-difluorobenzyl)-3-[(3-ethylbenzyl)amino]-2-hydroxypropyl}-4-(2,5-dioxo-2,5-dihydro-1H-pyrrol-1-yl)-2-hydroxybenzamide |
| 2503 | N-{(1S,2R)-1-(3,5-difluorobenzyl)-3-[(3-ethylbenzyl)amino]-2-hydroxypropyl}-4-(2,5-dioxopyrrolidin-1-yl)benzamide |
| 2507 | N-{(1S,2R)-1-(3,5-difluorobenzyl)-3-[(3-ethylbenzyl)amino]-2-hydroxypropyl}-4-[(trifluoroacetyl)amino]butanamide |
| 2510 | N-{(1S,2R)-1-(3,5-difluorobenzyl)-3-[(3-ethylbenzyl)amino]-2-hydroxypropyl}-2-[(1-hydroxycyclopentyl)thio]acetamide |
| 2511 | N-{(1S,2R)-1-(3,5-difluorobenzyl)-3-[(3-ethylbenzyl)amino]-2-hydroxypropyl}-3-(2-oxocyclohexyl)propanamide |
| 2512 | N-{(1S,2R)-1-(3,5-difluorobenzyl)-3-[(3-ethylbenzyl)amino]-2-hydroxypropyl}-4-(2-naphthyl)-4-oxobutanamide |
| 2513 | N-{(1S,2R)-1-(3,5-difluorobenzyl)-3-[(3-ethylbenzyl)amino]-2-hydroxypropyl}-3-oxo-2,3-dihydro-1H-indazole-4-carboxamide |
| 2514 | N-{(1S,2R)-1-(3,5-difluorobenzyl)-3-[(3-ethylbenzyl)amino]-2-hydroxypropyl}-1,3-dimethyl-1H-thieno[2,3-c]pyrazole-5-carboxamide |
| 2515 | $N^1$-{(1S,2R)-1-(3,5-difluorobenzyl)-3-[(3-ethylbenzyl)amino]-2-hydroxypropyl}-$N^2$-[(dimethylamino)sulfonyl]valinamide |
| 2516 | N-{(1S,2R)-1-(3,5-difluorobenzyl)-3-[(3-ethylbenzyl)amino]-2-hydroxypropyl}-4-(2-furyl)-4-oxobutanamide |
| 2517 | N-{(1S,2R)-1-(3,5-difluorobenzyl)-3-[(3-ethylbenzyl)amino]-2-hydroxypropyl}-4-(5-methyl-4-phenyl-1,3-oxazol-2-yl)benzamide |
| 2518 | N-{(1S,2R)-1-(3,5-difluorobenzyl)-3-[(3-ethylbenzyl)amino]-2-hydroxypropyl}-2,6-dioxohexahydropyrimidine-4-carboxamide |
| 2519 | N-{(1S,2R)-1-(3,5-difluorobenzyl)-3-[(3-ethylbenzyl)amino]-2-hydroxypropyl}-5,7-dimethoxy-1-oxoindane-2-carboxamide |
| 2521 | $N^1$-{(1S,2R)-1-(3,5-difluorobenzyl)-3-[(3-ethylbenzyl)amino]-2-hydroxypropyl}-$N^5$-(2-pyridin-2-ylethyl)pentanediamide |
| 2522 | N-{(1S,2R)-1-(3,5-difluorobenzyl)-3-[(3-ethylbenzyl)amino]-2-hydroxypropyl}-4-[4-(2-furoyl)piperazin-1-yl]-4-oxobutanamide |
| 2523 | N-{(1S,2R)-1-(3,5-difluorobenzyl)-3-[(3-ethylbenzyl)amino]-2-hydroxypropyl}-4-oxo-4,5,6,7-tetrahydro-1-benzofuran-3-carboxamide |
| 2524 | N-{(1S,2R)-1-(3,5-difluorobenzyl)-3-[(3-ethylbenzyl)amino]-2-hydroxypropyl}-5-oxo-1-(thien-2-ylmethyl)pyrrolidine-3-carboxamide |
| 2525 | 2-[(cyanomethyl)thio]-N-{(1S,2R)-1-(3,5-difluorobenzyl)-3-[(3-ethylbenzyl)amino]-2-hydroxypropyl}nicotinamide |
| 2526 | N-{(1S,2R)-1-(3,5-difluorobenzyl)-3-[(3-ethylbenzyl)amino]-2-hydroxypropyl}-1-(2-furoyl)-4-hydroxyprolinamide |
| 2527 | N-{(1S,2R)-1-(3,5-difluorobenzyl)-3-[(3-ethylbenzyl)amino]-2-hydroxypropyl}-4,5-dihydrofuro[2,3-g][2,1]benzisoxazole-8-carboxamide |
| 2528 | methyl 3-[({(1S,2R)-1-(3,5-difluorobenzyl)-3-[(3-ethylbenzyl)amino]-2-hydroxypropyl}amino)carbonyl]-5-methylthiophene-2-sulfenate |
| 2529 | 2-(acetylamino)-2-(1H-1,2,3-benzotriazol-1-yl)-N-{(1S,2R)-1-(3,5-difluorobenzyl)-3-[(3-ethylbenzyl)amino]-2-hydroxypropyl}acetamide |
| 2530 | 1-{[(cyclohexylamino)carbonyl]amino}-N-{(1S,2R)-1-(3,5-difluorobenzyl)-3-[(3-ethylbenzyl)amino]-2-hydroxypropyl}cyclopropanecarboxamide |
| 2531 | N-{(1S,2R)-1-(3,5-difluorobenzyl)-3-[(3-ethylbenzyl)amino]-2-hydroxypropyl}-2-(2-ethyl-4H-[1,2,4]triazolo[1,5-a]benzimidazol-4-yl)acetamide |
| 2532 | (2E)-$N^1$-{(1S,2R)-1-(3,5-difluorobenzyl)-3-[(3-ethylbenzyl)amino]-2-hydroxypropyl}-$N^4$-[4-(1,3-oxazol-5-yl)phenyl]but-2-enediamide |
| 2533 | N-{(1S,2R)-1-(3,5-difluorobenzyl)-3-[(3-ethylbenzyl)amino]-2-hydroxypropyl}-1,3,4,5-tetrahydrothiopyrano[4,3-b]indole-8-carboxamide |
| 2535 | N-{(1S,2R)-1-(3,5-difluorobenzyl)-3-[(3-ethylbenzyl)amino]-2-hydroxypropyl}-4-(3,4-dihydro-2H-1,5-benzodioxepin-7-yl)-4-oxobutanamide |
| 2536 | N-{(1S,2R)-1-(3,5-difluorobenzyl)-3-[(3-ethylbenzyl)amino]-2-hydroxypropyl}-4-(1-oxidothiomorpholin-4-yl)butanamide |
| 2537 | N-{(1S,2R)-1-(3,5-difluorobenzyl)-3-[(3-ethylbenzyl)amino]-2-hydroxypropyl}-4-oxo-4-(2-thioxo-1,3-benzothiazol-3(2H)-yl)butanamide |
| 2538 | N-{(1S,2R)-1-(3,5-difluorobenzyl)-3-[(3-ethylbenzyl)amino]-2-hydroxypropyl}-8H-thieno[2,3-b]indole-2-carboxamide |
| 2539 | N-{(1S,2R)-1-(3,5-difluorobenzyl)-3-[(3-ethylbenzyl)amino]-2-hydroxypropyl}-3,4-dihydro-2H-1,5-benzodioxepine-7-carboxamide |

| | Compound Name(s) |
|---|---|
| 2540 | N-{(1S,2R)-1-(3,5-difluorobenzyl)-3-[(3-ethylbenzyl)amino]-2-hydroxypropyl}-4H-chromeno[3,4-d]isoxazole-4-carboxamide |
| 2542 | N-{(1S,2R)-1-(3,5-difluorobenzyl)-3-[(3-ethylbenzyl)amino]-2-hydroxypropyl}-4-(3,4-difluorophenyl)-4-oxobutanamide |
| 2543 | N-{(1S,2R)-1-(3,5-difluorobenzyl)-3-[(3-ethylbenzyl)amino]-2-hydroxypropyl}-4-(3,4-difluorophenyl)-2-methyl-4-oxobutanamide |
| 2544 | N-{(1S,2R)-1-(3,5-difluorobenzyl)-3-[(3-ethylbenzyl)amino]-2-hydroxypropyl}-4-(3,4-difluorophenyl)-2-methoxy-4-oxobutanamide |
| 2545 | N-{(1S,2R)-1-(3,5-difluorobenzyl)-3-[(3-ethylbenzyl)amino]-2-hydroxypropyl}-2-hydroxy-4-oxo-4-[3-(trifluoromethyl)phenyl]butanamide |
| 2546 | N-{(1S,2R)-1-(3,5-difluorobenzyl)-3-[(3-ethylbenzyl)amino]-2-hydroxypropyl}-2-hydroxy-4-oxo-4-thien-2-ylbutanamide |
| 2548 | N-{(1S,2R)-1-(3,5-difluorobenzyl)-3-[(3-ethylbenzyl)amino]-2-hydroxypropyl}-2-[(2-ethyl-1-oxo-2,3-dihydro-1H-isoindol-5-yl)oxy]propanamide |
| 2549 | N-{(1S,2R)-1-(3,5-difluorobenzyl)-3-[(3-ethylbenzyl)amino]-2-hydroxypropyl}-3-oxoisoindoline-1-carboxamide |
| 2550 | N-{(1S,2R)-1-(3,5-difluorobenzyl)-3-[(3-ethylbenzyl)amino]-2-hydroxypropyl}-4-(7-methoxy-1-benzofuran-2-yl)-4-oxobutanamide |
| 2551 | N-{(1S,2R)-1-(3,5-difluorobenzyl)-3-[(3-ethylbenzyl)amino]-2-hydroxypropyl}-4H-chromeno[3,4-d]isoxazole-8-carboxamide |
| 2552 | N-{(1S,2R)-1-(3,5-difluorobenzyl)-3-[(3-ethylbenzyl)amino]-2-hydroxypropyl}-2-methyl-4-oxo-4H-chromene-6-carboxamide |
| 2553 | N-{(1S,2R)-1-(3,5-difluorobenzyl)-3-[(3-ethylbenzyl)amino]-2-hydroxypropyl}-2-([1,2,4]triazolo[4,3-b]pyridazin-6-ylthio)acetamide |
| 2554 | N-{(1S,2R)-1-(3,5-difluorobenzyl)-3-[(3-ethylbenzyl)amino]-2-hydroxypropyl}-2-(1,1-dioxidotetrahydrothien-2-yl)acetamide |
| 2555 | N-{(1S,2R)-1-(3,5-difluorobenzyl)-3-[(3-ethylbenzyl)amino]-2-hydroxypropyl}-4-(3,4-dihydro-2H-chromen-6-yl)-4-oxobutanamide |
| 2556 | N-{(1S,2R)-1-(3,5-difluorobenzyl)-3-[(3-ethylbenzyl)amino]-2-hydroxypropyl}-2-ethyl-3-oxoisoindoline-1-carboxamide |
| 2558 | N-{(1S,2R)-1-(3,5-difluorobenzyl)-3-[(3-ethylbenzyl)amino]-2-hydroxypropyl}-4-(4-hydroxyphenyl)-4-oxobutanamide |
| 2559 | 2-[(6-chloro[1,2,4]triazolo[4,3-b]pyridazin-3-yl)oxy]-N-{(1S,2R)-1-(3,5-difluorobenzyl)-3-[(3-ethylbenzyl)amino]-2-hydroxypropyl}acetamide |
| 2560 | N-{(1S,2R)-1-(3,5-difluorobenzyl)-3-[(3-ethylbenzyl)amino]-2-hydroxypropyl}-2-hydroxy-4-(3-methoxyphenyl)-4-oxobutanamide |
| 2561 | N-{(1S,2R)-1-(3,5-difluorobenzyl)-3-[(3-ethylbenzyl)amino]-2-hydroxypropyl}-2-hydroxy-4-oxo-4-thien-3-ylbutanamide |
| 2562 | 3-chlorophenyl 4-({(1S,2R)-1-(3,5-difluorobenzyl)-3-[(3-ethylbenzyl)amino]-2-hydroxypropyl}amino)-4-oxobutanoate |
| 2563 | 4-(4-chloro-2-hydroxyphenyl)-N-{(1S,2R)-1-(3,5-difluorobenzyl)-3-[(3-ethylbenzyl)amino]-2-hydroxypropyl}-4-oxobutanamide |
| 2565 | N-{(1S,2R)-1-(3,5-difluorobenzyl)-3-[(3-ethylbenzyl)amino]-2-hydroxypropyl}-6-{[(4-methylphenyl)sulfonyl]amino}-4-oxohexanamide |
| 2566 | N-{(1S,2R)-1-(3,5-difluorobenzyl)-3-[(3-ethylbenzyl)amino]-2-hydroxypropyl}-2-(6-hydroxy-3-oxo-2,3-dihydroimidazo[2,1-b][1,3]thiazol-2-yl)acetamide |
| 2567 | N-{(1S,2R)-1-(3,5-difluorobenzyl)-3-[(3-ethylbenzyl)amino]-2-hydroxypropyl}-2-(4,5-dihydro-1,3-thiazol-2-ylthio)acetamide |
| 2568 | N-{(1S,2R)-1-(3,5-difluorobenzyl)-3-[(3-ethylbenzyl)amino]-2-hydroxypropyl}-1H-imidazo[1,2-b]pyrazole-6-carboxamide |
| 2570 | N-{(1S,2R)-1-(3,5-difluorobenzyl)-3-[(3-ethylbenzyl)amino]-2-hydroxypropyl}-4-(6-methoxy-1,1'-biphenyl-3-yl)-4-oxobutanamide |
| 2571 | N-{(1S,2R)-1-(3,5-difluorobenzyl)-3-[(3-ethylbenzyl)amino]-2-hydroxypropyl}-4-(4-methoxyphenyl)-4-oxobutanamide |
| 2572 | N-{(1S,2R)-1-(3,5-difluorobenzyl)-3-[(3-ethylbenzyl)amino]-2-hydroxypropyl}-4-(2,3-dihydro-1,4-benzodioxin-6-yl)-4-oxobutanamide |
| 2573 | N-{(1S,2R)-1-(3,5-difluorobenzyl)-3-[(3-ethylbenzyl)amino]-2-hydroxypropyl}-2-(2-oxo-2,3-dihydro-1,3-benzoxazol-5-yl)acetamide |
| 2574 | N-{(1S,2R)-1-(3,5-difluorobenzyl)-3-[(3-ethylbenzyl)amino]-2-hydroxypropyl}-2-(2-oxo-2,3-dihydro-1H-benzimidazol-5-yl)acetamide |
| 2575 | N-{(1S,2R)-1-(3,5-difluorobenzyl)-3-[(3-ethylbenzyl)amino]-2-hydroxypropyl}-9-oxo-1,2,3,9-tetrahydrocyclopenta[b]chromene-7-carboxamide |
| 2576 | N-{(1S,2R)-1-(3,5-difluorobenzyl)-3-[(3-ethylbenzyl)amino]-2-hydroxypropyl}-1-methyl-1H-benzo[g]indazole-3-carboxamide |
| 2577 | N-{(1S,2R)-1-(3,5-difluorobenzyl)-3-[(3-ethylbenzyl)amino]-2-hydroxypropyl}-4,5-dihydronaphtho[2,1-d]isoxazole-3-carboxamide |
| 2578 | N-{(1S,2R)-1-(3,5-difluorobenzyl)-3-[(3-ethylbenzyl)amino]-2-hydroxypropyl}-2-(tetraazolo[1,5-b]pyridazin-6-ylthio)acetamide |
| 2580 | N-{(1S,2R)-1-(3,5-difluorobenzyl)-3-[(3-ethylbenzyl)amino]-2-hydroxypropyl}-4-(5-methyl-1H-pyrrol-2-yl)-4-oxobutanamide |
| 2581 | N-{(1S,2R)-1-(3,5-difluorobenzyl)-3-[(3-ethylbenzyl)amino]-2-hydroxypropyl}-4-{[(trifluoromethyl)sulfonyl]amino}butanamide |
| 2582 | N-(1S,2R)-3-(2-acetyl-1-ethylhydrazino)-1-benzyl-2-hydroxypropyl}-2-[(methylsulfonyl)amino]-1,3-thiazole-4-carboxamide |
| 2583 | N-{(1S,2R)-1-(3,5-difluorobenzyl)-3-[(3-ethylbenzyl)amino]-2-hydroxypropyl}-3-(1-hydroxy-2-propylpentyl)benzamide |
| 2587 | $N^1$-[(1S,2R)-3-[(2-{4-[(3-chlorobenzyl)oxy]phenyl}ethyl)amino]-1-(3,5-difluorobenzyl)-2-hydroxypropyl]-5-methyl-$N^3,N^3$-dipropylisophthalamide |
| 2589 | $N^1$-{(1S,2R)-1-(3,5-difluorobenzyl)-2-hydroxy-3-[(3-morpholin-4-ylpropyl)amino]propyl]-5-methyl-$N^3,N^3$-dipropylisophthalamide |
| 2597 | $N^1$-{(1S,2R)-1-(3,5-difluorobenzyl)-3-[(3-ethylbenzyl)amino]-2-hydroxypropyl}-$N^2$-[(methylsulfonyl)acetyl]-$N^2$-pentylglycinamide |
| 2598 | N-{(1S,2R)-1-(3,5-difluorobenzyl)-3-[(3-ethylbenzyl)amino]-2-hydroxypropyl}-3-{[(2R)-2-(methoxymethyl)pyrrolidin-1-yl]sulfonyl}propanamide |
| 2599 | N-{(1S,2R)-1-(3,5-difluorobenzyl)-3-[(3-ethylbenzyl)amino]-2-hydroxypropyl}-3-{[(2S)-2-(methoxymethyl)pyrrolidin-1-yl]sulfonyl}propanamide |
| 2600 | ethyl 4-{[(2R,3S)-3-({3-[(dipropylamino)carbonyl]benzoyl}amino)-2-hydroxy-4-phenylbutyl]amino}piperidine-1-carboxylate |
| 2601 | $N^1$-((1S,2R)-1-benzyl-3-{[(3R)-1-benzylpyrrolidin-3-yl]amino}-2-hydroxypropyl)-$N^3,N^3$-dipropylisophthalamide |
| 2602 | methyl (2E)-2-[2-({(1S,2R)-1-benzyl-2-hydroxy-3-[(3-methoxybenzyl)amino]propyl}amino)-2-oxoethyl]-4-methylpent-2-enoate |
| 2603 | $N^1$-{(1S,2R)-1-benzyl-2-hydroxy-3-[(3-methoxybenzyl)amino]propyl}-$N^4$-(4-methoxybenzyl)succinamide |
| 2604 | N-{(1S,2R)-1-benzyl-2-hydroxy-3-[(3-methoxybenzyl)amino]propyl}-3-{[(4-fluorophenyl)sulfonyl]amino}-3-methylbutanamide |
| 2605 | N-{(1S,2R)-1-benzyl-2-hydroxy-3-[(3-methoxybenzyl)amino]propyl}-9,10-dioxo-9,10-dihydroanthracene-2-carboxamide |
| 2606 | N-{(1S,2R)-1-benzyl-2-hydroxy-3-[(3-methoxybenzyl)amino]propyl}-4-(benzyloxy)benzamide |
| 2607 | N'-{(1S,2R)-1-benzyl-2-hydroxy-3-[(3-methoxybenzyl)amino]propyl}-N-methyl-N-phenylurea |

| | Compound Name(s) |
|---|---|
| 2608 | N'-{(1S,2R)-1-benzyl-2-hydroxy-3-[(3-methoxybenzyl)amino]propyl}-N,N-diisopropylurea |
| 2609 | N'-{(1S,2R)-1-benzyl-2-hydroxy-3-[(3-methoxybenzyl)amino]propyl}-N,N-diphenylurea |
| 2610 | N'-{(1S,2R)-1-benzyl-2-hydroxy-3-[(3-methoxybenzyl)amino]propyl}-N,N-dimethylurea |
| 2611 | methyl 2-{[({(1S,2R)-1-benzyl-2-hydroxy-3-[(3-methoxybenzyl)amino]propyl}amino)carbonyl]amino}benzoate |
| 2613 | 2-methoxyethyl (1S,2R)-1-benzyl-2-hydroxy-3-[(3-methoxybenzyl)amino]propylcarbamate |
| 2612 | phenyl (1S,2R)-1-benzyl-2-hydroxy-3-[(3-methoxybenzyl)amino]propylcarbamate |
| 2614 | 2-(benzyloxy)ethyl (1S,2R)-1-benzyl-2-hydroxy-3-[(3-methoxybenzyl)amino]propylcarbamate |
| 2615 | prop-2-ynyl (1S,2R)-1-benzyl-2-hydroxy-3-[(3-methoxybenzyl)amino]propylcarbamate |
| 2616 | (1R,2S,5R)-2-isopropyl-5-methylcyclohexyl (1S,2R)-1-benzyl-2-hydroxy-3-[(3-methoxybenzyl)amino]propylcarbamate |
| 2617 | pentyl (1S,2R)-1-benzyl-2-hydroxy-3-[(3-methoxybenzyl)amino]propylcarbamate |
| 2618 | neopentyl (1S,2R)-1-benzyl-2-hydroxy-3-[(3-methoxybenzyl)amino]propylcarbamate |
| 2621 | $N^1$-((1S,2R)-1-(3,5-difluorobenzyl)-2-hydroxy-3-{[(4-oxo-4H-chromen-3-yl)methyl]amino}propyl)-5-methyl-$N^3,N^3$-dipropylisophthalamide |
| 2622 | $N^1$-{(1S,2R)-1-(3,5-difluorobenzyl)-2-hydroxy-3-[(1,7,7-trimethylbicyclo[2.2.1]hept-2-yl)amino]propyl}-5-methyl-$N^3,N^3$-dipropylisophthalamide |
| 2623 | N-{(1S,2R)-1-(3,5-difluorobenzyl)-2-hydroxy-3-[(3-iodobenzyl)amino]propyl}-4-(3-methyl-5-oxo-4,5-dihydro-1H-pyrazol-1-yl)benzamide |
| 2625 | $N^1$-[(1S,2R)-3-[(1-acetylpiperidin-3-yl)amino]-1-(3,5-difluorobenzyl)-2-hydroxypropyl]-5-methyl-$N^3,N^3$-dipropylisophthalamide |
| 2627 | $N^1$-{(1S,2R)-1-(3,5-difluorobenzyl)-3-[(3-ethylbenzyl)amino]-2-hydroxypropyl}-$N^3$-ethoxy-5-methylisophthalamide |
| 2628 | $N^1$-(allyloxy)-$N^3$-{(1S,2R)-1-(3,5-difluorobenzyl)-3-[(3-ethylbenzyl)amino]-2-hydroxypropyl}-5-methylisophthalamide |
| 2629 | $N^1$-{(1S,2R)-1-(3,5-difluorobenzyl)-3-[(3-ethylbenzyl)amino]-2-hydroxypropyl}-$N^3$-isobutoxy-5-methylisophthalamide |
| 2630 | $N^1$-{(1S,2R)-1-(3,5-difluorobenzyl)-3-[(3-ethylbenzyl)amino]-2-hydroxypropyl}-5-methyl-$N^3$-(2,2,3,3,3-pentafluoropropyl)isophthalamide |
| 2631 | ethyl 4-({3-[({(1S,2R)-1-(3,5-difluorobenzyl)-3-[(3-ethylbenzyl)amino]-2-hydroxypropyl}amino)carbonyl]-5-methylbenzoyl}amino)butanoate |
| 2632 | $N^1$-{(1S,2R)-1-(3,5-difluorobenzyl)-3-[(3-ethylbenzyl)amino]-2-hydroxypropyl}-5-methyl-$N^3,N^3$-bis(2,2,2-trifluoroethyl)isophthalamide |
| 2633 | $N^1$-{(1S,2R)-1-(3,5-difluorobenzyl)-3-[(3-ethylbenzyl)amino]-2-hydroxypropyl}-$N^3$-ethyl-$N^3$-[(1-ethylpiperidin-4-yl)carbonyl]-5-methylisophthalamide |
| 2634 | $N^1$-{(1S,2R)-1-(3,5-difluorobenzyl)-3-[(3-ethylbenzyl)amino]-2-hydroxypropyl}-$N^3$-(2,2,3,3,4,4,4-heptafluorobutyl)-5-methylisophthalamide |
| 2635 | $N^1$-(1-benzylpyrrolidin-3-yl)-$N^3$-{(1S,2R)-1-(3,5-difluorobenzyl)-3-[(3-ethylbenzyl)amino]-2-hydroxypropyl}-$N^1$-ethyl-5-methylisophthalamide |
| 2636 | $N^1$-{(1S,2R)-1-(3,5-difluorobenzyl)-3-[(3-ethylbenzyl)amino]-2-hydroxypropyl}-5-methyl-$N^3$-(tetrahydrofuran-2-ylmethyl)isophthalamide |
| 2638 | $N^1$-((1S,2R)-1-(3,5-difluorobenzyl)-2-hydroxy-3-{[(3R)-2-oxoazepan-3-yl]amino}propyl)-5-methyl-$N^3,N^3$-dipropylisophthalamide |
| 2639 | $N^1$-{(1S,2R)-1-(3,5-difluorobenzyl)-3-[(1,1-dioxido-3,4-dihydro-2H-1,2-benzothiazin-4-yl)amino]-2-hydroxypropyl}-5-methyl-$N^3,N^3$-dipropylisophthalamide |
| 2640 | $N^1$-{(1S,2R)-1-(3,5-difluorobenzyl)-2-hydroxy-3-[2-(4-methylpentanoyl)hydrazino]propyl}-5-methyl-$N^3,N^3$-dipropylisophthalamide |
| 2641 | N-{(1S,2R)-1-(3,5-difluorobenzyl)-3-[(3-ethylbenzyl)amino]-2-hydroxypropyl}-3-[(3-ethylphenyl)sulfonyl]propanamide |
| 2642 | $N^1$-{(1S,2R)-1-(3,5-difluorobenzyl)-3-[(3-ethylbenzyl)amino]-2-hydroxypropyl}-2,2,3,3,4,4-hexafluoro-$N^5,N^5$-dipropylpentanediamide |
| 2643 | $N^5$-{(1S,2R)-1-(3,5-difluorobenzyl)-3-[(3-ethylbenzyl)amino]-2-hydroxypropyl}-2-phenyl-$N^1,N^1$-dipropylpentanediamide |
| 2644 | N-{(1S,2R)-1-(3,5-difluorobenzyl)-3-[(3-ethylbenzyl)amino]-2-hydroxypropyl}-3-[(3-hydroxypropyl)(methylsulfonyl)amino]benzamide |
| 2645 | N-{(1S,2R)-1-(3,5-difluorobenzyl)-3-[(3-ethylbenzyl)amino]-2-hydroxypropyl}-4-[(2-hydroxyethyl)(methylsulfonyl)amino]benzamide |
| 2646 | $N^1$-{(1S,2R)-1-(3,5-difluorobenzyl)-3-[(3-ethylbenzyl)amino]-2-hydroxypropyl}-5-{[(2R)-2-(methoxymethyl)pyrrolidin-1-yl]sulfonyl}-$N^3,N^3$-dipropylisophthalamide |
| 2647 | N-{(1S,2R)-1-(3,5-difluorobenzyl)-3-[(3-ethylbenzyl)amino]-2-hydroxypropyl}-4-[(3-hydroxypropyl) (methylsulfonyl)amino]benzamide |

The compounds in the table immediately below were prepared essentially using the methods described above and illustrated below in the schemes.

The following compounds were named using the Advanced Chemistry Development Inc. (ACD) nomenclature program, IUPAC Name Batch Version 4.5. The website for ACD is www.acdlabs.com.

| | Compound Name(s) | mass spec |
|---|---|---|
| 2648 | 5-bromo-$N^1$-{(1S,2R)-1-(3,5-difluorobenzyl)-2-hydroxy-3-[(3-iodobenzyl)amino]propyl}-$N^3,N^3$-dipropylisophthalamide | |
| 2649 | N-{(1S,2R)-1-(3,5-difluorobenzyl)-3-[(3-ethylbenzyl)amino]-2-hydroxypropyl}-3-{[(trifluoromethyl)sulfonyl]amino}benzamide | 586.1 |
| 2657 | $N^1$-{(1S,2R)-1-(3,5-dichlorobenzyl)-3-[(3-[(3-methoxybenzyl)amino]propyl}-$N^3,N^3$-dipropylbenzene-1,3,5-tricarboxamide | 643.2 |
| 2664 | $N^1$-[(1S,2R)-2-hydroxy-3-[(3-methoxybenzyl)amino]-1-(thien-2-ylmethyl)propyl]-$N^3,N^3$-dipropylbenzene-1,3,5-tricarboxamide | 581.3 |

-continued

| | Compound Name(s) | mass spec |
|---|---|---|
| 2665 | N$^1$-{(1S,2R)-1-(4-fluorobenzyl)-2-hydroxy-3-[(3-methoxybenzyl)amino]propyl}-N$^3$,N$^3$-dipropylbenzene-1,3,5-tricarboxamide | 593.3 |
| 2666 | N$^1$-{(1S,2R)-1-(3,5-difluorobenzyl)-3-[(3-ethylbenzyl)amino]-2-hydroxypropyl}-5-(4-methyl-1,3-oxazol-2-yl)-N$^3$,N$^3$-dipropylisophthalamide | 647 |
| 2667 | N$^1$-{(1S,2R)-1-(3,5-difluorobenzyl)-3-[(3-ethylbenzyl)amino]-2-hydroxypropyl}-N$^3$,N$^3$-dipropyl-5-(1,3-thiazol-2-yl)isophthalamide | 649 |
| 2668 | N-{(1S,2R)-1-(3,5-difluorobenzyl)-3-{(3-ethylbenzyl)amino]-2-hydroxypropyl)-3-[(methylsulfonyl)amino]benzamide | 532.2 |
| 2671 | N$^1$-{(1S,2R)-1-(3,5-difluorobenzyl)-3-[(3-ethylbenzyl)amino]-2-hydroxypropyl}-5-(1,3-oxazol-2-yl)-N$^3$,N$^3$-dipropylisophthalamide | 633 |
| 2672 | N$^1$-{(1S,2R)-1-(3,5-difluorobenzyl)-3-[(3-ethylbenzyl)amino]-2-hydroxypropyl}-5-(1,3-oxazol-2-yl)-N$^3$,N$^3$-dipropylisophthalamide hydrochloride | 633.4 |
| 2675 | N$^1$-{(1S,2R)-1-(3,5-difluorobenzyl)-3-[(3-ethylbenzyl)amino]-2-hydroxypropyl}-3-[(1-propylbutyl)sulfonyl]propanamide hydrochloride | 553 |
| 2677 | N$^1$-{(1S,2R)-1-(3,5-difluorobenzyl)-2-hydroxy-3-[(3-methoxybenzyl)amino]propyl}-5-(1,3-oxazol-2-yl)-N$^3$,N$^3$-dipropylisophthalamide | 635 |
| 2678 | N-{(1S,2R)-1-(3,5-difluorobenzyl)-2-hydroxy-3-[(3-iodobenzyl)amino]propyl}-2-[(methylsulfonyl)amino]-1,3-thiazole-4-carboxamide | 637.6 |
| 2679 | N$^1$-[(1S,2R)-1-(3,5-difluorobenzyl)-2-hydroxy-3-(isopentylamino)propyl]-N$^3$,N$^3$-dipropyl-5-{[(trifluoromethyl)sulfonyl]amino}isophthalamide | 665 |
| 2680 | N-{(1S,2R)-1-(3,5-difluorobenzyl)-3-[(3-ethylbenzyl)amino]-2-hydroxypropyl}-3-(isopentylsulfonyl)propanamide | 525 |
| 2681 | N-{(1S,2R)-1-(3,5-difluorobenzyl)-3-[(3-ethylbenzyl)amino]-2-hydroxypropyl}-3-{[(1-methyl-1H-imidazol-4-yl)sulfonyl]amino}benzamide trihydrochloride | 598.1 |
| 2682 | N-{(1S,2R)-1-(3,5-difluorobenzyl)-3-[(3-ethylbenzyl)amino]-2-hydroxypropyl}-4-{[(trifluoromethyl)sulfonyl]amino}benzamide | 586 |
| 2684 | N-{(1S,2R)-1-(3,5-difluorobenzyl)-3-[(3-ethylbenzyl)amino]-2-hydroxypropyl)-3-{[(2-hydroxyethyl)(propyl)amino]sulfonyl}propanamide | 556 |
| 2685 | N-{(1S,2R)-1-(3,5-difluorobenzyl)-3-[(3-ethylbenzyl)amino]-2-hydroxypropyl}-3-(1,3-oxazol-2-yl)benzamide hydrochloride | 506 |
| 2686 | N$^1$-{(1S,2R)-1-(3,5-difluorobenzyl)-3-[(3-ethylbenzyl)amino]-2-hydroxypropyl}-5-{[(2-hydroxy-1,1-dimethylethyl)amino]sulfonyl}-N$^3$,N$^3$-dipropylisophthalamide | 717 |
| 2687 | N-{(1S,2R)-1-(3,5-difluorobenzyl)-3-[(3-ethylbenzyl)amino]-2-hydroxypropyl}-3-{[(2-hydroxy-1,1-dimethylethyl)amino]sulfonyl}benzamide | 590 |
| 2688 | N-{(1S,2R)-1-(3,5-difluorobenzyl)-3-[(3-ethylbenzyl)amino]-2-hydroxypropyl}-5-{[(3-hydroxypropyl)amino]sulfonyl}-N$^3$,N$^3$-dipropylisophthalamide | 703 |
| 2689 | N-{(1S,2R)-1-(3,5-difluorobenzyl)-3-[(3-ethylbenzyl)amino]-2-hydroxypropyl}-2-[(methylsulfonyl)amino}-1,3-thiazole-4-carboxamide | 539.1 |
| 2690 | N$^1$-{(1S,2R)-1-(3,5-difluorobenzyl)-3-[(3-ethylbenzyl)amino]-2-hydroxypropyl}-N$^2$-(phenylacetyl)-3-[(1-propylbutyl)sulfonyl]alaninamide | 686 |

-continued

| Compound Name(s) | mass spec |
|---|---|
| 2691 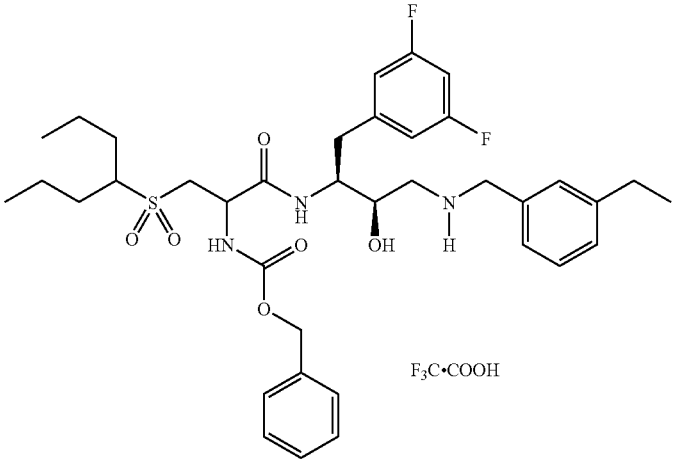 | 702 |
| 2692 N$^1$-{(1S,2R)-1-(3,5-difluorobenzyl)-3-[(3-ethylbenzyl)amino]-2-hydroxypropyl}-5-(3-methylisoxazol-4-yl)-N$^3$,N$^3$-dipropylisophthalamide hydrochloride | 647 |
| 2693 N$^1$-{(1S,2R)-1-(3,5-difluorobenzyl)-3-[(3-ethylbenzyl)amino]-2-hydroxypropyl}-5-({[2-(methylamino)ethyl]amino}sulfonyl)-N$^3$,N$^3$-dipropylisophthalamide hydrochloride | 702 |
| 2694 N$^1$-{(1S,2R)-1-(3,5-difluorobenzyl)-3-[(3-ethylbenzyl)amino]-2-hydroxypropyl}-5-{[2-hydroxyethyl)amino]sulfonyl}N$^3$,N$^3$-dipropylisophthalamide | 689 |
| 2695 N-{(1S,2R)-1-(3,5-difluorobenzyl)-3-[(3-ethylbenzyl)amino]-2-hydroxypropyl}-4-[(methylsulfonyl)amino]butanamide | 499 |
| 2696 N$^1$-{(1S,2R)-1-(3,5-difluorobenzyl)-3-[(3-ethylbenzyl)amino]-2-hydroxypropyl}-5-(piperazin-1-ylsulfonyl)-N$^3$,N$^3$-dipropylisophthalamide | 714 |
| 2697 N-{(1S,2R)-1-(3,5-difluorobenzyl)-3-[(3-ethylbenzyl)amino]-2-hydroxypropyl}-3-[methyl(methylsulfonyl)amino]benzamide | 546 |
| 2698 5-{[bis(2-hydroxyethyl)amino]sulfonyl}-N$^1$-{(1S,2R)-1-(3,5-difluorobenzyl)-3-[(3-ethylbenzyl)amino]-2-hydroxypropyl}-N$^3$,N$^3$-dipropylisophthalamide | 733 |
| 2699 N-{(1S,2R)-1-(3,5-difluorobenzyl)-3-[(3-ethylbenzyl)amino]-2-hydroxypropyl}-2,8-dimethylquinoline-3-carboxamide | 518.3 |
| 2702 2-{[(2R,3S)-4-(3,5-difluorophenyl)-3-({3-[(dipropylamino)carbonyl]-5-methylbenzoyl}amino)-2-hydroxybutyl]amino}ethyl 2,4-difluorophenylcarbamate | 661.7 |
| 2704 N$^1$-{(1S,2R)-1-(3,5-difluorobenzyl)-3-[(3-ethylbenzyl)amino]-2-hydroxypropyl}-N$^3$,N$^3$-dipropyl-5-(1H-pyrazol-4-yl)isophthalamide | 632 |
| 2706 N-{(1S,2R)-1-(3,5-difluorobenzyl)-3-[(3-ethylbenzyl)amino]-2-hydroxypropyl}-3-hydroxyisoxazole-5-carboxamide | 446.2 |
| 2707 N$^1$-{(1S,2R)-1-(3,5-difluorobenzyl)-3-[(3-ethylbenzyl)amino]-2-hydroxypropyl}-5-(1-methyl-1H-imidazol-2-yl)-N$^3$,N$^3$-dipropylisophthalamide | 646 |
| 2708 N-{(1S,2R)-1-(3,5-difluorobenzyl)-3-[(3-ethylbenzyl)amino]-2-hydroxypropyl}-3-{[(2R)-2-(methoxymethyl)pyrrolidin-1-yl]carbonyl}-5-methylbenzamide hydrochloride | 594.3 |
| 2709 N$^1$-{(1S,2R)-1-(3,5-difluorobenzyl)-3-[(3-ethylbenzyl)amino]-2-hydroxypropyl}-5-{[(2-hydroxyethyl)amino]sulfonyl}-N$^3$-propylisophthalamide | 647 |
| 2710 N$^1$-{(1S,2R)-1-(3,5-difluorobenzyl)-3-[(3-ethylbenzyl)amino]-2-hydroxypropyl}-5-({[(1S)-2-hydroxy-1-methylethyl]amino}sulfonyl)-N$^3$,N$^3$-dipropylisophthalamide | 703 |
| 2711 N$^1$-{(1S,2R)-1-(3,5-difluorobenzyl)-3-[(3-ethylbenzyl)amino]-2-hydroxypropyl}-N$^3$,N$^3$-diethyl-5-(1,3-oxazol-2-yl)isophthalamide | 605.4 |
| 2712 N-{(1S,2R)-1-(3,5-difluorobenzyl)-3-[(3-ethylbenzyl)amino]-2-hydroxypropyl}-3-{[(2S)-2-(methoxymethyl)pyrrolidin-1-yl]carbonyl}-5-methylbenzamide hydrochloride | 594.3 |
| 2713 N$^1$-{(1S,2R)-1-(3,5-difluorobenzyl)-3-[(3-ethylbenzyl)amino]-2-hydroxypropyl}-5-{[(2S)-2-(hydroxymethyl)pyrrolidin-1-yl]sulfonyl}-N$^3$,N$^3$-dipropylisophthalamide | 729 |
| 2714 N$^1$-{(1S,2R)-1-(3,5-difluorobenzyl)-3-[(3-ethylbenzyl)amino]-2-hydroxypropyl}-5-({[(1R)-2-hydroxy-1-methylethyl]amino}sulfonyl)-N$^3$,N$^3$-dipropylisophthalamide | 703 |

| | Compound Name(s) | mass spec |
|---|---|---|
| 2716 | N-{(1S,2R)-1-(3,5-difluorobenzyl)-3-[(3-ethylbenzyl)amino]-2-hydroxypropyl}-3-(2-ethyl-1-hydroxybutyl)benzamide | 539.3 |
| 2717 | $N^1$-{(1S,2R)-1-(3,5-difluorobenzyl)-3-[(3-ethylbenzyl)amino]-2-hydroxypropyl}-5-[(dimethylamino)sulfonyl]-$N^3,N^3$-dipropylisophthalamide | 673.1 |
| 2719 | $N^1$-[(1S,2R)-3-{[2-(aminosulfonyl)ethyl]amino}-1-(3,5-difluorobenzyl)-2-hydroxypropyl]-5-methyl-$N^3,N^3$-dipropylisophthalamide | 569.6 |
| 2723 | $N^1$-{(1S,2R)-1-(3,5-difluorobenzyl)-2-hydroxy-3-[(4-phenylbutyl)amino]propyl}-5-methyl-$N^3,N^3$-dipropylisophthalamide | 594.5 |
| 2729 | $N^1$-{(1S,2R)-1-(3,5-difluorobenzyl)-3-[(3-ethylbenzyl)amino]-2-hydroxypropyl}-$N^3$-ethyl-$N^3$-methyl-5-(1,3-oxazol-2-yl)isophthalamide | 591.4 |
| 2730 | $N^1$-{(1S,2R)-1-(3,5-difluorobenzyl)-3-[(3-ethylbenzyl)amino]-2-hydroxpropyl}-$N^3$-methyl-5-(1,3-oxazol-2-yl)-$N^3$-propylisophthalamide | 605.4 |
| 2731 | $N^1$-{(1S,2R)-1-(3,5-difluorobenzyl)-3-[(3-ethylbenzyl)amino]-2-hydroxypropyl}-$N^3,N^3$-dipropyl-5-(pyrrolidin-1-ylsulfonyl)isophthalamide hydrochloride | 699.1 |
| 2732 | $N^1$-[(1S,2R)-1-(3,5-difluorobenzyl)-2-hydroxy-3-(isopentylamino)propyl]-5-{[(2-hydroxy-1,1-dimethylethyl)amino]sulfonyl}-$N^3,N^3$-dipropylisophthalamide | 669 |
| 2733 | $N^1$-{(1S,2R)-1-(3,5-difluorobenzyl)-3-[(3-ethylbenzyl)amino]-2-hydroxypropyl{-5-(1,3-oxazol-5-yl)-$N^3,N^3$-dipropylisophthalamide hydrochloride | 633 |
| 2734 | $N^1$-{(1S,2R)-1-(3,5-difluorobenzyl)-3-[(3-ethynylbenzyl)amino]-2-hydroxypropyl)-5-(1,3-oxazol-2-yl)-$N^3,N^3$-dipropylisophthalamide hydrochloride | 629 |
| 2735 | $N^1$-butyl-$N^3$-{(1S,2R)-1-(3,5-difluorobenzyl)-3-[(3-ethylbenzyl)amino]-2-hydroxypropyl)-$N^1$-methyl-5-(1,3-oxazol-2-yl)isophthalamide | 619.4 |
| 2736 | $N^1$-{(1S,2R)-1-(3,5-difluorobenzyl)-3-[(3-ethylbenzyl)amino]-2-hydroxypropyl}-$N^3,N^3$-dimethyl-5-(1,3-oxazol-2-yl)isophthalamide | 577.3 |
| 2737 | $N^1$-{(1S,2R)-1-(3,5-difluorobenzyl)-3-[(3-ethylbenzyl)amino]-2-hydroxypropyl}-$N^3$-ethyl-5-(1,3-oxazol-2-yl)-$N^3$-propylisophthalamide | 619.4 |
| 2738 | $N^1$-{(1S,2R)-1-(3,5-difluorobenzyl)-3-[(3-ethynylbenzyl)amino]-2-hydroxypropyl)-$N^3,N^3$-dipropyl-5-(1,3-thiazol-2-yl)isophthalamide hydrochloride | 645 |
| 2739 | N-{(1S,2R)-1-(3,5-difluorobenzyl)-3-[(3-ethylbenzyl)amino]-2-hydroxypropyl}-3-{[(1-propylbutyl)amino]sulfonyl}propanamide | 568 |
| 2740 | $N^1$-{(1S,2R)-1-(3,5-difluorobenzyl)-3-[(3-ethylbenzyl)amino]-2-hydroxypropyl{-5-{[(2R)-2-(hydroxymethyl)pyrrolidin-1-yl]sulfonyl)-$N^3,N^3$-dipropylisophthalamide | 729 |
| 2741 | $N^1$-{(1S,2R)-1-(3,5-difluorobenzyl)-3-[(3-ethynylbenzyl)amino]-2-hydroxypropyl}-5-{[(2-hydroxy-1,1-dimethylethyl)amino]sulfonyl}-$N^3,N^3$-dipropylisophthalamide | 713 |
| 2742 | $N^1$-{(1S,2R)-1-(3,5-difluorobenzyl)-2-hydroxy-3-(isobutylamino)propyl]-5-(1,3-oxazol-2-yl)-$N^3,N^3$-dipropylisophthalamide hydrochloride | 571 |
| 2743 | 5-bromo-$N^1$-((1S,2R)-1-[3-fluoro-4-(trifluoromethyl)benzyl]-2-hydroxy-3-{[3-(trifluoromethyl)benzyl]amino}propyl)-$N^3,N^3$-dipropylisophthalamide | 734.1 |
| 2744 | 5-bromo-$N^1$-((1S,2R)-2-hydroxy-1-(2,3,4-trifluorobenzyl)-3-{[3-(trifluoromethyl)benzyl]amino}propyl)-$N^3,N^3$-dipropylisophthalamide | |
| 2745 | N-{(1S,2R)-1-(3,5-difluorobenzyl)-3-[(3-ethylbenzyl)amino]-2-hydroxypropyl}-3-(2-ethylbutanoyl)-5-methylbenzamide hydrochloride | 551.3 |
| 2746 | N-{(1S,2R)-1-(3,5-difluorobenzyl)-3-[(3-ethylbenzyl)amino]-2-hydroxypropyl}-3-methyl-5-[(2-propylpiperidin-1-yl)carbonyl]benzamide hydrochloride | 606.3 |
| 2747 | N-{(1S,2R)-1-(3,5-difluorobenzyl)-3-[(3-ethylbenzyl)amino]-2-hydroxypropyl}-3-methyl-5-[(2-methylpyrrolidin-1-yl)carbonyl]benzamide hydrochloride | 564.4 |
| 2748 | N-{(1S,2R)-1-(3,5-difluorobenzyl)-3-[(3-ethylbenzyl)amino]-2-hydroxypropyl}-3-[(2,6-dimethylpiperidin-1-yl)carbonyl]-5-methylbenzamide hydrochloride | 592.3 |
| 2749 | $N^1$-{(1S,2R)-1-(3,5-difluorobenzyl)-3-[(3-ethylbenzyl)amino]-2-hydroxypropyl}-5-{[(2-methoxyethyl)amino]sulfonyl}-$N^3,N^3$-dipropylisophthalamide | 703 |
| 2750 | $N^1$-((1S,2R)-1-(3,5-difluorobenzyl)-2-hydroxy-3-{[3-(trifluoromethyl)benzyl]amino}propyl)-$N^3,N^3$-dipropyl-5-(1,3-thiazol-2-yl)isophthalamide dihydrochloride | 689.6 |

| | Compound Name(s) | mass spec |
|---|---|---|
| 2751 | N$^1$-{(1S,2R)-1-(3,5-difluorobenzyl)-3-[(3-ethynylbenzyl)amino]-2-hydroxypropyl}-5-{[(2-hydroxyethyl)amino]sulfonyl}-N$^3$,N$^3$-dipropylisophthalamide | 685.2 |
| 2752 | N-((1S,2R)-1-(3,5-difluorobenzyl)-3-[(3-ethylbenzyl)amino]-2-hydroxypropyl}-3-methyl-5-(2-propylpentanoyl)benzamide hydrochloride | 579.3 |
| 2753 | N$^1$-(sec-butyl)-N$^3$-{(1S,2R)-1-(3,5-difluorobenzyl)-3-[(3-ethylbenzyl)amino]-2-hydroxypropyl}-5-methyl-N$^1$-propylisophthalamide | 594.6 |
| 2754 | N$^1$-butyl-N$^3$-{(1S,2R)-1-(3,5-difluorobenzyl)-3-[(3-ethylbenzyl)amino]-2-hydroxypropyl}-5-methyl-N$^1$-propylisophthalamide | 594.6 |
| 2755 | N$^1$-allyl-N$^1$-cyclopentyl-N$^3$-{(1S,2R)-1-(3,5-difluorobenzyl)-3-[(3-ethylbenzyl)amino]-2-hydroxypropyl}-5-methylisophthalamide | 600.5 |
| 2756 | N$^1$,N$^1$-dibutyl-N$^3$-{(1S,2R)-1-(3,5-difluorobenzyl)-3-[(3-ethylbenzyl)amino]-2-hydroxypropyl}-5-methylisophthalamide | 608.6 |
| 2757 | N$^1$-{(1S,2R)-1-(3,5-difluorobenzyl)-3-[(3-ethylbenzyl)amino]-2-hydroxypropyl}-N$^3$,N$^3$-diisobutyl-5-methylisophthalamide | 608.6 |
| 2758 | N$^1$-[(1S,2R)-1-(3,5-difluorobenzyl)-2-hydroxy-3-({3-[(1Z)-prop-1-enyl]benzyl}amino)propyl]-5-methyl-N$^3$,N$^3$-dipropylisophthalamide | |
| 2759 | N$^1$-((1S,2R)-1-(3,5-difluorobenzyl)-3-{[3-(ethylsulfonyl)benzyl]amino}-2-hydroxypropyl)-5-methyl-N$^3$,N$^3$-dipropylisophthalamide | 644.2 |
| 2760 | N$^1$-((1S,2R)-1-(3,5-difluorobenzyl)-2-hydroxy-3-{[1-(3-iodophenyl)cyclopropyl]amino}propyl)-5-methyl-N$^3$,N$^3$-dipropylisophthalamide | 704.1 |
| 2761 | | 561.2 |

| | Compound Name(s) | mass spec |
|---|---|---|
| 2762 | N$^1$-[(1S,2R)-3-[(1,1'-biphenyl-3-ylmethyl)amino]-1-(3,5-difluorobenzyl)-2-hydroxypropyl]-5-methyl-N$^3$,N$^3$-dipropylisophthalamide | |
| 2763 | N$^1$-{(1S,2R)-1-(3,5-difluorobenzyl)-2-hydroxy-3-[(3-hydroxy-1-phenylpropyl)amino]propyl}-5-methyl-N$^3$,N$^3$-dipropylisophthalamide | 593.3 |
| 2764 | N$^1$-cyclohexyl-N$^3$-{(1S,2R)-1-(3,5-difluorobenzyl)-3-[(3-ethylbenyl)amino]-2-hydroxypropyl}-N$^1$,5-dimethylisophthalamide | 594.6 |
| 2765 | N$^1$-cyclohexyl-N$^3$-{(1S,2R)-1-(3,5-difluorobenzyl)-3-[(3-ethylbenyl)amino]-2-hydroxypropyl}-N$^1$-ethyl-5-methylisophthalamide | 606.6 |
| 2766 | N$^1$-[(1S,2R)-3-{[3-(1-benzothien-2-yl)benzyl]amino}-1-(3,5-difluorobenzyl)-2-hydroxypropyl]-5-methyl-N$^3$,N$^3$-dipropylisophthalamide | 684.5 |
| 2767 | N$^1$-((1S,2R)-1-(3,5-difluorobenzyl)-2-hydroxy-3-{[3-(trifluoromethyl)benzyl]amino}propyl)-5-ethynyl-N$^3$,N$^3$-dipropylisophthalamide | 630.2 |
| 2768 | N$^1$-{(1S,2R)-1-(3,5-difluorobenzyl)-2-hydroxy-3-[(3-thien-3-ylbenzyl)amino]propyl}-5-methyl-N$^3$,N$^3$-dipropylisophthalamide | 633.0 |
| 2769 | N$^1$-((1S,2R)-1-(3,5-difluorobenzyl)-2-hydroxy-3-{[3-(5-methylthien-2-yl)benzyl]amino}propyl)-5-methyl-N$^3$,N$^3$-dipropylisophthalamide | 647.0 |
| 2770 | N$^1$-{(1S,2R)-1-(3,5-difluorobenzyl)-2-hydroxy-3-[(3-pyridin-4-ylbenzyl)amino]propyl}-5-methyl-N$^3$,N$^3$-dipropylisophthalamide | 629.6 |
| 2771 | N$^1$-((1S,2R)-1-(3,5-difluorobenzyl)-2-hydroxy-3-{[3-(4-methylthien-2-yl)benzyl]amino}propyl)-5-methyl-N$^3$,N$^3$-dipropylisophthalamide | 648.5 |
| 2772 | N$^1$-((1S,2R)-1-(3,5-difluorobenzyl)-3-{[3-(2,4-dimethoxypyrimidin-5-yl)benzyl]amino}-2-hydroxypropyl)-5-methyl-N$^3$,N$^3$-dipropylisophthalamide | 690.6 |

| Compound Name(s) | mass spec |
|---|---|
| 2773 N$^1$-((1S,2R)-1-(3,5-difluorobenzyl)-3-{[3-(3,5-dimethylisoxazol-4-yl)benzyl]amino}-2-hydroxypropyl)-5-methyl-N$^3$,N$^3$-dipropylisophthalamide | 647.6 |
| 2774 N$^4$-{(1S,2R)-1-(3,5-difluorobenzyl)-3-[(3-ethylbenzyl)amino]-2-hydroxypropyl}-6-methyl-N$^2$,N$^2$-dipropylpyridine-2,4-dicarboxamide | 581.3 |
| 2775 N$^1$-[(1S,2R)-3-{[3-(cyclopropylamino)benzyl]amino}-1-(3,5-difluorobenzyl)-2-hydroxypropyl]-5-methyl-N$^3$,N$^3$-dipropylisophthalamide | 607.3 |
| 2776 N$^1$-[(1S,2R)-3-{[3-(cyclopropylamino)benzyl)amino}-1-(3,5-difluorobenzyl)-2-hydroxypropyl]-5-ethynyl-N$^3$,N$^3$-dipropylisophthalamide | 617.3 |
| 2777 N$^1$-((1S,2R)-1-(3,5-difluorobenzyl)-2-hydroxy-3-{[1-(2-isobutyl-1,3-thiazol-5-yl)cyclopropyl)amino}propyl)-5-methyl-N$^3$,N$^3$-dipropylisophthalamide | 641.3 |
| 2778 N$^1$-((1S,2R)-1-(3,5-difluorobenzyl)-3-{[1-(3-ethylphenyl)cyclopropyl]amino)-2-hydroxypropyl)-5-(1,3-oxazol-2-yl)-N$^3$,N$^3$-dipropylisophthalamide | 659.3 |
| 2779 methyl 3-({[[(2R,3S)-4-(3,5-difluorophenyl)-3-({3-[(dipropylamino)carbonyl]-5-methylbenzoyl}amino)-2-hydroxybutyl]amino}methyl)phenyl(methyl)carbamate | 639.3 |
| 2780 N$^1$-[(1S,2R)-1-(3,5-difluorobenzyl)-2-hydroxy-3-({3-[methyl(methylsulfonyl)amino]benzyl}amino)propyl]-5-methyl-N$^3$,N$^3$-dipropylisophthalamide | 659.3 |
| 2781 N$^1$-[(1S,2R)-1-(3,5-difluorobenzyl)-3-({3-[(dimethylamino)sulfonyl]benzyl}amino)-2-hydroxypropyl]-5-methyl-N$^3$,N$^3$-dipropylisophthalamide | 659.3 |
| 2782 N$^1$-((1S,2R)-1-(3,5-difluorobenzyl)-3-{[1-(3-ethylphenyl)cyclopropyl]amino}-2-hydroxypropyl)-5-methyl-N$^3$,N$^3$-dipropylisophthalamide | 606.3 |
| 2783 N$^1$-((1S,2R)-1-(3,5-difluorobenzyl)-2-hydroxy-3-{[(2-isobutyl-1,3-thiazol-5-yl)methyl]amino}propyl)-5-(1,3-oxazol-2-yl)-N$^3$,N$^3$-dipropylisophthalamide | 668.2 |
| 2785 N$^1$-((1S,2R)-1-(3,5-difluorobenzyl)-3-{[1-(3-ethylphenyl)-1-methylethyl]amino}-2-hydroxypropyl)-5-ethynyl-N$^3$,N$^3$-dipropylisophthalamide | 618.3 |
| 2786 N$^1$-((1S,2R)-1-(3,5-difluorobenzyl)-3-{[1-(3-ethylphenyl)-1-methylethyl]amino}-2-hydroxypropyl)-5-methyl-N$^3$,N$^3$-dipropylisophthalamide | 608.3 |
| 2787 N$^1$-[(1S,2R)-1-(3,5-difluorobenzyl)-2-hydroxy-3-[(3-isopropylbenzyl)amino]propyl}-5-(1,3-oxazol-2-yl)-N$^3$,N$^3$-dipropylisophthalamide | 647.2 |
| 2788 N$^1$-((1S,2R)-1-(3,5-difluorobenzyl)-3-{[1-(3-ethylphenyl)-1-methylethyl]amino}-2-hydroxypropyl)-5-(1,3-oxazol-2-yl)-N$^3$,N$^3$-dipropylisophthalamide | 661.3 |
| 2789 N$^1$-((1S,2R)-1-(3,5-difluorobenzyl)-2-hydroxy-3-{[1-(3-isobutylisoxazol-5-yl)cyclopropyl]amino}propyl)-5-(1,3-oxazol-2-yl)-N$^3$,N$^3$-dipropylisophthalamide | 678.3 |
| 2790 N$^1$-((1S,2R)-1-(3,5-difluorobenzyl)-2-hydroxy-3-{[1-(3-isobutylisoxazol-5-yl)cyclopropyl]amino}propyl)-5-ethynyl-N$^3$,N$^3$-dipropylisophthalamide | 635.2 |
| 2791 N$^1$-((1S,2R)-1-(3,5-difluorobenzyl)-2-hydroxy-3-({3-[(methylsulfonyl)amino]benzyl}amino)propyl]-5-methyl-N$^3$,N$^3$-dipropylisophthalamide | 645.2 |
| 2792 N$^1$-((1S,2R)-1-(3,5-difluorobenzyl)-2-hydroxy-3-{[1-(3-isobutylisoxazol-5-yl)cyclopropyl]amino}propyl)-5-methyl-N$^3$,N$^3$-dipropylisophthalamide | 625.3 |
| 2793 N$^1$-{(1S,2R)-1-(3,5-difluorobenzyl)-3-[(3-ethynylbenzyl)amino]-2-hydroxypropyl}-5-(1,3-oxazol-2-yl)-N$^3$,N$^3$-dipropylisophthalamide | 629.2 |
| 2794 N$^1$-((1S,2R)-1-(3,5-difluorobenzyl)-2-hydroxy-3-{[3-(trifluoromethyl)benzyl]amino}propyl)-5-(1,3-oxazol-2-yl)-N$^3$,N$^3$-dipropylisophthalamide | 673.2 |
| 2795 N$^1$-[(1S,2R)-3-[(3-cyanobenzyl)amino]-1-(3,5-difluorobenzyl)-2-hydroxypropyl]-5-methyl-N$^3$,N$^3$-dipropylisophthalamide | 577.2 |

-continued

| Compound Name(s) | mass spec |
| --- | --- |
| 2796 [structure shown] | 649.0 |
| 2797 $N^1$-((1S,2R)-1-(3,5-difluorobenzyl)-3-{[1-(3-ethynylphenyl)cyclopropyl]amino}-2-hydroxpropyl)-5-(1,3-oxazol-2-yl)-$N^3$,$N^3$-dipropylisophthalamide | 655.3 |
| 2799 $N^1$-[(1S,2R)-1-(3,5-difluorobenzyl)-3-({3-[(1E)-hex-1-enyl]benzyl}amino)-2-hydroxypropyl]-5-methyl-$N^3$,$N^3$-dipropylisophthalamide | 634.6 |
| 2800 $N^1$-[(1S,2R)-3-{[3-(5-acetylthien-2-yl)benzyl]amino}-1-(3,5-difluorobenzyl)-2-hydroxypropyl]-5-ethyl-$N^3$,$N^3$-dipropylisophthalamide | 676.5 |
| 2801 $N^1$-[(1S,2R)-3-[(3-allylbenzyl)amino]-1-(3,5-difluorobenzyl)-2-hydroxypropyl]-5-methyl-$N^3$,$N^3$-dipropylisophthalamide | 592.6 |
| 2802 $N^1$-((1S,2R)-1-(3,5-difluorobenzyl)-2-hydroxy-3-{[3-(6-methoxypyridin-3-yl)benzyl]amino}propyl)-5-methyl-$N^3$,$N^3$-dipropylisophthalamide | 659.6 |
| 2803 $N^1$-[(1S,2R)-3-{[(2-tert-butylpyrimidin-4-yl)methyl]amino}-1-(3,5-difluorobenzyl)-2-hydroxypropyl]-5-methyl-$N^3$,$N^3$-dipropylisophthalamide | 610.3 |
| 2804 $N^4$-{(1S,2R)-1-(3,5-difluorobenzyl)-2-hydroxy-3-[(3-isopropylbenzyl)amino]propyl}-6-methyl-$N^2$,$N^2$-dipropylpyridine-2,4-dicarboxamide | 595.3 |
| 2805 $N^1$-[(1S,2R)-3-[(3-butylbenzyl)amino]-1-(3,5-difluorobenzyl)-2-hydroxypropyl]-5-methyl-$N^3$,$N^3$-dipropylisophthalamide | 608.6 |
| 2806 $N^1$-{(1S,2R)-1-(3,5-difluorobenzyl)-2-hydroxy-3-[(3-pentylbenzyl)amino]propyl}-5-methyl-$N^3$,$N^3$-dipropylisophthalamide | 622.6 |
| 2807 $N^1$-{(1S,2R)-1-(3,5-difluorobenzyl)-2-hydroxy-3-[(3-pent-4-enylbenzyl)amino]propyl}-5-methyl-$N^3$,$N^3$-dipropylisophthalamide | 620.6 |
| 2808 $N^1$-[(1S,2R)-3-[(3-cyclopentylbenzyl)amino]-1-(3,5-difluorobenzyl)-2-hydroxypropyl]-5-methyl-$N^3$,$N^3$-dipropylisophthalamide | 620.6 |
| 2809 $N^1$-[(1S,2R)-3-[(3-cyclohexylbenzyl)amino]-1-(3,5-difluorobenzyl)-2-hydroxypropyl]-5-methyl-$N^3$,$N^3$-dipropylisophthalamide | 634.6 |
| 2810 $N^1$-[(1S,2R)-3-{[3-(cyclohexylmethyl)benzyl]amino}-1-(3,5-difluorobenzyl)-2-hydroxypropyl]-5-methyl-$N^3$,$N^3$-dipropylisophthalamide | 648.6 |
| 2811 $N^1$-{(1S,2R)-1-(3,5-difluorobenzyl)-3-[(3-hex-5-enylbenzyl)amino]-2-hydroxypropyl}-5-methyl-$N^3$,$N^3$-dipropylisophthalamide | 634.6 |
| 2812 methyl (2S)-3-[3-({[(2R,3S)-4-(3,5-difluorophenyl)-3-({3-[(dipropylamino)carbonyl]-5-methylbenzoyl}amino)-2-hydroxybutyl]amino}methyl)phenyl]-2-methylpropanoate | 2812 |
| 2813 $N^1$-((1S,2R)-1-(3,5-difluorobenzyl)-2-hydroxy-3-{[3-(3-methylthien-2-yl)benzyl]amino}propyl)-5-methyl-$N^3$,$N^3$-dipropylisophthalamide | 648.5 |
| 2814 $N^1$-((1S,2R)-1-(3,5-difluorobenzyl)-2-hydroxy-3-{[3-(3-methylpyridin-2-yl)benzyl]amino}propyl)-5-methyl-$N^3$,$N^3$-dipropylisophthalamide | 643.6 |
| 2815 $N^1$-((1S,2R)-1-(3,5-difluorobenzyl)-2-hydroxy-3-{[3-(4-methylpyridin-2-yl)benzyl]amino}propyl)-5-methyl-$N^3$,$N^3$-dipropylisophthalamide | 643.6 |
| 2816 $N^1$-((1S,2R)-1-(3,5-difluorobenzyl)-2-hydroxy-3-{[3-(5-methylpyridin-2-yl)benzyl]amino}propyl)-5-methyl-$N^3$,$N^3$-dipropylisophthalamide | 643.6 |
| 2817 $N^1$-[(1S,2R)-3-{[3-(4-chlorobutyl)benzyl]amino}-1-(3,5-difluorobenzyl)-2-hydroxypropyl]-5-methyl-$N^3$,$N^3$-dipropylisophthalamide | 642.6 |

-continued

| | Compound Name(s) | mass spec |
|---|---|---|
| 2818 | $N^1$-[(1S,2R)-3-{[3-(3-cyanopropyl)benzyl]amino}-1-(3,5-difluorobenzyl)-2-hydroxypropyl]-5-methyl-$N^3$,$N^3$-dipropylisophthalamide | 619.6 |
| 2819 | $N^1$-[(1S,2R)-3-{[3-(4-cyanobutyl)benzyl]amino}-1-(3,5-difluorobenzyl)-2-hydroxypropyl]-5-methyl-$N^3$,$N^3$-dipropylisophthalamide | 633.6 |
| 2820 | $N^1$-[(1S,2R)-3-{[3-(6-cyanohexyl)benzyl]amino}-1-(3,5-difluorobenzyl)-2-hydroxypropyl]-5-methyl-$N^3$,$N^3$-dipropylisophthalamide | 661.6 |
| 2821 | $N^1$-((1S,2R)-1-(3,5-difluorobenzyl)-2-hydroxy-3-{[3-(6-methylpyridin-2-yl}benzyl]amino}propyl)-5-methyl-$N^3$,$N^3$-dipropylisophthalamide | 643.6 |
| 2822 | $N^1$-((1S,2R)-1-(3,5-difluorobenzyl)-2-hydroxy-3-{[3-(1,3-oxazol-2-yl)benzyl]amino}propyl)-5-methyl-$N^3$,$N^3$-dipropylisophthalamide | 619.2 |
| 2823 | methyl 3-{[((2R,3S)-4-(3,5-difluorophenyl)-3-{[3-[(dipropylamino)carbonyl]-5-(1,3-oxazol-2-yl)benzoyl]amino}-2-hydroxybutyl)amino]methyl}phenyl(methyl)carbamate | |
| 2824 | $N^1$-((1S,2R)-1-(3,5-difluorobenzyl)-2-hydroxy-3-{[(1S)-1-[(isobutylamino)carbonyl]-3-(methylsulfonyl)propyl]amino}propyl)-5-methyl-$N^3$,$N^3$-dipropylisophthalamide | 681.0 |
| 2825 | $N^1$-butyl-$N^3$-{(1S,2R)-1-(3,5-difluorobenzyl)-2-hydroxy-3-[(3-isopropylbenzyl)amino]propyl}-$N^1$,5-dimethylisophthalamide | 580.3 |
| 2826 | $N^1$-((1S,2R)-1-(3,5-difluorobenzyl)-3-{[1-(3-ethylphenyl)-1-methylethyl]amino}-2-hydroxypropyl)-5-{[(2-hydroxy-1,1-dimethylethyl)amino]sulfonyl}-$N^3$,$N^3$-dipropylisophthalamide | 745.1 |
| 2827 | $N^1$-{(1S,2R)-1-(3,5-difluorobenzyl)-3-[(3-ethylbenzyl)amino]-2-hydroxypropyl}-5-{methyl[(trifluoromethyl)sulfonyl]amino}-$N^3$,$N^3$-dipropylisophthalamide | 727 |
| 2828 | $N^1$-[(1S,2R)-3-(cyclopropylamino)-1-(3,5-difluorobenzyl)-2-hydroxypropyl]-5-{[(2-hydroxy-1,1-dimethylethyl)amino]sulfonyl}-$N^3$,$N^3$-dipropylisophthalamide | 639 |
| 2829 | $N^1$-((1S,2R)-1-(3,5-difluorobenzyl)-3-{[1-(3-ethylphenyl)-1-methylethyl]amino}-2-hydroxypropyl)-$N^3$,$N^3$-dipropyl-5-(1,3-thiazol-2-yl)isophthalamide | 677.1 |
| 2830 | $N^1$-{(1S,2R)-1-(3,5-difluorobenzyl)-3-[(3-ethylbenzyl)amino]-2-hydroxypropyl}-5-[methyl(methylsulfonyl)amino]-$N^3$,$N^3$-dipropylisophthalamide | 673.2 |
| 2831 | $N^1$-butyl-$N^3$-((1S,2R)-1-(3,5-difluorobenzyl)-3-{[1-(3-ethylphenyl)-1-methylethyl]amino}-2-hydroxypropyl)-$N^1$,5-dimethylisophthalamide | 594.3 |
| 2832 | $N^1$-((1S,2R)-1-(2,4-difluorobenzyl)-2-hydroxy-3-{[3-(trifluoromethyl)benzyl]amino}propyl)-5-methyl-$N^3$,$N^3$-dipropylisophthalamide | 620.2 |
| 2833 | 5-bromo-$N^1$-((1S,2R)-1-(2,4-difluorobenzyl)-2-hydroxy-3-{[3-(trifluoromethyl)benzyl]amino}propyl)-$N^3$,$N^3$-dipropylisophthalamide | 684.1 |
| 2834 | N-{(1S,2R)-1-(3,5-difluorobenzyl)-3-[(3-ethylbenzyl)amino]-2-hydroxypropyl}-3-[(2-ethylpiperidin-1-yl)sulfonyl]propanamide | 566 |
| 2835 | $N^1$-((1S,2R)-1-(3,5-difluorobenzyl)-3-{[1-(3-ethylphenyl)cyclopropyl]amino}-2-hydroxypropyl)-5-ethynyl-$N^3$,$N^3$-dipropylisophthalamide | 616.3 |
| 2836 | $N^1$-cyclobutyl-$N^3$-{(1S,2R)-1-(3,5-difluoro-benzyl)-3-[(3-ethylbenzyl)amino]-2-hydroxypropyl}-5-methylisophthalamide | 550.1 |
| 2837 | $N^1$-cyclopentyl-$N^3$-((1S,2R)-1-(3,5-difluorobenzyl)-3-[(3-ethylbenzyl)amino]-2-hydroxypropyl{-5-methylisophthalamide | 564.1 |
| 2838 | $N^1$-{(1S,2R)-1-(3,5-difluorobenzyl)-3-[(3-ethylbenzyl)amino]-2-hydroxypropyl}-5-methyl-$N^3$-pentylisophthalamide | 566.1 |
| 2839 | $N^1$-{(1S,2R)-1-(3,5-difluorobenzyl)-3-[(3-ethylbenzyl)amino]-2-hydroxypropyl}-$N^3$-isopentyl-5-methylisophthalamide | 566.1 |
| 2840 | $N^1$-{(1S,2R)-1-(3,5-difluorobenzyl)-3-[(3-ethylbenzyl)amino]-2-hydroxypropyl}-$N^3$-ethyl-$N^3$-(2-hydroxyethyl)-5-methylisophthalamide | 568.1 |
| 2841 | $N^1$-{(1S,2R)-1-(3,5-difluorobenzyl)-3-[(3-ethylbenzyl)amino]-2-hydroxypropyl}-$N^3$-(2-ethoxyethyl)-5-methylisophthalamide | 568.1 |
| 2842 | $N^1$-{(1S,2R)-1-(3,5-difluorobenzyl)-3-[(3-ethylbenzyl)amino]-2-hydroxypropyl}-$N^3$-(2-methoxyethyl)-$N^3$,5-dimethylisophthalamide | 568.1 |
| 2843 | $N^1$-{(1S,2R)-1-(3,5-difluorobenzyl)-3-[(3-ethylbenzyl)amino]-2-hydroxypropyl}-$N^3$-(2-furylmethyl)-$N^3$,5-dimethylisophthalamide | 590.1 |
| 2844 | N-{(1S,2R)-1-(3,5-difluorobenzyl)-3-[(3-ethylbenzyl)amino]-2-hydroxypropyl}-3-{[(2R,5R)-2,5-dimethylpyrrolidin-1-yl]carbonyl}-5-methylbenzamide | 578.1 |

-continued

| | Compound Name(s) | mass spec |
|---|---|---|
| 2845 | $N^1$-cyclopentyl-$N^3$-{(1S,2R)-1-(3,5-difluorobenzyl)-3-[(3-ethylbenzyl)amino]-2-hydroxypropyl}-$N^1$,5-dimethylisophthalamide | 578.1 |
| 2846 | $N^1${(1S,2R)-1-(3,5-difluorobenzyl)-3-[(3-ethylbenzyl)amino]-2-hydroxypropyl}-$N^3$,5-dimethyl-$N^3$-pentylisophthalamide | 580.1 |
| 2847 | $N^1$-{(1S,2R)-1-(3,5-difluorobenzyl)-3-[(3-ethylbenzyl)amino]-2-hydroxypropyl}-$N^3$-(2-hydroxyethyl)-5-methyl-$N^3$-propylisophthalamide | 582.1 |
| 2848 | $N^1$-{(1S,2R)-1-(3,5-difluorobenzyl)-3-[(3-ethylbenzyl)amino]-2-hydroxypropyl}-$N^3$-ethyl-$N^3$-(2-methoxyethyl)-5-methylisophthalamide | 582.1 |
| 2849 | $N^1$-{(1S,2R)-1-(3,5-difluorobenzyl)-3-[(3-ethylbenzyl)amino]-2-hydroxypropyl}-5-methyl-$N^3$-(2-methylcyclohexyl)isophthalamide | 592.1 |
| 2850 | $N^1$-{(1S,2R)-1-(3,5-difluorobenzyl)-3-[(3-ethylbenzyl)amino]-2-hydroxypropyl}-$N^3$-(2-methoxyethyl)-5-methyl-$N^3$-propylisophthalamide | 596.1 |
| 2851 | $N^1$-{(1S,2R)-1-(3,5-difluorobenzyl)-3-[(3-ethylbenzyl)amino]-2-hydroxypropyl}-$N^3$,$N^3$-bis(2-methoxyethyl)-5-methylisophthalamide | 612.1 |
| 2852 | $N^1$-allyl-$N^1$-cyclohexyl-$N^3$-{(1S,2R)-1-(3,5-difluorobenzyl)-3-[(3-ethylbenzyl)amino}-2-hydroxypropyl}-5-methylisophthalamide | 618.1 |
| 2853 | $N^1$-{(1S,2R)-1-(3,5-difluorobenzyl)-3-[(3-ethylbenzyl)amino}-2-hydroxypropyl}-5-methyl-$N^3$,$N^3$-dipentylisophthalamide | 636.2 |
| 2854 | $N^1$-{(1S,2R)-1-(3,5-difluorobenzyl)-3-[(3-ethylbenzyl)amino]-2-hydroxypropyl}-$N^3$,$N^3$-bis(2-ethoxyethyl)-5-methylisophthalamide | 640.1 |
| 2855 | $N^1$-{(1S,2R)-1-(3,5-difluorobenzyl)-2-hydroxy-3-[(2-naphthylmethyl)amino]propyl}-5-(1,3-oxazol-2-yl)-$N^3$,$N^3$-dipropylisophthalamide | 655.2 |
| 2856 | $N^1$-butyl-$N^3$-((1S,2R)-1-(3,5-difluorobenzyl)-3-{[1-(3-ethylphenyl)cyclopropyl]amino}-2-hydroxypropyl)-$N^1$,5-dimethylisophthalamide | 592.3 |
| 2857 | $N^1$-((1S,2R)-1-(3,5-difluorobenzyl)-3-{[1-(3-ethylphenyl)cyclopropyl]amino}-2-hydroxypropyl)-5-{[(2-hydroxy-1,1-dimethylethyl)amino]sulfonyl}-$N^3$,$N^3$-dipropylisophthalamide | 743.2 |
| 2860 | $N^1$-{(1S,2R)-1-(3,5-difluorobenzyl)-3-[(3-ethylbenzyl)amino]-2-hydroxypropyl}-5-[(3-hydroxypropyl)sulfonyl]-$N^3$,$N^3$-dipropylisophthalamide | 688 |
| 2861 | $N^1$-{(1S,2R)-1-(3,5-difluorobenzyl)-3-[(3-ethylbenzyl)amino]-2-hydroxypropyl}-5-(1H-imidazol-4-yl)-$N^3$,$N^3$-dipropylisophthalamide trifluoroacetate | 632 |
| 2862 | $N^1$-{(1S,2R)-1-(3,5-difluorobenzyl)-3-[(3-ethylbenzyl)amino]-2-hydroxypropyl}-5-isoxazol-3-yl-$N^3$,$N^3$-dipropylisophthalamide | 633 |
| 2863 | N-{(1S,2R)-1-(3,5-d1fluorobenzyl)-3-[3-ethylbenzyl)amino]-2-hydroxypropyl{-3-{[(2R)-2-(methoxymethyl)pyrrolidin-1-yl]carbonyl}-5-(1,3-oxazol-2-yl)benzamide | 647 |
| 2864 | $N^4$-{(1S,2R)-1-(3,5-difluorobenzyl)-3-[(3-ethynylbenzyl)amino]-2-hydroxypropyl}-6-methyl-$N^2$,$N^2$-dipropylpyridine-2,4-dicarboxamide | 577.2 |
| 2865 | $N^4$-((1S,2R)-1-(3,5-difluorobenzyl)-2-hydroxy-3-{[3-(trifluoromethyl)benzyl]amino}propyl)-6-methyl-$N^2$,$N^2$-dipropylpyridine-2,4-dicarboxamide | 621.2 |
| 2866 | $N^4$-((1S,2R)-1-(3,5-difluorobenzyl)-3-{[1-(3-ethylphenyl)cyclopropyl]amino}-2-hydroxypropyl)-6-methyl-$N^2$,$N^2$-dipropylpyridine-2,4-dicarboxamide | 607.3 |
| 2867 | $N^1$-((1S,2R)-1-(3,5-difluorobenzyl)-3-{[1-(3-ethylphenyl)cyclopropyl]amino}-2-hydroxypropyl)-$N^3$,$N^3$-dipropyl-5-(1,3-thiazol-2-yl)isophthalamide | 675.4 |
| 2868 | $N^1$-{(1S,2R)-1-(3,5-difluorobenzyl)-3-[(3-ethylbenzyl)amino]-2-hydroxypropyl}-5-[methyl(thien-2-ylsulfonyl)amino]-$N^3$,$N^3$-dipropylisophthalamide | 741 |
| 2869 | $N^1$-{(1S,2R)-1-(3,5-difluorobenzyl)-3-[(3-ethylbenzyl}amino]-2-hydroxypropyl}-5-({[(2R)-2-hydroxypropyl]amino}sulfonyl)-$N^3$,$N^3$-dipropylisophthalamide | 703 |
| 2870 | $N^1$-((1S,2R)-1-(3,5-difluorobenzyl)-2-hydroxy-3-{[1-(2-isobutyl-1,3-thiazol-5-yl)cyclopropyl]amino}propyl)-5-(1,3-oxazol-2-yl)-$N^3$,$N^3$-dipropylisophthalamide | 694.2 |
| 2871 | $N^1$-{(1S,2R)-1-(3,5-difluorobenzyl)-3-[(3-ethylbenzyl)amino]-2-hydroxypropyl}-3-hydroxy-$N^5$,$N^5$-dipropylpentanediamide | 548.1 |

-continued

| Compound Name(s) | mass spec |
|---|---|

2872 [structure] 534.1

2873 [structure] 550.1

2874 [structure] 656.3

| | |
|---|---|
| 2875 N-{(1S,2R)-1-(3,5-difluorobenzyl)-3-[(3-ethylbenzyl)amino]-2-hydroxypropyl}-4-[(methylsulfonyl)methyl]benzamide | 531 |
| 2876 N-{(1S,2R)-1-(3,5-difluorobenzyl)-3-[(3-ethylbenzyl)amino]-2-hydroxypropyl}-3-methyl-5-(2-methylpentanoyl)benzamide hydrochloride | 551.3 |
| 2877 $N^1$-{(1S,2R)-1-(3,5-difluorobenzyl)-3-[(3-ethylbenzyl)amino]-2-hydroxypropyl}-5-[(methylsulfonyl)amino]-$N^3,N^3$-dipropylisophthalamide | 659.2 |
| 2878 $N^1$-{(1S,2R)-1-(3,5-difluorobenzyl)-3-[(3-ethylbenzyl)amino]-2-hydroxypropyl}-3-[(1-propylbutyl)sulfonyl]-D-alaninamide dihydrochloride | 568 |
| 2879 $N^1$-{(1S,2R)-1-(3,5-difluorobenzyl)-3-[(3-ethylbenzyl)amino]-2-hydroxypropyl}-$N^2$-propionyl-3-[(1-propylbutyl)sulfonyl]-D-alaninamide | 624 |

-continued

| Compound Name(s) | mass spec |
|---|---|
| 2880 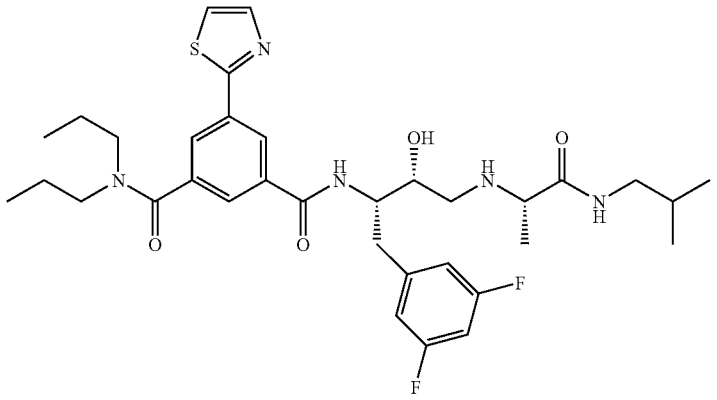 | 658.3 |
| 2881 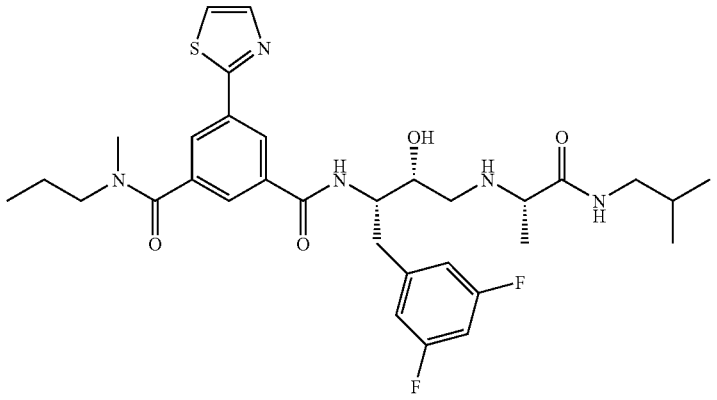 | 630.3 |
| 2882 N$^1$-butyl-N$^3$-{(1S,2R)-1-(3,5-difluorobenzyl)-3-[(3-ethylbenzyl)amino]-2-hydroxypropyl}-N$^1$-methyl-5-(1,3-thiazol-2-yl)isophthalamide | 635.4 |
| 2883 N-{(1S,2R)-1-(3,5-difluorobenzyl)-3-[(3-ethylbenzyl)amino]-2-hydroxypropyl}-3-[(3-hydroxypropyl)(methylsulfonyl)amino]benzamide | 590.2 |
| 2884 N-{(1S,2R)-1-(3,5-difluorobenzyl)-3-[(3-ethylbenzyl)amino]-2-hydroxypropyl}-4-(methylsulfonyl)benzamide | 517.2 |
| 2885 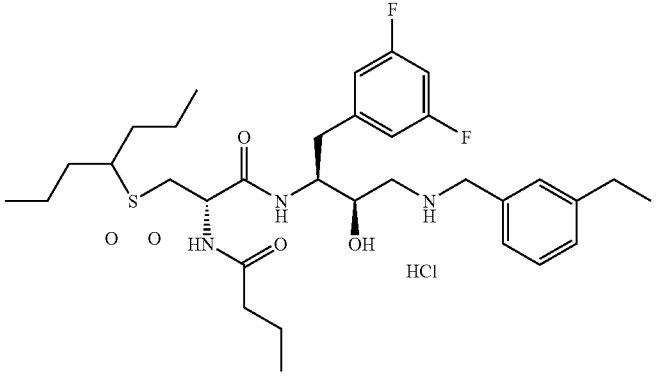<br>as drawn | 638 |
| 2886 N$^1${(1S,2R)-1-(3,5-difluorobenzyl)-3-[(3-ethylbenzyl)amino]-2-hydroxypropyl}-N$^3$,N$^3$-dipropyl-5-pyrimidin-2-ylisophthalamide | 644 |
| 2887 N$^1$-{(1S,2R)-1-(3,5-difluorobenzyl)-3-[(3-ethylbenzyl)amino]-2-hydroxypropyl}-5-({[(2S)-2-hydroxypropyl]amino}sulfonyl)-N$^3$,N$^3$-dipropylisophthalamide | 703 |

| Compound Name(s) | mass spec |
|---|---|
| 2888 $N^1$-{(1S,2R)-1-(3,5-difluorobenzyl)-3-[(3-ethylbenzyl)amino]-2-hydroxypropyl}-$N^3$-methyl-$N^3$-propyl-5-(1,3-thiazol-2-yl)isophthalamide | 621.3 |
| 2889 N-{(1S,2R)-1-(3,5-difluorobenzyl)-3-[(3-ethylbenzyl)amino]-2-hydroxypropyl}-3-(2-methylpentanoyl)-5-(1,3-oxazol-2-yl)benzamide | 604.3 |
| 2890 $N^1$-[(1S,2R)-1-(3,5-difluorobenzyl)-2-hydroxy-3-({3-[(methylsulfonyl)amino]benzyl}amino)propyl]-5-(1,3-oxazol-2-yl)-$N^3$,$N^3$-dipropylisophthalamide | 698.2 |
| 2891 $N^1$-{(1S,2R)-1-(3,5-difluorobenzyl)-3-[(3-ethylbenzyl)amino]-2-hydroxypropyl}-$N^2$-(2,2-dimethylpropanoyl)-3-[(1-propylbutyl)sulfonyl]-D-alaninamide hydrochloride | 652 |
| 2892 $N^1$-{(1S,2R)-1-(3,5-difluorobenzyl)-3-[(3-ethylbenzyl)amino]-2-hydroxypropyl}-5-{[(2R)-2-(methoxymethyl)pyrrolidin-1-yl]sulfonyl}-$N^3$,$N^3$-dipropylisophthalamide | 743 |
| 2893 N-{(1S,2R)-1-(3,5-difluorobenzyl)-3-[(3-ethylbenzyl)amino]-2-hydroxypropyl}-4-[(3-hydroxypropyl)(methylsulfonyl)amino]benzamide | 590.0 |
| 2894 $N^2$-acetyl-$N^1$-{(1S,2R)-1-(3,5-difluorobenzyl)-3-[(3-ethylbenzyl)amino]-2-hydroxypropyl}-3-[(1-propylbutyl)sulfonyl]-D-alaninamide hydrochloride | 610 |
| 2895 2-[allyl(methylsulfonyl)amino]-N-{(1S,2R)-1-(3,5-difluorobenzyl)-3-[(3-ethylbenzyl)amino]-2-hydroxypropyl}-1,3-thiazole-5-carboxamide | 579.2 |
| 2896 3-(butylsulfonyl)-$N^1$-{(1S,2R)-1-(3,5-difluorobenzyl)-3-[(3-ethylbenzyl)amino]-2-hydroxypropyl}-D-alaninamide bis(trifluoroacetate) | 526 |
| 2897 $N^1$-((1S,2R)-1-(3,5-difluorobenzyl)-3-{[1-(3-ethylphenyl)cyclopropyl]amino}-2-hydroxypropyl)-3-[(1-propylbutyl)sulfonyl]-D-alaninamide bis(trifluoroacetate) | 594 |
| 2898 $N^1$-{(1S,2R)-1-(3,5-difluorobenzyl)-3-[(3-ethylbenzyl)amino]-2-hydroxypropyl}-$N^2$-isobutyryl-3-[(1-propylbutyl)sulfonyl]-D-alaninamide hydrochloride | 638 |

The compounds in the table immediately below were prepared essentially using the methods described above and illustrated below in the schemes.

The following compounds were named using the Advanced Chemistry Development Inc. (ACD) nomenclature program, IUPAC Name Batch Version 4.5. The website for ACD is www.acdlabs.com.

| Compound Name(s) | mass spec |
|---|---|
| 2899 N-[(1S,2R)-3-(butylamino)-1-(3,5-difluorobenzyl)-2-hydroxypropyl]-4-(ethylthio)benzamide | |
| 2900 N-{(1S,2R)-1-(3,5-difluorobenzyl)-3-[(3-ethylbenzyl)amino]-2-hydroxypropyl}-1-(2-fluorophenyl)-5-oxopyrrolidine-3-carboxamide | 540.2 |
| 2901 $N^1$-(4-tert-butyl-1,3-thiazol-2-yl)-$N^4$-{(1S,2R)-1-(3,5-difluorobenzyl)-3-[(3-ethylbenzyl)amino]-2-hydroxypropyl}succinamide | |
| 2902 N-{(1S,2R)-1-(3,5-difluorobenzyl)-3-[(3-ethylbenzyl)amino]-2-hydroxypropyl}-3-hydroxy-6-(1-hydroxy-2,2-dimethylpropyl)pyridine-2-carboxamide | 542.3 |
| 2903 N-{(1S,2R)-1-(3,5-difluorobenzyl)-3-[(3-ethylbenzyl)amino]-2-hydroxypropyl}-2-{[(ethylamino)carbonyl]amino}benzamide | 525.3 |
| 2908 3-acetyl-N-[(1S,2R)-3-(benzylamino)-1-(3,5-difluorobenzyl)-2-hydroxypropyl]benzamide | |
| 2909 $N^1$-{(1S,2R)-1-(3,5-difluorobenzyl)-2-hydroxy-3-[(7-methoxy-1,2,3,4-tetrahydronaphthalen-1-yl)amino]propyl}-5-methyl-$N^3$,$N^3$-dipropylisophthalamide | |
| 2913 $N^1$-{(1S,2R)-1-(3,5-difluorobenzyl)-3-[(2,2-dioxido-3,4-dihydro-1,2-benzoxathiin-4-yl)amino]-2-hydroxypropyl}-5-methyl-$N^3$,$N^3$-dipropylisophthalamide | |
| 2916 $N^1$-{(1S,2R)-1-{[5-(cyanomethyl)-1H-imidazol-1-yl]methyl}-3-[(3-ethylbenzyl)amino]-2-hydroxypropyl}-5-methyl-$N^3$,$N^3$-dipropylisophthalamide | |
| 2918 $N^1$-((1S,2R)-1-(3,5-difluorobenzyl)-3-{[(2-ethylpyrimidin-4-yl)methyl]amino}-2-hydroxypropyl)-5-methyl-$N^3$,$N^3$-dipropylisophthalamide | |
| 2920 $N^1$-{(1S,2R)-1-(3,5-difluorobenzyl)-3-[(3-ethylbenzyl)amino]-2-hydroxypropyl}-5-{[ethyl(methyl)amino]sulfonyl}-$N^3$,$N^3$-dipropylisophthalamide | 687.3 |
| 2921 N-{(1S,2R)-1-(3,5-difluorobenzyl)-3-[(3-ethylbenzyl)amino]-2-hydroxypropyl}-3-[(2-hydroxyethyl)(methylsulfonyl)amino]benzamide | 575.9 |
| 2922 5-bromo-$N^1$-{(1S,2R)-1-(2,4-difluorobenzyl)-3-[(3-ethylbenzyl)amino]-2-hydroxypropyl}-$N^3$,$N^3$-dipropylisophthalamide | 646.4 |
| 2923 N-{(1S,2R)-1-(3,5-difluorobenzyl)-3-[(3-ethylbenzyl)amino]-2-hydroxypropyl}-3-[(2-methoxyethyl)(methylsulfonyl)amino]benzamide hydrochloride | 590.0 |
| 2924 N-{(1S,2R)-1-(3,5-difluorobenzyl)-3-[(3-ethylbenzyl)amino]-2-hydroxypropyl}-3-[(methylsulfonyl)methyl]benzamide | 531.2 |
| 2925 $N^1$-{(1S,2R)-1-(3,5-difluorobenzyl)-3-[(3-ethylbenzyl)amino]-2-hydroxypropyl}-5-[(4-hydroxybutyl)sulfonyl]-$N^3$,$N^3$-dipropylisophthalamide hydrochloride | 702.4 |
| 2926 N-{(1S,2R)-1-(3,5-difluorobenzyl)-3-[(3-ethylbenzyl)amino]-2-hydroxypropyl}-1-(dipropylamino)isoquinoline-7-carboxamide | 589.4 |
| 2927 $N^1$-{(1S,2R)-1-(3,5-difluorobenzyl)-3-[(3-ethylbenzyl)amino]-2-hydroxypropyl}-5-{[(2-hydroxyethyl)(methyl)amino]sulfonyl}-$N^3$,$N^3$-dipropylisophthalamide | 703.4 |

| | Compound Name(s) | mass spec |
|---|---|---|
| 2928 | $N^1$-{(1S,2R)-1-(3,5-difluorobenzyl)-3-[(3-ethylbenzyl)amino]-2-hydroxypropyl}-5-[(ethylamino)sulfonyl]-$N^3,N^3$-dipropylisophthalamide | 673.4 |
| 2929 | $N^1$-{(1S,2R)-1-(3,5-difluorobenzyl)-3-[(3-ethylbenzyl)amino]-2-hydroxypropyl}-5-(5-methyl-1,2,4-oxadiazol-3-yl)-$N^3,N^3$-dipropylisophthalamide hydrochloride | 648.4 |
| 2930 | N-{(1S,2R)-1-(3,5-difluorobenzyl)-3-[(3-ethylbenzyl)amino]-2-hydroxypropyl}-2-[methyl(methylsulfonyl)amino]-1,3-oxazole-4-carboxamide | |
| 2931 | 3-(butylsulfonyl)-N-{(1S,2R)-1-(3,5-difluorobenzyl)-3-[(3-ethylbenzyl)amino]-2-hydroxypropyl}propanamide | 511 |
| 2932 | $N^1$-{(1S,2R)-1-(3,5-difluorobenzyl)-3-[(3-ethylbenzyl)amino]-2-hydroxypropyl}-$N^3,N^3$-dipropylmalonamide | |
| 2933 | $N^2$-{(1S,2R)-1-(3,5-difluorobenzyl)-3-[(3-ethylbenzyl)amino]-2-hydroxypropyl}-$N^3,N^3$-dipropylbicyclo[2.2.1]hept-5-ene-2,3-dicarboxamide | |
| 2934 | $N^1$-{(1S,2R)-1-(3,5-difluorobenzyl)-3-[(3-ethylbenzyl)amino]-2-hydroxypropyl}-$N^3,N^3$-dipropylcyclopentane-1,3-dicarboxamide | |
| 2935 | $N^2$-{(1S,2R)-1-(3,5-difluorobenzyl)-3-[(3-ethylbenzyl)amino]-2-hydroxypropyl}-3,4-dimethyl-$N^5,N^5$-dipropylthieno[2,3-b]thiophene-2,5-dicarboxamide | |
| 2936 | $N^1$-{(1S,2R)-1-(3,5-difluorobenzyl)-3-[(3-ethylbenzyl)amino]-2-hydroxypropyl}-2-phenyl-$N^5,N^5$-dipropylpentanediamide | |
| 2937 | $N^2$-benzyl-$N^1$-{(1S,2R)-1-(3,5-difluorobenzyl)-3-[(3-ethylbenzyl)amino]-2-hydroxypropyl}-$N^2$-[2-(dipropylamino)-2-oxoethyl]glycinamide | |
| 2938 | 3-(4-chlorophenyl)-$N^1$-{(1S,2R)-1-(3,5-difluorobenzyl)-3-[(3-ethylbenzyl)amino]-2-hydroxypropyl}-$N^5,N^5$-dipropylpentanediamide | |
| 2939 | (2E)-$N^5$-{(1S,2R)-1-(3,5-difluorobenzyl)-3-[(3-ethylbenzyl)amino]-2-hydroxypropyl}-2-(methoxyimino)-$N^1,N^1$-dipropylpentanediamide | |
| 2940 | $N^1$-{(1S,2R)-1-(3,5-difluorobenzyl)-3-[(3-ethylbenzyl)amino]-2-hydroxypropyl}-$N^2$-[2-(dipropylamino)-2-oxoethyl]-$N^2$-phenylglycinamide | |
| 2941 | $N^1$-{(1S,2R)-1-(3,5-difluorobenzyl)-3-[(3-ethylbenzyl)amino]-2-hydroxypropyl}-$N^2,N^2$-dipropylcyclohexane-1,2-dicarboxamide | |
| 2942 | $N^1$-[(1S,2R)-3-[(benzyloxy)amino]-1-(3,5-difluorobenzyl)-2-hydroxypropyl]-5-(1,3-oxazol-2-yl)-$N^3,N^3$-dipropylisopthalamide | |
| 2943 | N-{(1S,2R)-1-(3,5-difluorobenzyl)-3-[(3-ethylbenzyl)amino]-2-hydroxypropyl}-3-phenylpropanamide | |
| 2945 | $N^1$-{(1S,2R)-1-(3,5-difluorobenzyl)-3-[(3-ethylbenzyl)amino]-2-hydroxypropyl}-5-(1H-imidazol-2-yl)-$N^3,N^3$-dipropylisophthalamide | 632.3 |
| 2946 | N-{(1S,2R)-1-(3,5-difluorobenzyl)-3-[(3-ethylbenzyl)amino]-2-hydroxypropyl}-3-(1-hydroxy-2-propylpentyl)benzamide | 567.3 |
| 2947 | N-{(1R,2R)-1-(3,5-difluorobenzyl)-3-[(3-ethylbenzyl)amino]-2-hydroxypropyl}-3-isobutyrylbenzamide hydrochloride | 536.2 |
| 2948 | N-{(1S,2R)-1-(3,5-difluorobenzyl)-3-[(3-ethylbenzyl)amino]-2-hydroxypropyl}-3-(2-propylpentanoyl)benzamide | 565.3 |
| 2949 | N-{(1S,2R)-1-(3,5-difluorobenzyl)-3-[(3-ethylbenzyl)amino]-2-hydroxypropyl}-3-(2-ethylbutanoyl)benzamide hydrochloride | 537.3 |

The compounds in the table immediately below were prepared essentially using the methods described above and illustrated below in the schemes.

The following compounds were named using the Advanced Chemistry Development Inc. (ACD) nomenclature program, IUPAC Name Batch Version 4.5; The website for ACD is www.acdlabs.com.

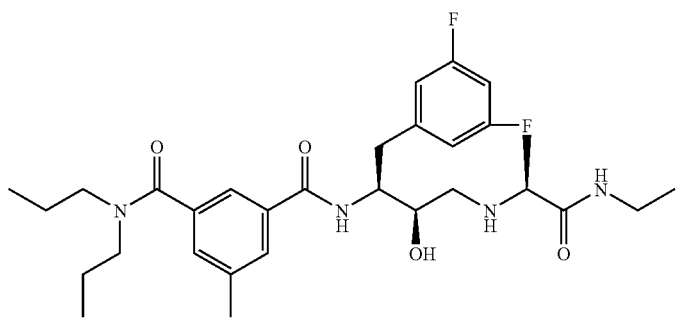

2951　　561.2

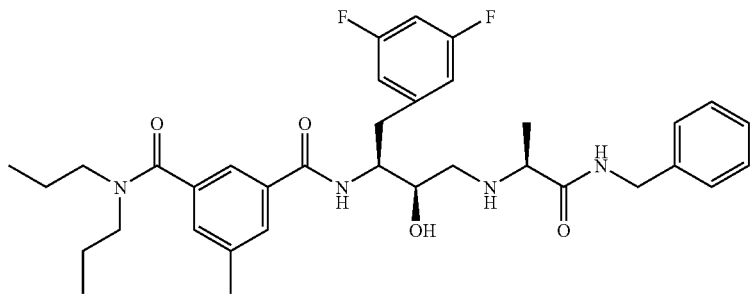

2953　　623.2

-continued

| | | |
|---|---|---|
| 2954 | N¹-{(1S,2R)-1-(3,5-difluorobenzyl)-3-[(3-ethylbenzyl)amino]-2-hydroxypropyl}-3,3-dimethyl-N²,N²-dipropylcyclopropane-1,2-dicarboxamide | 558.4 |
| 2956 | N¹-{(1S,2R)-1-(3,5-difluorobenzyl)-3-[(3-ethylbenzyl)amino]-2-hydroxypropyl}-3-methyl-N⁵,N⁵-dipropylpentanediamide | 546.5 |
| 2957 | N¹-{(1S,2R)-1-(3,5-difluorobenzyl)-3-[(3-ethylbenzyl)amino]-2-hydroxypropyl}-3,3-dimethyl-N⁵,N⁵-dipropylpentanediamide | 560.5 |
| 2958 | N¹-{(1S,2R)-1-(3,5-difluorobenzyl)-3-[(3-ethylbenzyl)amino]-2-hydroxypropyl}-3-ethyl-3-methyl-N⁵,N⁵-dipropylpentanediamide | 574.5 |
| 2959 | N¹-{(1S,2R)-1-(3,5-difluorobenzyl)-3-[(3-ethylbenzyl)amino]-2-hydroxypropyl}-3-hydroxy-3-methyl-N⁵,N⁵-dipropylpentanediamide | 562.5 |
| 2960 | 2-[allyl(methylsulfonyl)amino]-N-{(1S,2R)-1-(3,5-difluorobenzyl)-3-[(3-ethylbenzyl)amino]-2-hydroxypropyl}-1,3-oxazole-4-carboxamide | 563.2 |
| 2962 | N¹-[(1S,2R)-3-({2-[bis(2-hydroxyethyl)amino]ethyl}amino)-1-(3,5-difluorobenzyl)-2-hydroxypropyl]-5-methyl-N³,N³-dipropylisophthalamide | 593.5 |
| 2963 | N¹-[(1S,2R)-3-(cyclopropylamino)-1-(3,5-difluorobenzyl)-2-hydroxypropyl]-3-](1-propylbutyl)sulfonyl]-D-alaninamide dihydrochloride | |
| 2964 | N-{(1S,2R)-1-(3,5-difluorobenzyl)-3-[(3-ethylbenzyl)amino]-2-hydroxypropyl}-3-[4-(hydroxymethyl)-1,3-oxazol-2-yl]benzamide hydrochloride | 536.3 |

Example SP-131

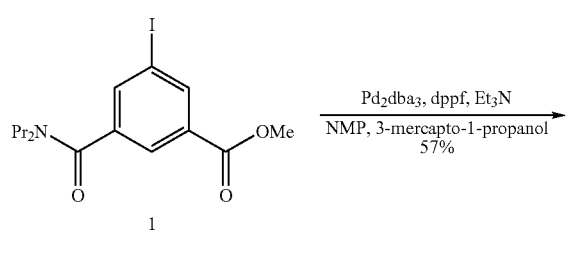

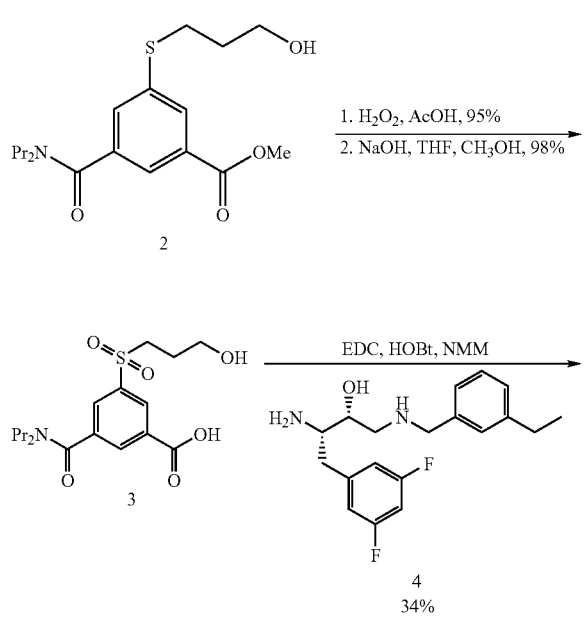

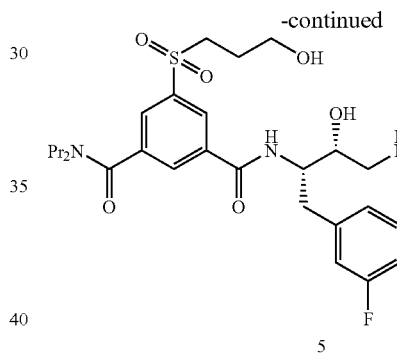

Step 1: A solution of iodide 1 (1.70 g, 4.36 mmol), Pd₂dba₃ (80 mg, 0.087 mmol), dppf (193 mg, 0.349 mmol), and triethylamine (882 mg, 8.72 mmol) in N-methylpyrrolidine (10 mL) was degassed under nitrogen for 15 min. 3-Mercapto-1-propanol (402 mg, 4.36 mmol) was added and the reaction mixture was heated at 60° C. for 2 h. The reaction mixture was cooled to room temperature and then partitioned between ethyl acetate and saturated sodium chloride. The organic layer was washed (2×) with saturated sodium chloride, dried (sodium sulfate), filtered, and concentrated under reduced pressure. Purification by flash column chromatography (silica, 1:1 hexanes/ethyl acetate) gave sulfide 2 (880 mg, 57%) as a yellow oil: ¹H NMR (300 Mz, CDCl₃) δ 8.00 (s, 1H), 7.85 (s, 1H), 7.50 (s, 1H), 3.92 (s, 3H), 3.77 (m, 2H), 3.47 (m, 4H), 3.11 (m, 4H), 1.92 (m, 2H), 1.70 (m, 2H), 0.98 (m, 3H), 0.78 (m, 3H); ESI MS m/z 354 [M+H]⁺.

Step 2: To a stirred solution of sulfide 2 (880 mg, 2.49 mmol) in 1:1 acetic acid/water (15 mL) was added excess 30% hydrogen peroxide. The reaction mixture was stirred overnight and then partitioned between ethyl acetate and water. The organic layer was washed with water, dried (sodium sulfate), filtered, and concentrated under reduced pressure to give a sulfone (912 mg, 95%) as a pale yellow oil: ¹H NMR (300 MHz, CDCl₃) δ 9.51 (s, 1H), 8.28 (s, 1H), 8.11 (s, 1H), 3.99 (s, 3H), 3.71 (m, 2H), 3.55 (m, 2H), 3.44 (m, 2H), 3.38 (m, 2H), 2.11 (m, 2H), 1.88 (m, 2H), 1.78 (m, 2H), 0.77 (m, 3H), 0.56 (m, 3H); APCI MS m/z 387 [M+H]+.

Step 3: A solution of the sulfone from step 2 (912 mg, 2.36 mmol) in 3:1:1 methanol/tetrahydrofuran/1 N sodium hydroxide (20 mL) was stirred at room temperature for 2 h. The reaction mixture was partitioned between ethyl acetate and water. The aqueous layer was acidified to pH 3 with 1 N hydrochloric acid and extracted with chloroform. The organic layer was dried (sodium sulfate), filtered, and concentrated to give acid 3 (860 mg, 98%) as a white foam: $^1$H NMR (300 MHz, CDCl$_3$) δ 8.48 (s, 1H), 8.24 (s, 1H), 8.08 (s, 1H), 4.11 (m, 2H), 3.69 (m, 2H), 3.33 (m, 2H), 3.13 (m, 2H), 1.98 (m, 2H), 1.75 (m, 2H), 1.58 (m, 2H), 1.03 (m, 3H), 0.79 (m, 3H).

Step 4: To a stirred solution of acid 3 (630 mg, 1.69 mmol), amine 4 (688 mg, 1.69 mmol), HOBt (251 mg, 1.86 mmol), and N-methylmorpholine (855 mg, 8.45 mmol) in methylene chloride (15 mL) was added EDC (583 mg, 3.04 mmol). The reaction mixture was stirred overnight and then partitioned between ethyl acetate and water. The organic layer was washed with 1 N hydrochloric acid, saturated sodium bicarbonate, and saturated sodium chloride, dried (sodium sulfate), filtered, and concentrated under reduced pressure. Purification by flash column chromatography (silica, 93:7:1 methylene chloride/methanol/ammonium hydroxide) gave ALB 8198 (5)(400 mg, 34%) as a white solid: mp 62-66° C.; IR (ATR) 3293, 2964, 2874, 1614 cm$^{-1}$; $^1$H NMR (300 MHz, CDCl$_3$) δ 8.18 (s, 1H), 8.06 (s, 1H), 7.85 (s, 1H), 7.28 (m, 2H), 7.15 (m, 2H), 6.85 (m, 2H), 6.62 (m, 1H), 4.31 (m, 1H), 3.79 (m, 2H), 3.67 (m, 2H), 3.55 (m, 2H), 3.24 (m, 2H), 3.05 (m, 2H), 2.91 (m, 4H), 2.86 (m, 1H), 2.60 (m, 2H), 1.95 (m, 2H), 1.73 (m, 2H), 1.56 (m, 2H), 1.22 (m, 3H), 1.03 (m, 3H), 0.72 (m, 3H); APCI MS m/z 688 [M+H]+; HPLC: Method A, 8.36 min (>99%, AUC). Anal. Calcd for C$_{36}$H$_{47}$F$_2$N$_3$O$_6$S.0.25H$_2$O: C, 62.45; H, 6.92; N, 6.07. Found: C, 62.21; H, 6.69; N, 5.97.

Example SP-132

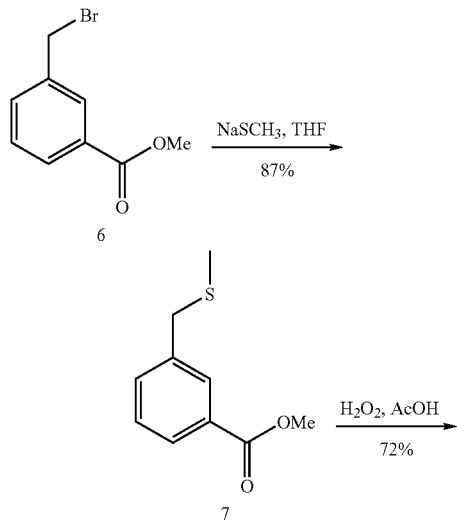

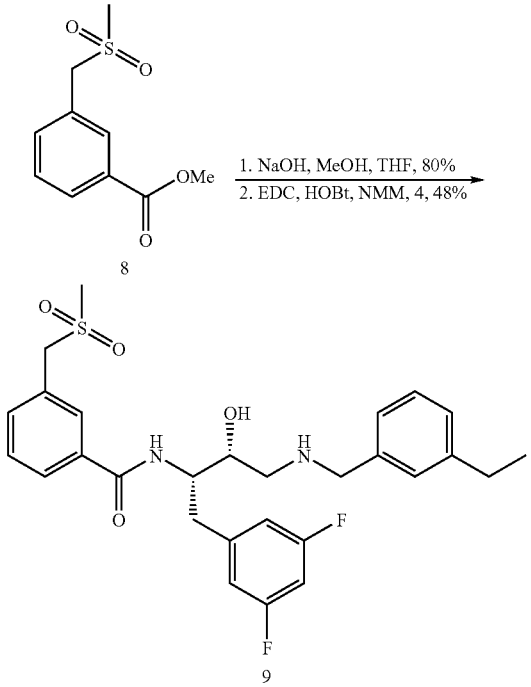

Step 1: A mixture of benzoate 6 (870 mg, 3.79 mmol) and sodium thiomethoxide (292 mg, 4.18 mmol) was stirred in THF (20 mL) at 40° C. After 48 h, the reaction mixture was cooled to room temperature and then partitioned between ethyl acetate and water. The organic layer was dried (sodium sulfate), filtered, and concentrated under reduced pressure to give sulfide 7 (650 mg, 87%) as a white foam: $^1$H NMR (300 MHz, CDCl$_3$) δ 7.97 (s, 1H), 7.88 (d, J=8 Hz, 1H), 7.40 (d, J=8 Hz, 1H), 7.27 (m, 1H), 3.92 (s, 3H), 3.71 (s, 2H), 1.99 (s, 3H).

Step 2: To a stirred solution of sulfide 7 (650 mg, 3.31 mmol) in 1:1 acetic acid/water (25 mL) was added excess 30% hydrogen peroxide. The reaction mixture was stirred overnight and then partitioned between ethyl acetate and water. The organic layer was washed with sodium bicarbonate, water, and saturated sodium chloride, dried (sodium sulfate), filtered, and concentrated under reduced pressure to give sulfone 8 (540 mg, 72%) as a clear oil: $^1$H NMR (500 MHz, DMSO-d$_6$) δ 58.12 (s, 1H), 8.04 (d, J=7 Hz, 1H), 7.74 (d, J=7 Hz, 1H), 7.54 (m, 1H), 4.62 (s, 2H), 3.98 (s, 3H), 2.98 (s, 3H).

Step 3: A mixture of sulfide 8 (540 mg, 2.37 mmol) in 3:1:1 methanol/THF/2 N sodium hydroxide (10 mL) was stirred overnight. The reaction mixture was partitioned between ethyl acetate and water. The aqueous layer was acidified to pH 3 with 1 N HCl and extracted with chloroform. The organic layer was dried (sodium sulfate), filtered, and concentrated under reduced pressure to provide an acid (406 mg, 80%) as a white solid: $^1$H NMR (300 MHz, DMSO-d$_6$) δ 8.02 (s, 1H), 7.96 (d, J=7 Hz, 1H), 7.64 (d, J=7 Hz, 1H), 7.57 (m, 1H), 4.59 (s, 2H), 2.92 (s, 3H).

Step 4: To a stirred solution of acid from step 3 (260 mg, 1.21 mmol), HOBt (163 mg, 1.21 mmol), amine 4 (495 mg, 1.21 mmol), and N-methylmorpholine (612 mg, 6.05 mmol) was added EDC (418 mg, 2.18 mmol). The reaction mixture was stirred overnight and then partitioned between ethyl acetate and water. The organic layer was washed with 1 N hydrochloric acid, saturated sodium bicarbonate, and saturated sodium chloride, dried (sodium sulfate), filtered, and concentrated under reduced pressure. Purification by flash column chromatography (silica, 93:7:1 methylene chloride/methanol/ammonium hydroxide) gave ALB 8653 (9) (308 mg, 48%): mp 147-149° C.; IR (ATR) 3286, 2961, 1633, 1596 cm$^{-1}$; $^1$H NMR (300 MHz, DMSO-d$_6$) δ 8.39 (d, J=9 Hz, 1H), 7.77 (s, 1H), 7.72 (d, J=7 Hz, 1H), 7.54 (d, J=7 Hz, 1H), 7.48 (m, 1H), 7.18-6.93 (m, 7H), 5.03 (br s, 1H), 4.51 (s, 2H), 4.18 (br s, 1H), 3.68 (s, 2H), 3.67 (m, 1H), 3.12 (m, 1H), 2.91 (s, 3H), 2.88 (m, 1H), 2.61 (m, 1H), 2.45 (m, 2H), 2.43 (m, 2H), 1.13 (m, 3H); ESI MS m/z 531 [M+H]$^+$; HPLC: Method A, 6.81 min (>99%, AUC). Anal. Calcd for C$_{31}$H$_{40}$F$_2$N$_4$O$_4$.0.25H$_2$O: C, 62.85; H, 6.12; N, 5.23. Found: C, 62.96; H, 5.83; N, 5.09.

Example SP-133

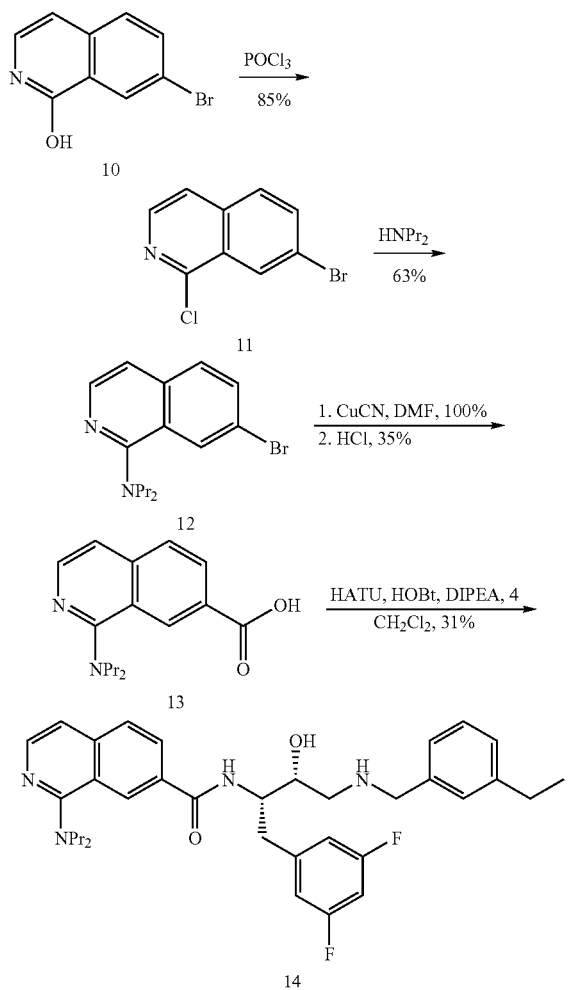

Step 1: A solution of hydroxide 10 (2.5 g, 11.1 mmol) and POCl$_3$ (10.4 mL, 111 mmol) was stirred at 70° C. for 2.5 h. The reaction mixture was cooled to room temperature, poured into ice water and the solution was stirred overnight. The aqueous mixture was diluted with CHCl$_3$, washed with a saturated solution of NaHCO$_3$, saturated NaCl, dried (MgsO$_4$), filtered, and concentrated under reduced pressure to afford chloride 11 (2.3 g, 85%) as a tan solid: $^1$H NMR (300 MHz, DMSO-d$_6$) δ 8.39-8.36 (m, 2H), 8.09-8.02 (m, 2H), 7.95 (d, J=6 Hz, 1H).

Step 2: A solution of chloride 11 (500 mg, 2.1 mmol) and dipropylamine (2.8 mL, 21 mmol) was heated at 150° C. in a sealed tube for 2 d. The reaction mixture was cooled, and the solvent was removed under reduced pressure to provide amine 12 (400 mg, 63%) as a brown oil: $^1$H NMR (300 MHz, DMSO-d$_6$) δ 8.55 (s, 1H), 7.90 (d, J=6 Hz, 1H), 7.75-7.64 (m, 2H), 6.87 (d, J=6 Hz, 1H), 3.42 (q, J=7 Hz, 4H), 1.65 (q, J=7 Hz, 4H), 0.94 (t, J=7 Hz, 6H)

Step 3: A solution of amine 12 (350 mg, 1.1 mmol) and CuCN (204 mg, 2.2 mmol) in DMF (2 mL) was stirred at reflux for 24 h. The reaction mixture was cooled to room temperature, diluted with water, and extracted with EtOAc (3×50 mL). The combined organics were washed with saturated NaCl, dried (MgSO$_4$), filtered, and concentrated under reduced pressure to provide a nitrile (279, mg, 100%) as a brown oil, which was used without any further characterization.

Step 4: A solution of the nitrile from step 4 (279 mg, 1.1 mmol) in concentrated HCl (4 mL) was heated at 150° C. in a sealed tube for 14 h. The reaction mixture was cooled to room temperature, the solvent was removed under reduced pressure, and the residue was dissolved in a 25% NH$_4$OH/H$_2$O solution and stirred for 1 h. The solution was acidified to pH 4, and extracted with CHCl$_3$ (3×50 mL). The combined organics were dried (Na$_2$SO$_4$), filtered, and concentrated under reduced pressure to provide acid 13 (104 mg, 35%) as a white solid: $^1$H NMR (300 MHz, CDCl$_3$) δ 8.85 (s, 1H), 8.15 (d, J=8 Hz, 1H), 8.01 (d, J=6 Hz, 1H), 7.79 (d, J=7 Hz, 1H), 7.21 (d, J=6 Hz, 1H), 3.47 (m, 4H), 1.68 (m, 4H), 0.83 (m, 6H); ESI MS m/z 273 [M+H]$^+$.

Step 5: To a stirred solution of acid 13 (103 mg, 0.38 mmol), amine 4 (154 mg, 0.38 mmol), HOBt (77 mg, 0.57 mmol), and DIPEA (0.2 mL, 1.1 mmol) in methylene chloride (4 mL) was added HATU (216 mg, 0.57 mmol). The reaction mixture was stirred overnight and then partitioned between methylene chloride and 1 N hydrochloric acid. The organic layer was washed with saturated sodium bicarbonate, saturated sodium chloride, dried (sodium sulfate), filtered, and concentrated under reduced pressure. Purification by flash column chromatography (silica, 9:1 methylene chloride/methanol) gave a ALB 8655 (70 mg, 31): mp: 142-151° C.; IR (ATR): 3222, 1621, 1585, 1114, 848, 700 cm$^{-1}$; $^1$H NMR (500 MHz, DMSO-d$_6$) δ 9.46 (s, 1H), 9.09 (s, 2H), 8.57 (s, 1H), 8.35 (s, 1H), 8.09 (s, 1H), 7.29 (s, 1H), 7.46 (d, J=6 Hz, 1H), 7.40 (s, 1H), 7.35 (d, J=7 Hz, 1H), 7.27 (t, J=7 Hz, 1H), 7.19 (d, J=7 Hz, 1H), 7.04-6.97 (m, 3H), 4.24-4.08 (m, 4H), 3.73 (br s, 4H), 3.54 (br s, 8H), 3.18 (d, J=8 Hz, 1H), 3.10 (br s, 1H), 3.00 (m, 1H), 2.87 (d, J=8 Hz, 1H), 2.56-2.50 (m, 2H), 1.75 (d, J=6 Hz, 4H), 1.12 (t, J=7 Hz, 3H), 0.88 (t, J=7 Hz, 6H); APCI MS m/z 589 [M+H]$^+$; HPLC: Method A, 7.21 min (99%, AUC). Anal. Calcd for C$_{35}$H$_{42}$F$_2$N$_4$O$_2$.2HCl.0.5H$_2$O: C, 62.68; H, 6.76; N, 8.35. Found: C, 62.60; H, 6.89; N, 8.29.

Example SP-134

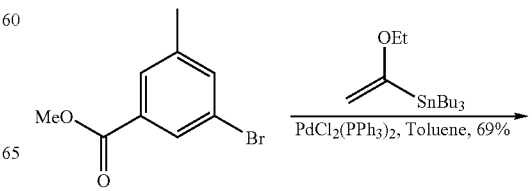

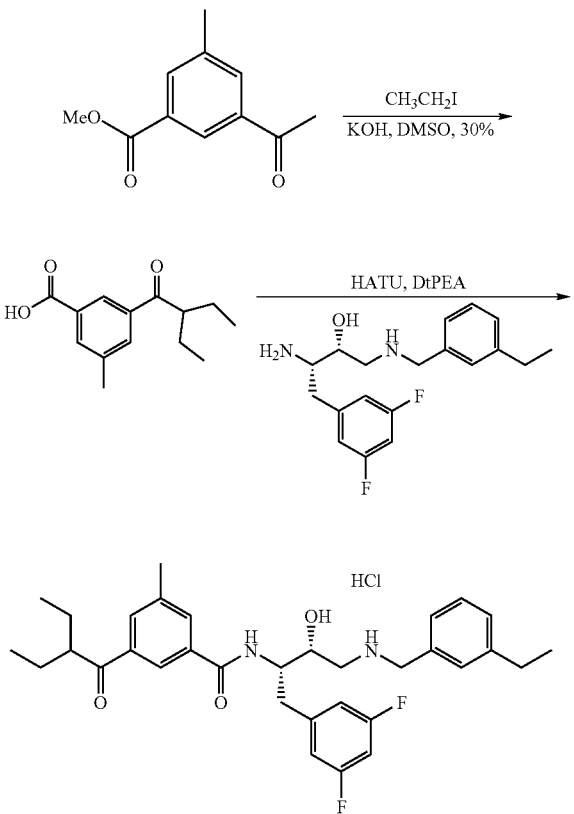

Ketones used in this Example can be generally prepared as shown in chart U.

Step 1

To a stirred solution of the halide (4.68 g, 20 mmol) in anhydrous toluene (10 mL) was added (α-ethyoxyvinyl)-tributyltin (7.66 ml, 22 mmol) and dichlorobis(triphenylphosphine)palladium (0.715 g, 1 mmol). The reaction was heated under nitrogen at 100° C. for 14 hours. After hydrolysis of the reaction mixture with 1N HCl (100 ml), the organic layer was extracted with diethyl ether (100 mL×2), washed with aqueous potassium fluoride (10%, 100 mL), dried with magnesium sulfate, and concentrated under vacuo. The crude product was purified by flash column chromatography (10-20% ethyl acetate: hexane) to afford 2.5 g of 3-Acetyl-5-methyl-benzoic acid methyl ester as a white solid (65% yield). IR (drift) 3090, 3078, 3019, 2998, 2952, 2920, 1716, 1681, 1608, 1596, 1448, 1435, 1273, 1237, 1234, 1197, 1118, 893 cm$^{-1}$; $^1$H NMR (CDCl$_3$) δ 8.44 (s, 1H), 8.10 (s, 1H), 8.01 (s, 1H), 3.99 (s, 3H), 2.68 (s, 3H), 2.51 (s, 3H); HRMS (FAB) calcd for C$_{11}$H$_{12}$O$_3$+H$^+$=193.0865, found 193.0868.

Step 2

To a stirred suspension of potassium hydroxide (pellets) (5.0 g, 90.0 mmol) in dimethylsulfoxide (10 mL) was added 3-Acetyl-5-methyl-benzoic acid methyl ester (0.8 g, 4.5 mmol) and 1-iodopropane (2.9 mL, 36 mmol) at room temperature. The reaction mixture was heated to 50-60° C. and stirred for additional 1 hour. After cooled to room temperature, the reaction was poured into 1N aqueous HCl solution (100 mL). The aqueous solution was extracted with diethyl ether (80 mL×2). The combined organic layer was washed with brine (80 mL×2), dried with magnesium sulfate, and concentrated under vacuo. The crude product was purified by flash column chromatography (30-40% ethyl acetate: hexane) to afford 0.316 g of the benzoic acid as a pale yellow solid (30% yield).

Step 3

To a stirred solution of acid the benzoic acid (138.2 mg, 0.59 mmol) in DMF (3 mL) was added HATU (281 mg, 0.74 mmol), diisopropylethylamine (0.31 mL, 1.77 mmol), and then the amine (240 mg, 0.59 mmol) at room temperature. After stirred for 1 hour at room temperature, the reaction mixture was poured into 40 mL water. The aqueous solution was extracted with chloroform (50 mL×2), and then organic layers were collected, washed with water (40 mL×2), 1N HCl (40 mL×2), sat. aq. sodium bicarbonate (40 mL×2) and brine (40 mL×2), dried over sodium sulfate, and concentrated under vacuo. The crude product was purified by flash column chromatography (10% methanol:dichloromethane) to afford 198 mg of the desired product as a pale yellow solid (61% yield).

Example SP-135

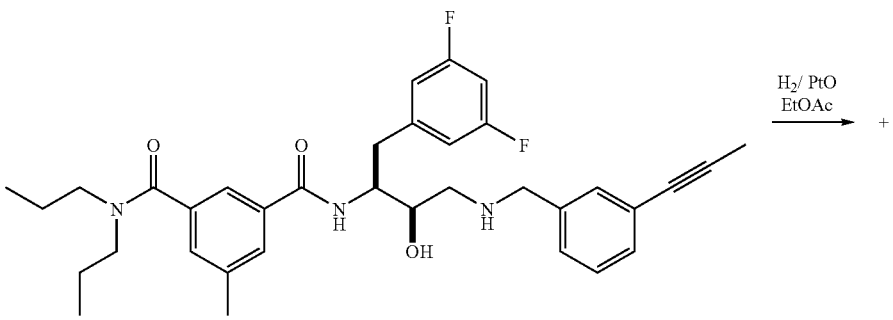

14b

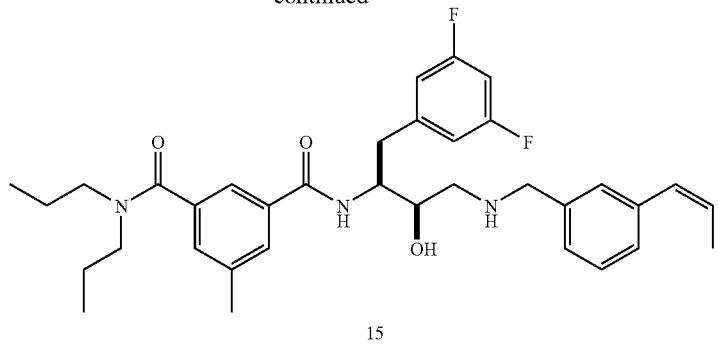

15

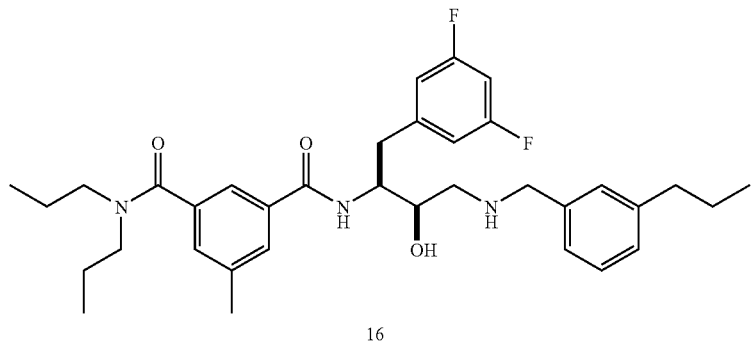

16

Compound 14b (1 equiv, 0.064 mmol, 37.6 mg) was dissolved in EtOAc before the addition of PtO (catalytic) and an H$_2$ balloon. The reaction was stirred for 4 hours at ambient temperature before LC-MS determined the two products: 15 and 16. The crude mixture was filtered through celite and the solvent was removed in vacuo before isolation by HPLC of each of the products: 15 (13 mg, 34%, M+H$^+$=592.3) and 16 (16 mg, 42%, M+H$^+$=594.3).

Example SP-136

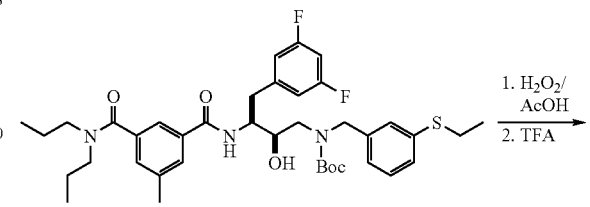

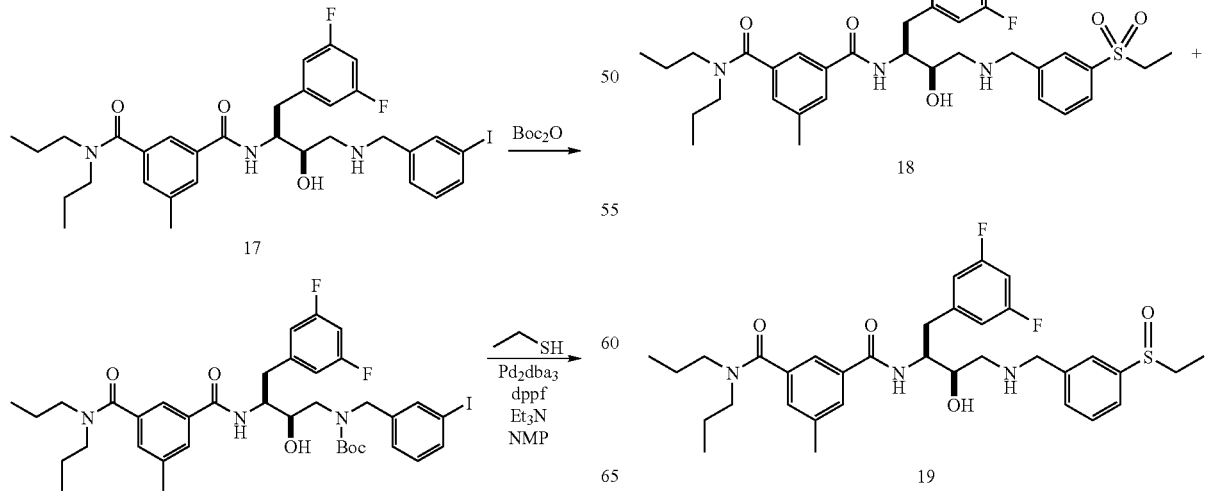

Compound 17 (1 equiv, 0.46 mmol, 0.31 g) was dissolved in CH$_2$Cl$_2$ and cooled to 0° C. before the addition of Boc$_2$O (1 equiv, 0.46 mmol, 0.1 g) and catalytic DMAP. After the reaction was judged to be done by TLC (4 h), the solvent was simply removed in vacuo and the product was used crude in the next step.

The iodo compound (1 equiv, 0.13 mmol, 100 mg), Pd$_2$dba$_3$ (0.02 equiv, 0.002 mmol, 2.4 mg), dppf (0.08 equiv, 0.01 mmol, 5.8 mg), Et$_3$N (2 equiv, 0.26 mmol, 0.04 mL), and NMP (0.3 M, 0.4 mL) were added to a sealed tube and flushed/bubbled with N$_2$ (g) for 15 minutes. Ethanethiol was then added and the tube was sealed and stirred for 3 h at 60° C. At this point the reaction was cooled to ambient temperature, diluted with brine, and extracted 3× with EtOAc. The combined organic extracts were then washed with brine (2×), dried over Na$_2$SO$_4$, filtered, and rotovapped to give the crude brown desired thioether. Column chromatography through SiO$_2$ with 25% EtOAc in hexanes gave the purified product (71.5 mg, 0.1 mmol, 77%).

The thioether (1 equiv, 0.08 mmol, 56.3 mg) was dissolved in AcOH (0.4 mL) and treated with 30% H2O2 (0.2 mL). The reaction was stirred 2 h. At this point, the crude mixture was partitioned between EtOAc and H$_2$O, and the products were extracted 3× with EtOAc. The organic extracts were dried over Na$_2$SO$_4$, filtered, and rotovapped before column chromatography purification through SiO$_2$ with 50% EtOAc in hexanes gave the separated Boc protected sulfone and sulfoxide. After TFA deprotection and HPLC purification, the final products 18 (17 mg, 33%, M+H$^+$=644.2) and 19 (18 mg, 35%, M+H$^+$=628.3) were achieved.

Example SP-137

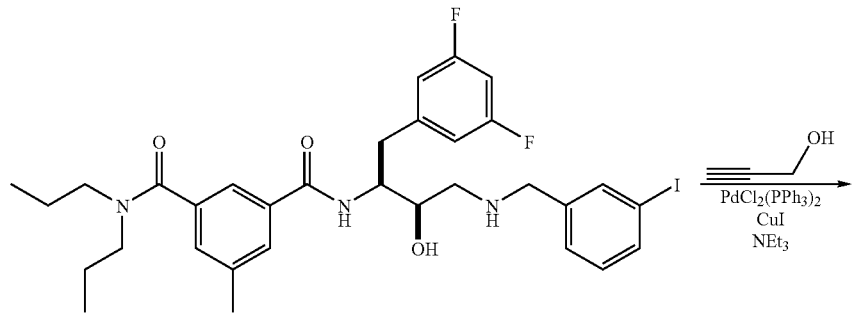

Example SP-138

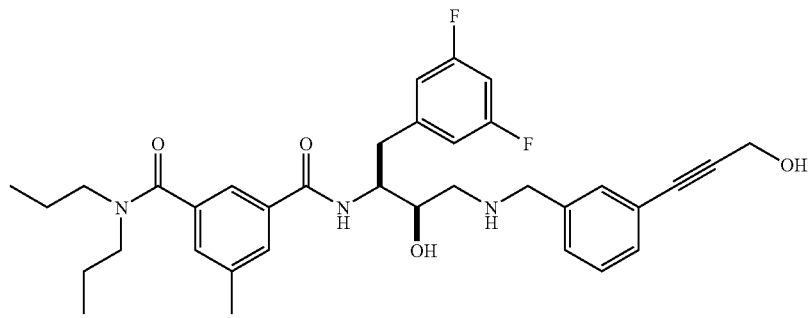

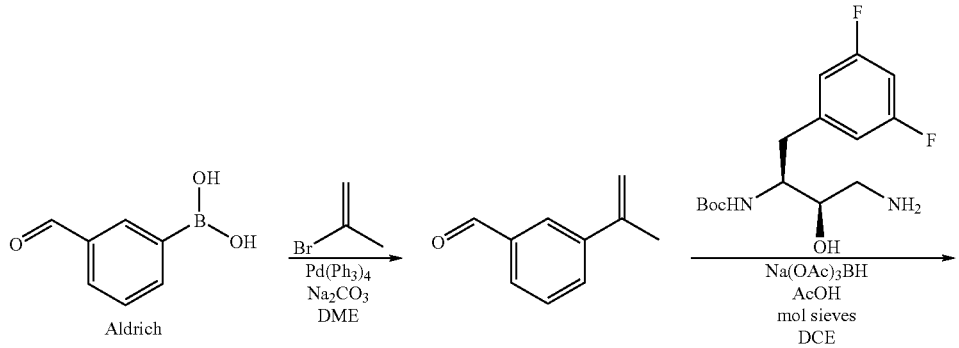

-continued
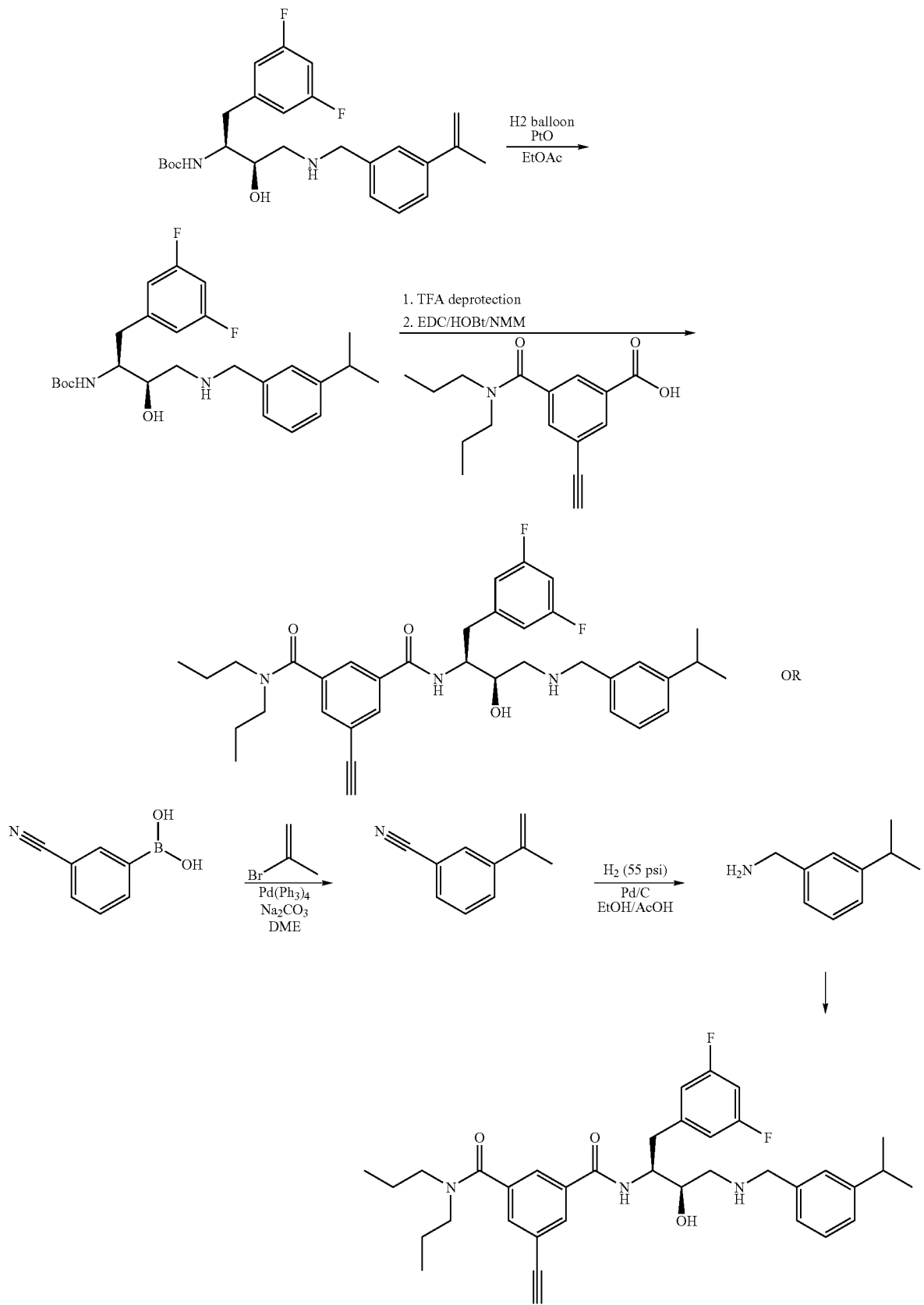

Example SP-139

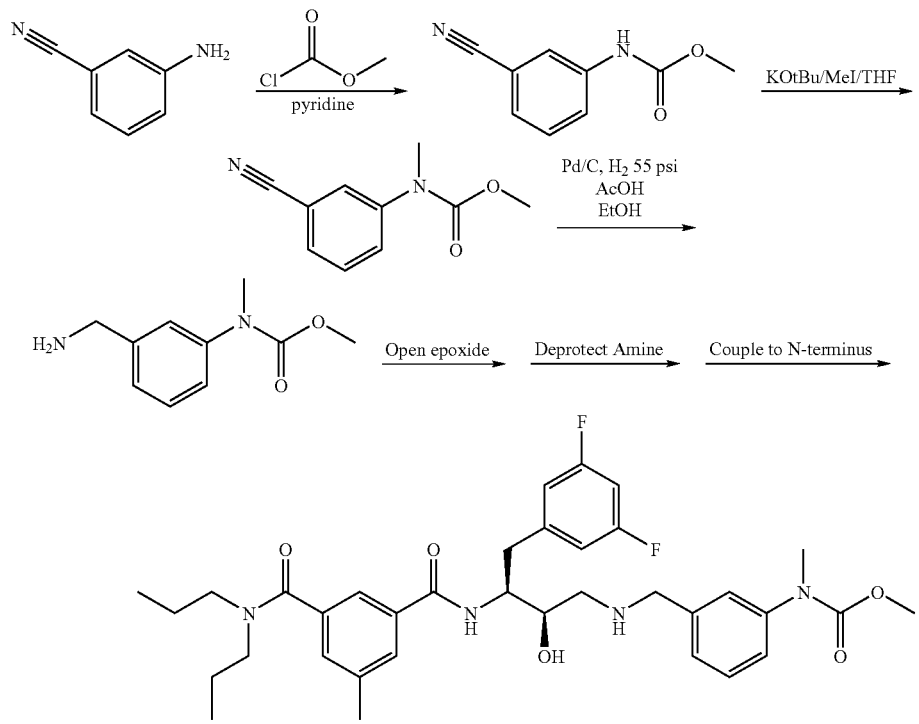

The aniline (1 equiv, 8.46 mmol, 1 g) was dissolved in pyridine (1 M, 8.5 mL) and cooled to 0° C. before the addition of methyl chloroformate (1.2 equiv, 10.2 mmol, 0.96 g, 0.78 mL). The reaction was allowed to warm to room temperature overnight with stirring. The reaction mixture was then rotovapped, and H$_2$O was added to the residual oil, at which point a white solid precipitated. The white precipitate was filtered and washed with H$_2$O, and then dried on the vacuum pump overnight to give the clean crude carbamate (1.4 g, 93%)

The carbamate (1 equiv, 3.98 mmol, 0.70 g) was dissolved in THF (8 mL) and cooled to 0° C. before the addition of a 1M THF solution of KOtBu (1.1 equiv, 4.37 mmol, 4.37 mL). Upon addition of KOtBu, the starting material crashed out of solution, and so more THF was added (5 mL) along with dioxane (2 mL). At this point, despite the continued lack of solubility, MeI (1.1 equiv, 4.37 mmol, 0.62 g, 0.27 mL) was added and the reaction was allowed to warm to room temperature overnight with stirring. After 12 hours, the reaction was still not in solution, and TLC showed incomplete consumption of starting material. Thus, DMF (5 mL) was added and the reaction finally went into solution. After stirring for 5 additional hours at ambient temperature, the reaction was complete. The crude reaction mixture was filtered through celite, rotovapped, partitioned between H$_2$O and EtOAc, extracted 3× with EtOAc, and washed with brine. The organic extracts were dried over Na$_2$SO$_4$, filtered, and rotovapped. Purification through a short plug of SiO$_2$ with 30% EtOAc in hexanes gave the desired methylated carbamate which still contained a colored impurity which was undetected by TLC and NMR. (0.76 g, Quantitative)

The nitrile (1 equiv, 3.98 mmol, 0.76 g) was dissolved in ethanol, and N$_2$ (g) was bubbled through the solution for 5 minutes before the addition of AcOH (1 equiv, 3.98 mmol, 2.27 mL) and 5% DeGussa Pd/C (1 scoop). N$_2$ (g) was bubbled again for 5 minutes before shaking on Parr Shaker at 55 psi H$_2$ overnight. The reaction was filtered through celite and rotovapped to give the acetic acid salt of the desired product. The product was then partitioned between 10% NaOH (aq) and 20% isopropanol/chloroform, and extracted 3× with 20% isopropanol/chloroform to give the desired freebase.

The crude free-base was used to open the epoxide. The M+H$^+$ mass of the final product is 639.3.

Example SP-140

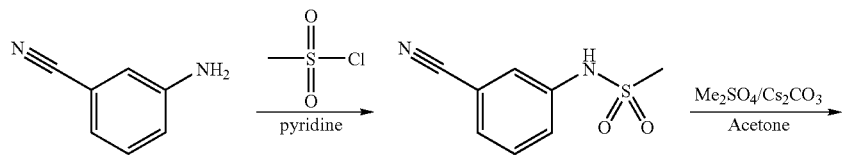

-continued

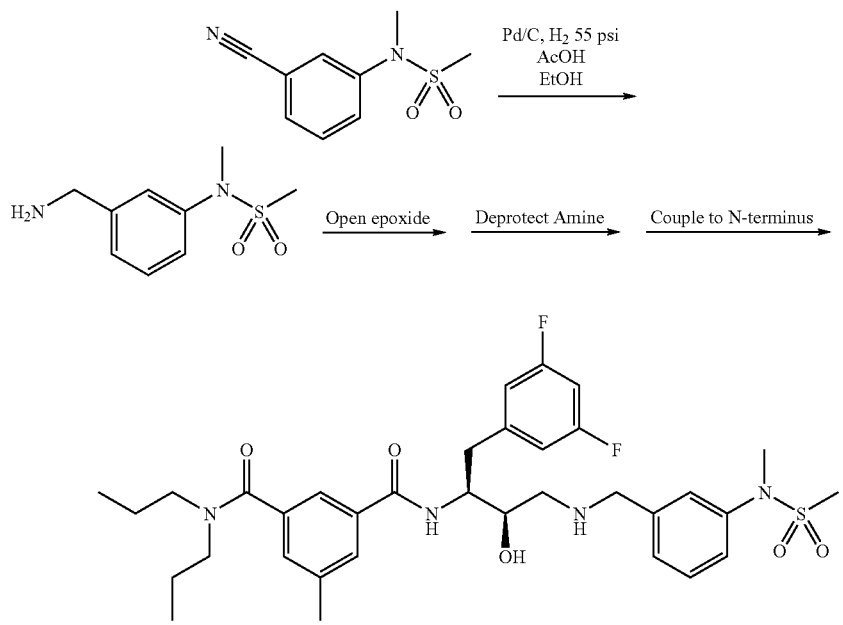

The aniline (1 equiv, 16.9 mmol, 2 g) was dissolved in pyridine and cooled to 0° C. before the addition of the sulfonyl chloride (1.5 equiv, 25.4 mmol, 2.91 g, 1.97 mL). Upon addition of the sulfonyl chloride, the reaction turned bright orange. The reaction was allowed to warm to room temperature overnight with stirring. After 12 hours, the reaction mixture was rotovapped, partitioned between $CH_2Cl_2$ and $NaHCO_3$ (aq), and extracted 3× with $CH_2Cl_2$. The combined organic extracts were washed with $KHSO_4$ (aq) and brine, dried over $Na_2SO_4$, filtered, and rotovapped to give the clean crude sulfonamide. (3.34 g, Quantitative)

The crude sulfonamide was dissolved in acetone before the addition of ground $Cs_2CO_3$, followed by $Me_2SO_4$. The $Cs_2CO_3$ did not dissolve completely. The reaction was stirred overnight at ambient temperature. After 12 h, the brownish reaction mixture was rotovapped in a fume hood, partitioned between EtOAc and $H_2O$, and extracted 3× with EtOAc. The combined organic extracts were then washed with $NaHCO_3$ (aq) and $KHSO_4$ (aq), dried over $Na_2SO_4$, filtered and rotovapped to give the crude methylated sulfonamide. By TLC the $R_f$ values of the starting sulfonamide and the final product were identical, however the spots were different colors. Quick purification through a plug of $SiO_2$ with 30%-40% EtOAc in hexanes gave the desired product. (1.88 g, 93%)

The nitrile (1 equiv, 8.94 mmol, 1.88 g) was dissolved in methanol, and $N_2$ (g) was bubbled through the solution for 5 minutes before the addition of AcOH (1 equiv, 8.94 mmol, 0.51 mL) and 5% DeGussa Pd/C (one scoop). $N_2$ (g) was bubbled again for 5 minutes before shaking on Parr Shaker at 55 psi $H_2$ for 2 hours. The reaction was filtered through celite and rotovapped to give the acetic acid salt of the desired product. The product was then partitioned between 10% NaOH (aq) and 20% isopropanol/chloroform, and extracted 3× with 20% isopropanol/chloroform to give the desired free-base.

The crude free-base was used to open the epoxide. The M+H⁺ mass of the final product is 659.3.

Example SP-141

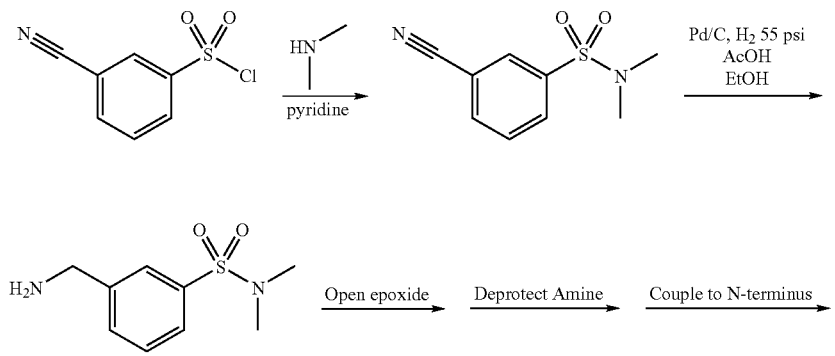

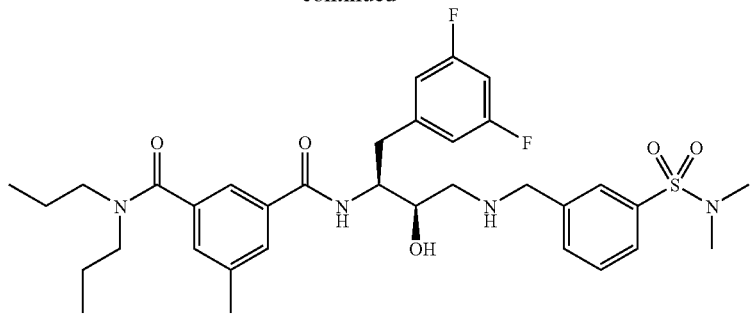

A 2M solution of dimethylamine in THF (1.2 equiv, 11.88 mmol, 5.94 mL) was dissolved in pyridine and cooled to 0° C. before the addition of the sulfonyl chloride (1 equiv, 9.9 mmol, 2 g). The reaction was allowed to warm to room temperature overnight with stirring. After 12 hours, the reaction mixture was rotovapped, partitioned between $CH_2Cl_2$ and $NaHCO_3$ (aq), and extracted 3× with $CH_2Cl_2$. The combined organic extracts were washed with $KHSO_4$ (aq) and brine, dried over $Na_2SO_4$, filtered, and rotovapped to give the clean crude sulfonamide. (2.04 g, 98%)

The nitrile (1 equiv, 9.7 mmol, 2.04 g) was dissolved in a mixture of ethanol, methanol, and THF until it finally went into solution. $N_2$ (g) was bubbled through the solution for 5 minutes before the addition of AcOH (1 equiv, 9.7 mmol, 0.56 mL) and 5% DeGussa Pd/C (one scoop). $N_2$ (g) was bubbled again for 5 minutes before shaking on Parr Shaker at 55 psi $H_2$ overnight. The reaction was filtered through celite and rotovapped to give the acetic acid salt of the desired product. The product was then partitioned between 10% NaOH (aq) and 20% isopropanol/chloroform, and extracted 3× with 20% isopropanol/chloroform to give the desired free-base.

The crude free-base was used to open the epoxide. The M+H⁺ mass of the final product is 659.3.

The aniline (1 equiv, 8.46 mmol, 1 g) was dissolved in pyridine (1 M, 8.5 mL) and cooled to 0° C. before the addition of methyl chloroformate (1.2 equiv, 10.2 mmol, 0.96 g, 0.78 mL). The reaction was allowed to warm to room temperature overnight. The reaction mixture was then rotovapped, and $H_2O$ was added to the residual oil, at which point a white solid precipitated. The white precipitate was filtered and washed with $H_2O$, and then dried on the vacuum pump overnight to give the clean crude carbamate (1.4 g, 93%)

The nitrile (1 equiv, 3.43 mmol, 0.604 g) was dissolved in ethanol, and $N_2$ (g) was bubbled through the solution for 5 minutes before the addition of AcOH (1 equiv, 3.43 mmol, 0.2 mL) and 5% DeGussa Pd/C (one scoop). $N_2$ (g) was bubbled again for 5 minutes before shaking on Parr Shaker at 55 psi $H_2$ overnight. The reaction was filtered through celite and rotovapped to give the acetic acid salt of the desired product. The product was then partitioned between $H_2O$ with $NH_4OH$ and 2.0% isopropanol/chloroform, and extracted 3× with 20% isopropanol/chloroform to give the desired free-base.

The crude free-base was used to open the epoxide. The M+H⁺ mass of the final product is 625.2.

Example SP-142

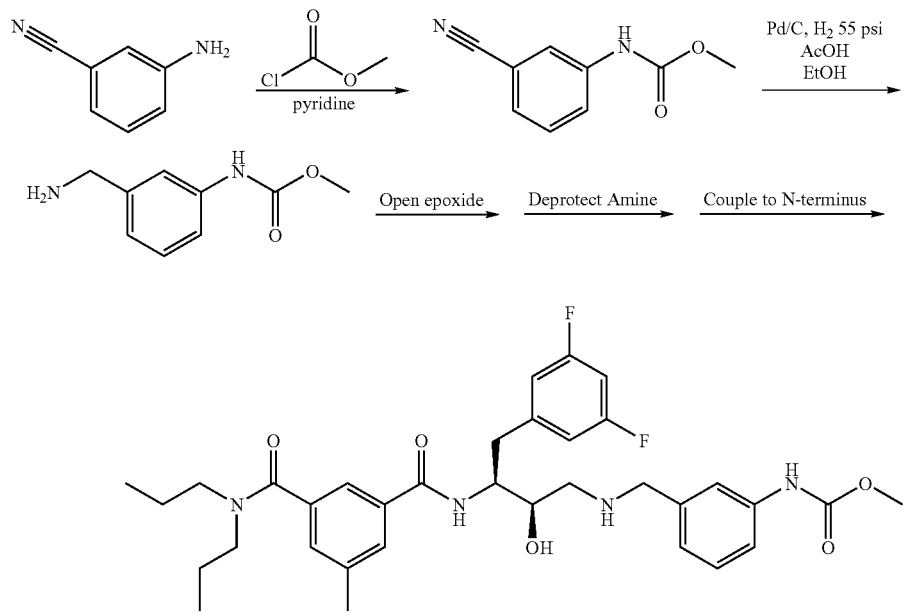

Example SP-143

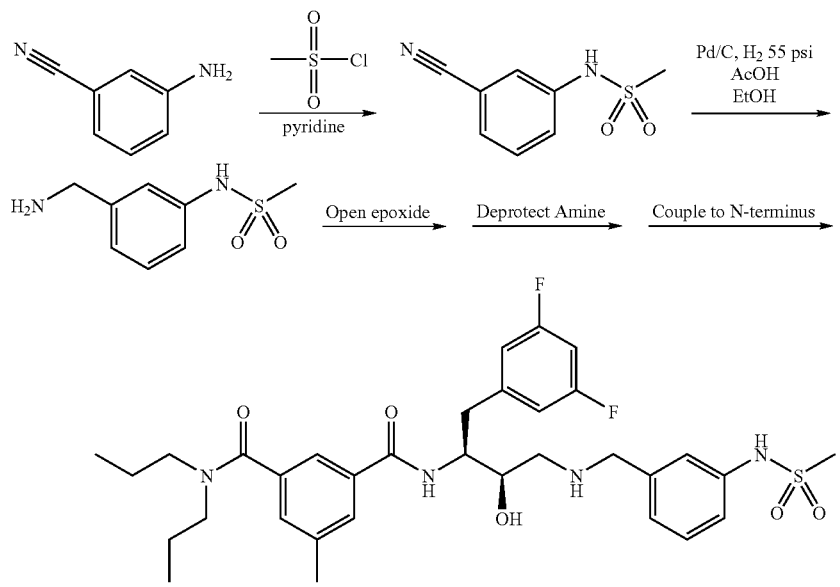

The aniline (1 equiv, 16.9 mmol, 2 g) was dissolved in pyridine and cooled to 0° C. before the addition of the sulfonyl chloride (1.5 equiv, 25.4 mmol, 2.91 g, 1.97 mL). Upon addition of the sulfonyl chloride, the reaction turned bright orange. The reaction was allowed to warm to room temperature overnight with stirring. After 12 hours, the reaction mixture was rotovapped, partitioned between $CH_2Cl_2$ and $NaHCO_3$ (aq), and extracted 3× with $CH_2Cl_2$. The combined organic extracts were washed with $KHSO_4$ (aq) and brine, dried over $Na_2SO_4$, filtered, and rotovapped to give the clean crude sulfonamide. (3.34 g, Quantitative)

The nitrile (1 equiv, 7.40 mmol, 1.45 g) was dissolved in methanol, and $N_2$ (g) was bubbled through the solution for 5 minutes before the addition of AcOH (1 equiv, 7.40, 0.42 mL) and 5% DeGussa Pd/C (one scoop). $N_2$ (g) was bubbled again for 5 minutes before shaking on Parr Shaker at 55 psi $H_2$ for 2 hours. The reaction was filtered through celite and rotovapped to give the acetic acid salt of the desired product. The product was then partitioned between $H_2O$ with $NH_4OH$ and 20% isopropanol/chloroform, and extracted 3× with 20% isopropanol/chloroform to give the desired free-base.

The crude free-base was used to open the epoxide. The M+H+ mass of the final product is 645.2

Example SP-144

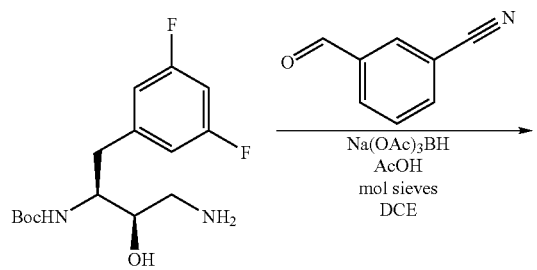

-continued

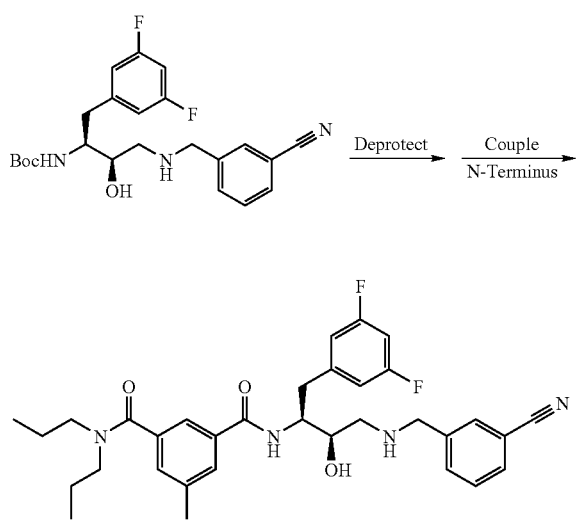

The aldehyde (1 equiv, 2.29 mmol, 0.3 g) and the amine (1.05 equiv., 2.40 mmol, 0.76 g) were dissolved in 1,2 dichloroethane (40 mL) and treated with molecular sieves (a small scoop) and a few drops of AcOH. The reaction was stirred for 1 h before adding $Na(OAc)_3BH$ (1.3 equiv, 2.98 mmol, 0.63 g). The reaction was stirred overnight at ambient temperature. After 12 h, the reaction mixture was filtered, and rotovapped. The residue was partitioned between EtOAc and $H_2O$, and the product was extracted 3× with EtOAc. The combined organic extracts were dried over $Na_2SO_4$, filtered, and rotovapped to give the clean crude desired amine. (Quantitative)

The crude material was deprotected with TFA and coupled to the N-terminus as usual. The M+H+ mass of the final product is 577.2.

Example SP-145

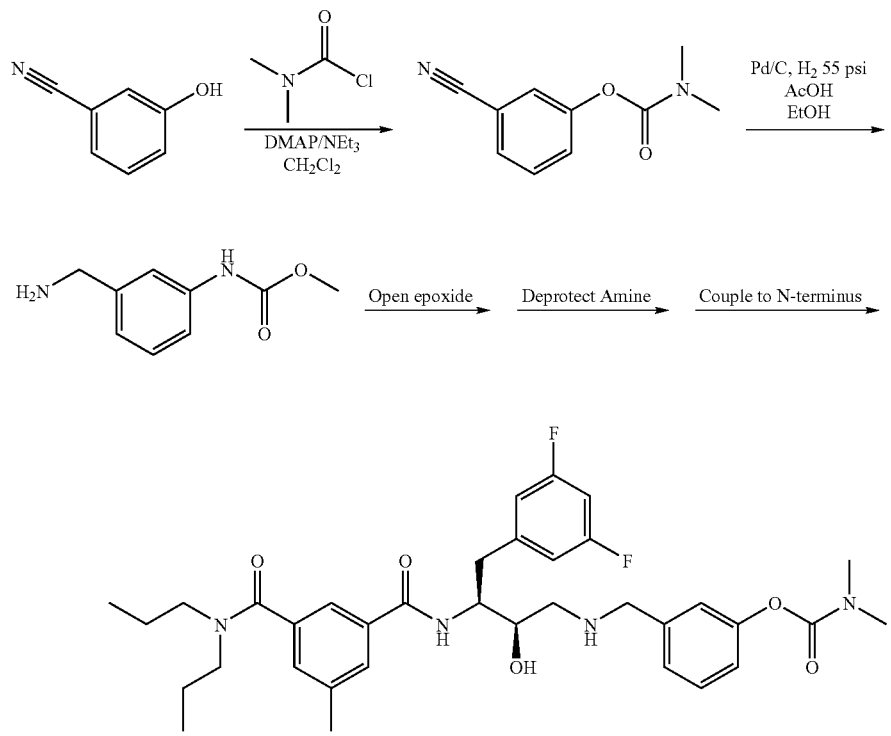

The phenol (1 equiv, 16.8 mmol, 2 g) was taken up in $CH_2Cl_2$, but did not dissolve, thus THF and acetone were added in a failed attempt to solubilize the phenol. The mixture was cooled to 0° C. before the addition of $NEt_3$ (1 equiv, 16.8 mmol, 1.7 g, 2.3 mL), DMAP (1 equiv, 16.8 mmol, 2.05 g), and dimethylcarbamyl chloride (1 equiv, 16.8 mmol, 1.81 g, 1.55 mL). Upon addition of $NEt_3$, the reagents dissolved. The reaction appeared to be complete after stirring for 2 hours, as judged by TLC. However, the reaction was stirred for 2 days. After 2 days, the reaction was partitioned between $CH_2Cl_2$ and $NaHCO_3$ (aq), and extracted 3× with $CH_2Cl_2$. The combined organic extracts were washed with 1 N HCl and brine, dried over $Na_2SO_4$, filtered, and rotovapped to afford the clean crude carbamate. (3.04 g, 95%)

The nitrile (1 equiv, 16.0 mmol, 3.04 g) was dissolved in ethanol, and $N_2$ (g) was bubbled through the solution for 5 minutes before the addition of 5% DeGussa Pd/C (one scoop). $N_2$ (g) was bubbled again for 5 minutes before shaking on Parr Shaker at 55 psi for 1 hour. The reaction was filtered through celite and rotovapped to give the desired free-base.

The crude free-base was used to open the epoxide. The M+H$^+$ mass of the final product is 639.3.

Example SP-146

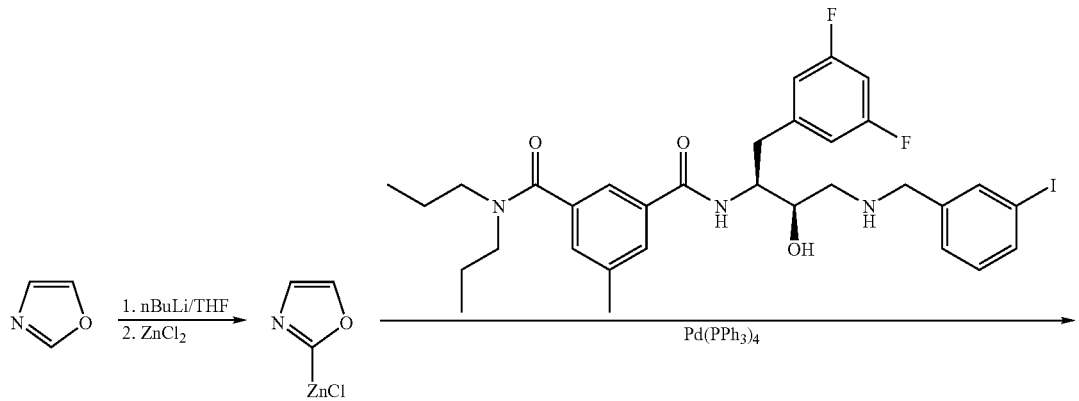

-continued

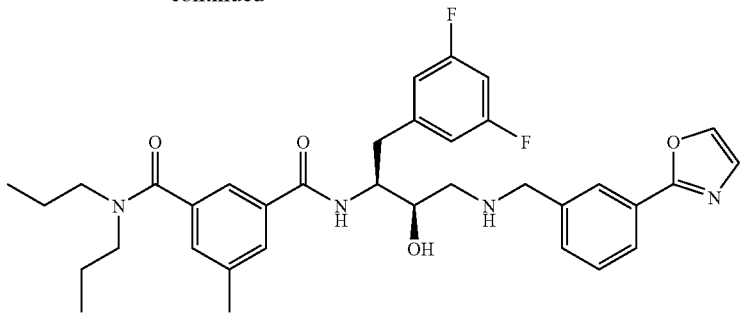

Oxazole (3.15 equiv, 1.89 mmol, 0.13 g) was weighed into an oven-dried round-bottom flask, dissolved in THF (3 mL), and cooled to −78° C. before the addition of a 1.6 M solution of nBuLi in hexanes (3.48 equiv, 2.09 mmol, 1.3 mL). After stirring for 30 minutes at −78° C., a 1.0 M solution of $ZnCl_2$ in THF (9.06 equiv, 5.4 mmol, 5.4 mL) was added dropwise. At this point the stirring stopped due to increased viscosity or stickiness within the reaction vessel. This solution was warmed to 0° C. for 1 hour before the HCl salt of AN 104574-7 (1 equiv, 0.6 mmol, 0.429 g), along with $Pd(PPh_3)_4$ were added. This mixture was heated to reflux for 1 hour. The reaction was then partitioned between EtOAc and $H_2O$, extracted 3× with EtOAc, washed with brine, dried over $Na_2SO_4$, filtered and rotovapped. Chromatography on $SiO_2$ with 2-5% $MeOH/CH_2Cl_2$ with a few drops of $NH_4OH$ yielded the clean desired product. (95%, 0.35 g, M+H$^+$ =619.2)

Example SP-147

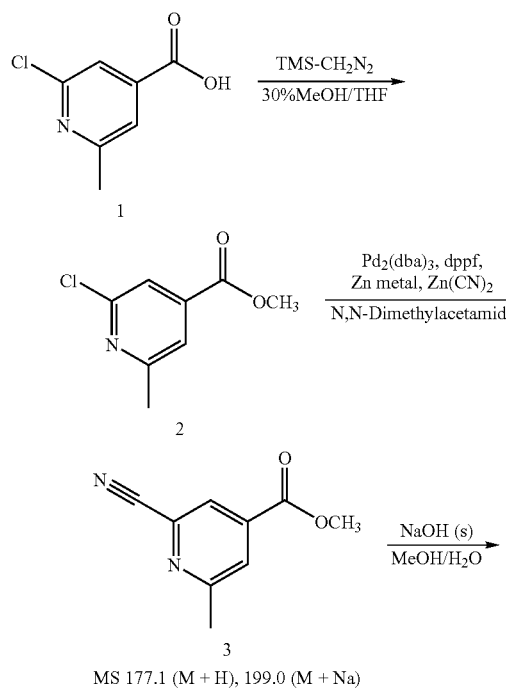

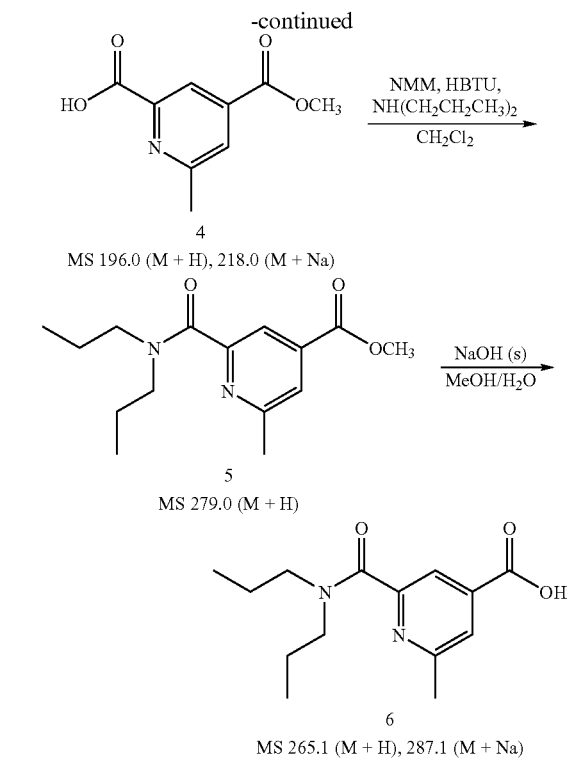

2-Dipropylcarbamoyl-6-methyl-isonicotinic acid

A solution of 23.7 mmole (1.0 eq.) of 2-chloro-6-methyl-isonicotinic acid in 32 mL of 30% MeOH/THF was prepared.

To the reaction mixture was added 30.0 mmole (1.3 eq) of (trimethylsilydiazo)methane dropwise. The reaction was complete after stirring at rt overnight. A few drops of glacial acetic acid were added to the reaction mixture prior to concentration by rotary evaporation to afford product 2, quantitatively.

To a dried 100 mL round bottom flask was added 22.0 mmole (1.0 eq.) of the methyl ester 2, 0.45 mmole (0.02 eq.) tris(dibenzlideneacetone)dipalladium (0), 0.90 (0.04 eq.) 1,1-bis(diphenylphosphine)ferrocene, 28.3 mmole (0.13 eq.) zinc metal dust and 10.7 (0.5 eq) zinc cyanide. The reaction flask was flushed with nitrogen gas for 5 min and 45 mL N,N-dimethylacetamide was added via syringe. The reaction was complete after refluxing while stirring vigorously for 4 h. The reaction mixture was diluted with EtOAc (50 mL) and washed with 2N $NH_4OH$ (3×50 mL) followed by sat. NaCl (50 mL). The combined organic extracts were dried over $Na_2SO_4$ and vacuum filtered. The filtrate was concentrated by rotary evaporation and purified via column chromatography Hex/EtOAc (8:2) to yield product 3, 34% yield.

A solution of 1.2 mmole (1.0 eq.) of the nitrile 3 in 5 mL of methanol was prepared. To the reaction mixture was added 6.7 mmole (5.7 eq) of sodium hydroxide. After 1 h of stirring at rt, 5 mL of H₂O were added to the reaction mixture. The reaction was complete after stirring for an additional 1.5 h. The mixture was diluted with CHCl₃ and washed with 2NHCl. The organic extracts were collected and dried over Na₂SO₄ and vacuum filtered. The filtrate was concentrated by rotary evaporation to afford product 4, 61% yield.

A solution of 0.7 mmole (1.0 eq.) of the carboxylic acid 4 in 6 mL of dichloromethane was prepared. To the reaction mixture was added 1.8 mmole (2.6 eq.) 4-methylmorpholine. The reaction flask was placed on ice to cool prior to addition of 0.8 mmole (1.1 eq.) HBTU and 0.8 mmole (1.2 eq.) diproplyamine. The reaction was complete after allowing to warm to rt overnight while stirring. The reaction mixture was diluted with EtOAc (25 mL) and washed with H₂O (2×25 mL) followed by sat. NaHCO₃ (2×25 mL). The combined organic extracts were dried over Na₂SO₄ and vacuum filtered. The filtrate was concentrated by rotary evaporation to afford product 5, 64% yield.

A solution of 0.5 (1.0 eq.) of the isophalate 5 in 2 mL of methanol was prepared. To the reaction mixture was added 4.5 mmole (9.3 eq) of sodium hydroxide. After 2 h of stirring at rt, 2 mL of H₂O were added to the reaction mixture. The reaction was complete after stirring for an additional 1.5 h. The mixture was diluted with EtOAc and washed with H₂O (2×) followed by sat. NaHCO₃ (2×). The aqueous extracts were collected and acidified with conc. HCl. A solution of CHCl₃/iPA (1:3) was utilized for extraction. The organic extracts were collected washed with sat. NaCl, dried over Na₂SO₄ and vacuum filtered. The filtrate was concentrated by rotary evaporation to afford product 6.

Example SP-148

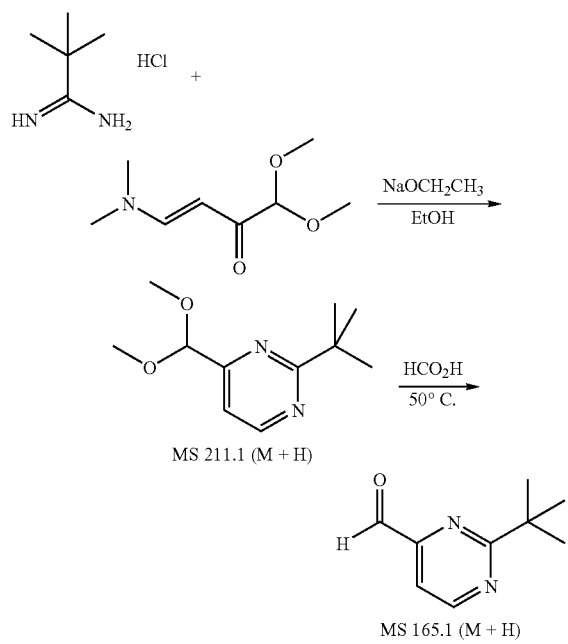

Bredereck, H., Sell, R. and Effenberger, F.; *Chem. Ber.;* 1964, 97, 3407.

Example SP-149

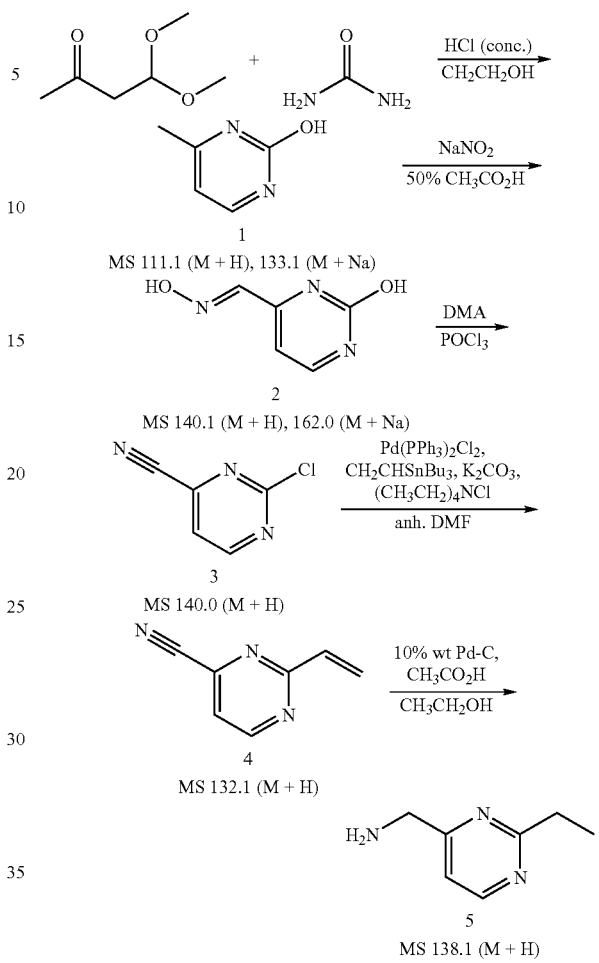

(2-Ethyl-pyrimidin-4-yl)-methylamine

Experimental procedures were utilized in order to yield products 1 through 3 as described in the following references. Burness, D. M.; *J. Org. Chem.,* 1956, 21, 97.

Daves, G. D., O'Brien, D. E., Lewis, L. and Cheng, C. C.; *J. Heterocycl. Chem.,* 1963, 1, 130.

Into a oven-dried 50 mL round bottom flask was added 3.6 mmole (1.0 eq.) of the halopyrimidine 3, 5.4 mmole (1.5 eq.) tributyl(vinyl)tin, 0.09 mmole (0.03 eq.) bis(triphenylphosphine)palladium (II) chloride, 4.1 mmole (1.1 eq.) tetraethylammonium chloride, 3.8 mmole (0.9 eq.) potassium carbonate and 7.5 mL of dry DMF. The reaction was complete after refluxing under condenser with nitrogen inlet for 2 hrs. The reaction mixture was diluted with EtOAc (30 mL) and washed with H₂O (2×30 mL) followed by sat. NaCl (30 mL). The combined organic extracts were dried over Na₂SO₄ and vacuum filtered. The filtrate was concentrated by rotary evaporation, purified via column chromatography Hex/EtOAc (9:1) to yield product 4, 42% yield.

In a small vial, a solution of 1.53 mmole (1.0 eq.) of the styrene 4 was prepared by dissolving in a minimal amount of EtOH. To the reaction mixture was added 0.1 mL of glacial acetic acid followed by a catalytic amount of 10% wt palladium on carbon. The reaction was complete after placement on the hydrogentator for 30 min. at 50 psi. The reaction mixture was vacuum filtered through Celite and rinsed with EtOAc. The filtrate was concentrated by rotary evaporation to afford product 5.

Example SP-150

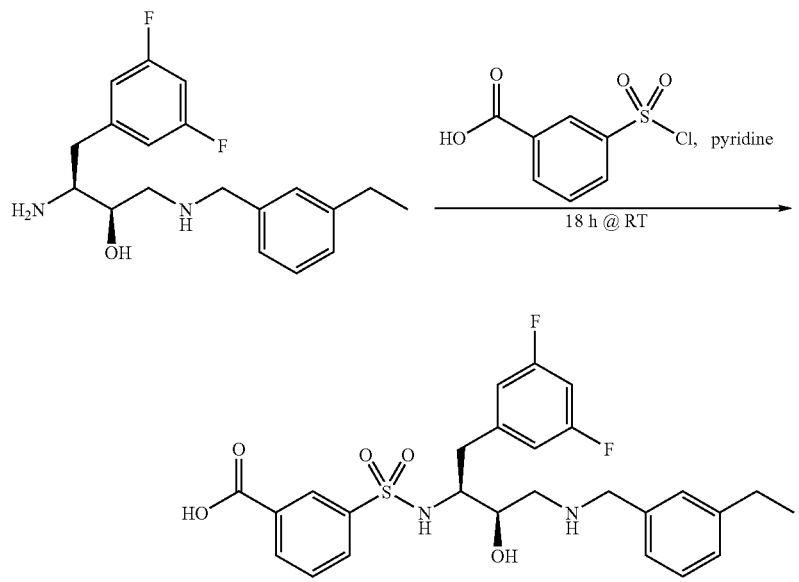

The starting diamine (~18 mgs, ~0.05 mmol) and 1 equiv. of sulfonyl chloride were dissolved in 1 ml of pyridine at −5.0° C. in a 1-dram vial. This mixture was allowed to react for 18 hours. After reaction time, the pyridine was dissolved and the product mixture was prepared for LC-MS analysis using a Hewlett-Packard 1050 Series HPLC coupled to a Thermo-Finnigan LCQ Deca MS. From the LC-MS results, the final product was purified using the Varian Pro Star Preparative HPLC.

Example SP-151

Synthesis of N-terminal Dipropylamine Replacement

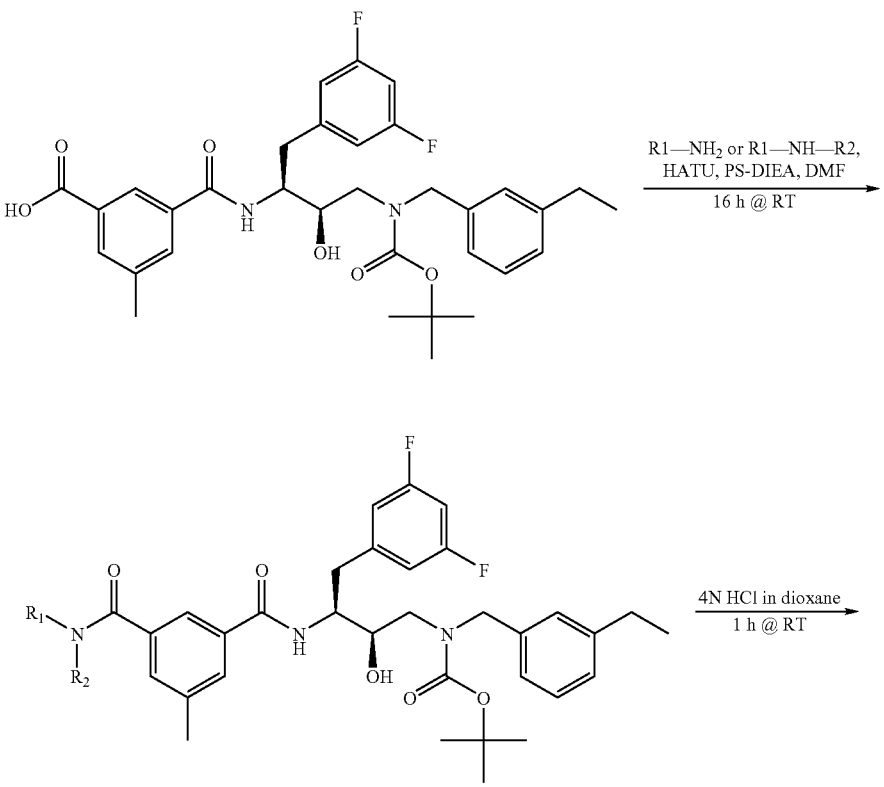

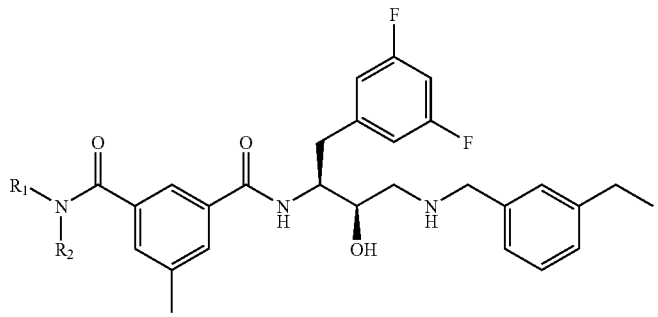

Example SP-152

Synthesis of N-terminal Glutarates

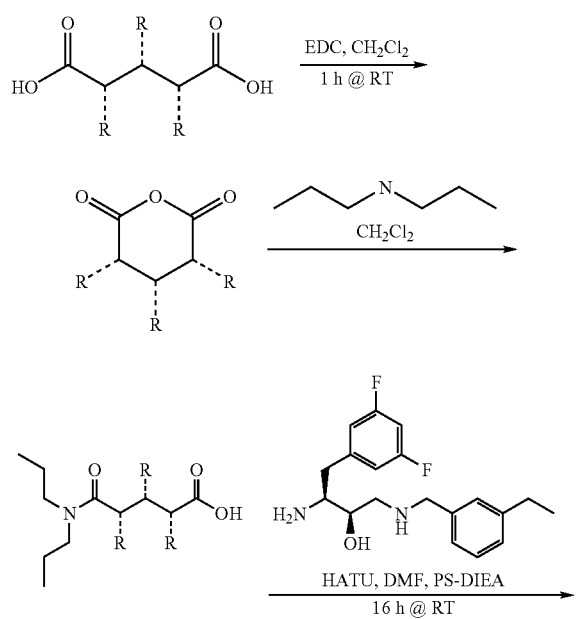

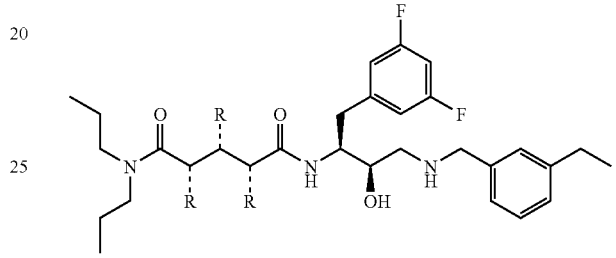

From the 11 compounds that were made in this library, 2 were made with the starting dicarboxylic acid and the other 9 were already in the glutaric anhydride form. To prevent the dicarboxylic acids from forming diamides, 0.1 mmol of each acid was reacted with 1 equiv. of EDC in 1 ml of dichloromethane for 1 hour at room temperature. With all of the starting materials in the glutaric anhydride form, 0.1 mmol of each glutaric anhydride was mixed with 0.1 mmol of dipropylamine in 1.5 ml of dichloromethane for 2 hours at room temperature. The resulting acids were then reacted with 1 equiv. of the HEA piece using 1.1 equiv. of HATU as the coupling agent. 3 equiv. of polystyrene-bound diisopropylethylamine was used as the base. These reactions were run in 1.5 ml of DMF for 4 hours at room temperature. The products were then purified via the Varian Pro Star Preparative HPLC.

Example SP-153

Representative Procedure of CHART Y (R=I)

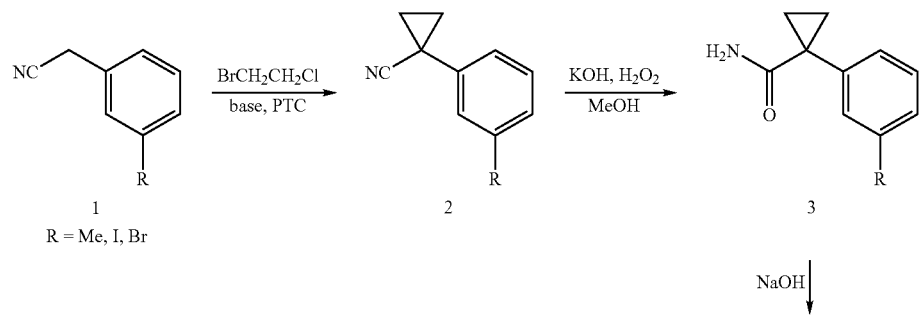

R = Me, I, Br

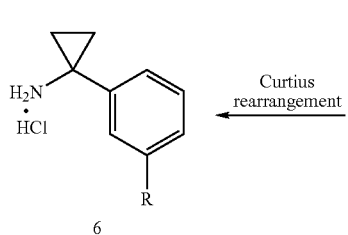
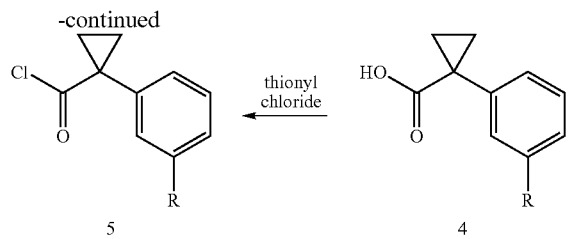

Preparation of 1-arylcyclopropanecarbonitriles (2)(R=I) Org. Prep. Proc. Inter. 1995, 27(3), 355-59

To a vigorously stirred mixture of the iodobenzyl cyanide 1 (3 g, 12.35 mM), benzyltriethylammonium chloride (TEBAC, 100 mg) and 1-bromo-2-chloroethane (BCE, 15 mL), 50% aq. NaOH solution (20 mL) was added dropwise over 35 min. (temp. 50° C.). After addition, the reaction was stirred at 50° C. for additional 2 hrs, then at RT for 2 hrs. Added water to 100 mL total and extracted with dichloromethane (3×25 mL). Organic extracts were washed with water, 5% aq. HCl, and water, then dried over $Na_2SO_4$ and concentrated. Purified by Kugelrohr distillation. Yield 2—3.3 g (99%); MH+ (CI) 269.9.

Preparation of amide 3. A mixture of 2 (13.3 mM), 25% aq. KOH (0.34 mL), 30% $H_2O_2$ (17.5 mL) and MeOH (100 mL) was heated at 55° C. for 7 hrs. TLC showed no SM. The reaction mixture was concentrated and dried under vacuum. Yield 95%; MH+ (CI) 288.0.

Hydrolysis of 3. An amide 3 (14 mM) was dissolved in a small amount of MeOH (5 mL) and 10% aq. NaOH solution (80 mL) and refluxed for 6 hrs. The mixture was cooled down and acidified with 15% HCl to pH~2. The solvent was partially evaporated and white solid was collected by filtration. Yield of an acid 4—85%; MH+ (CI).288.9.

Preparation of acid chloride 5. The reaction mixture: acid 4 (8 mM) and thionyl chloride (2.0 g, 1.23 mL) in $CH_2Cl_2$ (10 mL) was heated o/n at 50° C. (reflux). The next day a solvent was stripped on rotavapor and the residue was dried under vacuo. Used immediately without purification.

Curtius rearrangement. An acid chloride 5 (6.5 mM) was dissolved in acetone (15 mL), cooled to –10° C. and treated with sodium azide (1.8 g in 5 mL of water). After stirring for 1 hr at –10° C. the reaction mixture was poured into 100 mL of cold water and the azide was extracted into toluene. The toluene layer was washed with water and dried. The toluene solution was partially concentrated (to 15 mL) and the rest was carefully warmed to 100° C. for 1 hr. Conc. HCl (8-10 mL) was added and the reaction mixture was refluxed for 15 min. with vigorous stirring. White crystals were decanted and dried under vacuo. Yield 84% of 6 (R=I); MH+ (CI) 260.2.

Example SP-154

Synthesis of 2-isobutyl-5-(1-

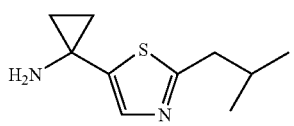

aminocycloprop-1-yl)thiazole

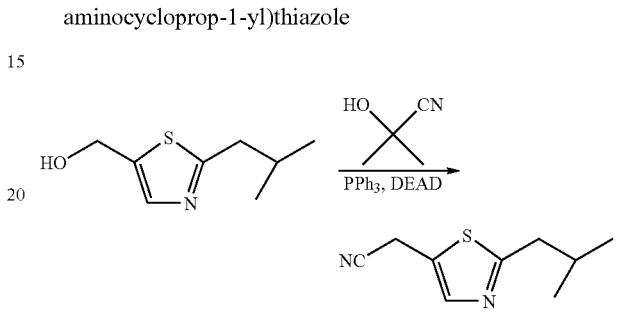

This procedure was adapted from: Wilk, B K. *Synth. Commun.* 1993, 23, 2481-4. To a solution of the thiazole methyl alcohol (753 mg, 4.4 mmol) and triphenylphosphine (1.74 g, 6.63 mmol) in dry THF (10 mL) at 0° C. was added diethyl azodicarboxylate (DEAD, 1.0 mL, 6.4 mmol) dropwise with stirring. After 10 min, acetone cyanohydrin (Aldrich, 0.6 mL, 6.6 mmol) was added dropwise with stirring. The resulting solution was stirred at 0° C. for 10 min, then at rt for 3 h, whereupon the mixture was concentrated under reduced pressure, and the residue purified by flash chromatography (EtOAc/hexanes elution; product $R_f$=0.73 in 60% EtOAc/hexanes) to give a yellow oil (516 mg, 65%) as product.

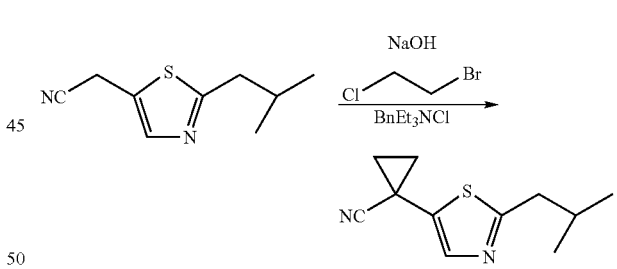

This procedure was adapted from: *Org. Prep. Proc. Int.* 1995, 27, 355-9. 50% Sodium hydroxide (aq, 5.0 mL total) was added to a solution of cyanide (516 mg, 2.9 mmol), 1-bromo-2-chloroethane (3.5 mL, 42 mmol), and benzyltriethylammonium chloride (25 mg, 0.09 mmol) at 50° C. This was maintained at 50° C. for 2 h, then at rt for 2 h. Water was added such that the total volume was 20 mL, and the mixture was extracted with $CH_2Cl_2$ (3×10 mL). The combined organic extracts were washed (water, 1 N HCl, water), dried ($Na_2SO_4$), filtered and concentrated under reduced pressure. The residue was purified by flash chromatography (20% EtOAc/hexanes elution) to give the product as an oil (403 mg, 68%); MH+ (CI) 207.1.

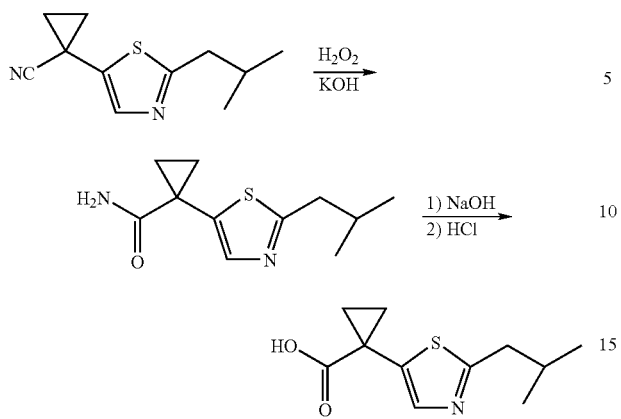

This procedure was adapted from: *Org. Prep. Proc. Int.* 1995, 27, 355-9. Cyclopropylarylcyanide (403 mg, 1.96 mmol) was dissolved in MeOH (15 mL), and 30% hydrogen peroxide (2.7 mL) and 25% KOH (aq, 0.05 mL) were added at rt. The solution was heated to 55° C. for 7 h. The reaction mixture was then concentrated in vacuo and stored in the freezer overnight. This crude product was used in the next reaction without further purification.

The crude amide was dissolved in minimal MeOH (1 mL), and 2.5 N NaOH (aq, 10 mL) was added. This suspension was heated to reflux (bath temp 105° C.) for 6 h, whereupon the mixture was cooled to 0° C., and acidified to pH 3 using 3 N HCl (aq). This was partially concentrated, then extracted with CHCl$_3$ (3×). The combined extracts were dried (Na$_2$SO$_4$), filtered and concentrated to give a solid (189 mg, 43%); MH+ (CI) 226.1.

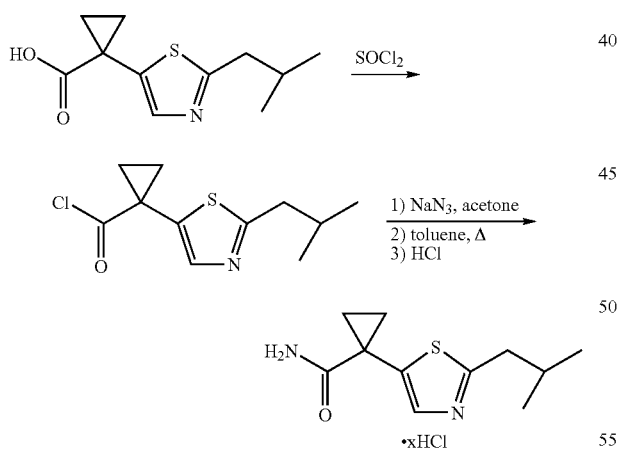

The carboxylic acid (189 mg, 0.84 mmol) was dissolved in CH2Cl2 (5 mL) and thionyl chloride (0.2 mL, 2.7 mmol) was added at rt. This was heated to reflux (bath temp 55° C.) for 3.5 h, whereupon the mixture was concentrated under reduced pressure. The crude acid chloride was dissolved in acetone (4 mL), and a solution of sodium azide (270 mg, 4.2 mmol) in water (1 mL) was added at −15° C. After 1 h at −15° C., water (20 mL) was added, and the acyl azide was extracted into toluene (3×). The combined organic extracts were dried (Na$_2$SO$_4$), filtered and partially concentrated (to ca. 30 mL). The solution was then warmed to 100° C. for 1 h. Conc. HCl (aq, 2 mL) was then added, and the mixture was heated to reflux for 15 min. The mixture was cooled to 0° C., basified with 10 N NaOH (aq), then extracted with CHCl$_3$ (3×). The combined organic layers were dried (Na$_2$SO$_4$), filtered and concentrated to give an oil (R$_f$=0.37 in 5% MeOH/CH$_2$Cl$_2$; ninhydrin visualization); MH+ (CI) 197.1.

Example SP-155

Procedure A: Synthesis of 2: 2,2-Dioxo-1,2,3,4-tetrahydro-2λ$^6$-benzo[c][1,2]thiazin-4-ylamine

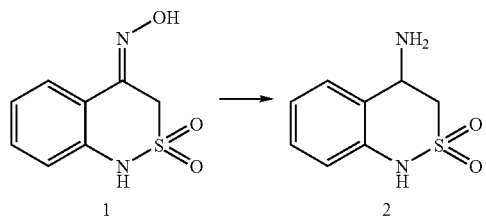

A solution of 0.58 g (2.7 mmol) of oxime 1 (prepared according to *J. Heterocyclic. Chem.* 17, 1281 (1980), the identical compound is described in this paper) in 13 ml of aqueous tetrahydrofurane (THF:H$_2$O, 10:1) was stirred under argon atmosphere. Aluminum amalgam (from 0.52 g, 19 mmol, 7 eq. of Reynolds heavy-duty aluminum foil), prepared by sequential exposure (10-20 seconds each) of small strips to 1 N KOH, distilled water, 0.5% mercuric chloride, distilled water, and dry THF, was then added to the solution of 1 over a period of 3 hours. The reaction mixture was stirred overnight, then filtered on a bed of celite and the solvent evaporated to yield 510 mg of 2 (94%) as an orange oil that slowly solidified. mass spec (CI)(MH+): 199.1

Example SP-155A

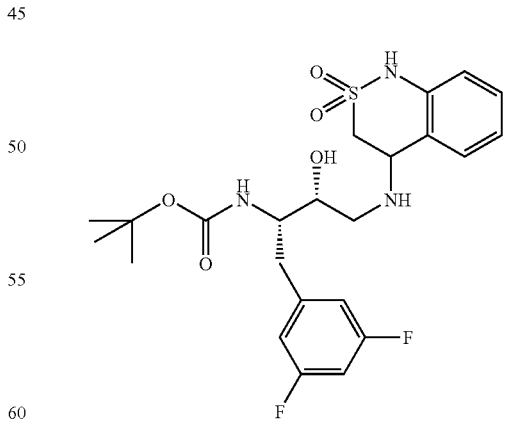

The compound of Example SP-155 can be used to open the appropriate boc protected amino epoxide to generate the compound of Example SP-155A. This compound can then be deprotected using methods well known in the art to generate the free amine, which can then be further manipulated.

Example SP-156

Procedure B: Synthesis of 4, 2,2-Dioxo-3,4-dihydro-2H-2λ⁶-benzo[e][1,2]oxathiin-4-ylamine

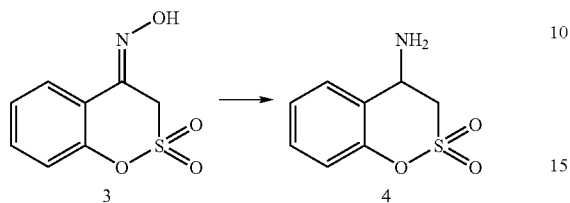

The amine 4 (mass spec (CI) (MH+): 200.0) was prepared according to the procedure A described above starting from 1H-2,1-Benzothiazin-4(3H)-one, oxime, 2,2-dioxide 3.

Oxime 3 was obtained starting from commercially available 1,2-Benzoxathiin-4(3H)-one, 2,2-dioxide [49670-47-5].

Example SP-156A

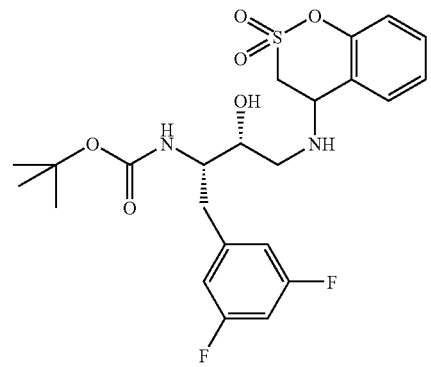

The compound of Example SP-156 can be used to open the appropriate boc protected amino epoxide to generate the compound of Example SP-156A. This compound can then be deprotected using methods well known in the art to generate the free amine, which can then be further manipulated.

Example SP-156-B

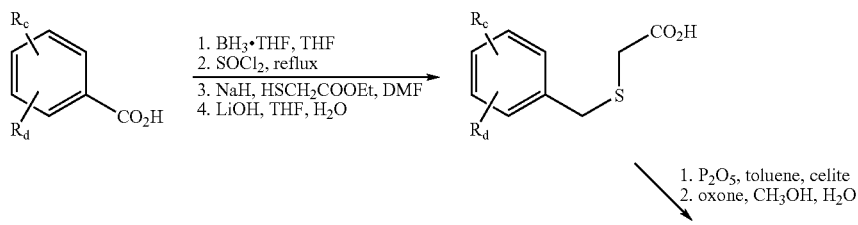

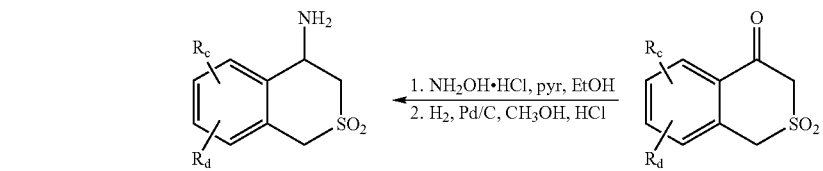

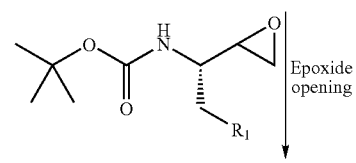

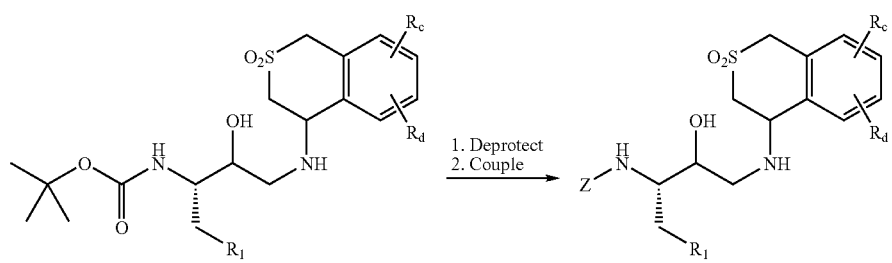

Rc and Rd are independently H, halogen, alkoxy, or alkyl. $R_1$ is 3,5-difluorobenzene; Z is residue from a group that will couple to an amine, including, for example, carboxylic acid derivates (such as an isophthalamide), sulfonic acid derivatives (such as para-toluenesulfonic acid), haloalkane derivatives (such as iodopentane, and arylhaloalkyl derivatives (such as benzylbromide.)

Example SP-157

Preparation of: tert-butyl (2R,3S)-4-(3,5-difluorophenyl)-2-hydroxy-3-({3-[(1-propylbutyl)sulfonyl]alanyl}amino)butyl(3-ethylbenzyl)carbamate

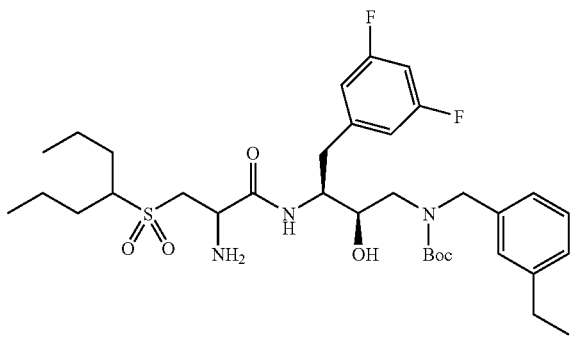

Part A.

A 250 ml round bottom flask equipped with magnetic stir bar and $N_2$ inlet was charged with 5.0 g (34 mmole) methyl 2-acetamidoacrylate, 4.6 g (34 mmole) 4-mercapto heptane in 50 ml methanol. The reaction vessel was charged with 3.6 g (36 mmole) triethylamine and stirred at room temperature for 45 minutes when HPLC indicated complete reaction. The reaction vessel was then treated with 47.2 g (77 mmole) Oxone. After 90 minutes HPLC indicated complete oxidation to the desired sulfone. The reaction was filtered and concentrated in vacuo. The residue was partitioned between ethyl acetate and water and the organic layer was washed with brine, dried over sodium sulfate, and concentrated in vacuo to 9.2 g (86%) of methyl N-acetyl-3-[(1-propylbutyl)sulfonyl]alaninate as a colorless oil. M+H=308 g/m.

Part B.

A 250 ml round bottom flask equipped with magnetic stir bar, reflux condenser, and $N_2$ inlet was charged with 9.2 g methyl N-acetyl-3-[(1-propylbutyl)sulfonyl]alaninate in 50 ml acetic acid and 50 ml conc. HCl. The solution was refluxed for 4 hours then concentrated in vacuo. The residue was chased with toluene (2x) then vacuum dried overnight to yield 7.8 g of the desired 3-[(1-propylbutyl)sulfonyl]alanine HCl salt.

Part C.

A 250 ml round bottom flask equipped with magnetic stir bar and $N_2$ inlet was charged with 7.8 g (27 mmole) 3-[(1-propylbutyl)sulfonyl]alanine and 7.4 g (30 mmole) N-Cbz succinamide in 100 ml methylene chloride. The reaction was cooled to 0° C., and 6.9 g NMK was added dropwise. The reaction was allowed to warm to room temperature and stirred for 4 hours at which point HPLC analysis indicated complete reaction. The reaction was concentrated in vacuo and partitioned between ethyl acetate and 1 N HCl. The organic layer was washed with water, brine, dried over sodium sulfate, and concentrated in vacuo to give 11.4 g of N-[(benzyloxy)carbonyl]-3-[(1-propylbutyl)sulfonyl]alanine that was used without further purification. M+H=386.

Part D.

A 250 ml round bottom flask equipped with magnetic stir bar and $N_2$ inlet was charged with 4.0 g (10 mmole) N-[(benzyloxy)carbonyl]-3-[(1-propylbutyl)sulfonyl]alanine and 1.2 g (12 mmole) (2R,3S)-3-amino-4-(3,5-difluorophenyl)-1-[(3-ethylbenzyl)amino]butan-2-ol dihydrochloride in 50 ml anhydrous methylene chloride. To the reaction mixture was added 5.6 ml (51 mmole) NMM, 1.7 g (13 mmole) hydroxybenzotriazole, and lastly 3.1 g (16 mmole) 1-(3-dimethylaminopropyl)-3-ethylcarbodiimide hydrochloride. After stirring at room temperature for 3 hours, HPLC analysis indicated complete reaction. The reaction was diluted with methylene chloride and washed with saturated sodium bicarbonate solution, 0.5 M citric acid, and brine. The organic layer was dried over sodium sulfate, filtered, and concentrated in vacuo to give the $N^2$-[(benzyloxy)carbonyl]-$N^1$-{(1S,2R)-1-(3,5-difluorobenzyl)-3-[(3-ethylbenzyl)amino]-2-hydroxypropyl}-3-[(1-propylbutyl)sulfonyl]alaninamide. A 50 ml round bottom flask equipped with magnetic stir bar and $N_2$ inlet was charged with the crude residue in anhydrous methylene chloride. The reaction was cooled to 0° C. and added 2.5 g (12 mmole) di-tert-butyl dicarbonate and 1.2 ml (11 mmole) N-methyl morpholine. The reaction was allowed to warm to room temperature and stirred for 18 hours at which point HPLC analysis indicated complete reaction. The reaction was diluted with methylene chloride and washed with saturated sodium bicarbonate solution, and brine. The organic layer was dried over sodium sulfate, filtered, and concentrated in vacuo. The crude material was purified on silica gel by flash chromatography using a gradient solvent of 5-40% ethyl acetate in hexane to give 3.4 g of $N^2$-[(benzyloxy-)carbonyl]-$N^1$-{(1S,2R)-N-[(t-butyloxy)carbonyl]-1-(3,5-difluorobenzyl)-3-[(3-ethylbenzyl)amino]-2-hydroxypropyl}-3-[(1-propylbutyl)sulfonyl]-D,L-alaninamide. M+Na=824.

Part E.

A Fisher-Porter bottle was charged with 3.4 g (4.2 mmole) of $N^2$-[(benzyloxy)-carbonyl]-$N^1$-{(1S,2R)-N-[(t-butyloxy)carbonyl]-1-(3,5-difluorobenzyl)-3-[(3-ethylbenzyl)amino]-2-hydroxypropyl}-3-[(1-propylbutyl)sulfonyl]alaninamide in 50 ml methanol. After degassing with nitrogen, 1.6 g of 5% Pd/C (Degussa E101 50% water) was added. The reaction vessel was purged with 40 psi nitrogen (4x) then pressurized to 50 psi with hydrogen. After 15 minutes, HPLC analysis indicated complete reaction. The catalyst was removed by filtration through celite, and the filtrate concentrated in vacuo to give 2.4 g of $N^1$-{(1S,2R)-N-[(t-butyloxy)carbonyl]-1-(3,5-difluorobenzyl)-3-[(3-ethylbenzyl)amino]-2-hydroxypropyl}-3-[(1-propylbutyl)sulfonyl]-D,L-alanine. M+H=668.

Example SP-158

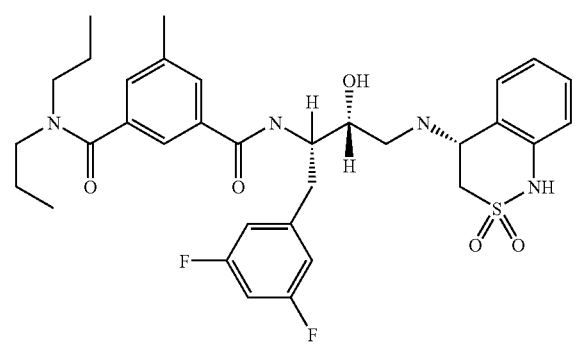

2,2-Dioxo-1,2,3,4-tetrahydro-$2\lambda^6$-benzo[c][1,2]thiazin4-ylamine 2 was prepared according to procedure A of Example SP-155. Also, epoxide opening with 2 (see procedure A of Example SP-155) was achieved according to the procedure described in Bennett, Frank. *Synlett* 1993, 703-704. Mass spec (CI) MH+ 643.7.

Example SP-159

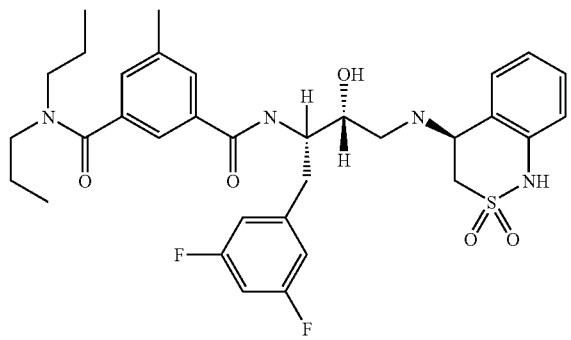

2,2-Dioxo-1,2,3,4-tetrahydro-2λ⁶-benzo[c][1,2]thiazin4-ylamine 2 was prepared according to procedure A in Example SP-155. Also, epoxide opening with 2 (see procedure A) was achieved according to the procedure described in Bennett, Frank. *Synlett* 1993, 703-704. Mass spec (CI) MH+ 643.7.

Example SP-160

Synthesis of t-Boc-NH-di-F-Phe-Hydroxyethylamine (HEA)-O-Bn

To 2.4 g (15 mmole, 3 eq.) of O-benzylhydroxylamine hydrochloride in 20 ml of EtOAc was added 20 ml of 1N KOH with stirring. The organic layer extracted and dried, stripping of solvent and reconstituted with 20 ml of DCM, 1.5 g (5 mmole) of erythro-di-F-Phe-epoxide and 0.62 g (1 mmole, 0.2 eq.) of Ytterbium(III) trifluoromethanesulfonate was added at room temperature. The mixture was stirred overnight and worked up by 1N HCl, bicarb and brine washings, dried, stripping of solvent gave 1.23 g crude which was subject to column purification, it afforded 0.76 g (1.8 mmole, 36%) of the targeted compound as a pale white solid.

Example SP-161

$N^1$-{(1S,2R)-1-(3,5-Difluorobenzyl)-3-[(3-ethylbenzyl)amino]-2-hydroxypropyl}-5-(5-methyl-1,2,4-oxadiazol-3-yl)-$N^3$,$N^3$-dipropylisophthalamide hydrochloride Step 1

Methyl 3-[(dipropylamino)carbonyl]-5-(5-methyl-1,2,4-oxadiazol-3-yl)benzoate

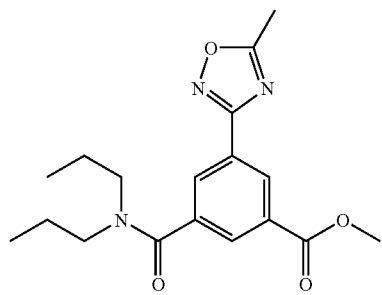

To a stirred solution of methyl 3-cyano-5-[(dipropylamino)carbonyl]benzoate prepared by the method in Example S-2510 (2.3 g, 7.9 mmol) in methanol (26 mL) is added hydroxylamine hydrochloride (1.1 g, 16 mmol) and potassium carbonate (2.2 g, 16 mmol). The resulting reaction mixture is refluxed for 20 h, and then cooled to room temperature. The inorganic salts are filtered, and the filtrate is concentrated under reduced pressure to provide an amidoxime in quantitative yield.

To the amidoxime (1.3 g, 4 mmol), and EDC (1.5 g, 8 mmol) in 2-methoxyethyl ether (8 mL) is added acetic acid (0.21 mL, 4 mmol). The resulting reaction mixture is stirred for 24 h and then refluxed for 3 h. The reaction mixture is cooled to room temperature, diluted with ethyl acetate, washed with water, 1 N hydrochloric acid, saturated sodium bicarbonate, and brine, dried (sodium sulfate), filtered, and concentrated under reduced pressure. Purification by flash column chromatography (silica, 50% ethyl acetate hexanes) provides the title compound. $^1$H NMR (500 MHz, CDCl$_3$) δ 8.69 (s, 1H), 8.18 (m, 1H), 8.11 (s, 1H), 3.91 (s, 3H), 3.43 (t, J=7 Hz, 2H), 3.12 (t, J=7 Hz, 2H), 2.63 (s, 3H), 1.66 (t, J=7 Hz, 2H), 1.50 (t, J=7 Hz, 2H), 0.95 (t, J=7 Hz, 3H), 0.70 (t, J=7 Hz, 3H).

Step 2

3-[(Dipropylamino)carbonyl]-5-(5-methyl-1,2,4-oxadiazol-3-yl)benzoic acid

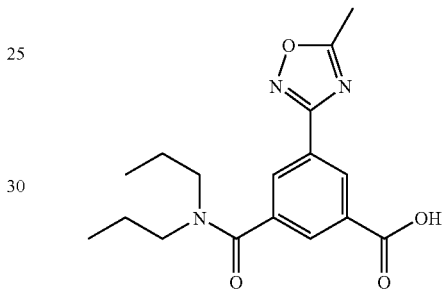

A stirred solution of methyl 3-[(dipropylamino)carbonyl]-5-(5-methyl-1,2,4-oxadiazol-3-yl)benzoate (629 mg, 1.8 mmol) and lithium iodide (2.4 g, 18 mmol) in pyridine (7 ml) is refluxed for 18 h. The reaction mixture is cooled to room temperature and the solvent is concentrated under reduced pressure. The residue is dissolved in water, washed with ethyl acetate, the aqueous layer is acidified to pH 3 with 1 N hydrochloric acid and extracted with chloroform (3×100 mL). The organic layer is dried (sodium sulfate), filtered, and concentrated to give the title compound. $^1$H NMR (500 MHz, CDCl$_3$) δ 11.11 (br s, 1H), 8.85 (t, J=1 Hz, 1H), 8.31 (t, J=1 Hz, 1H), 8.23 (t, J=1 Hz, 1H), 3.51 (s, 2H), 3.19 (s, 2H), 2.72 (s, 3H), 1.73 (d, J=7 Hz, 2H), 1.56 (d, J=7 Hz, 2H), 1.01 (t, J=7 Hz, 3H), 0.76 (t, J=7 Hz, 3H).

Step 3

$N^1$-{(1S,2R)-1-(3,5-Difluorobenzyl)-3-[(3-ethylbenzyl)amino]-2-hydroxypropyl}-5-(5-methyl-1,2,4-oxadiazol-3-yl)-$N^3$,$N^3$-dipropylisophthalamide hydrochloride

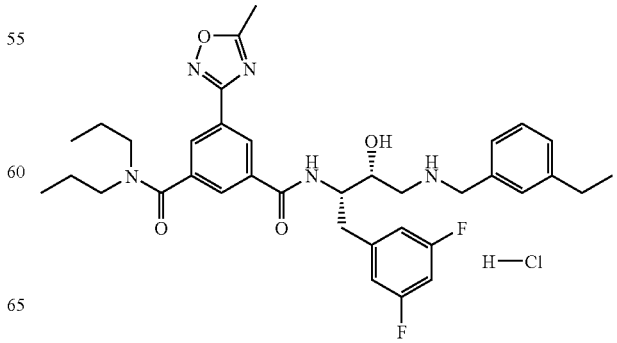

A solution of 3-[(dipropylamino)carbonyl]-5-(5-methyl-1,2,4-oxadiazol-3-yl)benzoic acid (209 mg, 0.63 mmol), HATU (359 mg, 0.95 mmol), HOBt (128 mg, 0.95 mmol), and diisopropylethylamine (165 µL, 0.95 mmol) is stirred in methylene chloride (2.0 mL) for 15 min. A solution of (2R,3S)-3-amino-4-(3,5-difluorophenyl)-1-[(3-ethylbenzyl)amino]butan-2-ol dihydrochloride prepared by the method in Example SP-272 (257 mg, 0.63 mmol) and diisopropylethylamine (165 µL, 0.95 mmol) in methylene chloride (2.0 mL) is added and the reaction mixture is stirred overnight. The reaction mixture is diluted with methylene chloride, washed with 1 N hydrochloric acid (25 mL), saturated sodium bicarbonate (25 mL), and brine, dried (magnesium sulfate), filtered, and concentrated under reduced pressure. Purification by flash column chromatography (silica, 1:9 methanol/chloroform) provides the title compound as the free base. The solid is dissolved in methanol (1 mL), and treated with hydrochloric acid (0.3 mL of a 1.0 M solution in diethyl ether, 0.3 mmol). The resulting precipitate is collected by filtration to provide the title compound. APCI MS m/z 648.4 [M+H]$^+$.

Example SP-162

N$^1$-{(1S,2R)-1-(3,5-difluorobenzyl)-3-[(3-ethylbenzyl)amino]-2-hydroxypropyl}-5-(1H-imidazol-2-yl)-N$^3$,N$^3$-dipropylisophthalamide Step 1

Methyl 3-[(dipropylamino)carbonyl]-5-(1H-imidazol-2-yl)benzoate

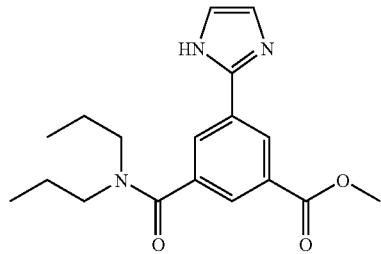

To a −70° C. stirred solution of 1-tert-butyldimethylsilylimidazole (602 mg, 3.3 mmol) in tetrahydrofuran (10 mL) is added n-butyllithium (1.6 M in hexanes, 2.3 mL, 3.63 mmol). After 30 min, zinc chloride (1 M in diethyl ether, 9.9 mL, 9.9 mmol) is added and the reaction mixture is warmed to 0° C. for 1 h. To this mixture is then added methyl 3-[(dipropylamino)carbonyl]-5-iodobenzoate prepared by the method in Example SP-281, step 2 (1.17 g, 3 mmol) followed by palladium(0)tetrakis(triphenylphosphine) (173 mg, 0.15 mmol). The reaction mixture is heated at reflux for 15 h. The reaction mixture is diluted with ethyl acetate (50 mL), washed with water, and brine, dried (sodium sulfate), filtered, and concentrated under reduced pressure. Purification by flash column chromatography (silica gel, 1-5% methanol/methylene chloride) provides the title compound in pure form. $^1$H NMR (300 MHz, CDCl$_3$) δ 8.64 (s, 1H), 8.14 (s, 1H), 7.97 (s, 1H), 7.19 (s, 2H), 3.96 (s, 3H), 3.51 (m, 2H), 3.32 (m, 2H), 1.73 (m, 2H), 1.57 (m, 2H), 1.01 (m, 3H), 0.73 (m, 3H).

Step 2

3-[(Dipropylamino)carbonyl]-5-(1H-imidazol-2-yl)benzoic acid

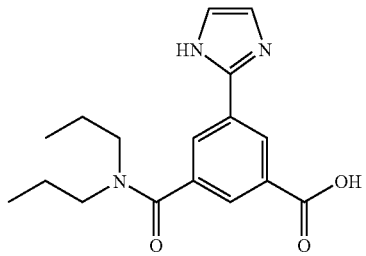

To a stirred solution of the ester from step 1 (260 mg, 0.79 mmol) in 2:1:1 tetrahydrofuran/methanol/water (8 mL) is added lithium hydroxide (140 mg, 3.3 mmol). The reaction mixture is stirred at room temperature for 2 h, and concentrated under reduced pressure. The residue is partitioned between water (10 mL) and diethyl ether (10 mL). The aqueous layer is acidified to pH 4-5 with 1 N hydrochloric acid and extracted with 3:1 chloroform/2-propanol (3×30 mL). The combined organic layers are dried (sodium sulfate), filtered, and concentrated under reduced pressure to provide the title compound. $^1$H NMR (300 MHz, CD$_3$OD) δ 8.64 (s, 1H), 8.10 (s, 1H), 8.01 (s, 1H), 7.28 (s, 2H), 3.52 (m, 2H), 3.26 (m, 2H), 1.75 (m, 2H), 1.59 (m, 2H), 1.02 (t, J=7 Hz, 3H), 0.75 (t, J=7 Hz, 3H).

Step 3

N$^1$-{(1S,2R)-1-(3,5-difluorobenzyl)-3-[(3-ethylbenzyl)amino]-2-hydroxypropyl}-5-(1H-imidazol-2-yl)-N$^3$,N$^3$-dipropylisophthalamide

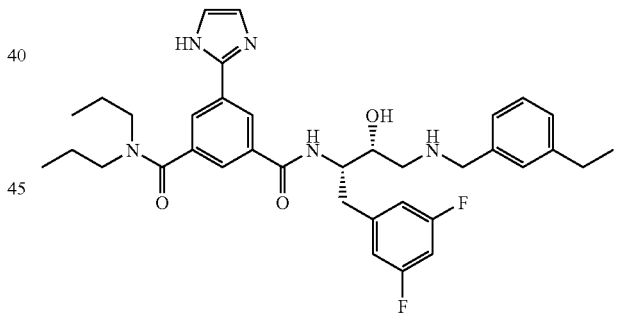

To a stirred solution of 3-[(dipropylamino)carbonyl]-5-(1H-imidazol-2-yl)benzoic acid (250 mg, 0.79 mmol), diisopropylethylamine (103 mg, 0.8 mmol), and HBTU (330 mg, 0.87 mmol) in methylene chloride (5 mL) is added a mixture of (2R,3S)-3-amino-4-(3,5-difluorophenyl)-1-[(3-ethylbenzyl)amino]butan-2-ol prepared by the method of Example SP-272 (322 mg, 0.79 mmol) and diisopropylethylamine (206 mg, 1.6 mmol) in methylene chloride (5 mL). The reaction mixture is stirred at room temperature for 4 h and concentrated under reduced pressure. The residue is diluted with ethyl acetate (20 mL), washed with saturated sodium bicarbonate, and brine, dried (sodium sulfate), filtered, and concentrated under reduced pressure. Purification by flash column chromatography (silica gel, 5:95 methanol/methylene chloride) provides the title compound in pure form. APCI MS m/z 632.3 [M+H]$^+$.

Example SP-163

N¹-{(1S,2R)-1-Benzyl-3-[(3-ethylbenzyl)amino]-2-hydroxypropyl}-N³-methyl-5-(1,3-oxazol-2-yl)-N³-propyl-isophthalamide Step 1

Methyl 3-iodo-5-{[methyl(propyl)amino]carbonyl}benzoate

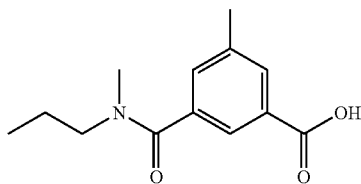

To 3-iodo-5-(methoxycarbonyl)benzoic acid (1.0 g, 3.3 mmol), prepared as in Example SP-281, step 1, and diisopropylethylamine (1.7 mL, 9.8 mmol) in DMF (10 mL) is added O-(7-Azabenzotriazol-1-yl)-N,N,N',N'-tetramethyluronium hexafluorophosphate (HATU, 1.5 g, 3.9 mmol) then N-methylpropylamine (503 µL, 4.9 mmol). The solution is stirred at room temperature 2 h. The solution is diluted in ethyl acetate and washed with water, saturated sodium bicarbonate, and brine. The organic layer is dried over sodium sulfate, filtered and concentrated under reduced pressure to give the title compound in crude form. This material is purified by flash chromatography (40% ethyl acetate/hexane) to give the purified title compound. MS (ESI) [M+H⁺]=362.4.

Step 2

3-{[Methyl(propyl)amino]carbonyl}-5-(1,3-oxazol-2-yl)benzoic acid

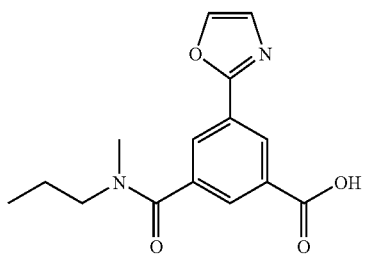

To a −70° C. stirred solution of oxazole (330 mg, 4.8 mmol) in tetrahydrofuran (4 mL) is added n-butyllithium (1.6 M in hexanes, 3.3 mL, 5.3 mmol). After 30 min, zinc chloride (1 M in diethyl ether, 14.5 mL, 14.5 mmol) is added and the reaction mixture is warmed to 0° C. for 1 h. To this mixture is added a solution of methyl 3-iodo-5-{[methyl(propyl)amino] carbonyl}benzoate (1.6 g, 4.5 mmol) in anhydrous tetrahydrofuran (3 mL) followed by palladium(0)tetrakis(triphenylphosphine) (221 mg, 0.19 mmol). The reaction mixture is heated at reflux for 2 h. The reaction mixture is cooled, diluted with ethyl acetate, washed with water, and brine, dried (sodium sulfate), filtered, and concentrated under reduced pressure. Purification by flash column chromatography (silica gel, 60% ethyl acetate/hexane) provides a solid. The solid is redissolved in 1:1:1 tetrahydrofuran/methanol/water (9 mL), and lithium hydroxide monohydrate (311 mg, 7.4 mmol) is added and stirred 2 h at room temperature. The reaction is diluted in chloroform and washed with 1N hydrochloric acid (aq), water, and brine, dried (sodium sulfate), filtered and concentrated under reduced pressure to give the title compound. ESI MS m/z 287.3 [M−H]⁻.

Step 3

N¹-{(1S,2R)-1-Benzyl-3-[(3-ethylbenzyl)amino]-2-hydroxypropyl}-N³-methyl-5-(1,3-oxazol-2-yl)-N³-propyl-isophthalamide

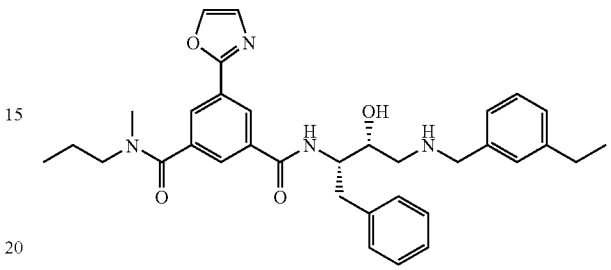

To 3-{[methyl(propyl)amino]carbonyl}-5-(1,3-oxazol-2-yl)benzoic acid (206 mg, 0.71 mmol) in DMF (5 mL) is added diisopropylethylamine (174 µL, 1.1 mmol), HATU (323 mg, 0.85 mmol), then (2R,3S)-3-amino-1-[(3-ethylbenzyl)amino]-4-phenylbutan-2-ol dihydrochloride prepared by the method of Example SP-272 (292 mg, 0.79 mmol). The reaction is stirred 4 h at room temperature. The reaction is partitioned between chloroform and water. The organic layer is washed with 1 N hydrochloric acid, saturated sodium bicarbonate, and brine, dried (sodium sulfate), filtered, and concentrated under reduced pressure. Purification by flash column chromatography (silica, 8% methanol/chloroform) gives the title compound. ESI MS m/z 569.3 [M+H]⁺.

Example SP-164

Step 1

N¹-Isobutyl-L-alaninamide

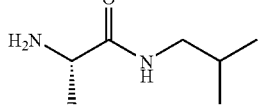

Boc-L-alanine (5.0 g, 26.4 mmol), isobutylamine (2.9 mL, 29.1 mmol), diisopropylethylamine (11.5 mL, 66 mmol), and HOBt (3.6 g, 26.4 mmol) in anhydrous DMF (15 mL) is stirred 15 min. EDC is added, and the reaction is stirred at room temperature 16 h. The reaction is diluted in ethyl acetate and washed with 1 N hydrochloric acid, saturated sodium bicarbonate, and brine, dried (magnesium sulfate), filtered, and concentrated under reduced pressure. The residue is redissolved in 4N hydrochloric acid in dioxane (30 mL) and stirred for 2 h. The solution is concentrated under reduced pressure, dissolved in chloroform and washed with 1 N NaOH (aq). The aqueous layer is extracted with chloroform, and the pooled organics are dried (sodium sulfate), filtered, and concentrated under reduced pressure to give the title compound. ESI MS m/z 145.2 [M+H]⁺.

Step 2

[1-(3,5-Difluoro-benzyl)-2-hydroxy-3-(1-isobutylcarbamoyl-ethylamino)-propyl]-carbamic acid tert-butyl ester

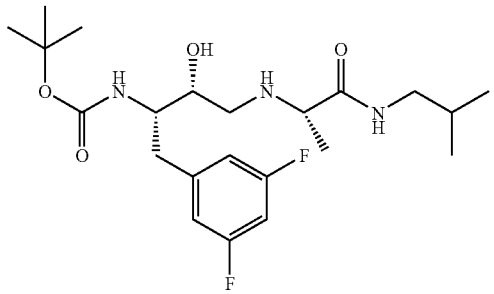

$N^1$-Isobutyl-L-alaninamide (3.8 g, 26 mmol) and tert-butyl (1S)-2-(3,5-difluorophenyl)-1-[(2S)-oxiran-2-yl]ethylcarbamate prepared by the method in Example S-3 (3.1 g, 10.4 mmol) in isopropanol (50 mL) are refluxed 4 h. The reaction is cooled and concentrated under reduced pressure. Purification by flash column chromatography (silica, 8% methanol/chloroform) gives the title compound. ESI MS m/z 444.1 $[M+H]^+$.

Step 3

$N^2$-[(2R,3S)-3-Amino-4-(3,5-difluorophenyl)-2-hydroxybutyl]-$N^1$-isobutyl-L-alaninamide dihydrochloride

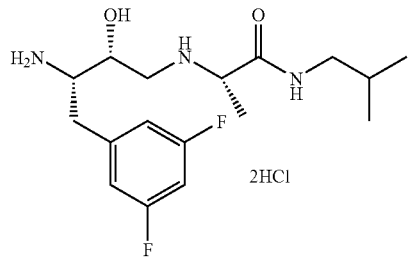

[1-(3,5-Difluoro-benzyl)-2-hydroxy-3-(1-isobutylcarbamoyl-ethylamino)-propyl]-carbamic acid tert-butyl ester (2.7 g, 6 mmol) is dissolved in excess 4N hydrochloric acid in dioxane, and the reaction is stirred 2 h at room temperature. The solution is concentrated under reduced pressure to give the title compound. ESI MS m/z 344.3 $[M+H]^+$.

Step 4

Methyl 3-[(dipropylamino)carbonyl]-5-(1,3-oxazol-2-yl)benzoate

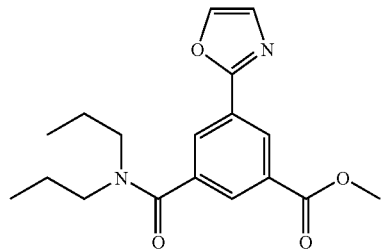

3-[(Dipropylamino)carbonyl]-5-iodobenzoic acid (12 g, 32 mmol) is dissolved in 20% methanol/benzene (480 mL), and 2M trimethylsilyldiazomethane in hexane (19 mL, 38 mmol) is added slowly. Upon completion of the addition, the solution is concentrated under reduced pressure to give methyl 3-[(dipropylamino)carbonyl]-5-iodobenzoate for use without further purification in the following reaction. To a −70° C. stirred solution of oxazole (120 mg, 1.7 mmol) in tetrahydrofuran (4 mL) is added n-butyllithium (1.6 M in hexanes, 1.2 mL, 1.9 mmol). After 30 min, zinc chloride (1 M in diethyl ether, 5.2 mL, 5.2 mmol) is added and the reaction mixture is warmed to 0° C. for 1 h. To this mixture is added a solution of methyl 3-[(dipropylamino)carbonyl]-5-iodobenzoate (643 mg, 1.6 mmol) in anhydrous tetrahydrofuran (3 mL) followed by palladium(0)tetrakis(triphenylphosphine) (80 mg, 0.07 mmol). The reaction mixture is heated at reflux for 3 h. The reaction mixture is cooled, diluted with ethyl acetate, filtered, washed with saturated sodium bicarbonate, water, and brine, dried (sodium sulfate), filtered, and concentrated under reduced pressure. Purification by flash column chromatography (silica gel, 60% ethyl acetate/hexane) provides the title compound in pure form. $^1$H NMR (400 MHz, CDCl$_3$) δ 8.77 (s, 1H), 8.27 (s, 1H), 8.14 (s, 1H), 7.80 (s, 1H) 7.32 (s, 1H), 3.52 (t, 2H), 3.22 (t, 2H), 1.75 (m, 2H), 1.30 (m, 2H), 0.97 (t, 3H), 0.79 (t, 3H).

Step 5

N-[1-(3,5-Difluoro-benzyl)-2-hydroxy-3-(1-isobutylcarbamoyl-ethylamino)-propyl]-5-oxazol-2-yl-N',N'-dipropyl-isophthalamide

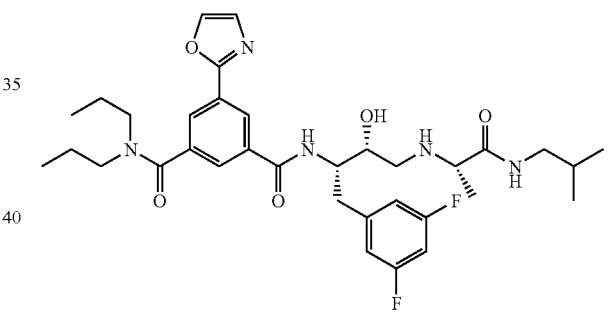

Methyl 3-[(dipropylamino)carbonyl]-5-(1,3-oxazol-2-yl) benzoate (430 mg, 1.3 mmol) is dissolved in 1:1:1 tetrahydrofuran/methanol/water (9 mL), and lithium hydroxide monohydrate (110 mg, 2.6 mmol) is added and stirred 2 h at room temperature. The reaction is concentrated under reduced pressure and chloroform is added. The solution is washed with 1N hydrochloric acid (aq). The aqueous layer is reextracted with chloroform, and the pooled organics are washed with brine. The solution is concentrated under reduced pressure.

To this residue redissolved in DMF (5 mL) is added diisopropylethylamine (438 μL, 2.52 mmol), HATU (289 mg, 0.76 mmol), then $N^2$-[(2R,3S)-3-amino-4-(3,5-difluorophenyl)-2-hydroxybutyl]-$N^1$-isobutyl-L-alaninamide dihydrochloride (288 mg, 0.69 mmol). The reaction is stirred 4 h at room temperature. The reaction is partitioned between chloroform and water. The organic layer is washed with 1 N hydrochloric acid, saturated sodium bicarbonate, and brine, dried (sodium sulfate), filtered, and concentrated under reduced pressure. Purification by flash column chromatography (silica, 8% methanol/chloroform) gives the title compound. ESI MS m/z 642.3 $[M+H]^+$.

Example SP-165

N-[1-(3,5-Difluoro-benzyl)-2-hydroxy-3-(1-isobutylcarbamoylethylamino)-propyl]-N'-methyl-5-oxazol-2-yl-N'-propylisophthalamide

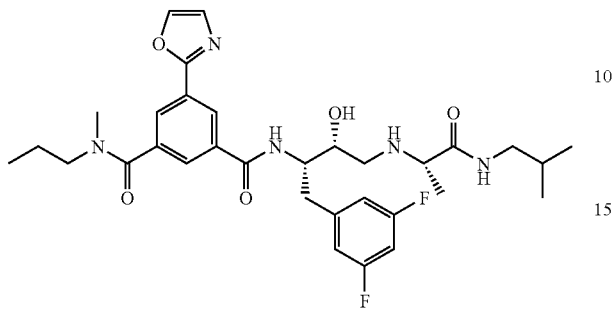

To 3-{[Methyl(propyl)amino]carbonyl}-5-(1,3-oxazol-2-yl)benzoic acid prepared by the method in Example SP-163 in DMF (5 mL) is added diisopropylethylamine (361 μL, 2.1 mmol), HATU (237 mg, 0.62 mmol), then dihydrochloride prepared by the method of Example SP-164 (237 mg, 0.57 mmol). The reaction is stirred 2 h at room temperature. The reaction is partitioned between chloroform and water. The organic layer is washed with 1 N hydrochloric acid, saturated sodium bicarbonate, and brine, dried (sodium sulfate), filtered, and concentrated under reduced pressure. Purification by flash column chromatography (silica, 8% methanol/chloroform) gives the title compound. ESI MS m/z 614.4 [M+H]$^+$.

Example SP-166

N'-{(1S,2R)-1-(3,5-difluorobenzyl)-3-[(3-ethylbenzyl)amino]-2-hydroxypropyl}-5-[1-(ethoxymethyl)-1H-imidazol-2-yl]-N$^3$,N$^3$-dipropylisophthalamide Step 1
Methyl 3-[(dipropylamino)carbonyl]-5-[1-(ethoxymethyl)-1H-imidazol-2-yl]benzoate

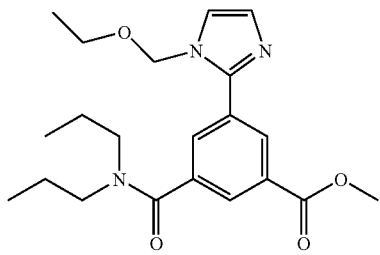

To a −70° C. stirred solution of 1-ethoxylmethylimidazole (J. Am. Chem. Soc. 1978, 100, 3918) (420 mg, 3.3 mmol) in tetrahydrofuran (10 mL) is added n-butyllithium (1.6 M in hexanes, 2.3 mL, 3.6 mmol). After 30 min, zinc. chloride (9.9 mL of a 1 M solution in diethyl ether, 9.9 mmol) is added and the reaction mixture is warmed to 0° C. for 1 h. To this mixture is then added methyl 3-[(dipropylamino)carbonyl]-5-iodobenzoate (1.17 g, 3 mmol) followed by palladium(0)tetrakis (triphenylphosphine) (173 mg, 0.15 mmol). The reaction mixture is heated at reflux for 2 h. The reaction mixture is diluted with ethyl acetate (50 mL)), washed with water, and brine, dried (sodium sulfate), filtered, and concentrated under reduced pressure. Purification by flash column chromatography (silica gel, 1-5% methanol/methylene chloride) provides the title compound in pure form. $^1$H NMR (300 MHz, CDCl$_3$) δ 8.52 (s, 1H), 8.10 (s, 1H), 8.03 (s, 1H), 8.19 (s, 2H), 5.28 (s, 2H), 3.95 (s, 3H), 3.59 (q, J=7 Hz, 2H), 3.49 (m, 2H), 3.21 (m, 2H), 1.70 (m, 2H), 1.54 (m, 2H), 1.25 (t, J=7 Hz, 3H), 0.99 (m, 3H), 0.75 (m, 3H).

Step 2
3-[(Dipropylamino)carbonyl]-5-[1-(ethoxymethyl)-1H-imidazol-2-yl]benzoic acid

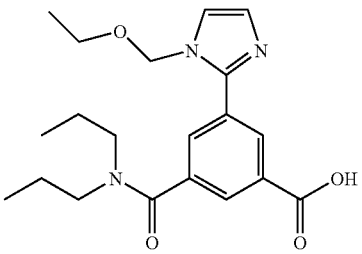

To a stirred solution of the ester from step 1 (756 mg, 1.95 mmol) in 2:1:1 tetrahydrofuran/methanol/water (12 mL) is added lithium hydroxide (170 mg, 4 mmol). The reaction mixture is stirred at room temperature for 42 h, and concentrated under reduced pressure. The residue is partitioned between water (10 mL) and chloroform (10 mL). The aqueous layer is acidified to pH 4-5 with 1 N hydrochloric acid and extracted with 3:1 chloroform/2-propanol (3×30 mL). The combined organic layers are dried (sodium sulfate), filtered, and concentrated under reduced pressure to provide the title compound. $^1$H NMR (300 MHz, CD$_3$OD) δ 8.51 (s, 1H), 8.06 (s, 1H), 8.00 (s, 1H), 7.49 (s, 1H), 7.17 (s, 1H), 5.39 (s, 2H), 3.62 (q, J=7 Hz, 2H), 3.51 (m, 2H), 3.27 (m, 2H), 1.72 (m, 2H), 1.59 (m, 2H), 1.21 (t, J=7 Hz, 3H), 1.00 (m, 3H), 0.75 (m, 3H).

Step 3
N$^1$-{(1S,2R)-1-(3,5-difluorobenzyl)-3-[(3-ethylbenzyl)amino]-2-hydroxypropyl}-5-[1-(ethoxymethyl)-1H-imidazol-2-yl]-N$^3$,N$^3$-dipropylisophthalamide

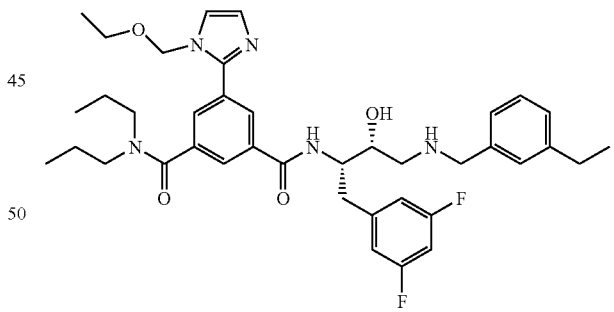

To a stirred solution of 3-[(dipropylamino)carbonyl]-5-[1-(ethoxymethyl)-1H-imidazol-2-yl]benzoic acid (177 mg, 0.47 mmol), diisopropylethylamine (651 mg, 0.5 mmol), and HBTU (209 mg, 0.55 mmol) in methylene chloride (5 mL) is added a mixture of (2R,3S)-3-amino-4-(3,5-difluorophenyl)-1-[(3-ethylbenzyl)amino]butan-2-ol prepared by the method of Example SP-272 (196 mg, 0.48 mmol) and diisopropylethylamine (130 mg, 1.0 mmol) in methylene chloride (5 mL). The reaction mixture is stirred at room temperature for 15 h and concentrated under reduced pressure. The residue is diluted with ethyl acetate (20 mL), washed with saturated sodium bicarbonate, and brine, dried (sodium sulfate), filtered, and concentrated under reduced pressure. Purification

Example SP-168

Methyl 3-[({(1S,2R)-1-(3,5-difluorobenzyl)-3-[(3-ethylbenzyl)amino]-2-hydroxypropyl}amino)carbonyl]benzoate

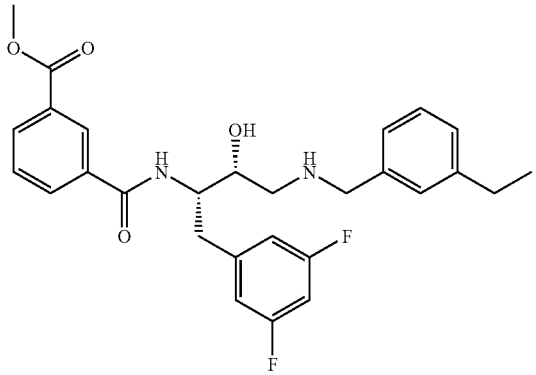

To methyl hydrogen isophthalate (1.0 g, 5.6 mmol) in DMF/chloroform (1:2, 15 mL) is added diisopropylethylamine (3.9 mL, 22 mmol), HATU (2.5 g, 6.7 mmol), then (2R,3S)-3-amino-4-(3,5-difluorophenyl)-1-[(3-ethylbenzyl)amino]butan-2-ol dihydrochloride prepared by the method of Example SP-272 (2.5 g, 6.1 mmol). The reaction is stirred 1 h at room temperature. The reaction is partitioned between ethyl acetate and water. The organic layer is washed with 1 N hydrochloric acid, saturated sodium bicarbonate, and brine, dried (sodium sulfate), filtered, and concentrated under reduced pressure. Purification by flash column chromatography (silica, 8% methanol/chloroform) gives the title compound. ESI MS m/z 497.3 [M+H]$^+$.

Example SP-169

N-{(1S,2R)-1-(3,5-difluorobenzyl)-3-[(3-ethylbenzyl)amino]-2-hydroxypropyl}-3-[4-(2-hydroxyethyl)-1,3-oxazol-2-yl]benzamide Step 1
Methyl O-benzyl-N-(tert-butoxycarbonyl)homoserinate

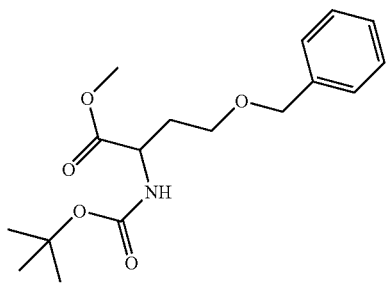

To O-benzyl-N-(tert-butoxycarbonyl)homoserine (5.8 g, 18.9 mmol) in 20% methanol/benzene (72 mL) is added 2M trimethylsilyldiazomethane in hexane (12.3 mL, 24.5 mmol), and the reaction stirred at room temperature 1.5 h. The solution is concentrated under reduced pressure to give the title compound in pure form. ESI MS m/z 324.2 [M+H]$^+$.

Step 2
tert-Butyl 3-(benzyloxy)-1-(hydroxymethyl)propylcarbamate

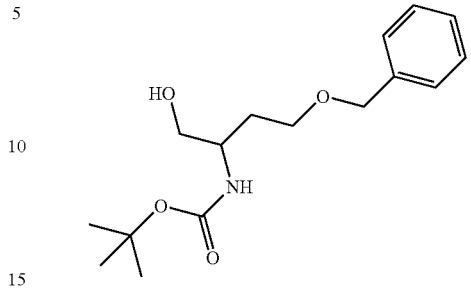

To an ice-cold solution of methyl O-benzyl-N-(tert-butoxycarbonyl)homoserinate (6 g, 18.6 mmol) in absolute ethanol (100 mL) is added sodium borohydride (2.8 g, 74.2 mmol), and the reaction is refluxed 2 h. The solution is cooled, excess saturated potassium carbonate added, and stirred 16 h at room temperature. The ethanol is removed under reduced pressure, and the aqueous solution is extracted with chloroform. The organic layer is washed with saturated sodium bicarbonate, saturated sodium sulfate, dried (magnesium sulfate), filtered, and concentrated under reduced pressure to give the title compound. ESI MS m/z 296.2 [M+H]$^+$.

Step 3
2-Amino-4-(benzyloxy)butan-1-ol hydrochloride

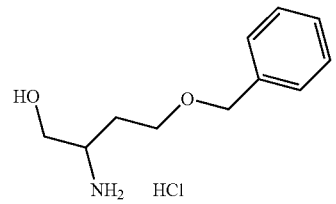

tert-Butyl 3-(benzyloxy)-1-(hydroxymethyl)propylcarbamate (5 g, 17 mmol) is dissolved in 4 N hydrochloric acid in dioxane (21 mL) and stirred for 3 h at room temperature. The solution is concentrated under reduced pressure to give the title compound in pure form. ESI MS m/z 196.1 [M+H]$^+$.

Step 4
Methyl 3-({[3-(benzyloxy)-1-(hydroxymethyl)propyl]amino}carbonyl)benzoate

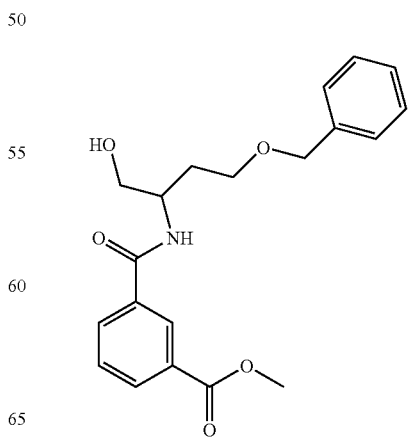

Methyl hydrogen isophthalate (1.5 g, 8.2 mmol), 2-amino-4-(benzyloxy)butan-1-ol hydrochloride (2 g, 8.6 mmol), diisopropylethylamine (4.2 mL, 24.7 mmol), and HATU (3.8 mg, 9.9 mmol), in DMF (15 mL) are stirred at room temperature 1 h. The reaction is diluted in ethyl acetate and washed with water, 1N hydrochloric acid (aq), saturated sodium bicarbonate, brine, dried (magnesium sulfate), filtered, and concentrated under reduced pressure. Purification by flash column chromatography (silica gel, 4% methanol/chloroform) provides the title compound. $^1$H NMR (400 MHz, CDCl$_3$) δ 8.44 (s, 1H), 8.18 (d, 1H, J=7.9 Hz), 7.86 (d, 1H, J=7.9 Hz), 7.43 (t, 1H, J=7.6 Hz), 7.42-7.35 (m, 5H), 4.59 (s, 2H), 4.33 (m, 1H), 3.96 (s, 3H), 3.88-3.72 (m, 4H), 3.53 (s, 1H), 2.08 (m, 2H).

Step 5

Methyl 3-{4-[2-(benzyloxy)ethyl]-1,3-oxazol-2-yl}benzoate

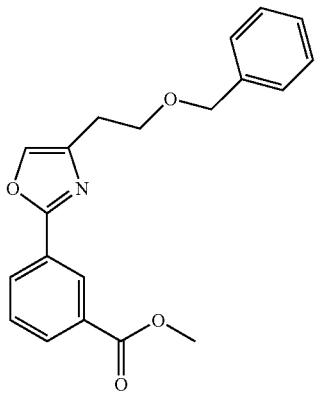

To methyl 3-({[3-(benzyloxy)-1-(hydroxymethyl)propyl]amino}carbonyl)benzoate (1.3 g, 3.6 mmol) in water-saturated methylene chloride (20 mL) is added sodium bromide (187 mg, 1.8 mmol) and water (2.75 mL), then TEMPO (6 mg, 0.04 mmol) with vigorous stirring. Sodium bicarbonate (115 mg) and 6% sodium hypochlorite (5 mL) is added and stirred 1 h. 6% sodium hypochlorite (1 mL) is added each hour for 3 h.

Excess saturated sodium thiosulfate is added and stirred 30 min. The mixture is partitioned, and the organic layer is washed with brine, dried (sodium sulfate), filtered and concentrated under reduced. The residue is dissolved in anhydrous tetrahydrofuran (4 mL), and (methoxycarbonylsulfamoyl)triethylammonium hydroxide, inner salt (670 mg, 2.8 mmol). The reaction is microwaved (100 W, 2 min) in a sealed vessel, cooled, filtered, and concentrated under reduced pressure. Purification by flash chromatography (silica gel, 40% ethyl acetate/hexanes) gives the title compound. ESI MS m/z 338.3 [M+H]$^+$.

Step 6

N-{(1S,2R)-1-(3,5-difluorobenzyl)-3-[(3-ethylbenzyl)amino]-2-hydroxypropyl}-3-[4-(2-hydroxyethyl)-1,3-oxazol-2-yl]benzamide

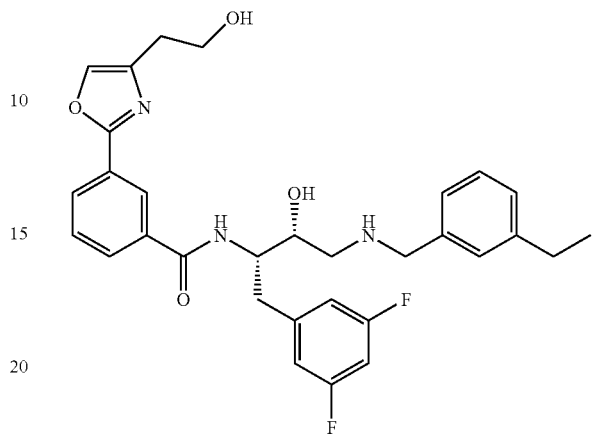

Methyl 3-{4-[2-(benzyloxy)ethyl]-1,3-oxazol-2-yl}benzoate (300 mg, 0.9 mmol), 20% palladium(II) hydroxide on carbon (65 mg), and cyclohexene (3 mL) in absolute ethanol (3 mL) are refluxed 1 h. The reaction is cooled, filtered through diatomaceous earth, and concentrated under reduced pressure. The residue is redissolved in 2:1:1 tetrahydrofuran/methanol/water (4 mL) is added lithium hydroxide (75 mg, 1.8 mmol). The reaction mixture is stirred at room temperature for 3 h, and concentrated under reduced pressure. The residue is dissolved in DMF (5 mL), and diisopropylethylamine (625 μL, 3.6 mmol), HATU (540 mg, 1.4 mmol), and (2R,3S)-3-amino-4-(3,5-difluorophenyl)-1-[(3-ethylbenzyl)amino]butan-2-ol dihydrochloride prepared by the method in Example SP-272 (407 mg, 1 mmol) are added. The reaction stirred at room temperature 16 h. The reaction mixture is diluted with chloroform, washed with water, 1N hydrochloric acid (aq), saturated sodium bicarbonate, brine, dried (sodium sulfate), filtered, and concentrated under reduced pressure. Purification by flash column chromatography (silica, 8% methanol/chloroform) provides the title compound. ESI MS m/z 550.3 [M+H]$^+$.

Example SP-170

N$^1$-{(1S,2R)-1-(3,5-Difluorobenzyl)-2-hydroxy-3-[(3-isopropylbenzyl)amino]propyl}-N$^3$,N$^3$-dipropyl-5-(1,3-thiazol-2-yl)isophthalamide Step 1
3-Isopropenylbenzonitrile

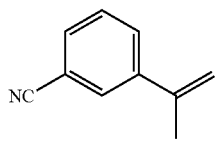

To a stirred solution of 3-cyanophenylboronic acid (10.0 g, 68.05 mmol) dissolved in DME (340 mL) is added 2-bromopropene (6.86 g, 56.7 mmol), and sodium carbonate (62.3 mL of a 2 M solution in water, 124.7 mmol). The reaction mixture is degassed for 20 min with nitrogen. Tetrakis(triphenylphosphine)palladium(0) (2.54 g, 2.2 mmol) is added, the reaction mixture degassed for 10 min, and heated at reflux overnight. The reaction mixture is cooled to room temperature and then partitioned between hexanes and water. The aqueous layer is extracted with hexanes (3×75 mL). The combined organic layers are washed with brine, dried (magnesium sulfate), filtered, and concentrated under reduced pressure. Purification by flash column chromatography (9:1 hexanes/ethyl acetate) provides the title compound. $^1$H NMR (300 MHz, DMSO-$d_6$) δ 7.96 (m, 1H), 7.85 (d, J=8 Hz, 1H), 7.75 (d, J=8 Hz, 1H), 7.56 (m, 1H) 5.58 (s, 1H), 5.23 (m, 1H), 2.13 (s, 3H).

Step 2

3-Isopropylbenzylamine hydrochloride

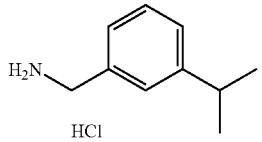

A solution of 3-isopropenylbenzonitrile (6.0 g, 41.9 mmol) and 10% Pd/C (600 mg) in ethanol (65 mL) and acetic acid (2.4 mL) is degassed with nitrogen for 15 min, and shaken under an atmosphere of hydrogen at 50 psi for 12 h. The reaction mixture is filtered through diatomaceous earth and concentrated under reduced pressure to provide an oil. The oil is dissolved in methanol (5 mL) and hydrochloric acid (15 mL of a 1 M solution in diethyl ether) is added. The resulting precipitate is collected by filtration to provide the title compound. APCI MS m/z 149 [M+H]$^+$.

Step 3 tert-Butyl (1S,2R)-1-(3,5-difluorobenzyl)-2-hydroxy-3-[(3-isopropylbenzyl)amino]propylcarbamate

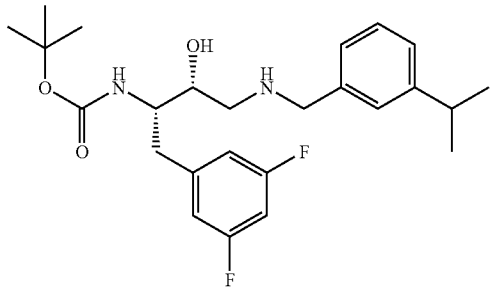

tert-Butyl (1S)-2-(3,5-difluorophenyl)-1-[(2S)-oxiran-2-yl]ethylcarbamate (2.0 g, 6.7 mmol) and 3-isopropylbenzylamine hydrochloride (2.5 g, 13.5 mmol) in isopropanol (60 mL) are refluxed 3 h. The reaction is cooled and stirred 16 h. The solution is concentrated under reduced pressure, redissolved in chloroform, washed with 1N hydrochloric acid, saturated sodium bicarbonate, brine, dried (sodium sulfate), filtered and concentrated under reduced pressure. Purification by flash chromatography (silica, 7% methanol/chloroform) gives the title compound in pure form. ESI MS m/z 449.3 [M+H]$^+$.

Step 4

(2R,3S)-3-amino-4-(3,5-difluorophenyl)-1-[(3-isopropylbenzyl)amino]butan-2-ol dihydrochloride

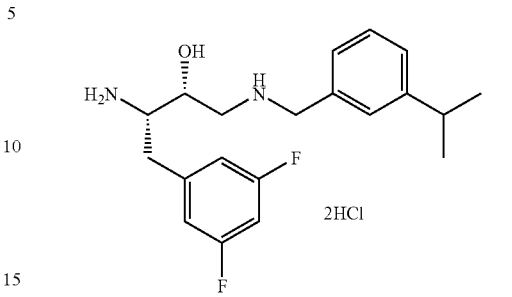

tert-Butyl (1S,2R)-1-(3,5-difluorobenzyl)-2-hydroxy-3-[(3-isopropylbenzyl)amino]propylcarbamate (1.5 g, 3.3 mmol) is dissolved in 4 N hydrochloric acid in dioxane (20 mL), and the reaction is stirred at room temperature 3 h. The mixture is concentrated under reduced pressure to afford the title compound. ESI MS m/z 349.2 [M+H]$^+$.

Step 5

Methyl 3-[(dipropylamino)carbonyl]-5-(1,3-thiazol-2-yl)benzoate

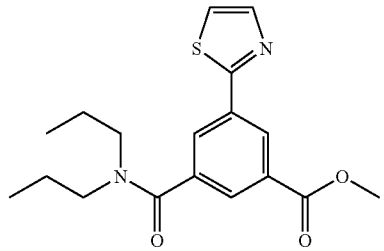

To 0.5 M thiazole zinc bromide in tetrahydrofuran (45 mL) is added methyl 3-[(dipropylamino)carbonyl]-5-iodobenzoate (8.6 g, 21.4 mmol) in anhydrous tetrahydrofuran (130 mL) followed by palladium(0)tetrakis(triphenylphosphine) (2 g, 1.7 mmol). The reaction mixture is heated at reflux for 16 h. The reaction mixture is diluted with ethyl acetate (50 mL), washed with water, saturated sodium bicarbonate, and brine, dried (magnesium sulfate), filtered, and concentrated under reduced pressure. Purification by flash column chromatography (silica gel, 35% ethyl acetate/hexanes) provides the title compound. ESI MS m/z 347.1 [M+H]$^+$.

Step 6

3-[(Dipropylamino)carbonyl]-5-(1,3-thiazol-2-yl)benzoic acid

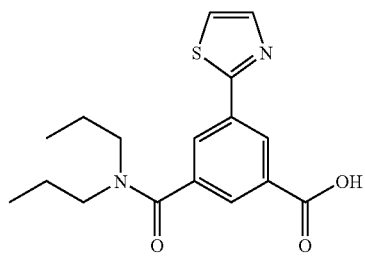

Methyl 3-[(dipropylamino)carbonyl]-5-(1,3-thiazol-2-yl)benzoate (4.4 g, 12.8 mmol) is dissolved in 1:1:1 tetrahydrofuran/methanol/water (60 mL), and lithium hydroxide monohydrate is added (1.1 g, 25.6 mmol). The reaction is stirred 15 min and is concentrated under reduced pressure. The residue is diluted in chloroform and washed with water, brine, dried (magnesium sulfate), filtered, and concentrated under reduced pressure to give the title compound. ESI MS m/z 333.1 [M+H]$^+$.

Step 7
$N^1$-{(1S,2R)-1-(3,5-Difluorobenzyl)-2-hydroxy-3-[(3-isopropylbenzyl)amino]propyl}-$N^3$,$N^3$-dipropyl-5-(1,3-thiazol-2-yl)isophthalamide

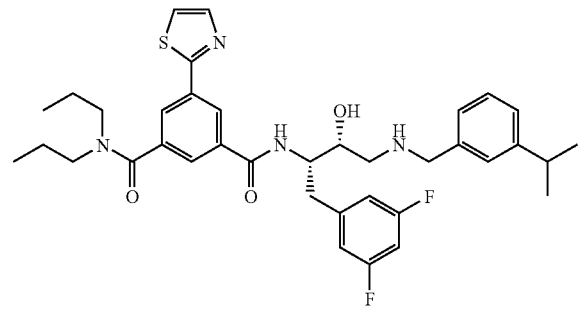

3-[(Dipropylamino)carbonyl]-5-(1,3-thiazol-2-yl)benzoic acid is dissolved in DMF (8 mL), and diisopropylethylamine (456 µL, 2.6 mmol), HATU (342 mg, 0.9 mmol), and (2R,3S)-3-amino-4-(3,5-difluorophenyl)-1-[(3-isopropylbenzyl)amino]butan-2-ol dihydrochloride (350 mg, 0.83 mmol) are added. The reaction stirred at room temperature 1 h. The reaction is partitioned between ethyl acetate and water. The organic layer is washed with 1 N hydrochloric acid, saturated sodium bicarbonate, and brine, dried (sodium sulfate), filtered, and concentrated under reduced pressure. Purification by flash column chromatography (silica, 8% methanol/chloroform) provides the title compound as the free base. The residue is dissolved in diethyl ether (5 mL) and 1N hydrochloric acid in diethyl ether (2 mL) is added. The mixture is concentrated under reduced pressure to yield the title compound. ESI MS m/z 663.3 [M+H]$^+$.

Example SP-171

$N^1$-{(1S,2R)-1-(3,5-Difluorobenzyl)-2-hydroxy-3-[(3-isopropylbenzyl)amino]propyl}-$N^3$,$N^3$-dipropyl-5-(1,3-thiazol-2-yl)isophthalamide hydrochloride

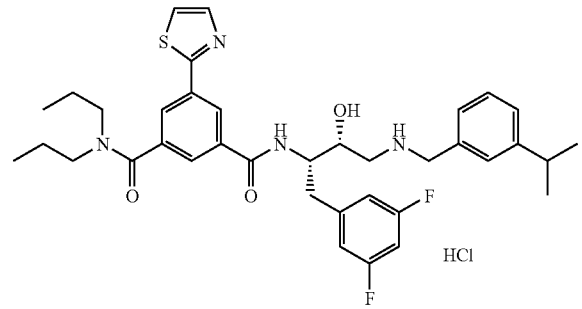

$N^1$-{(1S,2R)-1-(3,5-Difluorobenzyl)-2-hydroxy-3-[(3-isopropylbenzyl)amino]propyl}-$N^3$,$N^3$-dipropyl-5-(1,3-thiazol-2-yl)isophthalamide (180 mg, 0.27 mmol) is dissolved in diethyl ether (5 mL) and 1N hydrochloric acid in diethyl ether (2 mL) is added. The mixture is concentrated under reduced pressure to yield the title compound. ESI MS m/z 663.3 [M+H]$^+$.

Example SP-172

Methyl 3-(2-{3-[({(1S,2R)-1-(3,5-difluorobenzyl)-3-[(3-ethylbenzyl)amino]-2-hydroxypropyl}amino)carbonyl]phenyl}-1,3-oxazol-5-yl)propanoate Step 1
Methyl 3-{[(5-methoxy-2,5-dioxopentyl)amino]carbonyl}benzoate

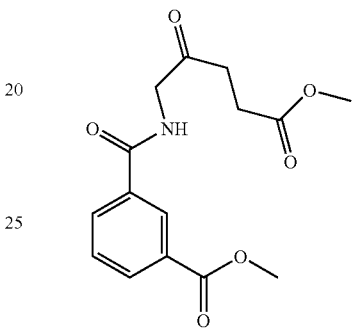

Methyl hydrogen isophthalate (1.8 g, 10.2 mmol) is dissolved in methylene chloride (10 mL) and DMF (10 mL), and diisopropylethylamine (4.4 mL, 25.5 mmol), HATU (4.6 g, 12.2 mmol), and 5-aminolevulinic acid methyl ester hydrochloride (2 g, 11.2 mmol) are added. The reaction stirred at room temperature 1 h. The reaction is partitioned between ethyl acetate and water. The organic layer is washed with 1 N hydrochloric acid, saturated sodium bicarbonate, and brine, dried (magnesium sulfate), filtered, and concentrated under reduced pressure. Purification by flash column chromatography (silica, 4% methanol/chloroform) provides the title compound. ESI MS m/z 306.1 [M–H]$^-$.

Step 2
Methyl 3-[5-(3-methoxy-3-oxopropyl)-1,3-oxazol-2-yl]benzoate

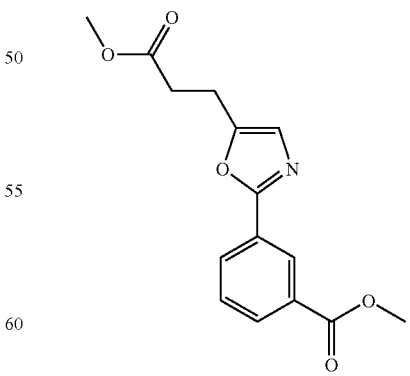

Methyl 3-{[(5-methoxy-2,5-dioxopentyl)amino]carbonyl}benzoate (520 mg, 1.7 mmol) is dissolved in anhydrous tetrahydrofuran (4 mL), and (methoxycarbonylsulfamoyl)triethylammonium hydroxide, inner salt (810 mg, 3.4 mmol). The reaction is microwaved (100 W, 2 min) in a sealed vessel, cooled, filtered, and concentrated under reduced pressure. Purification by flash chromatography (silica gel, 40% ethyl acetate/hexanes) gives the title compound. ESI MS m/z 290.1 [M+H]$^+$.

Step 3

3-[5-(2-Carboxyethyl)-1,3-oxazol-2-yl]benzoic acid

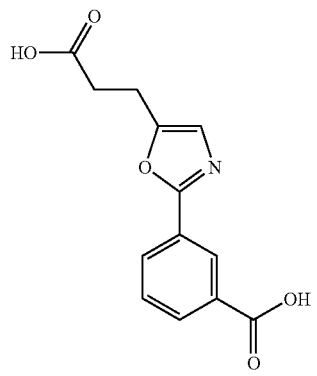

To methyl 3-[5-(3-methoxy-3-oxopropyl)-1,3-oxazol-2-yl]benzoate (400 mg, 1.3 mmol) in 2:1:1 tetrahydrofuran/methanol/water (8 mL) is added lithium hydroxide monohydrate (112 mg, 2.7 mmol), and the reaction is stirred 2 h at room temperature. More lithium hydroxide monohydrate (225 mg, 5.4 mmol) is added and the reaction is stirred 16 h at room temperature. The reaction is treated with excess concentrated hydrochloric acid resulting in a precipitate. The precipitate is filtered to give the title compound. ESI MS m/z 260.1 [M–H]$^-$.

Step 4

3-[5-(3-Methoxy-3-oxopropyl)-1,3-oxazol-2-yl]benzoic acid

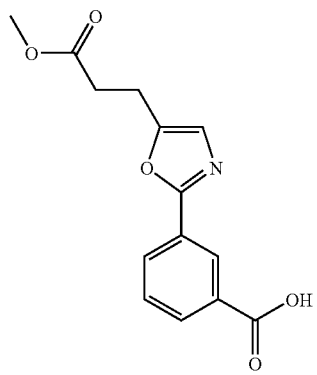

To 3-[5-(2-carboxyethyl)-1,3-oxazol-2-yl]benzoic acid (317 mg, 1.2 mmol) in methanol (5 mL) is added thionyl chloride (4.4 µL, 0.06 mmol), and the reaction is stirred at room temperature 16 h. The solution is concentrated under reduced pressure to give the title compound. ESI MS m/z 274.1 [M–H]$^-$.

Step 5

Methyl 3-(2-{3-[({(1S,2R)-1-(3,5-difluorobenzyl)-3-[(3-ethylbenzyl)amino]-2-hydroxypropyl}amino)carbonyl]phenyl}-1,3-oxazol-5-yl)propanoate

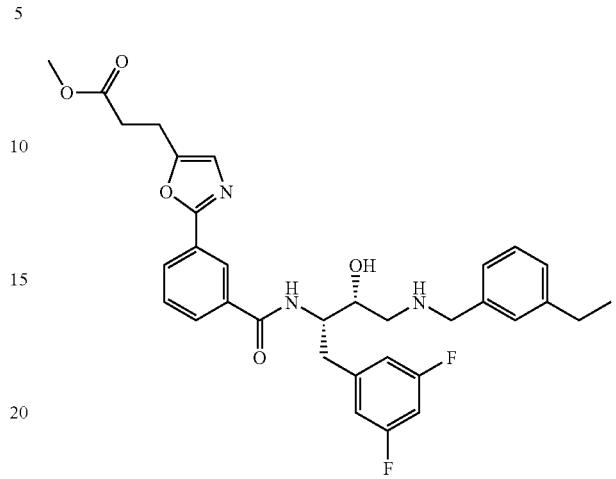

3-[5-(3-Methoxy-3-oxopropyl)-1,3-oxazol-2-yl]benzoic acid (285 mg, 1.0 mmol) is dissolved in methylene chloride (5 mL) and DMF (5 mL), and diisopropylethylamine (695 µL, 4.0 mmol), HATU (472 g, 1.2 mmol), and (2R,3S)-3-amino-4-(3,5-difluorophenyl)-1-[(3-ethylbenzyl)amino]butan-2-ol dihydrochloride prepared by the method of Example SP-272 (448 mg, 1.1 mmol) are added. The reaction stirred at room temperature 1 h. The reaction is partitioned between ethyl acetate and saturated sodium bicarbonate. The organic layer is washed with 1 N hydrochloric acid, saturated sodium bicarbonate, and brine, dried (sodium sulfate), filtered, and concentrated under reduced pressure. Purification by flash column chromatography (silica, 8% methanol/chloroform) provides the title compound. ESI MS m/z 591.9 [M+H]$^+$.

Example SP-173

3-(2-{3-[({(1S,2R)-1-(3,5-bifluorobenzyl)-3-[(3-ethylbenzyl)amino]-2-hydroxypropyl}amino)carbonyl]phenyl}-1,3-oxazol-5-yl)propanoic acid

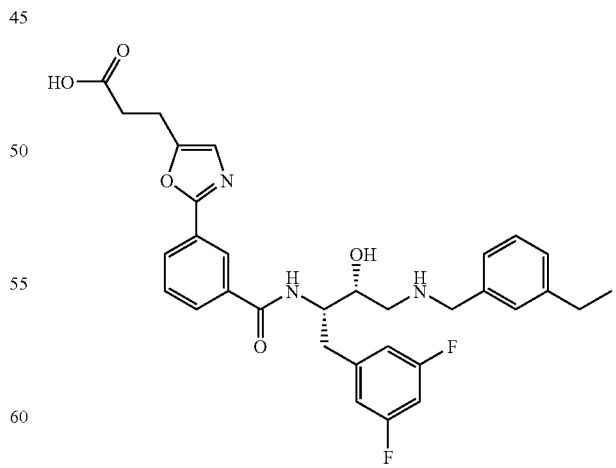

Methyl 3-(2-{3-[({(1S,2R)-1-(3,5-difluorobenzyl)-3-[(3-ethylbenzyl)amino]-2-hydroxypropyl}amino)carbonyl]phenyl}-1,3-oxazol-5-yl)propanoate (70 mg, 0.12 mmol) and lithium hydroxide monohydrate (10 mg, 0.24 mmol) in 2:1:1 tetrahydrofuran/methanol/water (6 mL) is stirred at room temperature 1.5 h. The reaction is concentrated under reduced pressure. The residue is washed with 1N hydrochloric acid (aq), then chloroform, and the solid is dried under reduced pressure to give the title compound. ESI MS m/z 578.2 [M+H]+.

Example SP-174

N-{(1S,2R)-1-(3,5-Difluorobenzyl)-3-[(3-ethylbenzyl)amino]-2-hydroxypropyl}-4-(1,3-oxazol-2-yl)benzamide Step 1
Methyl 4-(1,3-oxazol-2-yl)benzoate

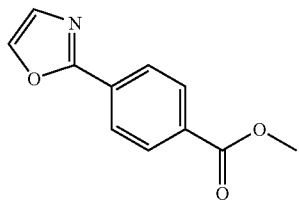

To a −70° C., stirred solution of oxazole (190 µL, 3.8 mmol) in tetrahydrofuran (10 mL) is added n-butyl lithium (2.6 mL of a 1.6 M solution in hexanes, 4.2 mmol). After 30 min, zinc chloride (11.5 mL of a 1.0 M solution in diethyl ether, 11.5 mmol) is added. The reaction mixture is warmed to 0° C. and methyl 4-iodobenzoate (1 g, 3.8 mmol) and palladium(0)tetrakis(triphenylphosphine) (530 mg, 0.4 mmol) are added. The reaction mixture is heated at 70° C. for 20 h under argon, cooled to room temperature, and then partitioned between ethyl acetate and water. The organic layer is washed with water and brine, dried (sodium sulfate), filtered, and concentrated under reduced pressure. Purification by flash column chromatography (3:1 hexanes/ethyl acetate) yields the title compound. ¹H NMR (300 MHz, CDCl₃) δ 8.14 (s, 4H), 8.07-8.05 (m, 1H), 7.36-7.35 (m, 1H), 3.95 (s, 3H).

Step 2
4-(1,3-Oxazol-2-yl)benzoic acid

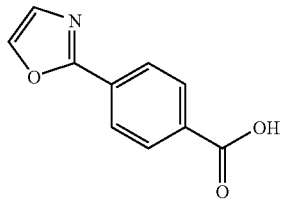

To a stirred solution of methyl 4-(1,3-oxazol-2-yl)benzoate (690 mg, 3.4 mmol) in a mixture of 2:1:1 tetrahydrofuran/methanol/water (20 mL) is added lithium hydroxide (430 mg, 3 mmol). The reaction mixture is stirred at room temperature for 2 h. The solvent is removed under reduced pressure and the residue is partitioned between diethyl ether and water. The aqueous layer is acidified to pH 1 with 1 N hydrochloric acid and a precipitate is observed. The solid is collected by filtration to afford the title compound. ¹H NMR (300 MHz, CD₃OD) δ 8.14 (s, 4H), 8.05 (s, 1H), 7.36 (s, 1H).

Step 3
N-{(1S,2R)-1-(3,5-Difluorobenzyl)-3-[(3-ethylbenzyl)amino]-2-hydroxypropyl}-4-(1,3-oxazol-2-yl)benzamide

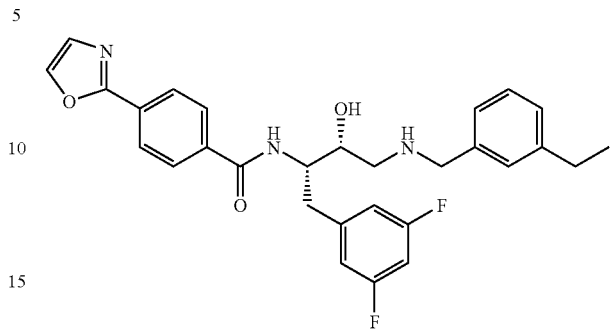

To a solution of 4-(1,3-oxazol-2-yl)benzoic acid (105 mg, 0.6 mmol), (2R,3S)-3-amino-4-(3,5-difluorophenyl)-1-[(3-ethylbenzyl)amino]butan-2-ol dihydrochloride (220 mg, 0.6 mmol), and HATU (210 mg, 0.6 mmol) stirring in methylene chloride (5 mL) is added N,N-diisopropylethylamine (340 µL, 1.9 mmol). The reaction mixture is stirred at room temperature for 18 h. The reaction mixture is partitioned between methylene chloride and water. The organic layer is washed with water, dried (sodium sulfate), filtered, and concentrated under reduced pressure to afford a crude solid. Purification by flash column chromatography (silica, gradient 96:4 to 93:7 methylene chloride/methanol) provided the title compound. ESI MS m/z 506.2 [M+H]+.

Example SP-173

N-{(1S,2R)-1-(3,5-difluorobenzyl)-3-[(3-ethylbenzyl)amino]-2-hydroxypropyl}-4-(1,3-thiazol-2-yl)benzamide Step 1
Methyl 4-(1,3-thiazol-2-yl)benzoate

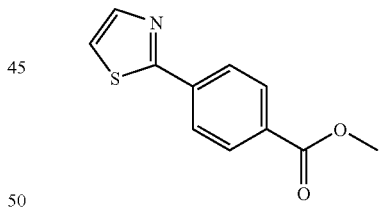

To a −70° C., stirred solution of thiazole (270 µL, 3.8 mmol) in tetrahydrofuran (10 mL) is added n-butyl lithium (2.6 mL of a 1.6 M solution in hexanes, 4.2 mmol). After 30 min, zinc chloride (11.4 mL of a 1.0 M solution in diethyl ether, 11.4 mmol) is added. The reaction mixture is warmed to 0° C. and methyl 4-iodobenzoate (1 g, 3.8 mmol) and palladium(0)tetrakis(triphenylphosphine) (530 mg, 0.4 mmol) are added. The reaction mixture is heated at 70° C. for 20 h under argon, cooled to room temperature, and then partitioned between ethyl acetate and water. The organic layer is washed with water, and brine, dried (sodium sulfate), filtered, and concentrated under reduced pressure. Purification by flash column chromatography (3:1 hexanes/ethyl acetate) yields the title compound. ¹H NMR (300 MHz, CDCl₃) δ 8.14-8.03 (m, 4H), 7.93-7.92 (m, 1H), 7.42-7.41 (m, 1H), 3.95 (s, 3H).

Step 2
4-(1,3-Thiazol-2-yl)benzoic acid

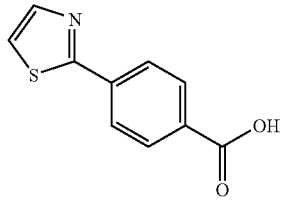

To a stirred solution of methyl 4-(1,3-thiazol-2-yl)benzoate (560 mg, 2.6 mmol) in a mixture of 2:1:1 tetrahydrofuran/methanol/water (20 mL) is added lithium hydroxide (322 mg, 3 mmol). The reaction mixture is stirred at room temperature for 2 h. The solvent is removed under reduced pressure and the residue is partitioned between diethyl ether and water. The aqueous layer is acidified to pH 1 with 1 N hydrochloric acid and a precipitate is observed. The solid is collected by filtration to afford the title compound. $^1$H NMR (300 MHz, CD$_3$OD) δ 8.14-8.05 (m, 4H), 7.95-7.93 (m, 1H), 7.71-7.69 (m, 1H).

Step 3
N-{(1S,2R)-1-(3,5-difluorobenzyl)-3-[(3-ethylbenzyl)amino]-2-hydroxypropyl}-4-(1,3-thiazol-2-yl)benzamide

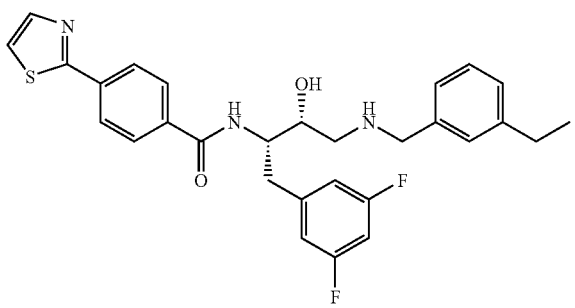

To a solution of 4-(1,3-thiazol-2-yl)benzoic acid (110 mg, 0.6 mmol), (2R,3S)-3-amino-4-(3,5-difluorophenyl)-1-[(3-ethylbenzyl)amino]butan-2-ol dihydrochloride (220 mg, 0.6 mmol), and HATU (210 mg, 0.6 mmol) stirring in methylene chloride (5 mL) is added N,N-diisopropylethylamine (340 µL, 1.9 mmol). The reaction mixture is stirred at room temperature for 18 h. The reaction mixture is partitioned between methylene chloride and water. The organic layer is washed with water, dried (sodium sulfate), filtered, and concentrated under reduced pressure. Purification by flash column chromatography (silica, gradient 95:5 to 92:8 methylene chloride/methanol) provides the title compound. ESI MS m/z 522.2 [M+H]$^+$.

Example SP-176

N-{(1S,2R)-1-(3,5-Difluorobenzyl)-3-[(3-ethylbenzyl)amino]-2-hydroxypropyl}-3-[(3H-[1,2,3]triazolo[4,5-b]pyridin-3-yloxy)methyl]benzamide

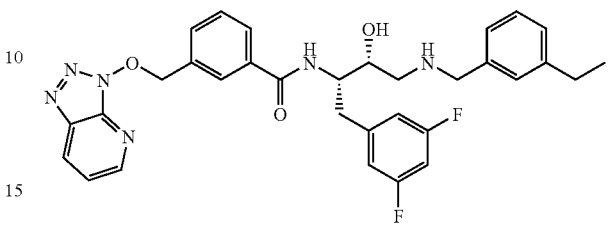

To 3-(bromomethyl)benzoic acid (200 mg, 0.93 mmol) and diisopropylethylamine (566 µL, 3.26 mmol) in DMF (5 mL) is added HATU (424 mg, 1.12 mmol), and the reaction is stirred 5 min. To the reaction is added (2R,3S)-3-amino-4-(3,5-difluorophenyl)-1-[(3-ethylbenzyl)amino]butan-2-ol dihydrochloride prepared by the method in Example SP-272 (379 mg, 0.93 mmol), and the reaction stirred 30 min. The reaction mixture is diluted with methylene chloride, washed with 1 N hydrochloric acid (15 mL), saturated sodium bicarbonate (15 mL), and brine. The organic layer is then dried (sodium sulfate), filtered, and concentrated under reduced pressure. Purification by flash column chromatography (silica, 8% methanol/chloroform) provides the title compound. ESI MS m/z 587.4 [M+H]$^+$.

Example SP-177

N-{(1S,2R)-1-(3,5-Difluorobenzyl)-2-hydroxy-3-[(3-iodobenzyl)amino]propyl}-3-{[(2-hydroxyethyl)(propyl)amino]methyl}-5-methylbenzamide dihydrochloride

Step 1
3-Bromo-5-(hydroxymethyl)benzoic acid

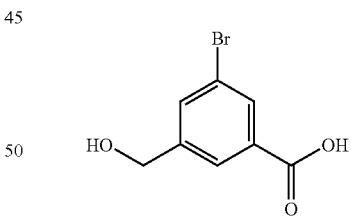

To an ice-cold solution of 3-bromo-5-(methoxycarbonyl)benzoic acid prepared by the method in Preparation 2 (10.3 g, 40 mmol) in anhydrous tetrahydrofuran (100 mL) is added lithium borohydride (12 g, 550 mmol) portion-wise. The reaction is stirred 4 h at this temperature. Absolute ethanol (20 mL) is added dropwise, and the reaction is stirred 1.5 h. The reaction is slowly poured on ice, and 10% hydrochloric acid (aq) is added until gas evolution ceased. The aqueous layer is extracted with chloroform, and the organic layer is washed with brine, dried (magnesium sulfate), filtered, and concentrated under reduced pressure to give the title compound. ESI MS m/z 229, 231 [M−H]$^-$.

Step 2
Methyl 3-bromo-5-(hydroxymethyl)benzoate

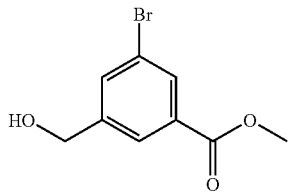

To 3-bromo-5-(hydroxymethyl)benzoic acid (7.0 g, 30 mmol) in 20% methanol/benzene (100 mL) is added trimethylsilyldiazomethane (2M in hexanes), and the reaction is stirred 16 h. The reaction is concentrated under reduced pressure to afford the title compound. ESI MS m/z 244.0 [M+H]$^+$.

Step 3
Methyl 3-(hydroxymethyl)-5-methylbenzoate

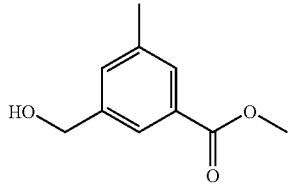

To a stirred solution of methyl 3-bromo-5-(hydroxymethyl)benzoate (3.0 g, 12.2 mmol) in dioxane (27 mL) is added cesium carbonate (4.0 g, 12.2 mmol), potassium carbonate (34 g, 24.4 mmol), and palladium(0)tetrakis(triphenylphosphine) (704 mg, 0.61 mmol), followed by trimethyl boroxine (1.7 mL, 12.2 mmol). The reaction mixture is refluxed for 5 h, cooled to room temperature, and then partitioned between water and ethyl acetate. The organic layer is washed with water, saturated sodium bicarbonate, and brine, dried (magnesium sulfate), filtered, and concentrated under reduced pressure. Purification by flash column chromatography (silica, 20% ethyl acetate/hexanes) provides the title compound. ESI MS m/z 181.2 [M+H]$^+$.

Step 4
N-{(1S,2R)-1-(3,5-Difluorobenzyl)-2-hydroxy-3-[(3-iodobenzyl)amino]propyl}-3-{[(2-hydroxyethyl)(propyl)amino]methyl}-5-methylbenzamide dihydrochloride

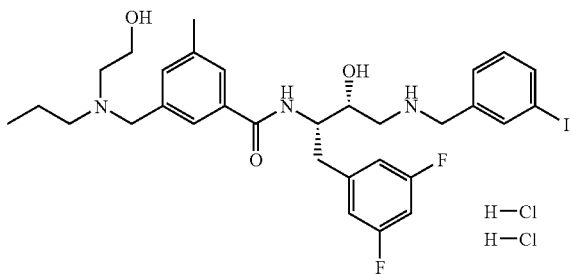

To a stirred solution of methyl 3-(hydroxymethyl)-5-methylbenzoate (1.25, 7 mmol) in methylene chloride (30 mL) at −30° C. is added methanesulfonyl chloride (752 µL, 9.7 mmol) followed by triethylamine (1.95 mL, 14 mmol). The reaction mixture is stirred for 15 min at 0° C. The reaction is diluted in diethyl ether and washed with water and cold brine, dried (magnesium sulfate), filtered and concentrated under reduced pressure to give an oil. The residue is redissolved in anhydrous methylene chloride (22 mL). From this stock solution, 2 mL is added to a solution of N-hydroxyethylpropylamine (115 µL, 1 mmol) in anhydrous methylene chloride (1 mL), and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 4% methanol/chloroform) provided the amine. The amine is dissolved in 1:1:1 tetrahydrofuran/methanol/water (3 mL), and lithium hydroxide monohydrate is added (33 mg, 0.75 mmol). The reaction is stirred 2 h and is concentrated under reduced pressure. The residue is redissolved in DMF (3 mL), and diisopropylethylamine (261 µL, 1.5 mmol), HATU (214 mg, 0.56 mmol), and (2R,3S)-3-amino-4-(3,5-difluorophenyl)-1-[(3-iodobenzyl)amino]butan-2-ol dihydrochloride (189 mg, 0.37 mmol) are added. The reaction stirred at room temperature 16 h. Purification by flash column chromatography (silica, 8% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 666.2 [M+H]$^+$.

Example SP-178

N-{(1S,2R)-1-(3,5-Difluorobenzyl)-2-hydroxy-3-[(3-iodobenzyl)amino]propyl}-3-{[ethyl(propyl)amino]methyl}-5-methylbenzamide dihydrochloride

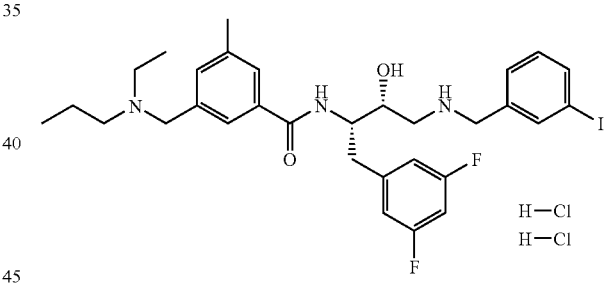

Analogous to the method described in Example SP-177, Step 4, 2 mL of the stock solution is added to a solution of N-ethylpropylamine (143 µL, 1 mmol) in anhydrous methylene chloride (1 mL), and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 4% methanol/chloroform) provided the amine. The amine is dissolved in 1:1:1 tetrahydrofuran/methanol/water (3 mL), and lithium hydroxide monohydrate is added (42 mg, 1 mmol). The reaction is stirred 2 h and is concentrated under reduced pressure. The residue is redissolved in DMF (5 mL), and diisopropylethylamine (265 µL, 1.5 mmol), (2R,3S)-3-amino-4-(3,5-difluorophenyl)-1-[(3-iodobenzyl)amino]butan-2-ol dihydrochloride (252 mg, 0.5 mmol), and HATU (237 mg, 0.62 mmol) are added. The reaction stirred at room temperature 16 h. Purification by flash column chromatography (silica, 10% methanol/chloroform) provides the title compound as the free base. The residue is dissolved in diethyl

Example SP-179

N-{(1S,2R)-1-(3,5-Difluorobenzyl)-2-hydroxy-3-[(3-iodobenzyl)amino]propyl}-3-{[(2-hydroxyethyl)(propyl)amino]methyl}benzamide dihydrochloride Step 1

Methyl 3-{[(2-hydroxyethyl)(propyl)amino]methyl}benzoate

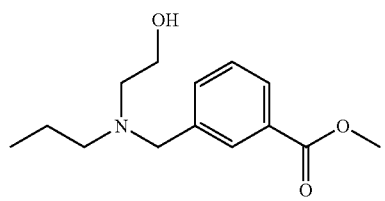

To 2-propylaminomethanol (505 μL, 4.4 mmol) in chloroform (20 mL) is added methyl bromomethylbenzoate (1 g, 4.4 mmol), and the reaction stirred at room temperature 16 h. The reaction is washed with saturated sodium bicarbonate and brine. The organic layer is then dried (sodium sulfate), filtered, and concentrated under reduced pressure. Purification by flash column chromatography (silica, 80% ethyl acetate/hexanes) provides the title compound. ESI MS m/z 252.3 [M+H]$^+$.

Step 2

N-{(1S,2R)-1-(3,5-Difluorobenzyl)-2-hydroxy-3-[(3-iodobenzyl)amino]propyl}-3-{[(2-hydroxyethyl)(propyl)amino]methyl}benzamide dihydrochloride

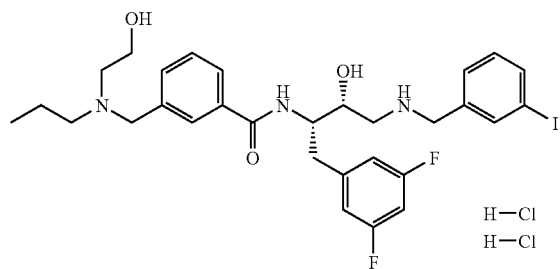

Methyl 3-{[(2-hydroxyethyl)(propyl)amino]methyl}benzoate (500 mg, 2 mmol) and lithium hydroxide monohydrate (170 mg, 4 mmol) are stirred in 2:1:1 tetrahydrofuran/methanol/water (4 mL) at room temperature for 16 h. The reaction is concentrated under reduced pressure and redissolved in DMF (15 mL). To this solution is added (2R,3S)-3-amino-4-(3,5-difluorophenyl)-1-[(3-iodobenzyl)amino]butan-2-ol dihydrochloride (1 g, 2 mmol), diisopropylethylamine (1.4 mL, 8 mmol), then HATU (1.1 g, 3 mmol), and the reaction stirred 2 h. Purification by flash column chromatography (silica, 10% methanol/chloroform) provides the title compound as the free base. The residue is dissolved in diethyl ether (5 mL) and 1N hydrochloric acid in diethyl ether (3 mL) is added. The mixture is concentrated under reduced pressure to yield the title compound. ESI MS m/z 652.2 [M+H]$^+$.

Example SP-180

N-{(1S,2R)-1-(3,5-Difluorobenzyl)-2-hydroxy-3-[(3-iodobenzyl)amino]propyl}-3-methyl-5-{[methyl(propyl)amino]methyl}benzamide dihydrochloride

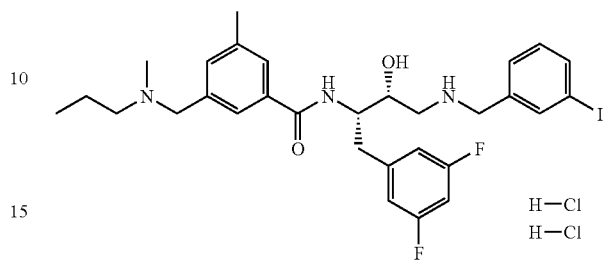

Analogous to the method described in Example SP-177, Step 4, 2 mL of the stock solution is added to a solution of N-methylpropylamine (103 μL, 1 mmol) in anhydrous methylene chloride (1 mL), and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 4% methanol/chloroform) provided the amine. The amine is dissolved in 1:1:1 tetrahydrofuran/methanol/water (3 mL), and lithium hydroxide monohydrate is added (33 mg, 0.75 mmol). The reaction is stirred 2 h and is concentrated under reduced pressure. The residue is redissolved in DMF (3 mL), and diisopropylethylamine (261 μL, 1.5 mmol), HATU (214 mg, 0.56 mmol), and (2R,3S)-3-amino-4-(3,5-difluorophenyl)-1-[(3-iodobenzyl)amino]butan-2-ol dihydrochloride (189 mg, 0.37 mmol) are added. The reaction stirred at room temperature 16 h. Purification by flash column chromatography (silica, 8% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 636.2 [M+H]$^+$.

Example SP-181

N-{(1S,2R)-1-(3,5-Difluorobenzyl)-2-hydroxy-3-[(3-iodobenzyl)amino]propyl}-3-[(dipropylamino)methyl]-5-methylbenzamide dihydrochloride

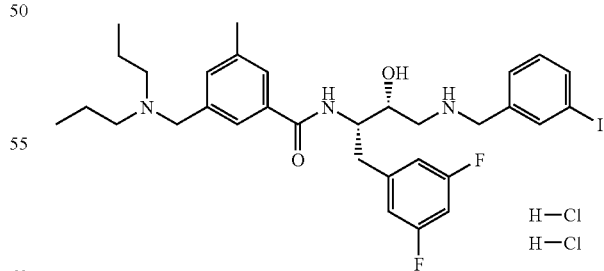

Analogous to the method described in Example SP-177, Step 4, 2 mL of the stock solution is added to a solution of dipropylamine (137 μL, 1 mmol) in anhydrous methylene chloride (1 mL), and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 4% methanol/chloroform) provided the amine. The amine is dissolved in 1:1:1 tetrahydrofuran/methanol/water (3 mL), and lithium hydroxide monohydrate is added (33 mg, 0.75 mmol). The reaction is stirred 2 h and is concentrated under reduced pressure. The residue is redissolved in DMF (3 mL), and diisopropylethylamine (261 µL, 1.5 mmol), HATU (214 mg, 0.56 mmol), and (2R,3S)-3-amino-4-(3,5-difluorophenyl)-1-[(3-iodobenzyl)amino]butan-2-ol dihydrochloride (189 mg, 0.37 mmol) are added. The reaction stirred at room temperature 16 h. Purification by flash column chromatography (silica, 8% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 664.2 [M+H]$^+$.

Example SP-182

3-{[Butyl(methyl)amino]methyl}-N-{(1S,2R)-1-(3,5-difluorobenzyl)-2-hydroxy-3-[(3-iodobenzyl)amino]propyl}-5-methylbenzamide dihydrochloride

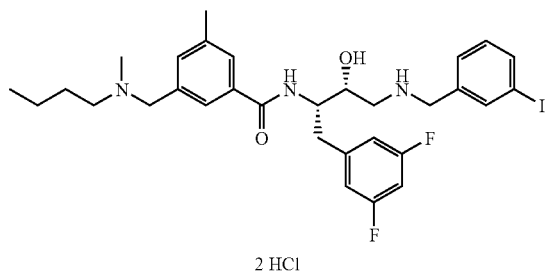

2 HCl

Analogous to the method described in Example SP-177 Step 4, 2 mL of the stock solution is added to a solution of N-methylbutylamine (118 µL, 1 mmol) in anhydrous methylene chloride (1 mL)), and the reaction mixture is stirred at room temperature for 5 h. The reaction mixture is diluted with methylene chloride (10 mL), washed with 1 N hydrochloric acid, and saturated sodium bicarbonate, dried (magnesium sulfate) filtered, and concentrated under reduced pressure. Purification by flash column chromatography (silica, 4% methanol/chloroform) provided the amine. The amine is dissolved in 1:1:1 tetrahydrofuran/methanol/water (3 mL), and lithium hydroxide monohydrate is added (33 mg, 0.75 mmol). The reaction is stirred 2 h and is concentrated under reduced pressure. The residue is redissolved in DMF (3 µL), and diisopropylethylamine (261 µL, 1.5 mmol), HATU (214 mg, 0.56 mmol), and (2R,3S)-3-amino-4-(3,5-difluorophenyl)-1-[(3-iodobenzyl)amino]butan-2-ol dihydrochloride (189 mg, 0.37 mmol) are added. The reaction stirred at room temperature 16 h. Purification by flash column chromatography (silica, 8% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 650.2 [M+H]$^+$.

Example SP-183

3-[(Cyclohexylamino)methyl]-N-{(1S,2R)-1-(3,5-difluorobenzyl)-2-hydroxy-3-[(3-iodobenzyl)amino]propyl}-5-methylbenzamide dihydrochloride

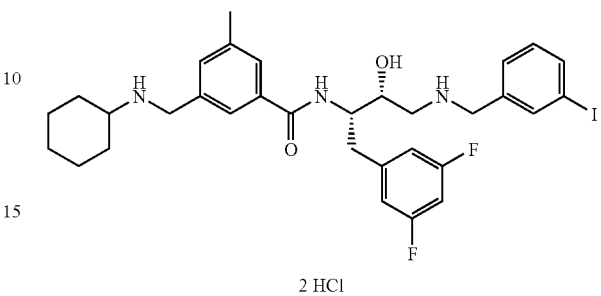

2 HCl

Analogous to the method described in Example SP-177, Step 4, 2 mL of the stock solution is added to a solution of cyclohexylamine (114 µL, 1 mmol) in anhydrous methylene chloride (1 mL), and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 4% methanol/chloroform) provided the amine. The amine is dissolved in 1:1:1 tetrahydrofuran/methanol/water (3 mL), and lithium hydroxide monohydrate is added (33 mg, 0.75 mmol). The reaction is stirred 2 h and is concentrated under reduced pressure. The residue is redissolved in DMF (3 mL), and diisopropylethylamine (261 µL, 1.5 mmol), HATU (214 mg, 0.56 mmol), and (2R,3S)-3-amino-4-(3,5-difluorophenyl)-1-[(3-iodobenzyl)amino]butan-2-ol dihydrochloride (189 mg, 0.37 mmol) are added. The reaction stirred at room temperature 16 h. Purification by flash column chromatography (silica, 8% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 662.2 [M+H]$^+$.

Example SP-184

3-{[benzyl(methyl)amino]methyl}-N-{(1S,2R)-1-(3,5-difluorobenzyl)-2-hydroxy-3-[(3-iodobenzyl)amino]propyl}-5-methylbenzamide dihydrochloride

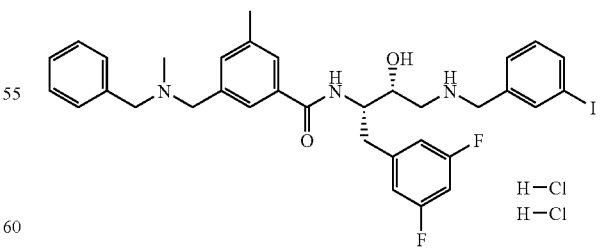

H—Cl
H—Cl

Analogous to the method described in Example SP-177, a stirred solution of methyl 3-(hydroxymethyl)-5-methylbenzoate (1.0, 5.6 mmol) in methylene, chloride (9 mL) at −30° C. is added methanesulfonyl chloride (600 µL, 7.8 mmol) followed by triethylamine (1.55 mL, 11 mmol). The reaction mixture is stirred for 1 h at 0° C., then filtered. From this stock solution, 2 mL is added to a solution of N-methylbenzylamine (538 μL, 4.2 mmol) in anhydrous methylene chloride (1 mL), and the reaction mixture is stirred at room temperature for 16 h. The reaction mixture is diluted with methylene chloride (10 mL), washed with saturated sodium bicarbonate and brine, dried (magnesium sulfate), filtered, and concentrated under reduced pressure. Purification by flash column chromatography (silica, 4% methanol/chloroform) provided the amine. The amine is dissolved in 2:1:1 tetrahydrofuran/methanol/water (4 mL), and lithium hydroxide monohydrate is added (90 mg, 2 mmol). The reaction is stirred 16 h and is concentrated under reduced pressure. The residue is redissolved in DMF (5 mL), and diisopropylethylamine (695 μL, 4 mmol), HATU (570 mg, 1.5 mmol), and (2R,3S)-3-amino-4-(3,5-difluorophenyl)-1-[(3-iodobenzyl)amino]butan-2-ol dihydrochloride (505 mg, 1 mmol) are added. The reaction stirred at room temperature 16 h. Purification by flash column chromatography (silica, 7% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 684.2 [M+H]$^+$.

Example SP-185

2-Butyl-N-{(1S,2R)-1-(3,5-difluorobenzyl)-3-[(3-ethyl-benzyl)amino]-2-hydroxypropyl}-1,2,3,4-tetrahydroisoquinoline-7-carboxamide dihydrochloride Step 1
2-Butyl-1,2,3,4-tetrahydroisoquinoline-7-carbonitrile

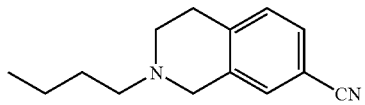

To an ice-cold, stirred solution of 1,2,3,4-tetrahydroisoquinoline-7-carbonitrile (J. Med. Chem. 1997, 40, 3997) (485 mg, 3.1 mmol) and triethylamine (0.47 mL, 3.4 mmol) in methylene chloride (5 mL) is added DMAP (37 mg, 0.3 mmol) and bromobutane (0.5 mL, 4.6 mmol). The reaction mixture is stirred for 20 h, diluted with methylene chloride, washed with water, and brine, dried (magnesium sulfate), filtered, and concentrated under reduced pressure. Purification by flash column chromatography (silica, 50% ethyl acetate/hexanes) affords the title compound. ESI MS m/z 215 [M+H]$^+$.

Step 2
2-Butyl-1,2,3,4-tetrahydroisoquinoline-7-carboxylic acid

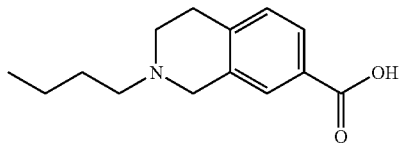

A sealed tube containing a solution of 2-butyl-1,2,3,4-tetrahydroisoquinoline-7-carbonitrile (480 mg, 2.2 mmol) in concentrated hydrochloric acid (10 mL) is stirred at 90° C. for 16 h. The reaction mixture is cooled to room temperature, concentrated ammonium hydroxide is added, and the precipitate formed is then collected by filtration to provide the title compound. ESI MS m/z 234 [M+H]$^+$.

Step 3
2-Butyl-N-{(1S,2R)-1-(3,5-difluorobenzyl)-3-[(3-ethyl-benzyl)amino]-2-hydroxypropyl}-1,2,3,4-tetrahydroisoquinoline-7-carboxamide dihydrochloride

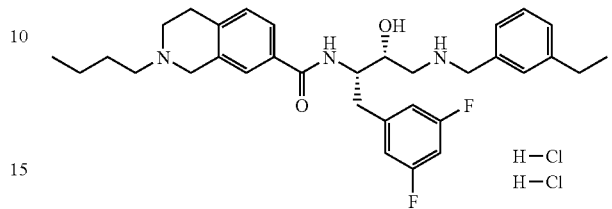

A solution of 2-butyl-1,2,3,4-tetrahydroisoquinoline-7-carboxylic acid (190 mg, 0.81 mmol), HATU (465 mg, 1.2 mmol), HOBt (162 mg, 1.2 mmol), and diisopropylethylamine (250 μL, 1.6 mmol) is stirred in methylene chloride (2.0 mL) for 15 min. A solution of (2R,3S)-3-amino-4-(3,5-difluorophenyl)-1-[(3-ethylbenzyl)amino]butan-2-ol prepared by the method in Example SP-272 (332 mg, 0.81 mmol) and diisopropylethylamine (250 μL, 1.6 mmol) in methylene chloride (2.0 mL) is added, and the reaction mixture is stirred overnight. The reaction mixture is diluted with methylene chloride, washed with 1 N hydrochloric acid (15 mL), saturated sodium bicarbonate (15 mL), and brine. The organic layer is then dried (magnesium sulfate), filtered, and concentrated under reduced pressure. Purification by flash column chromatography (silica, 1:9 methanol/chloroform) provides the title compound as the free base. The solid is dissolved in methanol (1 mL), and treated with hydrochloric acid (0.2 mL, 1.0 M diethyl ether, 0.2 mmol). The resulting precipitate was collected by filtration to provide the title compound. ESI MS m/z 550.3 [M+H]$^+$.

Example SP-186

3-{[Cyclohexyl(methyl)amino]methyl}-N-{(1S,2R)-1-(3,5-difluorobenzyl)-2-hydroxy-3-[(3-iodobenzyl)amino]propyl}-5-methylbenzamide dihydrochloride

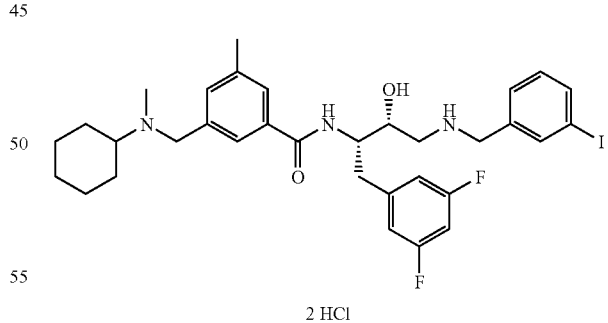

Analogous to the method described in Example SP-184, 2 mL of the stock solution is added to a solution of N-methyl-cyclohexylamine (545 μL, 4.2 mmol) in anhydrous methylene chloride (1 mL), and the reaction mixture is stirred at room temperature for 16 h. The reaction mixture is diluted with methylene chloride (10 mL), washed with saturated sodium bicarbonate and brine, dried (magnesium sulfate), filtered, and concentrated under reduced pressure. Purification by flash column chromatography (silica, 4% methanol/ chloroform) provided the amine. The amine is dissolved in 2:1:1 tetrahydrofuran/methanol/water (4 mL), and lithium hydroxide monohydrate is added (60 mg, 1.4 mmol). The reaction is stirred 16 h and is concentrated under reduced pressure. The residue is redissolved in DMF (4 mL), and diisopropylethylamine (465 µL, 2.7 mmol), HATU (380 mg, 1 mmol), and (2R,3S)-3-amino-4-(3,5-difluorophenyl)-1-[(3-iodobenzyl)amino]butan-2-ol dihydrochloride (340 mg, 0.67 mmol) are added. The reaction stirred at room temperature 16 h. Purification by flash column chromatography (silica, 7% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 676.2 [M+H]$^+$.

Example SP-187

5-{[Butyl(methyl)amino]methyl}-N-{(1S,2R)-1-(3,5-difluorobenzyl)-3-[(3-ethylbenzyl)amino]-2-hydroxypropyl}thiophene-2-carboxamide dihydrochloride Step 1

Methyl 5-(bromomethyl)thiophene-2-carboxylate

To an ice-cold solution of methyl 5-(hydroxymethyl)thiophene-2-carboxylate (375 mg, 2.17 mmol) in methylene chloride (9.0 mL) is added phosphorus tribromide (100 µL, 1.08 mmol) and the reaction mixture is stirred at 0° C. for 0.5 h. Saturated sodium bicarbonate (10 mL) is carefully added to the reaction mixture and the phases are separated. The organic phase is washed with water, dried (sodium sulfate), filtered, and concentrated under reduced pressure to yield the title compound in pure form. ESI MS m/z 235 [M+H]$^+$.

Step 2

Methyl 5-{[butyl(methyl)amino]methyl}thiophene-2-carboxylate

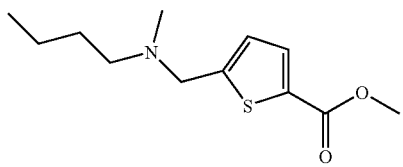

To a solution of methyl 5-(bromomethyl)thiophene-2-carboxylate (350 mg, 1.49 mmol) in dry acetone (6.0 mL) is added N-methylbutylamine (533 µL, 4.47 mmol) and the solution stirred at room temperature overnight. The reaction is then concentrated under reduced pressure, redissolved in methylene chloride, washed with saturated sodium bicarbonate, water, and brine. The organic layer is then dried (sodium sulfate), filtered, and concentrated under reduced pressure to yield the title compound in pure form. $^1$H NMR (300 MHz, CDCl$_3$) δ 7.65 (d, J=3 Hz, 1H), 6.88 (d, J=3 Hz, 1H), 3.86 (s, 3H), 3.69 (s, 2H), 2.41-2.36 (m, 2H), 2.25 (s, 3H), 1.53-1.43 (m, 2H), 1.34-1.25 (m, 2H), 0.91 (t, J=7 Hz, 3H).

Step 3

5-{[Butyl(methyl)amino]methyl}thiophene-2-carboxylic acid

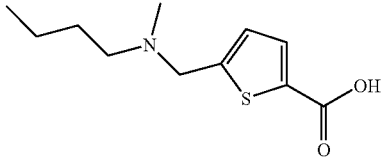

To a solution of methyl 5-{[butyl(methyl)amino]methyl}thiophene-2-carboxylate (280 mg, 1.16 mmol) in 2:1:1 dioxane/methanol/water (8.0 mL) is added lithium hydroxide monohydrate (146 mg, 3.38 mmol) and the reaction mixture stirred at room temperature overnight. The reaction mixture is concentrated under reduced pressure and the solid residue partitioned between ethyl acetate and water The aqueous phase is acidified to pH 1 with 1 N hydrochloric acid and extracted several times with 3:1 chloroform/2-propanol. The combined organic phase is washed with water, and brine, dried (sodium sulfate), filtered, and concentrated under reduced pressure to provide the title compound in pure form. $^1$H NMR (300 MHz, CD$_3$OD) δ 7.75 (d, J=4 Hz, 1H), 7.41 (d, J=4 Hz, 1H), 4.63 (s, 2H), 3.20-3.14 (m, 2H), 2.85 (s, 3H), 1.82-1.72 (m, 2H), 1.42 (tq, J 8, 7 Hz, 2H), 0.99 (t, J=7 Hz, 3H).

Step 4

5-{[Butyl(methyl)amino]methyl}-N-{(1S,2R)-1-(3,5-difluorobenzyl)-3-[(3-ethylbenzyl)amino]-2-hydroxypropyl}thiophene-2-carboxamide dihydrochloride

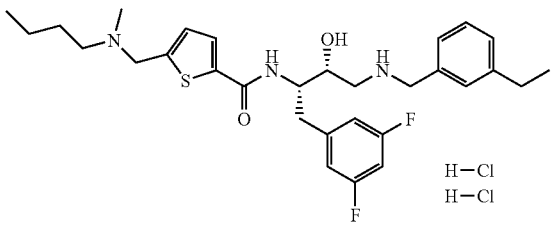

To a solution 5-{[butyl(methyl)amino]methyl}thiophene-2-carboxylic acid (171 mg, 0.75 mmol) and N,N-diisopropylethylamine (250 µL, 1.43 mmol) in methylene chloride (5.0 mL) is added HBTU (285 mg, 0.75 mmol) and the reaction stirred for 0.5 h. To this is added a solution of (2R,3S)-3-amino-4-(3,5-difluorophenyl)-1-[(3-ethylbenzyl)amino]butan-2-ol prepared by the method in Example SP-272 (306 mg, 0.75 mmol) in methylene chloride (5.0 mL) containing N,N-diisopropylethylamine (250 µL, 1.43 mmol). The reaction mixture is then stirred at room temperature overnight. The reaction mixture is diluted with methylene chloride, washed with saturated sodium bicarbonate, and brine. The organic layer is then dried (sodium sulfate), filtered, and concentrated under reduced pressure. Purification by flash column chromatography (silica, 95:5 chloroform/methanol) gives the title compound as the free base. The solid is dissolved in methanol (1 mL) and treated with hydrochloric acid (1.0 M diethyl ether). The resulting precipitate was collected by filtration to provide the title compound. ESI MS m/z 544.3 [M+H]+.

Example SP-188

3-{[Butyl(methyl)amino]methyl}-N-((1S,2R)-1-(3,5-difluorobenzyl)-3-{[1-(3-ethynylphenyl)cyclopropyl]amino}-2-hydroxypropyl)-5-methylbenzamide dihydrochloride Step 1

Methyl 3-{[butyl(methyl)amino]methyl}-5-methylbenzoate

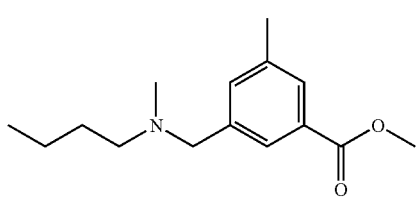

To methyl 3-(hydroxymethyl)-5-methylbenzoate prepared by the method in Example SP-177 (1.1 g, 6.1 mmol), in anhydrous methylene chloride (10 mL) is added methanesulfonyl chloride (663 µL, 8.6 mmol) at −30° C., and the reaction is warmed to 0° C. The reaction stirred 1 h, then filtered. The filtrate is added to N-methylbutylamine (2.1 mL, 18.3 mmol), and the reaction stirred at room temperature 16 h. The solution is concentrated under reduced pressure. Purification by flash chromatography affords the title compound in pure form. ESI MS m/z 250.2 [M+H]+.

Step 2

3-{[Butyl(methyl)amino]methyl}-N-((1S,2R)-1-(3,5-difluorobenzyl)-3-{[1-(3-ethynylphenyl)cyclopropyl]amino}-2-hydroxypropyl)-5-methylbenzamide dihydrochloride

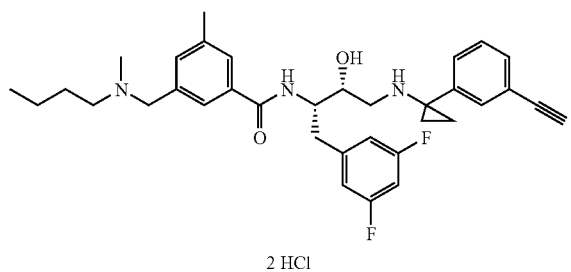

2 HCl

Methyl 3-{[butyl(methyl)amino]methyl}-5-methylbenzoate (122 mg, 0.49 mmol) is dissolved in 2:1:1 tetrahydrofuran/methanol/water (4 mL), and lithium hydroxide monohydrate is added (41 mg, 1 mmol), and the reaction stirred 16 h. The solution is concentrated under reduced pressure. The residue is redissolved in DMF (5 mL), and diisopropylethylamine (350 µL, 2 mmol), HATU (240 mg, 0.63 mmol), and (2R,3S)-3-amino-4-(3,5-difluorophenyl)-1-{[1-(3-ethynylphenyl)cyclopropyl]amino}butan-2-ol dihydrochloride prepared by the method in Example SP-272 (215 mg, 0.5 mmol) are added. The reaction stirred at room temperature 16 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 574.3 [M+H]+.

Example SP-189

3-{[Butyl(methyl)amino]methyl}-N-((1S,2R)-1-(3,5-difluorobenzyl)-2-hydroxy-3-{[3-(trifluoromethyl)benzyl]amino}propyl)-5-methylbenzamide dihydrochloride

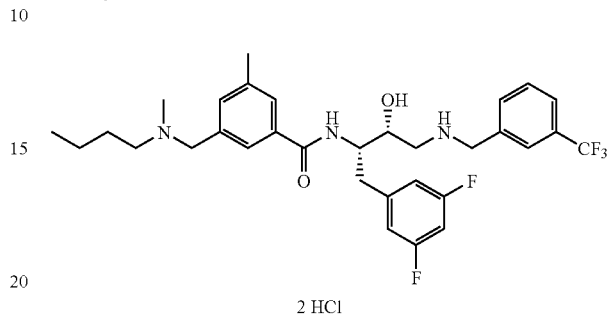

2 HCl

Analogous to the method in Example SP-188, methyl 3-{[butyl(methyl)amino]methyl}-5-methylbenzoate (112 mg, 0.45 mmol) is dissolved in 2:1:1 tetrahydrofuran/methanol/water (4 mL), and lithium hydroxide monohydrate is added (38 mg, 0.9 mmol), and the reaction stirred 16 h. The solution is concentrated under reduced pressure. The residue is redissolved in DMF (5 mL), and diisopropylethylamine (350 µL, 2 mmol), HATU (240 mg, 0.63 mmol), and (2R,3S)-3-amino-4-(3,5-difluorophenyl)-1-{[1-(3-ethynylphenyl)cyclopropyl]amino}butan-2-ol dihydrochloride prepared by the method in Example SP-272 (201 mg, 0.44 mmol) are added. The reaction stirred at room temperature 16 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 592.3 [M+H]+.

Example SP-190

3-Bromo-5-{[butyl(methyl)amino]methyl}-N-((1S,2R)-1-(3,5-difluorobenzyl)-3-{[1-(3-ethynylphenyl)cyclopropyl]amino}-2-hydroxypropyl)benzamide dihydrochloride Step 1

Methyl 3-bromo-5-{[butyl(methyl)amino]methyl}benzoate

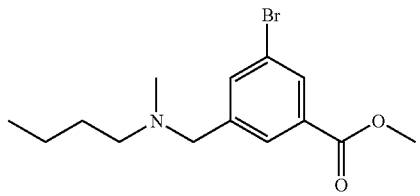

To a solution of methyl 3-bromo-5-(hydroxymethyl)benzoate (4.1 g, 16.8 mmol) in anhydrous methylene chloride (35 mL) at −30° C. is added methanesulfonyl chloride (1.82 mL, 23.5 mmol) followed by triethylamine (4.7 mL, 33.6 mmol). The reaction mixture is stirred for 45 min at 0° C., and then filtered. The filtrate is added to N-methylbutylamine (6 mL, 50.4 mmol) and stirred at room temperature for 16 h. The solution is concentrated under reduced pressure, and the residue is purified by flash column chromatography (silica, 8% ethyl acetate/hexanes) to give the title compound. ESI MS m/z 314.1 [M+H]+.

Step 2

3-Bromo-5-{[butyl(methyl)amino]methyl}-N-((1S,2R)-1-(3,5-difluorobenzyl)-3-{[1-(3-ethynylphenyl)cyclopropyl]amino}-2-hydroxypropyl)benzamide dihydrochloride

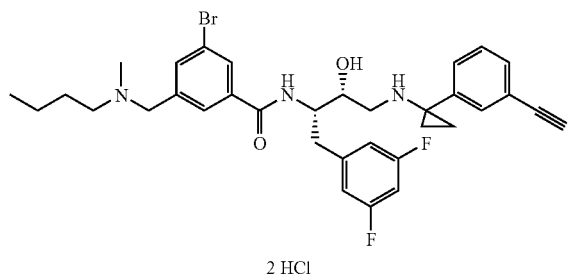

Methyl 3-bromo-5-{[butyl(methyl)amino]methyl}benzoate (113 mg, 0.36 mmol) is dissolved in 2:1:1 tetrahydrofuran/methanol/water (4 mL), and lithium hydroxide monohydrate is added (30 mg, 0.72 mmol), and the reaction stirred 16 h. The solution is concentrated under reduced pressure. The residue is redissolved in DMF (5 mL), and diisopropylethylamine (250 µL, 1.44 mmol), HATU (170 mg, 0.45 mmol), and (2R,3S)-3-amino-4-(3,5-difluorophenyl)-1-{[1-(3-ethynylphenyl)cyclopropyl]amino}-3-methylbutan-2-ol dihydrochloride prepared as in Example SP-264 (170 mg, 0.4 mmol) are added. The reaction stirred at room temperature 16 h. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 638.2 [M+H]+.

Example SP-191

3-{[Butyl(methyl)amino]methyl}-N-((1S,2R)-1-(3,5-difluorobenzyl)-3-{[1-(3-ethylphenyl)cyclopropyl]amino}-2-hydroxypropyl)-5-methylbenzamide dihydrochloride

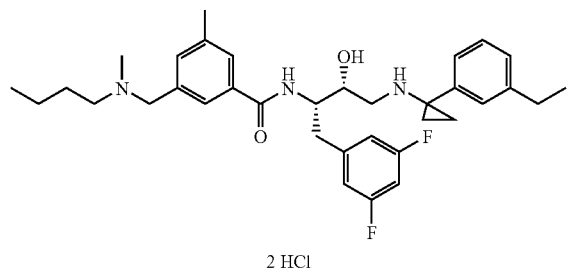

Analogous to the method in Example SP-188, methyl 3-{[butyl(methyl)amino]methyl}-5-methylbenzoate (132 mg, 0.53 mmol) is dissolved in 2:1:1 tetrahydrofuran/methanol/water (4 mL), and lithium hydroxide monohydrate is added (45 mg, 1.06 mmol), and the reaction stirred 16 h. The solution is concentrated under reduced pressure. The residue is redissolved in DMF (5 mL), and diisopropylethylamine (350 µL, 2 mmol), HATU (240 mg, 0.63 mmol), and (2R,3S)-3-amino-4-(3,5-difluorophenyl)-1-{[1-(3-ethylphenyl)cyclopropyl]amino}butan-2-ol prepared by the method in Example SP-272 (191 mg, 0.5 mmol) are added. The reaction stirred at room temperature 16 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 578.4 [M+H]+.

Example SP-192

3-{[Butyl(methyl)amino]methyl}-N-{(1S,2R)-1-(3,5-difluorobenzyl)-3-[(3-ethylbenzyl)amino]-2-hydroxypropyl}-5-methylbenzamide dihydrochloride

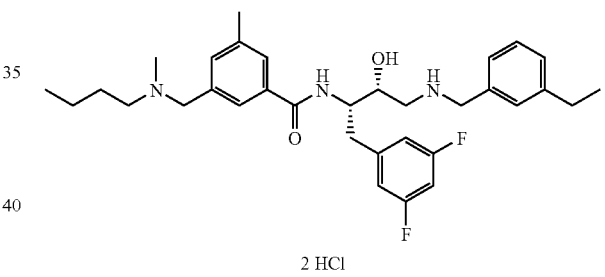

Analogous to the method in Example SP-188, methyl 3-{[butyl(methyl)amino]methyl}-5-methylbenzoate (122 mg, 0.49 mmol) is dissolved in 2:1:1 tetrahydrofuran/methanol/water (4 mL), and lithium hydroxide monohydrate is added (41 mg, 1.0 mmol), and the reaction stirred 16 h. The solution is concentrated under reduced pressure. The residue is redissolved in DMF (5 mL), and diisopropylethylamine (350 µL, 2 mmol), HATU (240 mg, 0.63 mmol), and (2R,3S)-3-amino-4-(3,5-difluorophenyl)-1-[(3-ethylbenzyl)amino]butan-2-ol dihydrochloride prepared by the method in Example SP-272 (203 mg, 0.5 mmol) are added. The reaction stirred at room temperature 16 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 552.3 [M+H]+.

Example SP-193

N-{(1S,2R)-1-(3,5-Difluorobenzyl)-2-hydroxy-3-[(3-iodobenzyl)amino]propyl}-3-{[isopentyl(methyl)amino]methyl}-5-methylbenzamide dihydrochloride

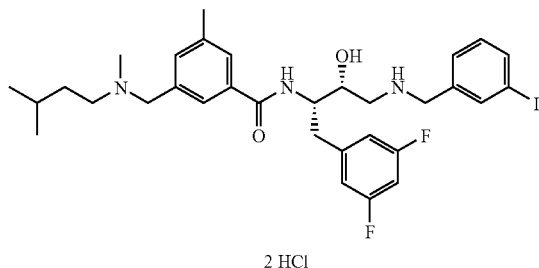

2 HCl

Analogous to the method described in Example SP-184, 2 mL of the stock solution is added to a solution of N-isoamylmethylamine (526 µL, 4.2 mmol) in anhydrous methylene chloride (1 mL), and the reaction mixture is stirred at room temperature for 16 h. The reaction mixture is diluted with methylene chloride (10 mL), washed with saturated sodium bicarbonate and brine, dried (magnesium sulfate), filtered, and concentrated under reduced pressure. Purification by flash column chromatography (silica, 4% methanol/chloroform) provided the amine. The amine is dissolved in 2:1:1 tetrahydrofuran/methanol/water (4 mL), and lithium hydroxide monohydrate is added (42 mg, 1 mmol). The reaction is stirred 16 h and is concentrated under reduced pressure. The residue is redissolved in DMF (5 mL), and diisopropylethylamine (355 µL, 2 mmol), HATU (242 mg, 0.64 mmol), and (2R,3S)-3-amino-4-(3,5-difluorophenyl)-1-[(3-iodobenzyl)amino]butan-2-ol dihydrochloride (257 mg, 0.5 mmol) are added. The reaction stirred at room temperature 16 h. Purification by flash column chromatography (silica, 7% methanol/chloroform) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 664.2 [M+H]$^+$.

Example SP-194

3-{[Butyl(methyl)amino]methyl}-N-{(1S,2R)-1-(3,5-difluorobenzyl)-2-hydroxy-3-[(1-phenylcyclopropyl)amino]propyl}-5-methylbenzamide dihydrochloride

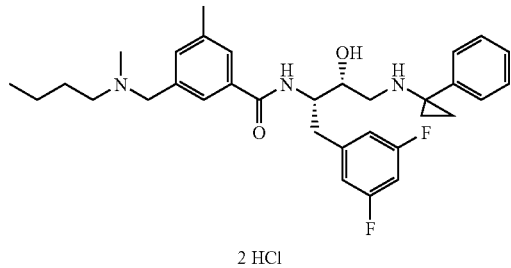

2 HCl

Analogous to the method in Example SP-188, methyl 3-{[butyl(methyl)amino]methyl}-5-methylbenzoate (170 mg, 0.68 mmol) is dissolved in 2:1:1 tetrahydrofuran/methanol/water (4 mL), and lithium hydroxide monohydrate is added (57 mg, 1.4 mmol), and the reaction stirred 2 h. The solution is concentrated under reduced pressure. The residue is redissolved in DMF (3 mL), and diisopropylethylamine (472 µL, 2.7 mmol), HATU (322 mg, 0.85 mmol), and (2R,3S)-3-amino-4-(3,5-difluorophenyl)-1-[(1-phenylcyclopropyl)amino]butan-2-ol dihydrochloride prepared by the method in Example S-XYZ (275 mg, 0.68 mmol) are added. The reaction stirred at room temperature 16 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 550.3 [M+H]$^+$.

Example SP-195

3-{[Butyl(methyl)amino]methyl}-N-{(1S,2R)-1-(3,5-difluorobenzyl)-2-hydroxy-3-[(3-isopropylbenzyl)amino]propyl}-5-methylbenzamide dihydrochloride

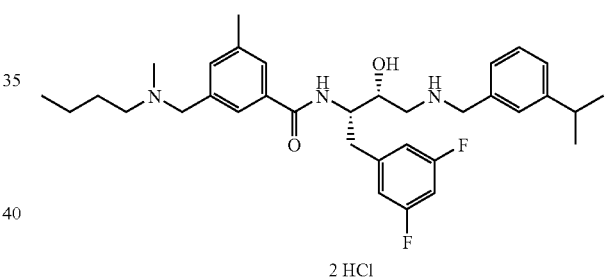

2 HCl

Analogous to the method in Example SP-188, methyl 3-{[butyl(methyl)amino]methyl}-5-methylbenzoate (50 mg, 0.2 mmol) is dissolved in 2:1:1 tetrahydrofuran/methanol/water (4 mL), and lithium hydroxide monohydrate is added (17 mg, 0.4 mmol), and the reaction stirred 16 h. The solution is concentrated under reduced pressure. The residue is redissolved in DMF (2 mL), and diisopropylethylamine (140 µL, 0.8 mmol), HATU (95 mg, 0.25 mmol), and (2R,3S)-3-amino-4-(3,5-difluorophenyl)-1-[(3-isopropylbenzyl)amino]butan-2-ol dihydrochloride prepared by the method in Example SP-170, Step 4 (85 mg, 0.2 mmol) are added. The reaction stirred at room temperature 16 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 566.3 [M+H]$^+$.

Example SP-196

3-{[Butyl(methyl)amino]methyl}-N-((1S,2R)-1-(3,5-difluorobenzyl)-3-{[1-(3-ethynylphenyl)cyclopropyl]amino}-2-hydroxypropyl)-5-(1,3-oxazol-2-yl)benzamide dihydrochloride

Step 1
3-(Methoxycarbonyl)-5-(1,3-oxazol-2-yl)benzoic acid

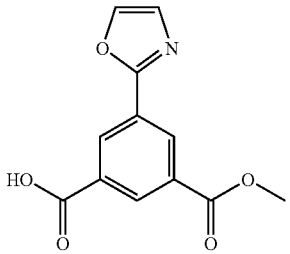

To a −70° C. stirred solution of oxazole (432 mg, 6.3 mmol) in tetrahydrofuran (10 mL) is added n-butyllithium (2.5 M in hexanes, 2.75 mL, 6.9 mmol). After 30 min, zinc chloride (1 M in diethyl ether, 18.75 mL, 18.75 mmol) is added and the reaction mixture is warmed to 0° C. for 1 h. To this mixture is added a solution of 3-iodo-5-(methoxycarbonyl)benzoic acid prepared by the method in Example SP-281, step 1 (1.8 g, 6 mmol) in anhydrous tetrahydrofuran (10 mL) followed by palladium(0)tetrakis(triphenylphosphine) (291 mg, 0.25 mmol). The reaction mixture is heated at reflux for 15 h. The reaction mixture is cooled, filtered through diatomaceous earth, diluted with ethyl acetate (50 mL), washed with water, and brine, dried (sodium sulfate), filtered, and concentrated under reduced pressure. Purification by flash column chromatography (silica gel, 5% methanol/methylene chloride) provides the title compound in pure form. ESI MS m/z 246.1 [M−H]−.

Step 2
Methyl 3-{[butyl(methyl)amino]methyl}-5-(1,3-oxazol-2-yl)benzoate

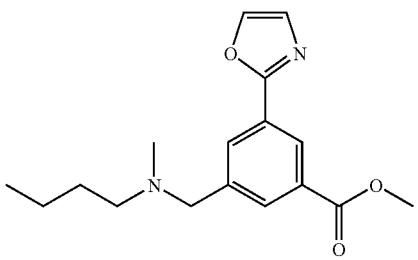

To an ice-cold solution of 3-(methoxycarbonyl)-5-(1,3-oxazol-2-yl)benzoic acid (340 mg, 1.4 mmol) in anhydrous tetrahydrofuran (10 mL) is added lithium borohydride (250 mg, 11 mmol) slowly. The reaction is stirred 30 min, then absolute ethanol (4 mL) is added, and the reaction is stirred 1 h. The solution is poured onto ice containing excess hydrochloric acid and extracted with ethyl acetate. The organic layer is washed with water, brine, dried (sodium sulfate), filtered, and concentrated under reduced pressure. The residue is redissolved in 20% methanol/benzene (50 mL), and 2M trimethylsilyldiazomethane in hexane (0.9 mL, 1.8 mmol) is added. The reaction is stirred 2 h at room temperature, then concentrated under reduced pressure. The residue is redissolved in anhydrous methylene chloride (10 mL), cooled to −30° C., then methanesulfonyl chloride (150 μL, 1.9 mmol) and triethylamine (380 μL, 2.7 mmol) are added. The reaction is stirred at 0° C. 15 min, then N-methylbutylamine (480 μL, 4 mmol) is added, and the reaction is stirred 16 h at room temperature. The solution is concentrated under reduced pressure. Purification by flash column chromatography (silica gel, 40-100% ethyl acetate/hexane gradient) provides the title compound in pure form. ESI MS m/z 303.3 [M+H]+.

Step 3
3-{[Butyl(methyl)amino]methyl}-N-((1S,2R)-1-(3,5-difluorobenzyl)-3-{[1-(3-ethynylphenyl)cyclopropyl]amino}-2-hydroxypropyl)-5-(1,3-oxazol-2-yl)benzamide dihydrochloride

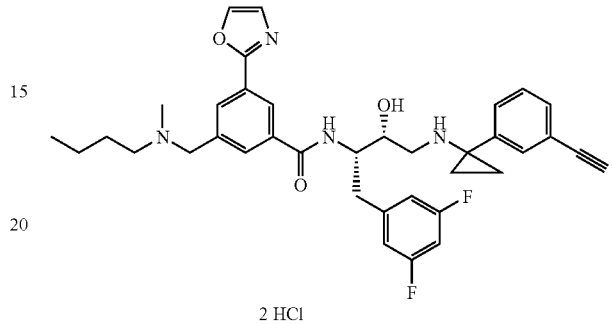

2 HCl

Methyl 3-{[butyl(methyl)amino]methyl}-5-(1,3-oxazol-2-yl)benzoate (30 mg, 0.1 mmol) is dissolved in 2:1:1 tetrahydrofuran/methanol/water (4 mL), and lithium hydroxide monohydrate is added (10 mg, 0.2 mmol), and the reaction stirred 16 h. The solution is concentrated under reduced pressure. The residue is redissolved in DMF (1 mL), and diisopropylethylamine (70 μL, 0.4 mmol), HATU (57 mg, 0.15 mmol), and (2R,3S)-3-amino-4-(3,5-difluorophenyl)-1-{[1-(3-ethynylphenyl)cyclopropyl]amino}butan-2-ol dihydrochloride (203 mg, 0.5 mmol) are added. The reaction stirred at room temperature 2 h. The reaction mixture is diluted with ethyl acetate, washed with water, saturated sodium bicarbonate, brine, dried (sodium sulfate), filtered, and concentrated under reduced pressure. Purification by flash column chromatography (silica, 9-10% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 627.3 [M+H]+.

Example SP-197

3-{[Butyl(methyl)amino]methyl}-5-cyano-N-((1S,2R)-1-(3,5-difluorobenzyl)-3-{[1-(3-ethynylphenyl)cyclopropyl]amino}-2-hydroxypropyl)benzamide dihydrochloride

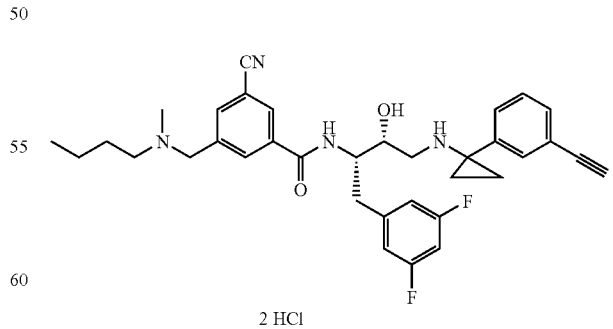

2 HCl

3-Bromo-5-(methoxycarbonyl)benzoic acid (4 g, 15.4 mmol) and copper(I) cyanide (4.1 g, 89.5 mmol) in N-methylpyrrolidinone (20 mL) is heated at 175° C. for 4 h. The reaction is cooled, and water is added. The aqueous solution is extracted with methylene chloride, washed with 1N hydrochloric acid (aq), brine, dried (sodium sulfate), filtered, and concentrated under reduced pressure. The residue is dissolved in tetrahydrofuran (20 mL), cooled in an ice bath, and lithium borohydride (475 mg, 22 mmol) is added slowly. The reaction stirred at this temperature 2 h. Absolute ethanol (4 mL) is added dropwise, and the reaction stirred 30 min. The mixture is poured on ice containing excess hydrochloric acid. After gas evolution ceases, the solution is extracted with methylene chloride and concentrated under reduced pressure.

The residue is dissolved in 20% methanol/benzene (20 mL), and 2M trimethylsilyldiazomethane in hexane (1.3 mL, 2.6 mmol) is added. The reaction stirred at room temperature 2 h and is concentrated under reduced pressure. The residue is then dissolved in anhydrous methylene chloride (10 mL), cooled to −30° C., then methanesulfonyl chloride (216 µL, 2.8 mmol) and triethylamine (556 µL, 4 mmol) are added. The reaction is warmed to 0° C. and stirred 15 min, then filtered. The filtrate is added to N-methylbutylamine (5 mL) and stirred 16 h. The solution is concentrated under reduced pressure and purification by flash chromatography (silica gel, 40% ethyl acetate/hexane) gives an oil. The oil (107 mg) is dissolved in 2:1:1 tetrahydrofuran/methanol/water (4 mL), and lithium hydroxide monohydrate is added (35 mg, 0.8 mmol), and the reaction stirred 1.5 h. The solution is concentrated under reduced pressure.

The residue is redissolved in DMF (3 mL), and diisopropylethylamine (280 µL, 1.6 mmol), HATU (230 mg, 0.6 mmol), and (2R,3S)-3-amino-4-(3,5-difluorophenyl)-1-{[1-(3-ethynylphenyl)cyclopropyl]amino}butan-2-ol dihydrochloride (206 mg, 0.5 mmol) are added. The reaction stirred at room temperature 16 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 585.3 [M+H]+.

Example SP-198

N-{(1S,2R)-1-(3,5-Difluorobenzyl)-3-[(3-ethylbenzyl)amino]-2-hydroxypropyl}-3-{[(2-furylmethyl)(methyl)amino]methyl}-5-methylbenzamide dihydrochloride Step 1
Methyl 3-bromo-5-(hydroxymethyl)benzoate

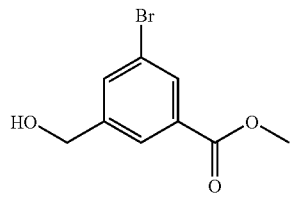

To an ice-cold, stirred solution of 3-bromo-5-(methoxycarbonyl)benzoic acid (5.0 g, 19.3 mmol) in tetrahydrofuran (77.2 mL) is added borane dimethyl sulfide complex (10.6 mL, 2.0 M tetrahydrofuran, 21.1 mmol). The reaction mixture is heated at 50° C. for 2 h. The reaction mixture is quenched with methanol (50 mL) and concentrated under reduced pressure. Purification by flash column chromatography (silica, 50% ethyl acetate/hexanes) affords the title compound. 1H NMR (300 MHz, CDCl3) δ 8.03 (s, 1H), 7.90 (s, 1H), 7.69 (s, 1H), 4.69 (s, 1H), 3.91 (s, 3H), 2.83 (br s, 1H).

Step 2
Methyl 3-(hydroxymethyl)-5-methylbenzoate

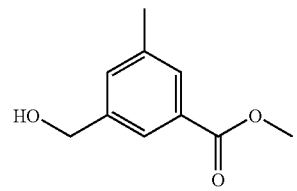

To a stirred solution of methyl 3-bromo-5-(hydroxymethyl)benzoate (4.53 g, 18.5 mmol) in dioxane (74 mL) is added cesium carbonate (6.0 g, 18.5 mmol), potassium carbonate (5.1 g, 37 mmol), and palladium(0)tetrakis(triphenylphosphine) (2.1 g, 1.85 mmol), followed by trimethyl boroxine (5.1 mL, 37 mmol). The reaction mixture is refluxed for 12 h, cooled to room temperature, and then partitioned between water and ethyl acetate. The organic layer is washed with water and brine, dried (magnesium sulfate), filtered, and concentrated under reduced pressure. The black oil is adsorbed onto silica gel followed by purification by flash column chromatography (silica, 25% ethyl acetate/hexanes) to provide the title compound. 1H NMR (300 MHz, CDCl3) δ 7.75 (s, 1H), 7.65 (s, 1H), 7.39 (s, 1H), 5.31 (br s, 1H), 4.53 (s, 1H), 3.84 (s, 3H), 2.36 (s, 3H).

Step 3
Methyl 3-{[(2-furylmethyl)(methyl)amino]methyl}-5-methylbenzoate

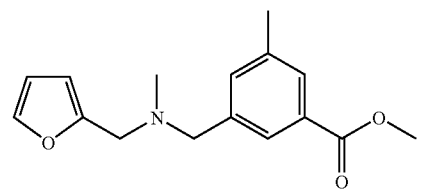

To an ice-cold, stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. N-Methylfurfurylamine (367 mg, 3.3 mmol) is added to the filtrate and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 50% ethyl acetate/hexanes) provided the title compound. 1H NMR (300 MHz, CDCl3) δ 7.76 (d, J=11 Hz, 2H), 3.79 (d, J=6 Hz, 2H), 6.32 (d, J=2 Hz, 1H), 6.21 (d, J=3 Hz, 1H), 3.90 (s, 3H), 3.59 (s, 3H), 3.53 (s, 2H), 2.39 (s, 3H), 2.23 (s, 3H).

Step 4

3-{[(2—Furylmethyl)(methyl)amino]methyl}-5-methyl-benzoic acid

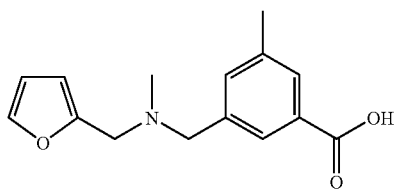

To a stirred solution of methyl 3-{[(2-furylmethyl)(methyl)amino]methyl}-5-methylbenzoate (180 mg, 0.66 mmol) in methanol (2 mL), tetrahydrofuran (1 mL), and water (1 mL) is added lithium hydroxide (277 mg, 6.6 mmol), and the reaction mixture stirred at room temperature for 2 h. The reaction mixture is concentrated under reduced pressure, dissolved in methylene chloride, filtered, and the filtrate concentrated under reduced pressure to provide the title compound. ESI MS m/z 258 [M+H]$^+$.

Step 5

N-{(1S,2R)-1-(3,5-Difluorobenzyl)-3-[(3-ethylbenzyl)amino]-2-hydroxypropyl}-3-{[(2-furylmethyl)(methyl)amino]methyl}-5-methylbenzamide dihydrochloride

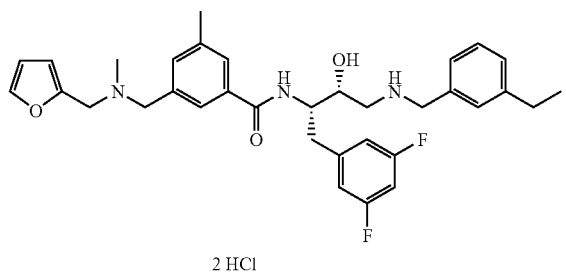

2 HCl

To a stirred solution of 3-{[(2-furylmethyl)(methyl)amino]methyl}-5-methylbenzoic acid (170 mg, 0.66 mmol) in methylene chloride (3 mL) is added HBTU (375 mg, 0.99 mmol), HOBt (134 mg, 0.99 mmol), and N,N-diisopropylethylamine (0.334 mL, 1.98 mmol), followed by (2R,3S)-3-amino-4-(3,5-difluorophenyl)-1-[(3-ethylbenzyl)amino]butan-2-ol prepared by the method in Example SP-272 (269 mg, 0.66 mmol), and the reaction mixture is stirred for 12 h at room temperature. The reaction mixture is diluted with methylene chloride, washed with water, and saturated sodium bicarbonate, dried (magnesium sulfate), filtered, and concentrated under reduced pressure. Purification by flash column chromatography (silica, 10% methanol/chloroform) affords the title compound as the free base. The compound is dissolved in methanol (2 mL), and to this solution is added hydrochloric acid (5 mL, 4 N dioxane, 20 mmol). The reaction mixture is stirred for 1 h at room temperature. The reaction mixture is then diluted with ethyl ether (10 mL). The precipitate that is formed is collected by filtration to provide the title compound. ESI MS m/z 576 [M+H]$^+$.

Example SP-199

N-{(1S,2R)-1-(3,5-Difluorobenzyl)-3-[(3-ethylbenzyl)amino]-2-hydroxypropyl}-3-{[(2-methoxyethyl)(methyl)amino]methyl}-5-methylbenzamide dihydrochloride

Step 1

Methyl 3-{[(2-methoxyethyl)(methyl)amino]methyl}-5-methylbenzoate

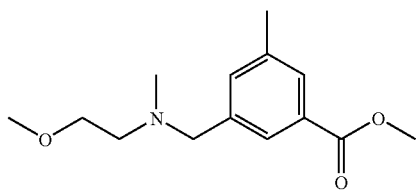

To an ice-cold stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. 2-Methoxy-N-methyleneamine (0.354 mL, 3.3 mmol) is added to the filtrate, and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 50% ethyl acetate/hexanes) provided the title compound. $^1$H NMR (300 MHz, CDCl$_3$) δ 7.75 (d, J=5 Hz, 2H), 7.37 (s, 3H), 3.90 (s, 1H), 3.56 (s, 2H), 3.52 (t, J=6 Hz, 2H), 3.34 (s, 3H), 2.61 (t, J=6 Hz, 2H), 2.39 (s, 3H), 2.26 (s, 3H).

Step 2

3-{[(2-Methoxyethyl)(methyl)amino]methyl}-5-methyl-benzoic acid

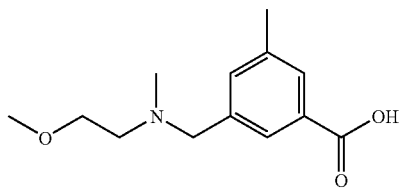

To a stirred solution of methyl 3-{[(2-methoxyethyl)(methyl)amino]methyl}-5-methylbenzoate (180 mg, 0.72 mmol) in methanol (2 mL), tetrahydrofuran (1 mL), and water (1 mL) is added lithium hydroxide (302 mg, 7.2 mmol) and the reaction mixture stirred at room temperature for 2 h. The reaction mixture is concentrated under reduced pressure, dissolved in methylene chloride, filtered, and the filtrate concentrated under reduced pressure to provide the title compound. ESI MS m/z 238 [M+H]$^+$.

Step 3
N-{(1S,2R)-1-(3,5-Difluorobenzyl)-3-[(3-ethylbenzyl)amino]-2-hydroxypropyl}-3-{[(2-methoxyethyl)(methyl)amino]methyl}-5-methylbenzamide dihydrochloride

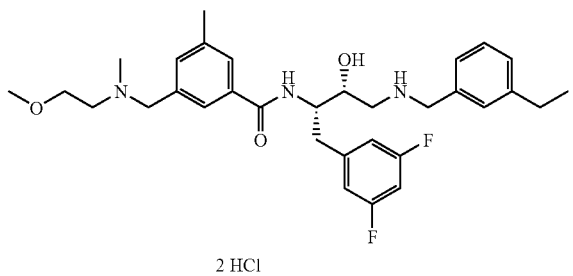

2 HCl

To a stirred solution of 3-{[(2-methoxyethyl)(methyl)amino]methyl}-5-methylbenzoic acid (140 mg, 0.56 mmol) in methylene chloride (3 mL) is added HBTU (318 mg, 0.84 mmol), HOBt (114 mg, 0.84 mmol), and N,N-diisopropylethylamine (0.284 mL, 1.68 mmol), followed by (2R,3S)-3-amino-4-(3,5-difluorophenyl)-1-[(3-ethylbenzyl)amino]butan-2-ol prepared by the method in Example SP-272 (228 mg, 0.56 mmol). The reaction mixture is stirred for 24 h at room temperature, diluted with methylene chloride, washed with water, and saturated sodium bicarbonate, dried (magnesium sulfate), filtered, and concentrated under reduced pressure. Purification by flash column chromatography (silica, 10% methanol/chloroform) affords the title compound as the free base. The compound is dissolved in methanol (2 mL), and to this solution is added hydrochloric acid (5 mL, 4 N dioxane, 20 mmol). The reaction mixture is stirred for 1 h at room temperature. The reaction mixture is then diluted with ethyl ether (10 mL). The precipitate that is formed is collected by filtration to provide the title compound. ESI MS m/z 554 [M+H]$^+$.

Example SP-200

3-{[[2-(Diethylamino)ethyl](methyl)amino]methyl}-N-{(1S,2R)-1-(3,5-difluorobenzyl)-3-[(3-ethylbenzyl)amino]-2-hydroxypropyl}-5-methylbenzamide trihydrochloride

Step 1
Methyl 3-{[[2-(diethylamino)ethyl](methyl)amino]methyl}-5-methylbenzoate

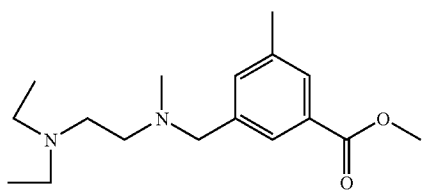

To an ice-cold, stirred solution of methyl 3-(hydroxymethyl)-5-methylbenzoate (200 mg, 1.19 mmol) and triethylamine (241 mg, 2.38 mmol) in methylene chloride (5 mL) is added methanesulfonyl chloride (191 mg, 1.67 mmol). The reaction mixture is stirred for 15 min, the precipitate that formed is removed by filtration, and N,N-diethyl-N'-methylethylenediamine (465 mg, 3.57 mmol) was added. The reaction mixture is stirred at room temperature for 2 h and then concentrated under reduced pressure. Purification by flash column chromatography (silica, 9:1 chloroform/methanol) gives the title compound. $^1$H NMR (300 MHz, CDCl$_3$) δ 8.02 (s, 2H), 7.33 (s, 1H), 3.56 (s, 3H), 3.48 (s, 2H), 2.95 (m, 4H), 2.75 (m, 4H), 2.41 (s, 3H), 2.31 (s, 3H), 1.21 (m, 6H).

Step 2
3-{[[2-(Diethylamino)ethyl](methyl)amino]methyl}-5-methylbenzoic acid

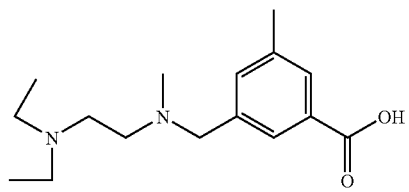

A mixture of methyl 3-{[[2-(diethylamino)ethyl](methyl)amino]methyl}-5-methylbenzoate (296 mg, 1.01 mmol) and 3:1:1 methanol/tetrahydrofuran/2 N sodium hydroxide (10 mL) is stirred overnight and then partitioned between ethyl acetate and water. The aqueous layer is acidified to pH 3 with 1 N hydrochloric acid and extracted with chloroform. The aqueous layer is concentrated under reduced pressure to give the title compound. $^1$H NMR (300 MHz, DMSO-d$_6$) δ 7.99 (s, 1H), 7.82 (s, 1H), 7.80 (s, 1H), 4.56 (m, 2H), 4.31 (m, 2H), 3.98 (m, 2H), 3.17 (m, 4H), 2.51 (s, 3H), 2.50 (s, 3H), 1.27 (m, 6H).

Step 3
3-{[[2-(Diethylamino)ethyl](methyl)amino]methyl}-N-{(1S,2R)-1-(3,5-difluorobenzyl)-3-[(3-ethylbenzyl)amino]-2-hydroxypropyl}-5-methylbenzamide trihydrochloride

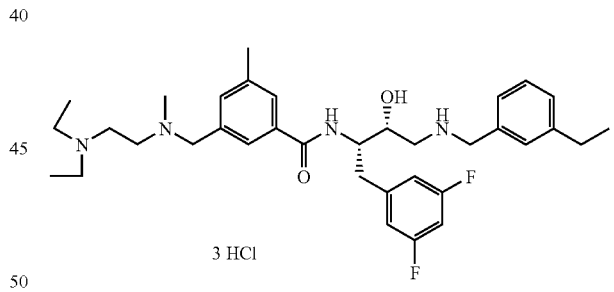

3 HCl

To a stirred solution of 3-{[[2-(diethylamino)ethyl](methyl)amino]methyl}-5-methylbenzoic acid (267 mg, 0.959 mmol), (2R,3S)-3-amino-4-(3,5-difluorophenyl)-1-[(3-ethylbenzyl)amino]butan-2-ol prepared by the method of Example SP-272 (391 mg, 0.959 mmol), HOBt (129 mg, 0.959 mmol), and N,N-diisopropylethylamine (496 mg, 3.84 mmol) in methylene chloride (5 mL) is added EDC (331 mg, 1.73 mmol). The reaction mixture is stirred overnight and then partitioned between ethyl acetate and water. The organic layer is washed with 1 N hydrochloric acid, saturated sodium bicarbonate, and brine, dried (sodium sulfate), filtered, and concentrated under reduced pressure. Purification by flash column chromatography (silica, 9:1:1 methylene chloride/methanol/ammonium hydroxide) gives the title compound. ESI MS m/z 595.4 [M+H]$^+$.

Example SP-201

N-{(1S,2R)-1-(3,5-Difluorobenzyl)-3-[(3-ethylbenzyl)amino]-2-hydroxypropyl}-3-oxoindane-5-carboxamide

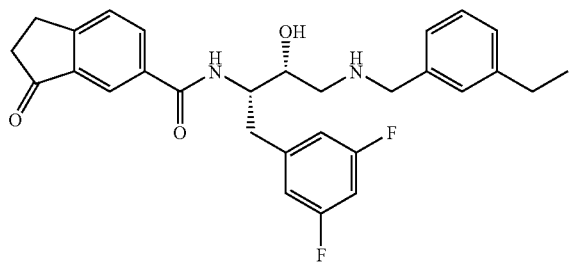

To 3-oxoindane-5-carboxylic acid (2.0 g, 11.5 mmol) in DMF (10 mL) is added diisopropylethylamine (8 mL, 46 mmol), HATU (5.5 g, 14.4 mmol), then (2R,3S)-3-amino-4-(3,5-difluorophenyl)-1-[(3-ethylbenzyl)amino]butan-2-ol dihydrochloride prepared by the method of Example SP-272 (5.6 g, 13.8 mmol). The reaction is stirred 1 h at room temperature. The reaction was partitioned between ethyl acetate and water. The organic layer is washed with 1 N hydrochloric acid, saturated sodium bicarbonate, and brine, dried (sodium sulfate), filtered, and concentrated under reduced pressure. Purification by flash column chromatography (silica, 8% methanol/methylene chloride) gives the title compound. ESI MS m/z 493.2 [M+H]$^+$.

Example SP-202

N-{(1S,2R)-1-(3,5-Difluorobenzyl)-3-[(3-ethylbenzyl)amino]-2-hydroxypropyl}-3-hydroxyindane-5-carboxamide

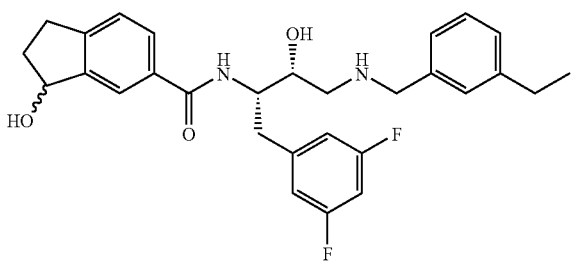

To an ice-cold solution of N-{(1S,2R)-1-(3,5-difluorobenzyl)-3-[(3-ethylbenzyl)amino]-2-hydroxypropyl}-3-oxoindane-5-carboxamide prepared by the method in Example SP-201 (66 mg, 0.13 mmol) in methanol (3 mL) is added sodium borohydride (20 mg, 0.52 mmol). The reaction stirred at room temperature 3 h. The reaction is concentrated under reduced pressure, redissolved in water (3 mL) and partitioned into ethyl acetate. The organic layer is washed with water, saturated sodium bicarbonate, and brine, dried (sodium sulfate), filtered, and concentrated under reduced pressure to give the title compound. ESI MS m/z 495.2 [M+H]$^+$.

Example SP-203

N-{(1S,2R)-1-(3,5-Difluorobenzyl)-3-[(3-ethylbenzyl)amino]-2-hydroxypropyl}-3-{[isobutyl(methyl)amino]methyl}-5-methylbenzamide hydrochloride Step 1

Methyl 3-{[isobutyl(methyl)amino]methyl}-5-methylbenzoate

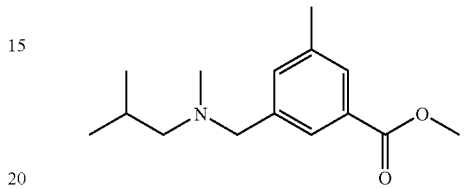

To an ice-cold, stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. N-Methylisobutylamine (287 mg, 3.3 mmol) is added to the filtrate, and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 15% ethyl acetate/hexanes) provides the title compound. $^1$H NMR (300 MHz, CDCl$_3$) δ 7.77 (s, 1H), 7.73 (s, 1H), 7.36 (s, 1H), 3.90 (s, 3H), 3.44 (s, 2H), 2.38 (s, 3H), 2.14 (s, 3H), 2.10 (d, J=8 Hz, 2H), 1.81 (m, 1H), 0.90 (d, J=7 Hz, 6H).

Step 2

3-{[Isobutyl(methyl)amino]methyl}-5-methylbenzoic acid

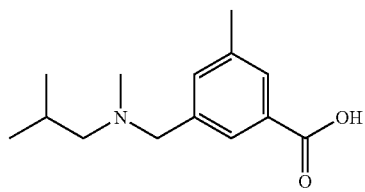

To a stirred solution of methyl 3-{[isobutyl(methyl)amino]methyl}-5-methylbenzoate (120 mg, 0.48 mmol) in methanol (2 mL), tetrahydrofuran (1 mL), and water (1 mL) is added lithium hydroxide (200 mg, 4.8 mmol), and the reaction mixture stirred at room temperature for 2 h. The reaction mixture is concentrated under reduced pressure, dissolved in methylene chloride, filtered, and the filtrate concentrated under reduced pressure to provide the title compound. ESI MS m/z 236 [M+H]$^+$.

Step 3

N-{(1S,2R)-1-(3,5-Difluorobenzyl)-3-[(3-ethylbenzyl)amino]-2-hydroxypropyl}-3-{[isobutyl(methyl)amino]methyl}-5-methylbenzamide hydrochloride

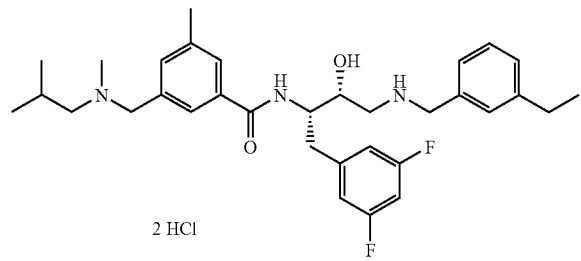

2 HCl

To a stirred solution of 3-{[isobutyl(methyl)amino]methyl}-5-methylbenzoic acid (110 mg, 0.48 mmol) in methylene chloride (3 mL) is added HBTU (273 mg, 0.72 mmol), HOBt (97 mg, 0.72 mmol), and N,N-diisopropylethylamine (0.243 mL, 1.44 mmol), followed by (2R,3S)-3-amino-4-(3,5-difluorophenyl)-1-[(3-ethylbenzyl)amino]butan-2-ol prepared by the method of Example SP-272 (196 mg, 0.48 mmol), and the reaction mixture is stirred for 12 h at room temperature. The reaction mixture is diluted with methylene chloride, washed with water, and saturated sodium bicarbonate, dried (magnesium sulfate), filtered, and concentrated under reduced pressure. Purification by flash column chromatography (silica, 10% methanol/chloroform) affords a clear oil, which is dissolved in methanol (2 mL). To this solution is added hydrochloric acid (5 mL, 4 N dioxane, 20 mmol), and the reaction mixture is stirred for 1 h at room temperature. The reaction mixture is then diluted with ethyl ether (10 mL). The precipitate that is formed is collected by filtration to provide the title compound. ESI MS m/z 552.5 [M+H]$^+$.

Example SP-204

N-{(1S,2R)-1-(3,5-Difluorobenzyl)-3-[(3-ethylbenzyl)amino]-2-hydroxypropyl}-3-methyl-5-{[methyl(pentyl)amino]methyl}benzamide dihydrochloride

Step 1

Methyl 3-methyl-5-{[methyl(pentyl)amino]methyl}benzoate

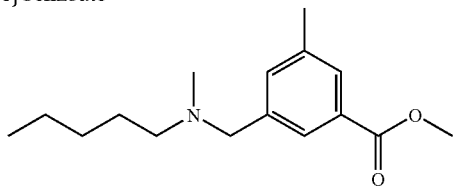

To an ice-cold, stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. N-Methylpentylamine (333 mg, 3.3 mmol) is added to the filtrate, and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 15% ethyl acetate/hexanes) provides the title compound. $^1$H NMR (300 MHz, CDCl$_3$) δ 7.75 (d, J=4 Hz, 2H), 7.36 (s, 1H), 3.90 (s, 3H), 3.47 (s, 2H), 3.13 (t, J=9 Hz, 3H), 2.39 (s, 2H), 2.34 (d, J=8 Hz, 2H), 2.18 (s, 3H), 1.45 (m, 5H), 1.32 (m, 2H).

Step 2

3-Methyl-5-{[methyl(pentyl)amino]methyl}benzoic acid

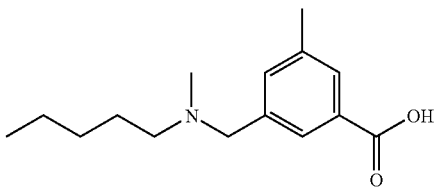

To a stirred solution of methyl 3-methyl-5-{[methyl(pentyl)amino]methyl}benzoate (120 mg, 0.46 mmol) in methanol (2 mL), tetrahydrofuran (1 mL), and water (1 mL) is added lithium hydroxide (191 mg, 4.6 mmol), and the reaction mixture stirred at room temperature for 2 h. The reaction mixture is concentrated under reduced pressure, dissolved in methylene chloride, filtered, and the filtrate concentrated under reduced pressure to provide the title compound. ESI MS m/z 250 [M+H]$^+$.

Step 3

N-{(1S,2R)-1-(3,5-Difluorobenzyl)-3-[(3-ethylbenzyl)amino]-2-hydroxypropyl}-3-methyl-5-{[methyl(pentyl)amino]methyl}benzamide dihydrochloride

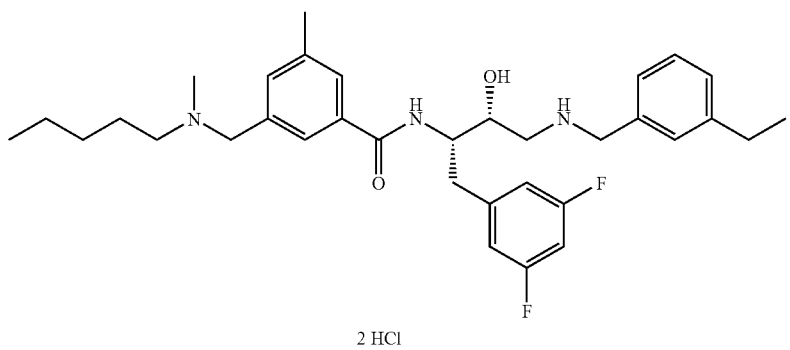

2 HCl

To a stirred solution of 3-methyl-5-{[methyl(pentyl) amino]methyl}benzoic acid (110 mg, 0.44 mmol) in methylene chloride (3 mL) is added HBTU (250 mg, 0.66 mmol), HOBt (90 mg, 0.66 mmol), and N,N-diisopropylethylamine (0.222 mL, 1.32 mmol), followed by (2R,3S)-3-amino-4-(3, 5-difluorophenyl)-1-[(3-ethylbenzyl)amino]butan-2-ol prepared by the method of Example SP-272 (180 mg, 0.44 mmol), and the reaction mixture is stirred for 12 h at room temperature. The reaction mixture is diluted with methylene chloride, washed with water, and saturated sodium bicarbonate, dried (magnesium sulfate), filtered, and concentrated under reduced pressure. Purification by flash column chromatography (silica, 10% methanol/chloroform) affords a clear oil, which is dissolved in methanol (2 mL). To this solution is added hydrochloric acid (5 mL, 4 N dioxane, 20 mmol), and the reaction mixture is stirred for 1 h at room temperature. The reaction mixture is then diluted with ethyl ether (10 mL). The precipitate that is formed is collected by filtration to provide the title compound. ESI MS m/z 566.5 [M+H]$^+$.

Example SP-205

N-{(1S,2R)-1-(3,5-Difluorobenzyl)-3-[(3-ethylbenzyl) amino]-2-hydroxypropyl}-3-{[(2R)-2-(methoxymethyl)pyrrolidin-1-yl]methyl}-5-methylbenzamide dihydrochloride Step 1

Methyl 3-{[(2R)-2-(methoxymethyl)pyrrolidin-1-yl]methyl}-5-methylbenzoate

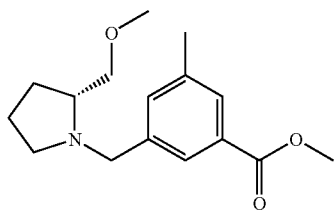

To an ice-cold, stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. (R)-2-(Methoxymethyl)pyrrolidine (380 mg, 3.3 mmol) is added to the filtrate, and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 50% ethyl acetate/hexanes) provides the title compound. $^1$H NMR (300 MHz, CDCl$_3$) δ 7.77 (s, 1H), 7.73 (s, 1H), 7.37 (s, 1H), 4.11 (d, J=13 Hz, 1H), 3.90 (d, J=6 Hz, 2H), 3.41 (m, 2H), 3.34 (m, 3H), 2.89 (m, 1H), 2.71 (m, 1H), 2.38 (s, 3H), 2.19 (m, 1H), 1.93 (m, 2H), 1.54 (m, 3H).

Step 2

3-{[(2R)-2-(Methoxymethyl)pyrrolidin-1-yl]methyl}-5-methylbenzoic acid

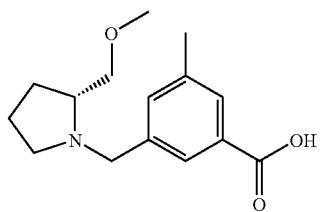

To a stirred solution of methyl 3-{[(2R)-2-(methoxymethyl)pyrrolidin-1-yl]methyl}-5-methylbenzoate (120 mg, 0.43 mmol) in methanol (2 mL), tetrahydrofuran (1 mL), and water (1 mL) is added lithium hydroxide (180 mg, 4.3 mmol), and the reaction mixture stirred at room temperature for 2 h. The reaction mixture is concentrated under reduced pressure, dissolved in methylene chloride, filtered, and the filtrate concentrated under reduced pressure to provide the title compound. ESI MS m/z 264 [M+H]$^+$.

Step 3

N-{(1S,2R)-1-(3,5-Difluorobenzyl)-3-[(3-ethylbenzyl) amino]-2-hydroxypropyl}-3-{[(2R)-2-(methoxymethyl)pyrrolidin-1-yl]methyl}-5-methylbenzamide dihydrochloride

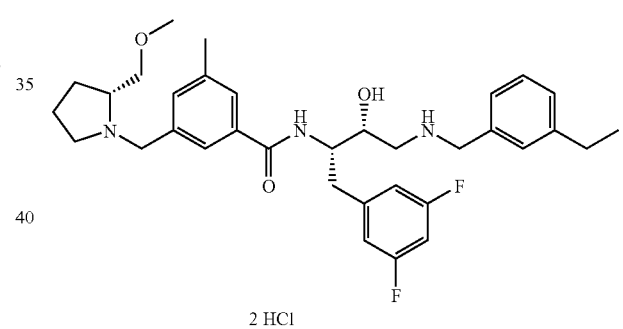

2 HCl

To a stirred solution of 3-{[(2R)-2-(methoxymethyl)pyrrolidin-1-yl]methyl}-5-methylbenzoic acid (113 mg, 0.43 mmol) in methylene chloride (3 mL) is added HBTU (165 mg, 0.66 mmol), HOBt (89 mg, 0.66 mmol), and N,N -diisopropylethylamine (0.220 mL, 1.30 mmol), followed by (2R, 3S)-3-amino-4-(3,5-difluorophenyl)-1-[(3-ethylbenzyl) amino]butan-2-ol prepared by the method of Example SP-272 (175 mg, 0.43 mmol), and the reaction mixture is stirred for 12 h at room temperature. The reaction mixture is diluted with methylene chloride, washed with water, and saturated sodium bicarbonate, dried (magnesium sulfate), filtered, and concentrated under reduced pressure. Purification by flash column chromatography (silica, 10% methanol/chloroform) affords a clear oil, which was dissolved in methanol (2 mL). To this solution is added hydrochloric acid (5 mL, 4 N dioxane, 20 mmol), and the reaction mixture is stirred for 1 h at room temperature. The reaction mixture is then diluted with ethyl ether (10 mL). The precipitate that is formed is collected by filtration to provide the title compound. ESI MS m/z 580.4 [M+H]$^+$.

Example SP-206

3-Bromo-5-{[butyl(methyl)amino]methyl}-N-{(1S,2R)-1-(3,5-difluorobenzyl)-3-[(3-ethylbenzyl)amino]-2-hydroxypropyl}benzamide dihydrochloride

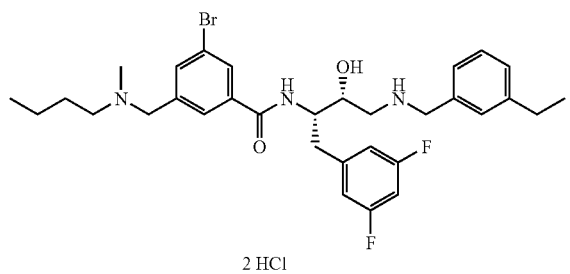

Methyl 3-bromo-5-{[butyl(methyl)amino]methyl}benzoate prepared by the method in Example SP-190, Step 1 (170 mg, 0.54) is dissolved in 2:1:1 tetrahydrofuran/methanol/water (4 mL), and lithium hydroxide monohydrate is added (45 mg, 1.1 mmol), and the reaction stirred 16 h. The solution is concentrated under reduced pressure. The residue is redissolved in DMF (5 mL), and diisopropylethylamine (375 µL, 2.16 mmol), HATU (256 mg, 0.68 mmol), and (2R,3S)-3-amino-4-(3,5-difluorophenyl)-1-[(3-ethylbenzyl)amino]butan-2-ol dihydrochloride prepared by the method in Example SP-272 (265 mg, 0.65 mmol) are added. The reaction stirred at room temperature 1 h. The reaction mixture is diluted with methylene chloride, washed with water, and saturated sodium bicarbonate, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (1 mL) is added. The mixture is concentrated under reduced pressure to yield the title compound. ESI MS m/z 616.2 [M+H]⁺.

Example SP-207

3-[(Butylamino)methyl]-N-{(1S,2R)-1-(3,5-difluorobenzyl)-3-[(3-ethylbenzyl)amino]-2-hydroxypropyl}-5-methylbenzamide dihydrochloride Step 1
Methyl 3-[(butylamino)methyl]-5-methylbenzoate

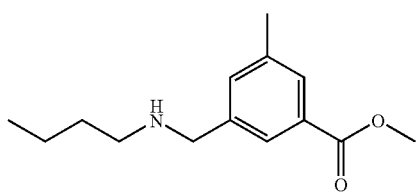

To an ice-cold, stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. Butylamine (0.543 mL, 5.5 mmol) is added to the filtrate, and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 89:10:1 chloroform/methanol/ammonium hydroxide) provides the title compound. ¹H NMR (300 MHz, CDCl₃) δ 7.75 (s, 1H), 7.70 (s, 1H), 7.24 (br s, 1H), 4.42 (d, J=9 Hz, 2H), 3.90 (s, 3H), 3.16 (m, 2H), 2.38 (s, 3H), 1.64 (s, 2H), 1.44 (m, 9H), 1.27 (m, 2H), 0.89 (t, J=7 Hz, 3H).

Step 2
Methyl 3-{[(tert-butoxycarbonyl)(butyl)amino]methyl}-5-methylbenzoate

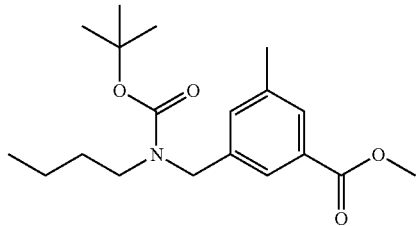

To a stirred solution of methyl 3-[(butylamino)methyl]-5-methylbenzoate (70 mg, 0.30 mmol) in methylene chloride is added triethylamine (0.046 mL, 0.33 mmol), and 4-dimethylaminopyridine (4.0 mg, 0.03 mmol) followed by di-tert-butyl-dicarbonate (72 mg, 0.30 mmol). The reaction mixture is stirred at room temperature for 24 h, diluted with methylene chloride, washed with 1 N hydrochloric acid, and brine. The organic solution is dried (magnesium sulfate), filtered, and concentrated under reduced pressure to afford the title compound. 1H NMR (300 MHz, CDCl₃) δ 7.75 (s, 1H), 7.70 (s, 1H), 7.24 (br s, 1H), 4.42 (d, J=9 Hz, 2H), 3.90 (s, 3H), 3.16 (m, 2H), 2.38 (s, 3H), 1.64 (s, 2H), 1.44 (m, 9H), 1.27 (m, 2H), 0.89 (t, J=7 Hz, 3H).

Step 3
3-{[(tert-Butoxycarbonyl)(butyl)amino]methyl}-5-methylbenzoic acid

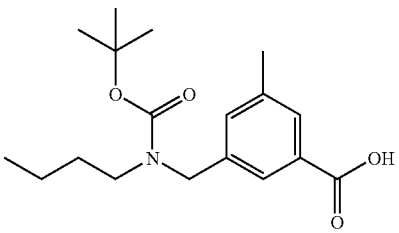

To a stirred solution of methyl 3-{[(tert -butoxycarbonyl)(butyl)amino]methyl}-5-methylbenzoate (70 mg, 0.21 mmol) in methanol (2 mL), tetrahydrofuran (1 mL), and water (1 mL) is added lithium hydroxide (88 mg, 2.1 mmol), and the reaction mixture stirred at room temperature for 2 h. The reaction mixture is concentrated under reduced pressure, dissolved in methylene chloride, filtered, and the filtrate concentrated under reduced pressure to provide the title compound.

Step 4

3-[(Butylamino)methyl]-N-{(1S,2R)-1-(3,5-difluorobenzyl)-3-[(3-ethylbenzyl)amino]-2-hydroxypropyl}-5-methylbenzamide dihydrochloride

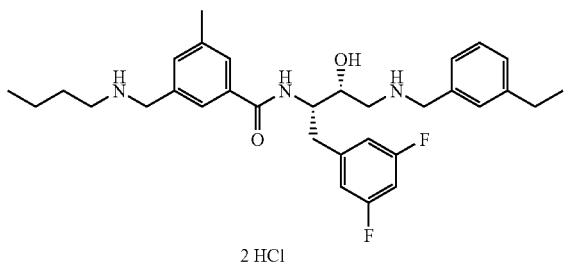

2 HCl

To a stirred solution of 3-{[(tert-butoxycarbonyl)(butyl)amino]methyl}-5-methylbenzoic acid (90 mg, 0.28 mmol) in methylene chloride (3 mL) is added HBTU (160 Mg, 0.42 mmol), HOBt (57 mg, 0.42 mmol), and N,N-diisopropylethylamine (0.142 mL, 0.84 mmol), followed by (2R,3S)-3-amino-4-(3,5-difluorophenyl)-1-[(3-ethylbenzyl)amino]butan-2-ol prepared by the method of Example SP-272 (114 mg, 0.28 mmol), and the reaction mixture is stirred for 12 h at room temperature. The reaction mixture is diluted with methylene chloride, washed with water, and saturated sodium bicarbonate, dried (magnesium sulfate), filtered, and concentrated under reduced pressure. Purification by flash column chromatography (silica, 10% methanol/chloroform) affords a clear oil, which is dissolved in methanol (2 mL). To this solution is added hydrochloric acid (5 mL, 4 N dioxane, 20 mmol), and the reaction mixture is stirred for 1 h at room temperature. The reaction mixture is then diluted with ethyl ether (10 mL). The precipitate that is formed is collected by filtration to provide the title compound. ESI MS m/z 538.5 [M+H]⁺.

Example SP-208

N-{(1S,2R)-1-(3,5-Difluorobenzyl)-3-[(3-ethylbenzyl)amino]-2-hydroxypropyl}-3-{[(2S)-2-(methoxymethyl)pyrrolidin-1-yl]methyl}-5-methylbenzamide dihydrochloride Step 1

Methyl 3-{[(2S)-2-(methoxymethyl)pyrrolidin-1-yl]methyl}-5-methylbenzoate

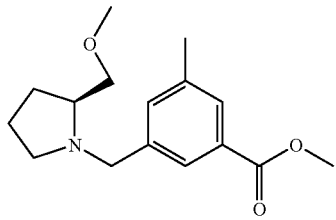

To an ice-cold, stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. (S)-(+)-2-(Methoxymethyl)pyrrolidine (380 mg, 3.3 mmol) is added to the filtrate, and the reaction mixture is stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (silica, 15% ethyl acetate/hexanes) provides the title compound. ¹H NMR (300 MHz, CDCl₃) δ 7.77 (s, 1H), 7.73 (s, 1H), 7.37 (s, 1H), 4.12 (d, J=17 Hz, 1H), 3.90 (s, 3H), 3.85 (m, 2H), 3.51 (m, 2H), 3.44 (m, 2H), 3.15 (s, 1H), 2.38 (s, 3H), 1.94 (m, 3H), 1.72 (m, 3H).

Step 2

3-{[(2S)-2-(Methoxymethyl)pyrrolidin-1-yl]methyl}-5-methylbenzoic acid

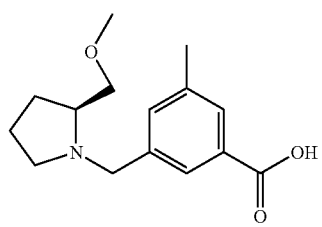

To a stirred solution of methyl 3-{[(2S)-2-(methoxymethyl)pyrrolidin-1-yl]methyl}-5-methylbenzoate (170 mg, 0.50 mmol) in methanol (2 mL), tetrahydrofuran (1 mL), and water (1 mL) is added lithium hydroxide (211 mg, 5.0 mmol), and the reaction mixture stirred at room temperature for 2 h. The reaction mixture is concentrated under reduced pressure, dissolved in methylene chloride, filtered, and the filtrate concentrated under reduced pressure to provide the title compound. ESI MS m/z 264 [M+H]⁺.

Step 3

N-{(1S,2R)-1-(3,5-Difluorobenzyl)-3-[(3-ethylbenzyl)amino]-2-hydroxypropyl}-3-{[(2S)-2-(methoxymethyl)pyrrolidin-1-yl]methyl}-5-methylbenzamide dihydrochloride

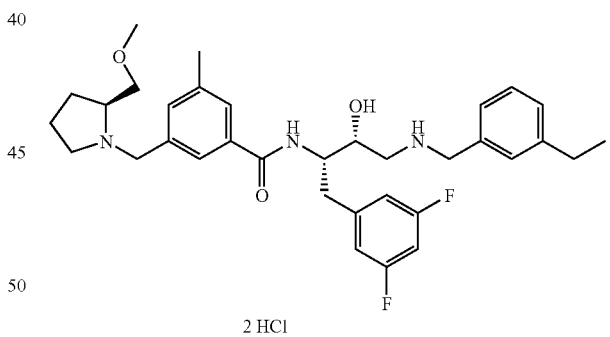

2 HCl

To a stirred solution of 3-{[(2S)-2-(methoxymethyl)pyrrolidin-1-yl]methyl}-5-methylbenzoic acid (110 mg, 0.42 mmol) in methylene chloride (3 mL) is added HBTU (240 mg, 0.63 mmol), HOBt (85 mg, 0.63 mmol), and N,N-diisopropylethylamine (0.212 mL, 1.26 mmol), followed by (2R,3S)-3-amino-4-(3,5-difluorophenyl)-1-[(3-ethylbenzyl)amino]butan-2-ol prepared by the method of Example SP-272 (171 mg, 0.42 mmol). The reaction mixture is stirred for 12 h at room temperature. The reaction mixture is diluted with methylene chloride, washed with water, and saturated sodium bicarbonate, dried (magnesium sulfate), filtered, and concentrated under reduced pressure. Purification by flash column chromatography (silica, 10% methanol/chloroform) affords a clear oil, which is dissolved in methanol (2 mL). To this solution is added hydrochloric acid (5 mL, 4 N dioxane, 20 mmol), and the reaction mixture is stirred for 1 h at room temperature. The reaction mixture is then diluted with ethyl ether (10 mL)). The precipitate that is formed was collected by filtration to provide the title compound. ESI MS m/z 580.4 [M+H]+.

Example SP-209

N-{(1S,2R)-1-(3,5-Difluorobenzyl)-3-[(3-ethylbenzyl)amino]-2-hydroxypropyl}-3-{[(2-hydroxyethyl)(methyl)amino]methyl}-5-methylbenzamide dihydrochloride Step 1

Methyl 3-{[(2-hydroxyethyl)(methyl)amino]methyl}-5-methylbenzoate

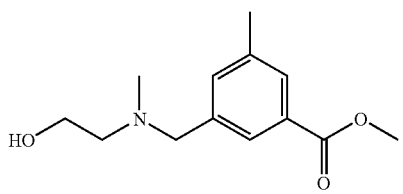

To an ice-cold stirred solution of methyl 3-(hydroxymethyl)-5-methylbenzoate (200 mg, 1.1 mmol) in methylene chloride (2.2 mL) is added triethylamine (0.304 mL, 2.2 mmol) followed by methanesulfonyl chloride (0.116 mL, 1.5 mmol). The reaction mixture is stirred for 15 min and filtered. 2-Methoxy-N-methyleneamine (0.354 mL, 3.3 mmol) is added to the filtrate and stirred at room temperature for 5 h. The reaction mixture is diluted with methylene chloride (10 mL), washed with 1 N hydrochloric acid, and saturated sodium bicarbonate, dried (magnesium sulfate), filtered, and concentrated under reduced pressure. Purification by flash column chromatography (50% ethyl acetate/hexanes) provides the title compound. ESI MS m/z 238 [M+H]+.

Step 2

3-{[(2-Hydroxyethyl)(methyl)amino]methyl}-5-methylbenzoic acid

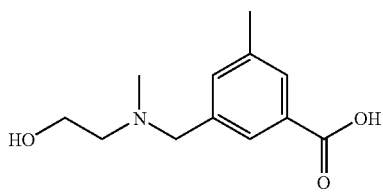

To a stirred solution of methyl 3-{[(2-hydroxyethyl)(methyl)amino]methyl}-5-methylbenzoate (180 mg, 0.72 mmol) in methanol (2 mL), tetrahydrofuran (1 mL), and water (1 mL) is added lithium hydroxide (302 mg, 7.2 mmol), and the reaction mixture is stirred at room temperature for 2 h. The reaction mixture is concentrated under reduced pressure, dissolved in methylene chloride, filtered, and concentrated under reduced pressure to provide the title compound. ESI MS m/z 224 [M+H]+.

Step 3

N-{(1S,2R)-1-(3,5-Difluorobenzyl)-3-[(3-ethylbenzyl)amino]-2-hydroxypropyl}-3-{[(2-hydroxyethyl)(methyl)amino]methyl}-5-methylbenzamide dihydrochloride

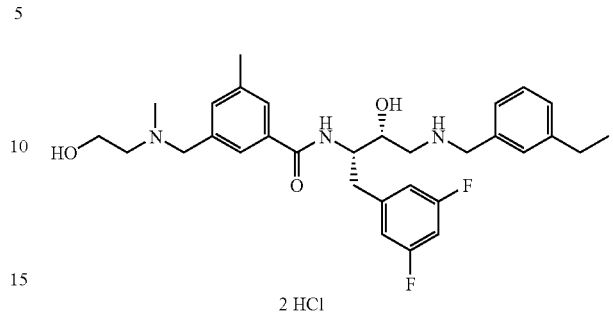

2 HCl

To a stirred solution of 3-{[(2-hydroxyethyl)(methyl)amino]methyl}-5-methylbenzoic acid (140 mg, 0.56 mmol) in methylene chloride (3 mL) is added HBTU (318 mg, 0.84 mmol), HOBt (114 mg, 0.84 mmol), and N,N-diisopropylethylamine (0.284 mL, 1.68 mmol), followed by (2R,3S)-3-amino-4-(3,5-difluorophenyl)-1-[(3-ethylbenzyl)amino]butan-2-ol prepared by the method of Example SP-272 (228 mg, 0.56 mmol). The reaction mixture is stirred for 24 h at room temperature, diluted with methylene chloride, washed with water, and saturated sodium bicarbonate, dried (magnesium sulfate), filtered, and concentrated under reduced pressure. Purification by flash column chromatography (10% methanol/chloroform) affords a clear oil, which is dissolved in methanol (2 mL). To this is added hydrochloric acid (5 mL of a 4 N solution in dioxane, 20 mmol), and the reaction mixture is stirred for 1 h at room temperature. The reaction mixture is diluted with ethyl ether (10 mL) The precipitate that is formed is collected by filtration to provide the title compound. ESI MS m/z 540.4 [M+H]+.

Example SP-210

3-Bromo-5-{[butyl(methyl)amino]methyl}-N-((1S,2R)-1-(3,5-difluorobenzyl)-2-hydroxy-3-{[3-(trifluoromethyl)benzyl]amino}propyl)benzamide dihydrochloride

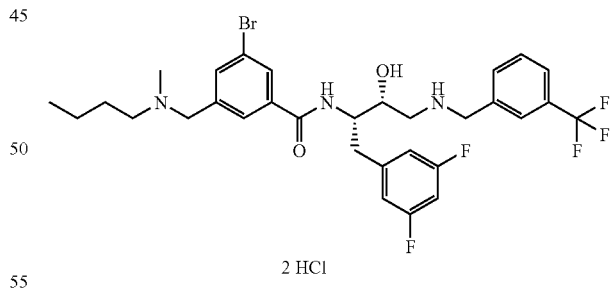

2 HCl

Methyl 3-bromo-5-{[butyl(methyl)amino]methyl}benzoate prepared by the method in Example SP-190, Step 1 (200 mg, 0.64) is dissolved in 2:1:1 tetrahydrofuran/methanol/water (4 mL), and lithium hydroxide monohydrate is added (60 mg, 1.3 mmol), and the reaction stirred 16 h. The solution is concentrated under reduced pressure. The residue is redissolved in DMF (5 mL), and diisopropylethylamine (445 µL, 2.6 mmol), HATU (304 mg, 0.8 mmol), and (2R,3S)-3-amino-4-(3,5-difluorophenyl)-1-{[3-(trifluoromethyl)benzyl]amino}butan-2-ol dihydrochloride prepared by the method in Example S-2511 (315 mg, 0.7 mmol) are added. The reaction stirred at room temperature 16 h. The reaction mixture is diluted with ethyl acetate, washed with water, and saturated sodium bicarbonate, brine, dried (sodium sulfate), filtered, and concentrated under reduced pressure. Purification by flash column chromatography (silica, 9% methanol/methylene chloride) provides the title compound as the free base. The residue is dissolved in diethyl ether (3 mL) and 1N hydrochloric acid in diethyl ether (2 mL) is added. The mixture is concentrated under reduced pressure to yield the title compound. ESI MS m/z 656.2 [M+H]$^+$.

Example SP-211

N-((1S,2R)-1-(3,5-Difluorobenzyl)-3-{[1-(3-ethynylphenyl)cyclopropyl]amino}-2-hydroxypropyl)-3-{[isopentyl(methyl)amino]methyl}-5-methylbenzamide dihydrochloride Step 1

Methyl 3-{[isopentyl(methyl)amino]methyl}-5-methylbenzoate

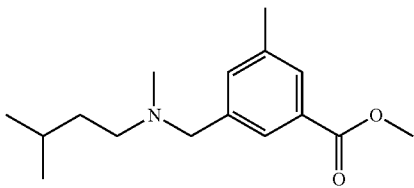

To methyl 3-(hydroxymethyl)-5-methylbenzoate prepared by the method in Example SP-198, Step 2 in anhydrous methylene chloride at −30° C. is added methanesulfonyl chloride (601 µL, 7.8 mmol), then triethylamine (1.5 mL, 11.1 mmol), and the reaction is stirred at 0° C. 15 min. The resulting precipitate is filtered, and the filtrate is added to N-methylisoamylamine (2.1 mL, 16.7 mmol). The reaction stirred at room temperature 16 h. The solution is concentrated under reduced pressure, redissolved in ethyl acetate and washed with saturated sodium bicarbonate, brine, dried (sodium sulfate), filtered, and concentrated under reduced pressure. Purification by flash column chromatography (silica, 20% ethyl acetate/hexanes) provides the title compound. ESI MS m/z 264.2 [M+H]$^+$.

Step 2

N-((1S,2R)-1-(3,5-Difluorobenzyl)-3-{[1-(3-ethynylphenyl)cyclopropyl]amino}-2-hydroxypropyl)-3-{[isopentyl(methyl)amino]methyl}-5-methylbenzamide dihydrochloride

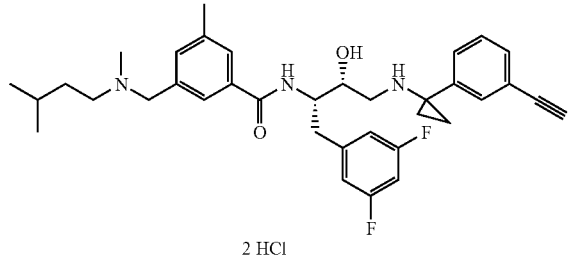

2 HCl

To methyl 3-{[isopentyl(methyl)amino]methyl}-5-methylbenzoate (250 mg, 0.95 mmol) in tetrahydrofuran/methanol/water (2:1:1, 8 mL) is added lithium hydroxide monohydrate (80 mg, 1.9 mmol), and the reaction is stirred at room temperature 16 h. The solution is concentrated under reduced pressure, redissolved in DMF (5 mL), and diisopropylethylamine (660 µL, 3.8 mmol), HATU (540 mg, 1.4 mmol), and (2R,3S)-3-amino-4-(3,5-difluorophenyl)-1-{[1-(3-ethynylphenyl)cyclopropyl]amino}-3-methylbutan-2-ol dihydrochloride (450 mg, 1.05 mmol) are added. The reaction stirred at room temperature 2 h. The reaction mixture is diluted with ethyl acetate, washed with water, saturated sodium bicarbonate, brine, dried (sodium sulfate), filtered, and concentrated under reduced pressure. Purification by flash column chromatography (silica, 9% methanol/methylene chloride) provides the title compound as the free base. The residue is dissolved in diethyl ether (3 mL) and 1N hydrochloric acid in diethyl ether (2 mL) is added. The mixture is concentrated under reduced pressure to yield the title compound. ESI MS m/z 588.3 [M+H]$^+$.

Example SP-212

N-((1S,2R)-1-(3,5-Difluorobenzyl)-3-{[1-(3-ethylphenyl)cyclopropyl]amino}-2-hydroxypropyl)-3-{[isopentyl(methyl)amino]methyl}-5-methylbenzamide dihydrochloride

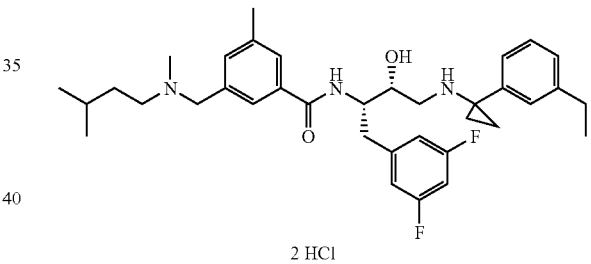

2 HCl

To methyl 3-{[isopentyl(methyl)amino]methyl}-5-methylbenzoate prepared by the method in Example SP-211, Step 1 (160 mg, 0.61 mmol) in tetrahydrofuran/methanol/water (2:1:1, 8 mL) is added lithium hydroxide monohydrate (51 mg, 1.2 mmol), and the reaction is stirred at room temperature 16 h. The solution is concentrated under reduced pressure, redissolved in DMF (5 mL), and diisopropylethylamine (424 µL, 2.4 mmol), HATU (290 mg, 0.8 mmol), and (2R,3S)-3-amino-4-(3,5-difluorophenyl)-1-{[1-(3-ethylphenyl)cyclopropyl]amino}-3-methylbutan-2-ol dihydrochloride prepared by the method in Example SP-272 (291 mg, 0.7 mmol) are added. The reaction stirred at room temperature 2 h. The reaction mixture is diluted with ethyl acetate, washed with water, saturated sodium bicarbonate, brine, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (2 mL) is added. The mixture is concentrated under reduced pressure to yield the title compound. ESI MS m/z 592.3 [M+H]$^+$.

Example SP-213

1-Butyl-N-{(1S,2R)-1-(3,5-difluorobenzyl)-3-[(3-ethylbenzyl)amino]-2-hydroxypropyl}-1H-indole-6-carboxamide Step 1: Methyl 1H-indole-5-carboxylate

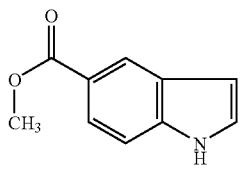

To a mixture of indole-5-carboxylic acid (3.0 g) and triethylamine (1.9 g) in dry THF (100 mL) was added 1,1-carbonyldiimidazole (3.08 g). The mixture was stirred for 30 minutes at room temperature, at which time methanol (25 mL) was added. The mixture was stirred at room temperature for 1 h, partitioned between water and ethyl acetate. The layers were separated and the organic layer washed twice with water, dried over anhydrous magnesium sulfate, filtered and concentrated under reduced pressure. Column chromatography on silica gel (200 mL) using $CH_2Cl_2$ as eluent to give 0.794 g of the title compound: $^1$H NMR ($CDCl_3$) δ 3.93, 6.66, 7.28, 7.41, 7.91, 8.34, 8.42.

Step 2: Methyl 1-butyl-1H-indole-5-carboxylate

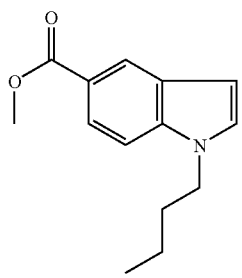

To a mixture of methyl 1H-indole-5-carboxylate (6.0 g) in methylsulfoxide (30 mL) was added potassium t-butoxide (3.88 g). The mixture was stirred at room temperature for 10 minutes at which time 1-iodobutane (1.8 mL) was added. The mixture was stirred at room temperature for 5 h then partitioned between water and methylene chloride. The layers were separated and the organic layer washed three times with brine, dried over anhydrous magnesium sulfate and concentrated under reduced pressure. Column chromatography on silica gel (100 mL) using 10% ethyl acetate in hexanes as eluent to give 6.18 g of the title compound: $^1$H NM ($CDCl_3$) δ 0.923, 1.38, 1.83, 3.9, 4.14, 6.58, 7.15, 7.34, 7.9, 8.39.

Step 3: 1-Butyl-1H-indole-6-carboxylic acid

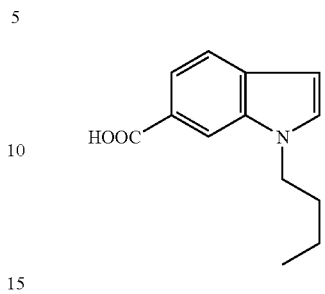

To a mixture of 1-butyl-1H-indole-6-carboxylic acid (0.52 g) in methanol (25.0 mL) and water (5.0 mL) was added lithium hydroxide monohydrate (2.0 g). The mixture was heated to 60° C. for 6 h, cooled to room temperature, poured into 1N HCl (50 mL) and extracted into ethyl acetate. The ethyl acetate extract was dried over anhydrous magnesium sulfate and concentrated under reduced pressure to give 0.496 g (72%) of the title compound: $^1$H NMR ($CDCl_3$) δ 0.98 (t, J=7.3 Hz, 3H), 1.4 (m, 2 H), 1.9 (m, 2H), 4.2 (m, 2H), 6.57 (ss, J=2.6. Hz, 1H), 7.31 (ss, J=3.1 Hz, 1H), 7.68 (d, J=8.4 Hz, 1H), 7.89 (dd, J=1.4, 8.4 Hz, 1H), 8.24 (s, 1H).

Step 4: 1-Butyl-N-{(1S,2R)-1-(3,5-difluorobenzyl)-3-[(3-ethylbenzyl)amino]-2-hydroxypropyl}-1H-indole-6-carboxamide

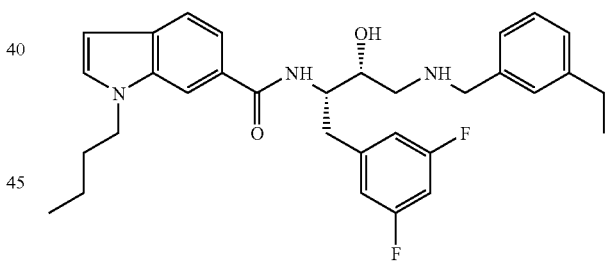

To a mixture of 1-butyl-1H-indole-6-carboxylic acid (0.278 g) in methylene chloride (10 mL) was added triethylamine (0.129 g), HOBT (0.175 g) and, HATU (0.486 g). The mixture was stirred at room temperature for 30 minutes at which time (2R,3S)-3-amino-4-(3,5-difluorophenyl)-1-[(3-ethylbenzyl)amino]butan-2-ol (0.408 g) was added. The resulting mixture was stirred at room temperature for 18 h then partitioned between water and methylene chloride. The layers were separated and the organic layer washed with water followed by brine and dried over anhydrous magnesium sulfate. Column chromatography on silica gel (100 mL) using 3% methanol in methylene chloride as eluent to give 0.256 g of the title compound: MS (ESI+) for $C_{32}H_{37}F_2N_3O_2$ m/z 542.2 (M+H).

Example SP-201

1-Butyl-N-{(1S,2R)-1(3,5-difluorobenzyl)-3-[(3-ethyl-benzyl)amino]-2-hydroxypropyl}indoline-6-carboxamide hydrochloride Step 1: Methyl 1-butylindoline-6-carboxylate

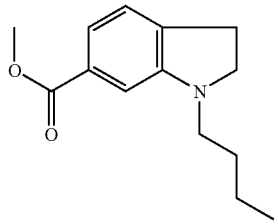

To a mixture of methyl 1-butyl-1H-indole-6-carboxylate, (2.1 g) in glacial acetic acid (25 mL) was added sodium cyanoborohydride (2.28 g). The mixture was heated at 40° C. for 3 h then cooled to room temperature, partitioned between water and ethyl acetate and the layers were separated. The organic layer was washed three times with brine, dried over anhydrous sodium sulfate and concentrated to give 1.64 g of the title compound: $^1$H NMR (CDCl$_3$) δ 0.969, 1.43, 1.59, 2.99, 3.1, 3.4, 3.88, 7.07, 7.34.

Step 2: 1-Butylindoline-6-carboxylic acid

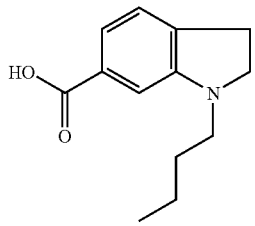

To a mixture of Methyl 1-butylindoline-6-carboxylate (1.6 g) in methanol (20 mL) was added 1N NaOH (5.0 mL). The mixture was heated at 60° C. for 2 h then cooled to room temperature, poured into 1N HCl and extracted into ethyl acetate. The ethyl acetate extract was dried over anhydrous magnesium sulfate and concentrated to give 1.16 g of the title compound: $^1$H NMR (CDCl$_3$) δ 0.974, 1.43, 1.60, 3.01, 3.11, 3.42, 7.1, 7.43.

Step 3: 1-Butyl-N-{(1S,2R)-1-(3,5-difluorobenzyl)-3-[(3-ethylbenzyl)amino]-2-hydroxypropyl}indoline-6-carboxamide hydrochloride

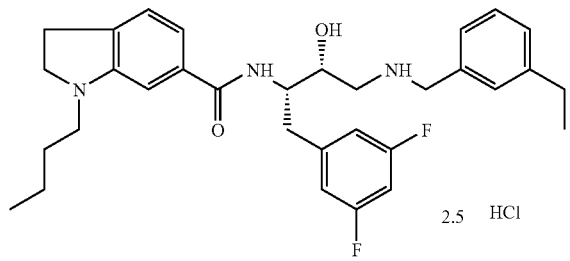

To a mixture of 1-butylindoline-6-carboxylic acid (0.2 g) in methylene chloride was added triethylamine (0.0.27 g), HOBT (0.125 g) and, HATU (0.347 g). The mixture was stirred at 40° C. for 15 minutes at which time (2R,3S)-3-amino-4-(3,5-difluorophenyl)-1-[(3-ethylbenzyl)amino]butan-2-ol (0.346 g) was added. The resulting mixture was stirred at 40° C. for 5 h then partitioned between water and methylene chloride. The layers were separated and the organic layer washed with water followed by brine and dried over anhydrous magnesium sulfate. Column chromatography on silica gel (100 mL) using 5% methanol in methylene chloride as eluent to give 0.100 g of the title compound: MS (ESI+) for C$_{32}$H$_{39}$F$_2$N$_3$O$_2$ m/z 535.9 (M+H)$^+$.

Example SP-215

1-Butyl-N-{(1S,2R)-1-(3,5-difluorobenzyl)-3-[(3-ethyl-benzyl)amino]-2-hydroxypropyl}-1H-indazole-6-carboxa-mide Step 1: 3-[(E)-(Tert-butylthio)diazenyl]-4-methylbenzoic acid

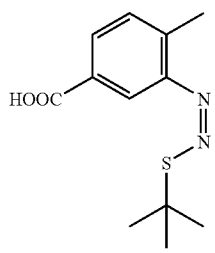

To a mixture of 3-amino-4-methyl benzoic acid (5.0 g) in water (50 mL) was added concentrated hydrochloric acid (15 mL). The mixture was chilled to 0° C. in an ice/acetone bath. Sodium nitrite (2.28 g) was dissolved in water (10 mL) and slowly added to the mixture at 0° C. The pH was adjusted to 6 with saturated sodium acetate and 2-methyl-2-propanethiol (1.8 mL) was added. The mixture was stirred for 1 h and the resulting solids were collected by filtration, washed with water and dried under reduced pressure to give 5.7 g of the title compound: $^1$H NMR (CDCl$_3$) δ 1.61, 2.20, 7.38, 7.55, 9.67.

Step 2: 1H-Indazole-6-carboxylic acid

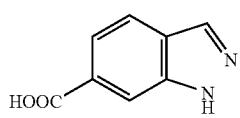

To a mixture of 3-[(E)-(tert-butylthio)diazenyl]-4-methyl-benzoic acid (5.7 g) in nitrogen degassed methylsulfoxide (90 mL) was added potassium t-butoxide (25.0 g). The mixture was stirred at room temperature for 24 h then poured onto ice and acidified to pH 4 with concentrated hydrochloric acid. The mixture was extracted with diethyl ether and the organic layer washed with brine. The organic layer was dried over anhydrous magnesium sulfate and decolorizing carbon then concentrated under reduced pressure to give 1.2 g of the title compound: $^1$H NMR (CDCl$_3$) δ 0.963, 1.36, 1.95, 4.48, 7.81, 7.88, 8.08, 8.29.

Step 3: Methyl 1H-indazole-6-carboxylate

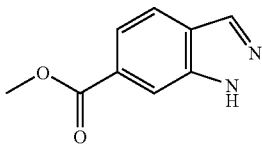

To a mixture of 1H-indazole-6-carboxylic acid (1.0 g) in methylene chloride (15 mL) was added EDC (1.8 g), HOBT (1.27 g), and triethylamine (1.29 mL). The mixture was heated to 40° C. for 30 minutes at which time methanol (10.0 mL) was added. The mixture was stirred at 40° C. for 18 h. The mixture was removed from heat, cooled to room temperature and poured into methylene chloride. The mixture was washed twice with water then brine, dried over anhydrous sodium sulfate and concentrated under reduced pressure to give 0.955 g of the title compound: $^1$H NMR (CDCl$_3$) δ 3.98, 7.81, 7.86, 8.16, 8.29, 10.6.

Step 4: Methyl 1-butyl-1H-indazole-6-carboxylate

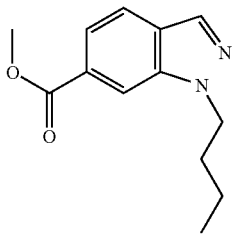

To a mixture of methyl 1H-indazole-6-carboxylate (0.95 g) in DMF (10 mL) was added 60% NaH (0.216 g). The mixture was heated to 60° C. and 1-iodobutane (0.61 mL) was added. The mixture was heated at 60° C. for 72 h and 1-iodobutane (0.61 mL) was added every 24 h. The mixture was removed from heat and cooled to room temperature and partitioned between water and ethyl acetate. The layers were separated and the organic layer washed three times with brine, dried over anhydrous magnesium sulfate and concentrated under reduced pressure. Column chromatography on silica gel (100 mL) using 5% ethyl acetate in hexanes as eluent to give 0.356 g of the title compound: $^1$H NMR (CDCl$_3$) δ 0.938, 1.34, 1.92, 3.97, 4.43, 7.73, 7.79, 8.03, 8.18.

Step 5: 1-Butyl-1H-indazole-6-carboxylic acid

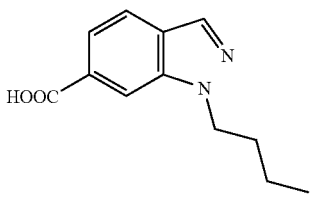

To a mixture of methyl 1-butyl-1H-indazole-6-carboxylate (0.356 g) in methanol (10 mL) was added saturated sodium bicarbonate (5 mL). The mixture was heated at 60° C. for 2 h at which time 1N NaOH (5 mL) was added and the mixture heated to 80° C. for 18 h. The mixture was cooled to room temperature, poured into 1N HCl (50 mL), and extracted with ethyl acetate. The ethyl acetate extract dried over anhydrous magnesium sulfate and concentrated under reduced pressure to give 0.310 g of the title compound: $^1$H NMR (CDCl$_3$) δ 0.964, 1.96, 4.48, 7.81, 7.89, 8.29, 8.46.

Step 6: 1-Butyl-N-{(1S,2R)-1-(3,5-difluorobenzyl)-3-[(3-ethylbenzyl)amino]-2-hydroxypropyl}-1H-indazole-6-carboxamide

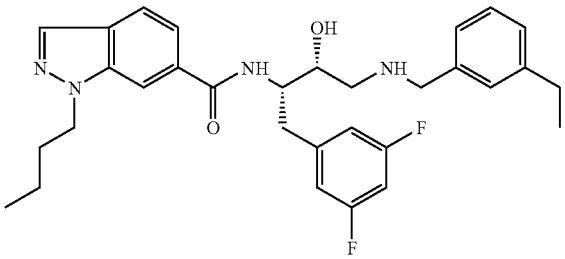

To a mixture of 1-butyl-1H-indazole-6-carboxylic acid (0.2 g) in methylene chloride (20 mL) was added triethylamine (0.182 g), HOBT (126 g), and HATU (0.348 g). The mixture was stirred at 40° C. for 10 minutes at which time (2R,3S)-3-amino-4-(3,5-difluorophenyl)-1-[(3-ethylbenzyl)amino]butan-2-ol (0.35 g) was added. The mixture was stirred at 40° C. for 3 h then poured into methylene chloride (50 mL), washed with water then brine, dried over anhydrous magnesium sulfate and concentrated under vacuum. Column chromatography on silica gel (100 mL) using 5% methanol in methylene chloride as eluent to give 0.2 g of the title compound: MS (ESI+) for C$_{31}$H$_{36}$F$_2$N$_4$O$_2$ m/z 534.9 (M+H)$^+$.

Example SP-216

1-Butyl-N-{(1S,2R)-1-(3,5-difluorobenzyl)-3-[(3-ethylbenzyl)amino]-2-hydroxypropyl}-4-[methyl(methylsulfonyl)amino]-1H-indole-6-carboxamide Step 1: Methyl 4-methyl-3,5-dinitrobenzoate

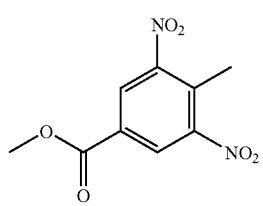

To a mixture of 3,5 dinitrotoluic acid (16 g) in methanol (10 mL) was added sulfuric acid (15 mL). The mixture was heated to 75° C. for 72 h, removed from heat and cooled to room temperature. The solvents were removed under pressure and the residue was partitioned between water and ethyl acetate. The layers were separated and the organic layer washed with 2 N NaOH followed by water. The organic layer was dried over anhydrous magnesium sulfate, filtered and concentrated to give 16.28 g (96%) of the title compound: $^1$H NMR (CDCl$_3$) δ 2.65 (s, 3H), 4.02 (s, 3H), 8.61 (s, 2 H Step 2: Methyl 4-[(E)-2-(dimethylamino)ethenyl]-3,5-dinitrobenzoate

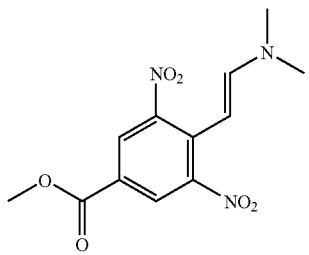

To a mixture of methyl 4-methyl-3,5-dinitrobenzoate (5.6 g) in toluene (20 mL) was added dimethylformamide dimethyl acetal (4.17 g) and 5-sulfo salycylic acid hydrate (0.1 g). The mixture was heated to 110° C. for 19 h, removed from heat and cooled to room temperature. The solvents were removed under reduced pressure at which time hexanes was added to the residue and the residue was filtered to give 6.85 g of the title compound: ¹H NMR (CDCl₃) δ 2.97, 3.96, 5.54, 6.74, 8.33.

Step 3: Methyl 4-amino-1H-indole-6-carboxylate

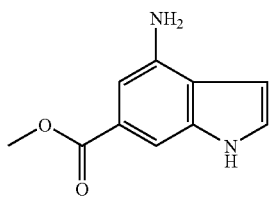

To a mixture of methyl 4-[(E)-2-(dimethylamino)ethenyl]-3,5-dinitrobenzoate (19.3 g) in ethyl acetate (200 mL) was added 5% palladium on carbon (1.5 g). The mixture was placed under 45 PSI H₂ and shaken overnight. The mixture was filtered through celite and concentrated. The residue was dissolved in CH₂Cl₂ to which was added ((1:1) H₂O:conc. HCl (250 mL)). The resulting solids were collected by filtration, dissolved in ethyl acetate and washed with 2N NaOH. The ethyl acetate layer with anhydrous magnesium sulfate, filtered and concentrated to give 7.4 g if the title compound: ¹H NMR (CDCl₃) δ 3.91, 4.01, 6.51, 7.09, 7.27, 8.40.

Step 4: Methyl 4-[(methylsulfonyl)amino]-1H-indole-6-carboxylate

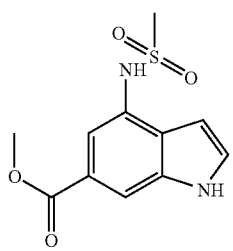

To a mixture of methyl 4-amino-1H-indole-6-carboxylate (1.0 g) in DMF (10 mL) was added 4-dimethylaminopyridine (1.46 g) and methanesulfonyl chloride (0.6 g). The mixture was heated to 60° C. for 3 h, cooled to room temperature, and partitioned between water and ethyl acetate. The layers were separated and the organic layer washed three times with brine, dried over anhydrous sodium sulfate and concentrated to give 0.71 g of the title compound: ¹H NMR (CDCl₃) δ 3.02, 3.94, 6.69, 7.42, 7.81, 8.04.

Step 5: Methyl 4-[methyl(methylsulfonyl)amino]-1H-indole-6-carboxylate

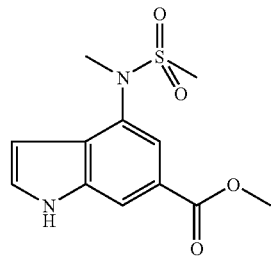

To a mixture of Methyl 4-[(methylsulfonyl)amino]-1H-indole-6-carboxylate (0.6 g) in THF (10 mL) was added potassium carbonate (0.309 g) and iodomethane (0.63 mL). The mixture was stirred at room temperature for 4 h then heated to 40° C. overnight. Iodomethane (0.3 mL) was added and the mixture heated an additional 3 h. The mixture was cooled to room temperature, partitioned between water and diethyl ether, dried over anhydrous sodium sulfate and concentrated. The residue was dissolved in ether and decolorizing carbon (2 g) was added and the mixture refluxed for 5 minutes then filtered through celite while hot. The ether was removed under reduced pressure to give 0.437 g of the title compound: MS (ESI+) for C12 H14 N2 O4 Si m/z 321.1 (M+K).

Step 6: 1-Butyl-4-[methyl(methylsulfonyl)amino]-1H-indole-6-carboxylic acid

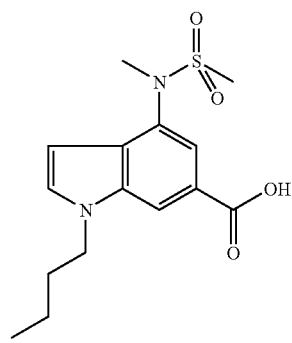

To a mixture of methyl 4-[methyl(methylsulfonyl)amino]-1H-indole-6-carboxylate (0.437 g) in DMF (15 mL) was added potassium hydroxide (0.087 g) and iodobutane (0.34 mL). The mixture was heated to 70° C. for 6 h. then stirred at room temperature for 72 h. The mixture was partitioned between water and ethyl acetate, the layers were separated and the organic layer washed three times with water. The organic layer was dried over anhydrous sodium sulfate, filtered and concentrated. The residue was dissolved in methanol (5 mL) to which was added 1N NaOH (2 mL) and the mixture heated to 50° C. for 1 h. The mixture was cooled to room temperature and poured into water and washed with ether. The aqueous layer was acidified to pH 4 with 1N HCl and the product extracted into ethyl acetate which was dried over anhydrous sodium sulfate, filtered and concentrated to dryness to give 0.377 g of the title compound: ¹H NMR (CDCl₃) δ 0.973, 1.38, 1.87, 3.01, 3.45, 4.21, 6.71, 7.36, 7.82, 8.18.

Step 7: 1-Butyl-N-{(1S,2R)-1-(3,5-difluorobenzyl)-3-[(3-ethylbenzyl)amino]-2-hydroxypropyl}-4-[methyl(methylsulfonyl)amino]-1H-indole-6-carboxamide

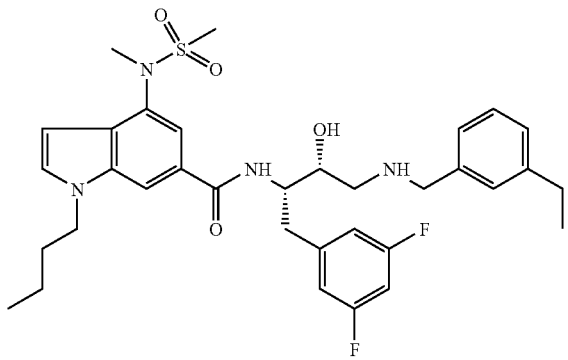

To a mixture of 1-Butyl-4-[methyl(methylsulfonyl)amino]-1H-indole-6-carboxylic acid (0.2 g) in methylene chloride (15 mL) was added triethylamine (0.156 g), HOBT (0.105 g), and HATU (0.293 g). The mixture was stirred at 39° C. for 10 minutes at which time (2R,3S)-3-amino-4-(3,5-difluorophenyl)-1-[(3-ethylbenzyl)amino]butan-2-ol (0.293 g) was added. The mixture was stirred at 40° C. for 4 h then poured into methylene chloride (50 mL), washed with water followed by brine then dried over anhydrous magnesium sulfate and concentrated under reduced pressure. Column chromatography on silica gel (100 mL) using 5% methanol in methylene chloride as eluent to give 0.21 g of the title compound: MS (ESI+) for $C_{34}H_{42}F_2N_4O_4S_1$ m/z 640.8 (M+H).

Example SP-217

N-{(1S,2R)-1-(3,5-Difluorobenzyl)-3-[(3-ethylbenzyl)amino]-2-hydroxypropyl}-2-(dipropylamino)isonicotinamide hydrochloride Step 1: 2-Chloroisonicotinonitrile

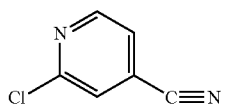

4-cyanopyridine-N-oxide (10.0 g) was added to phosphorus oxychloride (85 mL) and heated to 110° C. for 2.5 h. The mixture was cooled to room temperature and the excess phosphorus oxychloride removed under reduced pressure. The residue was dissolved in water and made basic with concentrated ammonia. The product was extracted into methylene chloride, dried over anhydrous magnesium sulfate and concentrated under reduced pressure. Column chromatography on silica gel (100 mL) using methylene chloride as eluent to give 7.19 g of the title compound: 1H NMR (CDCl₃) δ 7.48, 7.6, 8.6.

Step 2: 2-(Dipropylamino)isonicotinonitrile

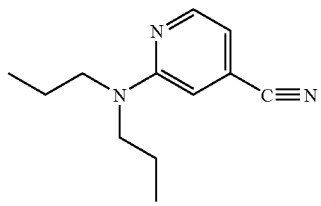

2-Chloroisonicotinonitrile (1.0 g) and dipropylamine (10 mL) were placed in a sealed heavy wall tube and heated to 100° C. for 18 h. The mixture was removed from heat and cooled to room temperature. The dipropylamine was removed under reduced pressure and the residue chromatographed on silica gel using 2% ethyl acetate in hexanes as eluent to give 1.06 g of the title compound: MS (ESI+) for $C_{12}H_{17}N_3$ m/z 204.1 (M+H)⁺.

Step 3: 2-(Dipropylamino)isonicotinic acid hydrochloride

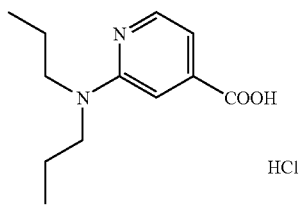

2-(Dipropylamino)isonicotinonitrile (1.0 g) was dissolved in concentrated hydrochloric acid (30 mL) and heated at 65° C. for 3 h. The solvents were removed under reduced pressure to give 1.27 g of the title compound: MS (ESI+) for $C_{13}H_{20}N_2O_2$ m/z 237.3 (M+H)⁺.

Step 4: N-{(1S,2R)-1-(3,5-Difluorobenzyl)-3-[(3-ethylbenzyl)amino]-2-hydroxypropyl}-2-(dipropylamino)isonicotinamide hydrochloride

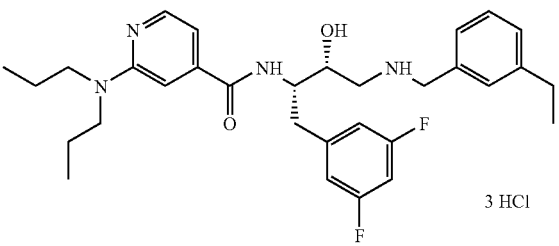

To a mixture of 2-(Dipropylamino)isonicotinic acid hydrochloride (0.2 g) in methylene chloride (15 mL) was added triethylamine (0.195 g), HOBT (0.105 g), and HATU (0.293 g). The mixture was stirred at 39° C. for 10 minutes at which time (2R,3S)-3-amino-4-(3,5-difluorophenyl)-1-[(3-ethylbenzyl)amino]butan-2-ol (0.285 g) was added. The mixture was stirred at 40° C. for 4 h then poured into methylene chloride (50 mL), washed with water then brine, dried over anhydrous magnesium sulfate and concentrated under vacuum. Column chromatography on silica gel (100 mL) using 5% methanol in methylene chloride as eluent and con-

Example SP-218

1-Butyl-N-{(1S,2R)-1-(3,5-difluorobenzyl)-3-[(3-ethylbenzyl)amino]-2-hydroxypropyl}-4-(1,3-oxazol-2-yl)-1H-indole-6-carboxamide Step 1: Methyl 4-iodo-1H-indole-6-carboxylate

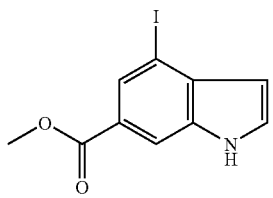

To a mixture of methyl 4-amino-1H-indole-6-carboxylate (Example SP-216, step 3) (3.2 g) in water (50 mL) was added concentrated hydrochloric acid (5 mL). The mixture was chilled to below 5° C. with the addition of ice. To this was added sodium nitrite (1.16 g) dissolved in water (10 mL). The mixture was stirred chilled for 1 h followed by addition of sodium iodide (3 g) in water (20 mL). The mixture was stirred for 30 minutes, filtered and the solids collected by filtration were washed with water and dried at 50° C. The solids turned black and gas evolved rapidly upon drying. Column chromatography on silica gel (200 mL) using 20% hexanes in CH$_2$Cl$_2$ as eluent to give 0.82 g of the title compound: $^1$H NMR (CDCl$_3$) δ 3.94, 6.55, 7.43, 8.14, 8.22, 8.62.

Step 2: Methyl 1-butyl-4-iodo-1H-indole-6-carboxylate

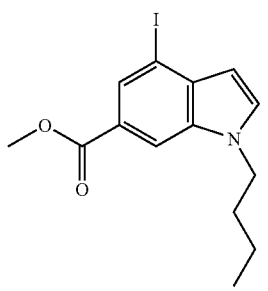

To a mixture of methyl 4-iodo-1H-indole-6-carboxylate (1.0 g) in DMF (10 mL) was added potassium hydroxide (0.392 g) and 1-iodobutane (0.8 mL). The mixture was heated to 80° C. for 18 h. The mixture was cooled to room temperature and partitioned between water and ethyl acetate. The layers were separated and the organic layer washed twice with water, dried over anhydrous magnesium sulfate and concentrated under reduced pressure. Column chromatography on silica gel (100 mL) using 20% ethyl acetate in hexanes as eluent to give 0.73 g of the title compound: $^1$H NMR (CDCl$_3$) δ 0.940, 1.32, 1.81, 3.95, 4.15, 6.45, 7.31, 8.09, 8.18.

Step 3: 1-Butyl-4-(1,3-oxazol-2-yl)-1H-indole-6-carboxylic acid

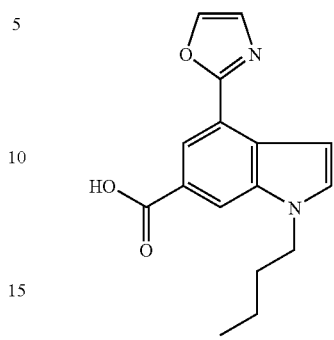

To a −72° C. solution of oxazole (0.069 g) in dry THF (20 mL) was added dropwise 1.6 M N-butyl lithium (0.68 mL). The mixture was stirred at −72° C. for 30 minutes at which time 1.0 M zinc chloride (3.3 mL) was added. The mixture was allowed to warm to 0° C. at which time methyl 1-butyl-4-iodo-1H-indole-6-carboxylate (0.37 g) and tetrakis triphenylphosphine palladium(0) (0.07 g) were added and the mixture heated to 85° C. The mixture was heated at 85° C. for 20 h then cooled to room temperature and partitioned between water and ethyl acetate. The layers were separated and the organic layer washed with water, dried over anhydrous sodium sulfate and concentrated under reduced pressure. Column chromatography was performed on silica gel (100 mL) using 20% ethyl acetate in hexanes as eluent. The residue was dissolved in methanol (10 mL) and 1N NaOH (3 mL) and heated at 60° C. for 2 h. The mixture was acidified to pH 4 with 1N HCl and extracted with ethyl acetate. The ethyl acetate extracts were dried over anhydrous sodium sulfate and concentrated to dryness under reduced pressure to give 0.2 g of the title compound: MS (ESI+) for C$_{16}$H$_{16}$N$_2$O$_3$ m/a 283.16 (M+H)$^+$.

Step 4: 1-Butyl-N-{(1S,2R)-1-(3,5-difluorobenzyl)-3-[(3-ethylbenzyl)amino]-2-hydroxypropyl}-4-(1,3-oxazol-2-yl)-1H-indole-6-carboxamide

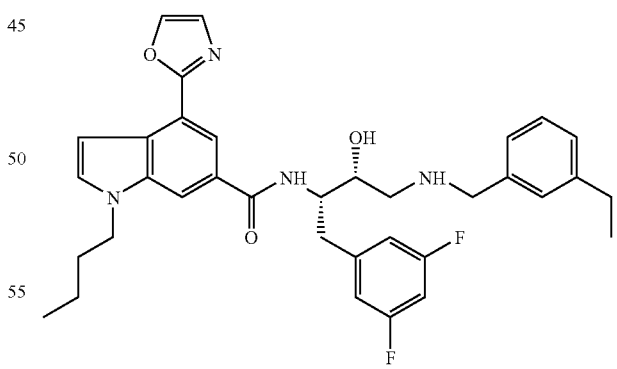

To a mixture of 1-butyl-4-(1,3-oxazol-2-yl)-1H-indole-6-carboxylic acid (0.2 g) in methylene chloride (20 mL) was added 1,1-carbonyldiimidazole (0.114 g). The mixture was stirred at room temperature for 1 h at which time (2R,3S)-3-amino-4-(3,5-difluorophenyl)-1-[(3-ethylbenzyl)amino]butan-2-ol (0.265 g) dissolved in methylene chloride (10 mL) was added. The mixture was stirred at room temperature for 18 h then poured into methylene chloride (50 mL), washed version to the hydrochloride salt gave 0.105 g of the title compound: MS (ESI+) for C$_{31}$H$_{40}$F$_2$N$_4$O$_2$ m/z 539.3 (M+H)$^+$.

515 with water followed by brine, dried over anhydrous magnesium sulfate and concentrated under reduced pressure. Column chromatography on silica gel (100 mL) using 65% methylene chloride, 30% hexanes, and 5% methanol as eluent to give 0.0985 g of the title compound: MS (ESI+) for $C_{35}H_{38}F_2N_4O_3$ m/z 601.99 (M+H)$^+$.

Example SP-219

1-Butyl-4-cyano-N-{(1S,2R)-1-(3,5-difluorobenzyl)-3-[(3-ethylbenzyl)amino]-2-hydroxypropyl}-1H-indole-6-carboxamide Step 1: Methyl 1-butyl-4-cyano-1H-indole-6-carboxylate

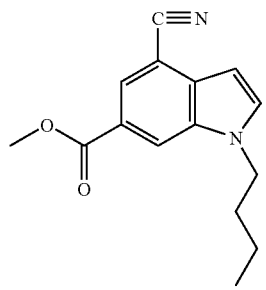

To a mixture of methyl 1-butyl-4-iodo-1H-indole-6-carboxylate (Example SP-218, Step 4) (1.47 g) in N-methyl pyrrolidinone (15 mL) was added copper (I) cyanide (1.1 g). The mixture was heated to 150° C. for 6 h, removed from heat and cooled to room temperature. The mixture was partitioned between water and ethyl acetate and the layers were separated. The organic layer was washed three times with water, dried over anhydrous sodium sulfate and concentrated under reduced pressure. Column chromatography on silica gel (100 mL) using 20% ethyl acetate as eluent to give 0.5 g of the title compound: $^1$H NMR (CDCl$_3$) δ 0.955, 1.32, 1.85, 3.98, 4.23, 6.76, 7.43, 8.16, 8.30.

Step 2: 1-Butyl-4-cyano-1H-indole-6-carboxylic acid

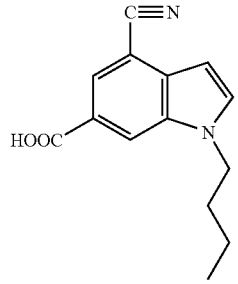

To a mixture of methyl 1-butyl-4-cyano-1H-indole-6-carboxylate (10.5 g) in methanol (15 mL) was added 1N NaOH (3.0 mL). The mixture was heated at 40° C. for 2 h then cooled to room temperature. The mixture was poured into 1N HCl and extracted into ethyl acetate. The ethyl acetate extract was dried over anhydrous magnesium sulfate and concentrated to give 0.45 g of the title compound: $^1$H NMR (CDCl$_3$) δ 0.973, 1.38, 1.88, 4.27, 6.79, 7.48, 8.24, 8.38.

516

Step 3: 1-Butyl-4-cyano-N-{(1S,2R)-1-(3,5-difluorobenzyl)-3-[(3-ethylbenzyl)amino]-2-hydroxypropyl}-1H-indole-6-carboxamide

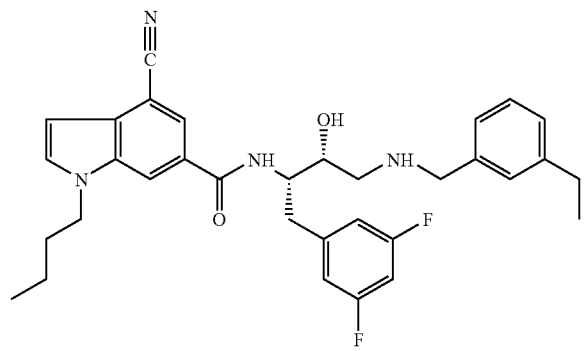

To a mixture of 1-butyl-4-cyano-1H-indole-6-carboxylic acid (0.29 g) in methylene chloride (10 mL) was added 1,1-carbonyldiimidazole (0.194 g) and triethylamine (0.267 g). The mixture was stirred at room temperature for 45 minutes at which time (2R,3S)-3-amino-4-(3,5-difluorophenyl)-1-[(3-ethylbenzyl)amino]butan-2-ol (0.5 g) dissolved in methylene chloride (10 mL) was added. The mixture was stirred at room temperature for 18 h then poured into methylene chloride (50 mL), washed with water followed by brine, dried over anhydrous magnesium sulfate and concentrated under vacuum. Column chromatography on silica gel (100 mL) using 5% methanol in methylene chloride as eluent to give 0.47 g of the title compound: MS (ESI+) for $C_{33}H_{36}F_2N_4O_2$ m/z 559.0 (M+H)$^+$.

Example SP-220

4-Butyl-N-{(1S,2R)-1-(3,5-difluorobenzyl)-3-[(3-ethylbenzyl)amino]-2-hydroxypropyl}-8-(1,3-oxazol-2-yl)-3,4-dihydro-2H-1,4-benzoxazine-6-carboxamide Step 1: Methyl 4-hydroxy-3-iodo-5-nitrobenzoate

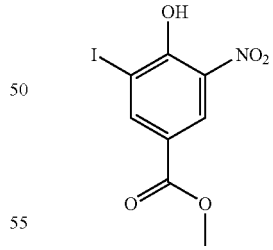

To a solution of methyl 4-hydroxy-3-nitrobenzoate (2.0 g) in acetic acid (15 mL) was added iodine monochloride (1.65 mg) in acetic acid, and the mixture was stirred at 100° C. for 1.5 h. After cooling to room temperature, the mixture was poured into water (200 mL), and stirred for 30 min. The mixture was filtered and washed with water and hexanes. The yellow powder was collected by filtration and dried in vacuum oven overnight to give 2.99 g of the title compound: $^1$H NMR (300 MHz, CDCl$_3$) δ 11.68, 8.81, 8.72, 3.96.

Step 2: Methyl 3-amino-4-hydroxy-5-iodobenzoate

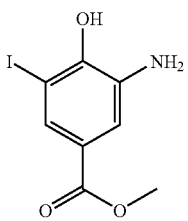

To a mixture of methyl 4-hydroxy-3-iodo-5-nitrobenzoate (2.99 g) in ethanol (40 mL) was added tin (II) chloride (10 g) portion wise. After stirring for 1 h at reflux, the mixture was cooled to 0° C. and quenched by saturated potassium carbonate (100 mL). The mixture was filtered through diatomaceous earth and the filtrate was extracted with ethyl acetate (4×100 mL). The combined organic extracts were dried (sodium sulfate), filtered, and concentrated under reduced pressure to give 2.5 g of the title compound: $^1$H NMR (300 MHz, DMSO-$d_6$) δ 7.50, 7.24, 3.75.

Step 3: Methyl 8-iodo-3-oxo-3,4-dihydro-2H-1,4-benzoxazine-6-carboxylate

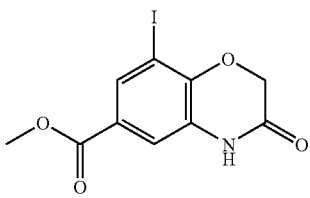

To an ice-cold, stirred solution of Methyl 3-amino-4-hydroxy-5-iodobenzoate (2.3 g) and sodium bicarbonate (1.5 g) in 1:1 isobutyl methyl ketone/water (80 mL) was added chloroacetyl chloride (1.1 g), and the reaction mixture was stirred for 1 h. The mixture was warmed to room temperature and heated at reflux for 18 h. After overnight, a beige solid formed. The mixture was filtered, and washed with water and hexanes to give 2.4 g of the title compound: $^1$H NMR (300 MHz, DMSO-$d_6$) δ 10.98, 7.89, 7.47, 4.79, 3.82.

Step 4: Methyl 4-butyl-8-iodo-3-oxo-3,4-dihydro-2H-1,4-benzoxazine-6-carboxylate

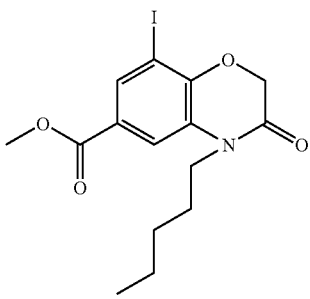

To a solution of Methyl 8-iodo-3-oxo-3,4-dihydro-2H-1,4-benzoxazine-6-carboxylate (2.64 g) and potassium carbonate (5 g) in DMSO (20 mL) was added bromobutane (5 g), and the reaction mixture was stirred for 1 h at 80° C. The mixture was cooled to room temperature, diluted with 1:1 ethyl acetate/hexanes (100 mL) and water (160 mL), and separated. The organic layer was washed with water, and brine, dried (magnesium sulfate), filtered, and concentrated under reduced pressure. Purification by flash column chromatography (silica, 1:10 ethyl acetate/hexanes) afforded 2.24 g of the title compound: $^1$H NMR (300 MHz, CDCl$_3$) δ 8.13, 7.63, 4.74, 3.96, 3.92, 1.64, 1.42, 0.97.

Step 5: Methyl 4-butyl-8-iodo-3,4-dihydro-2H-1,4-benzoxazine-6-carboxylate

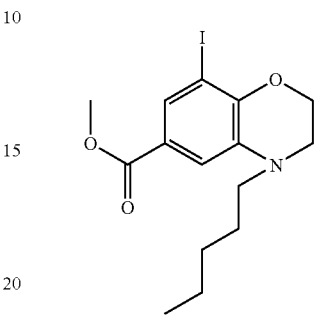

A solution of Methyl 4-butyl-8-iodo-3-oxo-3,4-dihydro-2H-1,4-benzoxazine-6-carboxylate (680 mg) and 9-BBN (900 mg) in tetrahydrofuran (30 mL) was heated at reflux for 1.5 h. The mixture was cooled to room temperature, ethanolamine (0.22 mL) was added, and the resulting solution was concentrated under reduced pressure. The residue was washed with hexanes, filtered, and the filtrate was concentrated under reduced pressure. Purification by flash column chromatography (silica, 10% ethyl acetate/hexanes) afforded 600 mg of the title compound: $^1$H NMR (300 MHz, CDCl$_3$) δ 7.75, 7.28, 4.34, 3.86, 3.36, 3.28, 1.58, 1.40, 0.96.

Step 6: Methyl 4-butyl-8-(1,3-oxazol-2-yl)-3,4-dihydro-2H-1,4-benzoxazine-6-carboxylate

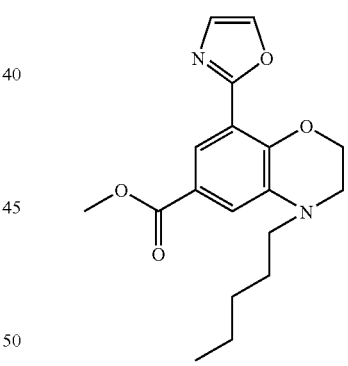

To a −70° C. solution of oxazole (227 mg) in tetrahydrofuran (10 mL) was added n-butyllithium (2.5 M in hexanes, 2 mL). After stirred at −70° C. for 30 min, zinc chloride (1 M in ethyl ether, 13 mL) was added. The mixture was warmed to 0° C. for 1 h. To this mixture was then added ethyl 4-butyl-8-iodo-3,4-dihydro-2H-1,4-benzoxazine-6-carboxylate (600 mg, 1.6 mmol) in THF (5 mL) followed by tetrakis triphenylphosphine palladium(0) (115 mg). The mixture was heated at reflux for 3 h, diluted with ethyl acetate (300 mL) and washed with water followed by brine. The organic solution was dried (sodium sulfate) and concentrated under reduced pressure. Purification by silica gel plug (1:1 acetate/hexanes) provided 363 mg of the title compound: $^1$H NMR (300 MHz, CDCl$_3$) δ 7.96, 7.73, 7.40, 7.28, 4.44, 3.90, 3.43, 3.34, 1.61, 1.41, 0.98.

519

Step 7: 4-Butyl-8-(1,3-oxazol-2-yl)-3,4-dihydro-2H-1,4-benzoxazine-6-carboxylic acid

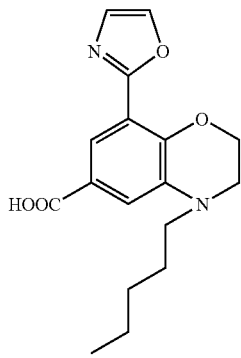

To a stirred solution of Methyl 4-butyl-8-(1,3-oxazol-2-yl)-3,4-dihydro-2H-1,4-benzoxazine-6-carboxylate (474 mg) in methanol (20 mL) was added potassium hydroxide (15 mL of a 1.0 M solution in water). The mixture was stirred at room temperature overnight then concentrated under reduced pressure. The residue was diluted with water and washed with ethyl acetate. The aqueous layer was acidified to pH 4 with 1 N hydrochloric acid and extracted with chloroform (4×100 mL). The combined organic extracts were dried (sodium sulfate), filtered, and concentrated under reduced pressure to give 450 mg of the title compound: $^1$H NMR (300 MHz, CDCl$_3$) δ 11.60, 8.08, 7.74, 7.46, 7.37, 4.46, 3.43, 3.34, 1.62, 1.41, 0.98.

Step 8: 4-Butyl-N-{(1S,2R)-1-(3,5-difluorobenzyl)-3-[(3-ethylbenzyl)amino]-2-hydroxypropyl}-8-(1,3-oxazol-2-yl)-3,4-dihydro-2H-1,4-benzoxazine-6-carboxamide

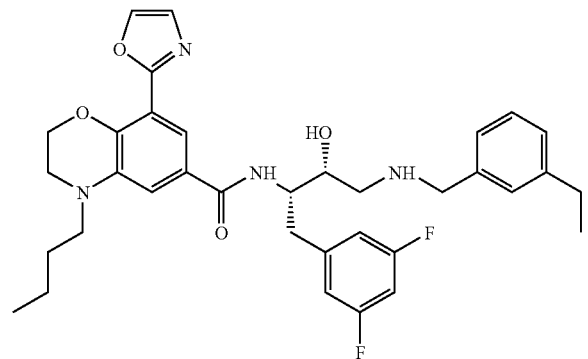

A solution of 4-Butyl-8-(1,3-oxazol-2-yl)-3,4-dihydro-2H-1,4-benzoxazine-6-carboxylic acid (450 mg, HBTU (853 mg), and diisopropylethylamine (580 mg) was stirred in methylene chloride (15 mL) for 15 min. A solution of (2R,3S)-3-amino-4-(3,5-difluorophenyl)-1-[(3-ethylbenzyl)amino]butan-2-ol (606 mg) in methylene chloride (7 mL) was added and the reaction mixture was stirred overnight. The mixture was filtered with methylene chloride, dried (magnesium sulfate), and concentrated under reduced pressure. Purification by flash column chromatography (silica, 1:9 methanol/chloroform) provided 400 mg of the title compound: ESI MS m/z 619 [M+H]$^+$.

520

Example SP-221

4-Butyl-8-cyano-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide Step 1: Methyl 3-bromo-5-(butylamino)-4-methoxybenzoate

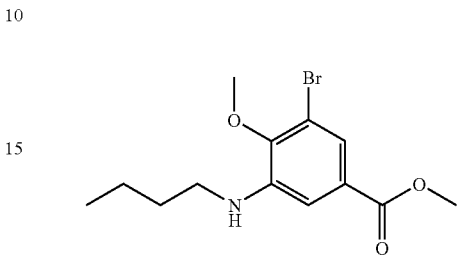

To a stirred solution of Pd(OAc)$_2$ (144 mg), BINAP (1.2 g), and cesium carbonate (8.4 g) in toluene (100 mL) was added butylamine (1.6 mL), and the mixture was heated at 80° C. for 15 min. A solution methyl 3,5-dibromo-4-methoxybenzoate (4.2 g) in toluene (30 mL) was added dropwise over 20 min. The mixture was refluxed overnight. The mixture was cooled to room temperature, filtered through diatomaceous earth, and concentrated under reduced pressure. Purification by flash column chromatography (silica, 1:9 ethyl acetate/hexanes) provided 3.5 g of the title compound: $^1$H NMR (300 MHz, CDCl$_3$) δ 7.52, 7.19, 3.90, 3.88, 3.18, 1.66, 1.46, 0.97.

Step 2: Methyl 3-bromo-5-(butylamino)-4-hydroxybenzoate

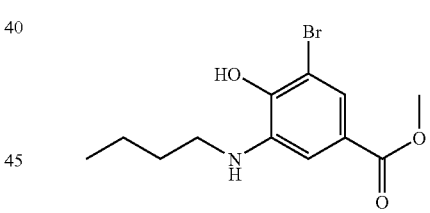

To a −78° C. solution of the Methyl 3-bromo-5-(butylamino)-4-methoxybenzoate (520 mg) in methylene chloride (10 mL) was added BBr$_3$ (8 ml of 1.0 M solution in methylene chloride) dropwise and the reaction mixture was stirred for 18 h. The mixture was concentrated under reduced pressure, and the residue was dissolved in methylene chloride and saturated sodium bicarbonate was added. The mixture was cooled to 0° C. and methanol was added dropwise. After stirring for 30 min, the mixture was stirred at room temperature for 1 h. The solvent was removed, and the residue dissolved in methylene chloride, washed with water, saturated sodium bicarbonate (15 mL), and brine, dried (magnesium sulfate), filtered, and concentrated under reduced pressure. Purification by flash column chromatography (silica, 1:20, ethyl acetate/hexanes) provided 440 mg of the title compound: $^1$H NMR (300 MHz, CDCl$_3$) δ 7.52, 7.19, 3.88, 3.18, 1.65, 1.46, 0.97.

Step 3: Methyl 8-bromo-4-butyl-3,4-dihydro-2H-1,4-benzoxazine-6-carboxylate

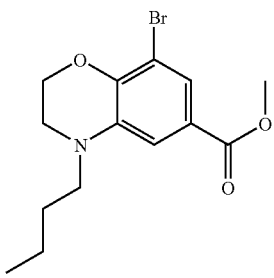

To an ice-cold, stirred solution of Methyl 3-bromo-5-(butylamino)-4-hydroxybenzoate (440 mg) and sodium bicarbonate (280 mg) in 1:1 isobutyl methyl ketone/water (10 mL) was added chloroacetyl chloride (226 mg). The mixture was stirred for 1 h, warmed to room temperature, and heated at reflux for 14 h. The mixture was cooled to room temperature, diluted with chloroform, and the layer separated. The organic layer was washed with water, and brine, dried (magnesium sulfate), filtered, and concentrated under reduced pressure to give a white solid: $^1$H NMR (300 MHz, CDCl$_3$) δ 7.94, 7.62, 4.76, 3.98, 3.93, 1.65, 1.43, 0.97, which was used in the next step without further purification or characterization.

Step 4: A solution of the amide from step 3 and 9-BBN (780 mg) in tetrahydrofuran (10 mL) was heated at reflux for 1.5 h. The mixture was cooled to room temperature, ethanolamine (0.2 mL) was added, and the resulting solution was concentrated under reduced pressure. The residue was washed with hexanes, filtered, and the filtrate was concentrated under reduced pressure. Purification by flash column chromatography (silica, 10% ethyl acetate/hexanes) afforded (330 mg, over 2 steps) of the title compound: $^1$H NMR (300 MHz, CDCl$_3$) δ 7.55, 7.27, 4.36, 3.87, 3.37, 3.30, 1.60, 1.41, 0.97.

Step 5: Methyl 4-butyl-8-cyano-3,4-dihydro-2H-1,4-benzoxazine-6-carboxylate

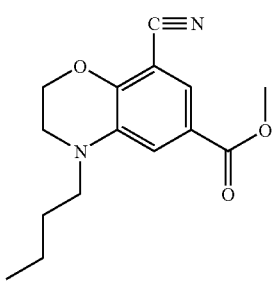

To a flask containing methyl 8-bromo-4-butyl-3,4-dihydro-2H-1,4-benzoxazine-6-carboxylate (0.33 g) was added NMP (7 mL), followed by copper cyanide (0.18 g). The mixture was then heated to 175° C. and stirred overnight. The resulting mixture was cooled to room temperature and poured into 1 N hydrochloric acid. The acidic aqueous layer was extracted with ethyl acetate, washed with 1 N hydrochloric acid (15 mL), saturated sodium bicarbonate (15 mL), and brine, dried (magnesium sulfate), filtered, and concentrated under reduced pressure. Purification by flash column chromatography (silica, 1:9 ethyl acetate/hexanes) provided 184 mg of the title compound: $^1$H NMR (300 MHz, CDCl$_3$) δ 7.55, 7.43, 4.41, 3.89, 3.39, 3.31, 1.58, 1.40, 0.97.

Step 6: 4-Butyl-8-cyano-3,4-dihydro-2H-1,4-benzoxazine-6-carboxylic acid

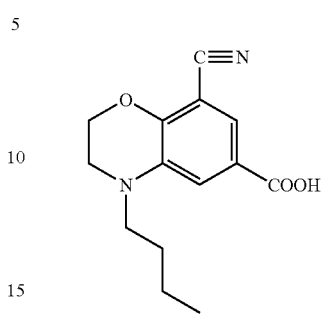

To a stirred solution of Methyl 4-butyl-8-cyano-3,4-dihydro-2H-1,4-benzoxazine-6-carboxylate (184 mg) in methanol (3 mL) was added potassium hydroxide (7 mL of a 1.0 M solution in water). The mixture was stirred at room temperature overnight then concentrated under reduced pressure. The residue was diluted with water and washed with ethyl acetate. The aqueous layer was acidified to pH 4 with 1 N hydrochloric acid and extracted with chloroform (4×100 mL). The combined organic extracts were dried (sodium sulfate), filtered, and concentrated under reduced pressure to give 154 mg of the title compound: $^1$H NMR (300 MHz, CDCl$_3$) δ 7.62, 7.46, 4.44, 3.41, 3.33, 1.60, 1.41, 0.98.

Step 7: 4-Butyl-8-cyano-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide

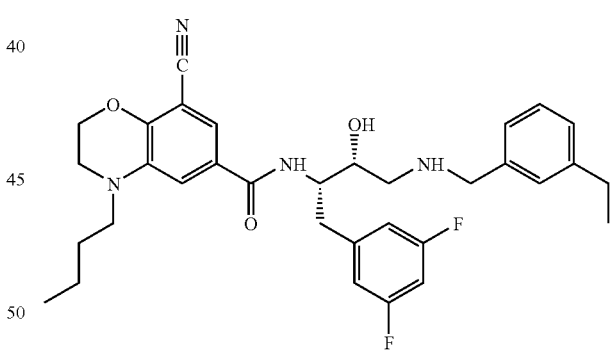

A solution of 4-Butyl-8-cyano-3,4-dihydro-2H-1,4-benzoxazine-6-carboxylic acid (129 mg), HBTU (284 mg), and diisopropylethylamine (0.26 mL) was stirred in methylene chloride (6 mL) for 15 min. A solution of (2R,3S)-3-amino-4-(3,5-difluorophenyl)-1-[(3-ethylbenzyl)amino]butan-2-ol (204 mg) in methylene chloride (4 mL) was added and the reaction mixture was stirred overnight. The mixture was diluted with methylene chloride, washed with 1 N hydrochloric acid (15 mL), saturated sodium bicarbonate (15 mL), and brine, dried (magnesium sulfate), filtered, and concentrated under reduced pressure. Purification by flash column chromatography (silica, 1:9 methanol/chloroform) provided 20 mg of the title compound: ESI MS m/z 577 [M+H]$^+$.

Example SP-222

4-Butyl-N-{(1S,2R)-1-(3,5-difluorobenzyl)-3-[(3-ethylbenzyl)amino]-2-hydroxypropyl}-1-(methylsulfonyl)-1,2,3,4-tetrahydroquinoxaline-6-carboxamide Step 1: Methyl 4-nitro-3-{[(trifluoromethyl)sulfonyl]oxy}benzoate

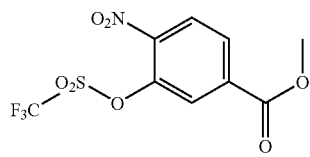

To an ice-cold, stirred solution of methyl 3-hydroxy-4-nitrobenzoate (1.5 g) and triethylamine (1.1 mL) in methylene chloride (15 mL) was added trifluoromethane sulfonic anhydride (1.4 mL), and the reaction mixture was stirred for 30 min. The mixture was diluted with methylene chloride, washed with saturated sodium bicarbonate, and brine, dried (magnesium sulfate), filtered, and concentrated under reduced pressure provided 2.4 g of the title compound: $^1$H NMR (300 MHz, DMSO-$d_6$) δ 8.47, 8.27, 8.15, 3.99.

Step 2: Methyl 3-(butylamino)-4-nitrobenzoate

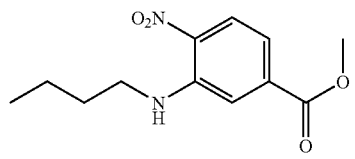

To a stirred solution of Pd$_2$(dba)$_3$ (139 mg), BINAP (284 mg), and cesium carbonate (2.0 g) in toluene (50 mL) was added butylamine (0.45 mL), and the reaction mixture was heated at 80° C. for 15 min. A solution of methyl 4-nitro-3-{[(trifluoromethyl)sulfonyl]oxy}benzoate (1.0 g) in toluene (15 mL) was added dropwise over 1 h. The mixture was cooled to room temperature, filtered through diatomaceous earth, and concentrated under reduced pressure. Purification by flash column chromatography (silica, 3:1 ethyl acetate/hexanes) provided 670 mg of the title compound as a yellow oil: ESI MS m/z 550 [M+H]$^+$.

Step 3: Methyl 4-amino-3-(butylamino)benzoate

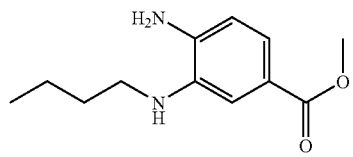

A solution of methyl 3-(butylamino)-4-nitrobenzoate (1.1 g) and 10% Pd/C (110 mg) in methanol (20 mL) was shaken under an atmosphere of hydrogen at 50 psi for 2 h. The mixture was filtered through diatomaceous earth, and concentrated under reduced pressure to provide 940 mg of the title compound: $^1$H NMR (300 MHz, DMSO-$d_6$) δ 7.13, 6.94, 6.52, 3.72, 3.02, 1.60, 1.42, 0.93.

Step 4: Methyl 4-butyl-3-oxo-1,2,3,4-tetrahydroquinoxaline-6-carboxylate

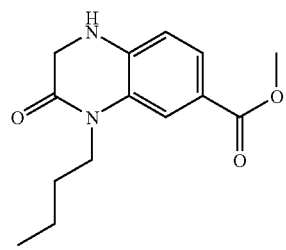

To an ice-cold, stirred solution of methyl 4-amino-3-(butylamino)benzoate (950 mg) and sodium bicarbonate (862 mg) in 1:1 isobutyl methyl ketone/water (20 mL) was added chloroacetyl chloride (0.41 mL), and the mixture was stirred for 1 h. The mixture was warmed to room temperature and refluxed for 14 h. The mixture was cooled to room temperature, diluted with chloroform, and separated. The organic layer was washed with water, and brine, dried (magnesium sulfate), filtered, and concentrated under reduced pressure. Purification by flash column chromatography (silica, 1:1 ethyl acetate/hexanes) afforded 850 mg of the title compound: $^1$H NMR (300 MHz, CDCl$_3$) δ 7.89, 7.72, 6.80, 3.97, 3.88, 3.30-3.25, 1.68-1.58, 1.47-1.35, 0.94-0.88.

Step 5: Methyl 4-butyl-1,2,3,4-tetrahydroquinoxaline-6-carboxylate

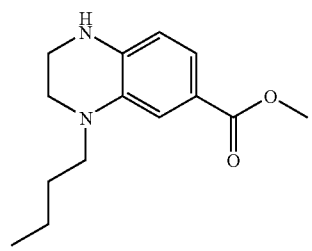

To an ice-cold, stirred solution of methyl 4-butyl-3-oxo-1,2,3,4-tetrahydroquinoxaline-6-carboxylate (840 mg) in tetrahydrofuran (32 mL) was added borane dimethylsulfide complex (3.2 mL, 2.0 M tetrahydrofuran) and the resulting mixture was refluxed for 24 h. The mixture was cooled to room temperature, quenched with methanol, and the solvent was removed under reduced pressure. Purification by flash column chromatography (silica, 1:1 ethyl acetate/hexanes) provided 364 mg of the title compound: $^1$H NMR (300 MHz, CDCl$_3$) δ 7.27, 7.22, 6.41, 3.84, 3.47-3.45, 3.32-3.23, 1.60-1.58, 1.42-1.37, 0.99-0.94.

Step 6: Methyl 4-butyl-1-(methylsulfonyl)-1,2,3,4-tetrahydroquinoxaline-6-carboxylate

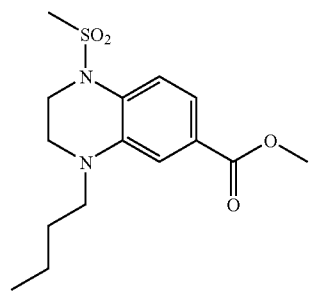

To an ice-cold, stirred solution of methyl 4-butyl-1,2,3,4-tetrahydroquinoxaline-6-carboxylate (180 mg) and triethylamine (62 µL) in methylene chloride (2 mL) was added methanesulfonyl chloride (101 µL) and the mixture was stirred for 1 h. The mixture was warmed to room temperature, diluted with methylene chloride, washed with washed with 1 N hydrochloric acid, and brine. The organic layer was then dried (magnesium sulfate), filtered, and concentrated under reduced pressure. Purification by flash column chromatography (silica, 1:3 ethyl acetate/hexanes) provided 150 mg of the title compound: $^1$H NMR (300 MHz, CDCl$_3$) δ 7.57, 7.41, 7.32, 3.90, 3.84, 3.45, 3.38, 1.61, 1.41, 0.98.

Step 7: 4-Butyl-1-(methylsulfonyl)-1,2,3,4-tetrahydroquinoxaline-6-carboxylic acid

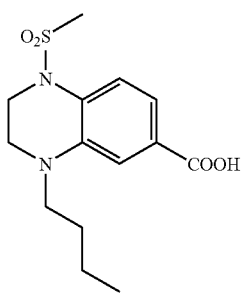

To a stirred solution of methyl 4-butyl-1-(methylsulfonyl)-1,2,3,4-tetrahydroquinoxaline-6-carboxylate (144 mg) in methanol (1.3 mL) was added 1 M potassium hydroxide (13 mL). The mixture was stirred at room temperature for 48 h and concentrated under reduced pressure. The residue was diluted with water and washed with ethyl acetate. The aqueous layer was acidified to pH 4 with 1 N hydrochloric acid and extracted with chloroform (4×100 mL). The combined organic extracts were dried (sodium sulfate), filtered, and concentrated under reduced pressure to give 99 mg of the title compound: $^1$H NMR (300 MHz, CDCl$_3$) δ 7.43, 7.39, 7.24, 3.77, 3.39, 3.32, 1.56, 1.33, 0.90.

Step 8: 4-Butyl-N-{(1S,2R)-1-(3,5-difluorobenzyl)-3-[(3-ethylbenzyl)amino]-2-hydroxypropyl}-1-(methylsulfonyl)-1,2,3,4-tetrahydroquinoxaline-6-carboxamide

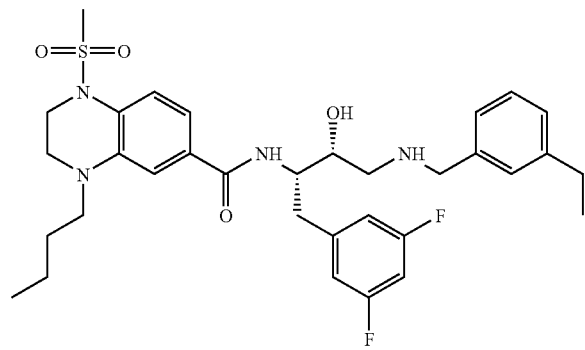

A solution of 4-butyl-1-(methylsulfonyl)-1,2,3,4-tetrahydroquinoxaline-6-carboxylic acid (99 mg), HATU (181 mg), HOBt (64 mg), and diisopropylethylamine (100 µL) was stirred in methylene chloride (1.0 mL) for 15 min. A solution of (2R,3S)-3-amino-4-(3,5-difluorophenyl)-1-[(3-ethylbenzyl)amino]butan-2-ol (129 mg) and diisopropylethylamine (100 µL) in methylene chloride (1.0 mL) was added and the mixture was stirred overnight. The mixture was diluted with methylene chloride, washed with 1 N hydrochloric acid (10 mL), saturated sodium bicarbonate (10 mL), and brine. The organic layer was then dried (magnesium sulfate), filtered, and concentrated under reduced pressure. Purification by flash column chromatography (silica, 1:9 methanol/chloroform) provided a clear solid. The solid was dissolved in methanol (1 mL), and treated with hydrochloric acid (0.5 mL, 1.0 M diethyl ether). The resulting precipitate was collected by filtration to provide 90 mg of the title compound: ESI MS m/z 629 [M+H]$^+$.

Example SP-223

4-Butyl-N-{(1S,2R)-1-(3,5-difluorobenzyl)-3-[(3-ethylbenzyl)amino]-2-hydroxypropyl}-1,2,3,4-tetrahydroquinoxaline-6-carboxamide hydrochloride Step 1: 1-Tert-butyl 6-methyl 4-butyl-3-oxo-3,4-dihydroquinoxaline-1,6(2H)-dicarboxylate

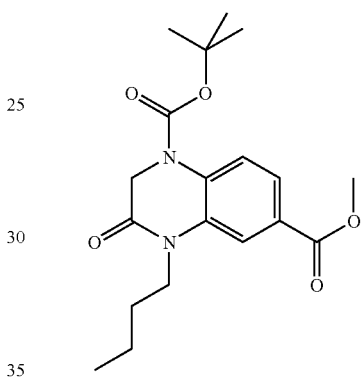

To an ice-cold, stirred solution of methyl 4-butyl-3-oxo-1,2,3,4-tetrahydroquinoxaline-6-carboxylate (1.1 g), and triethylamine (0.9 mL). in methylene chloride (10 mL) was added DMAP (51.3 mg) and di-tert-butyl dicarbonate (1.4 g), and the resulting mixture was stirred for 4 d. The mixture was diluted with methylene chloride, washed with water, and brine. The organic layer was then dried (magnesium sulfate), filtered, and concentrated under reduced pressure.

Purification by flash column chromatography (silica, 1:1 ethyl acetate/hexanes) provided 440 mg of the title compound: ESI MS m/z 363 [M+H]$^+$.

Step 2: 1-Tert-butyl 6-methyl 4-butyl-3,4-dihydroquinoxaline-1,6(2H)-dicarboxylate

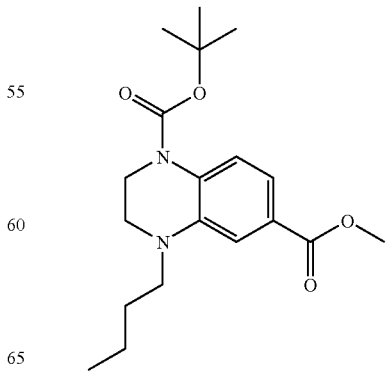

A solution of 1-tert-butyl 6-methyl 4-butyl-3-oxo-3,4-dihydroquinoxaline-1,6(2H)-dicarboxylate (440 mg) and 9-BBN dimer (600 mg) in tetrahydrofuran (10 mL) was heated at 65° C. for 10 h. The mixture was cooled to room temperature, ethanolamine (0.15 mL) was added and the resulting solution was concentrated under reduced pressure. The residue was washed with hexanes, filtered, and the filtrate was concentrated under reduced pressure. Purification by flash column chromatography (silica, 1:9 ethyl acetate/hexanes) afforded 158 mg of the title compound: 1H NMR (300 MHz, CDCl$_3$) δ 7.50, 7.34, 7.28, 3.88, 3.77, 3.38-3.30, 1.65-1.51, 1.42-1.34, 0.99-0.94.

Step 3: 1-(Tert-butoxycarbonyl)-4-butyl-1,2,3,4-tetrahydroquinoxaline-6-carboxylic acid

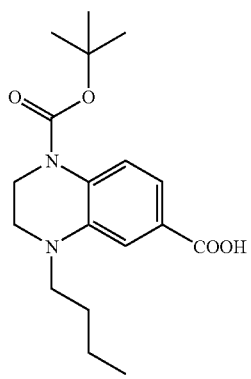

To a stirred solution of 1-tert-butyl 6-methyl 4-butyl-3,4-dihydroquinoxaline-1,6(2H)-dicarboxylate (158 mg) in methanol (1.4 mL) was added 1 M potassium hydroxide (1.4 mL). The mixture was stirred at 40° C. for 12 h and then concentrated under reduced pressure. The residue was diluted with water and washed with ethyl acetate. The aqueous layer was acidified to pH 4 with 1 N hydrochloric acid and extracted with chloroform (4×100 mL). The combined organic extracts were dried (sodium sulfate), filtered, and concentrated under reduced pressure to give 120 mg of the title compound: $^1$H NMR (300 MHz, CDCl$_3$) δ 7.55, 7.40, 7.37, 3.79, 3.38, 3.34, 1.60, 1.53, 1.39, 0.97.

Step 4: 4-Butyl-N-{(1S,2R)-1-(3,5-difluorobenzyl)-3-[(3-ethylbenzyl)amino]-2-hydroxypropyl}-1,2,3,4-tetrahydroquinoxaline-6-carboxamide hydrochloride

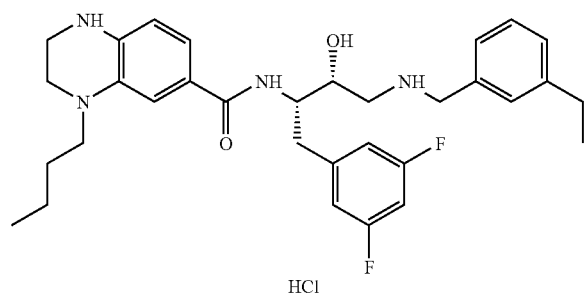

A solution of 1-(tert-butoxycarbonyl)-4-butyl-1,2,3,4-tetrahydroquinoxaline-6-carboxylic acid (120 mg), HBTU (204 g), and diisopropylethylamine (100 μL) was stirred in methylene chloride (2.0 mL) for 15 min. A solution of (2R,3S)-3-amino-4-(3,5-difluorophenyl)-1-[(3-ethylbenzyl)amino]butan-2-ol (146 mg) and diisopropylethylamine (100 μL) in methylene chloride (2.0 mL) was added and the mixture was stirred overnight. The mixture was diluted with methylene chloride, washed with 1 N hydrochloric acid (10 mL), saturated sodium bicarbonate (10 mL), and brine. The organic layer was then dried (magnesium sulfate), filtered, and concentrated under reduced pressure. Purification by flash column chromatography (silica, 1:9 methanol/chloroform) provided a clear solid. The solid was dissolved in methanol (1 mL), and treated with hydrochloric acid (0.5 mL, 1.0 M diethyl ether, 0.5 mmol). The resulting precipitate was collected by filtration to provide 45 mg of the title compound: ESI MS m/z 551 [M+H]$^+$.

Example SP-224

N-{(1S,2R)-1-(3,5-difluorobenzyl)-3-[(3-ethylbenzyl)amino]-2-hydroxypropyl}-6-[(methylsulfonyl)methyl]nicotinamide Step 1: Methyl 6-[(acetyloxy)methyl]nicotinate

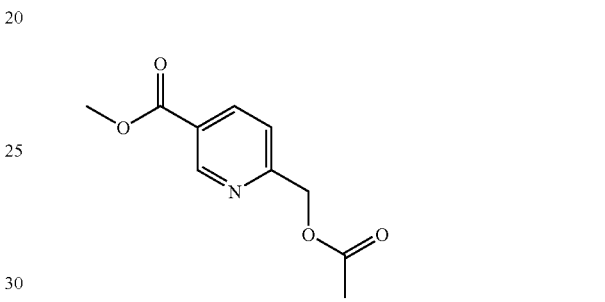

To a solution of methyl 6-methylnicotinate (6.05 g) in methylene chloride (100 mL) was added m-chloroperbenzoic acid (77%, 13.5 g). The reaction mixture was stirred at room temperature for 2 h and then diluted with chloroform (100 mL). The mixture was washed successively with aqueous sodium sulfite, saturated sodium bicarbonate, and brine. The organic later was then dried (sodium sulfate), filtered, and concentrated under reduced pressure to provide 6.21 g of methyl 6-methylnicotinate 1-oxide. A solution of methyl 6-methylnicotinate 1-oxide (4.35 g) in acetic anhydride (50 mL) was heated at 120° C. for 2 h and then concentrated under reduced pressure. Purification by flash column chromatography (silica gel, 1:2 to 3:5 ethyl acetate/hexanes) provided 3.3 g of the title compound: 3H NMR (300 MHz, CDCl$_3$) δ 9.18, 8.31, 7.44, 5.29, 3.96, 2.19.

Step 3: 6-[(Methylsulfonyl)methyl]nicotinic acid

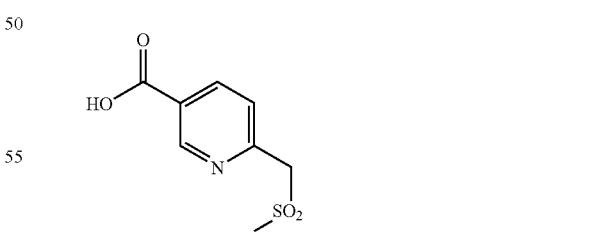

To a solution of methyl 6-[(acetyloxy)methyl]nicotinate (3.0 g) in dry methanol (100 mL) was added potassium carbonate (4.56 g). The mixture was stirred at room temperature for 2 h and then diluted with methylene chloride (200 mL) and water (200 mL). The organic layer was washed with brine, dried (sodium sulfate), filtered, and concentrated under reduced pressure to provide 1.70 g of the alcohol. This material was used without further purification. To an ice-cold solution of methyl 6-(hydroxymethyl)nicotinate (1.6 g) in methylene chloride (40 mL) was added diisopropylethylamine (1.5 g) followed by methanesulfonyl chloride (1.21 g). The mixture was stirred at room temperature for 1 h and then diluted with methylene chloride (100 mL). The mixture was washed successively with 0.5 N potassium hydrogen sulfate, water, and brine. The organic layer was then dried (sodium sulfate), filtered, and concentrated under reduced pressure to provide mesylate 2.34 g. This mesylate was used without further purification.

To a solution of methyl 6-{[(methylsulfonyl)oxy]methyl}nicotinate (2.34 g) in N,N-dimethylformamide (10 mL) was added sodium thiomethoxide (850 mg). The mixture was stirred at 50° C. for 15 h. The mixture was diluted with ethyl acetate (100 mL) and washed successively with water, saturated sodium bicarbonate, and brine. The organic layer was then dried (sodium sulfate), filtered, and concentrated under reduced pressure to provide 1.61 g of the methyl thioether. This material was used without further purification. To an ice-cold solution of methyl 6-[(methylthio)methyl]nicotinate (1.61 g) in methanol (35 mL) was added a solution of oxone (7.52 g) in water (35 mL). The resulting slurry was stirred at room temperature for 2 h. The resulting mixture was diluted with water (50 mL), and extracted with chloroform (3×100 mL). The combined organic extracts were washed with brine, dried (sodium sulfate), filtered, and concentrated under reduced pressure to provide 1.77 g of the methyl sulfone, which was used without further purification.

To a stirred solution of methyl 6-[(methylsulfonyl)methyl]nicotinate (800 mg) in 1:1.1 tetrahydrofuran/methanol/water (30 mL) was added lithium hydroxide (440 mg). The mixture was stirred at room temperature for 1 h, and concentrated under reduced pressure. The residue was partitioned between water (10 mL) and chloroform (10 mL). The aqueous layer was acidified to pH 4 with 1 N hydrochloric acid and extracted with 3:1 chloroform/2-propanol (3×30 mL). The combined organic layers were dried (sodium sulfate), filtered, and concentrated under reduced pressure to provide 700 mg of the title compound: $^1$H NMR (300 MHz, $CD_3OD$) δ 9.07, 8.33, 7.65, 4.77, 3.06.

Step 4: N-{(1S,2R)-1-(3,5-difluorobenzyl)-3-[(3-ethylbenzyl)amino]-2-hydroxypropyl}-6-[(methylsulfonyl)methyl]nicotinamide

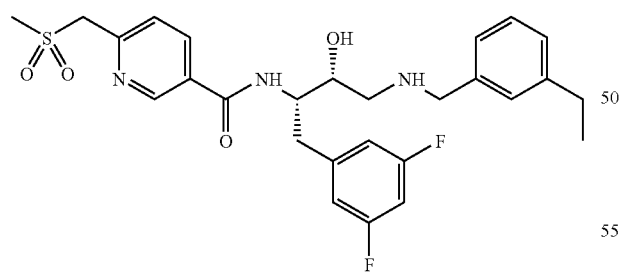

To a stirred solution of 6-[(methylsulfonyl)methyl]nicotinic acid (181 mg), diisopropylethylamine (116 mg), and HBTU (341 mg) in methylene chloride (5 mL) was added a mixture of (2R,3S)-3-amino-4-(3,5-difluorophenyl)-1-[(3-ethylbenzyl)amino]butan-2-ol (326 mg) and N,N-diisopropylethylamine (233 mg) in methylene chloride (5 mL). The mixture was stirred at room temperature for 15 h and concentrated under reduced pressure. The residue was diluted with ethyl acetate (50 mL), washed with saturated sodium bicarbonate, and brine, dried (sodium sulfate), filtered, and concentrated under reduced pressure. Purification by flash column chromatography (silica gel, 5:95 to 10:90 methanol/methylene chloride) provided 165 mg of the title compound: ESI MS m/z 532 [M+H]$^+$.

Example SP-225

3-Butyl-N-{(1S,2R)-1-(3,5-difluorobenzyl)-3-[(3-ethylbenzyl)amino]-2-hydroxypropyl}-1-methyl-1H-indole-5-carboxamide Step 1: Ethyl 4-hydrazinobenzoate hydrochloride

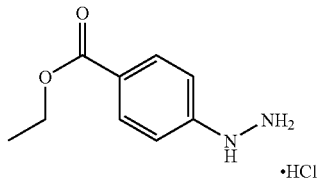

To a 0° C. mixture of 4-ethylaminobenzoate (10.0 g) in water (56 mL) and concentrated hydrochloric acid (20 mL) was added portion wise a solution of sodium nitrite (4.25 g) in water (20 mL). The mixture was stirred at 0° C. for 15 minutes at which time the mixture was poured into a solution of tin (II) chloride (50 gm) in water (34 mL). The resulting mixture was removed from the ice bath and allowed to slowly come to room temperature over 1 h at which time the resulting solids were collected by filtration and washed with chilled concentrated hydrochloric acid (30 mL) followed by ether. The solids were dried under vacuum to give 13 g of the title compound: $^1$H NMR (DMSO-$d_6$) δ 1.29, 4.25, 7.03, 7.85, 9.0, 9.06, 10.6.

Step 2: Ethyl 3-butyl-1H-indole-5-carboxylate

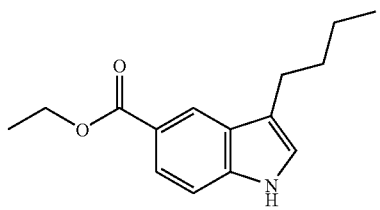

To a mixture of ethyl 4-hydrazinobenzoate hydrochloride (10 gm) in ethanol:water (5:1 100 mL) was added hexanal (4.62 gm). The mixture was refluxed at 100° C. for 3 h. The solvents were removed and toluene (100 mL) and p-toluene sulfonic acid (0.1 g) were added. The mixture was refluxed at 120° C. for 18 h, cooled to room temperature and concentrated under reduced pressure. Column chromatography on silica gel (100 mL) using 90:9:1 (hexanes: methylene chloride: ethyl acetate) as eluent to give 0.8 g of the title compound: $^1$H NMR ($CDCl_3$) δ 0.957, 1.44, 1.72, 2.78, 4.40, 7.02, 7.34, 7.90, 8.13, 8.38.

Step 3: Ethyl 3-butyl-1-methyl-1H-indole-5-carboxylate

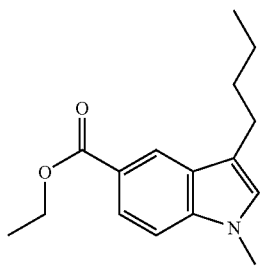

To a mixture of ethyl 3-butyl-1H-indole-5-carboxylate (0.6 g) in methylsulfoxide (10 mL) was added potassium t-butoxide (0.29 g) and iodomethane (2.0 mL). The mixture was stirred at 50° C. for 18 H, at which time the mixture was pored into water (50 mL). The solution was extracted with ethyl acetate and the organic extracts washed three times with brine, dried over anhydrous sodium sulfate and concentrated under reduced pressure. Column chromatography on silica gel (100 mL) using 5% ethyl acetate in hexanes as eluent to give 0.294 g of the title compound: $^1$H NMR (CDCl$_3$) δ 0.953, 1.44, 1.69, 2.77, 3.76, 4.40, 6.87, 7.26, 7.91, 8.35.

Step 4: 3-Butyl-1-methyl-1H-indole-5-carboxylic acid

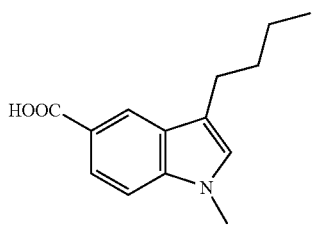

To a mixture of ethyl 3-butyl-1-methyl-1H-indole-5-carboxylate (0.294 g) in methanol (20 mL) was added 1N NaOH (10 mL). The mixture was stirred at 50° C. for 18 h, cooled to room temperature and poured into 1N HCl (50 mL). The mixture was extracted with ethyl acetate and the ethyl acetate extract was dried over anhydrous sodium sulfate and concentrated to dryness under reduced pressure to give 0.234 g (89%) of the title compound: $^1$H NMR (CD$_3$OD) δ 0.965, 1.42, 1.69, 2.76, 3.77, 7.02, 7.35, 7.84, 8.29.

Step 5: 3-Butyl-N-{(1S,2R)-1-(3,5-difluorobenzyl)-3-[(3-ethylbenzyl)amino]-2-hydroxypropyl}-1-methyl-1H-indole-5-carboxamide

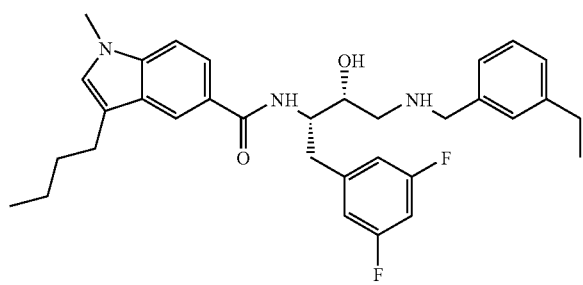

To a mixture of 3-Butyl-1-methyl-1H-indole-5-carboxylic acid (0.15 g) in methylene chloride (5 mL) and tetrahydrofuran (10 mL) was added 1,1-carbonyldiimidazole (0.105 g). The mixture was stirred at 40° C. at which time (2R,3S)-3-amino-4-(3,5-difluorophenyl)-1-[(3-ethylbenzyl)amino]butan-2-ol (0.2 g) in methylene chloride (5 mL) was added. The mixture was stirred at 40° C. for 18 h then poured into methylene chloride (50 mL). The mixture was washed with water then brine, dried over anhydrous sodium sulfate and concentrated under reduced pressure. Column chromatography on silica gel (100 mL) using 85:10:5 (methylene chloride: hexanes: methanol) as eluent to give 0.102 g of the title compound: MS (ESI+) for C$_{33}$H$_{39}$F$_2$N$_3$O$_2$ m/z 547.9 (M+H)$^+$.

Example SP-226

3-Butyl-N-{(1S,2R)-1-(3,5-difluorobenzyl)-3-[(3-ethylbenzyl)amino]-2-hydroxypropyl}-1H-indole-5-carboxamide Step 1: 3-Butyl-1H-indole-5-carboxylic acid

To a mixture of Ethyl 3-butyl-1H-indole-5-carboxylate, Example SP-225, step 2, (0.4 g) in methanol (15 mL) was added 1N NaOH (5 mL). The mixture was stirred at 50° C. for 18 h, cooled to room temperature and poured into 1N HCl (50 mL). The mixture was extracted with ethyl acetate. The ethyl acetate extract was dried over anhydrous sodium sulfate and concentrated to dryness under reduced pressure to give 0.145 g of the title compound: MS (ESI+) for C$_{13}$H$_{15}$N$_1$O$_2$ m/z 216.12 (M+H)$^+$.

Step 2: 3-Butyl-N-{(1S,2R)-1-(3,5-difluorobenzyl)-3-[(3-ethylbenzyl)amino]-2-hydroxypropyl}-1H-indole-5-carboxamide

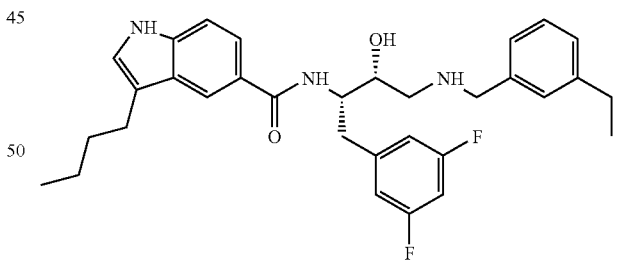

To a mixture of 3-Butyl-1H-indole-5-carboxylic acid (0.145 g) in methylene chloride (15 mL) was added triethylamine (0.068 g), and HATU (0.255 g). The mixture was stirred at room temperature for 15 minutes at which time (2R,3S)-3-amino-4-(3,5-difluorophenyl)-1-[(3-ethylbenzyl)amino]butan-2-ol (0.224 g) was added. The mixture was stirred at room temperature for 72 h then poured into methylene chloride (50 mL), washed with water then saturated sodium bicarbonate, dried over anhydrous magnesium sulfate and concentrated under vacuum. Column chromatography on silica gel (100 mL) using 5% methanol in methylene chloride with 0.15% HOAc as eluent to give 0.247 g of the title compound: MS (ESI+) for $C_{32}H_{37}F_2N_3O_2$ m/z 534.3 $(M+H)^+$.

Example SP-227

4-Butyl-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide Step 1: Methyl 4-butyl-3-oxo-3,4-dihydro-2H-1,4-benzoxazine-6-carboxylate

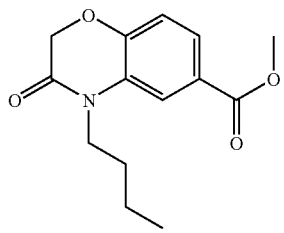

To an ice-cold, stirred solution of methyl 3-amino-4-hydroxybenzoate (3.0 g) and sodium bicarbonate (3.3 g) in 1:1 isobutyl methyl ketone/water (40 mL) was added chloroacetyl chloride (1.7 mL), and the mixture was stirred for 1 h. The mixture was warmed to room temperature and refluxed for 14 h, cooled to room temperature, diluted with chloroform, and separated. The organic layer was washed with water, and brine, dried (magnesium sulfate), filtered, and concentrated under reduced pressure. Purification by flash column chromatography (silica, 1:9 methanol/chloroform) afforded a phenoxazine 3.2 g as a white solid, which was used without further purification or characterization. To a solution of phenoxazine from step 1 (700 mg) and potassium carbonate (934 mg) in methanol (8 mL) was added bromobutane (1.8 mL), and the mixture was refluxed for 6 d. The mixture was cooled to room temperature, concentrated under reduced pressure, and the residue was partitioned between ethyl acetate and water. The organic layer washed with brine, dried (magnesium sulfate), filtered, and concentrated under reduced pressure to afforded 800 mg of the title compound: $^1$H NMR (300 MHz, CDCl$_3$) δ 7.72-7.68, 7.02-6.99, 4.66, 4.00-3.92, 1.69-1.64, 1.46-1.38, 1.01-0.95.

Step 2: Methyl 4-butyl-3,4-dihydro-2H-1,4-benzoxazine-6-carboxylate

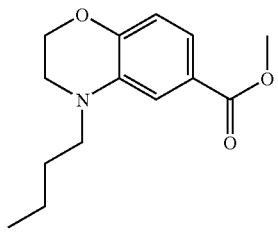

A solution of methyl 4-butyl-3-oxo-3,4-dihydro-2H-1,4-benzoxazine-6-carboxylate (800 mg) and 9-BBN (1.6 g) in tetrahydrofuran (13 mL) was refluxed for 1.5 h. The mixture was cooled to room temperature, ethanolamine (0.4 mL) was added, and the resulting solution was concentrated under reduced pressure. The residue was washed with hexanes, filtered, and the filtrate was concentrated under reduced pressure. Purification by flash column chromatography (silica, 25% ethyl acetate/hexanes) afforded 607 mg of the title compound: $^1$H NMR (300 MHz, DMSO-d$_6$) δ 7.21, 7.16, 6.75, 4.24-4.21, 3.78, 3.34-3.24, 1.55-1.47, 1.38-1.30, 0.95-0.90.

Step 3: 4-Butyl-3,4-dihydro-2H-1,4-benzoxazine-6-carboxylic acid

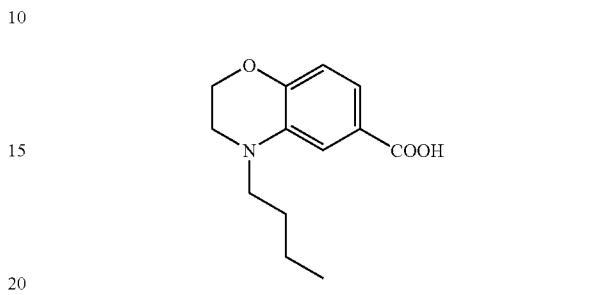

To a stirred solution of methyl 4-butyl-3,4-dihydro-2H-1,4-benzoxazine-6-carboxylate (412 mg) in methanol (5 mL) was added 1 M potassium hydroxide (17 mL). The mixture was stirred at room temperature for 5 h and concentrated under reduced pressure. The residue was diluted with water and washed with ethyl acetate. The aqueous layer was acidified to pH 4 with 1 N hydrochloric acid and extracted with chloroform (4×50 mL). The combined organic extracts were dried (sodium sulfate), filtered, and concentrated under reduced pressure to provide 384 mg of the title compound: ESI MS m/z 236 $[M+H]^+$.

Step 4: 4-Butyl-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide

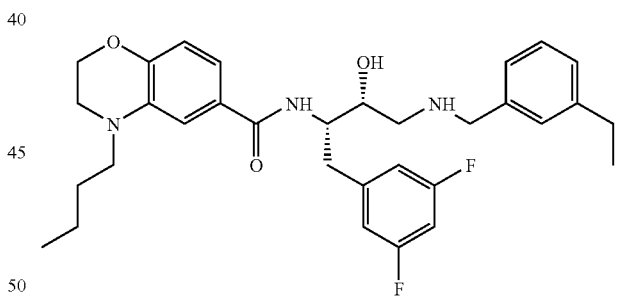

A solution of 4-Butyl-3,4-dihydro-2H-1,4-benzoxazine-6-carboxylic acid (43 mg), HATU (104 mg), HOBt (37 mg), and diisopropylethylamine (47 μL) was stirred in methylene chloride (1.0 mL) for 15 min. A solution of (2R,3S)-3-amino-4-(3,5-difluorophenyl)-1-[(3-ethylbenzyl)amino]butan-2-ol dihydrochloride (62 mg) and diisopropylethylamine (47 μL) in methylene chloride (1.0 mL) was added and the reaction mixture was stirred overnight. The mixture was diluted with methylene chloride, washed with 1 N hydrochloric acid (15 mL), saturated sodium bicarbonate (15 mL), and brine, dried (magnesium sulfate), filtered, and concentrated under reduced pressure. Purification by flash column chromatography (silica, 1:9 methanol/chloroform) provided 15 mg of the title compound: APCI MS m/z 552 $[M+H]^+$.

Example SP-228

3-acetyl-1-butyl-N-{(1S,2R)-1-(3,5-difluorobenzyl)-3-[(3-ethylbenzyl)amino]-2-hydroxypropyl}-1H-indole-6-carboxamide Step 1. Methyl 1-butyl-1H-indole-6-carboxylate

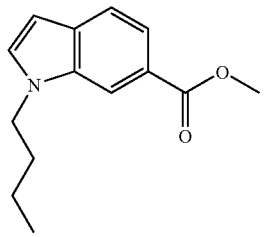

Methyl 1H-indole-6-carboxylate (4.17 g) was dissolved in DMSO (30 mL), and potassium tert-butoxide (2.93 g) was added. The mixture was stirred for ten min at room temperature. Iodobutane (3.0 mL) was added. The mixture was allowed to stir for three additional hours. The mixture was partitioned between ethyl acetate and water and brine, dried over sodium sulfate, filtered, and concentrated to give methyl 1-butyl-1H-indole-6-carboxylate (4.53 g). MS (ESI+) for $C_{14}H_{17}NO_2+H_1$ m/z 232.12 (M+H)$^+$.

Step 2. Methyl 3-acetyl-1-butyl-1H-indole-6-carboxylate

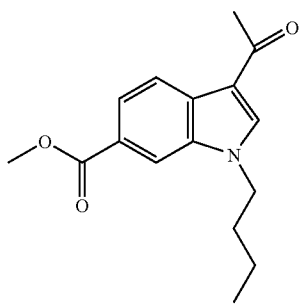

Methyl 1-butyl-1H-indole-6-carboxylate (4.53 g) was dissolved in dichloromethane (25 ml). The mixture was cooled to 0° C. Diethyl aluminum chloride was added dropwise (29.5 mL) and the mixture was allowed to stir at 0° C. for 30 min. A solution of dichloromethane (25 mL) and acetyl chloride (2.1 mL) was added dropwise, and the mixture was stirred for 2 h at 0° C. The mixture was then partitioned between dichloromethane, water, and brine, dried over sodium sulfate, filtered, and concentrated. The concentrate was chromatographed on silica gel using ethyl acetate/heptane (40/60) to give methyl 3-acetyl-1-butyl-1H-indole-6-carboxylate (3.38 g). MS (ESI+) for $C_{16}H_{19}N_1O_3+H_1$ m/z 274.14 (M+H)$^+$.

Step 3. 3-acetyl-1-butyl-1H-indole-6-carboxylic acid

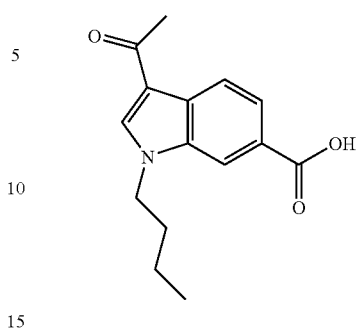

Methyl 3-acetyl-1-butyl-1H-indole-6-carboxylate (2.00 g) was dissolved in methanol (100 mL). Sodium hydroxide (1N) was added until the mixture became slightly cloudy. Methanol was again added (20 mL) until the solution was clear. Sodium hydroxide was again added until the mixture was slightly cloudy. The mixture was allowed to stir at room temperature overnight. The solution was concentrated to half its original volume and hydrochloric acid (2N) was added until the aqueous layer indicated a pH of about one. The mixture was extracted with dichloromethane and the organic layer was washed with brine, dried over sodium sulfate, filtered, and concentrated. The resulting material was chromatographed on silica gel using MeOH/heptane/dichloromethane (4/20/76) to give 3-acetyl-1-butyl-1H-indole-6-carboxylic acid (1.60 g). MS (ESI+) for $Cl_5H_{17}N_1O_3+H_1$ m/z 260.13 (M+H)$^+$.

Step 4. 3-acetyl-1-butyl-N-{(1S,2R)-1-(3,5-difluorobenzyl)-3-[(3-ethylbenzyl)amino]-2-hydroxypropyl}-1H-indole-6-carboxamide

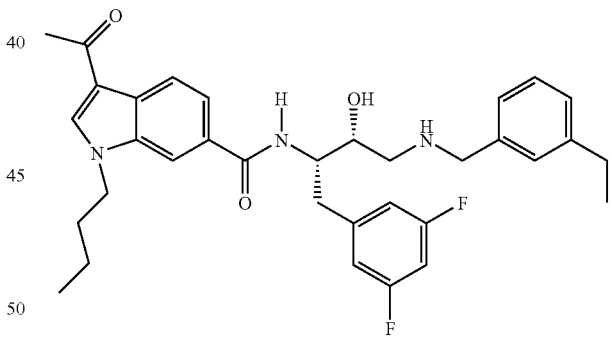

3-Acetyl-1-butyl-1H-indole-6-carboxylic acid (0.322 g) was dissolved in dichloromethane (15 mL). 1,1'-Carbonyldiimidazole was added (0.171 g). The mixture was stirred for 2 h and then a mixture of (2R,3S)-3-amino-4-(3,5-difluorophenyl)-1-[(3-ethylbenzyl)amino]butan-2-ol (0.250 g) in dichloromethane (15 mL) was added. After stirring overnight, the mixture was partitioned between dichloromethane, water, and brine. The organic layer was dried over sodium sulfate, filtered, and concentrated. The residue was chromatographed on silica gel using MeOH/dichloromethane (4/96) to give 3-acetyl-1-butyl-N-{(1S,2R)-1-(3,5-difluorobenzyl)-3-[(3-ethylbenzyl)amino]-2-hydroxypropyl}-1H-indole-6-carboxamide (0.335 g). MS (ESI+) for $C_{34}H_{39}F_2N_3O_3+H_1$ m/z 576.30 (M+H)$^+$.

Example SP-229

1-butyl-N-{(1S,2R)-1-(3,5-difluorobenzyl)-3-[(3-ethylbenzyl)amino]-2-hydroxypropyl}-3-(trifluoroacetyl)-1H-indole-6-carboxamide Step 1. Butyl 1-butyl-1H-indole-6-carboxylate

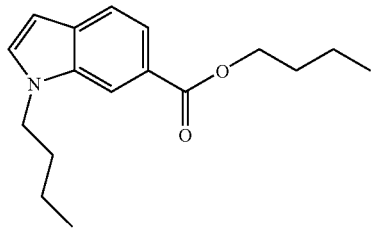

1-Butyl-1H-indole-6-carboxylic acid (0.450 g) was dissolved in dimethyl sulfoxide (10 mL). Potassium tert-butoxide (0.317 g) was added and the mixture was stirred for 10 min at room temperature. Iodobutane (0.33 mL) was added and the mixture was allowed to stir at room temperature for 6 h. Water was then added and the mixture was partioned between ethyl acetate, water, and brine, and dried over magnesium sulfate, filtered, and concentrated. Silica gel chromatography using heptane/dichloromethane (30/70) gave butyl 1-butyl-1H-indole-6-carboxylate (0.429 g). MS (ESI+) for $C_{17}H_{23}NO_2+H_1$ m/z 274.20 (M+H)$^+$.

Step 2. Butyl 1-butyl-3-(trifluoroacetyl)-1H-indole-6-carboxylate

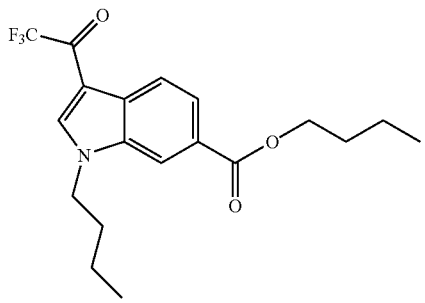

Boron trifluoride-methyl sulfide complex (0.238 g) was dissolved in dichloromethane (10 mL). The solution was cooled to −78° C. and a solution of trifluoroacetic anhydride (0.384 g) in dichloromethane (2 mL) was added. The mixture was stirred at −78° C. for 10 min, at which time a solution of butyl 1-butyl-1H-indole-6-carboxylate (0.250 g) in dichloromethane (3 mL) was added. The mixture was allowed to stir at −78° C. for 15 min and then allowed to warm to room temperature overnight. The mixture was then poured into aqueous sodium bicarbonate and extracted with dichloromethane. The organic layer was dried over sodium sulfate, filtered, and concentrated and the resulting material was chromatographed on silica gel using ethyl acetate/heptane (20/80) to give butyl 1-butyl-3-(trifluoroacetyl)-1H-indole-6-carboxylate (0.302 g). MS (ESI+) for $C_{19}H_{22}F_3N_1O_3+H_1$ m/z 370.16 (M+H)$^+$.

Step 3. 1-butyl-3-(trifluoroacetyl)-1H-indole-6-carboxylic acid

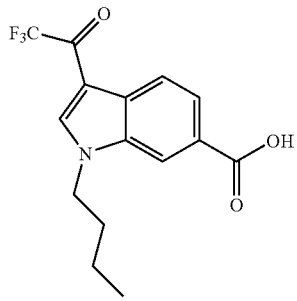

Butyl 1-butyl-3-(trifluoroacetyl)-1H-indole-6-carboxylate (0.277 g), LiOH.H$_2$O (0.040 g), THF (1.5 mL), water (0.5 mL), and methanol (0.5 mL) were stirred overnight at room temperature. The solvents were then removed under reduced pressure and HCl (2N, 0.5 mL) was added to the residue. The residue was extracted with ethyl acetate, dried over magnesium sulfate, filtered, and concentrated. Chromatography on silica gel using methanol/dichloromethane (6/94) gave 1-butyl-3-(trifluoroacetyl)-1H-indole-6-carboxylic acid (0.166 g). MS (ESI+) for $C_{15}H_{14}F_3N_1O_3+H_1$ m/z 314.10 (M+H)$^+$.

Step 4. 1-butyl-N-{(1S,2R)-1-(3,5-difluorobenzyl)-3-[(3-ethylbenzyl)amino]-2-hydroxypropyl}-3-(trifluoroacetyl)-1H-indole-6-carboxamide

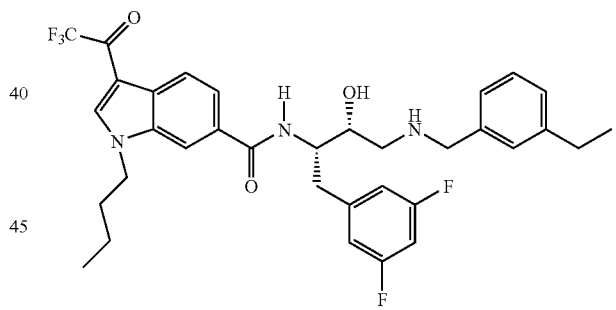

1-Butyl-3-(trifluoroacetyl)-1H-indole-6-carboxylic acid (0.141 g) was dissolved in dichloromethane (10 mL). 1,1'-Carbonyldiimidazole (0.080 g) was added and the mixture was stirred at room temperature for 2 h. A solution of (2R,3S)-3-amino-4-(3,5-difluorophenyl)-1-[(3-ethylbenzyl)amino]butan-2-ol (0.166 g) in dichloromethane was added and the mixture was allowed to stir overnight at room temperature. The mixture was then partitioned between dichloromethane and water, dried over sodium sulfate, filtered, and concentrated. Chromatography on silica gel using methanol/ethyl acetate/heptane/dichloromethane (3/10/10/77 to 6/10/10/74) gave 1-butyl-N-{(1S,2R)-1-(3,5-difluorobenzyl)-3-[(3-ethylbenzyl)amino]-2-hydroxypropyl}-3-(trifluoroacetyl)-1H-indole-6-carboxamide (0.155 g). MS (ESI+) for $C_{34}H_{36}F_5N_3O_3+H_1$ m/z 630.28 (M+H)$^+$.

Example SP-230

N-((1S,2R)-1-(3,5-difluorobenzyl)-3-{[1-(3-ethynylphenyl)cyclopropyl]amino}-2-hydroxypropyl)-2-(dipropylamino)isonicotinamide

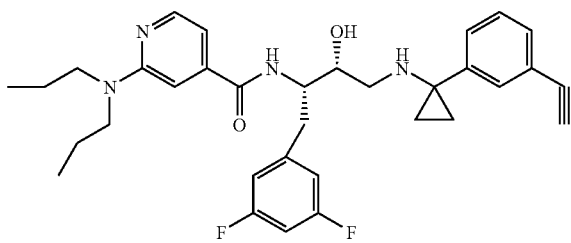

2-(Dipropylamino)isonicotinic acid (0.206 g) was dissolved in dichloromethane (10 mL). 1,1'-Carbonyldiimidazole was added (0.142 g) and the mixture was stirred for 2 h at room temperature, at which time (2R,3S)-3-amino-4-(3,5-difluorophenyl)-1-{[1-(3-ethynylphenyl)cyclopropyl]amino}butan-2-ol (0.284 g) in dichloromethane was added. The mixture was allowed to stir overnight and then was partitioned between dichloromethane, water, and brine, dried over sodium sulfate, filtered, and concentrated under reduced pressure. The concentrate was chromatographed on silica gel using methanol/dichloromethane (4/96) to give N-((1S,2R)-1-(3,5-difluorobenzyl)-3-{[1-(3-ethynylphenyl)cyclopropyl]amino}-2-hydroxypropyl)-2-(dipropylamino)isonicotinamide (0.268g). MS (ESI+) for $C_{33}H_{38}F_2N_4O_2+H_1$ m/z 561.30 $(M+H)^+$.

Example SP-231

1-butyl-N-((1S,2R)-1-(3,5-difluorobenzyl)-3-{[1-(3-ethynylphenyl)cyclopropyl]amino}-2-hydroxypropyl)-1H-indole-6-carboxamide

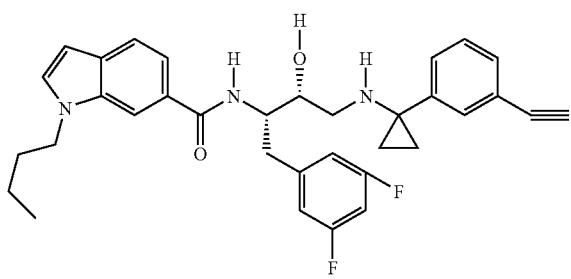

In the same manner as for N-((1S,2R)-1-(3,5-difluorobenzyl)-3-{[1-(3-ethynylphenyl)cyclopropyl]amino}-2-hydroxypropyl)-2-(dipropylamino)isonicotinamide, 1-butyl-1H-indole-6-carboxylic acid (0.119 g) gave 1-butyl-N-((1S,2R)-1-(3,5-difluorobenzyl)-3-{[1-(3-ethynylphenyl)cyclopropyl]amino}-2-hydroxypropyl)-1H-indole-6-carboxamide (0.076 g). MS (ESI+) for $C_{34}H_{35}F_2N_3O_2+H_1$ m/z 556.28 $(M+H)^+$.

Example SP-231

3-(allylthio)-N-((1S,2R)-1-(3,5-difluorobenzyl)-3-{[1-(3-ethylphenyl)cyclopropyl]amino}-2-hydroxypropyl)benzamide Step 1. 3-(Allylthio)benzoic acid 3-Thiobenzoic acid (Aldrich, 4.3 g, 28 mmol) was dissolved in THF (100 mL), cooled to 0° C., and treated with KO-tBu (6.3 g, 56 mmol), followed by allyl bromide (2.4 mL, 28 mmol). The solvent was removed from the reaction mixture and the residue was partitioned between 3M HCl and EtOAc. The organic layer was separated, dried (MgSO$_4$) and concentrated to give the title compound (5.3 g). (LRMS (M–H) m/z 193.2)

Step 2. 3-(allylthio)-N-((1S,2R)-1-(3,5-difluorobenzyl)-3-{[1-(3-ethylphenyl)cyclopropyl]amino}-2-hydroxypropyl)benzamide 3-(Allylthio)benzoic acid (717 mg, 3.69 mmol), (2R,3R)-3-amino-4-(3,5-difluorophenyl)-1-{[1-(3-ethylphenyl)cyclopropyl]amino}butan-2-ol (247mg, 0.685 mmol), and HATU (Aldrich, 2.1 g, 5.54 mmol) were dissolved in dichloromethane (35 mL), at ambient temperature, and treated with diisopropylethylamine (1.6 mL, 9.225 mmol). Upon completion, the reaction mixture was concentrated and chromatographed (SiO2, 2:1 to 1:1 Hexanes: EtOAc) to give the desired compound (650 mg). (LRMS (M+H) m/z=537.8)

Example SP-232

3-(allylsulfinyl)-N-((1S,2R)-1-(3,5-difluorobenzyl)-3-{[1-(3-ethylphenyl)cyclopropyl]amino}-2-hydroxypropyl)benzamide 3-(allylthio)-N-((1S,2R)-1-(3,5-difluorobenzyl)-3-{[1-(3-ethylphenyl)cyclopropyl]amino}-2-hydroxypropyl)benzamide (325 mg, 0.606 mmol) was dissolved in CH$_2$Cl$_2$ (10 mL) and AcOH (1 mL) and treated with mCPBA (104 mg, 0.606 mmol). The reaction mixture was stirred for 2.5 h, at which time more mCPBA (20 mg, 0.11 mmol) was added and stirring continued for 30 min. more. The organic layer was diluted with Et$_2$O and washed with 15% sodium thiosulfite solution. The organic was washed with brine, then dried (MgSO$_4$) and concentrated to give an oil, which was chromatographed with 25% to 50% EtOAc in hexanes to give the title compound. (LRMS (M+H) m/z 553.8)

Example SP-233

3-(allylsulfonyl)-N-((1S,2R)-1-(3,5-difluorobenzyl)-3-{[1-(3-ethylphenyl)cyclopropyl]amino}-2-hydroxypropyl)benzamide 3-(allylthio)-N-((1S,2R)-1-(3,5-difluorobenzyl)-3-{[1-(3-ethylphenyl)cyclopropyl]amino}-2-hydroxypropyl)benzamide (245 mg, 0.456 mmol) was dissolved in MeOH:H$_2$O (9:1, 6 mL) and treated with oxone (561 mg, 0.913 mmol). When the reaction was complete, the mixture was concentrated to 0.5× volume and poured onto EtOAc. This was washed with a 15% sodium thiosulfite solution, dried (MgSO$_4$) and concentrated to give the title compound. (LRMS (M+H) m/z 569.8)

Example SP-234

N-{(1S,2R)-1-(3,5-difluorobenzyl)-3-[(3-ethylbenzyl)amino]-2-hydroxypropyl}-2-(dipropylamino)-6-methylisonicotinamide Step 1. 2-chloro-6-methylisonicotinonitrile

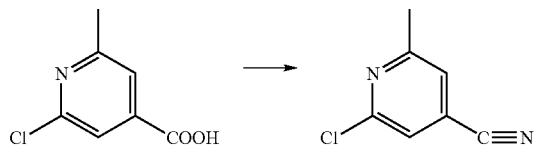

Using the method of Org. Prep. Proceed. Intern. (1982) 396, 2-chloro-6-methylisonicotinic acid (0.405 g, 2.36 mmol) was converted to 2-chloro-6-methylisonicotinonitrile (0.241 g).

Step 2. 2-(dipropylamino)-6-methylisonicotinonitrile

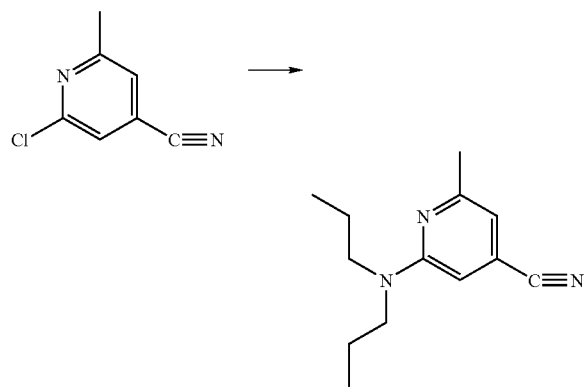

To 2-chloro-6-methylisonicotinonitrile (0.230 g, 1.51 mmol) was added di-n-propylamine (5 mL). The mixture was heated at 80° C. in a sealed, thick-walled glass vessel for 12 h and then at room temperature for 17 h. Excess di-n-propylamine was removed under reduced pressure and the residue was partitioned between dichloromethane and aq. sodium bicarbonate. After drying over sodium sulfate and concentration, the residue was chromatographed on silica gel using ethyl acetate-hexane (10/90) to give 0.14 g of 2-chloro-6-methylisonicotinonitrile and 0.059 g of 2-(dipropylamino)-6-methylisonicotinonitrile. Using the above conditions, 2-chloro-6-methylisonicotinonitrile (0.14 g) was converted to an additional 0.043 g of 2-(dipropylamino)-6-methylisonicotinonitrile.

Step 3. 2-(dipropylamino)-6-methylisonicotinic acid hydrochloride

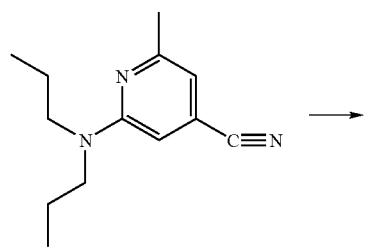

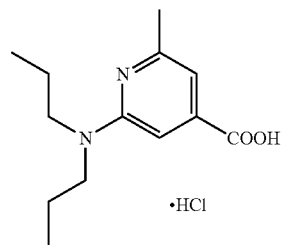

To 2-(dipropylamino)-6-methylisonicotinonitrile (0.094 g, 0.433 mmol) was added 4N HCl (2 mL) and THF (1 mL). The mixture was stirred at 100° C. (THF allowed to distill off) for 12 h, then the aqueous layer was removed under reduced pressure and using a toluene azeotrope to give 2-(dipropylamino)-6-methylisonicotinic acid hydrochloride, which was used without further purification in the next step.

Step 4. N-{(1S,2R)-1-(3,5-difluorobenzyl)-3-[(3-ethylbenzyl)amino]-2-hydroxypropyl}-2-(dipropylamino)-6-methylisonicotinamide

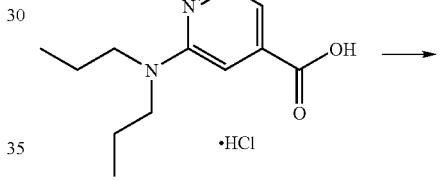

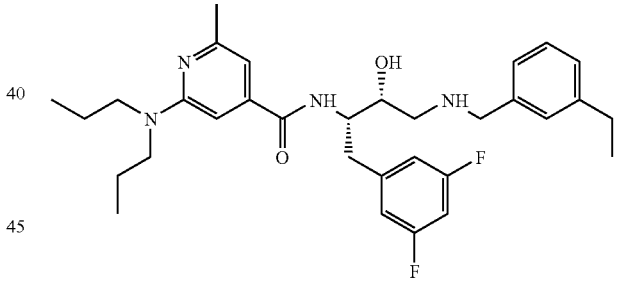

To 2-(dipropylamino)-6-methylisonicotinic acid hydrochloride (approx. 0.4 mmol) in THF (3 mL) was added triethylamine (0.17 mL), followed by dichloromethane (2 mL) and then CDI (0.071 g, 0.44 mmol). After stirring for 1 h, a mixture of (2R,3S)-3-amino-4-(3,5-difluorophenyl)-1-[(3-ethylbenzyl)amino]butan-2-ol dihydrochloride (0.163 g, 0.400 mmol), triethylamine (0.11 mL), and dichloromethane (approx. 2 mL) was added to the CDI mixture. The mixture was allowed to stir overnight, after which an additional 0.12 mL of triethylamine and 0.045 g of (2R,3S)-3-amino-4-(3,5-difluorophenyl)-1-[(3-ethylbenzyl)amino]butan-2-ol dihydrochloride was added. After stirring for several more hours, the mixture was partitioned between dichloromethane and aq. sodium bicarbonate. The organic layer was dried with sodium sulfate, concentrated, and the residue was chromatographed on silica gel using MeOH-dichloromethane (5/95) to give 0.04 g of the title compound.

Example SP-235

N-{(1S,2R)-1-(3,5-difluorobenzyl)-3-[(3-ethylbenzyl)amino]-2-hydroxypropyl}-2-(dipropylamino)-6-methylpyrimidine-4-carboxamide Step 1. methyl 2-(dipropylamino)-6-methylpyrimidine-4-carboxylate

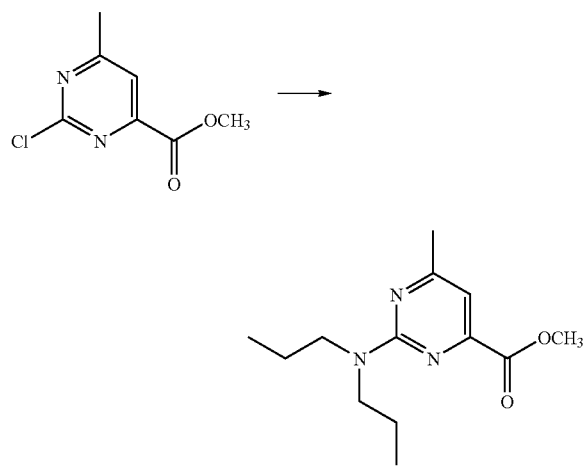

A mixture of methyl 2-chloro-6-methylpyrimidine-4-carboxylate (0.411 g, 2.20 mmol), di-n-propylamine (0.668 g, 6.60 mmol), triethylamine (0.267 g, 2.64 mmol), and THF (5 ml) was stirred at room temperature for 55 min and then at reflux for 1.3 h, at which time is was cooled and partitioned between ethyl acetate and a mixture of brine and aq. sodium bicarbonate. The organic layer was dried over magnesium sulfate and concentrated and then chromatographed on silica gel using ethyl acetate-hexane (90/10) to give methyl 2-(dipropylamino)-6-methylpyrimidine-4-carboxylate (0.457 g) as a pale yellow liquid.

Step 2. 35137-ret-135 2-(dipropylamino)-6-methylpyrimidine-4-carboxylic acid

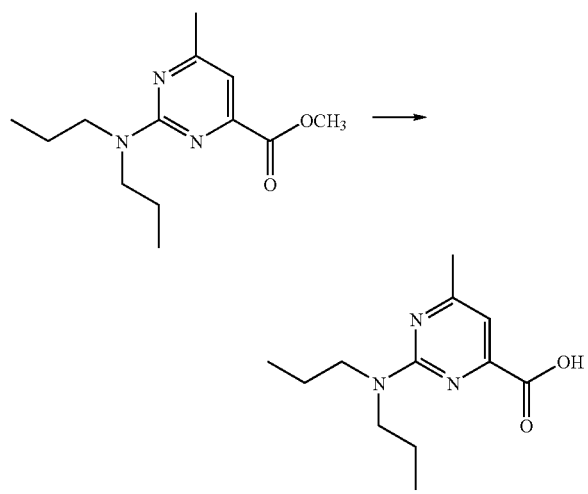

To methyl 2-(dipropylamino)-6-methylpyrimidine-4-carboxylate (0.450 g, 1.79 mmol) in MeOH (2 mL), water (1 mL), and THF (1 mL) was added lithium hydroxide monohydrate (0.113 g, 2.68 mmol). The mixture was stirred at room temperature for 1 h and then MeOH and THF were removed under reduced pressure. The pH of the residue was adjusted to approximately 5 and the resulting mixture was extracted with dichloromethane, dried over sodium sulfate, and concentrated to give 2-(dipropylamino)-6-methylpyrimidine-4-carboxylic acid (0.351 g) as a yellow solid.

Step 3. N-{(1S,2R)-1-(3,5-difluorobenzyl)-3-[(3-ethylbenzyl)amino]-2-hydroxypropyl}-2-(dipropylamino)-6-methylpyrimidine-4-carboxamide

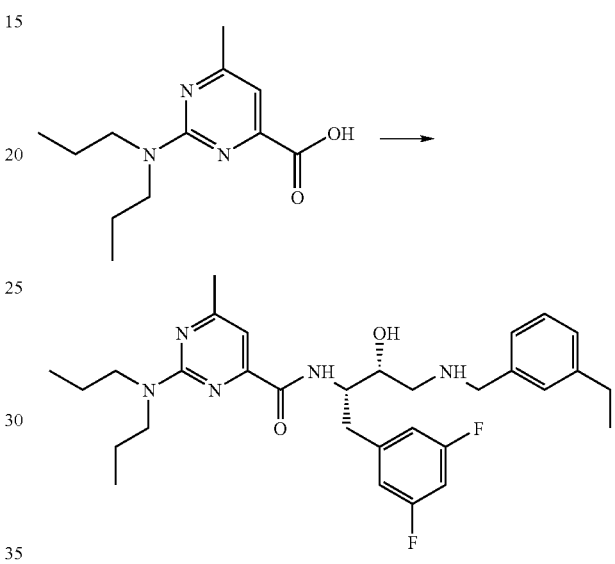

To 2-(dipropylamino)-6-methylpyrimidine-4-carboxylic acid (0.101 g, 0.426 mmol) in THF (0.5 mL) was added 1,1'-carbonyldiimidazole (CDI) (0.076 g, 0.468 mmol). After 50 min the CDI mixture was added to a mixture of (2R,3S)-3-amino-4-(3,5-difluorophenyl)-1-[(3-ethylbenzyl)amino]butan-2-ol dihydrochloride (0.173 g, 0.425 mmol) and triethylamine (0.18 mL, 1.28 mmol) in THF (6 mL) and dichloromethane (2 mL). After stirring overnight, the solvents were removed under reduced pressure and the residue was partitioned between dichloromethane, aq. sodium bicarbonate, and aq. sodium bicarbonate-brine mixture. The organic layer was dried over sodium sulfate, concentrated, and the residue was chromatographed on silica gel using MeOH-dichloromethane (5/95) to give 0.199 g of the title compound as a solid.

Example SP-236

3-butyl-N-{(1S,2R)-1-(3,5-difluorobenzyl)-3-[(3-ethylbenzyl)amino]-2-hydroxypropyl}imidazo[1,2-a]pyridine-6-carboxamide Step 1. 3-butylimidazo[1,2-a]pyridine-6-carboxylic acid

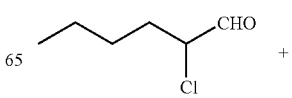 +

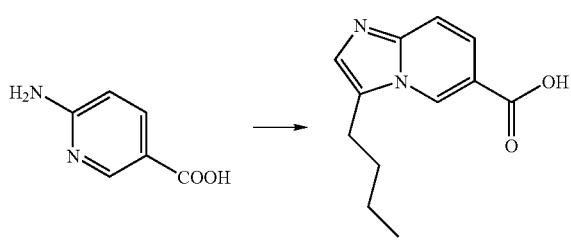

To hexanal (1.02 g, 10.2 mmol) in 15 mL of isopropyl alcohol-water (4:1 v/v) was added CuCl$_2$ (1.37 g, 10.2 mmol). The mixture was heated at 80° C. for 2.5 h, then cooled. The solids were removed by filtration and the filtrate was added to 6-aminonicotinic acid (1.35 g, 10 mmol). The mixture was stirred overnight at room temperature, then heated at reflux 32 h. After cooling, the solvents were removed under reduced pressure and MeOH was added to the residue. The resulting solid was removed by filtration and the filtrate was concentrated to dryness. MeOH was again added, and the resulting solid removed by filtration. After concentration of the filtrate, the residue was chromatographed on silica gel using MeOH-dichloromethane (33/67) to give 0.26 g of 3-butylimidazo[1,2-a]pyridine-6-carboxylic acid.

3-butyl-N-{(1S,2R)-1-(3,5-difluorobenzyl)-3-[(3-ethylbenzyl)amino]-2-hydroxypropyl}imidazo[1,2-a]pyridine-6-carboxamide

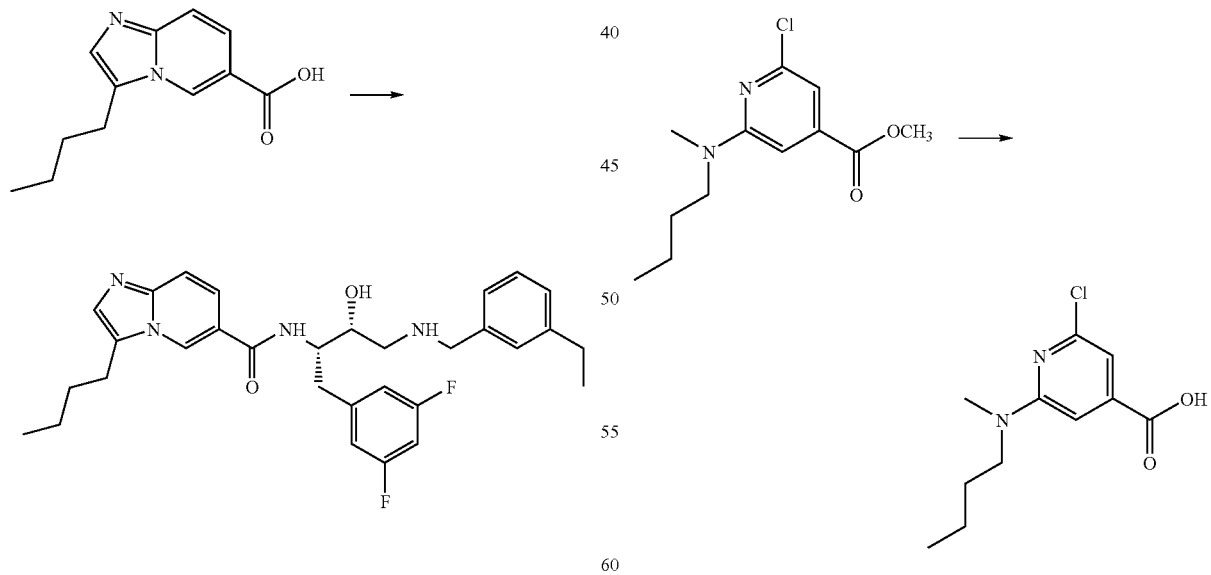

Step 2. In the same manner as for N-{(1S,2R)-1-(3,5-difluorobenzyl)-3-[(3-ethylbenzyl)amino]-2-hydroxypropyl}-2-(dipropylamino)-6-methylpyrimidine-4-carboxamide {Example S-SP-235}, Step 3, 3-butylimidazo[1,2-a]pyridine-6-carboxylic acid (0.16 g) was converted to 0.30 g of the title compound.

Example SP-237

2-[butyl(methyl)amino]-6-chloro-N-{(1S,2R)-1-(3,5-difluorobenzyl)-3-[(3-ethylbenzyl)amino]-2-hydroxypropyl}isonicotinamide Step 1. methyl 2-[butyl(methyl)amino]-6-chloroisonicotinate

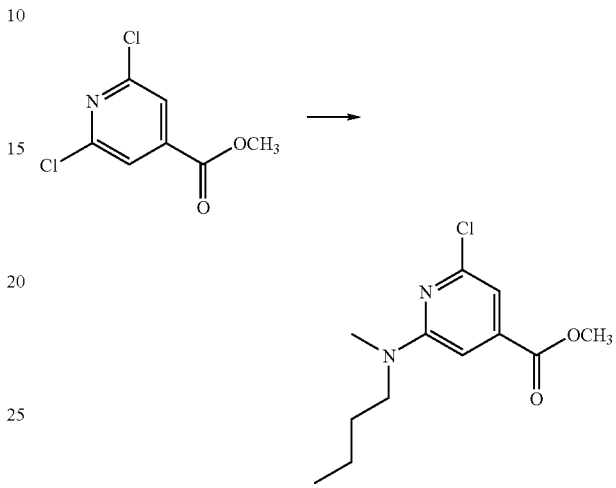

In the same manner as for N-{(1S,2R)-1-(3,5-difluorobenzyl)-3-[(3-ethylbenzyl)amino]-2-hydroxypropyl}-2-(dipropylamino)-6-methylisonicotinamide {Example SP-234, Step 2,} methyl 2,6-dichloroisonicotinate (1.0 g) was converted to methyl 2-[butyl(methyl)amino]-6-chloroisonicotinate (0.87 g).

Step 2. 2-[butyl(methyl)amino]-6-chloroisonicotinic acid

In the same manner as for N-{(1S,2R)-1-(3,5-difluorobenzyl)-3-[(3-ethylbenzyl)amino]-2-hydroxypropyl}-2-(dipropylamino)-6-methylpyrimidine-4-carboxamide {Example S-2435}, Step 2, methyl 2-[butyl(methyl)amino]-6-chloroisonicotinate. (0.17 g) was converted to 2-[butyl(methyl)amino]-6-chloroisonicotinic acid (0.15 g).

Step 3. 2-[butyl(methyl)amino]-6-chloro-N-{(1S,2R)-1-(3,5-difluorobenzyl)-3-[(3-ethylbenzyl)amino]-2-hydroxypropyl}isonicotinamide

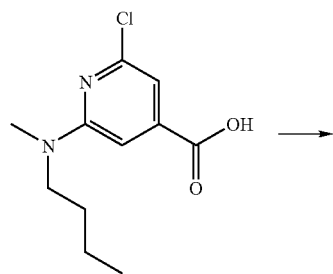

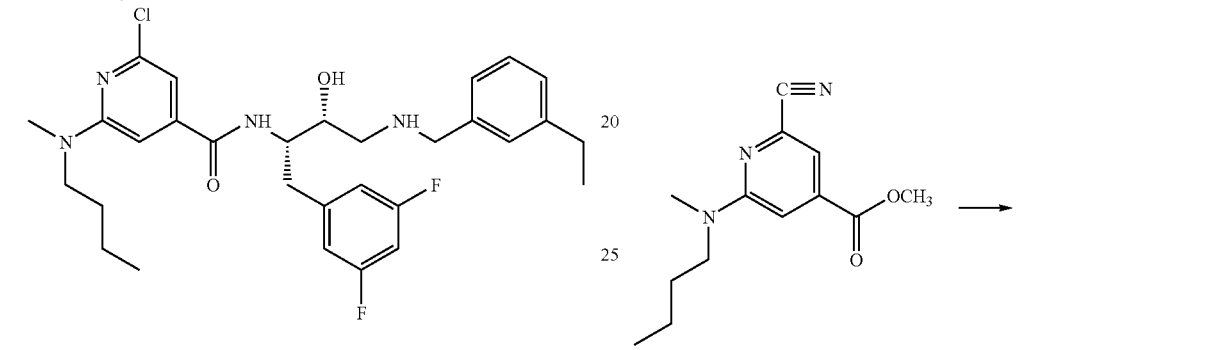

In the same manner as for N-{(1S,2R)-1-(3,5-difluorobenzyl)-3-[(3-ethylbenzyl)amino]-2-hydroxypropyl}-2-(dipropylamino)-6-methylpyrimidine-4-carboxamide {Example S-2435}, Step 3, 2-[butyl(methyl)amino]-6-chloroisonicotinic acid (0.15 g) was converted to 0.13 g of the title compound.

Example SP-238

2-[butyl(methyl)amino]-6-cyano-N-{(1S,2R)-1-(3,5-difluorobenzyl)-3-[(3-ethylbenzyl)amino]-2-hydroxypropyl}isonicotinamide Step 1. methyl 2-[butyl(methyl)amino]-6-cyanoisonicotinate

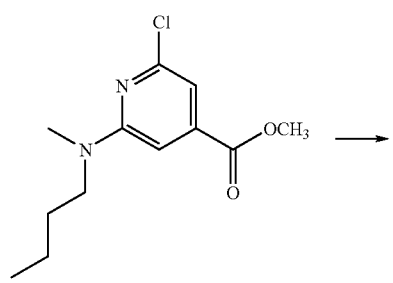

A flask containing methyl 2-[butyl(methyl)amino]-6-chloroisonicotinate (0.306 g, 1.19 mmol), zinc cyanide (0.0839 g, 0.714 mmol), Pd₂dba₃ (0.0218 g, 0.024 mmol), dppf (0.0264 g, 0.048 mmol), and zinc dust (0.0093 g, 0.143 g) was flushed with nitrogen. N-Methylpyrrolidinone (2 mL) was added and the mixture was heated at 120° C. for 2 h, at which time it was cooled and partitioned between ethyl acetate and aq. ammonium hydroxide and brine. The organic layer was dried over magnesium sulfate and concentrated, followed by silica gel chromatography using ethyl acetate-hexane (10/90) to give 0.161 g of methyl 2-[butyl(methyl)amino]-6-cyanoisonicotinate.

Step 2. 2-[butyl(methyl)amino]-6-cyanoisonicotinic acid

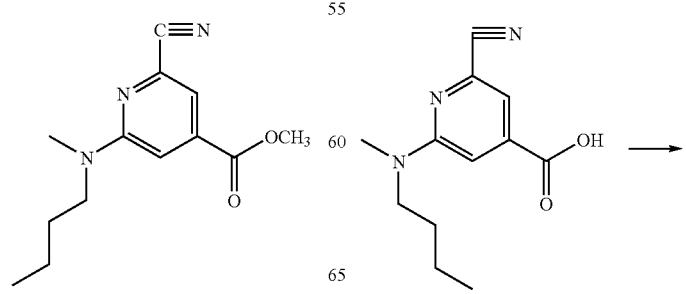

In the same manner as for N-{(1S,2R)-1-(3,5-difluorobenzyl)-3-[(3-ethylbenzyl)amino]-2-hydroxypropyl}-2-(dipropylamino)-6-methylpyrimidine-4-carboxamide {Example S-2435}, Step 2, methyl 2-[butyl(methyl)amino]-6-cyanoisonicotinate (0.157 g) was converted to 2-[butyl(methyl)amino]-6-cyanoisonicotinic acid (0.151 g).

Step 3. 2-[butyl(methyl)amino]-6-cyano-N-{(1S,2R)-1-(3,5-difluorobenzyl)-3-[(3-ethylbenzyl)amino]-2-hydroxypropyl}isonicotinamide

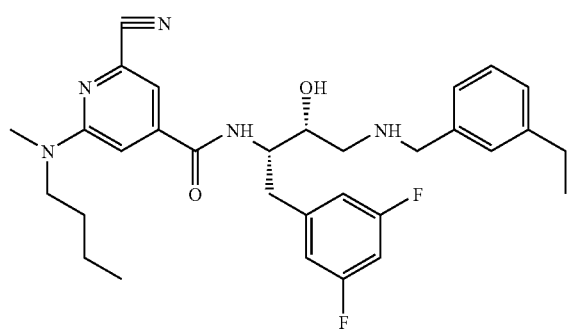

In the same manner as for N-{(1S,2R)-1-(3,5-difluorobenzyl)-3-[(3-ethylbenzyl)amino]-2-hydroxypropyl}-2-(dipropylamino)-6-methylpyrimidine-4-carboxamide {Example S-2435}, Step 3, 2-[butyl(methyl)amino]-6-cyanoisonicotinic acid (0.135 g) was converted to the title compound (0.223 g).

Example SP-239

2-cyano-N-{(1S,2R)-1-(3,5-difluorobenzyl)-3-[(3-ethylbenzyl)amino]-2-hydroxypropyl}-6-[methyl(propyl)amino]isonicotinamide

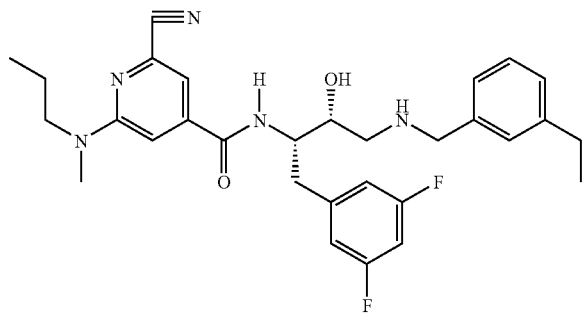

In the same manner as for N-{(1S,2R)-1-(3,5-difluorobenzyl)-3-[(3-ethylbenzyl)amino]-2-hydroxypropyl}-2-(dipropylamino)-6-methylpyrimidine-4-carboxamide {Example S-2435}, Step 3, 2-cyano-6-[methyl(propyl)amino]isonicotinic acid (0.13 g) gave 0.23 g of the title compound.

Example SP-240

Reaction scheme for the preparation of 1-butyl-N-{(1S,2R)-1-(3,5-difluorobenzyl)-3-[(3-ethylbenzyl)amino]-2-hydroxypropyl}-1,2,3,4-tetrahydroquinoline-7-carboxamide

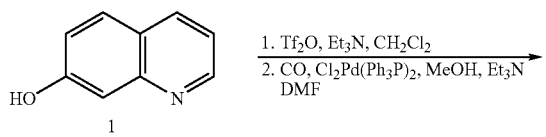

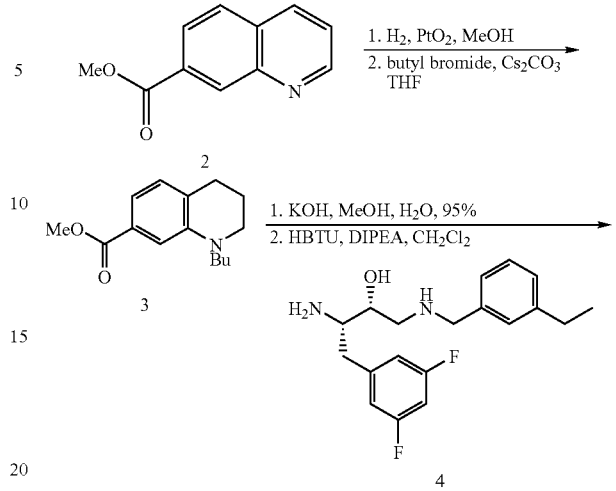

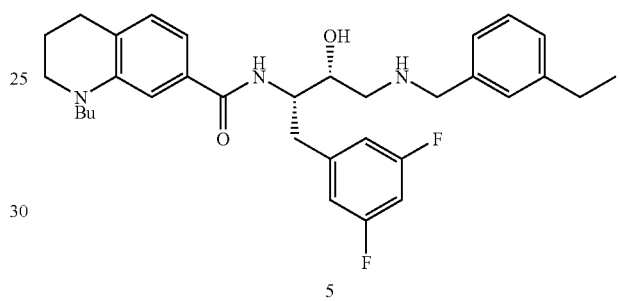

1-butyl-N-{(1S,2R)-1-(3,5-difluorobenzyl)-3-[(3-ethylbenzyl)amino]-2-hydroxypropyl}-1,2,3,4-tetrahydroquinoline-7-carboxamide Step 1: To an ice-cold, stirred solution of quinolin-7-ol (1.0 g, 6.9 mmol) and triethylamine (1.0 mL, 7.6 mmol) in methylene chloride (14 mL) was added trifluoromethane sulfonic anhydride (1.3 mL, 7.6 mmol), and the mixture was stirred for 30 min. The mixture was diluted with methylene chloride, washed with saturated sodium bicarbonate, and brine, dried (magnesium sulfate), filtered, and concentrated under reduced pressure provided quinolin-7-yl trifluoroacetate (1.5 g): ESI MS m/z 278 [M+H]$^+$.

Step 2: To a stirred solution of quinolin-7-yl trifluoroacetate (750 mg, 2.7 mmol), PdCl$_2$(Ph$_3$P) (95 mg, 0.14 mmol), and triethylamine (1.2 mL, 8.4 mmol) in 1:2 DMF/MeOH (39 mL) was degassed and sparged with CO, and the mixture was heated at 60° C. for 48 h. The mixture was cooled to room temperature, filtered through diatomaceous earth, and concentrated under reduced pressure. The residue was diluted with a 5% solution of LiCl, and washed with CHCl$_3$ (3×250 mL). The combined organics were dried (Na$_2$SO$_4$), filtered, and concentrated under reduced pressure. Purification by flash column chromatography (silica, 3:1 ethyl acetate/hexanes) provided methyl quinoline-7-carboxylate (185 mg): ESI MS m/z 188 [M+H]$^+$.

Step 3: A solution of methyl quinoline-7-carboxylate (185 mg, 1.0 mmol) and PtO$_2$ (20 mg) in methanol (10 mL) was shaken under an atmosphere of hydrogen for 2 h. The reaction mixture was filtered through diatomaceous earth, and concentrated under reduced pressure to provide methyl 1,2,3,4-tetrahydroquinoline-7-carboxylate (189 mg): ESI MS m/z 192 [M+H]$^+$.

Step 4: To a stirred solution of methyl 1,2,3,4-tetrahydroquinoline-7-carboxylate (180 mg, 0.94 mmol) and cesium bicarbonate (1.5 g, 4.7 mmol) in THF (2 mL) was added n-butyl bromide (1.0 mL, 9.4 mmol), and the reaction mixture was heated at reflux for 48 h. The reaction mixture was cooled to room temperature, and diluted with EtOAc. The organic layer was washed with water, and brine, dried (magnesium sulfate), filtered, and concentrated under reduced pressure. Purification by flash column chromatography (silica, 1:3 ethyl acetate/hexanes) afforded methyl 1-butyl-1,2,3,4-tetrahydroquinoline-7-carboxylate (156 mg): ESI MS m/z 248 [M+H]$^+$.

Step 5: To a stirred solution of methyl 1-butyl-1,2,3,4-tetrahydroquinoline-7-carboxylate (156 mg, 0.63 mmol) in methanol (1.3 mL) was added potassium hydroxide (6.3 mL of a 1 M solution in water, 6.3 mmol). The reaction mixture was stirred at room temperature for 48 h and concentrated under reduced pressure. The residue was diluted with water and washed with ethyl acetate. The aqueous layer was acidified to pH 4 with 1 N hydrochloric acid and extracted with chloroform (4×100 mL). The combined organic extracts were dried (sodium sulfate), filtered, and concentrated under reduced pressure. Purification by flash column chromatography (silica, 1:9 methanol/chloroform) afforded 1-butyl-1,2,3,4-tetrahydroquinoline-7-carboxylic acid (139 mg): ESI MS m/z 234 [M+H]$^+$.

Step 6: A solution of 1-butyl-1,2,3,4-tetrahydroquinoline-7-carboxylic acid (134 mg, 0.57 mmol), HBTU (327 mg, 0.86 mmol), and diisopropylethylamine (150 μL, 0.86 mmol) was stirred in methylene chloride (3.0 mL) for 15 min. A solution of (2R,3S)-3-amino-4-(3,5-difluorophenyl)-1-[(3-ethylbenzyl)amino]butan-2-ol (Example SP-272) (234 mg, 0.57 mmol) and diisopropylethylamine (150 μL, 0.86 mmol) in methylene chloride (3.0 mL) was added and the reaction mixture was stirred overnight. The reaction mixture was diluted with methylene chloride, washed with 1 N hydrochloric acid (10 mL), saturated sodium bicarbonate (10 mL), and brine. The organic layer was then dried (magnesium sulfate), filtered, and concentrated under reduced pressure. Purification by flash column chromatography (silica, 1:9 methanol/chloroform) provided 1-butyl-N-{(1S,2R)-1-(3,5-difluorobenzyl)-3-[(3-ethylbenzyl)amino]-2-hydroxypropyl}-1,2,3,4-tetrahydroquinoline-7-carboxamide (130 mg): ESI MS m/z 550 [M+H]$^+$ Example SP-241

N-{(1S,2R)-1(3,5-difluorobenzyl)-3-[(3-ethylbenzyl)amino]-2-hydroxypropyl}-3-propyl-1,2-benzisoxazole-5-carboxamide General Synthesis of Benzisoxazole Furan 1 was hydrogenated to afford amine 2. Diels-Alder reaction of amine 2 and 1-hexen-3-one afforded ketone 3.[1] Ketone 3 was then treated with p-toluenesulfonic acid to afford diketone 4. Diketone 4 was rearomatized with boron trifluoride to give phenol 5. Phenol 5 was then converted to oxime 6 with hydroxylamine. Oxime 6 was cyclized with thionyl chloride to afford methyl ester 7.[2] Methyl ester 7 was then saponified to acid 8. Coupling of acid 8 and amine 9 in the presence of HATU, provided benzoxazole 10.

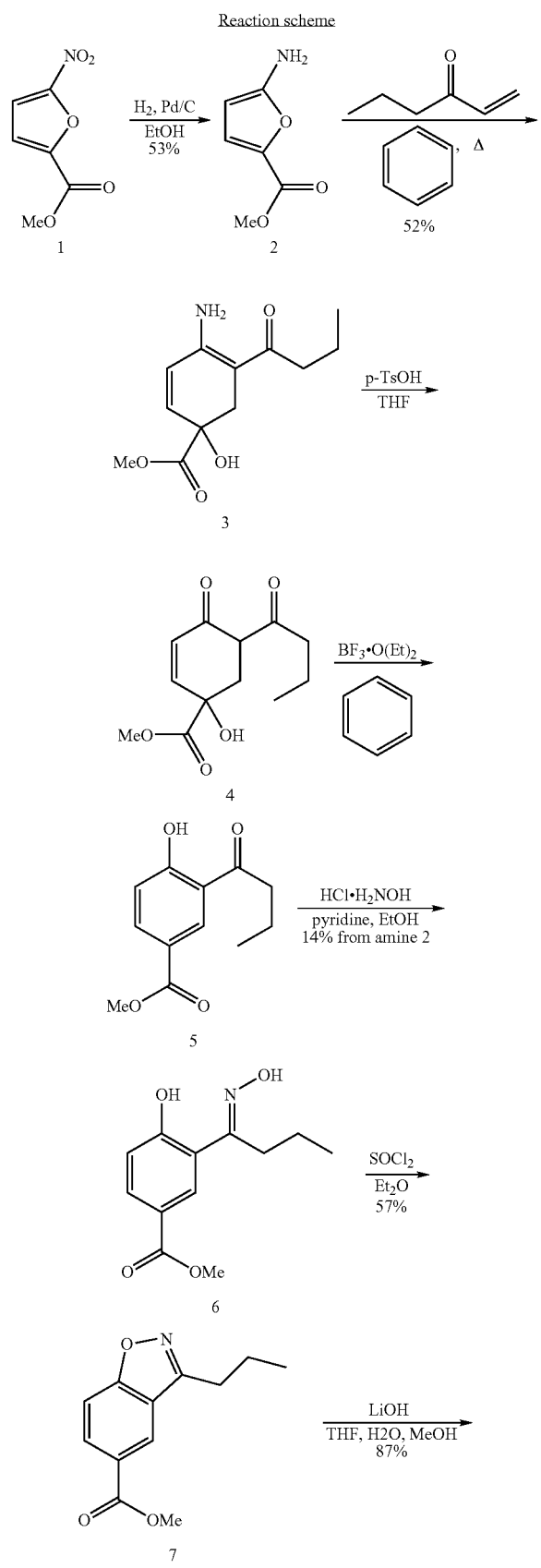

Reaction scheme

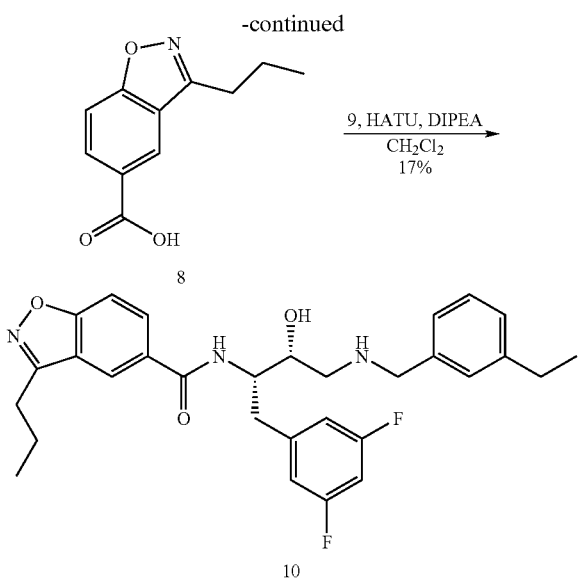

N-{(1S,2R)-1(3,5-difluorobenzyl)-3-[(3-ethylbenzyl) amino]-2-hydroxypropyl}-3-propyl-1,2-benzisoxazole-5-carboxamide Step 1: A mixture of methyl 5-nitro-2-furoate (13 g, 76 mmol) and 10% Pd/C (1.3 g) in ethanol (150 mL) was shaken under an atmosphere of hydrogen at 40 psi for 18 h. The reaction mixture was filtered through diatomaceous earth and concentrated under reduced pressure to afford a crude oil. Purification by flash column chromatography (silica, 1:1 hexanes/ethyl acetate) provided methyl 5-amino-2-furoate (5.6 g): $^1$H NMR (500 MHz, CDCl$_3$) δ 7.11-7.10 (m, 1H), 5.31-5.29 (m, 1H), 4.31 (br s, 2H), 3.84 (s, 3H).

Step 2: A stirred solution of methyl 5-amino-2-furoate (1.4 g, 10 mmol) and 1-hexen-3-one (7 mL, 60 mmol) in benzene (50 mL) was heated to reflux for 2 h. The reaction mixture was concentrated under reduced pressure to afford a crude oil. Purification by flash column chromatography (silica, 2:1 hexanes/ethyl acetate) provided methyl 4-amino-5-butyryl-1-hydroxycyclohexa-2,4-diene-1-carboxylate (1.25 g): $^1$H NMR (300 MHz, CDCl$_3$): δ 6.26-6.23 (m, 1H), 6.09-6.05 (m, 1H), 3.80 (s, 3H), 3.02-2.96 (m, 1H), 2.89-2.84 (m, 1H), 2.42-2.37 (m, 2H), 1.64-1.57 (m, 2H), 0.96-0.88 (m, 3H).

Step 3: To a stirred solution of methyl 4-amino-5-butyryl-1-hydroxycyclohexa-2,4-diene-1-carboxylate (1.25 g, 5.2 mmol) in a 1:1 mixture of water/tetrahydrofuran (10 mL) was added p-toluenesulfonic acid monohydrate (1.1 g, 5.8 mmol). The reaction mixture was stirred for 18 h and then partitioned between dichloromethane and water. The organic layer was dried (sodium sulfate), filtered, and concentrated under reduced pressure to afford methyl 5-butyryl-1-hydroxy-4-oxocyclohex-2-ene-1-carboxylate which was used without further purification or characterization.

Step 4: To a stirred solution of methyl 5-butyryl-1-hydroxy-4-oxocyclohex-2-ene-1-carboxylate in benzene was added BF$_3$.O(Et)$_2$ (1.3 mL, 10 mmol). The mixture was stirred for 0.25 h and then quenched with saturated sodium bicarbonate followed by extraction with dichloromethane. The organic layer was dried (sodium sulfate), filtered, and concentrated under reduced pressure to afford methyl 3-butyryl-4-hydroxybenzoate which was used without further purification or characterization.

Step 5: A stirred solution of methyl 3-butyryl-4-hydroxybenzoate, pyridine (3.7 mL, 46 mmol), and hydroxylamine hydrochloride (3.55 g, 51 mmol) in ethanol (30 mL) was heated reflux for 2 h. The mixture was concentrated under reduced pressure and partitioned between water and ethyl acetate. The organic layer was washed with 1 N hydrochloric acid, saturated sodium bicarbonate, dried (sodium sulfate), filtered, and concentrated under reduced pressure to afford a crude oil. Purification by flash column chromatography (silica, 10:1 hexanes/ethyl acetate) provided methyl 4-hydroxy-3-[(1E)-N-hydroxybutanimidoyl]benzoate (170 mg): $^1$H NMR (500 MHz, CD$_3$OD): δ 8.30-8.28 (m, 1H), 7.85-7.82 (m, 1H), 6.92-6.89 (m, 1H), 3.88 (s, 3H), 2.87-2.84 (m, 2H), 1.67-1.60 (m, 2H), 1.05-1.00 (m, 3H).

Step 6: To an ice-cold stirred solution of methyl 4-hydroxy-3-[(1E)-N-hydroxybutanimidoyl]benzoate (170 mg, 0.7 mmol) in diethyl ether (5 mL) was added a mixture of thionyl chloride (60 µL, 0.8 mmol) and pyridine (580 µL, 7.2 mmol) in diethyl ether (5 mL). After 2.5 h the mixture was poured over ice-water and acidified to pH=1 with 1 N hydrochloric acid. The mixture was then partitioned between water and ethyl acetate. The organic layer was washed with saturated sodium bicarbonate, dried (sodium sulfate), filtered, and concentrated under reduced pressure to afford a crude oil. Purification by flash column chromatography (silica, 10:1 hexanes/ethyl acetate) provided methyl 3-propyl-1,2-benzisoxazole-5-carboxylate (90 mg): $^1$H NMR (300 MHz, CDCl$_3$): δ 8.36-8.35 (m, 1H), 8.07-8.04 (m, 1H), 7.52-7.49 (m, 1H), 3.95 (s, 3H), 2.96-2.91 (m, 2H), 2.00-1.87 (m, 2H), 1.09-1.04 (m, 3H).

Step 7: To a solution of methyl 3-propyl-1,2-benzisoxazole-5-carboxylate (90 mg, 0.4 mmol) in a 2:1:1 mixture of tetrahydrofuran, water, and methanol (4 mL) was added lithium hydroxide (50 mg, 1.2 mmol) and the resulting reaction mixture stirred at room temperature for 2.5 h. The reaction mixture was concentrated under reduced pressure, and partitioned between water and ethyl ether. The aqueous layer was washed twice with ether and acidified to pH 1 with 6 M hydrochloric acid. The resulting aqueous layer was extracted with ethyl acetate, dried (sodium sulfate), and concentrated under reduced pressure to afford 3-propyl-1,2-benzisoxazole-5-carboxylic acid (73 mg): $^1$H NMR (300 MHz, CD$_3$OD): δ 8.28-8.27 (m, 1H), 8.09-8.06 (m, 1H), 7.64-7.61 (m, 1H), 2.99-2.94 (m, 2H), 1.96-1.86 (m, 2H), 1.08-1.02 (m, 3H).

Step 8: To a stirred solution of 3-propyl-1,2-benzisoxazole-5-carboxylic acid (70 mg, 0.3 mmol) and HATU (130 mg, 0.3 mmol) in methylene chloride (5 mL) was added N,N-diisopropylethylamine (110 µL, 0.6 mmol). In a separate flask, N,N-diisopropylethylamine (110 µL, 0.6 mmol) was added to (2R,3S)-3-amino-4-(3,5-difluorophenyl)-1-[(3-ethylbenzyl)amino]butan-2-ol (EXA xxx)(140 mg, 0.3 mmol) in methylene chloride (2 mL). This solution was added to the above solution containing the acid and the resulting reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 97:3 to 94:6 methylene chloride/methanol) provided N-{(1S,2R)-1-(3,5-difluorobenzyl)-3-

[(3-ethylbenzyl)amino]-2-hydroxypropyl}-3-propyl-1,2-benzisoxazole-5-carboxamide (30 mg). ESI-MS m/z 522 [M+H]+

Example SP-242

N-{(1S,2R)-1-(3,5-difluorobenzyl)-3-[(3-ethylbenzyl)amino]-2-hydroxypropyl}isoquinoline-7-carboxamide dihydrochloride

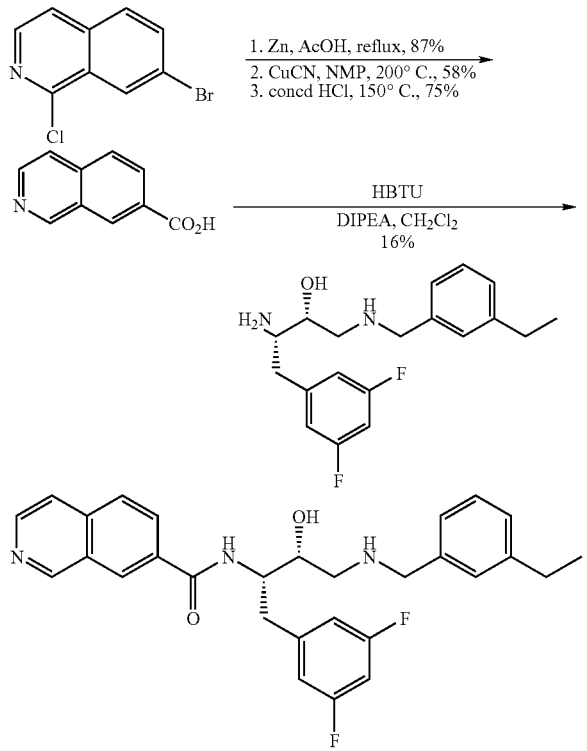

Step 1: A solution of 7-bromo-1-chloroisoquinoline (2.50 g, 10.3 mmol) and activated zinc (1.40 g, 21.65 mmol) in acetic acid (20 mL) was heated at reflux for 2 h. The reaction mixture was cooled to room temperature and concentrated under reduced pressure. The resulting residue was partitioned between ethyl acetate and water. The organic layer was washed with saturated sodium chloride, dried (sodium sulfate), filtered, and concentrated under reduced pressure to provide 7-bromoisoquinoline (1.86 g): ESI MS m/z 208 [M+H]+.

Step 2: A solution of 7-bromoisoquinoline (1.80 g, 8.65 mmol) and cuprous cyanide (1.16 g, 12.97 mmol) in N-methyl pyrrolidinone (17 mL) was heated to 200° C. for 2 h. The reaction mixture was cooled to room temperature and partitioned between ethyl acetate and water. The aqueous phase was back-extracted with additional ethyl acetate and the combined organic layers were washed with saturated sodium chloride, dried (sodium sulfate), filtered, and concentrated under reduced pressure to yield 7-cyano-isoquinoline (770 mg): $^1$H NMR (300 MHz, CDCl$_3$) δ 9.35 (s, 1H), 8.70 (d, J=5 Hz, 1H), 8.40 (s, 1H), 7.95 (d, J=8 .Hz, 1H), 7.84 (d, J=8 Hz, 1H), 7.73 (d, J=5 Hz, 1H); ESI MS m/z 155 [M+H]+.

Step 3: A solution of 7-cyanoisoquinoline (770 mg, 5.0 mmol) in concentrated hydrochloric acid (25 mL) was heated in a sealed tube to 150° C. for 18 h. The reaction mixture was cooled to room temperature and concentrated under reduced pressure. The residue was dissolved in water (10 mL) and neutralized to pH 7.0 with concentrated ammonium hydroxide. The solution was vacuum filtered and the filtrate concentrated under reduced pressure to provide isoquinoline-7-carboxylic acid (640 mg): ESI MS m/z 174 [M+H]+.

Step 4: To a stirred solution of isoquinoline-7-carboxylic acid (200 mg, 1.15 mmol) and N,N-diisopropyl ethylamine (1.20 mL, 6.88 mmol) in methylene chloride (14.0 mL) was added HBTU (438 mg, 1.15 mmol) and the reaction stirred for 0.5 h. (2R,3S)-3-Amino-4-(3,5-difluorophenyl)-1-[(3-ethylbenzyl)amino]butan-2-ol (470 mg, 1.15 mmol) was added in one portion and the reaction mixture was stirred under nitrogen for 18 h. The reaction mixture was then diluted with additional methylene chloride and washed with saturated sodium bicarbonate, saturated sodium chloride, dried (sodium sulfate), filtered, and concentrated under reduced pressure. Purification by flash column chromatography (silica, 0-5% methanol/methylene chloride) gave N-{(1S,2R)-1-(3,5-difluorobenzyl)-3-[(3-ethylbenzyl)amino]-2-hydroxypropyl}isoquinoline-7-carboxamide (100 mg) which was characterized as its bis-HCl salt: mp 142-143° C.; ESI MS m/z 490 [M+H]+

Example SP-243

N-{(1S,2R)-1-(3,5-difluorobenzyl)-3-[(3-ethylbenzyl)amino]-2-hydroxypropyl}-1-(propylamino)isoquinoline-7-carboxamide dihydrochloride

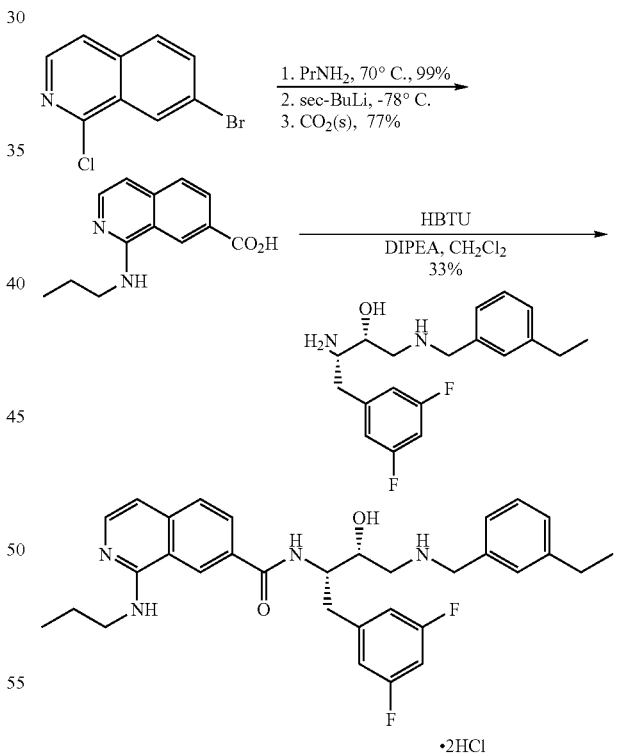

Step 1: A solution of 7-bromo-1-chloroisoquinoline in propylamine (15.0 mL) was heated at 70° C. in a sealed tube overnight. The reaction mixture was concentrated under reduced pressure, then dissolved in chloroform and washed with saturated sodium bicarbonate, saturated sodium chloride, dried (sodium sulfate), filtered, and concentrated under reduced pressure to yield 7-bromo-2-(N-propylamino)isoquinoline (820 mg): ESI MS m/z 266 [M+H]+.

Step 2: A solution of 7-bromo-2-(N-propylamino)isoquinoline (200 mg, 0.754 mmol) in anhydrous diethyl ether (1.0 mL) was cooled to −65° C. To this solution sec-butyllithium was added dropwise (1.30 mL of a 1.3 M solution in cyclohexane, 1.69 mmol) and the reaction mixture stirred at −60° C. for 10 min. The reaction mixture was quenched by addition of pulverized dry ice ($CO_2$) and the reaction allowed to slowly warm to room temperature over 1 h. The resulting solution was acidified with 1 N hydrochloric acid and the reaction mixture extracted with ethyl acetate (3×15 mL). The combined organic phase was washed with water, dried (sodium sulfate), filtered, and concentrated under reduced pressure to yield a brown solid. Purification by flash column chromatography (silica, 66:20:10:4 ethyl acetate/chloroform/methanol/concentrated ammonium hydroxide) gave 1-(propylamino)isoquinoline-7-carboxylic acid (133 mg): ESI MS m/z 231 [M+H]$^+$.

Step 3: To a stirred solution of 1-(propylamino)isoquinoline-7-carboxylic acid (81 mg, 0.396 mmol) and N,N-diisopropyl ethylamine (3.75 µL, 2.16 mmol) in methylene chloride (5.0 mL) was added HBTU (152 mg, 0.396 mmol) and the reaction stirred for 0.5 h. (2R,3S)-3-Amino-4-(3,5-difluorophenyl)-1-[(3-ethylbenzyl)amino]butan-2-ol (150 mg, 0.36 mmol) was added in one portion and the reaction mixture was stirred under nitrogen for 18 h. The reaction mixture was then diluted with additional methylene chloride and washed with saturated sodium bicarbonate, saturated sodium chloride, dried (sodium sulfate), filtered, and concentrated under reduced pressure. Purification by flash column chromatography (silica, 0-5% methanol/methylene chloride) gave N-{(1S,2R)-1-(3,5-difluorobenzyl)-3-[(3-ethylbenzyl)amino]-2-hydroxypropyl}-1-(propylamino)isoquinoline-7-carboxamide (67 mg) which was characterized as its bis-HCl salt: mp 262° C. dec; ESI MS m/z 547 [M+H]$^+$ Example SP-244

N-{(1S,2R)-1-(3,5-difluorobenzyl)-3-[(3-ethylbenzyl)amino]-2-hydroxypropyl}-1-(dipropylamino)isoquinoline-7-carboxamide

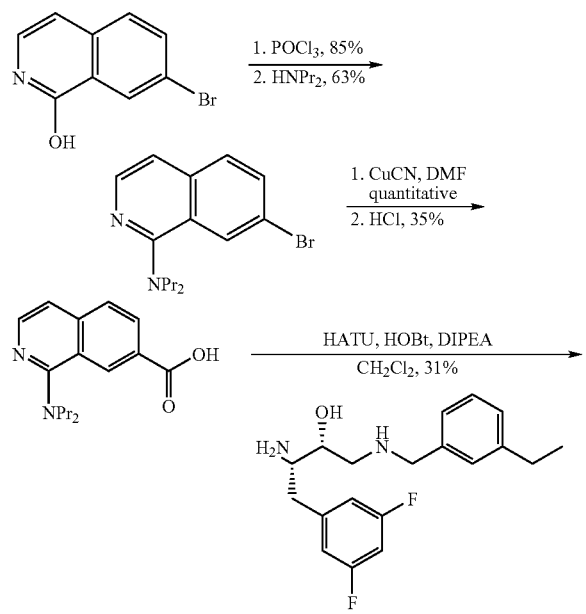

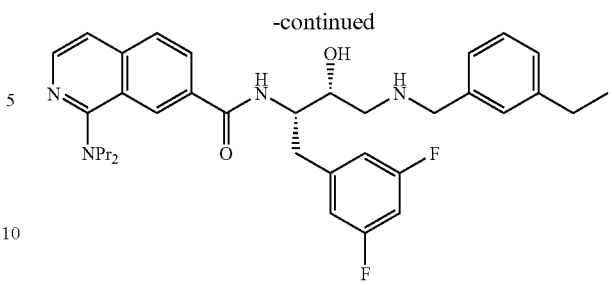

Step 1: A solution of 7-bromoisoquinolin-1-ol (2.5 g, 11.1 mmol) and POCl$_3$ (10.4 mL, 111 mmol) was stirred at 70° C. for 2.5 h. The reaction mixture was cooled to room temperature, poured into ice water, and the solution was stirred overnight. The aqueous mixture was diluted with chloroform, washed with a saturated solution of NaHCO$_3$, saturated NaCl, dried (MgSO$_4$), filtered, and concentrated under reduced pressure to afford 7-bromo-1-chloroisoquinoline (2.3 g): $^1$H NMR (300 MHz, DMSO-d$_6$) δ 8.39-8.36 (m, 2H), 8.09-8.02 (m, 2H), 7.95 (d, J=6 Hz, 1H).

Step 2: A solution of 7-bromo-1-chloroisoquinoline from step 1 (500 mg, 2.1 mmol) and dipropylamine (2.8 mL, 21 mmol) was heated at 150° C. in a sealed tube for 2 d. The reaction mixture was cooled, and the solvent was removed under reduced pressure to provide 7-bromo-N,N-dipropylisoquinolin-1-amine (400 mg): $^1$H NMR (300 MHz, DMSO-d$_6$) δ 8.55 (s, 1H), 7.90 (d, J=6 Hz, 1H), 7.75-7.64 (m, 2H), 6.87 (d, J=6 Hz, 1H), 3.42 (q, J=7 Hz, 4H), 1.65 (q, J=7 Hz, 4H), 0.94 (t, J=7 Hz, 6H).

Step 3: A solution of 7-bromo-N,N-dipropylisoquinolin-1-amine (350 mg, 1.1 mmol) and CuCN (204 mg, 2.2 mmol) in N,N-dimethylformamide (2 mL) was stirred at reflux for 24 h. The reaction mixture was cooled to room temperature, diluted with water, and extracted with ethyl acetate (3×50 mL). The combined organics were washed with saturated sodium chloride, dried (magnesium sulfate), filtered, and concentrated under reduced pressure to provide 1-(dipropylamino)isoquinoline-7-carbonitrile (279 mg, which was used without any further characterization.

Step 4: A solution of 1-(dipropylamino)isoquinoline-7-carbonitrile from step 3 (279 mg, 1.1 mmol) in concentrated hydrochloric acid (4 mL) was heated at 150° C. in a sealed tube for 14 h. The reaction mixture was cooled to room temperature, the solvent was removed under reduced pressure, and the residue was dissolved in a 25% ammonium hydroxide/water solution and stirred for 1 h. The solution was acidified to pH 4 with concentrated hydrochloric acid, and extracted with chloroform (3×50 mL). The combined organics were dried (Na$_2$SO$_4$), filtered, and concentrated under reduced pressure to provide 1-(dipropylamino)isoquinoline-7-carboxylic acid (104 mg): ESI MS m/z 273 [M+H]$^+$.

Step 5: To a stirred solution of 1-(dipropylamino)isoquinoline-7-carboxylic acid (103 mg, 0.38 mmol), (2R,3S)-3-Amino-4-(3,5-difluorophenyl)-1-[(3-ethylbenzyl)amino]butan-2-ol (154 mg, 0.38 mmol), HOBt (77 mg, 0.57 mmol), and DIPEA (0.2 mL, 1.1 mmol) in methylene chloride (4 mL) was added HATU (216 mg, 0.57 mmol). The reaction mixture was stirred overnight and then partitioned between methylene chloride and 1 N hydrochloric acid. The organic layer was washed with saturated sodium bicarbonate, saturated sodium chloride, dried (sodium sulfate), filtered, and concentrated under reduced pressure. Purification by flash column chromatography (silica, 9:1 chloroform/methanol) gave N-{(1S,2R)-1-(3,5-difluorobenzyl)-3-[(3-ethylbenzyl)amino]-2-hydroxypropyl}-1-(dipropylamino)isoquinoline-7-carboxamide (70 mg): mp: 142-151° C.; APCI MS m/z 589 [M+H]+

Example SP-244

1-[butyl(methyl)amino]-N-{(1S,2R)-1-(3,5-difluorobenzyl)-3-[(3-ethylbenzyl)amino]-2-hydroxypropyl}isoquinoline-7-carboxamide

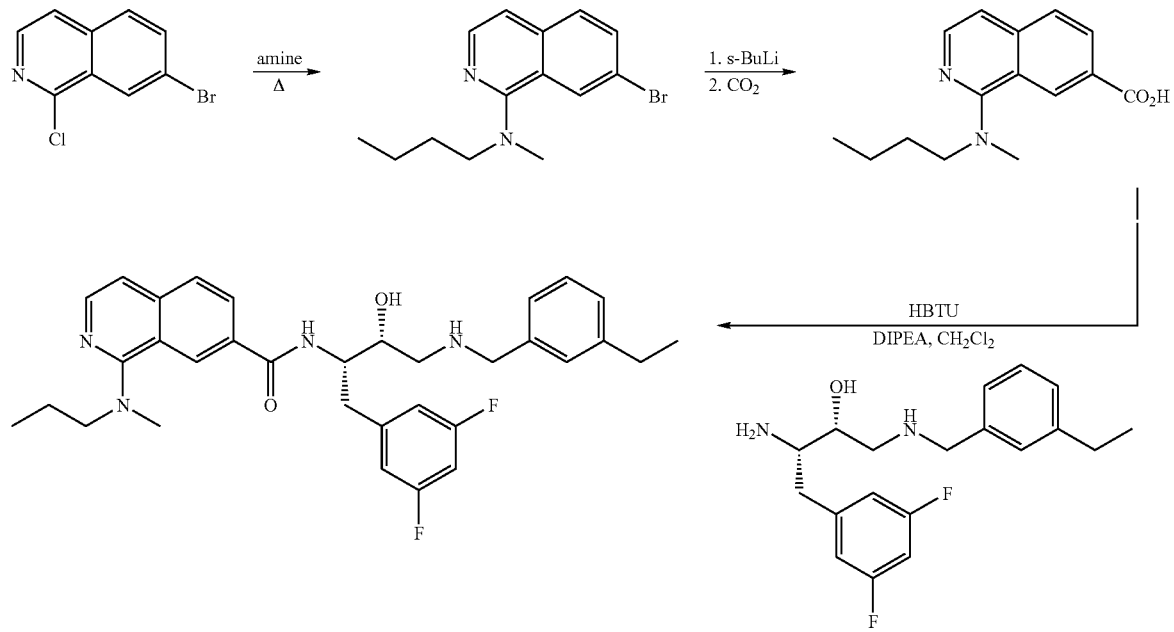

Step 1: A solution of 7-bromo-1-chloroisoquinoline (750 mg, 3.09 mmol) in N-methylbutylamine (7.0 mL) was heated at 65° C. in a sealed tube for 18 h. The reaction mixture was concentrated under reduced pressure. The residue was diluted with chloroform and washed with saturated sodium bicarbonate, dried (sodium sulfate), filtered, and concentrated under reduced pressure to yield a brown oil. Purification by flash column chromatography (silica, 3:1 hexanes/diethyl ether) provided 7-bromo-N-butyl-N-methylisoquinolin-1-amine (730 mg): ESI MS m/z 293 [M+H]+.

Step 2: To a −60° C. solution of 7-bromo-N-butyl-N-methylisoquinolin-1-amine (230 mg, 0.78 mmol) in diethyl ether was added sec-butyllithium (1.00 mL of a 1.3 M solution in cyclohexanes, 1.30 mmol). The solution was stirred at −60° C. for 20 min then excess dry ice ($CO_2$) was added and the reaction mixture was allowed to warm to room temperature. The reaction mixture was then acidified with 1 N hydrochloric acid and extracted with ethyl acetate. The aqueous phase was concentrated under reduced pressure to yield a yellow oil. Purification by flash column chromatography (silica, 50:30:15:5 ethyl acetate/chloroform/methanol/ammonium hydroxide) provided 1-[butyl(methyl)amino]isoquinoline-7-carboxylic acid (90 mg): ESI MS m/z 259 [M+H]+.

Step 3: To a solution of 1-[butyl(methyl)amino]isoquinoline-7-carboxylic acid (130 mg, 0.5 mmol) and N,N-diisopropylethylamine (525 μL, 3.0 mmol) in methylene chloride (6.25 mL) was added HBTU (190 mg, 0.5 mmol) and the reaction mixture was stirred for 0.5 h. (2R,3S)-3-Amino-4-(3,5-difluorophenyl)-1-[(3-ethylbenzyl)amino]butan-2-ol (174 mg, 0.42 mmol) was added in one portion and the reaction mixture was stirred at room temperature 18 h. The reaction mixture was diluted with methylene chloride and washed with saturated sodium bicarbonate, and saturated sodium chloride, dried (sodium sulfate), filtered, and concentrated under reduced pressure. Purification by flash chromatography (silica, 1-5% methanol in chloroform) gave 1-[butyl(methyl)amino]-N-{(1S,2R)-1-(3,5-difluorobenzyl)-3-[(3-ethylbenzyl)amino]-2-hydroxypropyl}isoquinoline-7-carboxamide (101 mg): mp 120-121° C.; ESI MS m/z 575 [M+H]+

Example SP-244

N-{(1S,2R)-1-(3,5-difluorobenzyl)-3-[(3-ethylbenzyl)amino]-2-hydroxypropyl}-1-[methyl(propyl)amino]isoquinoline-7-carboxamide was prepared in a manner similar to that outlined above for 1-[butyl(methyl)amino]-N-{(1S,2R)-1(3,5-difluorobenzyl)-3-[(3-ethylbenzyl)amino]-2hydroxypropyl}isoquinoline-7-carboxamide. ESI MS m/z 561 [M+H]+

Example SP-245

1-butyl-N-{(1S,2R)-1(3,5-difluorobenzyl)-3-[(3-ethylbenzyl)amino]-2-hydroxypropyl}isoquinoline-7-carboxamide

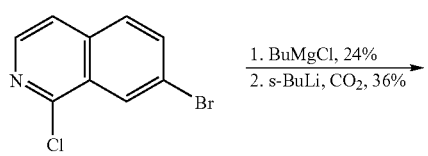

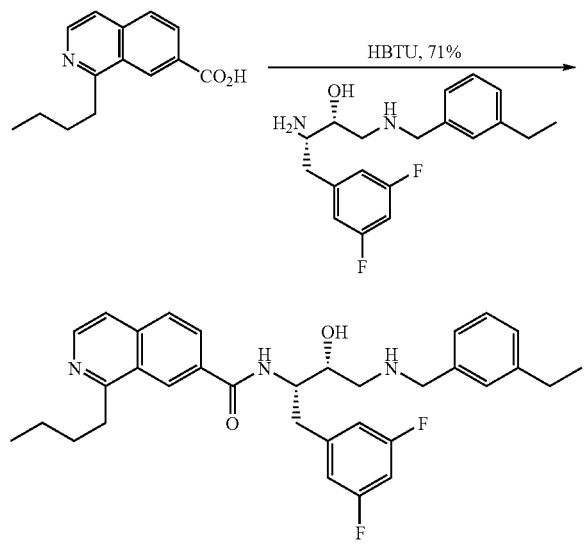

Step 1: To a refluxing solution of 7-bromo-1-chloroisoquinoline (4.85 g, 23.28 mmol) in diethyl ether (75 mL) was added butylmagnesium chloride (17.8 mL, 2.0 M ether, 35.6 mmol) and the reaction maintained at reflux for 2 h. The reaction mixture was cooled to room temperature, carefully diluted with an equal volume of ethyl acetate, washed with saturated sodium bicarbonate, water, and saturated sodium chloride, dried (sodium sulfate), filtered, and concentrated under reduced pressure to give an brown oil. Purification by flash column chromatography (silica, 1-10% ether/hexanes) gave the desired 7-bromo-1-butylisoquinoline (1.50 g): ESI MS m/z 264 [M+H]$^+$.

Step 2: To a –60° C. solution of 7-bromo-1-butylisoquinoline prepared in step 1 (940 mg, 3.55 mmol) in diethyl ether (15 mL) was added sec-butyl lithium (3.0 nL, 1.3 M cyclohexanes, 3.90 mmol) to yield a dark green solution. The reaction mixture was stirred at –60° C. for an additional 15 minutes at which time carbon dioxide gas was bubbled through the solution for 20 minutes with the aid of a gas dispersion tube. The resulting solution was then allowed to warm to room temperature and concentrated under reduced pressure to yield a pink solid. The residue was partitioned between ethyl acetate and water and then acidified to pH 7 with 1 N hydrochloric acid. The aqueous phase was extracted again with ethyl acetate and the combined organic phases were washed with saturated sodium chloride, dried (sodium sulfate), filtered, and concentrated to yield 1-butylisoquinoline-7-carboxylic acid (299 mg). ESI MS m/z 230 [M+H]$^+$.

Step 3: To a solution of 1-butylisoquinoline-7-carboxylic acid (79 mg, 0.26 mmol) and N,N-diisopropylethylamine (150 μL, 0.86 mmol) in methylene chloride (1.8 mL) was added HBTU (100 mg, 0.264 mmol) and the reaction mixture stirred for 0.5 h. To this was added a solution of (2R,3S)-3-amino-4-(3,5-difluorophenyl)-1-[(3-ethylbenzyl)amino]butan-2-ol (107 mg, 0.264 mmol) in methylene chloride (1.8 mL) containing N,N-diisopropylethylamine (150 μL, 0.86 mmol). The reaction mixture was then stirred at room temperature overnight. The reaction mixture was diluted with methylene chloride, washed with saturated sodium bicarbonate, and saturated sodium chloride. The organic layer was then dried (sodium sulfate), filtered, and concentrated under reduced pressure. Purification by flash column chromatography (silica, 93:7 chloroform/methanol) gave 1-butyl-N-{(1S,2R)-1-(3,5-difluorobenzyl)-3-[(3-ethylbenzyl)amino]-2-hydroxypropyl}isoquinoline-7-carboxamide (103 mg): mp 109-110° C.; ESI MS m/z 546 [M+H]$^+$.

Example SP-246

1-butyl-N-{(1S,2R)-1-(3,5-difluorobenzyl)-3-[(3-ethylbenzyl)amino]-2-hydroxypropyl}-1,2,3,4-tetrahydroisoquinoline-7-carboxamide

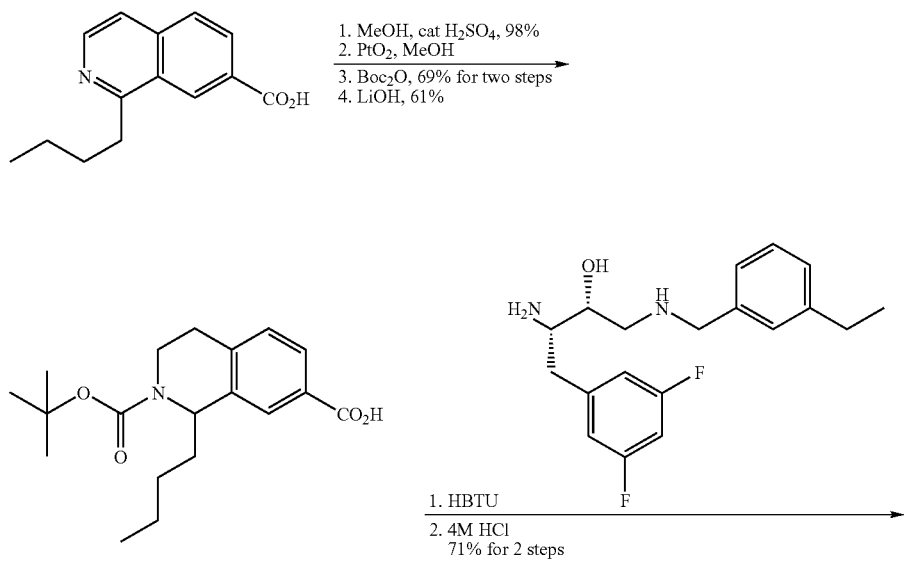

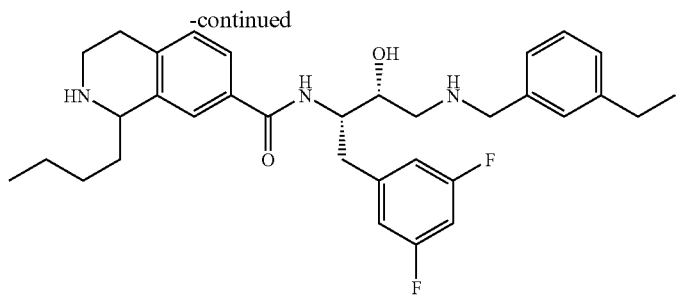

Step 1: A solution of 1-butylisoquinoline-7-carboxylic acid (325 mg, 1.41 mmol) in methanol (25 mL) containing concentrated sulfuric acid (800 µL) was refluxed overnight. The reaction mixture was then concentrated under reduced pressure, diluted with methylene chloride, washed with water, and saturated sodium chloride. The organic layer was then dried (sodium sulfate), filtered, and concentrated to yield methyl 1-butylisoquinoline-7-carboxylate (350 mg): ESI MS m/z 244 [M+H]$^+$;

Step 2: To a solution of methyl 1-butylisoquinoline-7-carboxylate prepared in step 1 (350 mg, 1.44 mmol) in methanol (6.0 mL) was added platinum(IV) oxide (35 mg) and the reaction mixture stirred under one atmosphere of hydrogen at room temperature overnight. The reaction mixture was concentrated under reduced pressure and redissolved in methylene chloride (15 mL). To this solution was added di-tert-butyl dicarbonate (350 mg, 1.6 mmol), triethylamine (500 µL, 3.11 mcol), 4-dimethylaminopyridine (20 mg, 0.16 mmol), and the reaction mixture stirred at room temperature for 4 h. The reaction mixture was then diluted with methylene chloride, washed with saturated sodium bicarbonate, water, and saturated sodium chloride. The organic layer was then dried (sodium sulfate), filtered, and concentrated under reduced pressure to yield a colorless oil. Purification by flash column chromatography (silica, 85:15 hexanes/ethyl acetate) yielded 2-tert-butyl 7-methyl 1-butyl-3,4-dihydroisoquinoline-2,7 (1H)-dicarboxylate (347 mg)l: ESI MS m/z 248 [M+H]$^+$.

Step 3: To a solution of 2-tert-butyl 7-methyl 1-butyl-3,4-dihydroisoquinoline-2,7(1H)-dicarboxylate prepared in step 2 (347 mg, 1.0 mmol) in 2:1:1 dioxane/methanol/water (6.6 mL) was added lithium hydroxide monohydrate (125 mg, 3.0 mmol) and the reaction mixture stirred 24 h at room temperature. The reaction mixture was concentrated under reduced pressure and the solid residue partitioned between ethyl acetate and water. The aqueous phase was acidified with 1 N hydrochloric acid to pH 1 and extracted several times with 3:1 chloroform/2-propanol. The combined organic phases were washed with water and saturated sodium chloride, dried (sodium sulfate), filtered, and concentrated under reduced pressure to provide 2-(tert-butoxycarbonyl)-1-butyl-1,2,3,4-tetrahydroisoquinoline-7-carboxylic acid (205 mg). ESI MS m/z 332 [M–H]$^-$.

Step 4: To a solution of 2-(tert-butoxycarbonyl)-1-butyl-1,2,3,4-tetrahydroisoquinoline-7-carboxylic acid (205 mg, 0.61 mmol) and N,N-diisopropylethylamine (150 µL, 0.86 mmol) in methylene chloride (4.0 mL) was added HBTU (233 mg, 0.61 mmol) and the reaction mixture stirred for 0.5 h. To this was added a solution of (2R,3S)-3-amino-4-(3,5-difluorophenyl)-1-[(3-ethylbenzyl)amino]butan-2-ol (250 mg, 0.61 mmol) in methylene chloride (4.0 mL) containing N,N-diisopropylethylamine (150 µL, 0.86 mmol). The reaction mixture was then stirred at room temperature overnight. The reaction mixture was diluted with methylene chloride, washed with saturated sodium bicarbonate, and saturated sodium chloride. The organic layer was then dried (sodium sulfate), filtered, and concentrated under reduced pressure. Purification by flash column chromatography (silica, 95:5 chloroform/methanol) gave the desired amide product. The amide was then dissolved in dioxane (5.0 mL) to which was added hydrochloric acid (20 mL, 4.0 M dioxanes, 80 mmol) and the reaction mixture stirred overnight. The reaction mixture was then concentrated to dryness and purified by flash column chromatography (silica, 90:6:3:1 ethyl acetate/chloroform/methanol/ammonium hydroxide) to yield a colorless oil. The oil was partitioned between 3:1 chloroform/2-propanol, washed with water, and saturated sodium chloride. The organic layer was then dried (sodium sulfate), filtered, and concentrated to yield a white solid. The solid was dried under high vacuum at 45° C. in the presence of $P_2O_5$ to yield 1-butyl-N-{(1S,2R)-1-(3,5-difluorobenzyl)-3-[(3-ethylbenzyl)amino]-2-hydroxypropyl}-1,2,3,4-tetrahydroisoquinoline-7-carboxamide(140 mg) characterized as a mixture of diastereomers: mp 121-124° C.; ESI MS m/z 550 [M+H]$^+$.

Example SP-247

N-{(1S,2R)-1-(3,5-difluorobenzyl)-3-[(3-ethylbenzyl)amino]-2-hydroxypropyl}-3-{[(2S)-2-ethylpyrrolidin-1-yl]carbonyl}-5-methylbenzamide hydrochloride

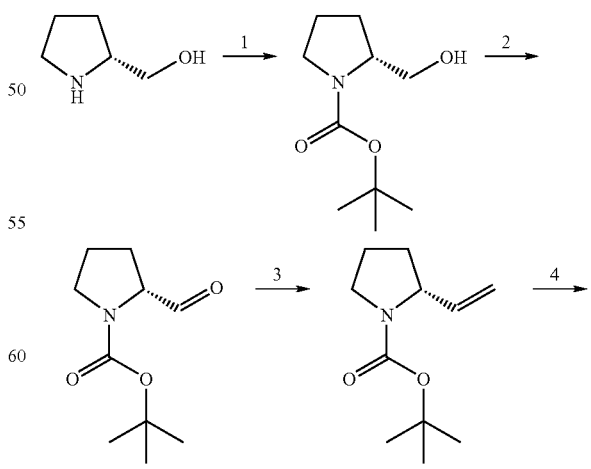

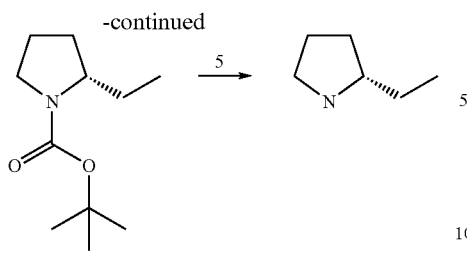

Step 1: Di-tert-butyl-dicarbonate (10.8 g, 49 mmol) was added to an ice-cold solution of R-pyrrolidinemethanol (5.0 g, 49 mmol) and triethylamine (7.6 mL, 55 mmol) in 125 mL of $CH_2Cl_2$. The resultant solution was warmed to ambient temperature and stirred overnight. The reaction solution was then concentrated, diluted with EtOAc, washed 2× with 1 M $KH_2PO_4$ and 2× with brine, dried over $Na_2SO_4$, filtered, and concentrated to afford tert-butyl (2R)-2-(hydroxymethyl) pyrrolidine-1-carboxylate (9.9 g).

Step 2: Oxalyl chloride (9.0 mL, 100 mmol) was added to a solution of DMSO (10.5 mL, 150 mmol) in 80 mL of $CH_2Cl_2$ at −78° C., under a nitrogen atmosphere. The solution was stirred for 20 min at −78° C., tert-butyl (2R)-2-(hydroxymethyl)pyrrolidine-1-carboxylate (9.9 g, 49 mmol) was added, and the resultant solution stirred at −78° C. for 20 min. Triethylamine (28 mL, 200 mmol) was added to the reaction solution, the dry ice-acetone bath was removed, and the resultant solution was allowed to stir for two hours, slowly warming to ambient temperature. The reaction solution was quenched with brine, the phases were separated, and the organic phase was washed with 1 M $KH_2PO_4$ and saturated $NaHCO_3$. The organic solution was then dried over $Na_2SO_4$, filtered, and concentrated to an orange oil. This oil was then dissolved in heptane, filtered through a plug of silica gel eluting with heptane, and the filtrate was concentrated to yield tert-butyl (2R)-2-formylpyrrolidine-1-carboxylate (7.87 g).

Step 3: n-Butyl lithium (1.6 M in hexanes)(27 mL, 43 mmol) was added to ice-cold hexamethyldisilazane (9.2 mL, 44 mmol) under a nitrogen atmosphere. The solution was stirred for 10 min and was then added to a suspension of methyl(triphenylphosphonium)bromide (15.5 g, 43 mmol) in 100 mL of THF at ambient temperature. After stirring for 1 h, the mixture was cooled to −78° C. and a solution of tert-butyl (2R)-2-formylpyrrolidine-1-carboxylate (7.9 g, 40 mmol) in 50 mL of THF was added. The cold bath was removed and the mixture stirred overnight at ambient temperature. The reaction mixture was then quenched with saturated $NH_4Cl$, the phases were separated, and the organic phase was washed with saturated $NH_4Cl$, brine, dried over $Na_2SO_4$, filtered, and concentrated to give an orange oil. The oil was purified on a Biotage 40M column eluting with heptane to give tert-butyl (2R)-2-vinylpyrrolidine-1-carboxylate (5.0 g).

Step 4: To a suspension of palladium (II) hydroxide on activated carbon (20% by wt, 1.2 g) in 10 mL of ethanol was added tert-butyl (2R)-2-vinylpyrrolidine-1-carboxylate (2.0 g, 10 mmol) as a solution in 15 mL of ethanol and the mixture was placed under 12 psi of $H_2$ on a parr hydrogenator overnight. The resultant mixture was then filtered and concentrated to give tert-butyl (2S)-2-ethylpyrrolidine-1-carboxylate (1.5 g).

Step 5: To a solution of tert-butyl (2S)-2-ethylpyrrolidine-1-carboxylate (1.0 g, 5.0 mmol) in 10 mL of dioxane was added 8 mL of 6N HCl and the resultant solution stirred overnight at ambient temperature. The reaction solution was then concentrated, turned basic with solid KOH, and extracted with EtOAc. The combined organic extracts were dried over $Na_2SO_4$, filtered and concentrated to give (2S)-2-ethylpyrrolidine hydrochloride (0.30 g).

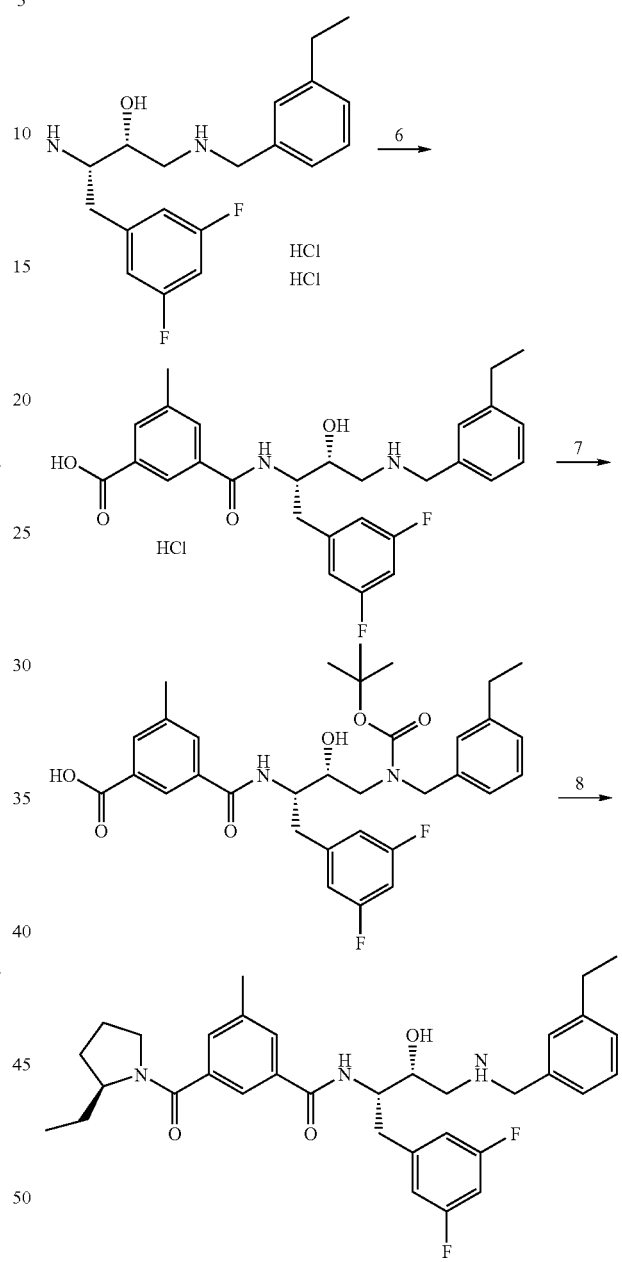

Step 6: A solution of 3-(methoxycarbonyl)-5-methylbenzoic acid (0.48 g, 2.5 mmol), HATU (1.0 g, 2.6 mmol), and HOAt (0.37 g, 2.7 mmol) in 10 mL of dry DMF was stirred for an hour over ice, under a nitrogen atmosphere prior to the addition of (2R,3S)-3-amino-4-(3,5-difluorophenyl)-1-[(3-ethylbenzyl)amino]butan-2-ol dihydrochloride (1.0 g, 2.5 mmol) and DIPEA (1.8 mL, 10 mmol). The solution was stirred overnight at ambient temperature. The reaction solution was then quenched with 1 M HCl, diluted with EtOAc, and the phases were separated. The organic phase was washed with 1 M HCl, the combined acid washings were back-extracted with EtOAc, and the organic phases combined. The combined organic phases were then washed with saturated NaHCO$_3$, brine and dried over Na$_2$SO$_4$ The mixture was filtered and concentrated to give the coupled product as an orange oil. This oil was dissolved in 35 mL of MeOH and solid LiOH.H$_2$O (0.6 g, 14 mmol) was added with 2 mL of water. The mixture was stirred overnight at ambient temperature. The solution was concentrated, diluted with water, neutralized with 1 M HCl, and concentrated. The resulting oily residue was purified on a Biotage 40S column eluting with 5% MeOH in CH$_2$Cl$_2$ to give a colorless oil. This was dissolved in 10 mL of MeOH and 3 mL of 1 M HCl in ether was added. The solution was concentrated and the residue triturated with heptane to give 3-[({(1S,2R)-1-(3,5-difluorobenzyl)-3-[(3-ethylbenzyl)amino]-2-hydroxypropyl}amino)carbonyl]-5-methylbenzoic acid hydrochloride (0.65 g).

Step 7: To a solution of 3-[({(1S,2R)-1-(3,5-difluorobenzyl)-3-[(3-ethylbenzyl)amino]-2-hydroxypropyl}amino)carbonyl]-5-methylbenzoic acid hydrochloride (0.50 g, 0.94 mmol) and di-tert-butyldicarbonate (0.20 g, 0.92 mmol) in 10 mL of methanol and 10 mL of CH$_2$Cl$_2$ was added triethylamine (0.40 mL, 2.9 mmol). The solution was stirred for 2.5 hours at ambient temperature, at which time it was concentrated, partitioned between EtOAc and 1 M KH$_2$PO$_4$, and the phases were separated. The organic phase was washed with M KH$_2$PO$_4$, dried over Na$_2$SO$_4$, filtered, concentrated, and triturated with heptane to give 3-({[(1S,2R)-3-[(tert-butoxycarbonyl)(3-ethylbenzyl)amino]-1-(3,5-difluorobenzyl)-2-hydroxypropyl]amino}carbonyl)-5-methylbenzoic acid (0.50 g).

Step 8: A solution of 3-({[(1S,2R)-3-[(tert-butoxycarbonyl)(3-ethylbenzyl)amino]-1-(3,5-difluorobenzyl)-2-hydroxypropyl]amino}carbonyl)-5-methylbenzoic acid (0.30 g, 0.50 mmol), HATU (0.19 g, 0.50 mmol) and HOAt (0.07 g, 0.51 mmol) in 5 mL of dry DMF under a nitrogen atmosphere was stirred for 15 minutes. A solution of (2S)-2-ethylpyrrolidine hydrochloride (0.05 g, 0.50 mmol) and DIPEA (0.35 mL, 2.0 mmol) in 5 mL of DMF was added. The solution was stirred overnight at ambient temperature. It was then quenched with 1 M HCl, diluted with EtOAc, and the phases were separated. The organic phase was washed with 1 M HCl, saturated NaHCO$_3$, dried over Na$_2$SO$_4$, filtered, and concentrated to give an orange-brown oil. This oil was purified on a Biotage 40S column eluting with 200 mL of CH$_2$Cl$_2$, then 3% MeOH in CH$_2$Cl$_2$. The yellow oil obtained was dissolved in 4 mL of CH$_2$Cl$_2$ and 4 mL of TFA was added. After stirring for two hours at ambient temperature the reaction solution was concentrated and the residue was purified by reverse phase prep hplc using a 1-inch Kromasil c18 column to give the product as the formic acid salt. This was then converted to the HCl salt by the addition of 2 mL of 1 M HCl in ether. Upon concentration and trituration with heptane N-{(1S,2R)-1-(3,5-difluorobenzyl)-3-[(3-ethylbenzyl)amino]-2-hydroxypropyl}-3-{[(2S)-2-ethylpyrrolidin-1-yl]carbonyl}-5-methylbenzamide hydrochloride was obtained (0.010 g). MS m/z 579.0 [M+H].

Example SP-248

The following compounds,
3-{[(2S)-2-butylpyrrolidin-1-yl]carbonyl}-N-{(1S,2R)-1-(3,5-difluorobenzyl)-3-[(3-ethylbenzyl)amino]-2-hydroxypropyl}-5-methylbenzamide, MS m/z 606.4 [M+H];
N-{(1S,2R)-1-(3,5-difluorobenzyl)-3-[(3-ethylbenzyl)amino]-2-hydroxypropyl}-3-methyl-5-{[(2S)-2-propylpyrrolidin-1-yl]carbonyl}benzamide formic acid salt, MS m/z 638.6 [M+H];
N-{(1S,2R)-1-(3,5-difluorobenzyl)-3-[(3-ethylbenzyl)amino]-2-hydroxypropyl}-3-{[(2R)-2-(2-methoxyethyl)pyrrolidin-1-yl]carbonyl}-5-methylbenzamide, MS m/z 608.6[M+H]; and
N-{(1S,2R)-1-(3,5-difluorobenzyl)-3-[(3-ethylbenzyl)amino]-2-hydroxypropyl}-3-{[(2S)-2-ethylpyrrolidin-1-yl]carbonyl}-5-methylbenzamide hydrochloride; were prepared in a manner similar to that outlined above for Example SP-247.

Example SP-249

The following compounds;
N-{(1S,2R)-1-(3,5-difluorobenzyl)-2-hydroxy-3-[(3-isopropylbenzyl)amino]propyl}-3-{[(2R)-2-(methoxymethyl)pyrrolidin-1-yl]carbonyl}-5-methylbenzamide hydrochloride, MS m/z 608.3 [M+H];
N-{(1S,2R)-1-(3,5-difluorobenzyl)-3-[(3-ethynylbenzyl)amino]-2-hydroxypropyl}-3-{[(2R)-2-(methoxymethyl)pyrrolidin-1-yl]carbonyl}-5-methylbenzamide hydrochloride, MS m/z 590.3 [M+H]; and
N-((1S,2R)-1-(3,5-difluorobenzyl)-3-{[1-(3-ethylphenyl)cyclopropyl]amino}-2-hydroxypropyl)-3-{[(2R)-2-(methoxymethyl)pyrrolidin-1-yl]carbonyl}-5-methylbenzamide hydrochloride, MS m/z 620.3 [M+H]; were also prepared using the methods disclosed herein.

Example SP-250

Preparation of: N-[(1S,2R)-3-{[1-(3-bromophenyl)cyclopropyl]amino}-1-(3,5-difluorobenzyl)-2-hydroxypropyl]acetamide Step 1: A stirred solution of N-{(1S)-2-(3,5-difluorophenyl)-1-[(2S)-oxiran-2-yl]ethyl}acetamide (4.96 g) and 1-(3-bromophenyl)cyclopropylamine (8.6 g) in 60 mL of i-PrOH was heated to 75° C. for 3 h. The cooled solution was evaporated and the residue re-dissolved in ethyl acetate (200 mL). The organic layer was washed with 10% aqueous HCl (25 mL×2). The aqueous washings were extracted once with EtOAc (75 mL) and the combined organic layers washed with a saturated solution of NaCl (100 mL). The organic layers were then dried over Na$_2$SO$_4$ and evaporated to yield a residue that was purified by column chromatography to give 5.0 g of tert-butyl (1S,2R)-3-{[1-(3-bromophenyl)cyclopropyl]amino}-1-(3,5-difluorobenzyl)-2-hydroxypropylcarbamate.

Step 2: To a suspension of tert-butyl (1S,2R)-3-{[1-(3-bromophenyl)cyclopropyl]amino}-1-(3,5-difluorobenzyl)-2-hydroxypropylcarbamate (1.3 g) in 5.0 mL of dichloromethane was added 5.0 mL of trifluoroacetic acid at 23° C. After stirring for 1 h, 10.0 mL of toluene was added and the solution evaporated. The resulting residue was re-dissolved in toluene and the solution evaporated. This procedure was repeated once more. After drying under high vacuum for 2 h, the residue was suspended in dichloromethane (10.0 mL) and triethylamine (0.5 g) and acetylimidazole (0.3 g) were added. The solution was stirred for 4 h and concentrated under reduced pressure. The residue was purified by column chromatography to yield 0.90 g of the title compound. ES+ found (M+H$^+$):455.

Example SP-251

Preparation of N-((1S,2R)-1-(3,5-difluorobenzyl)-2-hydroxy-3-{[1-(3'-methoxy-1,1'-biphenyl-3-yl)cyclopropyl]amino}propyl)acetamide
To a solution of N-[(1S,2R)-3-{[1-(3-bromophenyl)cyclopropyl]amino}-1-(3,5-difluorobenzyl)-2-hydroxypropyl]acetamide (0.030 g) in DMF (0.75 mL) was added 3-methoxyphenylboronic acid (0.030 g), $Cs_2CO_3$ (0.085 g) and $Pd(Ph_3P)_4$. The mixture was heated for 12 h at 90° C. The cooled solution was diluted with EtOAc (15 mL) and washed with brine (10 mL×2). The organic layer was dried over $Na_2SO_4$, filtered, and evaporated under reduced pressure. The resulting residue was purified by column chromatography to give 0.010 g of the title compound. ES+ found $(M+H^+)$:481.

Example SP-251

N-[(1S,2R)-1-(3,5-difluorobenzyl)-2-hydroxy-3-({1-[3'-(hydroxymethyl)-1,1'-biphenyl-3-yl]cyclopropyl}amino)propyl]acetamide, was prepared by the method of N-((1S,2R)-1-(3,5-difluorobenzyl)-2-hydroxy-3-{[1-(3'-methoxy-1,1'-biphenyl-3-yl)cyclopropyl]amino}propyl)acetamide step 1, using 3-(hydroxymethyl)phenylboronic acid (0.036 g) to give 0.008 g of the title compound. ES+ found $(M+H^+)$: 481.

Example SP-252A

N-[(1S,2R)-3-{[1-(2'-acetyl-1,1'-biphenyl-3-yl)cyclopropyl]amino}-1-(3,5-difluorobenzyl)-2-hydroxypropyl]acetamide was prepared by the method of N-((1S,2R)-1-(3,5-difluorobenzyl)-2-hydroxy-3-{[1-(3'-methoxy-1,1'-biphenyl-3-yl)cyclopropyl]amino}propyl)acetamide step 1, using 2-acetylphenylboronic acid (0.032 g) to give 0.012 g of the title compound. ES+ found $(M+H^+)$:493.

Example SP-252B

N-[(1S,2R)-1-(3,5-difluorobenzyl)-3-({1-[3-(5-formylthien-2-yl)phenyl]cyclopropyl}amino)-2-hydroxypropyl]acetamide was prepared by the method of N-((1S,2R)-1-(3,5-difluorobenzyl)-2-hydroxy-3-{[1-(3'-methoxy-1,1'-biphenyl-3-yl)cyclopropyl]amino}propyl)acetamide step 1, using 5-formylthien-2-ylboronic acid (0.030 g) to give 0.005 g of the title compound. ES+ found $(M+H^+)$:484.

Examples 2453A to 2453D

Example SP-253A $N^1$-{(1S,2R)-1-(cyclopentylmethyl)-3-[(3-ethylbenzyl)amino]-2-hydroxypropyl}-5-methyl-$N^3$,$N^3$-dipropylisophthalamide hydrochloride;

Example SP-253B $N^1$-[(1S,2R)-3-[(3-bromobenzyl)amino]-1-(cyclopentylmethyl)-2-hydroxypropyl]-5-methyl-$N^3$,$N^3$-dipropylisophthalamide hydrochloride;

Example SP-253C $N^1$-{(1S,2R)-1-(cyclohexylmethyl)-3-[(3-ethylbenzyl)amino]-2-hydroxypropyl}-5-methyl-$N^3$,$N^3$-dipropylisophthalamide hydrochloride;

Example SP-253D $N^1$-[(1S,2R)-3-[(3-bromobenzyl)amino]-1-(cyclohexylmethyl)-2-hydroxypropyl]-5-methyl-$N^3$,$N^3$-dipropylisophthalamide hydrochloride;

Example SP-254A

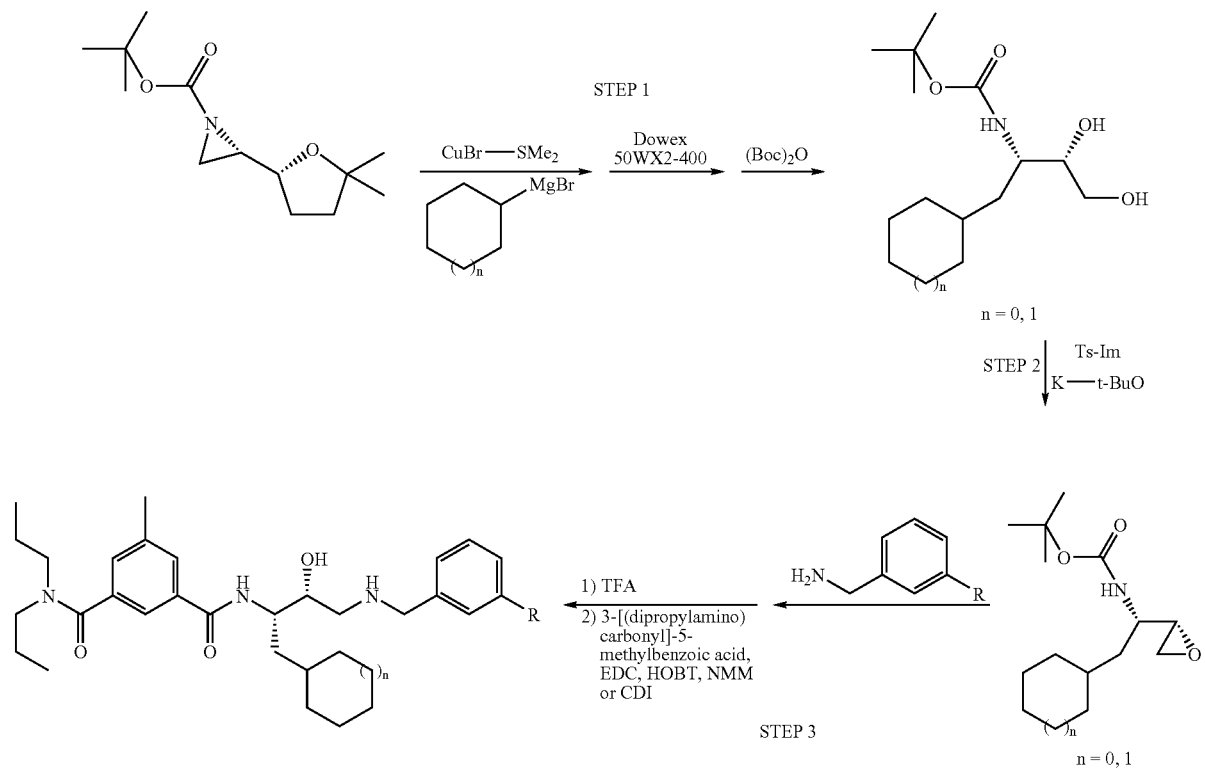

N$^1$-{(1S,2R)-1-(cyclopentylmethyl)-3-[(3-ethylbenzyl)amino]-2-hydroxypropyl}-5-methyl-N$^3$,N$^3$-dipropylisophthalamide hydrochloride (EXAMPLE SP-254) and N$^1$-[(1S,2R)-3-[(3-bromobenzyl)amino]-1-(cyclopentylmethyl)-2-hydroxypropyl]-5-methyl-N$^3$,N$^3$-dipropylisophthalamide hydrochloride (EXAMPLE SP-255)

Step 1: Cyclopentyl magnesium bromide (8 mL of 2M ethereal solution) was added to cuprous bromide/dimethylsulfide complex (0.33 g, 1.6 mmol) in 10 mL of dry THF cooled to −25° C. under nitrogen. After 20 min, a solution of tert-butyl (2R)-2-[(4S)-2,2-dimethyl-1,3-dioxolan-4-yl]aziridine-1-carboxylate (1.95 g, 8 mmol) in 4 mL of dry THF was introduced. The mixture was allowed to warm to ambient temperature overnight. It was quenched with saturated aqueous NH$_4$Cl and extracted with ethyl ether. The organic phase was washed with aqueous saturated NH$_4$Cl, 1 N NaHCO$_3$, and brine. It was dried over anhydrous Na$_2$SO$_4$ and concentrated to 2.38 g of a solid. This material was dissolved in 70 mL of methanol, 12 g of Dowex 50WX2-400 was added, and the mixture was refluxed for 2 h. The mixture was filtered, washing with methanol and dichloromethane. A clean receiver was attached, and the resin was washed with 100 mL of 1:1 concentrated NH$_4$OH:ethanol. The filtrate was concentrated to 1.16 g of tan crystals. The crystals were dissolved in 30 mL of dry THF, and 1.5 g (6.9 mmol) of di-t-butyldicarbonate was introduced. The mixture was stirred under nitrogen overnight. It was concentrated, extracted with ether and the ether was washed with several portions of water and brine. Drying over Na$_2$SO$_4$ and concentration afforded 1.8 g (6.7 mmol, 84% from tert-butyl (2R)-2-[(4S)-2,2-dimethyl-1,3-dioxolan-4-yl]aziridine-1-carboxylate) of tert-butyl (1S,2S)-1-[cyclopentylmethy]-2,3-dihydroxypropylcarbamate: $^1$H NMR (CDCl$_3$) δ 4.5 (d, 1H, NH), 3.7 (m, 1H), 3.6-3.49 (m, 2H), 3.36 (m, 1 H), 3.26 (t, 1H, OH), 2.76 (d, 1H, OH), 1.45 (s, 9H), 1.88-1.36 (m, 9H), 1.17-1.08 (m, 2H).

Step 2: Toluenesulfonyl imidazole (Ts-Im, 2.22 g, 10 mmol) was added to tert-butyl (1S,2S)-1-[cyclopentylmethyl]-2,3-dihydroxypropylcarbamate (1.8 g, 6.7 mmol) in 15 mL of dry THF under nitrogen, cooled in an ice bath. To this was added 13.4 mL (13.4 mmol) of a 1M solution of potassium-t-butoxide in THF over 8 min. After 5 min, the ice bath was removed and the orange mixture was stirred for 3 h. It was quenched with 1 N KH$_2$PO$_4$ and diluted with ether. The organic phase was washed with 1 N KH$_2$PO$_4$, water, and brine. The solution was dried over Na$_2$SO$_4$, concentrated, and chromatographed over silica gel, eluting with 5% dichloromethane, 15% ethyl acetate, and 80% heptane. Fraction 4 afforded 900 mg of a 2:1 mixture of tert-butyl (1S)-2-(cyclopentyl)-1-[(2S)-oxiran-2-yl]ethylcarbamate and a side product. Fraction 5 afforded 230 mg of tert-butyl (1S)-2-(cyclopentyl)-1-[(2S)-oxiran-2-yl]ethylcarbamate: $^1$H NMR (CDCl$_3$) δ 4.56 (d, 1H), 3.45 (m, 1H), 2.85 (m, 1H), 2.75 (m, 2H), 1.91 (m, 1H), 1.8 (m, 2H), 1.6-1.4 (m, 6H), 1.44 (s, 9H), 1.13-1.07 (m, 2H).

Example SP-254B

N$^1$-{(1S,2R)-1-(cyclopentylmethyl)-3-[(3-ethylbenzyl)amino]-2-hydroxypropyl}-5-methyl-N$^3$,N$^3$-dipropylisophthalamide hydrochloride Step 3: To tert-butyl (1S)-2-(cyclopentyl)-1-[(2S)-oxiran-2-yl]ethylcarbamate (230 mg, 0.9 mmol) was added 260 mg (1.9 mmol) of m-ethylbenzylamine in 5 mL of isopropanol. The mixture was refluxed for 1.5 h under nitrogen, the solvent was removed in vacuo, and the residue was dissolved in ethyl acetate. It was washed three times with small portions of 10% HCl, and the aqueous phases were back-extracted with ethyl acetate. The combined organic phases were washed with 1 N NaHCO$_3$ and brine, dried over Na$_2$SO$_4$, and concentrated. The residue was partially purified by forming the HCl salt, triturating with pentane, and then neutralizing to the free base (290 mg, 0.74 mmol). To this was added 2 mL of trifluoroacetic acid (TFA) and 2 mL of dichloromethane, and the mixture was stirred under nitrogen for 30 min. It was concentrated to an oil which was dissolved in 2 mL of dry THF and neutralized with 0.2 mL of 4-methyl morpholine. To this mixture was added a solution of 3-[(dipropylamino)carbonyl]-5-methylbenzoic acid (0.2 g, 0.76 mmol) and carbonyldiimidazole (CDI, 0.13 g, 0.8 mmol) in 3 mL of dry THF, which had been stirring together for 35 min. The reaction was stirred under nitrogen overnight. To the mixture was added 1 N KH$_2$PO$_4$ and ethyl acetate. The organic phase was washed with 1 N KH$_2$PO$_4$, 1 N NaHCO$_3$ (2×) and brine, dried over Na$_2$SO$_4$, and concentrated. Chromatography over silica gel, eluting with 6% methanol (containing 1% NH$_4$OH) in dichloromethane afforded 109 mg (0.19 mmol) of N$^1$-{(1S,2R)-1-(cyclopentylmethyl)-3-[(3-ethylbenzyl)amino]-2-hydroxypropyl}-5-methyl-N$^3$,N$^3$-dipropylisophthalamide hydrochloride (EXAMPLE SP-254) after formation of the salt with ethereal HCl: CI MS m/z 536 [M+H]$^+$.

Example SP-255

N$^1$-[(1S,2R)-3-[(3-bromobenzyl)amino]-1-(cyclopentylmethyl)-2-hydroxypropyl]-5-methyl-N$^3$,N$^3$-dipropylisophthalamide hydrochloride Step 3: The fraction containing tert-butyl (1S)-2-(cyclopentyl)-1-[(2S)-oxiran-2-yl]ethylcarbamate (ca. 2 mmol) and a side product, described in the above example, was reacted with m-bromobenzylamine (10 mmol) in 12 mL of isopropanol at reflux for 3 h. The solvent was removed and the residue was dissolved-in ethyl acetate. This was washed with several portions of 10% HCl, 1 N NaHCO$_3$, and brine, dried (Na$_2$SO$_4$), concentrated. Chromatography on silica gel, eluting with dichloromethane, then up to 2% of methanol (containing 1% NH$_4$OH) in dichloromethane afforded 523 mg (1.19 mmol, 60% based on epoxide) of the oily addition product. This material (0.31 g, 0.7 mmol) was dissolved in 2 mL of dichloromethane, and 1 mL of TFA was added. After 1 h it was concentrated, dissolved in ethyl acetate, neutralized with 1 N NaHCO$_3$, washed with brine, and concentrated to the free base. To this was added 4 mL of dry THF and a pre-mixed (for 2 h) solution of 3-[(dipropylamino)carbonyl]-5-methylbenzoic acid (190 mg, 0.72 mmol) and CDI (120 mg, 0.74 mmol) in 3 mL of dry THF. After 2 days the reaction was quenched with 1 N KH$_2$PO$_4$ and dissolved in ethyl acetate.

The organic phase was washed with 1 N KH$_2$PO$_4$, 1 N NaHCO$_3$ (2×) and brine, dried over Na$_2$SO$_4$, and concentrated. Chromatography over silica gel, eluting with 5% methanol (containing 1% NH$_4$OH) in dichloromethane afforded 184 mg (0.29 mmol) of N$^1$-[(1S,2R)-3-[(3-bromobenzyl)amino]-1-(cyclopentylmethyl)-2-hydroxypropyl]-5-methyl-N$^3$, N$^3$-dipropylisophthalamide hydrochloride Example SP-255 as a white solid after formation of the salt with ethereal HCl: CI MS m/z 586 [M+H]$^+$.

N$^1$-{(1S,2R)-1-(cyclohexylmethyl)-3-[(3-ethylbenzyl)amino]-2-hydroxypropyl}-5-methyl-N$^3$,N$^3$-dipropylisophthalamide hydrochloride (EXAMPLE SP-256) and N$^1$-[(1S,2R)-3-[(3-bromobenzyl)amino]-1-(cyclohexylmethyl)-2-hydroxypropyl]-5-methyl-N$^3$,N$^3$-dipropylisophthalamide hydrochloride (EXAMPLE SP-257)

Step 1: Cyclohexyl magnesium bromide was prepared by adding cyclohexyl bromide (2.46 mL, 20 mmol) to magnesium turnings (0.97 g, 40 mmol) in dry THF (20 mL) and refluxing for 1.5 h. Following the procedures described in step 1 for the previous EXAMPLE S-tert-butyl (1S,2S)-1-

[cyclohexylmethy]-2,3-dihydroxypropylcarbamate was obtained as 1.66 g (5.8 mmol, 70% from tert-butyl (2R)-2-[(4S)-2,2-dimethyl-1,3-dioxolan-4-yl]aziridine-1-carboxylate) of a slightly yellow oil which solidified on standing: $^1$H NMR (CDCl$_3$) δ 4.43 (d, 1H, NH), 3.69 (m, 1H), 3.59 (m, 2H), 3.32 (m, 1H), 3.24 (t, 1H, OH), 2.70 (d, 1H, OH), 1.45 (s, 9H), 1.8-1.13 (m, 11H), 1.01 (m, 1H), 0.87 (m, 1H).

Step 2: tert-Butyl (1S,2S)-1-[cyclohexylmethyl]-2,3-dihydroxypropylcarbamate (1.6 g, 5.5 mmol) was reacted with Ts-Im (1.5 g, 6.75 mmol) and potassium t-butoxide (11 mL of a 1 M solution in THF) in 20 mL of dry THF according to the procedure described in step 2 for the preceding example. Chromatography on silica gel, eluting with 5% dichloromethane and 5%, increasing to 15% ethyl acetate in heptane afforded 456 mg 1.7 mmol, of tert-butyl (1S)-2-(cyclohexyl)-1-[(2S)-oxiran-2-yl]ethylcarbamate: $^1$H NMR (CDCl$_3$) δ 4.41 (m, 1H), 3.55 (m, 1H), 2.84 (m, 1H), 2.75 (m, 2H), 1.8-1.6 (m, 4H), 1.45 (s, 9H), 1.4-1.1 (m, 7H), 0.98 (m, 1H), 0.86 (m, 1H).

Example SP-256

$N^1$-{(1S,2R)-1-(cyclohexylmethyl)-3-[(3-ethylbenzyl) amino]-2-hydroxypropyl}-5-methyl-$N^3$,$N^3$-dipropylisophthalamide hydrochloride Step 3: tert-Butyl (1S)-2-(cyclohexyl)-1-[(2S)-oxiran-2-yl]ethylcarbamate (225 mg, 0.84 mmol) was refluxed with m-ethyl benzylamine (254 mg, 1.9 mmol) in 5 mL of isopropanol under nitrogen for 1.5 h, the solvent was removed in vacuo, and the residue was dissolved in ethyl acetate. It was washed three times with small portions of 10% HCl, and the aqueous phases were back-extracted with ethyl acetate. The combined organic phases were washed with 1 N NaHCO$_3$ and brine, dried over Na$_2$SO$_4$, and concentrated. The resulting oil (300 mg) was dissolved in 2 mL of dichloromethane and 2 mL of TFA and stirred for 30 min. It was concentrated, and by weight determined to contain 4 eq. of TFA. This was dissolved in 2 mL of dry THF, and 0.4 mL (3.6 mmol) of 4-methyl morpholine was added. This was cooled to −30° C., and a mixture of 3-[(dipropylamino)carbonyl]-5-methylbenzoic acid (238 mg, 0.9 mmol) and CDI (165 mg, 1 mmol) in 3 mL of dry THF, which had previously been stirred together for 1 h at room temperature, was added. The mixture was allowed to warm to ambient temperature. After 3 days the reaction was quenched with 1 N KH$_2$PO$_4$ and dissolved in ethyl acetate. The organic phase was washed with 1 N KH$_2$PO$_4$, 1 N NaHCO$_3$ (2×) and brine, dried over Na$_2$SO$_4$, and concentrated. Chromatography over silica gel, eluting with 4% to 10% methanol (containing 1% NH$_4$OH) in dichloromethane afforded 124 mg (0.21 mmol) of $N^1$-{(1S,2R)-1-(cyclohexylmethyl)-3-[(3-ethylbenzyl)amino]-2-hydroxypropyl}-5-methyl-$N^3$,$N^3$-dipropylisophthalamide hydrochloride (EXAMPLE SP-256) as a white solid after formation of the salt with ethereal HCl: CI MS m/z 550 [M+H]$^+$.

Example SP-257

$N^1$-[(1S,2R)-3-[(3-bromobenzyl)amino]-1-(cyclohexylmethyl)-2-hydroxypropyl]-5-methyl-$N^3$,$N^3$-dipropylisophthalamide hydrochloride Step 3: tert-Butyl (1S)-2-(cyclohexyl)-1-[(2S)-oxiran-2-yl]ethylcarbamate (225 mg, 0.84 mmol) was refluxed with m-bromobenzylamine (380 mg, 2.0 mmol) in 7 mL of isopropanol under nitrogen for 2 h, the solvent was removed in vacuo, and the residue was dissolved in ethyl acetate. It was washed three times with small portions of 10% HCl, and the aqueous phases were back-extracted with ethyl acetate. The combined organic phases were washed with 1 N NaHCO$_3$ and brine, dried over Na$_2$SO$_4$, and concentrated. The resulting oil (356 mg) was dissolved in 3 mL of dichloromethane and 2 mL of TFA and stirred for 1.5 h. It was concentrated, and by weight determined to contain 3 eq. of TFA. To this was added 2 mL of dry dimethylformamide (DMF) and 0.35 mL (3.2 mmol) of 4-methyl morpholine. To this was added a premixed solution of 3-[(dipropylamino)carbonyl]-5-methylbenzoic acid (240 mg, 0.9 mmol), 1-(3-dimethylaminopropyl)-3-ethylcarbodiimide hydrochloride (EDC, 190 mg, 1 mmol), and 1-hydroxybenzotriazole hydrate (HOBT, 135 mg, 1 mmol) in 3 mL of dry DMF, which had been stirring together for 1.5 h. After 3 days the reaction was quenched with 1 N KH$_2$PO$_4$ and dissolved in ethyl acetate. The organic phase was washed with 1 N KH$_2$PO$_4$, 1 N NaHCO$_3$ (2×) and brine, dried over Na$_2$SO$_4$, and concentrated. Chromatography over silica gel, eluting with 5% methanol (containing 1% NH$_4$OH) in dichloromethane afforded 208 mg (0.32 mmnol) of $N^1$-[(1S,2R)-3-[(3-bromobenzyl)amino]-1-(cyclohexylmethyl)-2-hydroxypropyl]-5-methyl-$N^3$,$N^3$-dipropylisophthalamide hydrochloride (EXAMPLE SP-257) after formation of the salt with ethereal HCl: CI MS m/z 600 [M+H]$^+$.

Example SP-258

Synthesis of $N^1$-{(1S,2R)-1-(3,5-difluorobenzyl)-3-[({2-[(dimethylamino)methyl]pyridin-4-yl}methyl)amino]-2-hydroxypropyl}-5-(1,3-oxazol-2-yl)-$N^3$,$N^3$-dipropylisophthalamide

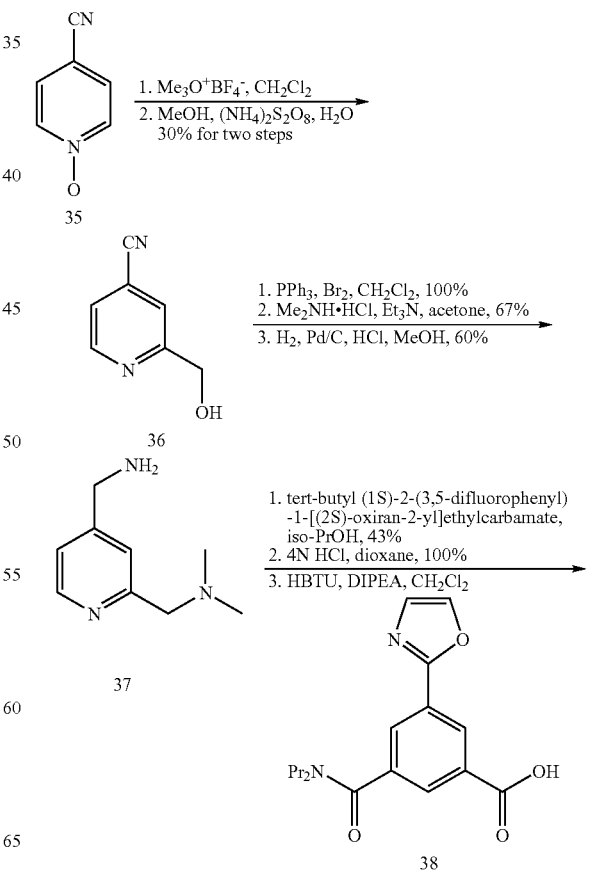

-continued

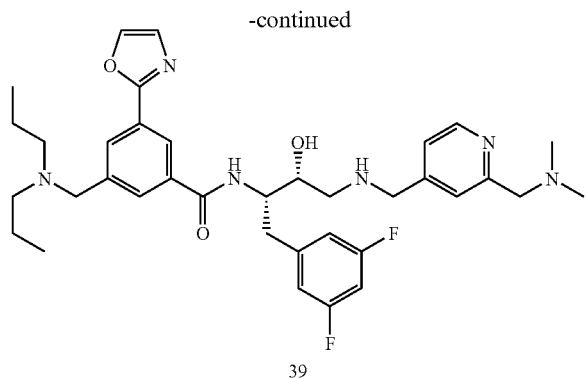

39

Step 1: Trimethyloxonium tetrafluoroborate (2.46 g, 16.7 nmmol) was added dropwise at room temperature to a solution of 4-cyanopyridine N-oxide (compound 35, above) (2.0 g, 16.7 mmol) in methylene chloride (260 mL) and the reaction mixture stirred at room temperature overnight. The reaction was concentrated under reduced pressure to give the desired 4-cyanopyridinum N-methoxy tetrafluoroborate: $^1$H NMR (300 MHz, DMSO-$d_6$) δ 9.80 (d, J=6.0 Hz, 2H), 8.87 (d, J=6.0 Hz, 2H), 4.48 (s, 3H).

Step 2: An aqueous solution of ammonium persulfate (8.3 mL, 8.3 mmol) was added to a refluxing solution of the N-methoxypyridinium salt prepared in step 1 was dissolved in methanol (200 mL). After stirring for 0.5 h, additional 1 M ammonium persulfate was added (4.2 mL, 4.2 mmol) and the reaction mixture was heated at reflux overnight. The reaction mixture was cooled to room temperature and concentrated under reduced pressure. The residue was partitioned between methylene chloride and saturated sodium bicarbonate. The organic layer was separated and washed with water, saturated sodium chloride, dried (sodium sulfate), filtered, and concentrated under reduced pressure to give a white solid. Purification by flash column chromatography (silica, 98:2 methylene chloride/methanol) gave 4-cyano-2-hydroxymethylpyridine (36) as a white solid (670 mg, 30%): 1H NMR (300 MHz, CDCl$_3$) δ 8.75 (d, J=5.0 Hz, 1H), 7.59 (d, J=0.5 Hz, 1H), 7.46 (dd, J=5.3, 0.5 Hz, 1H), 4.85 (d, J=5.3 Hz, 2H), 3.25 (t, J=5.3 Hz, 1H).

Step 3: Bromine (1.07 mL, 20.8 mmol) was added slowly at 0° C. to a solution of triphenylphosphine (5.53 g, 21.1 mmol) in methylene chloride (97 mL). The solution was warmed to room temperature and a white precipitate was observed. 4-Cyano-2-hydroxymethylpyridine 36 (2.61 g, 19.5 mmol) in methylene chloride (20 mL) was added dropwise and the reaction mixture was stirred at room temperature overnight. The reaction mixture was partitioned between water and methylene chloride. The organic layer was washed with saturated sodium chloride, dried (sodium sulfate), filtered, and concentrated under reduced pressure to give a white solid. Purification by flash column chromatography (silica, 99:1 methylene chloride/methanol) gave 4-cyano-2-bromomethylpyridine (3.95 g), which was used immediately in the next step without further purification: $^1$H NMR (300 MHz, CDCl$_3$) δ 8.76 (d, J=5.0 Hz, 1H), 7.7 (s, 1H), 7.46 (dd, J=5.0, 1.3 Hz, 1H), 4.58 (s, 2H).

Step 4: Dimethylamine hydrochloride (4.78 g, 58.6 mmol) was added to a solution of 4-cyano-2-bromomethylpyridine (3.95 g, 19.5 mmol) and triethylamine (13.58 mL, 97.7 mmol) in acetone (40 mL). The reaction mixture was stirred overnight at room temperature in a sealed tube. The reaction mixture was concentrated under reduced pressure and partitioned between methylene chloride and saturated sodium bicarbonate. The organic layer was separated and washed with water, saturated sodium chloride, dried (sodium sulfate), filtered, and concentrated under reduced pressure. Purification by flash column chromatography (silica, 99:1 methylene chloride/methanol) gave the desired 4-cyano-2-(dimethylamino)methylpyridine (2.10 g): $^1$H NMR (300 MHz, CDCl$_3$) δ 8.73 (d, J=5.0 Hz, 1H), 7.71 (s, 1H), 7.41 (dd, J=5.0, 1.2 Hz, 1H), 3.65 (s, 2H), 2.31 (s, 6H); ESI MS m/z 162 [M+H]$^+$.

Step 5: A mixture of 4-cyano-2-(dimethylamino)methylpyridine (800 mg, 4.97 mmol), palladium (80 mg, 10% Pd/C) and concentrated hydrochloric acid (3 mL) in methanol (30 mL) was shaken under 60 psi of hydrogen overnight. The reaction mixture was filtered through diatomaceous earth and the filter cake rinsed with water and methanol. The filtrate was concentrated under reduced pressure and the residue partitioned between water and methylene chloride. The aqueous layer was made alkaline with 1 N sodium hydroxide and extracted with methylene chloride. The organic layer was washed with saturated sodium chloride, dried (sodium sulfate), filtered, and concentrated under reduced pressure to give an orange oil. Purification by flash column chromatography (97:3 2-propanol/ammonium hydroxide) gave 4-aminomethyl-2-(dimethylamino)methylpyridine 37 (492 mg): $^1$H NMR (500 Hz, CDCl$_3$) δ 8.50 (d, J=5.1 Hz, 1H), 7.37 (s, 1H), 7.15 (d, J=5.1 Hz, 1H), 3.91 (s, 2H), 3.58 (s, 2H), 2.30 (s, 6H); ESI MS m/z 166 [M+H]$^+$.

Step 6: A mixture of 4-aminomethyl-2-(dimethylamino) methylpyridine 37 (490 mg, 2.98 mmol) and tert-butyl (1S)-2-(3,5-difluorophenyl)-1-[(2S)-oxiran-2-yl]ethylcarbamate (892 mg, 2.98 mmol) in 2-propanol (20 mL) was heated at reflux overnight. The reaction mixture was cooled to room temperature and concentrated under reduced pressure. The residue was purified by flash column chromatography (99:1 2-propanol/ammonium hydroxide) to give product (590 mg): ESI MS m/z 465 [M+H]$^+$.

Step 7: Hydrogen chloride (6.3 mL of a 4 N solution in dioxane, 25 mmol) was added at room temperature to a solution of the yellow solid prepared in step 6 (590 mg, 1.26 mmol) in dioxane (6.3 mL) and the reaction mixture stirred at room temperature for 6 h. The reaction mixture was concentrated under reduced pressure and the residue dissolved in methylene chloride containing N,N-diisopropylethylamine (3 mL). The organic phase was washed with water, and saturated sodium chloride, dried (sodium sulfate), filtered, and concentrated under reduced pressure to give the product (523 mg): ESI MS m/z 365 [M+H]$^+$ Step 8: A solution of 3-[(dipropylamino)carbonyl]-5-(1,3-oxazol-2-yl)benzoic acid 38 (120 mg, 0.38 mmol) in methylene chloride (3.8 mL) containing N,N-diisopropylethylamine (132 μL, 0.76 mmol) and HBTU (151 mg, 0.40 mmol) was stirred at room temperature for 0.5 h. To the above solution was added a solution of the orange oil from step 7 (207 mg, 0.57 mmol) in methylene chloride (3.8 mL) containing N,N-diisopropylethylamine (132 μL, 0.76 mmol) and the reaction mixture was stirred at room temperature for 18 h. The reaction mixture was then diluted with additional methylene chloride and washed with saturated sodium bicarbonate and saturated sodium chloride, dried (sodium sulfate), filtered, and concentrated under reduced pressure to yield an oily residue. Purification by flash column chromatography (silica, 90:10 methylene chloride/methanol) gave N$^1$-{(1S,2R)-1-(3,5-difluorobenzyl)-3-[({2-(dimethylamino)methyl]pyridin-4-yl}methyl)amino]-2-hydroxypropyl}-5-(1,3-oxazol-2-yl)-N$^3$,N$^3$-dipropylisophthalamide (178 mg): mp 63-66° C.; ESI MS m/z 663 [M+H]$^+$.

Example SP-259

Synthesis of N¹-{(1S,2R)-1-(3,5-difluorobenzyl)-3-[({4-[(dimethylamino)methyl]pyridin-2-yl}methyl)amino]-2-hydroxypropyl}-5-(1,3-oxazol-2-yl)-N³,N³-dipropylisophthalamide, compound 94 in scheme 23, below

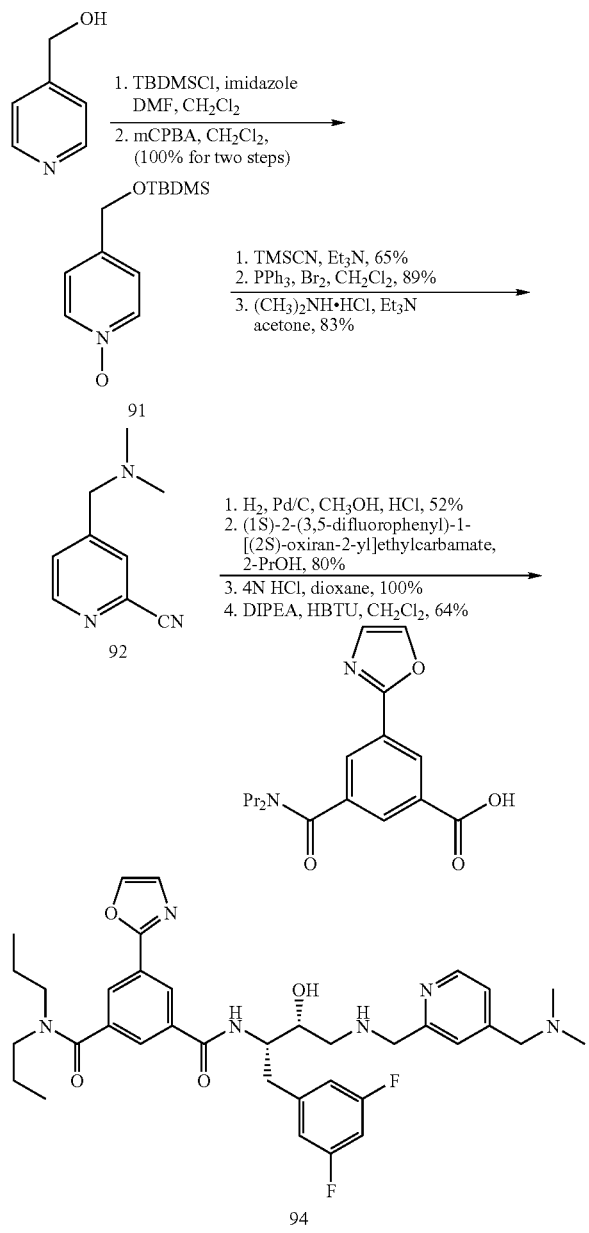

Synthesis of 2-cyano-4-(dimethylamino)methylpyridine (92)

Step 1: A mixture of 4-(hydroxymethyl)pyridine (17.4 g, 159 mmol), t-butyldimethylsilyl chloride (26.36 g, 174.88 mmol), and imidazole (13.31 g, 195.5 mmol) in N,N-dimethylformamide (200 mL) and methylene chloride (20 mL) was stirred overnight at room temperature. The reaction mixture was concentrated under reduced pressure and then partitioned between water and a mixture of ethyl acetate and hexanes (1:1). The organic layer was washed with saturated sodium chloride, dried (sodium sulfate), filtered, and concentrated under reduced pressure to give an oil (35.62 g): ¹H NMR (300 MHz, CDCl₃) δ 8.43 (d, J=6 Hz, 2H), 7.13 (d, J=6 Hz, 2H), 4.63 (s, 2H), 0.84 (s, 9H), 0.05 (s, 6H).

Step 2: To a stirred solution of the oil from step 1 (35.62 g, 159 mmol) in dry methylene chloride (470 mL) was added 3-chloroperoxybenzoic acid (47.03 g, 172.57 mmol). The reaction mixture was stirred at room temperature overnight and then partitioned between water and methylene chloride. The organic layer was washed with saturated sodium sulfite, saturated sodium bicarbonate, 1 N sodium hydroxide, and saturated sodium chloride, dried (sodium sulfate), filtered, and concentrated under reduced pressure to give 4-(t-butyldimethylsilyloxy)methylpyridine N-oxide 91 (37.8 g) ¹H NMR (300 MHz, CDCl₃) δ 8.07 (d, J=6 Hz, 2H), 7.13 (d, J=6 Hz, 2H), 4.59 (s, 2H), 0.83 (s, 9H), 0.05 (s, 6H).

Step 3: A mixture of 4-(t-butyldimethylsilyloxy)methylpyridine N-oxide 91 (30 g, 125 mmol), triethylamine (40 mL), and trimethylsilylcyanide (44 mL, 360 mmol) was refluxed overnight. The black solution was cooled to room temperature and concentrated under reduced pressure to give a black gum. Purification by flash column chromatography (silica, 10:90 ethyl acetate/hexanes) gave an oil (20.3 g): ¹H NMR (300 MHz, CDCl₃) δ 8.50 (d, J=5 Hz, 1H), 7.55 (s, 1H), 7.34 (d, J=5 Hz, 1H), 4.66 (s, 2H), 0.83 (s, 9H), 0.05 (s, 6H).

Step 4: Bromine (1.97 mL, 38.74 mmol) was added slowly at 0° C. to a solution of triphenylphosphine (10.29 g, 39.28 mmol) in methylene chloride (200 mL). The solution was warmed to room temperature and a white precipitate was observed. The brown oil from step 3 (9.0 g, 36.27 mmol) in methylene chloride (50 mL) was added and the reaction mixture was stirred at room temperature overnight. The reaction mixture was partitioned between water and methylene chloride. The organic layer was washed with saturated sodium chloride, dried (sodium sulfate), filtered, and concentrated under reduced pressure to give a brown solid. Purification by flash column chromatography (silica, 17:83 ethyl acetate/hexanes) gave a white solid (6.20 g): ¹H NMR (300 MHz, CDCl₃) δ 8.71 (d, J=3 Hz, 1H), 7.73 (s, 1H), 7.55 (dd, J=6, 3 Hz, 1H), 4.42 (s, 2H).

Step 5: To a stirred solution of the solid from step 4 (9.1 g, 46.44 mmol) in acetone (90 mL) was added dimethylamine hydrochloride (11.36 g, 139.3 mmol) and trimethylamine (38.73 mL, 278.6 mmol). The reaction mixture was stirred overnight in a sealed bottle. The reaction mixture was concentrated under reduced pressure. The residue was dissolved in water, made alkaline with 1 N sodium hydroxide to pH 10 and extracted with methylene chloride. The organic layer was washed with saturated sodium chloride, dried (sodium sulfate), filtered, and concentrated under reduced pressure to give 2-cyano-4-(dimethylamino)methylpyridine 92 (6.2 g): ESI MS m/z 162 [M+H]⁺.

Example SP-260

N¹-{(1S,2R)-1-(3,5-difluorobenzyl)-3-[({4-[(dimethylamino)methyl]pyridin-2-yl}methyl)amino]-2-hydroxypropyl}-5-(1,3-oxazol-2-yl)-N³,N³-dipropylisophthalamide Step 1: A mixture of 2-cyano-4-(dimethylamino)methylpyridine 92 (2.0 g, 12.4 mmol), 10% Pd/C (200 mg) and concentrated hydrochloric acid (8 mL) in methanol (180 mL) was shaken under 60 psi hydrogen overnight. The reaction mixture was filtered through diatomaceous earth and repeatedly washed with water and methanol. Methanol was removed under reduced pressure and the residue partitioned between water and methylene chloride. The aqueous layer was made alkaline with 1 N sodium hydroxide and extracted with methylene chloride. The organic layer was washed with saturated sodium chloride, dried (sodium sulfate), filtered, and concentrated under reduced pressure to give an oil (1.07 g): ¹H NMR (300 MHz, CDCl₃) δ 8.53 (d, J=5 Hz, 1H), 7.25

(s, 1H), 7.13 (d, J=5 Hz, 1H), 3.98 (s, 2H), 3.42 (s, 2H), 2.26 (s, 6H); ESI MS m/z 166 [M+H]⁺.

Step 2: A mixture of the orange oil from step 1 (500 mg, 3.03 mmol) and tert-butyl (1S)-2-(3,5-difluorophenyl)-1-[(2S)-oxiran-2-yl]ethylcarbamate (907 mg, 3.03 mmol) in 2-propanol (20 mL) was refluxed overnight. The reaction mixture was cooled to room temperature and concentrated under reduced pressure. The residue was purified by flash column chromatography (silica, 1:99 ammonium hydroxide/2-propanol) to give a solid (1.13 g): ESI MS m/z 465 [M+H]⁺.

Step 3: The yellow solid from step 2 (400 mg, 0.86 mmol) was dissolved in dioxane (4.3 mL) and hydrogen chloride (4.3 mL, 4 M dioxane, 17.22 mmol) was added. The reaction mixture was stirred at room temperature for 6 h. The reaction mixture was concentrated under reduced pressure and methylene chloride and N,N-diisopropylethylamine (3 mL) were added. The organic phase was washed with water, and saturated sodium chloride, dried (sodium sulfate), filtered, and concentrated under reduced pressure to give an oil (365 mg): ESI MS m/z 365 [M+H]⁺

Step 4: To a stirred solution of 3-[(dipropylamino)carbonyl]-5-(1,3-oxazol-2-yl)benzoic acid 93 (173.6 mg, 0.55 mmol) and N,N-diisopropyl ethylamine (191 µL, 1.10 mmol) in methylene chloride (6.0 mL) was added HBTU (218.62 mg, 0.58 mmol) and the reaction mixture stirred for 0.5 h. To the above solution was added a solution of the orange oil from step 3 (300 mg, 0.823 mmol) and N,N-diisopropylethylamine (191 µL, 1.10 mmol) in methylene chloride (6.0 mL), and the reaction mixture was stirred under nitrogen for 18 h. The reaction mixture was then diluted with additional methylene chloride and washed with saturated sodium bicarbonate, 0.5 N hydrochloric acid, and saturated sodium chloride,. The organic layer was then dried (sodium sulfate), filtered, and concentrated under reduced pressure to yield an oily residue. Purification by flash column chromatography (silica, 10:90 methanol/methylene chloride) gave N¹-{(1S,2R)-1-(3,5-difluorobenzyl)-3-[({4-[(dimethylamino)methyl]pyridin-2-yl}methyl)amino]-2-hydroxypropyl}-5-(1,3-oxazol-2-yl)-N³,N³-dipropylisophthalamide (94)(233 mg): mp 65-68° C.; ESI MS m/z 663 [M+H]⁺

Example SP-261

Synthesis of N¹-{(1S,2R)-1-(3,5-difluorobenzyl)-3-[(1-{4-[(dimethylamino)methyl]pyridin-2-yl}cyclopropyl)amino]-2-hydroxypropyl}-5-(1,3-oxazol-2-yl)-N³,N³-dipropylisophthalamide

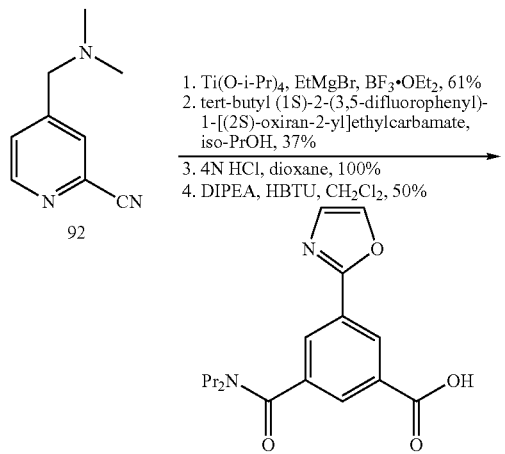

1. Ti(O-i-Pr)₄, EtMgBr, BF₃·OEt₂, 61%
2. tert-butyl (1S)-2-(3,5-difluorophenyl)-1-[(2S)-oxiran-2-yl]ethylcarbamate, iso-PrOH, 37%
3. 4N HCl, dioxane, 100%
4. DIPEA, HBTU, CH₂Cl₂, 50%

-continued

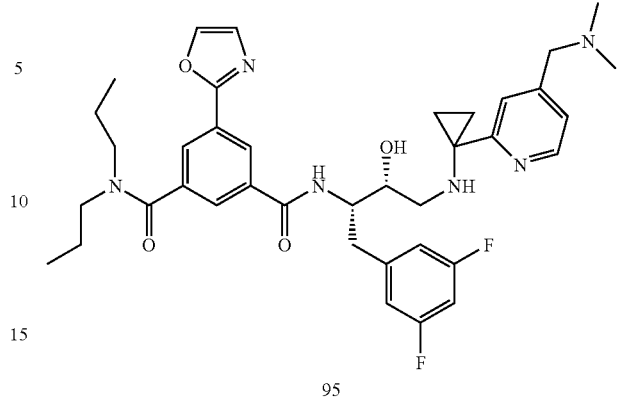

95

Step 1: To a solution of 2-cyano-4-(dimethylamino)methylpyridine 92 (prepared as in EXAMPLE SP-259) (500 mg, 3.10 mmol) in tetrahydrofuran (10 mL) was added titanium (IV) isopropoxide (1.01 mL, 3.41 mmol) and ethylmagnesium bromide (6.20 mL, 1 N THF, 6.20 mmol). After stirring for 0.5 h, boron trifluoride diethyl etherate (786 µL, 6.20 mmol) was added in one portion. The reaction mixture was stirred for 1 h at room temperature and 1 N sodium hydroxide was added to adjust the mixture to pH 9-10. The white solid generated was removed by filtration and the filtrate was partitioned between water and methylene chloride. The organic layer was washed with saturated sodium chloride, dried (sodium sulfate), filtered, and concentrated under reduced pressure to give a yellow oil. Purification by flash column chromatography (silica, 1:99 to 3:97 ammonium hydroxide/2-propanol) gave an oil (360 mg): ¹H NMR (300 MHz, CDCl₃) δ 8.42 (dd, J=6, 5 Hz, 1H), 3.41 (s, 2H), 7.02 (dd, J=6, 5 Hz, 1H), 3.98 (s, 2H), 3.42 (s, 2H), 2.25 (s, 6H), 2.08 (s, 2H), 1.31-1.27 (m, 2H), 1.15-1.11 (m, 2H); ESI MS m/z 192 [M+H]⁺.

Step 2: A mixture of the oil from step 1 (350 mg, 1.83 mmol) and tert-butyl (1S)-2-(3,5-difluorophenyl)-1-[(2S)-oxiran-2-yl]ethylcarbamate (496.8 mg, 1.66 mmol) in 2-propanol (13 mL) was refluxed overnight. The reaction mixture was cooled to room temperature and concentrated under reduced pressure. The residue was purified by flash column chromatography (silica, 1:99 ammonium hydroxide/2-propanol) to give a solid (300 mg): ESI MS m/z 491 [M+H]⁺.

Step 3: To a stirred solution of the solid from step 2 (300 mg, 0.61 mmol) in dioxane (6.0 mL) was added hydrochloric acid (6.0 mL, 4 N dioxane, 24.40 mmol). The reaction mixture was stirred at room temperature for 6 h. The reaction mixture was concentrated under reduced pressure and methylene chloride and N,N-diisopropylethylamine (3 mL) were added. The organic layer was washed with water, and saturated sodium chloride, dried (sodium sulfate), filtered, and concentrated under reduced pressure to give an oil (269 mg): ESI MS m/z 391 [M+H]⁺.

Step 4: To a stirred solution of 3-[(dipropylamino)carbonyl]-5-(1,3-oxazol-2-yl)benzoic acid 93 (prepared as in EXAMPLE S-2364, step 5) (124.3 mg, 0.39 mmol) and N,N-diisopropyl ethylamine (139 µL, 0.79 mmol) in methylene chloride (3.0 mL) was added HBTU (156.5 mg, 0.41 mmol) and the reaction mixture stirred for 0.5 h. To the above solution was added a solution of the orange oil from step 3 (269.6 mg, 0.823 mmol) and N,N-diisopropylethylamine (139 µL, 0.79 mmol) in methylene chloride (3.0 mL), and the reaction mixture was stirred under nitrogen for 18 h. The reaction mixture was then diluted with additional methylene chloride and washed with saturated sodium bicarbonate, and saturated sodium chloride, dried (sodium sulfate), filtered, and concentrated under reduced pressure to yield an oily residue. Purification by flash column chromatography (silica, 10:90 methanol/methylene chloride) gave $N^1$-{(1S,2R)-1-(3,5-difluorobenzyl)-3-[(1-{4-[(dimethylamino)methyl]pyridin-2-yl}cyclopropyl)amino]-2-hydroxypropyl}-5-(1,3-oxazol-2-yl)-$N^3$,$N^3$-dipropylisophthalamide (95) (134 mg): mp 70-72° C.; ESI MS m/z 689 [M+H]$^+$.

Example SP-262

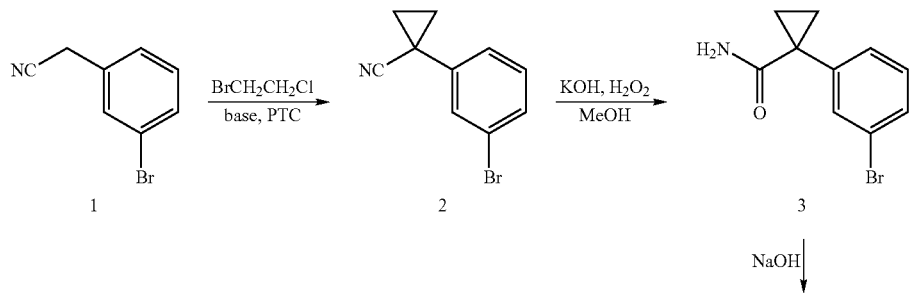

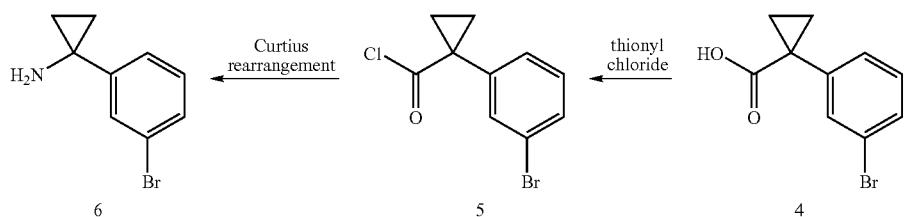

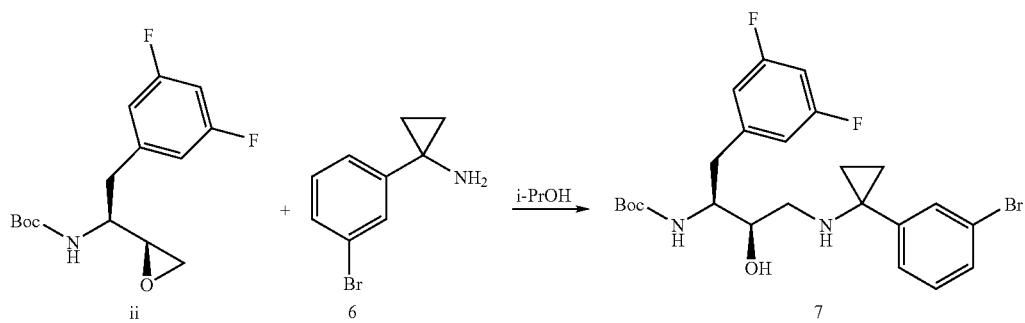

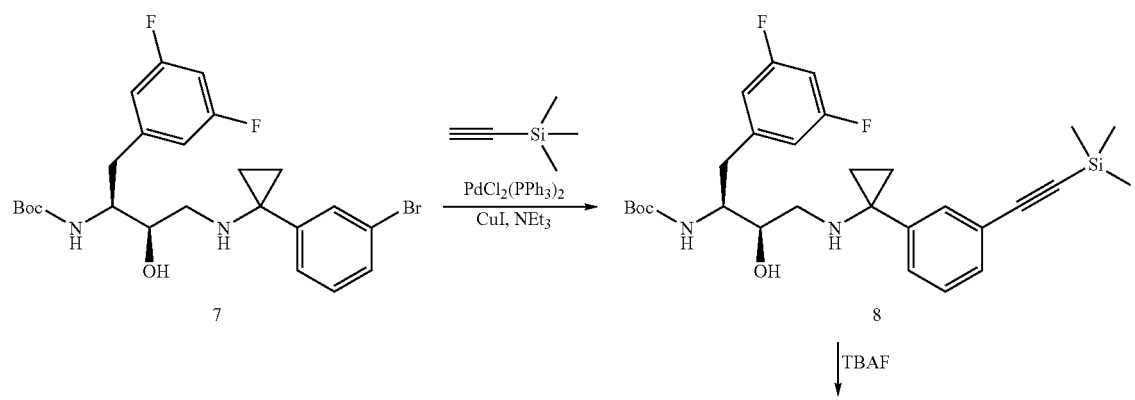

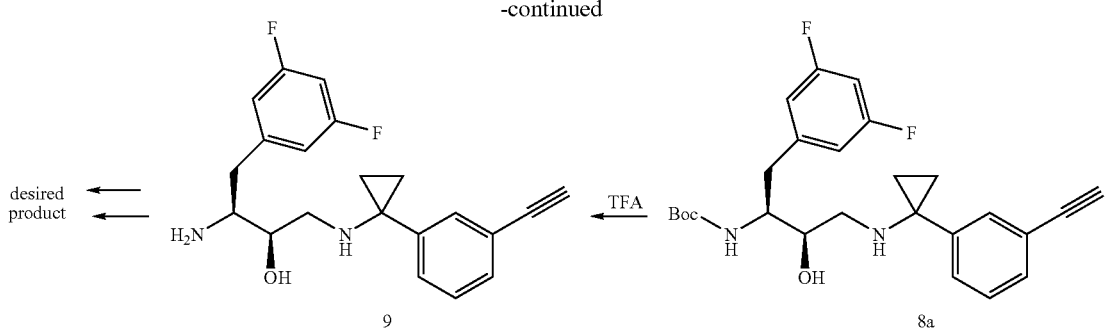

Preparation of Bromo-cyclopropyl Cyanide 2 (Modification of Procedure from Org. Prep. & Proc. Int., 1995, 27(3), 355)

A mixture of 1-bromo-2-chloroethane (BCE; 120 ml), 3-bromobenzyl cyanide (25 g) and benzyl-triethylammonium chloride (TEBAC, 1.1 g) was stirred at 40° C. while base (50% NaOH, 120 g) was added dropwise over 20 min. Temperature has risen to −80° C. within first 15 min. Very vigorous mechanical stirring was continued while temperature slowly dropped to 50° C. (over the next 3 hr). The mixture was deep red at this stage. After 3 hr there was no starting material (TLC). The reaction mixture was cooled down to RT, water (100 ml) was added and stirred for 5 min. Organic layer was separated and aqueous was extracted with dichloromethane (3×) Combined organic layers were washed with water and dil. aq. HCl. Solution was dried using $MgSO_4$, filtered and concentrated yielding deep yellow oil (126 g; still contains some BCE). Product was purified by a high vacuum fractionation using short-path set-up and single receiver. Collected fraction with bp 108-115° C./0.1-0.05 mmHg as a heavy oily liquid 26.6 g (94%). After cooling to RT this liquid solidified.

Preparation of Bromoamide 3

Bromocyanide 2 (5.9 g; 26.6 mmol) was dissolved in methanol (150 ml). To this solution while stirring KOH (25% aq soln., 0.68 ml) and hydrogen peroxide (30%, 35 ml) was added and the reaction mixture was heated at 55° C. for 5 hr. At that time there was no starting material (TLC). Mixture was evaporated yielding solid residue (7.1 g; contains KOH).

Preparation of Bromoacid 4

Crude bromoamide 3 from previous reaction was slurried in methanol (10 ml) and NaOH (10% aq, 150 ml) was added. Reaction mixture was refluxed 4.5 hr (TLC control). The mixture was cooled to RT, acidified with 15% HCl (to pH 2) and concentrated. Precipitated white solid was collected by filtration. Yield 6.8 g.

Preparation of Acid Chloride 5 (Slight Modification of Procedure from Synlett 1999, 11, 1763)

Thionyl chloride (2.73 ml) and benzotriazole (4.47 g) were dissolved in dry dichloromethane (25 ml). Crude bromoacid 4 (6.8 g) was dissolved in dichloromethane (120 ml) and to this stirred solution the prepared above thionyl chloride solution (22.2 ml; 1.25 eq) was added portionwise over a few minutes. Before the addition was complete, benzotriazole hydrochloride started separating out as a white solid. The reaction mixture was stirred for additional 15 min and at the end the solids were filtered off. Filtrate was stirred with anhydrous $MgSO_4$ (2 g) to destroy an excess of reagent. The solids were filtered off and filtrate was evaporated and dried under high vacuum for 1 hr to give viscous amber oil. Yield 6.6 g.

Preparation of Bromoamine 6

Crude acid chloride 5 was dissolved in dry acetone (40 ml), cooled to −10° C. and treated with sodium azide (4 g in 15 ml of waterl). After stirring for 1 hr at −10° C. a mixture was allowed to warm to 0° C. and was poured into cold water (300 ml). Azide was extracted into smallest possible amount of toluene (ca. 40 ml). The toluene layer was washed with water and dried. Solids were filtered off and resulting solution was stirred and heated cautiously at 100° C. for 1 hr. Conc. HCl (~25 ml) was added through condenser and mixture was refluxed for 15 min. On cooling white crystalline material precipitated and was filtered off. Filtrate was slightly concentrated, cooled down and additional portion of precipitate was collected. Combined solids were dried to give 4.1 g of bromocyclopropylamine 6 as hydrochloride salt.

Preparation of Compound 7

Crude bromoamine hydrochloride 6 (2 g; 8 mmol) was dissolved in sat. aq $Na_2CO_3$ (20 ml) and extracted with dichloromethane (5×10 ml). Combined extracts were dried, evaporated and kept overnight under vacuum. Yield of bromoamine 6 (1.68 g, 7.92 mmol). This amine was dissolved in isopropanol (20 ml) and epoxide (ii; 2.36 g, 7.92 mmol) was added. A mixture was stirred in a sealed tube at 80° C. until starting epoxide was not detected by TLC (2-6 hr). Reaction mixture was cooled and solvent was evaporated to give, after drying under vacuum, white solid (3.9 g, 82% pure).

Preparation of Compound 8

Crude BOC bromide 7 (3.9 g; 7.0 mmol; 1 eq) was dissolved in triethylamine (20 ml) and $PdCl_2(PPh_3)_2$ (0.196 g, 0.28 mmol; 0.04 eq) and CuI (0.068 g; 0.36 mmol; 0.05 eq) were added. Upon addition of CuI a reaction mixture turned yellow then changed color slowly to green. The reaction mixture was heated to reflux, at which point it turned orange-brown. Trimethylsilyl acetylene (0.82 g, 1.2 ml, 8.2 mmol, 1.2 eq) was added via syringe. A black precipitate formed immediately. The reaction mixture was refluxed for 3 hr under nitrogen, then it was cooled to RT before partitioning between aq. sat. $Na_2CO_3$ and ethyl acetate. Organic layer was separated and aqueous was extracted with ethyl acetate (3×25 ml). Combined extracts were washed with brine, dried and evaporated. The crude product was contaminated by acetylene derived from bromoamine 6.

Preparation of BOC-acetylene 8a

To a solution of crude silyl-protected acetylene 8 (from previous reaction) in THF (5 ml) the tetrabutylammonium fluoride (1M in THF, 8 ml) was added. Mixture was stirred for 1 hr at RT, solvent was evaporated, residue was dissolved in ether (30 ml), washed with brine, dried and concentrated. Crude product was purified by flash chromatography on silica gel using ethyl acetate/hexane (2:3) mixture to give purified BOC-acetylene 8a (1.54 g, 43% from 6).

Preparation of 9:

1-(3,5-difluorobenzyl)-3-[1-(3-ethynylphenyl)cyclopropylamino)]-2-hydroxypropyl amine dihydrochloride

[1-(3,5-difluorobenzyl)-3-[1-(3-ethynylphenyl)cyclopropylamino]-2-hydroxypropyl]-carbamic acid tert-butyl ester (2.34 g, 5.13 mmol) was treated with 4N HCl in dioxane (15.8 mL, 63.3. mmol). The resulting heterogeneous mixture was treated with methanol (10 mL) whereupon it became homogeneous over 30 min. The volatiles were evaporated in vacuo. Dioxane (20 mL) was added and the mixture was evaporated in vacuo to produce a white solid (2.33 g, 106%).

Example SP-263

Preparation of Cyclopropyl m-ethylbenzylamine (11)

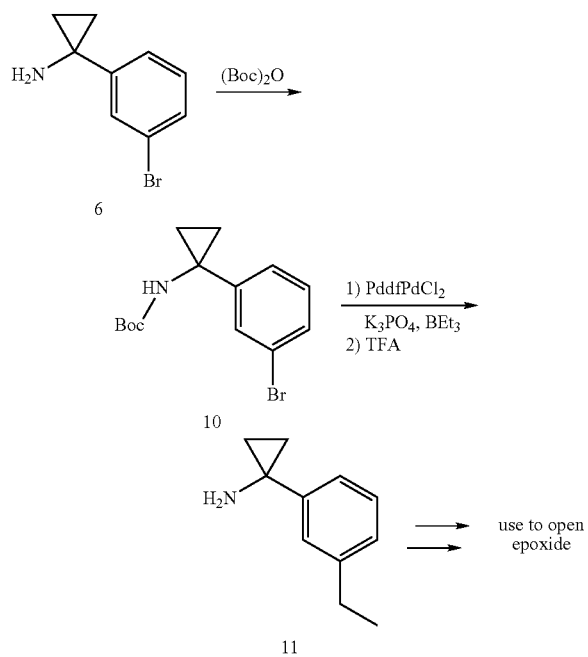

Preparation of 10.

1-(3-Bromo-phenyl)-cyclopropylamine 6 (25 g, 112 mmol), triethylamine (21.7 g, 2170 mmol) were mixed together in $CH_2Cl_2$ (300 mL). The solution was cooled to 0° C. and boc anhydride (25.07 g, 115 mmol) added in 4 equal portions at 15 minute intervals. (Gas evolution noted after each addition). Mixture stirred for 30 minutes and then an additional 5 grams of boc anhyrdide was added to drive reaction to completion (GC/MS). Solution worked up with 1 N HCl (2×100 mL), saturated aq. sodium bicarbonate (2×100 mL), and dried over sodium sulfate. Solvent was removed at reduced pressure and product was isolated by crystallization from cold hexanes (about 150 mL). Obtained 20.6 grams of white solid. Reduced volume of hexanes to about 75 ml and second crop was obtained (9.2 g)

Preparation of 11.

The Boc-bromobenzyl amine 10 (26.8 g, 94.03 mmol), and $PddfPdC_{12}$ (816 mg, 0.38 mmol, 0.004 eq) were mixed together in anhydrous THF (300 mL) and aqueous $K_3PO_4$ (100 mL of 2.0 M). To this red solution was added triethylborane (100 ml of 1.0 M in THF, 100 mmol). The solution turned black and was refluxed for 4 hours. GC/MS indicated the reaction was complete. The solution was poured into a separatory funnel and the aqueous layer separated. The organic layer was collected and solvent removed to a volume of 100 mL. Ethyl acetate/ hexanes (300 mL of 1:1) were added and the solution was extracted with 1N HCl (1×100 mL), sodium bicarbonate (2×100 mL) and brine (1×100 mL). The solution was dried over sodium sulfate and vacuum filtered through a bed of silica gel (125 ml of silica). The solvent was removed at reduced pressure to afford 20.6 grams of 11 as light yellow oil.

Example SP-264

Preparation of 6-Methyl-pyridine-2,4-dicarboxylic acid 4-({1-(3,5-difluoro-benzyl)-3-[1-(3-ethynyl-phenyl)-cyclopropylamino]-2-hydroxy-propyl}-amide) 2-dipropylamide

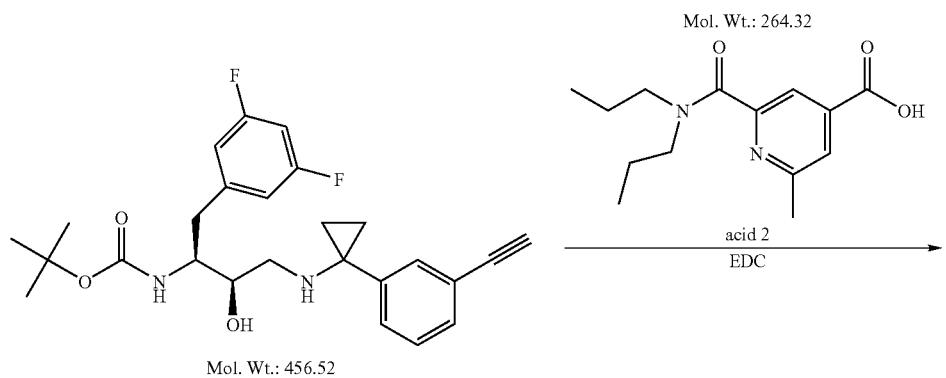

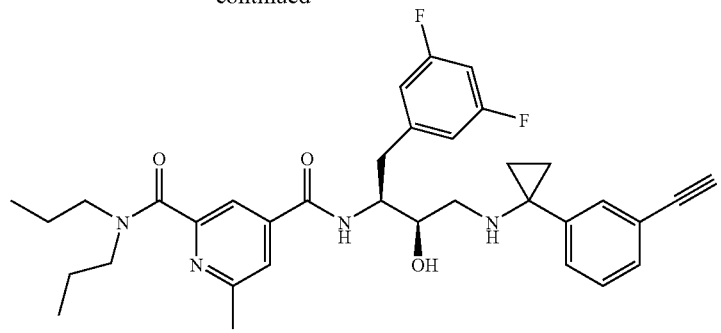

The Boc protected amine (prepared as in EXAMPLE SP-262) (0.912 g, 2 mM) was treated with 50% TFA in CH$_2$Cl$_2$ (1 hr, RT). Solvents were removed under reduced pressure to form an oil. Added toluene and evaporated; repeated stripping with toluene. After this operation and keeping residue under high vacuum for 1 hr off-white solid was obtained (free amine, most likely as a TFA salt). This amine was dissolved in CH$_2$Cl$_2$ (10 mL, slurry), added acid 2 (0.528 g; 2 mM), HOBt (0.297 g; 2.2 mM) and EDC (0.423 g; 2.2 mM). When EDC was added slurry rapidly became clear solution. At the end an excess of NEt$_3$ (2 mL) was added and a reaction mixture was stirred o/n at RT. The next day solvent was stripped and EtOAc solution was washed with aq. saturated solution of Na$_2$CO$_3$ (3×), brine, dried and concentrated. Initially purified by flash chromatography on Biotage (eluted with 20% hexane and 80% EtOAc). Final purification was done by HPLC. The TFA salt was converted into HCl mono salt by addition of 1.25M solution of HCl in MeOH (1.6 mL). Yield 0.971 g (76%).

Example SP-265

N$^1$-((1S,2R)-1-(3,5-difluorobenzyl)-3-{[-(3-ethylphenyl)cyclopropyl]amino}-2-hydroxypropyl)-5-(1,3-oxazol-2-yl)-N$^3$,N$^3$-dipropylisophthalamide

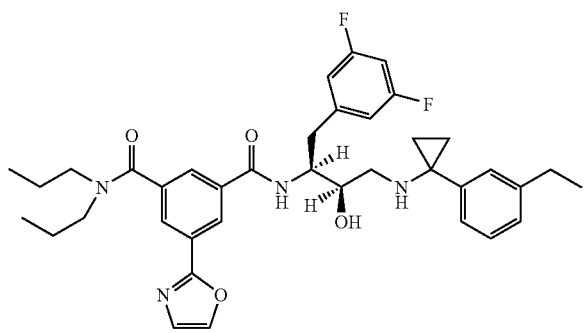

The above identified compound is prepared essentially using the procedure described in EXAMPLE SP-264.

M+659.3. Carbon NMR (CDCl$_3$): 11.00, 11.56, 11.78, 15.37, 20.80, 21.90, 28.71, 35.28, 44.45, 47.26, 49.97, 51.16, 53.75, 69.43, 77.12, 102.12, 112.02, 112.34, 126.23, 126.94, 127.29, 128.01, 128.68, 129.20, 129.51, 133.90, 134.70, 137.56, 139.59, 142.15, 145.53, 160.26, 161.43, 164.73, 166.98, 170.42.

Example SP-266

N$^1$-((1S,2R)-1-(3,5-difluorobenzyl)-3-{[1-(3-ethynylphenyl)cyclopropyl]amino}-2-hydroxypropyl)-5-(1,3-oxazol-2-yl)-N$^3$,N$^3$-dipropylisophthalamide

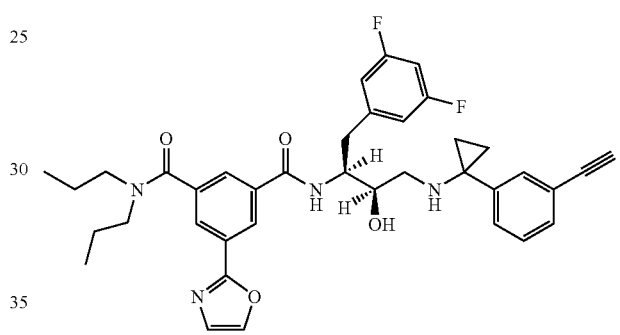

The above identified compound is prepared essentially using the procedure described in EXAMPLE SP-264.

M+655.3. Carbon NMR (CDCl$_3$): 11.01, 11.47, 11.58, 11.98, 20.82, 21.91, 35.22, 43.94, 47.28, 50.09, 51.17, 53.77, 69.49, 77.11, 78.63, 82.55, 102.17, 112.05, 123.22, 126.23, 126.82, 128.07, 128.76, 129.49, 130.68, 133.33, 134.50, 137.57, 139.61, 142.17, 160.23, 161.27, 164.56, 167.04, 170.44.

Example SP-267

N$^4$-((1S,2R)-1-(3,5-difluorobenzyl)-3-{[1-(3-ethylphenyl)cyclopropyl]amino}-2-hydroxypropyl)-6-methyl-N$^2$,N$^2$-dipropylpyridine-2,4-dicarboxamide

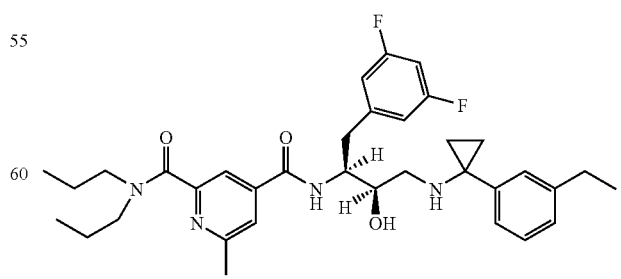

The above identified compound is prepared essentially using the procedure described in EXAMPLE SP-264.

M+607.3 Carbon NMR (CDCl$_3$): 10.96, 11.06, 11.53, 12.09, 15.43, 20.73, 21.90, 23.96, 28.75, 33.93, 44.32, 47.82, 49.60, 50.90, 53.98, 68.65, 77.11, 101.98, 112.064, 112.39, 117.03, 122.12, 127.25, 129.23, 129.49, 134.06, 142.21, 145.61, 153.63, 158.94, 161.19, 161.36, 164.48, 164.65, 165.65, 169.06.

Example SP-268

N$^4$-((1S,2R)-1-(3,5-difluorobenzyl)-3-{[1-(3-ethynylphenyl)cyclopropyl]amino}-2-hydroxypropyl)-6-methyl-N$^2$,N$^2$-dipropylpyridine-2,4-dicarboxamide

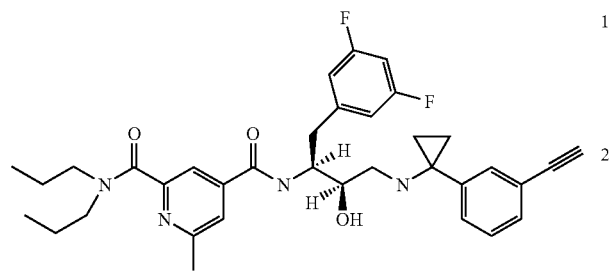

The above identified compound is prepared essentially using the procedure described in EXAMPLE SP-264.

M+603.3. Carbon NMR (CDCl$_3$): 10.99, 11.58, 12.29, 20.75, 21.92, 24.03, 33.98, 43.91, 47.91, 49.83, 50.96, 53.95, 68.74, 77.13, 78.72, 82.57, 102.08, 112.08, 112.41, 117.63, 122.16, 123.32, 129.51, 130.66, 133.37, 133.55, 134.63, 142.28, 153.56, 158.96, 161.20, 161.37, 164.66, 165.80.

Example SP-269

Preparation of 1-(3,5-difluorobenzyl)-3-(3-ethynyl)benzylamino)-2-hydroxypropyl amine dihydrochloride

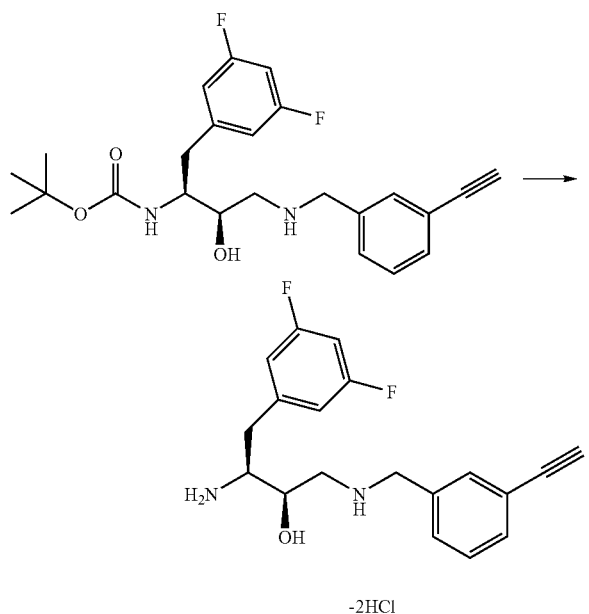

[1-(3,5-difluorobenzyl)-3-(3-ethynylbenzylamino)-2-hydroxypropyl]-carbamic acid tert-butyl ester (2.73 g, 6.33 mmol) was treated with 4N HCl in dioxane (15.8 mL, 63.3 mmol). The mixture became homogeneous after 5 min and then deposited a precipitate. Diethyl ether (15 mL) was added to aid stirring and the mixture was stirred for 2 h. The volatiles were evaporated in vacuo. Dioxane (20 mL) was added and the mixture was evaporated in vacuo to produce a white solid (2.67 g, 104%).

Example SP-270

N$^1$-{(1S,2R)-1-(3,5-difluorobenzyl)-3-[(3-ethynylbenzyl)amino]-2-hydroxypropyl}-5-ethynyl-N$^3$,N$^3$-dipropylisophthalamide

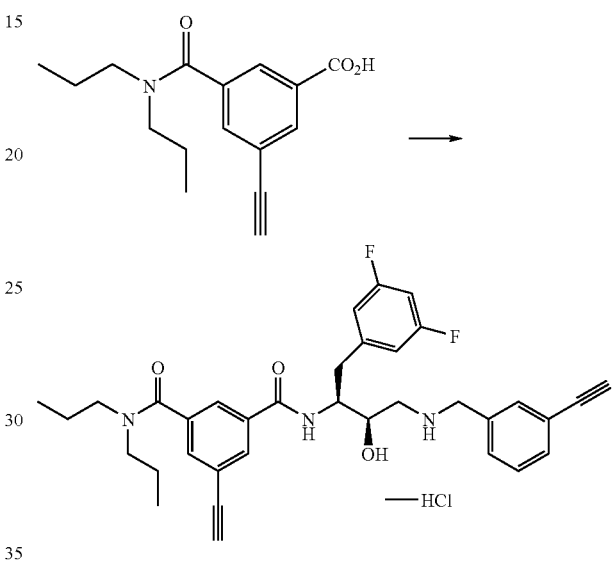

5-Ethynyl-N,N-dipropyl-iso-phthalamic acid (1.73 g, 6.32 mmol) was dissolved in anhydrous DMF (20 ml) under nitrogen. 1-Hydroxybenzotriazole (1.28 g, 9.48 mmol) and 1-(3-dimethylaminopropy)-3-ethylcarbodiimidehydrochloride (1.70 g, 8.85 mmol)) were added in succession. This mixture was stirred for 30 min at RT until homogeneous and then was added in one portion to a rapidly-stirred slurry of amine dihydrochloride (2.67, 6.32 mmol) and N-methylmorpholine (2.78 mL, 2.56 g, 25.3 mmol) in DMF (25 mL). The resulting mixture was stirred for 2 h before diluting with saturated aq sodium bicarbonate (200 mL). The mixture was extracted with ethyl acetate (3×100 mL) and the combined organic extracts were washed with saturated aq sodium bicarbonate (100 mL), water (2×100 mL), and brine (100 mL), dried (sodium sulfate), filtered and evaporated in vacuo to give an oil (3.7 g). The product was purified using flash column chromatography on silica gel (Flash 65i cartridge, eluting with 1 L 100% ethyl acetate, then 4 L 95:5 ethyl acetate/methanol ) to yield a pale yellow oil (2.74 g, 74%). LC-MS (m/e): 586 (M+1); 100% (254 nm). The ELN 152006 free base was dissolved in ethanol (25 mL) and treated with 4N HCl in dioxane (2.0 mL). The resulting mixture was evaporated in vacuo to remove volatiles, re-dissolved in 1:1 ethanol/water (25 mL) and evaporated in vacuo. The resulting solid was slurried in diethyl ether (50 mL), filtered and washed with diethyl ether to produce an off-white solid which was vacuumed dried to constant weight (2 d) to yield the desired product (2.43 g).

Analysis: for C$_{35}$H$_{37}$F$_2$N$_3$O$_3$+HCl: calcd.: C, 67.57; H, 6.16; N, 6.75; Cl, 5.50; found: C, 67.21; H, 6.04; N, 6.55; Cl, 5.71.

Example SP-271

Preparation of N¹-((1S,2R)-1-(3,5-difluorobenzyl)-3-{[1-(3-ethynylphenyl)cyclopropyl]amino}-2-hydroxypropyl)-5-methyl-N³,N³-dipropylisophthalamide

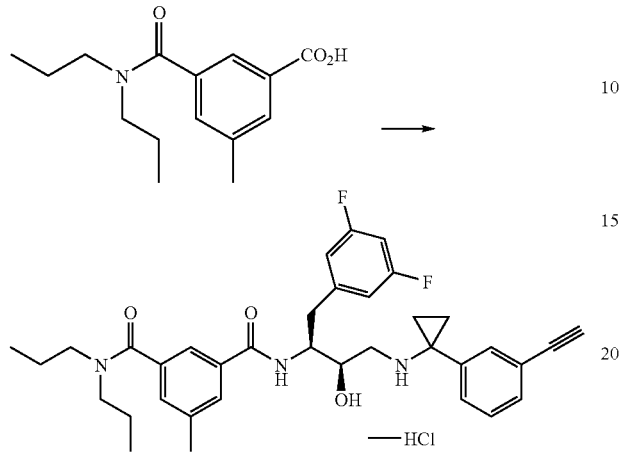

5-Methyl-N,N-dipropyl-iso-phthalamic acid (1.35 g, 5.13 mmol, was dissolved in anhydrous DMF (15 ml) under nitrogen. 1-Hydroxybenzotriazole (1.04 g, 7.69 mmol) and 1-(3-dimethylaminopropy)-3-ethylcarbodiimide hydrochloride (1.38 g, 7.18 mmol)) were added in succession. This mixture was stirred for 30 min at RT until homogeneous and then was added in one portion to a rapidly-stirred slurry of amine dihydrochloride (2.23 g, 5.13 mmol) and N-methylmorpholine (2.25 mL, 2.07 g, 20.5 mmol) in DMF (20 mL). The resulting mixture was stirred for 3.5 h before diluting with saturated aq sodium bicarbonate (150 mL). The mixture was extracted with ethyl acetate (3×100 mL) and the combined organic extracts were washed with saturated aq sodium bicarbonate (100 mL), water (2×100 mL), and brine (100 mL), dried (sodium sulfate), filtered and evaporated in vacuo to give an oil (3.0 g). The product was purified using flash column chromatography on silica gel (Flash 65i cartridge, eluting with 2.8L 1:1 ethyl acetate/hexane, 2.5 L 2:1 ethyl acetate/hexane, then 2 L 100% ethyl acetate) to yield a clear oil (2.34 g, 76%). LC-MS (m/e): 602 (M+1); 100% (254 nm). The ELN 152227 free base was dissolved in ethanol (25 mL) and treated with 4N HCl in dioxane (2.0 mL). The resulting mixture was evaporated in vacuo to remove volatiles, re-dissolved ethanol (25 mL) and evaporated in vacuo. The resulting solid was slurried in diethyl ether (50 mL) and filtered to produce a hygroscopic solid which was lyophilized to yield ELN 152227-3 (1.93 g).

Analysis: for $C_{36}H_{41}F_2N_3O_3$+HCl+0.8 $H_2O$: calcd.: C, 66.26; H, 6.73; N, 6.44; Cl, 5.43; found: C, 67.21; H, 6.40; N, 6.42; Cl, 5.34.

Example SP-272

Preparation of (2R,3S)-3-amino-4-(3,5-difluorophenyl)-1-[(3-ethylbenzyl)amino]butan-2-ol dihydrochloride

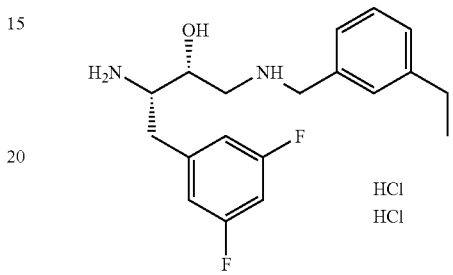

The slurry of [1-(3,5-difluorobenzyl)-3-(3-ethylbenzylamino)-2-hydroxypropyl]-carbamic acid tert-butyl ester (5.25 g, 0.012 m) in anhydrous dioxane (20 ml) was stirred (magnetic bar) at RT under nitrogen atmosphere in an 250 ml round-bottom flask, immersed in a cold water bath. The solution of hydrogen chloride in dioxane (4M, 32 ml) was added in one portion. The reaction mixture, initially homogeneous, became a thick slurry within ca. 20 min. Mixture was stirred for 70 min, and was monitored by the TLC (silica gel plates, 5×10 cm, eluted with ethyl acetate-methanol 95:5 mixture). Ethyl ether (100 ml) was added, precipitated product was filtered off and rinsed with ether (2×50 ml). The filter cake was air-dried for 1 hour then placed in an vacuum oven at 35° C. and the oven evacuated (5 torr). Product was dried to constant mass for 7 hours. Yield was 5.24 g. LC-MS (m/e): 335 (M+1); purity: 100% (254 nm).

Example SP-273

N¹-{(1S,2R)-1-(3,5-difluorobenzyl)-3-[(3-ethylbenzyl)amino]-2-hydroxypropyl}-5-ethynyl-N³,N³-dipropylisophthalamide

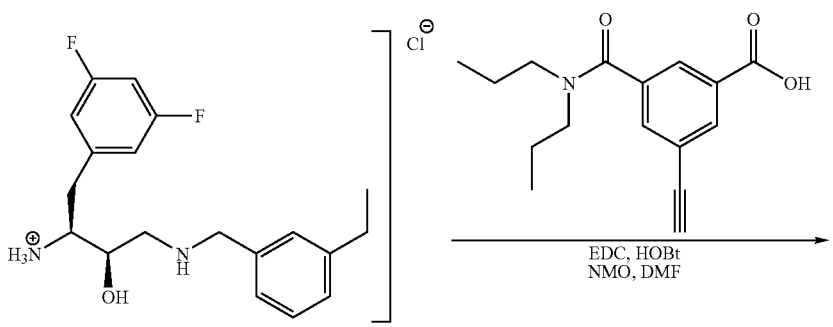

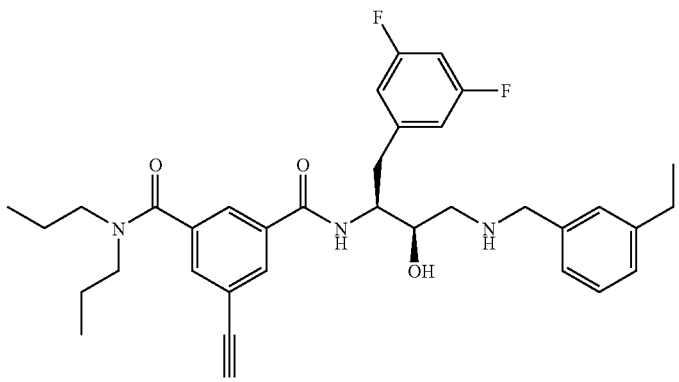

The 5-ethynyl-N,N-dipropyl-iso-phthalamic acid (1.64 g, 0.006m) was dissolved in anhydrous DMF (30 ml) in an round-bottom flask (50 ml) equipped with magnetic stirring bar. Flask was flushed with nitrogen and HOBt (1.23 g, 0.009 m, 1.5 eq), followed by EDC (1.63 g, 0.0084 m, 1.4 eq) were added. This mixture was stirred for 45 min at RT and then was added in one portion to the stirred solution of amine hydrochloride (2.45 g, 0.006 m) in anhydrous DMF (30 ml) and NMO (5.0 g, 0.05 m, 8.5 eq). The resulted heterogeneous mixture was vigorously stirred under nitrogen at RT for 2 hr. During that time all solids gradually dissolved, mixture remained however cloudy. Reaction progress was monitored by TLC (silica gel plates, 5×10 cm, eluted with ethyl acetate-methanol 95:5 mixture). Product was isolated by diluting reaction mixture with sat. aq. sodium bicarbonate (250 ml) and extraction with ethyl acetate (3×150 ml). Combined extracts were washed with brine and dried over magnesium sulfate. Solution was filtered and evaporated, yield of crude product was 4.6 g (yellow oil). Product was purified using flash column chromatography on silica gel (Flash 65i cartridge, applied in dichloromethane solution and eluted with ethyl acetate-methanol 93:7 mixture). Fractions containing product were combined and evaporated to give pale yellow oil, 2.7 g. LC-MS (m/e): 590 (M+1); 100% (254 nm). Purified product was treated with ethanolic hydrogen chloride (1.05 eq), filtered and lyophilized. Yield of final hydrochloride salt was 2.4 g. LC-MS (m/e) 590 (M+1); purity: 100% (254 nm), 100% (280 nm).

$^1$H—NMR (MeOH-d4): δ 0.70 (t, 3H), 1.01 (t, 3H), 1.23 (t, 3H), 1.53 (m, 2H), 1.73 (m, 2H), 2.67 (q, 2H), 2.87 (m, 1H), 3.05-3.35 (m, 8H), 4.00 (s, 1H), 4.01 (m, 1H), 4.25 (m, 3H), 4.91 (s), 6.77 (m, 1H), 6.91 (d, 2H), 7.29-7.38 (m, 4H), 7.56 (d, 2H), 7.79 (s, 1H). $^{13}$C-NMR: (MeOH-d4): 9.73, 10.17, 20.17, 21.33, 46.51-48.32, 49.27, 50.71, 54.04, 68.75, 79.79, 80.94, 101.17 (t), 111.56 (d), 123.26, 124.83, 127.00, 128.73, 129.23, 130.53, 130.95, 132.15, 134.29, 137.46, 142.69, 142.81, 145.17, 161.28 (d), 164.40 (d), 167.13, 170.28. Analysis: for $C_{35}H_{42}ClF_2N_3O_3 \times 0.5\ H_2O$ calcd.: C, 66.18; H, 6.82; N, 6.62; Cl, 5.58; found: C, 66.07; H, 6.85; N, 6.79; Cl, 5.17.

Example SP-274

Preparation of $N^1$-{(1S,2R)-1-(3,5-difluorobenzyl)-3-[(3-ethylbenzyl)amino]-2-hydroxypropyl}-$N^3$,$N^3$-dipropyl-5-(1,3-thiazol-2-yl)isophthalamide

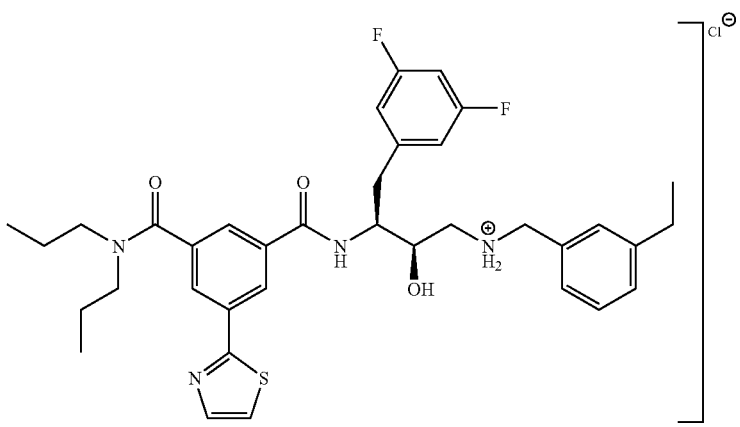

The N,N-dipropyl-5-thiazol-2-yl-iso-phthalamic acid (1.99 g, 0.006 m) was dissolved in anhydrous DMF (30 ml) in an round-bottom flask (50 ml) equipped with magnetic stirring bar. Flask was flushed with nitrogen and HOBt (1.24 g, 0.009 m, 1.5 eq), followed by EDC (1.63 g, 0.0084 m, 1.4 eq) were added. This mixture was stirred for 45 min at RT and then was added in one portion to the stirred solution of amine hydrochloride (2.45 g, 0.006 m) in anhydrous DMF (30 ml) and NMO (5.0 g, 0.05 m, 8.5 eq). The resulted heterogeneous mixture was vigorously stirred under nitrogen at RT for 2 hr. During that time all solids gradually dissolved, mixture remained however slightly cloudy. Reaction progress was monitored by TLC (silica gel plates, 5×10 cm, eluted with ethyl acetate-methanol 95:5 mixture). Product was isolated by diluting reaction mixture with sat. aq. sodium bicarbonate (250 ml) and extraction with ethyl acetate (3×150 ml). Combined extracts were washed with brine and dried over magnesium sulfate. Solution was filtered and evaporated, yield of crude product was 4.2 g (pale yellow oil). Product was purified using flash column chromatography on silica gel (Flash 65i cartridge, applied in dichloromethane solution and eluted with ethyl acetate-methanol 9:1 mixture),. Fractions containing product were combined and evaporated to give pale yellow oil, 2.75 g. LC-MS (m/e): 649 (M+1); purity: 100% (254 nm). Purified product was treated with ethanolic hydrogen chloride (1.05 eq) and lyophilized (added ethanol to improve solubility before filtration). Yield of final hydrochloride salt was 2.6 g. LC-MS (m/e): 649 (M+1); purity: 100% (254 nm).

$^1$H-NMR (MeOH-d4): δ 0.74 (t, 3H), 1.04 (t, 3H), 1.20 (t, 3H), 1.58 (m, 2H), 1.77 (m, 2H), 2.64 (q, 2H), 2.92 (m, 1H), 3.10-3.55 (m, 9H), 4.04 (m, 1H), 4.26 (m, 2H), 4.90 (s), 6.77 (m, 1H), 6.96 (d, 2H), 7.23-7.38 (m, 4H), 7.68 (t, 1H), 7.73 (d, 1H), 7.96 (d, 1H), 8.11 (t, 1H), 8.28 (t, 1H). $^{13}$C-NMR: (MeOH-d4): 9.76, 10.19, 14.75, 20.21, 21.39, 28.10, 35.38, 46.60-48.31, 50.75, 54.12, 68.78, 101.22 (t), 111.53 (d), 120.48, 125.65, 126.12, 126.97, 128.70, 129.218, 130.56, 133.96, 134.97, 138.00, 142.84, 143.53, 145.16, 161.31 (d), 164.52 (d), 165.96, 167.36, 170.47. Analysis for $C_{36}H_{43}ClF_2N_4O_3S\times0.5\ H_2O$ calcd.: C, 62.28; H, 6.39; N, 8.07; Cl, 5.11; found: C, 62.42; H, 6.24; N, 8.03; Cl, 5.10.

Example SP-275

2-Dipropylcarbamoyl-6-methyl-isonicotinic acid

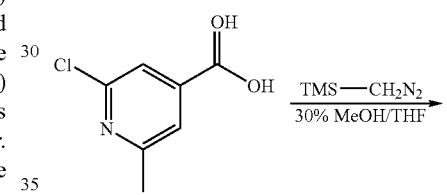

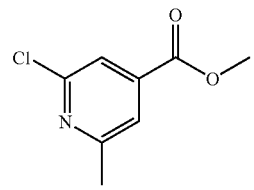

Commercially available, 2-chloro-methylisotinic acid (4.07 g, 23.72 mmol) was dissolved in a 30% MeOH/THF solution (32 ml). (Trimethylsilyl)diazomethane (2.0 M solution in hexanes) was added dropwise. Bubbling was observed and more reagent was added until bubbling ceased (15 mL). The reaction mixture was allowed to stir overnight at room temp. Prior to evaporation of solvent, glacial acetic acid was added to the reaction flask dropwise in order to rid of excess amine.

Example SP-276

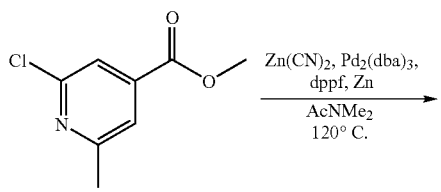

-continued

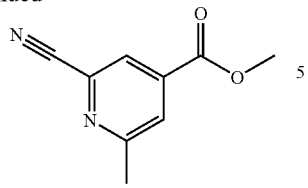

Reference: Fuqiang, J. and Confalone, N. Tet. Lett., 41, 2000, 3271-3273

Into a R.B flask equipped with a stir bar was added the methylated intermediate, tri(dibenzlideneacetone)dipalladium(0), 1,1-bis(diphenylphosphine), zinc metal dust and zinc cyanide. The flask was flushed with nitrogen gas for approx. 5 min. N,N-dimethylacetamide was added via syringe. The reaction mixture was refluxed in an oil bath set at 120° C. with a condenser under nitrogen atmosphere. Stir vigorously. After 4 h, the reaction mixture was partitioned between ethyl acetate (50 ml) and 2N NH$_4$OH (50 ml) Repeat washing with 2N NH$_4$OH (2×50 ml) followed by brine (50 ml). Organic phases were collected and dried over Na$_2$SO$_4$, filtered and evaporated. Purification by column chromatography was performed with eluting solvent (80:20;Hex/EtOac).

Example SP-277

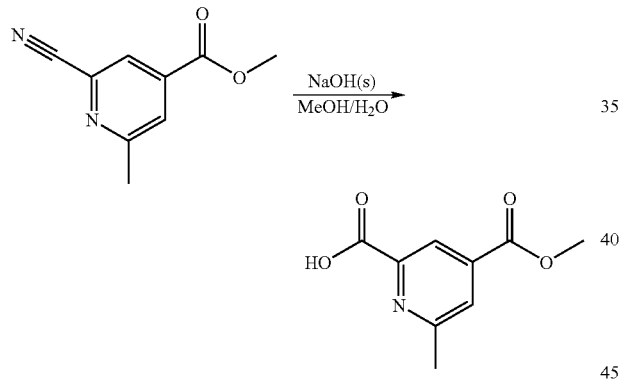

Dissolve nitrile intermediate (0.206 g, 1.170 mmol) in methanol (5 ml). Add sodium hydroxide (0.267 g, 6.675 mmol) and continue to stir at room temp. After 90 min add water (5 ml) and continue to stir for an additional 90 min. Partition between chloroform and 2 N HCl (aq). Add NaCl(s) to aqueous phase in order to saturate. Continue extraction with isopropanol:chloroform (1:3). Collect organic phases, dry over NaSO$_4$, filter and evaporate.

Example SP-278

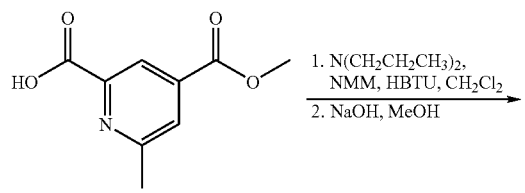

-continued

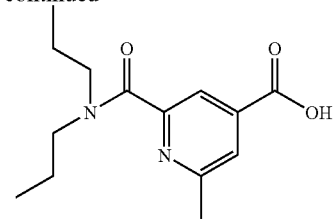

Anhydrous dichloromethane was added to the hydrolyzed intermediate (0.136, 0.697 mmol) followed by 4-methylmorpholine. The flask was placed on an ice bath to cool prior to addition of HBTU and dipropylamine. The mixture was allowed to warm to room temp. over night under nitrogen atmosphere. Partition reaction mixture between ethyl acetate (25 ml) and water (25 ml). Wash with water followed by sat. NaHCO$_3$ (2×25 ml). Organic phase was collected, dried over Na$_2$SO$_4$, filtered and evaporated.

Example SP-279

$N^1$-{(1S,2R)-1-(3,5-difluorobenzyl)-3-[(3-ethylbenzyl)amino]-2-hydroxypropyl}-5-(4-methyl-1,3-oxazol-2-yl)-$N^3$,$N^3$-dipropylisophthalamide

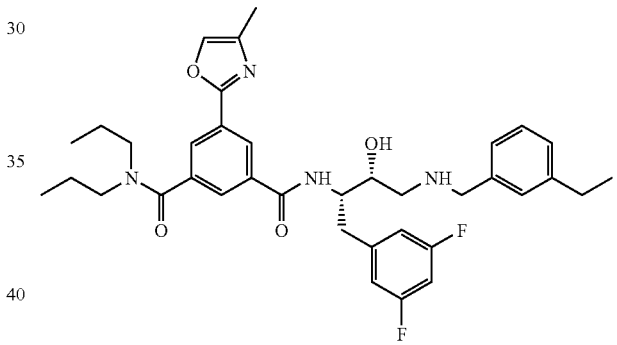

Step 1: A stirred solution of methyl 3-(aminocarbonyl)-5-[(dipropylamino)carbonyl]benzoate (200 mg, 0.65 mmol) chloroacetone (10 mL, 93 mmol) and potassium carbonate (90 mg, 0.65 mmol) was refluxed for 18 h. The reaction mixture was cooled to room temperature, diluted with ethyl acetate, washed with 2 N sodium hydroxide (2×50 mL), and saturated sodium chloride, dried (magnesium sulfate),. and concentrated under reduced pressure. Purification by flash column chromatography (silica, 1:1 ethyl acetate/hexanes) provided methyl 3-[(dipropylamino)carbonyl]-5-(4-methyl-1,3-oxazol-2-yl)benzoate (119 mg): $^1$H NMR (300 MHz, CDCl$_3$) δ 8.70 (d, J=1 Hz, 1H), 8.20 (d, J=1 Hz, 1H), 8.09 (d, J=1 Hz, 1H), 7.48 (s, 1H), 3.96 (s, 3H), 3.46 (d, J=7 Hz, 2H), 3.16 (t, J=7 Hz, 2H), 2.26 (s, 3H), 1.71 (d, J=7 Hz, 2H), 1.54 (d, J=7 Hz, 2H), 1.00 (t, J=7 Hz, 3H), 0.74 (t, J=7 Hz, 3H); ESI MS m/z 345 [M+H]$^+$.

Step 2: A solution of methyl 3-[(dipropylamino)carbonyl]-5-(4-methyl-1,3-oxazol-2-yl)benzoate (118 mg, 0.34 mmol) in methanol (1 mL) and potassium hydroxide (1 mL of a 1.0 M solution in water, 1 mmol) was stirred at room temperature for 45 min. The solvent was removed under reduced pressure, the residue was dissolved in water, extracted with ethyl acetate, the aqueous layer was acidified to pH 4 with 1 N hydrochloric acid, extracted with chloroform (3×100 mL), and the combined organics were concentrated under reduced pressure to afford 3-[(dipropylamino)carbonyl]-5-(4-methyl-1,3-oxazol-2-yl)benzoic acid (110 mg): $^1$H NMR (300 MHz, CD$_3$OD) δ 8.66 (d, J=1 Hz, 1H), 8.17 (d, J=1 Hz, 1H), 8.07 (d, J=1 Hz, 1H), 7.75 (d, J=1 Hz, 1H), 3.51 (t, J=7 Hz, 2H), 3.25 (t, J=7 Hz, 2H), 2.23 (s, 3H), 1.74 (d, J=7 Hz, 2H), 1.60 (d, J=7 Hz, 2H), 1.01 (t, J=7 Hz, 3H), 0.76 (t, J=7 Hz, 3H).

Step 3: A solution of 3-[(dipropylamino)carbonyl]-5-(4-methyl-1,3-oxazol-2-yl)benzoic acid (77.5 mg, 0.23 mmol), (2R,3S)-3-amino-4-(3,5-difluorophenyl)-1-[(3-ethylbenzyl)amino]butan-2-ol dihydrochloride (96 mg, 0.23 mmol), HOBt (32 mg, 0.23 mmol), and N-methylmorpholine (83 µL, 0.75 mmol) was stirred in dimethylformamide (2 mL) for 15 min. EDC (73 mg, 0.42 mmol) was added and the reaction mixture was stirred overnight. The reaction mixture was diluted with water, and extracted with ethyl acetate (3×25 mL) The organic layer was washed with 1 N hydrochloric acid (25 mL), saturated sodium bicarbonate (25 mL), saturated sodium chloride, dried (sodium sulfate), and concentrated under reduced pressure. Purification by flash column chromatography (silica, 1:9 methanol/chloroform) provided N$^1$-{(1S,2R)-1-(3,5-difluorobenzyl)-3-[(3-ethylbenzyl)amino]-2-hydroxypropyl}-5-(4-methyl-1,3-oxazol-2-yl)-N$^3$,N$^3$-dipropylisophthalamide (40 mg): $^1$H NMR (300 MHz, CDCl$_3$) δ 8.20 (br s, 1H, —NH), 8.17 (s, 1H), 8.05 (s, 1H), 7.52 (s, 1H), 7.38 (s, 1H), 7.24-7.08 (m, 5H), 7.02 (d, J=8 Hz, 2H), 6.61 (t, J=8 Hz, 1H), 4.27 (br s, 1H), 3.93 (d, J=4 Hz, 1H), 3.85 (s, 2H), 3.54 (br s, 2H), 3.43 (br s, 2H), 2.84 (d, J=5 Hz, 2H), 2.63 (q, J=8 Hz, 2H), 2.18 (s, 3H), 1.74 (t, J=5 Hz, 2H), 1.41 (d, J=7 Hz, 2H), 1.22 (t, J=8 Hz, 3H), 1.03 (t, J=7 Hz, 3H), 0.64 (t, J=7 Hz, 3H); ESI MS m/z 647 [M+H]$^+$ Example SP-280

N$^1$-{(1S,2R)-1-(3,5-difluorobenzyl)-3-[(3-ethylbenzyl)amino]-2-hydroxypropyl}-N$^3$,N$^3$-dipropyl-5-(1,3-thiazol-2-yl)isophthalamide

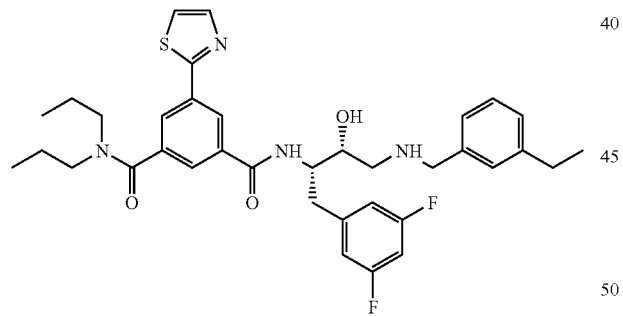

Step 1: To a −78° C. solution of thiazole (1.2 g) in THF (25 mL) was added n-butyl lithium (1.6 M in hexanes, 10 mL). The mixture was stirred for 30 min and then allowed to warm to 0° C. in an ice/water bath. Zinc chloride (1M in ethyl ether, 40 mL) was added and the mixture was stirred for 1 h, at which time methyl 3-[(dipropylamino)carbonyl]-5-iodobenzoate (5.1 g) in THF (20 mL) was added, followed by Pd(PPh$_3$)$_4$ (palladium tetrakis triphenylphosphine) (0.68 g). The mixture was then heated at 80° C. for 2 h, at which time it was allowed to cool and partitioned between ethyl acetate and water. The organic layers were washed with brine, dried (magnesium sulfate), and concentrated. The residue was chromatographed on silica gel using ethyl acetate/heptane (50/50) to give 4.5 g of methyl 3-[(dipropylamino)carbonyl]-5-(1,3-thiazol-2-yl)benzoate.

Step 2: Methyl 3-[(dipropylamino)carbonyl]-5-(1,3-thiazol-2-yl)benzoate (4.5 g) was dissolved in THF (20 mL), methanol (20 mL), and water (20 mL). Lithium hydroxide monohydrate (1.1 g) was added and the mixture was stirred at room temperature for 1.5 h, at which time the organic solvents were removed under reduced pressure. Some ethyl acetate and water were added and the pH was adjusted to about 0 with aq. HCl. The mixture was extracted with ethyl acetate and the organic layers were washed with brine, dried (magnesium sulfate), and concentrated to give 3.8 g of 3-[(dipropylamino)carbonyl]-5-(1,3-thiazol-2-yl)benzoic acid Step 3: A solution of 3-[(dipropylamino)carbonyl]-5-(1,3-thiazol-2-yl)benzoic acid (156 mg, 0.47 mmol), (2R,3S)-3-amino-4-(3,5-difluorophenyl)-1-[(3-ethylbenzyl)amino]butan-2-ol dihydrochloride (191 mg, 0.47 mmol), HOBt (64 mg, 0.47 mmol), and N-methylmorpholine (200 µL, 1.5 mmol) was stirred in dimethylformamide (2 mL) for 15 min. EDC (145 mg, 0.84 mmol) was added and the reaction mixture was stirred overnight. The reaction mixture was diluted with water, and extracted with ethyl acetate (3×25 mL). The organic layer was washed with 1 N hydrochloric acid (25 mL), saturated sodium bicarbonate (25 mL), saturated sodium chloride, dried (sodium sulfate), and concentrated under reduced pressure. Purification by flash column chromatography (silica, 1:9 methanol/chloroform) provided N$^1$-{(1S,2R)-1-(3,5-difluorobenzyl)-3-[(3-ethylbenzyl)amino]-2-hydroxypropyl}-N$^3$,N$^3$-dipropyl-5-(1,3-thiazol-2-yl)isophthalamide (33 mg): $^1$H NMR (500 MHz, CDCl$_3$) δ 8.40 (br s, 1H, —NH), 8.15 (br s, 1H), 7.94 (br s, 1H), 7.80 (d, J=3 Hz, 1H), 7.51 (br s, 1H), 7.34 (d, J=3 Hz, 1H), 7.27-7.24 (m, 1H), 7.21-7.18 (m, 2H), 7.11-7.10 (m, 1H), 7.00 (br s, 1H), 6.62-6.58 (m, 1H), 4.23 (d, J=5 Hz, 1H), 3.91-3.85 (m, 3H), 3.57 (br s, 2H), 3.31 (br s, 2H), 3.05 (d, J=5 Hz, 4H), 2.83 (d, , J=6 Hz, 2H), 2.64 (q, J=8 Hz, 2H), 1.75 (br s, 2H), 1.44 (t, J=7 Hz, 2H), 1.22 (t, J=8 Hz, 3H) 1.04 (t, J=7 Hz, 3H), 0.65 (t, J=7 Hz, 3H); ESI MS m/z 649 [M+H]$^+$;

Example SP-281

N$^1$-{(1S,2R)-1-(3,5-difluorobenzyl)-3-[(3-ethylbenzyl)amino]-2-hydroxypropyl}-5-(1,3-oxazol-2-yl)-N$^3$,N$^3$-dipropylisophthalamide

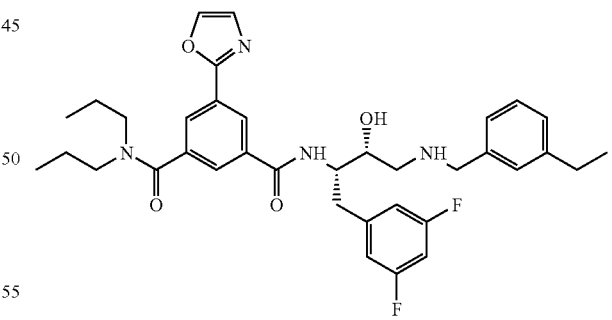

Step 1. To an ice-cold, stirred solution of 3-amino-5-(methoxycarbonyl)benzoic acid (5.19 g, 26.59 mmol) in a 2 N hydrochloric acid (156 mL) was added a solution of sodium nitrite (1.84 g, 26.67 mmol) in water (10.8 mL). This mixture was then added dropwise to an ice-cold, stirred solution of potassium iodide (8.84 g, 53.25 mmol) in water (26.2 mL). After stirring for 35 min, the reaction mixture was diluted with water and extracted with ethyl acetate. The organic layer was washed with 5% aqueous sodium thiosulfate, and saturated sodium chloride, dried (sodium sulfate), and concentrated under reduced pressure. Purification by flash column chromatography (silica, 50:50:2 hexanes/ethyl acetate/acetic acid) afforded 3-iodo-5-(methoxycarbonyl)benzoic acid (4.48 g): $^1$H NMR (500 MHz, DMSO-d$_6$): δ 13.49 (br s, 1H), 8.45-8.38 (m, 3H), 3.83 (s, 3H); ESI-MS (m/z): 305 [M+H]$^+$.

Step 2: To a mixture of 3-iodo-5-(methoxycarbonyl)benzoic acid (65.8 g, 0.215 mol), triethylamine (52.2 g, 0.516 mol), and dipropylamine (23.9 g, 0.237 mol) in methylene chloride (950 mL) was added 2-chloro-1-methylpyridinium iodide (65.9 g, 0.258 mol). The reaction mixture was stirred at room temperature for 15 h and then concentrated under reduced pressure. Purification by silica gel plug (3:1 hexanes/ethyl acetate) provided methyl 3-[(dipropylamino)carbonyl]-5-iodobenzoate (66.8 g): $^1$NMR (300 MHz, CDCl3) δ 8.39 (s, 1H), 7.98 (s, 1H), 7.88 (s, 1H), 3.93 (s, 3H), 3.45 (m, 2H), 3.14 (m, 2H), 1.69 (m, 2H), 1.54 (m, 2H), 0.98 (m, 3H), 0.77 (m, 3H).

Step 3: A stirred solution of 2-triethylstannyloxazole (Chem. Mater. 1994, 6, 1023) (1.5 g, 5.5 mmol) and methyl 3-[(dipropylamino)carbonyl]-5-iodobenzoate (1.8 g, 4.6 mmol) in dimethylformamide (12 mL) was degassed under reduced pressure for 15 min and purged with argon. Palladium(0)tetrakis(triphenylphosphine) (158 mg, 0.14 mmol) was added and the reaction mixture was degassed under reduced pressure for 15 min and then purged with argon. The reaction mixture was heated at reflux for 2 d, cooled to room temperature, diluted with ethyl acetate, washed with water (3×50 mL), dried (sodium sulfate), and concentrated under reduced pressure. Purification by flash column chromatography (silica, 1:1 ethyl acetate/hexanes) provided methyl 3-[(dipropylamino)carbonyl]-5-(1,3-oxazol-2-yl)benzoate (423 mg): $^1$H NMR (300 MHz, CDCl$_3$) δ 8.73 (s, 1H), 8.23 (s, 1H), 8.11 (s, 1H), 7.76 (s, 1H), 7.28 (s, 1H), 3.97 (s, 3H), 3.49 (br s, 2H), 3.18 (br s, 2H), 1.72 (d, J=7 Hz, 2H), 1.55 (d, J=7 Hz, 2H), 1.00 (t, J=7 Hz, 3H), 0.75 (t, J=7 Hz, 3H).

Step 4: A solution of methyl 3-[(dipropylamino)carbonyl]-5-(1,3-oxazol-2-yl)benzoate (315 mg, 0.95 mmol) in methanol (3 mL) and potassium hydroxide (3 mL of a 1.0 M solution in water, 3 mmol) was stirred at room temperature for 30 min. The solvent was removed under reduced pressure, the residue was dissolved in water, and extracted with ethyl acetate. The aqueous layer was acidified to pH 3 with 1 M hydrochloric acid, extracted with chloroform (3×100 mL), and the combined organic layers were concentrated under reduced pressure to afford 3-[(dipropylamino)carbonyl]-5-(1,3-oxazol-2-yl)benzoic acid (265 mg): $^1$H NMR (300 MHz, CD$_3$OD) δ 8.71 (s, 1H), 8.08 (s, 2H), 8.05 (s, 1H), 7.34 (s, 1H), 3.52 (t, J=8 Hz, 2H), 3.26 (t, J=8 Hz, 2H), 1.75 (q, J=8 Hz, 2H), 1.59 (q, J=8 Hz, 2H), 1.02 (t, J=8 Hz, 3H), 0.74 (t, J=8 Hz, 3H).

Step 5: A solution of 3-[(dipropylamino)carbonyl]-5-(1,3-oxazol-2-yl)benzoic acid (133 mg, 0.42 mmol), (2R,3S)-3-amino-4-(3,5-difluorophenyl)-1-[(3-ethylbenzyl)amino]butan-2-ol dihydrochloride (171 mg, 0.42 mmol), HOBt (57 mg, 0.42 mmol), and N-methylmorpholine (148 μL, 1.3 mmol) was stirred in dimethylformamide (2 mL) for 15 min. EDC (130 mg, 0.75 mmol) was added and the reaction mixture was stirred overnight. The reaction mixture was diluted with water, and extracted with ethyl acetate (3×25 mL). The organic layer was washed with 1 M hydrochloric acid (25 mL), saturated sodium bicarbonate (25 mL), saturated sodium chloride, dried (sodium sulfate), and concentrated under reduced pressure. Purification by flash column chromatography (silica, 1:9 methanol/chloroform) provided N$^1$-{(1S,2R)-1-(3,5-difluorobenzyl)-3-[(3-ethylbenzyl)amino]-2-hydroxypropyl}-5-(1,3-oxazol-2-yl)-N$^3$,N$^3$-dipropylisophthalamide (62 mg): mp 65-67° C.; $^1$H NMR (500 MHz, CDCl$_3$) δ 8.21 (br s, 1H), 8.15 (s, 2H), 7.69 (s, 1H), 7.60 (s, 1H), 7.25 (t, J=8 Hz, 1H), 7.19-7.17 (m, 3H), 7.10 (d, J=8 Hz, 1H), 6.96 (d, J=8 Hz, 2H), 6.60 (t, J=8 Hz, 1H), 4.27 (d, J=8 Hz, 1H), 3.88-3.80 (m, 3H), 3.53 (br s, 2H), 3.44 (br s, 2H), 3.09-3.01 (m, 4H), 2.85-2.82 (m, 2H), 2.62 (t, J=8 Hz, 2H), 1.74 (br s, 2H), 1.45 (br s, 2H), 1.21 (t, J=8 Hz, 3H), 1.03 (t, J=7 Hz, 3H), 0.66 (t, J=7 Hz, 3H); APCI MS m/z 633 [M+H]$^+$ Example SP-281

N$^1$-{(1S,2R) -1-(3,5-Difluorobenzyl)-3-[(3-ethylbenzyl)amino]-2-hydroxypropyl}-N$^3$-methyl-5-(1,3-oxazol-2-yl)-N$^3$-propylisophthalamide

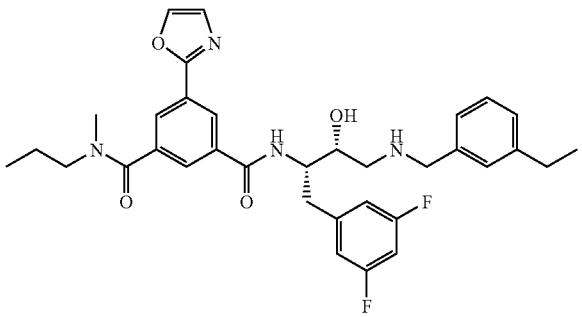

To 3-{[Methyl(propyl)amino]carbonyl}-5-(1,3-oxazol-2-yl)benzoic acid (350 mg, 1.2 mmol) in DMF (5 mL) is added diisopropylethylamine (835 μL, 4.8 mmol), HATU (554 mg, 1.5 mmol), then (2R,3S)-3-amino-4-(3,5-difluorophenyl)-1-[(3-ethylbenzyl)amino]butan-2-ol dihydrochloride prepared by the method of Example SP-272 (488 mg, 1.2 mmol). The reaction is stirred for 16 h at room temperature. The reaction is partitioned between chloroform and water. The organic layer is washed with 1 N hydrochloric acid, saturated sodium bicarbonate, and saturated sodium chloride, dried (sodium sulfate), filtered, and concentrated under reduced pressure. Purification by flash column chromatography (silica, 9% methanol/chloroform) gives the title compound. ESI MS m/z 605.3 [M+H]$^+$.

Example SP-282

Step 1
Methyl 3-{[butyl(methyl)amino]carbonyl}-5-iodobenzoate

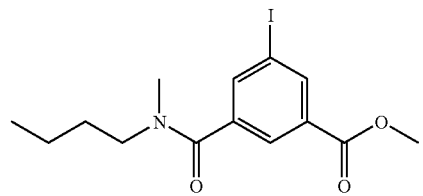

3-Iodo-5-(methoxycarbonyl)benzoic acid (1 g, 3.3 mmol) is dissolved in DMF (10 mL), and diisopropylethylamine (1.7 mL, 9.8 mmol), HATU (1.5 g, 3.9 mmol), and N-methylbutylamine (581 μL, 4.9 mmol) are added. The reaction stirred at room temperature 2 h. The reaction is partitioned between ethyl acetate and water. The organic layer is washed with saturated sodium bicarbonate, and saturated sodium chloride, dried (sodium sulfate), filtered, and concentrated under reduced pressure. Purification by flash column chromatography (silica, 40% ethyl acetate/hexane) provides the title compound. ESI MS m/z 376.1 [M+H]⁺.

Step 2

Methyl 3-{[butyl(methyl)amino]carbonyl}-5-(1,3-oxazol-2-yl)benzoate

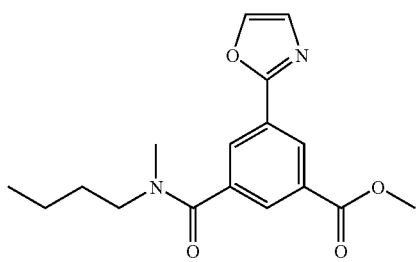

To a −70° C. stirred solution of oxazole (167 mg, 2.4 mmol) in tetrahydrofuran (4 mL) is added n-butyllithium (1.6 M in hexanes, 1.7 mL, 2.7 mmol). After 30 min, zinc chloride (1 M in diethyl ether, 7.3 mL, 7.3 mmol) is added and the reaction mixture is warmed to 0° C. for 1 h. To this mixture is added a solution of methyl 3-{[butyl(methyl)amino]carbonyl}-5-iodobenzoate (864 mg, 2.3 mmol) in anhydrous tetrahydrofuran (3 mL) followed by palladium(0)tetrakis(triphenylphosphine) (112 mg, 0.10 mmol). The reaction mixture is heated at reflux for 1.5 h. The reaction mixture is cooled, diluted with ethyl acetate, washed with water, and saturated sodium chloride, dried (sodium sulfate), filtered, and concentrated under reduced pressure. Purification by flash column chromatography (silica gel, 60% ethyl acetate/hexane) provides the title compound. ESI MS m/z 317.1 [M+H]⁺.

Step 3

3-{[Butyl(methyl)amino]carbonyl}-5-(1,3-oxazol-2-yl)benzoic acid

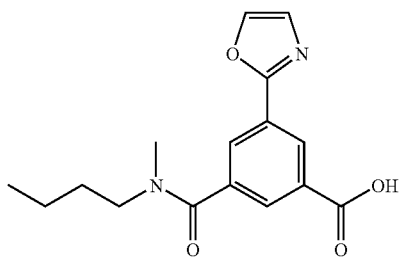

To methyl 3-{[butyl(methyl)amino]carbonyl}-5-(1,3-oxazol-2-yl)benzoate (660 mg, 2.1 mmol) in tetrahydrofuran/methanol/water (1:1:1, 9 mL) is added lithium hydroxide monohydrate (175 mg, 4.2 mmol), and the reaction is stirred at room temperature 16 h. The solution is diluted in chloroform and washed with water and saturated sodium chloride, dried (sodium sulfate), filtered, and concentrated under reduced pressure to give the title compound. ESI MS m/z 301.1 [M−H]⁻.

Step 4

N¹-butyl-N³-{(1S,2R)-1-(3,5-difluorobenzyl)-3-[(3-ethylbenzyl)amino]-2-hydroxypropyl}-N¹-methyl-5-(1,3-oxazol-2-yl)isophthalamide

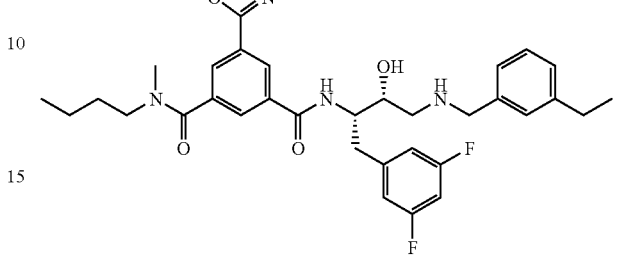

3-{[Butyl(methyl)amino]carbonyl}-5-(1,3-oxazol-2-yl)benzoic acid (237 mg, 0.78 mmol) is dissolved in DMF (5 mL), and diisopropylethylamine (546 µL, 3.1 mmol), HATU (358 mg, 0.94 mmol), and (2R,3S)-3-amino-4-(3,5-difluorophenyl)-1-[(3-ethylbenzyl)amino]butan-2-ol dihydrochloride prepared by the method of EXAMPLE SP-272 (319 mg, 0.78 mmol) are added. The reaction stirred at room temperature 5 h. The reaction mixture is diluted with chloroform, washed with water, 1N hydrochloric acid (aq), saturated sodium bicarbonate, saturated sodium chloride, dried (sodium sulfate), filtered, and concentrated under reduced pressure. Purification by flash column chromatography (silica, 9% methanol/methylene chloride) provides the title compound. ESI MS m/z 619.3 [M+H]⁺.

Example SP-283

N¹-{(1S,2R)-1-(3,5-difluorobenzyl)-3-[(3-ethylbenzyl)amino]-2-hydroxypropyl}-N³-ethyl-5-(1,3-oxazol-2-yl)-N³-propylisophthalamide Step 1

Methyl 3-{[ethyl(propyl)amino]carbonyl}-5-iodobenzoate

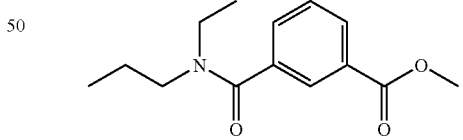

3-Iodo-5-(methoxycarbonyl)benzoic acid (1 g, 3.3 mmol) is dissolved in DMF (10 mL), and diisopropylethylamine (1.7 mL, 9.8 mmol), HATU (1.5 g, 3.9 mmol), and N-ethylpropylamine (572 µL, 4.9 mmol) are added. The reaction stirred at room temperature 16 h. The reaction is partitioned between ethyl acetate and water. The organic layer is washed with saturated sodium bicarbonate, and saturated sodium chloride, dried (sodium sulfate), filtered, and concentrated under reduced pressure. Purification by flash column chromatography (silica, 40% ethyl acetate/hexane) provides the title compound. ESI MS m/z 376.1 [M+H]⁺.

Step 2

Methyl 3-{[ethyl(propyl)amino]carbonyl}-5-(1,3-oxazol-2-yl)benzoate

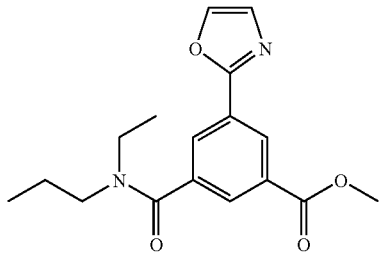

To a −70° C. stirred solution of oxazole (106 mg, 1.5 mmol) in tetrahydrofuran (4 mL) is added n-butyllithium (1.6 M in hexanes, 1.0 mL, 1.7 mmol). After 30 min, zinc chloride (1 M in diethyl ether, 4.6 mL, 4.6 mmol) is added and the reaction mixture is warmed to 0° C. for 1 h. To this mixture is added a solution of methyl 3-{[ethyl(propyl)amino]carbonyl}-5-iodobenzoate (535 mg, 1.45 mmol) in anhydrous tetrahydrofuran (1.8 mL) followed by palladium(0)tetrakis(triphenylphosphine) (120 mg, 0.10 mmol). The reaction mixture is heated at reflux for 2 h. The reaction mixture is cooled, diluted with ethyl acetate, washed with water, and saturated sodium chloride, dried (sodium sulfate), filtered, and concentrated under reduced pressure. Purification by flash column chromatography (silica gel, 60% ethyl acetate/hexane) provides the title compound. ESI MS m/z 317.1 $[M+H]^+$.

Step 3

3-{[Ethyl(propyl)amino]carbonyl}-5-(1,3-oxazol-2-yl)benzoic acid

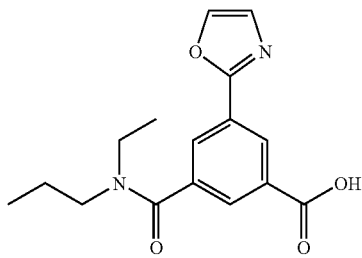

To methyl 3-{[ethyl(propyl)amino]carbonyl}-5-(1,3-oxazol-2-yl)benzoate (375 mg, 1.2 mmol) in tetrahydrofuran/methanol/water (1:1:1, 9 mL) is added lithium hydroxide monohydrate (100 mg, 2.4 mmol), and the reaction is stirred at room temperature 16 h. The solution is diluted in chloroform and washed with water and saturated sodium chloride, dried (sodium sulfate), filtered, and concentrated under reduced pressure to give the title compound. ESI MS m/z 301.1 $[M-H]^-$.

Step 4

$N^1$-{(1S,2R)-1-(3,5-Difluorobenzyl)-3-[(3-ethylbenzyl)amino]-2-hydroxypropyl}-$N^3$-ethyl-5-(1,3-oxazol-2-yl)-$N^3$-propylisophthalamide

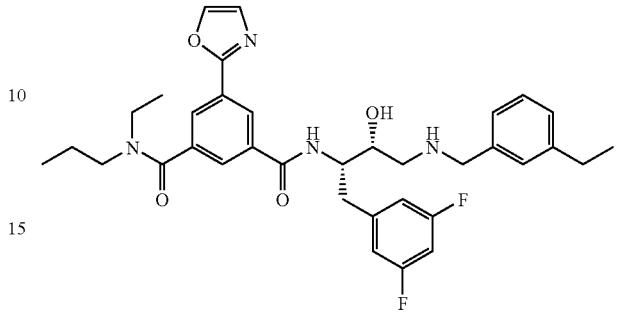

3-{[Ethyl(propyl)amino]carbonyl}-5-(1,3-oxazol-2-yl)benzoic acid (290 mg, 0.96 mmol) is dissolved in DMF (5 mL), and diisopropylethylamine (668 µL, 3.8 mmol), HATU (438 mg, 1.15 mmol), and (2R,3S)-3-amino-4-(3,5-difluorophenyl)-1-[(3-ethylbenzyl)amino]butan-2-ol dihydrochloride prepared by the method of EXAMPLE SP-272 (391 mg, 0.96 mmol) are added. The reaction stirred at room temperature 5 h. The reaction mixture is diluted with chloroform, washed with water, 1N hydrochloric acid (aq), saturated sodium bicarbonate, saturated sodium chloride, dried (sodium sulfate), filtered, and concentrated under reduced pressure. Purification by flash column chromatography (silica, 9% methanol/methylene chloride) provides the title compound. ESI MS m/z 619;3 $[M+H]^+$.

Example SP-284

$N^1$-((1S,2R)-1-(3,5-difluorobenzyl)-2-hydroxy-3-{[3-(trifluoromethyl)benzyl])amino}propyl)-$N^3$,$N^3$-dipropyl-5-(1,3-thiazol-2-yl)isophthalamide Step 1

Methyl 3-[(dipropylamino)carbonyl]-5-(1,3-thiazol-2-yl)benzoate

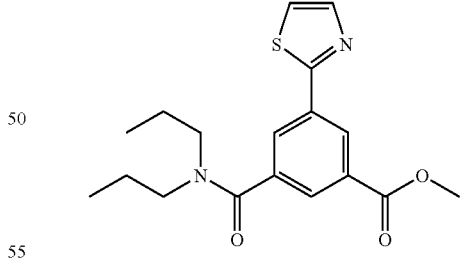

To 0.5M thiazole zinc bromide (45 mL) is added methyl 3-[(dipropylamino)carbonyl]-5-iodobenzoate (8.6 g, 21.4 mmol) in THF (130 mL), then palladium(0)tetrakis(triphenylphosphine) (2 g, 1.7 mmol) are added. The reaction mixture is heated at reflux for 16 h, cooled to room temperature, and then filtered. The solution is washed with water, saturated sodium bicarbonate, and saturated sodium chloride, dried (magnesium sulfate), filtered, and concentrated under reduced pressure. Purification by flash column chromatography (35% ethyl acetate/hexane) yields the title compound. ESI MS m/z 347.1 $[M+H]^+$.

Step 2

3-[(Dipropylamino)carbonyl]-5-(1,3-thiazol-2-yl)benzoic acid

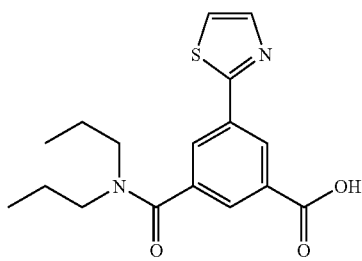

Methyl 3-[(dipropylamino)carbonyl]-5-(1,3-thiazol-2-yl)benzoate (4.4 g, 12.8 mmol) is dissolved in 1:1:1 tetrahydrofuran/methanol/water (60 mL), and lithium hydroxide monohydrate is added (1.1 g, 25.6 mmol), and the reaction stirred 15 min. The solution is concentrated under reduced pressure and diluted in chloroform. The solution is washed with water and saturated sodium bicarbonate, dried (magnesium sulfate), filtered, and concentrated under reduced pressure to give the title compound. ESI MS m/z 333.1 [M+H]$^+$.

Step 3

$N^1$-((1S,2R)-1-(3,5-Difluorobenzyl)-2-hydroxy-3-{[3-(trifluoromethyl)benzyl]amino}propyl)-$N^3$,$N^3$-dipropyl-5-(1,3-thiazol-2-yl)isophthalamide dihydrochloride

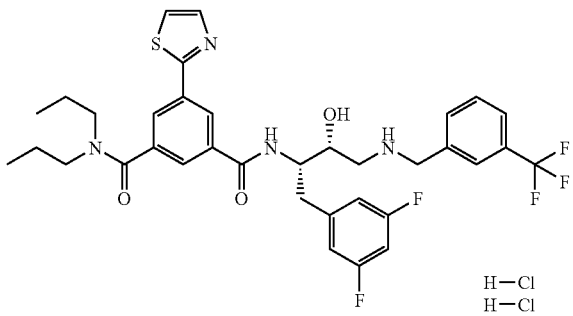

3-[(Dipropylamino)carbonyl]-5-(1,3-thiazol-2-yl)benzoic acid is dissolved in DMF (10 mL), and diisopropylethylamine (364 μL, 2.1 mmol), HATU (237 mg, 0.62 mmol), (2R,3S)-3-amino-4-(3,5-difluorophenyl)-1-{[3-(trifluoromethyl)benzyl]amino}butan-2-ol dihydrochloride prepared by the method of EXAMPLE SP-311 (250 mg, 0.52 mmol) are added. The reaction stirred at room temperature 4 h. The reaction mixture is diluted with chloroform, washed with water, saturated sodium bicarbonate, saturated sodium chloride, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (2 mL) is added. The mixture is concentrated under reduced pressure to yield the title compound. ESI MS m/z 689.3 [M+H]$^+$.

Example SP-285

Step 1

3-{[Butyl(methyl)amino]carbonyl}-5-(1,3-thiazol-2-yl)benzoic acid

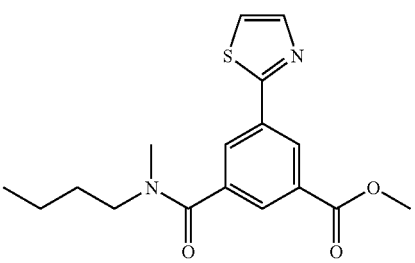

To 0.5M thiazole zinc bromide (4.5 mL) is added methyl 3-{[butyl(methyl)amino]carbonyl}-5-iodobenzoate (700 mg, 1.9 mmol) in THF (5 nL), then palladium(0)tetrakis(triphenylphosphine) (175 mg, 0.15 mmol) are added. The reaction mixture is heated at reflux for 16 h, cooled to room temperature, and then filtered. The solution is washed with water, saturated sodium bicarbonate, and saturated sodium chloride, dried (magnesium sulfate), filtered, and concentrated under reduced pressure. Purification by flash column chromatography (35% ethyl acetate/hexane) yields the title compound. ESI MS m/z 333.1 [M+H]$^+$.

Step 2

3-{[Butyl(methyl)amino]carbonyl}-5-(1,3-thiazol-2-yl)benzoic acid

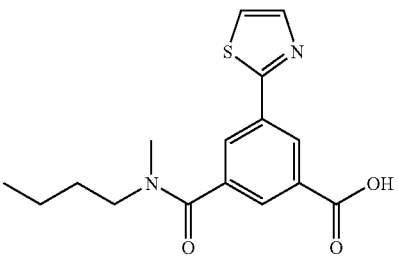

3-{[Butyl(methyl)amino]carbonyl}-5-(1,3-thiazol-2-yl)benzoic acid (410 mg, 1.23 mmol) is dissolved in 1:1:1 tetrahydrofuran/methanol/water (9 mL), and lithium hydroxide monohydrate is added (103 mg, 2.5 mmol), and the reaction stirred 16 h. The solution is concentrated under reduced pressure and diluted in ethyl acetate. The solution is washed with water and saturated sodium bicarbonate, dried (magnesium sulfate), filtered, and concentrated under reduced pressure to give the title compound. ESI MS m/z 319.1 [M+H]$^+$.

Step 3

N$^1$-Butyl-N$^3$-{(1S,2R)-1-(3,5-difluorobenzyl)-3-[(3-ethylbenzyl)amino]-2-hydroxypropyl}-N$^1$-methyl-5-(1,3-thiazol-2-yl)isophthalamide

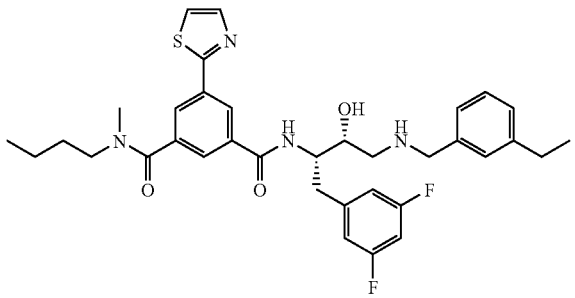

3-{[Butyl(methyl)amino]carbonyl}-5-(1,3-thiazol-2-yl)benzoic acid (125 mg, 0.39 mmol) is dissolved in DMF (3 mL), and diisopropylethylamine (271 µL, 1.6 mmol), HATU (178 mg, 0.47 mmol), (2R,3S)-3-amino-4-(3,5-difluorophenyl)-1-{[3-(trifluoromethyl)benzyl]amino}butan-2-ol dihydrochloride (176 mg, 0.43 mmol) are added. The reaction stirred at room temperature 4 h. The reaction mixture is diluted with chloroform, washed with water, saturated sodium bicarbonate, saturated sodium chloride, dried (sodium sulfate), filtered, and concentrated under reduced pressure. Purification by flash column chromatography (silica, 8% methanol/methylene chloride) provides the title compound as the free base. The residue is dissolved in diethyl ether (3 mL) and 1N hydrochloric acid in diethyl ether (2 mL) is added. The mixture is concentrated under reduced pressure to yield the title compound. ESI MS m/z 635.3 [M+H]$^+$.

Example SP-286

Step 1

Methyl 3-{[methyl(propyl)amino]carbonyl}-5-(1,3-thiazol-2-yl)benzoate

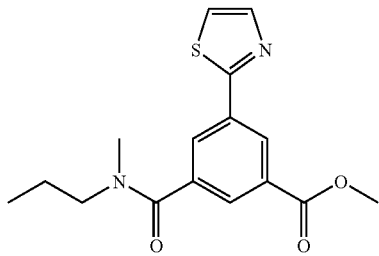

To 0.5M thiazole zinc bromide (4.1 mL) is added methyl 3-iodo-5-{[methyl(propyl)amino]carbonyl}benzoate (616 mg, 1.7 mmol) in THF (5 mL), then palladium(0)tetrakis(triphenylphosphine) (158 mg, 0.14 mmol) are added. The reaction mixture is heated at reflux for 16 h, cooled to room temperature, and then filtered. The solution is washed with water, saturated sodium bicarbonate, and saturated sodium chloride, dried (magnesium sulfate), filtered, and concentrated under reduced pressure. Purification by flash column chromatography (35% ethyl acetate/hexane) yields the title compound. ESI MS m/z 319.1 [M+H]$^+$.

Step 2

N$^1$-{(1S,2R)-1-(3,5-Difluorobenzyl)-3-[(3-ethylbenzyl)amino]-2-hydroxypropyl}-N$^3$-methyl-5-(1,3-thiazol-2-yl)-N$^3$-propylisophthalamide

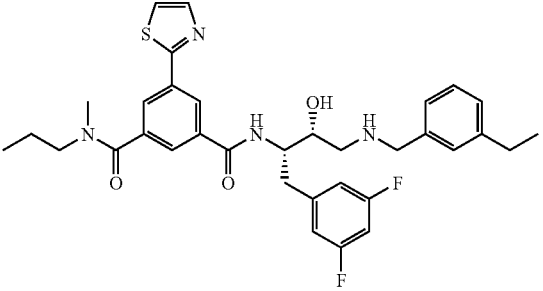

Methyl 3-{[methyl(propyl)amino]carbonyl}-5-(1,3-thiazol-2-yl)benzoate (390 mg, 1.22 mmol) is dissolved in 1:1:1 tetrahydrofuran/methanol/water (9 mL), and lithium hydroxide monohydrate is added (103 mg, 2.4 mmol), and the reaction stirred 2 h. The solution is concentrated under reduced pressure. The residue is redissolved in DMF (5 mL), and diisopropylethylamine (355 µL, 2.0 mmol), HATU (230 mg, 0.61 mmol), (2R,3S)-3-amino-4-(3,5-difluorophenyl)-1-[(3-ethylbenzyl)amino]butan-2-ol dihydrochloride prepared by the method of EXAMPLE SP-272 (206 mg, 0.51 mmol) are added. The reaction stirred at room temperature 16 h. The reaction mixture is diluted with ethyl acetate, washed with water, saturated sodium bicarbonate, saturated sodium chloride, dried (sodium sulfate), filtered, and concentrated under reduced pressure. Purification by flash column chromatography (silica, 9% methanol/methylene chloride) provides the title compound. ESI MS m/z 621.3 [M+H]$^+$.

Example SP-287

{(1S,2R)-1-(3,5-difluorobenzyl)-3-[(3-ethylbenzyl)amino]-2-hydroxypropyl}-dipropyl-5-pyridin-4-ylisophthalamide dihydrochloride Step 1: To a stirred solution of borate ester methyl 3-[(dipropylamino)carbonyl]-5-(3,3,4,4-tetramethylborolan-1-yl)benzoate dissolved in 1,4-dioxane (9.3 mL) was added sodium carbonate (2 mL of a 2 M solution in water, 4 mmol), 4-bromopyridine hydrochloride (250 mg, 1.3 mmol), and the reaction mixture was degassed for 15 min. The reaction mixture was flushed with argon and heated to reflux overnight. The reaction mixture was cooled to room temperature, diluted with water, extracted with ethyl acetate (3×50 mL), dried (magnesium sulfate), filtered, and concentrated under reduced pressure. Purification by flash column chromatography (silica, 1:1 ethyl acetate/hexanes) provided methyl 3-[(dipropylamino)carbonyl]-5-pyridin-4-ylbenzoate (240 mg): $^1$H NMR (300 MHz, CDCl$_3$) δ 8.46 (d, J=7 Hz, 2H), 8.10 (t, J=3 Hz, 1H), 8.04 (t, J=3 Hz, 1H), 7.97 (t, J=3 Hz, 1H), 7.48 (d, J=6 Hz, 2H), 3.45 (m, 2H), 3.16 (m, 2H), 2.09 (s, 3H), 1.69 (m, 2H), 1.54 (m, 2H), 0.94 (m, 3H), 0.74 (m, 3H).

Step 2: To a stirred solution of 1-methyl 3-[(dipropylamino)carbonyl]-5-pyridin-4-ylbenzoate (240 mg, 0.7 mmol) in methanol (1.5 mL), tetrahydrofuran (0.7 mL), and water (0.7 mL) was added lithium hydroxide (58 mg, 1.4 mmol). The reaction mixture was stirred for 4 h, and concentrated under reduced pressure. The residue was dissolved in water, and extracted with ethyl acetate (3×75 mL). The aqueous layer was acidified to pH 5 with 1 N hydrochloric acid and extracted with chloroform (4×50 mL). The combined organic extracts were dried (magnesium sulfate), filtered, and concentrated under reduced pressure to provide a pyridine (160 mg): $^1$H NMR (300 MHz, CDCl$_3$) δ 8.79 (d, J=5 Hz, 2H), 8.45 (s, 1H), 8.19 (s, 1H), 7.89 (s, 1H), 7.69 (d, J=6 Hz, 2H), 3.50 (d, J=7 Hz, 2H), 1.74 (d, J=7 Hz, 2H), 1.02 (m, 3H), 0.78 (m, 3H).

Step 3: To a stirred solution of pyridine from step 3 (160 mg, 0.49 mmol) in dichloromethane (1.96 mL) was added DIPEA (190 mg, 1.47 mmol), HATU (278 mg, 0.73 mmol), and HOBt (99 mg, 0.73 mmol), followed by amine 2 (200 mg, 0.49 mmol). The reaction mixture was stirred overnight at room temperature. The reaction mixture was partitioned between dichloromethane and water. The organic layer was washed with saturated sodium bicarbonate, saturated sodium chloride, dried (magnesium sulfate), filtered, and concentrated under reduced pressure. The resulting oil was dissolved in a minimal amount of methanol, and precipitated with hydrochloric acid (10 mL of a 1 M solution in diethyl ether, 10 mmol). The precipitate was filtered, washed with diethyl ether, and dried under vacuum to afford the title compound (100 mg): mp 166-169° C.; APCI MS m/z 643 [M+H]$^+$.

Example SP-288

N-{(1S,2R) -1-(3,5-difluorobenzyl)-3-[(3-ethylbenzyl) amino]-2-hydroxypropyl}-4-[(methylsulfonyl)methyl]piperidine-1-carboxamide Step 1: To an ice-cold, stirred solution of acid 1-(tert-butoxycarbonyl)piperidine-4-carboxylic acid (1.0 g, 4.4 mmol) in tetrahydrofuran (11 mL) was added borane-dimethylsulfide complex (3.4 mL of a 2.0 M solution in tetrahydrofuran, 6.8 mmol). After 2 h, the reaction mixture was quenched with methanol, and concentrated under reduced pressure to provide an alcohol (939 mg): $^1$H NMR (300 MHz, CDCl$_3$) δ 4.11 (br s, 2H), 3.50 (t, J=6 Hz, 2H), 2.68 (d, J=12 Hz, 2H), 1.74-1.65 (m, 3H), 1.45 (s, 9H), 1.31 (t, J=7 Hz, 1H), 1.14 (dd, J=12, 4 Hz, 2H).

Step 2: To an ice-cold, stirred solution of the alcohol from step 1 (450 mg, 2.1 mmol) and triethylamine (0.32 mL, 2.3 mmol) in tetrahydrofuran (6 mL) was added methanesulfonyl chloride (0.18 mL, 2.3 mmol). The reaction mixture was stirred for 5 min and then sodium iodide (375 mg, 2.3 mmol) was added. The reaction mixture was warmed to room temperature and filtered. To the collected filtrate was added sodium thiomethoxide (161 mg, 2.3 mmol) and the reaction mixture was heated at reflux for 24 h. The reaction mixture was cooled to room temperature, diluted with ethyl acetate, washed with water, and saturated sodium chloride, dried (sodium sulfate), filtered, and concentrated under reduced pressure to provide tert-butyl 4-[(methylthio)methyl]piperidine-1-carboxylate (430 mg): $^1$H NMR (300 MHz, CDCl$_3$) δ 4.11 (t, J=7 Hz, 2H), 2.69 (t, J=12 Hz, 2H), 2.42 (d, J=7 Hz, 2H), 2.10 (s, 3H), 1.83-1.78 (m, 2H), 1.66-1.59 (mn, 2H), 1.45 (s, 9H), 1.26-1.06 (m, 2H).

Step 3: A solution of sulfide from step 2 (420 mg, 1.7 mmol), hydrogen peroxide (11 mL of a 30% solution in water, 170 mmol), and sodium bicarbonate (143 mg, 1.7 mmol) in acetone (10 mL) was stirred for 18 h. The reaction mixture was washed with 1.3 N sodium hydroxide, and saturated sodium chloride, dried (magnesium sulfate), filtered, and concentrated under reduced pressure to provide a sulfone (390 mg): $^1$H NMR (300 MHz, CDCl$_3$) □ 4.11 (t, J=7 Hz, 2H), 2.94 (s, 3H), 2.81-2.73 (m, 2H), 2.35-2.20 (m, 2H), 1.96-1.91 (m, 2H), 1.45 (s, 9H), 1.38-1.23 (m, 3H).

Step 4: A solution of sulfone from step 3 (390 mg, 1.4 mmol) and hydrochloric acid (4 mL of a 4 M solution in dioxane, 14 mmol) was stirred for 18 h. The resulting precipitate was collected by filtration to provide tert-butyl 4-[(methylsulfonyl)methyl]piperidine-1-carboxylate (220 mg): $^1$H NMR (300 MHz, DMSO-d$_6$) δ 8.94 (br s, 1H), 8.70 (br s, 1H), 3.24-3.15 (m, 4H), 3.00 (s, 3H), 2.89 (q, J=7 Hz, 2H), 2.29-2.18 (m, 1H), 1.97 (d, J=13 Hz, 2H), 1.57-1.43 (m, 2H).

Step 5: To an ice-cold, stirred solution of triphosgene (108 mg, 0.36 mmol) and diisopropylethylamine (0.6 mL, 3.3 mmol) in methylene chloride (2.0 mL) was added amino sulfone from step 4 (210 mg, 0.98 mmol) in methylene chloride (3.5 mL) dropwise. After 5 min a solution of dihydrochloride of (2R,3S)-3-amino-4-(3,5-difluorophenyl)-1-[(3-ethylbenzyl)amino]butan-2-ol (401 mg, 0.98 mmol) was added and the reaction mixture was warmed until the solution became homogeneous. The reaction mixture was diluted with methylene chloride, washed with 1 N hydrochloric acid (25 mL), saturated sodium bicarbonate (25 mL), and saturated sodium chloride, dried (magnesium sulfate), filtered, and concentrated under reduced pressure. Purification by flash column chromatography (silica, 15:85 methanol/chloroform) provided a clear solid. The solid was dissolved in methanol (1 mL), and treated with hydrochloric acid (0.3 mL of a 1.0 M solution in diethyl ether, 0.3 mmol). The resulting precipitate was collected by filtration to provide the title compound (38 mg): mp 130-134° C.; APCI MS m/z 538 [M+H]$^+$.

Example SP-289

N-{(1S,2R)-1-(3,5-difluorobenzyl)-3-[(3-ethylbenzyl) amino]-2-hydroxypropyl}-4-[(methylsulfonyl)methyl]cyclohexane carboxamide Step 1: To a stirred solution of dimethyl cyclohexane-1,4-dicarboxylate (10.2 g, 51 mmol) in a mixture of 2:1:1 tetrahydrofuran/methanol/water (52 mL) was added lithium hydroxide (2.13 g, 51 mmol). The reaction mixture was stirred at room temperature for 18 h. The solvent was removed under reduced pressure and the residue was partitioned between diethyl ether and water. The aqueous layer was acidified to pH 4 with 1 N hydrochloric acid, and the precipitate collected, and dried under vacuum to afford 4-(methoxycarbonyl)cyclohexanecarboxylic acid (7.4 g): $^1$H NMR (300 MHz, CDCl$_3$) δ 3.68 (s, 3H), 2.33-2.27 (m, 2H), 2.11-2.06 (m, 4H), 1.50-1.43 (m, 4H).

Step 2: To an ice-cold, stirred solution of acid (3.2 g, 17 mmol) in tetrahydrofuran (40 mL) was added borane-dimethyl sulfide complex (12 mL, 22 mnol) The reaction mixture was heated at 70° C. for 2 h and a 1:1 mixture of acetic acid/water (10 mL) added. The resulting mixture was concentrated. Purification by flash column chromatography (silica, 1:1 hexanes/ethyl acetate) provided methyl 4(hydroxymethyl)cyclohexanecarboxylate (1.26 g): $^1$H NMR (300 MHz, CDCl$_3$) δ 3.67 (s, 3H), 3.48-3.46 (m, 2H), 2.26-2.15 (m, 1H), 2.05-1.85 (m, 4H), 1.52-1.42 (m, 3H), 1.02-0.97 (m, 2H).

Step 3: To an ice-cold, stirred solution of the alcohol (365 mg, 2.12 mmol) and triethylamine (440 µL, 4.8 mmol) in methylene chloride (5 mL) was added mesyl chloride (200 µL, 2.6 mmol). The reaction mixture was stirred for 20 min and then partitioned between methylene chloride and water. The organic layer was washed with 1 M hydrochloric acid, and saturated sodium bicarbonate, dried (magnesium sulfate), and concentrated under reduced pressure to afford a the desired mesylate, which was carried on without purification or characterization.

Step 4: To a stirred solution of the mesylate from step 3 (2.12 mmol) in tetrahydrofuran (5 mL) was added sodium iodide (640 mg, 4.3 mmol). The reaction mixture was heated to 60° C. for 5 h and then filtered. The reaction mixture was concentrated under reduced pressure, and carried on without purification or characterization.

Step 5: To a stirred solution of the iodide from step 4 (2.12 mmol) in a mixture of N,N-dimethylformamide (10 mL) and tetrahydrofuran (1 mL) was added sodium thiomethoxide (450 mg, 6.4 mmol). The reaction mixture was heated at 70° C. for 15 h. The reaction mixture was allowed to cool to room temperature, the solvents were removed, and the residue was partitioned between ether and water. The aqueous layer was acidified to pH 1 with 1 N hydrochloric acid, extracted with ethyl acetate, dried (sodium sulfate), filtered, and concentrated under reduced pressure to afford methyl 4-[(methylthio)methyl]cyclohexanecarboxylate (230 mg): $^1$H NMR (300 MHz, $CD_3OD$) δ 2.40-2.37 (m, 2H), 2.22-2.05 (m, 1H), 2.05 (s, 3H), 2.02-1.93 (m, 4H), 1.48-1.38 (m, 3H), 1.03-0.95 (m, 2H).

Step 6: To a stirred solution of the methyl sulfide (240 mg, 1.3 mmol) in sodium hydroxide solution (3.5 mL, 0.5 M solution) was added sodium bicarbonate (870 mg, 10.3 mmol) and acetone (1 mL) followed by the addition of a solution of oxone (1.0 g, 1.7 mmol) in 0.0004 M EDTA (4 mL). The reaction mixture was stirred at room temperature for 2 h and then quenched with sodium bisulfite. The reaction mixture was acidified with hydrochloric acid and extracted with ethyl acetate (3×100 mL). The combined organic layers were washed with water, dried (sodium sulfate), filtered, and concentrated under reduced pressure to provide acid 4-[(methylthio)methyl]cyclohexanecarboxylic acid (240 mg): $^1$H NMR (300 MHz, $CD_3OD$) δ 3.06-3.04 (m, 2H), 2.96 (s, 3H), 2.28-2.20 (m, 1H), 2.08-1.98 (m, 5H), 1.50-1.40 (m, 2H), 1.21-1.16 (m, 2H).

Step 7: To a stirred solution of the acid (120 mg, 0.6 mmol), (2R,3S)-3-amino-4-(3,5-difluorophenyl)-1-[(3-ethylbenzyl)amino]butan-2-ol (230 mg, 0.6 mmol), and HATU (210 mg, 0.6 mmol) in methylene chloride (5 mL) was added N,N-diisopropylethylamine (340 µL, 1.93 mmol). The reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 95:5 to 93:7 methylene chloride/methanol) provided the title compound (35 mg): mp 178-180° C.; ESI MS m/z 537 [M+H]$^+$.

Example SP-290

N-{(1S,2R)-1-(3,5-difluorobenzyl)-3-[(3-ethylbenzyl)amino]-2-hydroxypropyl}-5-piperidin-4-yl-N\(u)3\(d),N\(u)3\(d)-dipropylisophthalamide Step 1: To a −70° C. stirred solution of N-Boc-piperidone (500 mg, 2.5 mmol) in tetrahydrofuran (11 mL) was added lithium diisopropylamine (1.37 mL of a 2 M solution in tetrahydrofuran, 2.75 mmol). The reaction mixture was stirred for 2 h, warmed to 0° C., and N-phenyltriflamide (955 mg, 2.67 mmol) was added. The solution was allowed to warm to room temperature and was stirred for 12 h. The reaction mixture was concentrated under reduced pressure. Purification by flash column chromatography (3:1 hexanes/ethyl acetate) afforded tert-butyl 4-{[(trifluoromethyl)sulfonyl]oxy}-3,6-dihydropyridine-1(2H)-carboxylate (240 mg): $^1$H NMR (300 MHz, $CDCl_3$) δ 5.77 (s, 1H), 4.05 (m, 2H), 3.63 (m, 2H), 2.45 (m, 2H), 1.48 (s, 9H).

Step 2: To a stirred solution of the triflate (240 mg, 0.72 mmol) and borate ester methyl 3-[(dipropylamino)carbonyl]-5-(3,3,4,4-tetramethylborolan-1-yl)benzoate (280 mg, 0.72 mmol) in dioxane (3 mL) was added sodium carbonate (1.1 mL of a 2 M solution in water, 2.16 mmol). The reaction mixture was flushed with argon, palladium(0)tetrakis(triphenylphosphine) (34 mg, 0.03 mmol) was added, and the reaction mixture was heated at reflux for 12 h. The reaction mixture was cooled to room temperature, filtered through diatomaceous earth, dried (magnesium sulfate), filtered, and concentrated under reduced pressure. Purification by flash column chromatography (90:10 chloroform/methanol) afforded an acid (160 mg): $^1$H NMR (300 MHz, $CDCl_3$) δ 8.11 (s, 1H), 7.95 (s, 1H), 7.58 (s, 1H), 6.15 (br s, 1H), 4.10 (s, 2H), 3.65 (m, 2H), 3.48 (m, 2H), 3.16 (s, 2H), 2.54 (s, 2H), 1.70 (s, 2H), 1.50 (s, 9H), 1.25 (m, 2H), 0.99 (s, 3H), 0.76 (s, 3H).

Step 3: A solution of the acid from step 2 (160 mg, 0.37 mmol) and 10% Pd/C (25 mg) in ethanol (10 mL) was degassed with nitrogen for 15 min, and shaken under an atmosphere of hydrogen at 50 psi for 12 h. The reaction mixture was filtered through diatomaceous earth, and concentrated under reduced pressure to give acid 3-[1-(tert-butoxycarbonyl)piperidin-4-yl]-5-[(dipropylamino)carbonyl]benzoic acid (121 mg), which was carried on without further purification: $^1$H NMR (300 MHz, $CDCl_3$) δ 7.94 (d, J=12 Hz, 2H), 7.44 (s, 1H), 4.27 (br s, 2H), 3.43 (m, 2H), 3.14 (m, 2H), 2.78 (m, 4H), 1.84 (m, 3H), 1.63 (m, 6H), 1.49 (s, 9H), 1.23 (m, 3H), 0.86 (m, 3H), 0.75 (m, 3H).

Step 4: To a stirred solution of the acid (120 mg, 0.28 mmol) in methylene chloride (2 mL) was added N,N-diisopropylethylamine (0.141 mL, 0.84 mmol), HOBt (56 mg, 0.42 mmol), and HATU (160 mg, 0.42 mmol), followed by (2R,3S)-3-amino-4-(3,5-difluorophenyl)-1-[(3-ethylbenzyl)amino]butan-2-ol (114 mg, 0.28 mmol). The reaction mixture was stirred for 16 h at room temperature. The reaction mixture was diluted with methylene chloride (25 mL), washed with water, saturated sodium bicarbonate, and saturated sodium chloride, and dried (magnesium sulfate), filtered, and concentrated under reduced pressure. Purification by flash column chromatography (93:7 chloroform/methanol) afforded a piperidine (90 mg): $^1$H NMR (300 MHz, $CDCl_3$) δ 7.61 (s, 1H), 7.54 (s, 1H), 7.43 (s, 1H), 7.14 (m, 4H), 6.79 (m, 2H), 6.64 (m, 1H), 4.29 (m, 3H), 3.68 (m, 4H), 3.47 (m, 2H), 3.02 (m, 4H), 2.77 (m, 5H), 2.66 (m, 2H), 1.71 (m, 8H), 1.48 (s, 9H), 1.24 (m, 5H), 0.99 (m, 3H), 0.73 (m, 3H).

Step 5: A solution of piperidine from step 4 (90 mg, 0.12 mmol) and hydrochloric acid (0.3 mL of a 4.0 M solution in dioxane, 1.2 mmol) was stirred for 30 min at room temperature. The reaction mixture was concentrated under reduced pressure, washed with ether (50 mL), and filtered. Purification by flash column chromatography (89:10:1 chloroform/methanol/ammonium hydroxide) afforded the title compound (35 mg): mp 84-87° C.; ESI MS m/z 649 [M+H]$^+$.

Example SP-291

N-{(1S,2R)-1-(3,5-difluorobenzyl)-3-[(3-ethylbenzyl)amino]-2-hydroxypropyl}-3-methyl-5-(1,3-oxazol-2-yl)benzamide hydrochloride Step 1: To an ice-cold, stirred solution of acid 3-(methoxycarbonyl)-5-nitrobenzoic acid (24.6 g, 0.11 mol) in tetrahydrofuran (200 mL) was added borane-dimethylsulfide complex (82 mL of a 2.0 M solution in tetrahydrofuran, 0.16 mol) and the reaction mixture was heated at reflux for 24 h. The reaction mixture was cooled to room temperature, quenched with methanol, and the solvent was removed under reduced pressure. Purification by flash column chromatography (silica, 1:1 ethyl acetate/hexanes) provided an alcohol (16 g):

¹H NMR (300 MHz, DMSO-d₆) δ 8.51 (d, J=1 Hz, 1H), 8.42 (s, 1H), 8.32 (s, 1H), 5.69 (t, J=6 Hz, 1H), 4.70 (d, J=6 Hz, 2H), 3.93 (s, 3H).

Step 2: To an ice-cold, stirred solution of the alcohol from step 1 (6.6 g, 32 mmol) in methylene chloride was added phosphorus tribromide (1.5 mL, 16 mmol) and the reaction mixture was stirred for 40 min. The reaction mixture was diluted with methylene chloride, washed with saturated sodium bicarbonate, and saturated sodium chloride, dried (magnesium sulfate), filtered, and concentrated under reduced pressure to give a bromide (8.1 g): ¹H NMR (300 MHz, DMSO-d₆) δ 8.79 (t, J=2 Hz, 1H), 8.45 (t, J=2 Hz, 1H), 8.39 (d, J=2 Hz, 1H), 4.57 (s, 2H), 4.00 (s, 3H).

Step 3: A solution of bromide from step 2 (8.1 g, 32 mmol) and 10% Pd/C (1.0 g) in 13:4:1 methanol/ethyl acetate/acetic acid (90 mL) was shaken under an atmosphere of hydrogen at 45 psi for 24 h. The reaction mixture was filtered through diatomaceous earth, and concentrated under reduced pressure to provide 1 methyl 3-amino-5-methylbenzoate (2.8 g): ESI MS m/z 166 [M+H]⁺.

Step 4: To an ice-cold, stirred solution of the aniline (2.8 g, 17 mmol) in 2 N hydrochloric acid (48 mL) was added a solution of sodium nitrite (1.2 g, 17 mmol) in water (10 mL), and the reaction mixture was stirred for 30 min. This reaction mixture was added to an ice-cold, stirred solution of potassium iodide (5.6 g, 34 mmol) and copper(I) iodide (1.6 g, 8.6 mmol) in water (10 mL). The reaction mixture was warmed to room temperature over 2 h and then diluted with ethyl acetate. The organic layer was washed with a 10% solution of sodium thiosulfate, and saturated sodium chloride, dried (magnesium sulfate), filtered, and concentrated under reduced pressure. Purification by flash column chromatography (silica, 1:9 ethyl acetate/hexanes) provided an iodide (1.4 g): ¹H NMR (300 MHz, CDCl₃) δ 8.16 (s, 1H), 7.80 (d, J=1 Hz, 1H), 7.72 (d, J=1 Hz, 1H), 3.90 (s, 3H), 2.35 (s, 3H).

Step 5: To a −70° C. stirred solution of oxazole (174 mg, 2.5 mmol) in tetrahydrofuran (5 mL) was added n-butyllithium (1.7 mL of a 1.6 M solution in hexanes, 2.8 mmol). After 30 min, zinc chloride (7.5 mL of a 1 M solution in diethyl ether, 7.5 mmol) was added and the reaction mixture was warmed to 0° C. for 1 h. To this mixture was then added iodide from step 4 (695 mg, 2.5 mmol) followed by palladium (0)tetrakis(triphenylphosphine) (145 mg, 0.13 mmol). The reaction mixture was heated at reflux for 16 h. The reaction mixture was cooled, and diluted with ethyl acetate (50 mL). The organic layer was washed with water, and saturated sodium chloride, dried (magnesium sulfate), filtered, and concentrated under reduced pressure. Purification by flash column chromatography (silica, 1:1 ethyl acetate/hexanes) provided an oxazole (330 mg): ¹H NMR (300 MHz, CD₃OD) δ 8.45 (s, 1H), 8.08 (d, J=1 Hz, 1H), 8.01 (s, 1H), 7.97 (d, J=1 Hz, 1H), 7.32 (s, 1H), 3.95 (s, 3H), 2.48 (s, 3H); ESI MS m/z 218 [M+H]⁺.

Step 6: To a stirred solution of the ester from step 5 (384 mg, 1.7 mmol) in methanol (5 mL) was added potassium hydroxide (15 mL of a 1.0 M solution in water, 15 mmol). The reaction mixture was stirred at room temperature for 2 h and concentrated under reduced pressure. The residue was diluted with water and washed with ethyl acetate. The aqueous layer was acidified to pH 5 with 1 N hydrochloric acid and extracted with chloroform (4×100 mL). The combined organic extracts were dried (sodium sulfate), filtered, and concentrated under reduced pressure to give an acid (358 mg): ¹H NMR (300 MHz, DMSO-d₆) δ 13.2 (br s, 1H), 8.32 (s, 1H), 8.20 (s, 1H), 8.03 (s, 1H), 7.93 (s, 1H), 7.42 (s, 1H), 2.45 (s, 3H).

Step 7: A solution of the acid from step 6 (358 mg, 1.8 mmol), HATU (1.0 g, 2.6 mmol), HOBt (357 mg, 2.6 mmol), and diisopropylethylamine (500 μL, 2.6 mmol) was stirred in methylene chloride (2.0 mL) for 15 min. A solution of dihydrochloride of (2R,3S)-3-amino-4-(3,5-difluorophenyl)-1-[(3-ethylbenzyl)amino]butan-2-ol (718 mg, 1.8 mmol) and diisopropylethylamine (500 μL, 2.6 mmol) in methylene chloride (2.0 mL) was added and the reaction mixture was stirred overnight. The reaction mixture was diluted with methylene chloride, washed with 1 N hydrochloric acid (20 mL), saturated sodium bicarbonate (20 mL), and saturated sodium chloride, dried (magnesium sulfate), filtered, and concentrated under reduced pressure. Purification by flash column chromatography (silica, 1:9 methanol/chloroform) provided a clear solid. The solid was dissolved in methanol (2 mL), and treated with hydrochloric acid (0.5 mL of a 1.0 M solution in diethyl ether, 0.5 mmol). The resulting precipitate was collected by filtration to provide the title compound (250 mg): mp 105-107° C.; APCI MS m/z 520 [M+H]⁺.

Example SP-292

N-{(1S,2R)-1-(3,5-difluorobenzyl)-3-[(3-ethylbenzyl) amino]-2-hydroxypropyl}-5-[(methylsulfonyl)methyl] thiophene-2-carboxamide Step 1: To a solution of acid 5-(methoxycarbonyl) thiophene-2-carboxylic acid (1.00 g, 5.37 mmol) in tetrahydrofuran (21.5 mL) was added borane-dimethylsulfide complex (3.0 mL of a 2.0 M solution in tetrahydrofuran, 6.00 mmol). The reaction mixture was heated at reflux for 24 h and then carefully quenched with anhydrous methanol (1.0 mL) and cooled to room temperature. The reaction mixture was acidified with 1 N hydrochloric acid and extracted with ethyl acetate. The combined organic phases were washed with water, and saturated sodium chloride, dried (sodium sulfate), filtered, and concentrated to yield the desired alcohol (820 mg): ¹H NMR (300 MHz, CDCl₃) δ 7.65 (d, J=4 Hz, 1H), 6.96 (d, J=4 Hz, 1H), 4.83 (s, 2H), 3.87 (s, 3H).

Step 2: To a 0° C. solution of the alcohol prepared in step 1 (805 mg, 4.67) in tetrahydrofuran (31 mL) containing triethylamine (790 μL, 5.61 mmol) and dimethylaminopyridine (6 mg) was added methanesulfonyl chloride (400 μL, 5.14 mmol) and the reaction mixture was stirred for 0.5 h. The reaction mixture was filtered and the filtrate concentrated under reduced pressure to provide the crude mesylate, which was used in the next step without further purification: ¹H NMR (300 MHz, CDCl₃) δ 7.70 (m, 1H), 7.18 (m, 1H), 5.39 (s, 2H), 3.90 (s, 3H), 2.97 (s, 3H).

Step 3: To the mesylate prepared in step 2 in N,N-dimethylformamide (10 mL) was added sodium thiomethoxide (516 mg, 7.0 mmol) and the reaction mixture was warmed to 50° C. for 18 h. The reaction was diluted with water (200 mL) and extracted with chloroform (4×25 mL). The combined organic phases were washed with 5% lithium chloride, water, and saturated sodium chloride, dried (sodium sulfate), filtered, and concentrated under reduced pressure to give the desired sulfide (760 mg) which was used without further purification: ¹H NMR (300 MHz, CDCl₃) δ 7.64 (d, J=4 Hz, 1H), 6.93 (d, J=4 Hz, 1H), 3.89 (m, 5H), 2.08 (s, 3H).

Step 4: To a 0° C. solution of the sulfide prepared in step 3 (760 mg, 3.75 mmol) in chloroform (6.25 mL) was added 70% m-CPBA (2.31 g, 9.37 mmol) and the reaction stirred at 0° C. for 2.5 h. The reaction mixture was then diluted with chloroform and washed with 1 N sodium hydroxide, water, and saturated sodium chloride, dried (sodium sulfate), filtered, and concentrated under reduced pressure to provide the desired sulfone (780 mg) which was used without further purification: ¹H NMR (300 MHz, CDCl₃) δ 7.74 (d, J=4 Hz, 1H), 7.20 (d, J=4 Hz, 1H), 4.46 (s, 2H), 3.89 (m, 3H), 2.87 (s, 3H).

Step 5: To a solution of the sulfone prepared in step 4 (268 mg, 1.14 mmol) in 2:1:1 dioxane/methanol/water (7.6 mL) was added lithium hydroxide monohydrate (53 mg, 1.14 mmol) and the reaction mixture was stirred for 24 h at room temperature. The reaction mixture was concentrated under reduced pressure and the solid residue was partitioned between ethyl acetate and water. The aqueous phase was acidified with 1 N hydrochloric acid and extracted several times with diethyl ether. The combined ether extracts were washed with water, and saturated sodium chloride, dried (sodium sulfate), filtered, and concentrated under reduced pressure to provide 5-[(methylsulfonyl)methyl]thiophene-2-carboxylic acid (115 mg) which was used without further purification: ¹H NMR (300 MHz, CDCl₃) δ 7.73 (d, J=4 Hz, 1H), 7.20 (d, J=4 Hz, 1H), 4.52 (s, 2H), 2.90 (s, 3H); ESI MS (negative mode) m/z 219 [M−H]⁻.

Step 6: To a solution of acid from step 5 (115 mg, 0.52 mmol) and N,N-diisopropylethylamine (540 μL, 3.12 mmol) in methylene chloride (6.5 mL) was added HBTU (200 mg, 0.52 mmol) and the reaction mixture was stirred for 0.5 h. (2R,3S)-3-amino-4-(3,5-difluorophenyl)-1-[(3-ethylbenzyl)amino]butan-2-ol (211 mg, 0.52 mmol) was added in one portion and the reaction mixture was stirred at room temperature for 18 h. The reaction mixture was diluted with methylene chloride and washed with saturated sodium bicarbonate, and saturated sodium chloride, dried (sodium sulfate), filtered, and concentrated under reduced pressure. Purification by flash chromatography (silica, 1-5% methanol in chloroform) gave the title compound (45 mg): mp 128-131° C.; ESI MS m/z 537 [M+H]⁺.

Example SP-293

N-{(1S,2R)-1-(3,5-difluorobenzyl)-3-[(3-ethylbenzyl)amino]-2-hydroxypropyl}-3-methyl-5-(1,3-thiazol-2-yl)benzamide hydrochloride Step 1: To a −70° C. stirred solution of thiazole (214 mg, 2.5 mmol) in tetrahydrofuran (5 mL) was added n-butyllithium (1.7 mL of a 1.6 M solution in hexanes, 2.8 mmol). After 30 min, zinc chloride (7.5 mL of a 1 M solution in diethyl ether, 7.5 mmol) was added and the reaction mixture was warmed to 0° C. for 1 h. To this mixture was then added iodide described above (695 mg, 2.5 mmol) followed by palladium (0)tetrakis(triphenylphosphine) (145 mg, 0.13 mmol). The reaction mixture was heated at reflux for 16 h. The reaction mixture was cooled and diluted with ethyl acetate (50 mL). The organic layer was washed with water, and saturated sodium chloride, dried (magnesium sulfate), filtered, and concentrated under reduced pressure. Purification by flash column chromatography (silica, 1:1 ethyl acetate/hexanes) provided a thiazole (208 mg): ¹H NMR (300 MHz, CDCl₃) δ 8.38 (s, 1H), 8.02 (d, J=1 Hz, 1H), 7.92 (s, 1H), 7.88 (d, J=3 Hz, 1H), 7.37 (d, J=3 Hz, 1H), 3.95 (s, 3H), 2.48 (s, 3H).

Step 2: To a stirred solution of the ester from step 1 (208 mg, 0.89 mmol) in 2:1:1 methanol/tetrahydrofuran/water (4 mL) was added lithium hydroxide (75 mg, 1.8 mmol). The reaction mixture was stirred at room temperature for 3 h and concentrated under reduced pressure. The residue was diluted with water and washed with ethyl acetate. The aqueous layer was acidified to pH 5 with 1 N hydrochloric acid and extracted with chloroform (5×100 mL). The combined organic extracts were dried (sodium sulfate), filtered, and concentrated under reduced pressure to give an acid (146 mg): ¹H NMR (300 MHz, DMSO-d₆) δ 13.17 (br s, 1H), 8.28 (s, 1H), 8.01 (d, J=1 Hz, 1H), 7.96 (d, J=3 Hz, 1H), 7.85 (d, J=3 Hz, 2H), 2.45 (s, 3H).

Step 3: A solution of the acid from step 2 (140 mg, 0.64 mmol), HATU (364 mg, 0.96 mmol) and diisopropylethylamine (170 μL, 0.96 mmol) was stirred in methylene chloride (2.0 mL) for 15 min. A solution of dihydrochloride (2R,3S)-3-amino-4-(3,5-difluorophenyl)-1-[(3-ethylbenzyl)amino]butan-2-ol (318 mg, 0.64 mmol) and diisopropylethylamine (170 μL, 0.96 mmol) in methylene chloride (2.0 mL) was added and the reaction mixture was stirred overnight. The reaction mixture was diluted with methylene chloride, washed with 1 N hydrochloric acid (20 mL), saturated sodium bicarbonate (20 mL), and saturated sodium chloride, dried (magnesium sulfate), filtered, and concentrated under reduced pressure. Purification by flash column chromatography (silica, 1:9 methanol/chloroform) provided a clear solid. The solid was dissolved in methanol (1 mL), and treated with hydrochloric acid (0.5 mL of a 1.0 M solution in diethyl ether, 0.5 mmol). The resulting precipitate was collected by filtration to provide the title compound (100 mg): mp 178-180° C.; APCI MS m/z 536 [M+H]⁺.

Example SP-293

N-{(1S,2R)-1-(3,5-difluorobenzyl)-3-[(3-ethylbenzyl)amino]-2-hydroxypropyl}-4-[(methylsulfonyl)methyl]cyclohexanecarboxamide Step 1: To an ice-cold, stirred solution of cyclohexane-1,4-dicarboxylic acid (3.0 g, 17 mmol) in a mixture of 2:1 tetrahydrofuran/methanol (24 mL) was added trimethylsilyl diazomethane (9 mL of a 2.0 M in hexanes, 18 mmol). The reaction mixture was stirred at room temperature for 2 h. Acetic acid (5 mL) was added and the solvent was removed under reduced pressure. Purification by flash column chromatography (silica, 10:1:0.01 hexanes/ethyl acetate/acetic acid) provided 4-(methoxycarbonyl)cyclohexanecarboxylic acid (1.00 g): ¹H NMR (300 MHz, CDCl₃) δ 3.68 (s, 3H), 2.53-2.47 (m, 2H), 1.97-1.89 (m, 4H), 1.74-1.66 (m, 4H).

Step 2: To an ice-cold, stirred solution of acid from step 1 (700 mg, 3.8 mmol) in tetrahydrofuran (10 mL) was added borane-dimethyl sulfide complex (2 mL, 4.1 mmol). The reaction mixture was warmed to room temperature for 2 h and a 1:1 mixture of acetic acid/water (10 mL) was added. The resulting mixture was concentrated under reduced pressure. Purification by flash column chromatography (silica, 1:1 hexanes/ethyl acetate) provided methyl 4-(hydroxymethyl)cyclohexanecarboxylate (560 mg): ¹H NMR (500 MHz, CDCl₃) δ 3.68 (s, 3H), 3.51-3.46 (m, 2H), 2.59-2.57 (m, 1H), 2.05-2.00 (m, 2H), 1.65-1.55 (m, 5H), 1.31-1.27 (m, 2H).

Step 3: To an ice-cold, stirred solution of alcohol from step 2 (300 mg, 1.8 mmol) and triethylamine (370 μL, 2.7 mmol) in methylene chloride (5 mL) was added mesyl chloride (170 μL, 2.1 mmol). The reaction mixture was stirred for 20 min and then partitioned between methylene chloride and water. The organic layer was washed with 1 N hydrochloric acid, and saturated sodium bicarbonate, dried (magnesium sulfate), and concentrated under reduced pressure to afford a the desired mesylate, which was carried on without purification or characterization.

Step 4: To a stirred solution of the mesylate from step 3 (1.8 mmol) in tetrahydrofuran (5 mL) was added sodium iodide (530 mg, 3.5 mmol). The reaction mixture was heated at 60° C. for 5 h, cooled to room temperature, and then filtered. The reaction mixture was concentrated under reduced pressure, and carried on without purification or characterization.

Step 5: To a stirred solution of the iodide from step 4 (1.8 mmol) in a mixture of N,N-dimethylformaxmide (10 mL) and tetrahydrofuran (1 mL) was added sodium thiomethoxide (375 mg, 5.3 mmol). The reaction mixture was heated at 70° C. for 15 h. The reaction mixture was then cooled to room temperature, the solvents were removed, and the residue partitioned between ether and water. The aqueous layer was acidified to pH 1 with 1 N hydrochloric acid, extracted with ethyl acetate, dried (sodium sulfate), filtered, and concentrated under reduced pressure to afford 4-[(methylthio)methyl]cyclohexanecarboxylic acid (50 mg): $^1$H NMR (300 MHz, CD$_3$OD) δ 2.53-2.51 (m, 1H), 2.43-2.41 (m, 3H), 2.05 (s, 3H), 2.05-1.95 (m, 2H), 1.71-1.53 (m, 4H), 1.36-1.30 (m, 2H).

Step 6: To a stirred solution of methyl sulfide from step 5 (100 mg, 0.5 mmol) in sodium hydroxide solution (1.5 mL, 0.5 M solution in water) was added sodium bicarbonate (360 mg, 4.3 mmol) and acetone (1 mL) followed by the addition of a solution of oxone (430 mg, 0.7 mmol) in 0.0004 M EDTA (2 mL). The reaction mixture was stirred at room temperature for 2 h and then quenched with sodium bisulfite. The reaction mixture was acidified with 1 N hydrochloric acid and extracted with ethyl acetate (3×100 mL). The combined organic layers were washed with water, dried (sodium sulfate), filtered, and concentrated under reduced pressure to provide 4-[(methylsulfonyl)methyl]cyclohexanecarboxylic acid (100 mg): $^1$H NMR (300 MHz, CD$_3$OD) δ 3.11-3.08 (m, 2H), 2.96 (s, 3H), 2.53-2.51 (m, 1H), 2.18-2.16 (m, 1H), 1.99-1.93 (m, 2H), 1.79-1.25 (m, 6H).

Step 7: To a stirred solution of acid from step 6 (100 mg, 0.5 mmol), (2R,3S)-3-amino-4-(3,5-difluorophenyl)-1-[(3-ethylbenzyl)amino]butan-2-ol (190 mg, 0.5 mmol), and HATU (175 mg, 0.5 mmol) in methylene chloride (5 mL) was added N,N-diisopropylethylamine (280 µL, 1.6 mmol). The reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 95:5 to 92:8 methylene chloride/methanol) provided the title compound (60 mg): mp 45-50° C.; ESI MS m/z 537 [M+H]$^+$.

Example SP-293

N-{(1S,2R)-1-(3,5-difluorobenzyl)-3-[(3-ethylbenzyl)amino]-2-hydroxypropyl}-5-piperidin-3-yl-N,N-dipropylisophthalamide hydrochloride Step 1: To a stirred solution of 3-bromo-pyridine (205 mg, 1.3 mmol) and methyl 3-[(dipropylamino)carbonyl]-5-(3,3,4,4-tetramethylborolan-1-yl)benzoate (500 mg, 1.3 mmol) in dioxane (9 mL) was added sodium carbonate (2.0 mL of a 2 M solution in water, 3.9 mmol). The reaction mixture was flushed with argon, palladium(0)tetrakis(triphenylphosphine) (36 mg, 0.052 mmol) was added and the reaction mixture was heated at reflux for 12 h. The reaction mixture was cooled to room temperature, filtered through diatomaceous earth, dried (magnesium sulfate), filtered, and concentrated under reduced pressure. Purification by flash column chromatography (3:2 hexanes/ethyl acetate) afforded a pyridine (200 mg): $^1$H NMR (300 MHz, CDCl$_3$) δ 8.88 (m, 1H), 8.65 (m, 1H), 8.31 (m, 1H), 8.07 (m, 1H), 7.92 (m, 1H), 7.79 (m, 1H), 7.67 (m, 1H), 3.98 (m, 3H), 3.50 (m, 2H), 3.21 (m, 2H), 1.66 (m, 4H), 1.07 (m, 3H), 0.78 (m, 3H).

Step 2: A solution of the pyridine from step 1 (160 mg, 0.37 mmol) and platinum oxide (15 mg) in ethanol (2.5 mL), water (0.5 mL), and concentrated hydrochloric acid (1.0 mL) was degassed with nitrogen for 15 min, and shaken under an atmosphere of hydrogen at 50 psi for 12 h. The reaction mixture was filtered through diatomaceous earth and concentrated under reduced pressure to afford methyl 3-[(dipropylamino)carbonyl]-5-piperidin-3-ylbenzoate (204 mg, quantitative), which was carried forward without further purification: $^1$H NMR (300 MHz, CDCl$_3$) δ 9.62 (m, 3H), 8.02 (m, 3H), 4.78 (m, 2H), 3.96 (s, 3H), 3.61 (mn, 5H), 2.04 (m, 5H), 1.34 (m, 3H), 0.91 (m, 6H).

Step 3: To a stirred solution of piperidine from step 2 (204 mg, 0.59 mmol) in methylene chloride (1.6 mL) was added Boc anhydride (162 mg, 0.65 mmol) and triethylamine (0.122 mL, 0.88 mmol). The solution was stirred at room temperature for 2 d. The reaction mixture was filtered and concentrated under reduced pressure. Purification by flash column chromatography afforded a Boc-protected piperidine (100 mg): $^1$H NMR (300 MHz, CDCl$_3$) δ 7.93 (t, J=3 Hz, 1H), 7.88 (t, J=3 Hz, 1H), 7.42 (t, J=3 Hz, 1H), 4.16 (m, 2H), 3.93 (s, 3H), 3.46 (m, 2H), 3.13 (m, 2H), 2.78 (m, 3H), 2.03 (d, J=10 Hz, 1H), 1.70 (m, 7H), 1.48 (m, 9H), 1.00 (m, 3H), 0.75 (m, 3H).

Step 4: To a stirred solution of piperidine from step 3 (100 mg, 0.22 mmol) in methanol (2 mL) was added potassium hydroxide (2.2 mL of a 1 M solution in water, 2.2 mmol) and the reaction mixture was stirred at room temperature for 2 h. The reaction mixture was partitioned between ethyl acetate (50 mL) and water (50 mL). The aqueous layer was acidified to pH 4-5 with 1 N hydrochloric acid and extracted with chloroform (5×50 mL). The combined organic layers were dried (magnesium sulfate), filtered, and concentrated under reduced pressure to afford an acid (90 mg)l: $^1$H NMR (300 MHz, CDCl$_3$) δ 7.99 (s, 1H), 7.94 (s, 1H), 7.47 (s, 1H), 4.12 (m, 2H), 3.47 (m, 2H), 3.14 (m, 2H), 2.77 (m, 3H), 2.03 (m, 1H), 1.67 (m, 7H), 1.48 (s, 9H), 0.98 (m, 3H), 0.77 (m, 3H).

Step 5: To a stirred solution of piperidine from step 4 (90 mg, 0.21 mmol) in methylene chloride (1 mL) was added N,N-diisopropylethylamine (0.142 mL, 0.84 mmol), HOBt (42 mg, 0.31 mmol), and HATU (118 mg, 0.31 mmol) followed by (2R,3S)-3-amino-4-(3,5-difluorophenyl)-1-[(3-ethylbenzyl)amino]butan-2-ol (86 mg, 0.21 mmol). The reaction was stirred for 16 h at room temperature. The reaction mixture was diluted with methylene chloride (25 mL), washed with water, saturated sodium bicarbonate, and saturated sodium chloride, dried (magnesium sulfate), filtered, and concentrated under reduced pressure. Purification by flash column chromatography (95:5 chloroform/methanol) afforded a piperidine (100 mg) which was carried forward without further characterization.

Step 6: A solution of piperidine from step 5 (100 mg, 0.15 mmol) and hydrochloric acid (0.4 mL of a 4.0 M solution in dioxane, 1.5 mmol) was stirred for 30 min at room temperature. The reaction mixture was concentrated under reduced pressure and washed with ether (50 mL). The precipitate that formed was collected by filtration to give the title compound (60 mg): mp 145-145° C.; ESI MS m/z 649 [M+H]$^+$.

Example SP-294

1-butyl-N-{(1S,2R)-1-(3,5-difluorobenzyl)-3-[(3-ethylbenzyl)amino]-2-hydroxypropyl}-5-methyl-1H-pyrrole-2-carboxamide Step 1: To a stirred solution of ethanol (54 mL) was added sodium metal (1.29 g, 54.00 mmol). The reaction mixture was stirred for 1 h and then diethyl acetamidomaloante (2.37 g, 10.92 mmol) was added. The reaction mixture was heated at reflux for 1 h and 1,4-dichloro-2-butyne (1.14 mL, 11.64 mmol) was added. The reaction mixture was refluxed for 1 h, cooled to room temperature, and concentrated under reduced pressure. The resulting residue was partitioned between ethyl acetate and water. The organic layer was washed with saturated sodium chloride, dried (sodium sulfate), treated with activated charcoal, filtered through diatomaceous earth, and concentrated under reduced pressure to yield ethyl 5-methyl-1H-pyrrole-2-carboxylate (1.26 g): $^1$H NMR (300 MHz, CDCl$_3$) δ 8.82 (br s, 1H), 6.81 (s, 1H), 5.95 (s, 1H), 4.31 (q, J=6 Hz, 2H), 2.31 (s, 3H), 1.34 (t, J=6 Hz, 3H).

Step 2: A mixture of pyrrole from step 1 (240 mg, 1.71 mmol), potassium carbonate (306 mg, 2.21 mmol), and butyl bromide (328 mg, 2.39 mmol) in acetonitrile (10 mL) was heated to 40° C. for 2 d. The reaction mixture was cooled to room temperature and then partitioned between ethyl acetate and water. The organic layer was dried (sodium sulfate), filtered, and concentrated under reduced pressure to give a brown oil. Purification by flash column chromatography (silica, 5.5:1 hexanes/ethyl acetate) gave an ester (232 mg): $^1$H NMR (300 MHz, CDCl$_3$) δ 6.91 (d, J=3 Hz, 1H), 5.88 (d, J=3 Hz, 1H), 4.24 (m, 4H), 2.26 (s, 3H), 1.65 (m, 2H), 1.37 (m, 5H), 0.99 (m, 3H); ESI MS m/z 210 [M+H]$^+$.

Step 3: A mixture of the ester from step 2 (232 mg, 1.11 mmol) and 3:1:1 methanol/tetrahydrofuran/2 N sodium hydroxide (5 mL) was stirred overnight. The reaction was not complete after 24 h. The reaction mixture was heated to 40° C. for 4 h, cooled to room temperature, and then partitioned between ethyl acetate and water. The aqueous layer was acidified to pH 3 with 1 N hydrochloric acid and extracted with chloroform. The organic layer was dried (sodium sulfate), filtered, and concentrated under reduced pressure to give 1-butyl-5-methyl-1H-pyrrole-2-carboxylic acid (110 mg): $^1$H NMR (300 MHz, CDCl$_3$) δ 7.04 (d, J=3 Hz, 1H), 5.93 (d, J=3 Hz, 1H), 4.24 (m, 2H), 2.28 (s, 3H), 1.67 (m, 2H), 1.43 (m, 2H), 0.99 (m, 3H).

Step 4: To a stirred solution of (2R,3S)-3-amino-4-(3,5-difluorophenyl)-1-[(3-ethylbenzyl)amino]butan-2-ol (248 mg, 0.608 mmol), acid (110 mg, 0.608 mmol), HOBt (82 mg, 0.608 mmol), and N-methylmorpholine (99 mg, 2.43 mmol) in methylene chloride (5 mL) was added EDC (210 mg, 1.09 mmol). The reaction mixture was stirred overnight and then partitioned between ethyl acetate and water. The organic layer was washed with 1 N hydrochloric acid, saturated sodium bicarbonate, and saturated sodium chloride, dried (sodium sulfate), filtered, and concentrated under reduced pressure. Purification by flash column chromatography (silica, 9:1 methylene chloride/methanol) gave the title compound (100 mg): mp 116-121° C.; ESI LMS m/z 498 [M+H]$^+$.

Example SP-295

N-{(1S,2R)-1-(3,5-difluorobenzyl)-2-hydroxy-3-[(1H-pyrrol-2-ylmethyl)amino]propyl}-5-methyl-N,N-dipropyl-isophthalamide Step 1: A mixture of tert-butyl (1S,2R)-3-amino-1-(3,5-difluorobenzyl)-2-hydroxypropylcarbamate (170 mg, 0.538 mmol), 1H-pyrrole-2-carbaldehyde (51 mg, 0.538 mmol), and triethylamine (60 mg, 0.592 mmol) was stirred in chloroform (10 mL) containing magnesium sulfate for 4 h. The reaction mixture was filtered and concentrated under reduced pressure. The resulting residue was dissolved in 2-propanol (10 mL) and sodium borohydride (26 mg, 0.699 mmol) was added. The reaction mixture was stirred overnight and then treated with methanol. The reaction mixture was concentrated under reduced pressure. Purification by flash column chromatography (silica, 9:1 chloroform/methanol) gave tert-butyl (1S,2R)-1-(3,5-difluorobenzyl)-2-hydroxy-3-[(1H-pyrrol-2-ylmethyl)amino]propylcarbamate (132 mg): $^1$H NMR (300 MHz, CD$_3$OD) δ 6.82 (m, 4H), 6.21 (s, 1H), 6.09 (m, 1H), 4.09 (s, 2H), 3.66 (m, 2H), 3.19 (m, 1H), 3.13 (m, 1H), 3.03 (m, 1H), 2.88 (m, 1H), 1.31 (s, 9H).

Step 2: To a stirred solution of the pyrrole from step 1 (132 mg, 0.334 mmol) in dioxane (3 mL) was added hydrochloric acid (0.33 mL, 4 N dioxane, 1.34 mmol). The reaction mixture was stirred overnight and then concentrated under reduced pressure to give an amine (134 mg, quantitative) as a brown solid, which was used without any further characterization or purification.

Step 3: To a stirred mixture of the amine from step 2 (134 mg, 0.334 mmol), 3-[(dipropylamino)carbonyl]-5-methylbenzoic acid (88 mg, 0.334 mmol), HOBt (45 mg, 0.334 mmol), and N-methylmorpholine (203 mg, 2.00 mmol) in methylene chloride (5 mL) was added EDC (115 mg, 0.601 mmol). After 24 h, the reaction mixture was partitioned between ethyl acetate and water. The organic layer was washed with 1 N hydrochloric acid, saturated sodium bicarbonate, and saturated sodium chloride, dried (sodium sulfate), filtered, and concentrated under reduced pressure to give a white solid. Purification by flash column chromatography (silica, 9:1:1 methylene chloride/methanol/ammonium hydroxide) gave the title compound (27 mg): mp 63-74° C.; ESI MS m/z 541 [M+H]$^+$.

Example SP-296

N-{(1S,2R)-1-(3,5-difluorobenzyl)-3-[(3-ethylbenzyl)amino]-2-hydroxypropyl}-5-piperazin-1-yl-N,N-dipropyl-isophthalamide hydrochloride Step 1: In a sealed tube, a solution of dimethyl 5-bromoisophthalate (5.0 g, 18.3 mmol), N-benzylpiperazine (4.0 mL, 23.0 mmol), and cesium carbonate (8.4 g, 25.7 mmol) in toluene (36 mL) was degassed with nitrogen at room temperature for 20 minutes. Palladium (II) acetate (225 mg, 0.92 mmol) and BINAP (1.7 g, 2.74 mmol) were quickly added under nitrogen and the solution heated to 80° C. overnight to yield a yellow solution with a white suspension. The reaction mixture was cooled to room temperature, vacuum filtered, and the solid rinsed with fresh toluene. The filtrate was then concentrated under reduced pressure to yield a yellow oil. Purification by flash chromatography (silica, 80:20 hexanes/ethyl acetate) gave the desired dimethyl 5-(4-benzylpiperazin-1-yl)isophthalate (4.40 g): ESI MS m/z 369 [M+H]$^+$.

Step 2: To a solution of the ester from step 1 (1.0 g, 2.70 mmol) in 2:1:1 dioxane/methanol/water (18 mL) was added lithium hydroxide monohydrate (100 mg, 2.44 mmol) and the reaction mixture stirred for 24 h at room temperature. The reaction mixture was concentrated under reduced pressure and the solid residue partitioned between ethyl acetate and water. The organic layer was set aside and the aqueous phase acidified with 1 N hydrochloric acid and extracted three times with ethyl acetate. The combined ethyl acetate extracts were washed with water, and saturated sodium chloride, dried (sodium sulfate), filtered, and concentrated under reduced pressure to provide the desire monoacid (945 mg): $^1$H NMR (300 MHz, CDCl$_3$) δ 10.50-10.30 (br s, 1H), 8.19-8.12 (m, 1H), 7.80-7.60 (m, 2H), 7.35-7.26 (m, 5H), 3.91 (s, 3H), 3.73 (s, 2H), 3.36-3.33 (m, 4H), 2.77-2.71 (m, 4H); ESI MS m/z 355 [M+H]$^+$.

Step 3: To a solution of the monoacid prepared in step 2 (1.2 g, 3.38 mmol) in methylene chloride (22.5 mL) was added triethylamine (940 μL, 6.76 mmol), N,N-dipropylamine (554 μL, 4.0 mmol), and 2-chloro-1-methylpyridinium iodide (865 mg, 3.38 mmol). The reaction mixture was stirred at room temperature overnight. The residue was then diluted with methylene chloride, washed with saturated sodium bicarbonate, water, and saturated sodium chloride. The organic layer was then dried (sodium sulfate), filtered, and concentrated under reduced pressure to yield a yellow oil. Purification by flash column chromatography (silica, 80:20 hexanes/ethyl acetate) gave the desired amide (1.0 g): $^1$H NMR (300 MHz, CDCl$_3$) δ 7.59-7.58 (m, 1H), 7.44-7.42 (m, 1H), 7.35-7.26 (m, 5H), 7.05-7.04 (m, 1H), 3.89 (s, 3H), 3.56 (s, 2H), 3.50-3.35 (m, 2H), 3.28-3.25 (m, 4H), 3.20-3.05 (m, 2H), 2.62-2.58 (m, 4H), 1.70-1.40 (m, 4H), 1.00-0.95 (m, 3H), 0.80-0.70 (m, 3H).

Step 4: To a solution of the amide prepared in step 3 (1.00 g, 2.28 mmol) in absolute ethanol (120 mL) was added palladium(II) hydroxide (100 mg) and the reaction shaken under 55 psi of hydrogen at 60° C. overnight. The reaction was then cooled to room temperature, filtered through diatomaceous earth, and the filter cake rinsed with fresh ethanol. The filtrate was concentrated under reduced pressure and redissolved in dry acetonitrile (15 mL) To this was added di-tert-butyl dicarbonate (650 mg, 2.96 mmol) and N,N-diisopropylethylamine (450 uL, 2.50 mmol), and the reaction mixture stirred at room temperature overnight. The reaction mixture was then concentrated under reduced pressure, redissolved in chloroform, washed with saturated sodium bicarbonate, water, and saturated sodium chloride. The organic layer was then dried (sodium sulfate), filtered, and concentrated under reduced pressure to yield a colorless oil. Purification by flash column chromatography (silica, 66:33 hexanes/ethyl acetate) yielded the desired Boc-protected amine (953 mg): $^1$H NMR (300 MHz, CDCl$_3$) δ 7.60-7.59 (m, 1H), 7.48-7.47 (m, 1H), 7.08-7.07 (m, 1H), 3.92 (s, 3H), 3.60-3.51 (m, 4H), 3.46-3.44 (m, 2H), 3.22-3.16 (m, 6H), 1.70-1.48 (m, 13H), 1.10-0.98 (m, 3H), 0.78-0.74 (m, 3H); ESI MS m/z 448 [M+H]$^+$.

Step 5: To a solution of Boc-protected amine prepared in step 4 (953 mg, 2.13 mmol) in 2:1:1 dioxane/methanol/water (14.2 mL) was added lithium hydroxide monohydrate (268 mg, 6.39 mmol), and the reaction mixture stirred at room temperature overnight. The reaction mixture was concentrated under reduced pressure and then partitioned between ethyl acetate and water. The aqueous phase was acidified with 1 N hydrochloric acid and extracted three times with ethyl acetate. The combined ethyl acetate extracts were washed with water and saturated sodium chloride, dried (sodium sulfate), filtered, and concentrated under reduced pressure to provide the desired 3-[4-(tert-butoxycarbonyl)piperazin-1-yl]-5-[(dipropylamino)carbonyl]benzoic acid (770 mg): ESI MS m/z 434 [M+H]$^+$.

Step 6: A solution of the acid from step 5 (320 mg, 0.738 mmol) and HBTU (279 mg, 0.738 mmol) in methylene chloride (4.6 mL) containing N,N-diisopropylethylamine (770 μL, 4.42 mmol) as stirred at room temperature for 20 minutes. To this was added a solution of (2R,3S)-3-amino-4-(3,5-difluorophenyl)-1-[(3-ethylbenzyl)amino]butan-2-ol (300 mg, 0.738 mmol) and N,N-diisopropylethylamine (770 μL, 4.42 mmol) in methylene chloride (4.6 mL). The reaction mixture was stirred at room temperature overnight. The reaction mixture was then concentrated under reduced pressure, diluted with methylene chloride, washed with saturated sodium bicarbonate, water, and saturated sodium chloride. The organic layer was then dried (sodium sulfate), filtered, and concentrated under reduced pressure to yield a yellow syrup. Purification by flash column chromatography (silica, 93:7 chloroform/methanol) gave the desired amide (443 mg): ESI MS m/z 750 [M+H]$^+$.

Step 7: To a solution of the amide prepared in step 6 (220 mg, 0.293 mmol) in 1,4-dioxane (2.0 mL) was added hydrochloric acid (750 μL, 4 M dioxane, 3.0 mmol) and the reaction mixture was stirred at room temperature for 2 h. The reaction mixture was then concentrated under reduced pressure. The residue was taken up in methylene chloride and concentrated again under reduced pressure. This was repeated until a solid remained. No further purification was required. The recovered solid was dried under high vacuum over phosphorus pentoxide at 50° C. for 48 h to give the title compound (120 mg) which was characterized as its dihydrochloride salt: mp 135-136° C.; ESI MS m/z 650 [M+H]$^+$.

Example SP-297

N-{(1S,2R)-1-(3,5-difluorobenzyl)-3-[(3-ethylbenzyl)amino]-2-hydroxypropyl}-2-(3-oxo-4-propylcyclohexyl)acetamide Step 1: A solution of 2-propylphenol (26.83 g, 197 mmol), potassium carbonate (30.64 g, 221 mmol), methyl iodide (50.0 mL, 800 mmol), and 18-crown-6 (500 mg, 1.9. mmol) in acetone (300 mL) was refluxed for 48 h. The reaction mixture was cooled to room temperature, the solid removed by filtration, and the filtrate concentrated under reduced pressure. The resulting residue was partitioned between methylene chloride and water. The organic layer was washed with 2 N sodium hydroxide, water, and saturated sodium chloride, dried (sodium sulfate), filtered, and concentrated under reduced pressure to afford the desired methyl phenyl ether (23.46 g) as an oil, which was used without further purification: $^1$H NMR (300 MHz, CDCl$_3$) δ 7.16-7.11 (m, 2H), 6.90-6.82 (m, 2H), 3.81 (s, 3H), 2.58 (m, 2H), 1.60 (tq, J=7, 5 Hz, 2H), 0.95 (t, J=7 Hz, 3H).

Step 2: Absolute ethanol (200 mL) followed by tetrahydrofuran (50 mL) was added at −78° C. to a solution of methyl phenyl ether from step 1 (10.0 g, 66.58 mmol) suspended in anhydrous ammonia (700 mL). Lithium metal (2.3 g, 330 mmol) was added at −78° C. in small portions over 0.5 h to yield a deep blue solution. The reaction was stirred at −78° C. until a white solution resulted. The cooling bath was taken away, the flask exposed to the atmosphere, and the ammonia was removed under a stream of nitrogen. The solid residue remaining was dissolved in a minimum amount of water and acidified to pH 3 with 10% hydrochloric acid, and then extracted several times with diethyl ether. The combined ether phase was washed with saturated sodium chloride, dried (sodium sulfate), filtered, and carefully concentrated under reduced pressure at 0° C. to provide an oil. The oil was dissolved in 10% hydrochloric acid (200 mL) and refluxed for 3 h. The reaction mixture was then cooled to room temperature and extracted several times with diethyl ether. The combined ether extracts were washed with saturated sodium chloride, dried (sodium sulfate), filtered, and concentrated under reduced pressure to yield an oil. Purification by flash column chromatography (silica, 89:11 hexanes/ethyl acetate) gave 2-propylcyclohexenone (4.43 g): $^1$H NMR (300 MHz, CDCl$_3$) δ 6.95-6.89 (m, 1H), 5.97 (app dt, J=10, 2 Hz, 1H), 2.39-2.36 (m, 3H), 2.20-2.04 (m, 1H), 1.88-1.63 (m, 2H), 1.50-1.25 (m, 4H), 0.93 (t, J=7 Hz, 3H).

Step 3: A solution of sodium metal (30 mg, 1.30 mmol) in absolute ethanol (4.0 mL) was stirred at −10° C. for 0.5 h. Diethyl malonate (3.5 mL, 23 mmol) was added at −10° C. followed by addition of a solution of 2-propylcyclohexenone (3.0 g, 21.7 mmol) in absolute ethanol (3.0 mL). The reaction mixture was stirred an additional 12 h at room temperature. The reaction mixture was acidified to pH 3 with 10% hydrochloric acid and then extracted several times with diethyl ether. The combined ether extracts were washed with water, and saturated sodium chloride, dried (sodium sulfate), filtered, and concentrated under reduced pressure to yield a yellow oil. Purification by flash column chromatography (silica, 83:17 hexanes/ethyl acetate) gave 2-(3-oxo-4-propylcyclohexyl)-malonic acid diethyl ester (5.07 g): $^1$H NMR (300 MHz, CDCl$_3$) δ 4.21 (q, J=7 Hz, 2H), 4.20 (q, J=7 Hz, 2H), 3.30 (s, 0.5H), 3.28 (s, 0.5H), 2.67-1.55 (m, 8H), 1.43-1.11 (m, 10H), 0.90 (t, J=7 Hz, 1.5H), 0.90 (t, J=7.0 Hz, 1.5H).

Step 4: A solution of the diester from step 2 (2.37 g, 7.94 mmol) in 1 N potassium hydroxide (16.27 mL, 16.27 mmol) was refluxed for 2 h. The reaction mixture was cooled to room temperature, diluted with water, and extracted with methylene chloride. The aqueous phase was acidified to pH 1-2 with 6 N hydrochloric acid and then refluxed for 2 h. The reaction mixture was cooled to room temperature and extracted several times with methylene chloride. The combined organic phase was washed with water, and saturated sodium chloride, dried (sodium sulfate), filtered, and concentrated under reduced pressure to yield a light yellow oil. Purification by flash column chromatography (silica, 66:33 hexanes/ethyl acetate with 1% glacial acetic acid) gave (3-oxo-4-propyl-cyclohexyl)-acetic acid (1.42 g): $^1$H NMR (300 MHz, CDCl$_3$) δ 2.71-1.12 (m, 14H), 1.11-0.82 (m, 3H); ESI MS m/z 197 [M−H]$^−$.

Step 5: To a stirred solution of the acid from step 4 (244 mg, 1.23 mmol) and N,N-diisopropyl ethylamine (214 μL, 1.23 mmol) in methylene chloride (7.0 mL) was added HBTU (513 mg, 1.35 mmol) and the reaction mixture stirred for 0.5 h. To the above solution was added a solution of amine (2R, 3S)-3-amino-4-(3,5-difluorophenyl)-1-[(3-ethylbenzyl)amino]butan-2-ol (500 mg, 1.35 mmol) and N,N-diisopropylethylamine (428 μL, 2.46 mmol) in methylene chloride (7.0 mL) and the reaction mixture was stirred under nitrogen for 18 h. The reaction mixture was then diluted with additional methylene chloride and washed with saturated sodium bicarbonate, 0.5 N hydrochloric acid, and saturated sodium chloride. The organic layer was then dried (sodium sulfate), filtered, and concentrated under reduced pressure to yield an oily residue. Purification by flash column chromatography (silica, 7:93 methanol/methylene chloride) gave the title compound (360 mg): mp 52-54° C.; ESI MS m/z 515 [M+H]$^+$.

Example SP-298

N-{(1S,2R)-1-(3,5-difluorobenzyl)-3-[(3-ethylbenzyl)amino]-2-hydroxypropyl}-2-(3-oxocyclohexyl)acetamide Step 1 (3-Oxo-cyclohexyl)-malonic acid diethyl ester was prepared in 88% yield from cyclohexenone by the method described above for the synthesis of 2-(3-oxo-4-propylcyclohexyl)-malonic acid diethyl ester: $^1$H NMR (300 MHz, CDCl$_3$) δ 4.44-4.12 (m, 4H), 2.88-1.22 (m, 16H).

Step 2 (3-Oxo-cyclohexyl)-acetic acid was prepared in 70% yield from 2-(3-oxo-cyclohexyl)-malonic acid diethyl ester by the method described above for the synthesis of (3-oxo-4-propyl-cyclohexyl)-acetic acid: 1H NMR (300 MHz, CDCl$_3$) δ 2.58-1.92 (m, 7H), 1.80-1.61 (m, 1H), 1.52-1.42 (m, 1H); ESI MS m/z 155 [M−H]$^−$.

Step 3: N-{(1S,2R)-1-(3,5-difluorobenzyl)-3-[(3-ethylbenzyl)amino]-2-hydroxypropyl}-2-(3-oxocyclohexyl)acetamide was prepared in 23% yield from (3-Oxo-cyclohexyl)-acetic acid by the method described for the synthesis of N-{(1S,2R)-1-(3,5-difluorobenzyl)-3-[(3-ethylbenzyl)amino]-2-hydroxypropyl}-2-(3-oxo-4-propylcyclohexyl)acetamide (EXAMPLE SP-297.)

mp 139.5-149.8° C.;); ESI MS m/z 473 [M+H]$^+$.

Example SP-299

3-benzyl-4-(4-butylphenyl)-N-{(1S,2R)-1-(3,5-difluorobenzyl)-3-[(3-ethylbenzyl)amino]-2-hydroxypropyl}-4-oxobutanamide Step 1: Benzaldehyde (2.81 mL, 27.15 mL) was added at 0° C. to a solution of 4-butyl-acetophenone (5.26 mL, 27.15 mmol) in methanol (7.8 mL) and water (13.0 mL) containing sodium hydroxide (1.39 g, 34.75 mmol). The reaction was warmed to room temperature and stirred 48 h. The reaction mixture was diluted with ethyl acetate and washed with water, saturated sodium chloride, dried (sodium sulfate), filtered, and concentrated to yield a light yellow syrup. Volatile impurities were removed under high vacuum at 120° C. to yield the desired enone (6.3 g): ESI MS m/z 265 [M+H]$^+$.

Step 2: A solution of the enone prepared in step 1 (2.0 g, 7.56 mmol) in anhydrous diethyl ether (11 mL) was added at −78° C. to a solution of lithium metal (120 mg, 16.6 mmol) in dry liquid ammonia (11 mL). The reaction was stirred at −78° C. for 0.5 h and excess lithium was quenched with several drops of piperylene to yield a yellow solution. Lithium bromoacetate (2.75 g, 18.9 mmol) was added in one portion and the reaction stirred at −78° C. for 0.5 h then at −33° C. for 2 h. The reaction was then quenched with NH$_4$Cl and the open reaction vessel warmed to room temperature. The residue was partitioned between ethyl acetate and water and the phases separated. The organic phase was washed with water, saturated sodium chloride, dried (sodium sulfate), filtered and concentrated to yield a yellow syrup. Purification by flash column chromatography (silica, 74:25:1 hexanes/ethyl acetate/acetic acid) gave 3-benzyl-4-(4-butylphenyl)-4-oxobutanoic acid (60 mg): ESI MS m/z 325 [M+H]$^+$.

Step 3: A solution of 3-benzyl-4-(4-butylphenyl)-4-oxobutanoic acid (60 mg, 0.185 mmol) and HBTU (70 mg, 0.185 mmol) in methylene chloride (1.2 mL) containing N,N-diisopropylethylamine (100 μL, 0.55 mmol) was stirred at room temperature for 20 minutes. To this was added a solution of amine (2R,3S)-3-amino-4-(3,5-difluorophenyl)-1-[(3-ethylbenzyl)amino]butan-2-ol (75 mg, 0.185 mmol) and N,N-diisopropylethylamine (100 μL, 0.55 mmol) in methylene chloride (1.2 mL). The reaction mixture was stirred at room temperature overnight. The reaction mixture was then concentrated under reduced pressure, diluted with methylene chloride, washed with saturated sodium bicarbonate, water and saturated sodium chloride, dried (sodium sulfate), filtered, and concentrated under reduced pressure to yield a colorless syrup. Purification by flash column chromatography (silica, 93:7 chloroform/methanol) gave the title compound (36 mg) (diastereomeric mixture): mp 42-45° C.; ESI MS m/z 641 [M+H]$^+$.

Example SP-300

N-{(1S,2R)-1(3,5-difluorobenzyl)-2-hydroxy-3-[(1H-indol-6-ylmethyl)amino]propyl}-5-methyl-N$^3$,N$^3$-dipropyl-isophthalamide

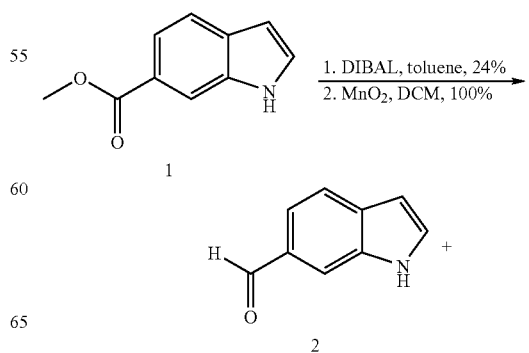

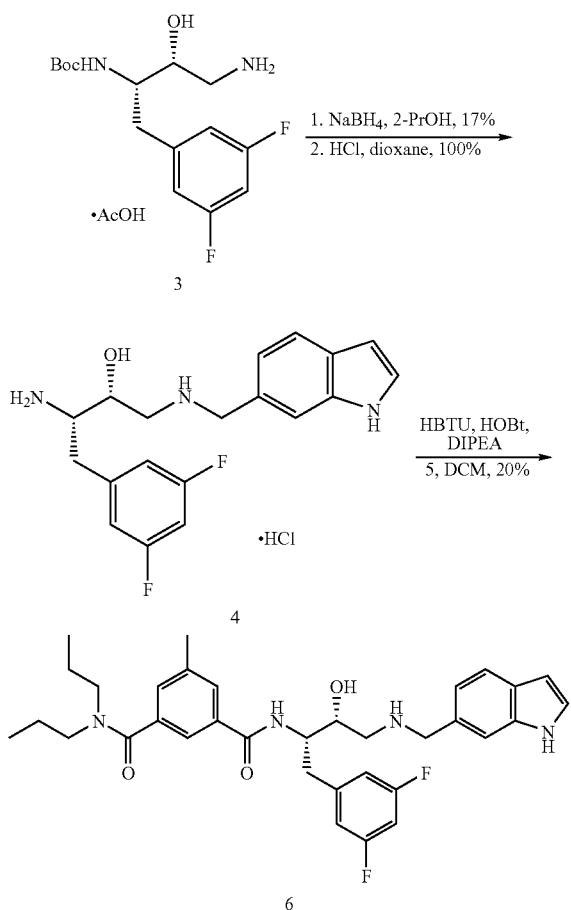

Step 1: To a −78° C., stirred solution of methyl 1H-indole-6-carboxylate (500 mg, 2.85 mmol) in methylene chloride (11.5 mL) was added diisobutylaluminum hydride (5.70 mL, 1.0 M solution in methylene chloride). The reaction mixture was stirred for 2 h at −78° C., and slowly warmed to room temperature for 10 h. The reaction mixture was quenched with methanol, washed with Rochelle's salt (saturated aqueous potassium sodium tartrate), dried (magnesium sulfate), and concentrated under reduced pressure. Purification by flash column chromatography (silica, 6:1 ethyl acetate/hexanes) afforded an alcohol (100 mg): $^1$H NMR (300 MHz, CDCl$_3$) δ 8.21 (br s, 1H), 7.62 (d, J=9 Hz, 1H), 7.39 (s, 1H), 7.20-7.22 (m, 1H), 7.10-7.13 (m, 1H), 6.54-6.56 (m, 1H), 4.77 (d, J=3 Hz, 2H), 1.60 (s, 1H).

Step 2: To a stirred solution of alcohol from step 1 (100 mg, 0.68 mmol) in methylene chloride (3 mL) was added magnesium oxide (590 mg, 6.8 mmol) and the reaction mixture was stirred for 1 h. The reaction mixture was filtered through diatomaceous earth and concentrated under reduced pressure to provide 1H-indole-6-carbaldehyde (99 mg) as a solid, which was carried forward without further purification or characterization. $^1$H NMR (300 MHz, CDCl$_3$) δ 10.03-10.88 (m, 1H), 8.56 (br s, 1H), 7.96 (s, 1H), 7.74 (d, J=8 Hz, 1H), 7.64-7.70 (m, 1H), 7.46 (t, J=3 Hz, 1H), 6.65 (s, 1H).

Step 3: To a stirred solution of 1H-indole-6-carbaldehyde (99 mg, 0.68 mmol) and tert-butyl (1S,2R)-3-amino-1-(3,5-difluorobenzyl)-2-hydroxypropylcarbamate acetate 3 (256 mg, 0.68 mmol) in 2-propanol (3 mL) was added sodium borohydride (30 mg, 0.82 mmol). The reaction mixture was stirred for 12 h., quenched with methanol, and concentrated under reduced pressure. Purification by flash column chromatography (silica, 1:1 ethyl acetate/hexanes) provided indole (50 mg): $^1$H NMR (300 MHz, CDCl$_3$) δ 8.41 (br s, 1H), 7.60 (d, J=8 Hz, 1H), 7.38 (s, 1H), 7.21 (t, J=3 Hz, 1H), 7.04 (dd, J=8, 1 Hz, 1H), 6.71-6.73 (m, 3H), 6.61-6.68 (m, 1H), 6.53 (s, 1H), 5.38 (br s, 2H), 4.66 (d, J=9 Hz, 1H), 3.89 (s, 2H), 3.49-3.54 (m, 1H), 2.91-2.98 (m, 1H), 2.62-2.73 (m, 3H), 1.35 (s, 9H).

Step 4: To a stirred solution of indole from step 3 (50 mg, 0.11 mmol) was added hydrochloric acid (0.27 mL, 4.0 M solution in dioxane). The reaction mixture was stirred for 1 h, diluted with ethyl ether, and concentrated under reduced pressure to provide (2R,3S)-3-amino-4-(3,5-difluorophenyl)-1-[(1H-indol-6-ylmethyl)amino]butan-2-ol hydrochloride 4 (70 mg): ESI MS m/z 346 [M+H]$^+$.

Step 5: To a stirred solution of 3-[(dipropylamino)carbonyl]-5-methylbenzoic acid (5) (29 mg, 0.11 mmol) in methylene chloride (3 mL) was added HBTU (64 mg, 0.17 mmol), HOBt (23 mg, 0.17 mmol), and N,N-diisopropylethylamine (0.075 mL, 0.44 mmol), followed by (2R,3S)-3-amino-4-(3,5-difluorophenyl)-1-[(1H-indol-6-ylmethyl)amino]butan-2-ol hydrochloride 4 (70 mg, 0.11 mmol). The reaction mixture was stirred for 12 h, diluted with methylene chloride, washed with water, saturated sodium bicarbonate, dried (magnesium sulfate), filtered, and concentrated under reduced pressure. Purification by flash column chromatography (silica, 89:10:1 chloroform/methanol/ammonium hydroxide) provided the title compound (6) (13 mg): mp 135-137° C.; ESI MS m/z 591 [M+H]$^+$.

Example SP-301

N-{(1S,2R)-1-(3,5-difluorobenzyl)-3-[(3-ethylbenzyl)amino]-2-hydroxypropyl}-1,3-benzodioxole-5-carboxamide

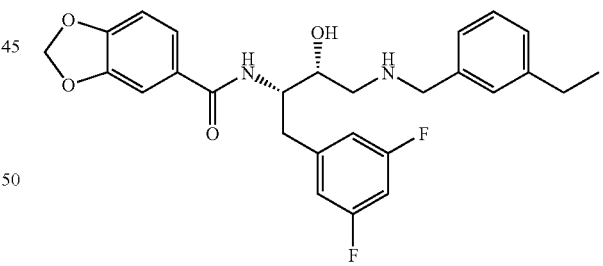

To a solution of piperonylic acid (0.500 g, 3.01 mmol), EDC (0.867 g, 4.52 mmol), HOBT (0.611 g, 4.52 mmol) in anhydrous DMF (10 mL) was added a solution of TEA (1.67 mL, 12.04 mmol), 3-Amino-4-(3,5-difluoro-phenyl)-1-(3-ethyl-benzylamino)-butan-2-ol (1.693 g, 3.01 mmol), and anhydrous DMF (5 mL). Reaction mixture was stirred under nitrogen overnight. Quenched reaction mixture with 10% sodium bicarbonate (aq.) then extracted with ethyl acetate. Washed organic layer with 1N HCl, followed by a wash with 10% sodium bicarbonate (aq.). Dried organic layer over magnesium sulfate, filtered, then concentrated in vacuo, yielding the product. (ES+: 483.2)

Example SP-302 tert-butyl (1S,2R)-1-[3-(benzyloxy)-5-fluorobenzyl]-3-[(3-ethylbenzyl)amino]-2-hydroxypropylcarbamate

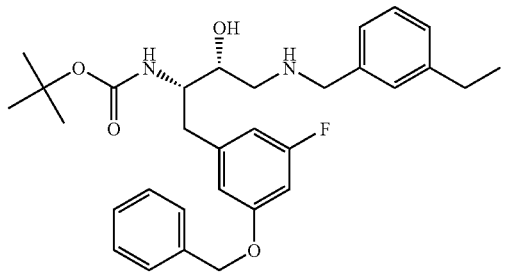

[2-(3-Benzyloxy-5-fluoro-phenyl)-1-oxiranyl-ethyl]-carbamic acid tert-butyl ester (3.33 g, 8.59 mmol) and m-ethyl benzylamine (2.32 g, 17.19 mmol) were dissolved in isopropyl alcohol (80 ml) and brought to reflux for 2 h. Reaction mixture was then concentrated in vacuo to remove isopropyl alcohol. Dissolved yellow liquid in ethyl acetate (30 ml), then washed with 1N HCl (3×100 ml). Aqueous layers were combined then extracted with ethyl acetate (2×100 ml). Organic layers were washed with 10% sodium bicarbonate (aq., 3×100 ml), followed by a brine wash. Organic layer was dried over sodium sulfate, filtered, then concentrated in vacuo, yielding the product (4.31 g). (ES+: 523.9)

Example SP-303

5-[((1S,2R)-1-(3,5-difluorobenzyl)-3-{[1-(3-ethylphenyl)cyclopropyl]amino}-2-hydroxypropyl)amino]-5-oxopentanoic acid

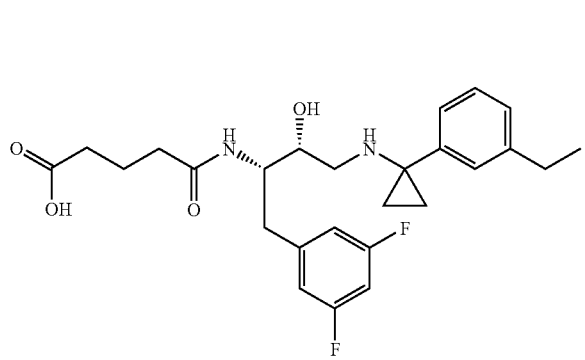

To a solution of 3-Amino-4-(3,5-difluoro-phenyl)-1-[1-(3-ethyl-phenyl)-cyclopropylamino]-butan-2-ol (0.500 g, 1.387 mmol) in chloroform (7 ml) was added TEA (0.58 ml, 4.161 mmol) with stirring under nitrogen for 30 min. To this solution was added glutaric anhydride (0.158 g, 1.387 mmol) and reaction was stirred overnight at 50° C. The reaction mixture was concentrated in vacuo, yielding the product. (ES+: 475.2)

Example SP-304

4-[((1S,2R)-1-(3,5-difluorobenzyl)-3-{[1-(3-ethylphenyl)cyclopropyl]amino}-2-hydroxypropyl)amino]-4-oxobutanoic acid

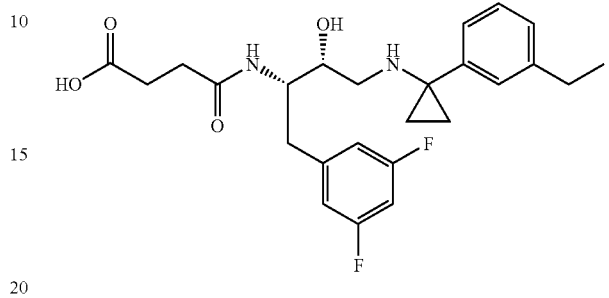

To a solution of 3-Amino-4-(3,5-difluoro-phenyl)-1-[1-(3-ethyl-phenyl)-cyclopropylamino]-butan-2-ol (0.500 g, 1.387 mmol) in chloroform (7 ml) was added TEA (0.58 ml, 4.161 mmol) with stirring under nitrogen for 30 min. To this solution was added succinic anhydride (0.138 g, 1.387 mmol) and reaction was stirred overnight at 50° C. The next morning reaction mixture was concentrated in vacuo, yielding the product. (ES+: 461.2)

Example SP-305 formic acid compound with $N^1$-[(3S)-1-azabicyclo[2.2.2]oct-3-yl]-$N^5$-((1S,2R)-1-(3,5-difluorobenzyl)-3-{[1-(3-ethylphenyl)cyclopropyl]amino}-2-hydroxypropyl)pentanediamide (1:1)

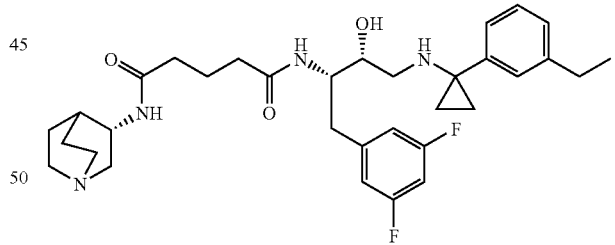

To a solution of R-aminoqtuinuclidine (0.084 g, 0.421 mmol) TEA (0.294 ml, 2.11 mmol), and anhydrous DMF (2.5 ml) was added 5-[((1S,2R)-1-(3,5-difluorobenzyl)-3-{[1-(3-ethylphenyl)cyclopropyl]amino}-2-hydroxypropyl)amino]-5-oxopentanoic acid (0.200 g, 0.421 mmol), EDC (0.121 g, 0.632 mmol), HOBT (0.085 g, 0.632 mmol) under nitrogen, with stirring at 45° C. overnight. Reaction mixture was quenched with 10% sodium bicarbonate (aq.) then extracted with ethyl acetate then concentrated in vacuo, yielding product (0.122 g). Prep-HPLC yielded the product as its formate salt. (ES+: 583.3)

Example SP-306 formic acid compound with N¹-[(3R)-1-azabicyclo[2.2.2]oct-3-yl]-N⁵-((1S,2R)-1-(3,5-difluorobenzyl)-3-{[1-(3-ethylphenyl)cyclopropyl]amino}-2-hydroxypropyl)pentanediamide (1:1)

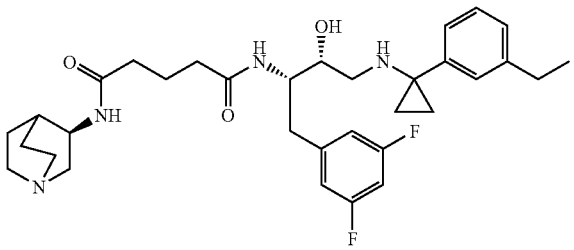

To a solution of S-aminoquinuclidine (0.084 g, 0.421 mmol) TEA (0.294 ml, 2.11 mmol), and anhydrous DMF (2.5 ml) was added 5-[((1S,2R)-1-(3,5-difluorobenzyl)-3-{[1-(3-ethylphenyl)cyclopropyl]amino}-2-hydroxypropyl)amino]-5-oxopentanoic acid (0.200 g, 0.421 mmol), EDC (0.121 g, 0.632 mmol), HOBT (0.085 g, 0.632 mmol) under nitrogen, with stirring at 45° C. overnight. Reaction mixture was quenched with 10% sodium bicarbonate (aq.) then extracted with ethyl acetate then concentrated in vacuo, yielding product (0.065 g). Prep-HPLC yielded the product as its formate salt. (ES+: 583.3)

Example SP-307 formic acid compound with N¹-[(3S)-1-azabicyclo[2.2.2]oct-3-yl]-N⁴-((1S,2R)-1-(3,5-difluorobenzyl)-3-{[1-(3-ethylphenyl)cyclopropyl]amino}-2-hydroxypropyl)succinamide (1:1)

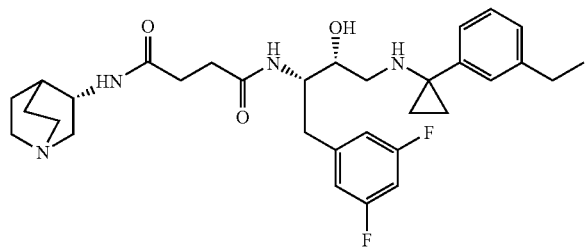

To a solution of R-aminoquinuclidine (0.086 g, 0.434 mmol) TEA (0.302 ml, 2.17 mmol), and anhydrous DMF (2.5 ml) was added 4-[((1S,2R)-1-(3,5-difluorobenzyl)-3-{[1-(3-ethylphenyl)cyclopropyl]amino}-2-hydroxypropyl)amino]-4-oxobutanoic acid (0.200 g, 0.434 mmol), EDC (0.125 g, 0.651 mmol), and HOBT (0.088 g, 0.651 mmol) under nitrogen, with stirring at 45° C. overnight. Reaction mixture was quenched with 10% sodium bicarbonate (aq.) then extracted with ethyl acetate then concentrated in vacuo, yielding product (0.200 g). Prep-HPLC yielded the product as its formate salt. (ES+: 569.3)

Example SP-308 formic acid compound with N¹-[(3R)-1-azabicyclo[2.2.2]oct-3-yl]-N⁴-((1S,2R)-1-(3,5-difluorobenzyl)-3-{[1-(3-ethylphenyl)cyclopropyl]amino}-2-hydroxypropyl)succinamide (1:1)

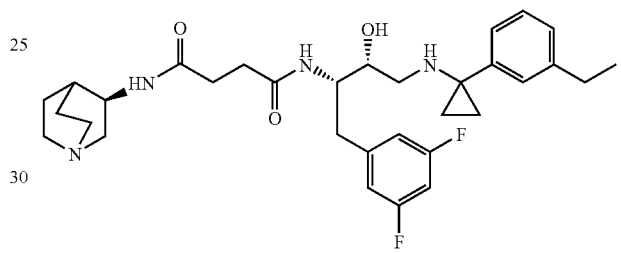

To a solution of S-aminoquinuclidine (0.086 g, 0.434 mmol) TEA (0.302 ml, 2.17 mmol), and anhydrous DMF (2.5 ml) was added 4-[((1S,2R)-1-(3,5-difluorobenzyl)-3-{[1-(3-ethylphenyl)cyclopropyl]amino}-2-hydroxypropyl)amino]-4-oxobutanoic acid (0.200 g, 0.434 mmol), EDC (0.125 g, 0.651 mmol), and HOBT (0.088 g, 0.651 mmol) under nitrogen, with stirring at 45° C. overnight. Reaction mixture was quenched with 10% sodium bicarbonate (aq.) then extracted with ethyl acetate then concentrated in vacuo, yielding product (0.093 g). Prep-HPLC yielded the product as its formate salt. (ES+: 569.3)

Example SP-309

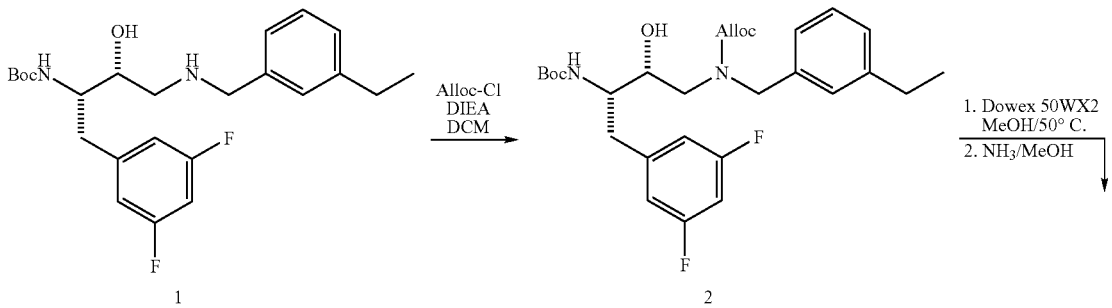

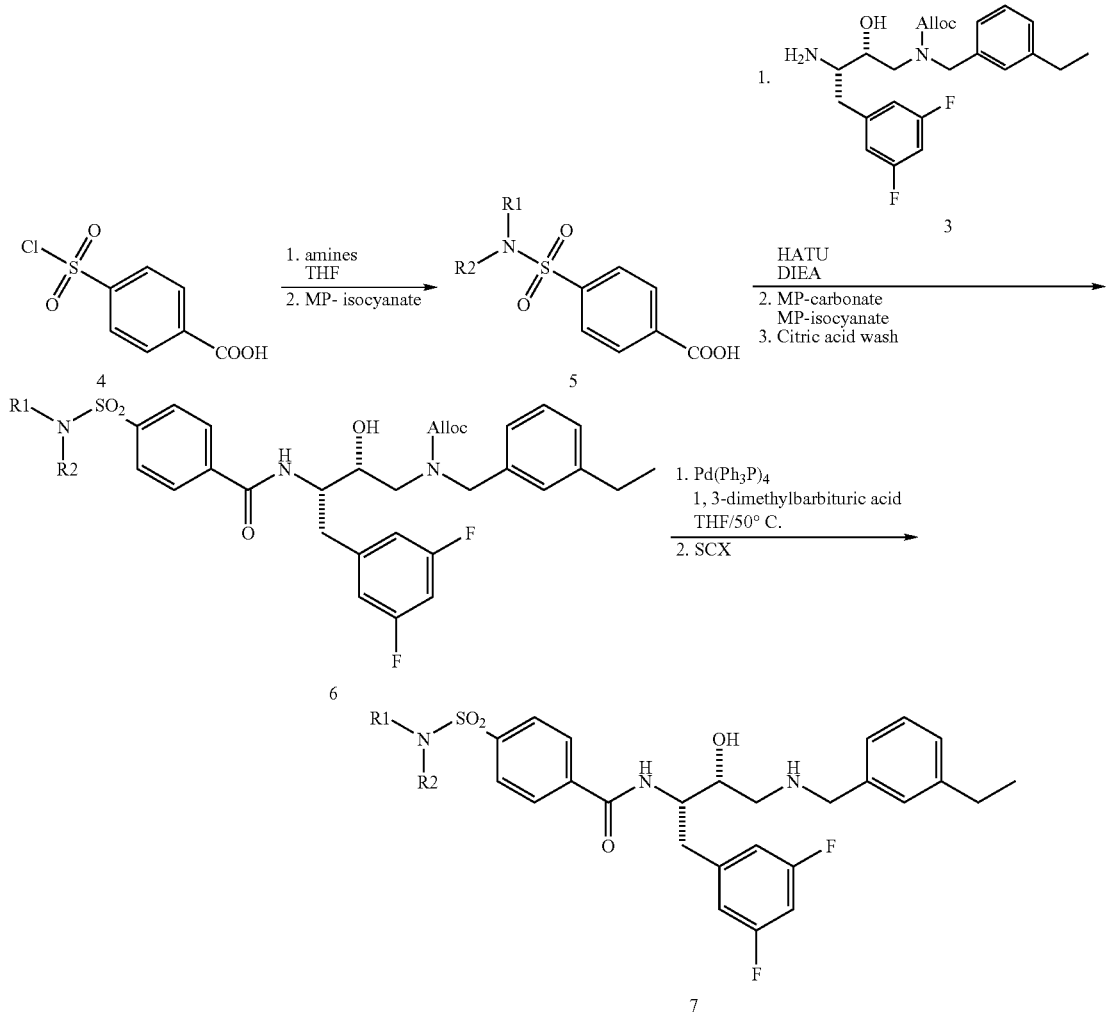

MP stands for macroporous resin.

2: A solution of 1 (2.50 g; 5.75 mmol) and DIEA (1.20 mL; 6.90 mmol) in DCM (100 mL) was cooled in an ice/water bath. Allyl chloroformate (0.73 mL; 6.90 mmol) was added, and the reaction was allowed to come to ambient temperature over 4 h. The reaction was washed with 10% $K_2CO_3$ (100 mL), water (100 mL), brine (100 mL), and dried over $Na_2CO_3$. Flash chromatography on 90 g silica gel with 0-30% EtOAc/heptane afforded 2.88 g (5.55 mmol; 96%) 2 as a white solid.

3: A solution of 2 (2.88 g; 5.55 mmol) and Dowex 50WX2 (Aldrich; 8.88 g; approx. 44.4 mmol) in MeOH (100 mL) was heated to 50° C. for 5.25 h. The reaction was cooled to ambient temperature and filtered. The resin was washed well with MeOH, and the product was eluted with approx. 3.5M ammonia in MeOH. After removal of solvent, 2.11 g (5.04 mmol; 91%) 3 was collected as an off-white waxy solid.

5: The appropriate amines (0.3 mmol) were added to vials containing 4-(chlorosulfonyl)benzoic acid 4 (2.0 mL of a 0.05M solution of THF) plus 1 eq. of DIEA if necessary (to liberate any amine hydrochloride salts). The vials were agitated on an orbital shaker at ambient temperature/250 rpm for 18 h. MP-isocyanate resin (approx. 0.6 mmol) was added to each vial, which were heated to 60° C. for 5 h. The reactions were filtered, the resin washed well with THF, and concentrated.

6: The acids 5 were coupled to Alloc-protected TSI 3 using HATU (1.2 eq.) and DIEA (2.4 eq.) in DMF for 18 h at ambient temperature. MP-isocyanate (3 eq.) and MP-carbonate (1 eq.) were then added, and the reactions rocked for 4 h at ambient temperature. The reactions were filtered, the resins washed well with 1,2-dichloroethane, and concentrated. The residues were dissolved in 1,2-dichloroethane (1.5 mL), washed with 1M citric acid (1.5 mL) and loaded onto 3 mL capacity Varian ChemElut Hydromatrix cartridges. After 5 min, the product was eluted with 1,2-dichloroethane (2×6 mL), and concentrated in vacuo.

7: Alloc intermediates 6 were deprotected using Pd(Ph3P)4 (0.15 eq.) and 1,3-dimethylbarbituric acid (20 eq.) in THF at 60° C./3 h. The reaction vials were concentrated in vacuo, and SCX was performed by loading the crude reaction mixture onto 1000 mg/3 mL SCX cartridges using 5 mL MeOH. The cartridges were washed well with MeOH, and the products eluted with approx. 3.5M ammonia in MeOH. If necessary, the final products were purified by high-throughput preparative UV HPLC.

The following compounds were prepared using the above described methodology.

| EXAMPLE | Structure | Compound Name(s) | OAMS |
|---|---|---|---|
| 2965 | 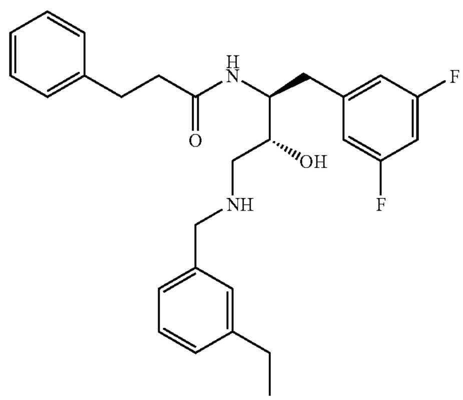 | N-{(1S,2R)-1-(3,5-difluorobenzyl)-3-[(3-ethylbenzyl)amino]-2-hydroxypropyl}-3-phenylpropanamide | 467.3 |
| 2966 | 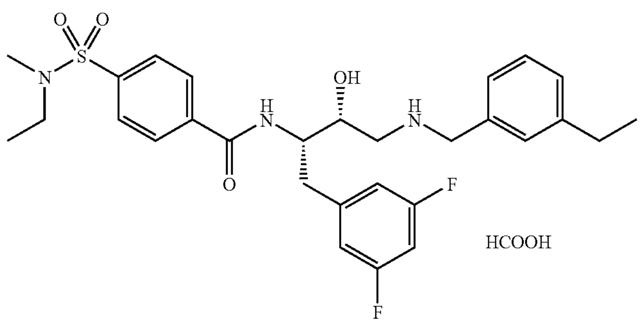 | formic acid compound with N-{(1S,2R)-1-(3,5-difluorobenzyl)-3-[(3-ethylbenzyl)amino]-2-hydroxypropyl}-4-{[ethyl(methyl)amino]sulfonyl}benzamide (1:1) | 560.1 |
| 2967 | 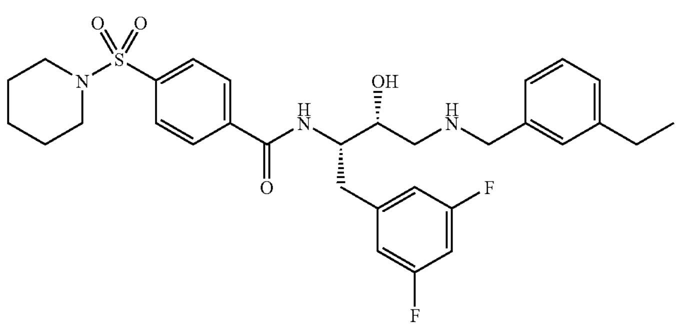 | N-{(1S,2R)-1-(3,5-difluorobenzyl)-3-[(3-ethylbenzyl)amino]-2-hydroxypropyl)-4-(piperidin-1-ylsulfonyl)benzamide | 586.2 |
| 2968 | 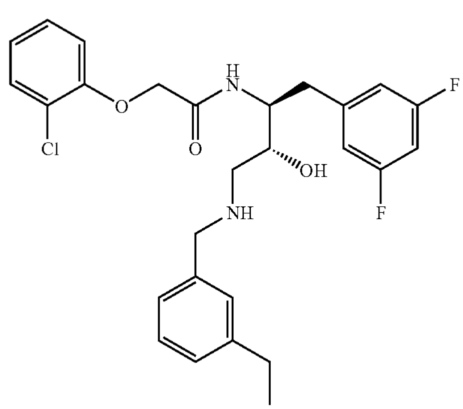 | 2-(2-chlorophenoxy)-N-{(1S,2R)-1-(3,5-difluorobenzyl)-3-[(3-ethylbenzyl)amino]-2-hydroxypropyl}acetamide | 503.3 |

-continued

| EXAMPLE | Structure | Compound Name(s) | OAMS |
|---|---|---|---|
| 2969 | 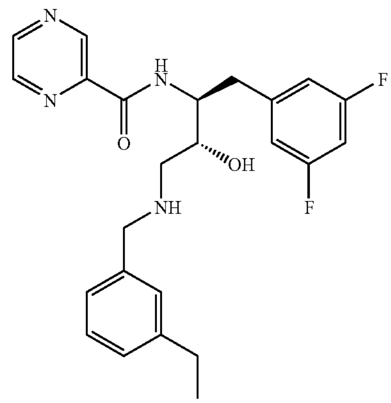 | N-{(1S,2R)-1-(3,5-difluorobenzyl)-3-[(3-ethylbenzyl)amino]-2-hydroxypropyl}pyrazine-2-carboxamide | 441.2 |
| 2970 | 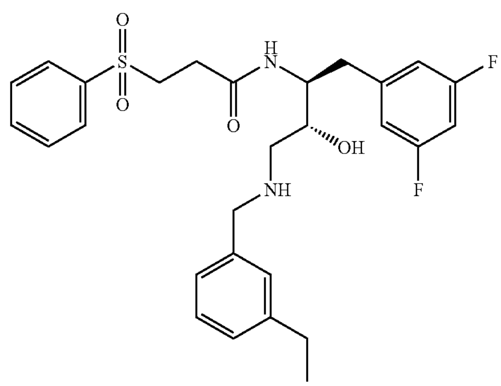 | N-{(1S,2R)-1-(3,5-difluorobenzyl)-3-[(3-ethylbenzyl)amino]-2-hydroxypropyl}-3-(phenylsulfonyl)propanamide | 531.2 |
| 2971 | 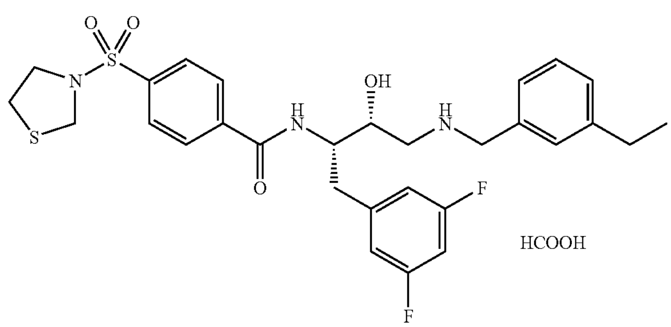 | formic acid compound with N-{(1S,2R)-1-(3,5-difluorobenzyl)-3-[(3-ethylbenzyl)amino]-2-hydroxypropyl}-4-(1,3-thiazolidin-3-yl-sulfonyl)benzamide (1:1) | 589.9 |
| 2972 | 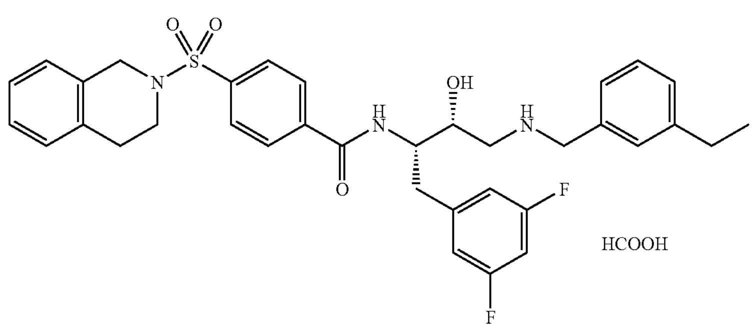 | formic acid compound with N-{(1S,2R)-1-(3,5-difluorobenzyl)-3-[(3-ethylbenzyl)amino]-2-hydroypropyl}-4-(3,4-dihydroisoquinolin-2(1H)-ylsulfonyl)benzamide (1:1) | 634.0 |

| EXAMPLE | Structure | Compound Name(s) | OAMS |
|---|---|---|---|
| 2973 | 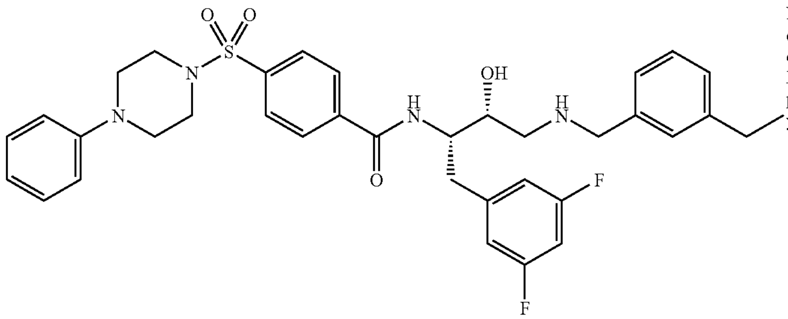 | N-{(1S,2R)-1-(3,5-difluorobenzyl)-3-[(3-ethylbenzyl)amino]-2-hydroxypropyl}-4-[(4-phenylpiperazin-1-yl)sulfonyl]benzamide | 663.0 |
| 2974 | 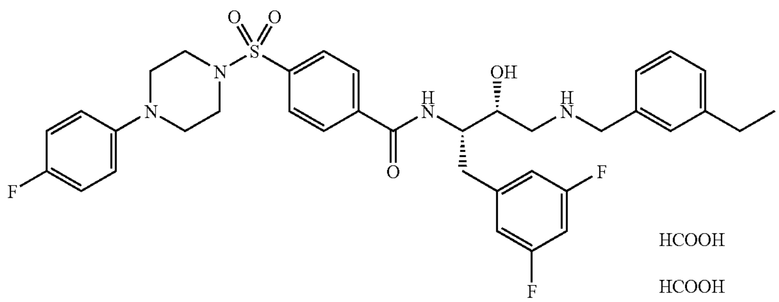 | formic acid compound with N-{(1S,2R)-1-(3,5-difluorobenzyl)-3-[(3-ethylbenzyl)amino]-2-hydroxypropyl}-4-{[4-(4-fluorophenyl)piperazin-1-yl]sulfonyl}benzamide (2:1) | 680.9 |
| 2975 | 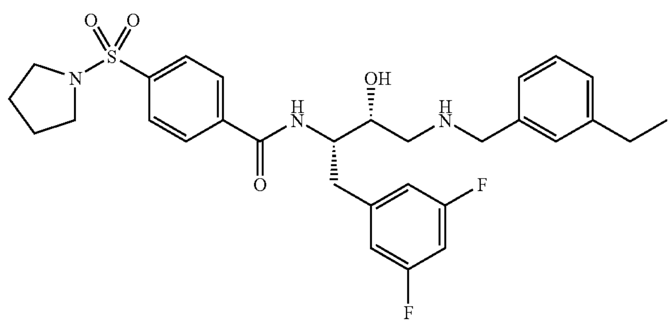 | N-{(1S,2R)-1-(3,5-difluorobenzyl)-3-[(3-ethylbenzyl)amino]-2-hydroxypropyl}-4-(pyrrolidin-1-ylsulfonyl)benzamide | 572 |
| 2976 | 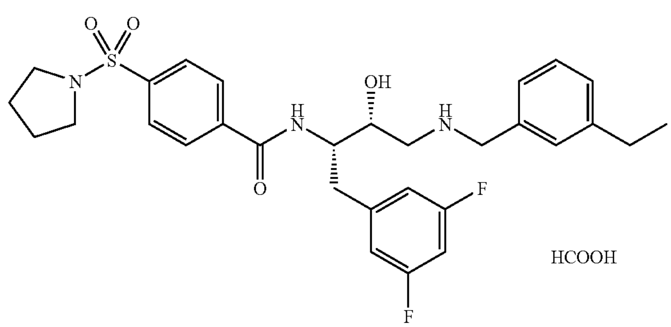 | formic acid compound with N-{(1S,2R)-1-(3,5-difluorobenzyl)-3-[(3-ethylbenzyl)amino]-2-hydroxypropyl}-4-(pyrrolidin-1-ylsulfonyl)benzamide (1:1) | 572.0 |
| 2977 | 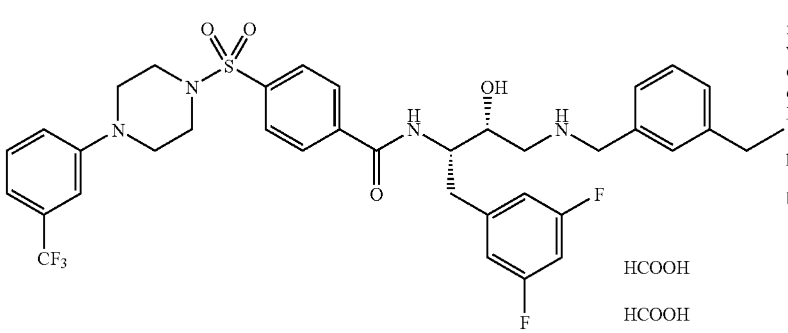 | formic acid compound with N-{(1S,2R)-1-(3,5-difluorobenzyl)-3-[(3-ethylbenzyl)amino]-2-hydroxypropyl}-4-(-55 4-[3-(trifluoromethyl)phenyl]piperazin-1-yl}sulfonyl)benzamide (2:1) | 731.0 |

| EXAMPLE | Structure | Compound Name(s) | OAMS |
|---|---|---|---|
| 2978 | 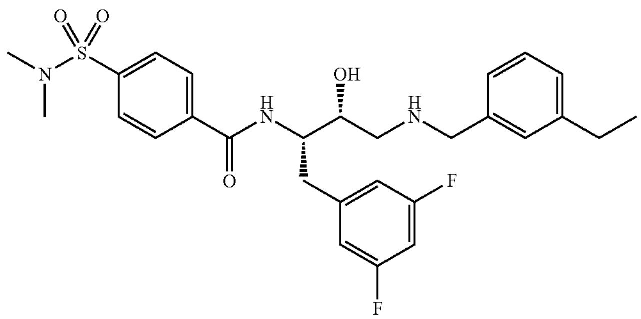 | N-{(1S,2R)-1-(3,5-difluorobenzyl)-3-[(3-ethylbenzyl)amino]-2-hydroxypropyl}-4-[(dimethylamino)sulfonyl]benzamide | 546 |
| 2979 | 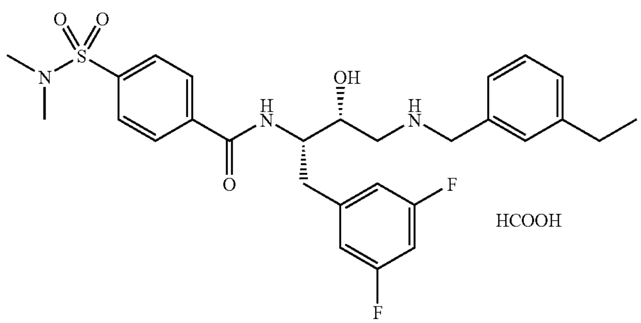 | formic acid compound with N-{(1S,2R)-1-(3,5-difluorobenzyl)-3-[(3-ethylbenzyl)amino]-2-hydroxypropyl}-4-[(dimethylamino)sulfoyl]benzamide (1:1) | 546.0 |
| 2980 | 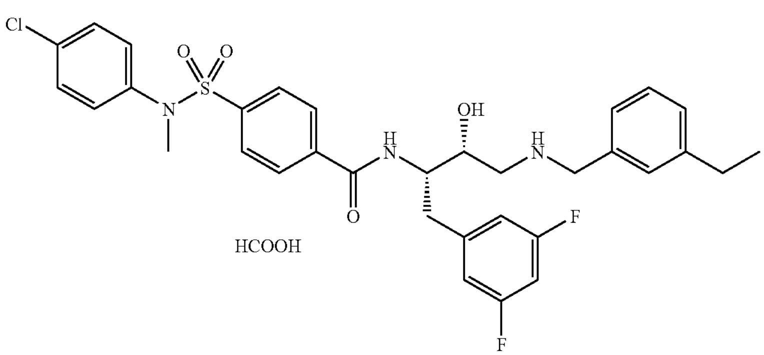 | formic acid compound with 4-{[(4-chlorophenyl)(methyl)amino]sulfonyl}-N-{(1S,2R)-1-(3,5-difluorobenzyl)-3-[(3-ethylbenzyl)amino]-2-hydroxypropyl}benzamide (1:1) | 642.0 |
| 2981 | 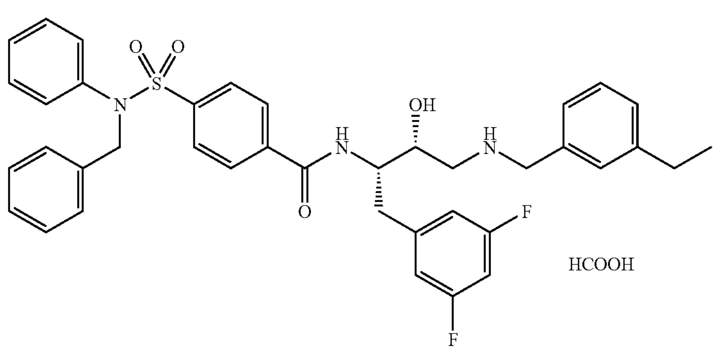 | formic acid compound with 4-{[benzyl(phenyl)amino]sulfonyl}-N-{(1S,2R)-1-(3,5-difluorobenzyl)-3-[(3-ethylbenzyl)amino]-2-hydroxypropyl}benzamide (1:1) | 684.1 |

-continued

| EXAMPLE | Structure | Compound Name(s) | OAMS |
|---|---|---|---|
| 2982 | 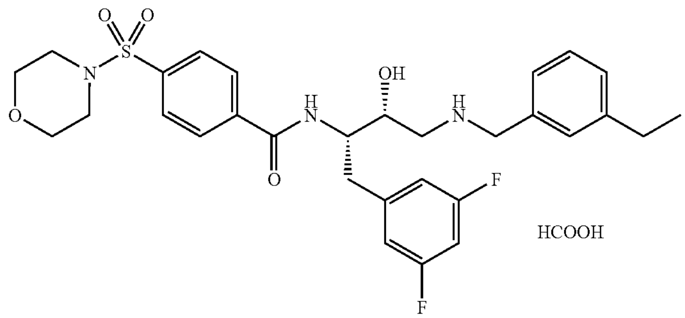 | formic acid compound with N-{(1S,2R)-1-(3,5-difluorobenzyl)-3-[(3-ethylbenzyl)amino]-2-hydroxypropyl}-4-(morpholin-4-ylsulfonyl)benzamide (1:1) | 588.1 |
| 2983 | 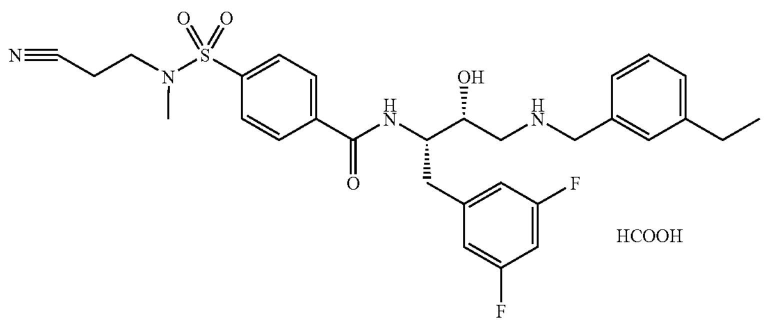 | formic acid compound with 4-{[(2-cyanoethyl)(methyl)amino]sulfonyl}-N-{(1S,2R)-1-(3,5-difluorobenzyl)-3-[(3-ethylbenzyl)amino]-2-hydroxypropyl}benzamide (1:1) | 585.0 |
| 2984 | 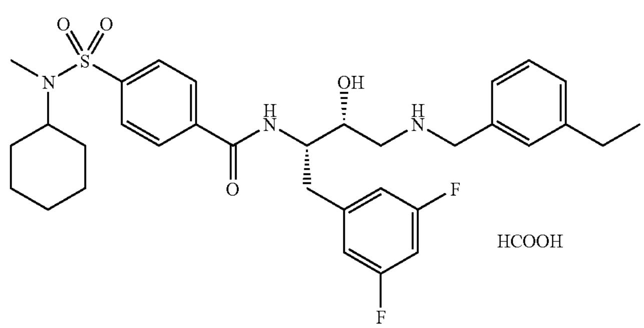 | formic acid compound with 4-{[cyclohexyl(methyl)amino]sulfonyl}-N-{(1S,2R)-1-(3,5-difluorobenzyl-3-[(3-ethylbenzyl)amino]-2-hydroxypropyl}benzamide (1:1) | 614.0 |
| 2985 | 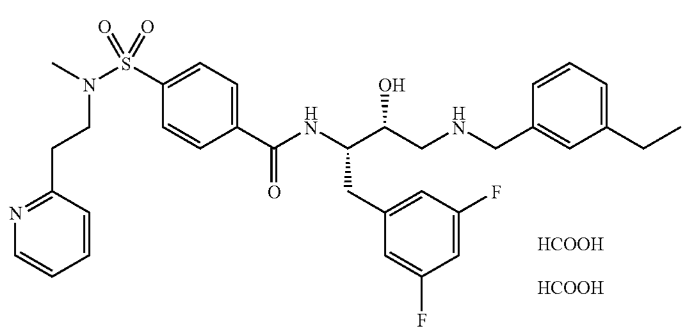 | formic acid compound with N-{(1S,2R)-1-(3,5-difluorobenzyl)-3-[(3-ethylbenzyl)amino]-2-hydroypropyl}-4-{[methyl(2-pyridin-2-ylethyl)amino]sulfonyl}benzamide (2:1) | 637.0 |

-continued

| EXAMPLE | Structure | Compound Name(s) | OAMS |
|---------|-----------|------------------|------|
| 2986 | HCOOH | formic acid compound with N-{(1S,2R)-1-(3,5-difluorobenzyl)-3-[(3-ethylbenzyl)amino]-2-hydroxypropyl}-4-{[methyl(phenyl)amino]sulfonyl}benzamide (1:1) | 608.1 |
| 2987 | HCOOH | formic acid compound with 4-{[benzyl(methyl)amino]sulfonyl}-N-{(1S,2R)-1-(3,5-difluorobenzyl)-3-[(3-ethylbenzyl)amino]-2-hydroxypropyl}benzamide (1:1) | 622.1 |
| 2988 | HCOOH | formic acid compound with N-{(1S,2R)-1-(3,5-difluorobenzyl)-3-[(3-ethylbenzyl)amino]-2-hydroxyproypl}-4-{[methyl(2-phenylethyl)amino]sulfonyl}benzamide (1:1) | 636.1 |
| 2989 | HCOOH | formic acid compound with 4-{[allyl(methyl)amino]sulfonyl}-N-{(1S,2R)-1-(3,5-difluorobenzyl)-3-[(3-ethylbenzyl)amino]-2-hydroxypropyl}benzamide (1:1) | 572.1 |

-continued

| EXAMPLE | Structure | Compound Name(s) | OAMS |
|---|---|---|---|
| 2990 | 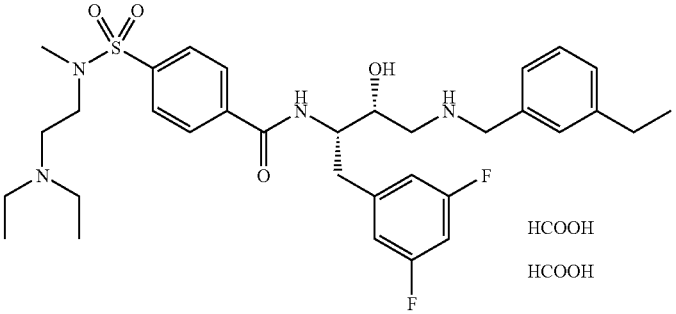 | formic acid compound with 4-{[[2-(diethyl-amino)ethyl](methyl)amino]sulfonyl}-N-{(1S,2R)-1-(3,5-difluoro-benzyl)-3-[(3-ethyl-benzyl)amino]-2-hydroxypropyl}benzamide (2:1) | 631.1 |
| 2991 | 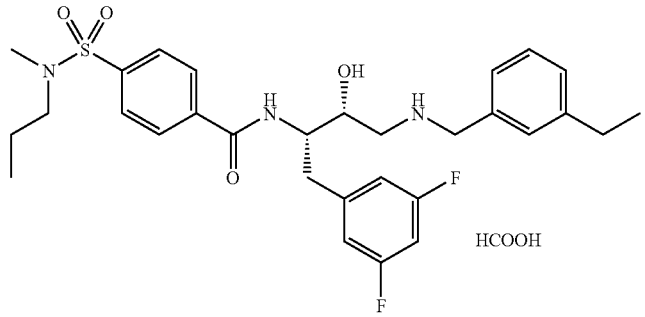 | formic acid compound with N-{(1S,2R)-1-(3,5-difluorobenzyl)-3-[(3-ethylbenzyl)amino]-2-hydroxypropyl}-4-{[methyl(propyl)amino]sulfonyl}benzamide (1:1) | 574.1 |
| 2992 | 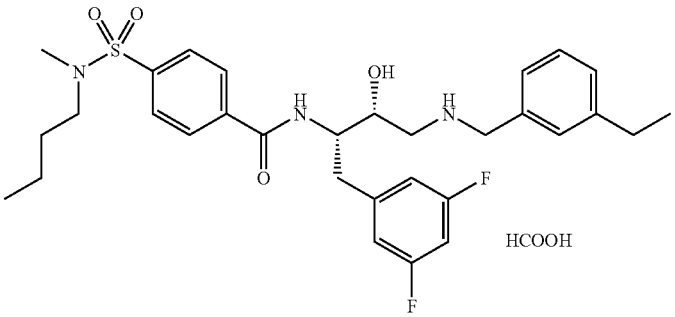 | formic acid compound with 4-{[butyl(methyl)amino]sulfonyl}-N-{(1S,2R)-1-(3,5-difluoro-benzyl-3-[(3-ethylbenzyl)amino]-2-hydroxy-propyl}benzamide (1:1) | 588.1 |
| 2993 | 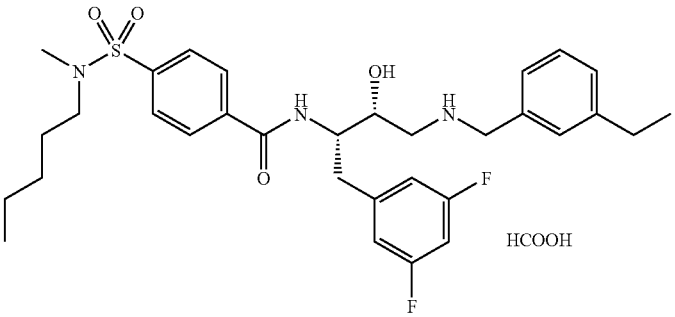 | formic acid compound with N-{(1S,2R)-1-(3,5-difluorobenzyl)-3-[(3-ethylbenzyl)amino]-2-hydroxypropyl}-4-{[methyl(pentyl)amino]sulfonyl}benzamide (1:1) | 602.1 |

-continued

| EXAMPLE | Structure | Compound Name(s) | OAMS |
|---|---|---|---|
| 2994 | 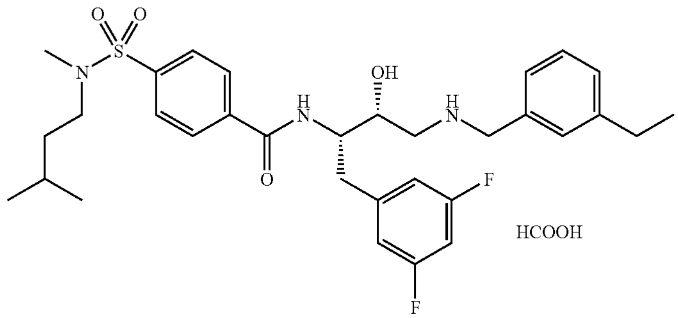 | formic acid compound with N-{(1S,2R)-1-(3,5-difluorobenzyl)-3-[(3-ethylbenzyl)amino]-2-hydroxypropyl}-4-{[isopentyl(methyl)amino]sulfonyl}benzamide (1:1) | 602.1 |
| 2995 | 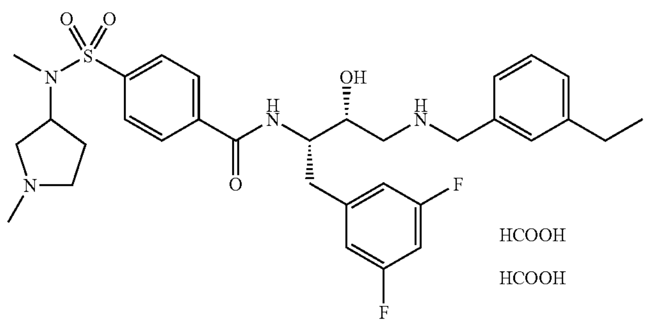 | formic acid compound with N-{(1S,2R)-1-(3,5-difluorobenzyl)-3-[(3-ethylbenzyl)amino]-2-hydroxypropyl}-4-{[methyl(1-methyl-pyrrolidin-3-yl)amino]sulfonyl}benzamide (2:1) | 615.0 |
| 2996 | 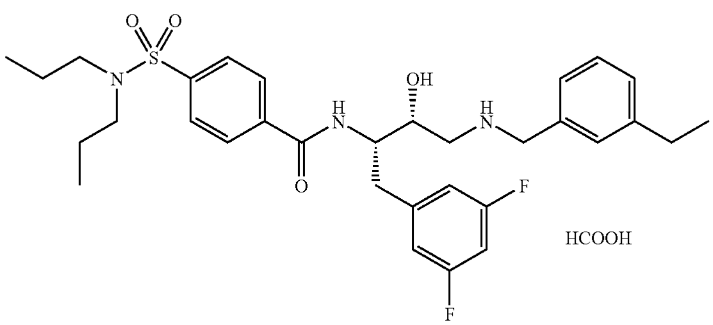 | formic acid compound with N-{(1S,2R)-1-(3,5-difluorobenzyl)-3-[(3-ethylbenzyl)amino]-2-hydroxypropyl}-4-[(dipropylamino)sulfonyl]benzamide (1:1) | 602.0 |
| 2997 | 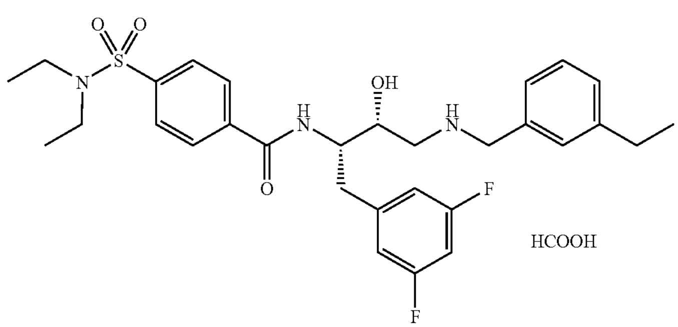 | formic acid compound with 4-[(diethylamino)sulfonyl]-N-{(1S,2R)-1-(3,5-difluorobenzyl)-3-[(3-ethylbenzyl)amino]-2-hydroxypropyl}benzamide (1:1) | 574.0 |

Example SP-310

N-{(1S,2R)-1-(3,5-difluorobenzyl)-3-[(3-ethylbenzyl)amino]-2-hydroxypropyl}-2-[methyl(methylsulfonyl)amino]-1,3-oxazole-4-carboxamide

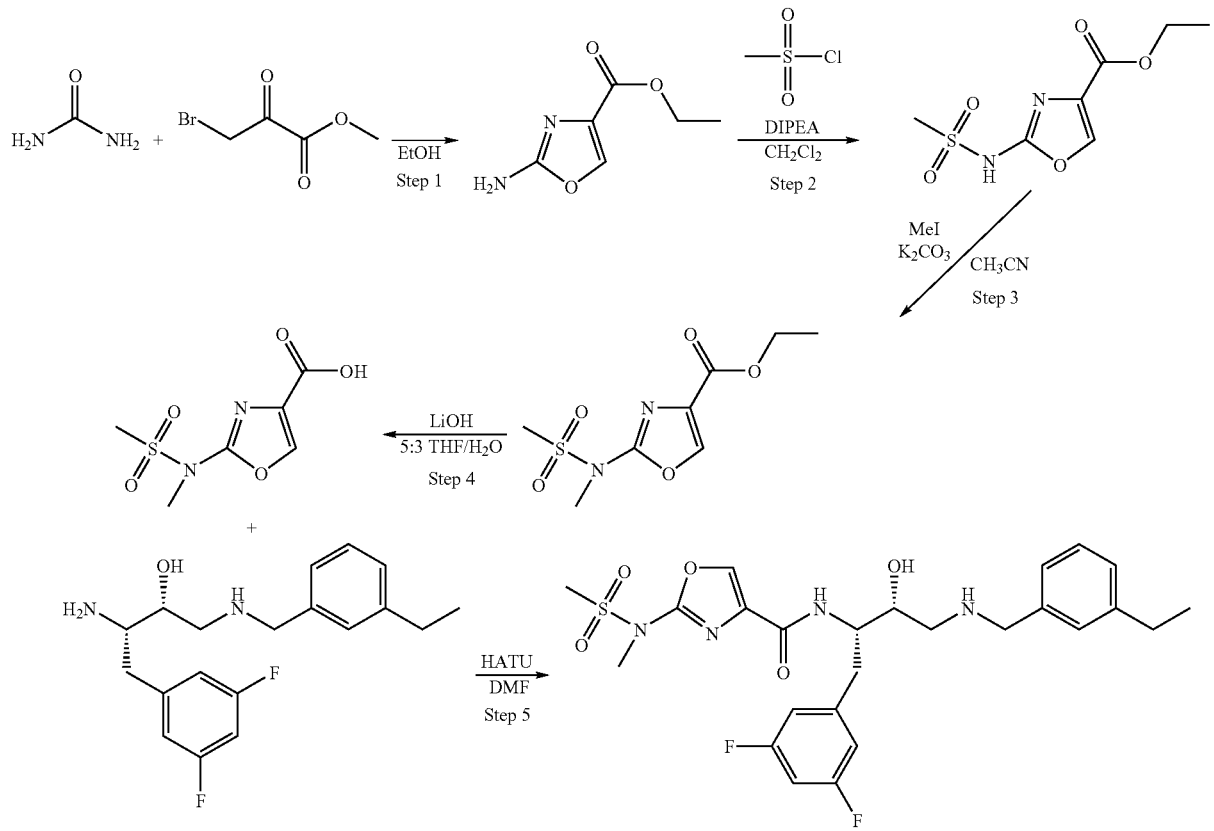

ethyl 2-amino-1,3-oxazole-4-carboxylate

Step 1. To a 250 ml 3-neck round bottom flask was added (20 g, 0.3332 moles) urea, (150 ml) ethanol and (42.42 g, 0.2175 moles, 0.65 eq) ethylbromopyruvate. The mixture was then heated under agitation to reflux for 16 hours. The reaction solution changed from yellow to red in color. The reaction solution was then evaporated to dryness and the crude product was taken up in (50 ml) water and (150 ml) ethyl acetate. The pH was adjusted from 1 to 10 using 2N sodium hydroxide, changing the biphasic mixture a dark red. The mixture was separated and the aqueous phase was extracted twice with ethyl acetate. The organic layers were then combined and washed with water and brine. The resulting yellow solution was concentrated to ~50 ml, causing an off-white solid to precipitate out. The solid was filtered off and washed with ethanol and diethyl ether. The mother liquor was then evaporated to dryness and the resulting oily solid was taken up in (150 ml) ethyl acetate and concentrated to ~50 ml. An off-white solid precipitated out. The mixture was cooled in an ice bath, and the solid was filtered off and washed with ethanol and diethyl ether to give ethyl 2-amino-1,3-oxazole-4-carboxylate (14.79 g).

ethyl 2-[(methylsulfonyl)amino]-1,3-oxazole-4-carboxylate

Step 2. To a 20 ml screw cap vial was added (1 g, 5.8069 mmoles) ethyl 2-amino-1,3-oxazole-4-carboxylate, (10 ml) dichloromethane and (1.39 ml, 7.9797 mmoles, 1.25 eq.) N,N-diisopropylethylamine. To the reaction was then added (0.545 ml, 7.0415 mmoles, 1.1 eq.) methanesulfonyl chloride, and the reaction was agitated for 14 hours. The reaction was then evaporated to dryness and purified using a Biotage silica gel column, resulting in (272 mg) of ethyl 2-[(methylsulfonyl)amino]-1,3-oxazole-4-carboxylate.

ethyl 2-[methyl(methylsulfonyl)amino]-1,3-oxazole-4-carboxylate

Step 3. To a 25 ml round bottom flask under $N_2$ was added (101.8mg, 0.4346 mmoles) ethyl 2-[(methylsulfonyl)amino]-1,3-oxazole-4-carboxylate, (180.2 mg, 1.3038 mmoles, 3.0 eq.) potassium carbonate, and (5 ml) acetonitrile. The mixture was then agitated at ambient temperature while (33.8 µl, 0.5429 mmoles, 1.25 eq.) iodomethane was added. The reaction was allowed to run at ambient temperature for 3 hours. An electrospray mass spec indicated mostly starting material. The $N_2$ line was removed and an additional (40 µl, 0.6425 mmoles, 1.5 eq.) iodomethane were added. The reaction was left at ambient temperature overnight. The reaction was quenched with (5 ml) 1N HCl and was extracted with dichloromethane. The organic layer was washed with water and then evaporated to dryness. The resulting oil was purified by preparative HPLC, yielding (70 mg) of ethyl 2-[methyl(methylsulfonyl)amino]-1,3-oxazole-4-carboxylate.

2-[methyl(methylsulfonyl)amino]-1,3-oxazole-4-carboxylic acid

Step 4. To a 50 ml round bottom flask was added (61 mg, 0.2457 mmoles) ethyl 2-[methyl(methylsulfonyl)amino]-1,3-oxazole-4-carboxylate, (51.5 mg, 1.2274 mmoles, 5.0 eq.) lithium hydroxide, (2.5 ml) tetrahydrofuran and (1.5 ml) water. The reaction was agitated at ambient temperature for ~2 hours. The reaction was complete by electrospray mass spec. The reaction was worked up by adding (5 ml) 1N HCl and then extracting with ethyl acetate. The organic layer was washed with water and brine and then dried with magnesium sulfate. The solution was then evaporated to dryness, leaving (44.6 mg) of 2-[methyl(methylsulfonyl)amino]-1,3-oxazole-4-carboxylic acid.

N-{(1S,2R)-1-(3,5-difluorobenzyl)-3-[(3-ethylbenzyl)amino]-2-hydroxypropyl}-2-[methyl(methylsulfonyl)amino]-1,3-oxazole-4-carboxamide Step 5. To a 7 ml screw cap vial was added (20.9 mg, 0.0949 mmoles) 2-[methyl(methylsulfonyl)amino]-1,3-oxazole-4-carboxylic acid, (36.7mg, 0.1097 mmoles, 1.15 eq.) (2R,3S)-3-amino-4-(3,5-difluorophenyl)-1-[(3-ethylbenzyl)amino]butan-2-ol and (54.6 mg, 0.1436 mmoles, 1.5 eq.) HATU, followed by (1.25 ml) N,N-dimethylformamide. The reaction was placed in an orbital shaker and was left at ambient temperature for 2 hours. The reaction was quenched with (2 ml) 1N HCl. The clear solution was extracted three times with ethyl acetate and the combined organic layers were washed with saturated sodium carbonate solution and then brine. The solution was then dried with magnesium sulfate and evaporated to a clear oil which was purified by preparative HPLC, resulting N-{(1S,2R)-1-(3,5-difluorobenzyl)-3-[(3-ethylbenzyl)amino]-2-hydroxypropyl}-2-[methyl(methylsulfonyl)amino]-1,3-oxazole-4-carboxamide (15.7 mg).

Example SP-311 methyl 3-cyano-5-[(dipropylamino)carbonyl]benzoate

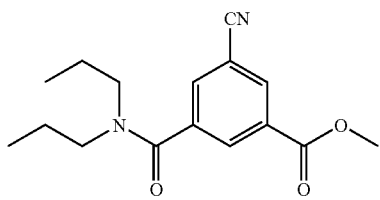

Methyl 3-bromo-5-[(dipropylamino)carbonyl]benzoate (Preparation 3) (0.15 g), copper (I) cyanide, and N-methylpyrrolidinone (1 mL) was heated at 150° C. overnight, at which time the mixture was cooled and partitioned between ethyl acetate and aq. HCl (1N). The organic layer was dried (magnesium sulfate), concentrated under reduced pressure, and the residue was chromatographed on silica gel using ethyl acetate-hexane (20/80) to give 0.066 g of the desired product. ms (m+H) 289.2. See also preparation 7 for the preparation of the acid.

Example SP-312

(2R,3S)-3-amino-4-(3,5-difluorophenyl)-1-{[3-(trifluoromethyl)benzyl]amino}butan-2-ol dihydrochloride

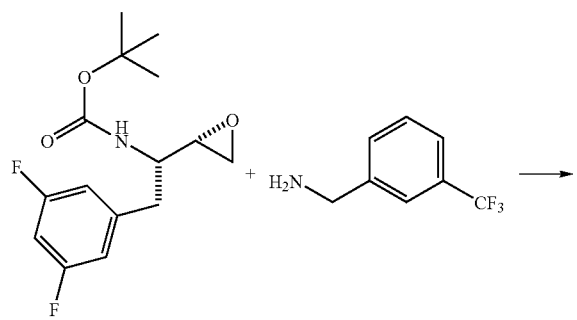

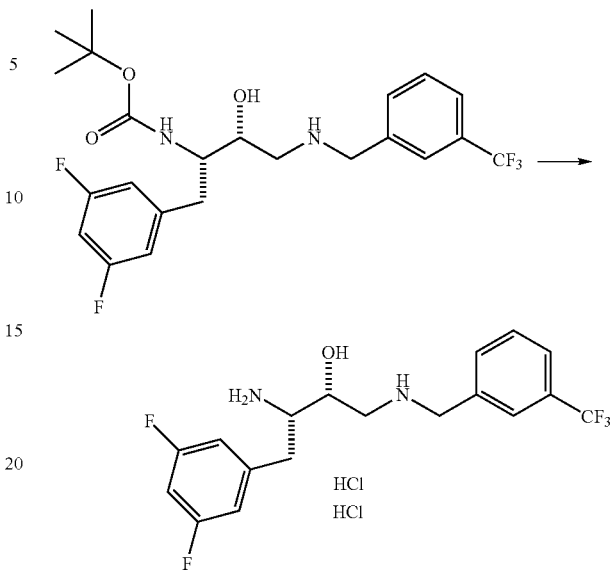

A mixture of oxirane (1.0 g) and 3-(trifluoromethyl)benzylamine (1.2 g) in isopropyl alcohol (25 mL) was stirred at reflux for 4 h, at which time the mixture was cooled and the solvent was removed under reduced pressure. The residue was partitioned between ethyl acetate and aq. HCl (1N) and the organic layers were dried (sodium sulfate), concentrated, and chromatographed on silica gel using methanol-dichloromethane (5/95) to give 1.0 g of tert-butyl (1S,2R)-1-(3,5-difluorobenzyl)-2-hydroxy-3-{[3-(trifluoromethyl)benzyl]amino}propylcarbamate.

The carbamate group was then removed essentially using the method described in EXAMPLE SP-272.

Example SP-313

3-[(dipropylamino)carbonyl]-5-ethynylbenzoic acid

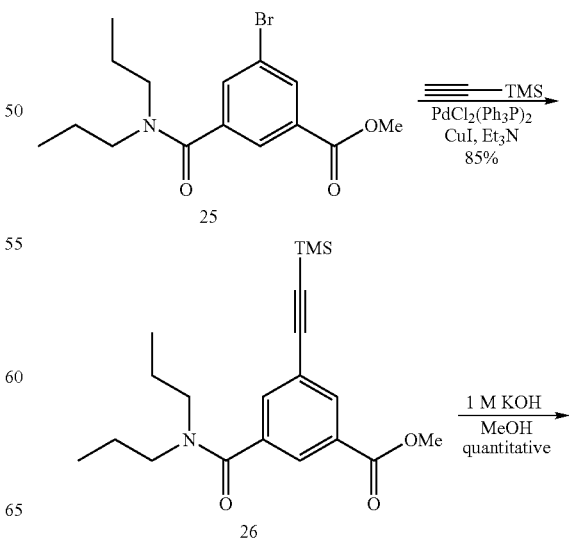

-continued

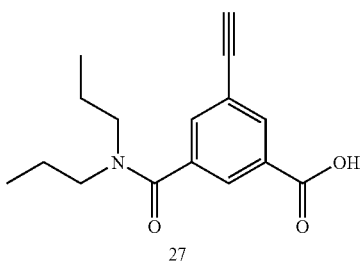

Step 1: A solution of methyl 3-bromo-5-[(dipropylamino)carbonyl]benzoate (25) (200 mg, 0.58 mmol), PdCl$_2$(Ph$_3$P)$_2$ (16 mg, 0.03 mol %) and CuI (6 mg, 0.05 mol %) in triethylamine (1.2 mL) was heated to reflux. (Trimethylsilyl)acetylene (100 μL, 0.7 mmol) was added, and the bright yellow solution quickly turned orange then went brown within a minute. The reaction mixture was stirred for 3 h, cooled to room temperature, diluted with H$_2$O (20 mL), and extracted with CHCl$_3$ (3×15 mL). The combined organics were washed with saturated NaCl (20 mL), dried (Na$_2$SO$_4$), filtered, and concentrated under reduced pressure to give methyl 3-[(dipropylamino)carbonyl]-5-[(trimethylsilyl)ethynyl]benzoate 26 (185.5 mg): $^1$H NMR (300 MHz, CDCl$_3$): δ 7.95 (s, 1H), 7.75 (s, 1H), 7.43 (s, 1H), 3.74 (s, 3H), 3.25 (br s, 2H), 2.95 (br s, 2H), 1.49 (br s, 2H), 1.34 (br s, 2H), 0.79 (br s, 3H), 0.56 (br s, 3H), 0.06 (s, 9H).

Step 2: To a stirred solution of methyl 3-[(dipropylamino)carbonyl]-5-[(trimethylsilyl)ethynyl]benzoate 26 (185.3 mg, 0.49 mmol) in MeOH (2.5 mL) was added a solution of KOH (2.9 mL of a 1 M solution in H$_2$O, 2.9 mmol). The resulting homogeneous brown solution turned to a white/brown suspension, then to a clear brown solution. The reaction mixture was stirred for 4 h, diluted with CHCl$_3$ (40 mL), separated and the organic layer was concentrated under reduced pressure to provide 3-[(dipropylamino)carbonyl]-5-ethynylbenzoic acid 27 (141.8 mg): $^1$H NMR (300 MHz, CDCl$_3$): δ 8.22 (d, J=1 Hz, 1H), 8.05 (d, J=1 Hz, 1H), 7.71 (d, J=1 Hz, 1H), 3.48 (br s, 2H), 3.17 (s, 1H), 3.16 (br s, 2H), 1.71 (d, J=7 Hz, 2H), 1.55 (d, J=7 Hz, 2H), 1.00 (d, J=7 Hz, 3H), 0.78 (d, J=7.Hz, 3H).

The following compounds were also prepared using the procedures described above and the schemes described below.

| EXAMPLE | Structure | Compound Name(s) | Mass Spec |
|---|---|---|---|
| 2999 | 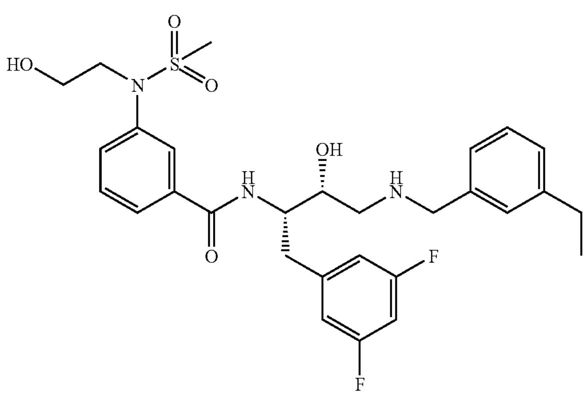 | N-{(1S,2R)-1-(3,5-difluorobenzyl)-3-[(3-ethylbenzyl)amino]-2-hydroxypropyl}-3-[(2-hydroxyethyl)(methylsulfonyl)amino]benzamide | *575.3 |
| 3000 | 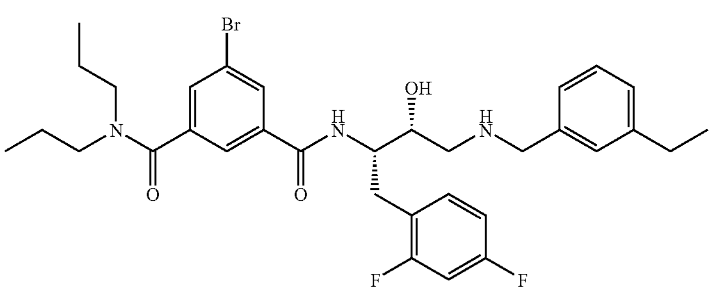 | 5-bromo-N$^1$-{(1S,2R)-1-(2,4-difluorobenzyl)-3-[(3-ethylbenzyl)amino]-2-hydroxypropyl}-N$^3$,N$^3$-dipropylisophthalamide | **644, 646 |

-continued

| EXAMPLE | Structure | Compound Name(s) | Mass Spec |
|---|---|---|---|
| 3001 | 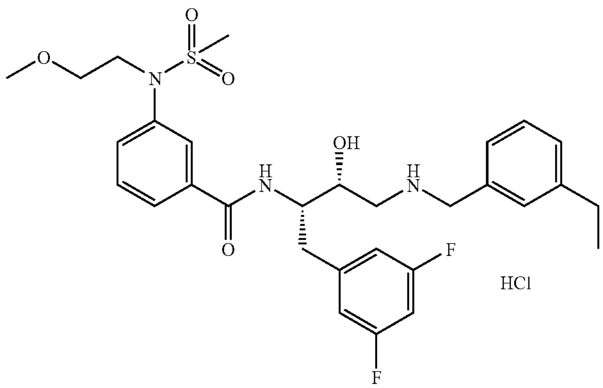 | N-{(1S,2R)-1-(3,5-difluorobenzyl)-3-[(3-ethylbenzyl)amino]-2-hydroxypropyl}-3-[(2-methoxyethyl)(methylsulfonyl)amino]benzamide hydrochloride | **590 |
| 3002 | 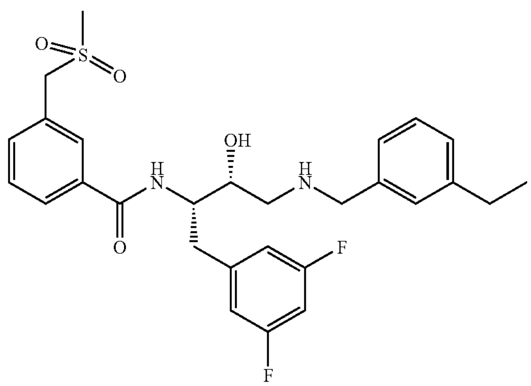 | N-{(1S,2R)-1-(3,5-difluorobenzyl)-3-[(3-ethylbenzyl)amino]-2-hydroxypropyl}-3-[(methylsulfonyl)methyl]benzamide | **531 |
| 3003 | 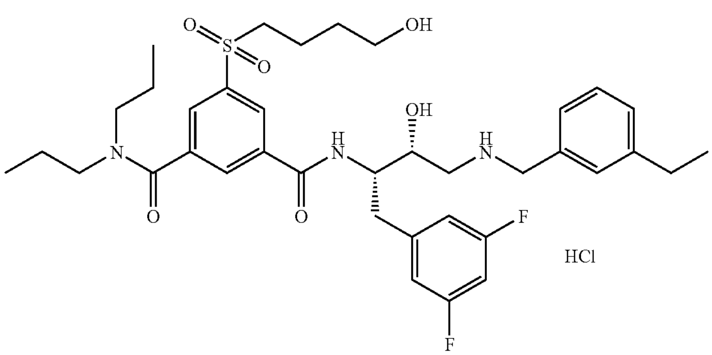 | $N^1$-{(1S,2R)-1-(3,5-difluorobenzyl)-3-[(3-ethylbenzyl)amino]-2-hydroxypropyl}-5-[(4-hydroxybutyl)sulfonyl]-$N^3,N^3$,-dipropylisophthalamide hydrochloride | **702 |
| 3004 | 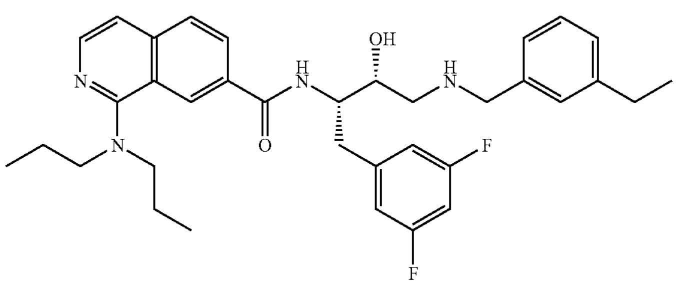 | N-{(1S,2R)-1-(3,5-difluorobenzyl)-3-[(3-ethylbenzyl)amino]-2-hydroxypropyl}-1-(dipropylamino)isoquinoline-7-carboxamide | **589.4 |

-continued

| EXAMPLE | Structure | Compound Name(s) | Mass Spec |
|---|---|---|---|
| 3005 | 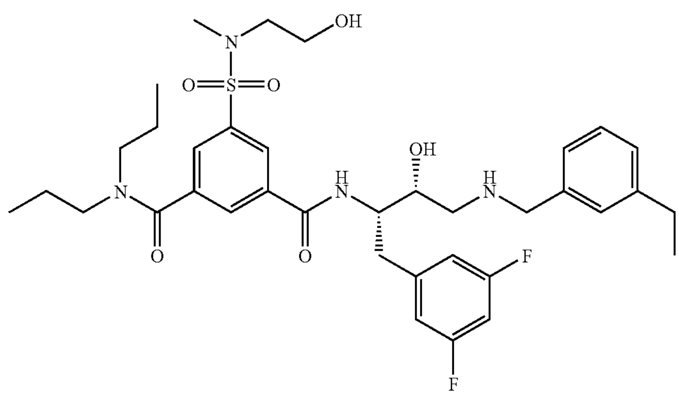 | $N^1$-{(1S,2R)-1-(3,5-difluorobenzyl)-3-[(3-ethylbenzyl)amino]-2-hydroxypropyl}-5-{[(2-hydroxyethyl)(methyl)amino]sulfonyl}-$N^3$,$N^3$-dipropylisophthalamide | **703 |
| 3006 | 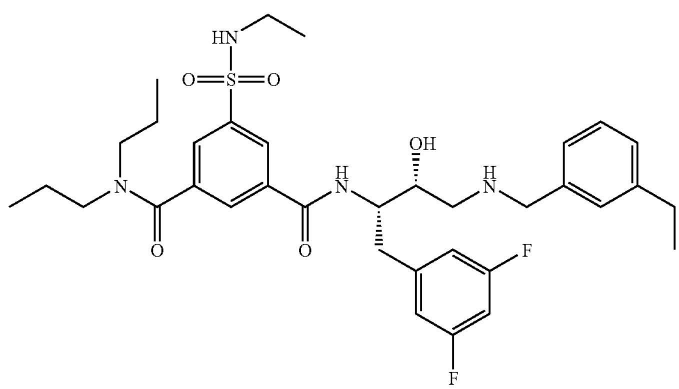 | $N^1$-{(1S,2R)-1-(3,5-difluorobenzyl)-3-[(3-ethylbenzyl)amino]-2-hydroxypropyl}-5-[(ethylamino)sulfonyl]-$N^3$,$N^3$-dipropylisophthalamide | **673 |
| 3007 | 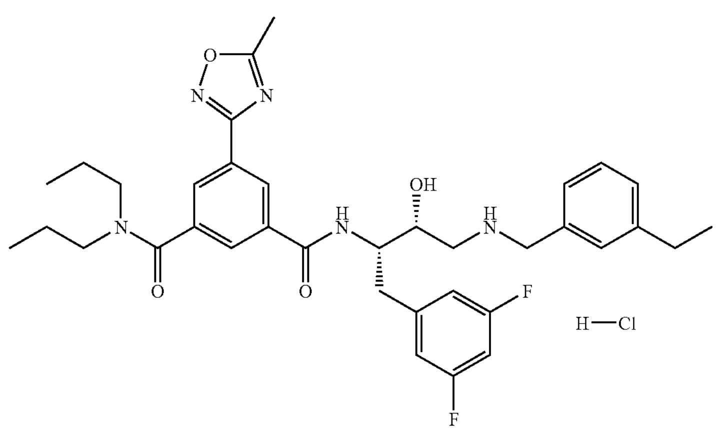 | $N^1$-{(1S,2R)-1-(3,5-difluorobenzyl)-3-[(3-ethylbenzyl)amino]-2-hydroxypropyl}-5-(5-methyl-1,2,4-oxadiazol-3-yl)-$N^3$,$N^3$-dipropylisophthalamide hydrochloride | **648.4 |
| 3008 | 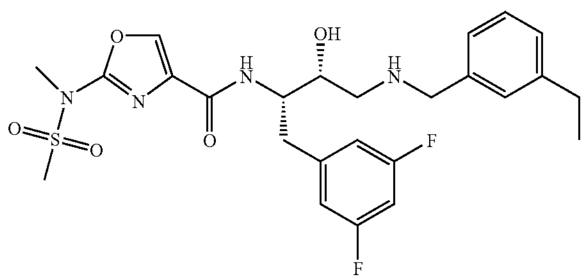 | N-{(1S,2R)-1-(3,5-difluorobenzyl)-3-[(3-ethylbenzyl)amino]-2-hydroxypropyl}-2-[(methyl(methylsulfonyl)amino]-1,3-oxazole-4-carboxamide | ****537.3 (+) |

-continued

| EXAMPLE | Structure | Compound Name(s) | Mass Spec |
|---|---|---|---|
| 3009 | 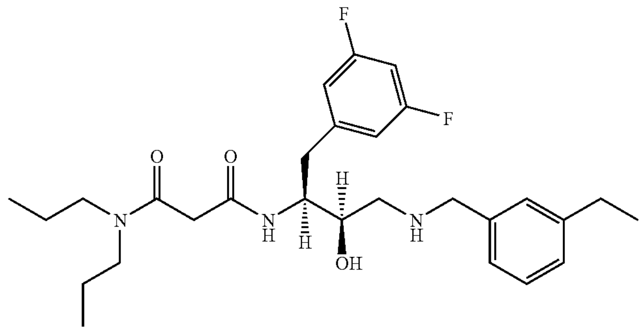 | $N^1$-{(1S,2R)-1-(3,5-difluorobenzyl)-3-[(3-ethylbenzyl)amino]-2-hydroxypropyl}-$N^3,N^3$-dipropylmalonamide | |
| 3010 | 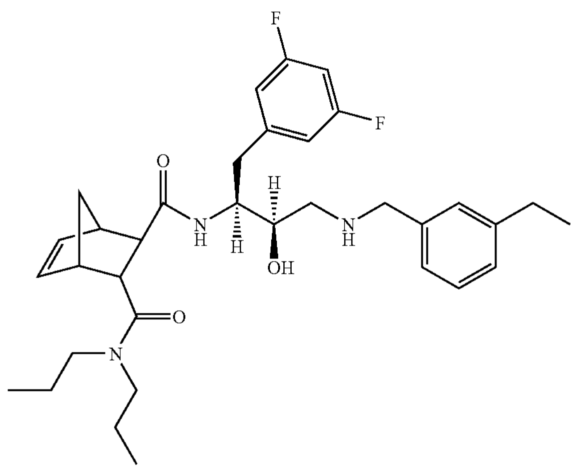 | $N^2$-{(1S,2R)-1-(3,5-difluorobenzyl)-3-[(3-ethylbenzyl)amino]-2-hydroxypropyl}-$N^3,N^3$-dipropylbicylo[2.2.1]hept-5-ene-2,3-dicarboxamide | |
| 3011 | 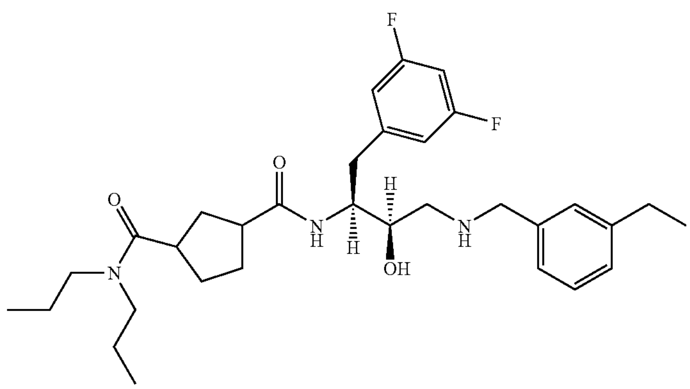 | $N^1$-{(1S,2R)-1-(3,5-difluorobenzyl)-3-[(3-ethylbenzyl)amino]-2-hydroxypropyl}-$N^3,N^3$-dipropylcyclopentane-1,3-dicarboxamide | |
| 3012 | 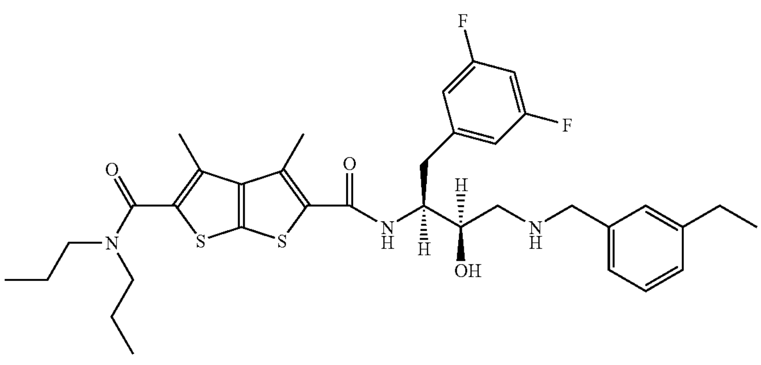 | $N^2$-{(1S,2R)-1-(3,5-difluorobenzyl)-3-[(3-ethylbenzyl)amino]-2-hydroxypropyl}-3,4-dimethyl-$N^5,N^5$-dipropylthieno[2,3-d]thiophene-2,5-dicarboxamide | |

-continued

| EXAMPLE | Structure | Compound Name(s) | Mass Spec |
|---|---|---|---|
| 3013 | 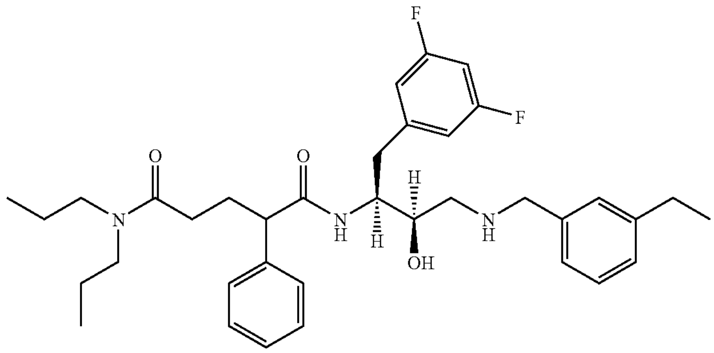 | $N^1$-{(1S,2R)-1-(3,5-difluorobenzyl)-3-[(3-ethylbenzyl)amino]-2-hydroxypropyl}-2-phenyl-$N^5$,$N^5$-dipropylpentanediamide | |
| 3014 | 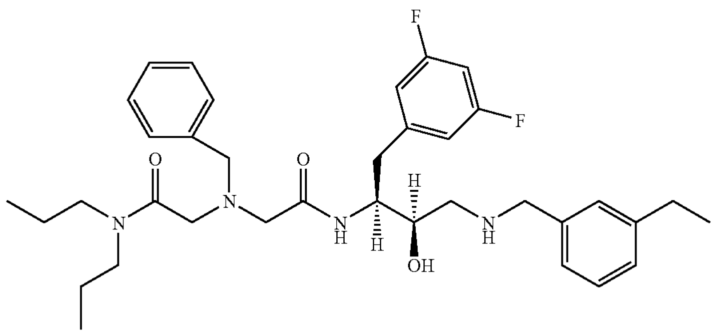 | $N^2$-benzyl-$N^1$-{(1S,2R)-1-(3,5-difluorobenzyl)-3-[(3-ethylbenzyl)amino]-2-hydroxypropyl}-$N^2$-[2-(dipropylamino)-2-oxoethyl]glycinamide | |
| 3015 | 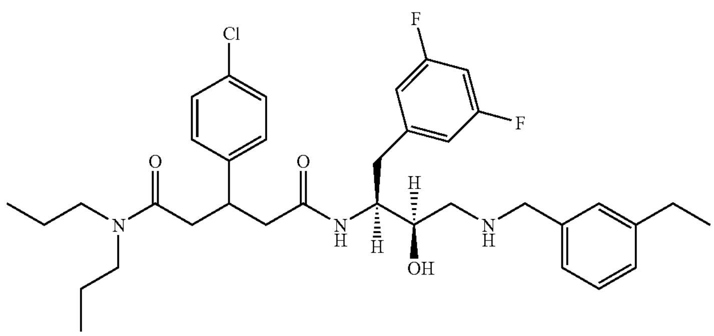 | 3-(4-chlorophenyl)-$N^1$-{(1S,2R)-1-(3,5-difluorobenzyl)-3-[(3-ethylbenzyl)amino]-2-hydroxypropyl}-$N^5$,$N^5$-dipropylpentanediamide | |
| 3016 | 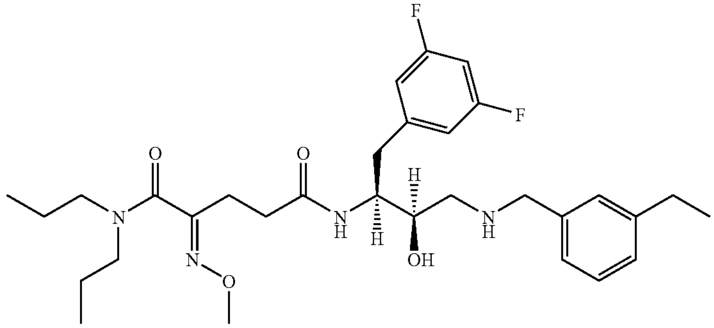 | (2E)-$N^5$-{(1S,2R)-1-(3,5-difluorobenzyl)-3-[(3-ethylbenzyl)amino]-2-hydroxypropyl}-2-(methoxyimino)-$N^1$,$N^1$-dipropylpentanediamide | |

-continued

| EXAMPLE | Structure | Compound Name(s) | Mass Spec |
|---|---|---|---|
| 3017 | 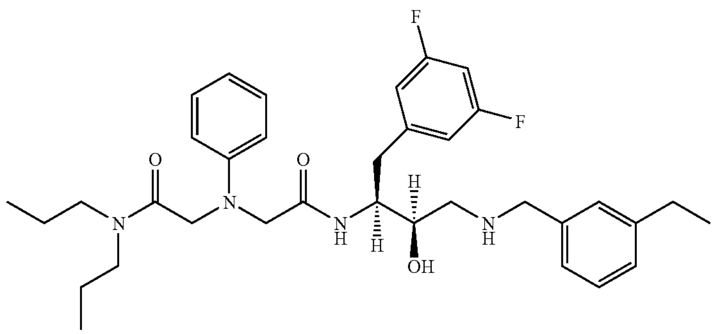 | N¹-{(1S,2R)-1-(3,5-difluoro-benzyl)-3-[(3-ethylbenzyl)amino]-2-hydroxypropyl}-N²-[2-(dipropylamino)-2-oxoethyl]-N²-phenylglycinamide | |
| 3018 | 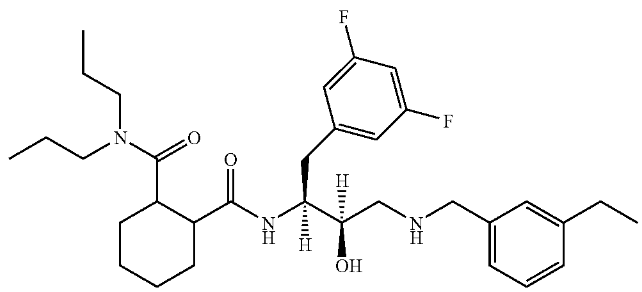 | N¹-{(1S,2R)-1-(3,5-difluoro-benzyl)-3-[(3-ethylbenzyl)amino]-2-hydroxypropyl}-N²,N²-dipropylcyclohexane-1,2-dicarboxamide | |
| 3019 | 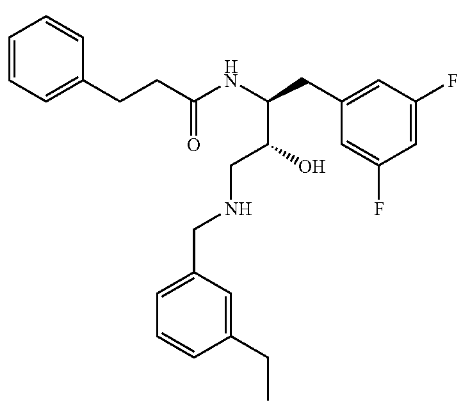 | N-{(1S,2R)-1-(3,5-difluoro-benzyl)-3-[(3-ethylbenzyl)amino]-2-hydroxypropyl}-2-phenylpropanamide | ***467.3 |
| 3020 | 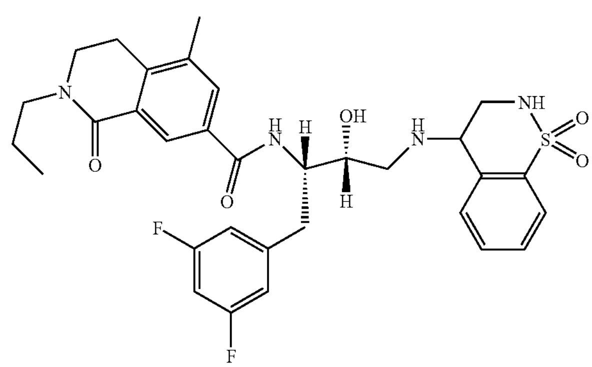 | N¹-{(1S,2R)-1-(3,5-difluoro-benzyl)-3-[(1,1-dioxido-3,4-dihydro-2H-1,2-benzothiazin-4-yl)amino]-2-hydroxy-propyl}-5-methyl-N³,N³-dipropylisophthalamide | |

| EXAMPLE | Structure | Compound Name(s) | Mass Spec |
|---|---|---|---|
| 3021 | 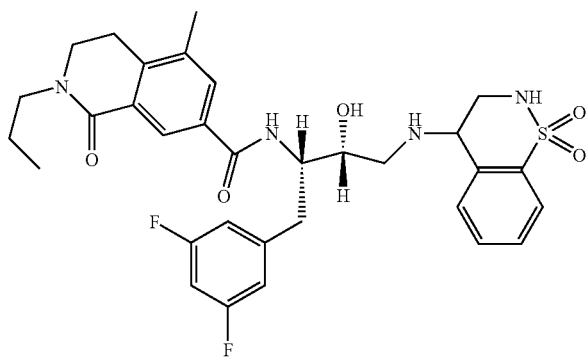 | N$^1$-{(1S,2R)-1-(3,5-difluorobenzyl)-3-[(1,1-dioxido-3,4-dihydro-2H-1,2-benzothiazin-4-yl)amino]-2-hydroxypropyl}-5-methyl-N$^3$,N$^3$-dipropylisophthalamide | |
| 3022 | 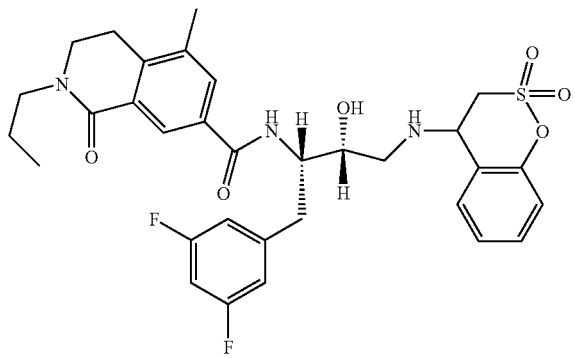 | N$^1$-{(1S,2R)-1-(3,5-difluorobenzyl)-3-[(2,2-dioxido-3,4-dihydro-1,2-benzoxathiin-4-yl)amino]-2-hydroxypropyl}-5-methyl-N$^3$,N$^3$-dipropylisophthalamide | |
| 3023 | 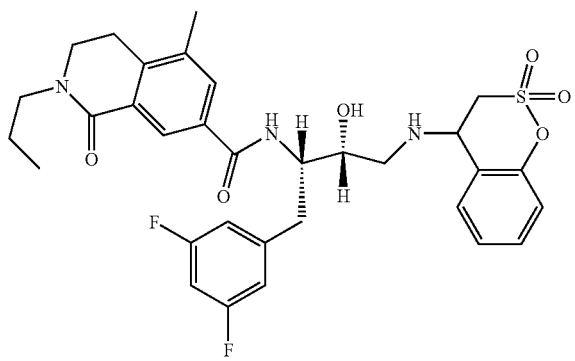 | N$^1$-{(1S,2R)-1-(3,5-difluorobenzyl)-3-[(2,2-dioxido-3,4-dihydro-1,2-benzoxathiin-4-yl)amino]-2-hydroxypropyl}-5-methyl-N$^3$,N$^3$-dipropylisophthalamide | |
| 3024 | 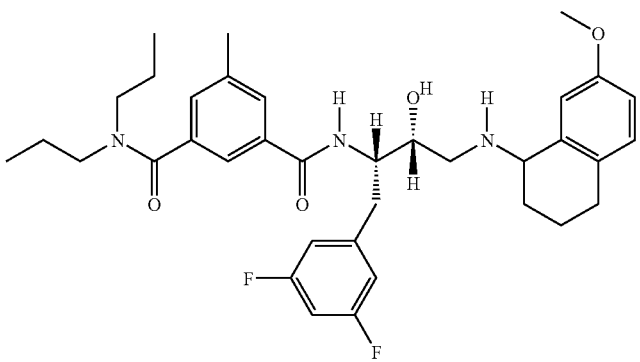 | N$^1$-{(1S,2R)-1-(3,5-difluorobenzyl)-2-hydroxy-3-[(7-methoxy-1,2,3,4-tetrahydronaphthalen-1-yl)amino]propyl}-5-methyl-N$^3$,N$^3$-dipropylisophthalamide | |

-continued

| EXAMPLE | Structure | Compound Name(s) | Mass Spec |
|---|---|---|---|
| 3025 | 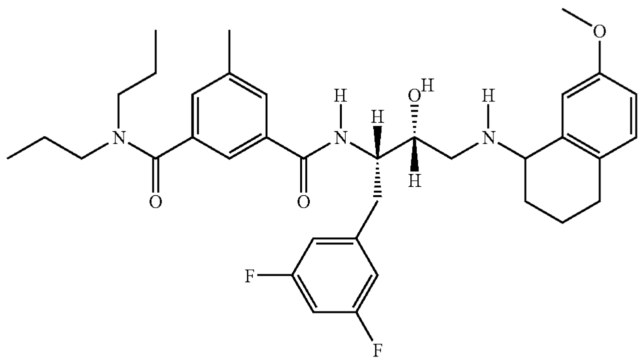 | $N^1$-{(1S,2R)-1-(3,5-difluorobenzyl)-2-hydroxy-3-[(7-methoxy-1,2,3,4-tetrahydronaphthalen-1-yl)amino]propyl}-5-methyl-$N^3$,$N^3$-dipropylisophthalamide | |
| 3026 | 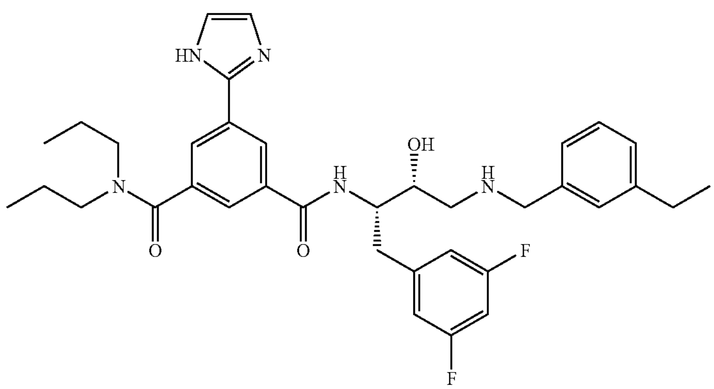 | $N^1$-{(1S,2R)-1-(3,5-difluorobenzyl)-3-[(3-ethylbenzyl)amino]-2-hydroxypropyl}-5-(1H-imidazol-2-yl)-$N^3$,$N^3$-dipropylisophthalamide | **632.3 |
| 3027 | 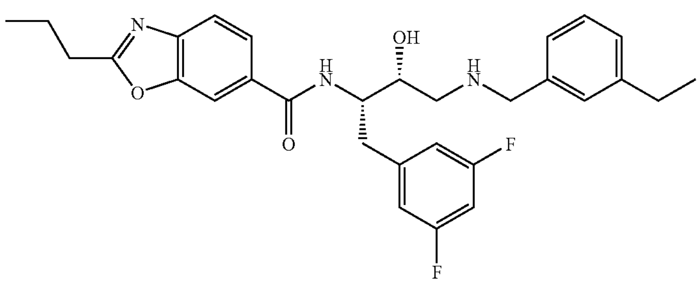 | $N^1$-{(1S,2R)-1-(3,5-difluorobenzyl)-3-[(3-ethylbenzyl)amino]-2-hydroxypropyl}-2-propyl-1,3-benzoxazole-6-carboxamide | **522 |
| 3028 | 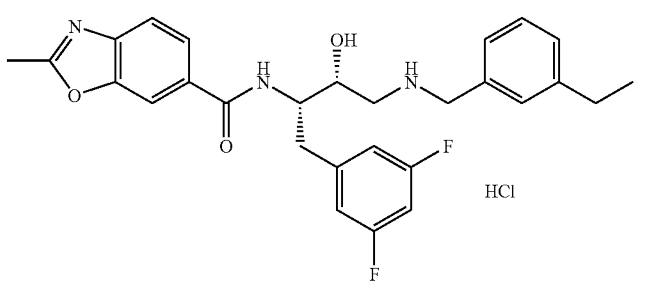 | N-{(1S,2R)-1-(3,5-difluorobenzyl)-3-[(3-ethylbenzyl)amino]-2-hydroxypropyl}-2-methyl-1,3-benzoxazole-6-carboxamide hydrochloride | **494 |

| EXAMPLE | Structure | Compound Name(s) | Mass Spec |
|---|---|---|---|
| 3029 | 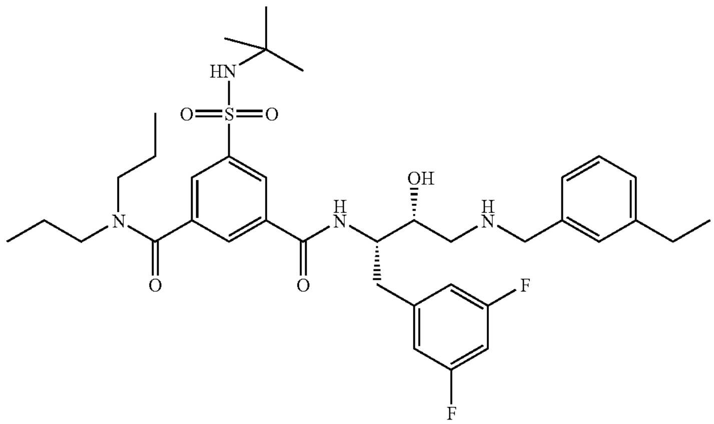 | 5-[(tert-butylamino)sulfonyl]-N¹-{(1S,2R)-1-(3,5-difluorobenzyl)-3-[(3-ethylbenzyl)amino]-2-hydroxypropyl}-N³,N³-dipropylisophthalamide | **701 |
| 3030 | 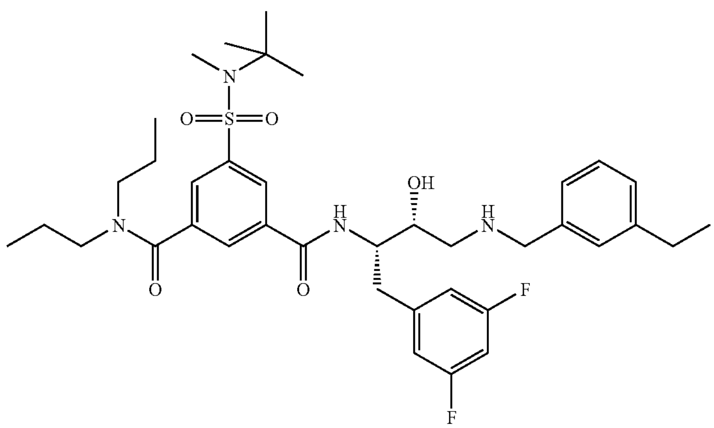 | 5-{[tert-butyl(methyl)amino]sulfonyl}-N¹-{(1S,2R)-1-(3,5-difluorobenzyl)-3-[(3-ethylbenzyl)amino]-2-hydroxypropyl}-N³,N³-dipropylisophthalamide | **715 |
| 3031 | 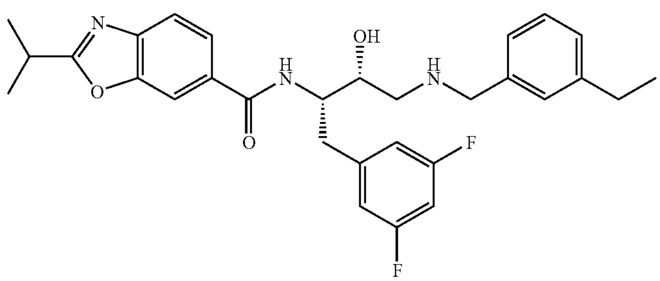 | N-{(1S,2R)-1-(3,5-difluorobenzyl)-3-[(3-ethylbenzyl)amino]-2-hydroxypropyl}-2-isopropyl-1,3-benzoxazole-6-carboxamide | **522 |
| 3032 | 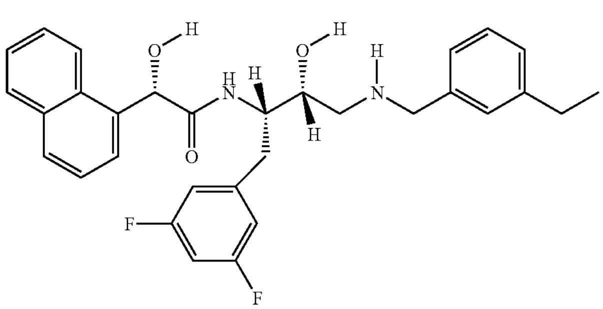 | (2S)-N-{(1S,2R)-1-(3,5-difluorobenzyl)-3-[(3-ethylbenzyl)amino]-2-hydroxypropyl}-2-hydroxy-2-(1-naphthyl)ethanamide | |

-continued

| EXAMPLE | Structure | Compound Name(s) | Mass Spec |
|---|---|---|---|
| 3033 | 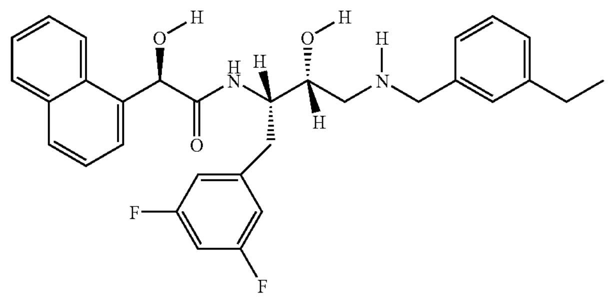 | (2R)-N-{(1S,2R)-1-(3,5-difluorobenzyl)-3-[(3-ethylbenzyl)amino]-2-hydroxypropyl}-2-hydroxy-2-(1-naphthyl)ethanamide | |
| 3034 | 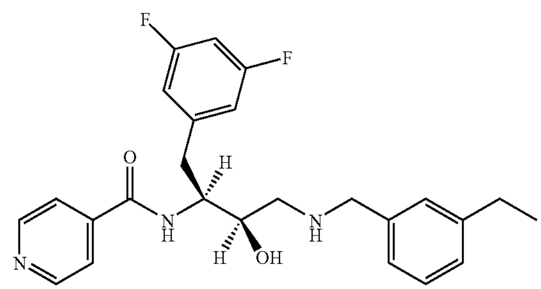 | N-{(1S,2R)-1-(3,5-difluorobenzyl)-3-[(3-ethylbenzyl)amino]-2-hydroxypropyl]isonicotinamide | |
| 3035 | 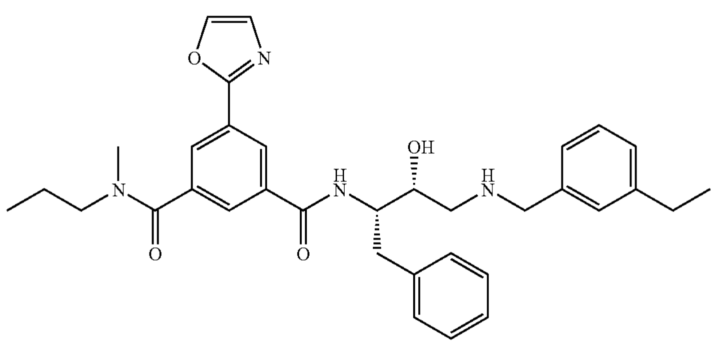 | N$^1$-{(1S,2R)-1-benzyl-3-[(3-ethylbenzyl)amino]-2-hydroxypropyl}-N$^3$-methyl-5-(1,3-oxazol-2-yl)-N$^3$-propylisophthalamide | **569.3 |
| 3036 | 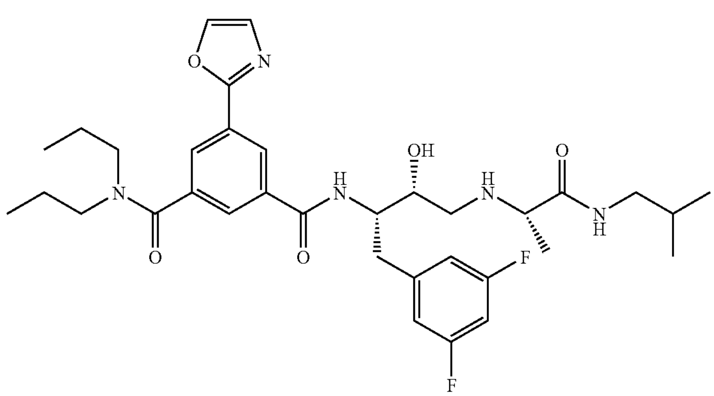 | | **642.3 |

-continued

| EXAMPLE | Structure | Compound Name(s) | Mass Spec |
|---|---|---|---|
| 3037 | 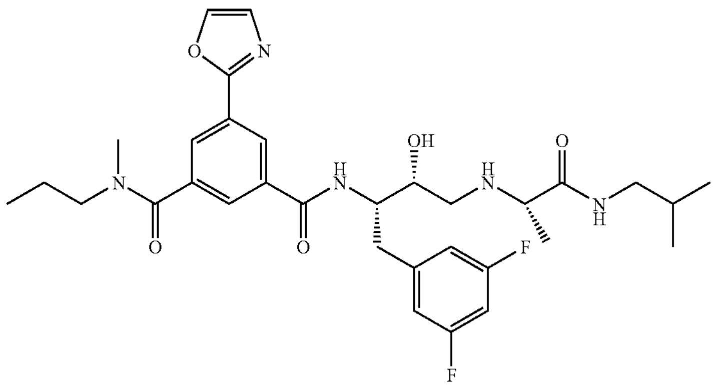 | | **614.4 |
| 3038 | 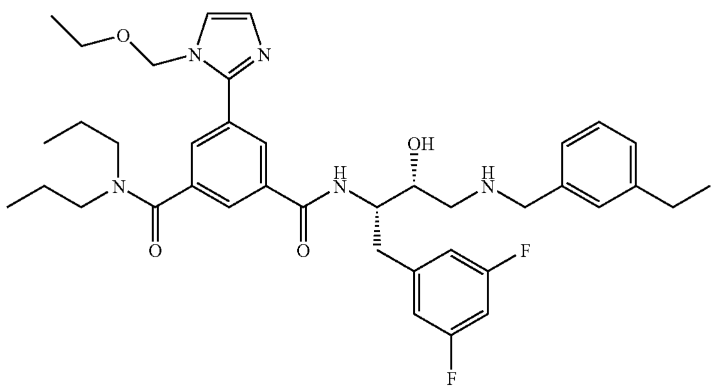 | N¹-{(1S,2R)-1-(3,5-difluorobenzyl)-3-[(3-ethylbenzyl)amino]-2-hydroxypropyl}-5-[1-(ethoxymethyl)-1H-imidazol-2-yl]-$N^3,N^3$-dipropylisophthalamide | **690.3 |
| 3039 | 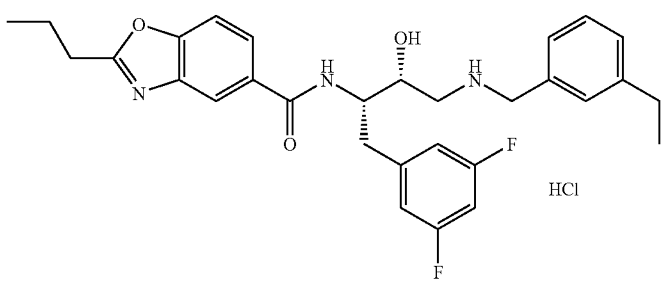 | N-{(1S,2R)-1-(3,5-difluorobenzyl)-3-[(3-ethylbenzyl)amino]-2-hydroxypropyl}-2-propyl-1,3-benzoxazole-5-carboxamide hydrochloride | **522 |
| 3040 | 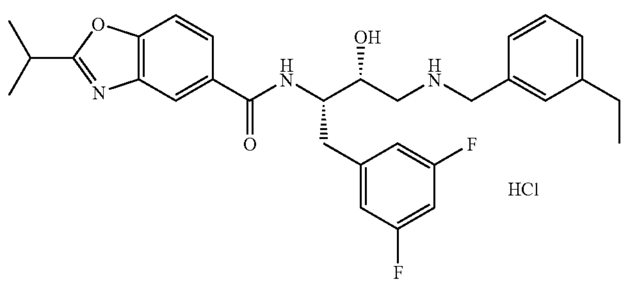 | N-{(1S,2R)-1-(3,5-difluorobenzyl)-3-[(3-ethylbenzyl)amino]-2-hydroxpropyl}-2-isopropyl-1,3-benzoxazole-5-carboxamide hydrochloride | **522 |

-continued

| EXAMPLE | Structure | Compound Name(s) | Mass Spec |
|---|---|---|---|
| 3041 | 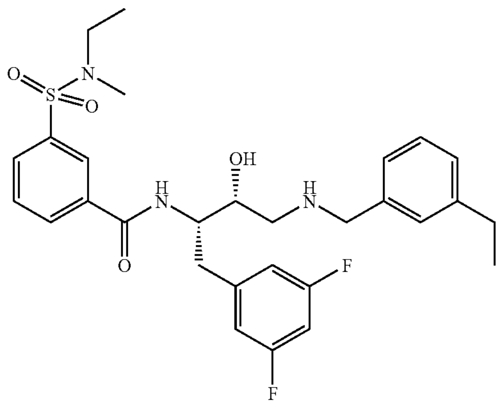 | N-{(1S,2R)-1-(3,5-difluorobenzyl)-3-[(3-ethylbenzyl)amino]-2-hydroxypropyl}-3-{[ethyl(methyl)amino]sulfonyl}benzamide | **560 |
| 3042 | 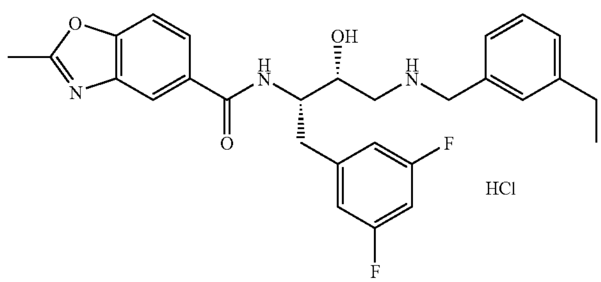 | N-{(1S,2R)-1-(3,5-difluorobenzyl)-3-[(3-ethylbenzyl)amino]-2-hydroxypropyl}-2-methyl-1,3-benzoxazole-5-carboxamide hydrochloride | **494 |
| 3043 | 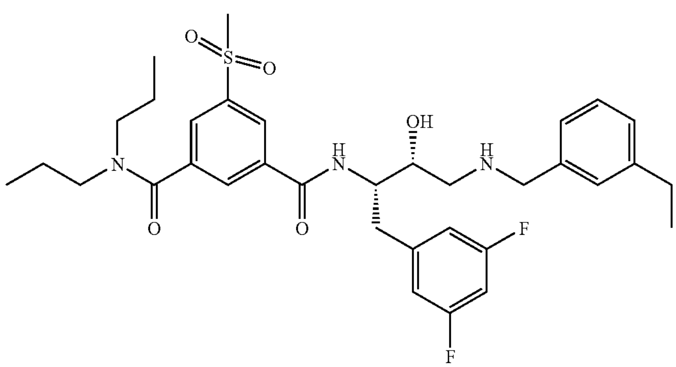 | $N^1$-{(1S,2R)-1-(3,5-difluorobenzyl)-3-[(3-ethylbenzyl)amino]-2-hydroxypropyl}-5-(methylsulfonyl)-$N^3$,$N^3$-dipropylisophthalamide | **644 |
| 3044 | 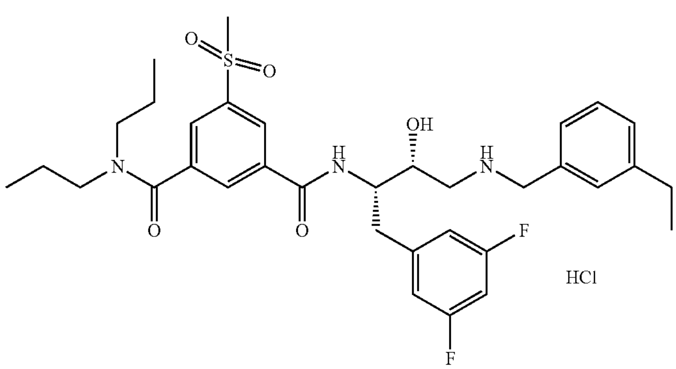 | $N^1$-{(1S,2R)-1-(3,5-difluorobenzyl)-3-[(3-ethylbenzyl)amino]-2-hydroxypropyl}-5-(methylsulfonyl)-$N^3$,$N^3$-dipropylisophthalamide hydrochloride | **645.04 |

-continued

| EXAMPLE | Structure | Compound Name(s) | Mass Spec |
|---|---|---|---|
| 3045 | 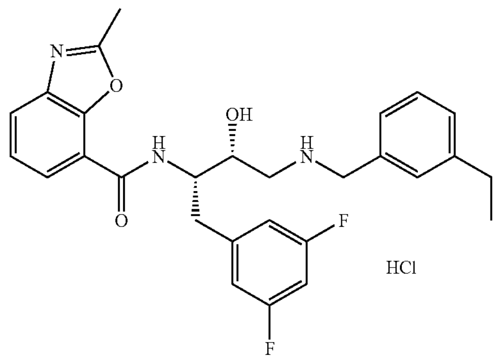 | N$^1$-{(1S,2R)-1-(3,5-difluorobenzyl)-3-[(3-ethylbenzyl)amino]-2-hydroxypropyl}-2-methyl-1,3-benzoxazole-7-carboxamide hydrochloride | **494 |
| 3046 | 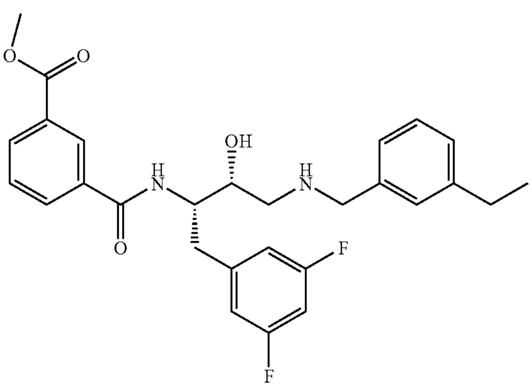 | methyl 3-[({(1S,2R)-1-(3,5-difluorobenzyl)-3-[(3-ethylbenzyl)amino]-2-hydroxypropyl}amino)carbonyl]benzoate | **497.3 |
| 3047 | 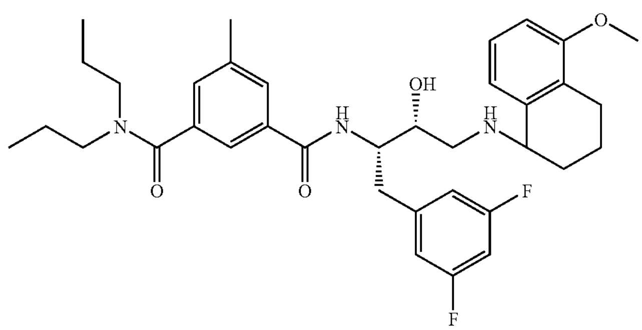 | N$^1$-{(1S,2R)-1-(3,5-difluorobenzyl)-2-hydroxy-3-[(5-methoxy-1,2,3,4-tetrahydronaphthalen-1-yl)amino]propyl}-5-methyl-N$^3$,N$^3$-dipropylisophthalamide | |
| 3048 | 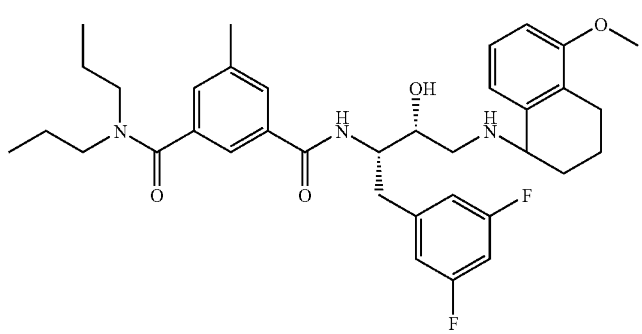 | N$^1$-{(1S,2R)-1-(3,5-difluorobenzyl)-2-hydroxy-3-[(5-methoxy-1,2,3,4-tetrahydronaphthalen-1-yl)amino]propyl}-5-methyl-N$^3$,N$^3$-dipropylisophthalamide | |

-continued

| EXAMPLE | Structure | Compound Name(s) | Mass Spec |
|---|---|---|---|
| 3049 | 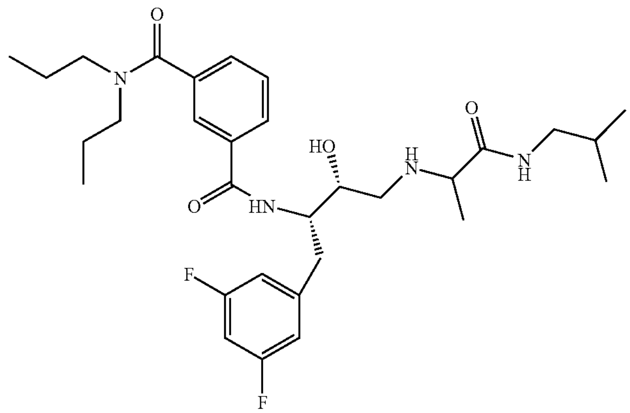 | ELAN-91970 | |
| 3050 | 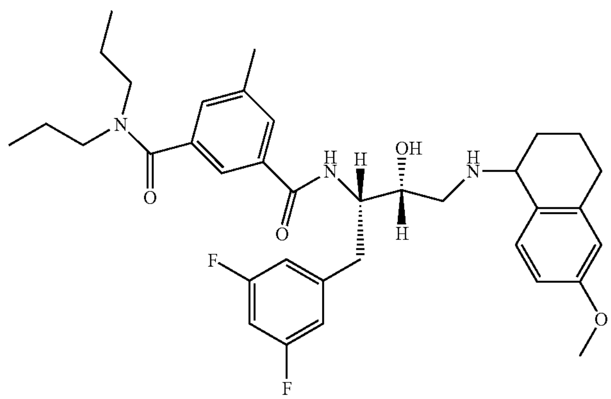 | N¹-{(1S,2R)-1-(3,5-difluorobenzyl)-2-hydroxy-3-[(6-methoxy-1,2,3,4-tetrahydronaphthalen-1-yl)amino]propyl}-5-methyl-N³,N³-dipropylisophthalamide | |
| 3051 | 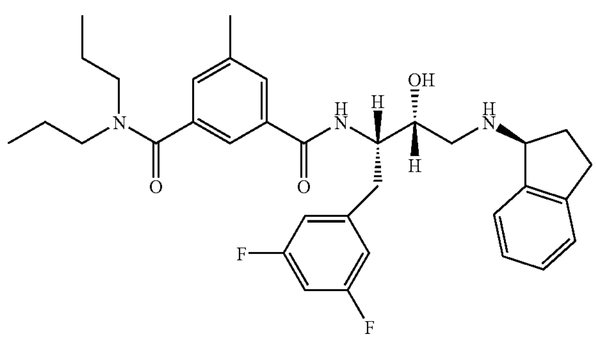 | N¹-{(1S,2R)-1-(3,5-difluorobenzyl)-3-[(1S)-2,3-dihydro-1H-inden-1-ylamino]-2-hydroxypropyl}-5-methyl-N³,N³-dipropylisophthalamide | |
| 3052 | 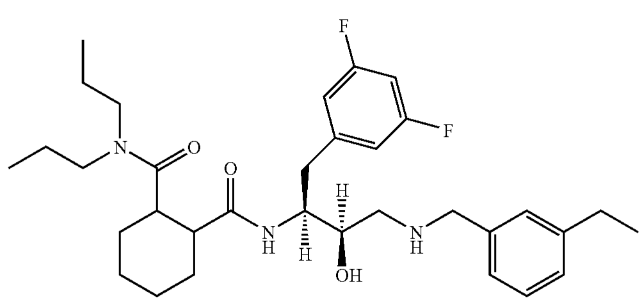 | N¹-{(1S,2R)-1-(3,5-difluorobenzyl)-3-[(3-ethylbenzyl)amino]-2-hydroxypropyl}-N²,N²-dipropylcyclohexane-1,2-dicarboxamide | |

| EXAMPLE | Structure | Compound Name(s) | Mass Spec |
|---|---|---|---|
| 3053 | 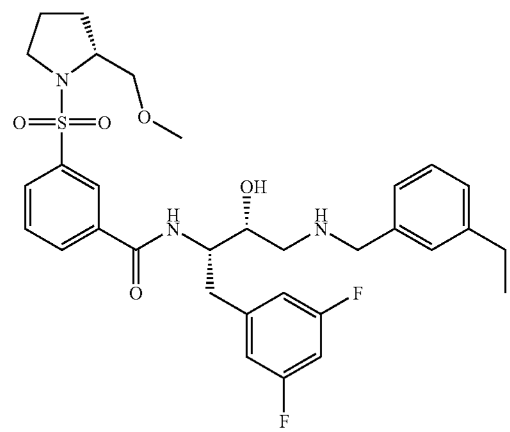 | N-{(1S,2R)-1-(3,5-difluorobenzyl)-3-[(3-ethylbenzyl)amino]-2-hydroxypropyl}-3-{[(2R)-2-(methoxymethyl)pyrrolidin-1-yl]sulfonyl}benzamide | **616 |
| 3054 | 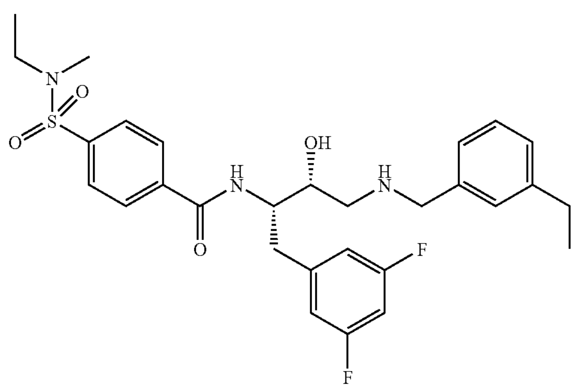 | N-{(1S,2R)-1-(3,5-difluorobenzyl)-3-[(3-ethylbenzyl)amino]-2-hydroxypropyl}-4-{[ethyl(methyl)amino]sulfonyl}benzamide | **560 |
| 3055 | 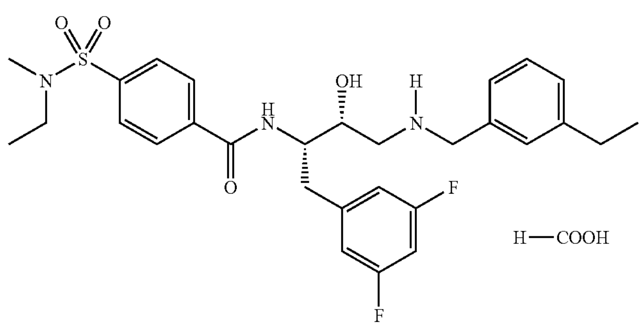 | formic acid compound with N-{(1S,2R)-1-(3,5-difluorobenzyl)-3-[(3-ethylbenzyl)amino]-2-hydroxypropyl}-4-{[ethyl(methyl)amino]sulfonyl}benzamide (1:1) | ***560.1 |
| 3056 | 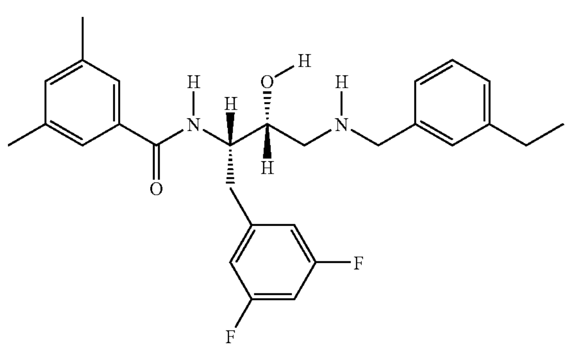 | N-{(1S,2R)-1-(3,5-difluorobenzyl)-3-[(3-ethylbenzyl)amino]-2-hydroxypropyl}-3,5-dimethylbenzamide | |

| EXAMPLE | Structure | Compound Name(s) | Mass Spec |
|---|---|---|---|
| 3057 | 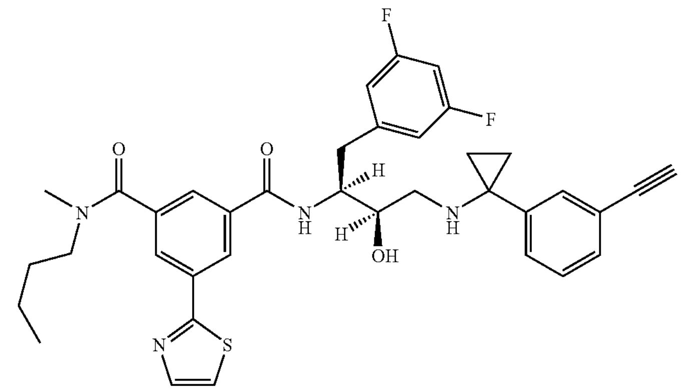 | N¹-butyl-N³-((1S,2R)-1-(3,5-difluorobenzyl)-3-{[1-(3-ethynylphenyl)cyclopropyl]amino}-2-hydroxypropyl)-N¹-methyl-5-(1,3-thiazol-2-yl)isophthalamide | |
| 3058 | 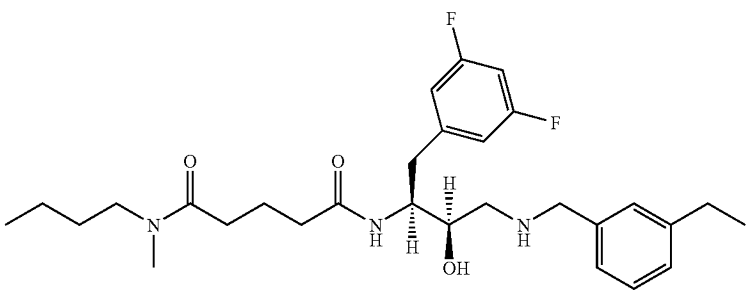 | N¹-butyl-N⁵-{(1S,2R)-1-(3,5-difluorobenzyl)-3-[(3-ethylbenzyl)amino]-2-hydroxypropyl}-N¹-methylpentanediamide | |
| 3059 | 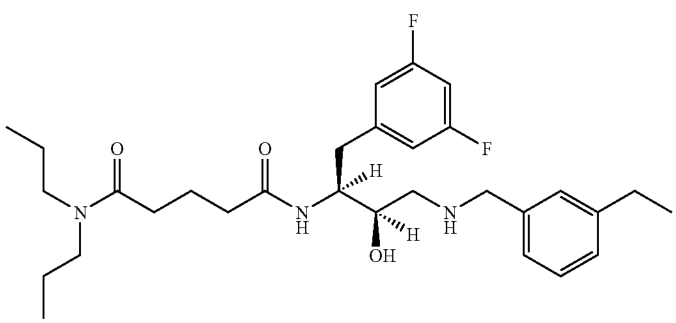 | N¹-{(1S,2R)-1-(3,5-difluorobenzyl)-3-[(3-ethylbenzyl)amino]-2-hydroxypropyl}-N⁵,N⁵-dipropylpentanediamide | |
| 3060 | 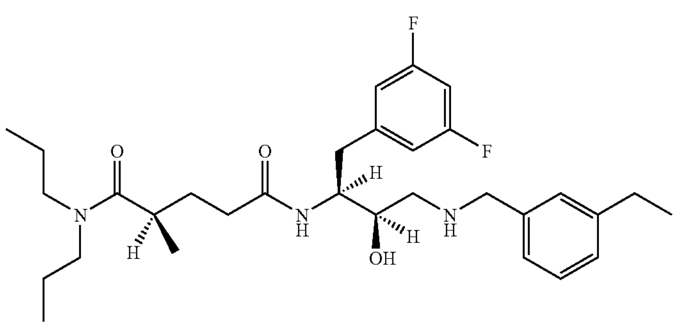 | (2R)-N⁵-{(1S,2R)-1-(3,5-difluorobenzyl)-3-[(3-ethylbenzyl)amino]-2-hydroxypropyl}-2-methyl-N¹,N¹-dipropylpentanediamide | |

| EXAMPLE | Structure | Compound Name(s) | Mass Spec |
|---|---|---|---|
| 3061 | 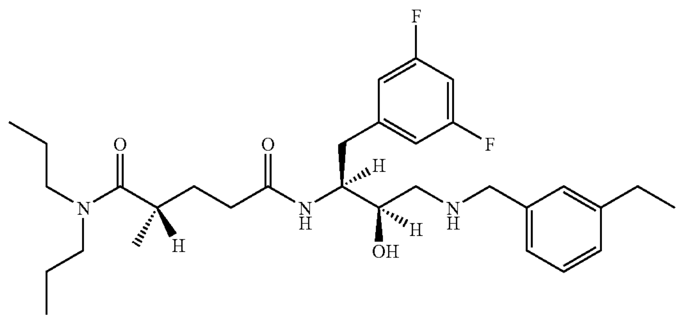 | (2S)-N$^5$-{(1S,2R)-1-(3,5-difluorobenzyl)-3-[(3-ethylbenzyl)amino]-2-hydroxypropyl}-2-methyl-N$^1$,N$^1$-dipropylpentanediamide | |
| 3062 | 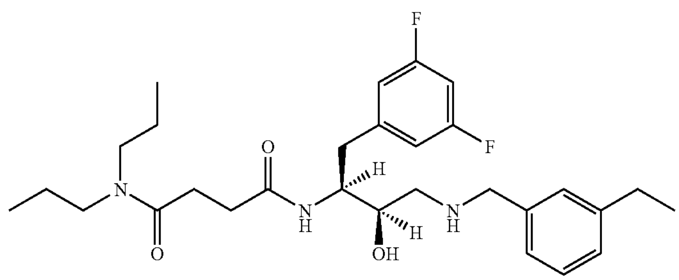 | N$^1$-{(1S,2R)-1-(3,5-difluorobenzyl)-3-[(3-ethylbenzyl)amino]-2-hydroxypropyl}-N$^4$,N$^4$-dipropylsuccinamide | |
| 3063 | 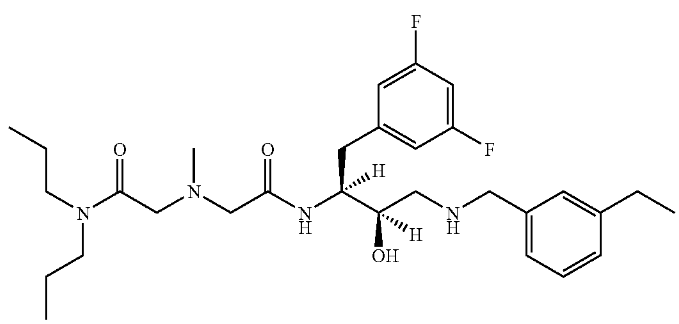 | N$^1$-{(1S,2R)-1-(3,5-difluorobenzyl)-3-[(3-ethylbenzyl)amino]-2-hydroxypropyl}-N$^2$-[2-(dipropylamino)-2-oxoethyl]-N$^2$-methylglycinamide | |
| 3064 | 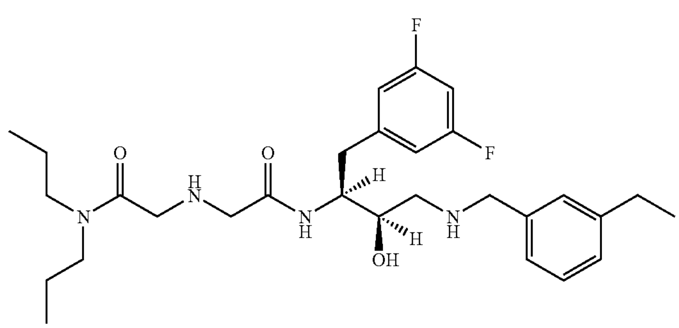 | N$^1$-{(1S,2R)-1-(3,5-difluorobenzyl)-3-[(3-ethylbenzyl)amino]-2-hydroxypropyl}-N$^2$-[2-(dipropylamino)-2-oxoethyl]-glycinamide | |

-continued

| EXAMPLE | Structure | Compound Name(s) | Mass Spec |
|---|---|---|---|
| 3065 | 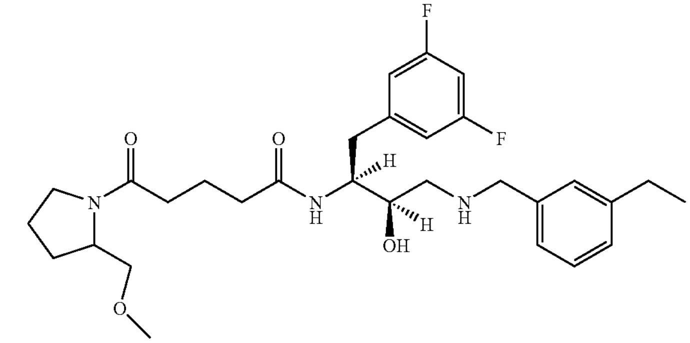 | N-{(1S,2R)-1-(3,5-difluoro-benzyl)-3-[(3-ethylbenzyl)amino]-2-hydroxypropyl}-5-[2-(methoxymethyl)pyrrolidin-1-yl]-5-oxopentanamide | |
| 3066 | 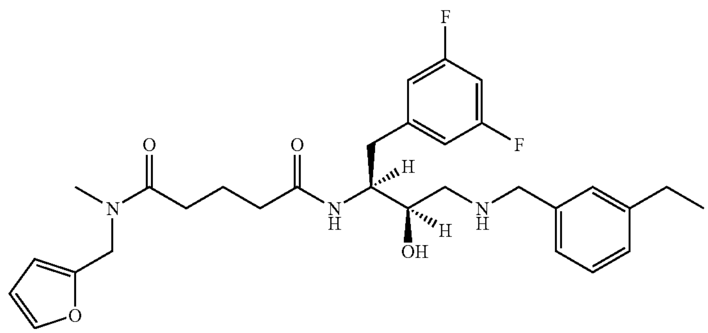 | $N^1$-{(1S,2R)-1-(3,5-difluoro-benzyl)-3-[(3-ethylbenzyl)amino]-2-hydroxypropyl}-$N^5$-(2-furylmethyl)-$N^5$-methylpentanediamide | |
| 3067 | 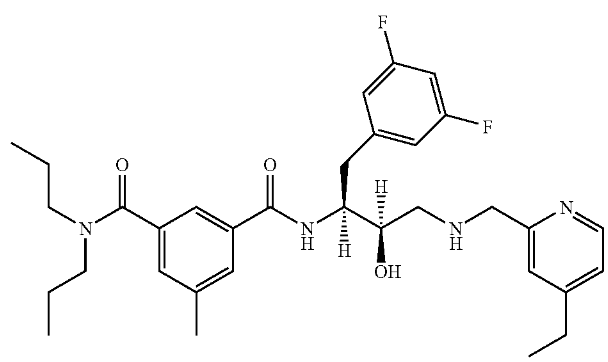 | $N^1$-((1S,2R)-1-(3,5-difluoro-benzyl)-3-{[(4-ethylpyridin-2-yl)methyl]amino}-2-hydroxypropyl)-5-methyl-$N^3,N^3$-dipropylisophthalamide | |
| 3068 | 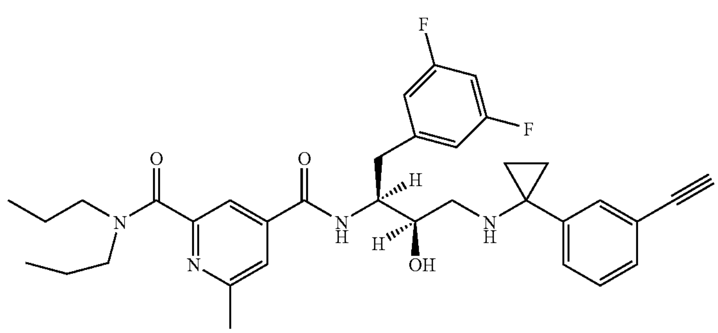 | $N^4$-((1S,2R)-1-(3,5-difluoro-benzyl)-3-{[1-(3-ethynyl-phenyl)cyclopropyl]amino}-2-hydroxypropyl)-6-methyl-$N^2,N^2$-dipropylpyridine-2,4-dicarboxamide | |

-continued

| EXAMPLE | Structure | Compound Name(s) | Mass Spec |
|---|---|---|---|
| 3069 | 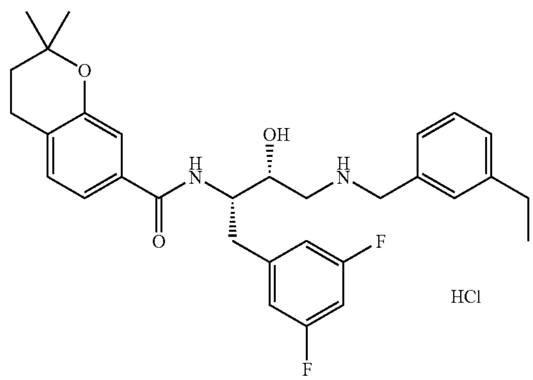 | N-{(1S,2R)-1-(3,5-difluoro-benzyl)-3-[(3-ethylbenzyl)amino]-2-hydroxypropyl}-2,2-dimethylchromane-7-carboxamide hydrochloride | **523 |
| 3070 | 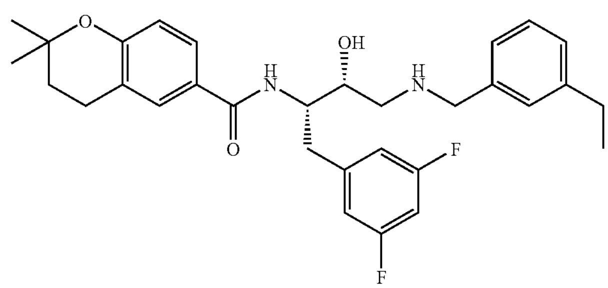 | N-{(1S,2R)-1-(3,5-difluoro-benzyl)-3-[(3-ethylbenzyl)amino]-2-hydroxypropyl}-2,2-dimethylchromane-6-carboxamide | **523 |
| 3071 | 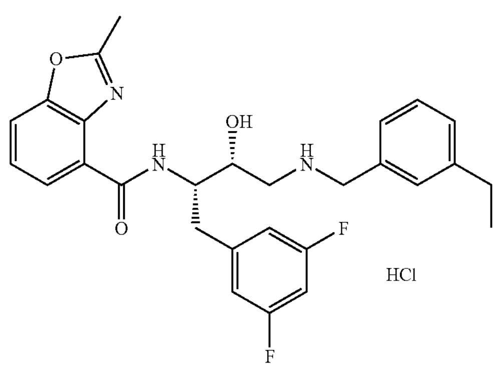 | N-{(1S,2R)-1-(3,5-difluoro-benzyl)-3-[(3-ethylbenzyl)amino]-2-hydroxypropyl}-2-methyl-1,3-benzoxazole-4-carboxamide hydrochloride | **494 |
| 3072 | 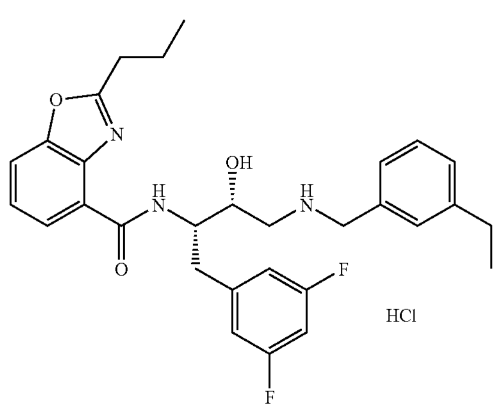 | N-{(1S,2R)-1-(3,5-difluoro-benzyl)-3-[(3-ethylbenzyl)amino]-2-hydroxypropyl}-2-propyl-1,3-benzoxazole-4-carboxamide hydrochloride | |

-continued

| EXAMPLE | Structure | Compound Name(s) | Mass Spec |
|---|---|---|---|
| 3073 | 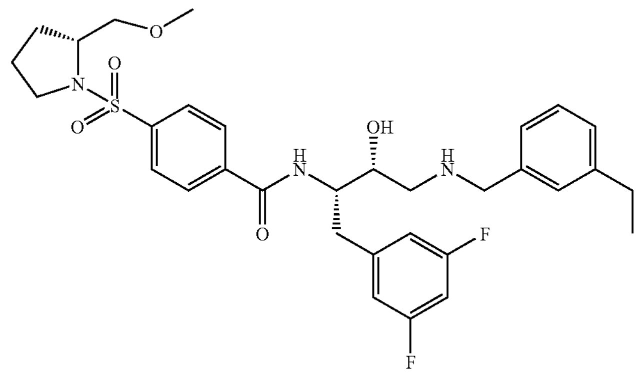 | N-{(1S,2R)-1-(3,5-difluorobenzyl)-3-[(3-ethylbenzyl)amino]-2-hydroxypropyl}-4-{[(2R)-2-(methoxymethyl)pyrrolidin-1-yl]sulfonyl}benzamide | **616 |
| 3074 | 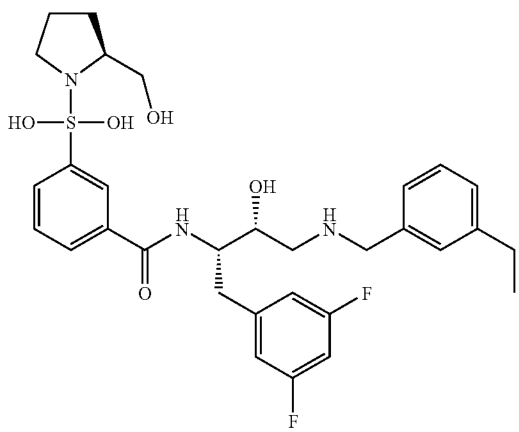 | N-{(1S,2R)-1-(3,5-difluorobenzyl)-3-[(3-ethylbenzyl)amino]-2-hydroxypropyl}-3-(dihydroxy[(2S)-2-(hydroxymethyl)pyrrolidin-1-yl]-lambda$^4$-sulfanyl}benzamide | **602 |
| 3075 | 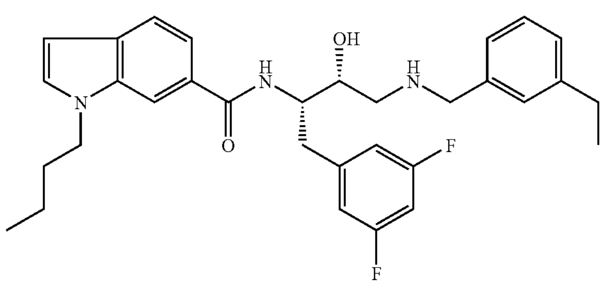 | 1-butyl-N-{(1S,2R)-1-(3,5-difluorobenzyl)-3-[(3-ethylbenzyl)amino]-2-hydroxypropyl}-1H-indole-6-carboxamide | **534 |
| 3076 | 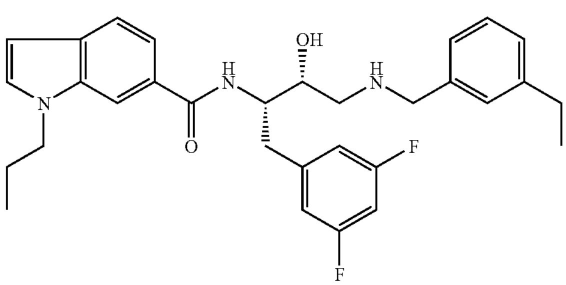 | N-{(1S,2R)-1-(3,5-difluorobenzyl)-3-[(3-ethylbenzyl)amino]-2-hydroxypropyl}-1-propyl-1H-indole-6-carboxamide | **520 |

| EXAMPLE | Structure | Compound Name(s) | Mass Spec |
|---|---|---|---|
| 3077 | 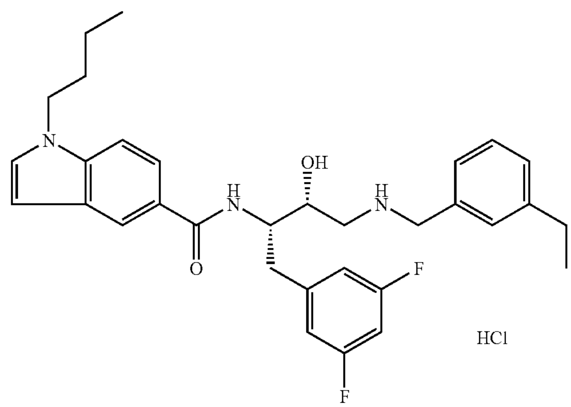 | 1-butyl-N-{(1S,2R)-1-(3,5-difluorobenzyl)-3-[(3-ethylbenzyl)amino]-2-hydroxypropyl}-1H-indole-5-carboxamide hydrochloride | **534 |
| 3078 | 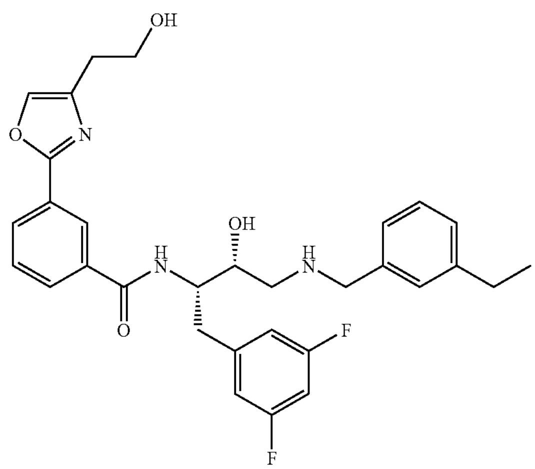 | N-{(1S,2R)-1-(3,5-difluorobenzyl)-3-[(3-ethylbenzyl)amino]-2-hydroxypropyl}-3-[4-(2-hydroxyethyl)-1,3-oxazol-2-yl]benzamide | **550.3 |
| 3079 | 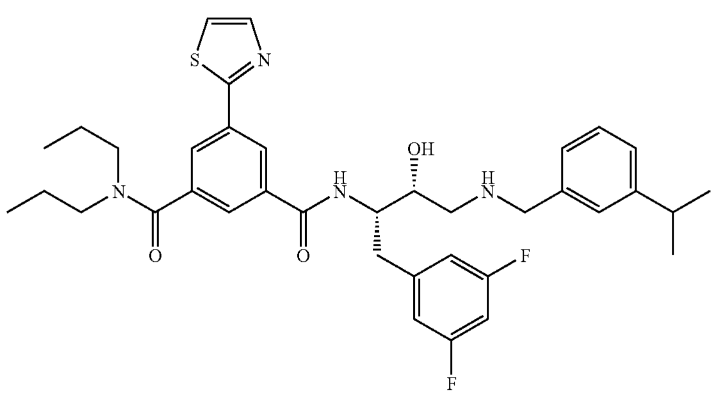 | $N^1$-{(1S,2R)-1-(3,5-difluorobenzyl)-2-hydroxy-3-[(3-isopropylbenzyl)amino]propyl}-$N^3$,$N^3$-dipropyl-5-(1,3-thiazol-2-yl)isophthalamide | **663.3 |

-continued

| EXAMPLE | Structure | Compound Name(s) | Mass Spec |
|---|---|---|---|
| 3080 | 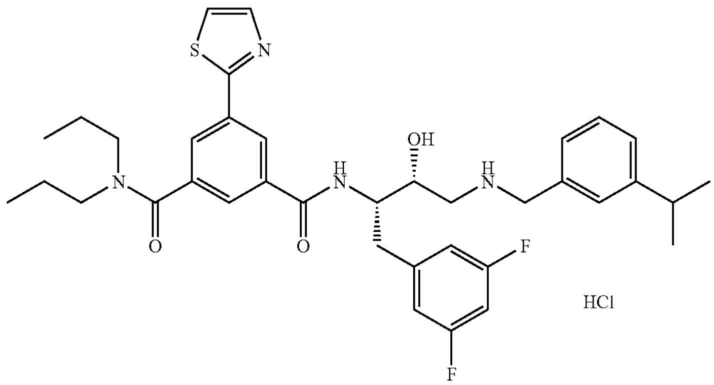 | $N^1$-{(1S,2R)-1-(3,5-difluorobenzyl)-2-hydroxy-3-[(3-isopropylbenzyl)amino]propyl}-$N^3$,$N^3$-dipropyl-5-(1,3-thiazol-2-yl)isophthalamide hydrochloride | **663.3 |
| 3081 | 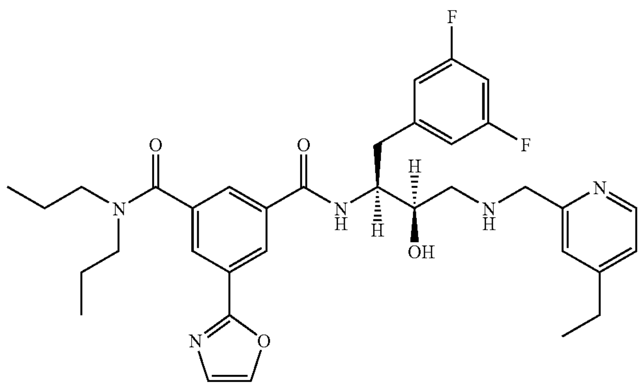 | $N^1$-((1S,2R)-1-(3,5-difluorobenzyl)-3-{[(4-ethylpyridin-2-yl)methyl]amino}-2-hydroxypropyl)-5-(1,3-oxazol-2-yl)-$N^3$,$N^3$-dipropylisophthalamide | |
| 3082 | 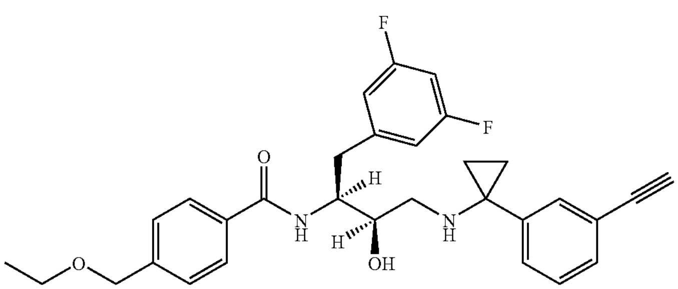 | N-((1S,2R)-1-(3,5-difluorobenzyl)-3-{[1-(3-ethynylphenyl)cyclopropyl]amino}-2-hydroxypropyl)-4-(ethoxymethyl)benzamide | |
| 3083 | 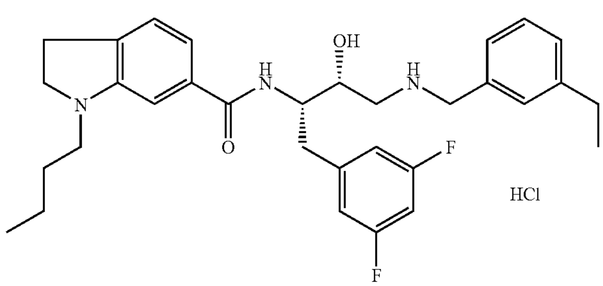 | 1-butyl-N-{(1S,2R)-1-(3,5-difluorobenzyl)-3-[(3-ethylbenzyl)amino]-2-hydroxypropyl}indoline-6-carboxamide hydrochloride | |

| EXAMPLE | Structure | Compound Name(s) | Mass Spec |
|---|---|---|---|
| 3084 | 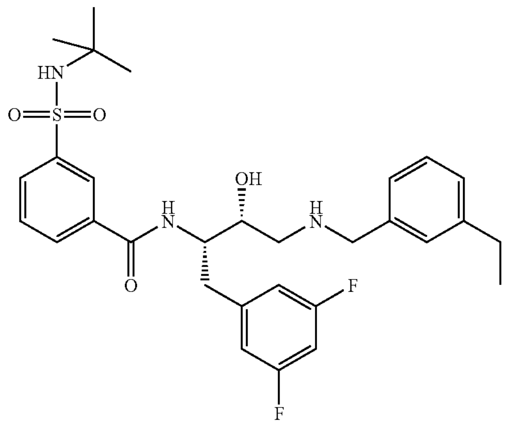 | 3-[(tert-butylamino)sulfonyl]-N-{(1S,2R)-1-(3,5-difluorobenzyl)-3-[(3-ethylbenzyl)amino]-2-hydroxypropyl}benzamide | **574 |
| 3085 | 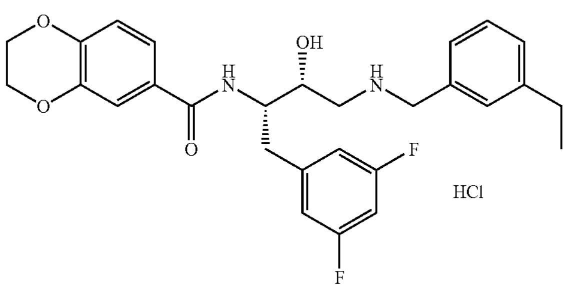 | N-{(1S,2R)-1-(3,5-difluorobenzyl)-3-[(3-ethylbenzyl)amino]-2-hydroxypropyl}-2,3-dihydro-1,4-benzodioxine-6-carboxamide hydrochloride | |
| 3086 | 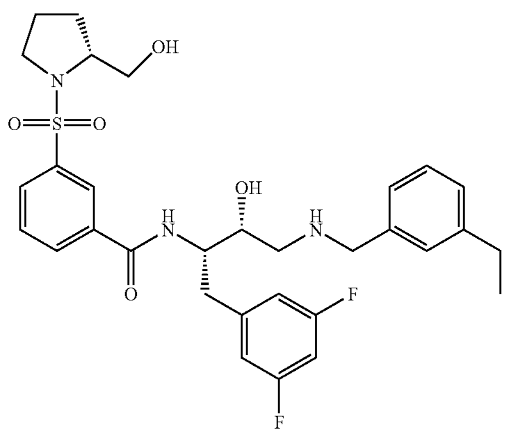 | N-{(1S,2R)-1-(3,5-difluorobenzyl)-3-[(3-ethylbenzyl)amino]-2-hydroxypropyl}-3-{[(2R)-2-(hydroxymethyl)pyrrolidin-1-yl]sulfonyl}benzamide | **602 |
| 3087 | 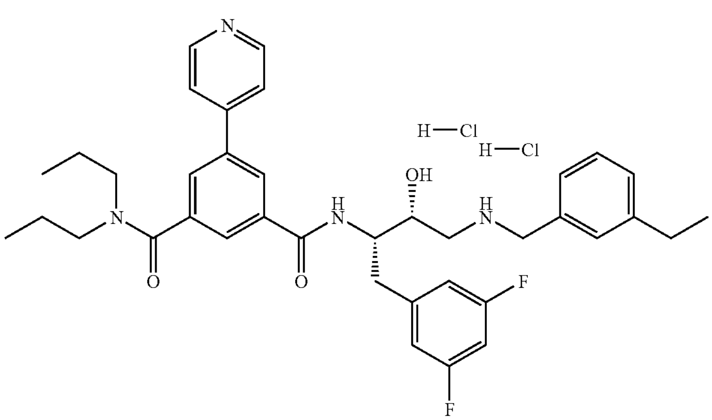 | $N^1$-{(1S,2R)-1-(3,5-difluorobenzyl)-3-[(3-ethylbenzyl)amino]-2-hydroxypropyl}-$N^3,N^3$-dipropyl-5-pyridin-4-ylisophthalamide dihydrochloride | **643.3 |

-continued

| EXAMPLE | Structure | Compound Name(s) | Mass Spec |
|---|---|---|---|
| 3088 | 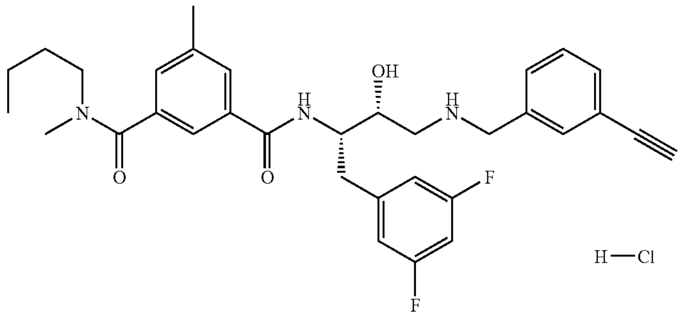 | $N^1$-butyl-$N^3$-{(1S,2R)-1-(3,5-difluorobenzyl)-3-[(3-ethynylbenzyl)amino]-2-hydroxypropyl}-$N^1$,5-dimethylisophthalamide hydrochloride | *561 |
| 3089 | 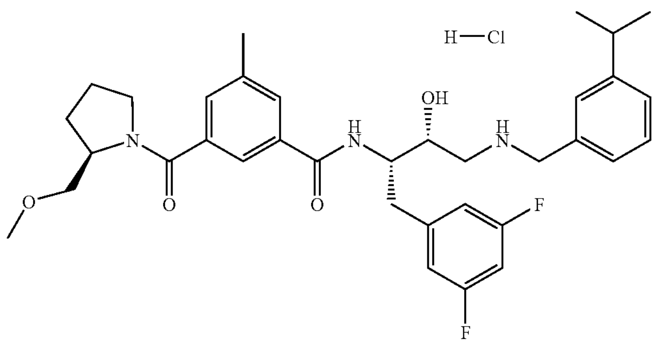 | N-{(1S,2R)-1-(3,5-difluorobenzyl)-2-hydroxy-3-[(3-isopropylbenzyl)amino]propyl}-3-{[(2R)-2-(methoxymethyl)pyrrolidin-1-yl]carbonyl}-5-methyl-benzamide hydrochloride | **608.3 |
| 3090 | 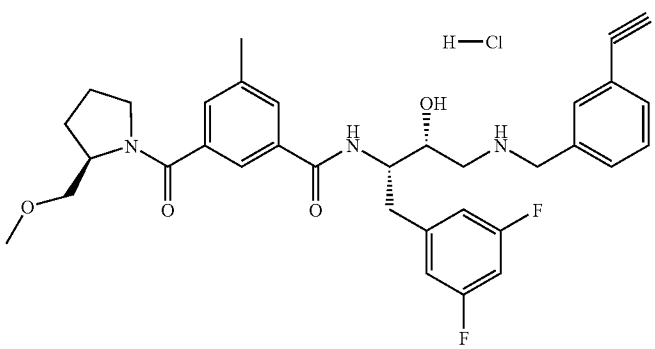 | N-{(1S,2R)-1-(3,5-difluorobenzyl)-3-[(3-ethynylbenzyl)amino]-2-hydroxypropyl}-3-{[(2R)-2-(methoxymethyl)pyrrolidin-1-yl]carbonyl}-5-methylbenzamide hydrochloride | **590.3 |
| 3091 | 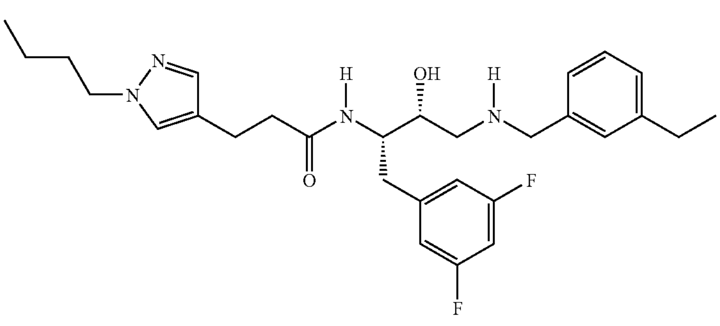 | 3-(1-butyl-1H-pyrazol-4-yl)-N-{(1S,2R)-1-(3,5-difluorobenzyl)-3-[(3-ethylbenzyl)amino]-2-hydroxypropyl}propanamide | |

-continued

| EXAMPLE | Structure | Compound Name(s) | Mass Spec |
|---|---|---|---|
| 3092 | 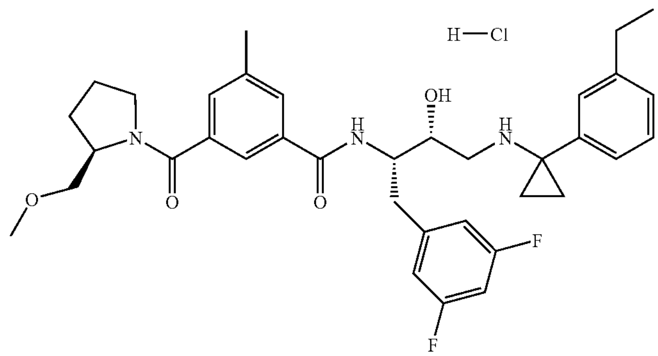 | N-((1S,2R)-1-(3,5-difluorobenzyl)-3-{[1-(3-ethylphenyl)cyclopropyl]amino}-2-hydroxypropyl)-3-{[(2R)-2-(methoxymethyl)pyrrolidin-1-yl]carbonyl}-5-methyl benzamide hydrochloride | **620.3 |
| 3093 | 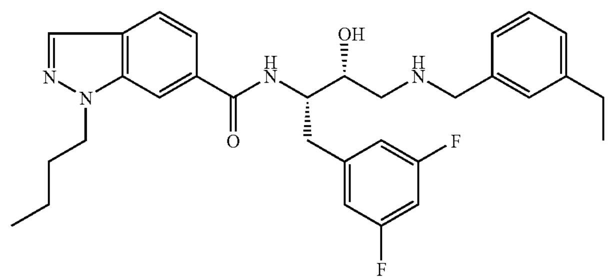 | 1-butyl-N-{(1S,2R)-1-(3,5-difluorobenzyl)-3-[(3-ethylbenzyl)amino]-2-hydroxypropyl}-1H-indazole-6-carboxamide | |
| 3094 | 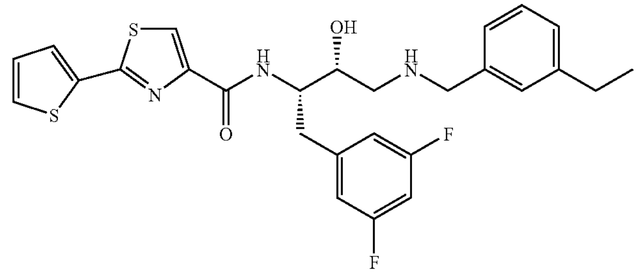 | N-{(1S,2R)-1-(3,5-difluorobenzyl)-3-[(3-ethylbenzyl)amino]-2-hydroxypropyl}-2-thien-2-yl-1,3-thiazole-4-carboxamide | ****528.2 (+) |
| 3095 | 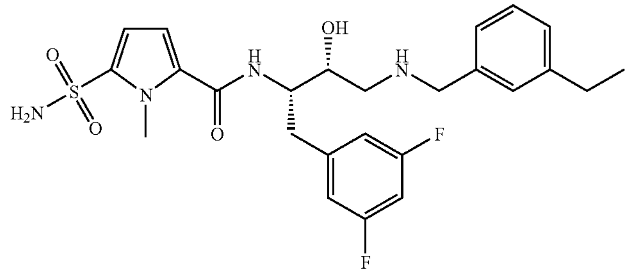 | 5-(aminosulfonyl)-N-[(1S,2R)-1-(3,5-difluorobenzyl)-3-[(3-ethylbenzyl)amino]-2-hydroxypropyl}-1-methyl-1H-pyrrole-2-carboxamide | ****521.2 (+) |
| 3096 | 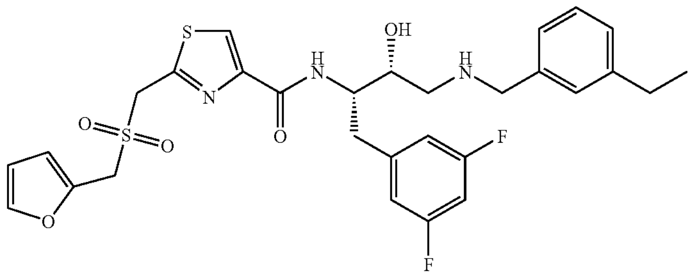 | N-{(1S,2R)-1-(3,5-difluorobenzyl)-3-[(3-ethylbenzyl)amino]-2-hydroxypropyl}-2-{[(2-furylmethyl)sulfonyl]methyl}-1,3-tiazole-4-carboxamide | ****604.1 (+) |

| EXAMPLE | Structure | Compound Name(s) | Mass Spec |
|---|---|---|---|
| 3097 | 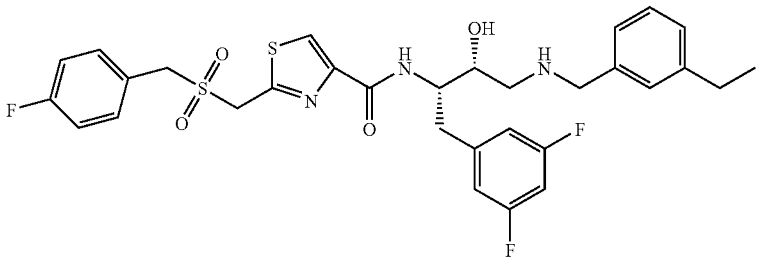 | N-{(1S,2R)-1-(3,5-difluorobenzyl)-3-[(3-ethylbenzyl)amino]-2-hydroxypropyl}-2-{[(4-fluorobenzyl)sulfonyl]methyl}-1,3-thiazole-4-carboxamide | |
| 3098 | 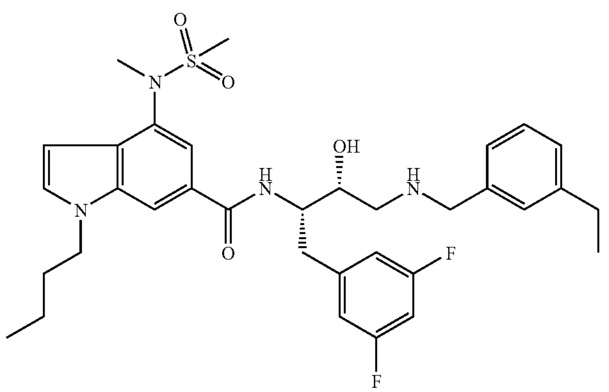 | 1-butyl-N-{(1S,2R)-1-(3,5-difluorobenzyl)-3-[(3-ethylbenzyl)amino]-2-hydroxypropyl}-4-[methyl(methylsulfonyl)amino]-1H-indole-6-carboxamide | **640.8 |
| 3099 | 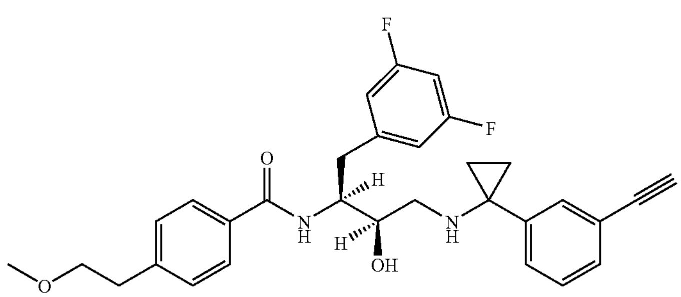 | N-((1S,2R)-1-(3,5-difluorobenzyl)-3-{[1-(3-ethynylphenyl)cyclopropyl]amino}-2-hydroxypropyl)-4-(2-methoxyethyl)benzamide | |
| 3100 | 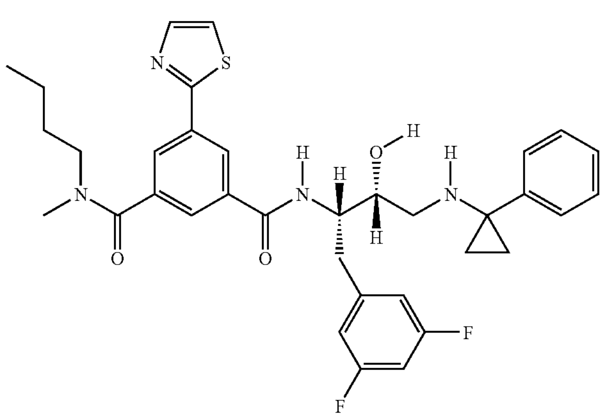 | N¹-butyl-N³-{(1S,2R)-1-(3,5-difluorobenzyl)-2-hydroxy-3-[(1-phenylcyclopropyl)amino]propyl}-N¹-methyl-5-(1,3-thiazol-2-yl)isophthalamide | |

-continued

| EXAMPLE | Structure | Compound Name(s) | Mass Spec |
|---|---|---|---|
| 3101 | 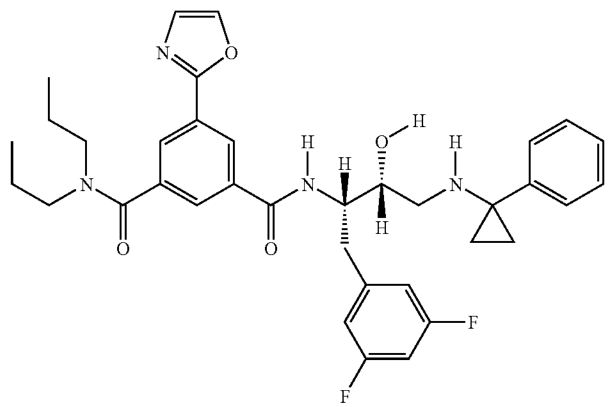 | N¹-{(1S,2R)-1-(3,5-difluorobenzyl)-2-hydroxy-3-[(1-phenylcyclopropyl)amino]propyl}-5-(1,3-oxazol-2-yl)-N³,N³-dipropylisophthalamide | |
| 3102 | 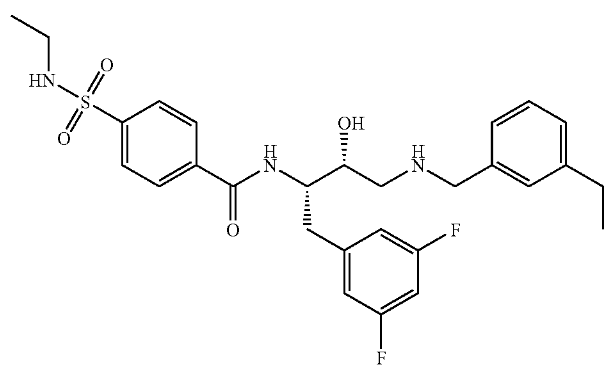 | N-{(1S,2R)-1-(3,5-difluorobenzyl)-3-[(3-ethylbenzyl)amino]-2-hydroxypropyl}-4-[(ethylamino)sulfonyl]benzamide | **546 |
| 3103 | 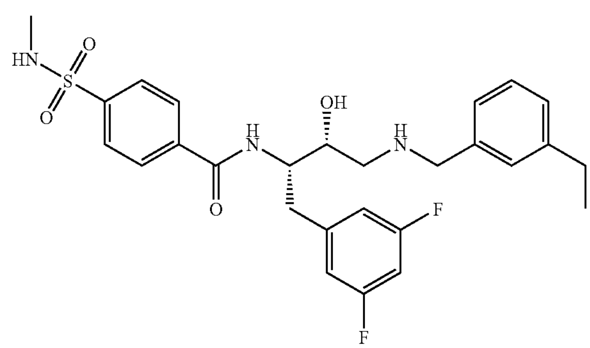 | N-{(1S,2R)-1-(3,5-difluorobenzyl)-3-[(3-ethylbenzyl)amino]-2-hydroxypropyl}-4-[(methylamino)sulfonyl]benzamide | **532 |
| 3104 | 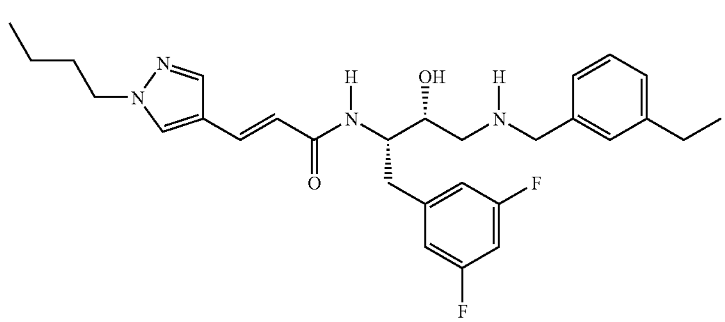 | (2E)-3-(1-butyl-1H-pyrazol-4-yl)-N-{(1S,2R)-1-(3,5-difluorobenzyl)-3-[(3-ethylbenzyl)amino]-2-hydroxypropyl}prop-2-enamide or (2E)-3-(1-butyl-1H-pyrazol-4-yl)-N-{(1S,2R)-1-(3,5-difluorobenzyl)-3-[(3-ethylbenzyl)amino]-2-hydroxypropyl}prop-2-enamide | |

-continued

| EXAM-PLE | Structure | Compound Name(s) | Mass Spec |
|---|---|---|---|
| 3105 | 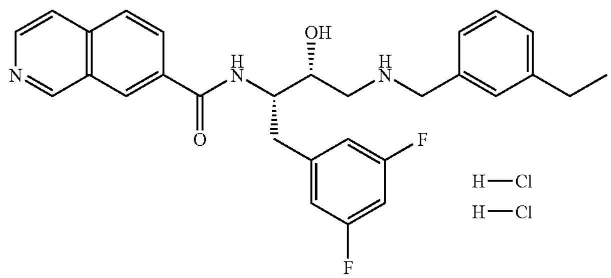 | N-{(1S,2R)-1-(3,5-difluoro-benzyl)-3-[(3-ethylbenzyl)amino]-2-hydroxypropyl}isoquinoline-7-carboxamide dihydrochloride | **490.1 |
| 3106 | 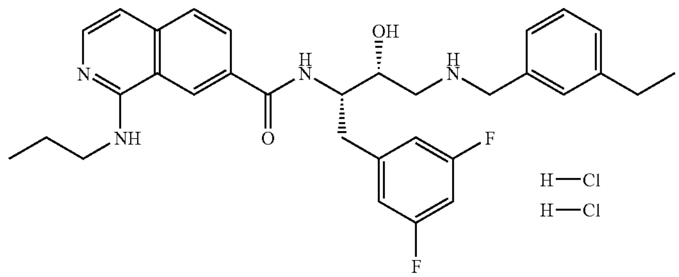 | N-{(1S,2R)-1-(3,5-difluoro-benzyl)-3-[(3-ethylbenzyl)amino]-2-hydroxypropyl}-1-(propylamino)isoquinoline-7-carboxamide dihydrochloride or N-{(1S,2R)-1-(3,5-difluorobenzyl)-3-[(3-ethylbenzyl)amino]-2-hydroxypropyl}-1-(propylamino)isoquinoline-7-carboxamide dihydrochloride | **547.3 |
| 3107 | 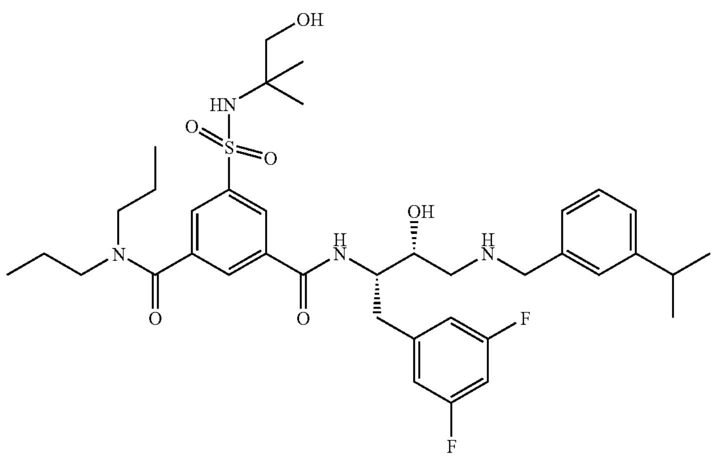 | $N^1$-{(1S,2R)-1-(3,5-difluoro-benzyl)-2-hydroxy-3-[(3-isopropylbenzyl)amino]propyl}-5-{[(2-hydroxy-1,1-dimethylethyl)amino]sulfonyl}-$N^3,N^3$-dipropyl-isophthalamide | **730.8 |
| 3108 | 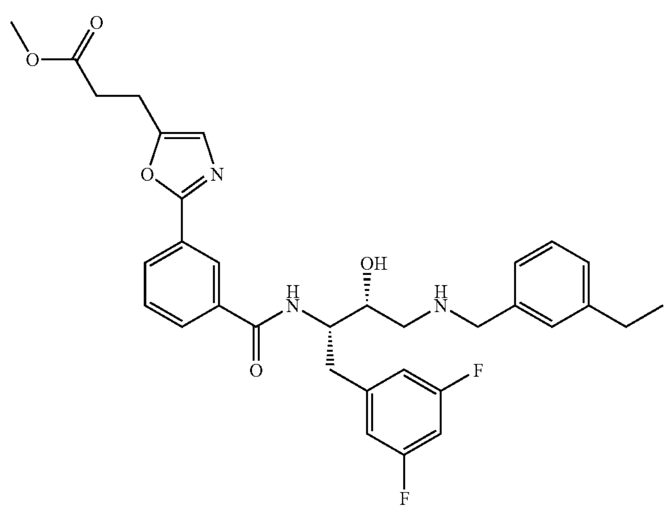 | methyl 3-(2-{3-[({(1S,2R)-1-(3,5-difluorobenzyl)-3-[(3-ethylbenzyl)amino]-2-hydroxypropyl}amino)carbonyl]phenyl}-1,3-oxazol-5-yl)propanoate | **591.9 |

-continued

| EXAMPLE | Structure | Compound Name(s) | Mass Spec |
|---|---|---|---|
| 3109 | 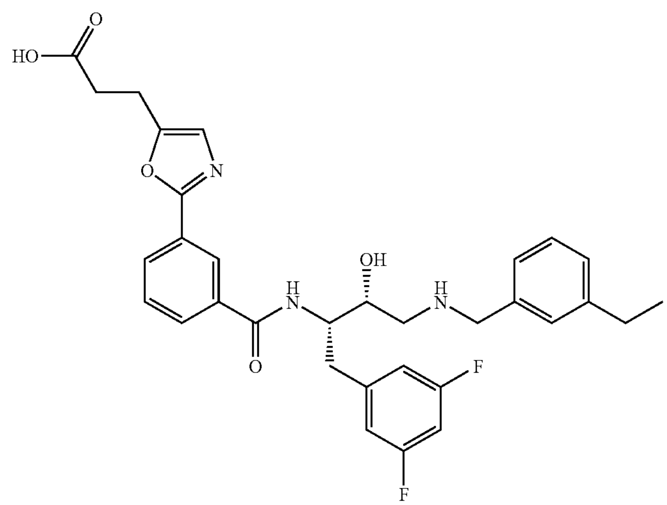 | 3-(2-{3-[({(1S,2R)-1-(3,5-difluorobenzyl)-3-[(3-ethylbenzyl)amino]-2-hydroxypropyl}amino)carbonyl]phenyl}-1,3-oxazol-5-yl)propanoic acid | **578.2 |
| 3110 | 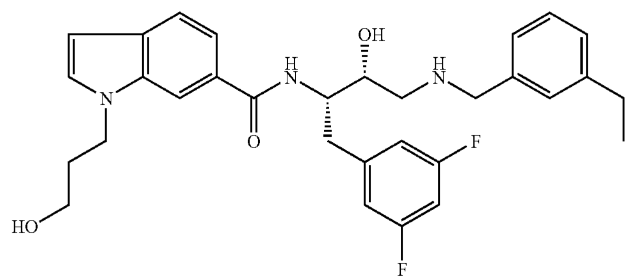 | N-{(1S,2R)-1-(3,5-difluorobenzyl)-3-[(3-ethylbenzyl)amino]-2-hydroxypropyl}-1-(3-hydroxypropyl)-1H-indole-6-carboxamide | **536.8 |
| 3111 | 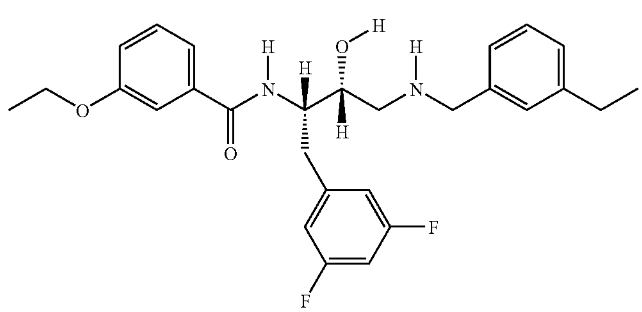 | N-{(1S,2R)-1-(3,5-difluorobenzyl)-3-[(3-ethylbenzyl)amino]-2-hydroxypropyl}-3-ethoxybenzamide | |
| 3112 | 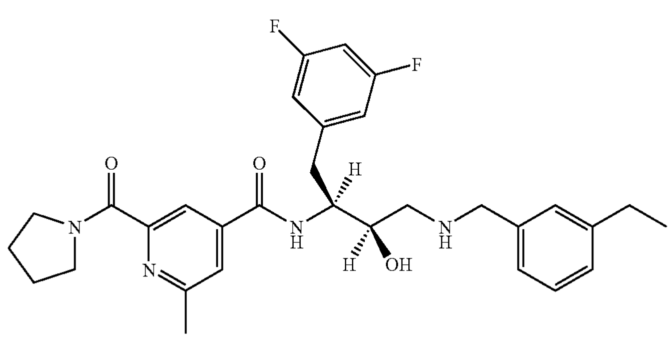 | N-{(1S,2R)-1-(3,5-difluorobenzyl)-3-[(3-ethylbenzyl)amino]-2-hydroxypropyl}-2-methyl-6-(pyrrolidin-1-ylcarbonyl)isonicotinamide | |

-continued

| EXAMPLE | Structure | Compound Name(s) | Mass Spec |
|---|---|---|---|
| 3113 | 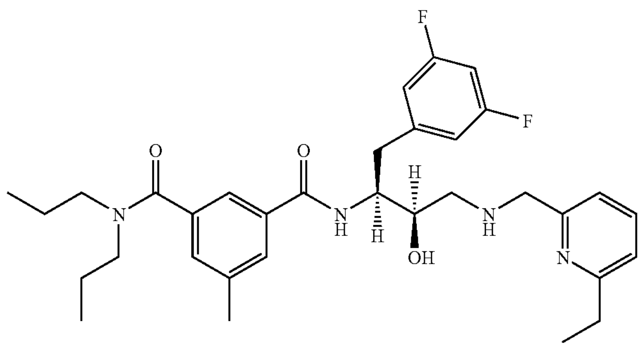 | $N^1$-((1S,2R)-1-(3,5-difluoro-benzyl)-3-{[(6-ethylpyridin-2-yl)methyl]amino}-2-hydroxypropyl)-5-methyl-$N^3,N^3$-dipropylisophthalamide | |
| 3114 | 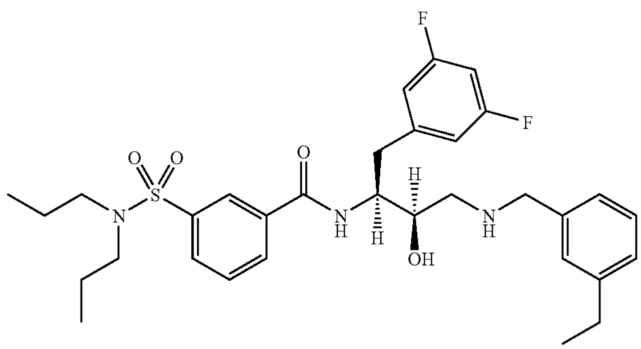 | N-{(1S,2R)-1-(3,5-difluoro-benzyl)-3-[(3-ethylbenzyl)amino]-2-hydroxypropyl}-3-[(dipropylamino)sulfonyl]benzamide | |
| 3115 | 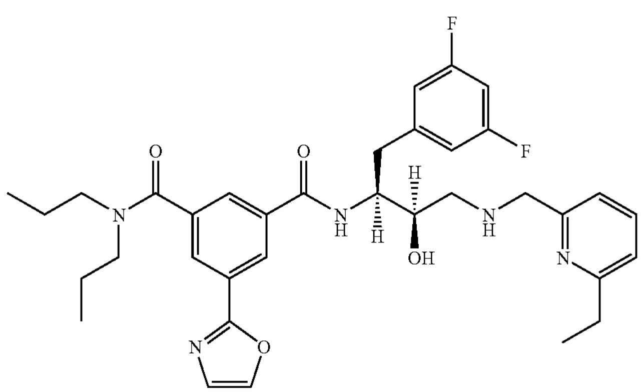 | $N^1$-((1S,2R)-1-(3,5-difluoro-benzyl)-3-{[(6-ethylpyridin-2-yl)methyl]amino}-2-hydroxypropyl)-5-(1,3-oxazol-2-yl)-$N^3,N^3$-dipropylisophthalamide | |
| 3116 | 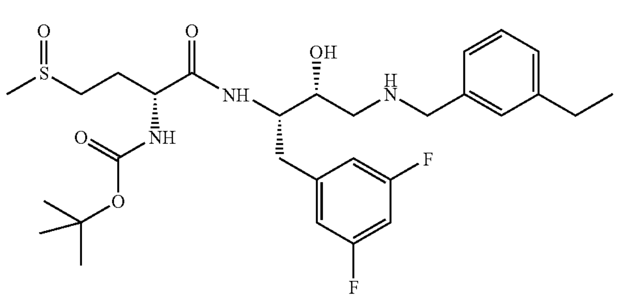 | tert-butyl (1R)-1-[({(1S,2R)-1-(3,5-difluorobenzyl)-3-[(3-ethylbenzyl)amino]-2-hydroxypropyl}amino)carbonyl]-3-(methylsulfinyl)propyl carbamate | ****582.1 (+) |

| EXAMPLE | Structure | Compound Name(s) | Mass Spec |
|---|---|---|---|
| 3117 | 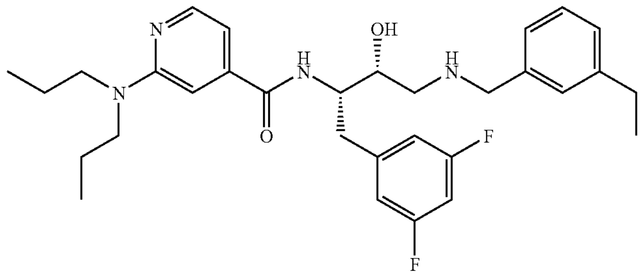 | N-{(1S,2R)-1-(3,5-difluoro-benzyl)-3-[(3-ethylbenzyl)amino]-2-hydroxypropyl}-2-dipropylamino)isonicotinamide or ELAN154894 | |
| 3118 | 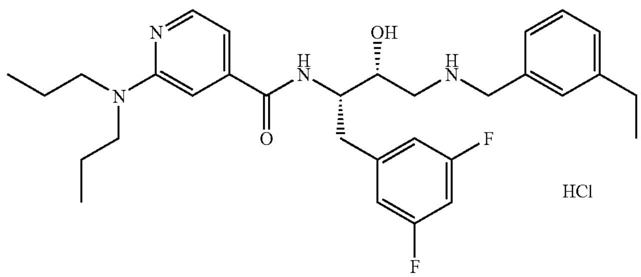 | N-{(1S,2R)-1-(3,5-difluoro-benzyl)-3-[(3-ethylbenzyl)amino]-2-hydroxypropyl}-2-dipropylamino)isonicotinamide hydrochloride | |
| 3119 | 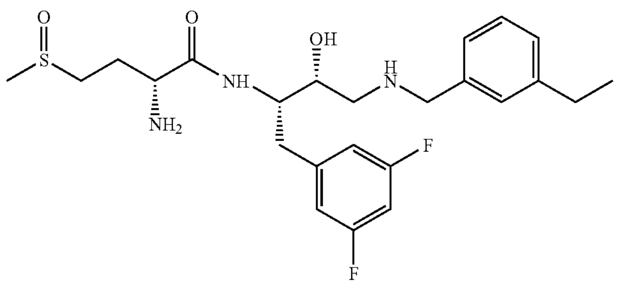 | (2R)-2-amino-N-{(1S,2R)-1-(3,5-difluorobenzyl)-3-[(3-ethylbenzyl)amino]-2-hydroxypropyl}-4-(methyl-sulfinyl)butanamide | ****482.2 (+) |
| 3120 | 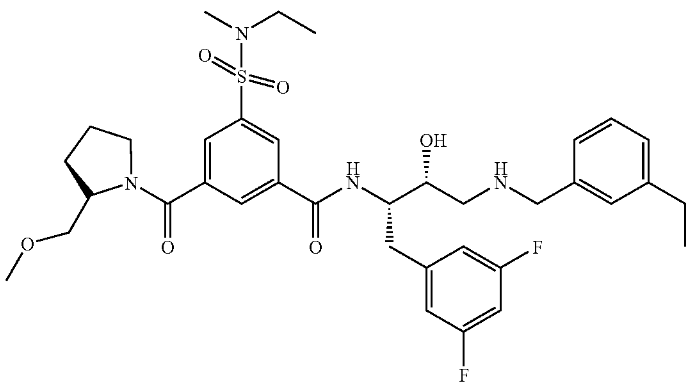 | N-{(1S,2R)-1-(3,5-difluoro-benzyl)-3-[(3-ethylbenzyl)amino]-2-hydroxypropyl}-3-{[ethyl(methyl)amino]sulfonyl}-5-{[(2S)-2-(methoxymethyl)pyrrolidin-1-yl]carbonyl}benzamide | **701 |
| 3121 | 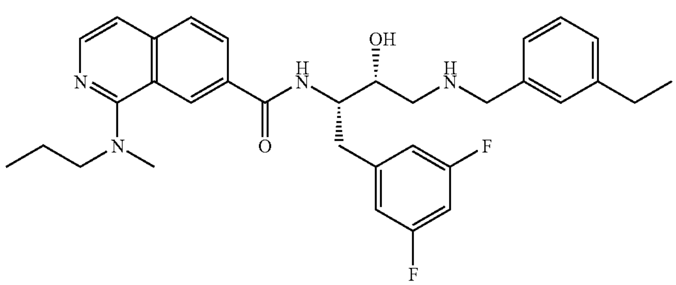 | N-{(1S,2R)-1-(3,5-difluoro-benzyl)-3-[(3-ethylbenzyl)amino]-2-hydroxypropyl}-1-[methyl(propyl)amino]iso-quinoline-7-carboxamide or N-{(1S,2R)-1-(3,5-difluoro-benzyl)-3-[(3-ethylbenzyl)amino]-2-hydroxypropyl}-1-[methyl(propyl)amino]isoquinoline-7-carboxamide | **561.4 |

| EXAMPLE | Structure | Compound Name(s) | Mass Spec |
|---|---|---|---|
| 3122 | 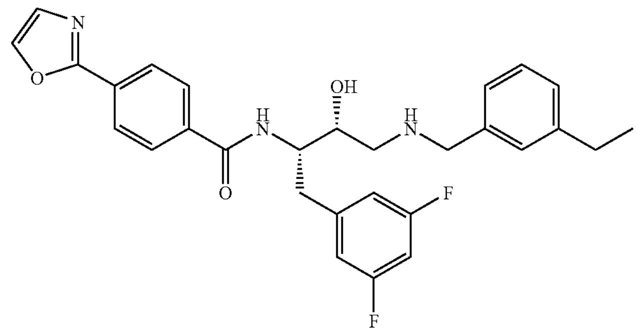 | N-{(1S,2R)-1-(3,5-difluorobenzyl)-3-[(3-ethylbenzyl)amino]-2-hydroxypropyl}-4-(1,3-oxazol-2-yl)benzamide | **506.2 |
| 3123 | 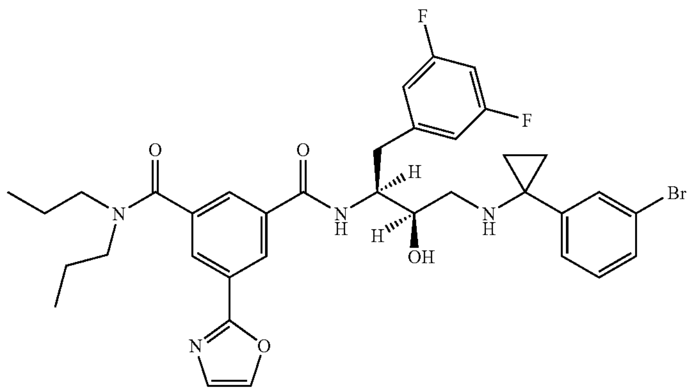 | $N^1$-[(1S,2R)-3-{[1-(3-bromophenyl)cyclopropyl]amino}-1-(3,5-difluorobenzyl)-2-hydroxypropyl]-5-(1,3-oxazol-2-yl)-$N^3$,$N^3$-dipropylisophthalamide | |
| 3124 | 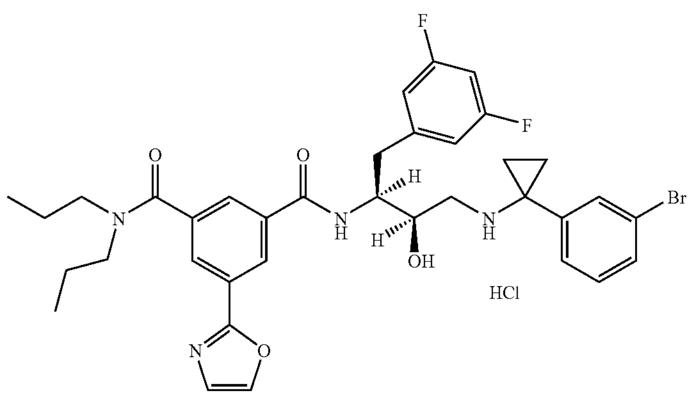 | $N^1$-[(1S,2R)-3-{[1-(3-bromophenyl)cyclopropyl]amino}-1-(3,5-difluorobenzyl)-2-hydroxypropyl]-5-(1,3-oxazol-2-yl)-$N^3$,$N^3$-dipropylisophthalamide hydrochloride | **709.2 + 711.2 |
| 3125 | 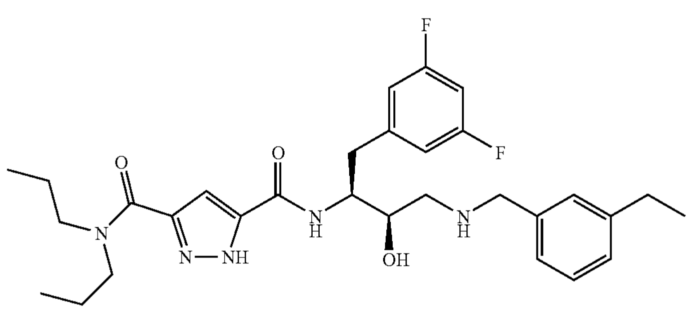 | $N^5$-{(1S,2R)-1-(3,5-difluorobenzyl)-3-[(3-ethylbenzyl)amino]-2-hydroxypropyl}-$N^3$,$N^3$-dipropyl-1H-pyrazole-3,5-dicarboxamide | |

-continued

| EXAMPLE | Structure | Compound Name(s) | Mass Spec |
|---|---|---|---|
| 3126 | 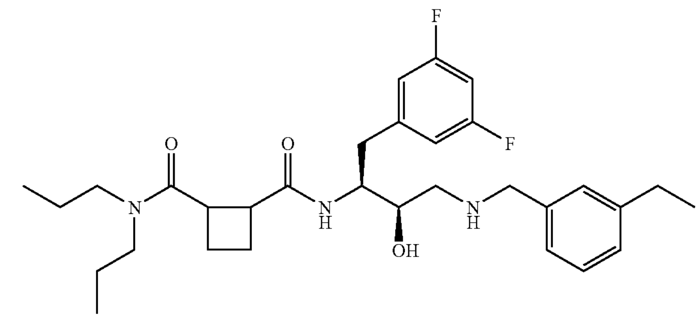 | $N^5$-{(1S,2R)-1-(3,5-difluoro-benzyl)-3-[(3-ethylbenzyl)amino]-2-hydroxypropyl}-$N^2,N^2$-dipropylcyclobutane-1,2-dicarboxamide | |
| 3127 | 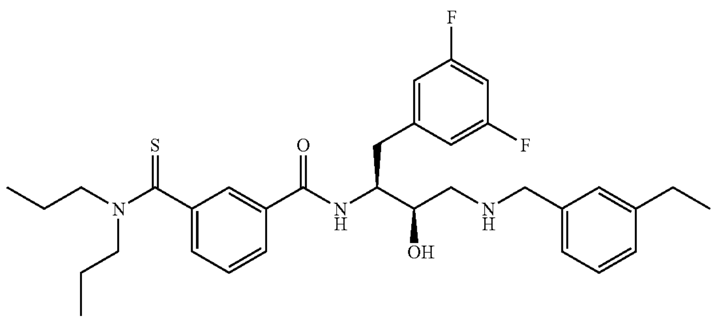 | N-{(1S,2R)-1-(3,5-difluoro-benzyl)-3-[(3-ethylbenzyl)amino]-2-hydroxypropyl}-3-[(dipropylamino)carbonothioyl]benzamide | |
| 3128 | 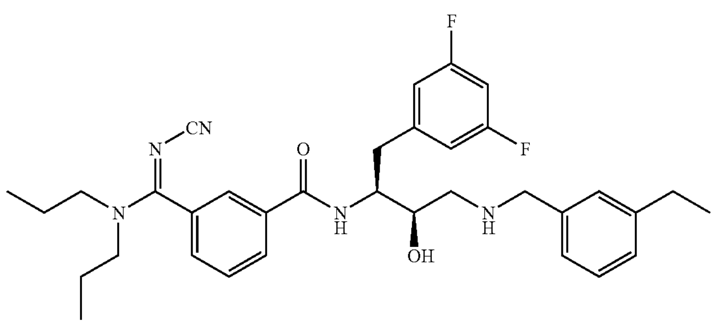 | 3-[(E)-(cyanoimino)(dipropylamino)methyl]-N-{(1S,2R)-1-(3,5-difluorobenzyl)-3-[(3-ethyl-benzyl)amino]-2-hydroxy-propyl}benzamide | |
| 3129 | 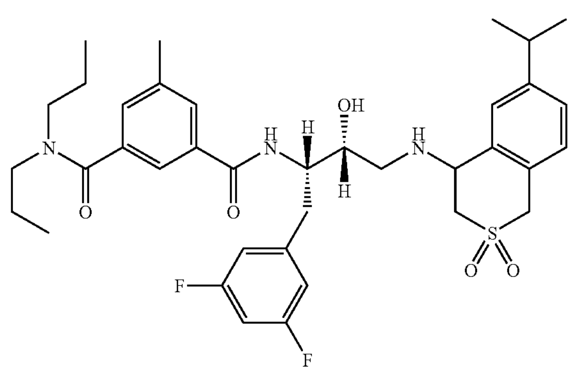 | $N^1$-{(1S,2R)-1-(3,5-difluorobenzyl)-2-hydroxy-3-[(6-isopropyl-2,2-dioxido-3,4-dihydro-1H-isothiochromen-4-yl)amino]proypl}-5-methyl-$N^3,N^3$-dipropylisophthalamide | |

-continued

| EXAMPLE | Structure | Compound Name(s) | Mass Spec |
|---|---|---|---|
| 3130 | 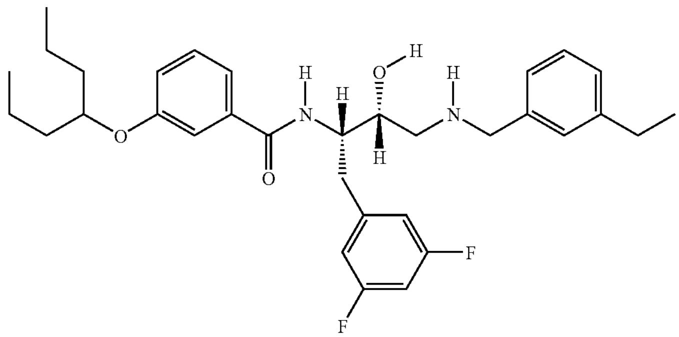 | N-{(1S,2R)-1-(3,5-difluorobenzyl)-3-[(3-ethylbenzyl)amino]-2-hydroxypropyl}-3-(1-propylbutoxy)benzamide | |
| 3131 | 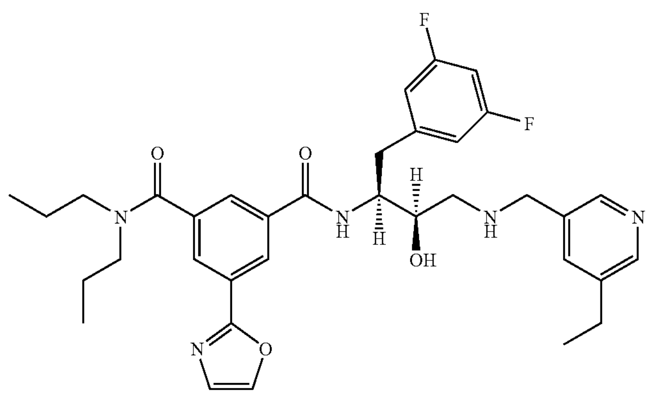 | N$^1$-((1S,2R)-1-(3,5-difluorobenzyl)-3-{[(5-ethylpyridin-3-yl)methyl]amino}-2-hydroxypropyl)-5-(1,3-oxazol-2-yl)-N$^3$,N$^3$-dipropylisophthalamide | |
| 3132 | 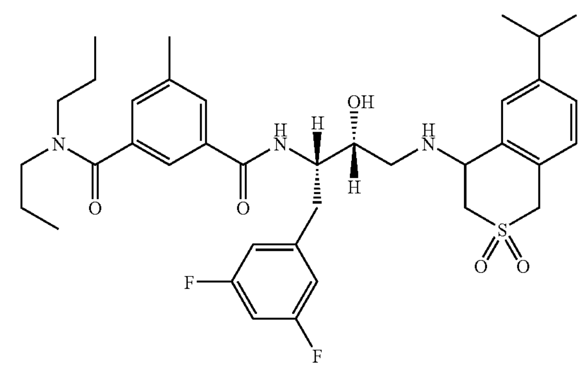 | N$^1$-{(1S,2R)-1-(3,5-difluorobenzyl)-2-hydroxy-3-[(6-isopropyl-2,2-dioxido-3,4-dihydro-1H-isothiochromen-4-yl)amino]propyl}-5-methyl-N$^3$,N$^3$-dipropylisophthalamide | |
| 3133 | 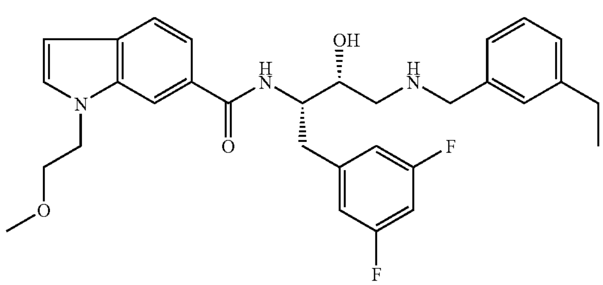 | N-{(1S,2R)-1-(3,5-difluorobenzyl)-3-[(3-ethylbenzyl)amino]-2-hydroxypropyl}-1-(2-methoxyethyl)-1H-indole-6-carboxamide | **536 |

-continued

| EXAMPLE | Structure | Compound Name(s) | Mass Spec |
|---|---|---|---|
| 3134 | 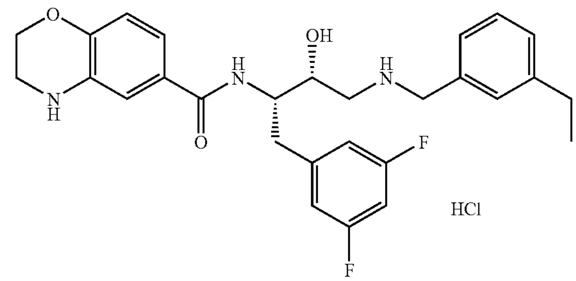 | N-{(1S,2R)-1-(3,5-difluoro-benzyl)-3-[(3-ethylbenzyl)amino]-2-hydroxypropyl}-3,4-dihydro-2H-1,4-benzoxazine-6-carboxamide hydrochloride | |
| 3135 | 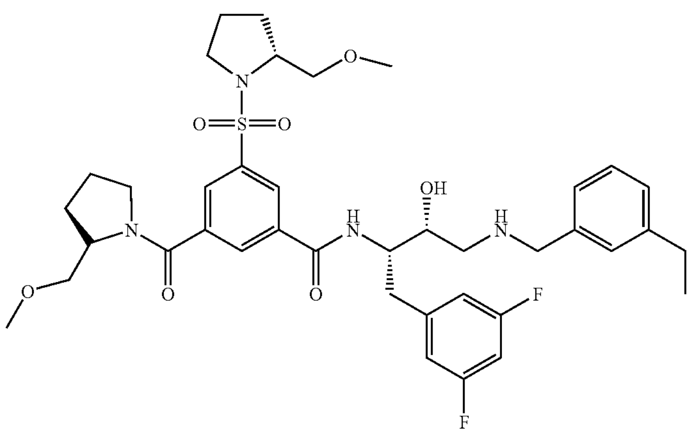 | N-{(1S,2R)-1-(3,5-difluoro-benzyl)-3-[(3-ethylbenzyl)amino]-2-hydroxypropyl}-3-{[(2S)-2-(methoxymethyl)pyrrolidin-1-yl]carbonyl}-5-{[(2R)-2-(methoxymethyl)pyrrolidin-1-yl]sulfonyl}benzamide | **757 |
| 3136 | 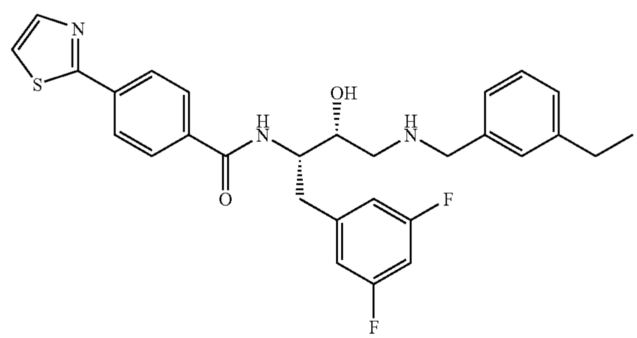 | N-{(1S,2R)-1-(3,5-difluoro-benzyl)-3-[(3-ethylbenzyl)amino]-2-hydroxypropyl}-4-(1,3-thiazol-2-yl)benzamide | **522.2 |
| 3137 | 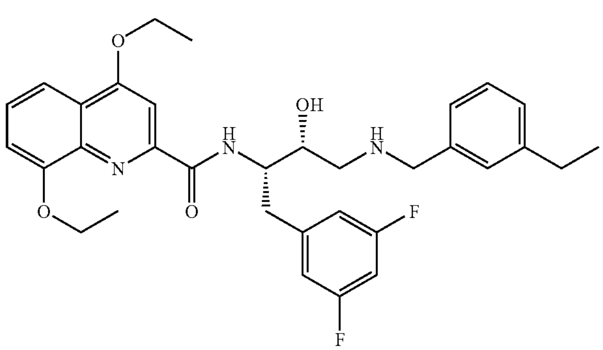 | N-{(1S,2R)-1-(3,5-difluoro-benzyl)-3-[(3-ethylbenzyl)amino]-2-hydroxypropyl}-4,8-diethoxyquinoline-2-carboxamide | ****578.3 (+) |

-continued

| EXAMPLE | Structure | Compound Name(s) | Mass Spec |
|---|---|---|---|
| 3138 | 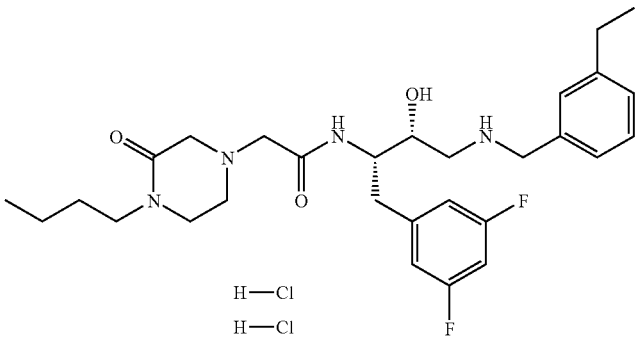 | 2-(4-butyl-3-oxopiperazin-1-yl)-N-{(1S,2R)-1-(3,5-difluorobenzyl)-3-[(3-ethylbenzyl)amino]-2-hydroxypropyl}acetamide dihydrochloride | |
| 3139 | 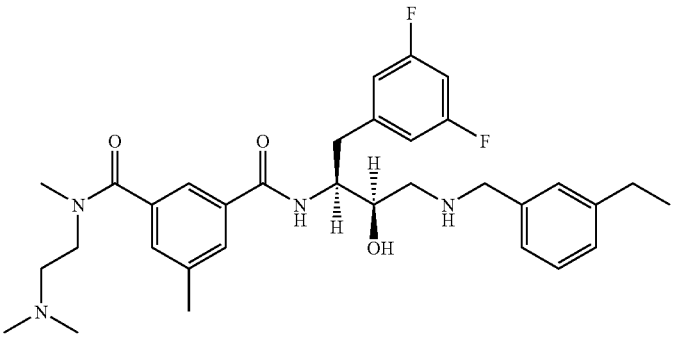 | $N^1$-{(1S,2R)-1-(3,5-difluorobenzyl)-3-[(3-ethylbenzyl)amino]-2-hydroxypropyl}-$N^3$-[2-(dimethylamino)ethyl]-$N^3$,5-dimethylisophthalamide | |
| 3140 | 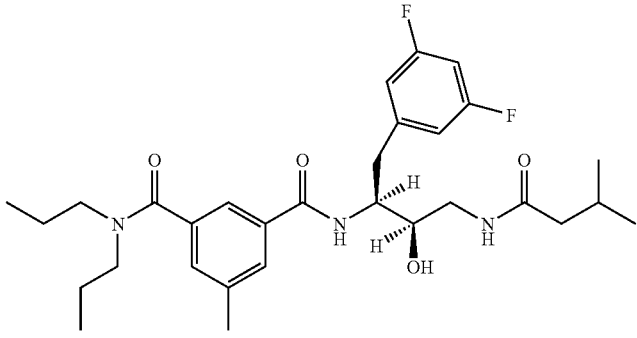 | $N^1$-{(1S,2R)-1-(3,5-difluorobenzyl)-2-hydroxy-3-[(3-methylbutanoyl)amino]propyl}-5-methyl-$N^3$,$N^3$-dipropylisophthalamide | |
| 3141 | 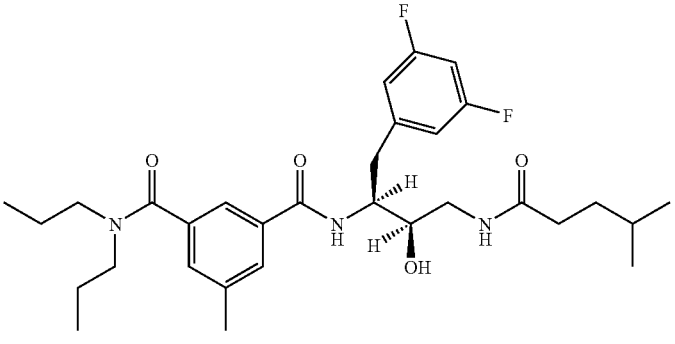 | $N^1$-{(1S,2R)-1-(3,5-difluorobenzyl)-2-hydroxy-3-[(4-methylbutanoyl)amino]propyl}-5-methyl-$N^3$,$N^3$-dipropylisophthalamide | |

-continued

| EXAMPLE | Structure | Compound Name(s) | Mass Spec |
|---|---|---|---|
| 3142 | 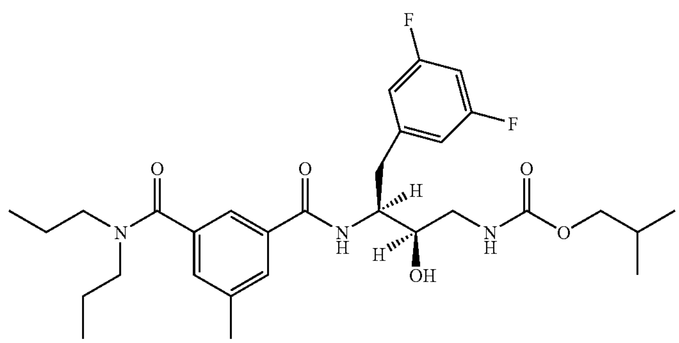 | isobutyl (2R,3S)-4-(3,5-difluorophenyl)-3-({3-[(dipropylamino)carbonyl]-5-methylbenzoyl}amino)-2-hydroxybutylcarbamate | |
| 3143 | 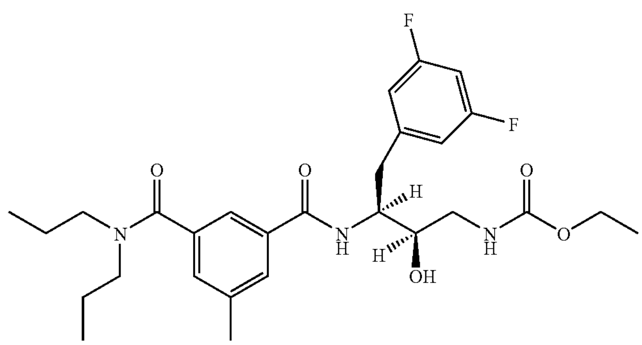 | ethyl (2R,3S)-4-(3,5-difluorophenyl)-3-({3-[(dipropylamino)carbonyl]-5-methylbenzoyl}amino)-2-hydroxybutylcarbamate | |
| 3144 | 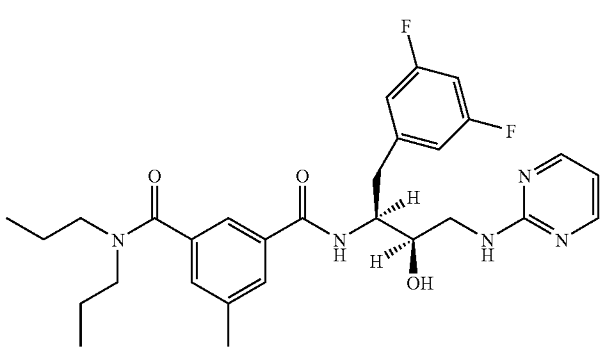 | $N^1$-[(1S,2R)-1-(3,5-difluorobenzyl)-2-hydroxy-3-(pyrimidin-2-ylamino)propyl]-5-methyl-$N^3$,$N^3$-dipropylisophthalamide | |
| 3145 | 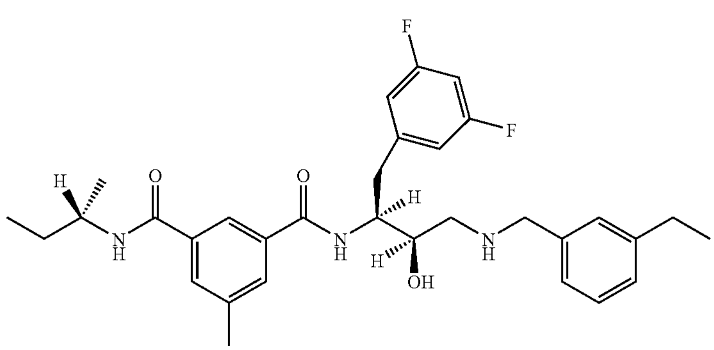 | $N^1$-{(1S,2R)-1-(3,5-difluorobenzyl)-3-[(3-ethylbenzyl)amino]-2-hydroxypropyl}-5-methyl-$N^3$-[(1S)-1-methylpropyl]isophthalamide | |

-continued

| EXAMPLE | Structure | Compound Name(s) | Mass Spec |
|---|---|---|---|
| 3146 | 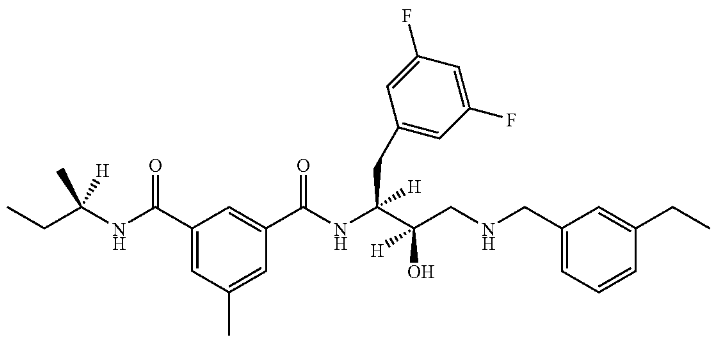 | N$^1$-{(1S,2R)-1-(3,5-difluoro-benzyl)-3-[(3-ethylbenzyl)amino]-2-hydroxypropyl)-5-methyl-N$^3$-[(1R)-1-methyl-propyl]isophthalamide | |
| 3147 | 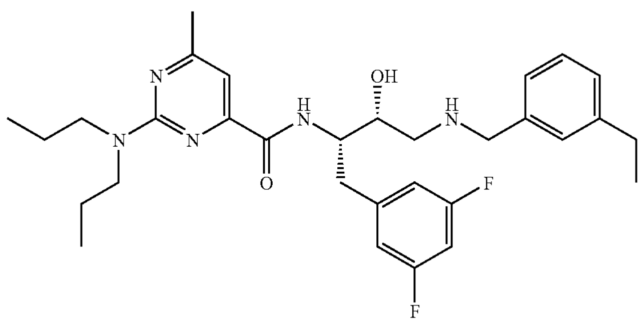 | N-{(1S,2R)-1-(3,5-difluoro-benzyl)-3-[(3-ethylbenzyl)amino]-2-hydroxypropyl}-2-(dipropylamino)-6-methyl-pyrimidine-4-carboxamide | **554.4 |
| 3148 | 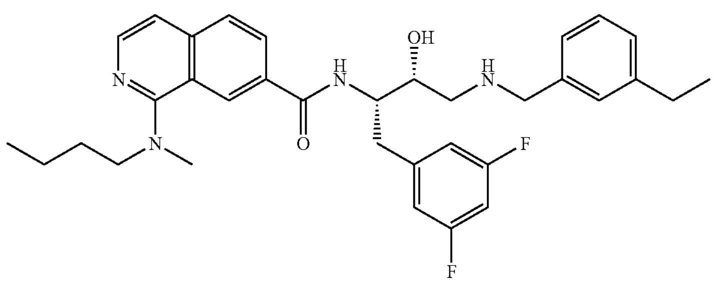 | 1-[butyl(methyl)amino]-N-{(1S,2R)-1-(3,5-difluoro-benzyl)-3-[(3-ethylbenzyl)amino]-2-hydroxypropyl}isoquinoline-7-carboxamide or 1-[butyl(methyl)amino]-N-{(1S,2R)-1-(3,5-difluoro-benzyl)-3-[(3-ethylbenzyl)amino]-2-hydroxypropyl}isoquinoline-7-carboxamide | **575.4 |
| 3149 | 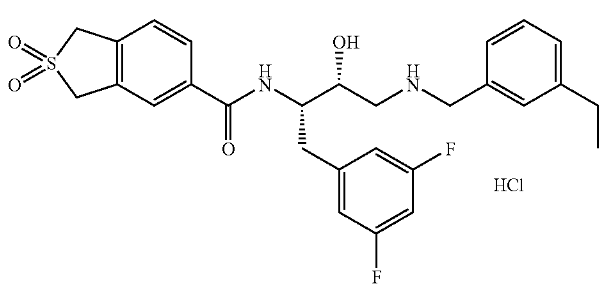 | N-{(1S,2R)-1-(3,5-difluoro-benzyl)-3-[(3-ethylbenzyl)amino]-2-hydroxypropyl}-1,3-dihydro-2-benzothiophene-5-carbaxamide 2,2-dioxide hydrochloride | **529 |

-continued

| EXAMPLE | Structure | Compound Name(s) | Mass Spec |
|---|---|---|---|
| 3150 | 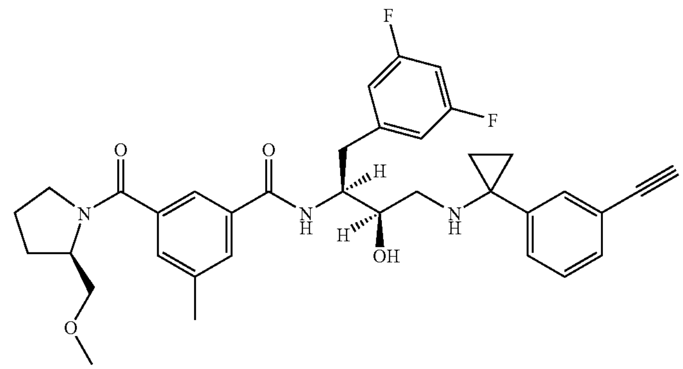 | N-((1S,2R)-1-(3,5-difluoro-benzyl)-3-{[1-(3-ethynyl-phenyl)cyclopropyl]amino}-2-hydroxypropyl)-3-{[(2R)-2-(methoxymethyl)pyrrolidin-1-yl]carbonyl}-5-methylbenzamide | |
| 3151 | 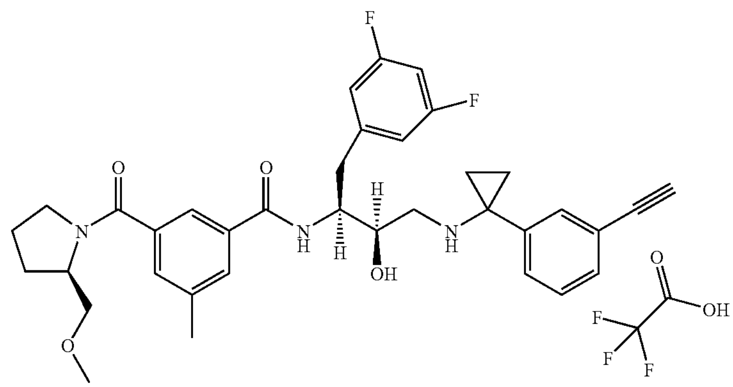 | N-((1S,2R)-1-(3,5-difluoro-benzyl)-3-{[1-(3-ethynyl-phenyl)cyclopropyl]amino}-2-hydroxypropyl)-3-{[(2R)-2-(methoxymethyl)pyrrolidin-1-yl]carbonyl}-5-methyl-benzamide trifluoroacetate | |
| 3152 | 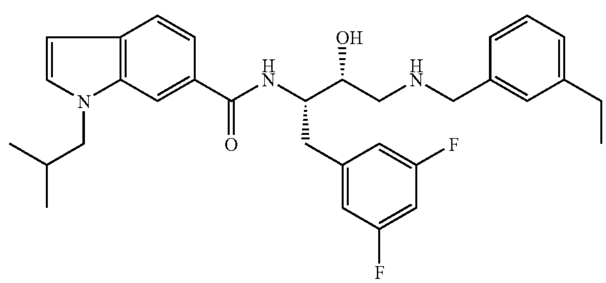 | N-{(1S,2R)-1-(3,5-difluoro-benzyl)-3-[(3-ethylbenzyl)amino]-2-hydroxypropyl}-1-isobutyl-1H-indole-6-carboxamide | **534.2 |
| 3153 | 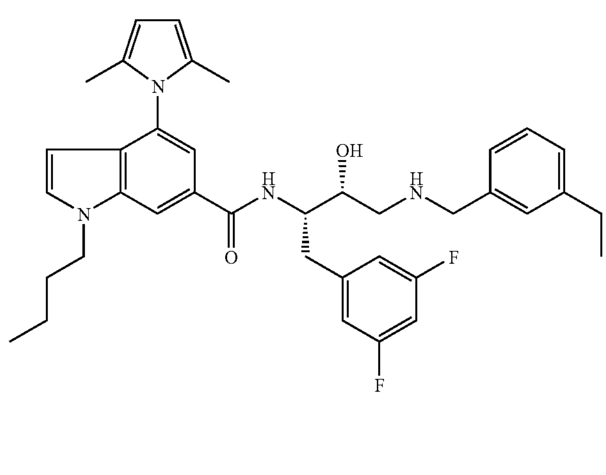 | 1-butyl-N-{(1S,2R)-1-(3,5-difluorobenzyl)-3-[(3-ethyl-benzyl)amino]-2-hydroxy-propyl}-4-(2,5-dimethyl-1H-pyrrol-1-yl)-1H-indole-6-carboxamide | **627.86 |

-continued

| EXAMPLE | Structure | Compound Name(s) | Mass Spec |
|---|---|---|---|
| 3154 | 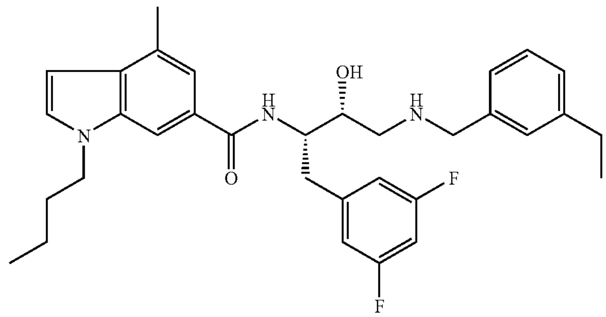 | 1-butyl-N-{(1S,2R)-1-(3,5-difluorobenzyl)-3-[(3-ethylbenzyl)amino]-2-hydroxypropyl}-4-methyl-1H-indole-6-carboxamide | **548.94 |
| 3155 | 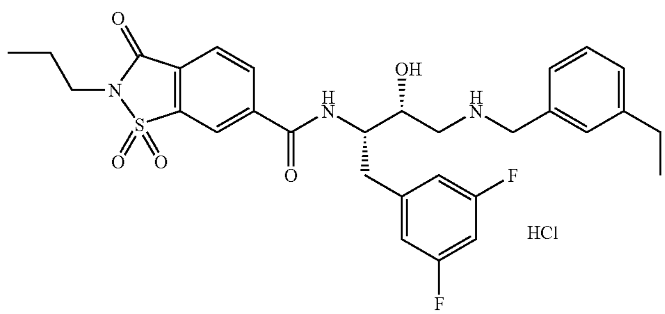 | N-{(1S,2R)-1-(3,5-difluorobenzyl)-3-[(3-ethylbenzyl)amino]-2-hydroxypropyl}-3-oxo-2-propyl-2,3-dihydro-1,2-benzisothiazole-6-carboxamide 1,1-dioxide hydrochloride | **586 |
| 3156 | 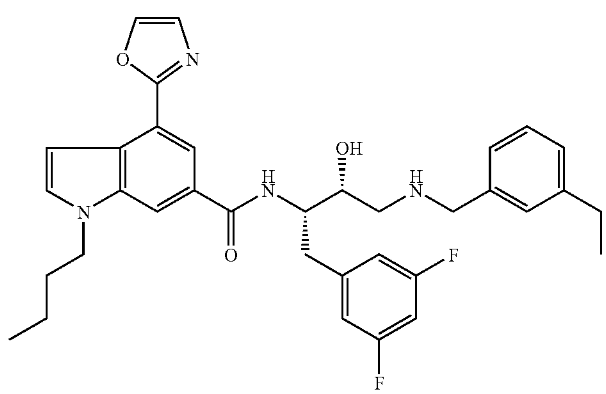 | 1-butyl-N-{(1S,2R)-1-(3,5-difluorobenzyl)-3-[(3-ethylbenzyl)amino]-2-hydroxypropyl}-4-(1,3-oxazol-2-yl)-1H-indole-6-carboxamide | **601.99 |
| 3157 | 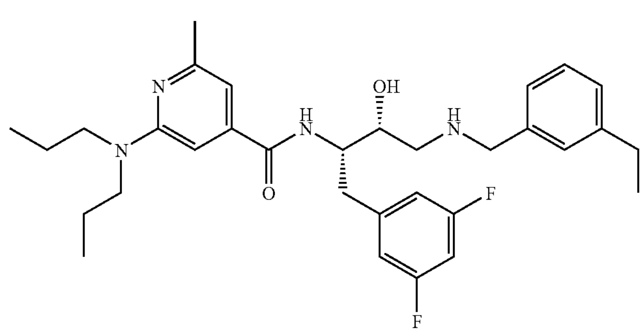 | N-{(1S,2R)-1-(3,5-difluorobenzyl)-3-[(3-ethylbenzyl)amino]-2-hydroxypropyl}-2-(dipropylamino)-6-methyl-isonicotinamide | **553 |

-continued

| EXAMPLE | Structure | Compound Name(s) | Mass Spec |
|---|---|---|---|
| 3158 | 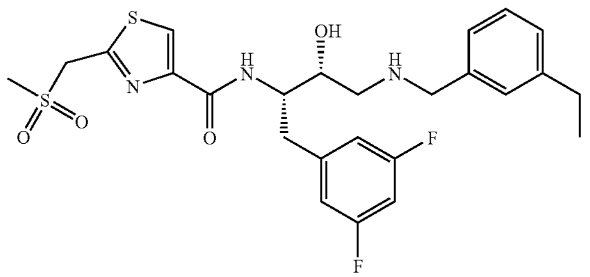 | N-{(1S,2R)-1-(3,5-difluorobenzyl)-3-[(3-ethylbenzyl)amino]-2-hydroxypropyl}-2-[(methylsulfonyl)methyl]-1,3-thiazole-4-carboxamide | **** (537.8) (+) |
| 3159 | 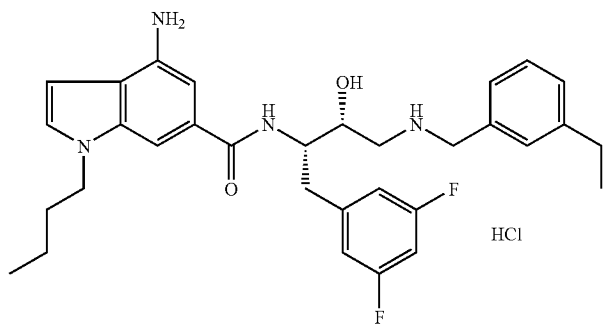 | 4-amino-1-butyl-N-{(1S,2R)-1-(3,5-difluorobenzyl)-3-[(3-ethylbenzyl)amino]-2-hydroxypropyl}-1H-indole-6-carboxamide hydrochloride | |
| 3160 | 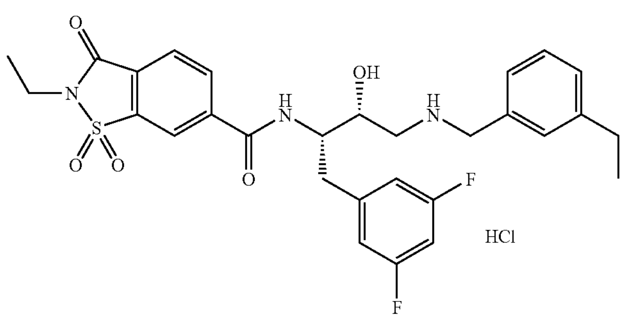 | N-{(1S,2R)-1-(3,5-difluorobenzyl)-3-[(3-ethylbenzyl)amino]-2-hydroxypropyl}-2-ethyl-3-oxo-2,3-dihydro-1,2-benzisothiazole-6-carboxamide 1,1-dioxide hydrochloride | |
| 3161 | 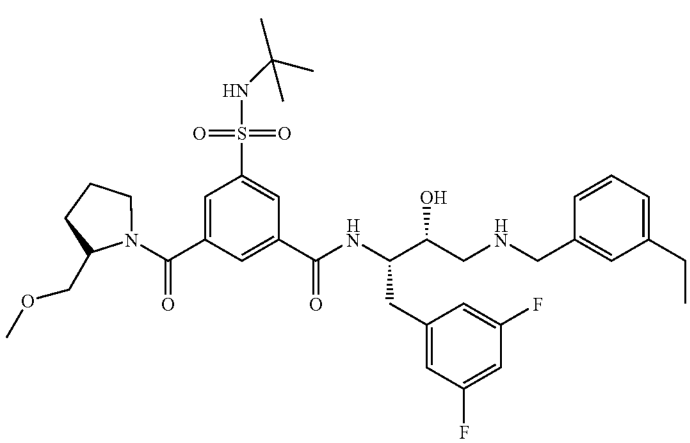 | 3-[(tert-butylamino)sulfonyl]-N-{(1S,2R)-1-(3,5-difluorobenzyl)-3-[(3-ethylbenzyl)amino]-2-hydroxypropyl}-5-{[(2S)-2-(methoxymethyl)pyrrolidin-1-yl]carbonyl}benzamide | |

-continued

| EXAMPLE | Structure | Compound Name(s) | Mass Spec |
|---|---|---|---|
| 3162 | 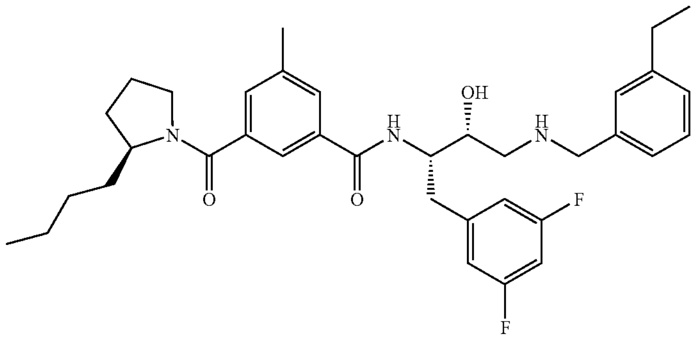 | 3-{[(2S)-2-butylpyrrolidin-1-yl]carbonyl}-N-{(1S,2R)-1-(3,5-difluorobenzyl)-3-[(3-ethylbenzyl)amino]-2-hydroxypropyl}-5-methylbenzamide | |
| 3163 | 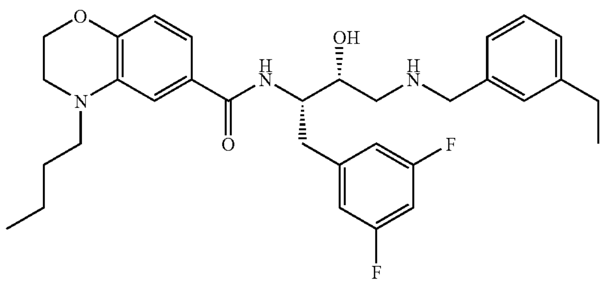 | 4-butyl-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide | |
| 3164 | 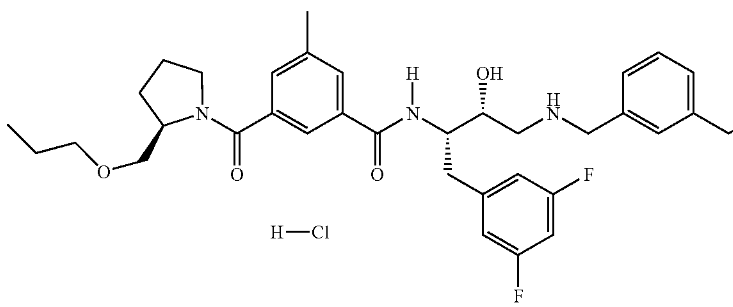 | N-{(1S,2R)-1-(3,5-difluorobenzyl)-3-[(3-ethylbenzyl)amino]-2-hydroxypropyl}-3-methyl-5-{[(2R)-2-(propoxymethyl)pyrrolidin-1-yl]carbonyl}benzamide hydrochloride | |
| 3165 | 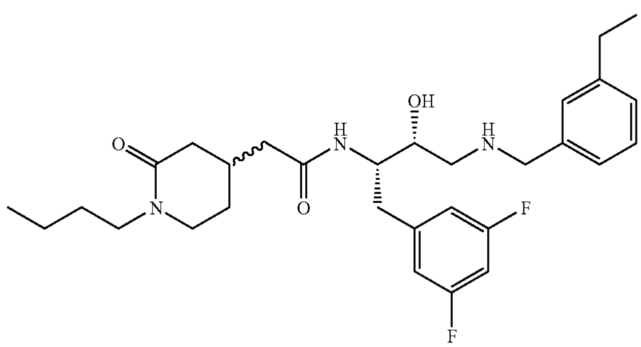 | 2-(1-butyl-2-oxopiperidin-4-yl)-N-{(1S,2R)-1-(3,5-difluorobenzyl)-3-[(3-ethylbenzyl)amino]-2-hydroxypropyl}acetamide | |
| 3166 | 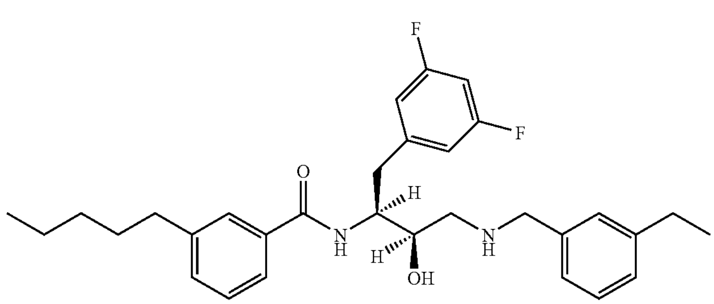 | N-{(1S,2R)-1-(3,5-difluorobenzyl)-3-[(3-ethylbenzyl)amino]-2-hydroxypropyl}-3-pentylbenzamide | |

-continued

| EXAMPLE | Structure | Compound Name(s) | Mass Spec |
|---|---|---|---|
| 3167 | 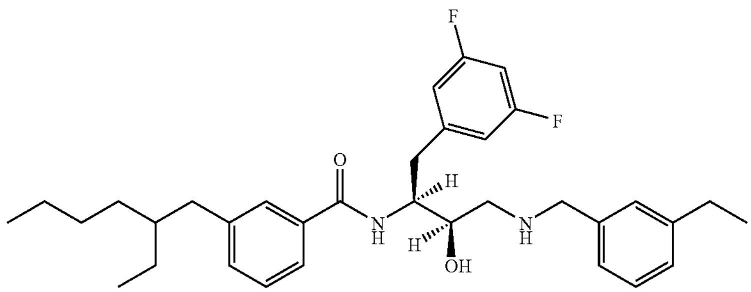 | N-{(1S,2R)-1-(3,5-difluorobenzyl)-3-[(3-ethylbenzyl)amino]-2-hydroxypropyl}-3-(2-ethylhexyl)benzamide | |
| 3168 | 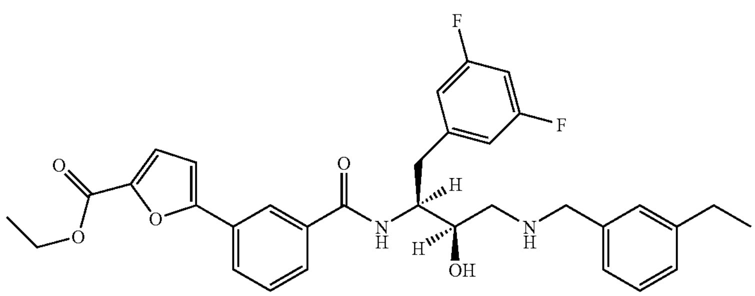 | ethyl 5-{3-[({(1S,2R)-1-(3,5-difluorobenzyl)-3-[(3-ethylbenzyl)amino]-2-hydroxypropyl}amino)carbonyl]phenyl}-2-furoate | |
| 3169 | 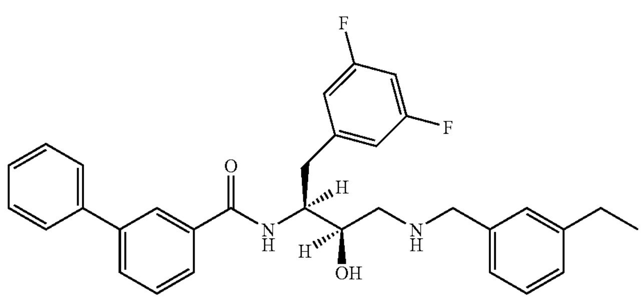 | N-{(1S,2R)-1-(3,5-difluorobenzyl)-3-[(3-ethylbenzyl)amino]-2-hydroxypropyl}-1,1'-biphenyl-3-carboxamide | |
| 3170 | 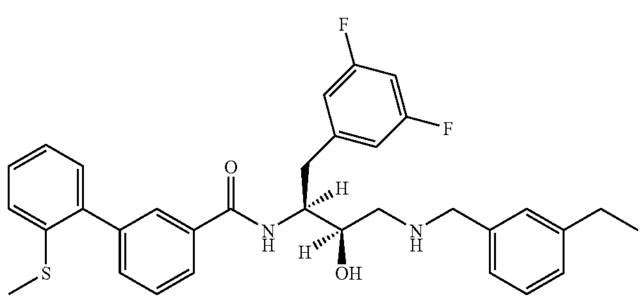 | N-{(1S,2R)-1-(3,5-difluorobenzyl)-3-[(3-ethylbenzyl)amino]-2-hydroxypropyl}-2'-(mthylthio)-1,1'-biphenyl-3-carboxamide | |
| 3171 | 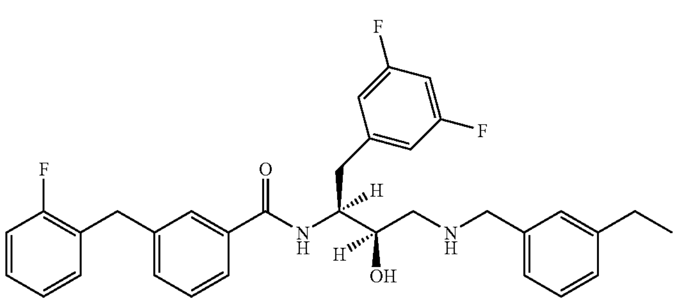 | N-{(1S,2R)-1-(3,5-difluorobenzyl)-3-[(3-ethylbenzyl)amino]-2-hydroxypropyl}-3-(2-fluorobenzyl)benzamide | |

-continued

| EXAMPLE | Structure | Compound Name(s) | Mass Spec |
|---|---|---|---|
| 3172 | 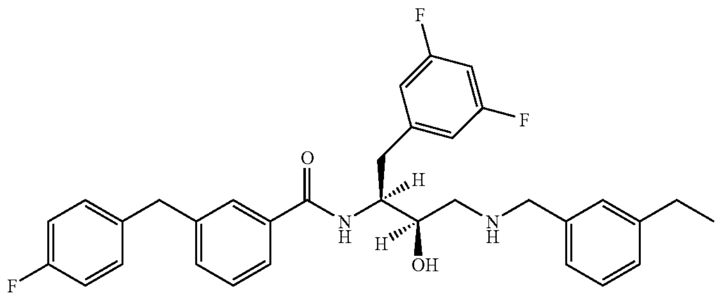 | N-{(1S,2R)-1-(3,5-difluorobenzyl)-3-[(3-ethylbenzyl)amino]-2-hydroxypropyl}-3-(4-fluorobenzyl)benzamide | |
| 3173 | 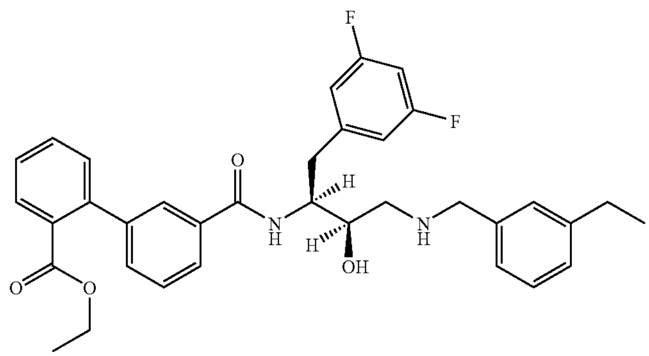 | ethyl 3'-[({(1S,2R)-1-(3,5-difluorobenzyl)-3-[(3-ethylbenzyl)amino]-2-hydroxypropyl}amino)carbonyl]-1,1'-biphenyl-2-carboxylate | |
| 3174 | 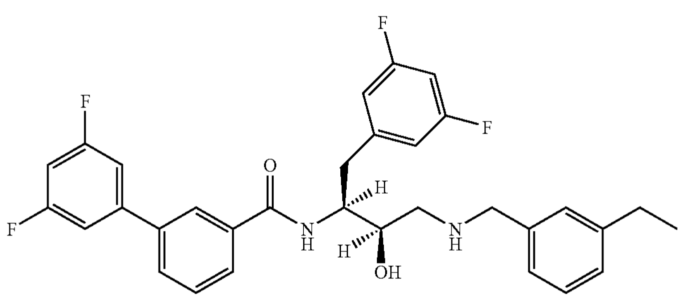 | N-{(1S,2R)-1-(3,5-difluorobenzyl)-3-[(3-ethylbenzyl)amino]-2-hydroxypropyl}-3',5'-difluoro-1,1'-biphenyl-3-carboxamide | |
| 3175 | 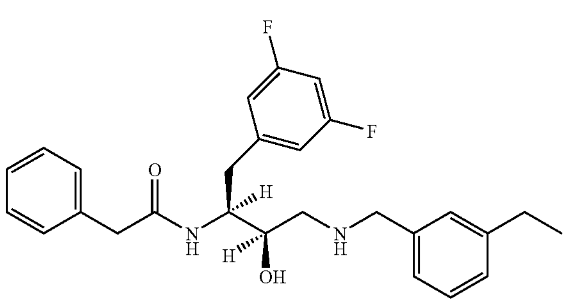 | N-{(1S,2R)-1-(3,5-difluorobenzyl)-3-[(3-ethylbenzyl)amino]-2-hydroxypropyl}-2-phenylacetamide | |

-continued

| EXAMPLE | Structure | Compound Name(s) | Mass Spec |
|---|---|---|---|
| 3176 | 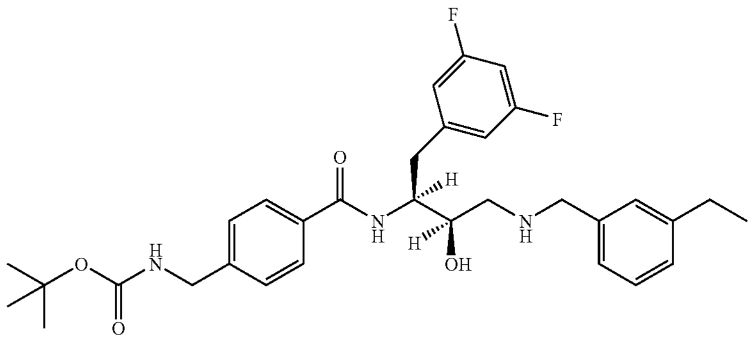 | tert-butyl 4-[({(1S,2R)-1-(3,5-difluorobenzyl)-3-[(3-ethylbenzyl)amino]-2-hydroxypropyl}amino)carbonyl]benzylcarbamate | |
| 3177 | 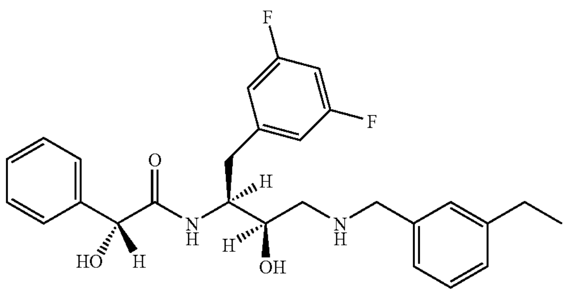 | (2R)-N-{(1S,2R)-1-(3,5-difluorobenzyl)-3-[(3-ethylbenzyl)amino]-2-hydroxypropyl}-2-hydroxy-2-phenylethanamide | |
| 3178 | 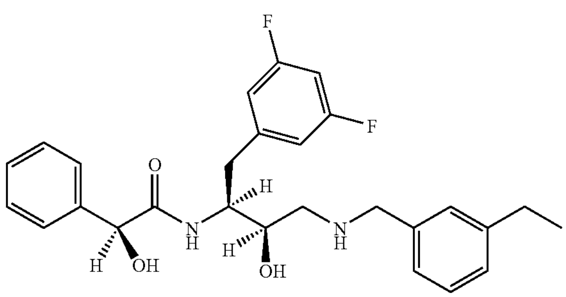 | (2R)-N-{(1S,2R)-1-(3,5-difluorobenzyl)-3-[(3-ethylbenzyl)amino]-2-hydroxypropyl}-2-hydroxy-2-phenylethanamide | |
| 3179 | 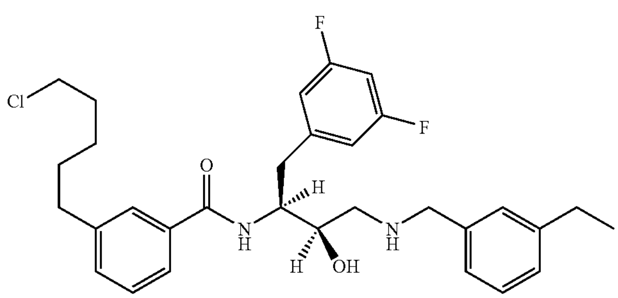 | 3-(5-chloropentyl)-N-{(1S,2R)-1-(3,5-difluorobenzyl)-3-[(3-ethylbenzyl)amino]-2-hydroxypropyl}benzamide | |
| 3180 | 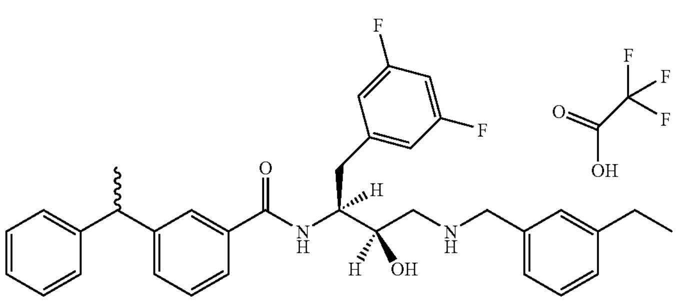 | N-{(1S,2R)-1-(3,5-difluorobenzyl)-3-[(3-ethylbenzyl)amino]-2-hydroxypropyl}-3-(1-phenylethyl)benzamide trifluoroacetate | |

-continued

| EXAMPLE | Structure | Compound Name(s) | Mass Spec |
|---|---|---|---|
| 3181 | 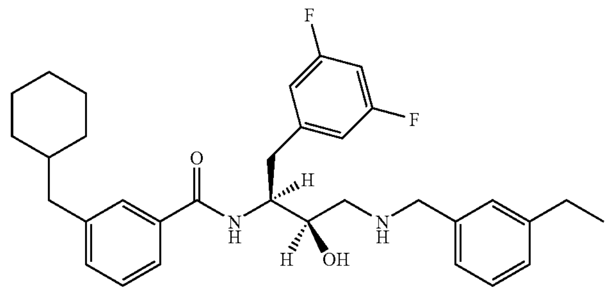 | 3-(cyclohexylmethyl)-N-{(1S,2R)-1-(3,5-difluorobenzyl)-3-[(3-ethylbenzyl)amino]-2-hydroxypropyl)benzamide | |
| 3182 | 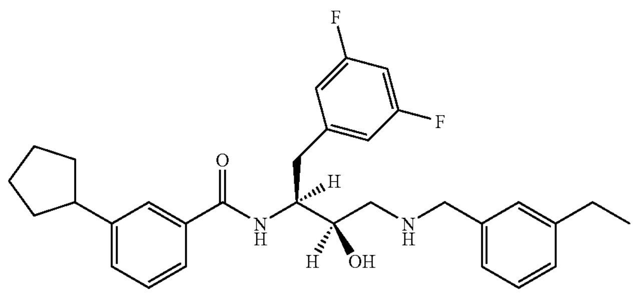 | 3-cyclopentyl-N-{(1S,2R)-1-(3,5-difluorobenzyl)-3-[(3-ethylbenzyl)amino]-2-hydroxypropyl}benzamide | |
| 3183 | 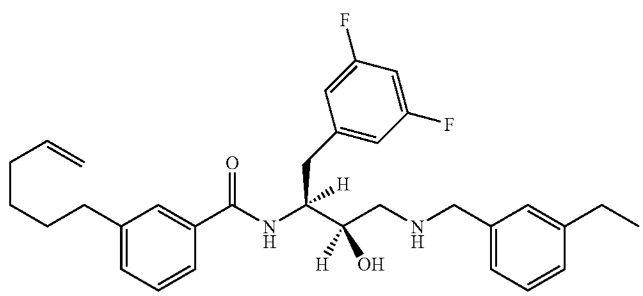 | N-{(1S,2R)-1-(3,5-difluorobenzyl)-3-[(3-ethylbenzyl)amino]-2-hydroxypropyl}-3-hex-5-enylbenzamide | |
| 3184 | 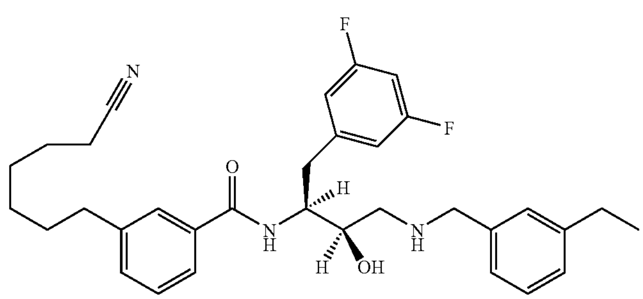 | 3-(6-cyanohexyl)-N-{(1S,2R)-1-(3,5-difluorobenzyl)-3-[(3-ethylbenzyl)amino]-2-hydroxypropyl}benzamide | |
| 3185 | 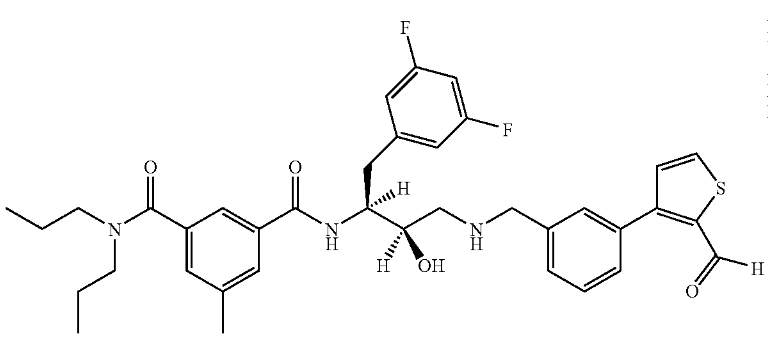 | $N^1$-((1S,2R)-1-(3,5-difluorobenzyl)-3-{[3-(2-formylthien-3-yl)benzyl]amino}-2-hydroxypropyl)-5-methyl-$N^3$,$N^3$-dipropylisophthalamide | |

-continued

| EXAMPLE | Structure | Compound Name(s) | Mass Spec |
|---|---|---|---|
| 3186 | 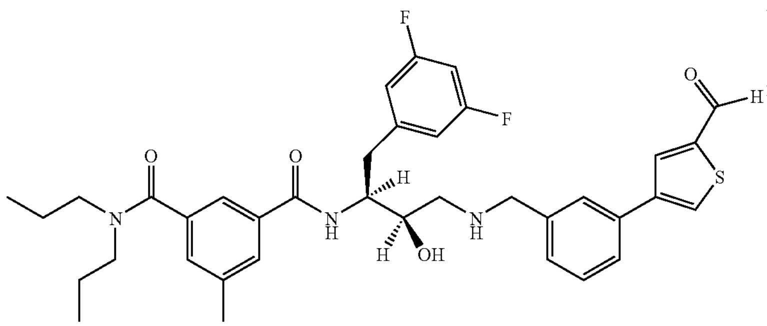 | N$^1$-((1S,2R)-1-(3,5-difluorobenzyl)-3-{[3-(5-formylthien-3-yl)benzyl]amino}-2-hydroxypropyl)-5-methyl-N$^3$,N$^3$-dipropylisophthalamide | |
| 3187 | 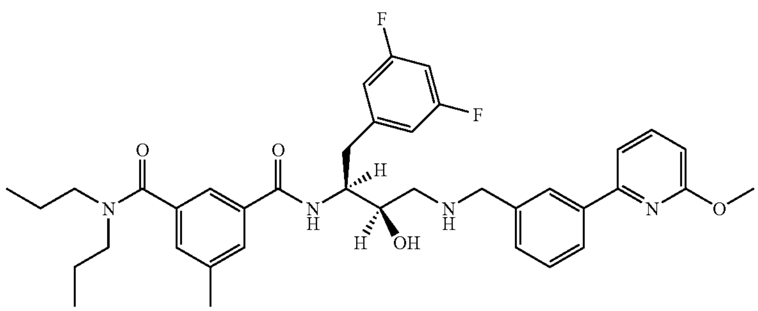 | N$^1$-((1S,2R)-1-(3,5-difluorobenzyl)-2-hydroxy-3-{[3-(6-methoxypyridin-2-yl)benzyl]amino}propyl)-5-methyl-N$^3$,N$^3$-dipropylisophthalamide | |
| 3188 | 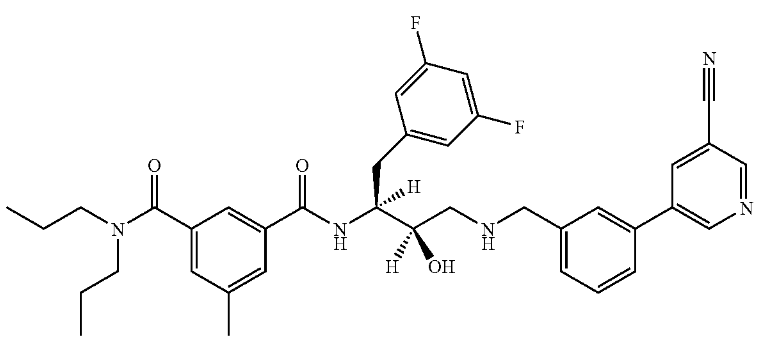 | N$^1$-[(1S,2R)-3-{[3-(5-cyanopyridin-3-yl)benzyl]amino}-1-(3,5-difluorobenzyl)-2-hydroxypropyl]-5-methyl-N$^3$,N$^3$-dipropylisophthalamide | |
| 3189 | 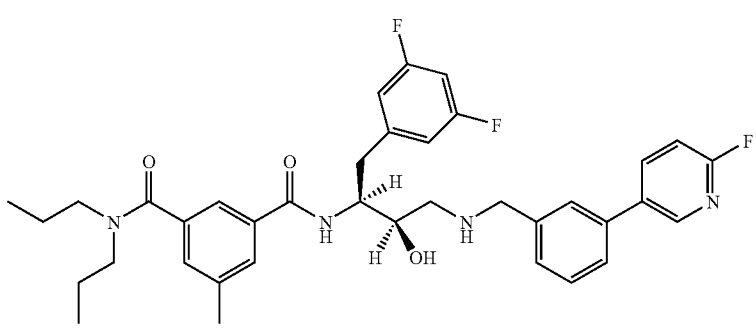 | N$^1$-((1S,2R)-1-(3,5-difluorobenzyl)-3-{[3-(6-fluoropyridin-3-yl)benzyl]amino}-2-hydroxypropyl)-5-methyl-N$^3$,N$^3$-dipropylisophthalamide | |

| EXAMPLE | Structure | Compound Name(s) | Mass Spec |
|---|---|---|---|
| 3190 | 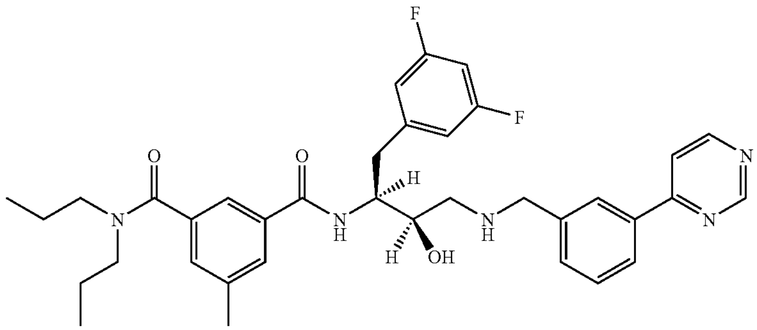 | N¹-{(1S,2R)-1-(3,5-difluorobenzyl)-2-hydroxy-3-[(3-pyrimidin-4-ylbenzyl)amino]propyl}-5-methyl-N³,N³-dipropylisophthalamide | |
| 3191 | 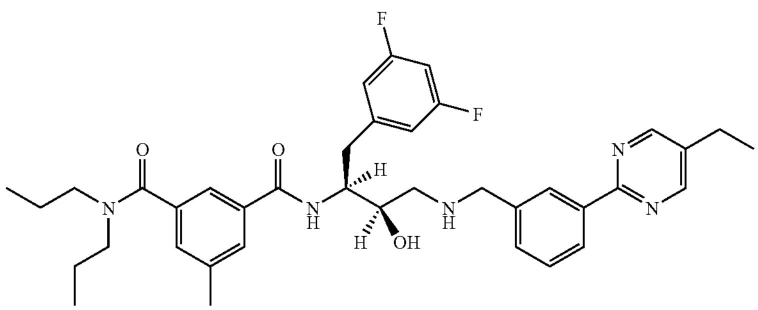 | N¹-((1S,2R)-1-(3,5-difluorobenzyl)-3-{[3-(5-ethylpyrimidin-2-yl)benzyl]amino}-2-hydroxypropyl)-5-methyl-N³,N³-dipropylisophthalamide | |
| 3192 | 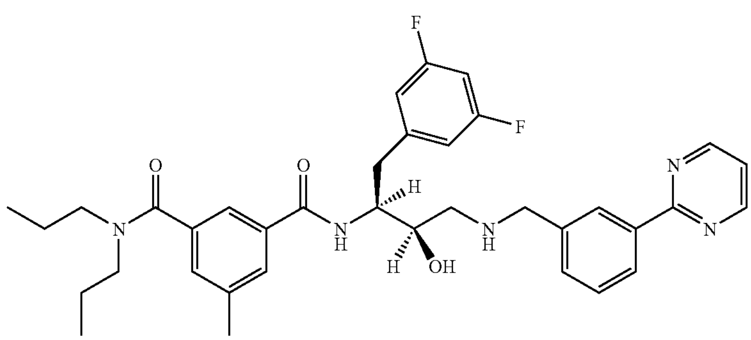 | N¹-{(1S,2R)-1-(3,5-difluorobenzyl)-2-hydroxy-3-[(3-pyrimidin-2-ylbenzyl)amino]propyl}-5-methyl-N³,N³-dipropylisophthalamide | |
| 3193 | 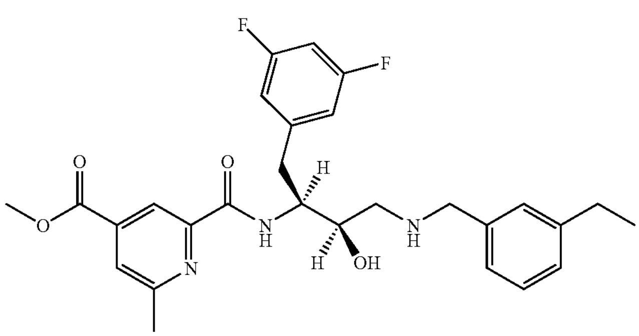 | methyl 2-[({(1S,2R)-1-(3,5-difluorobenzyl)-3-[(3-ethylbenzyl)amino]-2-hydroxypropyl}amino)carbonyl]-6-methylisonicotinate | |

| EXAMPLE | Structure | Compound Name(s) | Mass Spec |
|---|---|---|---|
| 3194 | 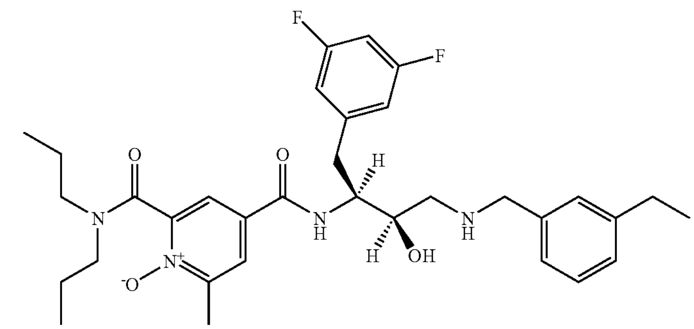 | $N^4$-{(1S,2R)-1-(3,5-difluorobenzyl)-3-[(3-ethylbenzyl)amino]-2-hydroxypropyl}-6-methyl-$N^2,N^2$-dipropylpyridine-2,4-dicarboxamide 1-oxide | |
| 3195 | 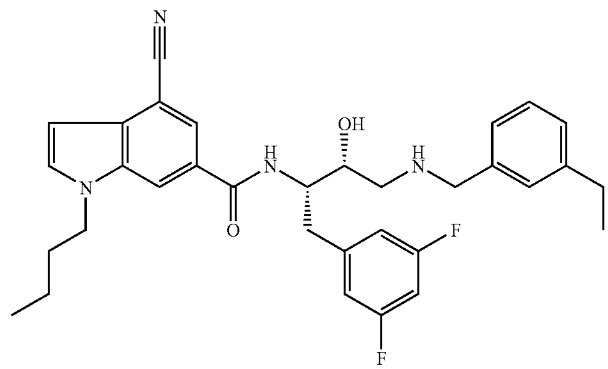 | 1-butyl-4-cyano-N-{(1S,2R)-1-(3,5-difluorobenzyl)-3-[(3-ethylbenzyl)amino]-2-hydroxypropyl}-1H-indole-6-carboxamide | |
| 3196 | 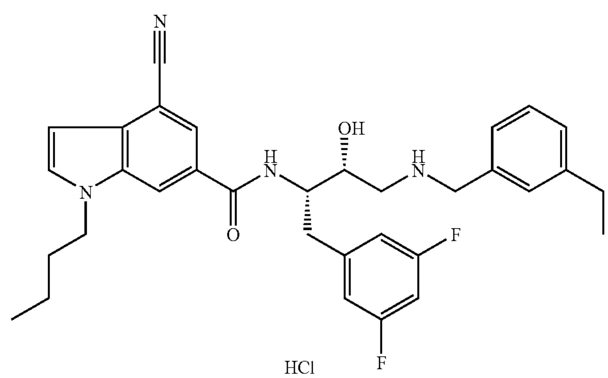 | 1-butyl-4-cyano-N-{(1S,2R)-1-(3,5-difluorobenzyl)-3-[(3-ethylbenzyl)amino]-2-hydroxypropyl}-1H-indole-6-carboxamide hydrochloride | |
| 3197 | 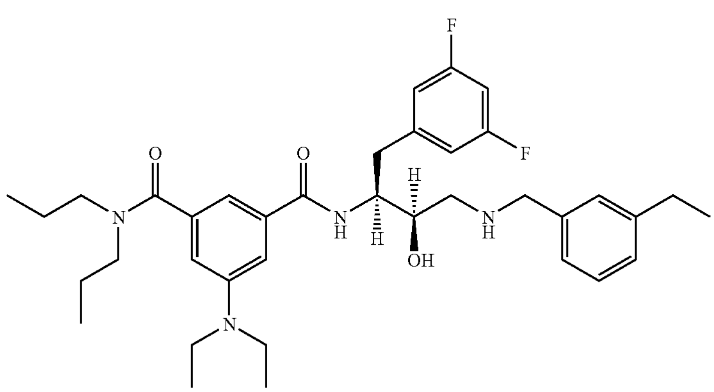 | 5-(diethylamino)-$N^1$-{(1S,2R)-1-(3,5-difluorobenzyl)-3-[(3-ethylbenzyl)amino]-2-hydroxypropyl}-$N^3,N^3$-dipropylisophthalamide | |

-continued

| EXAMPLE | Structure | Compound Name(s) | Mass Spec |
|---|---|---|---|
| 3198 | 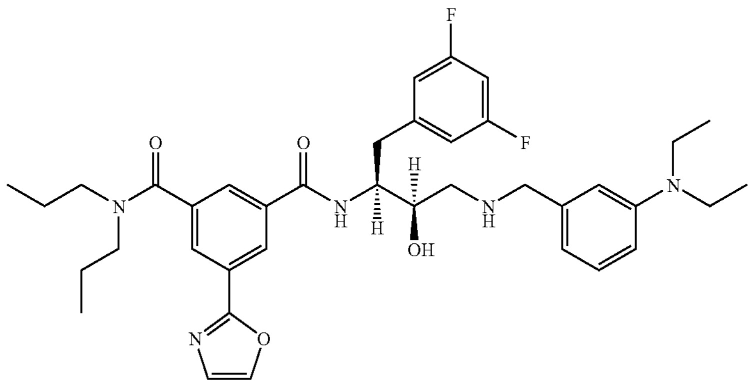 | N¹-[(1S,2R)-3-{[3-(diethylamino)benzyl]amino}-1-(3,5-difluorobenzyl)-2-hydroxypropyl]-5-(1,3-oxazol-2-yl)-N³,N³-dipropylisophthalamide | |
| 3199 | 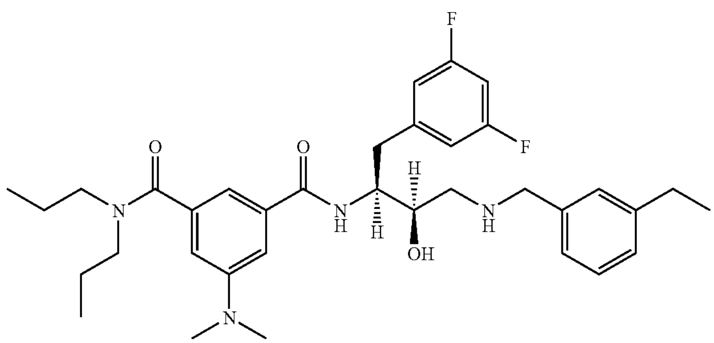 | N¹-{(1S,2R)-1-(3,5-difluorobenzyl)-3-[(3-ethylbenzyl)amino]-2-hydroxypropyl}-5-(dimethylamino)-N³,N³-dipropylisophthalamide | |
| 3200 | 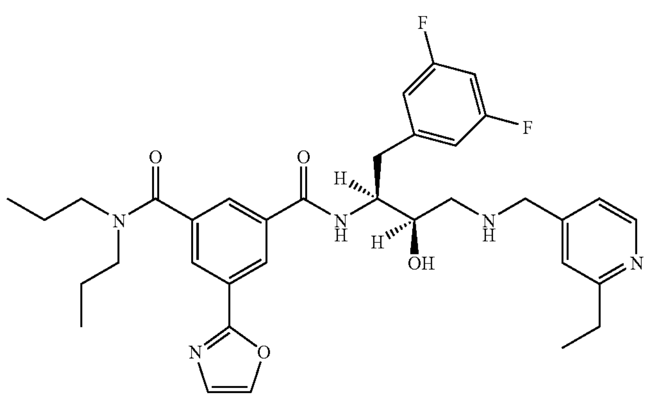 | N¹-((1S,2R)-1-(3,5-difluorobenzyl)-3-{[(2-ethylpyridin-4-yl)methyl]amino}-2-hydroxypropyl)-5-(1,3-oxazol-2-yl)-N³,N³-dipropylisophthalamide | |
| 3201 | 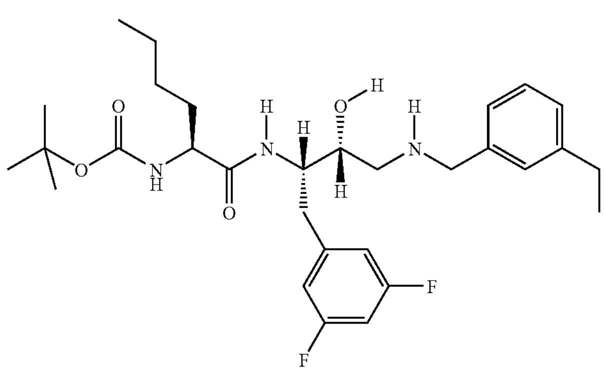 | N²-(tert-butoxycarbonyl)-N¹-{(1S,2R)-1-(3,5-difluorobenzyl)-3-[(3-ethylbenzyl)amino]-2-hydroxypropyl}-L-norleucinamide | |

-continued

| EXAMPLE | Structure | Compound Name(s) | Mass Spec |
|---|---|---|---|
| 3202 | 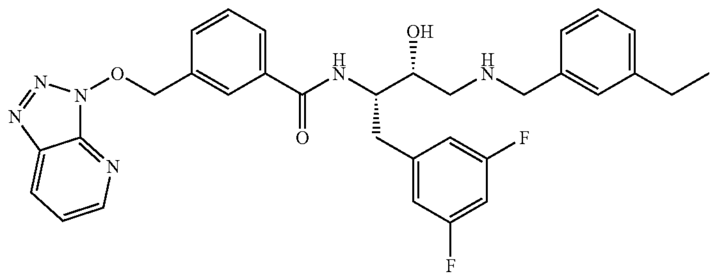 | N-{(1S,2R)-1-(3,5-difluoro-benzyl)-3-[(3-ethylbenzyl)amino]-2-hydroxypropyl}-3-[(3H-[1,2,3]triazolo[4,5-b]pyridin-3-yloxy)methyl]benzamide | |
| 3203 | 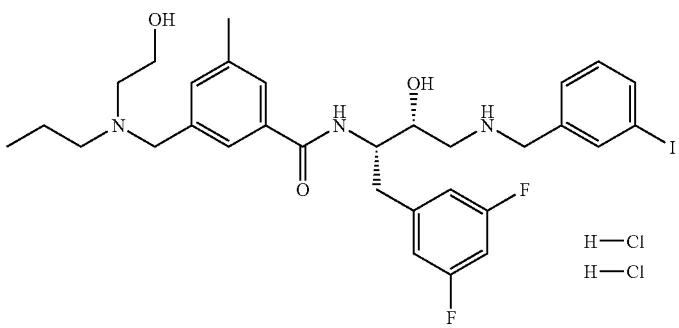 | N-{(1S,2R)-1-(3,5-difluoro-benzyl)-2-hydroxy-3-[(3-iodobenzyl)amino]propyl}-3-{[(2-hydroxyethyl)(propyl)amino]methyl}-5-methylbenzamide dihydrochloride | |
| 3204 | 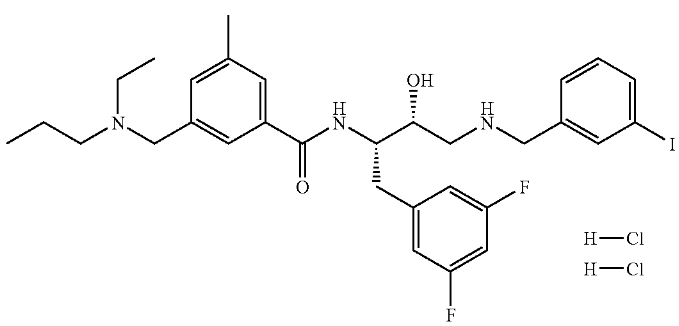 | N-{(1S,2R)-1-(3,5-difluoro-benzyl)-2-hydroxy-3-[(3-iodobenzyl)amino]propyl}-propyl}-3-{[ethyl(propyl)amino]methyl}-5-methyl-benzamide dihydrochloride | |
| 3205 | 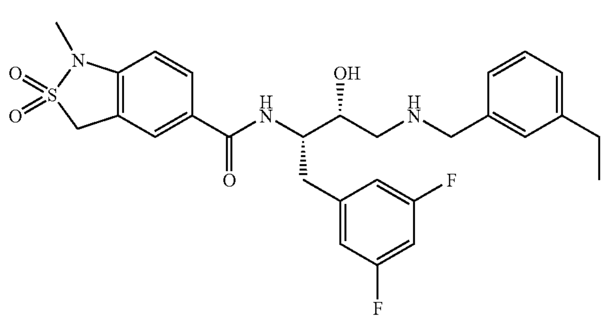 | N-{(1S,2R)-1-(3,5-difluoro-benzyl)-3-[(3-ethylbenzyl)amino]-2-hydroxypropyl}-1-methyl-1,3-dihydro-2,1-benzisothiazole-5-carboxamide 2,2-dioxide | |

-continued

| EXAMPLE | Structure | Compound Name(s) | Mass Spec |
|---|---|---|---|
| 3206 | 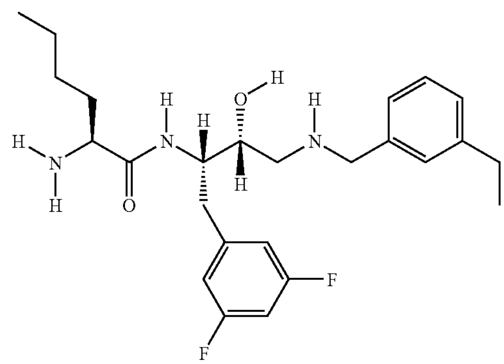 | N¹-{(1S,2R)-1-(3,5-difluorobenzyl)-3-[(3-ethylbenzyl)amino]-2-hydroxypropyl}-L-norleucinamide | |
| 3207 | 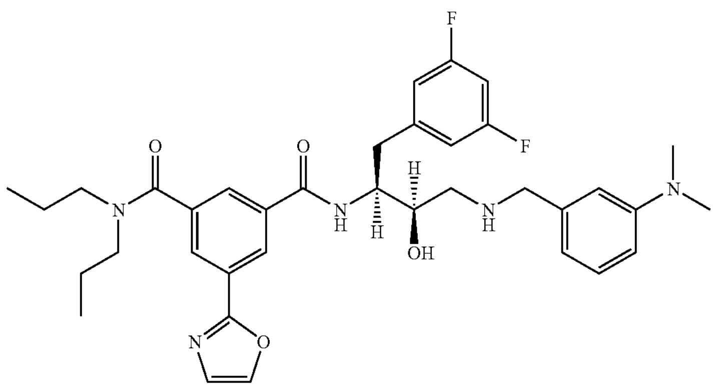 | N¹-((1S,2R)-1-(3,5-difluorobenzyl)-3-{[3-(dimethylamino)benzyl]amino}-2-hydroxypropyl)-5-(1,3-oxazol-2-yl)-N³,N³-dipropylisophthalamide | |
| 3208 | 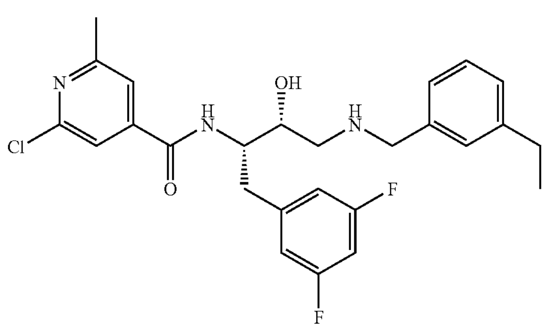 | 2-chloro-N-{(1S,2R)-1-(3,5-difluorobenzyl)-3-[(3-ethylbenzyl)amino]-2-hydroxypropyl}-6-methylisonicotinamide | |
| 3209 | 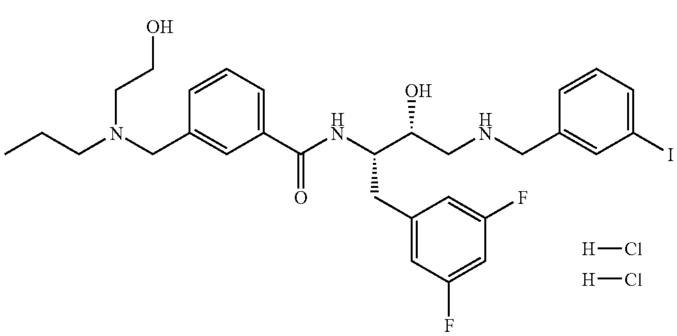 | N-{(1S,2R)-1-(3,5-difluorobenzyl)-2-hydroxy-3-[(3-iodobenzyl)amino]propyl}-3-{[(2-hydroxyethyl)(propyl)amino]methyl}benzamide dihydrochloride | |

-continued

| EXAMPLE | Structure | Compound Name(s) | Mass Spec |
|---|---|---|---|
| 3210 | 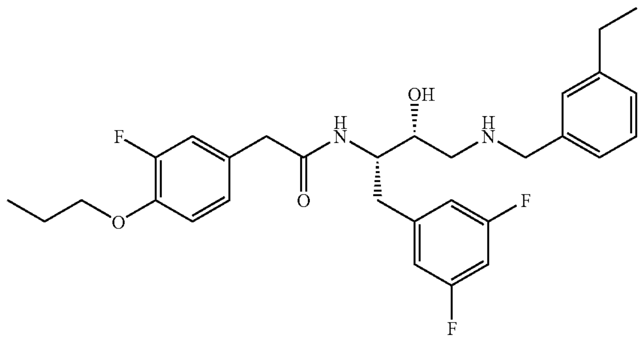 | N-{(1S,2R)-1-(3,5-difluorobenzyl)-3-[(3-ethylbenzyl)amino]-2-hydroxypropyl}-2-(3-fluoro-4-propoxyphenyl)acetamide | |
| 3211 | 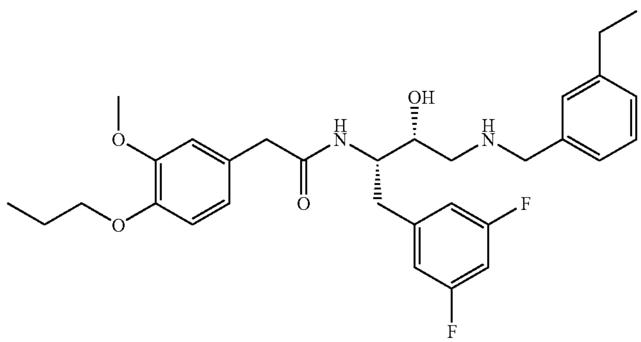 | N-{(1S,2R)-1-(3,5-difluorobenzyl)-3-[(3-ethylbenzyl)amino]-2-hydroxypropyl}-2-(3-methoxy-4-propoxyphenyl)acetamide | |
| 3212 | 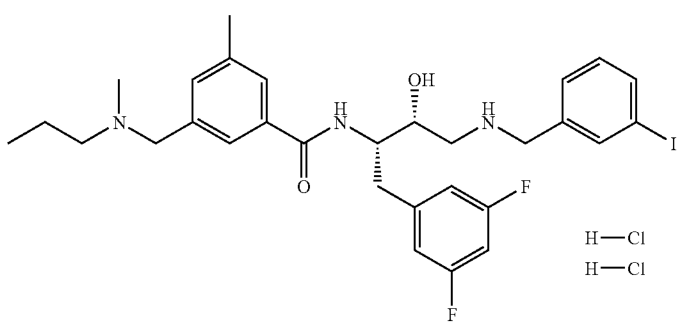 | N-{(1S,2R)-1-(3,5-difluorobenzyl)-2-hydroxy-3-[(3-iodobenzyl)amino]propyl}-3-methyl-5-{[methyl(propyl)amino]methyl}benzamide dihydrochloride | |
| 3213 | 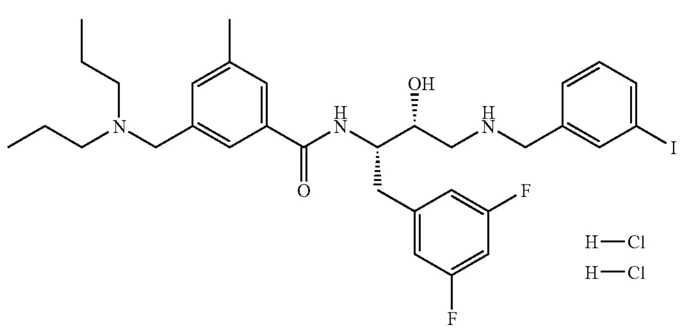 | N-{(1S,2R)-1-(3,5-difluorobenzyl)-2-hydroxy-3-[(3-iodobenzyl)amino]propyl}-3-[(dipropylamino)methyl]-5-methylbenzamide dihydrochloride | |

-continued

| EXAMPLE | Structure | Compound Name(s) | Mass Spec |
|---|---|---|---|
| 3214 | 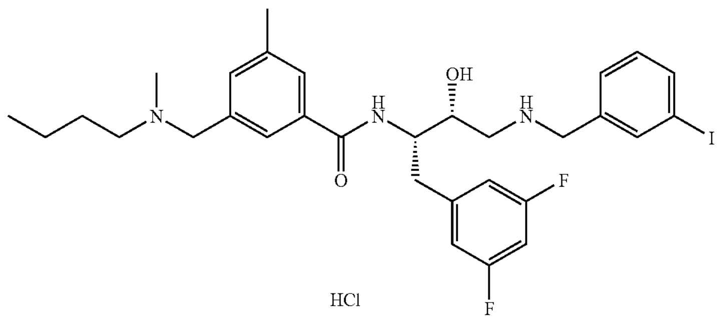 | 3-{[butyl(methyl)amino]methyl}-N-{(1S,2R)-1-(3,5-difluorobenzyl)-2-hydroxy-3-[(3-iodobenzyl)amino]propyl}-5-methylbenzamide hydrochloride | |
| 3215 | 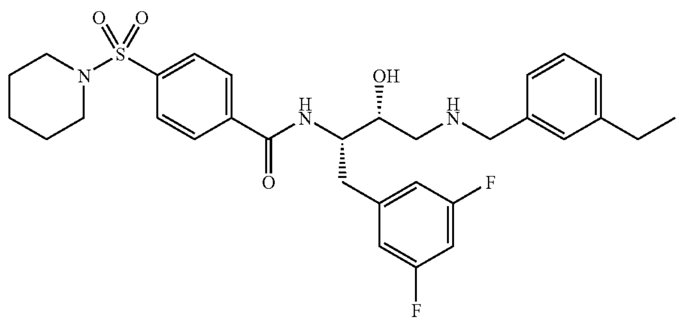 | N-{(1S,2R)-1-(3,5-difluorobenzyl)-3-[(3-ethylbenzyl)amino]-2-hydroxypropyl}-4-(piperidin-1-ylsulfonyl)benzamide | |
| 3216 | 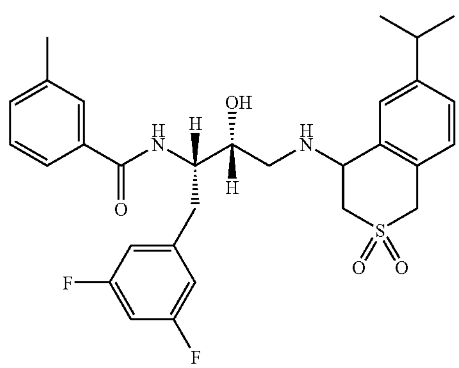 | N-{(1S,2R)-1-(3,5-difluorobenzyl)-2-hydroxy-3-[(6-isopropyl-2,2-dioxido-3,4-dihydro-1H-isothiochromen-4-yl)amino]propyl}-3-methylbenzamide | |
| 3217 | 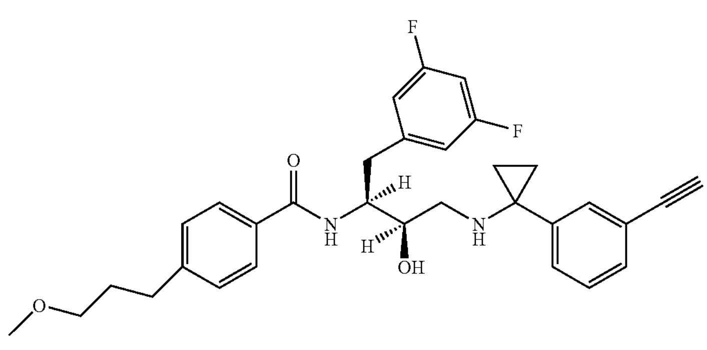 | N-((1S,2R)-1-(3,5-difluorobenzyl)-3-{[1-(3-ethynylphenyl)cyclopropyl]amino}-2-hydroxypropyl}-4-(3-methoxypropyl)benzamide | |

-continued

| EXAMPLE | Structure | Compound Name(s) | Mass Spec |
|---|---|---|---|
| 3218 | 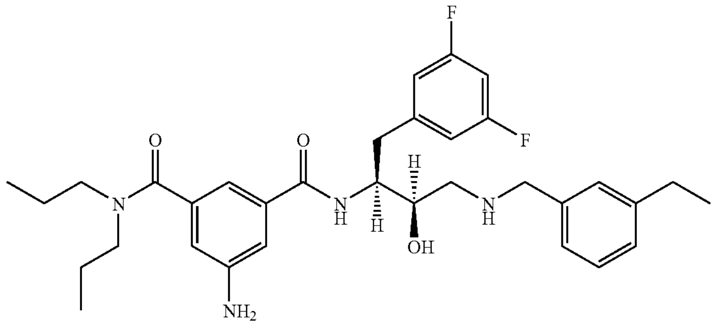 | 5-amino-$N^1$-{(1S,2R)-1-(3,5-difluorobenzyl)-3-[(3-ethylbenzyl)amino]-2-hydroxypropyl}-$N^3$,$N^3$-dipropylisophthalamide | |
| 3219 | 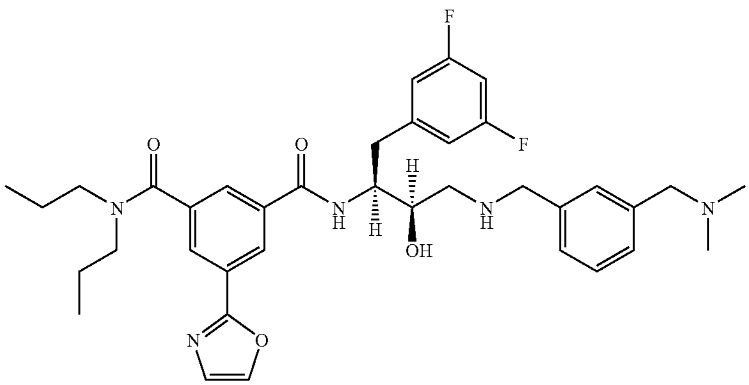 | $N^1$-[(1S,2R)-1-(3,5-difluorobenzyl)-3-({3-[(dimethylamino)methyl]benzyl}amino)-2-hydroxypropyl]-5-(1,3-oxazol-2-yl)-$N^3$,$N^3$-dipropylisophthalamide | |
| 3220 | 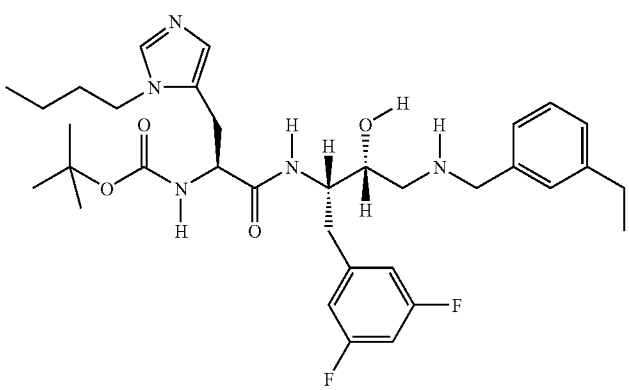 | N-(tert-butoxycarbonyl)-3-butyl-N-{(1S,2R)-1-(3,5-difluorobenzyl)-3-[(3-ethylbenzyl)amino]-2-hydroxypropyl}-L-histidinamide | |
| 3221 | 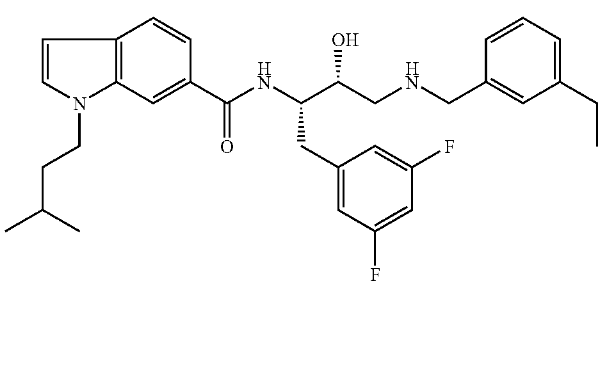 | N-{(1S,2R)-1-(3,5-difluorobenzyl)-3-[(3-ethylbenzyl)amino]-2-hydroxypropyl}-1-isopentyl-1H-indole-6-carboxamide | |

-continued

| EXAMPLE | Structure | Compound Name(s) | Mass Spec |
|---|---|---|---|
| 3222 | 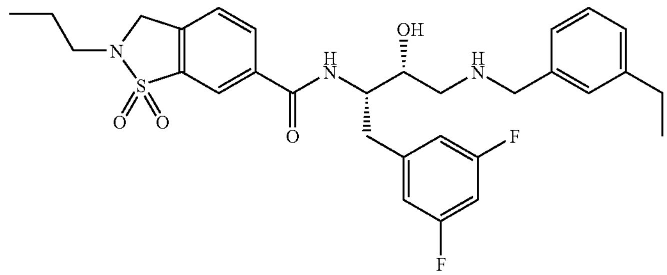 | N-{(1S,2R)-1-(3,5-difluorobenzyl)-3-[(3-ethylbenzyl)amino]-2-hydroxypropyl}-2-propyl-2,3-dihydro-1,2-benzisothiazole-6-carboxamide 1,1-dioxide | |
| 3223 | 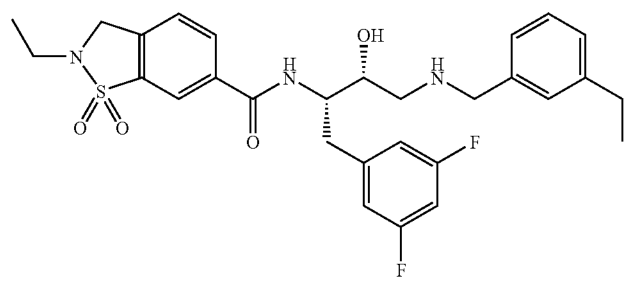 | N-{(1S,2R)-1-(3,5-difluorobenzyl)-3-[(3-ethylbenzyl)amino]-2-hydroxypropyl}-2-ethyl-2,3-dihydro-1,2-benzisothiazole-6-carboxamide 1,1-dioxide | |
| 3224 | 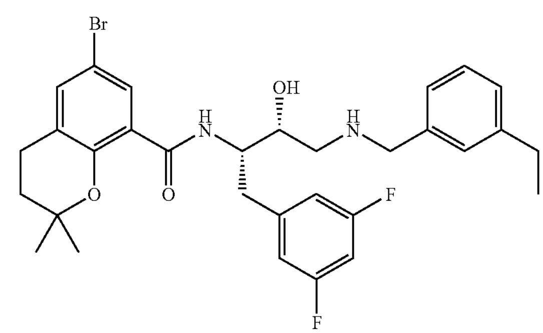 | 6-bromo-N-{(1S,2R)-1-(3,5-difluorobenzyl)-3-[(3-ethylbenzyl)amino]-2-hydroxypropyl}-2,2-dimethylchromane-8-carboxamide | |
| 3225 | 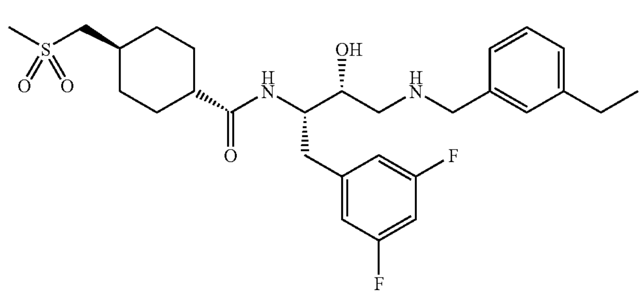 | N-{(1S,2R)-1-(3,5-difluorobenzyl)-3-[(3-ethylbenzyl)amino]-2-hydroxypropyl}-4-[(methylsulfonyl)methyl]cyclohexanecarboxamide | |

-continued

| EXAMPLE | Structure | Compound Name(s) | Mass Spec |
|---|---|---|---|
| 3226 | 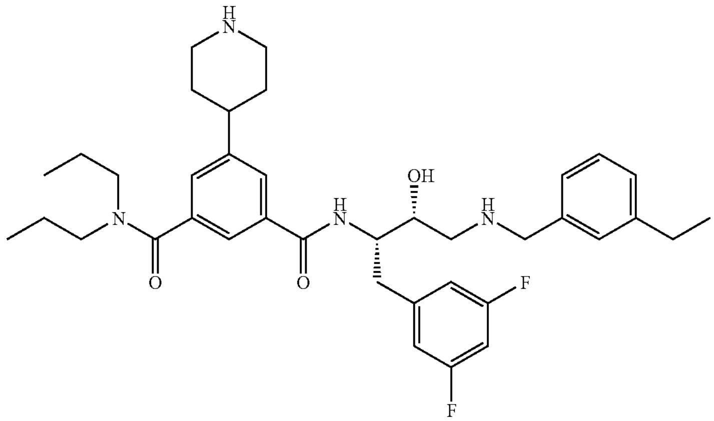 | N$^1$-{(1S,2R)-1-(3,5-difluorobenzyl)-3-[(3-ethylbenzyl)amino]-2-hydroxypropyl}-5-piperidin-4-yl-N$^3$,N$^3$-dipropylisophthalamide | |
| 3227 | 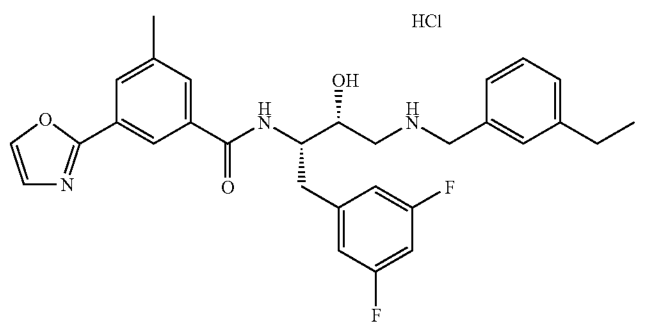 | N-{(1S,2R)-1-(3,5-difluorobenzyl)-3-[(3-ethylbenzyl)amino]-2-hydroxypropyl}-3-methyl-5-(1,3-oxazol-2-yl)benzamide hydrochloride | |
| 3228 | 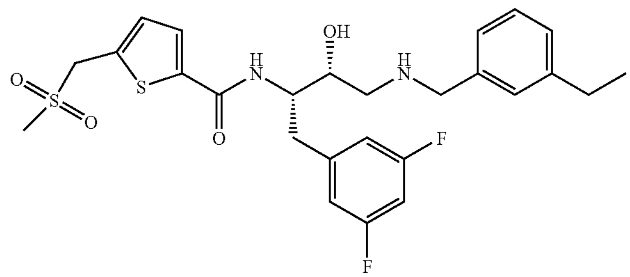 | N-{(1S,2R)-1-(3,5-difluorobenzyl)-3-[(3-ethylbenzyl)amino]-2-hydroxypropyl}-5-[(methylsulfonyl)methyl]thiophene-2-carboxamide | |
| 3229 | 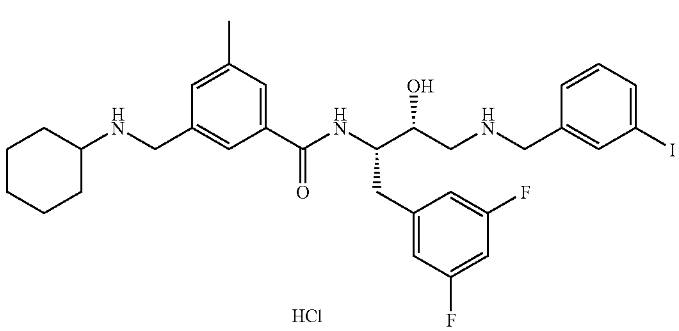 | 3-[(cyclohexylamino)methyl]-N-{(1S,2R)-1-(3,5-difluorobenzyl)-2-hydroxy-3-[(3-iodobenzyl)amino]propyl}-5-methylbenzamide hydrochloride | |

-continued

| EXAMPLE | Structure | Compound Name(s) | Mass Spec |
|---|---|---|---|
| 3230 | 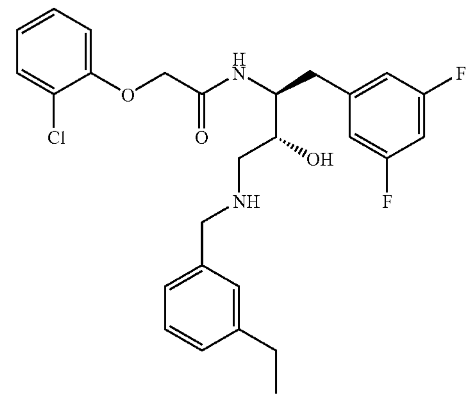 | 2-(2-chlorophenoxy)-N-{(1S,2R)-1-(3,5-difluorobenzyl)-3-[(3-ethylbenzyl)amino]-2-hydroxypropyl}acetamide | |
| 3231 | 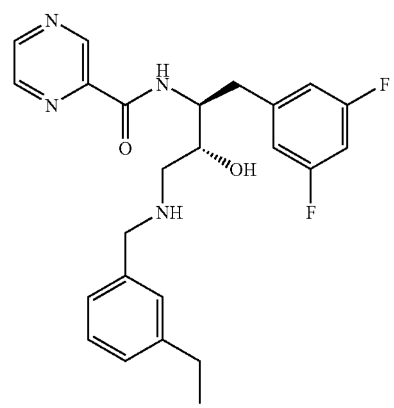 | N-{(1S,2R)-1-(3,5-difluorobenzyl)-3-[(3-ethylbenzyl)amino]-2-hydroxypropyl}pyrazine-2-carboxamide | |
| 3232 | 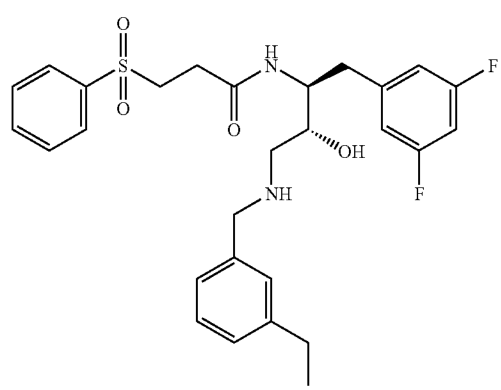 | N-{(1S,2R)-1-(3,5-difluorobenzyl)-3-[(3-ethylbenzyl)amino]-2-hydroxypropyl}-3-(phenylsulfonyl)propanamide | |
| 3233 | 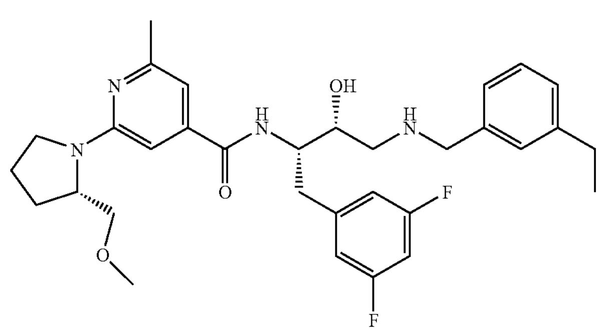 | N-{(1S,2R)-1-(3,5-difluorobenzyl)-3-[(3-ethylbenzyl)amino]-2-hydroxypropyl}-2-[(2S)-2-(methoxymethyl)pyrrolidin-1-yl]-6-methylisonicotinamide | |

-continued

| EXAMPLE | Structure | Compound Name(s) | Mass Spec |
|---|---|---|---|
| 3234 | 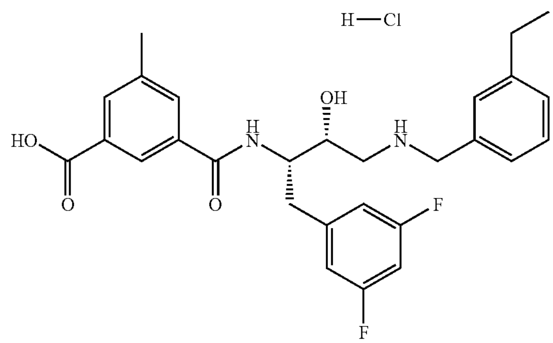 | 3-[({(1S,2R)-1-(3,5-difluorobenzyl)-3-[(3-ethylbenzyl)amino]-2-hydroxypropyl}amino)carbonyl]-5-methylbenzoic acid hydrochloride | |
| 3235 | 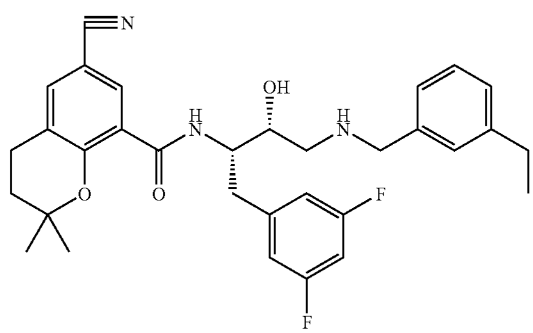 | 6-cyano-N-{(1S,2R)-1-(3,5-difluorobenzyl)-3-[(3-ethylbenzyl)amino]-2-hydroxypropyl}-2,2-dimethyl-chromane-8-carboxamide | |
| 3236 | 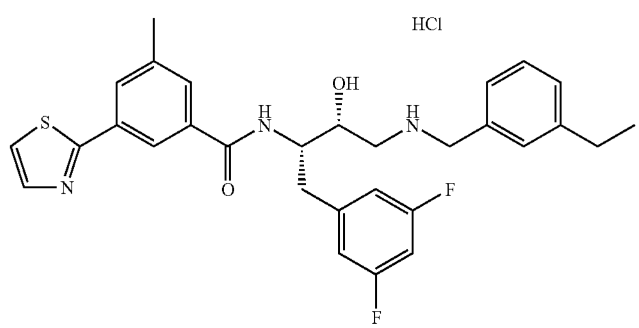 | N-{(1S,2R)-1-(3,5-difluorobenzyl)-3-[(3-ethylbenzyl)amino]-2-hydroxypropyl}-3-methyl-5-(1,3-thiazol-2-yl)benzamide hydrochloride | |
| 3237 | 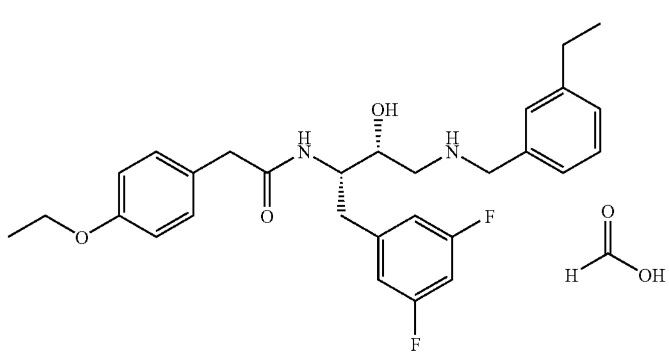 | formic acid compound with N-{(1S,2R)-1-(3,5-difluorobenzyl)-3-[(3-ethylbenzyl)amino]-2-hydroxypropyl}-2-(4-ethoxyphenyl)acetamide (1:1) | |

-continued

| EXAMPLE | Structure | Compound Name(s) | Mass Spec |
|---|---|---|---|
| 3238 | 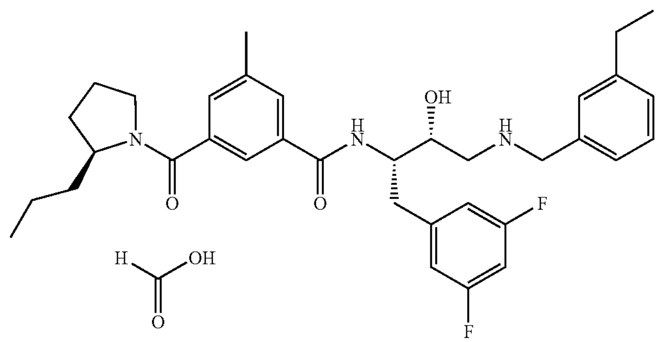 | formic acid compound with N-{(1S,2R)-1-(3,5-difluorobenzyl)-3-[(3-ethylbenzyl)amino]-2-hydroxypropyl}-3-methyl-5-{[(2S)-2-propylpyrrolidin-1-yl]carbonyl}benzamide (1:1) | |
| 3239 | 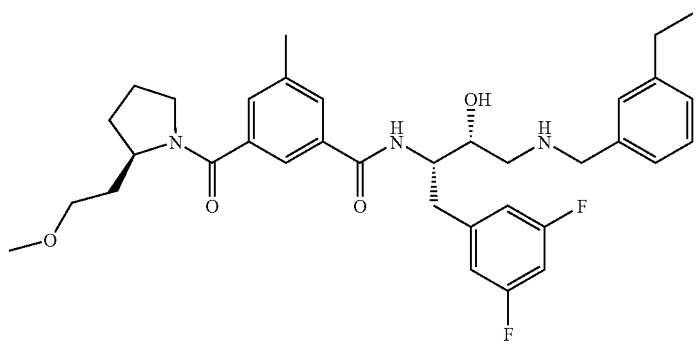 | N-{(1S,2R)-1-(3,5-difluorobenzyl)-3-[(3-ethylbenzyl)amino]-2-hydroxypropyl}-3-{[(2R)-2-(2-methoxyethyl)pyrrolidin-1-yl]carbonyl}-5-methylbenzamide | |
| 3240 | 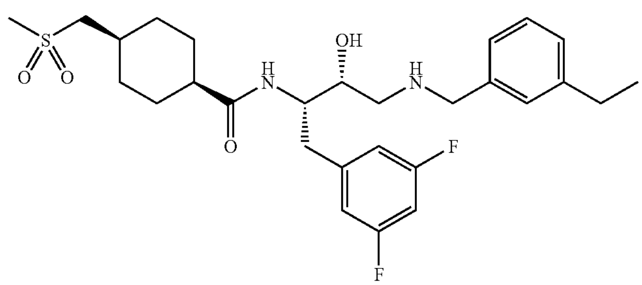 | N-{(1S,2R)-1-(3,5-difluorobenzyl)-3-[(3-ethylbenzyl)amino]-2-hydroxypropyl}-4-[(methylsulfonyl)methyl]cyclohexanecarboxamide | |
| 3241 | 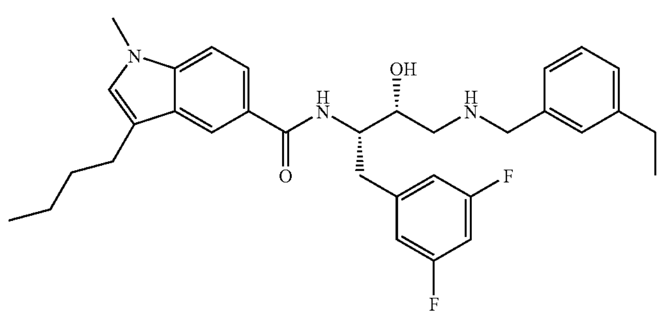 | 3-butyl-N-{(1S,2R)-1-(3,5-difluorobenzyl)-3-[(3-ethylbenzyl)amino]-2-hydroxypropyl}-1-methyl-1H-indole-5-carboxamide | |
| 3242 | 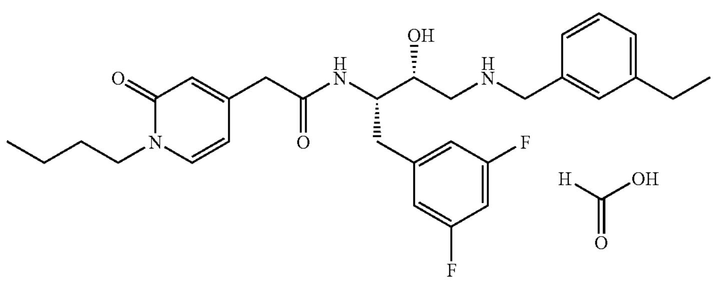 | formic acid compound with 2-(1-butyl-2-oxo-1,2-dihydropyridin-4-yl)-N-{(1S,2R)-1-(3,5-difluorobenzyl)-3-[(3-ethylbenzyl)amino]-2-hydroxypropyl}acetamide (1:1) | |

-continued

| EXAMPLE | Structure | Compound Name(s) | Mass Spec |
|---|---|---|---|
| 3243 | 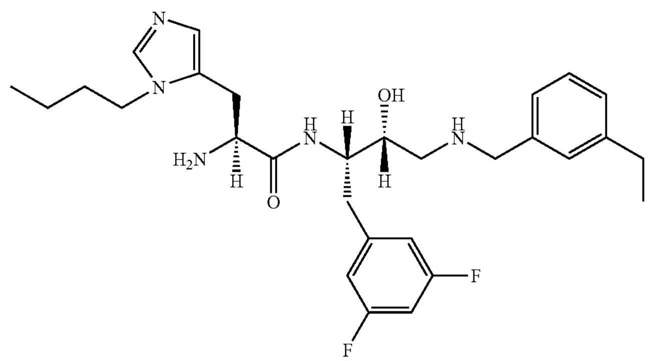 | 3-butyl-N-{(1S,2R)-1-(3,5-difluorobenzyl)-3-[(3-ethylbenzyl)amino]-2-hydroxypropyl}-L-histidinamide | |
| 3244 | 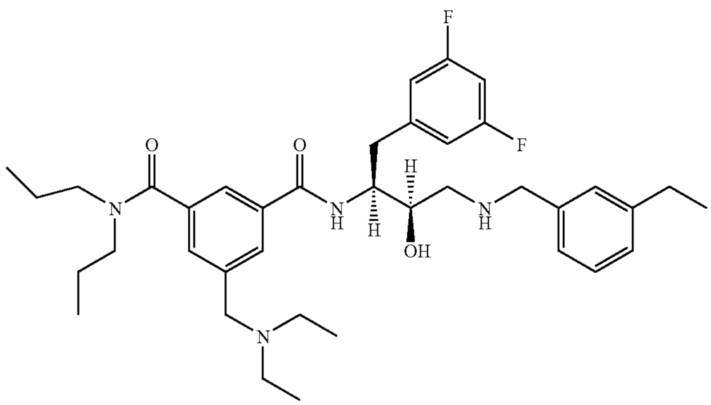 | 5-[(diethylamino)methyl]-N$^1$-{(1S,2R)-1-(3,5-difluorobenzyl)-3-[(3-ethylbenzyl)amino]-2-hydroxypropyl}-N$^3$,N$^3$-dipropylisophthalamide | |
| 3245 | 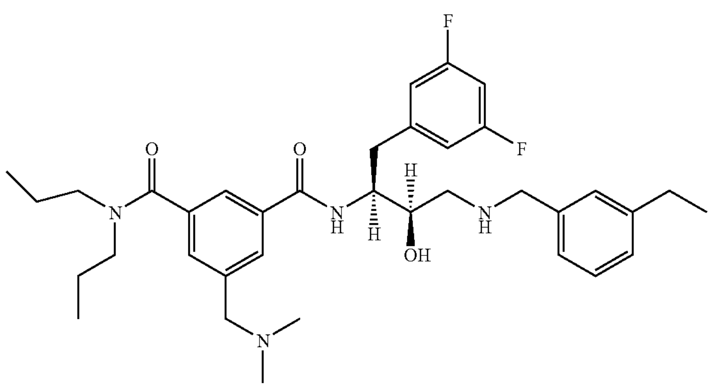 | N$^1$-{(1S,2R)-1-(3,5-difluorobenzyl)-3-[(3-ethylbenzyl)amino]-2-hydroxypropyl}-5-[(dimethylamino)methyl]-N$^3$,N$^3$-dipropylisophthalamide | |
| 3246 | 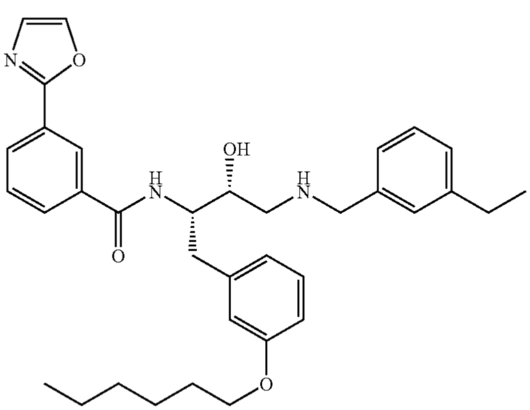 | N-{(1S,2R)-3-[(3-ethylbenzyl)amino]-1-[3-(hexyloxy)benzyl]-2-hydroxypropyl}-3-(1,3-oxazol-2-yl)benzamide | **570.2 |

-continued

| EXAMPLE | Structure | Compound Name(s) | Mass Spec |
|---|---|---|---|
| 3247 | 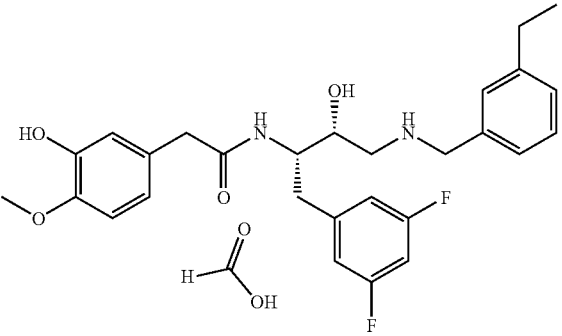 | formic acid compound with N-{(1S,2R)-1-(3,5-difluoro-benzyl)-3-[(3-ethylbenzyl)amino]-2-hydroxypropyl}-2-(3-hydroxy-4-methoxyphenyl)acetamide (1:1) | |
| 3248 | 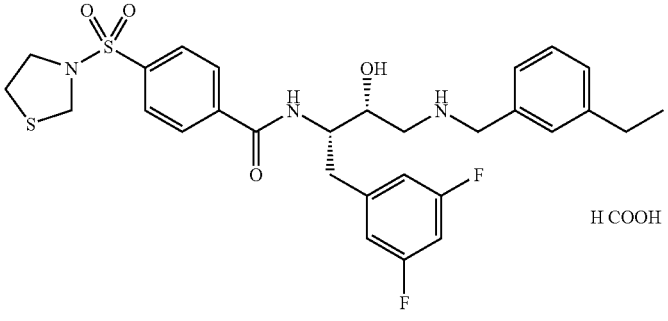 | formic acid compound with N-{(1S,2R)-1-(3,5-difluoro-benzyl)-3-[(3-ethylbenzyl)amino]-2-hydroxypropyl}-4-(1,3-thiazolidin-3-ylsulfonyl)benzamide (1:1) | ***589.9 |
| 3249 | 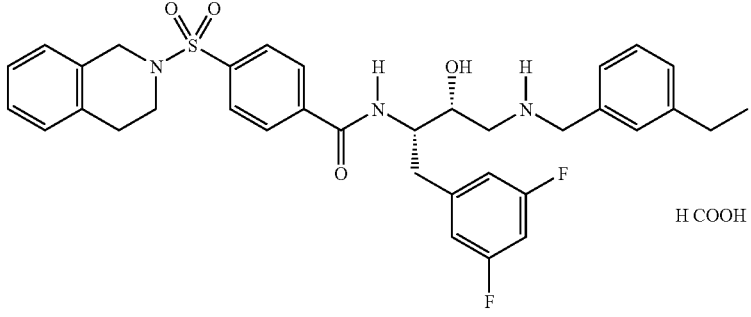 | formic acid compound with N-{(1S,2R)-1-(3,5-difluoro-benzyl)-3-[(3-ethylbenzyl)amino]-2-hydroxypropyl}-4-(3,4-dihydroisoquinolin-2(1H)-ylsulfonyl)benzamide (1:1) | ***634.0 |
| 3250 | 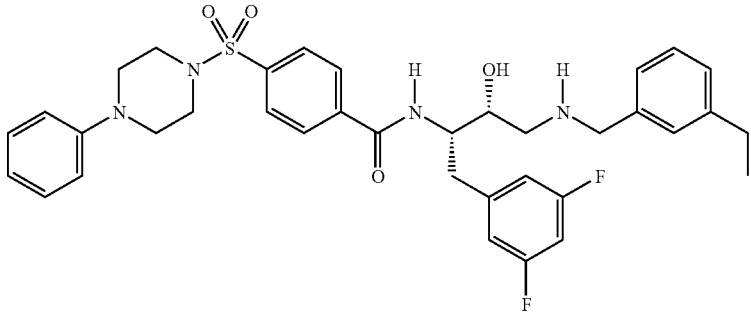 | N-{(1S,2R)-1-(3,5-difluoro-benzyl)-3-[(3-ethylbenzyl)amino]-2-hydroxypropyl}-4-[(4-phenylpiperazin-1-yl)sulfonyl]benzamide | ***663.0 |

-continued

| EXAMPLE | Structure | Compound Name(s) | Mass Spec |
|---|---|---|---|
| 3251 | 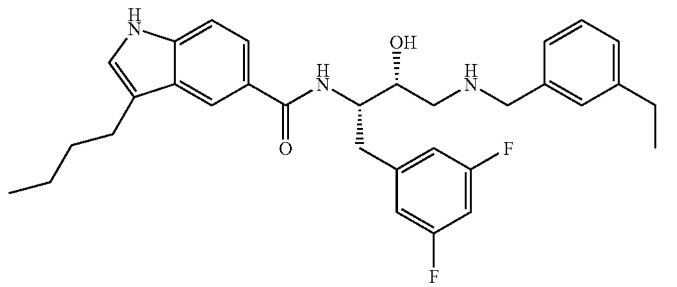 | 3-butyl-N-{(1S,2R)-1-(3,5-difluorobenzyl)-3-[(3-ethylbenzyl)amino]-2-hydroxypropyl}-1H-indole-5-carboxamide | |
| 3253 | 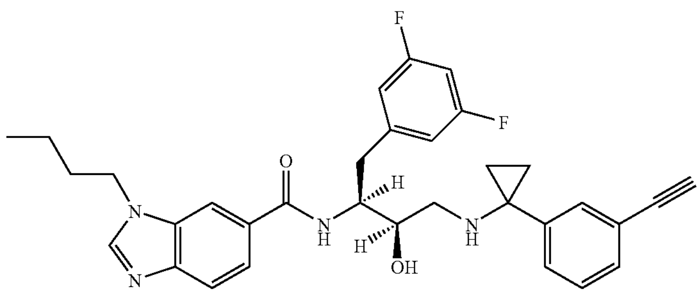 | 1-butyl-N-((1S,2R)-1-(3,5-difluorobenzyl)-3-{[1-(3-ethynylphenyl)cyclopropyl]amino}-2-hydroxypropyl)-1H-benzimidazole-6-carboxamide or ELAN155076 | |
| 3254 | 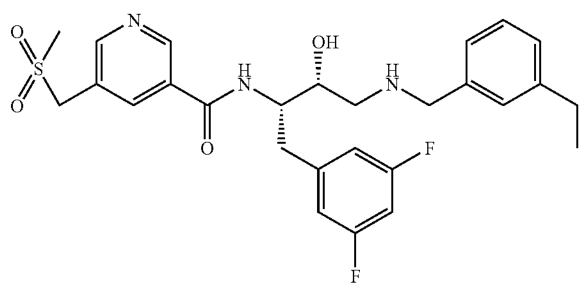 | N-{(1S,2R)-1-(3,5-difluorobenzyl)-3-[(3-ethylbenzyl)amino]-2-hydroxypropyl}-5-[(methylsulfonyl)methyl]nicotinamide | **532 |
| 3255 | 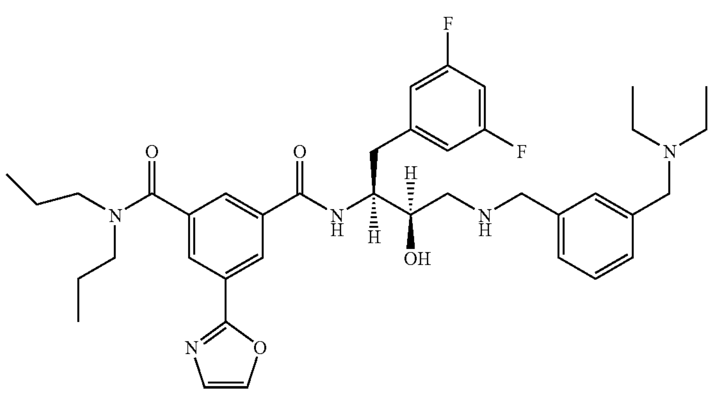 | $N^1$-[(1S,2R)-3-({3-[(diethylamino)methyl]benzyl}amino)-1-(3,5-difluorobenzyl)-2-hydroxypropyl]-5-(1,3-oxazol-2-yl)-$N^3$,$N^3$-dipropylisophthalamide | |
| 3256 | 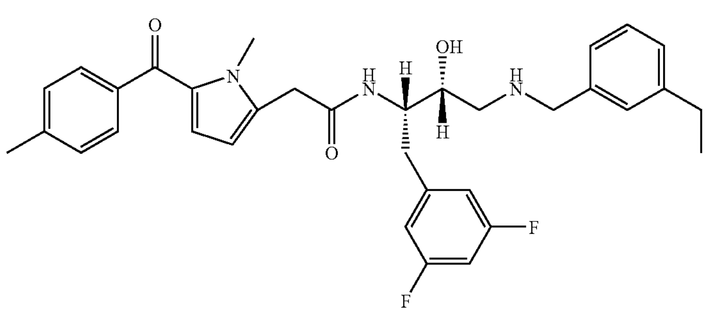 | N-{(1S,2R)-1-(3,5-difluorobenzyl)-3-[(3-ethylbenzyl)amino]-2-hydroxypropyl}-2-[1-methyl-5-(4-methylbenzoyl)-1H-pyrrol-2-yl]acetamide | |

-continued

| EXAMPLE | Structure | Compound Name(s) | Mass Spec |
|---|---|---|---|
| 3257 | 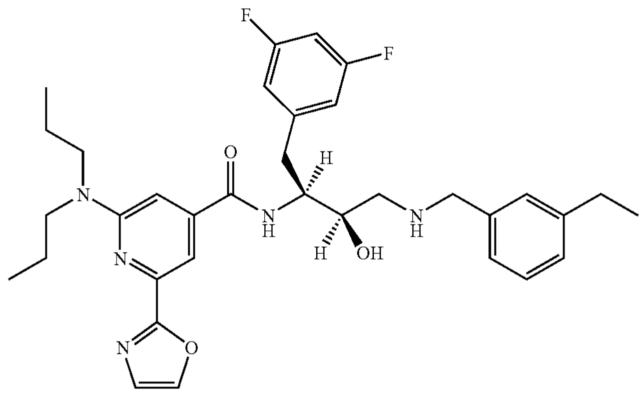 | N-{(1S,2R)-1-(3,5-difluoro-benzyl)-3-[(3-ethylbenzyl)amino]-2-hydroxypropyl}-2-(dipropylamino)-6-(1,3-oxazol-2-yl)isonicotinamide | |
| 3258 | 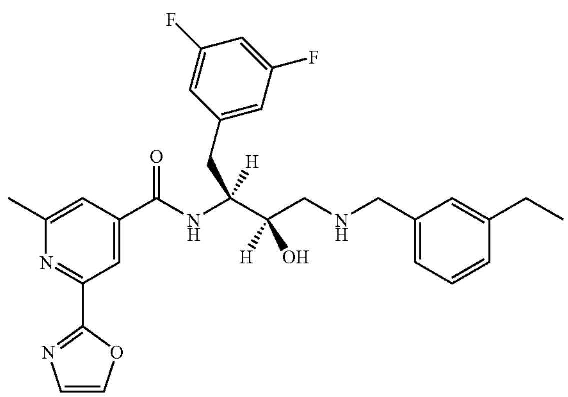 | N-{(1S,2R)-1-(3,5-difluoro-benzyl)-3-[(3-ethylbenzyl)amino]-2-hydroxypropyl}-2-methyl-6-(1,3-oxazol-2-yl)isonicotinamide | |
| 3259 | 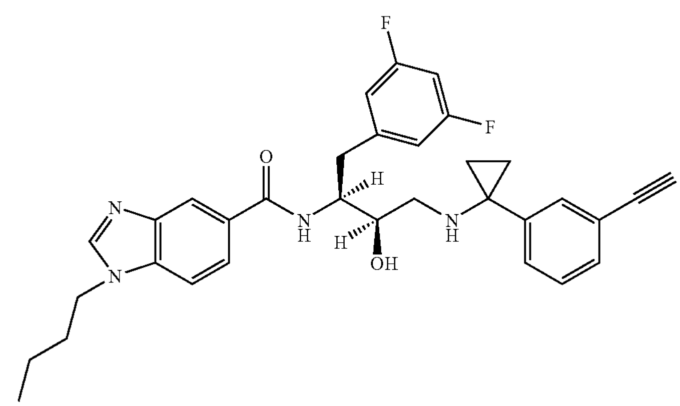 | 1-butyl-N-((1S,2R)-1-(3,5-difluorobenzyl)-3-{[1-(3-ethynylphenyl)cyclopropyl]amino}-2-hydroxypropyl)-1H-benzimidazole-5-carboxamide | |
| 3260 | 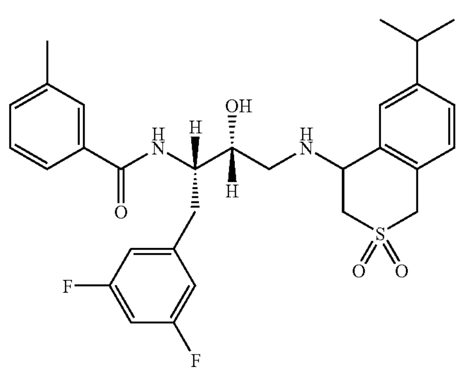 | N-{(1S,2R)-1-(3,5-difluoro-benzyl)-2-hydroxy-3-[(6-isopropyl-2,2-dioxido-3,4-dihydro-1H-isothiochromen-4-yl)amino]propyl}-3-methylbenzamide | |

-continued

| EXAMPLE | Structure | Compound Name(s) | Mass Spec |
|---|---|---|---|
| 3261 | 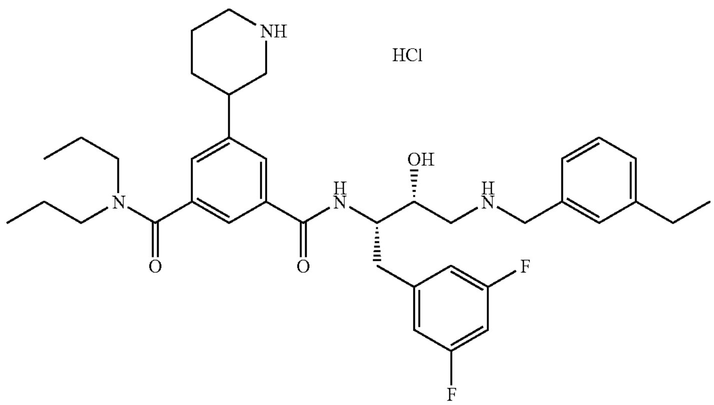 | N$^1$-{(1S,2R)-1-(3,5-difluorobenzyl)-3-[(3-ethylbenzyl)amino]-2-hydroxypropyl}-5-piperidin-3-yl-N$^3$,N$^3$-dipropylisophthalamide hydrochloride | **649.6 |
| 3262 | 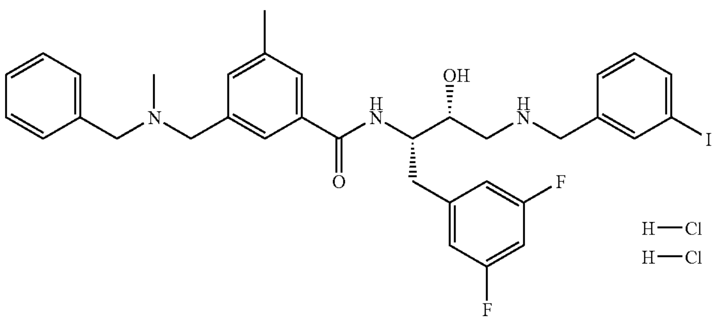 | 3-{[benzyl(methyl)amino]methyl}-N-{(1S,2R)-1-(3,5-difluorobenzyl)-2-hydroxy-3-[(3-iodobenzyl)amino]propyl}-5-methylbenzamide dihydrochloride | **684.2 |
| 3263 | 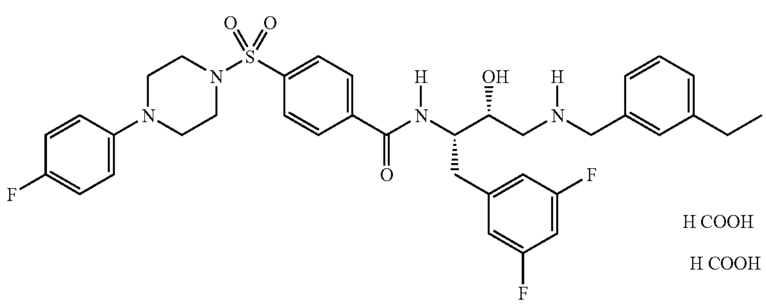 | formic acid compound with N-{(1S,2R)-1-(3,5-difluorobenzyl)-3-[(3-ethylbenzyl)amino]-2-hydroxypropyl}-4-{[4-(4-fluorophenyl)piperazin-1-yl]sulfonyl)benzamide (2:1) | ***680.9 |
| 3264 | 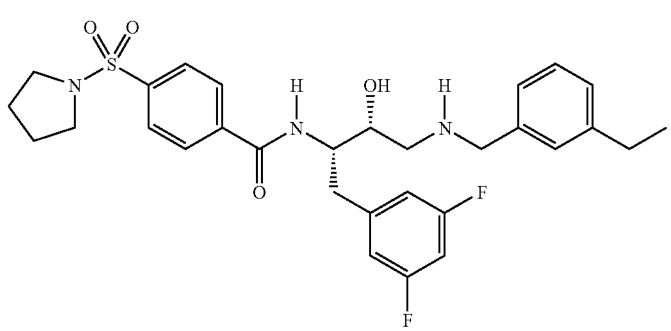 | N-{(1S,2R)-1-(3,5-difluorobenzyl)-3-[(3-ethylbenzyl)amino]-2-hydroxypropyl}-4-(pyrrolidin-1-ylsulfonyl)benzamide | ****572 |

-continued

| EXAMPLE | Structure | Compound Name(s) | Mass Spec |
|---|---|---|---|
| 3265 | 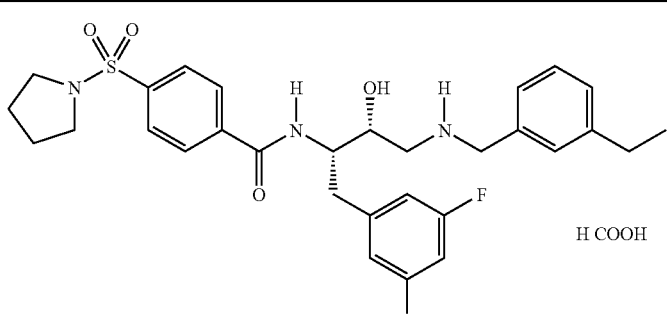 | formic acid compound with N-{(1S,2R)-1-(3,5-difluorobenzyl)-3-[(3-ethylbenzyl)amino]-2-hydroxypropyl}-4-(pyrrolidin-1-ylsulfonyl)benzamide (1:1) | ****572.0 |
| 3266 | 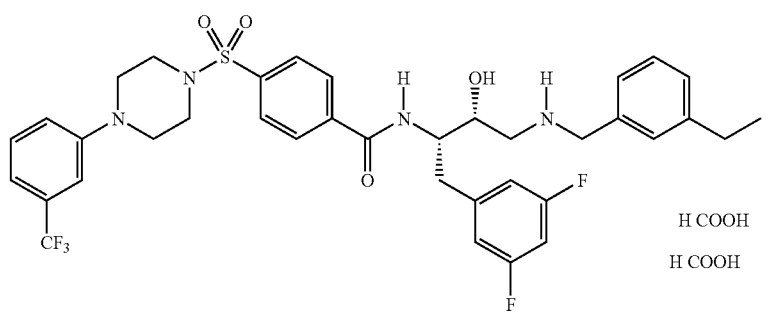 | formic acid compound with N-{(1S,2R)-1-(3,5-difluorobenzyl)-3-[(3-ethylbenzyl)amino]-2-hydroxypropyl}-4-({4-[3-(trifluoromethyl)phenyl]piperazin-1-yl}sulfonyl)benzamide (2:1) | ****731.0 |
| 3267 | 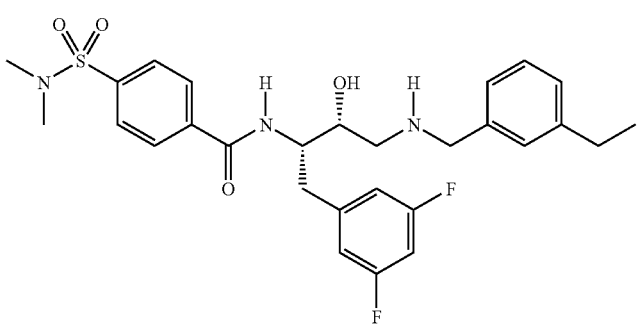 | N-{(1S,2R)-1-(3,5-difluorobenzyl)30[(3-ethylbenzyl)amino]-2-hydroxypropyl}-4-[(dimethylamino)sulfonyl]benzamide | ****546 |
| 3268 | 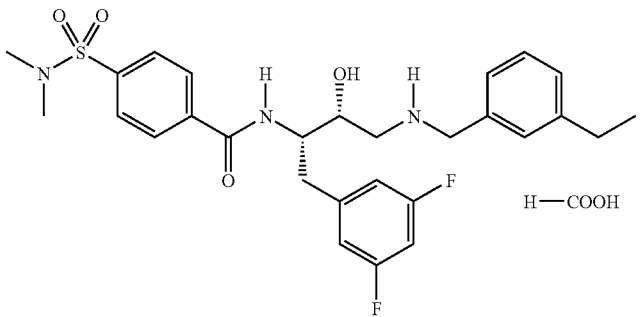 | formic acid compound with N-{(1S,2R)-1-(3,5-difluorobenzyl)-3-[(3-ethylbenzyl)amino]-2-hydroxypropyl}-4-[(dimethylamino)sulfonyl]benzamide (1:1) | ****546.0 |

-continued

| EXAMPLE | Structure | Compound Name(s) | Mass Spec |
|---|---|---|---|
| 3269 | 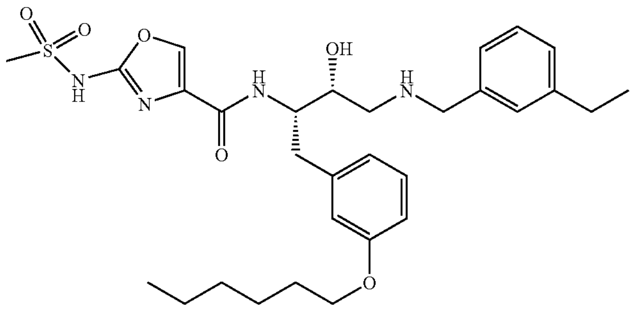 | N-{(1S,2R)-3-[(3-ethylbenzyl)amino]-1-[3-(hexyloxy)benzyl]-2-hydroxypropyl}-2-[(methylsulfonyl)amino]-1,3-oxazole-4-carboxamide | **587.5 |
| 3270 | 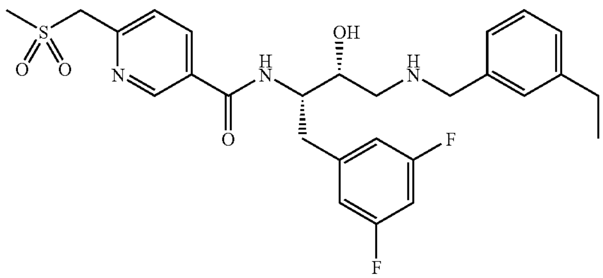 | N-{(1S,2R)-1-(3,5-difluorobenzyl)-3-[(3-ethylbenzyl)amino]-2-hydroxypropyl}-6-[(methylsulfonyl)methyl]nicotinamide | **532 |
| 3272 | 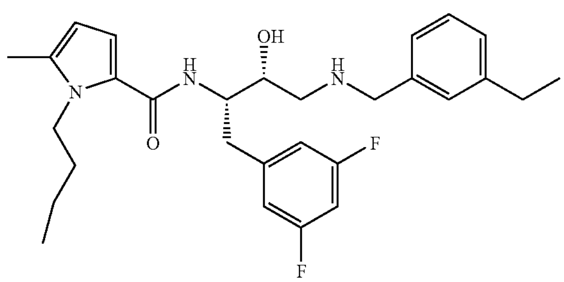 | 1-butyl-N-{(1S,2R)-1-(3,5-difluorobenzyl)-3-[(3-ethylbenzyl)amino]-2-hydroxypropyl}-5-methyl-1H-pyrrole-2-carboxamide | **498.4 |
| 3273 | 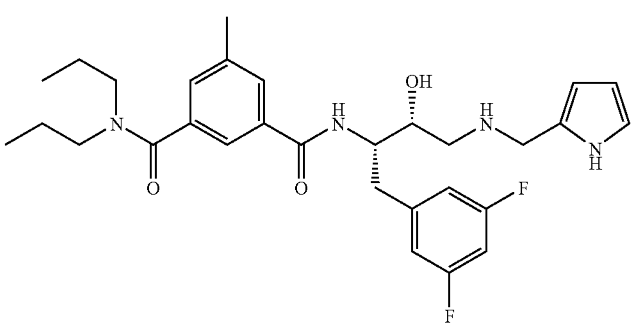 | $N^1$-{(1S,2R)-1-(3,5-difluorobenzyl)-2-hydroxy-3-[(1H-pyrrol-2-ylmethyl)amino]propyl}-5-methyl-$N^3$,$N^3$-dipropylisophthalamide | **541.2 |

-continued

| EXAMPLE | Structure | Compound Name(s) | Mass Spec |
|---|---|---|---|
| 3274 | 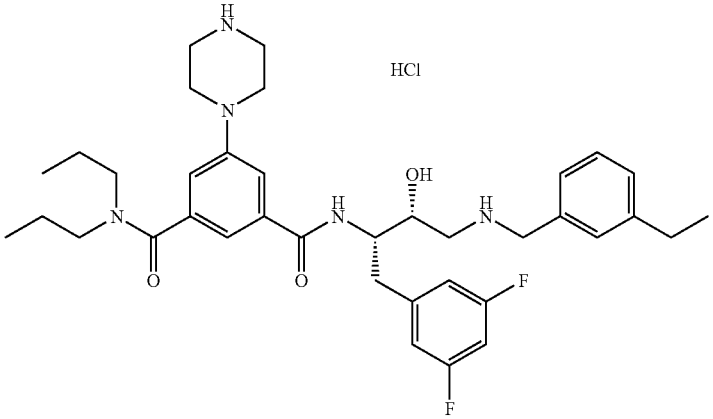 | $N^1$-{(1S,2R)-1-(3,5-difluorobenzyl)-3-[(3-ethylbenzyl)amino]-2-hydroxypropyl}-5-piperazin-1-yl-$N^3,N^3$-dipropylisophthalamide hydrochloride | **650.4 |
| 3276 | 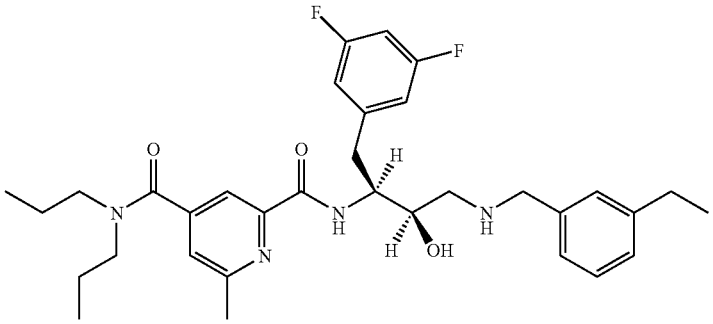 | $N^2$-{(1S,2R)-1-(3,5-difluorobenzyl)-3-[(3-ethylbenzyl)amino]-2-hydroxypropyl}-6-methyl-$N^4,N^4$-dipropylpyridine-2,4-dicarboxamide | |
| 3277 | 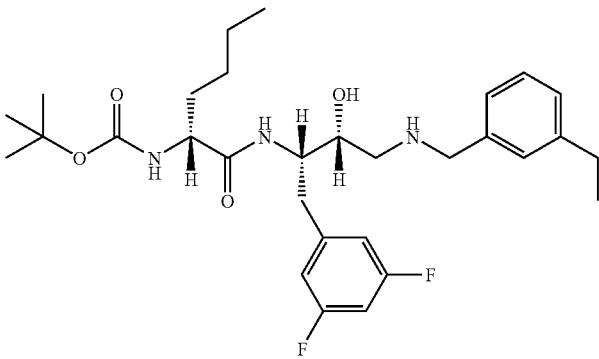 | $N^2$-(tert-butoxycarbonyl)-$N^1$-{(1S,2R)-1-(3,5-difluorobenzyl)-3-[(3-ethylbenzyl)amino]-2-hydroxypropyl}-D-norleucinamide | |
| 3278 | 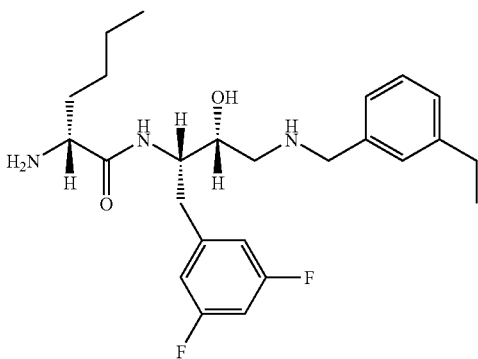 | $N^1$-{(1S,2R)-1-(3,5-difluorobenzyl)-3-[(3-ethylbenzyl)amino]-2-hydroxypropyl}-D-norleucinamide | |

-continued

| EXAMPLE | Structure | Compound Name(s) | Mass Spec |
|---|---|---|---|
| 3281 | 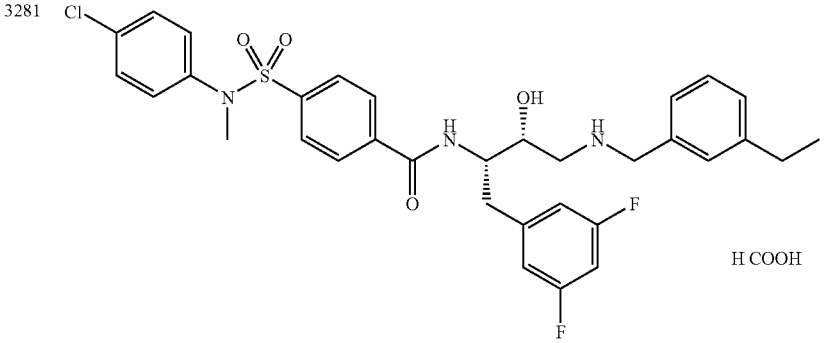 H COOH | formic acid compound with 4-{[(4-chlorophenyl)(methyl)amino]sulfonyl}-N-{(1S,2R)-1-(3,5-difluorobenzyl)-3-[(3-ethylbenzyl)amino]-2-hydroxypropyl}benzamide (1:1) | ***642.0 |
| 3282 | 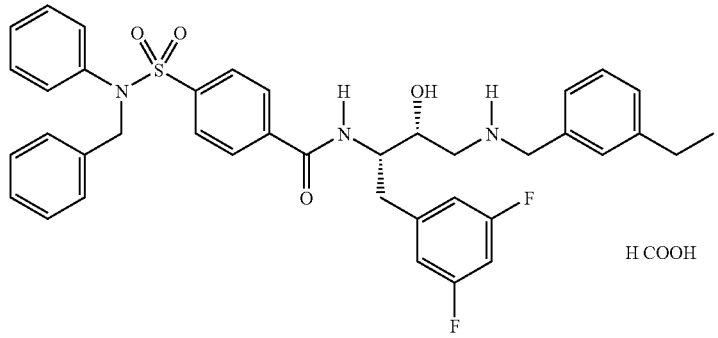 H COOH | formic acid compound with 4-{[benzyl(phenyl)amino]sulfonyl}-N-{(1S,2R)-1-(3,5-difluorobenzyl)-3-[(3-ethylbenzyl)amino]-2-hydroxypropyl}benzamide (1:1) | ***684.1 |
| 3283 | 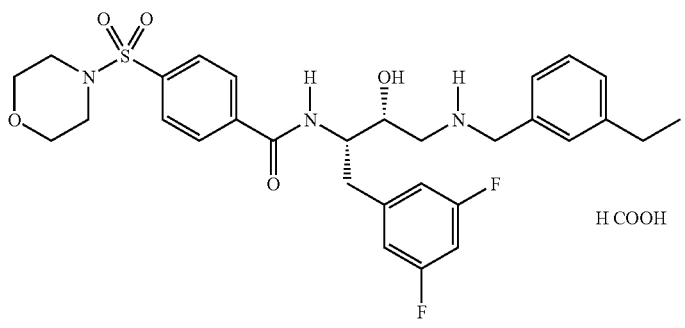 H COOH | formic acid compound with N-{(1S,2R)-1-(3,5-difluorobenzyl)-3-[(3-ethylbenzyl)amino]-2-hydroxypropyl}-4-(morpholin-4-ylsulfonyl)benzamide (1:1) | ***588.1 |
| 3285 | 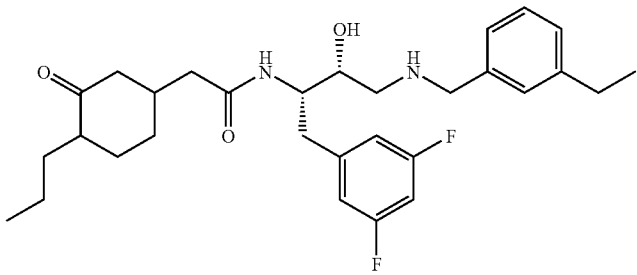 | N-{(1S,2R)-1-(3,5-difluorobenzyl)-3-[(3-ethylbenzyl)amino]-2-hydroxypropyl}-2-(3-oxo-4-propylcyclohexyl)acetamide | **515.4 |

-continued

| EXAMPLE | Structure | Compound Name(s) | Mass Spec |
|---|---|---|---|
| 3286 | 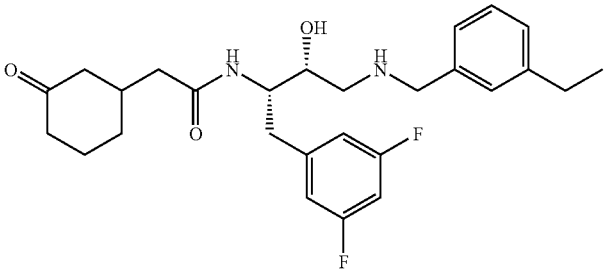 | N-{(1S,2R)-1-(3,5-difluorobenzyl)-3-[(3-ethylbenzyl)amino]-2-hydroxypropyl}-2-(3-oxocyclohexyl)acetamide | **473.3 |
| 3287 | 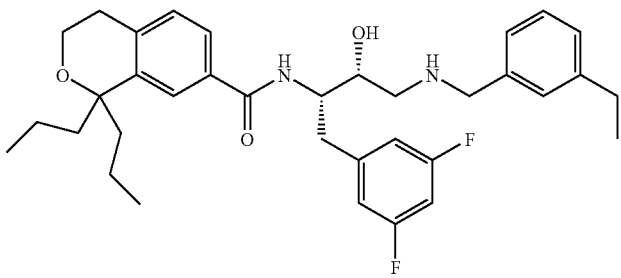 | N-{(1S,2R)-1-(3,5-difluorobenzyl)-3-[(3-ethylbenzyl)amino]-2-hydroxypropyl}-1,1-dipropyl-3,4-dihydro-1H-isochromene-7-carboxamide | **579.4 |
| 3288 | 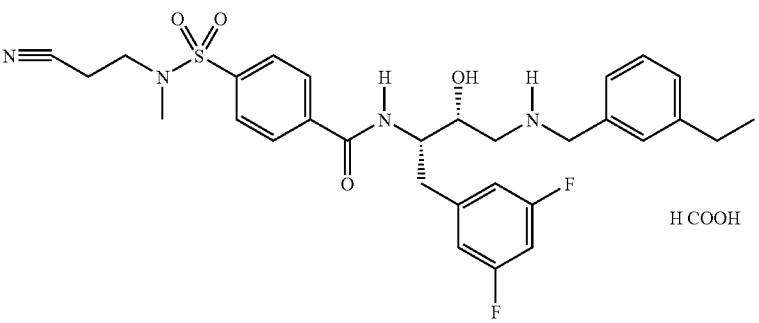 | formic acid compound with 4-{[(2-cyanoethyl)(methyl)amino]sulfonyl}-N-{(1S,2R)-1-(3,5-difluorobenzyl)-3-[(3-ethylbenzyl)amino]-2-hydroxypropyl}benzamide (1:1) | ***585.0 |
| 3289 | 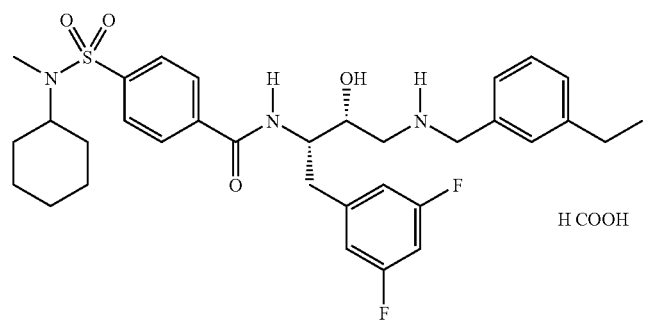 | formic acid compound with 4-{[cyclohexyl(methyl)amino]sulfonyl}-N-{(1S,2R)-1-(3,5-difluorobenzyl)-3-[(3-ethylbenzyl)amino]-2-hydroxypropyl}benzamide (1:1) | ***614.0 |
| 3290 | 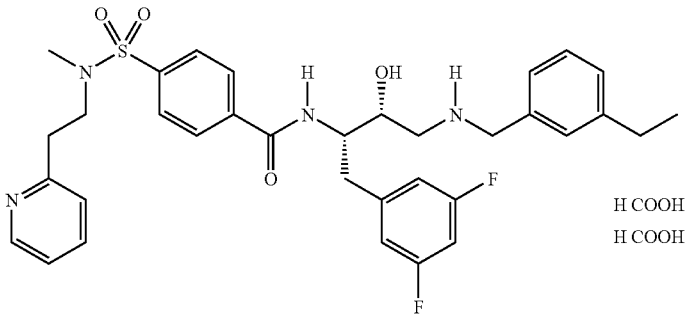 | formic acid compuond with N-{(1S,2R)-1-(3,5-difluorobenzyl)-3-[(3-ethylbenzyl)amino]-2-hydroxypropyl}-4-{[methyl(2-pyridin-2-ylethyl)amino]sulfonyl)benzamide (2:1) | ***637.0 |

-continued

| EXAMPLE | Structure | Compound Name(s) | Mass Spec |
|---|---|---|---|
| 3291 | 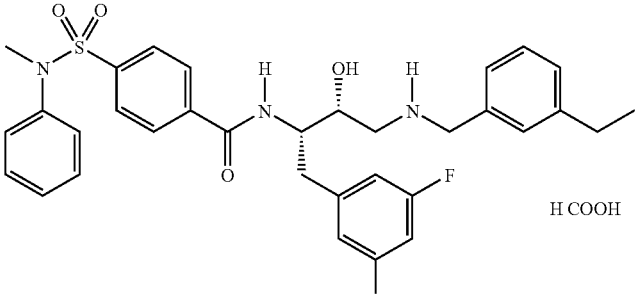 | formic acid compuond with N-{(1S,2R)-1-(3,5-difluorobenzyl)-3-[(3-ethylbenzyl)amino]-2-hydroxypropyl}-4-{[methyl(phenyl)amino]sulfonyl}benzamide (1:1) | ***608.1 |
| 3292 | 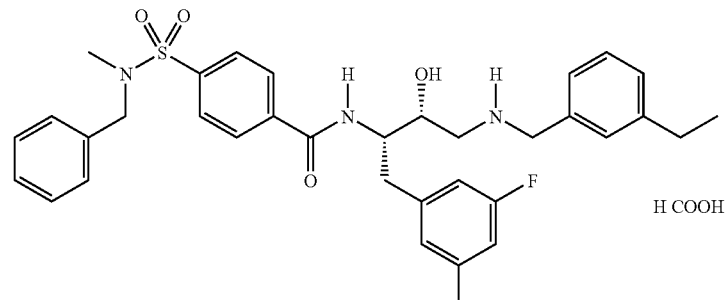 | formic acid compuond with 4-{[benzyl(methyl)amino]sulfonyl}-N-{(1S,2R)-1-(3,5-difluorobenzyl)-3-[(3-ethylbenzyl)amino]-2-hydroxypropyl}benzamide (1:1) | ***622.1 |
| 3293 | 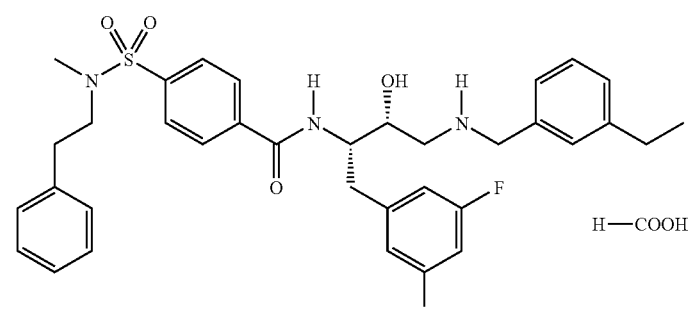 | formic acid compuond with N-{(1S,2R)-1-(3,5-difluorobenzyl)-3-[(3-ethylbenzyl)amino]-2-hydroxypropyl}-4-{[methyl(2-phenylethyl)amino]sulfonyl}benzamide (1:1) | ***636.1 |
| 3294 | 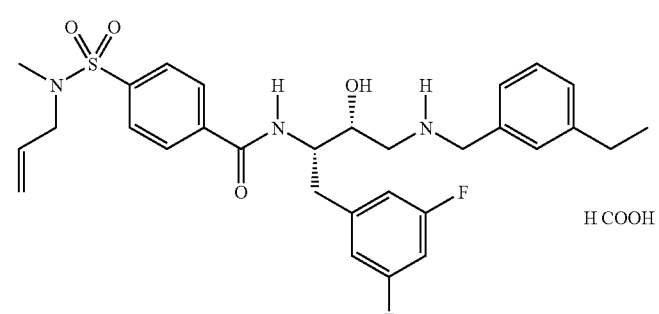 | formic acid compuond with 4-{[allyl(methyl)amino]sulfonyl}-N-{(1S,2R)-1-(3,5-difluorobenzyl)-3-[(3-ethylbenzyl)amino]-2-hydroxypropyl}benzamide (1:1) | ***572.1 |

-continued

| EXAMPLE | Structure | Compound Name(s) | Mass Spec |
|---|---|---|---|
| 3295 | 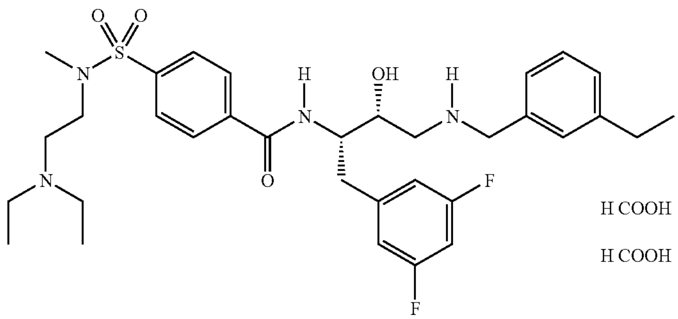 | formic acid compuond with 4-{[[2-(diethylamino)ethyl](methyl)amino]sulfonyl}-N-{(1S,2R)-1-(3,5-difluorobenzyl)-3-[(3-ethylbenzyl)amino]-2-hydroxypropyl}benzamide (2:1) | ***631.1 |
| 3296 | 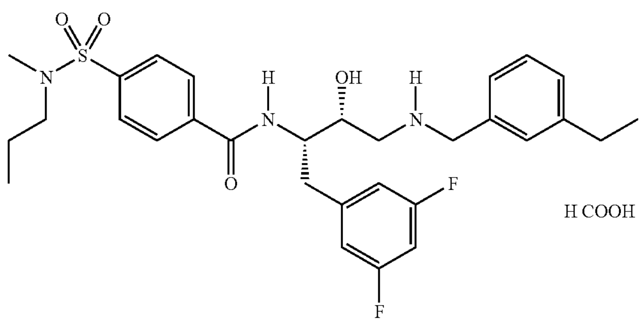 | formic acid compuond with N-{(1S,2R)-1-(3,5-difluorobenzyl)-3-[(3-ethylbenzyl)amino]-2-hydroxypropyl}-4-{[methyl(propyl)amino]sulfonyl}benzamide (1:1) | ***574.1 |
| 3297 | 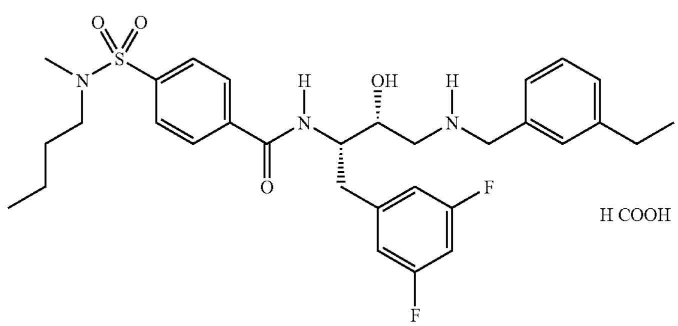 | formic acid compuond with 4-{[butyl(methyl)amino]sulfonyl}-N-{(1S,2R)-1-(3,5-difluorobenzyl)-3-[(3-ethylbenzyl)amino]-2-hydroxypropyl}benzamide (1:1) | ***588.1 |
| 3298 | 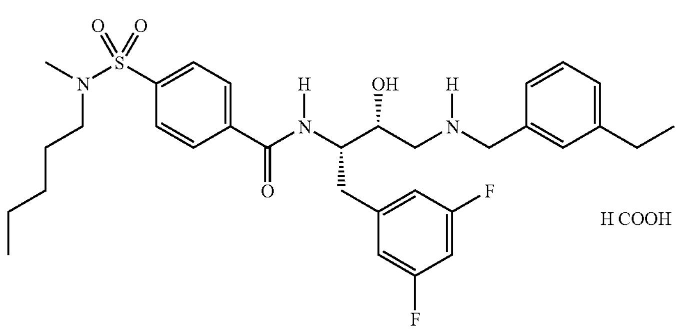 | formic acid compuond with N-{(1S,2R)-1-(3,5-difluorobenzyl)-3-[(3-ethylbenzyl)amino]-2-hydroxypropyl}-4-{[methyl(propyl)amino]sulfonyl}benzamide (1:1) | ***602.1 |

-continued

| EXAMPLE | Structure | Compound Name(s) | Mass Spec |
|---|---|---|---|
| 3299 | 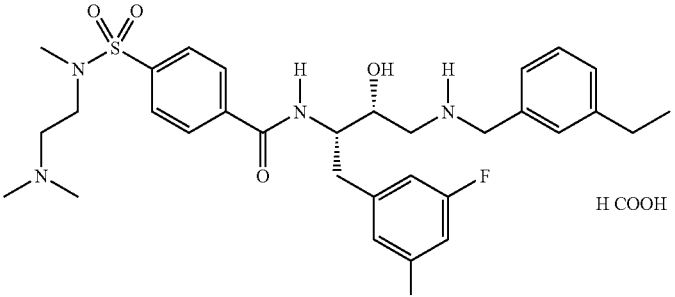 | formic acid compuond with N-{(1S,2R)-1-(3,5-difluoro-benzyl)-3-[(3-ethylbenzyl)amino]-2-hydroxypropyl}-4-{[isopentyl(methyl)amino]sulfonyl}benzamide (1:1) | ***602.1 |
| 3300 | 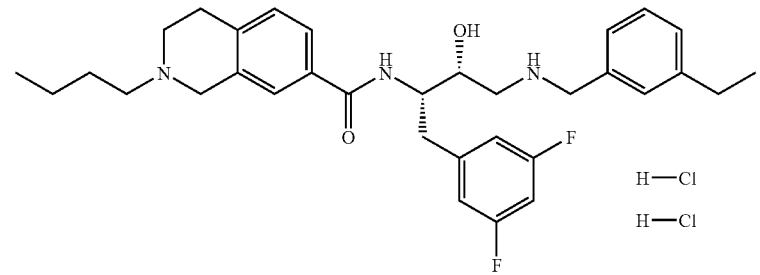 | 2-butyl-N-{(1S,2R)-1-(3,5-difluorobenzyl)-3-[(3-ethyl-benzyl)amino]-2-hydroxy-propyl}-1,2,3,4-tetrahydro-isoquinoline-7-carboxamide dihydrochloride | **550.3 |
| 3301 | 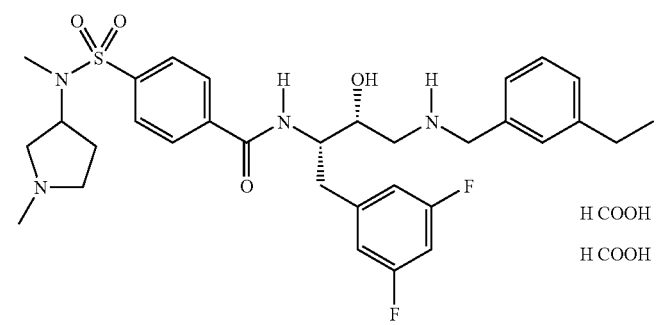 | formic acid compound with N-{(1S,2R)-1-(3,5-difluoro-benzyl)-3-[(3-ethylbenzyl)amino]-2-hydroxypropyl}-4-{[methyl(1-methylpyrrolidin-3-yl)amino]sulfonyl}benzamide (2:1) | ***615.0 |
| 3302 | 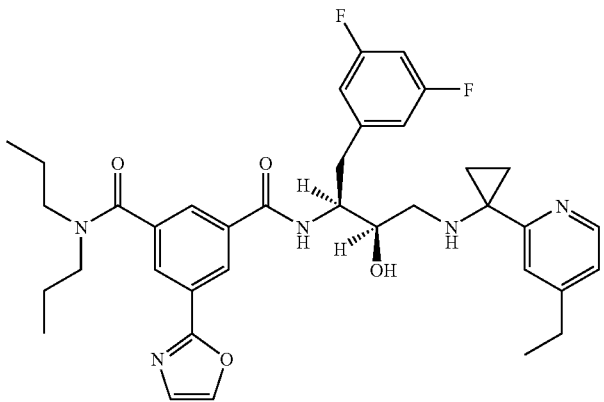 | $N^1$-((1S,2R)-1-(3,5-difluoro-benzyl)-3-{[1-(4-ethylpyridin-2-yl)cyclopropyl]amino}-2-hydroxypropyl)-5-(1,3-oxazol-2-yl)-$N^3$,$N^3$-dipropylisophthalamide | |

-continued

| EXAMPLE | Structure | Compound Name(s) | Mass Spec |
|---|---|---|---|
| 3303 | 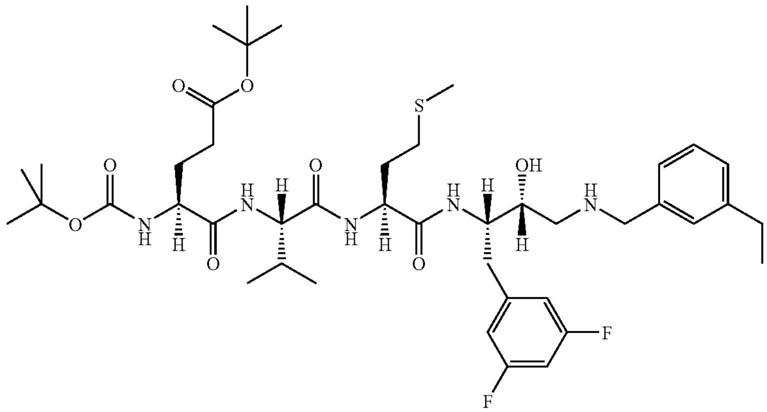 | ELAN-155957 | |
| 3304 | 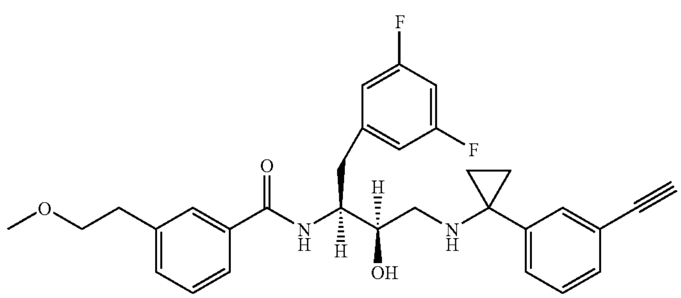 | N-((1S,2R)-1-(3,5-difluorobenzyl)-3-{[1-(3-ethynylphenyl)cyclopropyl]amino}-2-hydroxypropyl)-3-(2-methoxyethyl)benzamide | |
| 3305 | 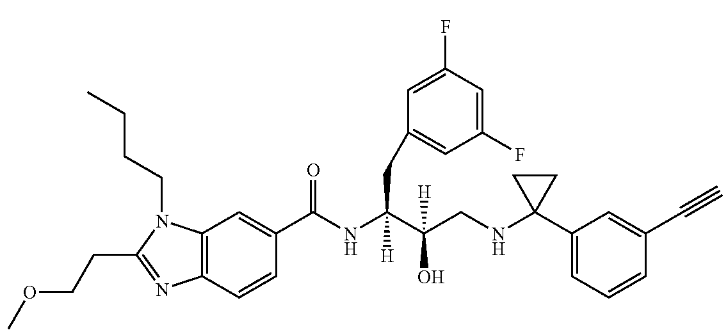 | 1-butyl-N-((1S,2R)-1-(3,5-difluorobenzyl)-3-{[1-(3-ethynylphenyl)cyclopropyl]amino}-2-hydroxypropyl)-2-(2-methoxyethyl)-1H-benzimidazole-6-carboxamide | |
| 3306 | 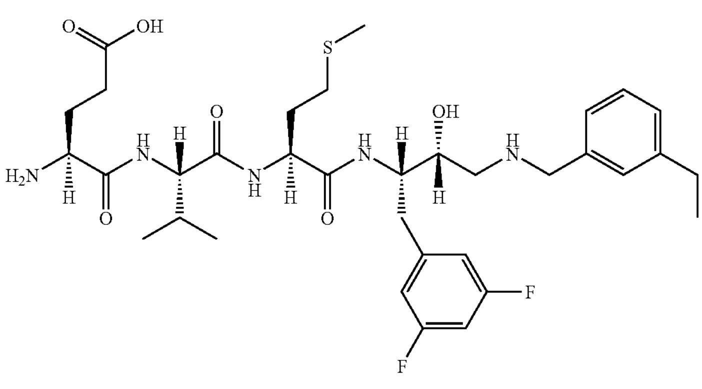 | L-alpha-glutamyl-L-valyl-$N^1$-((1S,2R)-1-(3,5-difluorobenzyl)-3-[(3-ethylbenzyl)amino]-2-hydroxypropyl}-L-methioninamide | |

-continued

| EXAMPLE | Structure | Compound Name(s) | Mass Spec |
|---|---|---|---|
| 3307 | 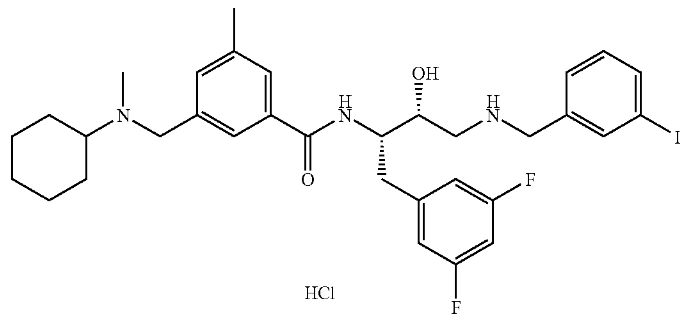 | 3-{[cyclohexyl(methyl)amino] methyl}-N-{(1S,2R)-1-(3,5-difluorobenzyl)-2-hydroxy-3-[(3-iodobenzyl)amino] propyl}-5-methylbenzamide hydrochloride | **676.2 |
| 3309 | 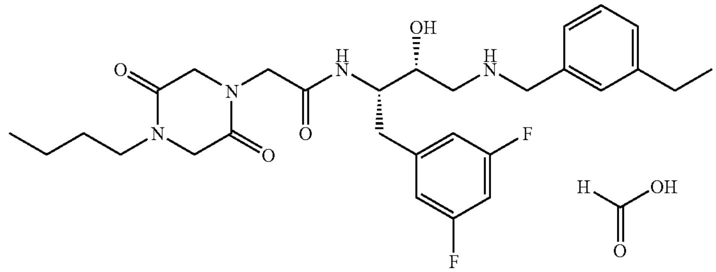 | formic acid compound with 2-(4-butyl-2,5-dioxopiperazin-1-yl)-N-{(1S,2R)-1-(3,5-difluorobenzyl)-3-[(3-ethylbenzyl)amino]-2-hydroxypropyl}acetamide (1:1) | |
| 3310 | 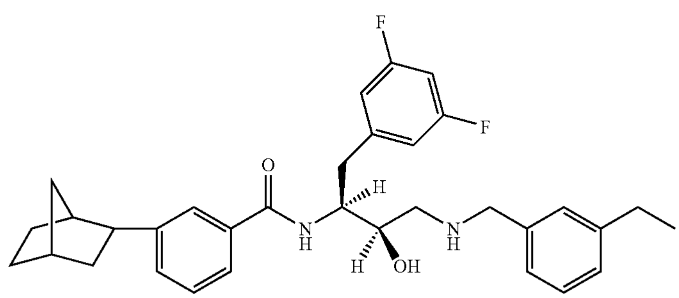 | 3-bicyclo[2.2.1]hept-2-yl-N-{(1S,2R)-1-(3,5-difluorobenzyl)-3-[(3-ethylbenzyl)amino]-2-hydroxypropyl}benzamide | |
| 3311 | 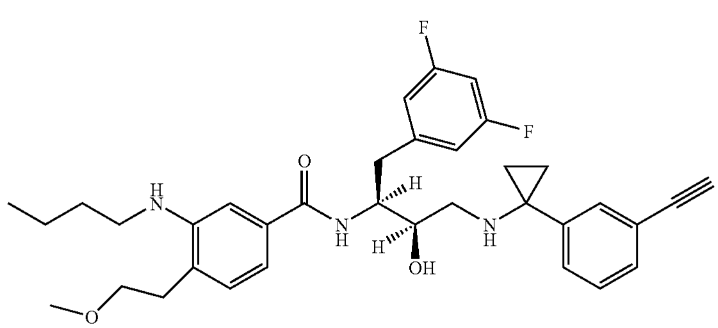 | 3-(butylamino)-N-((1S,2R)-1-(3,5-difluorobenzyl)-3-{[1-(3-ethynylphenyl)cyclopropyl]amino}-2-hydroxypropyl)-4-(2-methoxyethyl)benzamide | |

-continued

| EXAMPLE | Structure | Compound Name(s) | Mass Spec |
|---|---|---|---|
| 3312 | 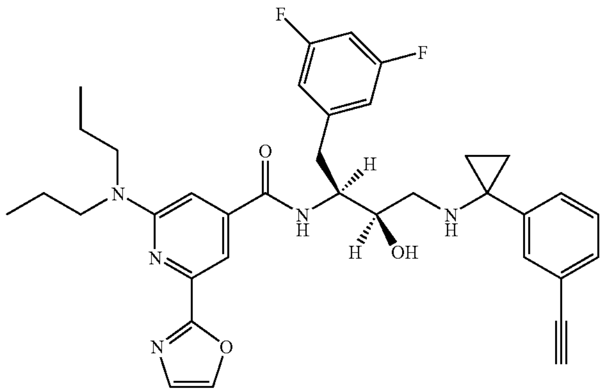 | N-((1S,2R)-1-(3,5-difluorobenzyl)-3-{[1-(3-ethynylphenyl)cyclopropyl]amino}-2-hydroxypropyl)-2-(dipropylamino)-6-(1,3-oxazol-2-yl)isonicotinamide | |
| 3313 | 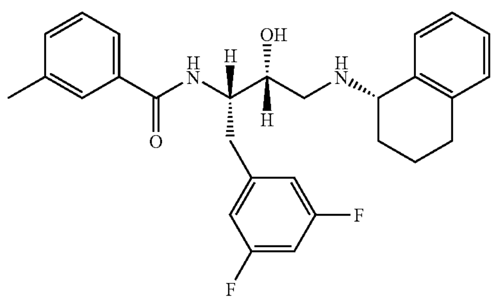 | N-{(1S,2R)-1-(3,5-difluorobenzyl)-2-hydroxy-3-[(1S)-1,2,3,4-tetrahydronaphthalen-1-ylamino]propyl}-3-methylbenzamide | |
| 3314 | 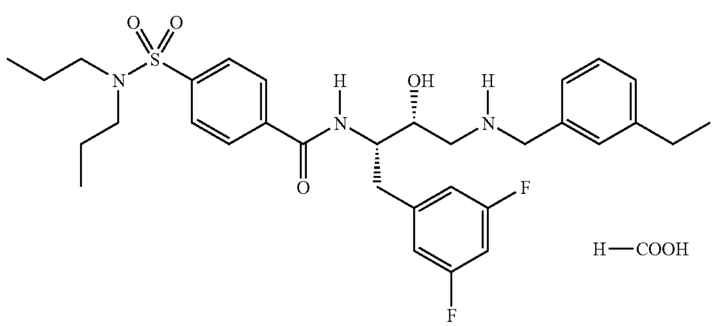 | formic acid compound with N-{(1S,2R)-1-(3,5-difluorobenzyl)-3-[(3-ethylbenzyl)amino]-2-hydroxypropyl}-4-[(dipropylamino)sulfonyl]benzamide (1:1) | ***602.0 |
| 3315 | 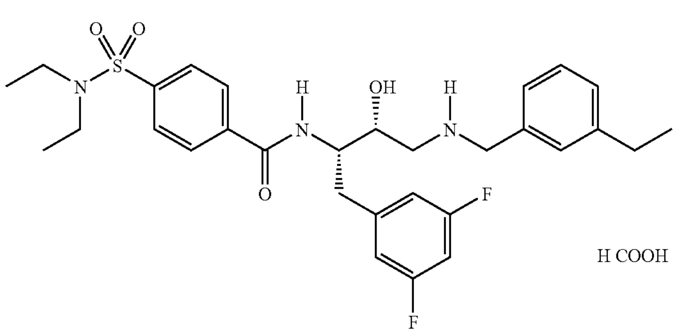 | formic acid compound with 4-[(diethylamino)sulfonyl]-N-{(1S,2R)-1-(3,5-difluorobenzyl)-3-[(3-ethylbenzyl)amino]-2-hydroxypropyl}benzamide (1:1) | ***574.0 |

-continued

| EXAMPLE | Structure | Compound Name(s) | Mass Spec |
|---|---|---|---|
| 3316 | 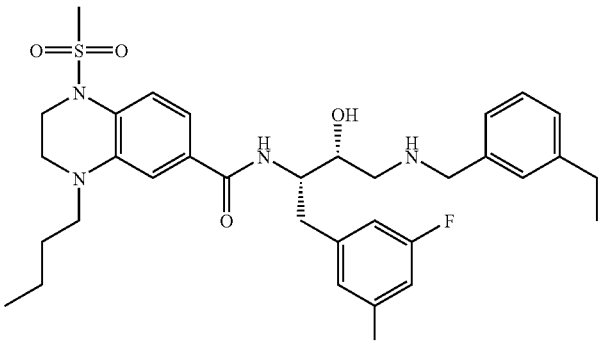 | 4-butyl-N-{(1S,2R)-1-(3,5-difluorobenzyl)-3-[(3-ethylbenzyl)amino]-2-hydroxypropyl}-1-(methylsulfonyl)-1,2,3,4-tetrahydroquinoxaline-6-carboxamide | **629 |
| 3317 | 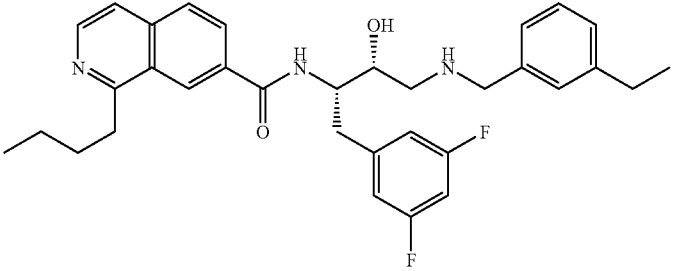 | 1-butyl-N-{(1S,2R)-1-(3,5-difluorobenzyl)-3-[(3-ethylbenzyl)amino]-2-hydroxypropyl}isoquinoline-7-carboxamide | **546.3 |
| 3318 | 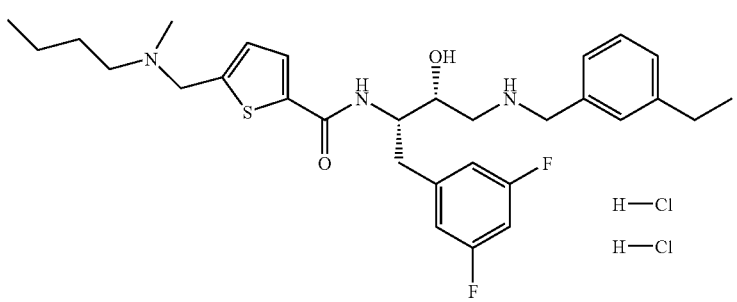 | 5-{[butyl(methyl)amino]methyl}-N-{(1S,2R)-1-(3,5-difluorobenzyl)-3-[(3-ethylbenzyl)amino]-2-hydroxypropyl}thiophene-2-carboxamide dihydrochloride | **544.3 |
| 3319 | 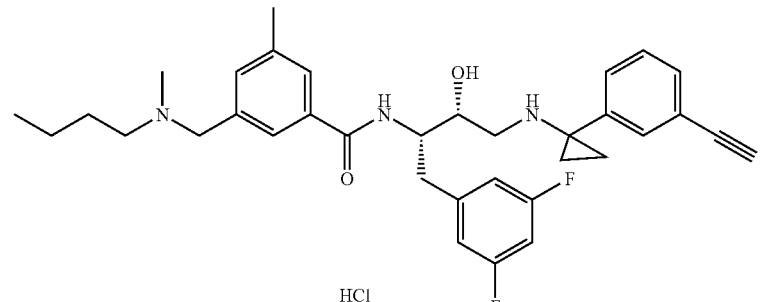 | 3-{[butyl(methyl)amino]methyl}-N-((1S,2R)-1-(3,5-difluorobenzyl)-3-{[1-(3-ethynylphenyl)cyclopropyl]amino}-2-hydroxypropyl)-5-methylbenzamide hydrochloride | **574.3 |

-continued

| EXAMPLE | Structure | Compound Name(s) | Mass Spec |
|---|---|---|---|
| 3320 | 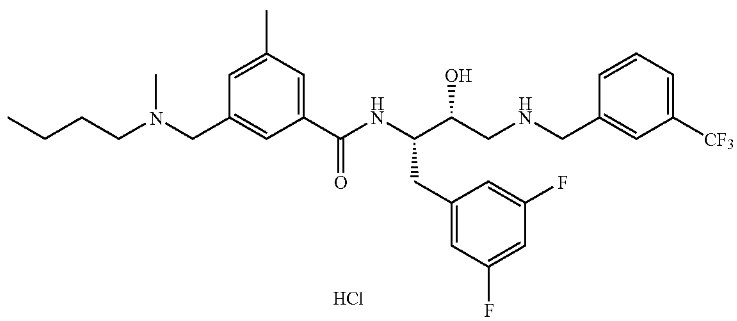 | 3-{[butyl(methyl)amino]methyl}-N-((1S,2R)-1-(3,5-difluorobenzyl)-2-hydroxy-3-{[3-(trifluoromethyl)benzyl]amino}propyl)-5-methylbenzamide hydrochloride | **592.3 |
| 3321 | 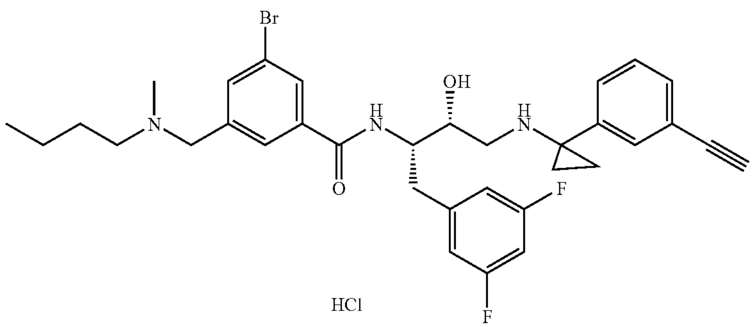 | 3-bromo-5-{[butyl(methyl)amino]methyl}-N-((1S,2R)-1-(3,5-difluorobenzyl)-3-{[1-(3-ethynylphenyl)cyclopropyl]amino}-2-hydroxypropyl)benzamide hydrochloride | **638.2 |
| 3322 | 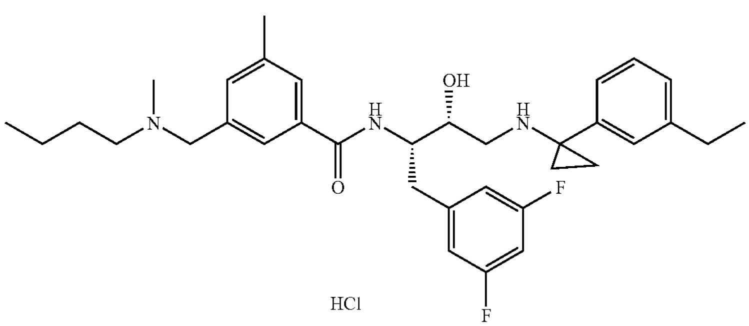 | 3-{[butyl(methyl)amino]methyl}-N-((1S,2R)-1-(3,5-difluorobenzyl)-3-{[1-(3-ethylphenyl)cyclopropyl]amino}-2-hydroxypropyl)-5-methylbenzamide hydrochloride | **578.4 |
| 3323 | 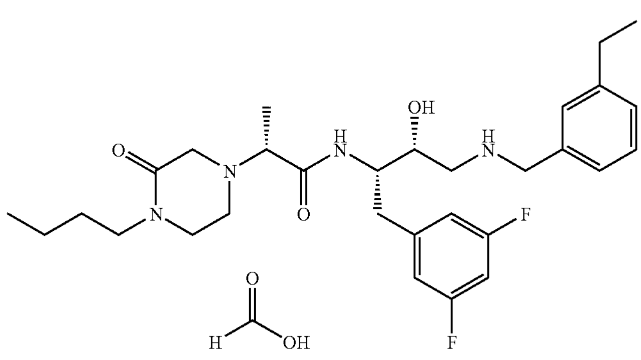 | (2R)-2-(4-butyl-3-oxopiperazin-1-yl)-N-{(1S,2R)-1-(3,5-difluorobenzyl)-3-[(3-ethylbenzyl)amino]-2-hydroxypropyl}propanamide | |

-continued

| EXAMPLE | Structure | Compound Name(s) | Mass Spec |
|---|---|---|---|
| 3324 | 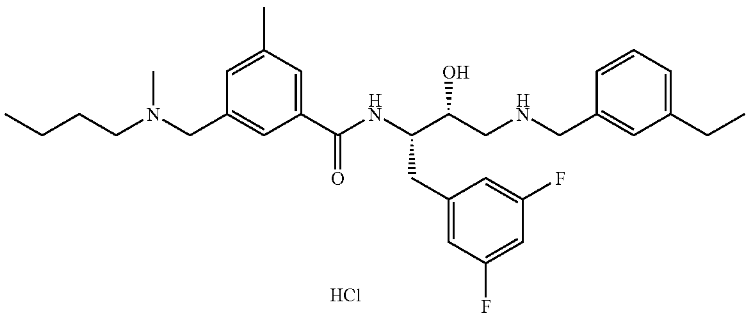 | 3-{[butyl(methyl)amino]methyl}-N-{(1S,2R)-1-(3,5-difluorobenzyl)-3-[(3-ethylbenzyl)amino]-2-hydroxypropyl}-5-methylbenzamide hydrochloride | **552.3 |
| 3325 | 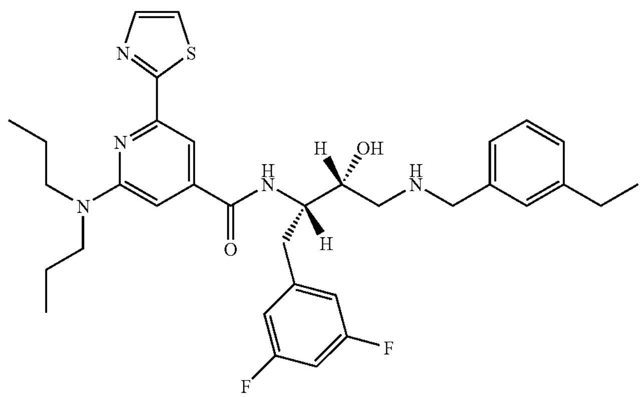 | N-{(1S,2R)-1-(3,5-difluorobenzyl)-3-[(3-ethylbenzyl)amino]-2-hydroxypropyl}-2-(dipropylamino)-6-(1,3-thiazol-2-yl)isonicotinamide | |
| 3326 | 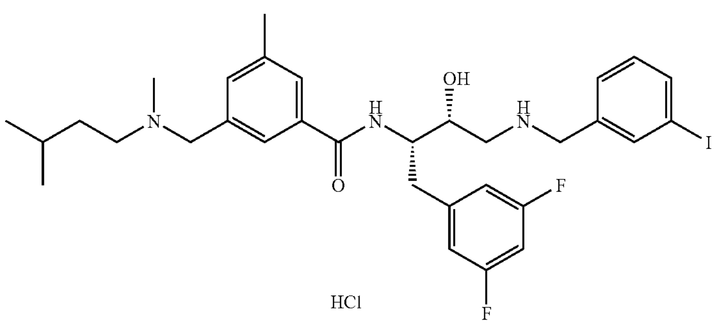 | N-{(1S,2R)-1-(3,5-difluorobenzyl)-2-hydroxy-3-[(3-iodobenzyl)amino]propyl}-3-{[isopentyl(methyl)amino]methyl}-5-methylbenzamide hydrochloride | **664.2 |
| 3327 | 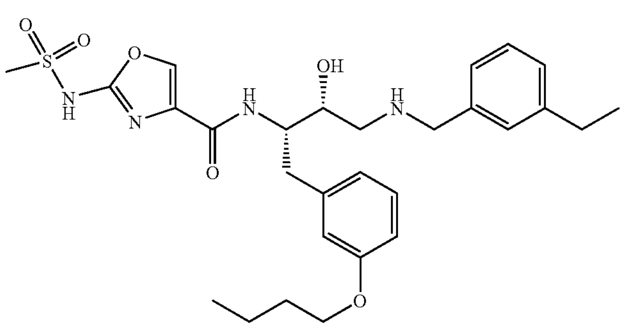 | N-{(1S,2R)-1-(3-butoxybenzyl)-3-[(3-ethylbenzyl)amino]-2-hydroxypropyl}-2-[(methylsulfonyl)amino]-1,3-oxazole-4-carboxamide | **559.1 |

-continued

| EXAMPLE | Structure | Compound Name(s) | Mass Spec |
|---|---|---|---|
| 3328 | 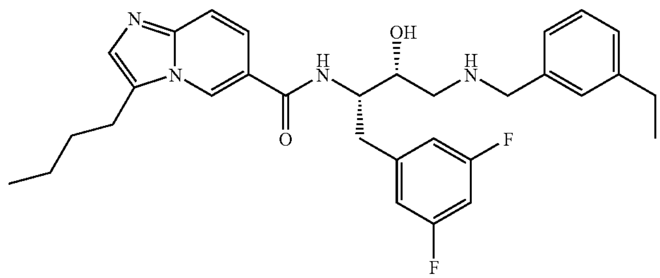 | 3-butyl-N-((1S,2R)-1-(3,5-difluorobenzyl)-3-[(3-ethylbenzyl)amino]-2-hydroxypropyl}imidazo[1,2-a]pyridine-6-carboxamide | |
| 3329 | 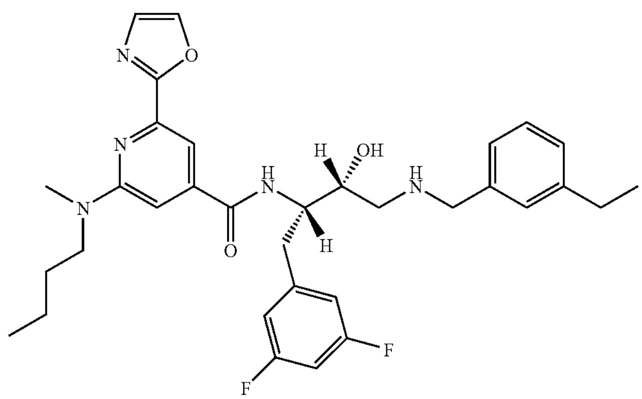 | 2-[butyl(methyl)amino]-N-{(1S,2R)-1-(3,5-difluorobenzyl)-3-[(3-ethylbenzyl)amino]-2-hydroxypropyl}-6-(1,3-oxazol-2-yl)isonicotinamide | |
| 3330 | 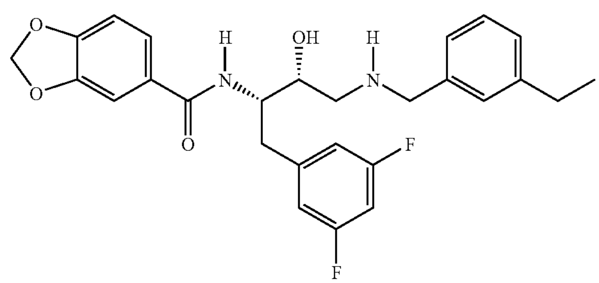 | N-{(1S,2R)-1-(3,5-difluorobenzyl)-3-[(3-ethylbenzyl)amino]-2-hydroxypropyl}-1,3-benzodioxole-5-carboxamide | **483.2 |
| 3333 | 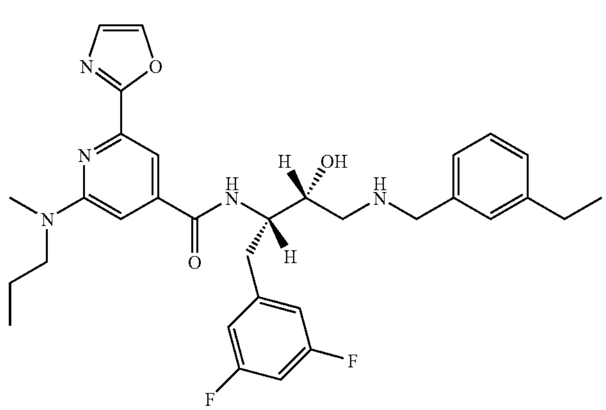 | N-{(1S,2R)-1-(3,5-difluorobenzyl)-3-[(3-ethylbenzyl)amino]-2-hydroxypropyl}-2-[methyl(propyl)amino]-6-(1,3-oxazol-2-yl)isonicotinamide | |

-continued

| EXAMPLE | Structure | Compound Name(s) | Mass Spec |
|---|---|---|---|
| 3334 | 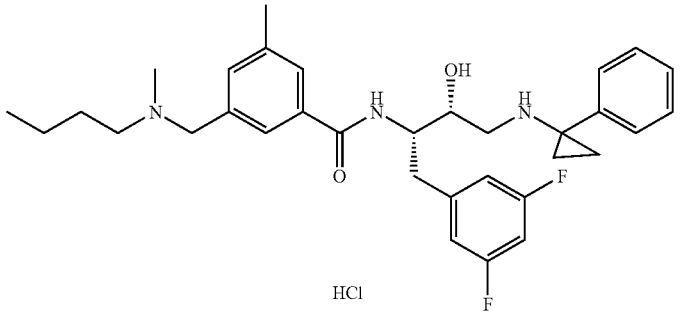 | 3-{[butyl(methyl)amino]methyl}-N-{(1S,2R)-1-(3,5-difluorobenzyl)-2-hydroxy-3-[(1-phenylcyclopropyl)amino]propyl}-5-methylbenzamide hydrochloride | **550.3 |
| 3335 | 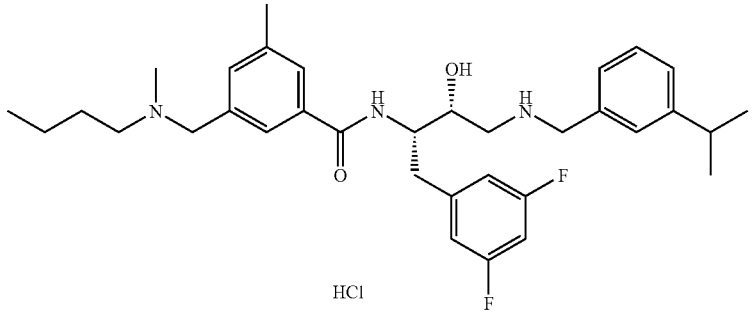 | 3-{[butyl(methyl)amino]methyl}-N-{(1S,2R)-1-(3,5-difluorobenzyl)-2-hydroxy-3-[(3-isopropylbenzyl)amino]propyl}-5-methylbenzamide hydrochloride | **566.3 |
| 3337 | 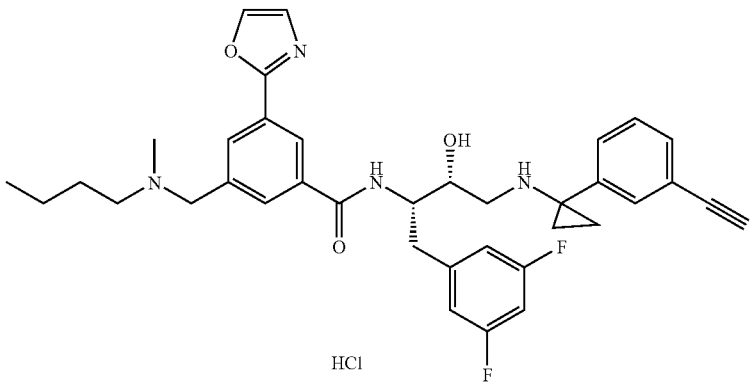 | 3-{[butyl(methyl)amino]methyl}-N-{(1S,2R)-1-(3,5-difluorobenzyl)-3-{[1-(3-ethynylphenyl)cyclopropyl]amino}-2-hydroxypropyl}-5-(1,3-oxazol-2-yl)benzamide hydrochloride | **627.3 |
| 3339 | 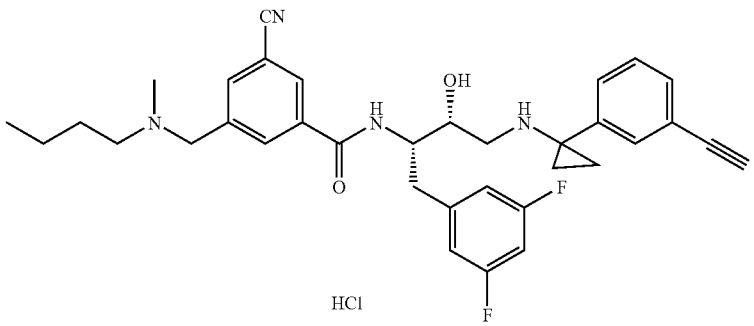 | 3-{[butyl(methyl)amino]methyl}-5-cyano-N-((1S,2R)-1-(3,5-difluorobenzyl)-3-{[1-(3-ethynylphenyl)cyclopropyl]amino}-2-hydroxypropyl)benzamide hydrochloride | **585.3 |

-continued

| EXAMPLE | Structure | Compound Name(s) | Mass Spec |
|---|---|---|---|
| 3342 | 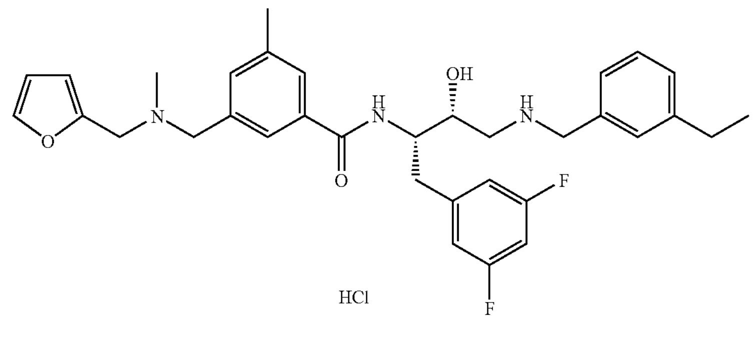 | N-{(1S,2R)-1-(3,5-difluorobenzyl)-3-[(3-ethylbenzyl)amino]-2-hydroxypropyl}-3-{[(2-furylmethyl)(methyl)amino]methyl}-5-methylbenzamide hydrochloride | **576.4 |
| 3343 | 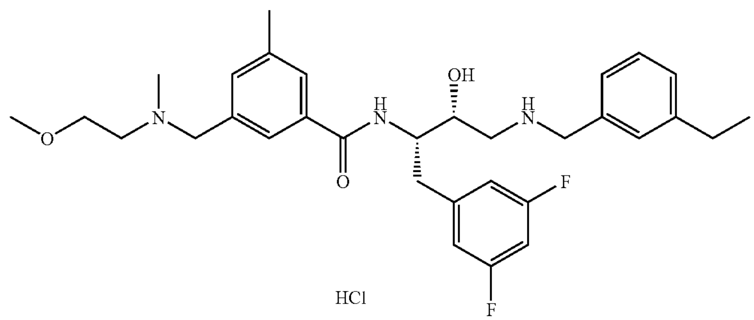 | N-{(1S,2R)-1-(3,5-difluorobenzyl)-3-[(3-ethylbenzyl)amino]-2-hydroxypropyl}-3-{[(2-methoxyethyl)(methyl)amino]methyl}-5-methylbenzamide hydrochloride | **554.5 |
| 3344 | 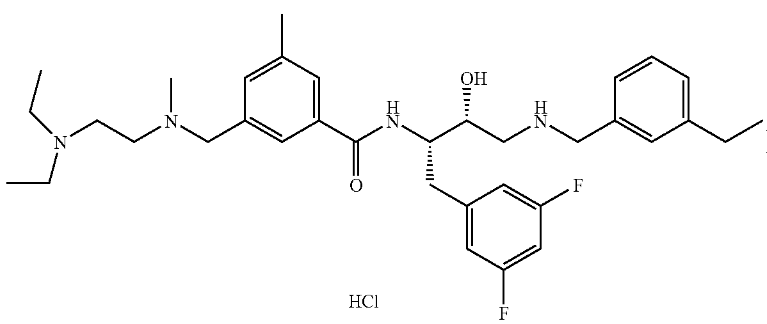 | 3-{[[2-(diethylamino)ethyl](methyl)amino]methyl}-N-{(1S,2R)-1-(3,5-difluorobenzyl)-3-[(3-ethylbenzyl)amino]-2-hydroxypropyl}-5-methylbenzamide hydrochloride | **595.4 |
| 3345 | 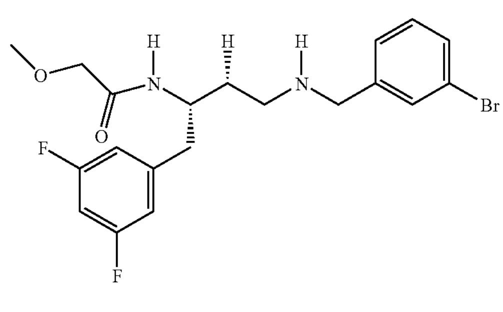 | N-[(1S,2R)-3-[(3-bromobenzyl)amino]-1-(3,5-difluorobenzyl)-2-hydroxypropyl]-2-methoxyacetamide | **457 |

-continued

| EXAMPLE | Structure | Compound Name(s) | Mass Spec |
|---|---|---|---|
| 3346 | 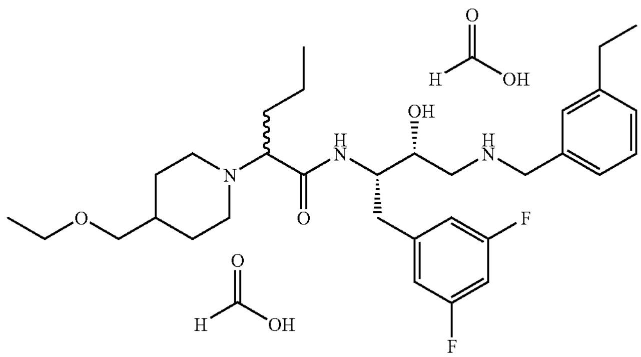 | formic acid compound with N-{(1S,2R)-1-(3,5-difluorobenzyl)-3-[(3-ethylbenzyl)amino]-2-hydroxypropyl}-2-[4-(ethoxymethyl)piperidin-1-yl]pentanamide (2:1) | |
| 3347 | 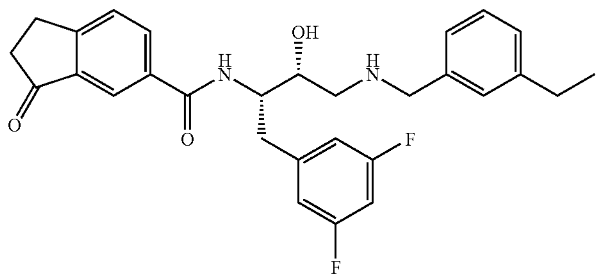 | N-{(1S,2R)-1-(3,5-difluorobenzyl)-3-[(3-ethylbenzyl)amino]-2-hydroxypropyl}-3-oxoindane-5-carboxamide | **493.2 |
| 3348 | 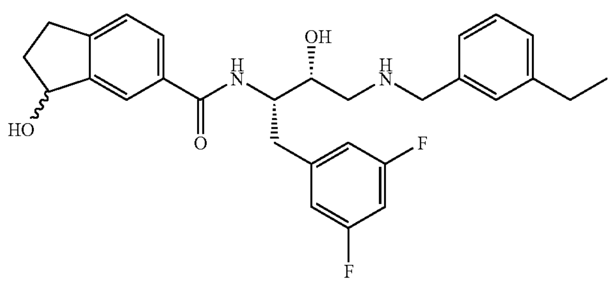 | N-{(1S,2R)-1-(3,5-difluorobenzyl)-3-[(3-ethylbenzyl)amino]-2-hydroxypropyl}-3-hydroxyindane-5-carboxamide | **495.2 |
| 3349 | 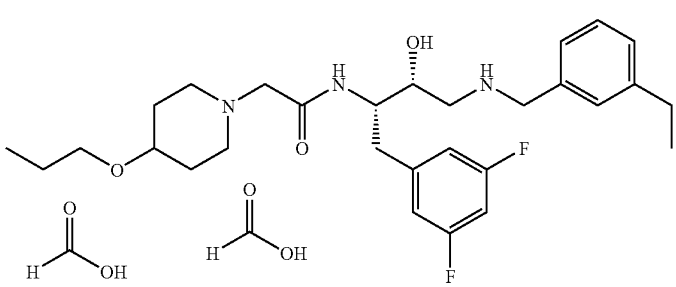 | formic acid compound with N-{(1S,2R)-1-(3,5-difluorobenzyl)-3-[(3-ethylbenzyl)amino]-2-hydroxypropyl}-2-(4-propoxypiperidin-1-yl)acetamide (2:1) | |
| 3350 | 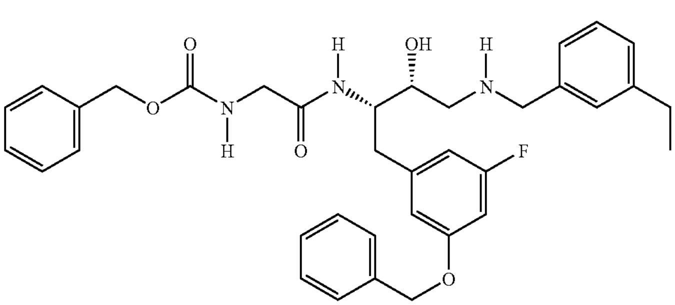 | | **614.3 |

-continued

| EXAMPLE | Structure | Compound Name(s) | Mass Spec |
|---|---|---|---|
| 3351 | 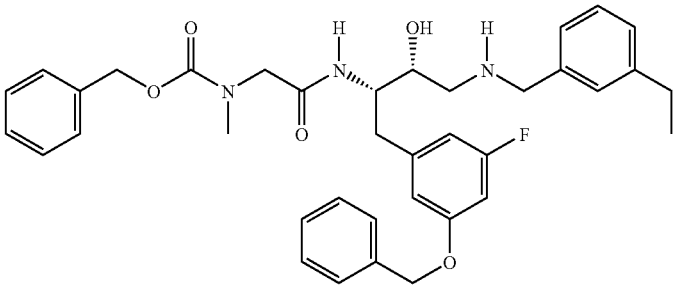 | | **628.3 |
| 3352 | 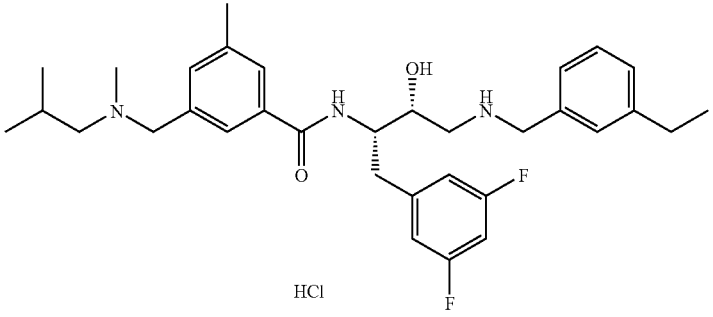 | N-{(1S,2R)-1-(3,5-difluorobenzyl)-3-[(3-ethylbenzyl)amino]-2-hydroxypropyl}-3-([isobutyl(methyl)amino]methyl}-5-methylbenzamide hydrochloride | **552.5 |
| 3353 | 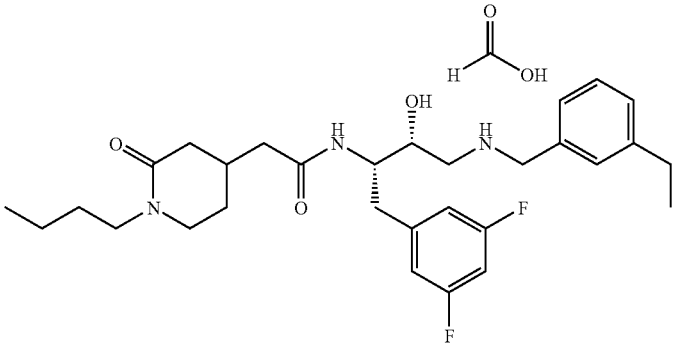 | formic acid compound with 2-(1-butyl-2-oxopiperidin-4-yl)-N-{(1S,2R)-1-(3,5-difluorobenzyl)-3-[(3-ethylbenzyl)amino]-2-hydroxypropyl}acetamide (1:1) | |
| 3354 | 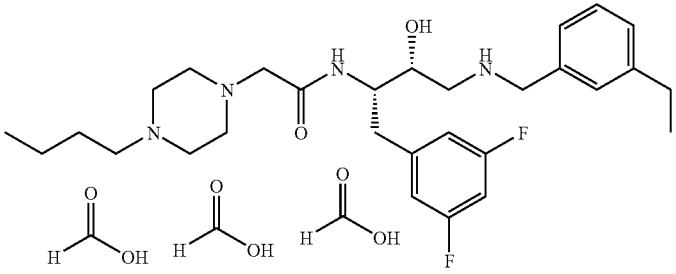 | formic acid compound with 2-(4-butylpiperazin-1-yl)-N-{(1S,2R)-1-(3,5-difluorobenzyl)-3-[(3-ethylbenzyl)amino]-2-hydroxypropyl}acetamide (3:1) | |

-continued

| EXAMPLE | Structure | Compound Name(s) | Mass Spec |
|---|---|---|---|
| 3355 | 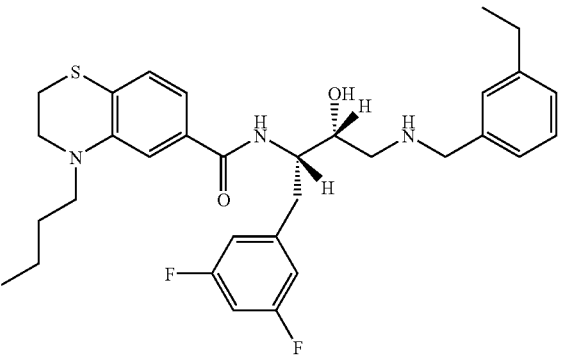 | 4-butyl-N-{(1S,2R)-1-(3,5-difluorobenzyl)-3-[(3-ethylbenzyl)amino]-2-hydroxypropyl}-3,4-dihydro-2H-1,4-benzothiazine-6-carboxamide or ELAN157245 | |
| 3357 | 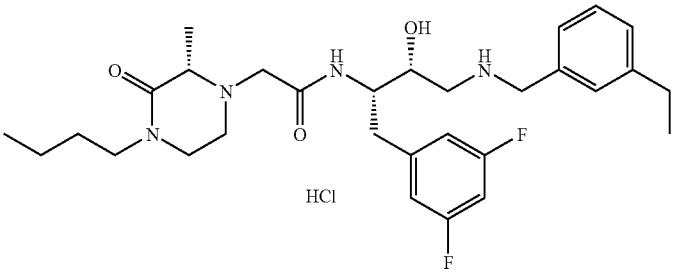 | 2-[(2S)-4-butyl-2-methyl-3-oxopiperazin-1-yl]-N-{(1S,2R)-1-(3,5-difluorobenzyl)-3-[(3-ethylbenzyl)amino]-2-hydroxypropyl}acetamide hydrochloride | |
| 3358 | 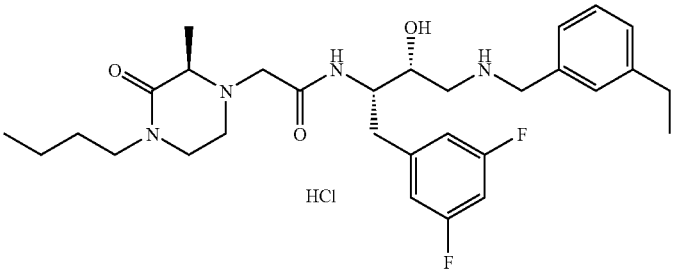 | 2-[(2R)-4-butyl-2-methyl-3-oxopiperazin-1-yl]-N-{(1S,2R)-1-(3,5-difluorobenzyl)-3-[(3-ethylbenzyl)amino]-2-hydroxypropyl}acetamide hydrochloride | |
| 3359 | 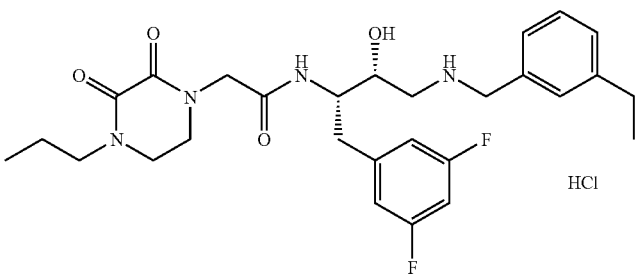 | N-{(1S,2R)-1-(3,5-difluorobenzyl)-3-[(3-ethylbenzyl)amino]-2-hydroxypropyl}-2-(2,3-dioxo-4-propylpiperazin-1-yl)acetamide hydrochloride | |
| 3360 | 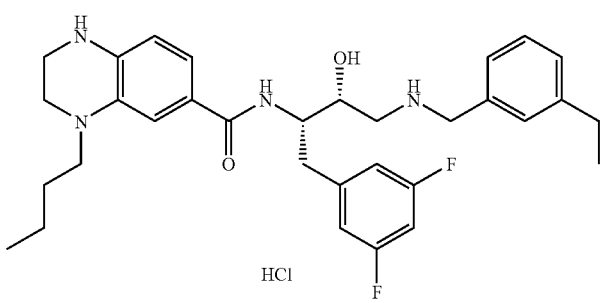 | 4-butyl-N-{(1S,2R)-1-(3,5-difluorobenzyl)-3-[(3-ethylbenzyl)amino]-2-hydroxypropyl}-1,2,3,4-tetrahydroquinoxaline-6-carboxamide hydrochloride | **551 |

| EXAMPLE | Structure | Compound Name(s) | Mass Spec |
|---|---|---|---|
| 3361 | 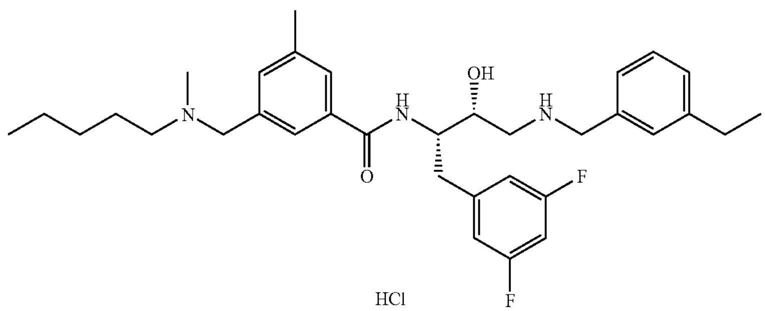 | N-{(1S,2R)-1-(3,5-difluorobenzyl)-3-[(3-ethylbenzyl)amino]-2-hydroxypropyl}-3-methyl-5-{[methyl(pentyl)amino]methyl}benzamide hydrochloride | **566.5 |
| 3362 | 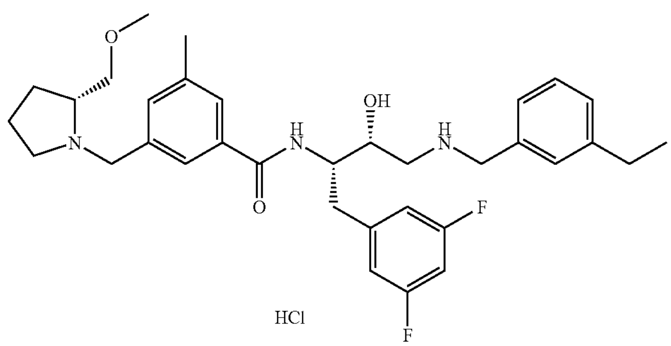 | N-{(1S,2R)-1-(3,5-difluorobenzyl)-3-[(3-ethylbenzyl)amino]-2-hydroxypropyl}-3-{[(2R)-2-(methoxymethyl)pyrrolidin-1-yl]methyl}-5-methylbenzamide hydrochloride | **580.4 |
| 3363 | 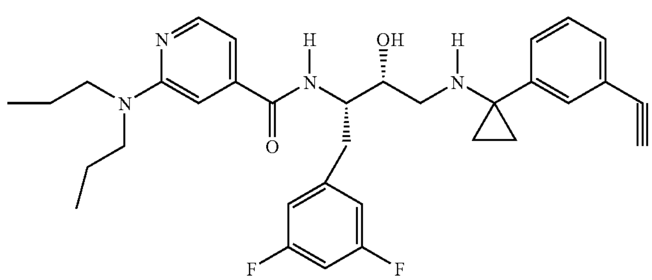 | N-((1S,2R)-1-(3,5-difluorobenzyl)-3-{[1-(3-ethynylphenyl)cyclopropyl]amino}-2-hydroxypropyl)-2-(dipropylamino)isonicotinamide | |
| 3364 | 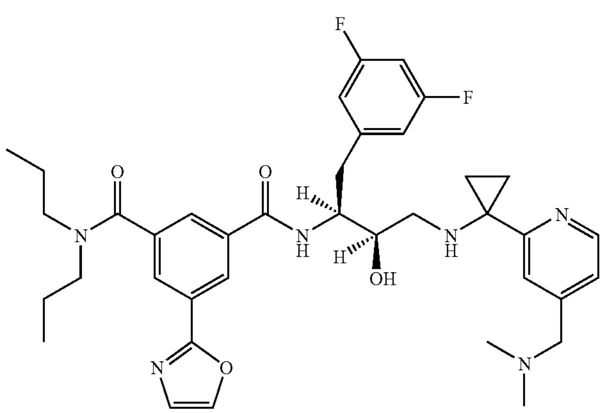 | $N^1$-{(1S,2R)-1-(3,5-difluorobenzyl)-3-[(1-{4-[(dimethylamino)methyl]pyridin-2-yl}cyclopropyl)amino]-2-hydroxypropyl}-5-(1,3-oxazol-2-yl)-$N^3$,$N^3$-dipropylisophthalamide | *689 |

| EXAMPLE | Structure | Compound Name(s) | Mass Spec |
|---|---|---|---|
| 3365 | 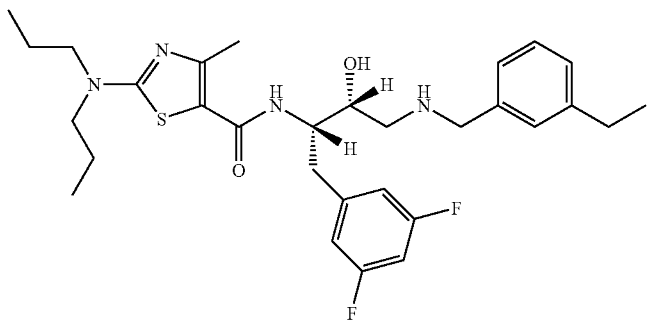 | N-{(1S,2R)-1-(3,5-difluorobenzyl)-3-[(3-ethylbenzyl)amino]-2-hydroxypropyl}-2-(dipropylamino)-4-methyl-1,3-thiazole-5-carboxamide | |
| 3367 | 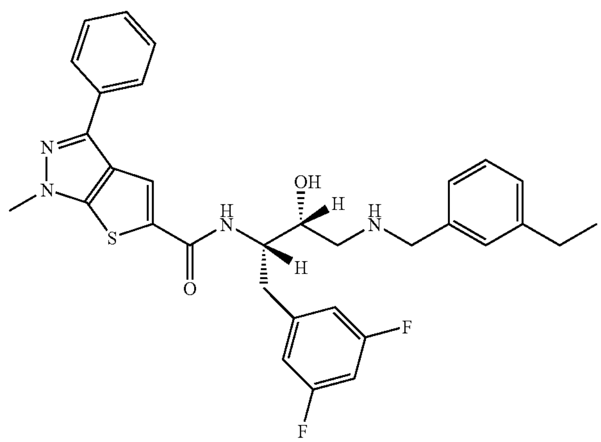 | N-{(1S,2R)-1-(3,5-difluorobenzyl)-3-[(3-ethylbenzyl)amino]-2-hydroxypropyl}-1-methyl-3-phenyl-1H-thieno[2,3-c]pyrazole-5-carboxamide | |
| 3368 | 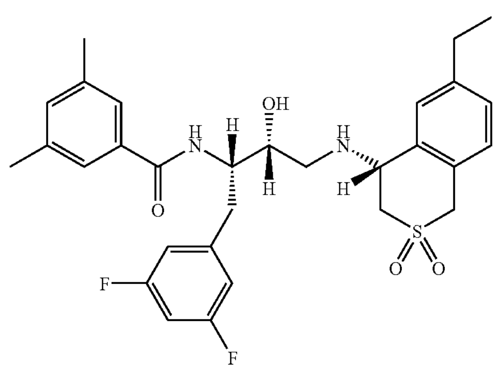 | N-((1S,2R)-1-(3,5-difluorobenzyl)-3-{[(4R)-6-ethyl-2,2-dioxido-3,4-dihydro-1H-isothiochromen-4-yl]amino}-2-hydroxypropyl)-3,5-dimethylbenzamide | **616.2 |
| 3370 | 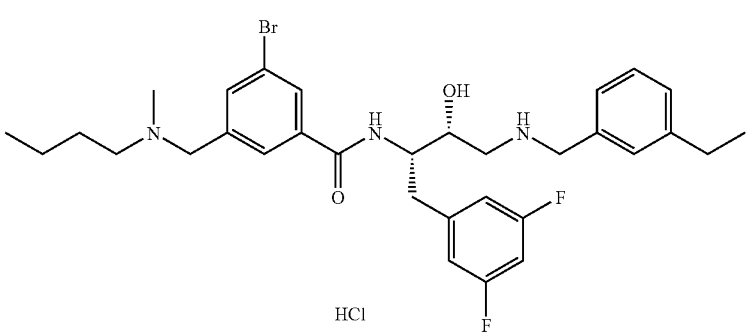 | 3-bromo-5-{[butyl(methyl)amino]methyl}-N-{(1S,2R)-1-(3,5-difluorobenzyl)-3-[(3-ethylbenzyl)amino]-2-hydroxypropyl}benzamide | |

-continued

| EXAMPLE | Structure | Compound Name(s) | Mass Spec |
|---|---|---|---|
| 3371 | 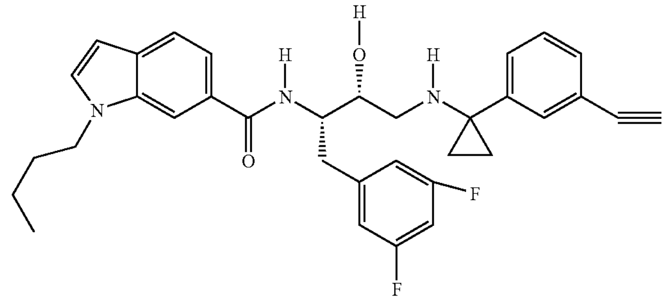 | 1-butyl-N-((1S,2R)-1-(3,5-difluorobenzyl)-3-{[1-(3-ethynylphenyl)cyclopropyl]amino}-2-hydroxypropyl)-1H-indole-6-carboxamide | |
| 3372 | 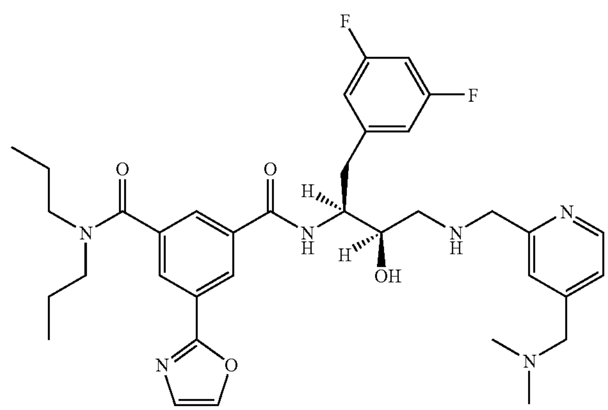 | ALB 12052 or $N^1$-{(1S,2R)-1-(3,5-difluorobenzyl)-3-[({4-[(dimethylamino)methyl]pyridin-2-yl}methyl)amino]-2-hydroxypropyl}-5-(1,3-oxazol-2-yl)-$N^3$,$N^3$-dipropylisophthalamide | *663 |
| 3373 | 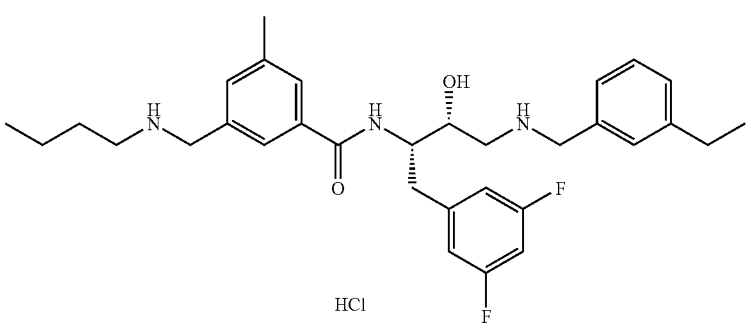 | 3-[(butylamino)methyl]-N-{(1S,2R)-1-(3,5-difluorobenzyl)-3-[(3-ethylbenzyl)amino]-2-hydroxypropyl}-5-methylbenzamide hydrochloride | **538.5 |
| 3374 | 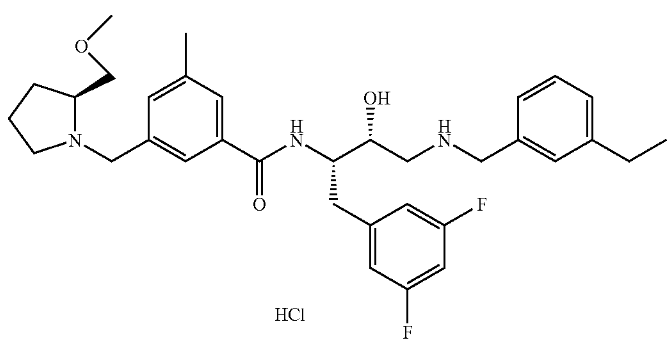 | N-{(1S,2R)-1-(3,5-difluorobenzyl)-3-[(3-ethylbenzyl)amino]-2-hydroxypropyl}-3-{[(2S)-2-(methoxymethyl)pyrrolidin-1-yl]methyl}-5-methylbenzamide hydrochloride | **580.4 |

-continued

| EXAMPLE | Structure | Compound Name(s) | Mass Spec |
|---|---|---|---|
| 3375 | 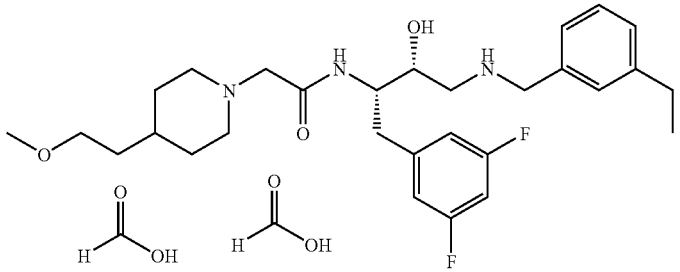 | formic acid compound with N-{(1S,2R)-1-(3,5-difluorobenzyl)-3-[(3-ethylbenzyl)amino]-2-hydroxypropyl}-2-[4-(2-methoxyethyl)piperidin-1-yl]acetamide (2:1) | |
| 3376 | 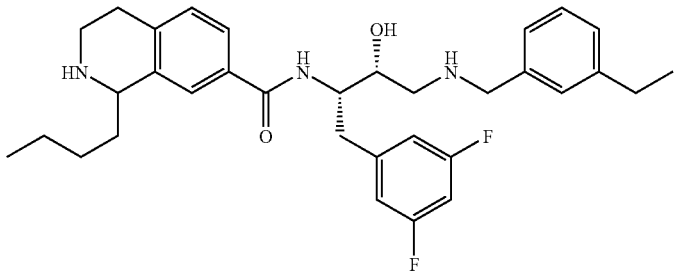 | 1-butyl-N-{(1S,2R)-1-(3,5-difluorobenzyl)-3-[(3-ethylbenzyl)amino]-2-hydroxypropyl}-1,2,3,4-tetrahydroisoquinoline-7-carboxamide | **550.4 |
| 3377 | 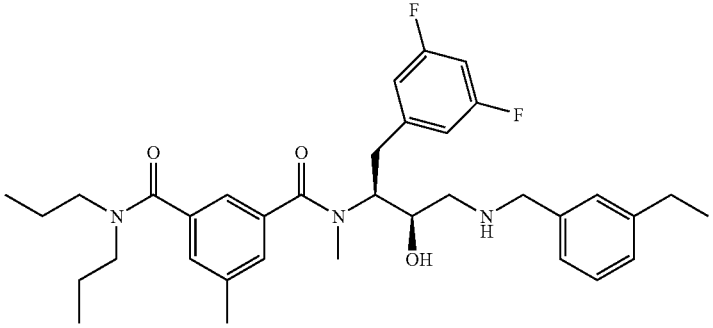 | $N^1$-{(1S,2R)-1-(3,5-difluorobenzyl)-3-[(3-ethylbenzyl)amino]-2-hydroxypropyl}-$N^1$,5-dimethyl-$N^3$,$N^3$-dipropylisophthalamide | |
| 3378 | 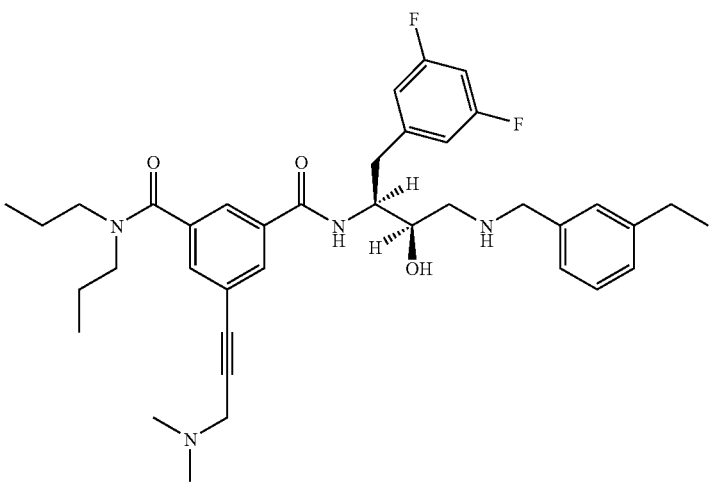 | $N^1$-{(1S,2R)-1-(3,5-difluorobenzyl)-3-[(3-ethylbenzyl)amino]-2-hydroxypropyl}-5-[3-(dimethylamino)prop-1-ynyl]-$N^3$,$N^3$-dipropylisophthalamide | |

| EXAMPLE | Structure | Compound Name(s) | Mass Spec |
|---|---|---|---|
| 3379 | 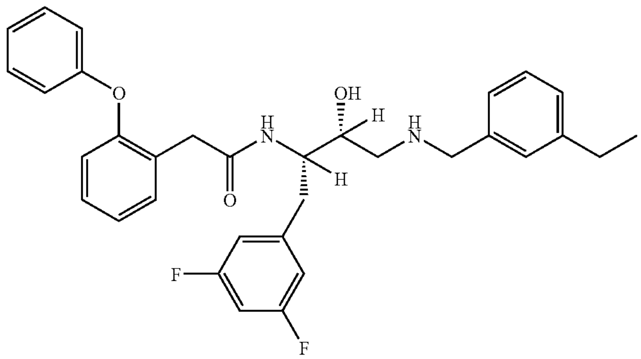 | N-{(1S,2R)-1-(3,5-difluorobenzyl)-3-[(3-ethylbenzyl)amino]-2-hydroxypropyl}-2-(2-phenoxyphenyl)acetamide | |
| 3380 | 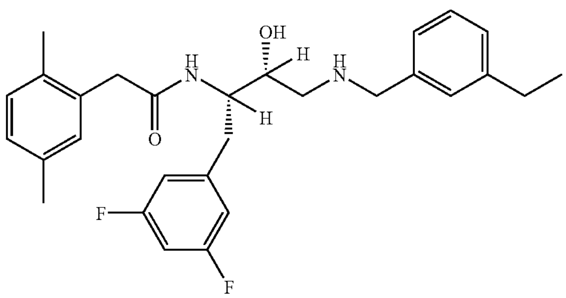 | N-{(1S,2R)-1-(3,5-difluorobenzyl)-3-[(3-ethylbenzyl)amino]-2-hydroxypropyl}-2-(2,5-dimethylphenyl)acetamide | |
| 3381 | 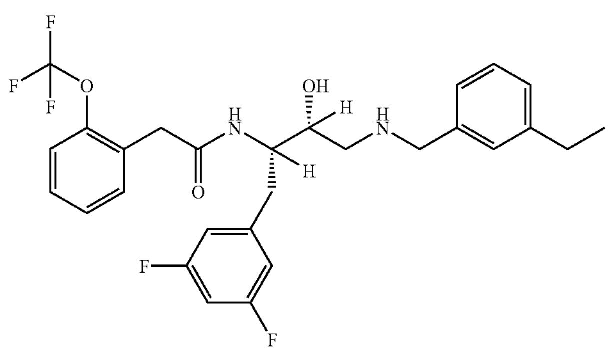 | N-{(1S,2R)-1-(3,5-difluorobenzyl)-3-[(3-ethylbenzyl)amino]-2-hydroxypropyl}-2-[2-(trifluoromethoxy)phenyl]acetamide | |
| 3382 | 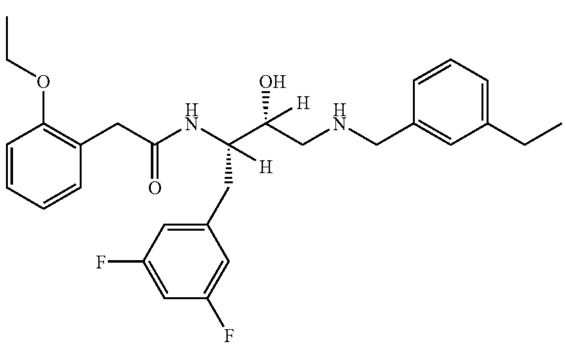 | N-{(1S,2R)-1-(3,5-difluorobenzyl)-3-[(3-ethylbenzyl)amino]-2-hydroxypropyl}-2-(2-ethoxyphenyl)acetamide | |

-continued

| EXAMPLE | Structure | Compound Name(s) | Mass Spec |
|---|---|---|---|
| 3383 | 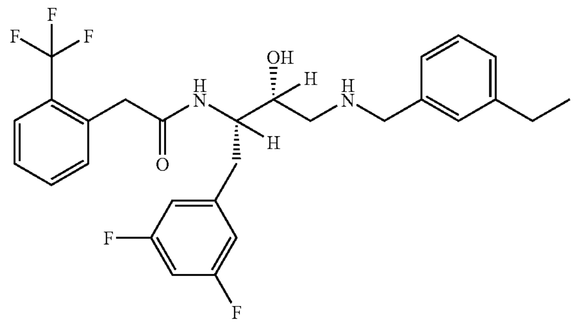 | N-{(1S,2R)-1-(3,5-difluorobenzyl)-3-[(3-ethylbenzyl)amino]-2-hydroxypropyl}-2-[2-(trifluoromethyl)phenyl]acetamide | |
| 3384 | 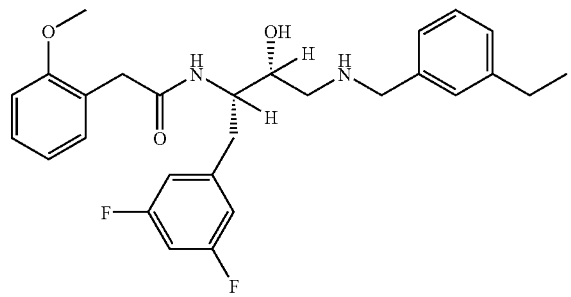 | N-{(1S,2R)-1-(3,5-difluorobenzyl)-3-[(3-ethylbenzyl)amino]-2-hydroxypropyl}-2-(2-methoxyphenyl)acetamide | |
| 3385 | 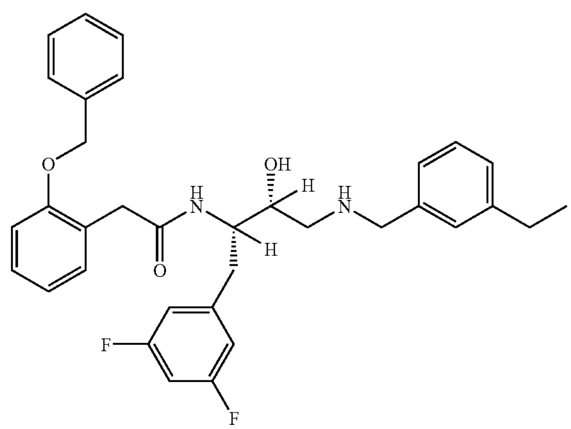 | 2-[2-(benzyloxy)phenyl]-N-{(1S,2R)-1-(3,5-difluorobenzyl)-3-[(3-ethylbenzyl)amino]-2-hydroxypropyl)acetamide | |
| 3386 | 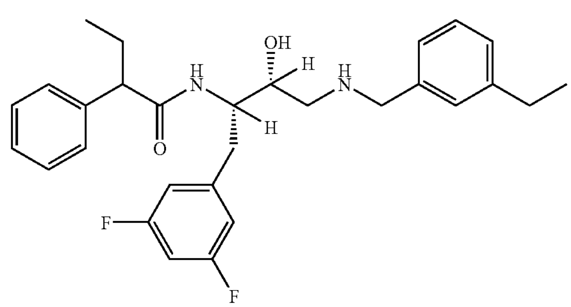 | N-{(1S,2R)-1-(3,5-difluorobenzyl)-3-[(3-ethylbenzyl)amino]-2-hydroxypropyl}-2-phenylbutanamide | |

-continued

| EXAMPLE | Structure | Compound Name(s) | Mass Spec |
|---|---|---|---|
| 3387 | 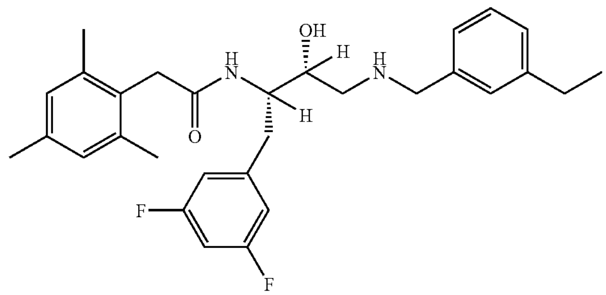 | N-{(1S,2R)-1-(3,5-difluoro-benzyl)-3-[(3-ethylbenzyl)amino]-2-hydroxypropyl}-2-mesitylacetamide | |
| 3388 | 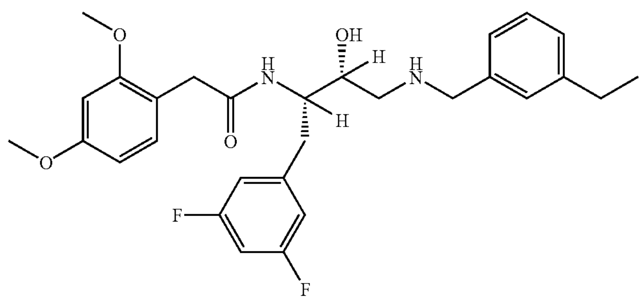 | N-{(1S,2R)-1-(3,5-difluoro-benzyl)-3-[(3-ethylbenzyl)amino]-2-hydroxypropyl}-2-(2,4-dimethoxyphenyl)acetamide | |
| 3389 | 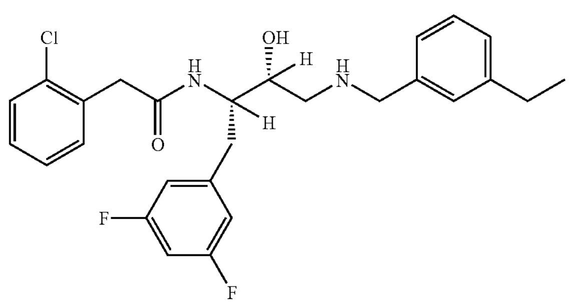 | 2-(2-chlorophenl)-N-{(1S,2R)-1-(3,5-difluoro-benzyl)-3-[(3-ethylbenzyl)amino]-2-hydroxypropyl}acetamide | |
| 3390 | 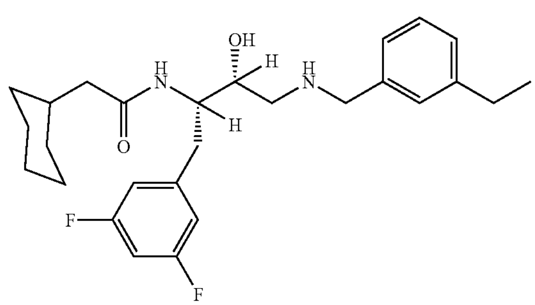 | 2-cyclohexyl-N-{(1S,2R)-1-(3,5-difluorobenzyl)-3-[(3-ethylbenzyl)amino]-2-hydroxypropyl}acetamide | |
| 3391 | 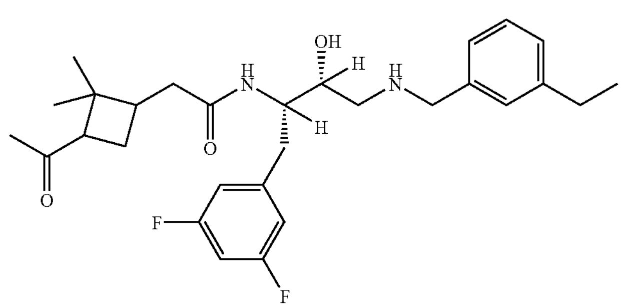 | ELAN-157393 | |

| EXAMPLE | Structure | Compound Name(s) | Mass Spec |
|---|---|---|---|
| 3392 | 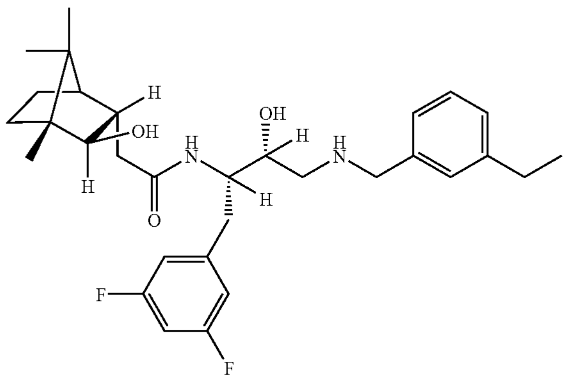 | ELAN-157394 | |
| 3393 | 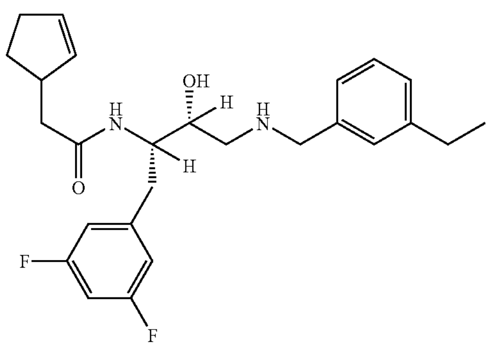 | 2-cyclopent-2-en-1-yl-N-{(1S,2R)-1-(3,5-difluorobenzyl)-3-[(3-ethylbenzyl)amino]-2-hydroxypropyl}acetamide | |
| 3394 | 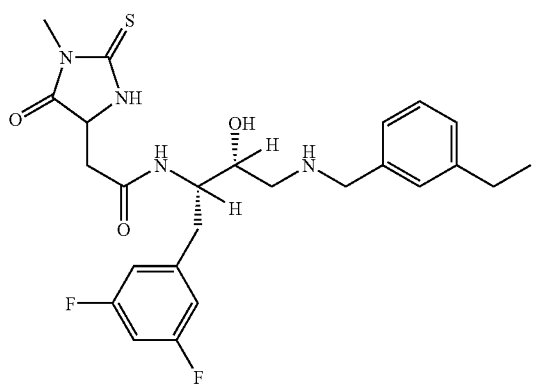 | N-{(1S,2R)-1-(3,5-difluorobenzyl)-3-[(3-ethylbenzyl)amino]-2-hydroxypropyl}-2-(1-methyl-5-oxo-2-thioxoimidazolidin-4-yl)acetamide | |
| 3395 | 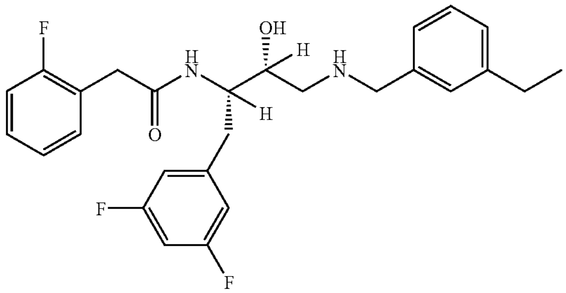 | N-{(1S,2R)-1-(3,5-difluorobenzyl)-3-[(3-ethylbenzyl)amino]-2-hydroxypropyl}-2-(2-fluorophenyl)acetamide | |

-continued

| EXAMPLE | Structure | Compound Name(s) | Mass Spec |
|---|---|---|---|
| 3396 | 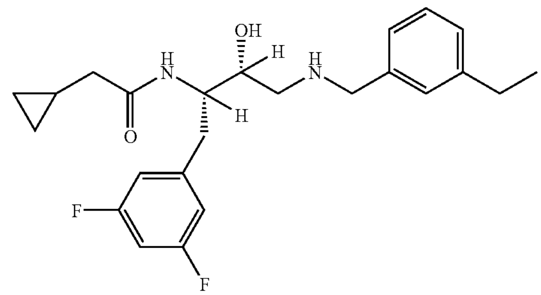 | 2-cyclopropyl-N-{(1S,2R)-1-(3,5-difluorobenzyl)-3-[(3-ethylbenzyl)amino]-2-hydroxypropyl}acetamide | |
| 3397 | 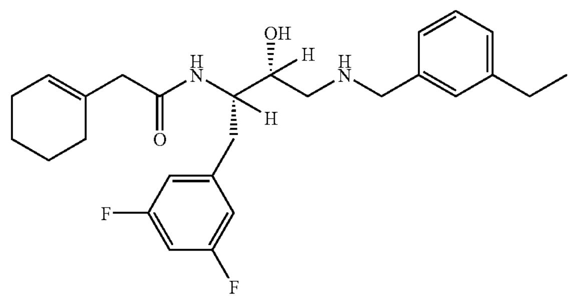 | 2-cyclohex-1-en-1-yl-N-{(1S,2R)-1-(3,5-difluorobenzyl)-3-[(3-ethylbenzyl)amino]-2-hydroxypropyl}acetamide | |
| 3398 | 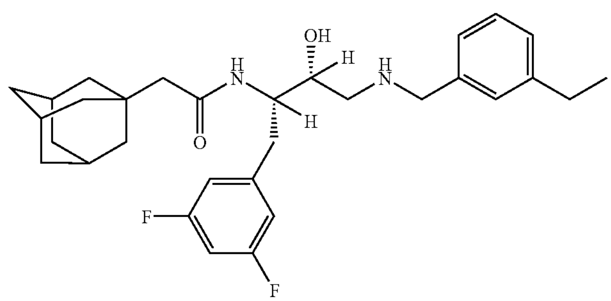 | 2-(1-adamantyl)-N-{(1S,2R)-1-(3,5-difluorobenzyl)-3-[(3-ethylbenzyl)amino]-2-hydroxypropyl}acetamide | |
| 3399 | 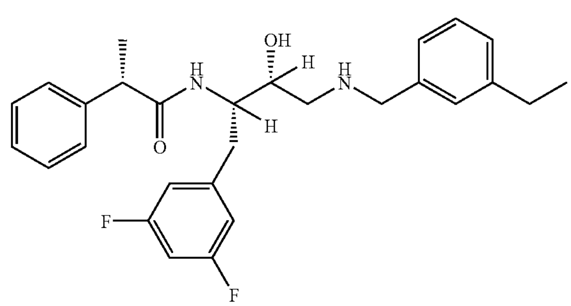 | (2S)-N-{(1S,2R)-1-(3,5-difluorobenzyl)-3-[(3-ethylbenzyl)amino]-2-hydroxypropyl}-2-phenylpropanamide | |
| 3400 | 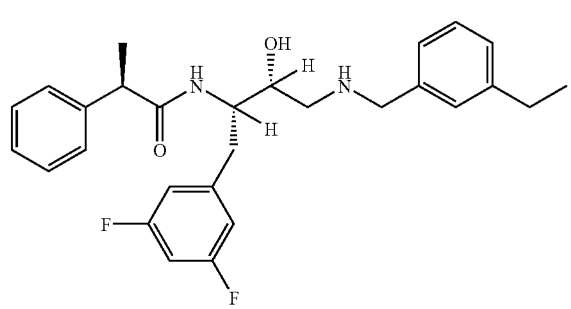 | (2R)-N-{(1S,2R)-1-(3,5-difluorobenzyl)-3-[(3-ethylbenzyl)amino]-2-hydroxypropyl}-2-phenylpropanamide | |

-continued

| EXAMPLE | Structure | Compound Name(s) | Mass Spec |
|---|---|---|---|
| 3401 | 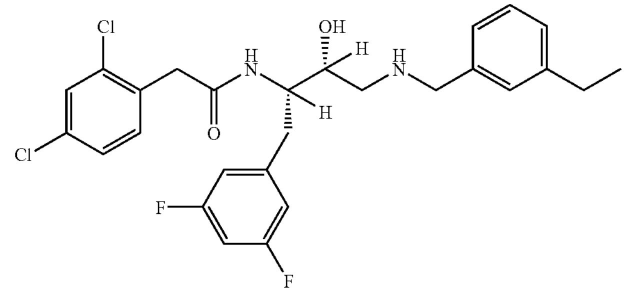 | 2-(2,4-dichlorophenyl)-N-{(1S,2R)-1-(3,5-difluoro-benzyl)-3-[(3-ethylbenzyl)amino]-2-hydroxypropyl}acetamide | |
| 3402 | 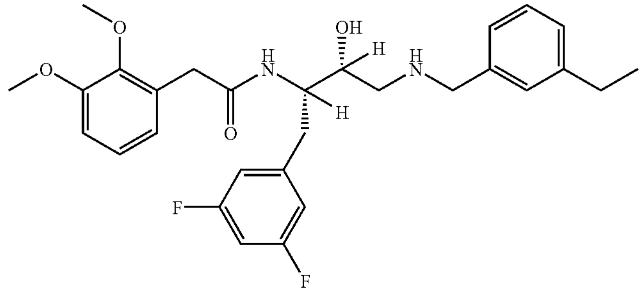 | N-{(1S,2R)-1-(3,5-difluoro-benzyl)-3-[(3-ethylbenzyl)amino]-2-hydroxypropyl}-2-(2,3-dimethoxyphenyl)acetamide | |
| 3403 | 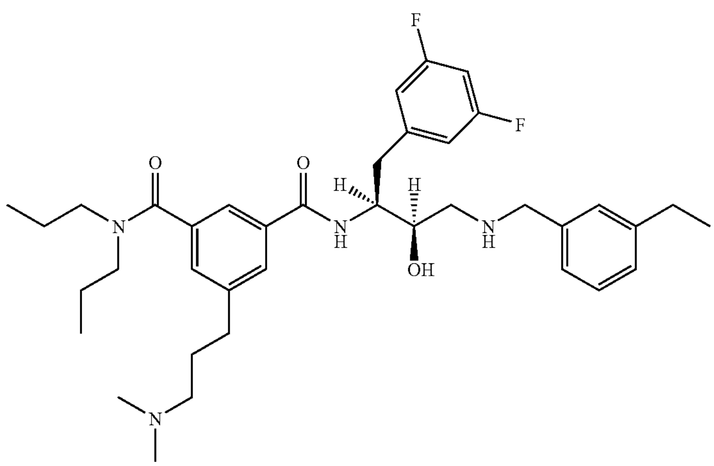 | $N^1$-{(1S,2R)-1-(3,5-difluoro-benzyl)-3-[(3-ethylbenzyl)amino]-2-hydroxypropyl}-5-[3-(dimethylamino)propyl]-$N^3,N^3$-dipropylisophthalamide | |
| 3406 | 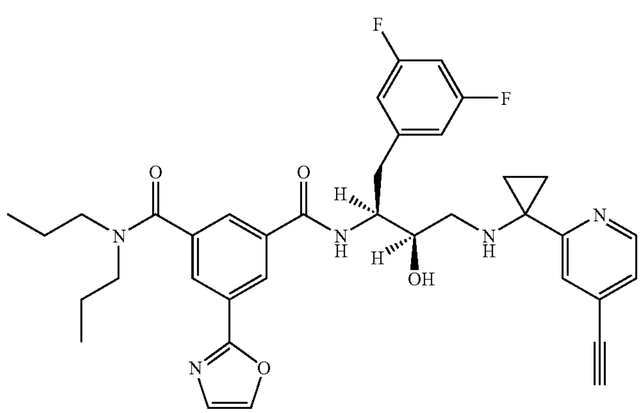 | $N^1$-((1S,2R)-1-(3,5-difluoro-benzyl)-3-{[1-(4-ethynylpyridin-2-yl)cyclopropyl]amino}-2-hydroxypropyl)-5-(1,3-oxazol-2-yl)-$N^3,N^3$-dipropylisophthalamide | |

| EXAMPLE | Structure | Compound Name(s) | Mass Spec |
|---|---|---|---|
| 3407 | 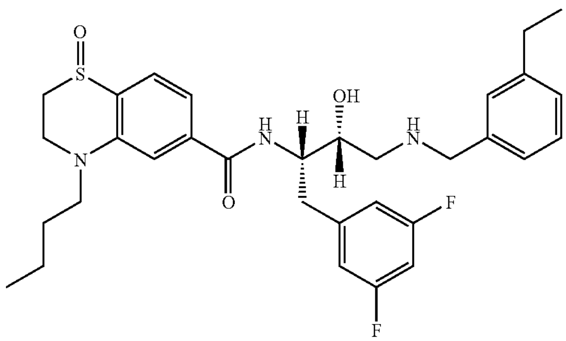 | 4-butyl-N-{(1S,2R)-1-(3,5-difluorobenzyl)-3-[(3-ethylbenzyl)amino]-2-hydroxypropyl}-3,4-dihydro-2H-1,4-benzothiazine-6-carboxamide 1-oxide | |
| 3408 | 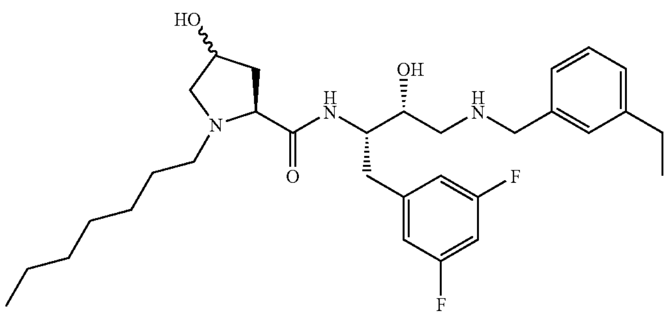 | N-{(1S,2R)-1-(3,5-difluorobenzyl)-3-[(3-ethylbenzyl)amino]-2-hydroxypropyl}-1-heptyp-4-hydroxy-L-prolinamide | |
| 3409 | 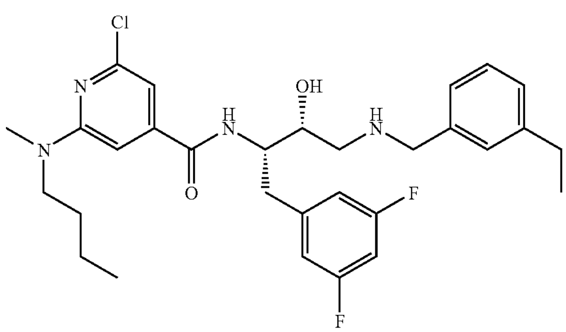 | 2-[butyl(methyl)amino]-6-chloro-N-{(1S,2R)-1-(3,5-difluorobenzyl)-3-[(3-ethylbenzyl)amino]-2-hydroxypropyl}isonicotinamide | |
| 3410 | 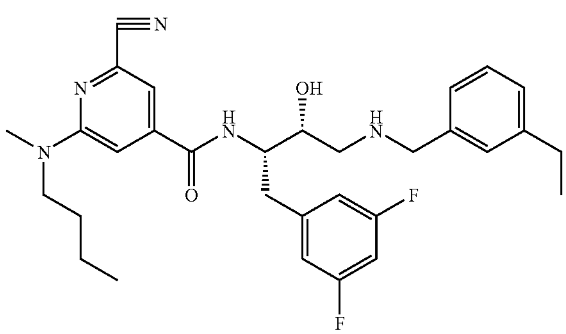 | 2-[butyl(methyl)amino]-6-cyano-N-{(1S,2R)-1-(3,5-difluorobenzyl)-3-[(3-ethylbenzyl)amino]-2-hydroxypropyl}isonicotinamide | |

-continued

| EXAMPLE | Structure | Compound Name(s) | Mass Spec |
|---|---|---|---|
| 3411 | 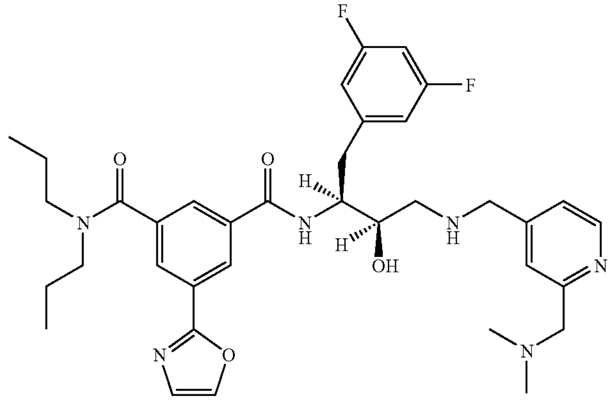 | ALB-12164 N'-{(1S,2R)-1-(3,5-difluorobenzyl)-3-[({2-[(dimethylamino)methyl]pyridin-4-yl}methyl)amino]-2-hydroxypropyl}-5-(1,3-oxazol-2-yl)-N,N-dipropylisophthalamide | *663 |
| 3412 | 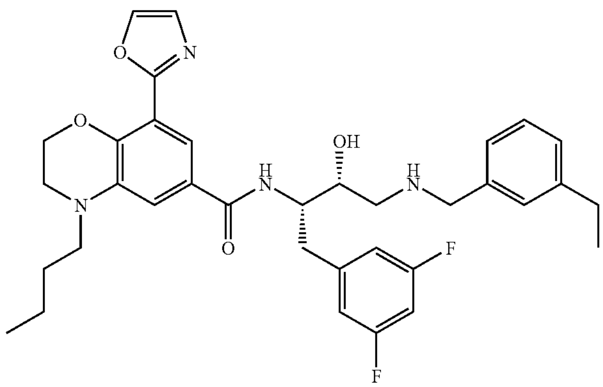 | 4-butyl-N-{(1R,2R)-1-(3,5-difluorobenzyl)-3-[(3-ethylbenzyl)amino]-2-hydroxypropyl}-8-(1,3-oxazol-2-yl)-3,4-dihydro-2H-1,4-benzoxazine-6-carboxamide or 4-butyl-N-{(1S,2R)-1-(3,5-difluorobenzyl)-3-[(3-ethylbenzyl)amino]-2-hydroxypropyl}-8-(1,3-oxazol-2-yl)-3,4-dhydro-2H-1,4-benzoxazine-6-carboxamide | **619 |
| 3413 | 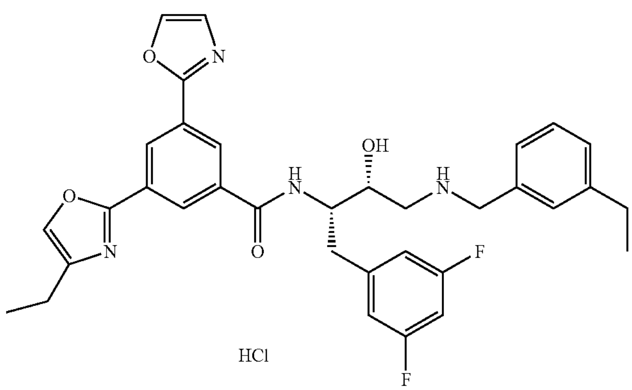 | N-{(1S,2R)-1-(3,5-difluorobenzyl)-3-[(3-ethylbenzyl)amino]-2-hydroxypropyl}-3-(4-ethyl-1,3-oxazol-2-yl)-5-(1,3-oxazol-2-yl)benzamide hydrochloride | **601 |
| 3414 | 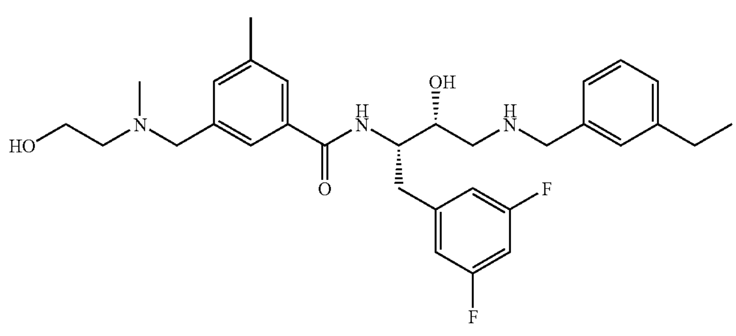 | | **540.4 |

-continued
| EXAMPLE | Structure | Compound Name(s) | Mass Spec |
|---|---|---|---|
| 3415 | 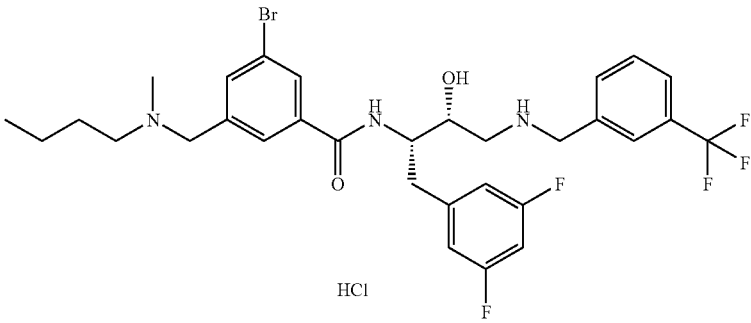 | | **656.2 |
| 3416 | 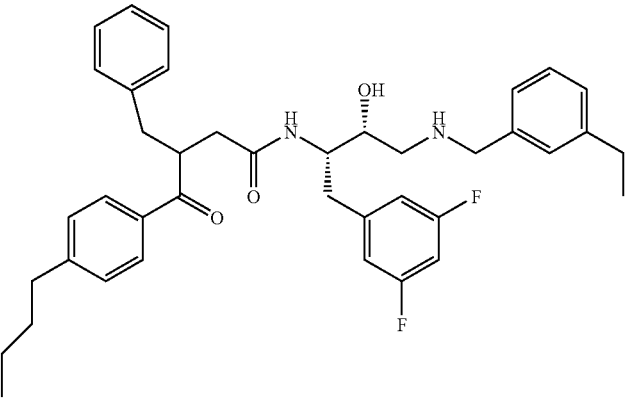 | 3-benzyl-4-(4-butylphenyl)-N-{(1S,2R)-1-(3,5-difluorobenzyl)-3-[(3-ethylbenzyl)amino]-2-hydroxypropyl}-4-oxobutanamide | **641.6 |
| 3417 | 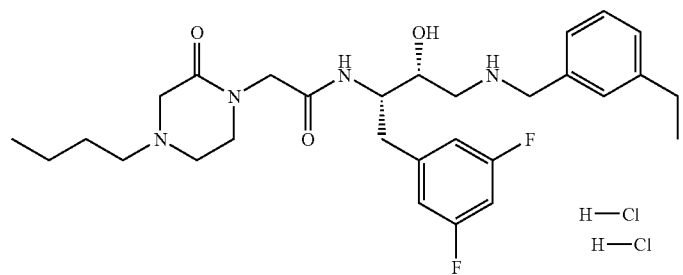 | 2-(4-butyl-2-oxopiperazin-1-yl)-N-{(1S,2R)-1-(3,5-difluorobenzyl)-3-[(3-ethylbenzyl)amino]-2-hydroxypropyl}acetamide dihydrochloride | |
| 3418 | 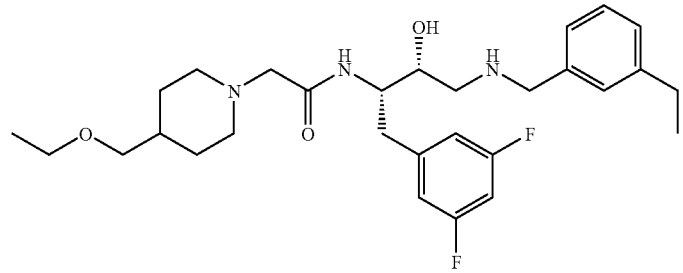 | N-{(1S,2R)-1-(3,5-difluorobenzyl)-3-[(3-ethylbenzyl)amino]-2-hydroxypropyl}-2-[4-(ethoxymethyl)piperidin-1-yl]acetamide | |

-continued

| EXAMPLE | Structure | Compound Name(s) | Mass Spec |
|---|---|---|---|
| 3419 | 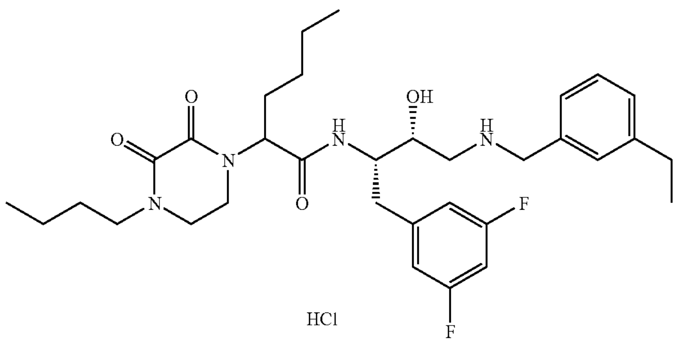 | 2-(4-butyl-2,3-dioxopiperazin-1-yl)-N-{(1S,2R)-1-(3,5-difluorobenzyl)-3-[(3-ethylbenzyl)amino]-2-hydroxypropyl}hexanamide hydrochloride | |
| 3421 | 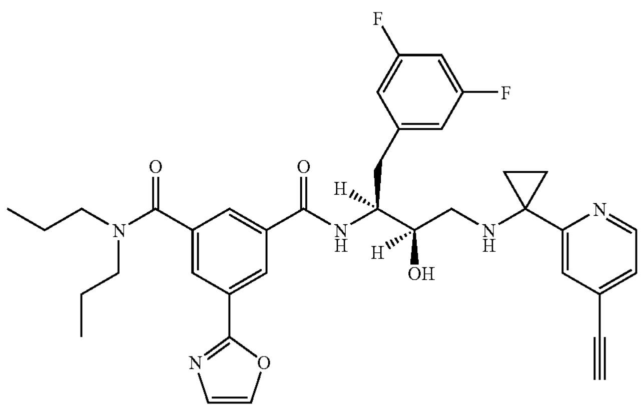 | N¹-((1S,2R)-1-(3,5-difluorobenzyl)-3-{[1-(4-ethynylpyridin-2-yl)cyclopropyl]amino}-2-hydroxypropyl)-5-(1,3-oxazol-2-yl)-N³,N³-dipropylisophthalamide | |
| 3422 | 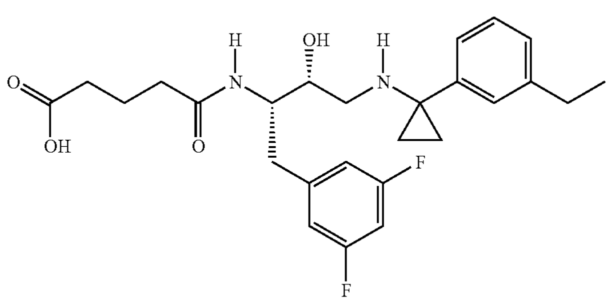 | 5-[((1S,2R)-1-(3,5-difluorobenzyl)-3-{[1-(3-ethylphenyl)cyclopropyl]amino}-2-hydroxypropyl)amino]-5-oxopentanoic acid | **475.2 |
| 3423 | 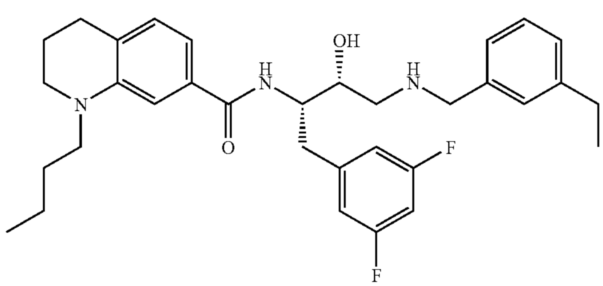 | 1-butyl-N-{(1S,2R)-1-(3,5-difluorobenzyl)-3-[(3-ethylbenzyl)amino]-2-hydroxypropyl}-1,2,3,4-tetrahydroquinoline-7-carboxamide or 1-butyl-N-{(1S,2R)-1-(3,5-difluorobenzyl)-3-[(3-ethylbenzyl)amino]-2-hydroxypropyl}-1,2,3,4-tetrahydroquinoline-7-carboxamide | |

-continued

| EXAMPLE | Structure | Compound Name(s) | Mass Spec |
|---|---|---|---|
| 3424 | 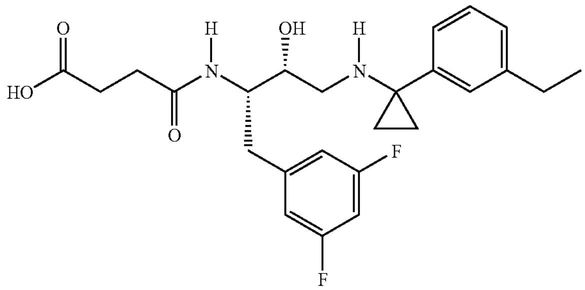 | 4-[((1S,2R)-1-(3,5-difluorobenzyl)-3-{[1-(3-ethylphenyl)cyclopropyl]amino}-2-hydroxypropyl)amino]-4-oxobutanoic acid | **461.2 |
| 3425 | 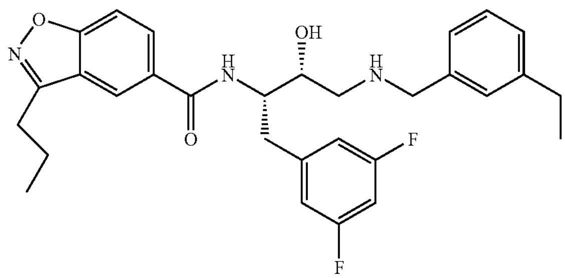 | N-{(1S,2R)-1-(3,5-difluorobenzyl)-3-[(3-ethylbenzyl)amino]-2-hydroxypropyl}-3-propyl-1,2-benzisoxazole-5-carboxamide | |
| 3426 | 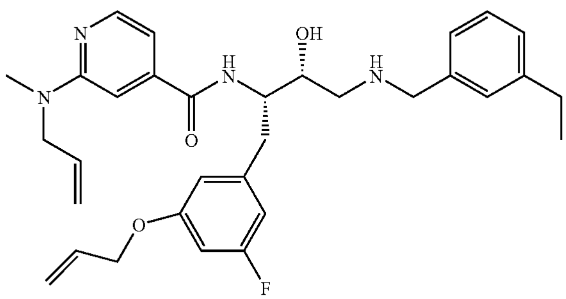 | 2-[allyl(methyl)amino]-N-{(1S,2R)-1-[3-(allyloxy)-5-fluorobenzyl]-3-](3-ethylbenzyl)amino]-2-hydroxypropyl}isonicotinamide | **547.5 |
| 3427 | 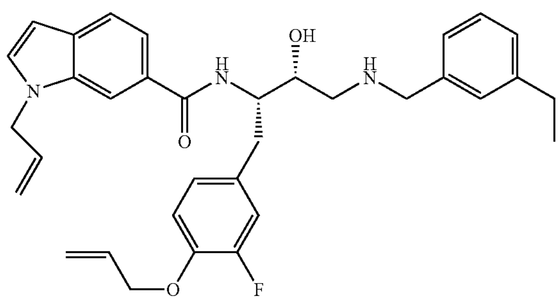 | 1-allyl-N-{(1S,2R)-1-[4-(allylxoy)-3-fluorobenzyl]-3-[(3-ethylbenzyl)amino]-2-hydroxypropyl}-1H-indole-6-carboxamide | **556.4 |
| 3428 | 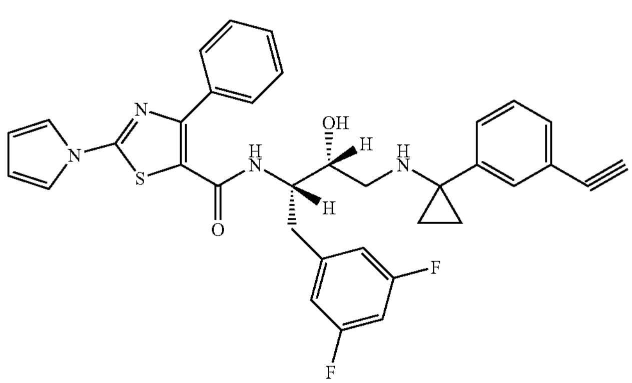 | N-((1S,2R)-1-(3,5-difluorobenzyl)-3-{[1-(3-ethynylphenyl)cyclopropyl]amino}-2-hydroxypropyl)-4-phenyl-2-(1H-pyrrol-1-yl)-1,3-thiazole-5-carboxamide | |

-continued

| EXAMPLE | Structure | Compound Name(s) | Mass Spec |
|---|---|---|---|
| 3429 | 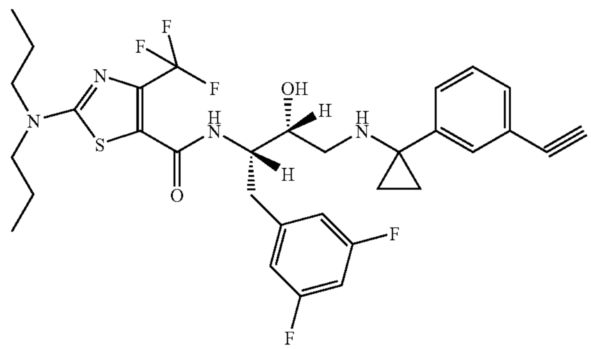 | N-((1S,2R)-1-(3,5-difluoro-benzyl)-3-{[1-(3-ethynyl-phenyl)cyclopropyl]amino}-2-hydroxypropyl)-2-(dipropyl-amino)-4-(trifluoromethyl)-1,3-thiazole-5-carboxamide | |
| 3432 | 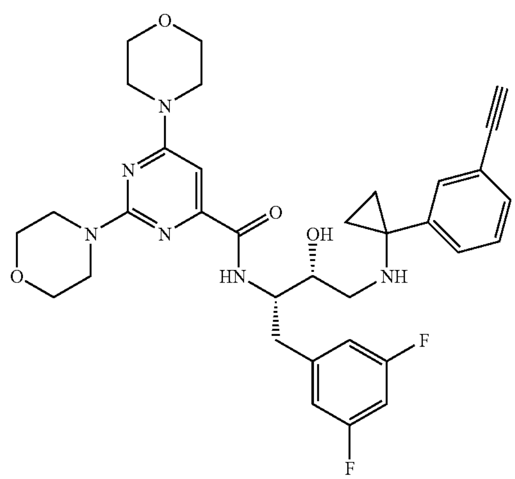 | N-((1S,2R)-1-(3,5-difluoro-benzyl)-3-{[1-(3-ethynyl-phenyl)cyclopropyl]amino}-2-hydroxypropyl)-2,6-dimorpholin-4-ylpyrimidine-4-carboxamide | |
| 3433 | 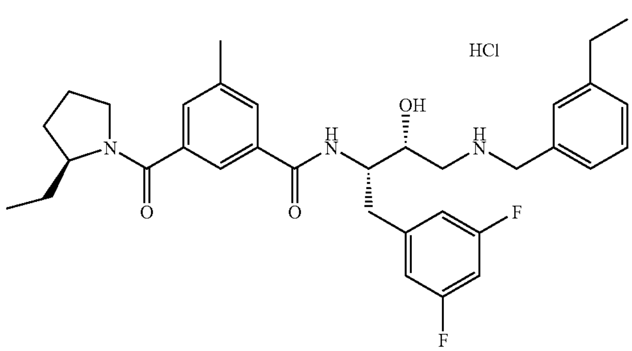 | N-{(1S,2R)-1-(3,5-difluoro-benzyl)-3-[(3-ethylbenzyl)amino]-2-hydroxypropyl}-3-{[(2S)-2-ethylpyrrolidin-1-yl]carbonyl}-5-methylbenzamide hydrochloride | |
| 3434 | 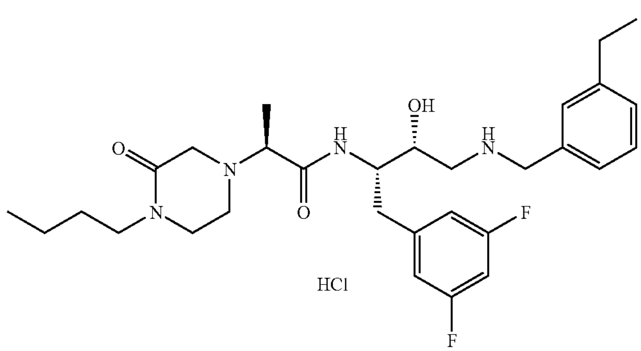 | (2S)-2-(4-butyl-3-oxopiperazin-1-yl)-N-{(1S,2R)-1-(3,5-difluoro-benzyl)-3-[(3-ethylbenzyl)amino]-2-hydroxypropyl}propanamide hydrochloride | |

| EXAMPLE | Structure | Compound Name(s) | Mass Spec |
|---|---|---|---|
| 3451 | 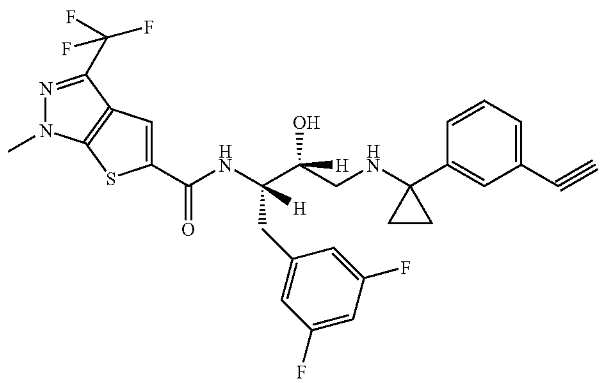 | N-((1S,2R)-1-(3,5-difluorobenzyl)-3-{[1-(3-ethynylphenyl)cyclopropyl]amino}-2-hydroxypropyl)-1-methyl-3-(trifluoromethyl)-1H-thieno[2,3-c]pyrazole-5-carboxamide | |
| 3452 | 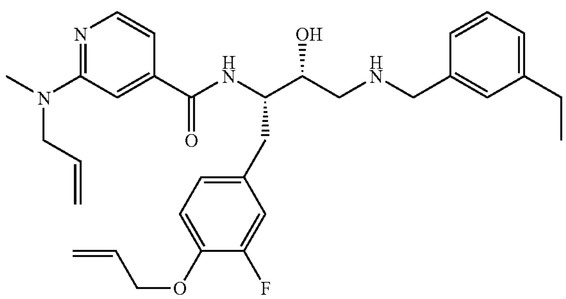 | 2-[allyl(methyl)amino]-N-{(1S,2R)-1-[4-(allyloxy)-3-fluorobenzyl]-3-[(3-ethylbenzyl)amino]-2-hydroxypropyl}isonicotinamide | **547.4 |
| 3453 | 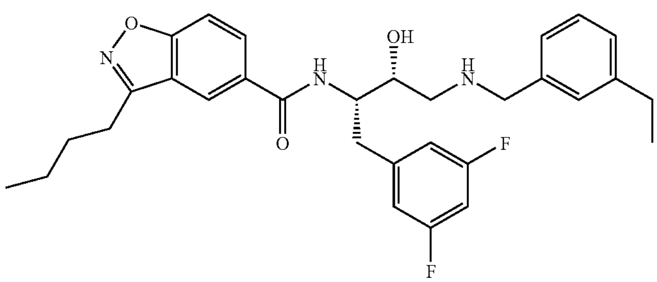 | 3-butyl-N-{(1S,2R)-1-(3,5-difluorobenzyl)-3-[(3-ethylbenzyl)amino]-2-hydroxypropyl}-1,2-benzisoxazole-5-carboxamide | **536 |
| 3454 | 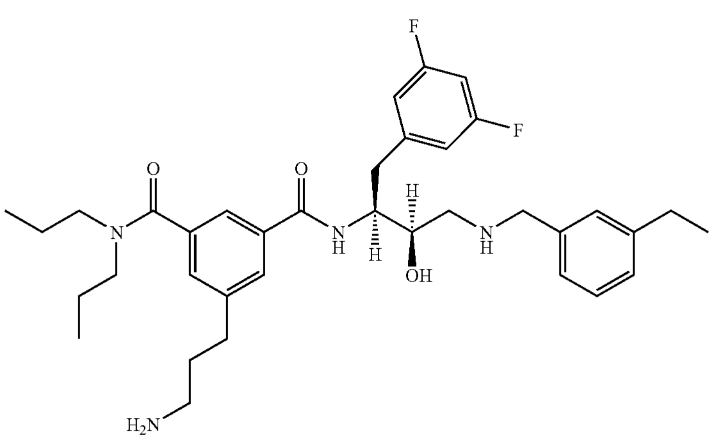 | 5-(3-aminopropyl)-N¹-{(1S,2R)-1-(3,5-difluorobenzyl)-3-[(3-ethylbenzyl)amino]-2-hydroxypropyl}-N³,N³-dipropylisophthalamide | |

-continued

| EXAMPLE | Structure | Compound Name(s) | Mass Spec |
|---|---|---|---|
| 3455 | 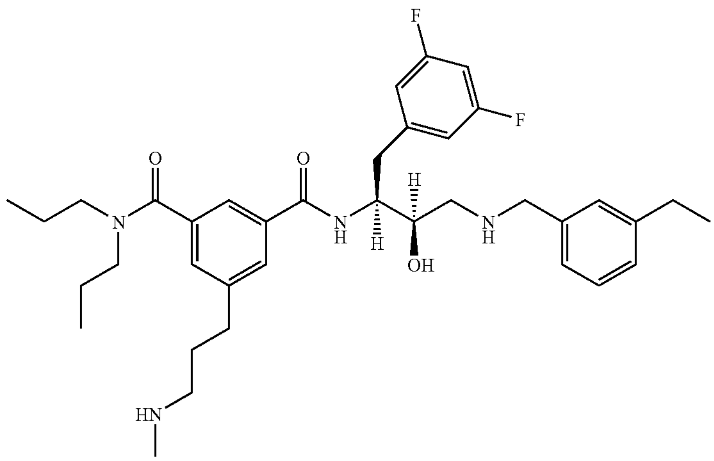 | $N^1$-{(1S,2R)-1-(3,5-difluorobenzyl)-3-[(3-ethylbenzyl)amino]-2-hydroxypropyl}-5-[3-(methylamino)propyl]-$N^3,N^3$-dipropylisophthalamide or ELAN157961 | |
| 3456 | 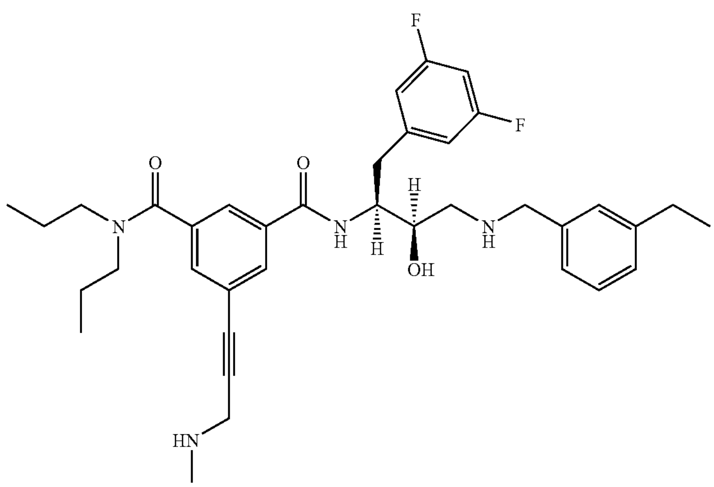 | $N^1$-{(1S,2R)-1-(3,5-difluorobenzyl)-3-[(3-ethylbenzyl)amino]-2-hydroxypropyl}-5-[3-(methylamino)prop-1-ynyl]-$N^3,N^3$-dipropylisophthalamide | |
| 3457 | 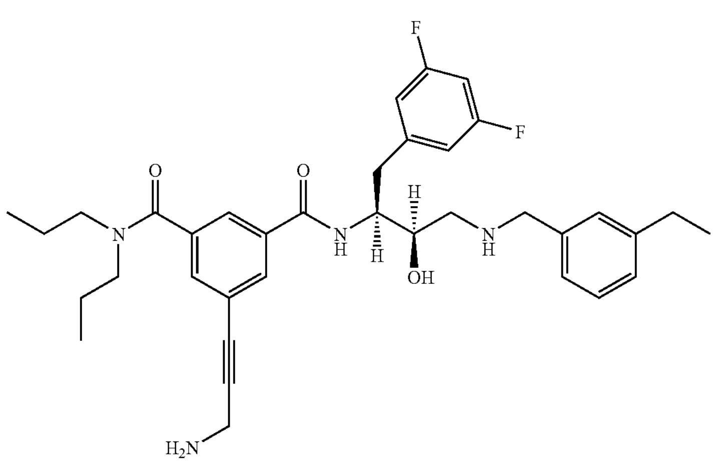 | 5-(3-aminoprop-1-ynyl)-$N^1$-{(1S,2R)-1-(3,5-difluorobenzyl)-3-[(3-ethylbenzyl)amino]-2-hydroxypropyl}-$N^3,N^3$-dipropylisophthalamide or ELAN57963 | |

| EXAMPLE | Structure | Compound Name(s) | Mass Spec |
|---|---|---|---|
| 3458 | 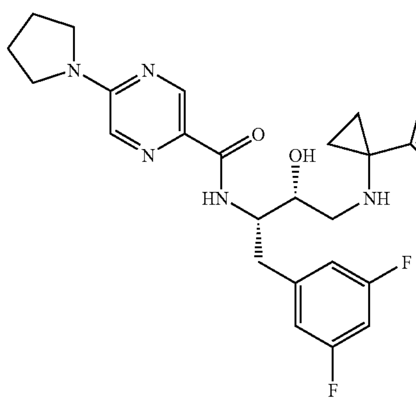 | N-((1S,2R)-1-(3,5-difluoro-benzyl)-3-{[1-(3-ethynyl-phenyl)cyclopropyl]amino}-2-hydroxypropyl)-5-pyrrolidin-1-ylpyrazine-2-carboxamide | |
| 3459 | 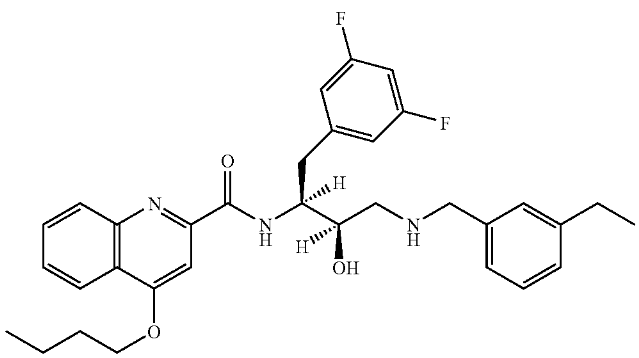 | 4-butoxy-N-{(1S,2R)-1-(3,5-difluorobenzyl)-3-[(3-ethyl-benzyl)amino]-2-hydroxy-propyl}quinoline-2-carboxamide | |
| 3461 | 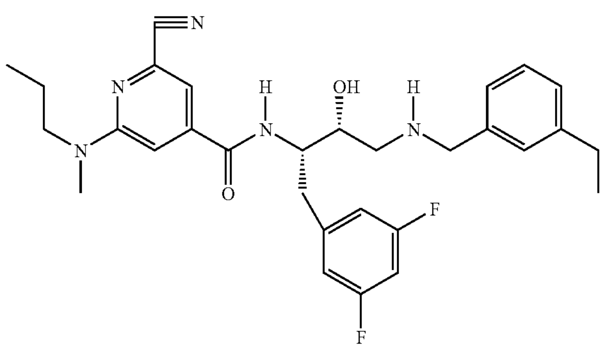 | 2-cyano-N-{(1S,2R)-1-(3,5-difluorobenzyl)-3-[(3-ethyl-benzyl)amino]-2-hydroxy-propyl}-6-[methyl(propyl)amino]isonicotinamide | |
| 3462 | 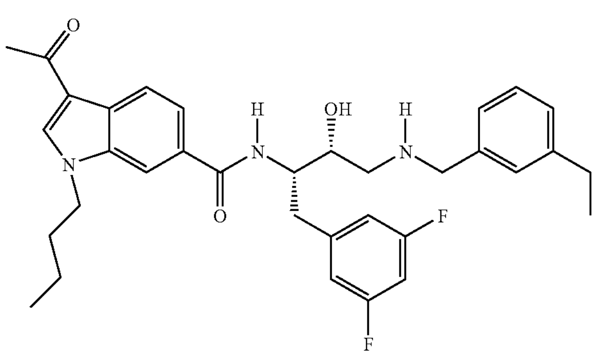 | 3-acetyl-1-butyl-N-{(1S,2R)-1-(3,5-difluorobenzyl)-3-[(3-ethylbenzyl)amino]-2-hydroxypropyl}-1H-indole-6-carboxamide | |

-continued

| EXAMPLE | Structure | Compound Name(s) | Mass Spec |
|---|---|---|---|
| 3463 | 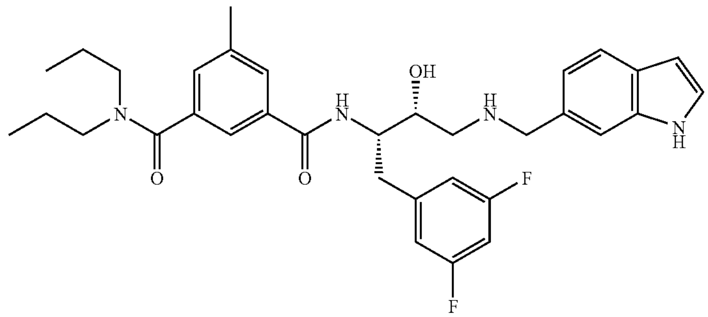 | N$^1$-{(1S,2R)-1-(3,5-difluoro-benzyl)-2-hydroxy-3-[(1H-indol-6-ylmethyl)amino]propyl}-5-methyl-N$^3$,N$^3$-dipropylisophthalamide | **591.5 |
| 3464 | 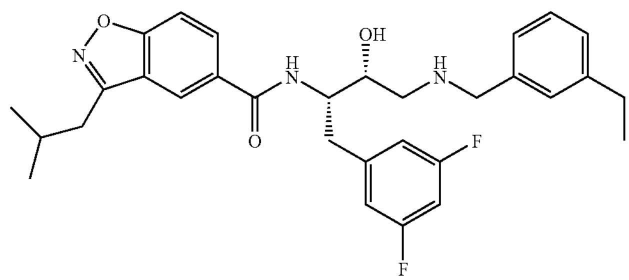 | N-{(1S,2R)-1-(3,5-difluoro-benzyl)-3-[(3-ethylbenzyl)amino]-2-hydroxypropyl}-3-isobutyl-1,2-benzisoxazole-5-carboxamide | **536 |
| 3465 | 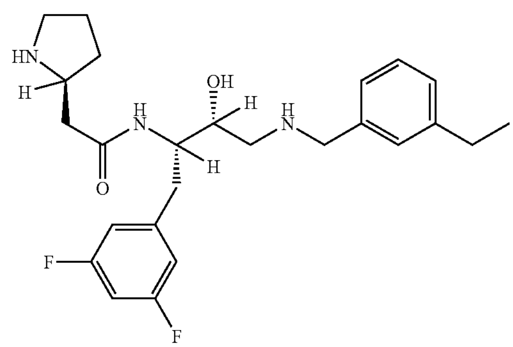 | N-{(1S,2R)-1-(3,5-difluoro-benzyl)-3-[(3-ethylbenzyl)amino]-2-hydroxypropyl}-2-[(2S)-pyrrolidin-2-yl]acetamide | |
| 3466 | 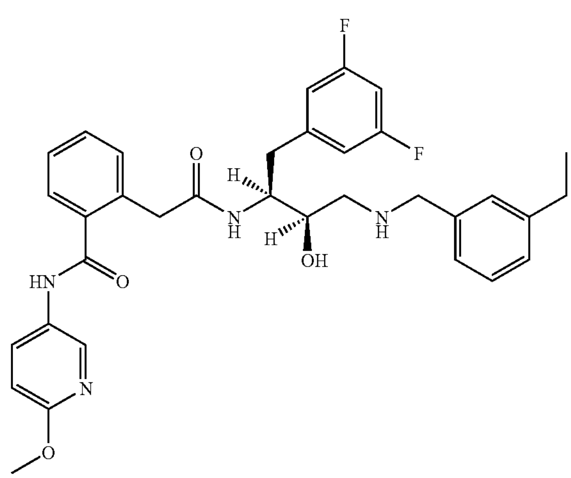 | 2-[2-({(1S,2R)-1-(3,5-difluorobenzyl)-3-[(3-ethylbenzyl)amino]-2-hydroxypropyl}amino)-2-oxoethyl]-N-(6-methoxypyridin-3-yl)benzamide | |

-continued

| EXAMPLE | Structure | Compound Name(s) | Mass Spec |
|---|---|---|---|
| 3467 | 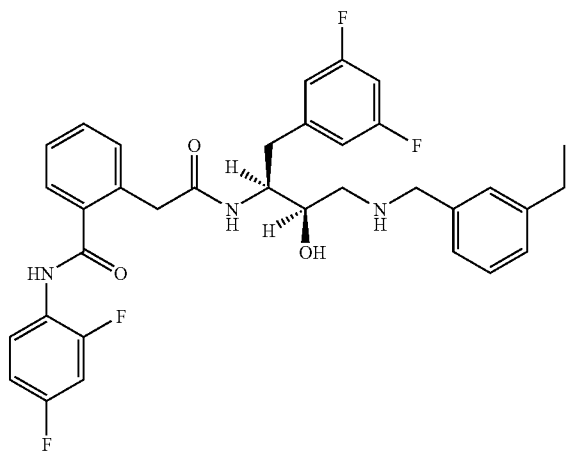 | 2-[2-({(1S,2R)-1-(3,5-difluorobenzyl)-3-[(3-ethylbenzyl)amino]-2-hydroxypropyl}amino)-2-oxoethyl]-N-(2,4-difluorophenyl)benzamide | |
| 3468 | 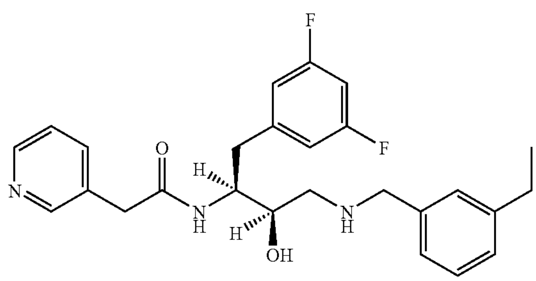 | N-{(1S,2R)-1-(3,5-difluorobenzyl)-3-[(3-ethylbenzyl)amino]-2-hydroxypropyl}-2-pyridin-3-ylacetamide | |
| 3469 | 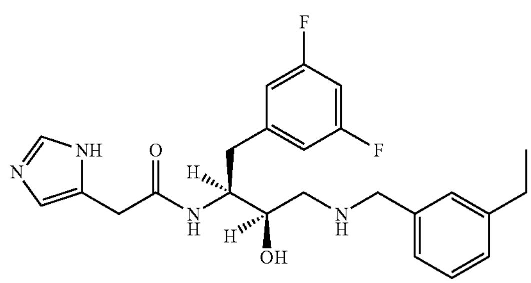 | N-{(1S,2R)-1-(3,5-difluorobenzyl)-3-[(3-ethylbenzyl)amino]-2-hydroxypropyl}-2-(1H-imidazol-5-yl)acetamide | |
| 3470 | 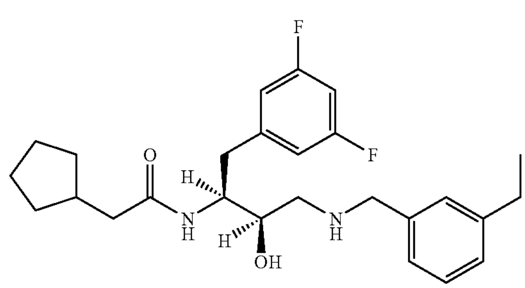 | 2-cyclopentyl-N-{(1S,2R)-1-(3,5-difluorobenzyl)-3-[(3-ethylbenzyl)amino]-2-hydroxypropyl}acetamide | |

-continued

| EXAMPLE | Structure | Compound Name(s) | Mass Spec |
|---|---|---|---|
| 3471 | 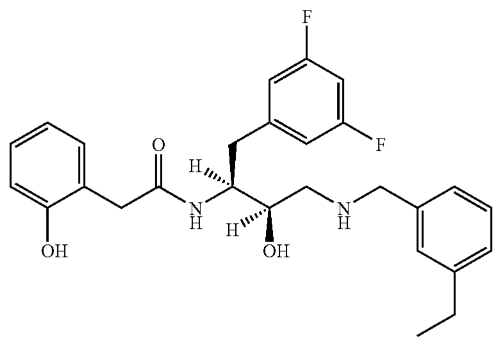 | 2-cyclopentyl-N-{(1S,2R)-1-(3,5-difluorobenzyl)-3-[(3-ethylbenzyl)amino]-2-hydroxypropyl}-2-(2-hydroxyphenyl)acetamide | |
| 3472 | 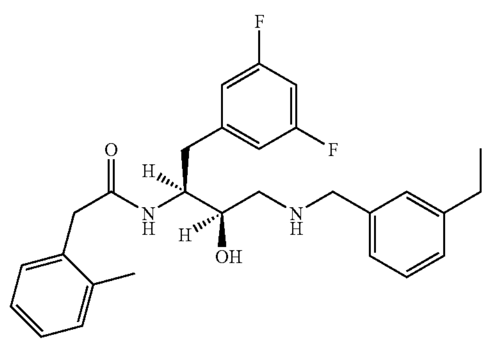 | N-{(1S,2R)-1-(3,5-difluoro-benzyl)-3-[(3-ethylbenzyl)amino]-2-hydroxypropyl}-2-(2-methylphenyl)acetamide | |
| 3473 | 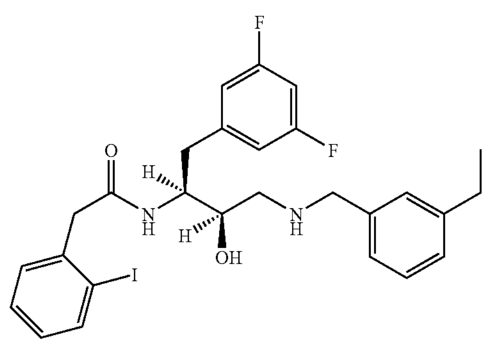 | N-{(1S,2R)-1-(3,5-difluoro-benzyl)-3-[(3-ethylbenzyl)amino]-2-hydroxypropyl}-2-(2-iodophenyl)acetamide | |
| 3474 | 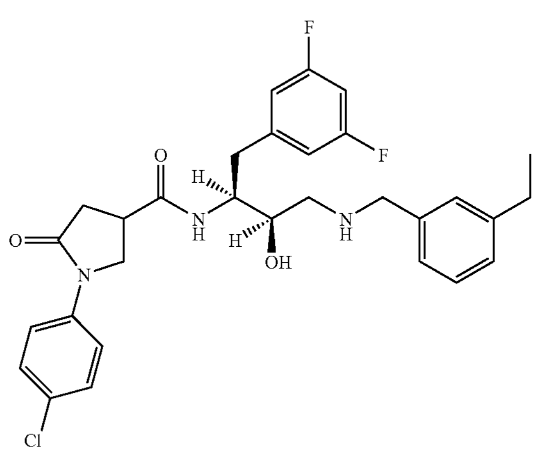 | 1-(4-chlorophenyl)-N-{(1S,2R)-1-(3,5-difluoro-benzyl)-3-[(3-ethylbenzyl)amino]-2-hydroxypropyl}-5-oxopyrrolidine-3-carboxamide | |

-continued

| EXAM-PLE | Structure | Compound Name(s) | Mass Spec |
|---|---|---|---|
| 3475 | 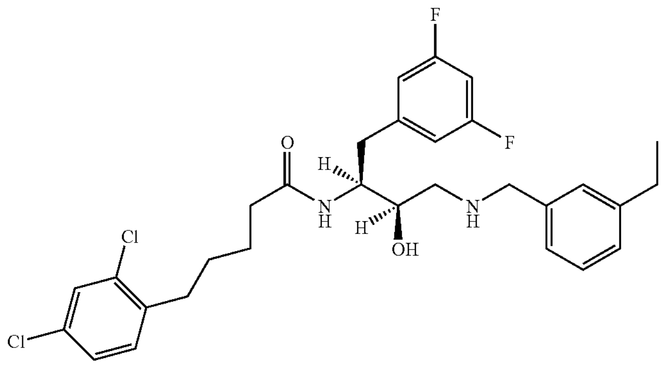 | 4-(2,4-dichlorophenoxy)-N-{(1S,2R)-1-(3,5-difluoro-benzyl)-3-[(3-ethylbenzyl)amino]-2-hydroxypropyl}butanamide | |
| 3476 | 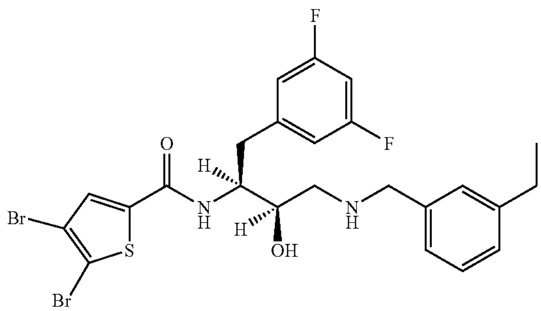 | 4,5-dibromo-N-{(1S,2R)-1-(3,5-difluorobenzyl)-3-[(3-ethylbenzyl)amino]-2-hydroxypropyl}thiophene-2-carboxamide | |
| 3477 | 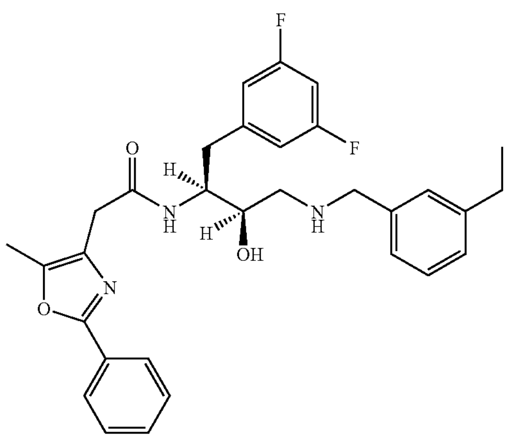 | N-{(1S,2R)-1-(3,5-difluoro-benzyl)-3-[(3-ethylbenzyl)amino]-2-hydroxypropyl}-2-(5-methyl-2-phenyl-1,3-oxazol-4-yl)acetamide | |
| 3478 | 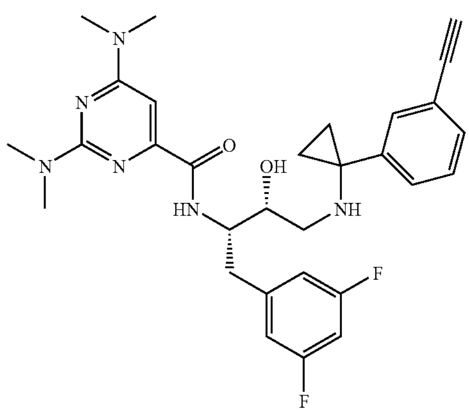 | N-((1S,2R)-1-(3,5-difluoro-benzyl)-3-{[1-(3-ethynyl-phenyl)cyclopropyl]amino}-2-hydroxypropyl)-2,6-bis(dimethylamino)pyrimidine-4-carboxamide | |

-continued

| EXAMPLE | Structure | Compound Name(s) | Mass Spec |
|---|---|---|---|
| 3479 | 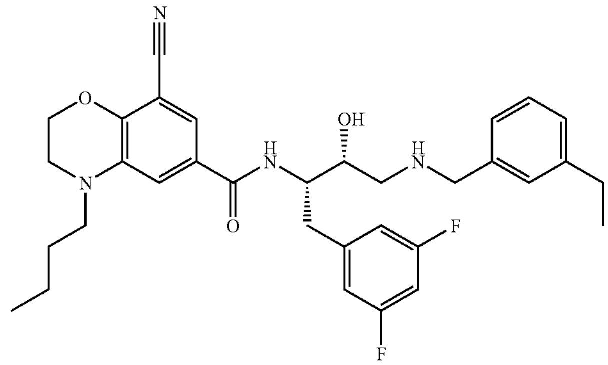 | 4-butyl-8-cyano-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide | **577 |
| 3480 | 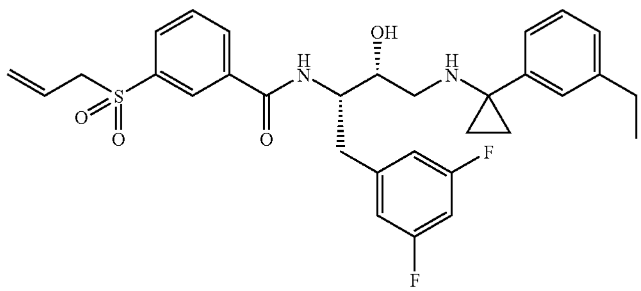 | 3-(allylsulfonyl)-N-((1S,2R)-1-(3,5-difluorobenzyl)-3-{[1-(3-ethylphenyl)cyclopropyl]amino}-2-hydroxypropyl)benzamide | **569.8 |
| 3481 | 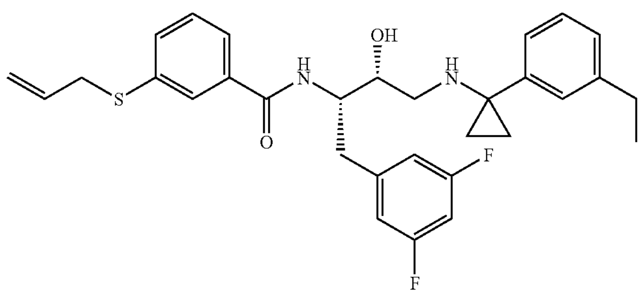 | 3-(allylthio)-N-((1S,2R)-1-(3,5-difluorobenzyl)-3-{[1-(3-ethylphenyl)cyclopropyl]amino}-2-hydroxypropyl)benzamide | **537.8 |
| 3484 | 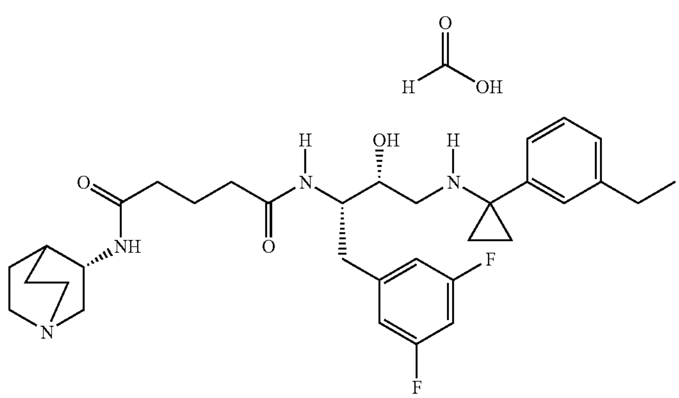 | formic acid compound with N¹-[(3S)-1-azabicyclo[2.2.2]oct-3-yl]-N⁵-((1S,2R)-1-(3,5-difluorobenzyl)-3-{[1-(3-ethylphenyl)cyclopropyl]amino}-2-hydroxypropyl)pentanediamide (1:1) | **583.3 |

-continued

| EXAMPLE | Structure | Compound Name(s) | Mass Spec |
|---|---|---|---|
| 3485 | 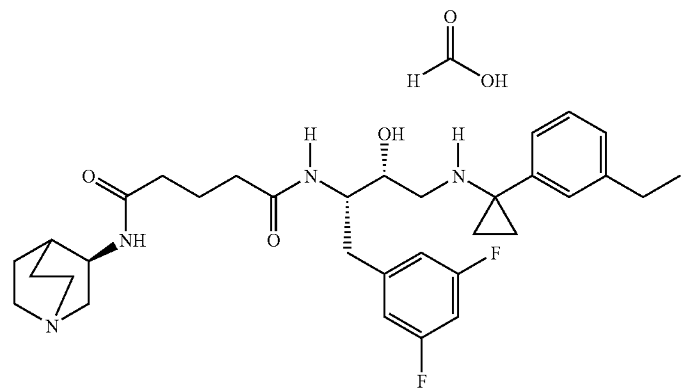 | formic acid compound with $N^1$-[(3R)-1-azabicyclo[2.2.2]oct-3-yl]-$N^5$-((1S,2R)-1-(3,5-difluorobenzyl)-3-{[1-(3-ethylphenyl)cyclopropyl]amino}-2-hydroxypropyl)pentanediamide (1:1) | **583.3 |
| 3486 | 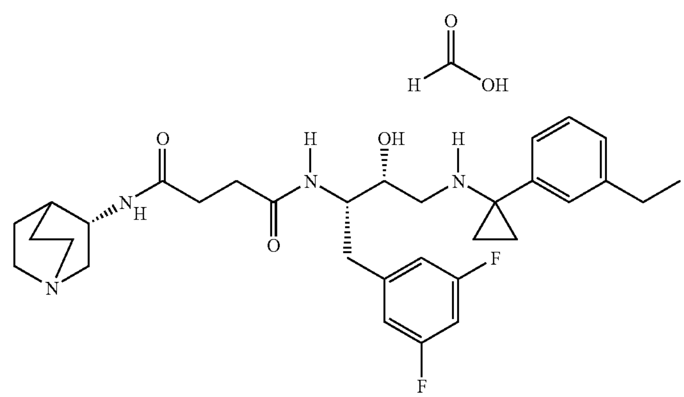 | formic acid compound with $N^1$-[(3S)-1-azabicyclo[2.2.2]oct-3-yl]-$N^4$-((1S,2R)-1-(3,5-difluorobenzyl)-3-{[1-(3-ethylphenyl)cyclopropyl]amino}-2-hydroxypropyl)succinamide (1:1) | **569.3 |
| 3487 | 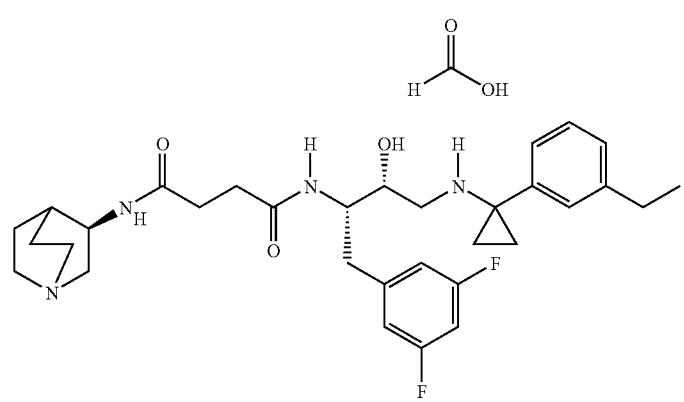 | formic acid compound with $N^1$-[(3R)-1-azabicyclo[2.2.2]oct-3-yl]-$N^4$-((1S,2R)-1-(3,5-difluorobenzyl)-3-{[1-(3-ethylphenyl)cyclopropyl]amino}-2-hydroxypropyl)succinamide (1:1) | **569.3 |

-continued

| EXAMPLE | Structure | Compound Name(s) | Mass Spec |
|---|---|---|---|
| 3490 | 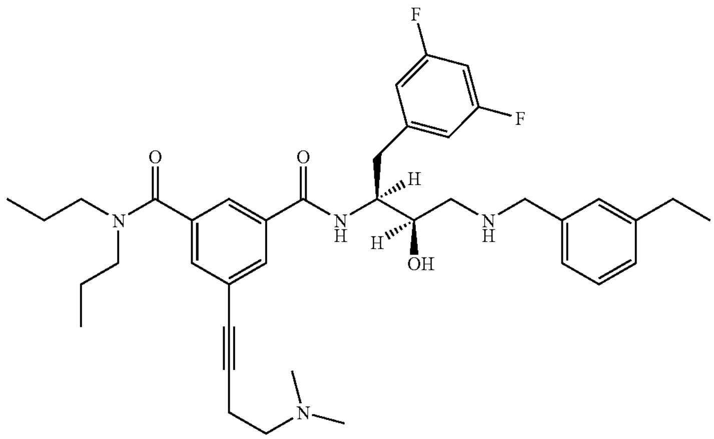 | $N^1$-{(1S,2R)-1-(3,5-difluorobenzyl)-3-[(3-ethylbenzyl)amino]-2-hydroxypropyl}-5-[4-(dimethylamino)but-1-ynyl]-$N^3$,$N^3$-dipropylisophthalamide or ELAN158095 | |
| 3491 | 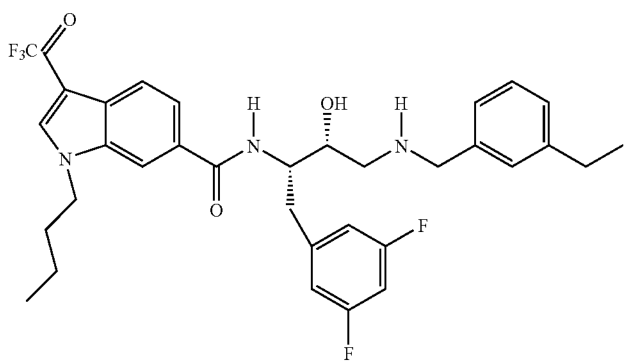 | 1-butyl-N-{(1S,2R)-1-(3,5-difluorobenzyl)-3-[(3-ethylbenzyl)amino]-2-hydroxypropyl}-3-(trifluoroacetyl)-1H-indole-6-carboxamide | |
| 3492 | 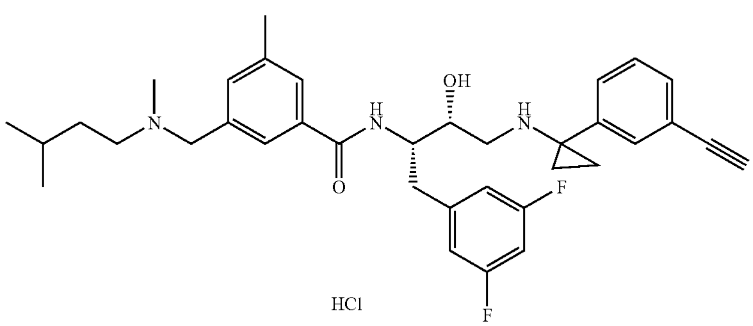 | N-((1S,2R)-1-(3,5-difluorobenzyl)-3-{[1-(3-ethynylphenyl)cyclopropyl]amino}-2-hydroxypropyl)-3-{[isopentyl(methyl)amino]methyl}-5-methylbenzamide hydrochloride | **588.3 |
| 3493 | 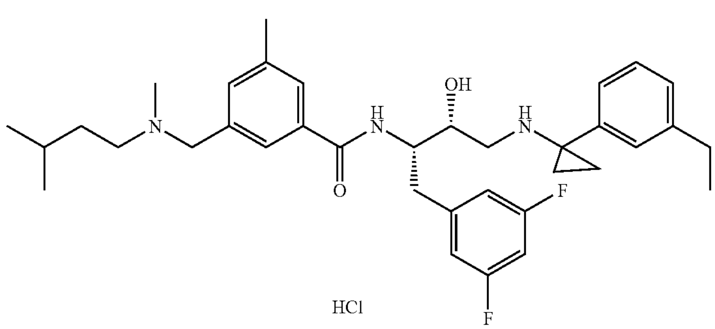 | N-((1S,2R)-1-(3,5-difluorobenzyl)-3-{[1-(3-ethylphenyl)cyclopropyl]amino}-2-hydroxypropyl)-3-{[isopentyl(methyl)amino]methyl}-5-methylbenzamide hydrochloride | **592.3 |

-continued

| EXAMPLE | Structure | Compound Name(s) | Mass Spec |
|---|---|---|---|
| 3494 | 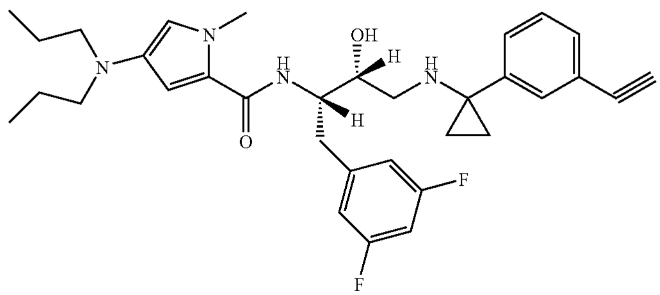 | N-((1S,2R)-1-(3,5-difluoro-benzyl)-3-{[1-(3-ethynyl phenyl)cyclopropyl]amino}-2-hydroxypropyl)-4-(dipropyl-amino)-1-methyl-1H-pyrrole-2-carboxamide | |
| 3495 | 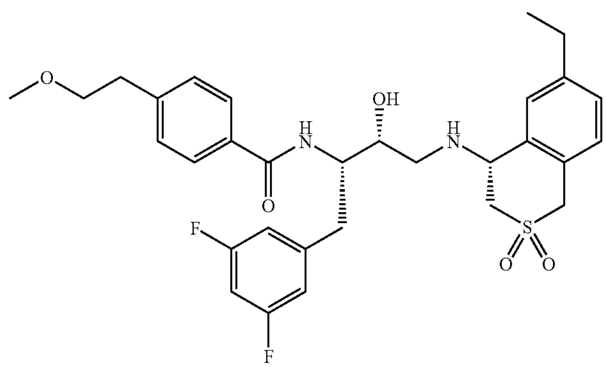 | N-((1S,2R)-1-(3,5-difluoro-benzyl)-3-{[(4R)-6-ethyl-2,2-dioxido-3,4-dihydro-1H-isothiochromen-4-yl]amino}-2-hydroxypropyl)-4-(2-methoxyethyl)benzamide | |
| 3496 | 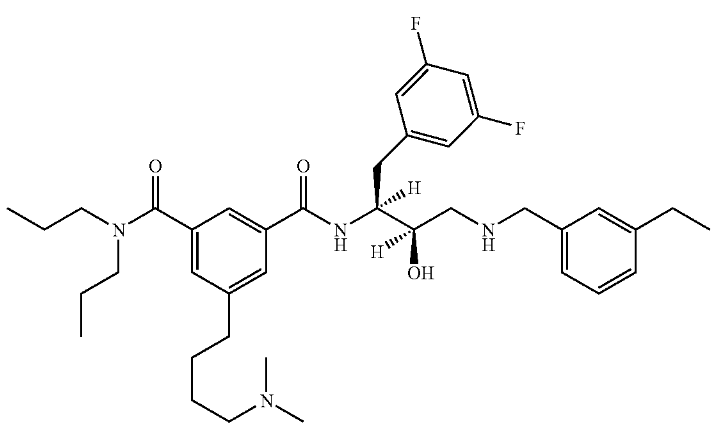 | $N^1$-{(1S,2R)-1-(3,5-difluoro-benzyl)-3-[(3-ethylbenzyl) amino]-2-hydroxypropyl}-5-[4-(dimethylamino)butyl]-$N^3,N^3$-dipropylisophthalamide or ELAN158113 | |
| 3497 | 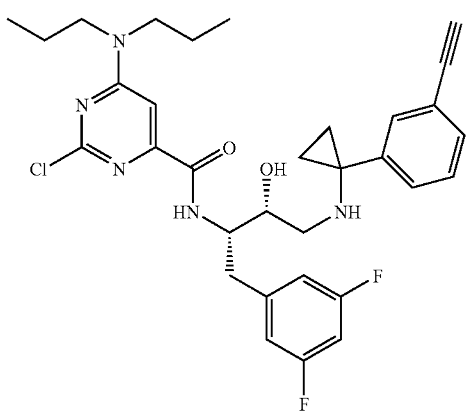 | ELAN-158116 | |

-continued

| EXAMPLE | Structure | Compound Name(s) | Mass Spec |
|---|---|---|---|
| 3500 | 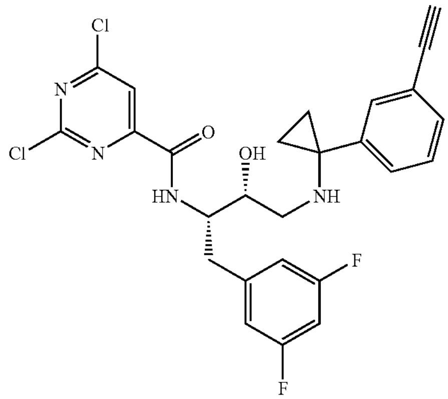 | ELAN-158128 2,6-dichloro-N-((1S,2R)-1-(3,5-difluorobenzyl)-3-{[1-(3-ethynylphenyl)cyclopropyl]amino}-2-hydroxypropyl)pyrimidine-4-carboxamide | |
| 3503 | 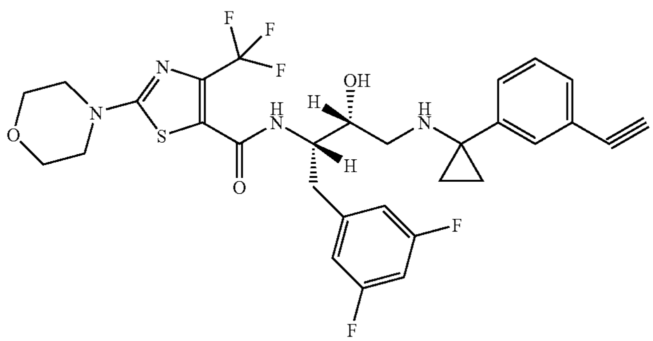 | N-((1S,2R)-1-(3,5-difluoro-benzyl)-3-{[1-(3-ethynyl-phenyl)cyclopropyl]amino}-2-hydroxypropyl)-2-morpholin-4-yl-4-(trifluoromethyl)-1,3-thiazole-5-carboxamide | |
| 3506 | 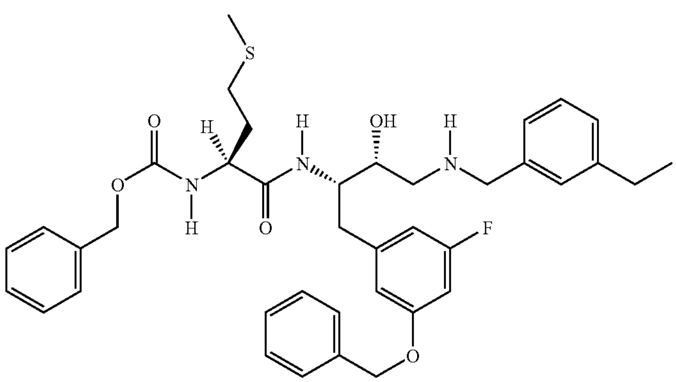 | | **688 |
| 3507 | 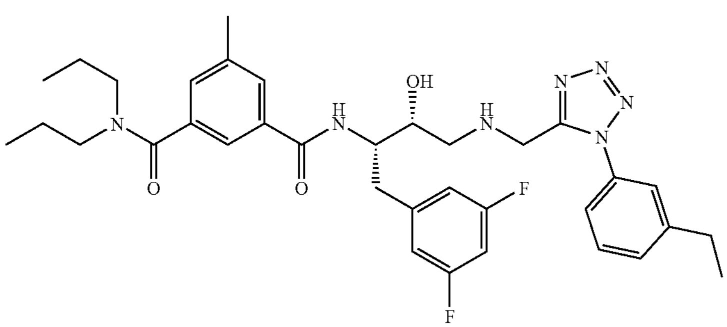 | $N^1$-[(1S,2R)-1-(3,5-difluoro-benzyl)-3-({[1-(3-ethyl-phenyl)-1H-tetraazol-5-yl]methyl}amino)-2-hydroxy-propyl]-5-methyl-$N^3,N^3$-dipropylisophthalamide | **648 |

-continued

| EXAMPLE | Structure | Compound Name(s) | Mass Spec |
|---|---|---|---|
| 3508 | 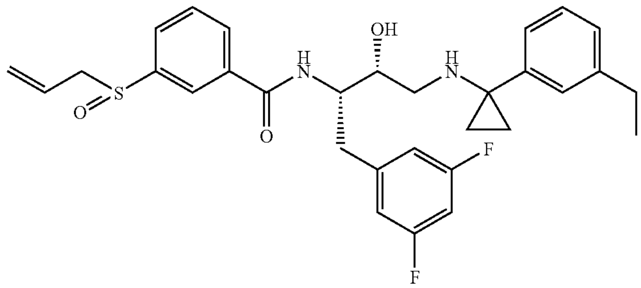 | 3-(allylsulfinyl)-N-((1S,2R)-1-(3,5-difluorobenzyl)-3-{[1-(3-ethylphenyl)cyclopropyl]amino}-2-hydroxypropyl)benzamide | **553.8 |
| 3520 | 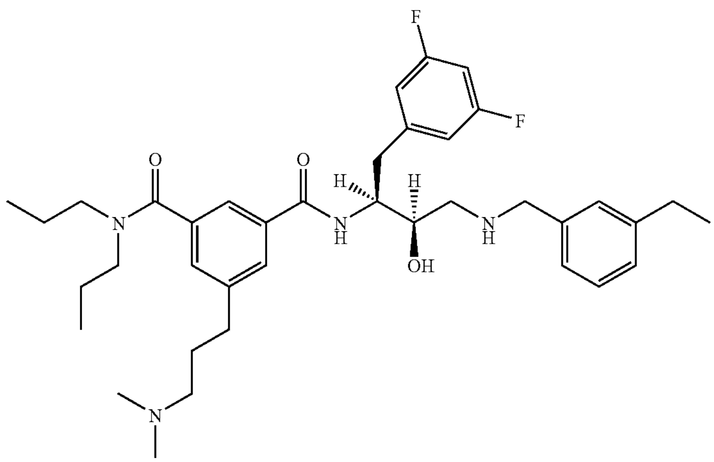 | $N^1$-{(1S,2R)-1-(3,5-difluorobenzyl)-3-[(3-ethylbenzyl)amino]-2-hydroxypropyl}-5-[3-(dimethylamino)propyl]-$N^3,N^3$-dipropylisophthalamide | |
| 3521 | 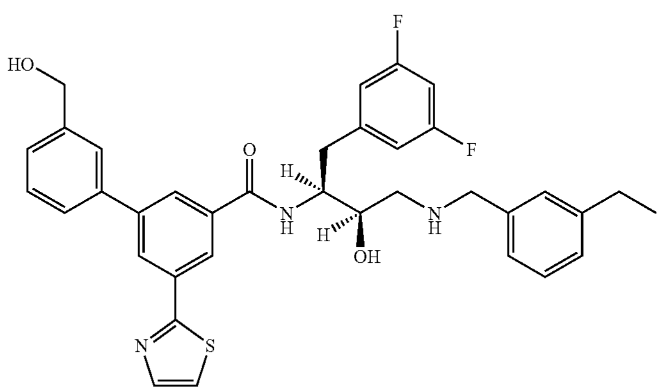 | N-{(1S,2R)-1-(3,5-difluorobenzyl)-3-[(3-ethylbenzyl)amino]-2-hydroxypropyl}-3'-(hydroxymethyl)-5-(1,3-thiazol-2-yl)-1,1'-biphenyl-3-carboxamide | |
| 3522 | 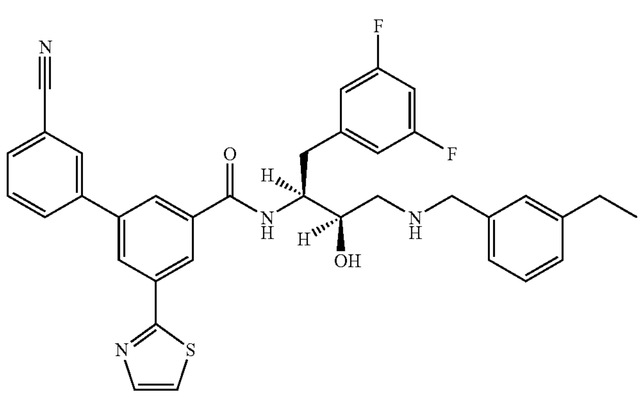 | 3'-cyano-N-{(1S,2R)-1-(3,5-difluorobenzyl)-3-[(3-ethylbenzyl)amino]-2-hydroxypropyl}-5-(1,3-thiazol-2-yl)-1,1'-biphenyl-3-carboxamide | |

| EXAMPLE | Structure | Compound Name(s) | Mass Spec |
|---|---|---|---|
| 3523 | 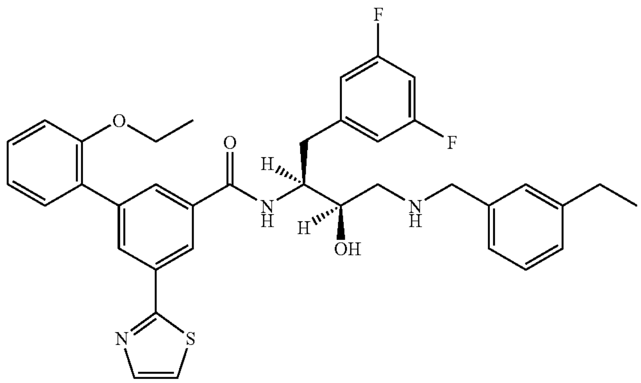 | N-{(1S,2R)-1-(3,5-difluorobenzyl)-3-[(3-ethylbenzyl)amino]-2-hydroxypropyl}-2'-ethoxy-5-(1,3-thiazol-2-yl)-1,1'-biphenyl-3-carboxamide | |
| 3524 | 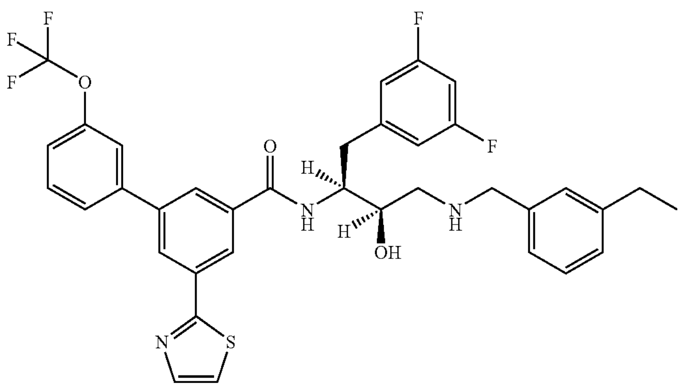 | N-{(1S,2R)-1-(3,5-difluorobenzyl)-3-[(3-ethylbenzyl)amino]-2-hydroxypropyl}-5-(1,3-thiazol-2-yl)-3'-(trifluoromethoxy)-1,1'-biphenyl-3-carboxamide | |
| 3525 | 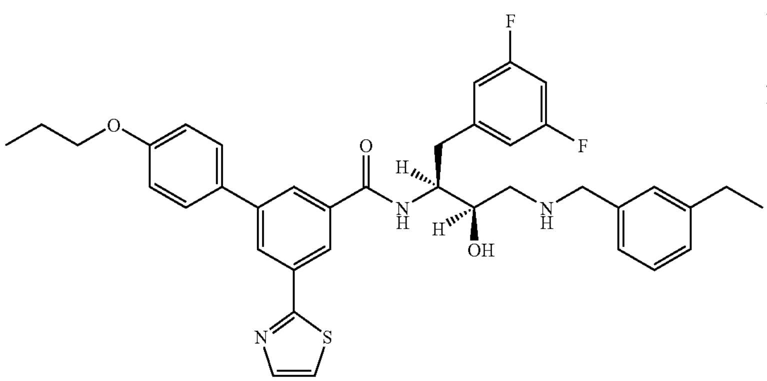 | N-{(1S,2R)-1-(3,5-difluorobenzyl)-3-[(3-ethylbenzyl)amino]-2-hydroxypropyl}-4'-propoxy-5-(1,3-thiazol-2-yl)-1,1'-biphenyl-3-carboxamide | |
| 3526 | 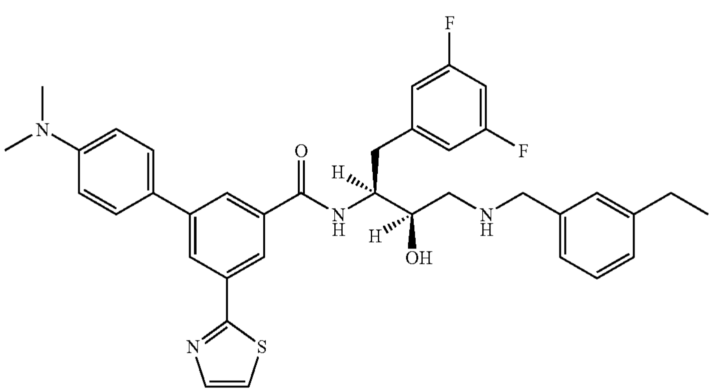 | N-{(1S,2R)-1-(3,5-difluorobenzyl)-3-[(3-ethylbenzyl)amino]-2-hydroxypropyl}-4'-(dimethylamino)-5-(1,3-thiazol-2-yl)-1,1'-biphenyl-3-carboxamide | |

-continued

| EXAMPLE | Structure | Compound Name(s) | Mass Spec |
|---|---|---|---|
| 3527 | 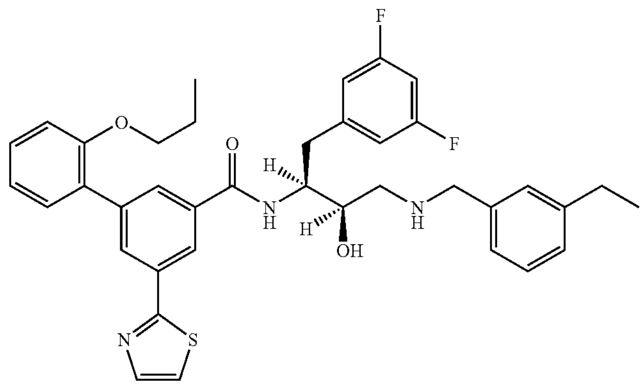 | N-{(1S,2R)-1-(3,5-difluorobenzyl)-3-[(3-ethylbenzyl)amino]-2-hydroxypropyl}-2'-propoxy-5-(1,3-thiazol-2-yl)-1,1'-biphenyl-3-carboxamide | |
| 3528 | 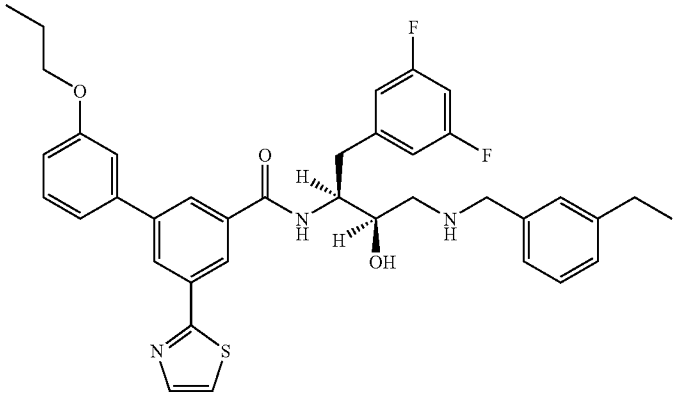 | N-{(1S,2R)-1-(3,5-difluorobenzyl)-3-[(3-ethylbenzyl)amino]-2-hydroxypropyl}-3'-propoxy-5-(1,3-thiazol-2-yl)-1,1'-biphenyl-3-carboxamide | |
| 3529 | 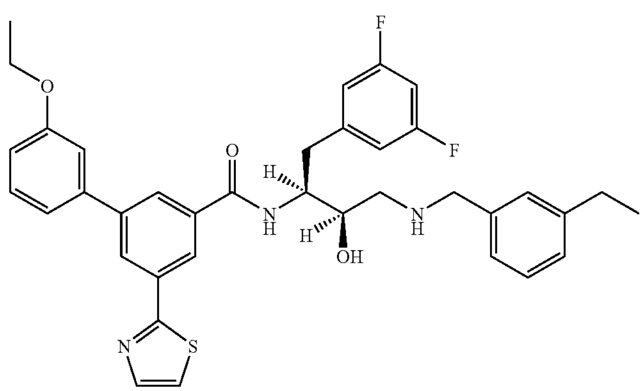 | N-{(1S,2R)-1-(3,5-difluorobenzyl)-3-[(3-ethylbenzyl)amino]-2-hydroxypropyl}-3'-ethoxy-5-(1,3-thiazol-2-yl)-1,1'-biphenyl-3-carboxamide | |
| 3530 | 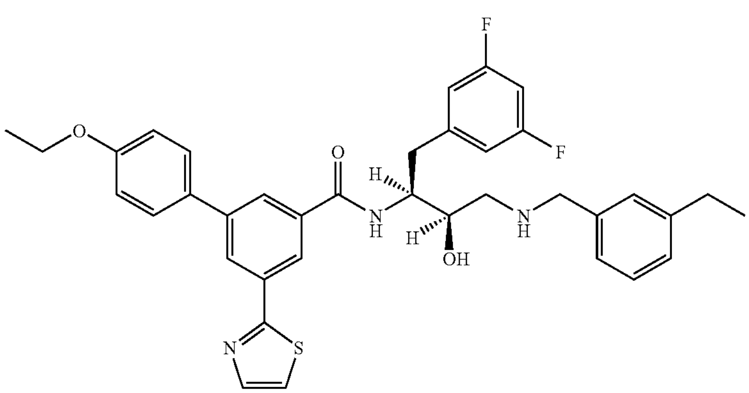 | N-{(1S,2R)-1-(3,5-difluorobenzyl)-3-[(3-ethylbenzyl)amino]-2-hydroxypropyl}-4'-ethoxy-5-(1,3-thiazol-2-yl)-1,1'-biphenyl-3-carboxamide | |

-continued

| EXAMPLE | Structure | Compound Name(s) | Mass Spec |
|---|---|---|---|
| 3531 | 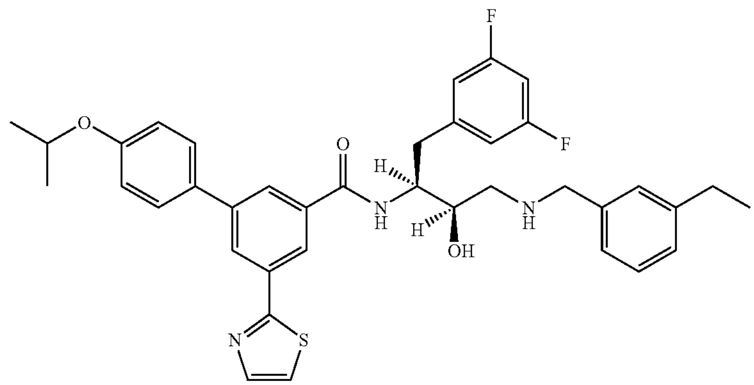 | N-{(1S,2R)-1-(3,5-difluorobenzyl)-3-[(3-ethylbenzyl)amino]-2-hydroxypropyl}-4'-isopropoxy-5-(1,3-thiazol-2-yl)-1,1'-biphenyl-3-carboxamide | |
| 3532 | 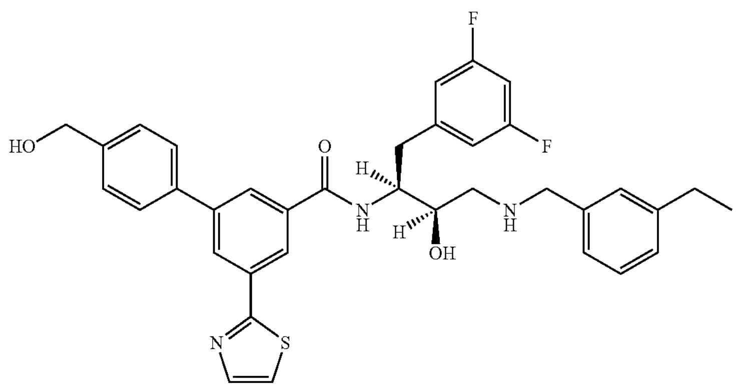 | N-{(1S,2R)-1-(3,5-difluorobenzyl)-3-[(3-ethylbenzyl)amino]-2-hydroxypropyl}-4'-(hydroxymethyl)-5-(1,3-thiazol-2-yl)-1,1'-biphenyl-3-carboxamide | |
| 3533 | 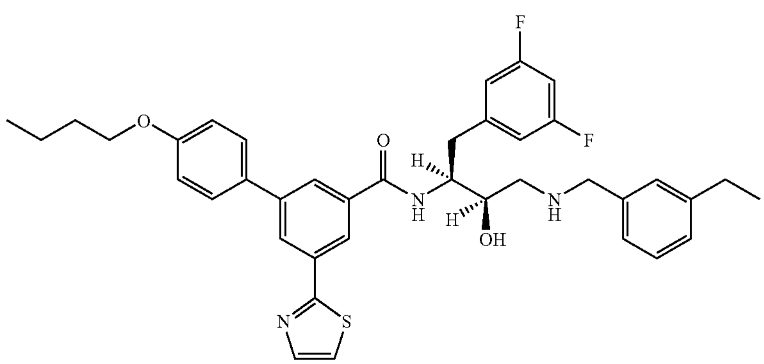 | 4'-butoxy-N-{(1S,2R)-1-(3,5-difluorobenzyl)-3-[(3-ethylbenzyl)amino]-2-hydroxypropyl}-5-(1,3-thiazol-2-yl)-1,1'-biphenyl-3-carboxamide | |
| 3534 | 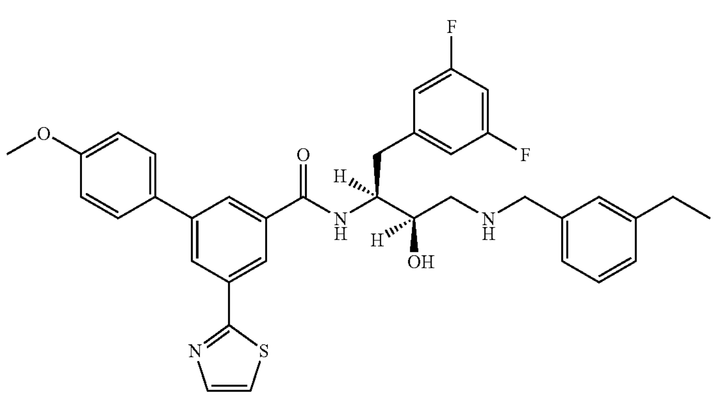 | N-{(1S,2R)-1-(3,5-difluorobenzyl)-3-[(3-ethylbenzyl)amino]-2-hydroxypropyl}-4'-methoxy-5-(1,3-thiazol-2-yl)-1,1'-biphenyl-3-carboxamide | |

-continued

| EXAMPLE | Structure | Compound Name(s) | Mass Spec |
|---|---|---|---|
| 3535 | 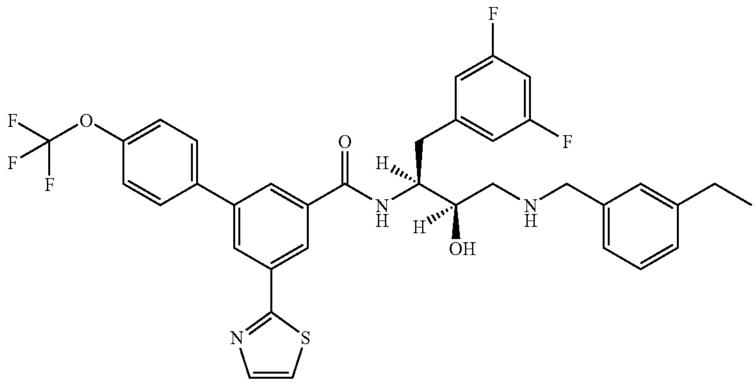 | N-{(1S,2R)-1-(3,5-difluorobenzyl)-3-[(3-ethylbenzyl)amino]-2-hydroxypropyl}-5-(1,3-thiazol-2-yl)-4'-(trifluoromethoxy)-1,1'-biphenyl-3-carboxamide | |
| 3536 | 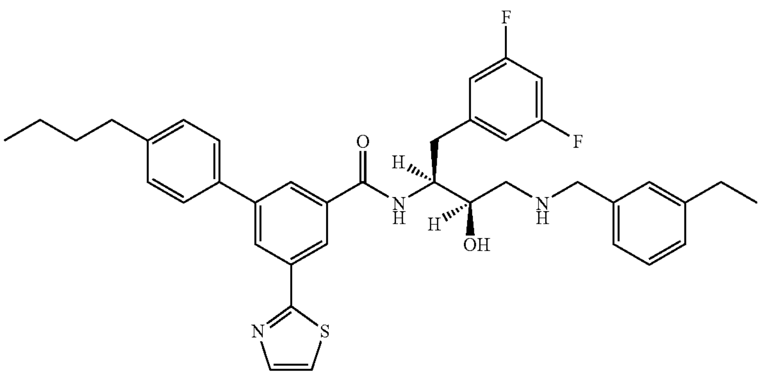 | 4'-butyl-N-{(1S,2R)-1-(3,5-difluorobenzyl)-3-[(3-ethylbenzyl)amino]-2-hydroxypropyl}-5-(1,3-thiazol-2-yl)-1,1'-biphenyl-3-carboxamide | |
| 3537 | 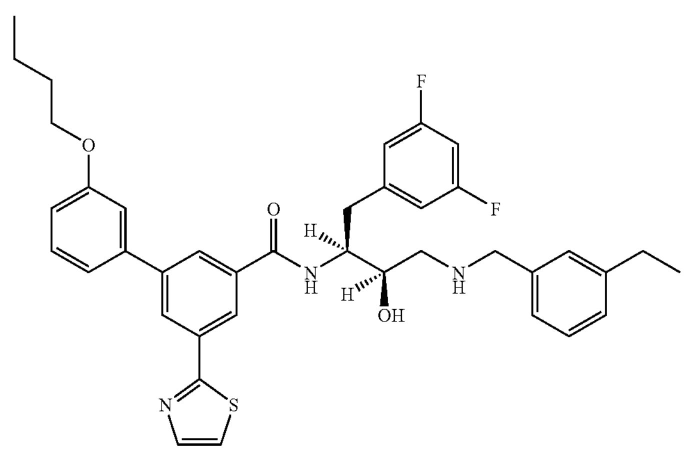 | 3'-butoxy-N-{(1S,2R)-1-(3,5-difluorobenzyl)-3-[(3-ethylbenzyl)amino]-2-hydroxypropyl}-5-(1,3-thiazol-2-yl)-1,1'-biphenyl-3-carboxamide | |

| EXAMPLE | Structure | Compound Name(s) | Mass Spec |
|---|---|---|---|
| 3538 | 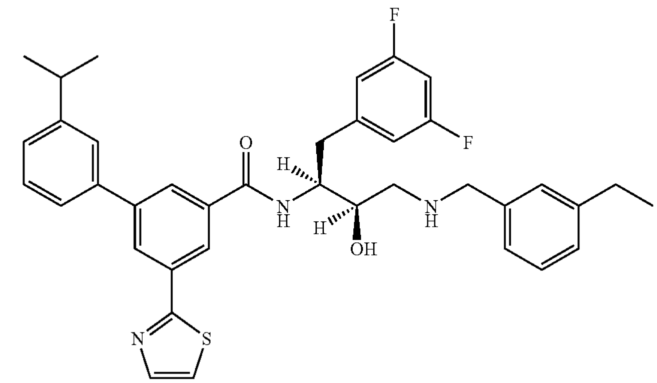 | N-{(1S,2R)-1-(3,5-difluorobenzyl)-3-[(3-ethylbenzyl)amino]-2-hydroxypropyl}-3'-isopropyl-5-(1,3-thiazol-2-yl)-1,1'-biphenyl-3-carboxamide | |
| 3539 | 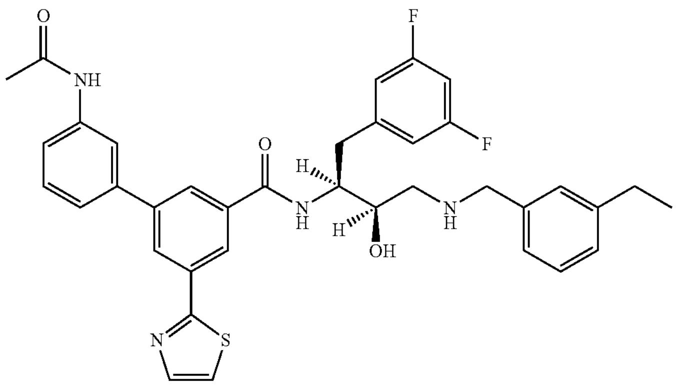 | 3'-(acetylamino)-N-{(1S,2R)-1-(3,5-difluorobenzyl)-3-[(3-ethylbenzyl)amino]-2-hydroxypropyl}-5-(1,3-thiazol-2-yl)-1,1'-biphenyl-3-carboxamide | |
| 3540 | 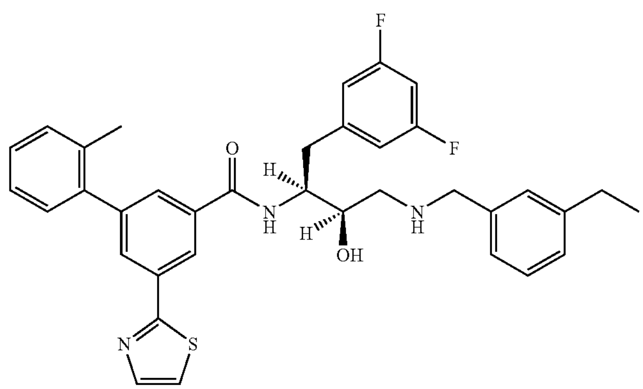 | N-{(1S,2R)-1-(3,5-difluorobenzyl)-3-[(3-ethylbenzyl)amino]-2-hydroxypropyl}-2'-methoxy-5-(1,3-thiazol-2-yl)-1,1'-biphenyl-3-carboxamide | |
| 3541 | 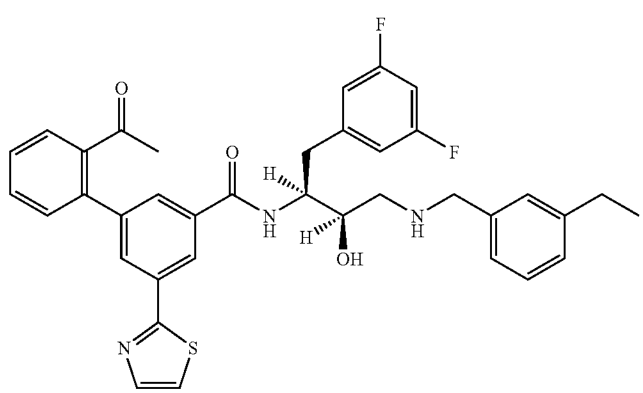 | 2'-acetyl-N-{(1S,2R)-1-(3,5-difluorobenzyl)-3-[(3-ethylbenzyl)amino]-2-hydroxypropyl}-5-(1,3-thiazol-2-yl)-1,1'-biphenyl-3-carboxamide | |

| EXAMPLE | Structure | Compound Name(s) | Mass Spec |
|---|---|---|---|
| 3542 | 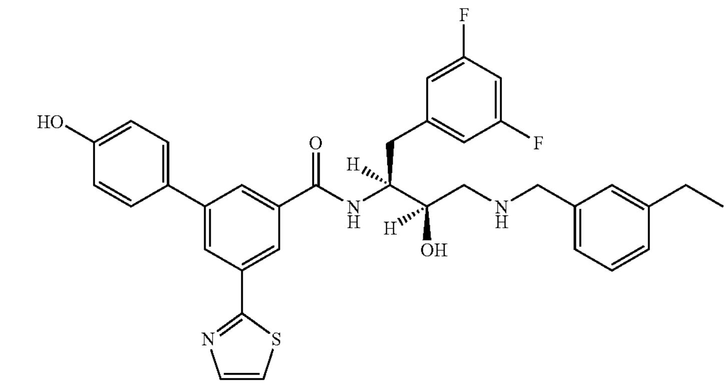 | N-{(1S,2R)-1-(3,5-difluorobenzyl)-3-[(3-ethylbenzyl)amino]-2-hydroxypropyl}-4'-hydroxy-5-(1,3-thiazol-2-yl)-1,1'-biphenyl-3-carboxamide | |
| 3543 | 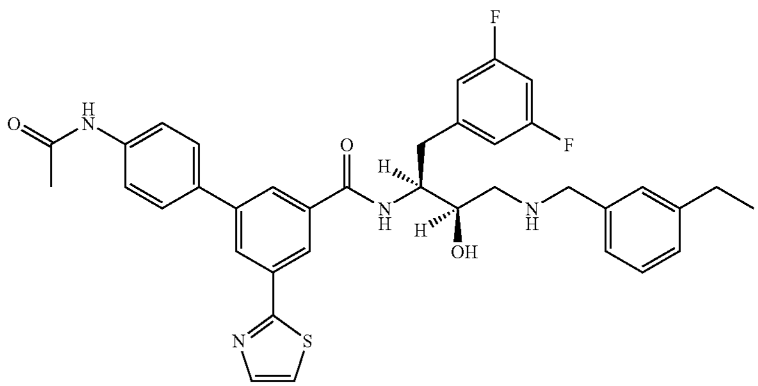 | 4'-(acetylamino)-N-{(1S,2R)-1-(3,5-difluorobenzyl)-3-[(3-ethylbenzyl)amino]-2-hydroxypropyl}-5-(1,3-thiazol-2-yl)-1,1'-biphenyl-3-carboxamide | |
| 3544 | 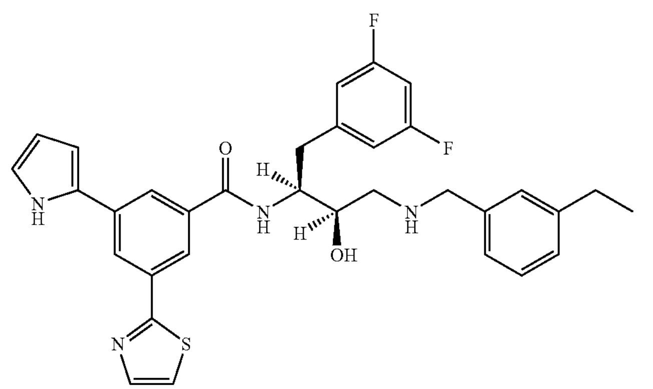 | N-{(1S,2R)-1-(3,5-difluorobenzyl)-3-[(3-ethylbenzyl)amino]-2-hydroxypropyl}-3-(1H-pyrrol-2-yl)-5-(1,3-thiazol-2-yl)benzamide | |
| 3545 | 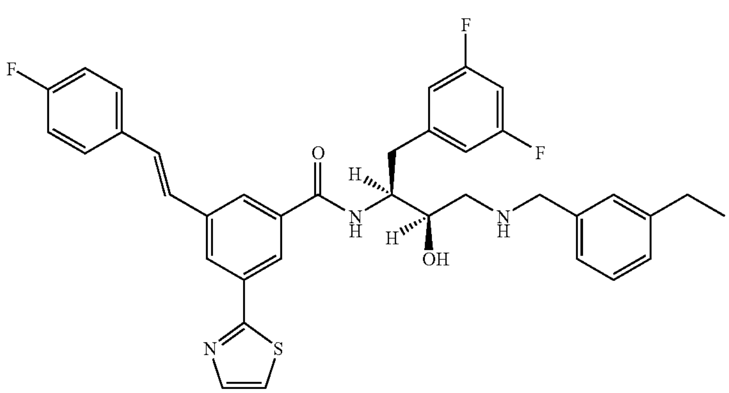 | N-{(1S,2R)-1-(3,5-difluorobenzyl)-3-[(3-ethylbenzyl)amino]-2-hydroxypropyl}-3-[(E)-2-(4-fluorophenyl)ethenyl]-5-(1,3-thiazol-2-yl)benzamide | |

| EXAMPLE | Structure | Compound Name(s) | Mass Spec |
|---|---|---|---|
| 3546 | 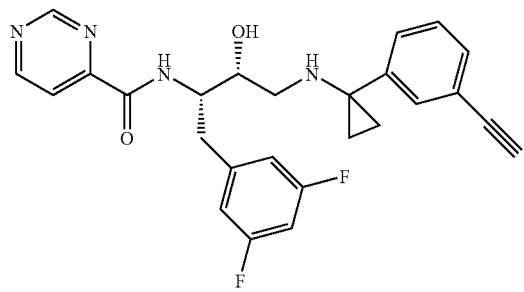 | N-((1S,2R)-1-(3,5-difluoro-benzyl)-3-{[1-(3-ethynyl-phenyl)cyclopropyl]amino}-2-hydroxypropyl)pyrimidine-4-carboxamide | |
| 3549 | 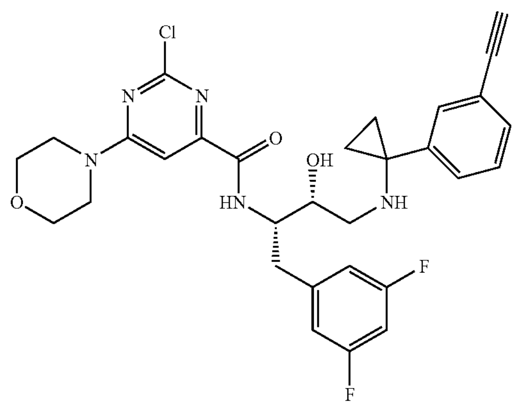 | 2-chloro-N-((1S,2R)-1-(3,5-difluorobenzyl)-3-{[1-(3-ethynylphenyl)cyclopropyl]amino}-2-hydroxypropyl)-6-morpholin-4-ylpyrimidine-4-carboxamide | |
| 3550 | 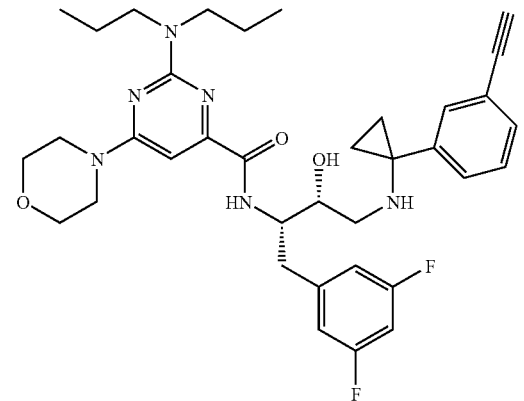 | N-((1S,2R)-1-(3,5-difluoro-benzyl)-3-{[1-(3-ethynyl-phenyl)cyclopropyl]amino}-2-hydroxypropyl)-2-(dipropylamino)-6-morpholin-4-ylpyrimidine-4-carboxamide | |

-continued
| EXAMPLE | Structure | Compound Name(s) | Mass Spec |
|---|---|---|---|
| 3551 | 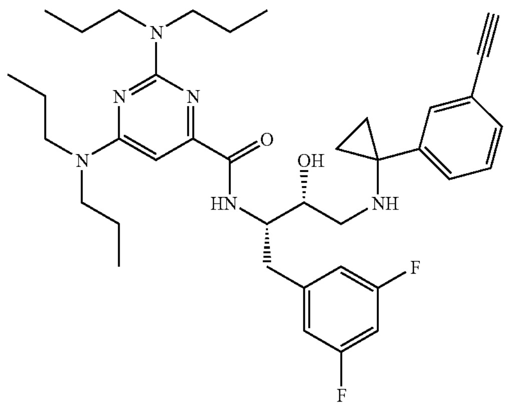 | N-((1S,2R)-1-(3,5-difluorobenzyl)-3-{[1-(3-ethynylphenyl)cyclopropyl]amino}-2-hydroxypropyl)-2,6-bis(dipropylamino)pyrimidine-4-carboxamide | |
*means M/Z (EI)
**means M + H (CI)
***means OAMS
****means MS Data
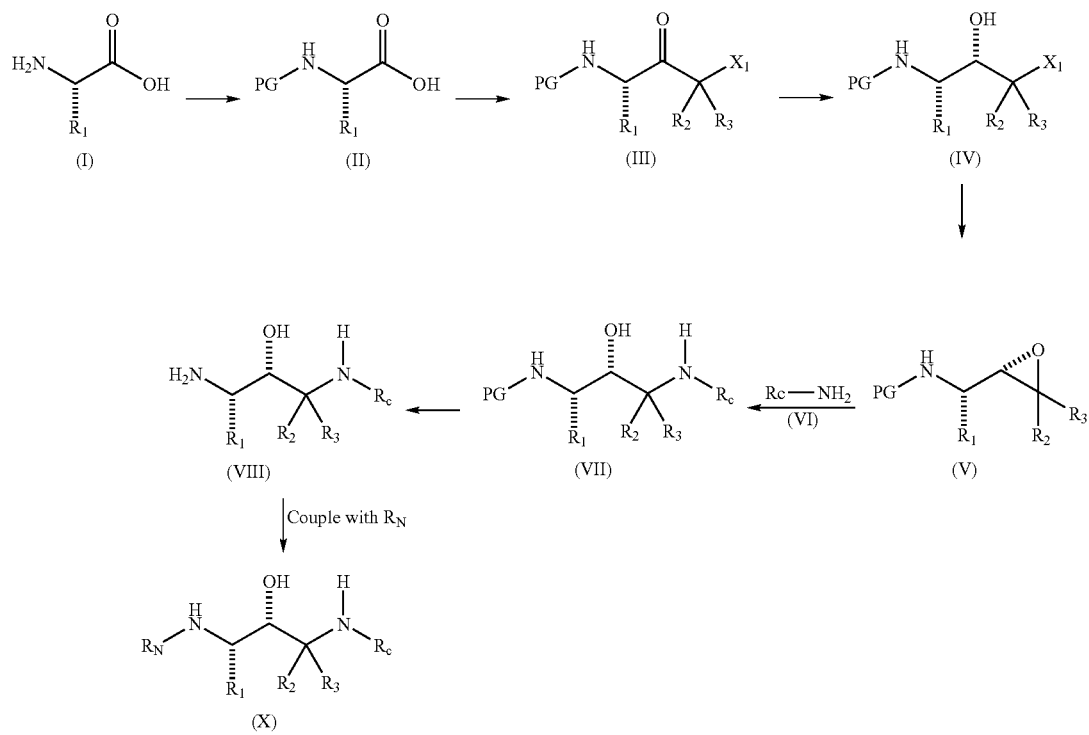
CHART A
PG = protecting group
$X_1$ is a leaving group

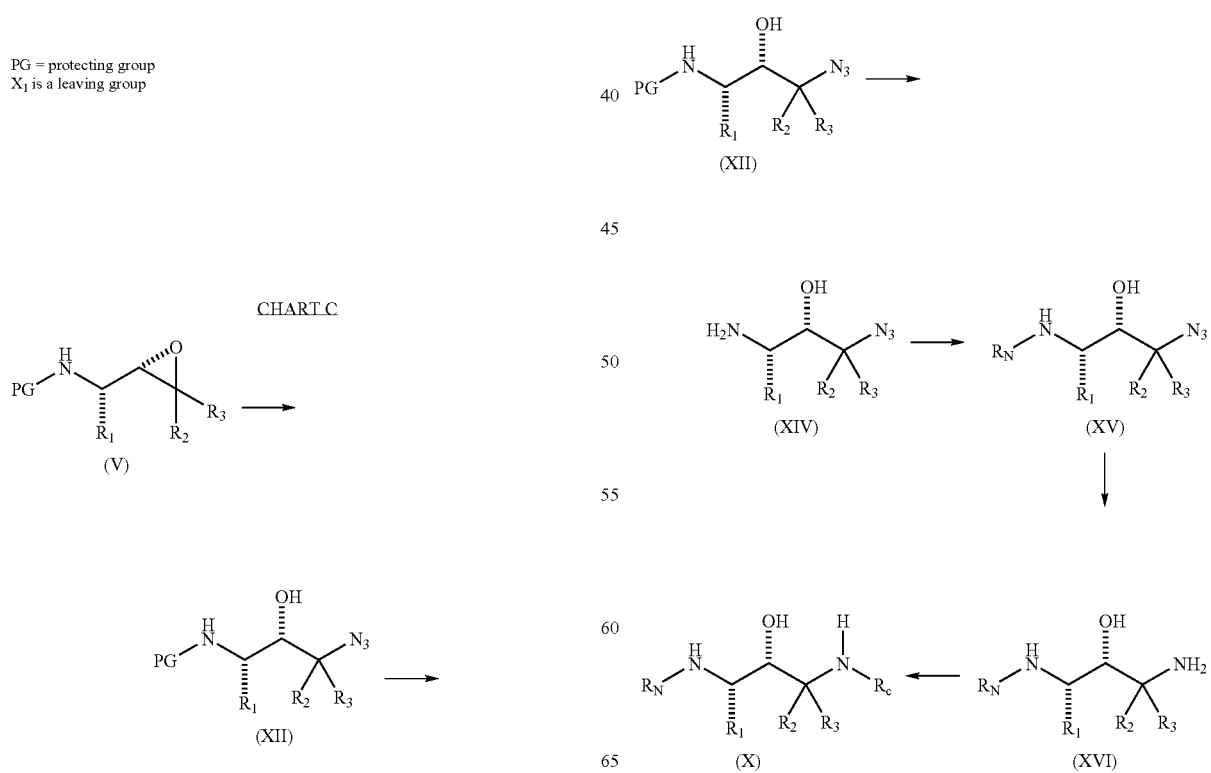

CHART E
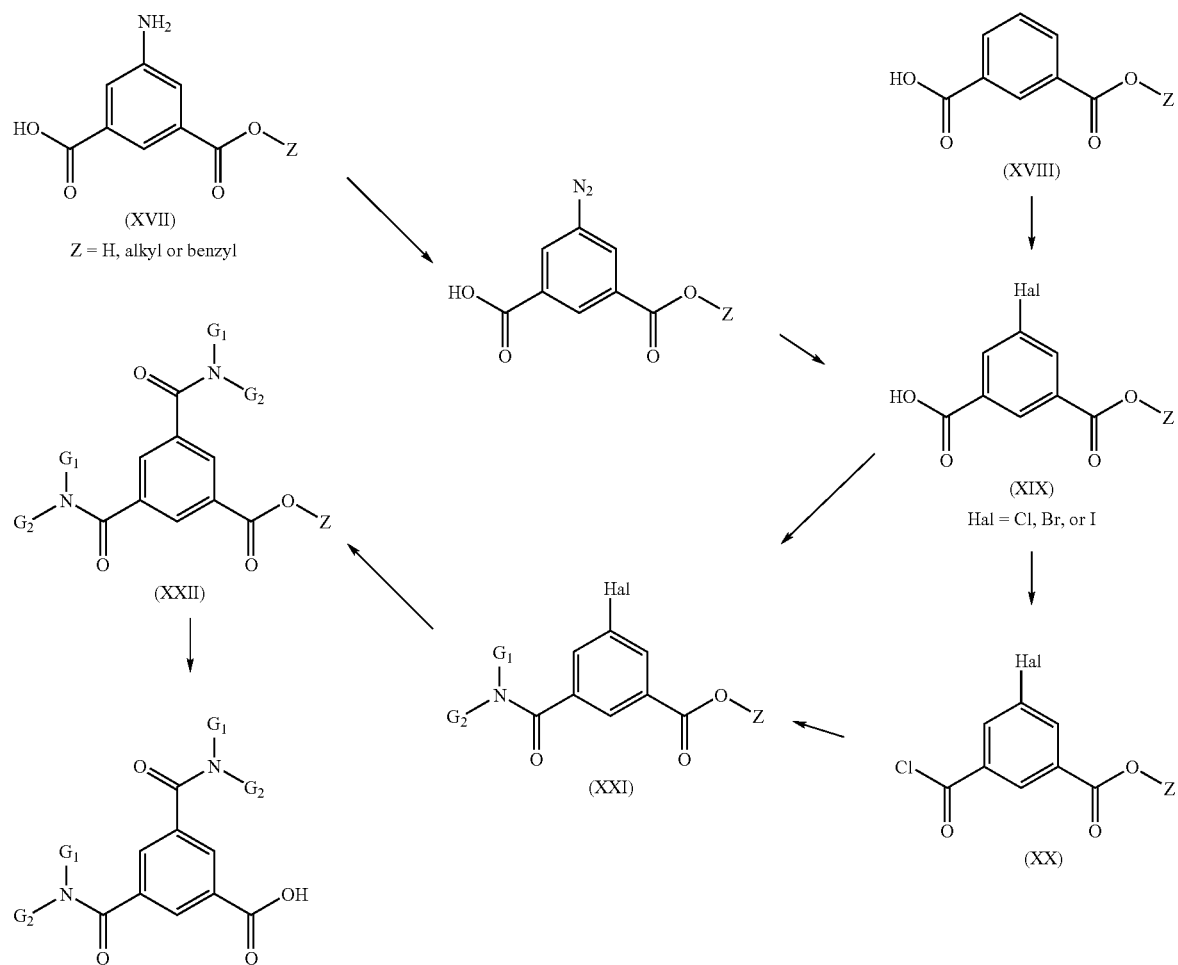
CHART F
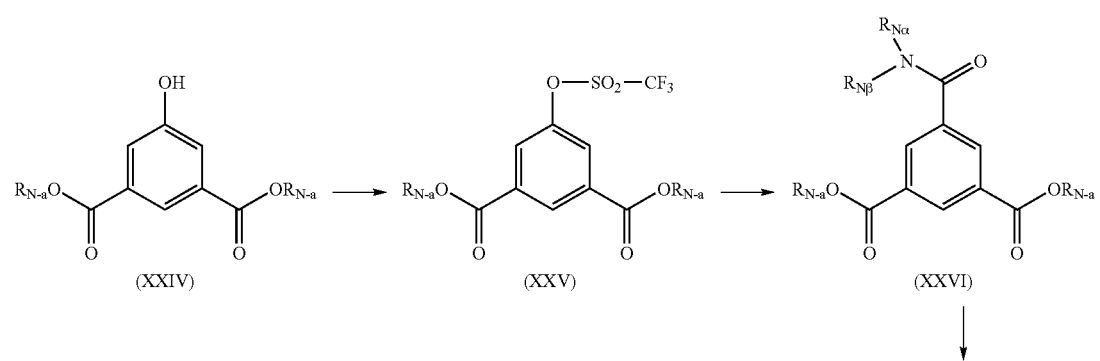

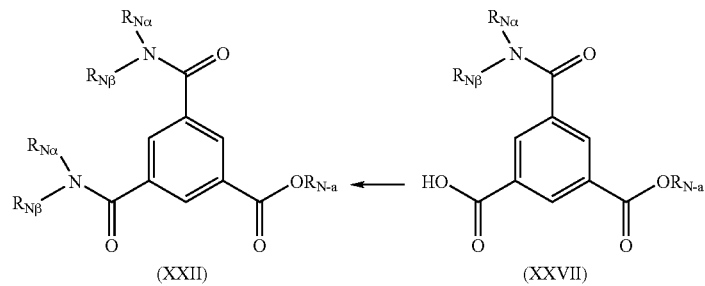
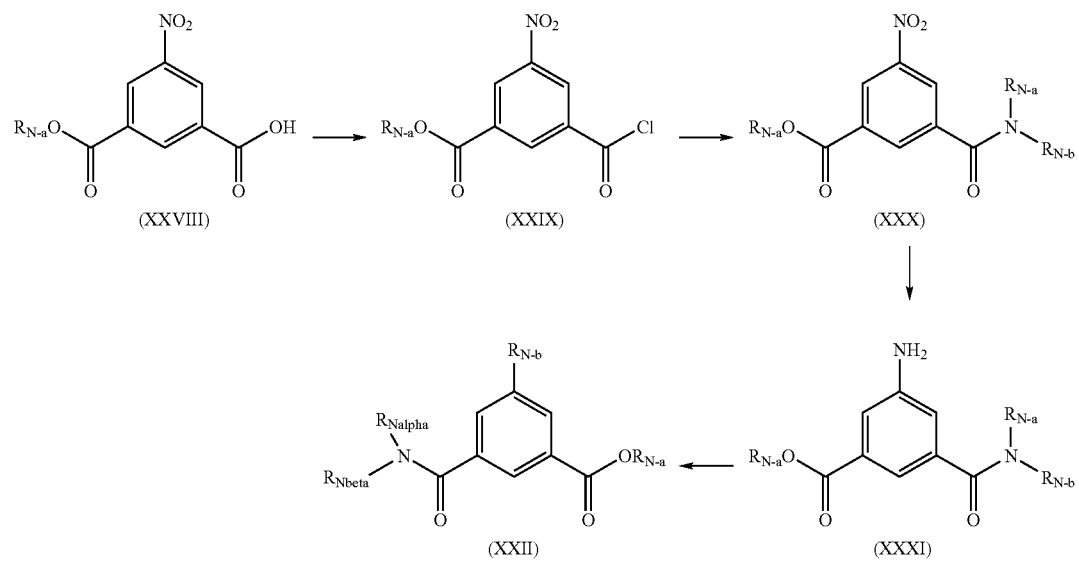
CHART G
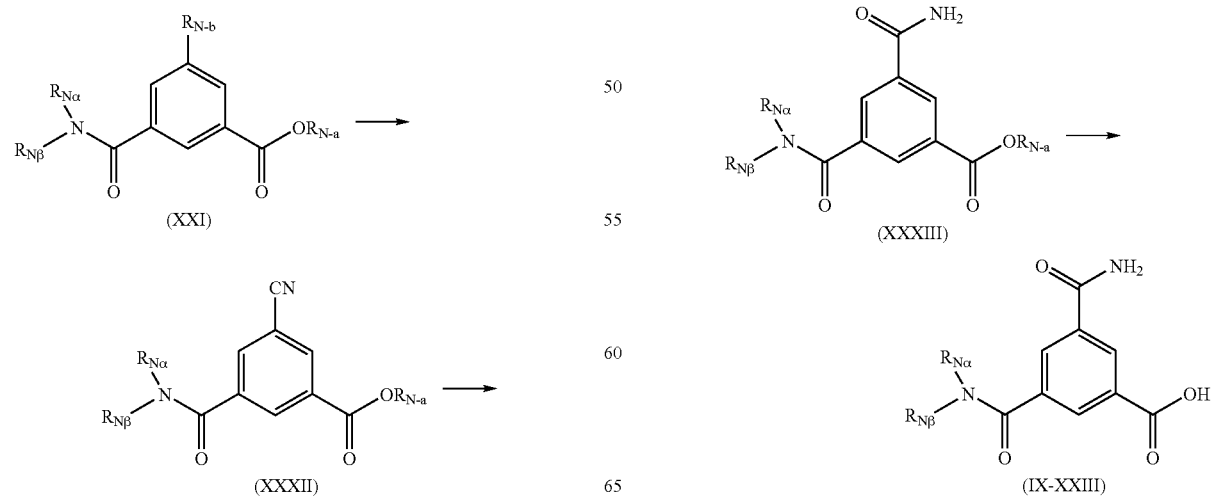
CHART H

CHART I
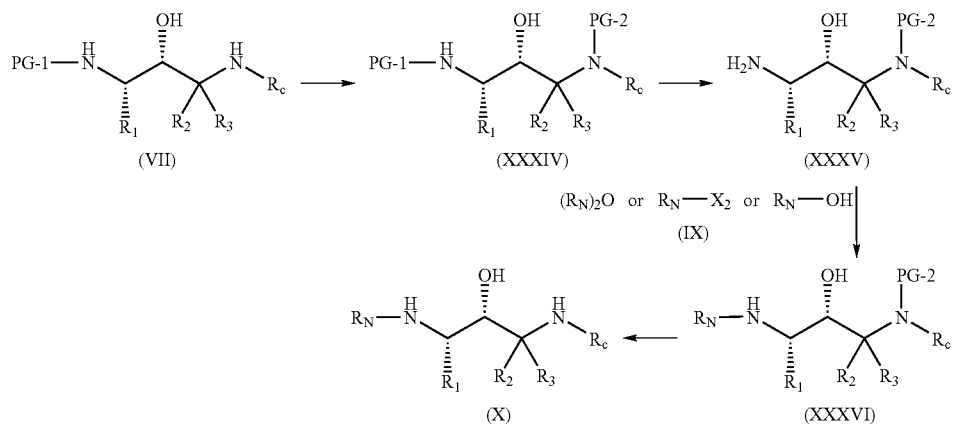
CHART J
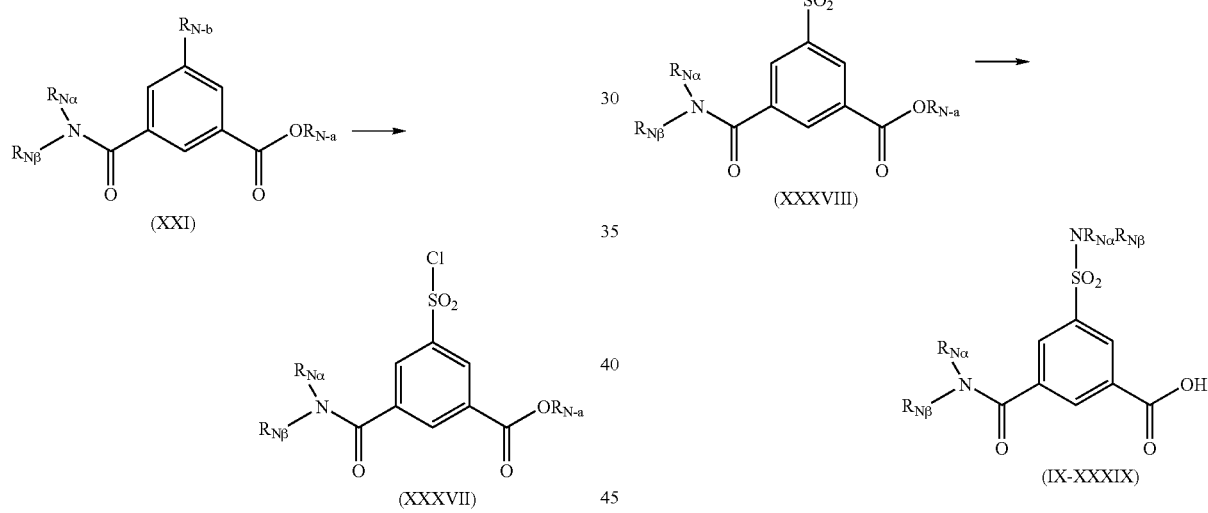
CHART K
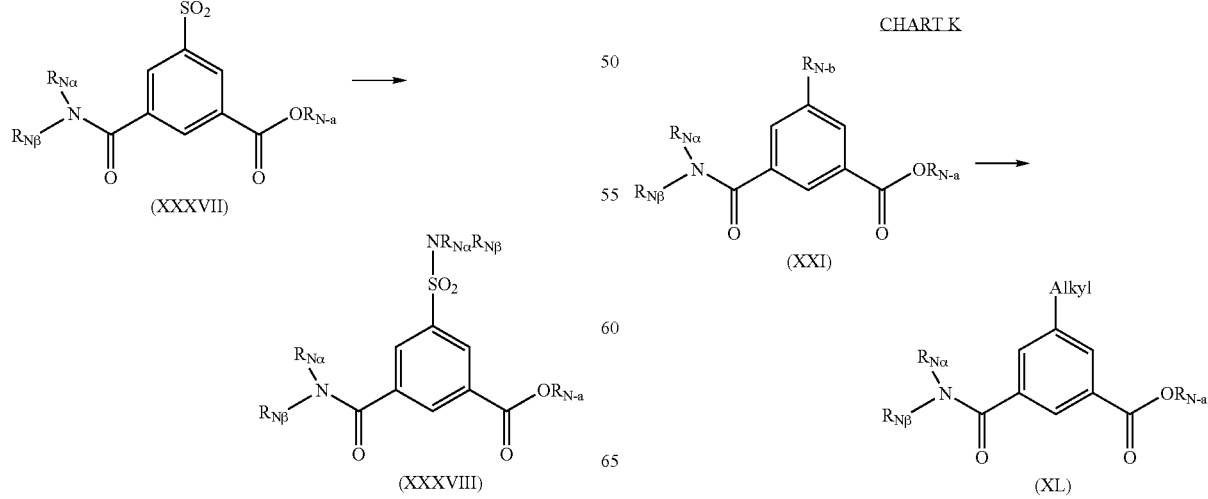

907
-continued
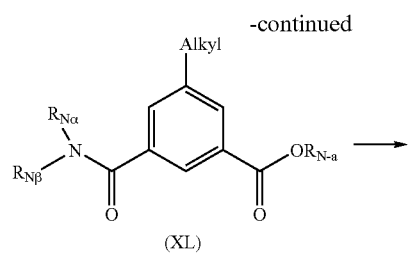
(XL)
→
908
-continued
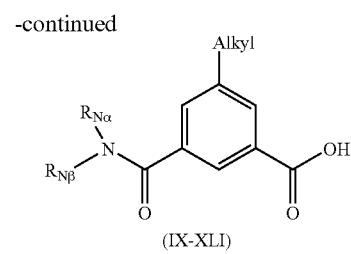
(IX-XLI)
CHART L
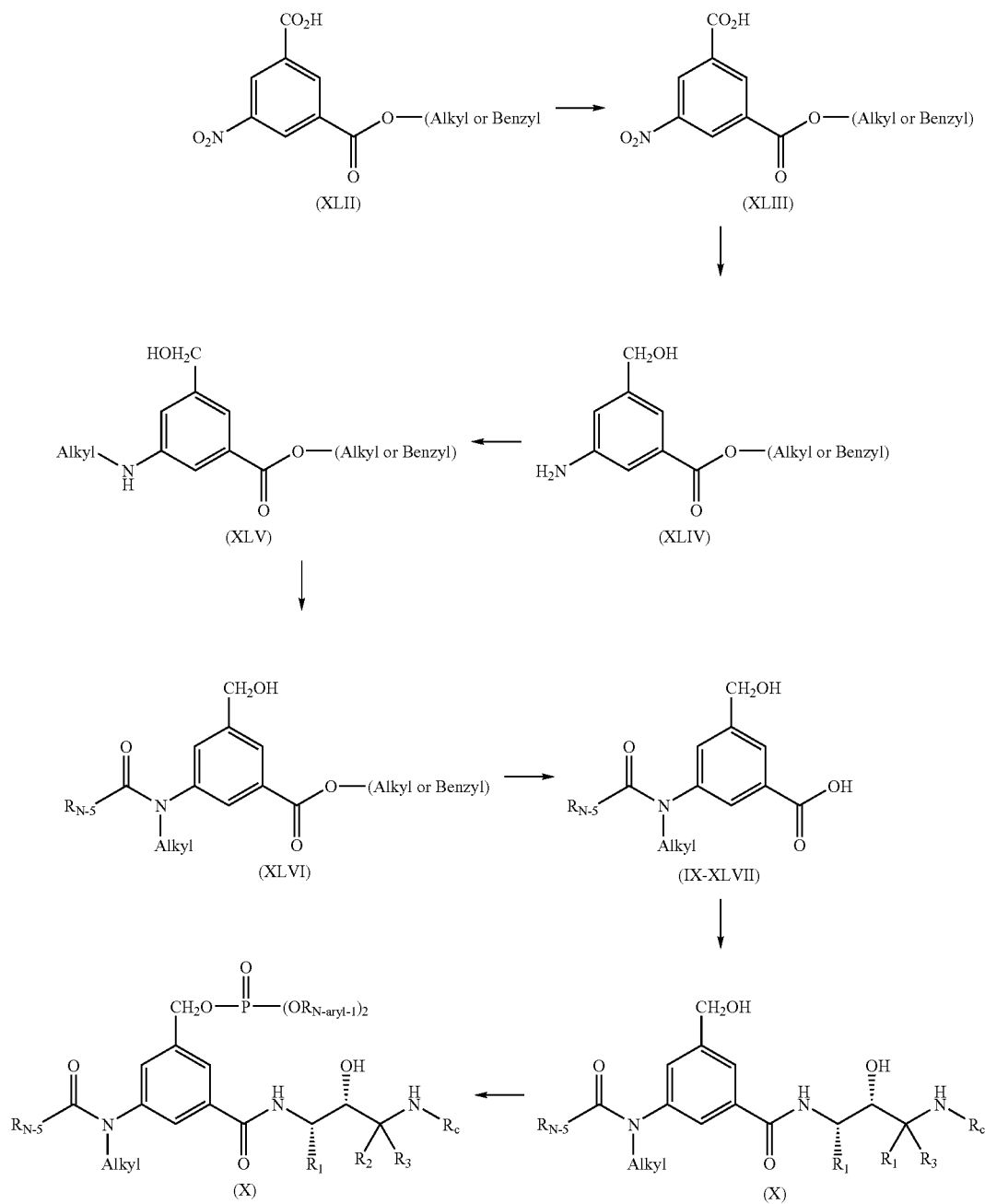

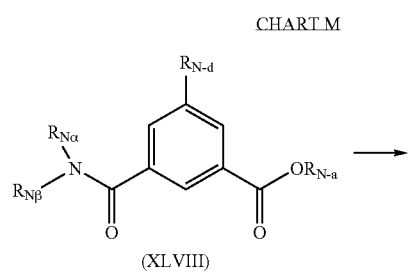
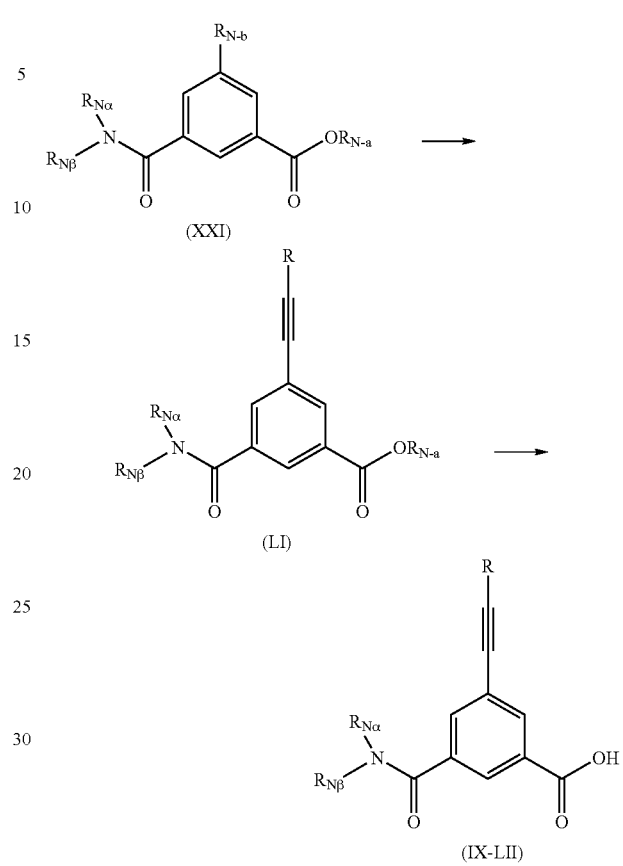
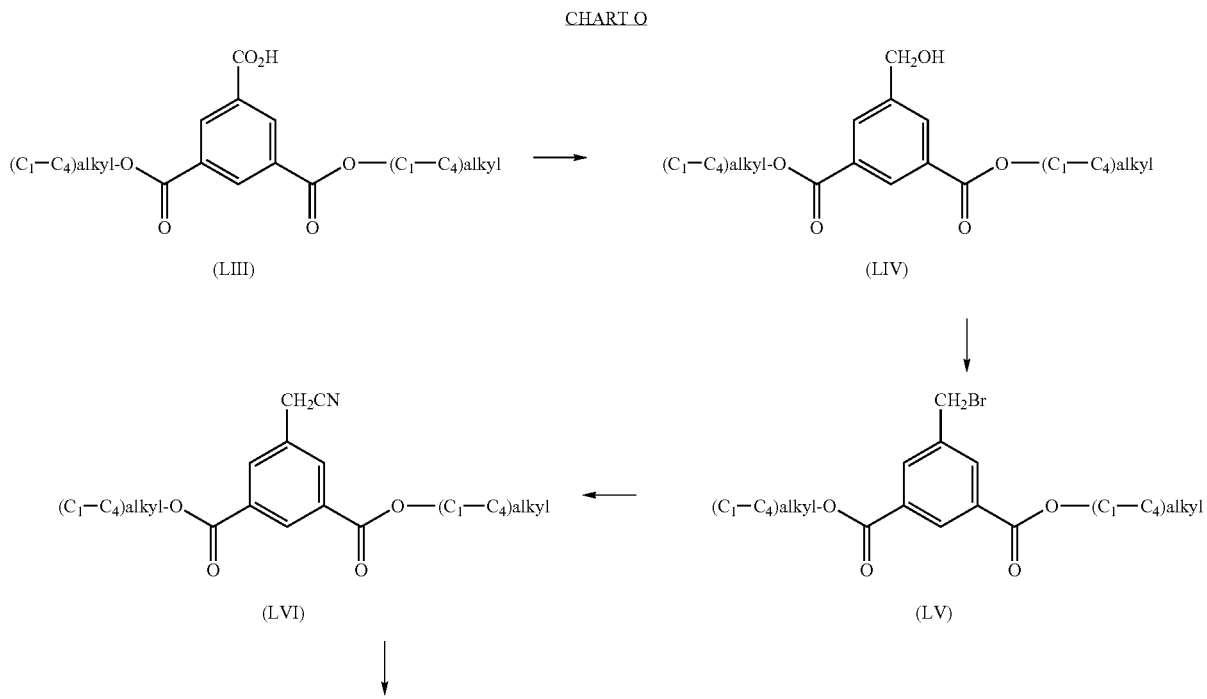

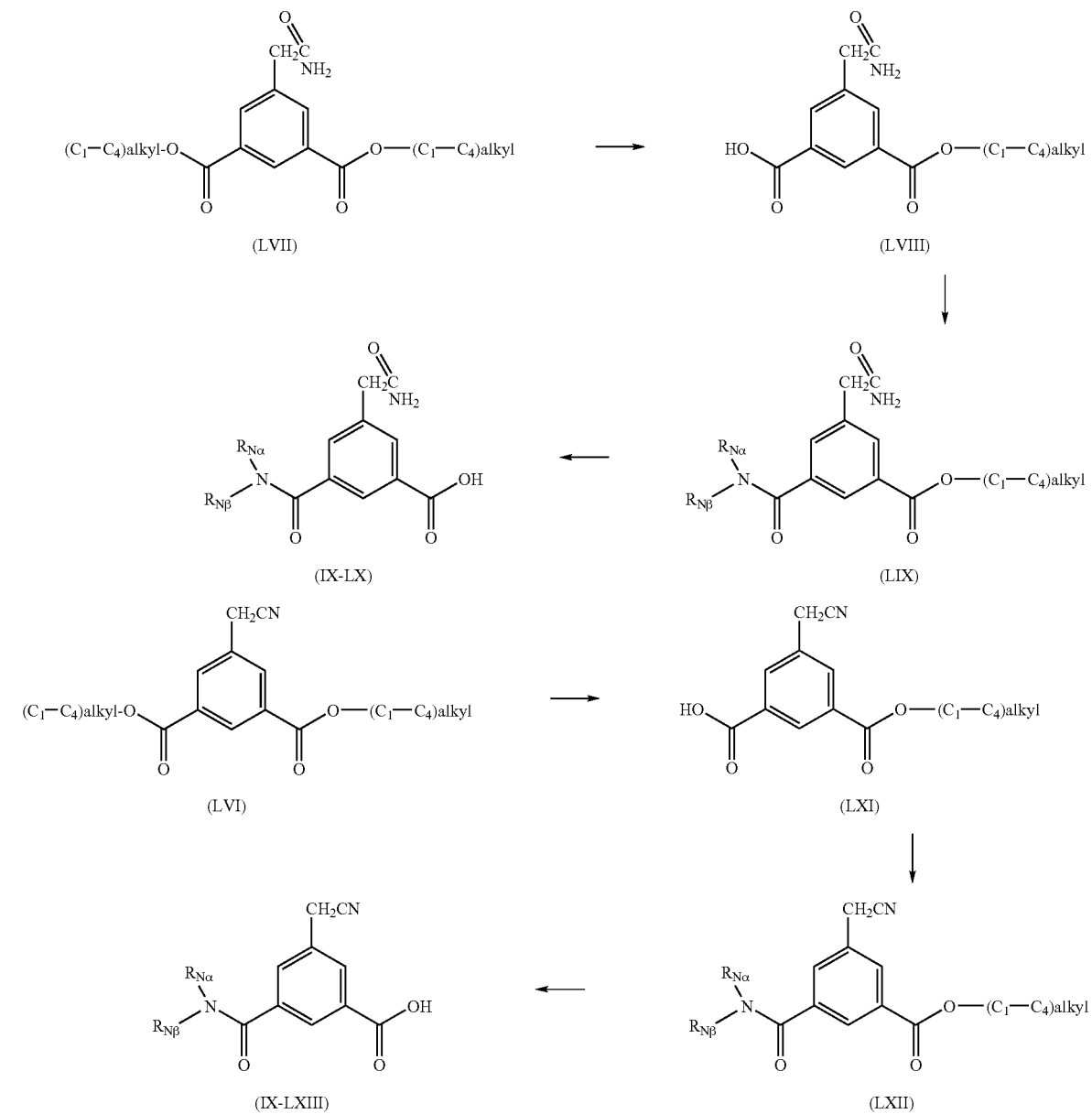
CHART P
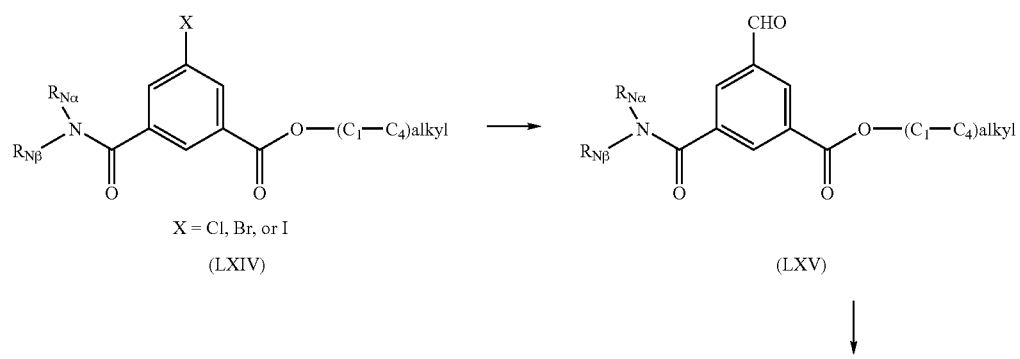

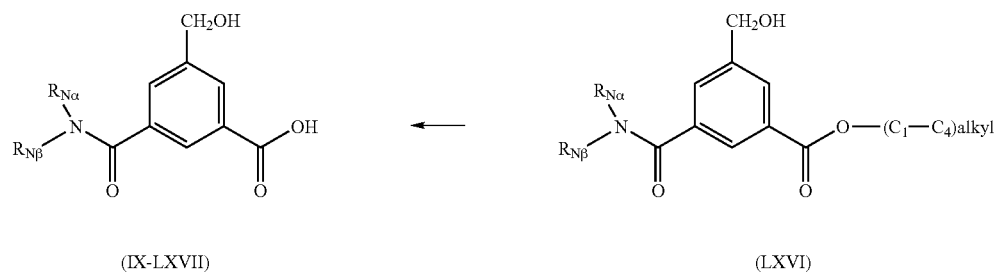
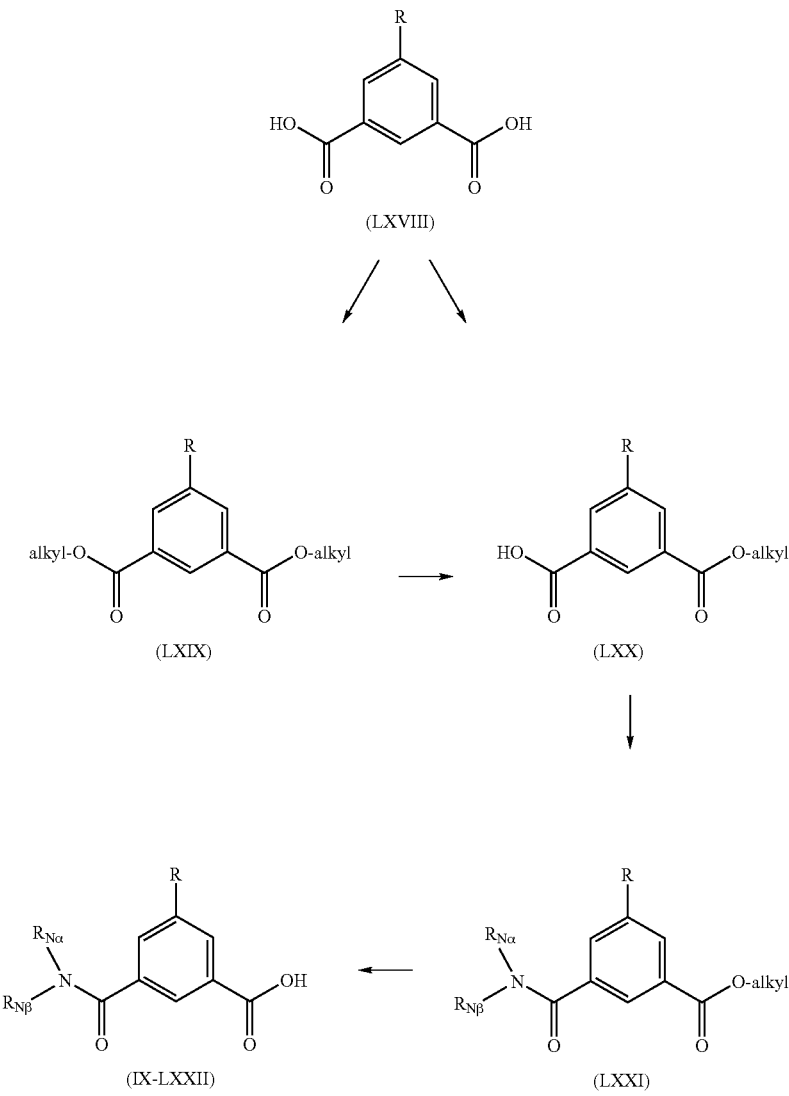
CHART Q

CHART R
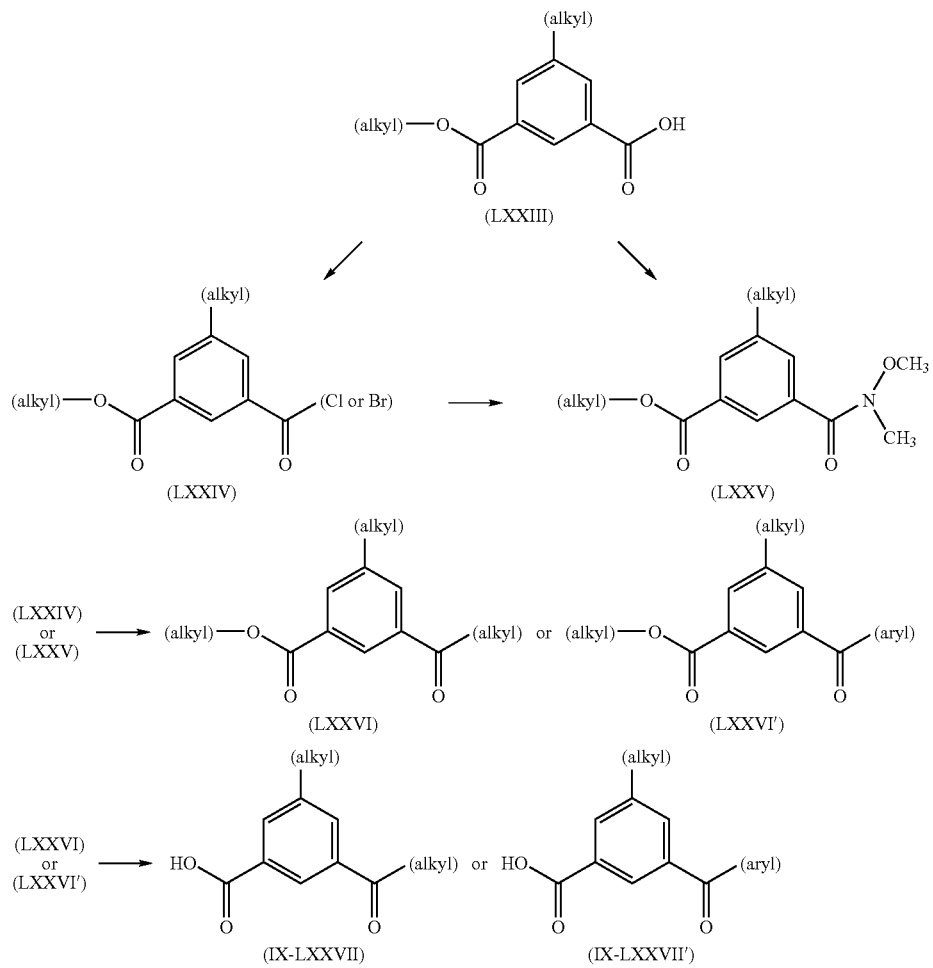
CHART S
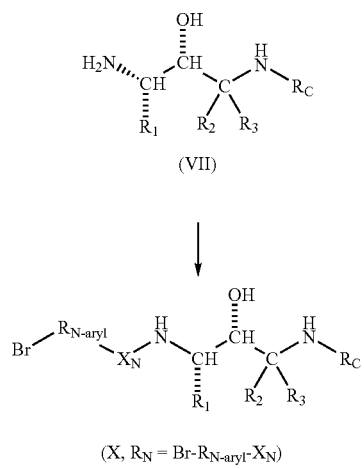

-continued
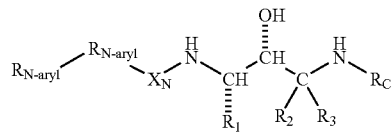
(X, $R_N = R_{N\text{-}aryl}\text{-}R_{N\text{-}aryl}\text{-}X_N$)
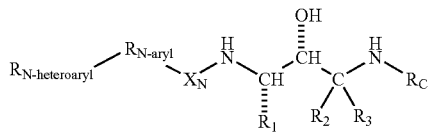
(X, $R_N = R_{N\text{-}heteroaryl}\text{-}R_{N\text{-}aryl}\text{-}X_N$)
CHART T
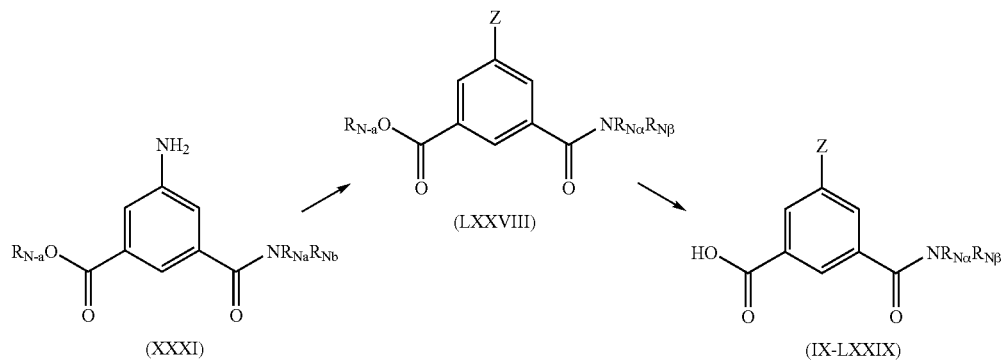
CHART U
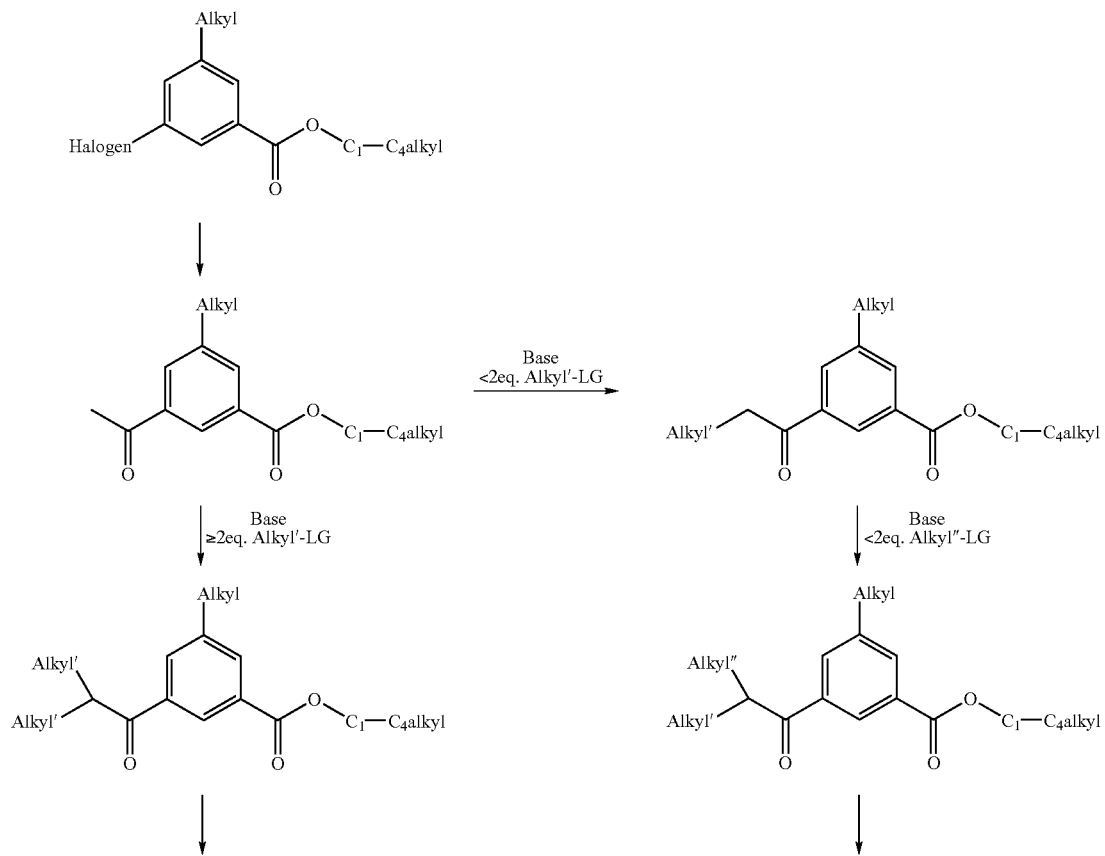

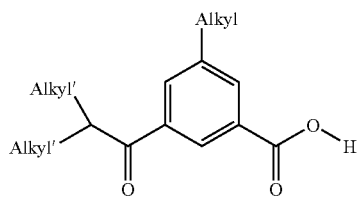
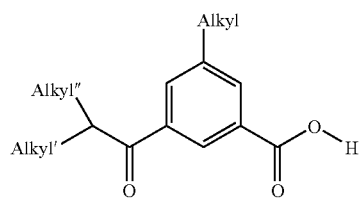

CHART U details a method for the preparation of ketones used in the invention. The preferred halogen is bromine or iodine. A commercially available halogenated benzoate is coupled with (α-ethoxyvinyl)-tributyl in the presence of a catalyst, for example a palladium catalyst like dichlorobis (triphenylphosphine)palladium, yielding a methylketone-substituted benzoate ester after hydrolytic workup. In a preferred embodiment of the invention, this reaction is conducted in an anhydrous organic solvent. In a further more preferred embodiment of the invention, this reaction is conducted in anhydrous toluene.(Kosugi and Migita, *Bull. Chem. Soc., Jpn.*, 1987, 60, 767-768). Base-catalyzed nucleophilic addition to a stoichiometric excess of alkyl'-LG (or alkyl"-LG) yields a symmetric dialkylated productthat, depending on the strength of the base, may be directly converted to the equivalent benzoate. Alternatively, the methylketone-substituted benzoate ester may be reacted with a lower excess of alkyl'-LG, yielding a mono-substituted derivative. Said derivative may be further alkylated by base-catalyzed reaction with alkyl"-LG. It is understood that LG is Leaving Group as defined above. It is understood by one skilled in the art how to perform alkylations. In a preferred embodiment of the invention, said alkylations are catalyzed by sodium hydroxide or potassium hydroxide. In an additional preferred embodiment of the invention, the alkylations are conducted in a dipolar aprotic solvent, e.g. dimethylsulfoxide.

CHART V

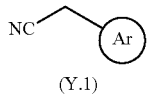

(Y.1)

Ar = substituted aryl or heteroaryl

| BrCH$_2$CH$_2$Cl
| base, PTC
▼

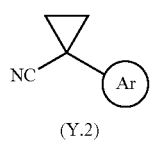

(Y.2)

| KOH, H$_2$O$_2$
| MeOH
▼

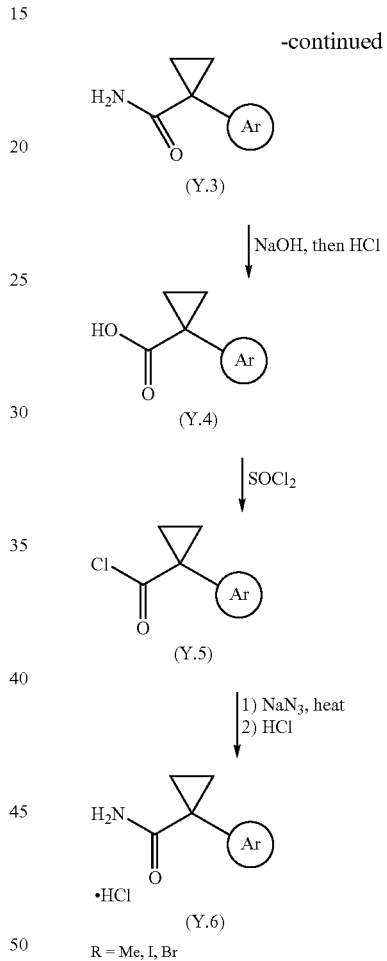

CHART V. Synthesis of 3-substituted cyclopropylbenzylamines and related heteroaryl amines (Y.6 in Chart V). A commercially available 3-substituted benzylonitrile is reacted with 1-bromo-2-chloroethanein the presence of an aqueous base and a phase transfer catalyst to yield the a cyclopropanated benzylnitrile (Y.2). The cyanide (Y.2) is converted to amide (Y.3), which is treated with 10 aqueous base, yielding acid (Y.4) after acidic workup. Acid (Y.4) is converted to acyl chloride (Y.5), which is reacted with azide, yielding an intermediate which undergoes rearrangement and decomposition to give product (Y.6). (Y.6)is then reacted according to Chart JJ to yield inhibitor (X). Representative procedures are provided in EXAMPLE 2353.

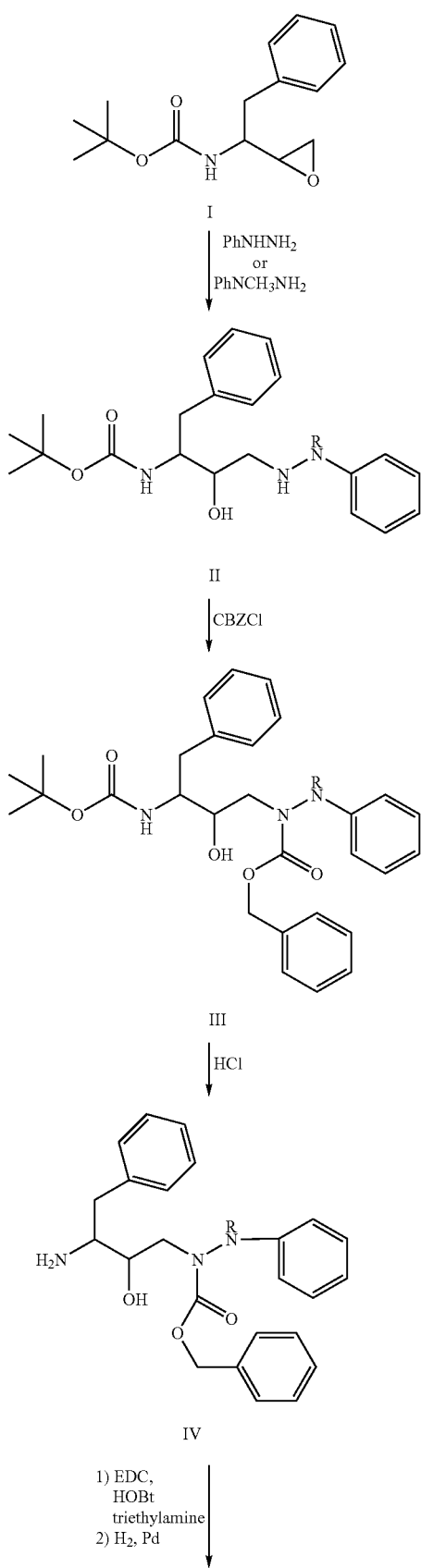

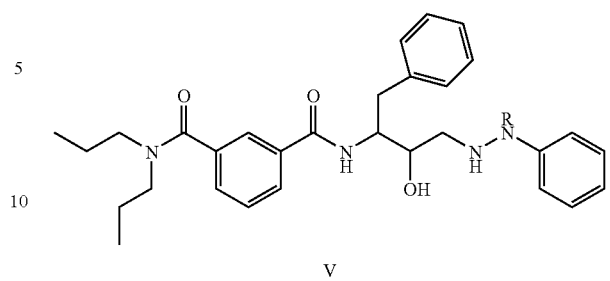

Chart Z. Reaction of epoxide I with an aromatic hydrazine in isopropanol produces the selective alkylation of the unsubstituted hydrazine nitrogen, yielding hydrazine II (M. Nakakata, *Tetrahedron Letters* 1993, 6095-6098). Acylation of one of the hydrazine nitrogens with an acylating agent, e.g. benzyloxycarbonyl, yields III and reduces the reactivity of this moiety to further acylation irrespective of which hydrazine nitrogen is the first to undergo acylation (B. Gisin, *Helv. Chim. Acta* 1970, vol 53, 1030-1043. S. Shinagawa, *Chem. Pharm. Bull.* 1981, vol 29, 3630-3638). Removal of the tert-butoxycarbonyl protecting group of III yields free amine IV, which is coupled to isophthalic acid (XIV)using carbodiimide or other known coupling agents. Deacylation of the hydrazine nitrogen yields compound V.

CHART AA

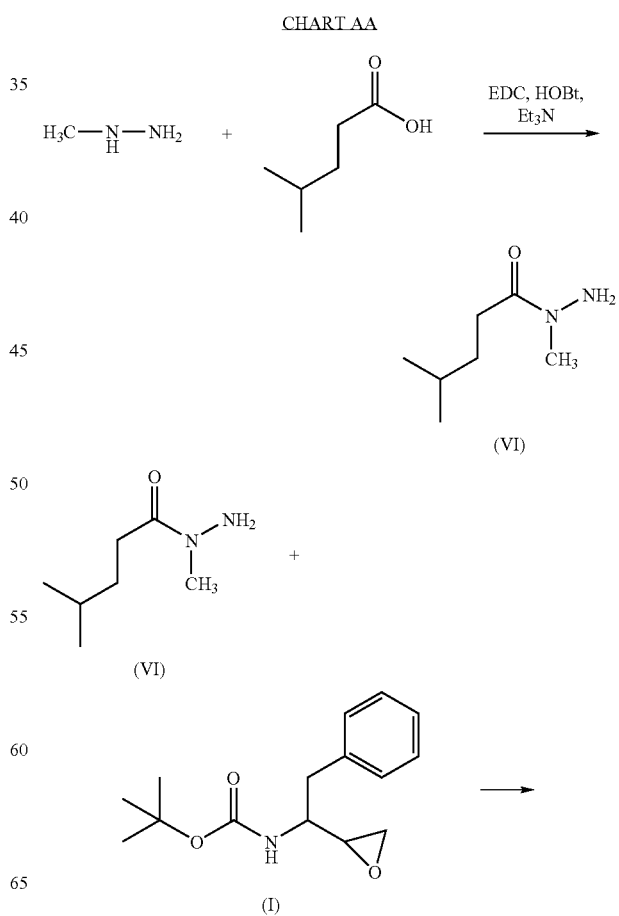

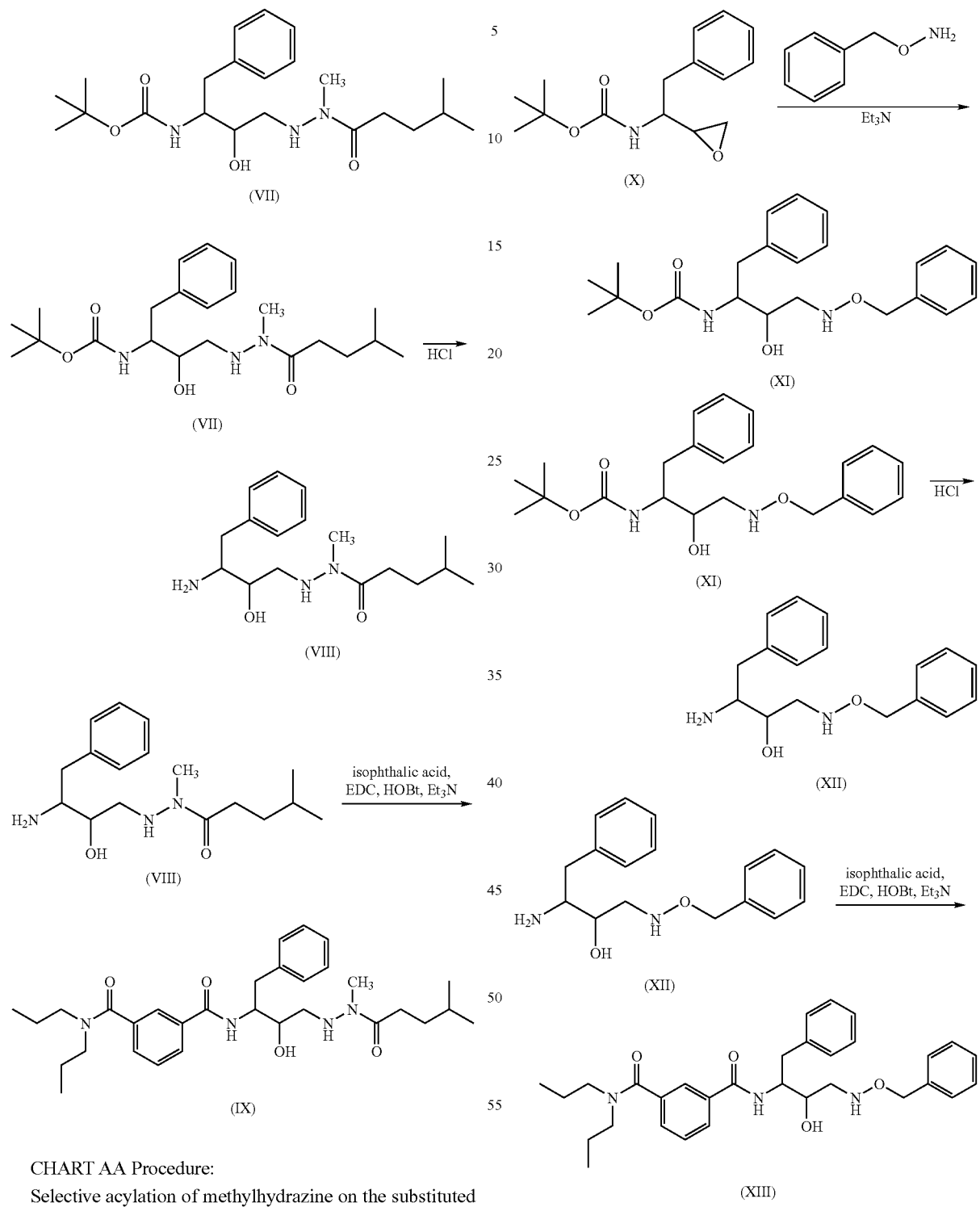

CHART AA Procedure:

Selective acylation of methylhydrazine on the substituted nitrogen (D. Butler, *J. Medicinal Chemistry* 1971, vol. 14, 1052-1054) yields acylhydrazine VI, which is reacted with epoxide I in isopropanol to form adduct VII (S. Wang, *J. Medicinal Chemistry* 1997, vol 40, 937-941. G. Bold, *J. Medicinal Chemistry* 1998, vol 41, 3387-3401). Removal of the tert-butoxycarbonyl protecting group, followed by coupling to isophthalic acid (XIV) yields final product IX.

Chart BB Procedure:

Epoxide X is reacted with 0-benzylhydroxylamine to yield adduct XI (S. Rosenberg, *J. Medicinal Chemistry* 1990, vol 33, 1582-1590). Removal of the tert-butoxycarbonyl protecting group, followed by acylation with isophthallic acid XIV yields target compound XIII.

CHART CC

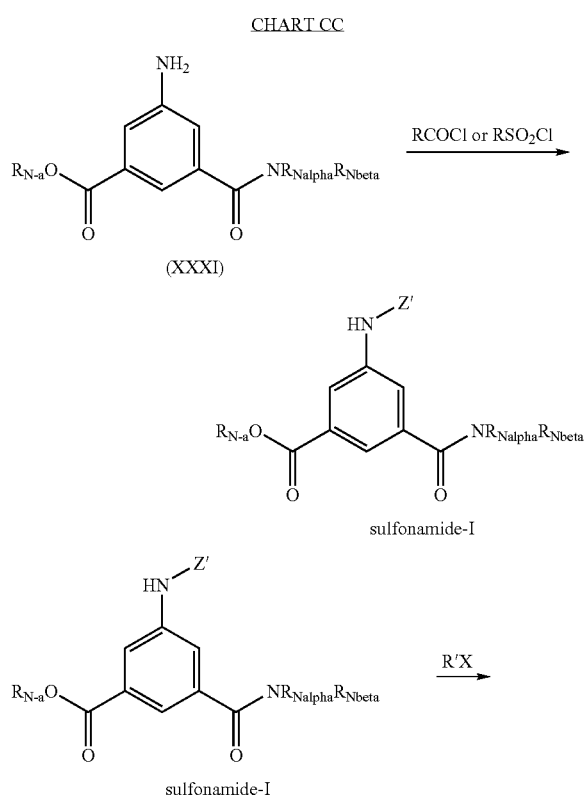

Chart CC. Aniline XXXI is acylated with acyl chlorides or anhydrides or sulfonated with sulfonyl halides or sulfonyl anhydrides to yield sulfonamide-I using methods well known to those skilled in the art. Sulfonamide-I is alkylated with RX, wherein X is a leaving group, for example Cl, Br, tosylate, or mesylate, in the presence of a base, e.g. trialkylamine, sodium hydride, pyridine, or potassium t-butoxide, to yield sulfonamide-II.

CHART DD

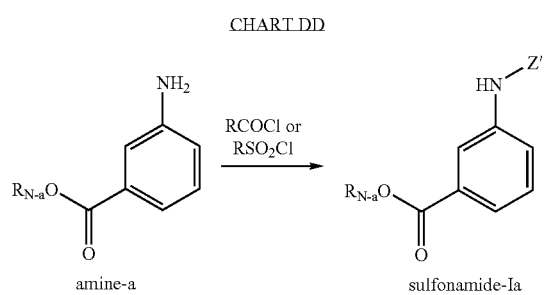

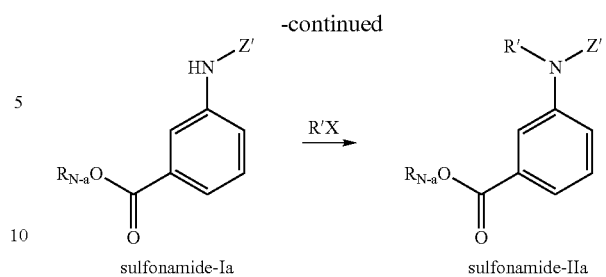

Chart DD. Amine-a is acylated with acyl chlorides or anhydrides or sulfonated with sulfonyl halides or sulfonyl anhydrides to yield sulfonamide-I using methods known to those skilled in the art. Sulfonamide-Ia is alkylated with RX, wherein X is a leaving group, for example Cl, Br, tosylate, or mesylate, in the presence of a base, e.g. trialkylamine, sodium hydride, pyridine, or potassium t-butoxide, to yield sulfonamide-IIa.

CHART EE

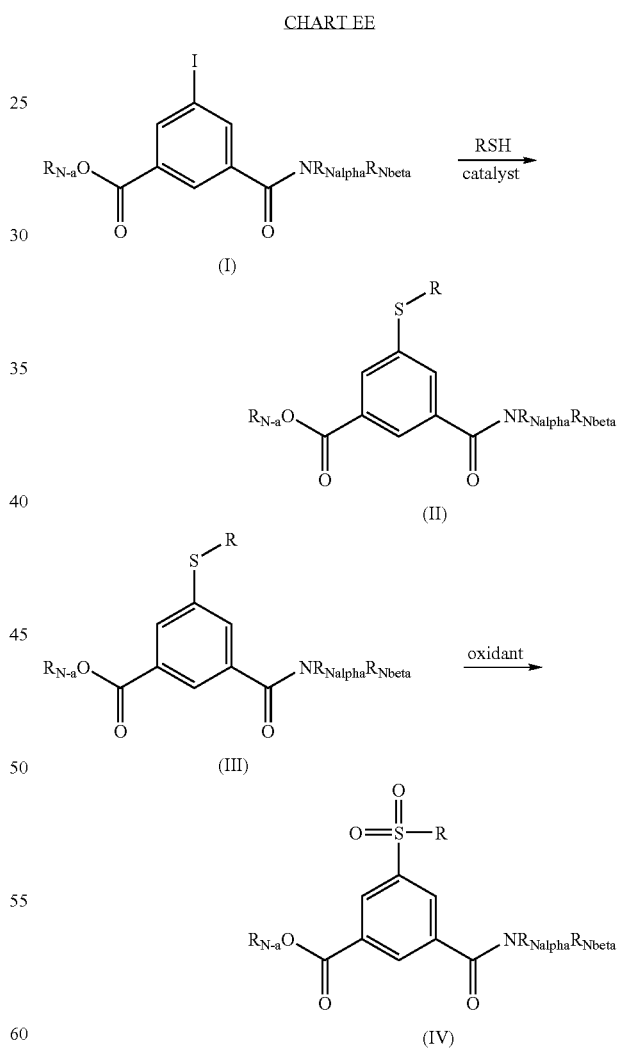

Chart EE. Iodo amide (I) is coupled to a thiol RSH in the presence of a catalyst, for example a palladium(0) catalyst like bis(dibenzylideneacetone)palladium(0), an additive, preferably 1,1'-bis(diphenylphosphino)ferrocene, and a base, e.g. a trialkyamine, in an organic solvent, for example N-methylpyrrolidinone (NMP) or DMF, at a temperature ranging from room temperature to reflux temperature to yield sulfide (II). Sulfide (II) is oxidized with hydrogen peroxide in the presence of an acid or with a peracid, e.g. m-chloroperoxybenzoic acid to yield sulfone (III). Other methods of oxidation are reported in references like Smith and March, Advanced Organic Chemistry: Reactions, Mechanisms, and Structure, 5$^{th}$ Ed., Wiley Interscience, 2001. If sulfone (III) is an ester, it is further hydrolyzed to yield a carboxylic acid (IV, not shown) by basic hydrosolisis with a base like lithium, sodium, or potassium hydroxide, followed by acidic workup. Acid (IV) is then coupled to an amine to yield the final target product.

CHART FF

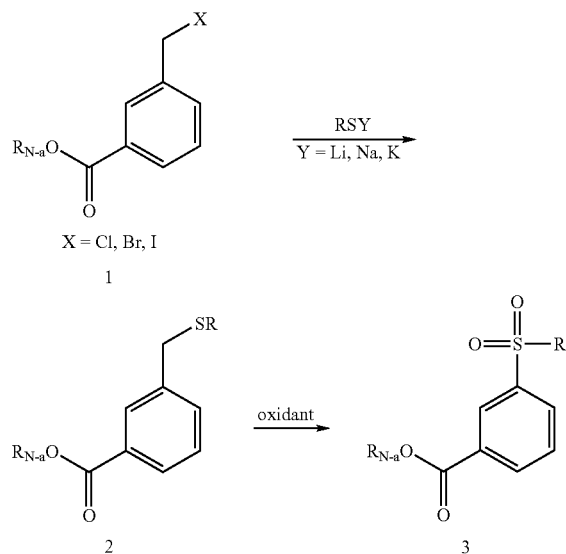

Chart FF. A halogenated benzyl-derivative of structure (1). (1) is reacted with thiolate, for example a lithium, sodium or potassium thiolate, in an organic solvent, for example THF, toluene, or acetonitrile, at temperatures ranging from room temperature to reflux, yielding a sulfanyl derivative of structure (2). (2) is peroxidated with an oxidant, for example hydrogen peroxide in the presence of an acid like acetic acid or m-chloroperoxybenzoic acid, in an organic solvent like dichloromethane to yield methylene sulfone (3). Other methods of oxidation are reported in references like Smith and March, Advanced Organic Chemistry: Reactions, Mechanisms, and Structure, 5$^{th}$ Ed., Wiley Interscience, 2001. If necessary, sulfone (3) is hydrolyzed to its acid derivative by methods known to those skilled in the art, or is used directly if already a carboxylic acid; coupling of said acid with amine yields the target product.

CHART GG

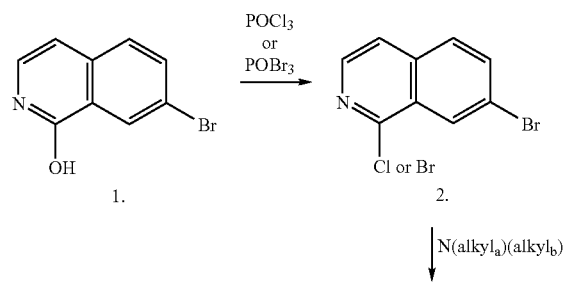

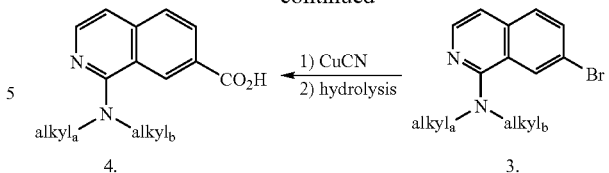

Chart GG. Isoquinoline (1) is reacted with phosphorus oxychloride or phosphorus oxybromide at temperatures ranging from room temperature to about 150° C. to yield halo-isoquinoline (2). Halo-isoquinoline (2) is reacted with an amine at temperatures ranging from room temperature to 200° C. to yield amino-isoquinoline (3). This reaction may be carried out in the presence of an organic solvent such as THF, acetonitrile, DMF, or NMP. Alternatively, the amine can be used as solvent, and a sealed reaction vessel may be used to contain volatile amine at high temperatures. Amino-isoquinoline (3) is reacted with copper (I) cyanide in an organic solvent, for example DMF or NMP (N-methylpyrrolidinone) at temperatures ranging from about 120° C. to reflux, followed by hydrolysis with an aqueous acid, for example aqueous HCl, to yield isoquinoline carboxylic acid (4). Additional methods for converting amino-isoquinoline (3) to isoquinoline carboxylic acid (4) are known to those skilled in the art and include, for example, reacting (3) with carbon monoxide and an alcohol in the presence of a catalyst, for example a palladium catalyst such as palladium acetate or palladium(0) tetrakis(triphenylphosphine), and an additive, for example 1,1-bis(diphenylphosphino)ferrocene or 1,3-bis(diphenylphosphino)propane, in an organic solvent, for example DMF or NMP, and in the presence of a base, for example a trialkylamine or aqueous sodium or potassium carbonate or sodium or potassium hydrogen carbonate, at temperatures ranging from about 50 to about 150° C., followed by hydroysis of the ester product to isoquinoline carboxylic acid (4). Isoquinoline carboxylic acid (4) is then coupled to an amine to yield the final target product.

CHART HH

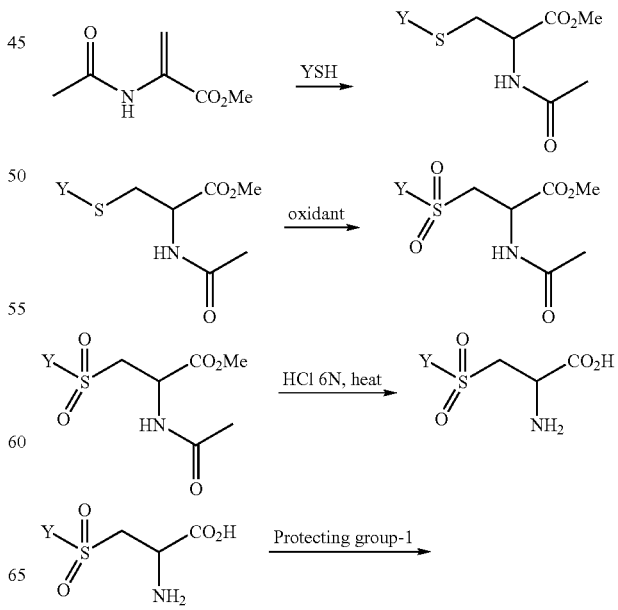

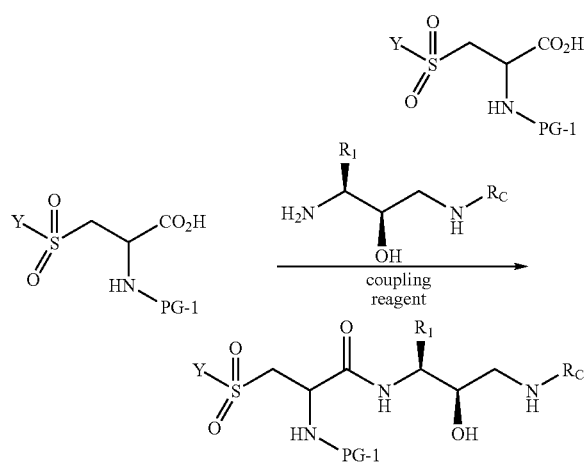

Charts HH and II. Chart HH discloses the synthesis of a set of racemic α-amino sulfones while Chart II discloses the synthesis of the active enantiomer. The Michael addition of a thiol to a protected dehydroalanine methyl ester yields a sulfanyl intermediate. The sulfanyl derivative is peroxidated to the corresponding sulfone according to one of the above-mentioned methods. Hydrolysis of the ester and protecting group may be carried out with a strong aqueous acid, for example 6N HCl, or acetic acid, optionally at high temperature to yield the free amino acid salt. A protecting group for example Cbz or Boc, may be added to the amine group. Standard peptide coupling to the unprotected diamine preferentially affords the product with an unreacted N—$R_C$ moiety which is then orthogonally protected to yield the diprotected diamine. Selective removal of the Rn protecting group affords a free amine. This amine can be converted according one of the above-mentioned methods into amides, carbamates,. Alternatively, it may be reacted with an isocyanate to yield a urea, or with a sulfonyl chloride to yield a sulfonamide. The removal of the Rc protecting yields the target compounds. Chart II is identical to chart HH with an addi-

CHART II

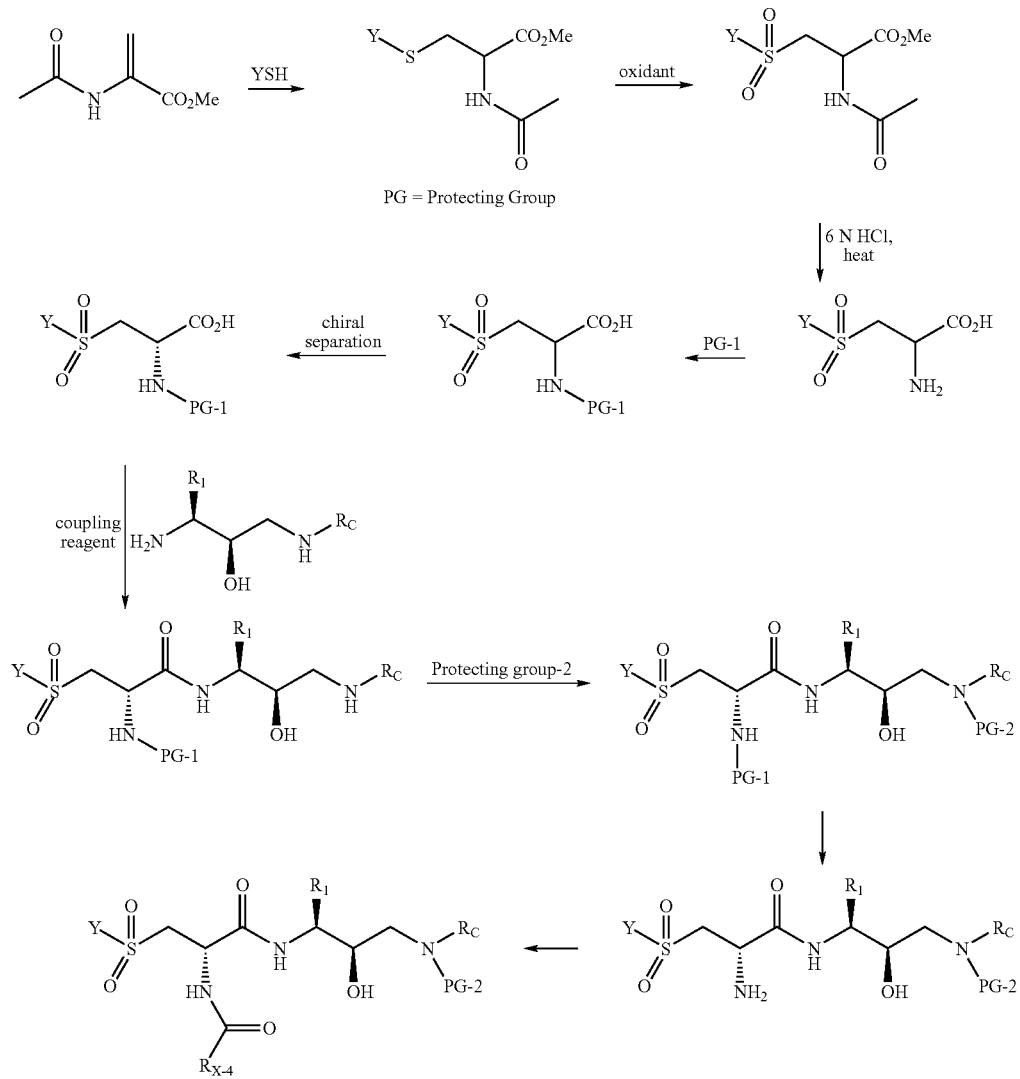

tional isomer separation step which may be carried out chemically, enzymatically, or by chiral chromatography, yielding the single isomer acid which is transformed into the target product as described above.
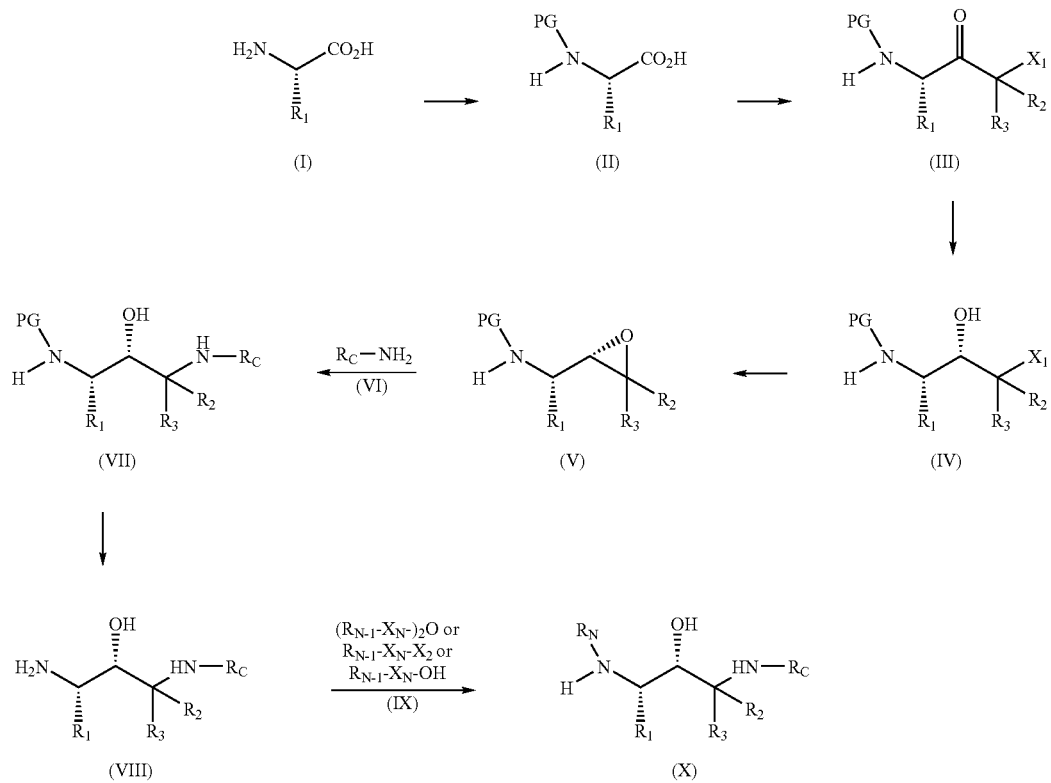
CHART JJ
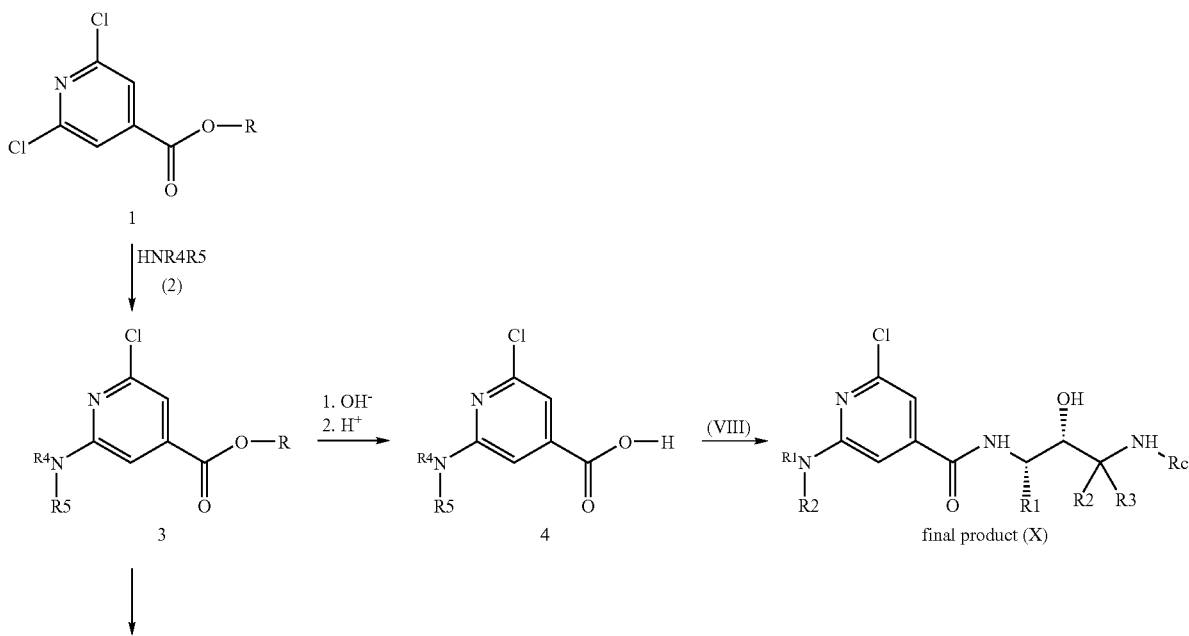
ChartKK

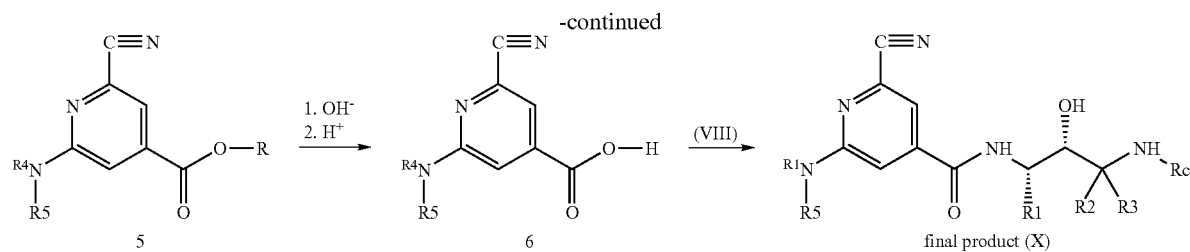

Pyridine 1 is reacted with an amine 2 in an organic solvent, for example THF, at reflux or by warming to a temperature ranging from about 80° C. to about 130° C. in a sealed vessel, to yield pyridine ester 3. Pyridine ester 3 is hydrolyzed using methods known to those skilled in the art to yield chloro-acid 4. Chloro-acid 4 is coupled to amine (VIII) using methods discussed above and known to those skilled in the art to yield final product (X).

Alternatively, ester pyridine 3 is cyanated as taught in Tet. Lett. 2000, 41, 3271 to yield nitrile ester 5. Additional methods of preparing nitrile ester 5 include but are not limited to treatment of ester pyridine 3 with copper cyanide in organic solvents, for example N-methylpyrrolidinone, DMF at temperatures ranging from about 80° C. to about 180° C. The ester moiety of 5 is converted to acid 6 via methods known to those skilled in the art. Acid 5 is then coupled to amine (VIII) using methods that are discussed above or known to those skilled in the art to give final product (X).

CHART LL

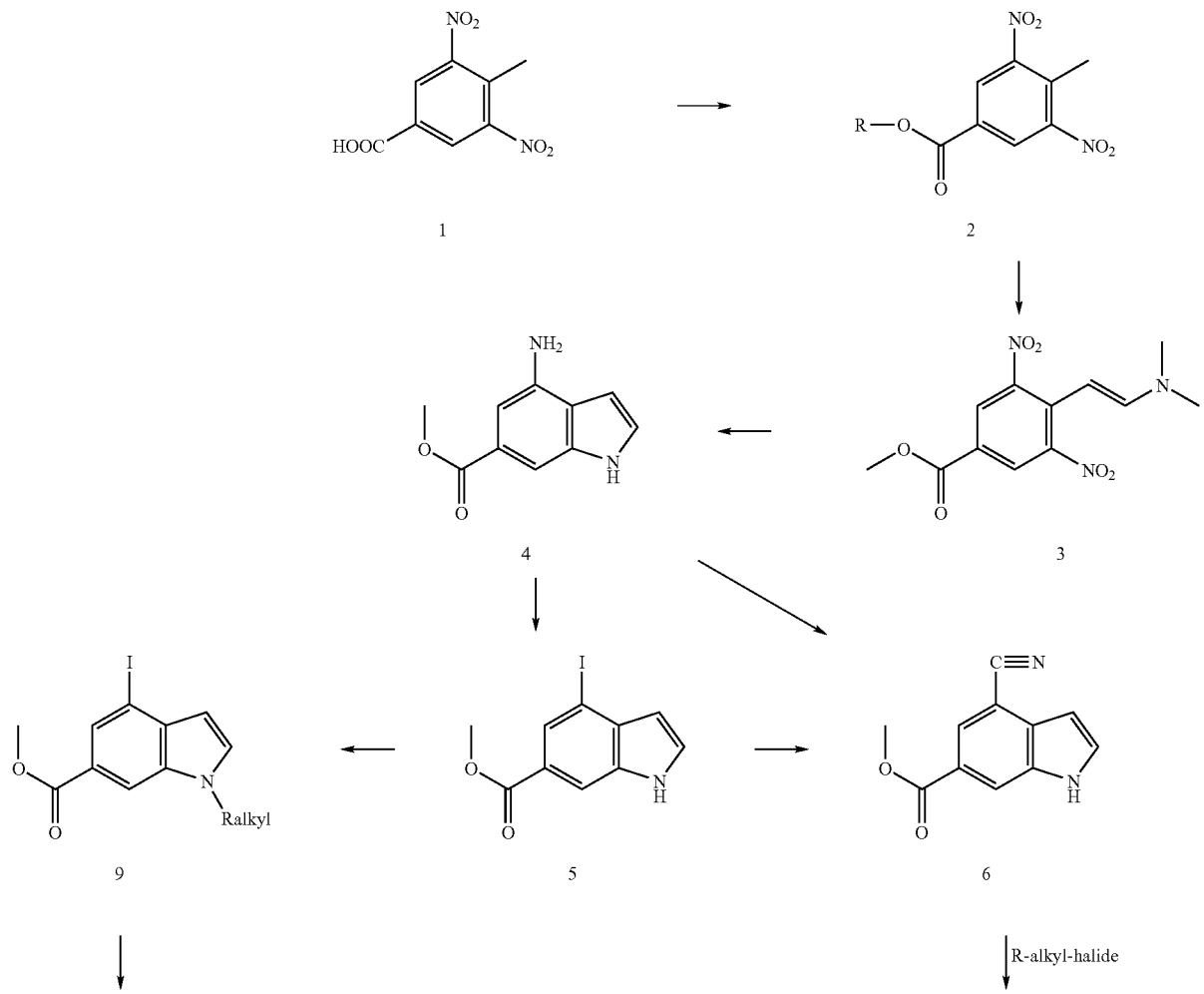

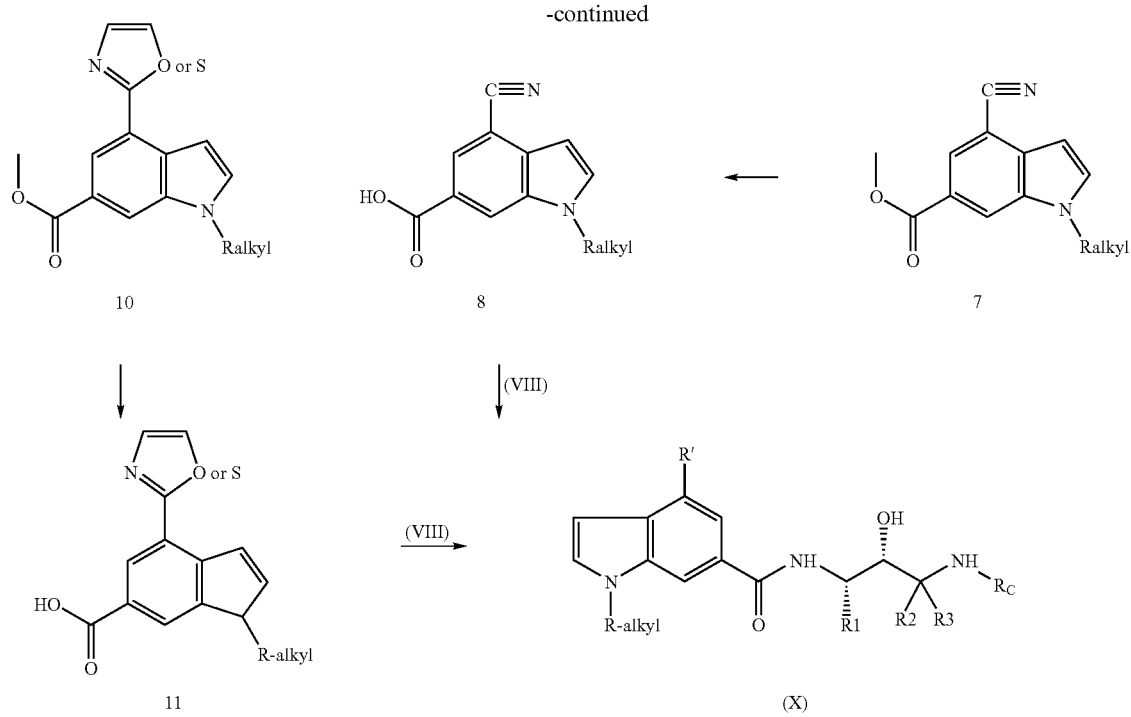

Dinitro acid 1 is esterified with an alcohol and an acid catalyst or by methods known to those skilled in the art to yield dinitro ester 2. Dinitro ester 2 is reacted with a protected aldehyde, for example an acetal or a ketal, in an organic solvent, for example toluene, at temperatures from about 50 to 150° C. and in the presence of an acid catalyst, for example concentrated sulfuric acid or sulfosalicylic acid, yielding dinitro amine 3. Dinitro amine 3 is treated with a palladium catalyst such as palladium on carbon in an organic solvent, for example methanol, ethanol, ethyl acetate, and acetonitrile, in the presence of an acid such as formic or acetic acid to yield amino-indole 4. Amino-indole 4 is reacted with sodium nitrite and aqueous hydrochloric or sulfuric acid, followed by potassium iodide, to give iodo-indole 5. Iodo-indole 5 is reacted with copper cyanide in an organic solvent, for example N-methylpyrrolidinone at temperatures from about 100 to about 200° C. to yield nitrile-indole 6. Nitrile-indole 6 is then alkylated with an alkyl halide, for example propyl or butyl iodide, bromide, or chloride in the presence of a base, for example sodium hydride or potassium tert-butoxide, preferably potassium tert-butoxide, in an organic solvent, for example THF, DMF or DMSO, preferably DMSO, at room temperature to 100° C., to yield ester indole 7.

Alternatively, amino-indole 4 may be reacted with an aqueous mineral acid and sodium nitrite, followed by neutralization with a base, for example sodium bicarbonate, and then reacted with potassium cyanide and copper cyanide to yield nitrile-indole 6. Ester indole 7 is then hydrolyzed to indole acid 8 using methods known to those skilled in the art. Indole 8 is then coupled to amine (VIII) using methods known to those skilled in the art and previously disclosed in this document.

Alternatively, iodo indole 5 is reacted with an alkyl halide, for example as propyl or butyl iodide, bromide, or chloride in the presence of a base, for example sodium hydride or potassium tert-butoxide, more preferably potassium tert-butoxide, in an organic solvent, for example THF, DMF or DMSO, preferably DMSO, at a temperature from room temperature to about 100° C., to yield iodo alkyl 9. An Oxazole or a thiazole in an organic solvent, for example dialkyl ether or THF, at a temperature from about 0 to about −78° C. is reacted with a base, preferably butyl lithium and optionally left stirring for from about 15 to about 60 min. Zinc chloride is then added and the mixture is allowed to warm to 0-30° C., at which time iodo alkyl 9 is added, followed by tetrakis triphenylphosphine palladium. The mixture is then optionally left stirring at a temperature from room temperature to about 80° C. to yield oxazole/thiazole indole 10.The hydrolysis of 10 by methods known to those skilled in the art yields oxazole/thiazole acid 11. Oxazole/thiazole acid 11 is coupled to amine (VIII) using methods known to those skilled in the art.

CHART MM

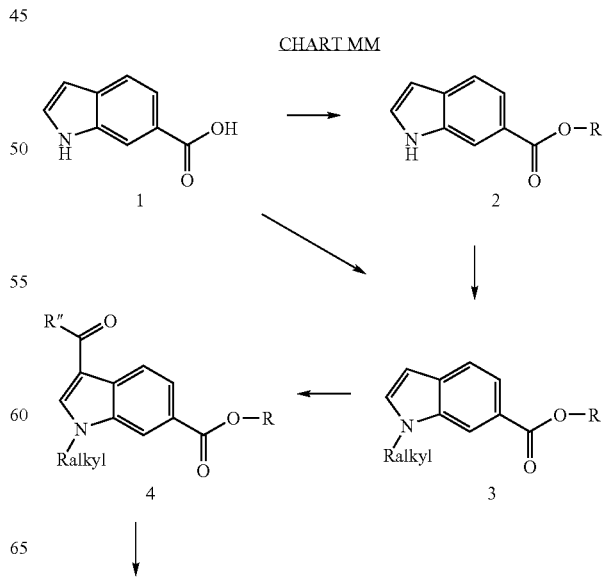

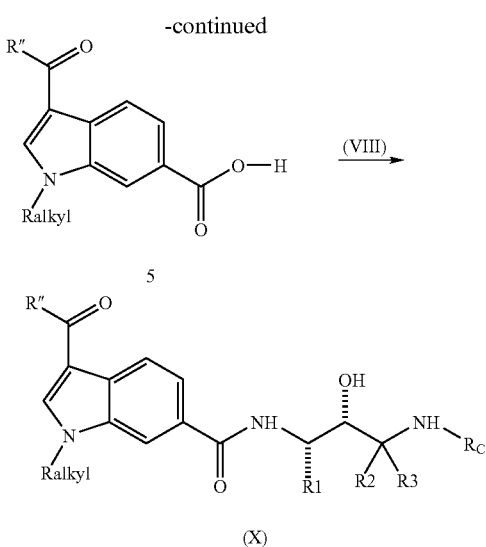

Indole acid 1 is converted to indole ester 2 by methods known to those skilled in the art. Indole ester 2 is then alkylated with an alkyl halide, for example propyl or butyl iodide, bromide, or chloride, in the presence of a base, for example sodium hydride or potassium tert-butoxide, preferably potassium tert-butoxide, in an organic solvent, for example THF, DMF or DMSO, preferably DMSO, at room temperature to about 100° C. to yield alkyl indole 3. Alternatively, indole acid 1 may be converted directly to alkyl indole 3 by reaction with an alkyl halide, for example propyl or butyl iodide, bromide, or chloride in the presence of a base, for example sodium hydride or potassium tert-butoxide, preferably potassium tert-butoxide, in an organic solvent, for example THF, DMF or DMSO, preferably DMSO at room temperature to about 100° C. Alkyl indole 3 is then treated by the method disclosed in Org. Lett. (2000) 1485 and references cited therein, Tet. Lett. (1995) 4005 and references cited therein, and Org. Lett. (2001) 1005 and references cited therein to yield acylindole 4. Acylindole 4 is hydrolyzed to indole acid 5 using methods known to those skilled in the art, and indole acid 5 is coupled to amine (VIII) using methods known to those skilled in the art to yield (X).

Biological Examples

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et. al, 1999, *Nature* 40:537-540) or recombinantly produced as the full-length enzyme (amino acids 1-501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-$C_{125}$SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well is transferred to a corresponding anti-MBP antibody coated ELISA plate for capture, containing 80 microliters/well specimen diluent. This reaction is incubated overnight at 4 degrees C. and the ELISA is developed the next day after a 2 hours incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than or equal to 20 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

```
Biotin-SEVNL-DAEFR[oregon green]KK    [SEQ ID NO:1]

Biotin-SEVKM-DAEFR[oregon green]KK    [SEQ ID NO:2]
```

-continued

Biotin-GLNIKTEEISEISY-EVEFRC[oregon green]KK [SEQ ID NO:3]

Biotin-ADRGLTTRPGSGLTNIKTEEISEVNL-DAEF[oregon green]KK [SEQ ID NO:4]

Biotin-FVNQHLCoxGSHLVEALY-LVCoxGERGFFYTPKA[oregon green]KK [SEQ ID NO:5]

The enzyme (0.1 nanomolar) and test compounds (0.001-100 micromolar) are incubated in pre-blocked, low affinity, black plates (384 well) at 37 degrees C. for 30 minutes. The reaction is initiated by addition of 150 millimolar substrate to a final volume of 30 microliter per well. The final assay conditions are: 0.001-100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an IC50 of less than 20 micromolar.

Example C

Beta-secretase Inhibition: P26-P4'SW Assay

Synthetic substrates containing the beta-secretase cleavage site of APP are used to assay beta-secretase activity, using the methods described, for example, in published PCT application WO00/47618. The P26-P4,SW substrate is a peptide of the sequence:

(biotin)CGGADRGLTTRPGSGLTNIKTEEISEVN LDAEF [SEQ ID NO:6]

The P26-P1 standard has the sequence:

(biotin)CGGADRGLTTRPGSGLTNIKTEEISEVNL [SEQ ID NO:7]

Briefly, the biotin-coupled synthetic substrates are incubated at a concentration of from about 0 to about 200 micromolar in this-assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51.millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with strepavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays Using Synthetic Oligopeptide-Substrates

Synthetic oligopeptides are. prepared that incorporate the known cleavage site of beta-secretase, and optionally detectable tags, such as fluorescent or chouromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys65IMet52 to Asn65μLeu652 (numbered for APP751), commonly called the Swedish mutation and shown to overproduce A beta (Citron et. al., 1992, Nature 360:672-674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et. al., 1995, Nature 373:523-527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1-30 mg/ml; preferably 1-10 mg/ml). After time, e.g., 3-10 hours, the animals are sacrificed, and brains removed for analysis.

Transgenic animals are administered an amount of the compound inhibitor preferably formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta-production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor preferably formulated in a carrier suitable for the chosen mode of administration. Administration is repeated daily for the duration of the test period. Beginning on day 0, cognitive and memory-tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

While this invention has been described with respect to various specific examples and embodiments, it is to be understood that the invention is not limited thereby and should only be construed by interpretation of the scope of the appended claims.

The following compounds were prepared using the above described methodology.

| Example | Structure | Compound Name(s) | Mass Spec +H⁺ |
|---|---|---|---|
| 3552 | 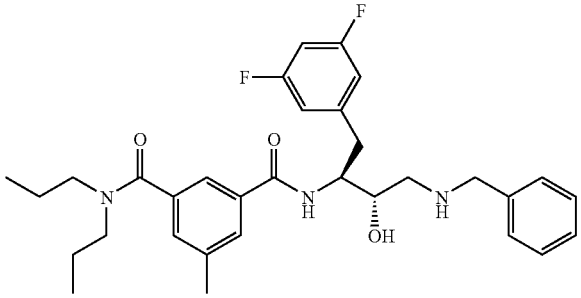 | N'-[(1S,2S)-3-(benzylamino)-1-(3,5-difluorobenzyl)-2-hydroxypropyl]-5-methyl-N,N-dipropylisophthalamide | 552.2 |

-continued

| Example | Structure | Compound Name(s) | Mass Spec +H+ |
|---|---|---|---|
| 3553 | 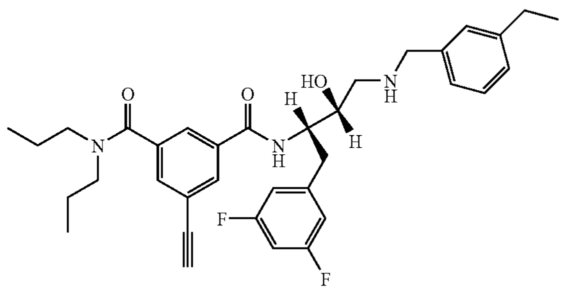 | N'-{(1S,2R)-1-(3,5-difluorobenzyl)-3-[(3-ethylbenzyl)amino]-5-ethynyl-N,N-dipropylisophthalamide | 590.3 |
| 3554 | 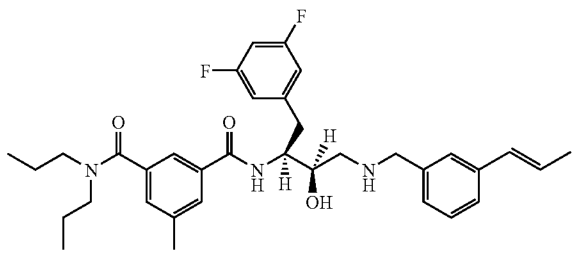 | N'-[(1S,2R)-1-(3,5-difluorobenzyl)-2-hydroxy-3-({3-[(1E)-prop-1-en-1-yl]benzyl}amino)propyl]-5-methyl-N,N-dipropylisophthalamide | 592.3 |
| 3555 | 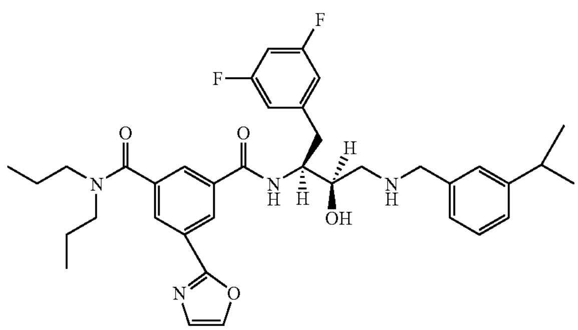 | N'-{(1S,2R)-1-(3,5-difluorobenzyl)-2-hydroxy-3-[(3-isopropylbenzyl)amino]propyl}-5-(1,3-oxazol-2-yl)-N,N-dipropylisophthalamide | 647.2 |
| 3556 | 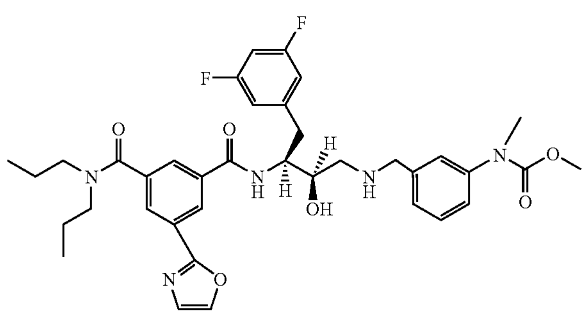 | methyl (3-{[((2R,3S)-4-(3,5-difluorophenyl)-3-{[3-[(dipropylamino)carbonyl]-5-(1,3-oxazol-2-yl)benzoyl]amino]-2-hydroxybutyl)amino]methyl}phenyl)methylcarbamate | 692.2 |
| 3557 | 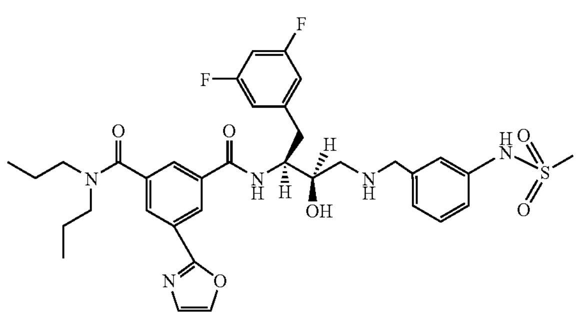 | n'-[(1S,2R)-1-(3,5-difluorobenzyl)-2-hydroxy-3-({3-[(methylsulfonyl)amino]benzyl}amino)propyl]-5-(1,3-oxazol-2-yl)-N,N-dipropylisophthalamide | 698.2 |

-continued

| Example | Structure | Compound Name (s) | Mass Spec +H⁺ |
|---------|-----------|-------------------|---------------|
| 3558 | 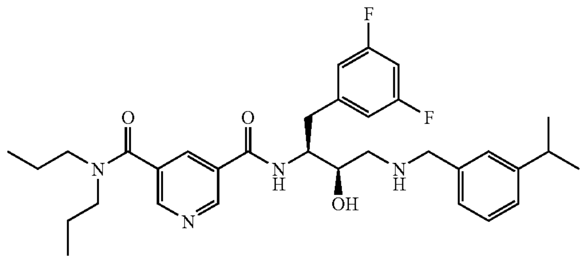 | N'-{(1S,2R)-1-(3,5-difluorobenzyl)-2-hydroxy-3-[(3-isopropylbenzyl)amino]propyl}-N,N-dipropylpyridine-3,5-dicarboxamide | MS 582 (M + H). |
| 3559 | 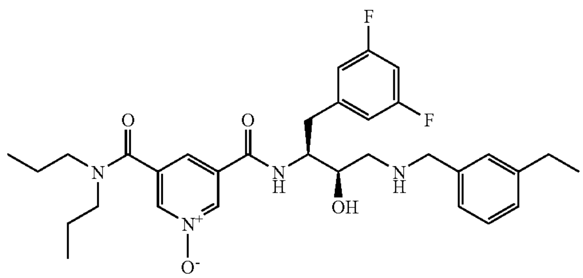 | N'-{(1S,2R)-1-(3,5-difluorobenzyl)-3-[(3-ethylbenzyl)amino]-2-hydroxypropyl}-N,N-dipropylpyridine-3,5-dicarboxamide 1-oxide | MS 584 (M + H). |
| 3560 | 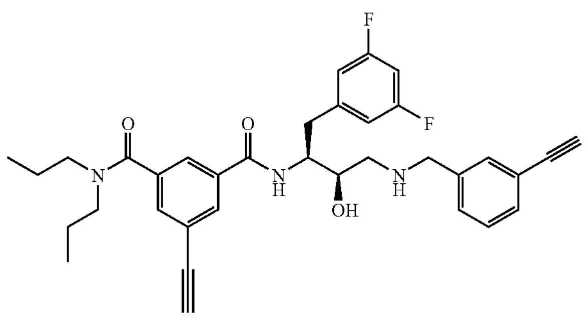 | N'-{(1S,2R)-1-(3,5-difluorobenzyl)-3-[(3-ethylbenzyl)amino]-2-hydroxypropyl}ehtynyl-N,N-dipropylisophthalamide | MS 587 (M + H). |
| 3561 | 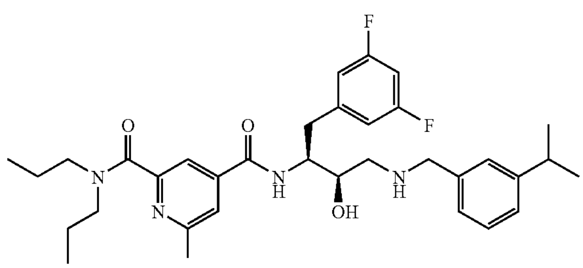 | N⁴-{(1S,2R)-1-(3,5-difluorobenzyl)-2-hydroxy-3-[(3-isopropylbenzyl)amino]propyl}-6-methyl-N²,N²-dipropylpyridine-2,4-dicarboxamide | MS 595 (M + H). |
| 3562 | 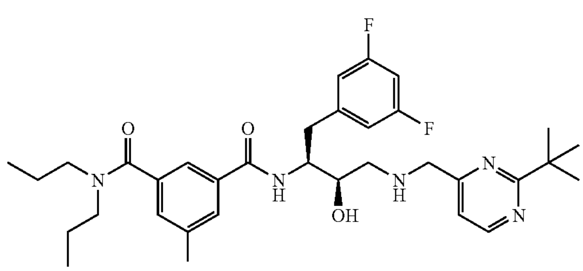 | N'-[(1S,2R)-3-{[(2-tert-butylpyrimidin-4-yl)methyl]amino}-1-(3,5-difluorobenzyl)-2-hydroxypropyl]-5-methyl-N,N-dipropylisophthalamide | 610 |

-continued

| Example | Structure | Compound Name (s) | Mass Spec +H+ |
|---|---|---|---|
| 3563 | 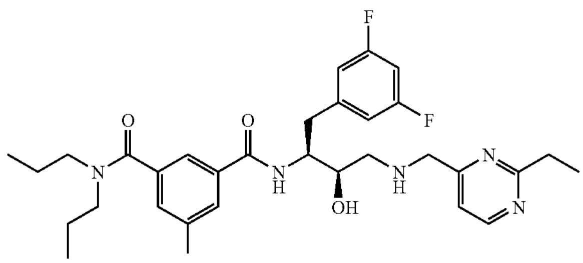 | N'-((1S,2R)-1-(3,5-difluorobenzyl)-3-{[(2-ethylpyrimidin-4-yl)methyl]amino}-2-hydroxypropyl)-5-methyl-N,N-dipropylisophthalamide | 583 605 (M + Na) |
| 3564 | 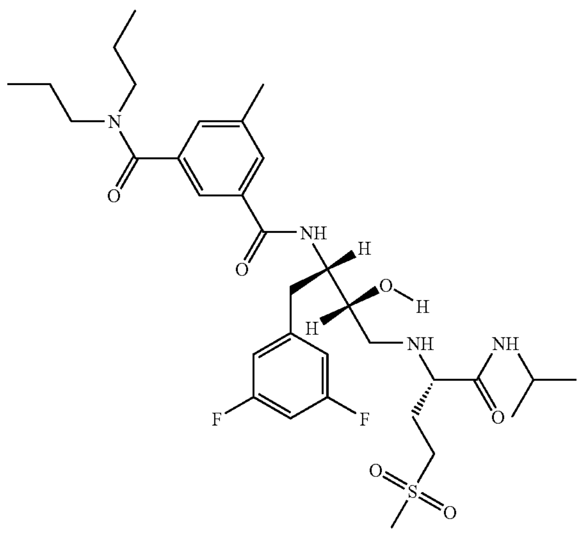 | N'-((1S,2R)-1-(3,5-difluorobenzyl)-2-hydroxy-3-{[(1S)-1-[(isobutylamino) carbonyl]-3-(methylsulfonyl)propyl]amino}propyl)-5-methyl-N,N-dipropylisophthalamide | 681.3 |
| 3565 | 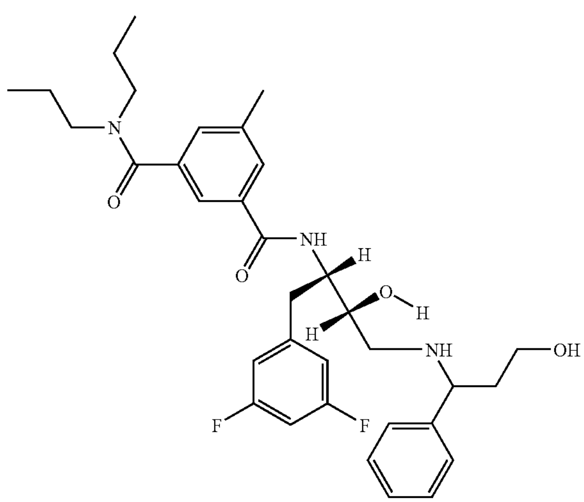 | N'-{(1S,2R)-1-(3,5-difluorobenzyl)-2-hydroxy-3-[(3-hydroxy-1-phenylpropyl)amino]propyl}-5-methyl-N,N-dipropylisophthalamide | 596.3 |

| Example | Structure | Compound Name(s) | Mass Spec +H+ |
|---|---|---|---|
| 3566 | 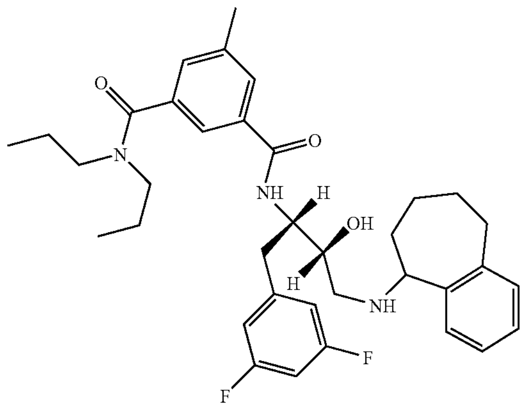 | N'-[(1S,2R)-1-(3,5-difluorobenzyl)-2-hydroxy-3-(6,7,8,9-tetrahydro-5H-benzo[7]annulen-5-ylamino)propyl]-5-methyl-N,N-dipropylisophthalamide | 606.3 |
| 3567 | 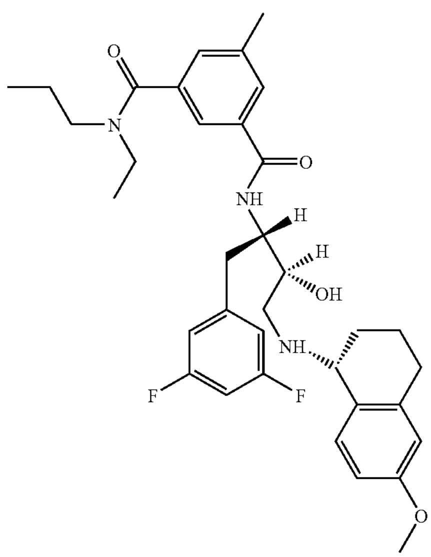 | N'-((1S,2S)-1-(3,5-difluorobenzyl)-2-hydroxy-3-{[(1R)-6-methoxy-1,2,3,4-tetrahydronaphthalen-1-yl]amino}propyl)-5-methyl-N,N-dipropylisophthalamide | Mass spec (CI) MH+-OMe-tetraline 462.2 |
| 3568 | 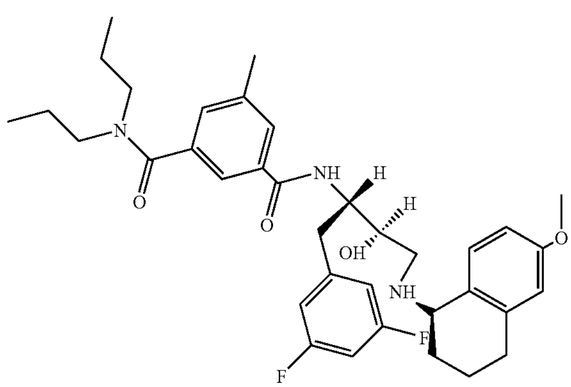 | N'-((1S,2R)-1-(3,5-difluorobenzyl)-2-hydroxy-3-{[(1R)-6-methoxy-1,2,3,4-tetrahydronaphthalen-1-yl]amino}propyl)-5-methyl-N,N-dipropylisophthalamide | Mass spec (CI) MH+-OMe-tetraline 462.2 |

| Example | Structure | Compound Name (s) | Mass Spec +H⁺ |
|---|---|---|---|
| 3569 | 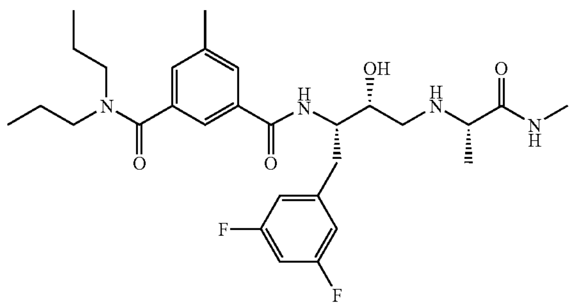 | N'-((1S,2R)-1-(3,5-difluorobenzyl)-2-hydroxy-3-{[(1S)-2-oxo-1-methyl-2-(methylamino)ethyl]amino}propyl)-5-methyl-N,N-dipropylisophthalamide | 547.4 |
| 3570 | 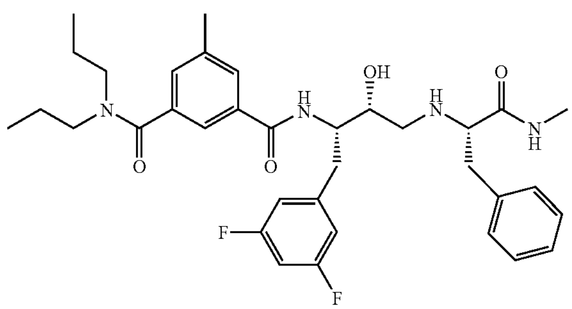 | N'-[(1S,2R)-3-}[(1S)-1-benzyl-2-oxo-2-(methylamino)ethyl]amino}-1-(3,5-difluorobenzyl)-2-hydroxypropyl]-5-methyl-N,N-dipropylisophthalamide | |
| 3571 | 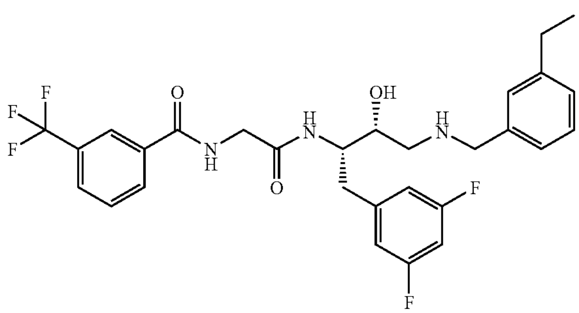 | N¹-{(1S,2R)-1-(3,5-difluorobenzyl)-3-[(3-ethylbenzyl)amino]-2-hydroxypropyl}-N²-{oxo[3-(trifluoromethyl)phenyl]methyl}glycinamide | |
| 3572 | 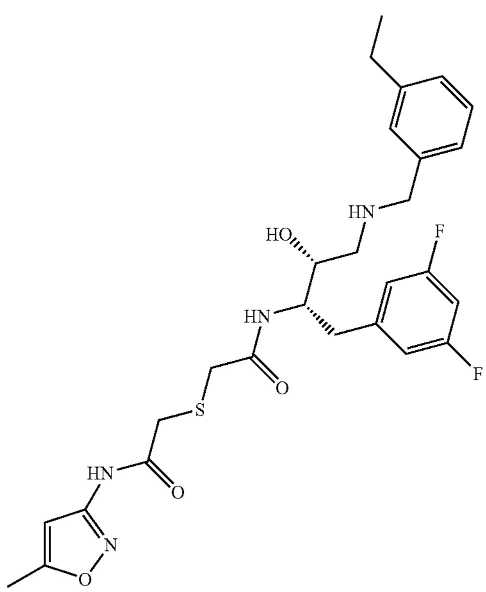 | 2-{[2-({(1S,2R)-1-(3,5-difluorobenzyl)-3-[(3-ethylbenzyl)amino]-2-hydroxypropyl}amino)-2-oxoethyl]thio)-N-(5-methylisoxazol-3-yl)acetamide | |

| Example | Structure | Compound Name (s) | Mass Spec +H+ |
|---|---|---|---|
| 3573 | 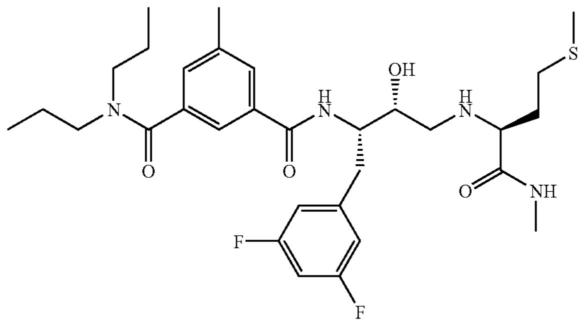 | N'-((1S,2R)-1-(3,5-difluorobenzyl)-2-hydroxy-3-{[(1S)-1-[oxo (methylamino)methyl]-3-(methylthio)propyl]amino}propyl)-5-methyl-N,N-dipropylisophthalamide | |
| 3574 | 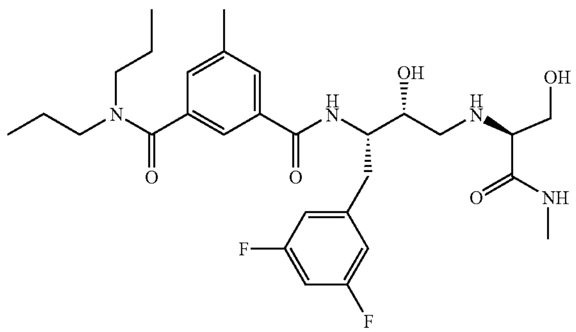 | N'-((1S,2R)-1-(3,5-difluorobenzyl)-2-hydroxy-3-{[(1R)-1-(hydroxymethyl)-2-oxo-2-(methylamino)ethyl]amino}propyl)-5-methyl-N,N-dipropylisophthalamide | |
| 3575 | 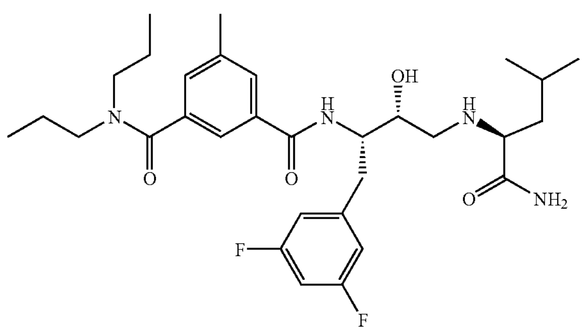 | N'-[(1S,2R)-3-({(1S)-1-[amino (oxo)methyl]-3-methylbutyl}amino)-1-(3,5-difluorobenzyl)-2-hydroxypropyl]-5-methyl-N,N-dipropylisophthalamide | |
| 3576 | 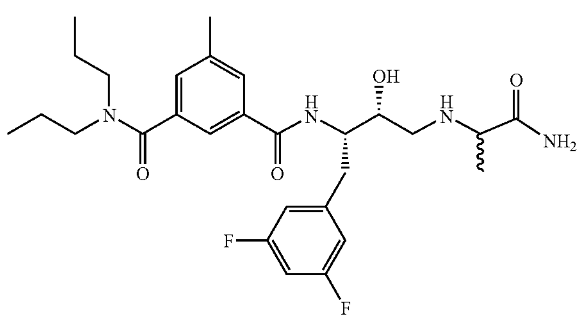 | N'-[(1S,2R)-3-[(2-amino-2-oxo-1-methylethyl)amino]-1-(3,5-difluorobenzyl)-2-hydroxypropyl]-5-methyl-N,N-dipropylisophthalamide | |

| Example | Structure | Compound Name (s) | Mass Spec +H+ |
|---|---|---|---|
| 3577 | 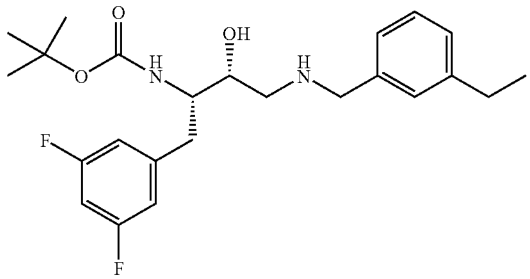 | tert-butyl (1S,2R)-1-(3,5-difluorobenzyl)-3-[(3-ethylbenzyl)amino]-2-hydroxypropylcarbamate | |
| 3578 | as drawn | tert-butyl (1S,2R)-3-(cyclopropylamino)-1-(3,5-difluorobenzyl)-2-hydroxypropylcarbamate | |
| 3579 | as drawn | tert-butyl (1S,2R)-3-(cyclopropylmethyl)amino]-1-(3,5-difluorobenzyl)-2-hydroxypropylcarbamate | |
| 3580 | 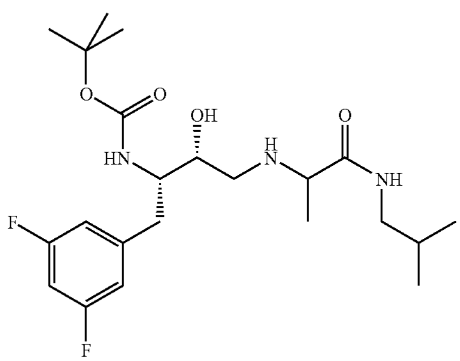 | tert-butyl ((1S,2R)-1-(3,5-difluorobenzyl)-2-hydroxy-3-{[2-oxo-2-(isobutylamino)-1-methylethyl]amino}propyl)carbamate | 416.1 |
| 3581 | 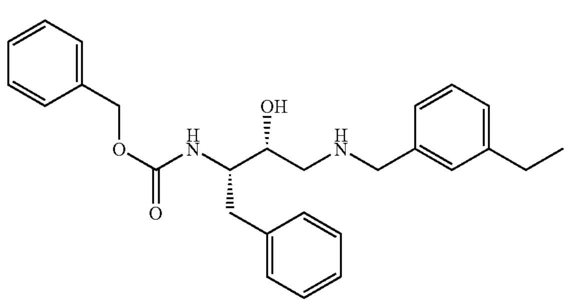 | benzyl (1S,2R)-1-benzyl-3-[(3-ethylbenzyl)amino]-2-hydroxypropylcarbamate | |

| Example | Structure | Compound Name(s) | Mass Spec +H+ |
|---|---|---|---|
| 3582 | 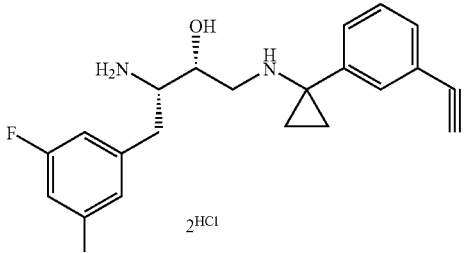 | (2R,3S)-3-amino-4-(3,5-difluorophenyl)-1-{[1-(3-ethynylphenyl)cyclopropyl]amino}butan-2-ol hydrochloride | 357.2 |
| 3583 | 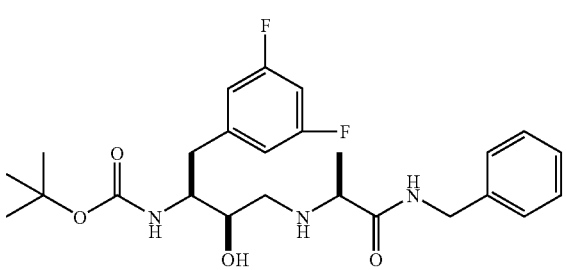 | tert-butyl [(1S,2R)-3-{[(1S)-2-(benzylamino)-2-oxo-1-methylethyl]amino]-1-(3,5-difluorobenzyl)-2-hydroxypropyl]carbamate | 478.1 |
| 3584 | 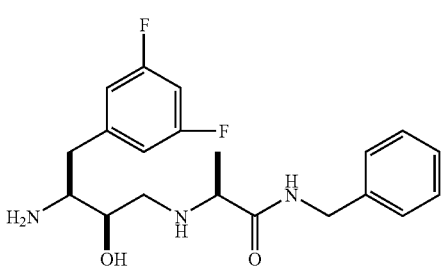 | N²-[(2R,3S)-3-amino-4-(3,5-difluorophenyl)-2-hydroxybutyl]-N¹-benzyl-L-alaninamide bis(trifluoroacetate)(salt) | |
| 3585 | 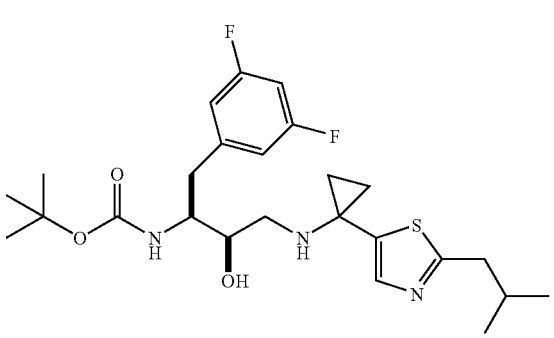 | tert-butyl ((1S,2R)-1-(3,5-difluorobenzyl)-2-hydroxy-3-{[1-(2-isobutyl-1,3-thiazol-5-yl)cyclopropyl]amino}propyl)carbamate | 496.2 |

| Example | Structure | Compound Name(s) | Mass Spec +H+ |
|---|---|---|---|
| 3586 | 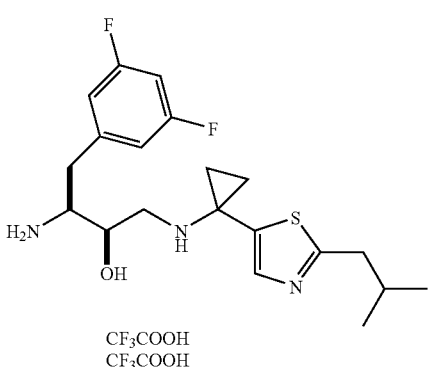 | (2R,3S)-3-amino-4-(3,5-difluorophenyl)-1-{[1-(2-isobutyl-1,3-thiazol-5-yl)cyclopropyl]amino}butan-2-ol bis(trifluoroacetate)(salt) | |
| 3587 | 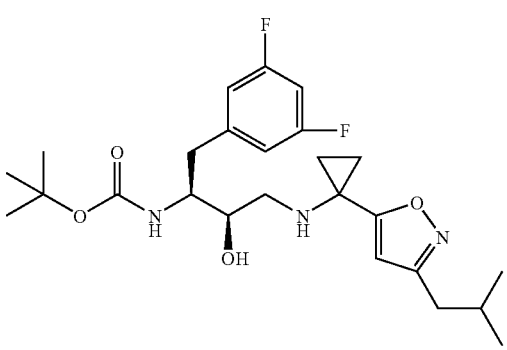 | tert-butyl ((1S,2R)-1-(3,5-difluorobenzyl)-2-hydroxy-3-{[1-(3-isobutylisoxazol-5-yl)cyclopropyl]amino}propyl)carbamate | 480.2 |
| 3588 | 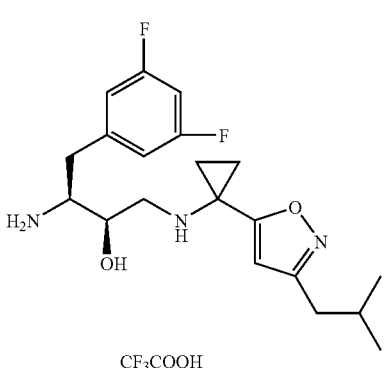 | (2R,3S)-3-amino-4-(3,5-difluorophenyl)-1-{[1-(3-isobutylisoxazol-5-yl)cyclopropyl]amino]butan-2-ol bis(trifluoroacetate)(salt) | |

-continued

| Example | Structure | Compound Name (s) | Mass Spec +H⁺ |
|---|---|---|---|
| 3589 | 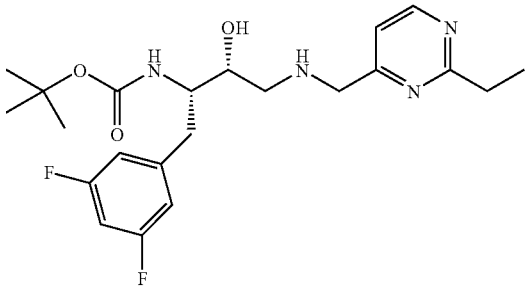 | tert-butyl ((1S,2R)-1-(3,5-difluorobenzyl)-3-{[(2-ethylpyrimidin-4-yl)methyl]amino}-2-hydroxypropyl)carbamate | 437.3 |
| 3590 | 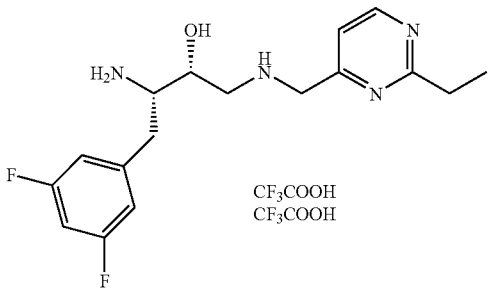 | (2R,3S)-3-amino-4-(3,5-difluorophenyl)-1-{[(2-ethylpyrimidin-4-yl)methyl]amino}butan-2-ol bis(trifluoroacetate)(salt) | |
| 3591 | 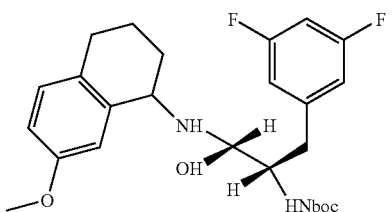 | tert-butyl {(1S,2R)-1-(3,5-difluorobenzyl)-2-hydroxy-3-[(7-methoxy-1,2,3,4-tetrahydronaphthalen-1-yl)amino]propyl}carbamate | 477.5 |
| 3592 | 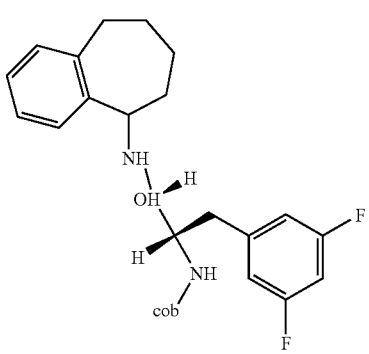 | tert-butyl [(1S,2R)-1-(3,5-difluorobenzyl)-2-hydroxy-3-(6,7,8,9-tetrahydro-5H-benzo[7]annulen-5-ylamino)propyl]carbamate | 461.2 |
| 3593 | 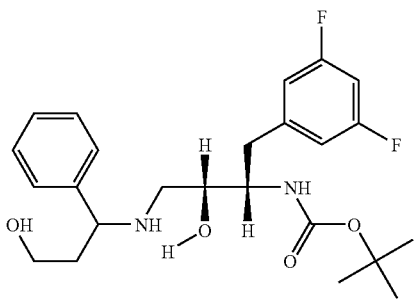 | tert-butyl {(1S,2R)-1-(3,5-difluorobenzyl)-2-hydroxy-3-[(3-hydroxy-1-phenylpropyl)amino]propyl}carbamate | 451.2 |

-continued

| Example | Structure | Compound Name (s) | Mass Spec +H+ |
|---|---|---|---|
| 3594 | 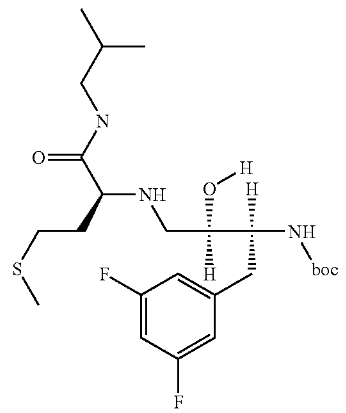 | tert-butyl ((1S,2R)-1-(3,5-difluorobenzyl)-2-hydroxy-3-{[(1S)-1-[oxo(isobutylamino)methyl]-3-(methylthio)propyl]amino}propyl carbamate | 504.3 |
| 3595 | 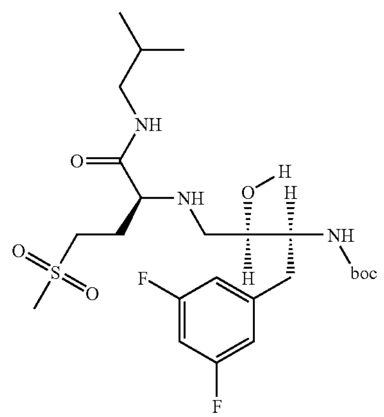 | tert-butyl ((1S,2R)-1-(3,5-difluorobenzyl)-2-hydroxy-3-{[(1S)-1-[(isobutylamino)carbonyl]-3-(methylsulfonyl)propyl)carbamate | 536.2 |
| 3596 | 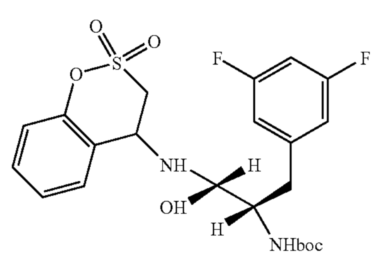 | tert-butyl {(1S,2R)-1-(3,5-difluorobenzyl)-3-[(2,2-dioxido-3,4-dihydro-1,2-benzoxathiin-4-yl)amino]-2-hydroxypropyl}carbamate | 499.1 |
| 3597 | 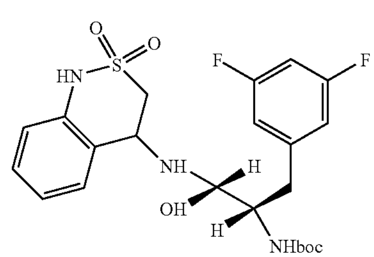 | tert-butyl {(1S,2R)-1-(3,5-difluorobenzyl)-3-[(2,2-dioxido-3,4-dihydro-1H-2,1-benzothiazin-4-yl)amino]-2-hydroxypropyl}carbamate | 498.1 |

-continued

| Example | Structure | Compound Name (s) | Mass Spec +H⁺ |
|---|---|---|---|
| 3598 | 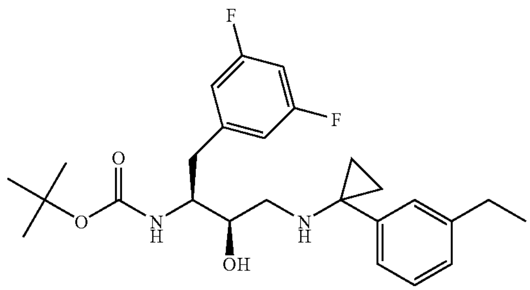 | tert-butyl ((1S,2R)-1-(3,5-difluorobenzyl)-3-{[1-(3-ethylphenyl)cyclopropyl]amino}-2-hydroxypropyl)carbamate | 461.3 |
| 3599 | 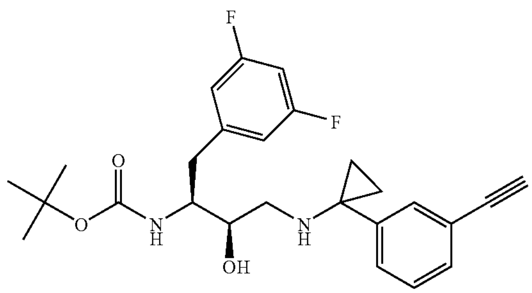 | tert-butyl ((1S,2R)-1-(3,5-difluorobenzyl)-3-{[1-(3-ethylphenyl)cyclopropyl]amino}-2-hydroxypropyl)carbamate | 457.2 |
| 3600 | 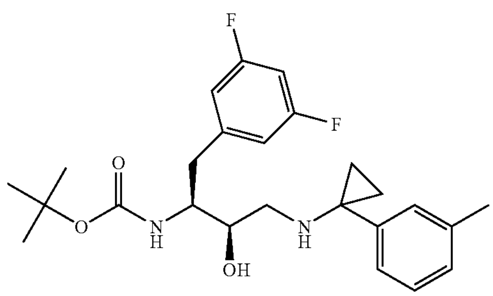 | tert-butyl ((1S,2R)-1-(3,5-difluorobenzyl)-2-hydroxy-3-{[1-(3-methylphenyl)cyclopropyl]amino}propyl)carbamate | 447.2 |
| 3601 | 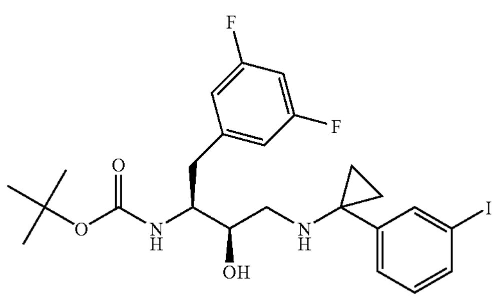 | tert-butyl ((1S,2R)-1-(3,5-difluorobenzyl)-2-hydroxy-3-{[1-(3-iodophenyl)cyclopropyl]amino}propyl)carbamate | 558.4 |
| 3602 | 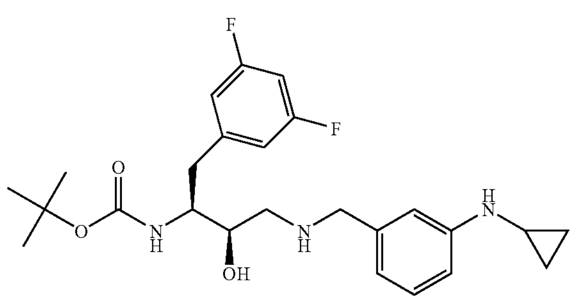 | tert-butyl [(1S,2R)-3-{[3-(cyclopropylamino)benzyl]amino}-1-(3,5-difluorobenzyl)-2-hydroxypropyl]carbamate | 462.2 |

| Example | Structure | Compound Name(s) | Mass Spec +H⁺ |
|---|---|---|---|
| 3603 | 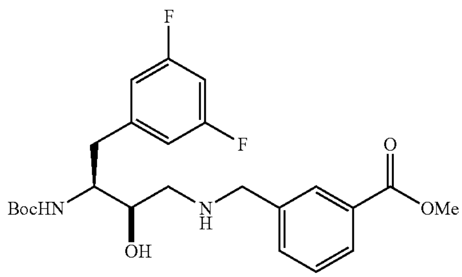 | methyl 3-({[(2R,3S)-3-[(tert-butoxycarbonyl)amino]-4-(3,5-difluorophenyl)-2-hydroxybutyl]amino}methyl)benzoate | 465.1 |
| 3604 | 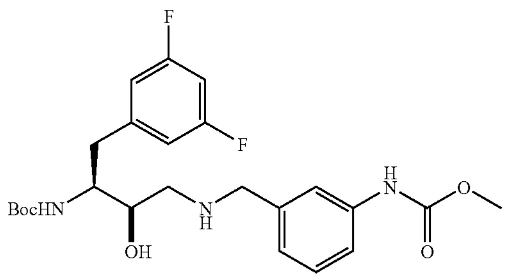 | methyl [3-({[(2R,3S)-3-[(tert-butoxycarbonyl)amino]-4-(3,5-difluorophenyl)-2-hydroxybutyl]amino}methyl)phenyl]carbamate | 480.1 |
| 3605 | 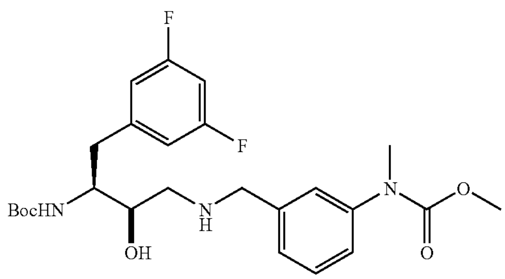 | methyl [3-({[(2R,3S)-3-[(tert-butoxycarbonyl)amino]-4-(3,5-difluorophenyl)-2-hydroxybutyl]amino}methyl)phenyl]methylcarbamate | 494.1 |
| 3606 | 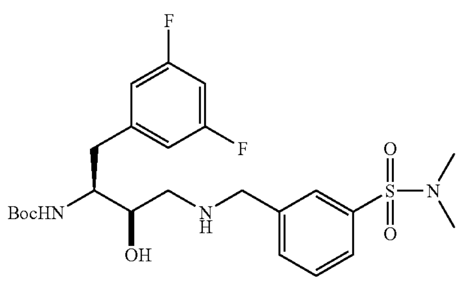 | tert-butyl [(1S,2R)-1-(3,5-difluorobenzyl)-3-({3-[(dimethylamino)sulfonyl]benzyl}amino)-2-hydroxypropyl]carbamate | 514.1 |
| 3607 | 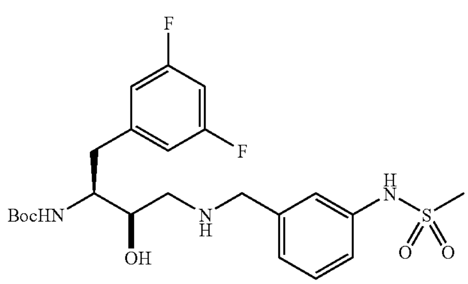 | tert-butyl [(1S,2R)-1-(3,5-difluorobenzyl)-2-hydroxy-3-({3-[(methylsulfonyl)amino]benzyl}amino)propyl]carbamate | 500.1 |

-continued

| Example | Structure | Compound Name (s) | Mass Spec +H⁺ |
|---|---|---|---|
| 3608 | 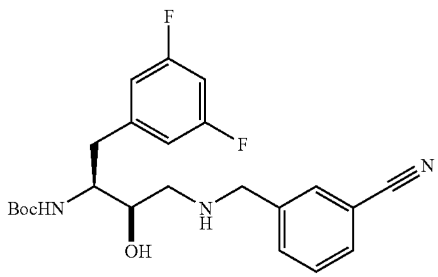 | tert-butyl [(1S,2R)-3-[(3-cyanobenzyl)amino]-1-(3,5-difluorobenzyl)-2-hydroxypropyl]carbamate | 432.1 |
| 3609 | 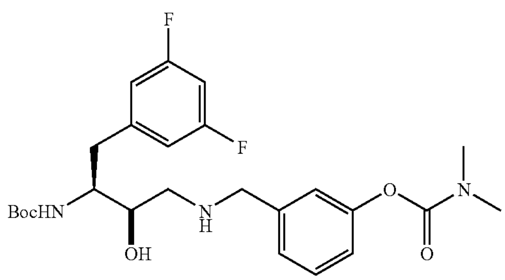 | 3-({[(2R,3S)-3-[(tert-butoxycarbonyl)amino]-4-(3,5-difluorophenyl)-2-hydroxybutyl]amino}methyl)phenyl dimethylcarbamate | 494.1 |
| 3610 | 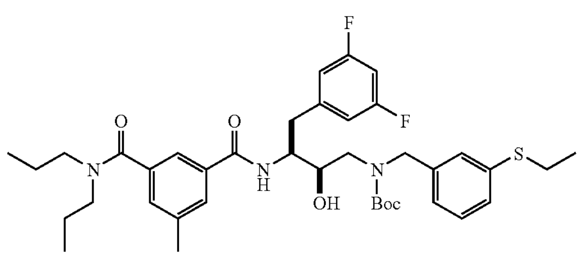 | tert-butyl [(2R,3S)-4-(3,5-difluorophenyl)-3-({3-[(dipropylamino)carbonyl]-5-methylbenzoyl}amino)-2-hydroxybutyl][3-(ethylthio)benzyl]carbamate | 612.3 |
| 3611 | 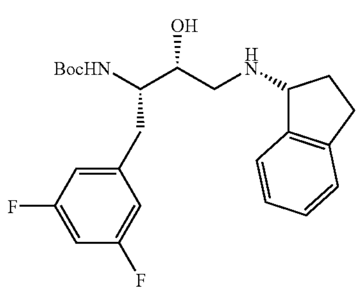 | tert-butyl {(1S,2R)-1-(3,5-difluorobenzyl)-3-[(1R)-2,3-dihydro-1H-inden-1-ylamino]-2-hydroxypropyl}carbamate | 433.2 |
| 3612 | 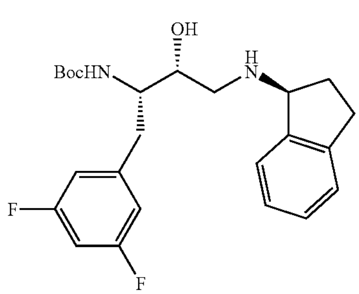 | tert-butyl {(1S,2R)-1-(3,5-difluorobenzyl)-3-[(1S)-2,3-dihydro-1H-inden-1-ylamino]-2-hydroxypropyl}carbamate | 433.2 |

-continued

| Example | Structure | Compound Name (s) | Mass Spec +H⁺ |
|---|---|---|---|
| 3613 | 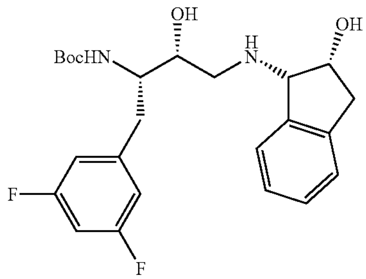 | tert-butyl ((1S,2R)-1-(3,5-difluorobenzyl)-2-hydroxy-3-{[(1S,2R)-2-hydroxy-2,3-dihydro-1H-inden-1-yl]amino}propyl)carbamate | 449.2 |
| 3614 | 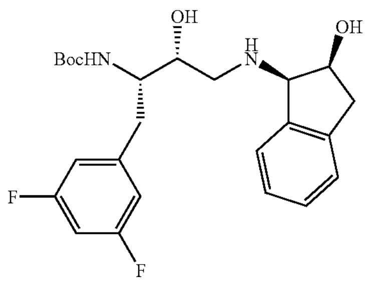 | tert-butyl ((1S,2R)-1-(3,5-difluorobenzyl)-2-hydroxy-3-{[(1R,2S)-2-hydroxy-2,3-dihydro-1H-inden-1-yl]amino}propyl)carbamate | 449.4 |
| 3615 | 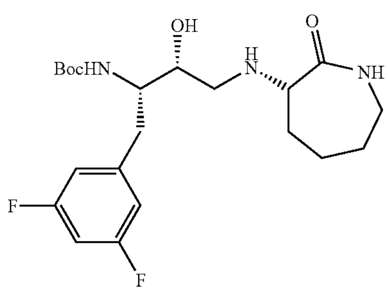 | tert-butyl ((1S,2R)-1-(3,5-difluorobenzyl)-2-hydroxy-3-{[(3S)-2-oxoazepan-3-yl]amino}propyl)carbamate | 428.2 |
| 3616 | 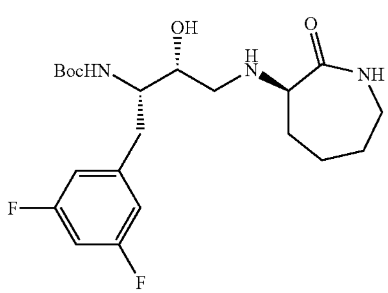 | tert-butyl ((1S,2R)-1-(3,5-difluorobenzyl)-2-hydroxy-3-{[(3R)-2-oxoazepan-3-yl]amino}propyl)carbamate | 428.2 |
| 3617 | 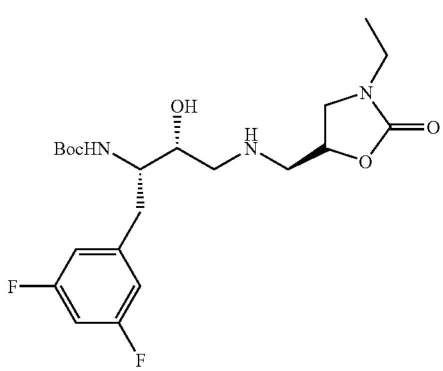 | tert-butyl [(1S,2R)-1-(3,5-difluorobenzyl)-3-({[(5S)-3-ethyl-2-oxo-1,3-oxazolidin-5-yl]methyl}amino)-2-hydroxypropyl]carbamate | 444.2 |

-continued

| Example | Structure | Compound Name (s) | Mass Spec +H+ |
|---|---|---|---|
| 3618 | 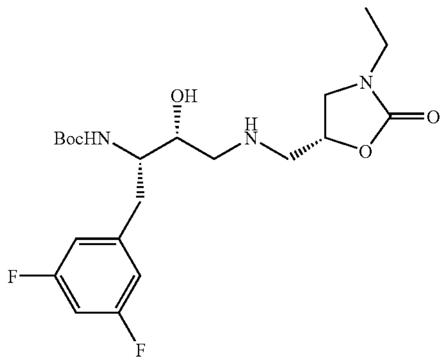 | tert-butyl [(1S,2R)-1-(3,5-difluorobenzyl)-3-({[(5R)-3-ethyl-2-oxo-1,3-oxazolidin-5-yl]methyl}amino)-2-hydroxypropyl]carbamate | 444.2 |
| 3619 | 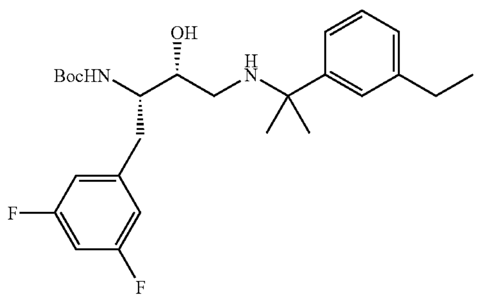 | tert-butyl ((1S,2R)-1-(3,5-difluorobenzyl)-3-{[1-(3-ethylphenyl)-1-methylethyl]amino}-2-hydroxypropyl)carbamate | 475.2 |
| 3620 | 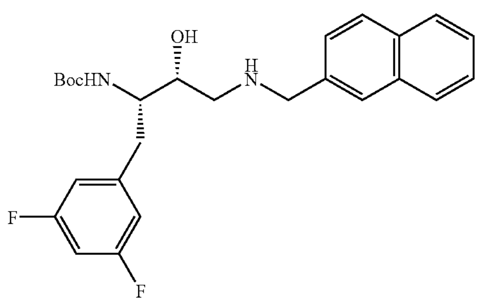 | tert-butyl ((1S,2R)-1-(3,5-difluorobenzyl)-2-hydroxy-3-[(2-naphthylmethyl)amino]propyl)carbamate | 463.3 |
| 3621 | 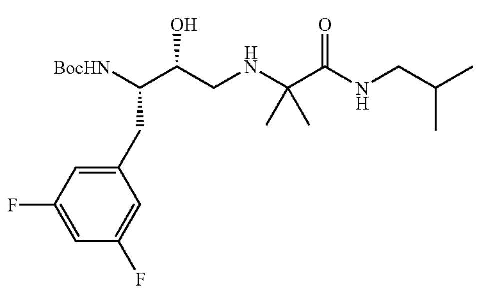 | tert-butyl ((1S,2R)-1-(3,5-difluorobenzyl)-2-hydroxy-3-{[2-oxo-2-(isobutylamino)-1,1-dimethylethyl]amino}propyl)carbamate | 458.2 |
| 3622 | 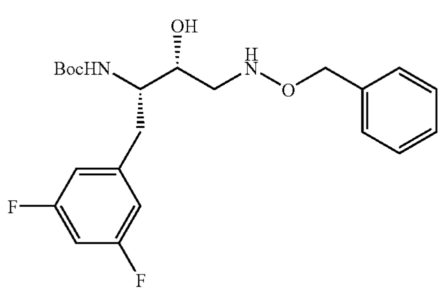 | tert-butyl [(1S,2R)-3-[(benzyloxy)amino]-1-(3,5-difluorobenzyl)-2-hydroxypropyl]carbamate | 423.1 |

-continued

| Example | Structure | Compound Name(s) | Mass Spec +H⁺ |
|---|---|---|---|
| 3623 | 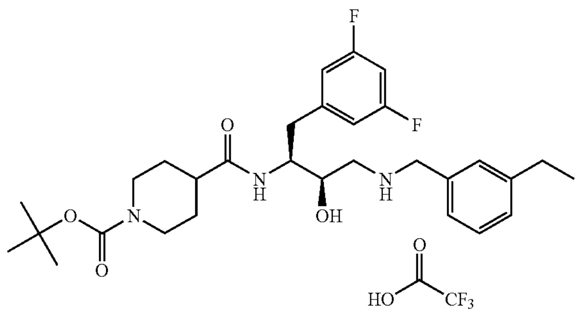 | tert-butyl 4-[({(1S,2R)-1-(3,5-difluorobenzyl)-3-[(3-ethylbenzyl)amino]-2-hydroxypropyl}amino)carbonyl]piperidine-1-carboxylate trifluoroacetate | |
| 3624 | 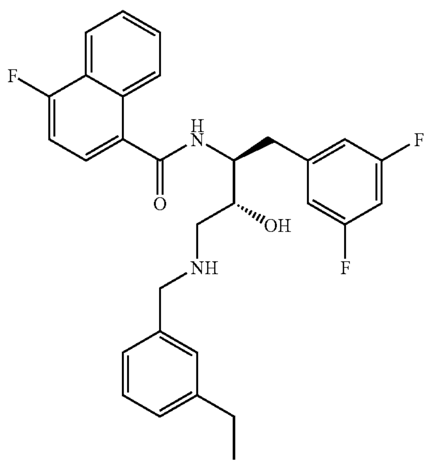 | N-{(1S,2R)-1-(3,5-difluorobenzyl)-3-[(3-ethylbenzyl)amino]-2-hydroxypropyl}-4-fluoro-1-naphthamide | |
| 3625 | 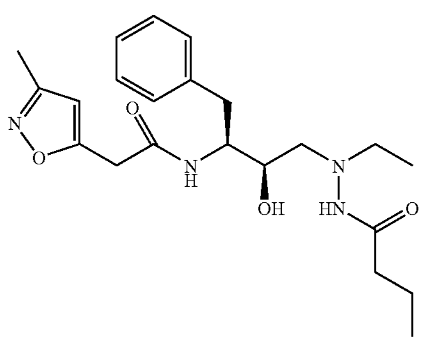 | N-[(1S,2R)-1-benzyl-3-(2-butyryl-1-ethylhydrazino)-2-hydroxypropyl]-2-(3-methylisoxazol-5-yl)acetamide | |
| 3626 | 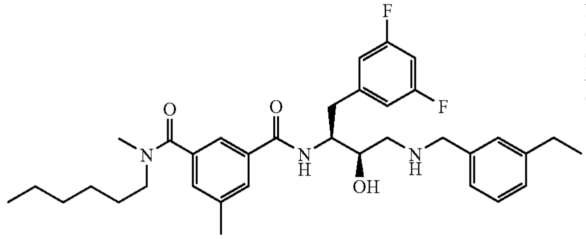 | N'-{(1S,2R)-1-(3,5-difluorobenzyl)-3-[(3-ethylbenzyl)amino]-2-hydroxypropyl}-N-hexyl-N,5-dimethylisophthalamide | |

-continued

| Example | Structure | Compound Name(s) | Mass Spec +H⁺ |
|---|---|---|---|
| 3627 | 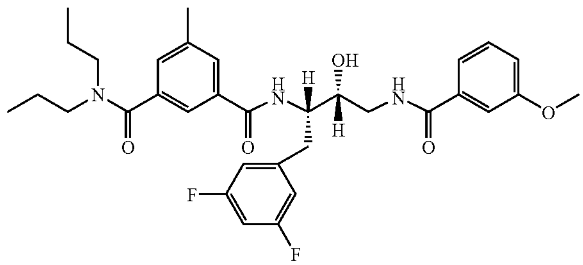 | N'-{(1S,2R)-1-(3,5-difluorobenzyl)-2-hydroxy-3-[(3-methoxybenzoyl)amino]propyl}-5-methyl-N,N-dipropylisophthalamide | |
| 3628 | single enantiomer | N'-{(1S,2R)-1-(3,5-difluorobenzyl)-3-[(3-ethylbenzyl)amino]-2-hydroxypropyl}-1-methyl-1H-imidazole-2-carboxamide | |
| 3629 | single diastereomer | N¹-{(1S,2R)-1-(3,5-difluorobenzyl-3-[(3-ethylbenzyl)amino]-2-hydroxypropyl}-3,3-dimethyl-N²,N²-dipropylcyclopropane-1,2-dicarboxamide | |
| 3630 | single enantiomer | tert-butyl 2-[({(1S,2R)-1-(3,5-difluorobenzyl)-3-[(3-ethylbenzyl)amino]-2-hydroxypropyl}amino)carbonyl]-1-methyl-1H-imidazol-4-ylcarbamate | |
| 3631 | 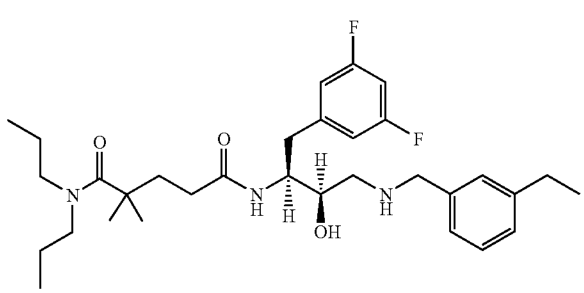 | N⁵-{(1S,2R)-1-(3,5-difluorobenzyl)-3-[(3-ethylbenzyl)amino]-2-hydroxypropyl}-2,2-dimethyl-N¹,N¹-dipropylpentanediamide | |

-continued

| Example | Structure | Compound Name(s) | Mass Spec +H⁺ |
|---|---|---|---|
| 3632 | 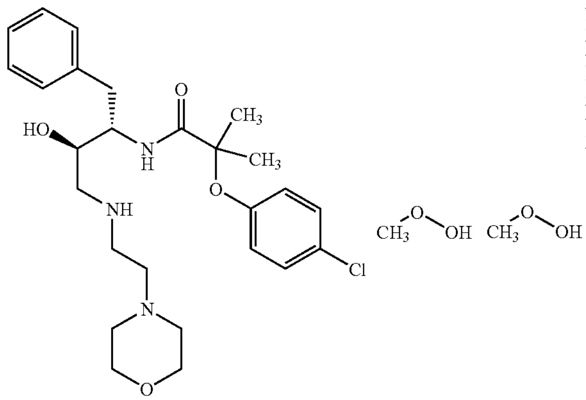 | N-{(1S,2R)-1-benzyl-2-hydroxy-3-[(2-morpholin-4-ylethyl)amino]propyl}-2-(4-chlorophenoxy)-2-methylpropanamide compound with methyl hydroperoxide (1:2) | |
| 3633 | 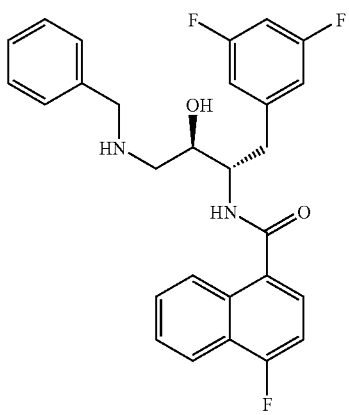 | N-[(1S,2R)-3-(benzylamino)-1-(3,5-difluorobenzyl)-2-hydroxypropyl]-4-fluoro-1-naphthamide | |
| 3634 | 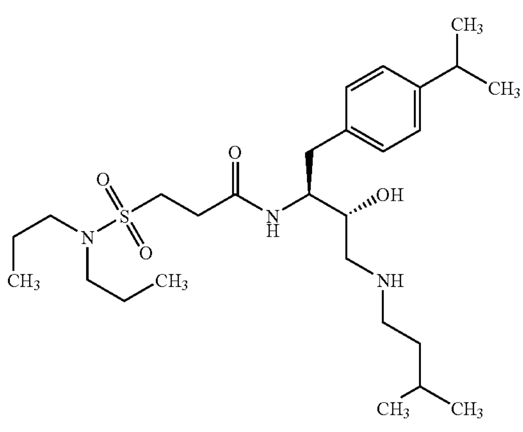 | 3-[(dipropylamino)sulfonyl]-N-[(1S,2R)-2-hydroxy-3-(isopentylamino)-1-(4-isopropylbenzyl)propyl]propanamide | |

| Example | Structure | Compound Name(s) | Mass Spec +H+ |
|---|---|---|---|
| 3635 | 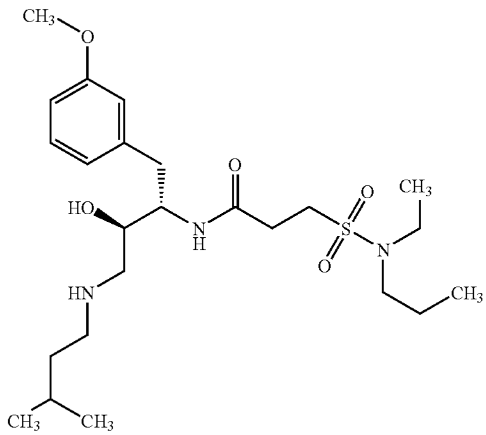 | 3-[(dipropylamino)sulfonyl]-N-[(1S,2R)-2-hydroxy-3-(isopentylamino)-1-(3-methoxybenzyl)propyl]propanamide | |
| 3636 | 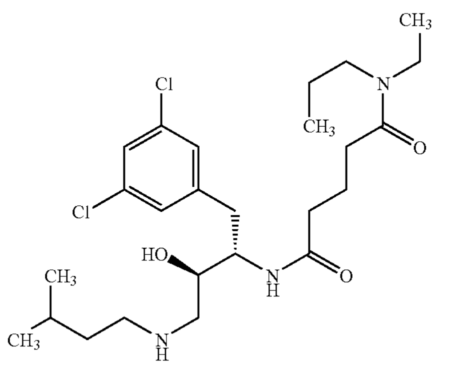 | N¹-[(1S,2R)-1-(3,5-dichlorobenzyl)-2-hydroxy-3-(isopentylamino)propyl]-N⁵,N⁵-dipropylpentanediamide | |
| 3637 | 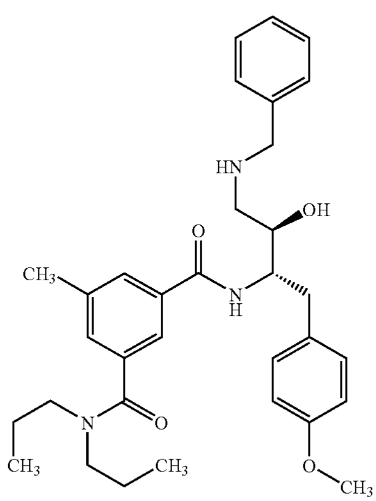 | N¹-[(1S,2R)-3-(benzylamino)-2-hydroxy-1-(4-methoxybenzyl)propyl]-5-methyl-N³,N³-dipropylisophthalamide | |

-continued

| Example | Structure | Compound Name (s) | Mass Spec +H+ |
|---|---|---|---|
| 3638 | 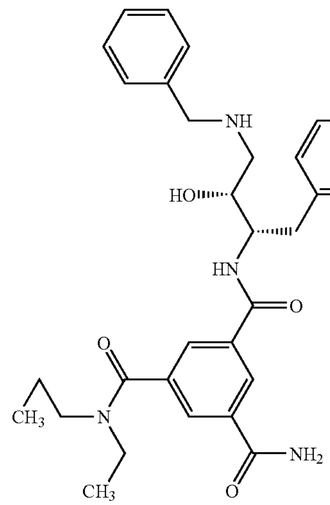 | N¹-[(1S,2R)-3-(benzylamino)-2-hydroxy-1-(4-methoxybenzyl)propyl]-N³,N³-dipropylbenzene-1,3,5-tricarboxamide | |
| 3639 | 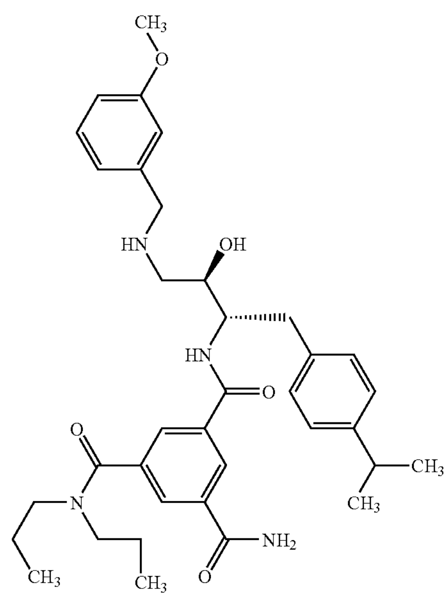 | N¹-{(1S,2R)-2-hydroxy-1-(4-isopropylbenzyl)-3-[(3-methoxybenzyl)amino]propyl}-N³,N³-dipropylbenzene-1,3,5-tricarboxamide | |
| 3640 | 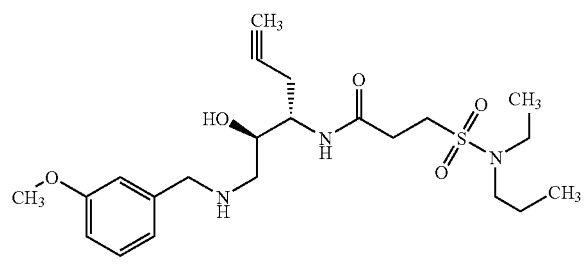 | 3-[(dipropylamino)sulfonyl]-N-((1S)-1-((1R)-1-hydroxy-2-[(3-methoxybenzyl)amino]ethyl}but-3-ynyl)propanamide | |

| | | |
|---|---|---|
| 3641 | 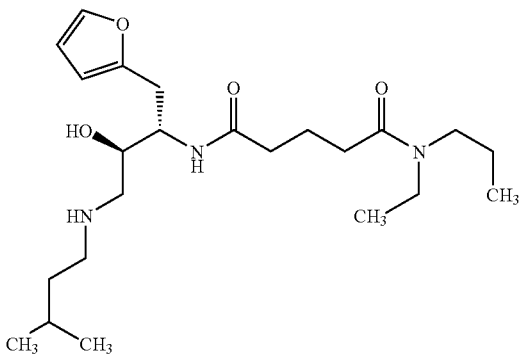 | N$^1$-[(1S,2R)-1-(2-furylmethyl)-2-hydroxy-3-(isopentylamino)propyl]-N$^5$,N$^5$-dipropylpentanediamide |
| 3642 | 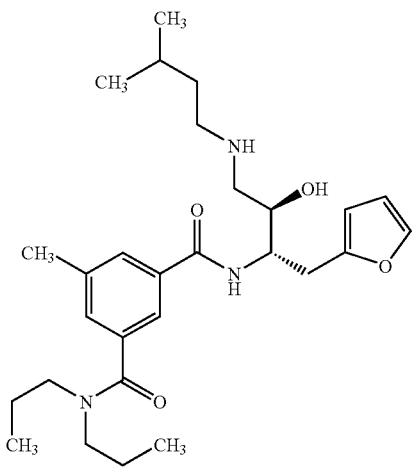 | N$^1$-[(1S,2R)-1-(2-furylmethyl)-2-hydroxy-3-(isopentylamino)propyl]-5-methyl-N$^3$,N$^3$-dipropylisophthalamide |
| 3643 | 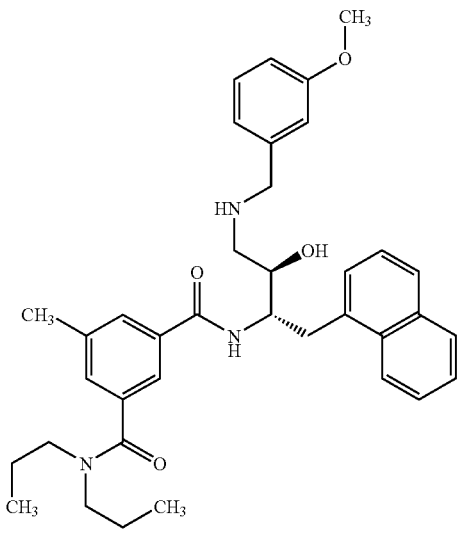 | N$^1$-[(1S,2R)-2-hydroxy-3-[(3-methoxybenzyl)amino]-1-(1-naphthylmethyl)propyl]-5-methyl-N$^3$,N$^3$-dipropylisophthalamide |

| | | |
|---|---|---|
| 3644 | 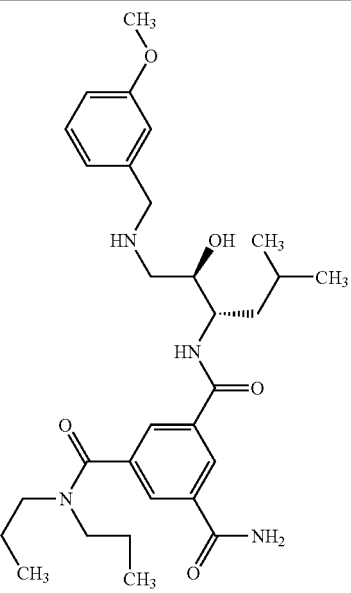 | N¹-((1S)-1-{(1R)-1-hydroxy-2-[(3-methoxybenzyl)amino]ethyl}-3-methylbutyl)-N³,N³-dipropylbenzene-1,3,5-tricarboxamide |
| 3645 | 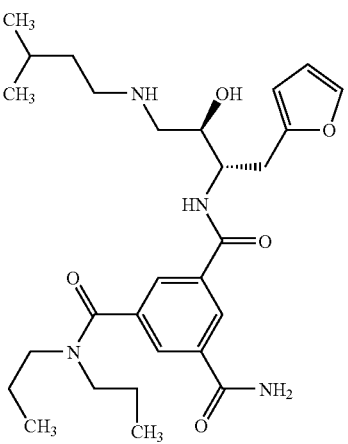 | N¹-[(1S,2R)-1-(2-furylmethyl)-2-hydroxy-3-(isopentylamino)propyl]-N³,N³-dipropylbenzene-1,3,5-tricarboxamide |
| 3646 | 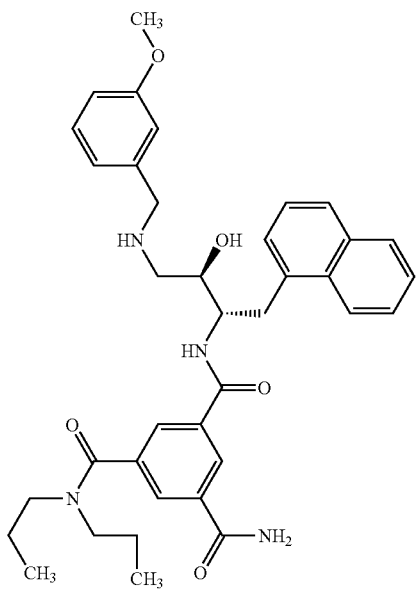 | N¹-[(1S,2R)-2-hydroxy-3-[(3-methoxybenzyl)amino]-1-(1-naphthylmethyl)propyl]-N³,N³-dipropylbenzene-1,3,5-tricarboxamide |

-continued
| | | |
|---|---|---|
| 3647 | 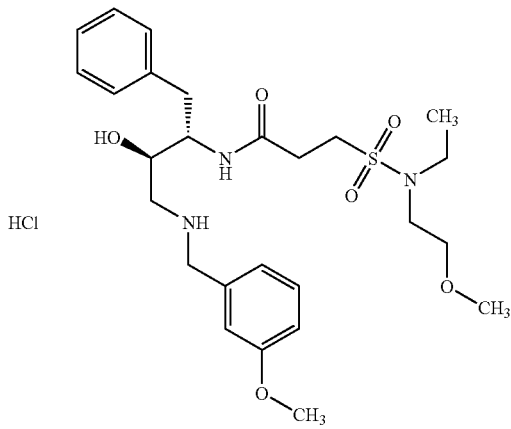 | N-{(1S,2R)-1-benzyl-2-hydroxy-3-[(3-methoxybenzyl)amino]propyl}-3-{[(2-methoxyethyl)(propyl)amino]sulfonyl}propanamide hydrochloride |
| 3648 | 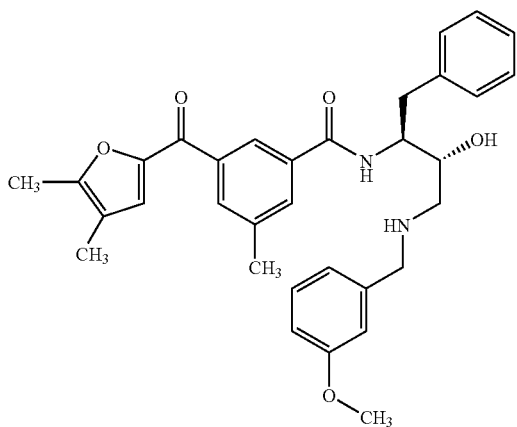 | N-{(1S,2R)-1-benzyl-2-hydroxy-3-[(3-methoxybenzyl)amino]propyl}-3-(4,5-dimethyl-2-furoyl)-5-methylbenzamide |
| 3649 | 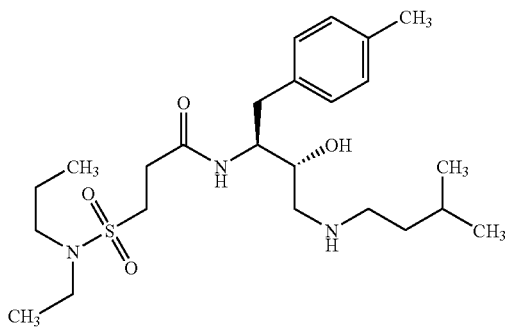 | 3-[(dipropylamino)sulfonyl]-N-[(1S,2R)-2-hydroxy-3-(isopentylamino)-1-(4-methylbenzyl)propyl]propanamide |

-continued

| | | |
|---|---|---|
| 3650 | 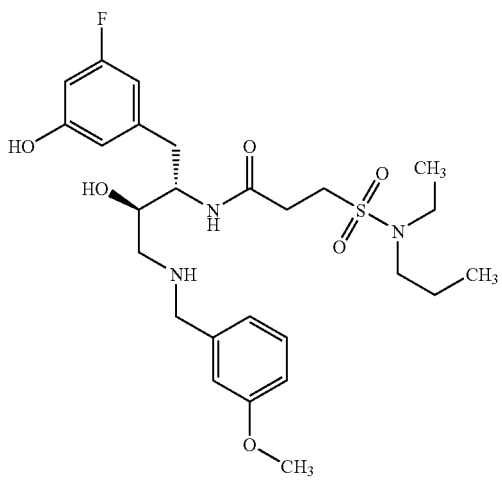 | 1 3-[(dipropylamino)sulfonyl]-N-{(1S,2R)-1-(3-fluoro-5-hydroxybenzyl)-2-hydroxy-3-[(3-methoxybenzyl)amino]propyl]propanamide |
| 3651 | 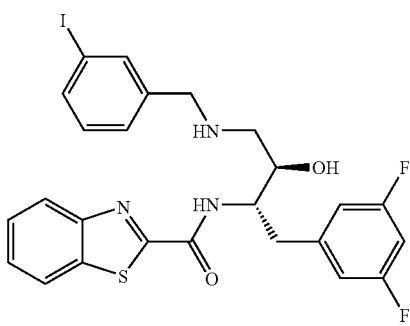 | N-{(1S,2R)-1-(3,5-difluorobenzyl)-2-hydroxy-3-{(3-iodobenzyl)amino]propyl}-1,3-benzothiazole-2-carboxamide |
| 3652 | 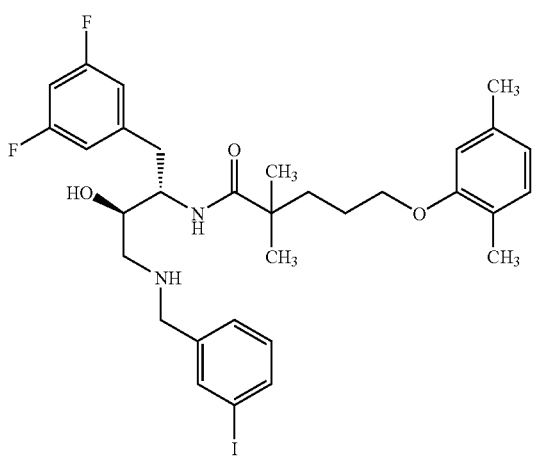 | N-{(1S,2R)-1-(3,5-difluorobenzyl)-2-hydroxy-3-{(3-iodobenzyl)amino]propyl}-5-(2,5-dimethylphenoxy)-2,2-dimethylpentanamide |
| 3653 | 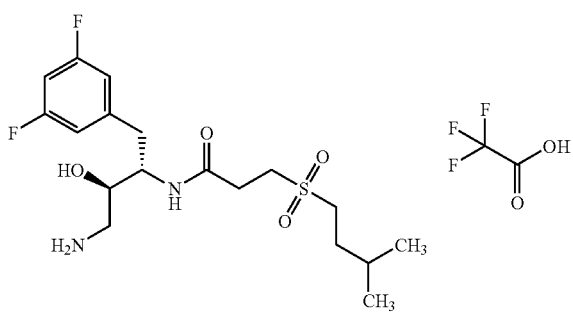 | N-[(1S,2R)-3-amino-1-(3,5-difluorobenzyl)-2-hydroxypropyl]-3-(isopentylsulfonyl)propanamide trifluoroacetate |

-continued

| | | |
|---|---|---|
| 3654 | 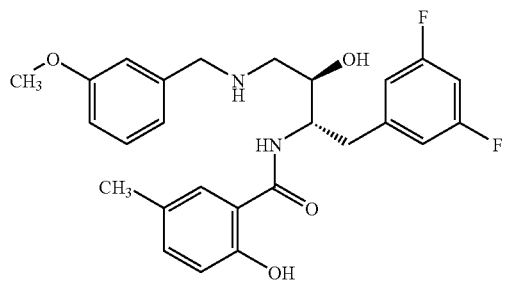 | N-{(1S,2R)-1-(3,5-difluorobenzyl)- 471.4 2-hydroxy-3-[(3-methoxybenzyl) amino]propyl}-2-hydroxy-5-methylbenzamide |
| 3655 | 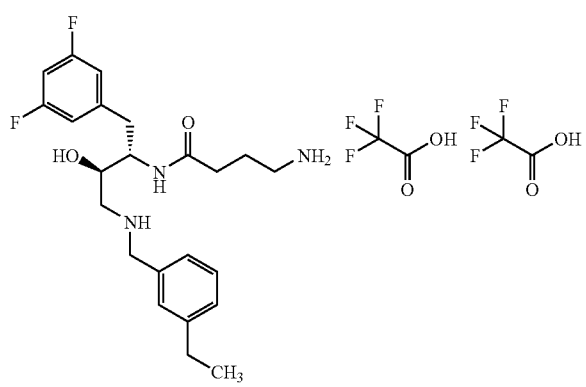 | 4-amino-N-[(1S,2R)-1-(3,5-difluorobenzyl)-3-[(3-ethylbenzyl)amino]-2-hydroxypropyl]butanamide bis (trifluoroacetate) |
| 3656 | 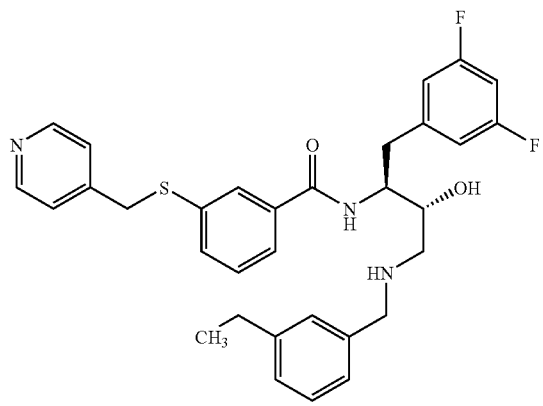 | N-{(1S,2R)-1-(3,5-difluorobenzyl)-3-[(3-ethylbenzyl)amino]-2-hydroxypropyl}-3-[(pyridin-4-ylmethyl)thio]benzamide |
| 3657 | 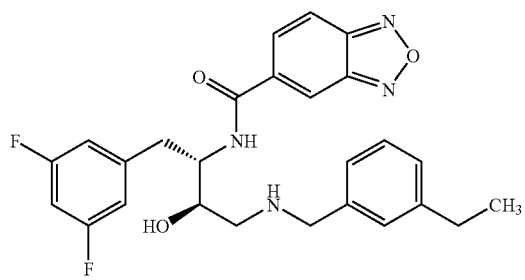 | N-{(1S,2R)-1-(3,5-difluorobenzyl)-3-[(3-ethylbenzyl)amino]-2-hydroxypropyl}-2,1,3-benzoxadiazole-5-carboxamide |

-continued
| | | |
|---|---|---|
| 3658 | 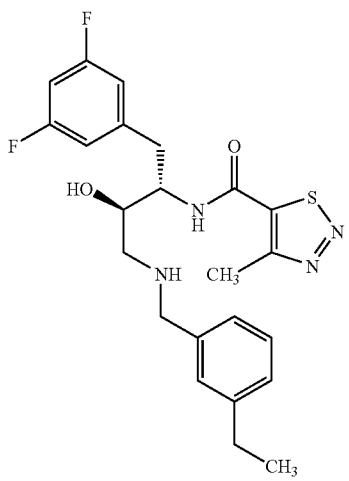 | N-{(1S,2R)-1-(3,5-difluorobenzyl)-3-[(3-ethylbenzyl)amino]-2-hydroxypropyl}-4-methyl 1,2,3-thiadiazole-5-carboxamide |
| 3659 | 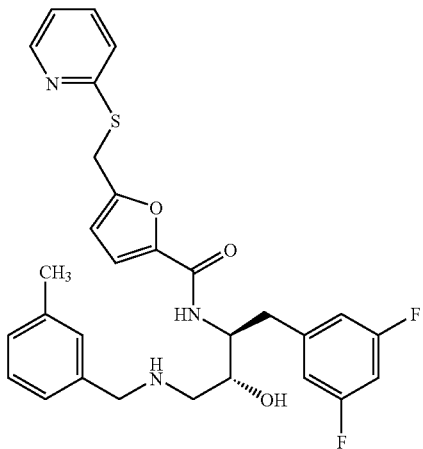 | N-{(1S,2R)-1-(3,5-difluorobenzyl)-3-[(3-ethylbenzyl)amino]-2-hydroxypropyl}-5-[(pyridin-2-ylthio)methyl]-2-furamide |
| 3660 | 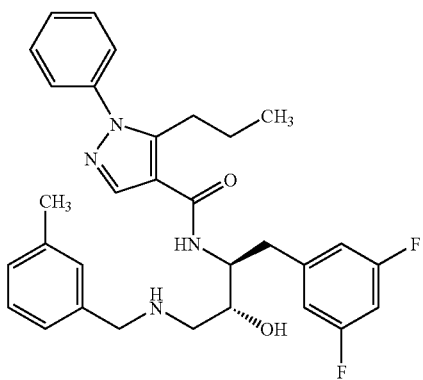 | N-{(1S,2R)-1-(3,5-difluorobenzyl)-3-[(3-ethylbenzyl)amino]-2-hydroxypropyl}-1-phenyl-5-propyl-1H-pyrazole-4-carboxamide |

| | | |
|---|---|---|
| 3661 | 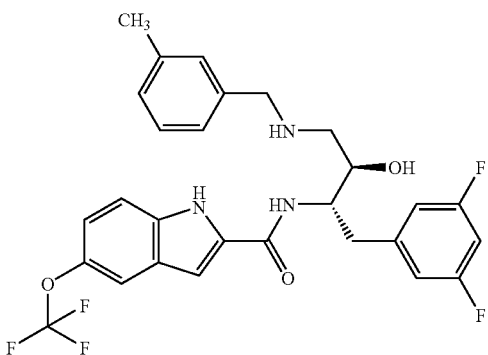 | N-{(1S,2R)-1-(3,5-difluorobenzyl)-3-[(3-ethylbenzyl)amino]-2-hydroxypropyl}-5-(trifluoromethoxy)-1H-indole-2-carboxamide |
| 3662 | 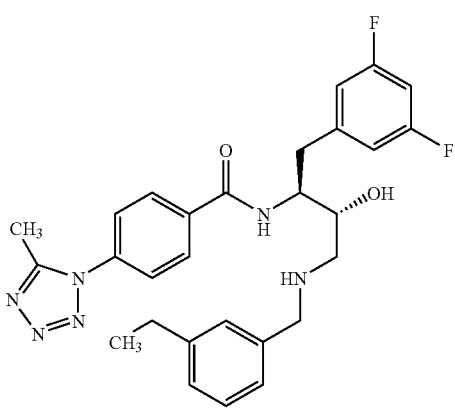 | N-{(1S,2R)-1-(3,5-difluorobenzyl)-3-[(3-ethylbenzyl)amino]-2-hydroxypropyl}-4-(5-methyl-1H-tetraazol-1-yl)benzamide |
| 3663 | 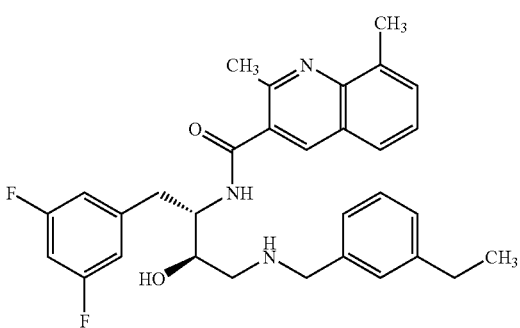 | N-{(1S,2R)-1-(3,5-difluorobenzyl)-3-[(3-ethylbenzyl)amino]-2-hydroxypropyl}-2,8-dimethylquinoline-3-carboxamide |
| 3664 | 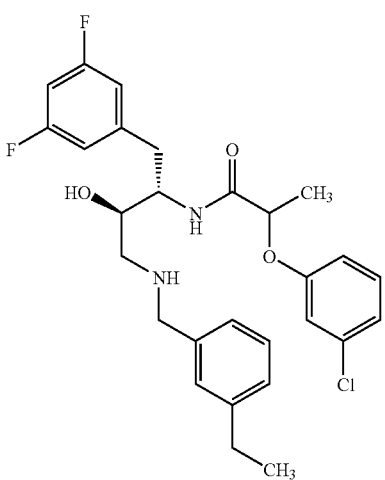 | 2-(3-chlorophenoxy)-N-{(1S,2R)-1-(3,5-difluorobenzyl)-3-[(3-ethylbenzyl)amino]-2-hydroxypropyl}propanamide |

-continued
| | | |
|---|---|---|
| 3665 | 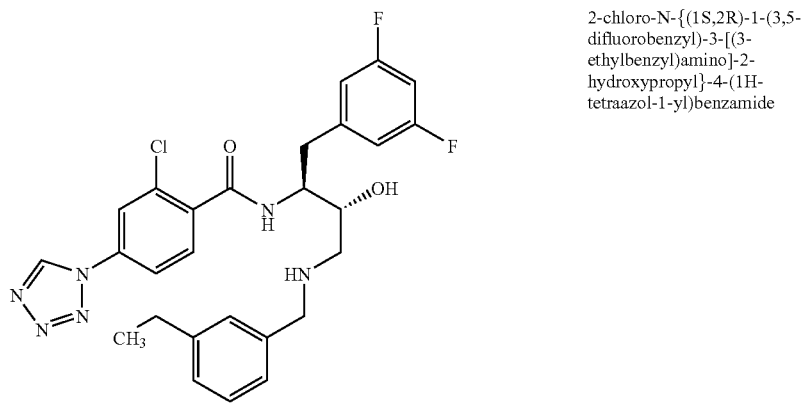 | 2-chloro-N-{(1S,2R)-1-(3,5-difluorobenzyl)-3-[(3-ethylbenzyl)amino]-2-hydroxypropyl}-4-(1H-tetraazol-1-yl)benzamide |
| 3666 | 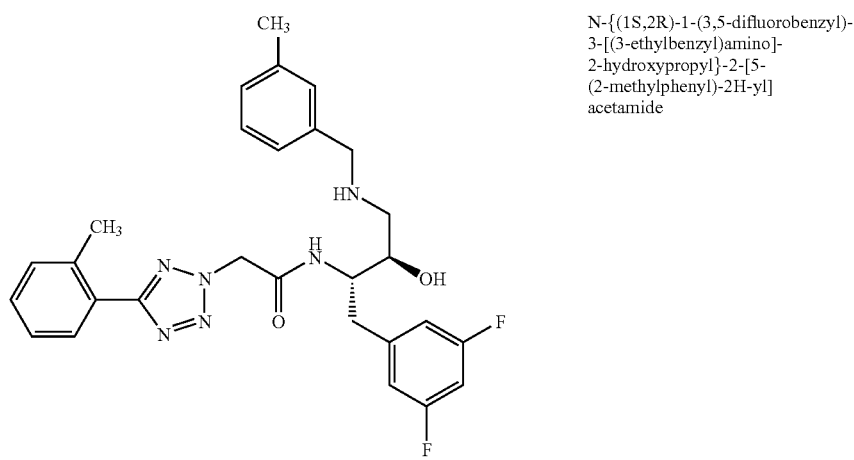 | N-{(1S,2R)-1-(3,5-difluorobenzyl)-3-[(3-ethylbenzyl)amino]-2-hydroxypropyl}-2-[5-(2-methylphenyl)-2H-yl]acetamide |
| 3667 | 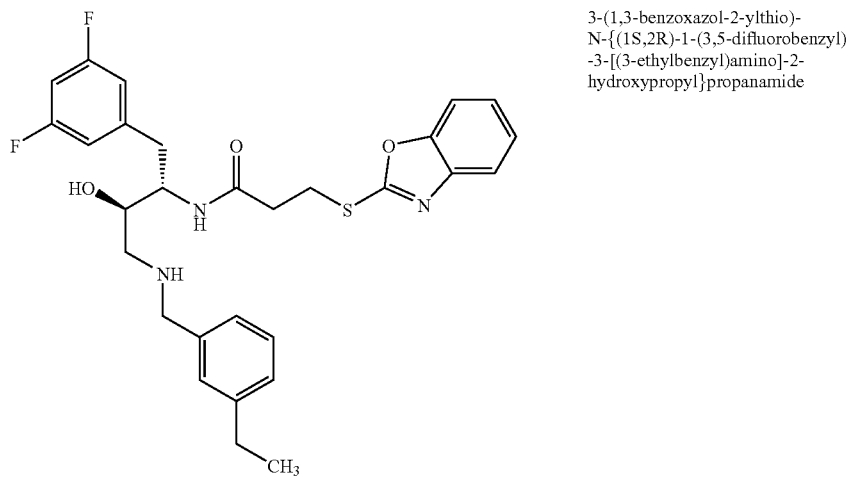 | 3-(1,3-benzoxazol-2-ylthio)-N-{(1S,2R)-1-(3,5-difluorobenzyl)-3-[(3-ethylbenzyl)amino]-2-hydroxypropyl}propanamide |

-continued

| | | |
|---|---|---|
| 3668 | 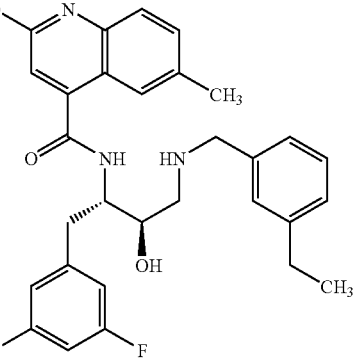 | N-{(1S,2R)-1-(3,5-difluorobenzyl)-3-[(3-ethylbenzyl)amino]-2-hydroxypropyl}-2-hydroxy-6-methylquinoline-4-caboxamide |
| 3669 | 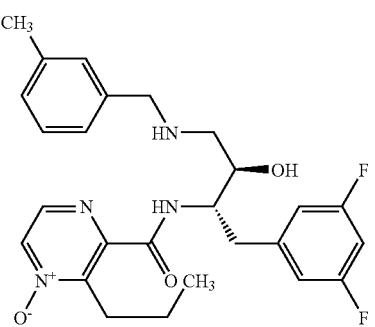 | N-{(1S,2R)-1-(3,5-difluorobenzyl)-3-[(3-ethylbenzyl)amino]-2-hydroxypropyl}-3-propylpyrazine-2-carboxamide 4-oxide |
| 3670 | 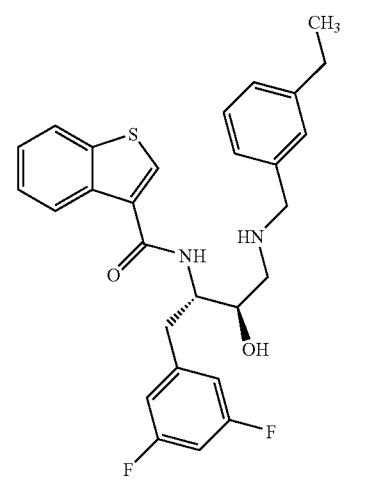 | N-{(1S,2R)-1-(3,5-difluorobenzyl)-3-[(3-ethylbenzyl)amino]-2-hydroxypropyl}-1-benzothiophene-3-carboxamide |
| 3671 | 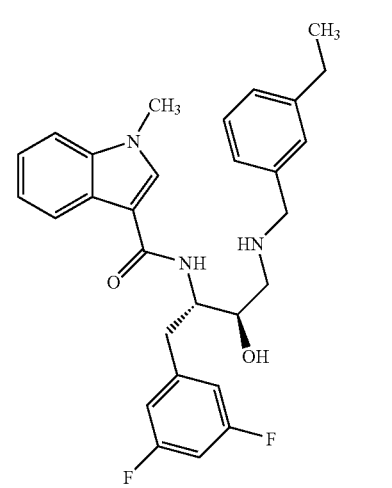 | N-{(1S,2R)-1-(3,5-difluorobenzyl)-3-[(3-ethylbenzyl)amino]-2-hydroxypropyl}-1-methyl-1H-indole-3-carboxamide |

| | | |
|---|---|---|
| 3672 | 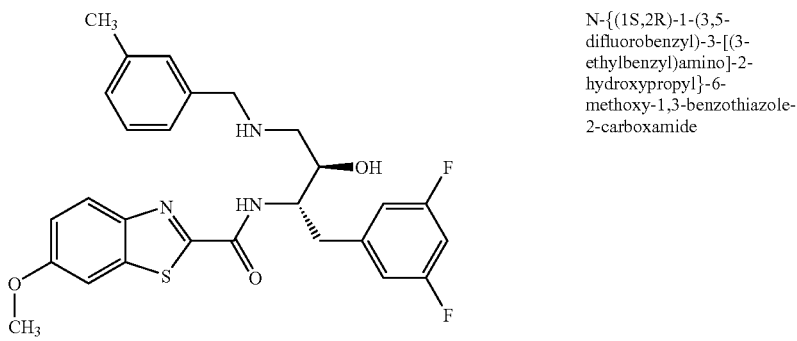 | N-{(1S,2R)-1-(3,5-difluorobenzyl)-3-[(3-ethylbenzyl)amino]-2-hydroxypropyl}-6-methoxy-1,3-benzothiazole-2-carboxamide |
| 3673 | 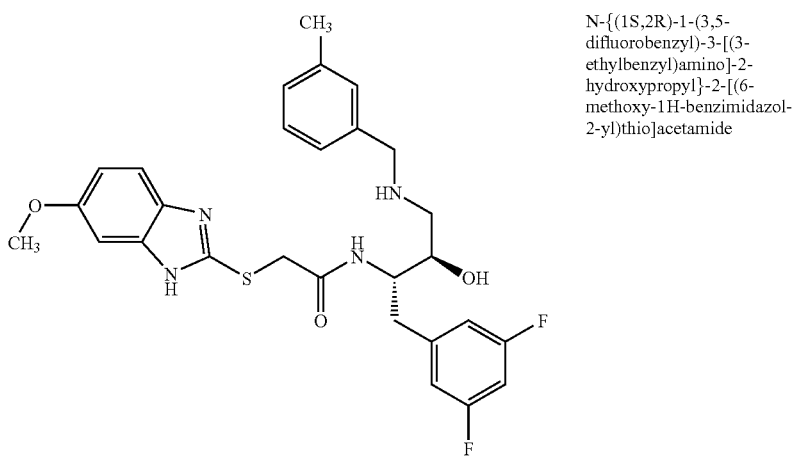 | N-{(1S,2R)-1-(3,5-difluorobenzyl)-3-[(3-ethylbenzyl)amino]-2-hydroxypropyl}-2-[(6-methoxy-1H-benzimidazol-2-yl)thio]acetamide |
| 3674 | 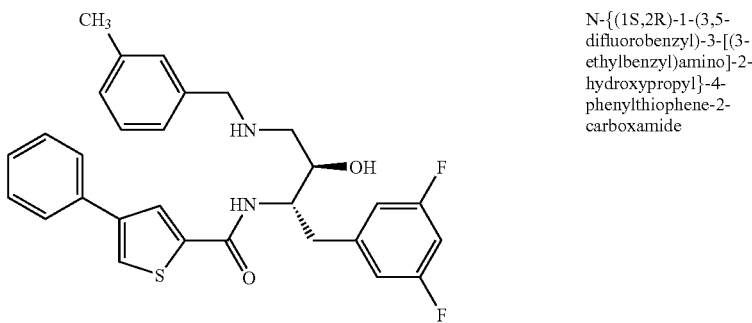 | N-{(1S,2R)-1-(3,5-difluorobenzyl)-3-[(3-ethylbenzyl)amino]-2-hydroxypropyl}-4-phenylthiophene-2-carboxamide |
| 3675 | 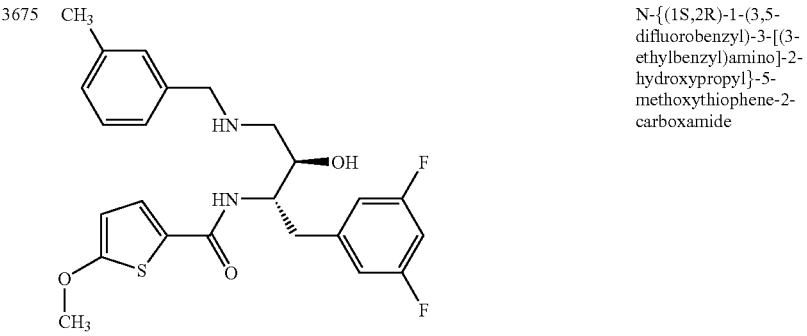 | N-{(1S,2R)-1-(3,5-difluorobenzyl)-3-[(3-ethylbenzyl)amino]-2-hydroxypropyl}-5-methoxythiophene-2-carboxamide |

| | | |
|---|---|---|
| 3676 | 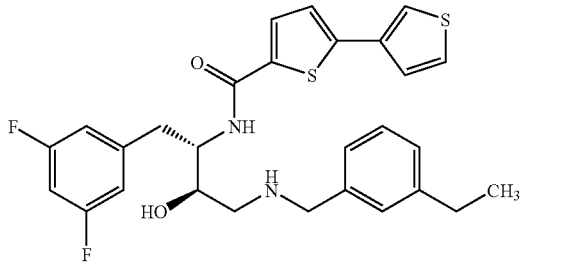 | N-{(1S,2R)-1-(3,5-difluorobenzyl)-3-[(3-ethylbenzyl)amino]-2-hydroxypropyl}-2,3'-bithiophene-5 carboxamide |
| 3677 | 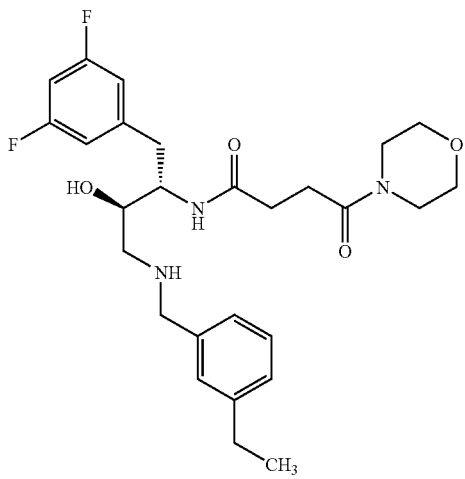 | N-{(1S,2R)-1-(3,5-difluorobenzyl)-3-[(3-ethylbenzyl)amino]-2-hydroxypropyl}-4-morpholin-4-yl-4-oxobutanamide |
| 3678 | 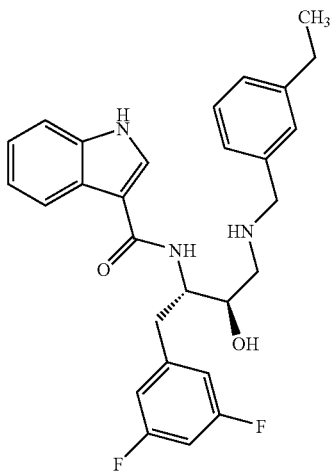 | N-{(1S,2R)-1-(3,5-difluorobenzyl)-3-[(3-ethylbenzyl)amino]-2-hydroxypropyl}-1H-indole-3-carboxamide |
| 3679 | 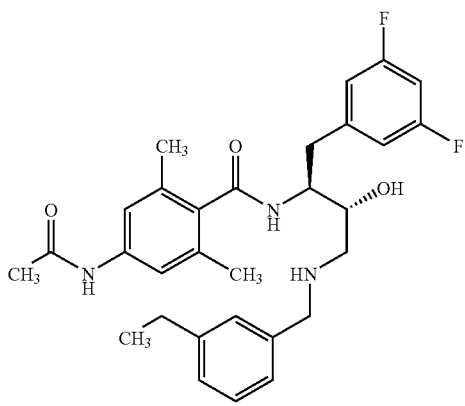 | 4-(acetylamino)-N-{(1S,2R)-1-(3,5-difluorobenzyl)-3-[(3-ethylbenzyl)amino]-2-hydroxypropyl}-2,6-dimethylbenzamide |

-continued
3680 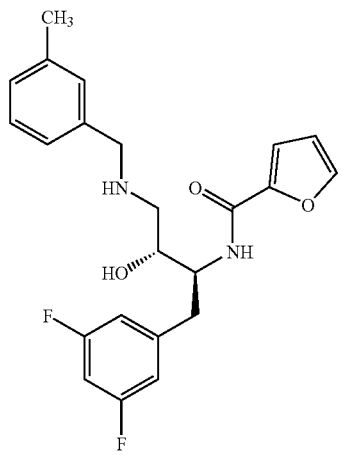
N-{(1S,2R)-1-(3,5-difluorobenzyl)-3-[(3-ethylbenzyl)amino]-2-hydroxypropyl}-2-furamide
3681 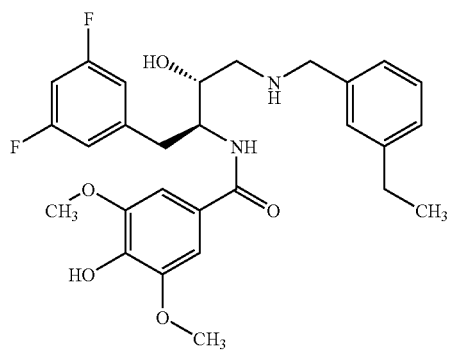
N-{(1S,2R)-1-(3,5-difluorobenzyl)-3-[(3-ethylbenzyl)amino]-2-hydroxypropyl}-4-hydroxy-3,5-dimethoxybenzamide
3682 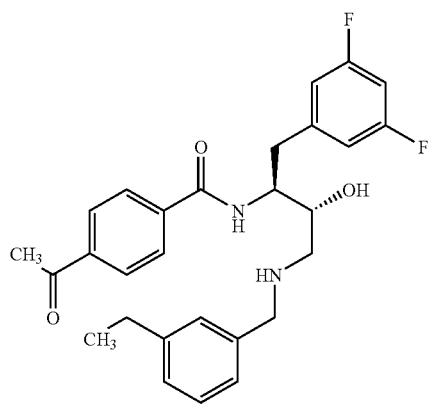
4-acetyl-N-{(1S,2R)-1-(3,5-difluorobenzyl)-3-[(3-ethylbenzyl)amino]-2-hydroxypropyl}benzamide -continued
| | | |
|---|---|---|
| 3683 | 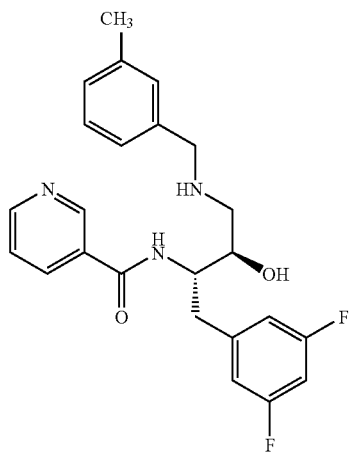 | N-{(1S,2R)-1-(3,5-difluorobenzyl)-3-[(3-ethylbenzyl)amino]-2-hydroxypropyl}nicotinamide |
| 3684 | 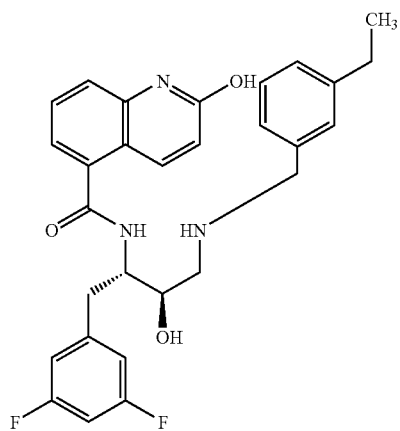 | N-{(1S,2R)-1-(3,5-difluorobenzyl)-3-[(3-ethylbenzyl)amino]-2-hydroxypropyl}-2-hydroxyquinoline-4-carboxamide |
| 3685 | 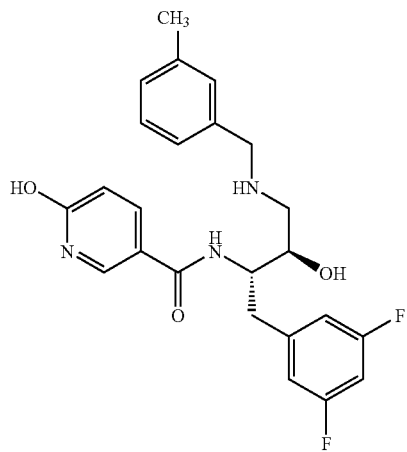 | N-{(1S,2R)-1-(3,5-difluorobenzyl)-3-[(3-ethylbenzyl)amino]-2-hydroxypropyl}-6-hydroxynicotinamide |

-continued

| | | |
|---|---|---|
| 3686 | 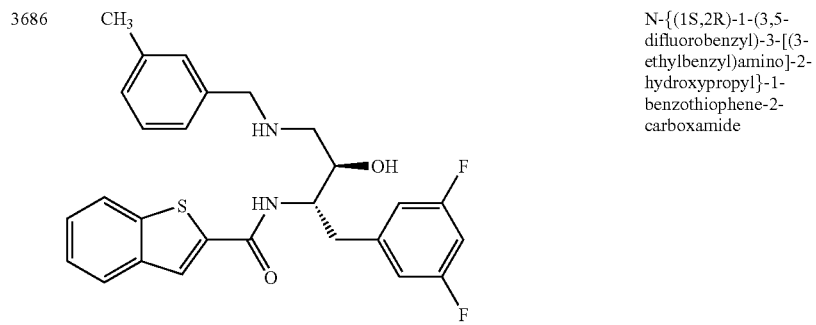 | N-{(1S,2R)-1-(3,5-difluorobenzyl)-3-[(3-ethylbenzyl)amino]-2-hydroxypropyl}-1-benzothiophene-2-carboxamide |
| 3687 | 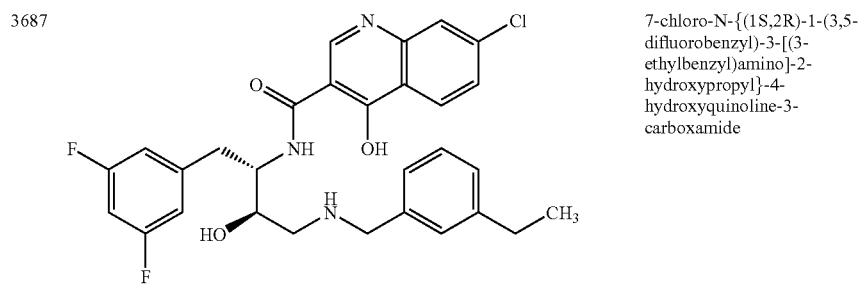 | 7-chloro-N-{(1S,2R)-1-(3,5-difluorobenzyl)-3-[(3-ethylbenzyl)amino]-2-hydroxypropyl}-4-hydroxyquinoline-3-carboxamide |
| 3688 | 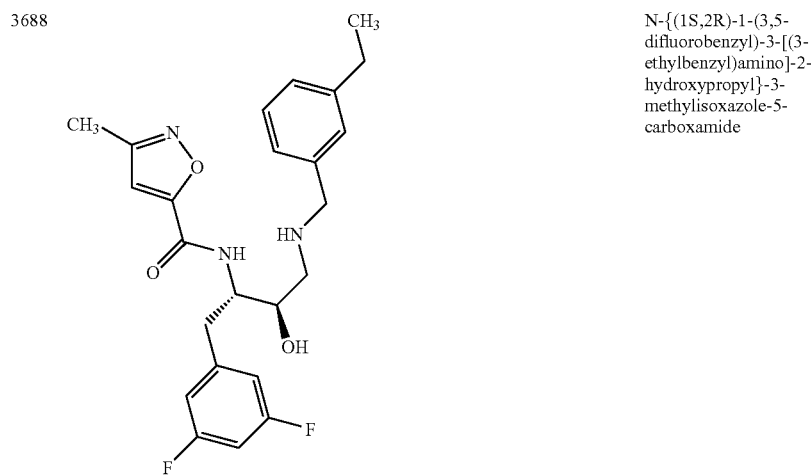 | N-{(1S,2R)-1-(3,5-difluorobenzyl)-3-[(3-ethylbenzyl)amino]-2-hydroxypropyl}-3-methylisoxazole-5-carboxamide |
| 3689 | 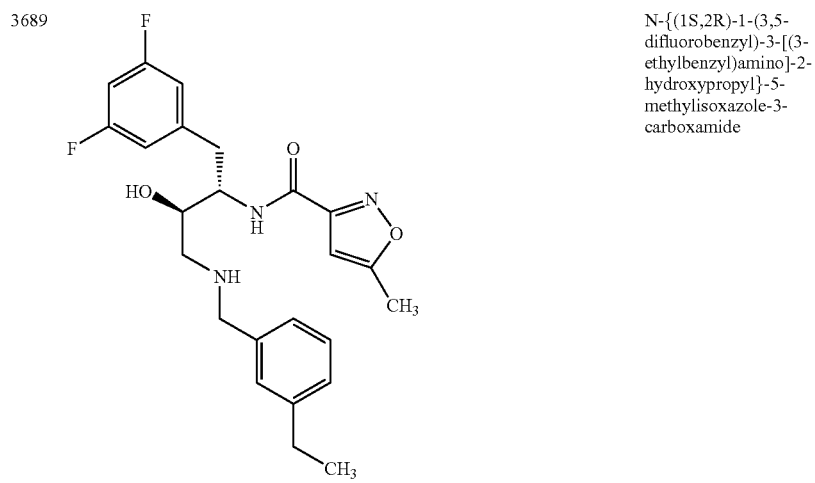 | N-{(1S,2R)-1-(3,5-difluorobenzyl)-3-[(3-ethylbenzyl)amino]-2-hydroxypropyl}-5-methylisoxazole-3-carboxamide |

-continued
| | | |
|---|---|---|
| 3690 | 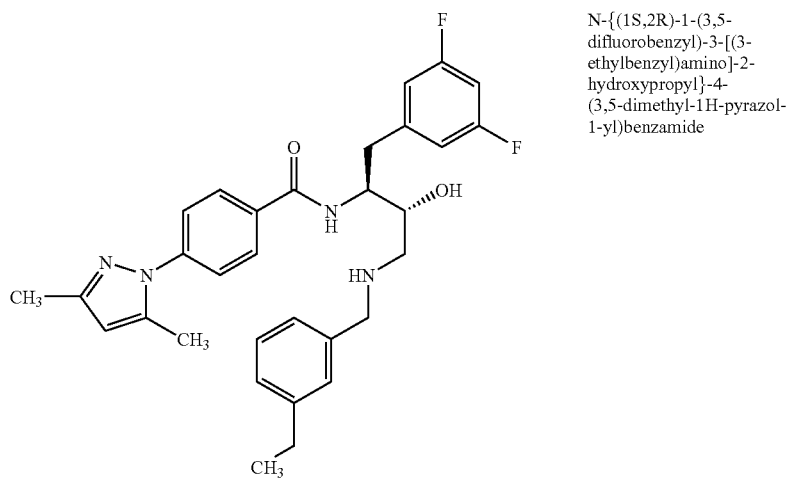 | N-{(1S,2R)-1-(3,5-difluorobenzyl)-3-[(3-ethylbenzyl)amino]-2-hydroxypropyl}-4-(3,5-dimethyl-1H-pyrazol-1-yl)benzamide |
| 3691 | 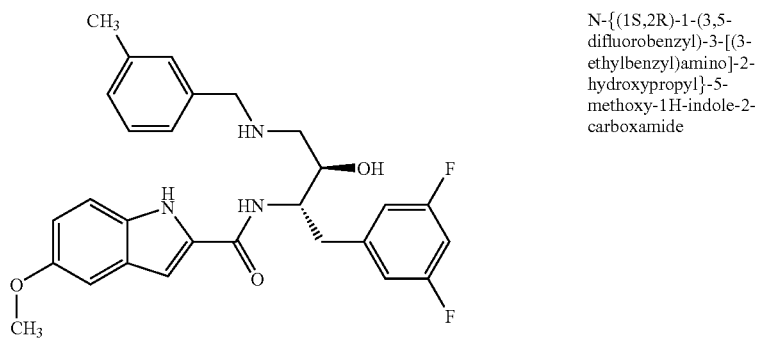 | N-{(1S,2R)-1-(3,5-difluorobenzyl)-3-[(3-ethylbenzyl)amino]-2-hydroxypropyl}-5-methoxy-1H-indole-2-carboxamide |
| 3692 | 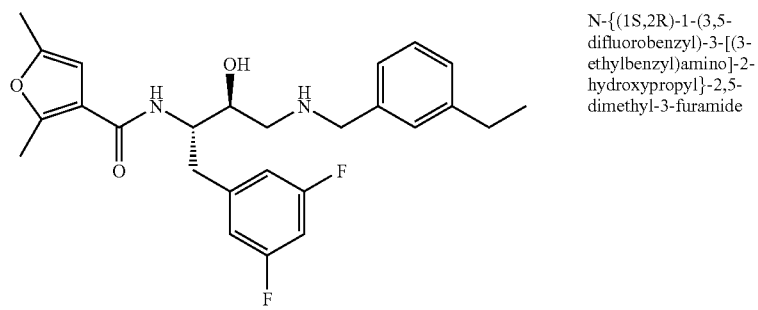 | N-{(1S,2R)-1-(3,5-difluorobenzyl)-3-[(3-ethylbenzyl)amino]-2-hydroxypropyl}-2,5-dimethyl-3-furamide |
| 3693 | 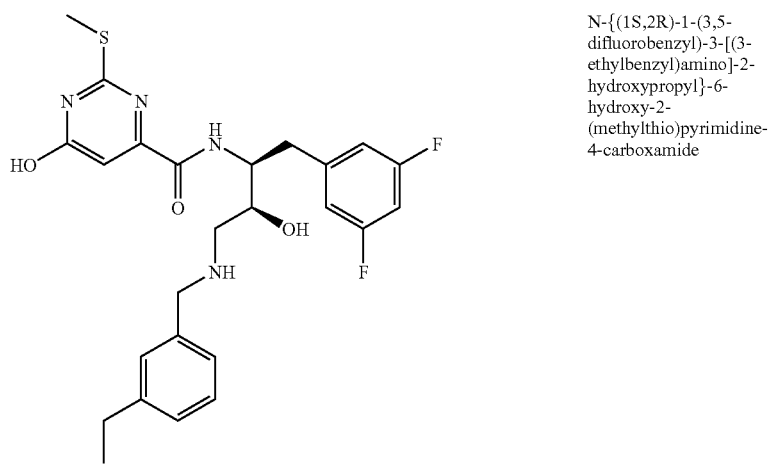 | N-{(1S,2R)-1-(3,5-difluorobenzyl)-3-[(3-ethylbenzyl)amino]-2-hydroxypropyl}-6-hydroxy-2-(methylthio)pyrimidine-4-carboxamide |

-continued
| | | |
|---|---|---|
| 3694 | 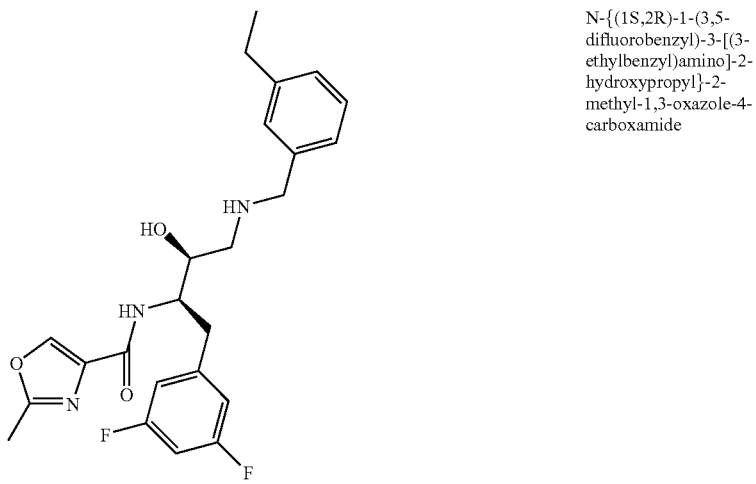 | N-{(1S,2R)-1-(3,5-difluorobenzyl)-3-[(3-ethylbenzyl)amino]-2-hydroxypropyl}-2-methyl-1,3-oxazole-4-carboxamide |
| 3695 | 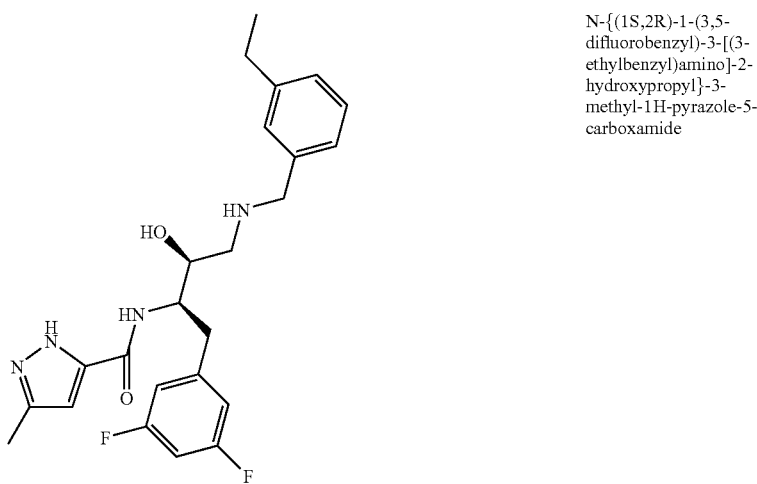 | N-{(1S,2R)-1-(3,5-difluorobenzyl)-3-[(3-ethylbenzyl)amino]-2-hydroxypropyl}-3-methyl-1H-pyrazole-5-carboxamide |
| 3696 | 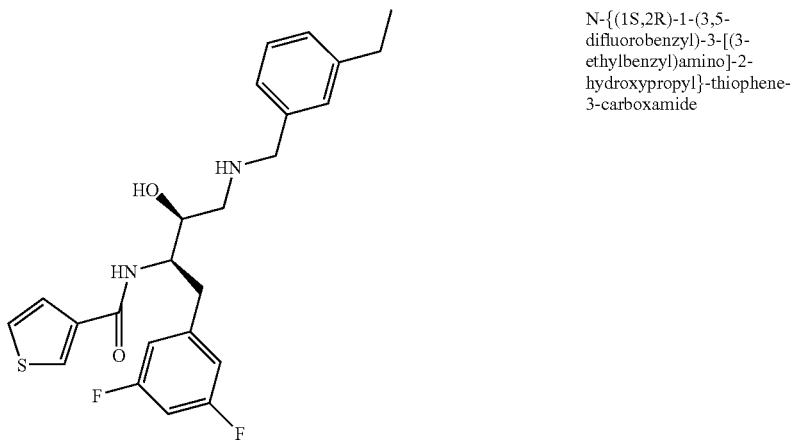 | N-{(1S,2R)-1-(3,5-difluorobenzyl)-3-[(3-ethylbenzyl)amino]-2-hydroxypropyl}-thiophene-3-carboxamide |

-continued
| | | |
|---|---|---|
| 3697 | 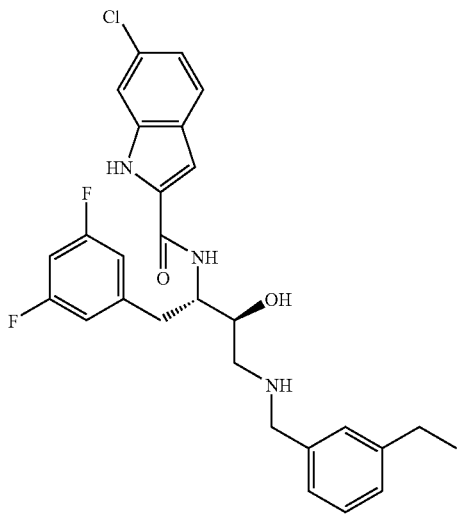 | 6-chloro-N-{(1S,2R)-1-(3,5-difluorobenzyl)-3-[(3-ethylbenzyl)amino]-2-hydroxypropyl}-1H-indole-2-carboxamide |
| 3698 | 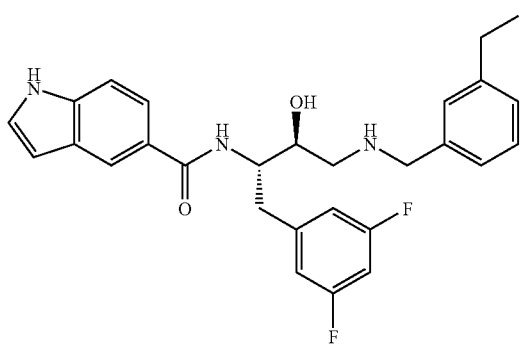 | N-{(1S,2R)-1-(3,5-difluorobenzyl)-3-[(3-ethylbenzyl)amino]-2-hydroxypropyl}-1H-indole-5-carboxamide |
| 3699 | 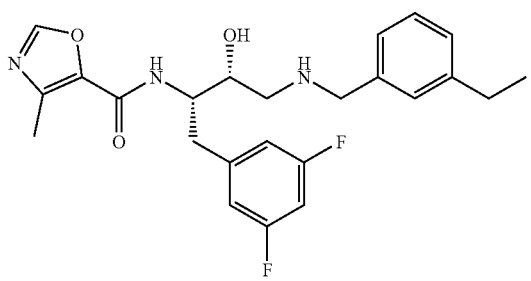 | N-{(1S,2R)-1-(3,5-difluorobenzyl)-3-[(3-ethylbenzyl)amino]-2-hydroxypropyl}-4-methyl-1,3-oxazole-5-carboxamide |
| 3700 | 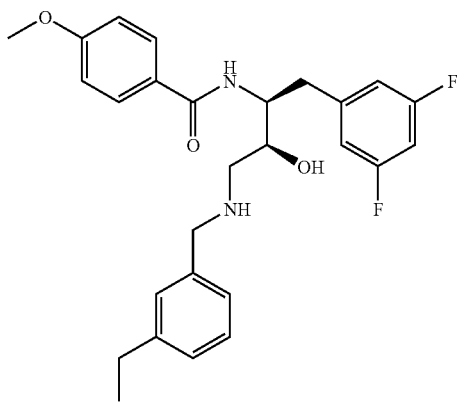 | N-{(1S,2R)-1-(3,5-difluorobenzyl)-3-[(3-ethylbenzyl)amino]-2-hydroxypropyl}-4-methoxybenzamide |

| | | |
|---|---|---|
| 3701 | 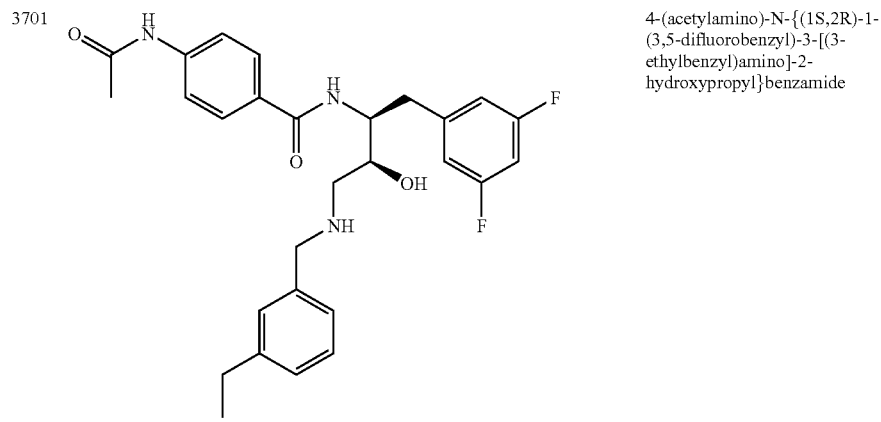 | 4-(acetylamino)-N-{(1S,2R)-1-(3,5-difluorobenzyl)-3-[(3-ethylbenzyl)amino]-2-hydroxypropyl}benzamide |
| 3702 | 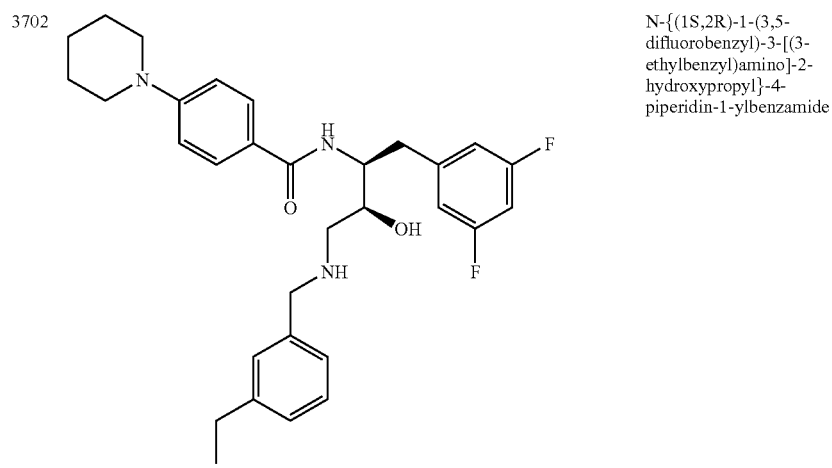 | N-{(1S,2R)-1-(3,5-difluorobenzyl)-3-[(3-ethylbenzyl)amino]-2-hydroxypropyl}-4-piperidin-1-ylbenzamide |
| 3703 | 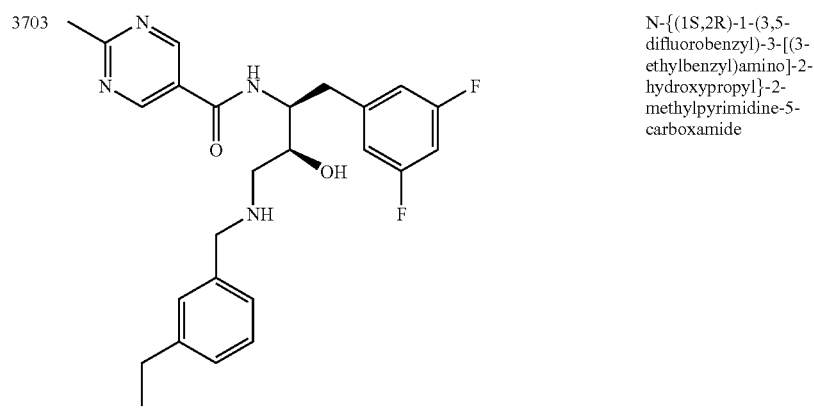 | N-{(1S,2R)-1-(3,5-difluorobenzyl)-3-[(3-ethylbenzyl)amino]-2-hydroxypropyl}-2-methylpyrimidine-5-carboxamide |

-continued

| | | |
|---|---|---|
| 3704 | 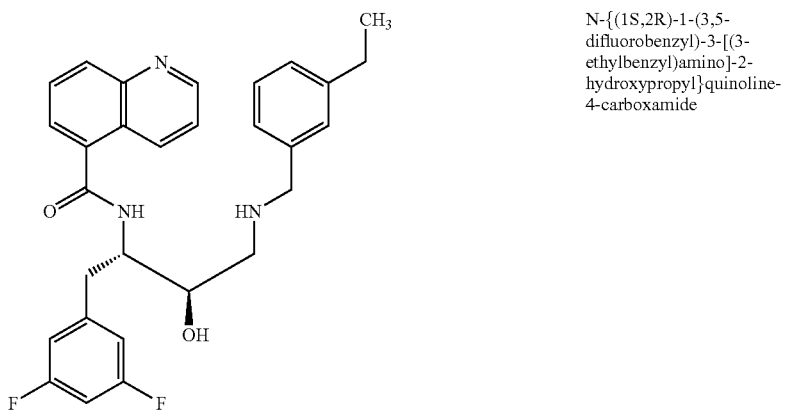 | N-{(1S,2R)-1-(3,5-difluorobenzyl)-3-[(3-ethylbenzyl)amino]-2-hydroxypropyl}quinoline-4-carboxamide |
| 3705 | 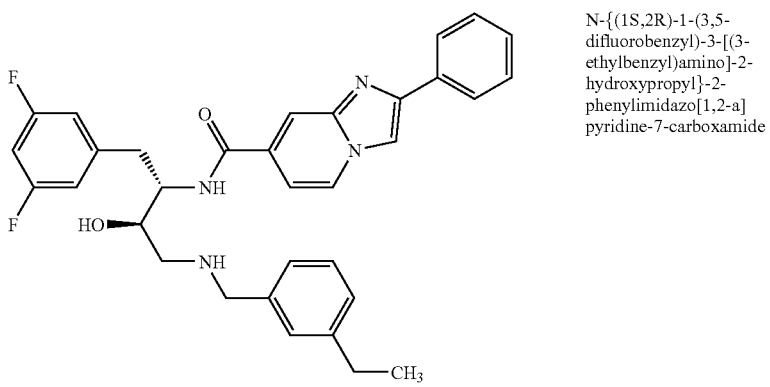 | N-{(1S,2R)-1-(3,5-difluorobenzyl)-3-[(3-ethylbenzyl)amino]-2-hydroxypropyl}-2-phenylimidazo[1,2-a]pyridine-7-carboxamide |
| 3706 | 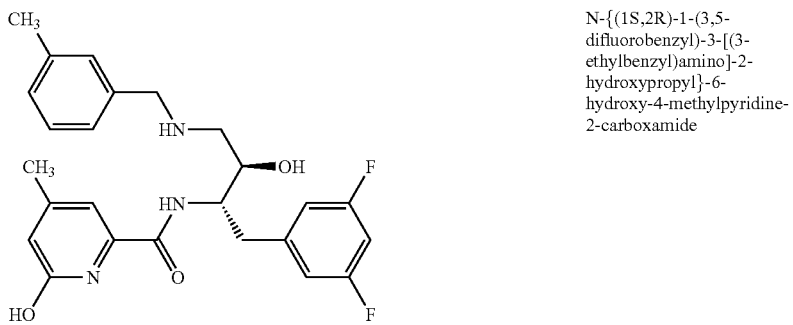 | N-{(1S,2R)-1-(3,5-difluorobenzyl)-3-[(3-ethylbenzyl)amino]-2-hydroxypropyl}-6-hydroxy-4-methylpyridine-2-carboxamide |
| 3707 | 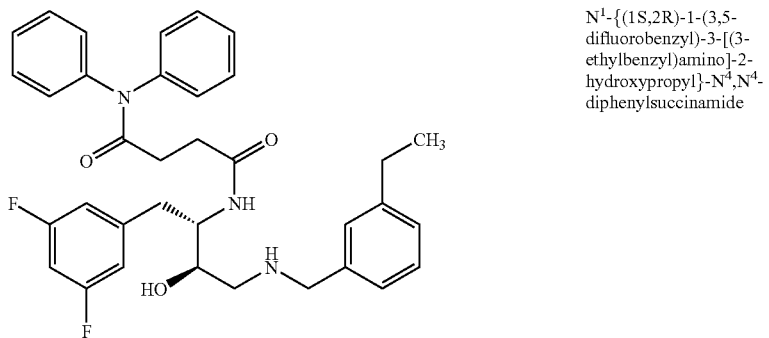 | $N^1$-{(1S,2R)-1-(3,5-difluorobenzyl)-3-[(3-ethylbenzyl)amino]-2-hydroxypropyl}-$N^4,N^4$-diphenylsuccinamide |

| | | |
|---|---|---|
| 3708 | 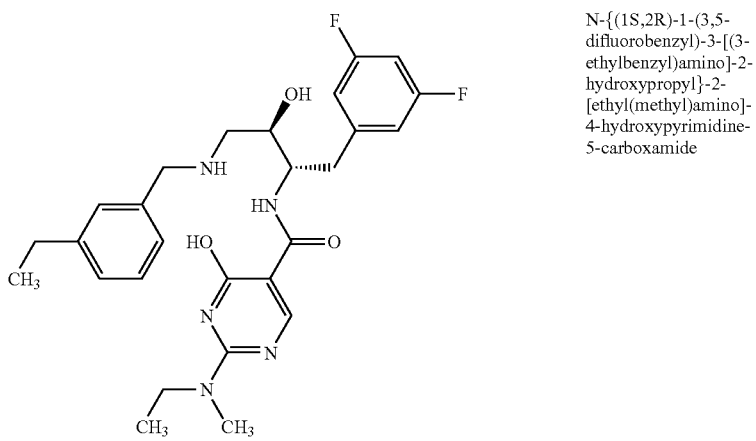 | N-{(1S,2R)-1-(3,5-difluorobenzyl)-3-[(3-ethylbenzyl)amino]-2-hydroxypropyl}-2-[ethyl(methyl)amino]-4-hydroxypyrimidine-5-carboxamide |
| 3709 | 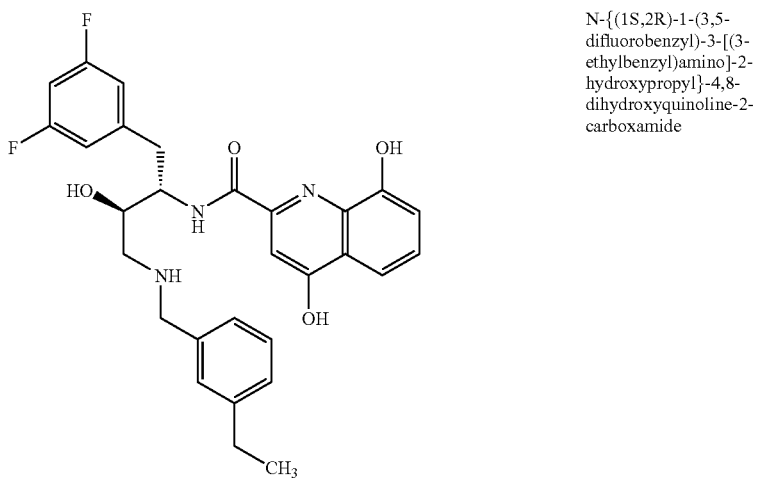 | N-{(1S,2R)-1-(3,5-difluorobenzyl)-3-[(3-ethylbenzyl)amino]-2-hydroxypropyl}-4,8-dihydroxyquinoline-2-carboxamide |
| 3710 | 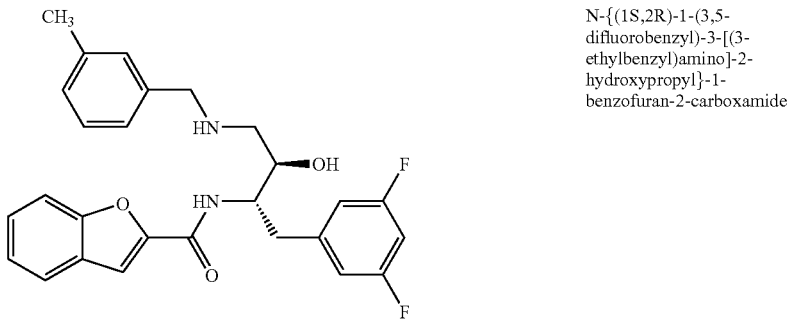 | N-{(1S,2R)-1-(3,5-difluorobenzyl)-3-[(3-ethylbenzyl)amino]-2-hydroxypropyl}-1-benzofuran-2-carboxamide |

-continued
| | | |
|---|---|---|
| 3711 | 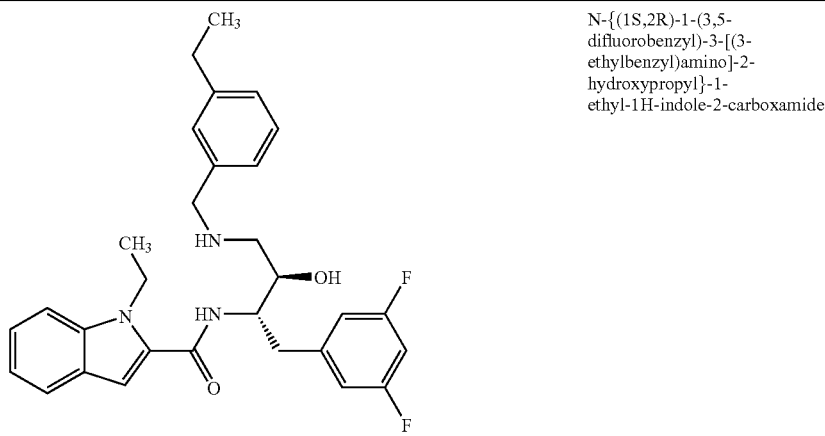 | N-{(1S,2R)-1-(3,5-difluorobenzyl)-3-[(3-ethylbenzyl)amino]-2-hydroxypropyl}-1-ethyl-1H-indole-2-carboxamide |
| 3712 | 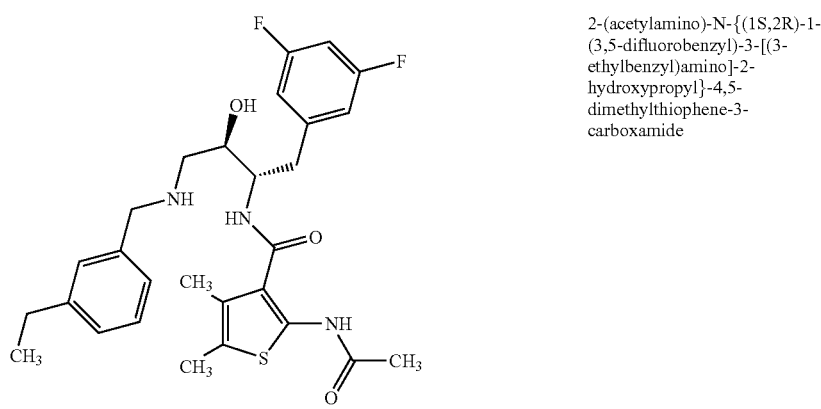 | 2-(acetylamino)-N-{(1S,2R)-1-(3,5-difluorobenzyl)-3-[(3-ethylbenzyl)amino]-2-hydroxypropyl}-4,5-dimethylthiophene-3-carboxamide |
| 3713 | 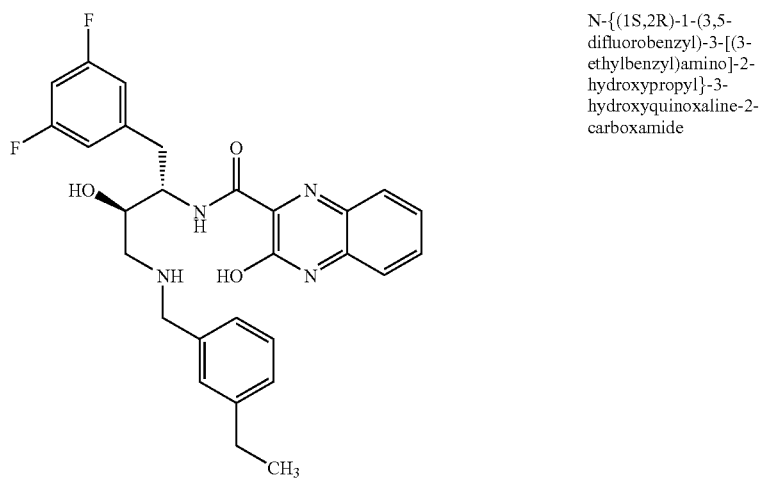 | N-{(1S,2R)-1-(3,5-difluorobenzyl)-3-[(3-ethylbenzyl)amino]-2-hydroxypropyl}-3-hydroxyquinoxaline-2-carboxamide |

-continued
| | | |
|---|---|---|
| 3714 | 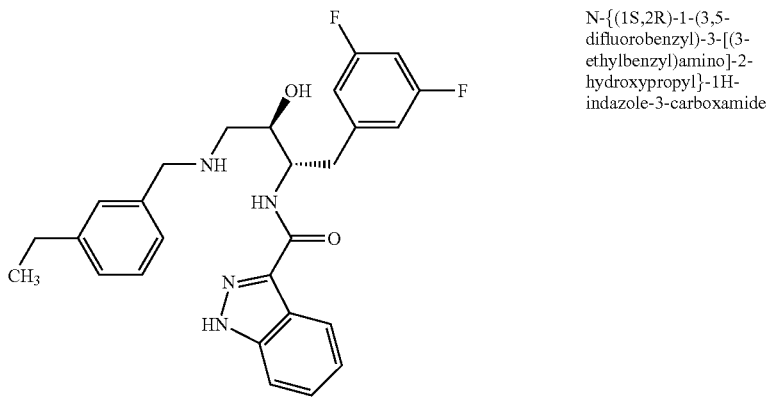 | N-{(1S,2R)-1-(3,5-difluorobenzyl)-3-[(3-ethylbenzyl)amino]-2-hydroxypropyl}-1H-indazole-3-carboxamide |
| 3715 | 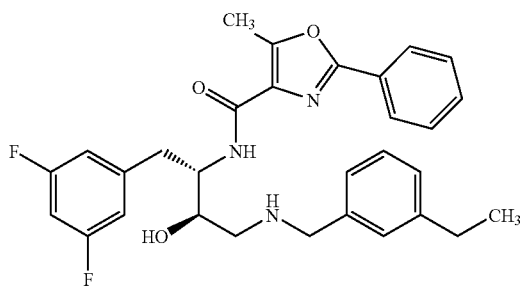 | N-{(1S,2R)-1-(3,5-difluorobenzyl)-3-[(3-ethylbenzyl)amino]-2-hydroxypropyl}-5-methyl-2-phenyl-1,3-oxazole-4-carboxamide |
| 3716 | 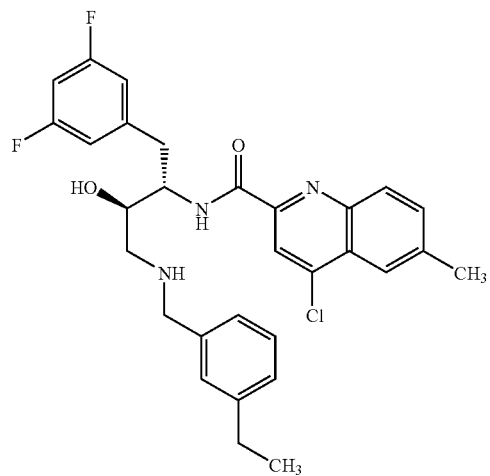 | 4-chloro-N-{(1S,2R)-1-(3,5-difluorobenzyl)-3-[(3-ethylbenzyl)amino]-2-hydroxypropyl}-6-methylquinoline-2-carboxamide |

| | | |
|---|---|---|
| 3717 | 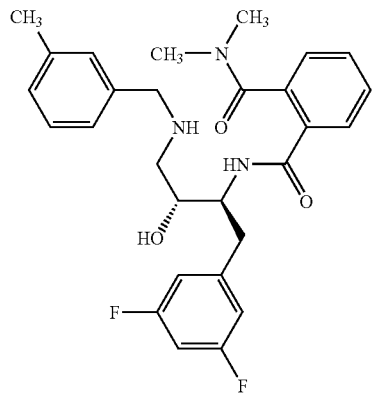 | N¹-{(1S,2R)-1-(3,5-difluorobenzyl)-3-[(3-ethylbenzyl)amino]-2-hydroxypropyl}N²,N²-dimethylphthalamide |
| 3718 | 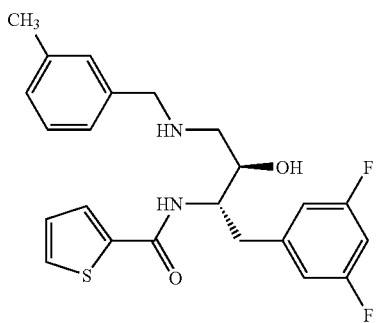 | N-{(1S,2R)-1-(3,5-difluorobenzyl)-3-[(3-ethylbenzyl)amino]-2-hydroxypropyl}thiophene-2-carboxamide |
| 3719 | 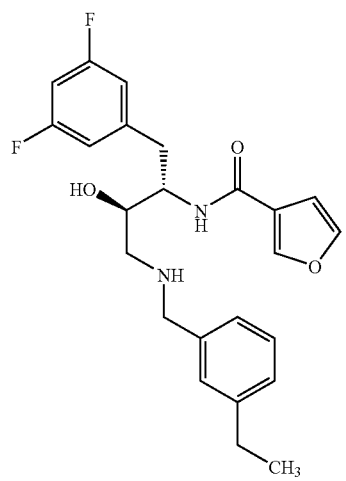 | N-{(1S,2R)-1-(3,5-difluorobenzyl)-3-[(3-ethylbenzyl)amino]-2-hydroxypropyl}-3-furamide |

-continued

| | | |
|---|---|---|
| 3720 | 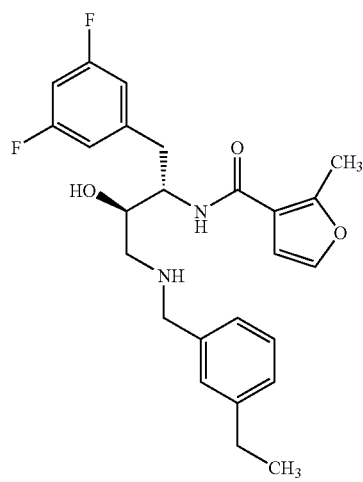 | N-{(1S,2R)-1-(3,5-difluorobenzyl)-3-[(3-ethylbenzyl)amino]-2-hydroxypropyl}-2-methyl-3-furamide |
| 3721 | 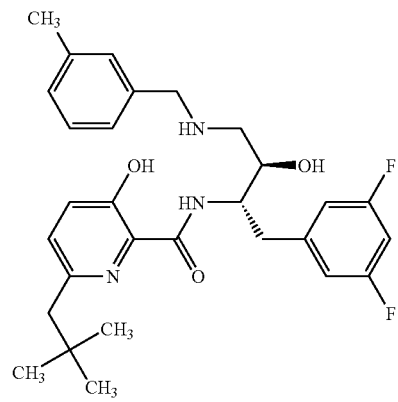 | N-{(1S,2R)-2-(3,5-difluorobenzyl)-3-[(3-ethylbenzyl)amino]-2-hydroxypropyl}-3-hydroxy-6-neopentylpyridine-2-carboxamide |
| 3722 | 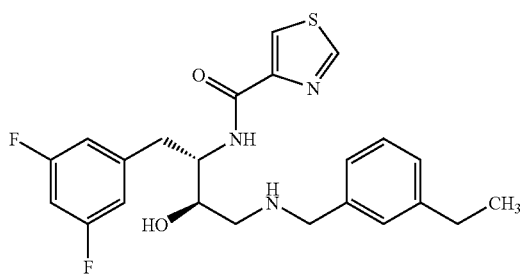 | N-{(1S,2R)-1-(3,5-difluorobenzyl)-3-[(3-ethylbenzyl)amino]-2-hydroxypropyl}-1,3-thiazole-4-carboxamide |
| 3723 | 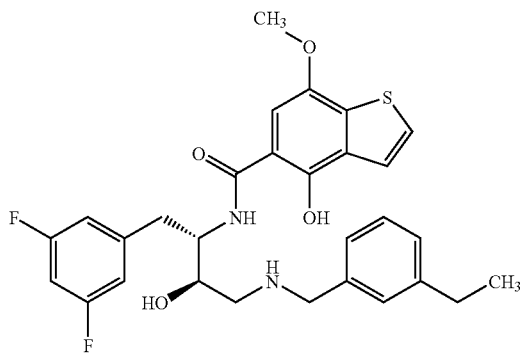 | N-{(1S,2R)-1-(3,5-difluorobenzyl)-3-[(3-ethylbenzyl)amino]-2-hydroxypropyl}-4-hydroxy-7-methoxy-1-benzothiophene-5-carboxamide |

-continued
| | | |
|---|---|---|
| 3724 | 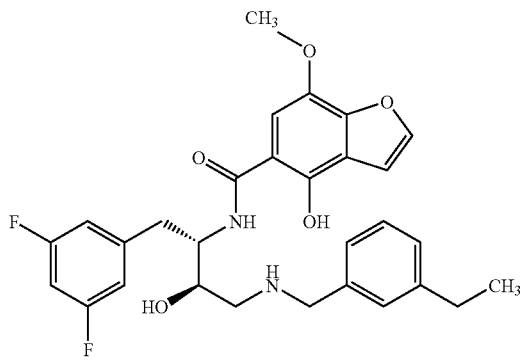 | N-{(1S,2R)-1-(3,5-difluorobenzyl)-3-[(3-ethylbenzyl)amino]-2-hydroxypropyl}-4-hydroxy-7-methoxy-1-benzofuran-5-carboxamide |
| 3725 | 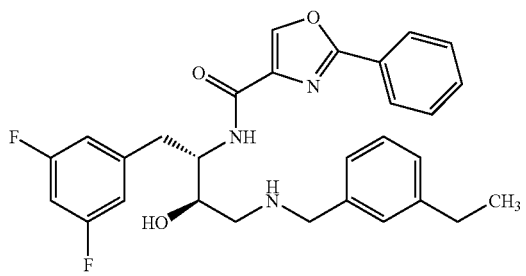 | N-{(1S,2R)-1-(3,5-difluorobenzyl)-3-[(3-ethylbenzyl)amino]-2-hydroxypropyl}-2-phenyl-1,3-oxazole-4-carboxamide |
| 3726 | 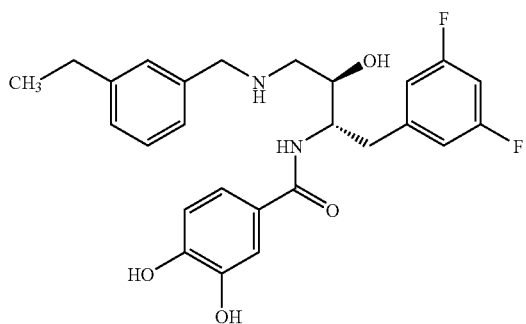 | N-{(1S,2R)-1-(3,5-difluorobenzyl)-3-[(3-ethylbenzyl)amino]-2-hydroxypropyl}-3,4-dihydroxybenzamide |
| 3727 | 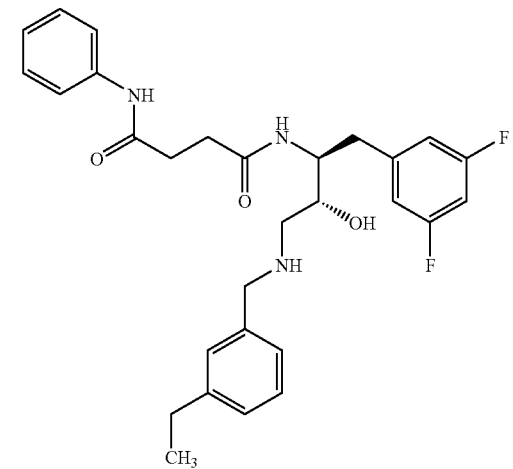 | $N^1$-{(1S,2R)-1-(3,5-difluorobenzyl)-3-[(3-ethylbenzyl)amino]-2-hydroxypropyl}-$N^4$-phenylsuccinamide |

-continued
| | | |
|---|---|---|
| 3728 | 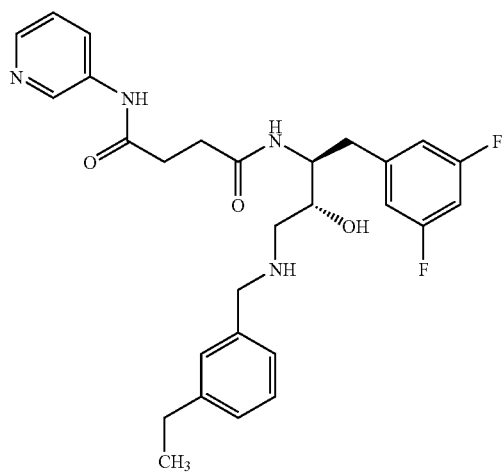 | N¹-{(1S,2R)-1-(3,5-difluorobenzyl)-3-[(3-ethylbenzyl)amino]-2-hydroxypropyl}-N⁴-pyridin-3-ylsuccinamide |
| 3729 | 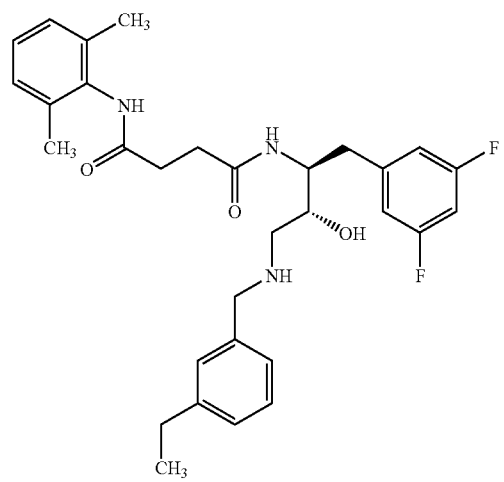 | N¹-{(1S,2R)-1-(3,5-difluorobenzyl)-3-[(3-ethylbenzyl)amino]-2-hydroxypropyl}-N⁴-(2,6-dimethylphenyl)succinamide |
| 3730 | 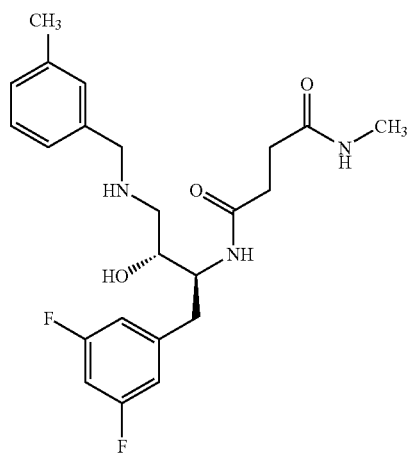 | N¹-{(1S,2R)-1-(3,5-difluorobenzyl)-3-[(3-ethylbenzyl)amino]-2-hydroxypropyl}-N⁴-methylsuccinamide |

-continued

| | | |
|---|---|---|
| 3731 | 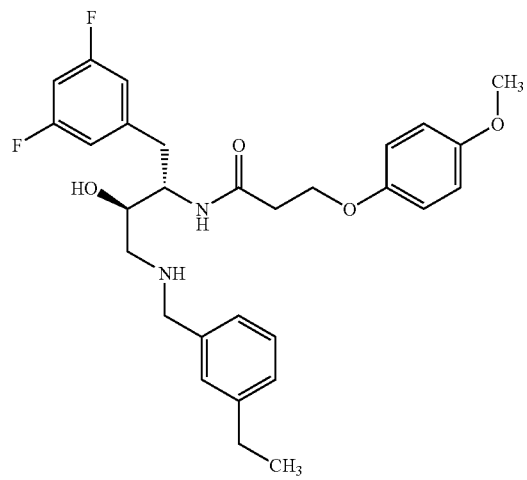 | N-{(1S,2R)-1-(3,5-difluorobenzyl)-3-[(3-ethylbenzyl)amino]-2-hydroxypropyl}-3-(4-methoxyphenoxy)propanamide |
| 3732 | 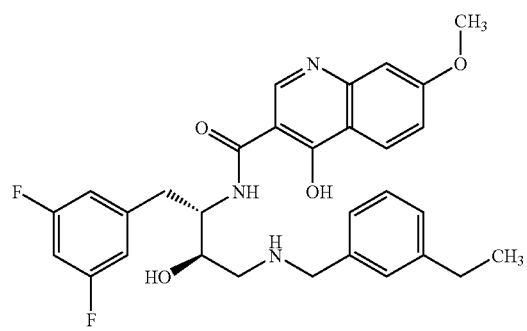 | N-{(1S,2R)-1-(3,5-difluorobenzyl)-3-[(3-ethylbenzyl)amino]-2-hydroxypropyl}-4-hydroxy-7-methoxyquinoline-3-carboxamide |
| 3733 | 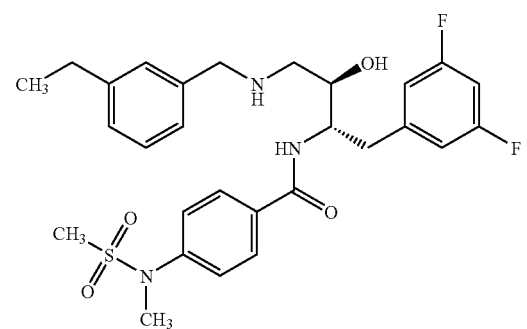 | N-{(1S,2R)-1-(3,5-difluorobenzyl)-3-[(3-ethylbenzyl)amino]-2-hydroxypropyl}-4-[methyl(methylsulfonyl)amino]benzamide |
| 3734 | 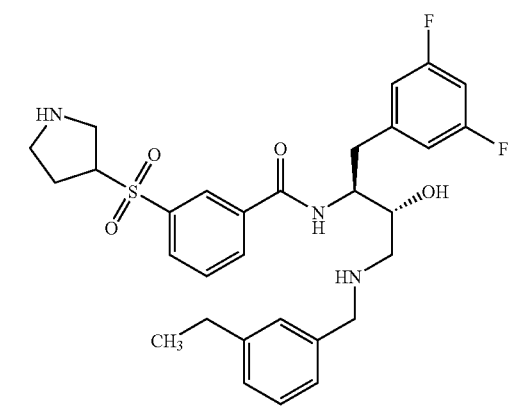 | N-{(1S,2R)-1-(3,5-difluorobenzyl)-3-[(3-ethylbenzyl)amino]-2-hydroxypropyl}-3-(pyrrolidin-3-ylsulfonyl)benzamide | 572.2 |

| | | |
|---|---|---|
| 3735 | 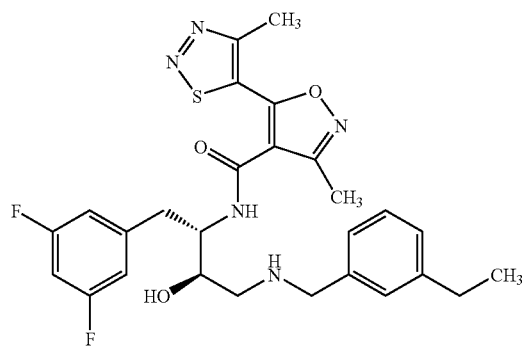 | N-{(1S,2R)-1-(3,5-difluorobenzyl)-3-[(3-ethylbenzyl)amino]-2-hydroxypropyl}-3-methyl-5-(4-methyl-1,2,3-thiadiazol-5-yl)isoxazole-4-carboxamide |
| 3736 | 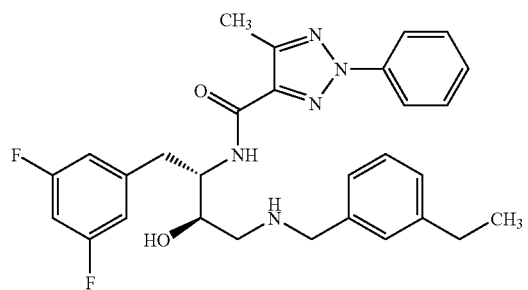 | N-{(1S,2R)-1-(3,5-difluorobenzyl)-3-[(3-ethylbenzyl)amino]-2-hydroxypropyl}-5-methyl-2-phenyl-2H-1,2,3-triazole-4-carboxamide |
| 3737 | 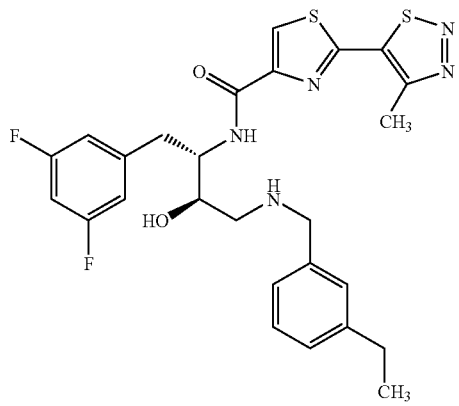 | N-{(1S,2R)-1-(3,5-difluorobenzyl)-3-[(3-ethylbenzyl)amino]-2-hydroxypropyl}-2-(4-methyl-1,2,3-thiadiazol-5-yl)-1,3-thiazole-4-carboxamide |
| 3738 | 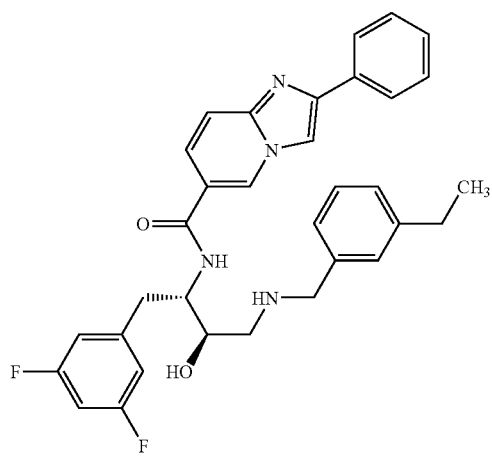 | N-{(1S,2R)-1-(3,5-difluorobenzyl)-3-[(3-ethylbenzyl)amino]-2-hydroxypropyl}-2-phenylimidazo[1,2-a]pyridine-6-carboxamide |

-continued
| | | |
|---|---|---|
| 3739 | 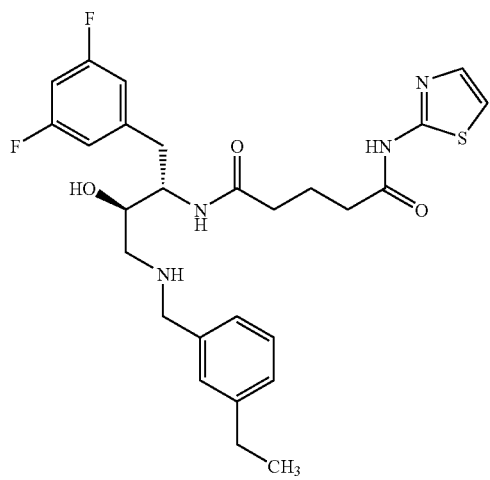 | N-{(1S,2R)-1-(3,5-difluorobenzyl)-3-[(3-ethylbenzyl)amino]-2-hydroxypropyl}-N⁵-(1,3-thiazol-2-yl)pentanediamide |
| 3740 | 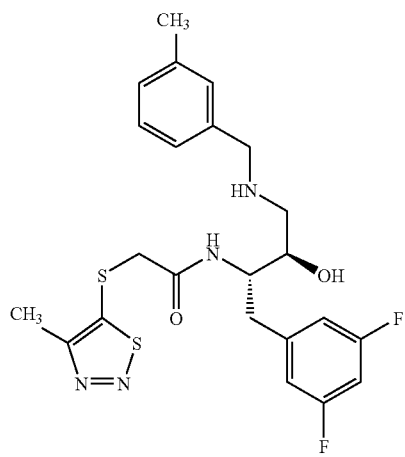 | N-{(1S,2R)-1-(3,5-difluorobenzyl)-3-[(3-ethylbenzyl)amino]-2-hydroxypropyl}-2-[(4-methyl-1,2,3-thiadiazol-5-yl)thio]acetamide |
| 3741 | 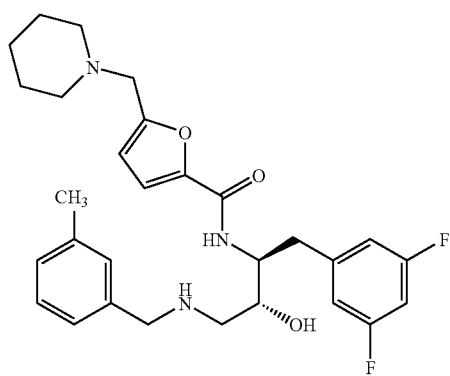 | N-{(1S,2R)-1-(3,5-difluorobenzyl)-3-[(3-ethylbenzyl)amino]-2-hydroxypropyl}-5-piperidin-1-ylmethyl)-2-furamide |

-continued
| | | |
|---|---|---|
| 3742 | 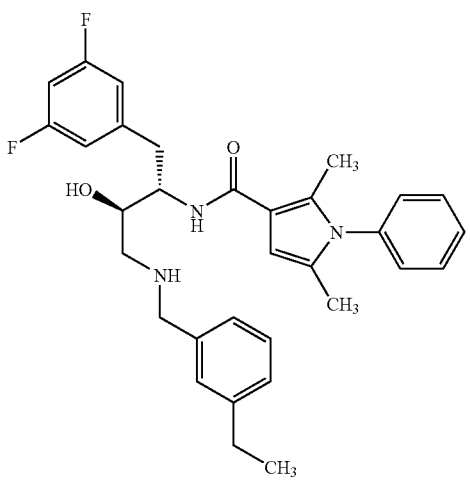 | N-{(1S,2R)-1-(3,5-difluorobenzyl)-3-[(3-ethylbenzyl)amino]-2-hydroxypropyl}-2,5-dimethyl-1-phenyl-1H-pyrrole-3-carboxamide |
| 3743 | 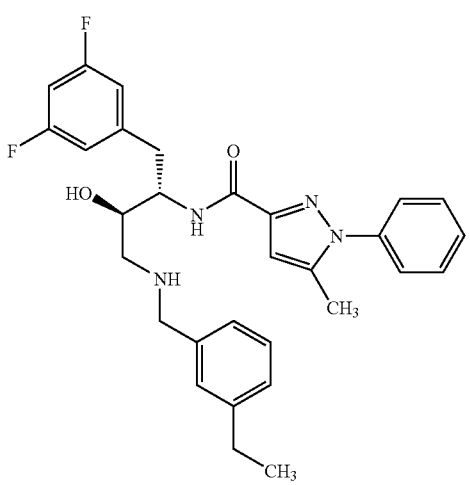 | N-{(1S,2R)-1-(3,5-difluorobenzyl)-3-[(3-ethylbenzyl)amino]-2-hydroxypropyl}-5-methyl-1-phenyl-1H-pyrazole-3-carboxamide |
| 3744 | 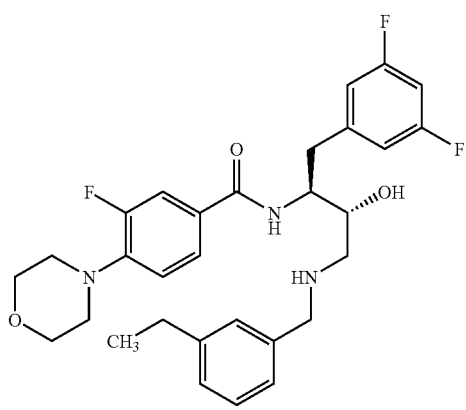 | N-{(1S,2R)-1-(3,5-difluorobenzyl)-3-[(3-ethylbenzyl)amino]-2-hydroxypropyl}-3-fluoro-4-morpholin-4-ylbenzamide |

-continued

| | | |
|---|---|---|
| 3745 | 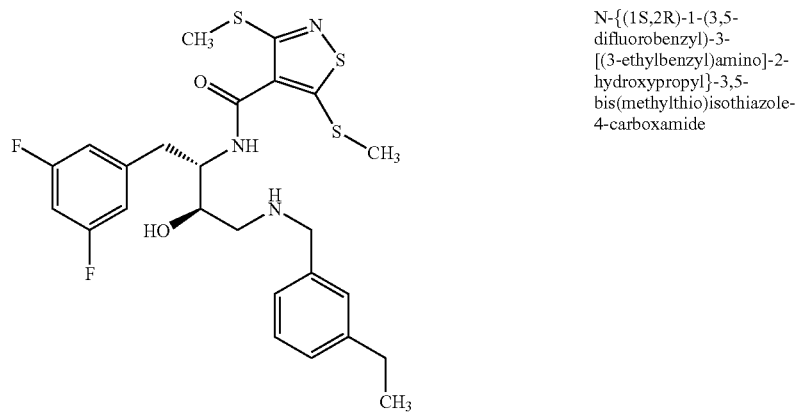 | N-{(1S,2R)-1-(3,5-difluorobenzyl)-3-[(3-ethylbenzyl)amino]-2-hydroxypropyl}-3,5-bis(methylthio)isothiazole-4-carboxamide |
| 3746 | 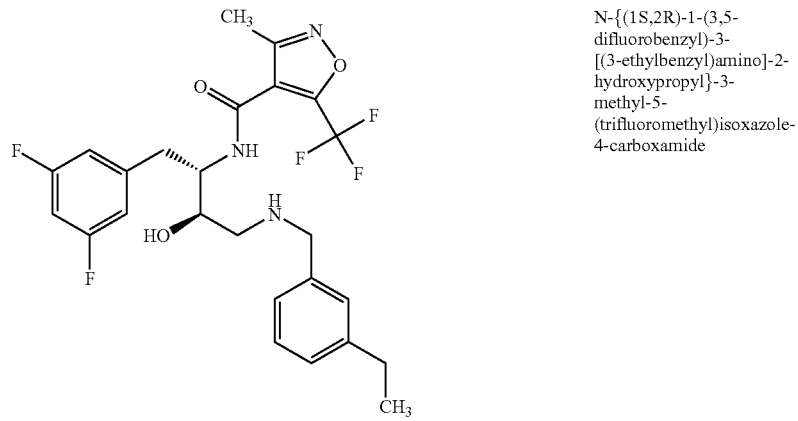 | N-{(1S,2R)-1-(3,5-difluorobenzyl)-3-[(3-ethylbenzyl)amino]-2-hydroxypropyl}-3-methyl-5-(trifluoromethyl)isoxazole-4-carboxamide |
| 3747 | 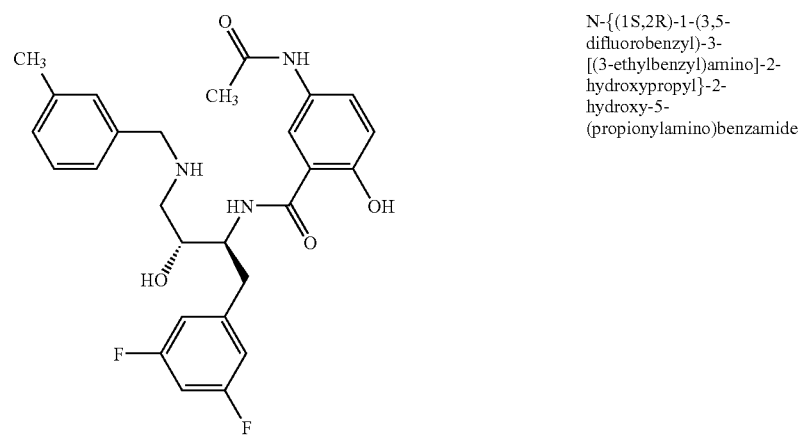 | N-{(1S,2R)-1-(3,5-difluorobenzyl)-3-[(3-ethylbenzyl)amino]-2-hydroxypropyl}-2-hydroxy-5-(propionylamino)benzamide |
| 3748 | 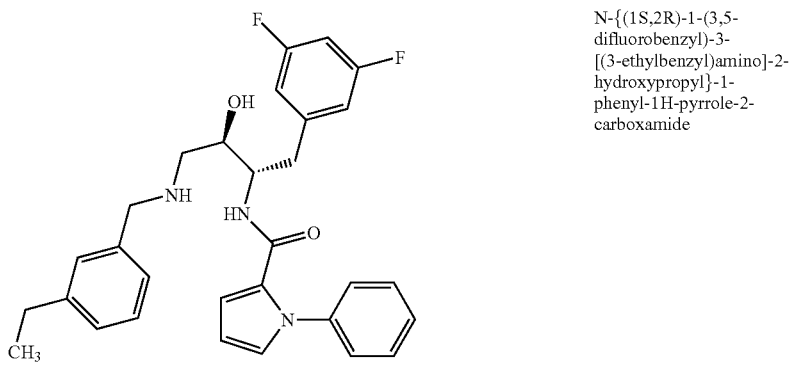 | N-{(1S,2R)-1-(3,5-difluorobenzyl)-3-[(3-ethylbenzyl)amino]-2-hydroxypropyl}-1-phenyl-1H-pyrrole-2-carboxamide |

| | | |
|---|---|---|
| 3749 | 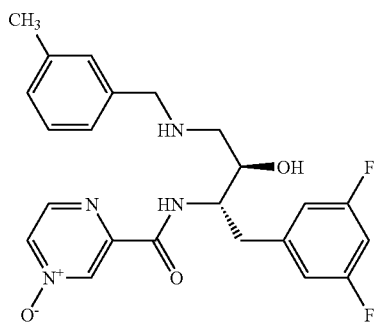 | N-{(1S,2R)-1-(3,5-difluorobenzyl)-3-[(3-ethylbenzyl)amino]-2-hydroxypropyl}pyrazine-2-carboxamide 4-oxide |
| 3750 | 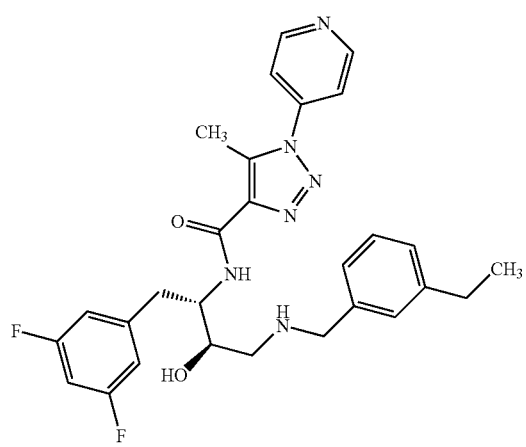 | N-{(1S,2R)-1-(3,5-difluorobenzyl)-3-[(3-ethylbenzyl)amino]-2-hydroxypropyl}-5-methyl-1-pyridin-4-yl-1H-1,2,3-triazole-4-carboxamide |
| 3751 | 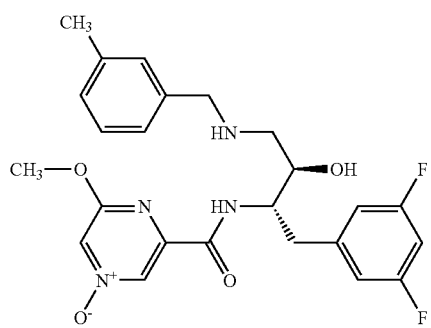 | N-{(1S,2R)-1-(3,5-difluorobenzyl)-3-[(3-ethylbenzyl)amino]-2-hydroxypropyl}-6-methoxypyrazine-2-carboxamide 4-oxide |
| 3752 | 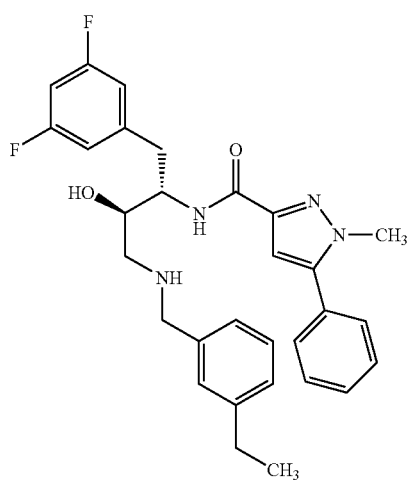 | N-{(1S,2R)-1-(3,5-difluorobenzyl)-3-[(3-ethylbenzyl)amino]-2-hydroxypropyl}-1-methyl-5-phenyl-1H-pyrazole-3-carboxamide |

-continued
| | | |
|---|---|---|
| 3753 | 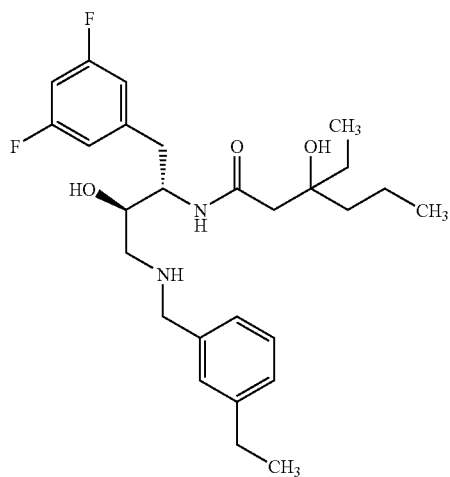 | N-{(1S,2R)-1-(3,5-difluorobenzyl)-3-[(3-ethylbenzyl)amino]-2-hydroxypropyl}-3-hydroxy-3-propylhexanamide |
| 3754 | 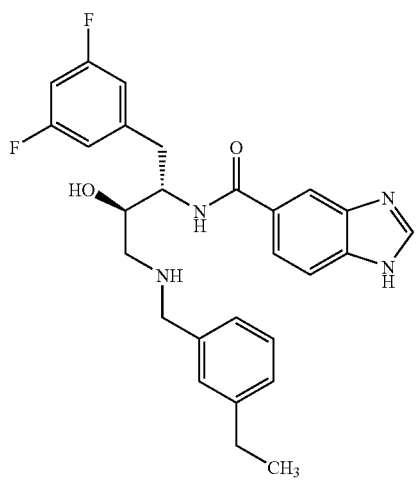 | N-{(1S,2R)-1-(3,5-difluorobenzyl)-3-[(3-ethylbenzyl)amino]-2-hydroxypropyl}-1H-benzimidazole-5-carboxamide |
| 3755 | 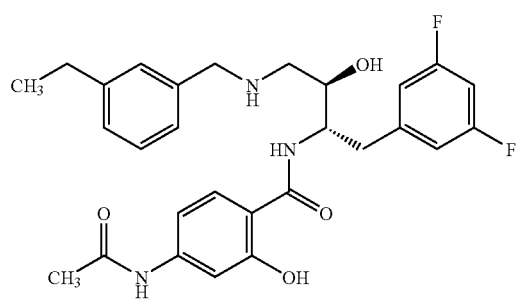 | N-{(1S,2R)-1-(3,5-difluorobenzyl)-3-[(3-ethylbenzyl)amino]-2-hydroxypropyl}-2-hydroxy-4-(propionylamino)benzamide |

-continued
| | | |
|---|---|---|
| 3756 | 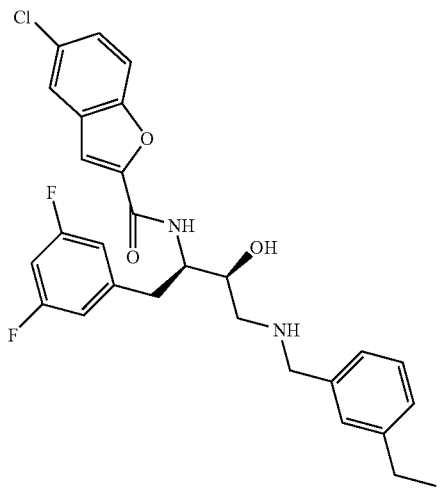 | 5-chloro-N-{(1S,2R)-1-(3,5-difluorobenzyl)-3-[(3-ethylbenzyl)amino]-2-hydroxypropyl}-1-benzofuran-2-carboxamide |
| 3757 | 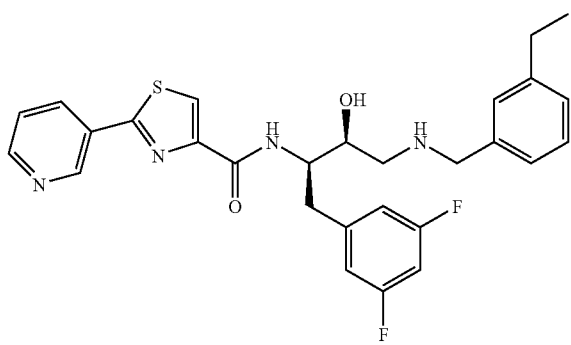 | N-{(1S,2R)-1-(3,5-difluorobenzyl)-3-[(3-ethylbenzyl)amino]-2-hydroxypropyl}-2-pyridin-3-yl-1,3-thiazole-4-carboxamide |
| 3758 | 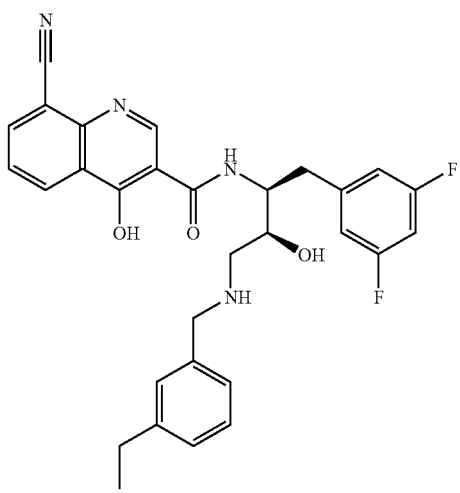 | 8-cyano-N-{(1S,2R)-1-(3,5-difluorobenzyl)-3-[(3-ethylbenzyl)amino]-2-hydroxypropyl}-4-hydroxyquinoline-3-carboxamide |

| | | |
|---|---|---|
| 3759 | 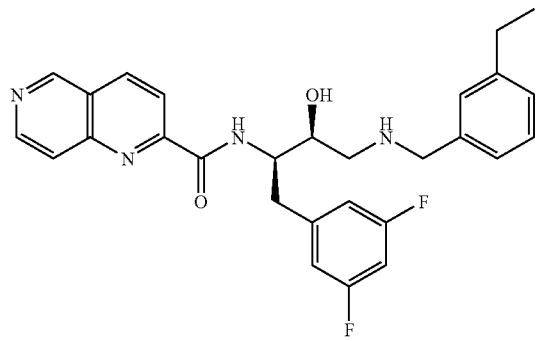 | N-{(1S,2R)-1-(3,5-difluorobenzyl)-3-[(3-ethylbenzyl)amino]-2-hydroxypropyl}-1,6-naphthyridine-2-carboxamide |
| 3760 | 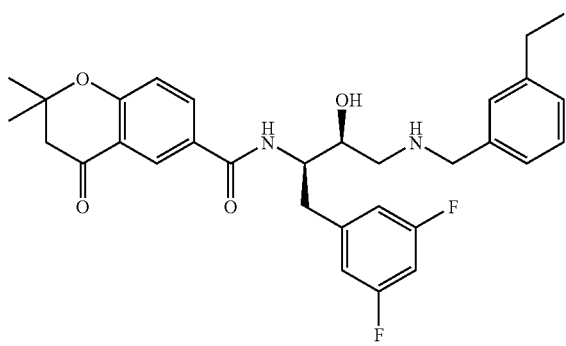 | N-{(1S,2R)-1-(3,5-difluorobenzyl)-3-[(3-ethylbenzyl)amino]-2-hydroxypropyl}-2,2-dimethyl-4-oxochromane-6-carboxamide |
| 3761 | 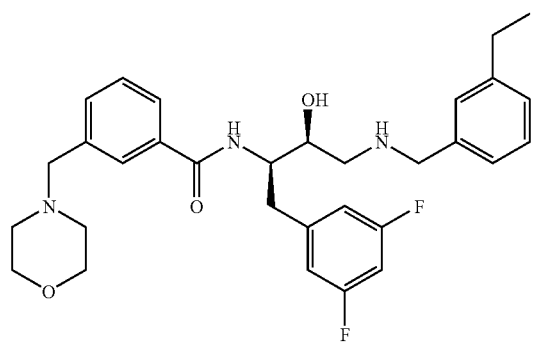 | N-{(1S,2R)-1-(3,5-difluorobenzyl)-3-[(3-ethylbenzyl)amino]-2-hydroxypropyl}-3-(morpholin-4-ylmethyl)benzamide |
| 3762 | 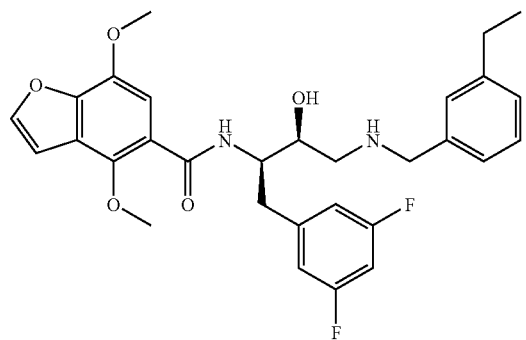 | N-{(1S,2R)-1-(3,5-difluorobenzyl)-3-[(3-ethylbenzyl)amino]-2-hydroxypropyl}-4,7-dimethoxy-1-benzofuran-5-carboxamide |

-continued
| | | |
|---|---|---|
| 3763 | 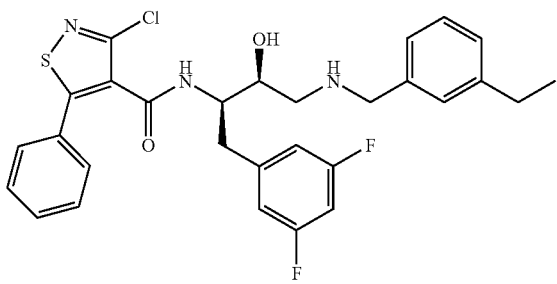 | 3-chloro-N-{(1S,2R)-1-(3,5-difluorobenzyl)-3-[(3-ethylbenzyl)amino]-2-hydroxypropyl}-5-phenylisothiazole-4-carboxamide |
| 3764 | 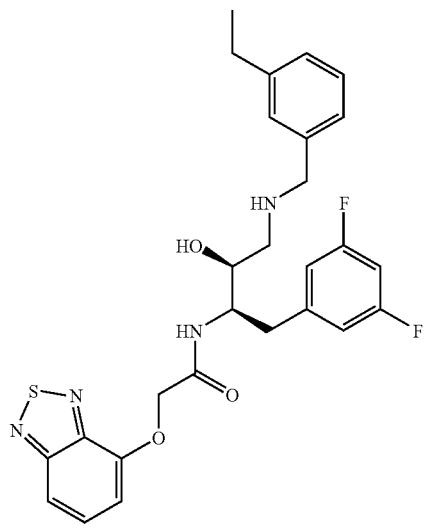 | 2-(2,1,3-benzothiadiazol-4-yloxy)-N-{(1S,2R)-1-(3,5-difluorobenzyl)-3-[(3-ethylbenzyl)amino]-2-hydroxypropyl}acetamide |
| 3765 | 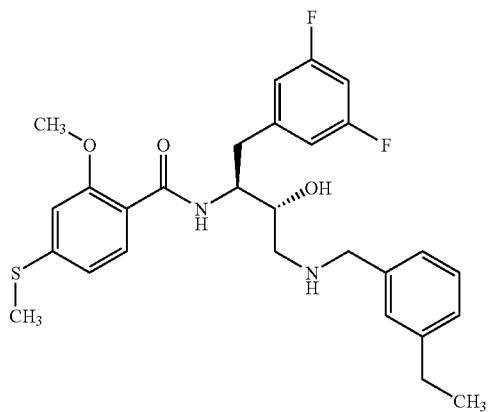 | N-{(1S,2R)-1-(3,5-difluorobenzyl)-3-[(3-ethylbenzyl)amino]-2-hydroxypropyl}-2-methoxy-4-(methylthio)benzamide |

| | | |
|---|---|---|
| 3766 | 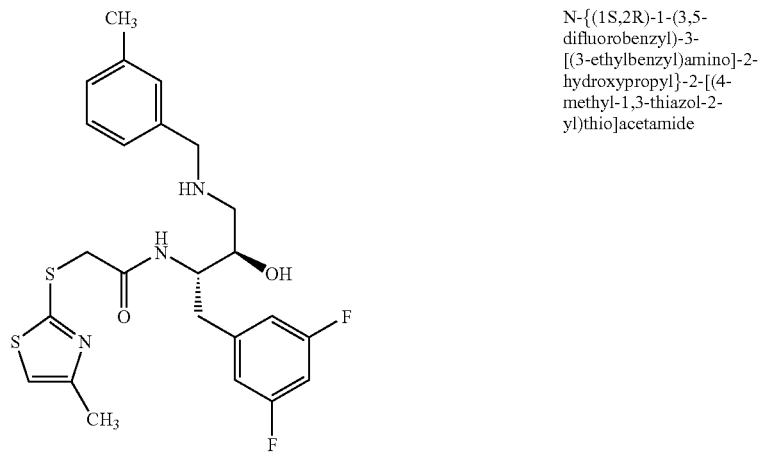 | N-{(1S,2R)-1-(3,5-difluorobenzyl)-3-[(3-ethylbenzyl)amino]-2-hydroxypropyl}-2-[(4-methyl-1,3-thiazol-2-yl)thio]acetamide |
| 3767 | 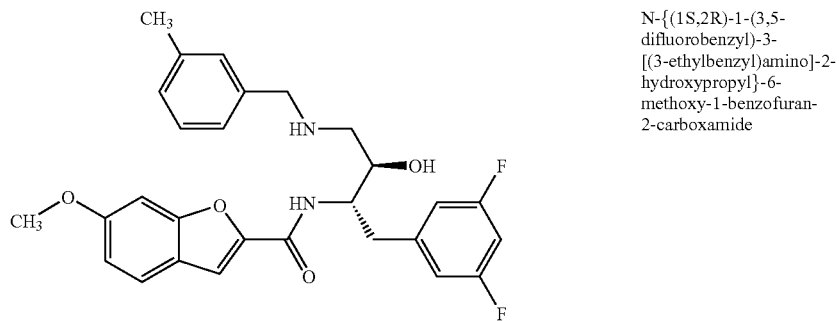 | N-{(1S,2R)-1-(3,5-difluorobenzyl)-3-[(3-ethylbenzyl)amino]-2-hydroxypropyl}-6-methoxy-1-benzofuran-2-carboxamide |
| 3768 | 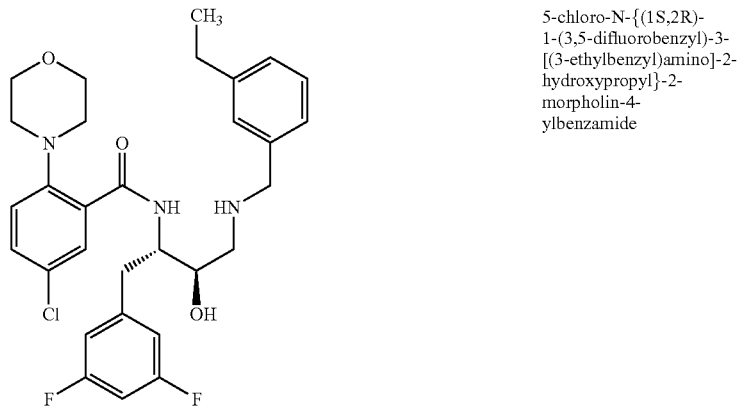 | 5-chloro-N-{(1S,2R)-1-(3,5-difluorobenzyl)-3-[(3-ethylbenzyl)amino]-2-hydroxypropyl}-2-morpholin-4-ylbenzamide |

| | | |
|---|---|---|
| 3769 | 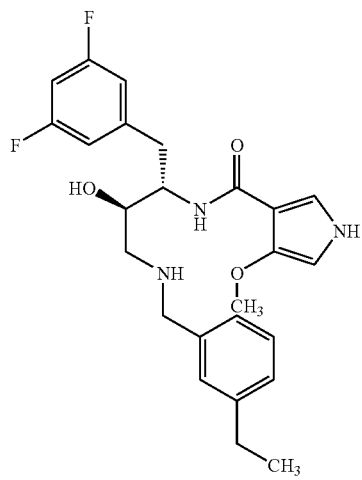 | N-{(1S,2R)-1-(3,5-difluorobenzyl)-3-[(3-ethylbenzyl)amino]-2-hydroxypropyl}-4-methoxy-1H-pyrrole-3-carboxamide |
| 3770 | 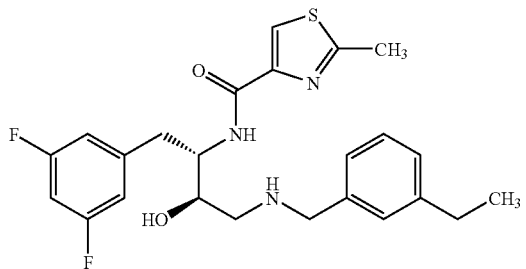 | N-{(1S,2R)-1-(3,5-difluorobenzyl)-3-[(3-ethylbenzyl)amino]-2-hydroxypropyl}-2-methyl-1,3-thiazole-4-carboxamide |
| 3771 | 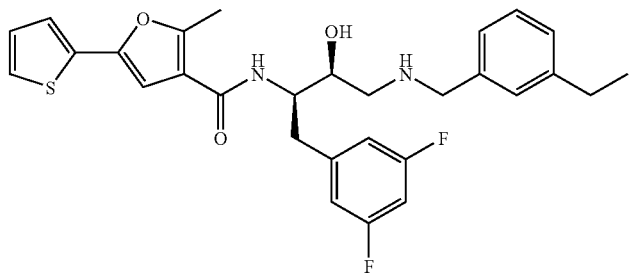 | N-{(1S,2R)-1-(3,5-difluorobenzyl)-3-[(3-ethylbenzyl)amino]-2-hydroxypropyl}-2-methyl-5-(2-thienyl)-3-furamide |
| 3772 | 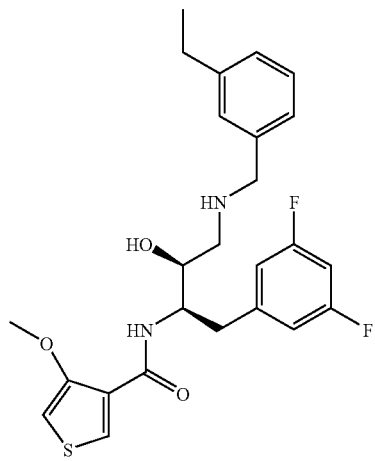 | N-{(1S,2R)-1-(3,5-difluorobenzyl)-3-[(3-ethylbenzyl)amino]-2-hydroxypropyl}-4-methoxythiophene-3-carboxamide |

| | | |
|---|---|---|
| 3773 | 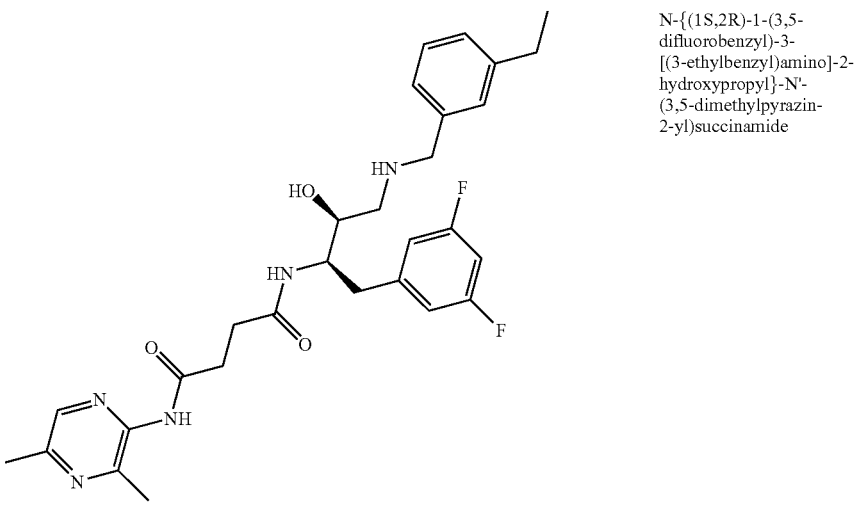 | N-{(1S,2R)-1-(3,5-difluorobenzyl)-3-[(3-ethylbenzyl)amino]-2-hydroxypropyl}-N'-(3,5-dimethylpyrazin-2-yl)succinamide |
| 3774 | 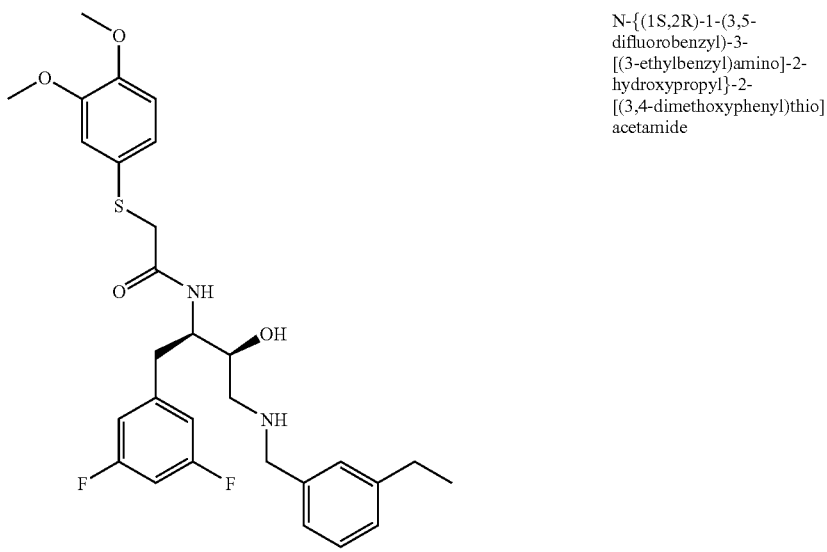 | N-{(1S,2R)-1-(3,5-difluorobenzyl)-3-[(3-ethylbenzyl)amino]-2-hydroxypropyl}-2-[(3,4-dimethoxyphenyl)thio]acetamide |
| 3775 | 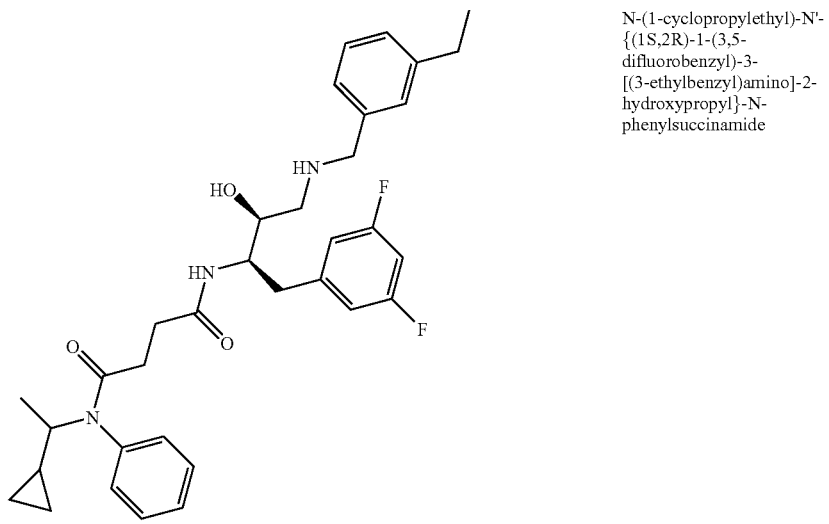 | N-(1-cyclopropylethyl)-N'-{(1S,2R)-1-(3,5-difluorobenzyl)-3-[(3-ethylbenzyl)amino]-2-hydroxypropyl}-N-phenylsuccinamide |

| | | |
|---|---|---|
| 3776 | 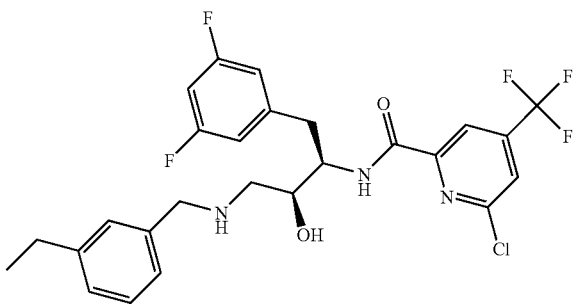 | 6-chloro-N-{(1S,2R)-1-(3,5-difluorobenzyl)-3-[(3-ethylbenzyl)amino]-2-hydroxypropyl}-4-(trifluoromethyl)pyridine-2-carboxamide |
| 3777 | 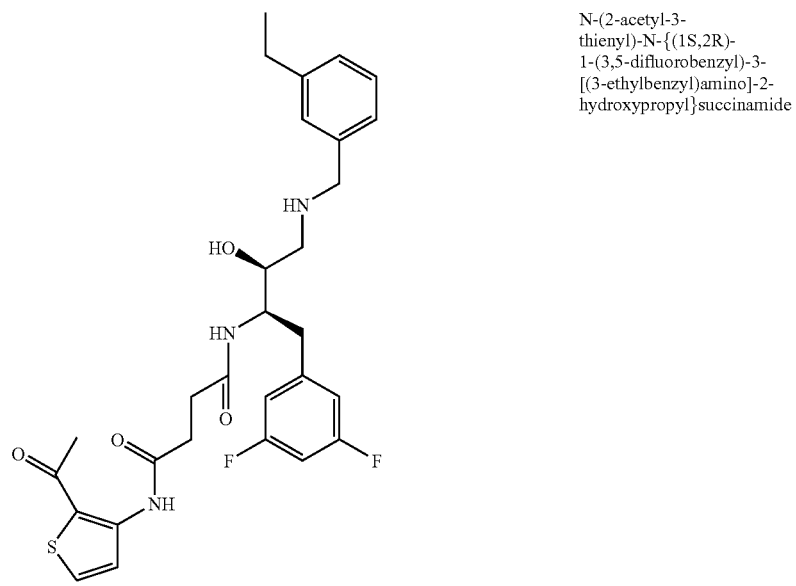 | N-(2-acetyl-3-thienyl)-N-{(1S,2R)-1-(3,5-difluorobenzyl)-3-[(3-ethylbenzyl)amino]-2-hydroxypropyl}succinamide |
| 3778 | 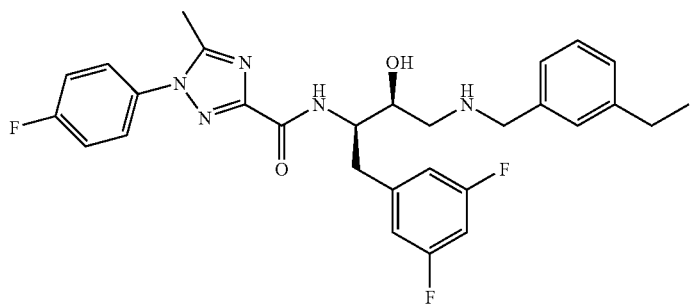 | N-{(1S,2R)-1-(3,5-difluorobenzyl)-3-[(3-ethylbenzyl)amino]-2-hydroxypropyl}-1-(4-fluorophenyl)-5-methyl-1H-1,2,4-triazole-3-carboxamide |
| 3779 | 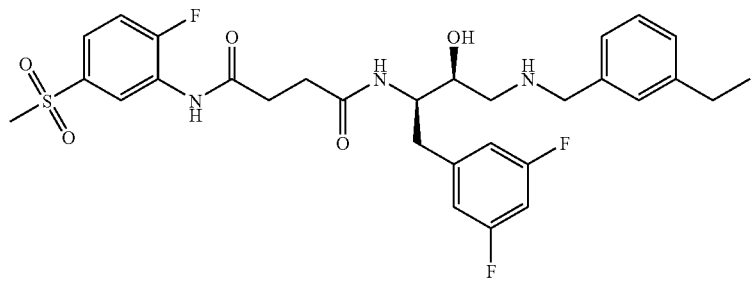 | N-{(1S,2R)-1-(3,5-difluorobenzyl)-3-[(3-ethylbenzyl)amino]-2-hydroxypropyl}-N'-[2-fluoro-5-(methylsulfonyl)phenyl]succinamide |

-continued
| | | |
|---|---|---|
| 3780 | 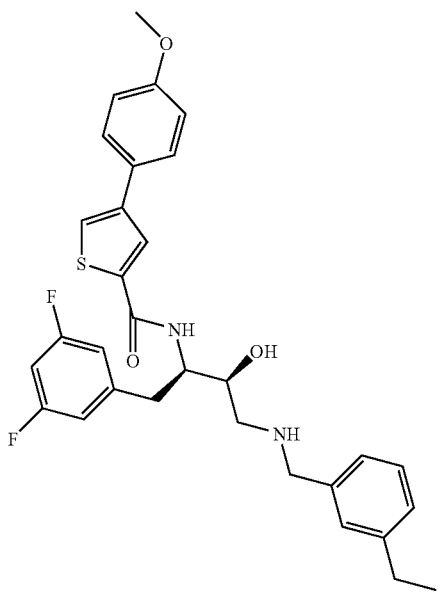 | N-{(1S,2R)-1-(3,5-difluorobenzyl)-3-[(3-ethylbenzyl)amino]-2-hydroxypropyl}-4-(4-methoxyphenyl)thiophene-2-carboxamide |
| 3781 | 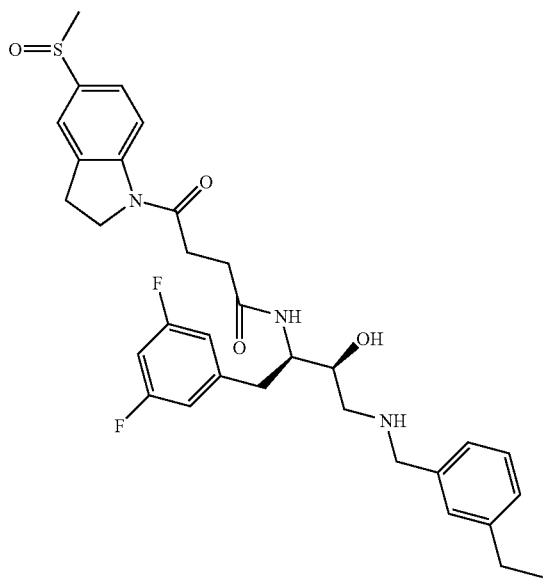 | N-{(1S,2R)-1-(3,5-difluorobenzyl)-3-[(3-ethylbenzyl)amino]-2-hydroxypropyl}-4-[5-(methylsulfinyl)-2,3-dihydro-1H-indol-1-yl]-4-oxobutanamide |
| 3782 | 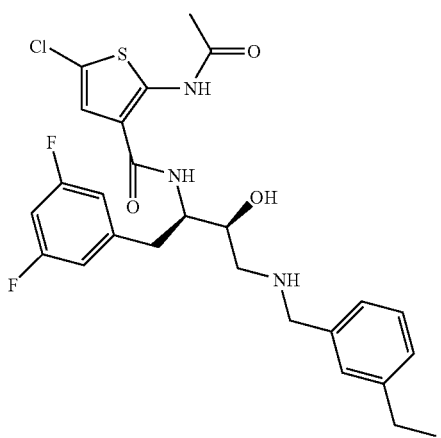 | 2-(acetylamino)-5-chloro-N-{(1S,2R)-1-(3,5-difluorobenzyl)-3-[(3-ethylbenzyl)amino]-2-hydroxypropyl}thiophene-3-carboxamide |

-continued
| | | |
|---|---|---|
| 3783 | 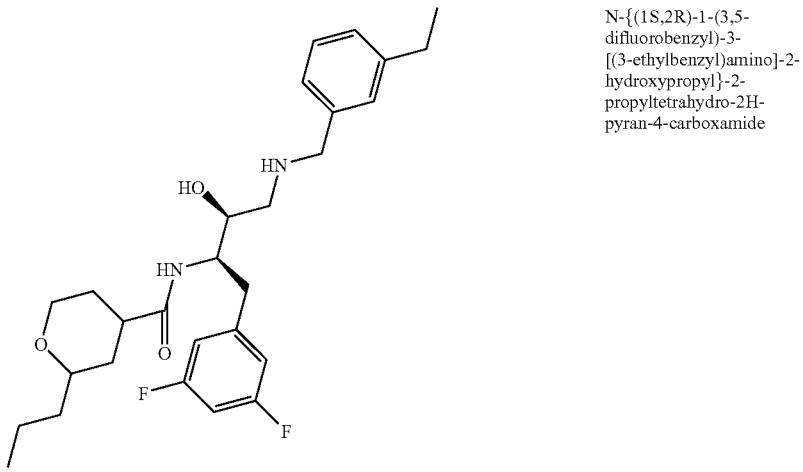 | N-{(1S,2R)-1-(3,5-difluorobenzyl)-3-[(3-ethylbenzyl)amino]-2-hydroxypropyl}-2-propyltetrahydro-2H-pyran-4-carboxamide |
| 3784 | 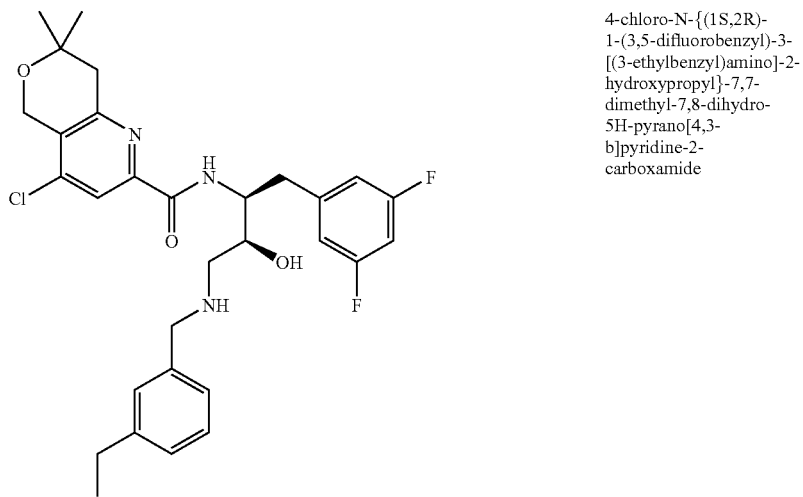 | 4-chloro-N-{(1S,2R)-1-(3,5-difluorobenzyl)-3-[(3-ethylbenzyl)amino]-2-hydroxypropyl}-7,7-dimethyl-7,8-dihydro-5H-pyrano[4,3-b]pyridine-2-carboxamide |
| 3785 | 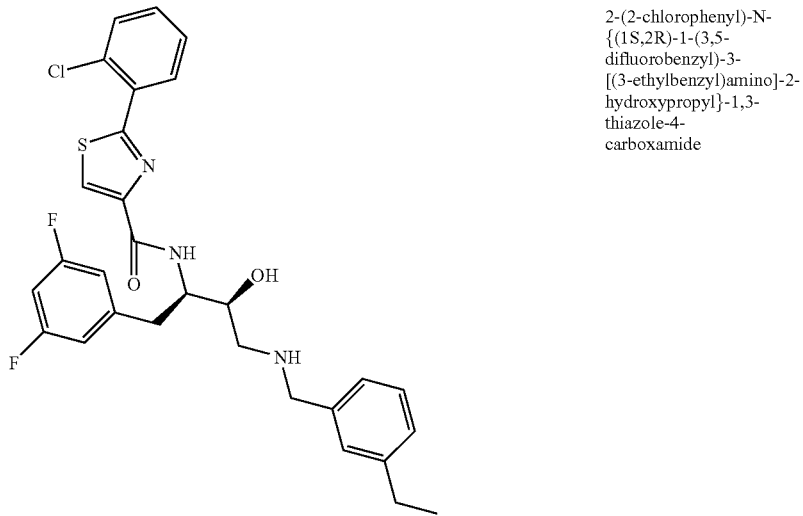 | 2-(2-chlorophenyl)-N-{(1S,2R)-1-(3,5-difluorobenzyl)-3-[(3-ethylbenzyl)amino]-2-hydroxypropyl}-1,3-thiazole-4-carboxamide |

| | | |
|---|---|---|
| 3786 | 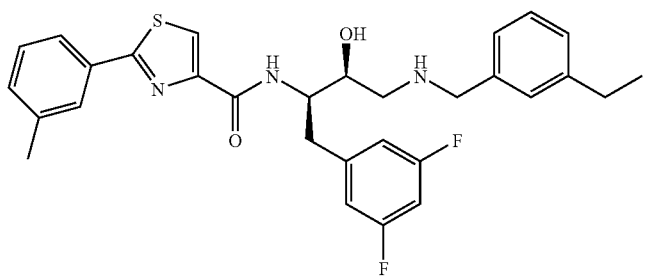 | N-{(1S,2R)-1-(3,5-difluorobenzyl)-3-[(3-ethylbenzyl)amino]-2-hydroxypropyl}-2-(3-methylphenyl)-1,3-thiazole-4-carboxamide |
| 3787 | 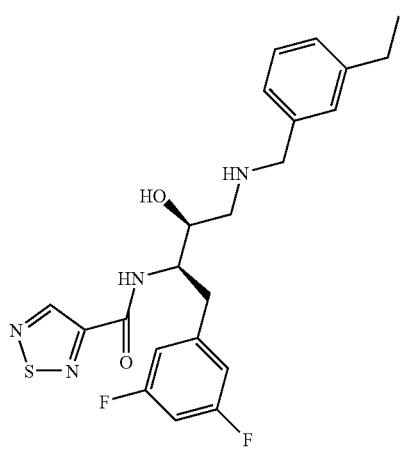 | N-{(1S,2R)-1-(3,5-difluorobenzyl)-3-[(3-ethylbenzyl)amino]-2-hydroxypropyl}-1,2,5-thiadiazole-3-carboxamide |
| 3788 | 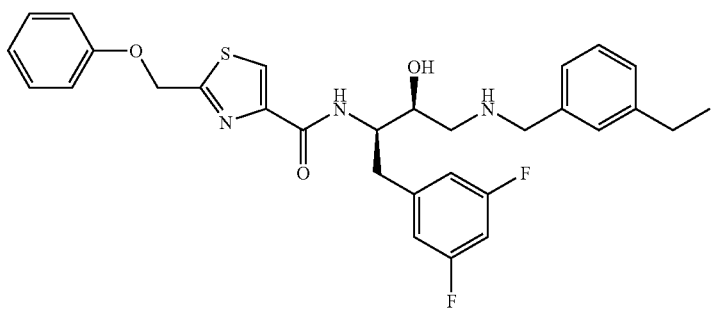 | N-{(1S,2R)-1-(3,5-difluorobenzyl)-3-[(3-ethylbenzyl)amino]-2-hydroxypropyl}-2-(phenoxymethyl)-1,3-thiazole-4-carboxamide |
| 3789 | 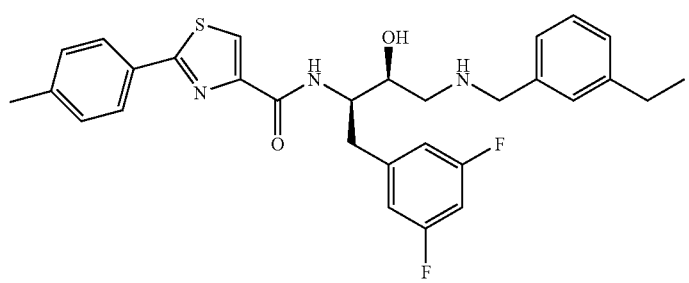 | N-{(1S,2R)-1-(3,5-difluorobenzyl)-3-[(3-ethylbenzyl)amino]-2-hydroxypropyl]-2-(4-methylphenyl)-1,3-thiazole-4-carboxamide |

-continued

3790 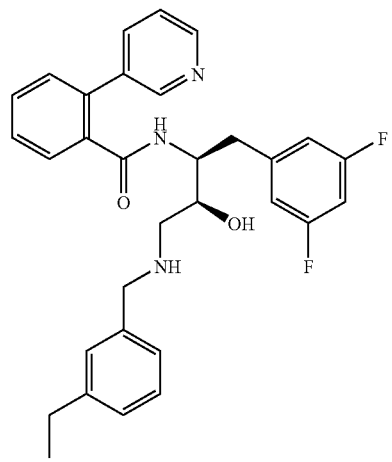 N-{(1S,2R)-1-(3,5-difluorobenzyl)-3-[(3-ethylbenzyl)amino]-2-hydroxypropyl}-2-pyridin-3-ylbenzamide 3791 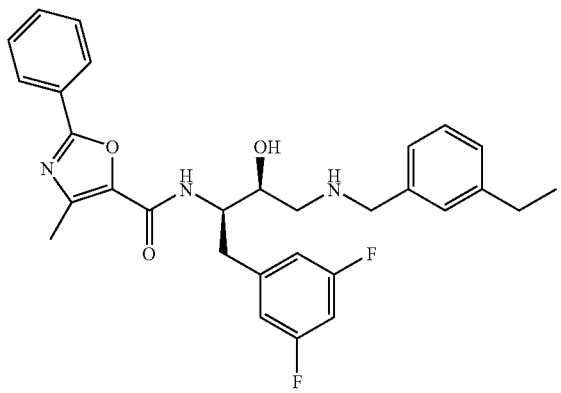 N-{(1S,2R)-1-(3,5-difluorobenzyl)-3-[(3-ethylbenzyl)amino]-2-hydroxypropyl}-4-methyl-2-phenyl-1,3-oxazole-5-carboxamide 3792 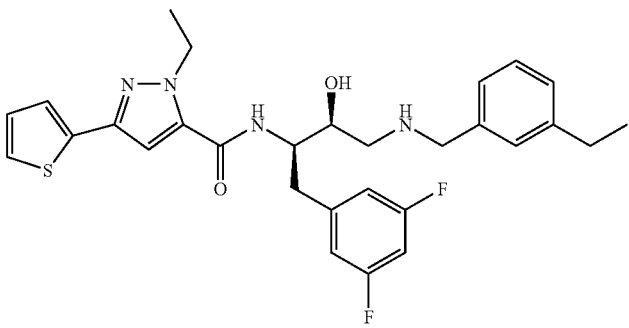 N-{(1S,2R)-1-(3,5-difluorobenzyl)-3-[(3-ethylbenzyl)amino]-2-hydroxypropyl}-1-ethyl-3-(2-thienyl)-1H-pyrazole-5-carboxamide 3793 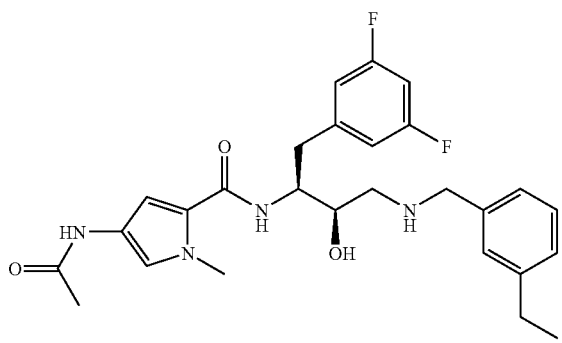 4-(acetylamino)-N-{(1S,2R)-1-(3,5-difluorobenzyl)-3-[(3-ethylbenzyl)amino]-2-hydroxypropyl}-1-methyl-1H-pyrrole-2-carboxamide -continued

| | | |
|---|---|---|
| 3794 | 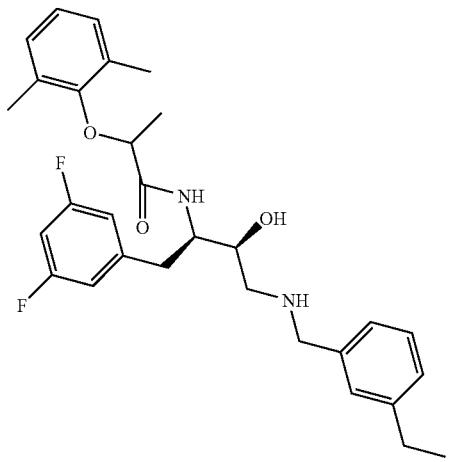 | N-{(1S,2R)-1-(3,5-difluorobenzyl)-3-[(3-ethylbenzyl)amino]-2-hydroxypropyl}-2-(2,6-dimethylphenoxy)propanamide |
| 3795 | 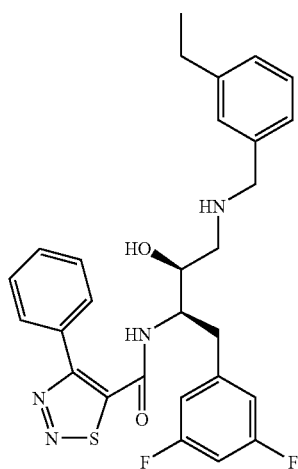 | N-{(1S,2R)-1-(3,5-difluorobenzyl)-3-[(3-ethylbenzyl)amino]-2-hydroxypropyl}-4-phenyl-1,2,3-thiadiazole-5-carboxamide |
| 3796 | 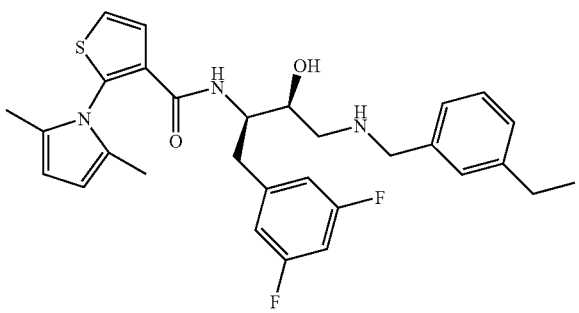 | N-{(1S,2R)-1-(3,5-difluorobenzyl)-3-[(3-ethylbenzyl)amino]-2-hydroxypropyl}-2-(2,5-dimethyl-1H-pyrrol-1-yl)thiophene-3-carboxamide |
| 3797 | 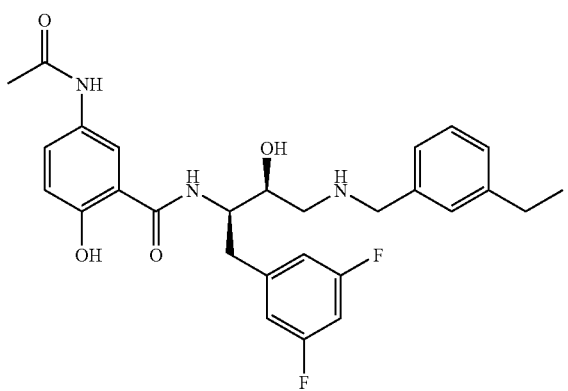 | 5-(acetylamino)-N-{(1S,2R)-1-(3,5-difluorobenzyl)-3-[(3-ethylbenzyl)amino]-2-hydroxypropyl}-2-hydroxybenzamide |

| | | |
|---|---|---|
| 3798 | 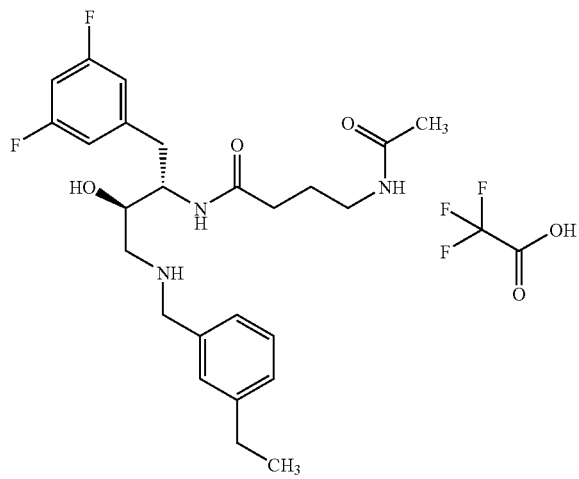 | 4-(acetylamino)-N-{(1S,2R)-1-(3,5-difluorobenzyl)-3-[(3-ethylbenzyl)amino]-2-hydroxypropyl}butanamide trifluoroacetate |
| 3799 | 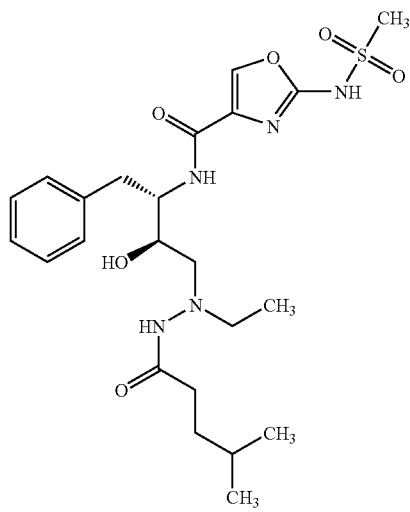 | N-{(1S,2R)-1-benzyl-3-[1-ethyl-2-(4-methylpentanoyl)hydrazino)-2-hydroxypropyl}-2-[(methylsulfonyl)amino]-1,3-oxazole-4-carboxamide |
| 3800 | 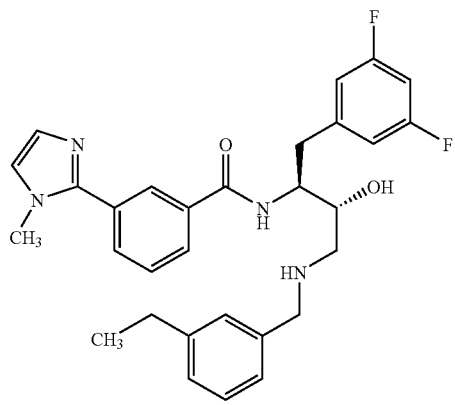 | N-{(1S,2R)-1-(3,5-difluorobenzyl)-3-[(3-ethylbenzyl)amino]-2-hydroxypropyl}-3-(1-methyl-1H-imidazol-2-yl)benzamide   519 |

-continued

| | | |
|---|---|---|
| 3801 | 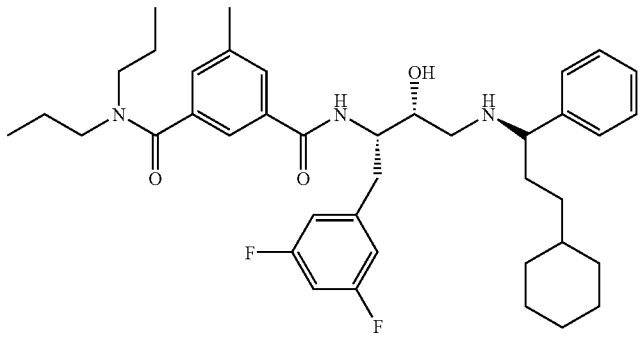 | N'-[(1S,2R)-3-{[(1R)-3-cyclohexyl-1-phenylpropyl]amino]}-1-(3,5-difluorobenzyl)-2-hydroxypropyl]-5-methyl-N,N-dipropylisophthalamide |
| 3802 | 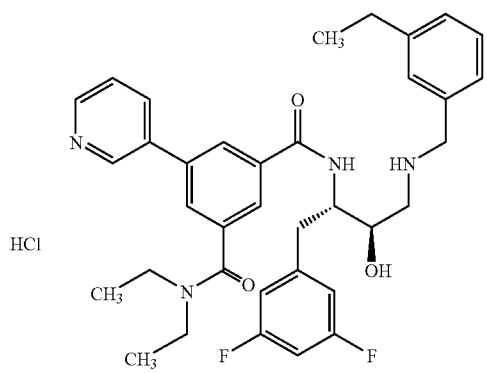 | $N^1$-{(1S,2R)-1-(3,5-difluorobenzyl)-3-[(3-ethylbenzyl)amino]-2-hydroxypropyl}-$N^3,N^3$-dipropyl-5-pyridin-3-ylisophthalamide hydrochloride |
| 3803 | 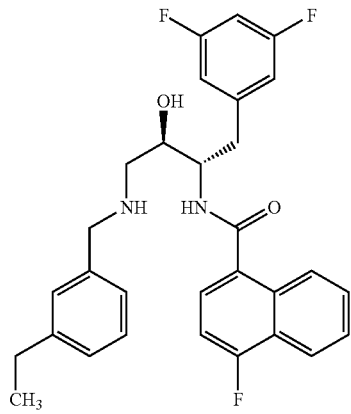 | N-{(1S,2R)-1-(3,5-difluorobenzyl)-3-[(3-ethylbenzyl)amino]-2-hydroxypropyl}-4-fluoro-1-naphthamide |
| 3804 | 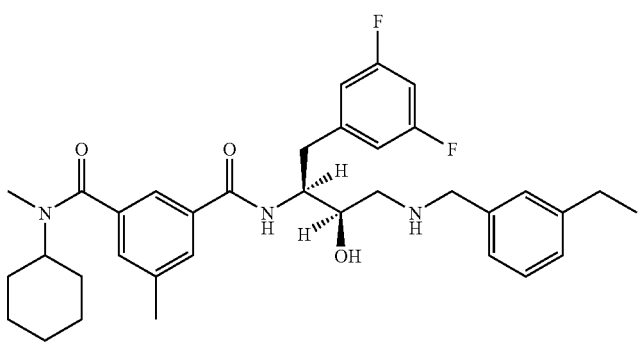 | N-cyclohexyl-N'-{(1S,2R)-1-(3,5-difluorobenzyl)-3-[(3-ethylbenzyl)amino]-2-hydroxypropyl}-N,5-dimethylisophthalamide |

-continued

| | | | |
|---|---|---|---|
| 3805 | 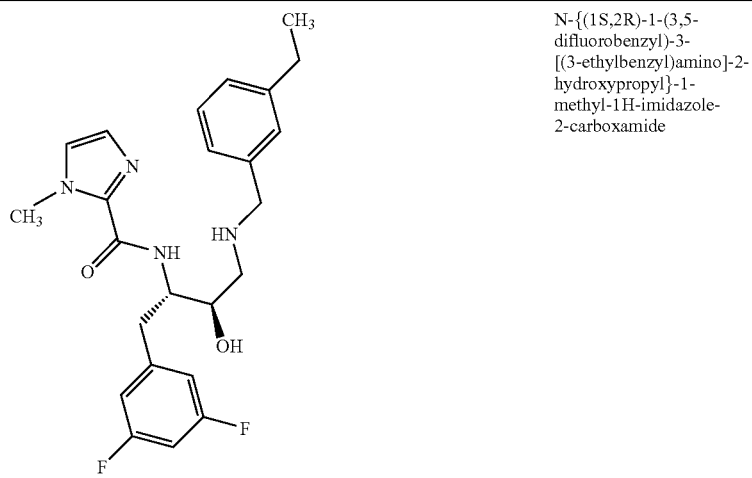 | N-{(1S,2R)-1-(3,5-difluorobenzyl)-3-[(3-ethylbenzyl)amino]-2-hydroxypropyl}-1-methyl-1H-imidazole-2-carboxamide | 443.2 |
| 3806 | 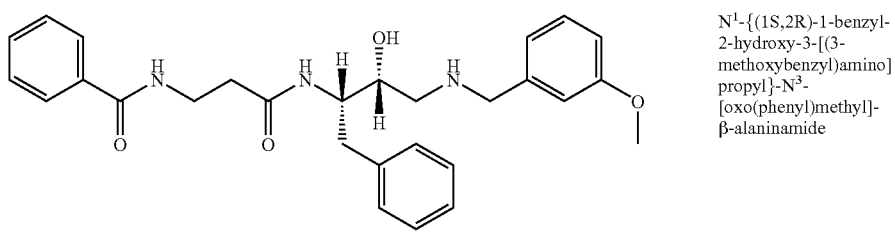 | N$^1$-{(1S,2R)-1-benzyl-2-hydroxy-3-[(3-methoxybenzyl)amino]propyl}-N$^3$-[oxo(phenyl)methyl]-β-alaninamide | |
| 3807 | 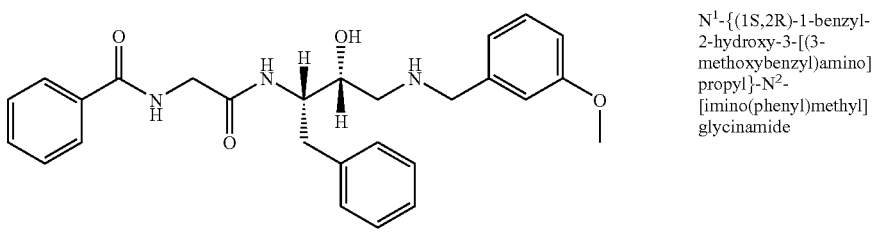 | N$^1$-{(1S,2R)-1-benzyl-2-hydroxy-3-[(3-methoxybenzyl)amino]propyl}-N$^2$-[imino(phenyl)methyl]glycinamide | |
| 3808 | 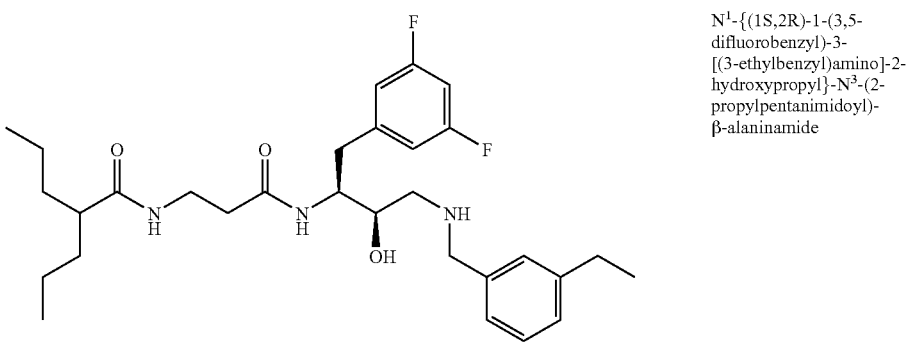 | N$^1$-{(1S,2R)-1-(3,5-difluorobenzyl)-3-[(3-ethylbenzyl)amino]-2-hydroxypropyl}-N$^3$-(2-propylpentanimidoyl)-β-alaninamide | |
| 3809 | 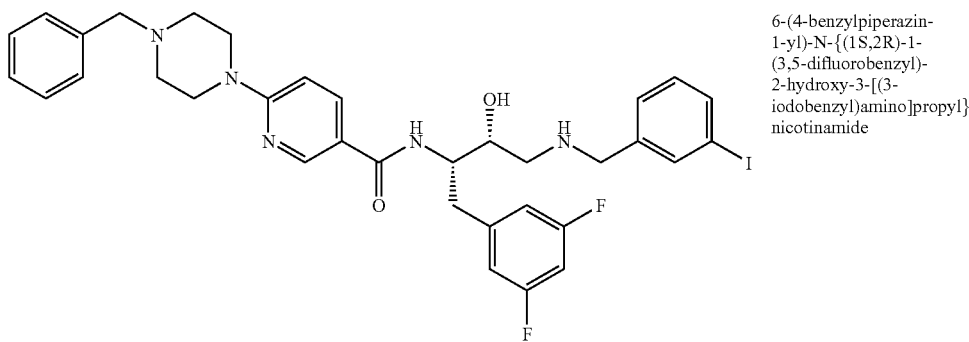 | 6-(4-benzylpiperazin-1-yl)-N-{(1S,2R)-1-(3,5-difluorobenzyl)-2-hydroxy-3-[(3-iodobenzyl)amino]propyl}nicotinamide | |

| | | |
|---|---|---|
| 3810 | 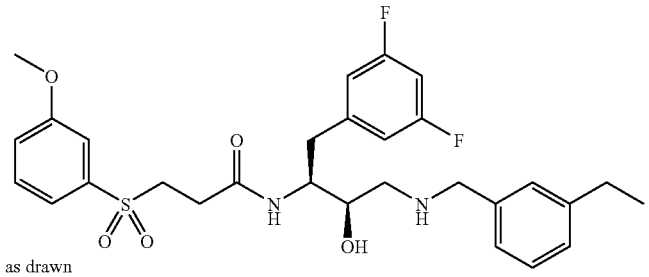 as drawn | N-{(1S,2R)-1-(3,5-difluorobenzyl)-3-[(3-ethylbenzyl)amino]-2-hydroxypropyl}-3-[(3-methoxyphenyl)sulfonyl]propanamide |
| 3811 | 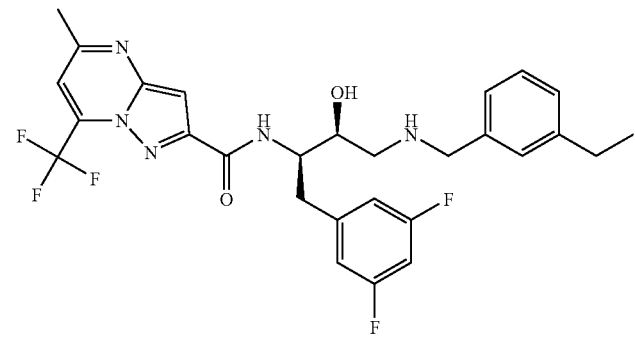 | N-{(1S,2R)-1-(3,5-difluorobenzyl)-3-[(3-ethylbenzyl)amino]-2-hydroxypropyl}-5-methyl-7-(trifluoromethyl)pyrazolo[1,5-a]pyrimidine-2-carboxamide |
| 3812 | 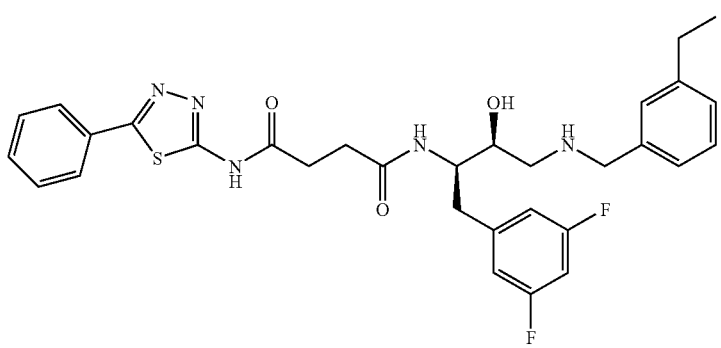 | N-{(1S,2R)-1-(3,5-difluorobenzyl)-3-[(3-ethylbenzyl)amino]-2-hydroxypropyl}-N'-(5-phenyl-1,3,4-thiadiazol-2-yl)succinamide |
| 3813 | 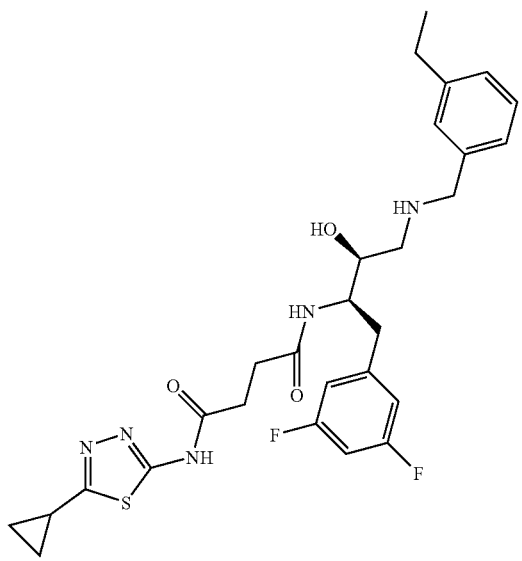 | N-(5-cyclopropyl-1,3,4-thiadiazol-2-yl)-N'-{(1S,2R)-1-(3,5-difluorobenzyl)-3-[(3-ethylbenzyl)amino]-2-hydroxypropyl}succinamide |

| | | |
|---|---|---|
| 3814 | 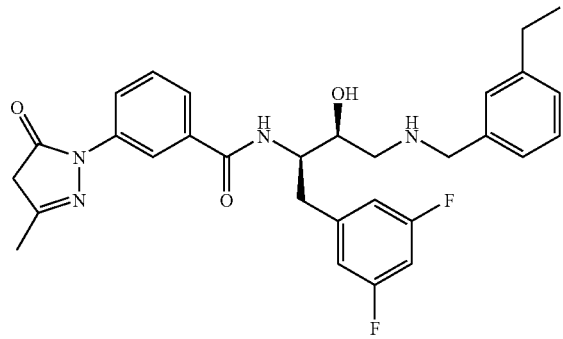 | N-{(1S,2R)-1-(3,5-difluorobenzyl)-3-[(3-ethylbenzyl)amino]-2-hydroxypropyl}-3-(3-methyl-5-oxo-4,5-dihydro-1H-pyrazol-1-yl)benzamide |
| 3815 | 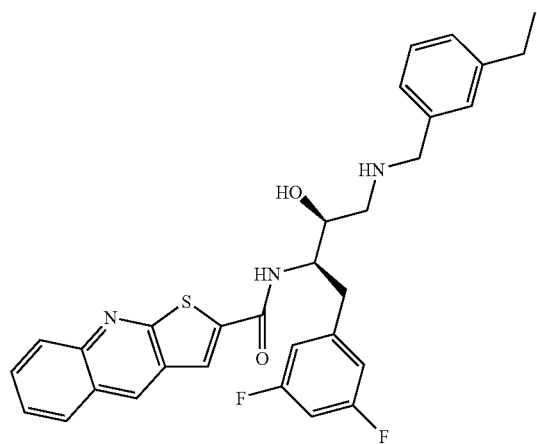 | N-{(1S,2R)-1-(3,5-difluorobenzyl)-3-[(3-ethylbenzyl)amino]-2-hydroxypropyl}thieno[2,3-b]quinoline-2-carboxamide |
| 3816 | 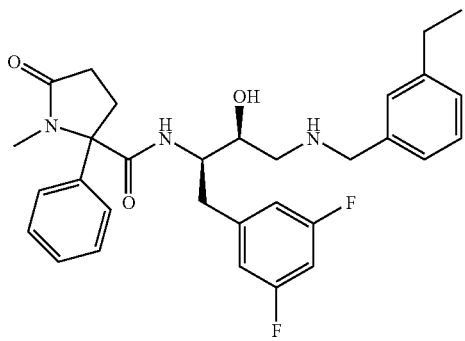 | N-{(1S,2R)-1-(3,5-difluorobenzyl)-3-[(3-ethylbenzyl)amino]-2-hydroxypropyl}-1-methyl-5-oxo-2-phenylprolinamide |
| 3817 | 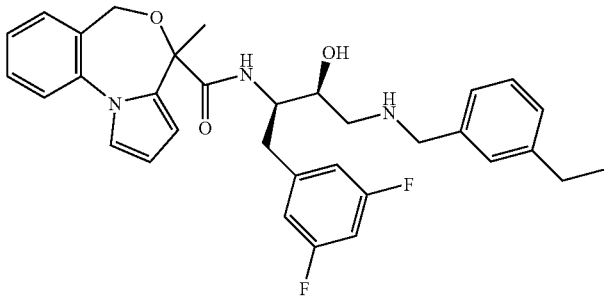 | N-{(1S,2R)-1-(3,5-difluorobenzyl)-3-[(3-ethylbenzyl)amino]-2-hydroxypropyl}-4-methyl-4H,6H-pyrrolo[1,2-a][4,1]benzoxazepine-4-carboxamide |

-continued

| | | |
|---|---|---|
| 3818 | 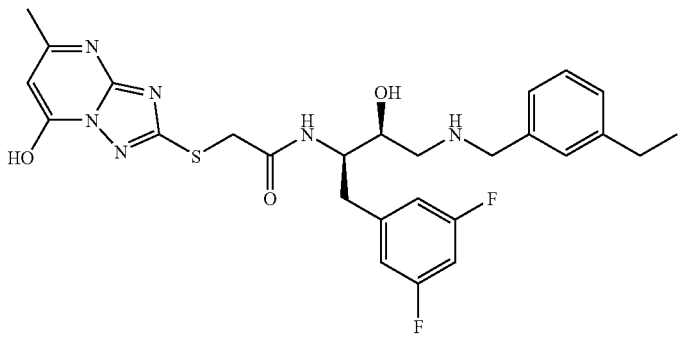 | N-{(1S,2R)-1-(3,5-difluorobenzyl)-3-[(3-ethylbenzyl)amino]-2-hydroxypropyl}-2-[(7-hydroxy-5-methyl[1,2,4]triazolo[1,5-a]pyrimidin-2-yl)thio]acetamide |
| 3819 | 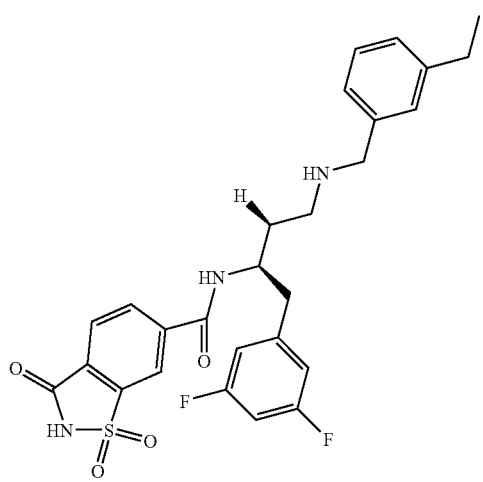 | N-{(1S,2R)-1-(3,5-difluorobenzyl)-3-[(3-ethylbenzyl)amino]-2-hydroxypropyl}-3-oxo-2,3-dihydro-1,2-benzisothiazole-6-carboxamide 1,1-dioxide |
| 3820 | 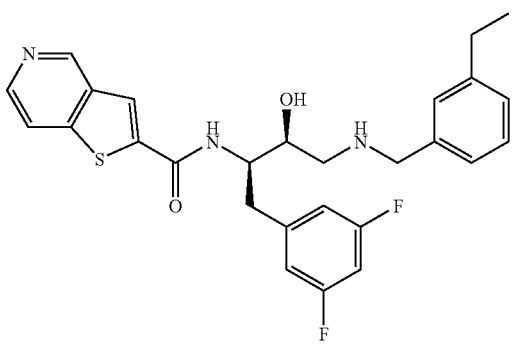 | N-{(1S,2R)-1-(3,5-difluorobenzyl)-3-[(3-ethylbenzyl)amino]-2-hydroxypropyl}thieno[3,2-c]pyridine-2-carboxamide |
| 3821 | 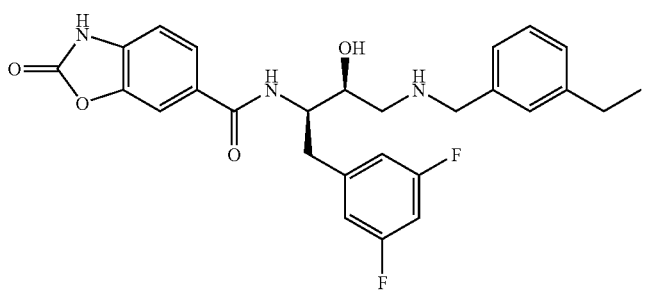 | N-{(1S,2R)-1-(3,5-difluorobenzyl)-3-[(3-ethylbenzyl)amino]-2-hydroxypropyl}-2-oxo-2,3-dihydro-1,3-benzoxazole-6-carboxamide |

-continued

| | | |
|---|---|---|
| 3822 | 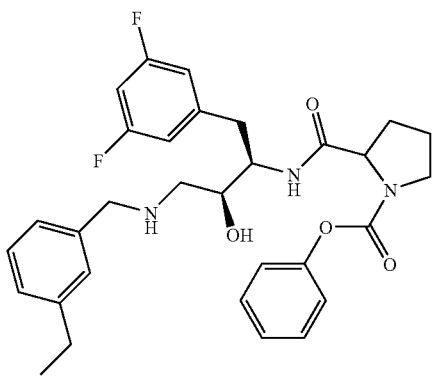 | N-{(1S,2R)-1-(3,5-difluorobenzyl)-3-[(3-ethylbenzyl)amino]-2-hydroxypropyl}-1-[oxo(phenoxy)methyl]prolinamide |
| 3823 | 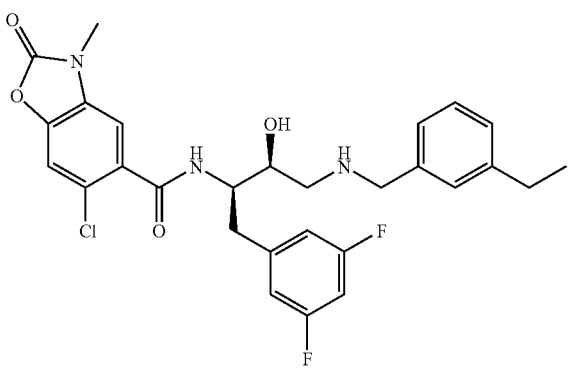 | 6-chloro-N-{(1S,2R)-1-(3,5-difluorobenzyl)-3-[(3-ethylbenzyl)amino]-2-hydroxypropyl}-3-methyl-2-oxo-2,3-dihydro-1,3-benzoxazole-5-carboxamide |
| 3824 | 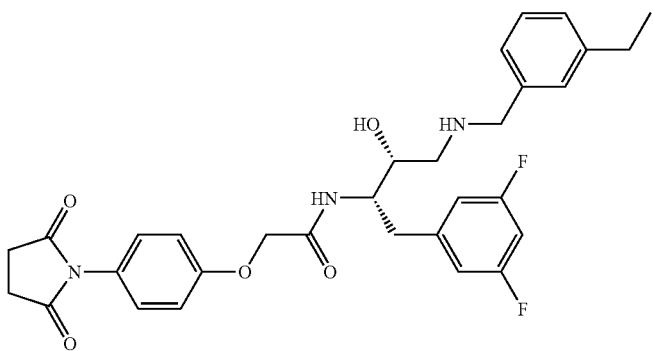 | N-{(1S,2R)-1-(3,5-difluorobenzyl)-3-[(3-ethylbenzyl)amino]-2-hydroxypropyl}-2-[4-(2,5-dioxopyrrolidin-1-yl)phenoxy]acetamide |
| 3825 | 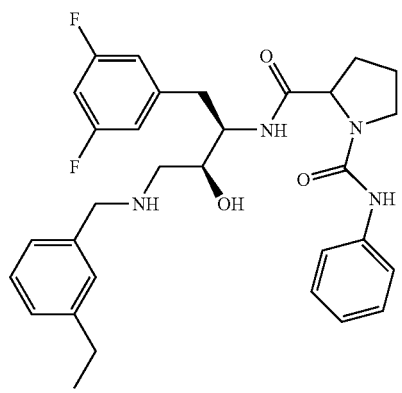 | $N^2$-{(1S,2R)-1-(3,5-difluorobenzyl)-3-[(3-ethylbenzyl)amino]-2-hydroxypropyl}-$N^1$-phenylpyrrolidine-1,2-dicarboxamide |

-continued

| | | |
|---|---|---|
| 3826 | 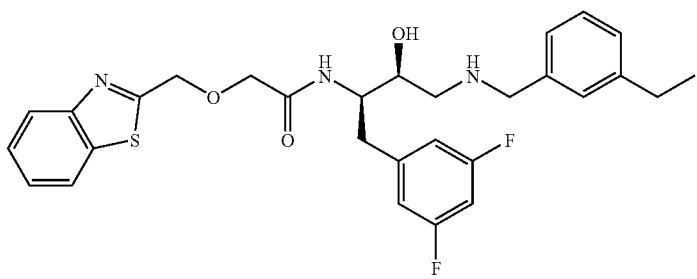 | 2-(1,3-benzothiazol-2-ylmethoxy)-N-{(1S,2R)-1-(3,5-difluorobenzyl)-3-[(3-ethylbenzyl)amino]-2-hydroxypropyl}acetamide |
| 3827 | 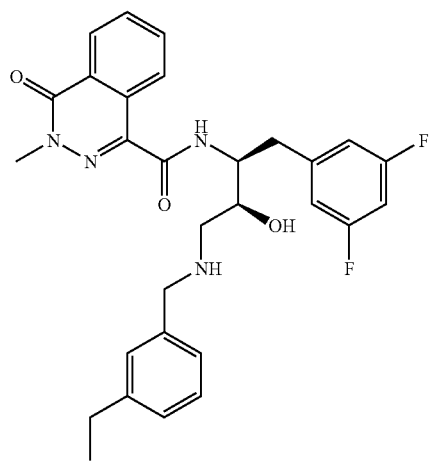 | N-{(1S,2R)-1-(3,5-difluorobenzyl)-3-[(3-ethylbenzyl)amino]-2-hydroxypropyl}-3-methyl-4-oxo-3,4-dihydrophthalazine-1-carboxamide |
| 3828 | 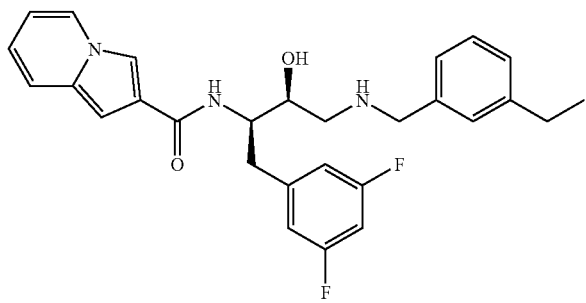 | N-{(1S,2R)-1-(3,5-difluorobenzyl)-3-[(3-ethylbenzyl)amino]-2-hydroxypropyl}indolizine-2-carboxamide |
| 3829 | 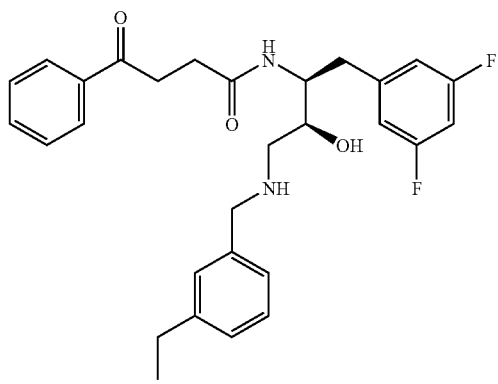 | N-{(1S,2R)-1-(3,5-difluorobenzyl)-3-[(3-ethylbenzyl)amino]-2-hydroxypropyl}-4-oxo-4-phenylbutanamide |

| | | |
|---|---|---|
| 3830 | 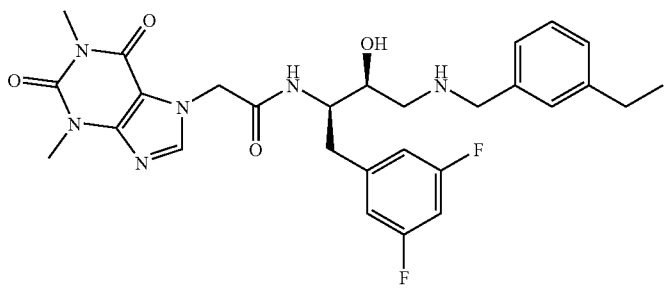 | N-{(1S,2R)-1-(3,5-difluorobenzyl)-3-[(3-ethylbenzyl)amino]-2-hydroxypropyl}-2-(1,3-dimethyl-2,6-dioxo-1,2,3,6-tetrahydro-7H-purin-7-yl)acetamide |
| 3831 | 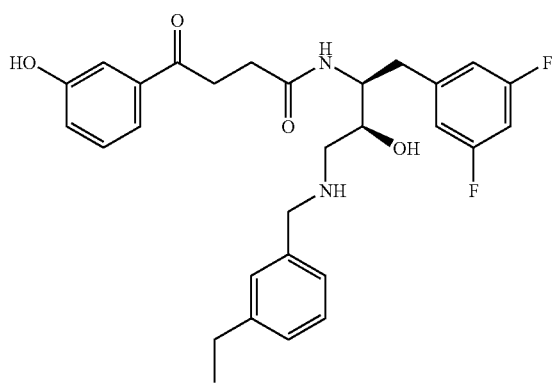 | N-{(1S,2R)-1-(3,5-difluorobenzyl)-3-[(3-ethylbenzyl)amino]-2-hydroxypropyl}-4-(3-hydroxyphenyl)-4-oxobutanamide |
| 3832 | 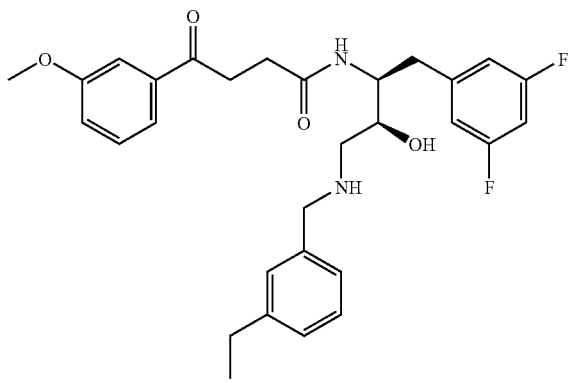 | N-{(1S,2R)-1-(3,5-difluorobenzyl)-3-[(3-ethylbenzyl)amino]-2-hydroxypropyl}-4-(3-methoxyphenyl)-4-oxobutanamide |
| 3833 | 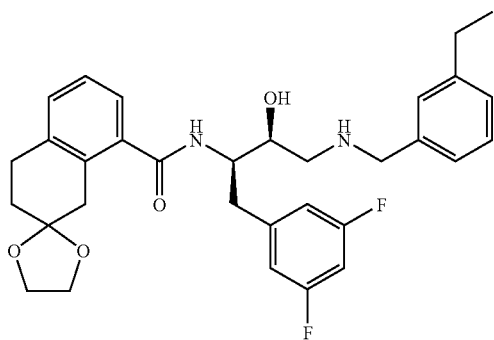 | N-{(1S,2R)-1-(3,5-difluorobenzyl)-3-[(3-ethylbenzyl)amino]-2-hydroxypropyl}-3',4'-dihydro-1'H-spiro[1,3-dioxolane-2,2'-naphthalene]-8'-carboxamide |

-continued

| | | |
|---|---|---|
| 3834 | 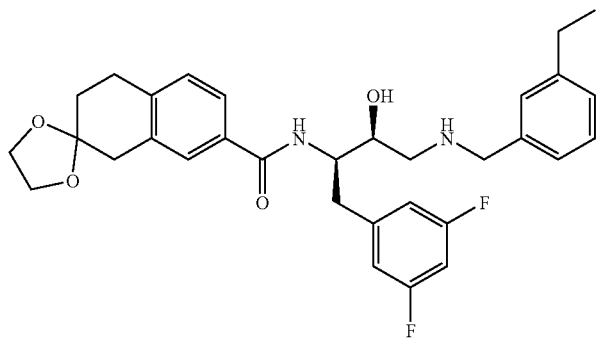 | N-{(1S,2R)-1-(3,5-difluorobenzyl)-3-[(3-ethylbenzyl)amino]-2-hydroxypropyl}-3',4'-dihydro-1'H-spiro[1,3-dioxolane-2,2'-naphthalene]-7'-carboxamide |
| 3835 | 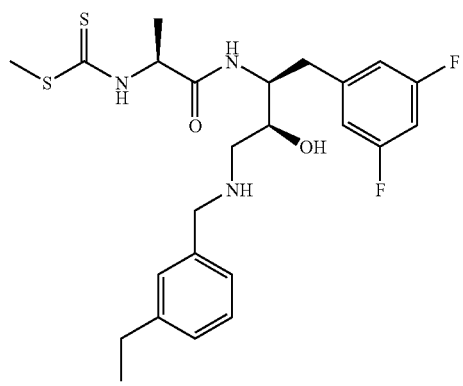 | N¹-{(1S,2R)-1-(3,5-difluorobenzyl)-3-[(3-ethylbenzyl)amino]-2-hydroxypropyl}-N²-[mercapto(methylthio)methyl]-D-alaninamide |
| 3836 | 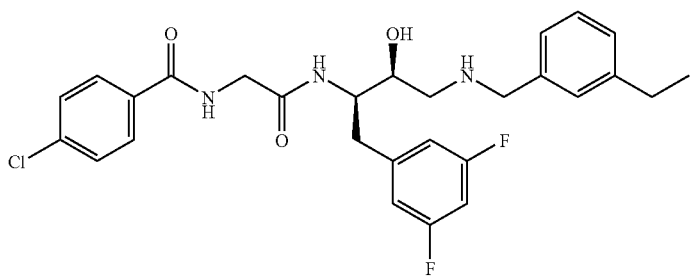 | N²-[(4-chlorophenyl)(oxo)methyl]-N¹-{(1S,2R)-1-(3,5-difluorobenzyl)-3-[(3-ethylbenzyl)amino]-2-hydroxypropyl}glycinamide |
| 3837 | 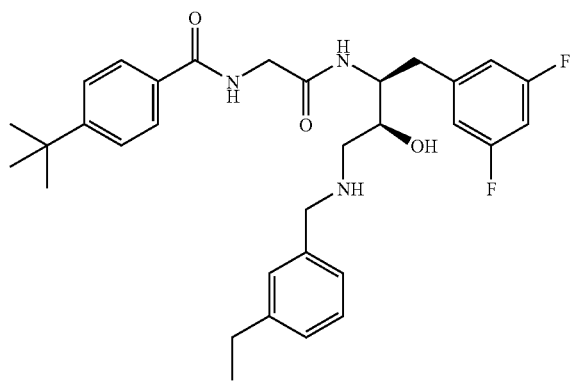 | N²-[(4-tert-butylphenyl)(oxo)methyl]-N¹-{(1S,2R)-1-(3,5-difluorobenzyl)-3-[(3-ethylbenzyl)amino]-2-hydroxypropyl}glycinamide |

| | | |
|---|---|---|
| 3838 | 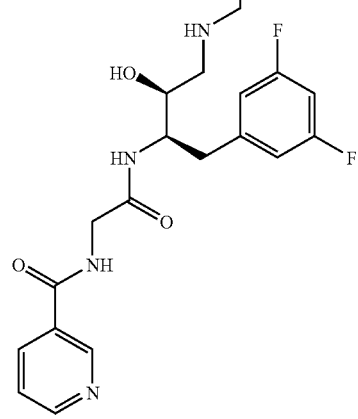 | N¹-{(1S,2R)-1-(3,5-difluorobenzyl)-3-[(3-ethylbenzyl)amino]-2-hydroxypropyl}-N²-[oxo(pyridin-3-yl)methyl]glycinamide |
| 3839 | 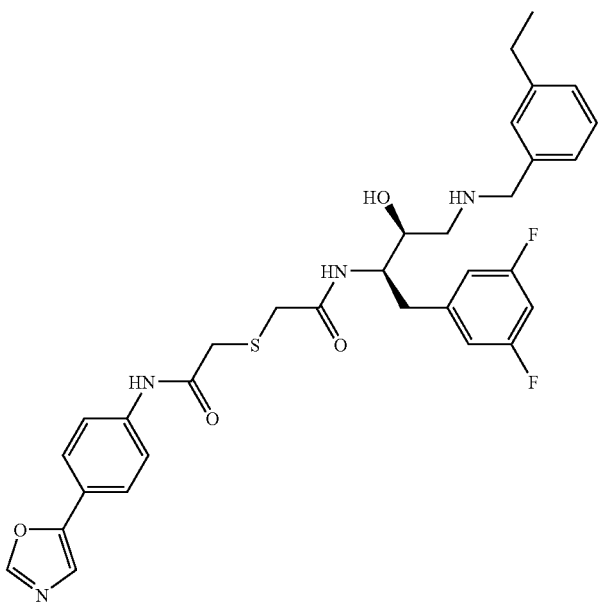 | 2-{[2-{(1S,2R)-1-(3,5-difluorobenzyl)-3-[(3-ethylbenzyl)amino]-2-hydroxypropyl}amino]-2-oxoethyl]thio}-N-[4-(1,3-oxazol-5-yl)phenyl]acetamide |
| 3840 | 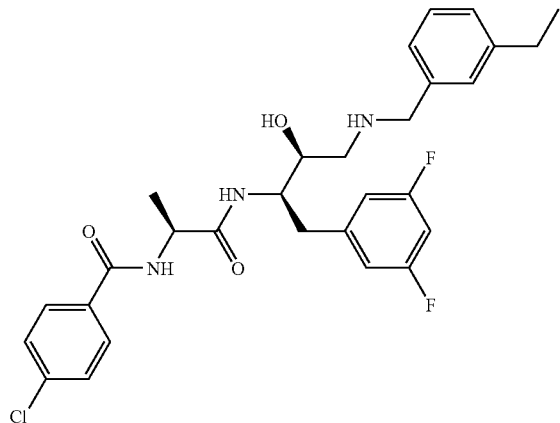 | N²-[(4-chlorophenyl)(oxo)methyl]-N¹-{(1S,2R)-1-(3,5-difluorobenzyl)-3-[(3-ethylbenzyl)amino]-2-hydroxypropyl}-D-alaninamide |

-continued

| | | |
|---|---|---|
| 3841 | 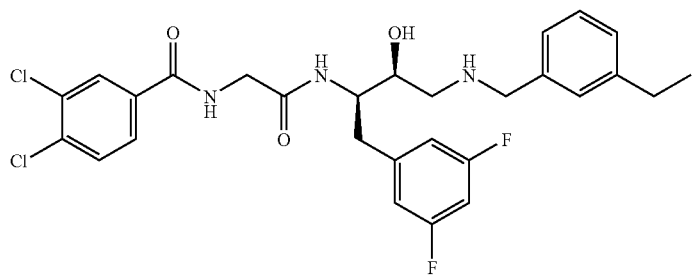 | N²-[(3,4-dichlorophenyl)(oxo)methyl]-N¹-{(1S,2R)-1-(3,5-difluorobenzyl)-3-[(3-ethylbenzyl)amino]-2-hydroxypropyl}glycinamide |
| 3842 | 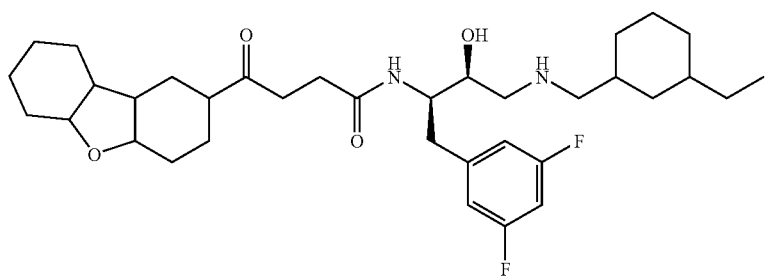 | N-{(1S,2R)-1-(3,5-difluorobenzyl)-3-[(3-ethylbenzyl)amino]-2-hydroxypropyl}-4-(5a,9a-dihydrodibenzo[b,d]furan-2-yl)-4-oxobutanamide |
| 3843 | 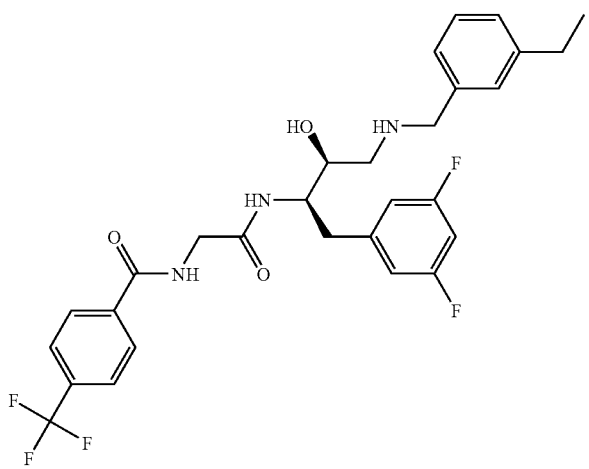 | N¹-{(1S,2R)-1-(3,5-difluorobenzyl)-3-[(3-ethylbenzyl)amino]-2-hydroxypropyl}-N²-(oxo[4-(trifluoromethyl)phenyl]methyl)glycinamide |
| 3844 | 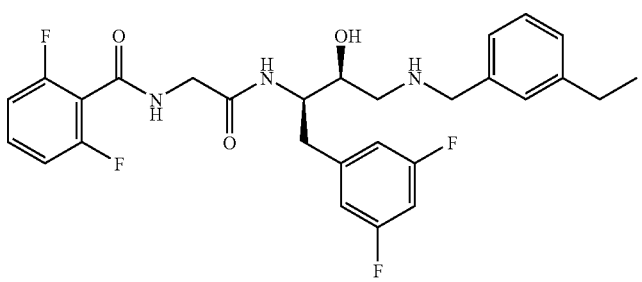 | N¹-{(1S,2R)-1-(3,5-difluorobenzyl)-3-[(3-ethylbenzyl)amino]-2-hydroxypropyl}-N²-[(2,6-difluorophenyl)(oxo)methyl]glycinamide |
| 3845 | 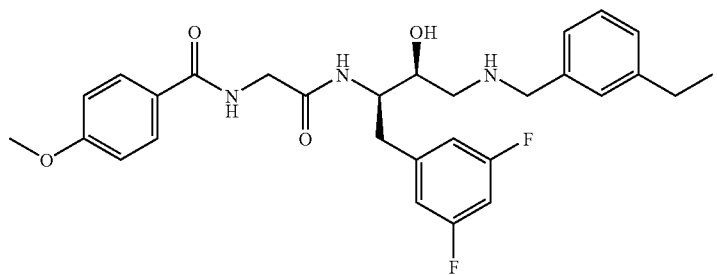 | N¹-{(1S,2R)-1-(3,5-difluorobenzyl)-3-[(3-ethylbenzyl)amino]-2-hydroxypropyl}-N²-[oxo(4-methoxyphenyl)methyl]glycinamide |

-continued

| | | |
|---|---|---|
| 3846 | 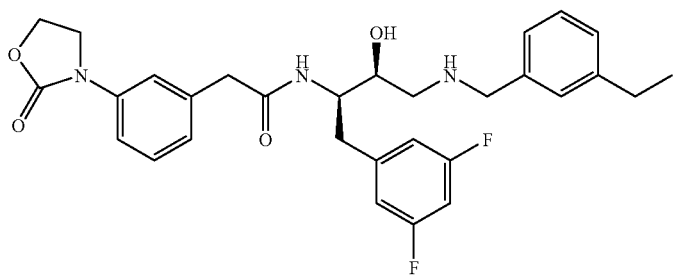 | N-{(1S,2R)-1-(3,5-difluorobenzyl)-3-[(3-ethylbenzyl)amino]-2-hydroxypropyl}-4-(2-oxo-1,3-oxazolidin-3-yl)benzamide |
| 3847 | 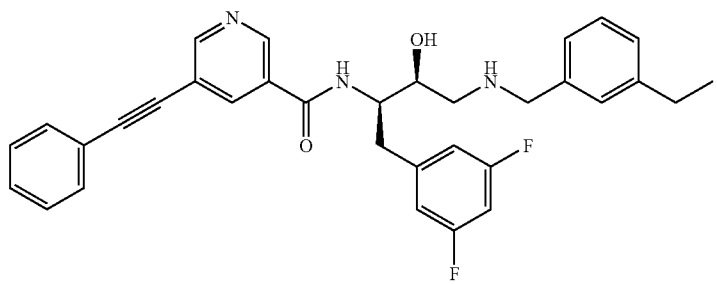 | N-{(1S,2R)-1-(3,5-difluorobenzyl)-3-[(3-ethylbenzyl)amino]-2-hydroxypropyl}-5-(phenylethynyl)nicotinamide |
| 3848 | 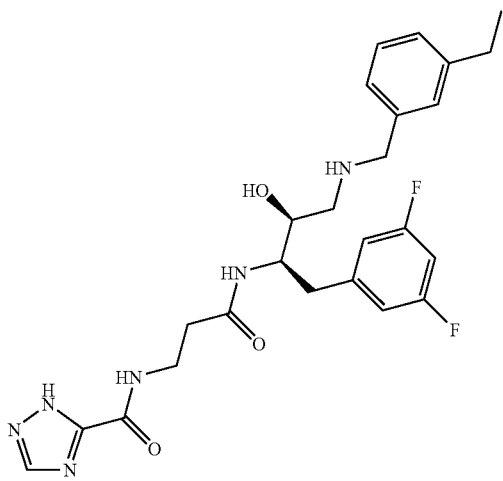 | $N^1$-{(1S,2R)-1-(3,5-difluorobenzyl)-3-[(3-ethylbenzyl)amino]-2-hydroxypropyl}-$N^3$-[oxo(1H-1,2,4-triazol-5-yl)methyl]-β-alaninamide |
| 3849 | 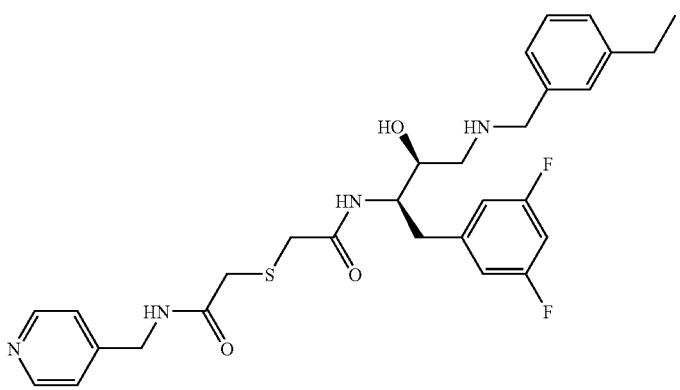 | 2-{[2-({(1S,2R)-1-(3,5-difluorobenzyl)-3-[(3-ethylbenzyl)amino]-2-hydroxypropyl}amino)-2-oxoethyl]thio}-N-(pyridin-4-ylmethyl)acetamide |

-continued

| | | |
|---|---|---|
| 3850 | 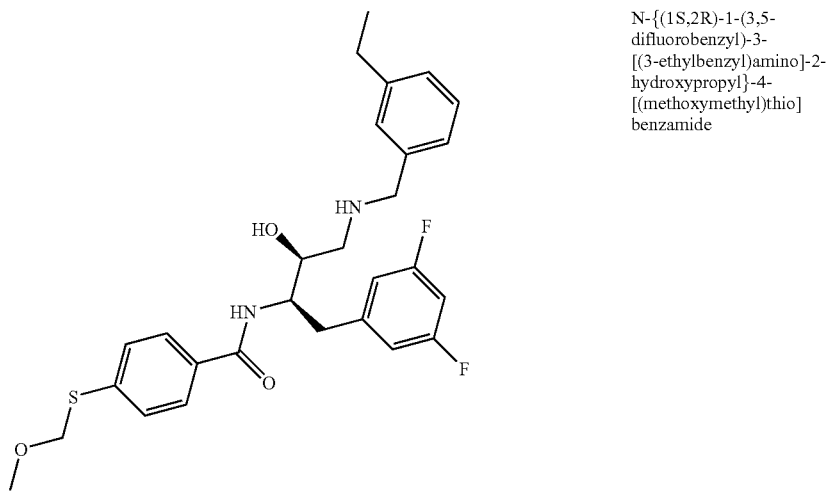 | N-{(1S,2R)-1-(3,5-difluorobenzyl)-3-[(3-ethylbenzyl)amino]-2-hydroxypropyl}-4-[(methoxymethyl)thio]benzamide |
| 3851 | 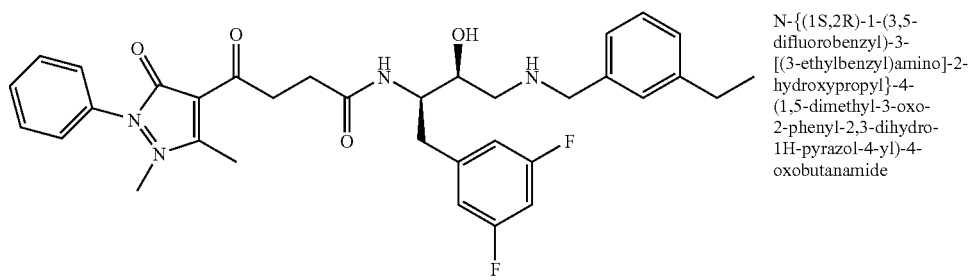 | N-{(1S,2R)-1-(3,5-difluorobenzyl)-3-[(3-ethylbenzyl)amino]-2-hydroxypropyl}-4-(1,5-dimethyl-3-oxo-2-phenyl-2,3-dihydro-1H-pyrazol-4-yl)-4-oxobutanamide |
| 3852 | 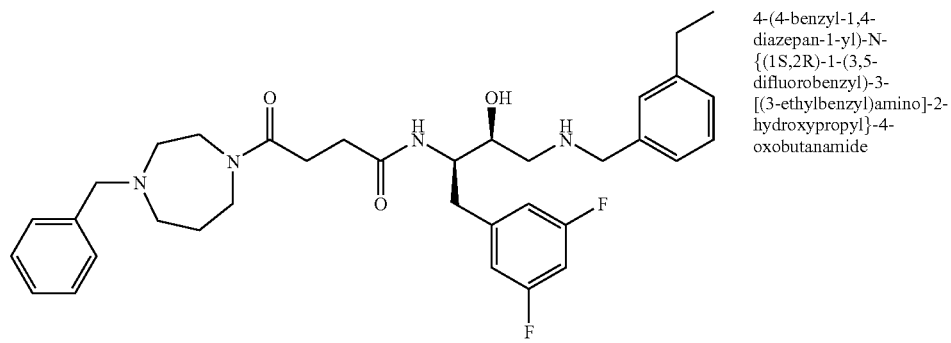 | 4-(4-benzyl-1,4-diazepan-1-yl)-N-{(1S,2R)-1-(3,5-difluorobenzyl)-3-[(3-ethylbenzyl)amino]-2-hydroxypropyl}-4-oxobutanamide |
| 3853 | 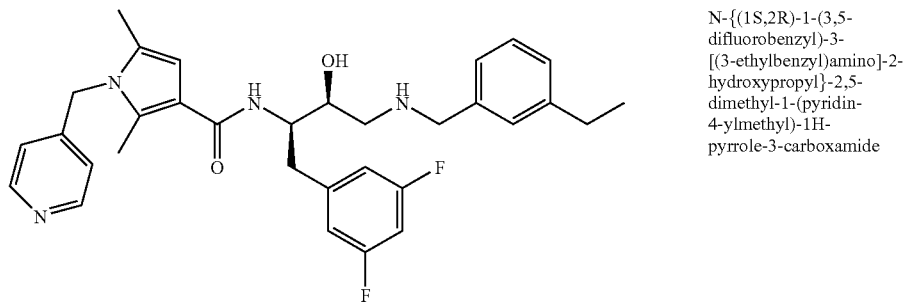 | N-{(1S,2R)-1-(3,5-difluorobenzyl)-3-[(3-ethylbenzyl)amino]-2-hydroxypropyl}-2,5-dimethyl-1-(pyridin-4-ylmethyl)-1H-pyrrole-3-carboxamide |

| | | |
|---|---|---|
| 3854 | 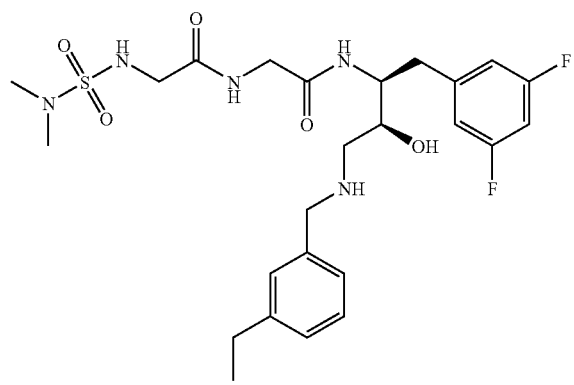 | N-[(dimethylamino)sulfonyl]glycyl-N¹-{(1S,2R)-1-(3,5-difluorobenzyl)-3-[(3-ethylbenzyl)amino]-2-hydroxypropyl}glycinamide |
| 3855 | 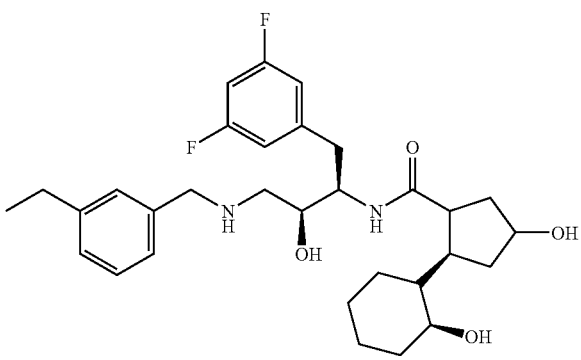 | N-{(1S,2R)-1-(3,5-difluorobenzyl)-3-[(3-ethylbenzyl)amino]-2-hydroxypropyl}-4-hydroxy-1-[(1R,2R)-2-hydroxycyclohexyl]prolinamide |
| 3856 | 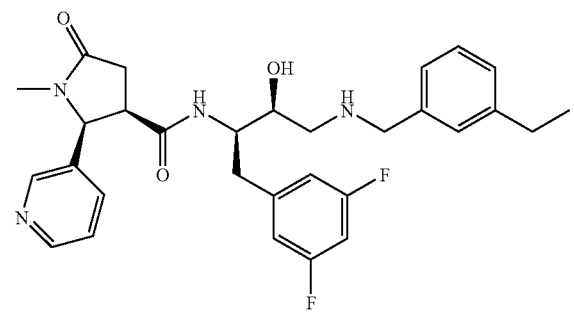 | (2S,3S)-N-{(1S,2R)-1-(3,5-difluorobenzyl)-3-[(3-ethylbenzyl)amino]-2-hydroxypropyl}-1-methyl-5-oxo-2-pyridin-3-ylpyrrolidine-3-carboxamide |
| 3857 | 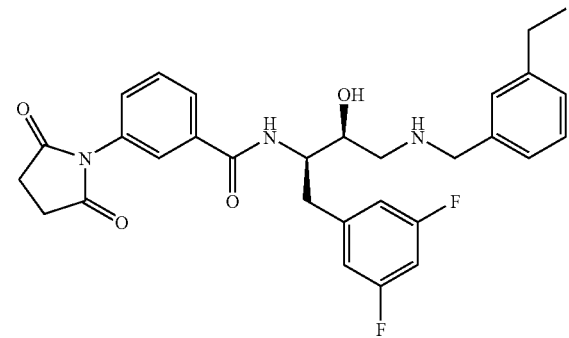 | N-{(1S,2R)-1-(3,5-difluorobenzyl)-3-[(3-ethylbenzyl)amino]-2-hydroxypropyl}-3-(2,5-dioxopyrrolidin-1-yl)benzamide |

-continued

3858 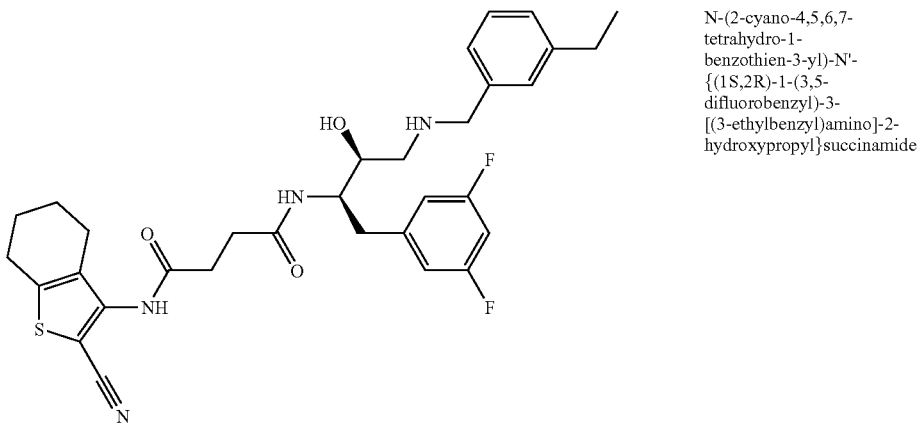
N-(2-cyano-4,5,6,7-tetrahydro-1-benzothien-3-yl)-N'-{(1S,2R)-1-(3,5-difluorobenzyl)-3-[(3-ethylbenzyl)amino]-2-hydroxypropyl}succinamide 3859 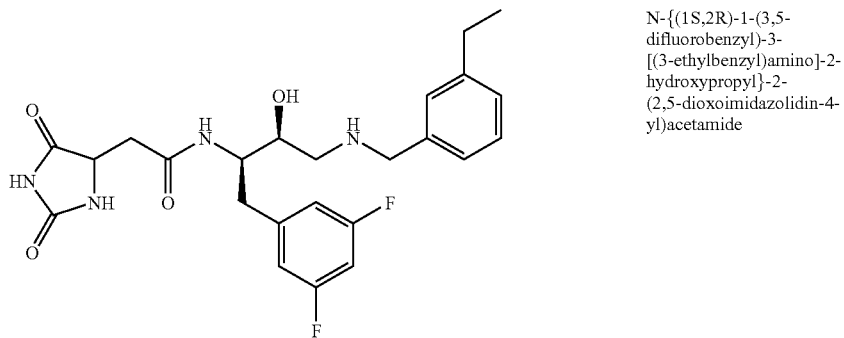
N-{(1S,2R)-1-(3,5-difluorobenzyl)-3-[(3-ethylbenzyl)amino]-2-hydroxypropyl}-2-(2,5-dioxoimidazolidin-4-yl)acetamide 3860 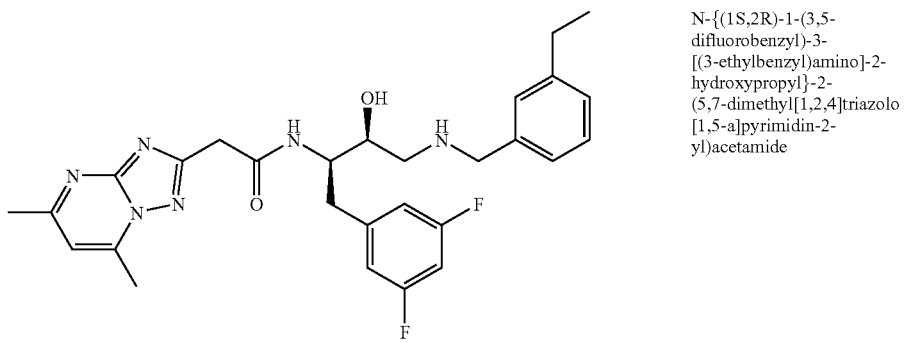
N-{(1S,2R)-1-(3,5-difluorobenzyl)-3-[(3-ethylbenzyl)amino]-2-hydroxypropyl}-2-(5,7-dimethyl[1,2,4]triazolo[1,5-a]pyrimidin-2-yl)acetamide 3861 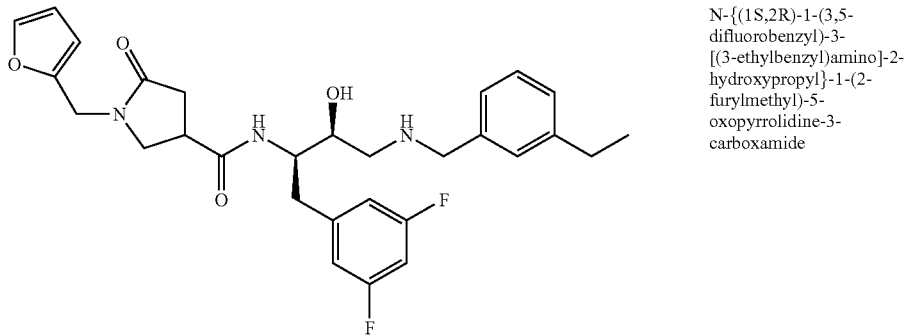
N-{(1S,2R)-1-(3,5-difluorobenzyl)-3-[(3-ethylbenzyl)amino]-2-hydroxypropyl}-1-(2-furylmethyl)-5-oxopyrrolidine-3-carboxamide -continued

| | | |
|---|---|---|
| 3862 | 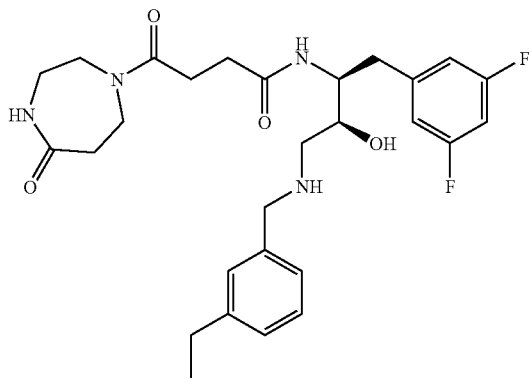 | N-{(1S,2R)-1-(3,5-difluorobenzyl)-3-[(3-ethylbenzyl)amino]-2-hydroxypropyl}-4-oxo-4-(5-oxo-1,4-diazepan-1-yl)butanamide |
| 3863 | 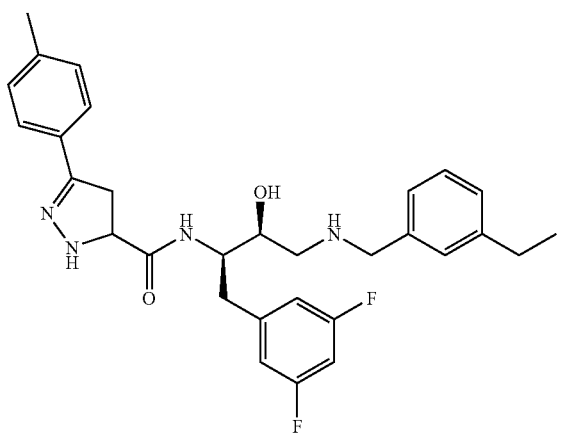 | N-{(1S,2R)-1-(3,5-difluorobenzyl)-3-[(3-ethylbenzyl)amino]-2-hydroxypropyl}-3-(4-methylphenyl)-4,5-dihydro-1H-pyrazole-5-carboxamide |
| 3864 | 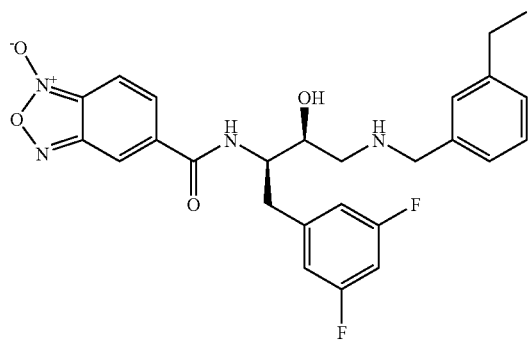 | N-{(1S,2R)-1-(3,5-difluorobenzyl)-3-[(3-ethylbenzyl)amino]-2-hydroxypropyl}-2,1,3-benzoxadiazole-5-carboxamide 1-oxide |
| 3865 | 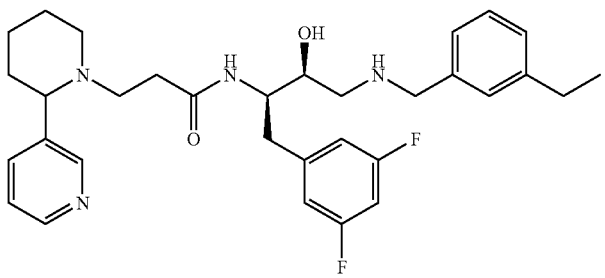 | N-{(1S,2R)-1-(3,5-difluorobenzyl)-3-[(3-ethylbenzyl)amino]-2-hydroxypropyl}-3-(2-pyridin-3-ylpiperidin-1-yl)propanamide |

| | | |
|---|---|---|
| 3866 | 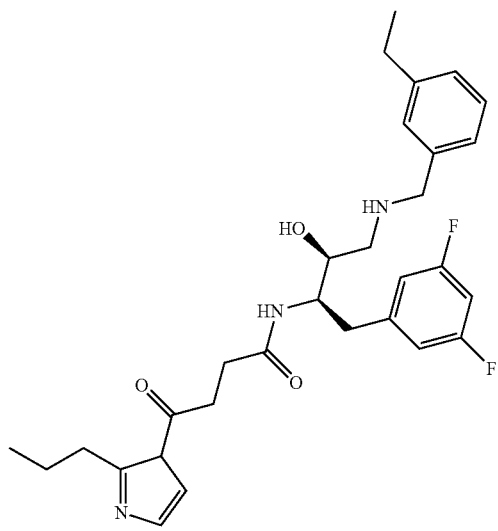 | N-{(1S,2R)-1-(3,5-difluorobenzyl)-3-[(3-ethylbenzyl)amino]-2-hydroxypropyl}-4-oxo-4-(2-propyl-1H-imidazol-1-yl)butanamide |
| 3867 | 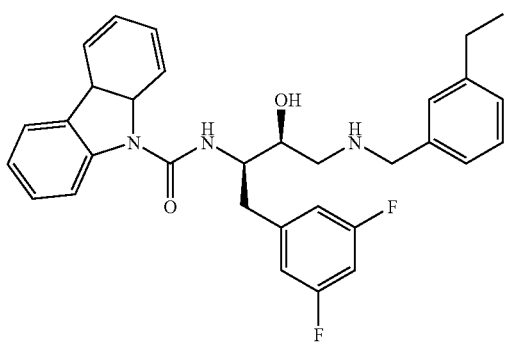 | N-{(1S,2R)-1-(3,5-difluorobenzyl)-3-[(3-ethylbenzyl)amino]-2-hydroxypropyl}-4a,9a-dihydro-9H-carbazole-9-carboxamide |
| 3868 | 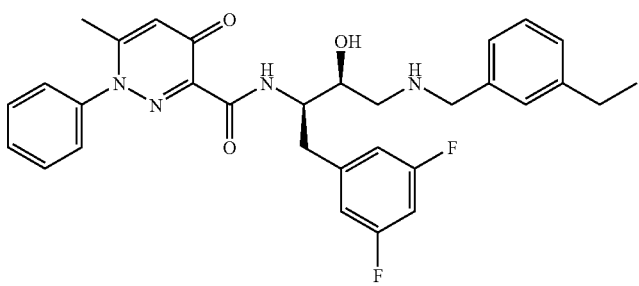 | N-{(1S,2R)-1-(3,5-difluorobenzyl)-3-[(3-ethylbenzyl)amino]-2-hydroxypropyl}-6-methyl-4-oxo-1-phenyl-1,4-dihydropyridazine-3-carboxamide |
| 3869 | 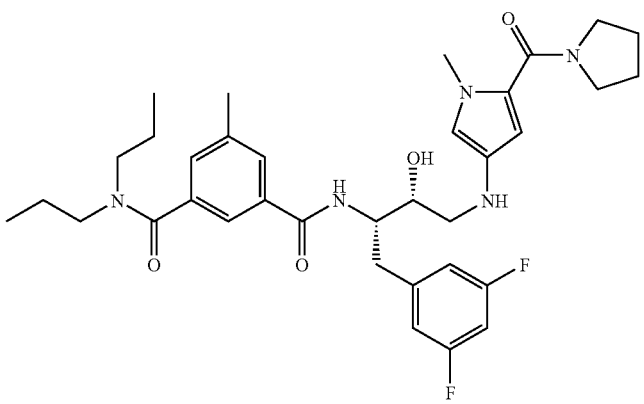 | N'-((1S,2R)-1-(3,5-difluorobenzyl)-2-hydroxy-3-{(1-methyl-5-(pyrrolidin-1-ylcarbonyl)-1H-pyrrol-3-yl]amino}propyl)-5-methyl-N,N-dipropylisophthalamide |

| | | |
|---|---|---|
| 3870 | 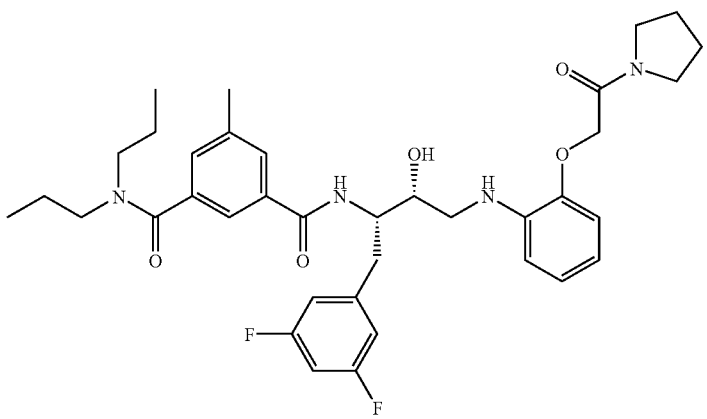 | N'-((1S,2R)-1-(3,5-difluorobenzyl)-2-hydroxy-3-{[2-(2-oxo-2-pyrrolidin-1-ylethoxy)phenyl]amino}propyl)-5-methyl-N,N-dipropylisophthalamide |
| 3871 | 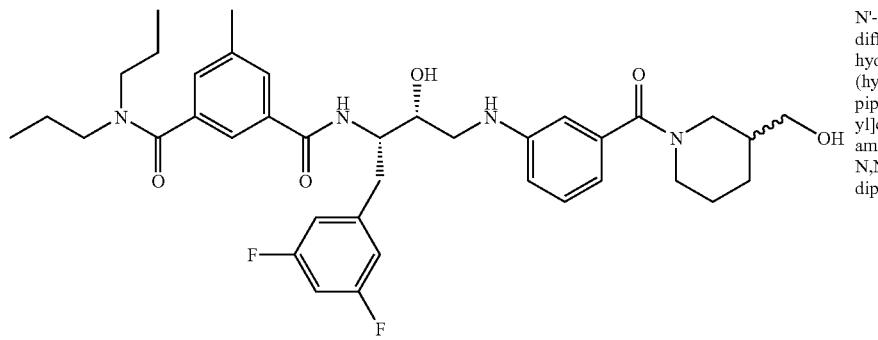 | N'-{(1S,2R)-1-(3,5-difluorobenzyl)-2-hydroxy-3-[(3-{[3-(hydroxymethyl)piperidin-1-yl]carbonyl}phenyl)amino]propyl}-5-methyl-N,N-dipropylisophthalamide |
| 3872 | 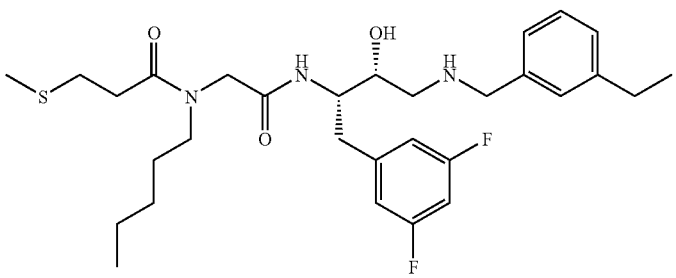 | N¹{(1S, 2R)-1-(3,5-difluorobenzyl)-3-[(3-ethylbenzyl)amino]-2-hydroxypropyl}-N²-[3-(methylthio)-1-oxopropyl]-N²-pentylglycinamide |
| 3873 | 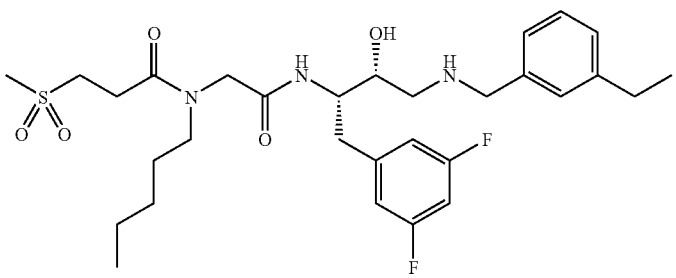 | N¹-{(1S,2R)-1-(3,5-difluorobenzyl)-3-[(3-ethylbenzyl)amino]-2-hydroxypropyl}-N²-[3-(methylsulfonyl)-1-oxopropyl]-N²-pentylglycinamide |

-continued

| | | |
|---|---|---|
| 3874 | 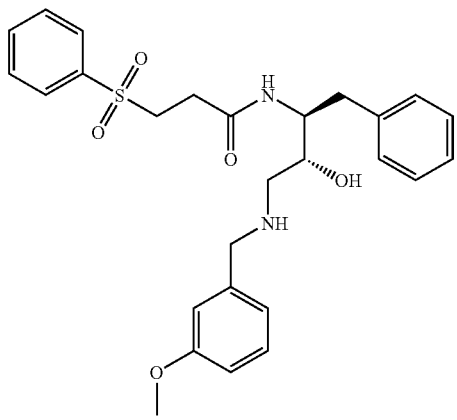 | N-{(1S,2R)-1-benzyl-2-hydroxy-3-[(3-methoxybenzyl)amino]propyl}-3-(phenylsulfonyl)propanamide |
| 3875 | 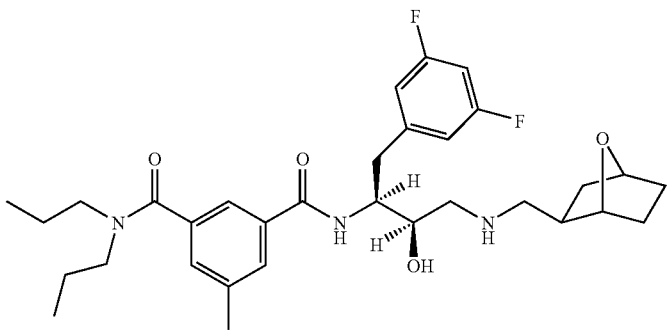 | N'-{(1S,2R)-1-(3,5-difluorobenzyl)-2-hydroxy-3-[(7-oxabicyclo[2.2.1]hept-2-ylmethyl)amino]propyl}-5-methyl-N,N-dipropylisophthalamide |
| 3876 | 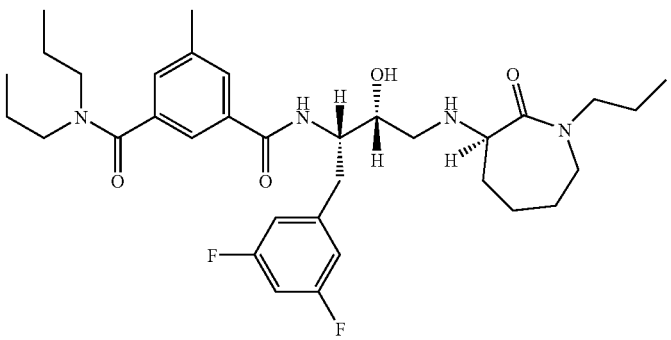 | N'-((1S,2R)-1-(3,5-difluorobenzyl)-2-hydroxy-3-{[(3R)-2-oxo-1-propylazepan-3-yl]amino}propyl)-5-methyl-N,N-dipropylisophthalamide |
| 3877 | 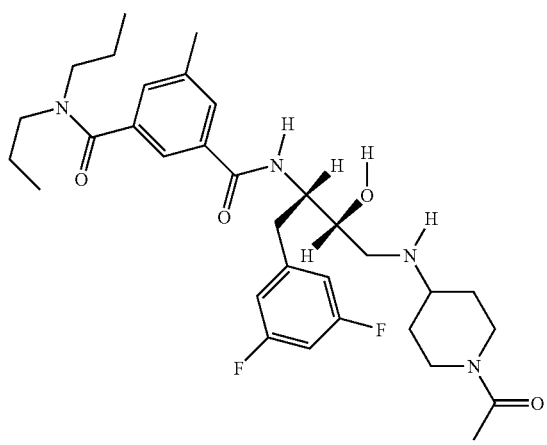 | N'-[(1S,2R)-3-[(1-acetylpiperidin-4-yl)amino]-1-(3,5-difluorobenzyl)-2-hydroxypropyl]-5-methyl-N,N-dipropylisophthalamide |

-continued

| | | |
|---|---|---|
| 3878 | 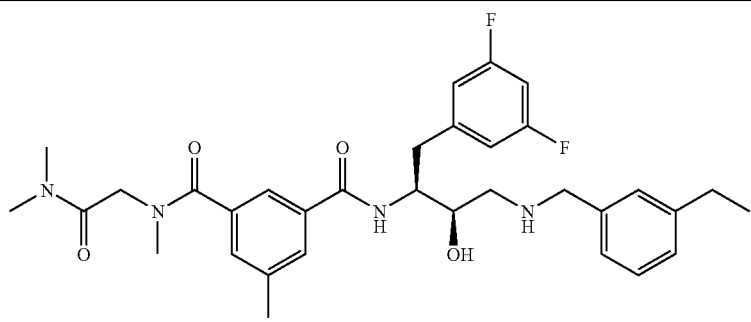 | N'-{(1S,2R)-1-(3,5-difluorobenzyl)-3-[(3-ethylbenzyl)amino]-2-hydroxpropyl}-N-[2-(dimethylamino)-2-oxoethyl]-N,5-dimethylisophthalamide |
| 3879 | 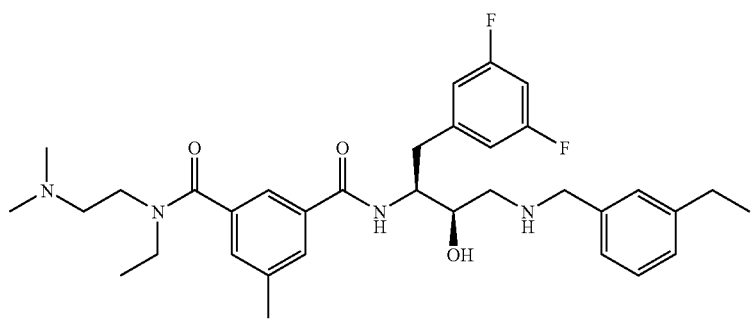 | N'-{(1S,2R)-1-(3,5-difluorobenzyl)-3-[(3-ethylbenzyl)amino]-2-hydroxypropyl}-N-(2-(dimethylamino)ethyl]-N-ethyl-5-methylisophthalamide |
| 3880 | 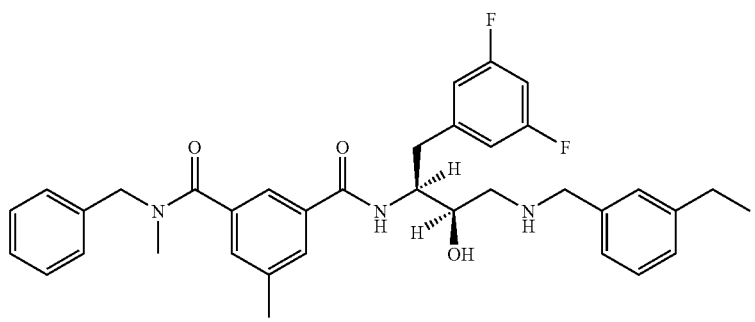 | N-benzyl-N'-{(1S,2R)-1-(3,5-difluorobenzyl)-3-[(3-ethylbenzyl)amino]-2-hydroxypropyl}-N,5-dimethylisophthalamide |
| 3881 | 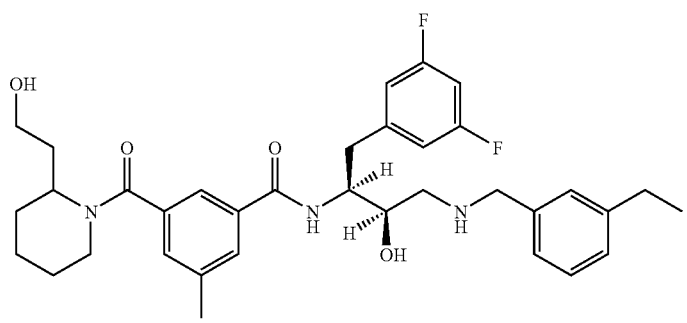 | N-{(1S,2R)-1-(3,5-difluorobenzyl)-3-[(3-ethylbenzyl)amino]-2-hydroxypropyl}-3-{[2-(2-hydroxyethyl)piperidin-1-yl]carbonyl}-5-methylbenzamide |
| 3882 | 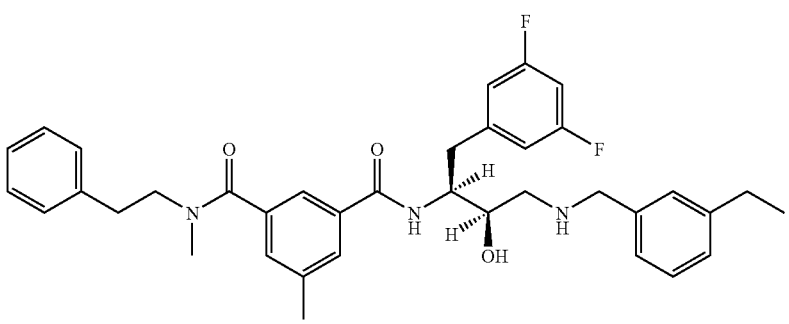 | N'-{(1S,2R)-1-(3,5-difluorobenzyl)-3-[(3-ethylbenzyl)amino]-2-hydroxypropyl}-N,5-dimethyl-N-(2-phenylethyl)isophthalamide |

-continued

| | | |
|---|---|---|
| 3883 | 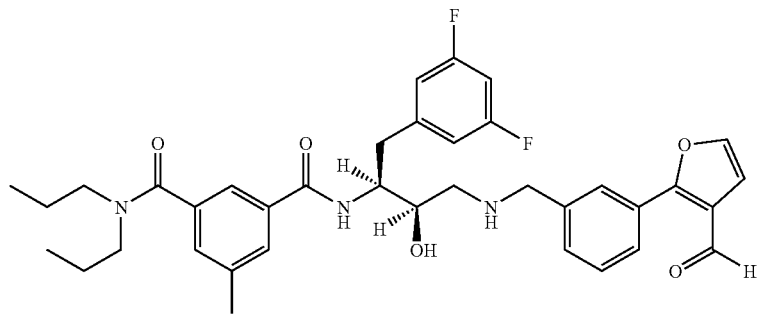 | N'-((1S,2R)-1-(3,5-difluorobenzyl)-3-{[3-(3-formyl-2-furyl)benzyl]amino}-2-hydroxypropyl)-5-methyl-N,N-dipropylisophthalamide |
| 3884 | 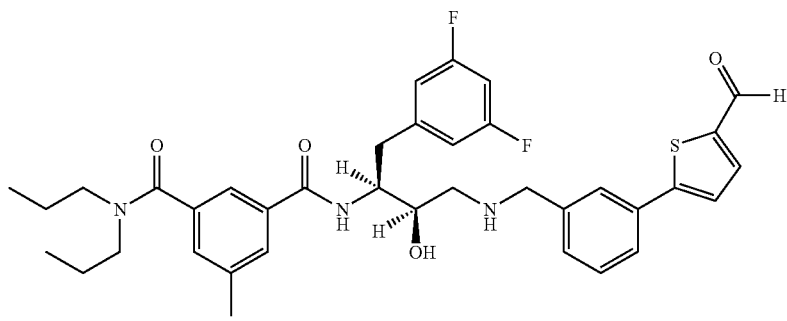 | N'-((1S,2R)-1-(3,5-difluorobenzyl)-3-{[3-(5-formyl-2-thienyl)benzyl]amino}-2-hydroxypropyl)-5-methyl-N,N-dipropylisophthalamide |
| 3885 | 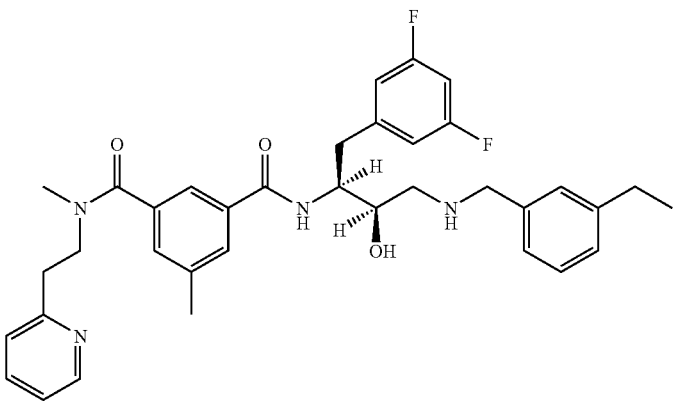 | N'-{(1S,2R)-1-(3,5-difluorobenzyl)-3-[(3-ethylbenzyl)amino]-2-hydroxypropyl}-N,5-dimethyl-N-(2-pyridin-2-ylethyl)isophthalamide |
| 3886 | 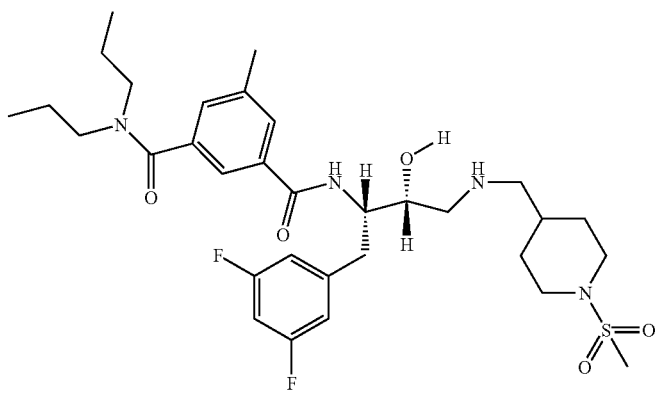 | N'-[(1S,2R)-1-(3,5-difluorobenzyl)-2-hydroxy-3-({[1-(methylsulfonyl)piperidin-4-yl]methyl}amino)propyl]-5-methyl-N,N-dipropylisophthalamide |

-continued

| | | |
|---|---|---|
| 3887 | 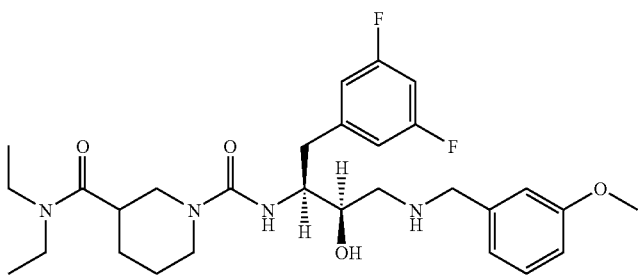 | N'-{(1S,2R)-1-(3,5-difluorobenzyl)-2-hydroxy-3-[(3-methoxybenzyl)amino]propyl}-N³,N³-diethylpiperidine-1,3-dicarboxamide |
| 3888 | 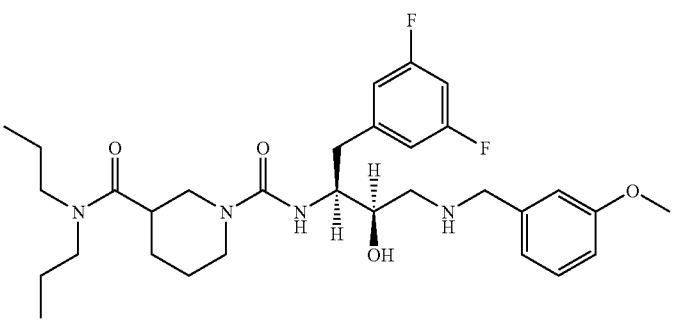 | N¹-{(1S,2R)-1-(3,5-difluorobenzyl)-2-hydroxy-3-[(3-methoxybenzyl)amino)propyl}-N³,N³-dipropylpiperidine-1,3-dicarboxamide |
| 3889 | 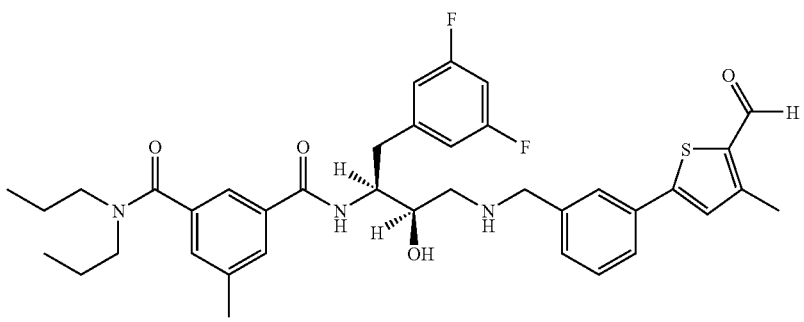 | N'-((1S,2R)-1-(3,5-difluorobenzyl)-3-{[3-(5-formyl-4-methyl-2-thienyl)benzyl]amino}-2-hydroxypropyl)-5-methyl-N,N-dipropylisophthalamide |
| 3890 | 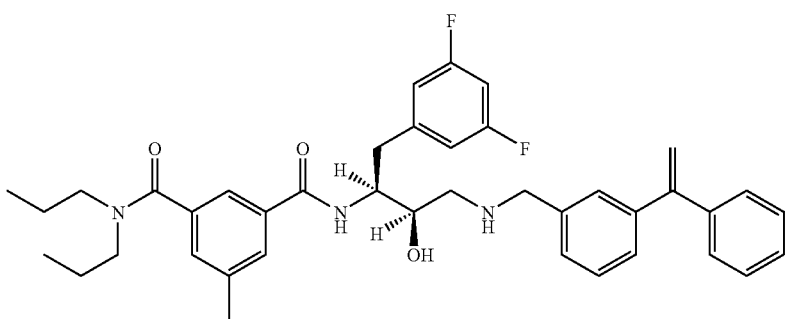 | N'-((1S,2R)-1-(3,5-difluorobenzyl)-2-hydroxy-3-{(3-(1-phenylvinyl)benzyl]amino}propyl)-5-methyl-N,N-dipropylisophthalamide |
| 3891 | 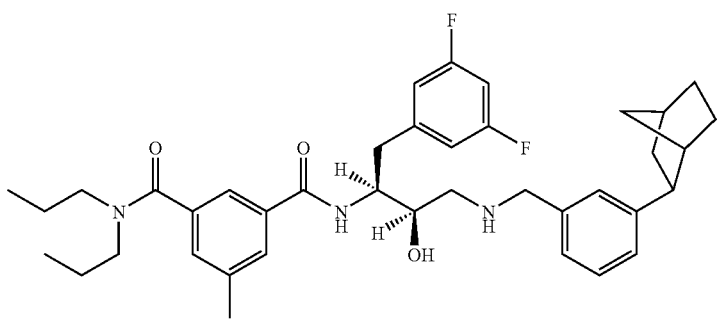 | N'-[(1S,2R)-3-[(3-bicyclo[2.2.1]hept-2-ylbenzyl)amino]-1-(3,5-difluorobenzyl)-2-hydroxypropyl]-5-methyl-N,N-dipropylisophthalamide |

-continued

3892 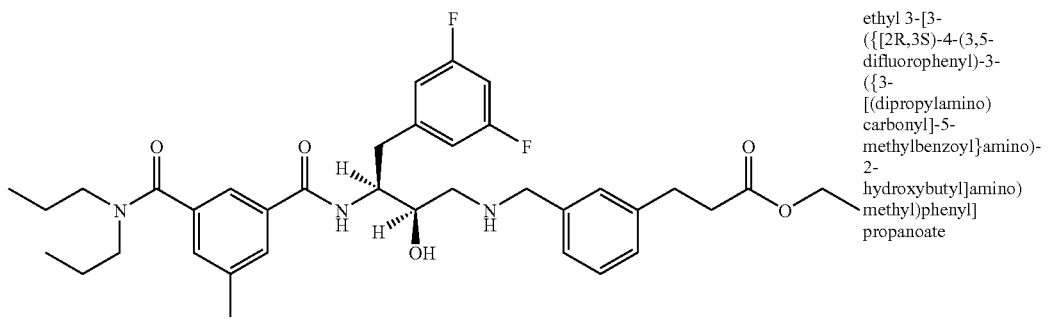 ethyl 3-[3-({[2R,3S)-4-(3,5-difluorophenyl)-3-({3-[(dipropylamino)carbonyl]-5-methylbenzoyl}amino)-2-hydroxybutyl]amino)methyl)phenyl]propanoate 3893 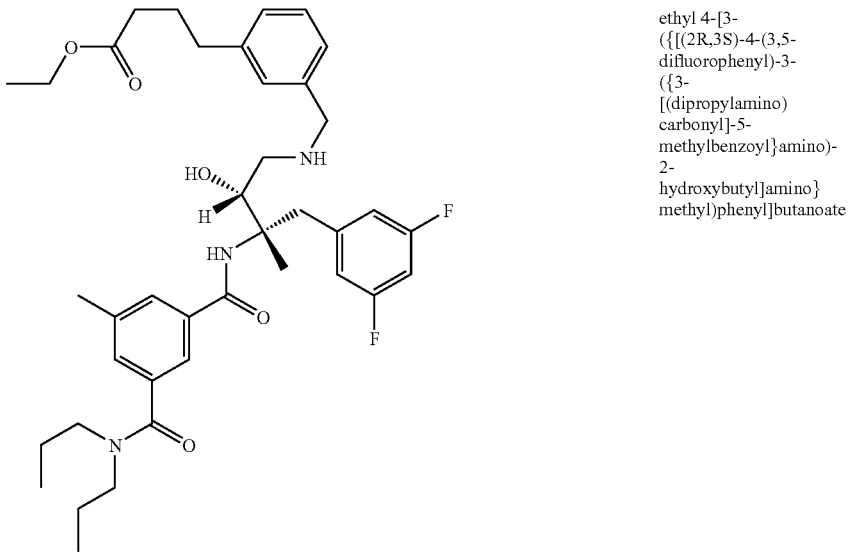 ethyl 4-[3-({[(2R,3S)-4-(3,5-difluorophenyl)-3-({3-[(dipropylamino)carbonyl]-5-methylbenzoyl}amino)-2-hydroxybutyl]amino}methyl)phenyl]butanoate 3894 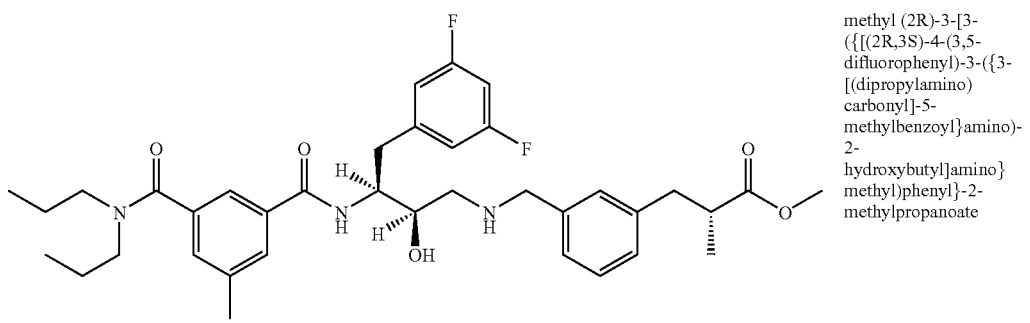 methyl (2R)-3-[3-({[(2R,3S)-4-(3,5-difluorophenyl)-3-({3-[(dipropylamino)carbonyl]-5-methylbenzoyl}amino)-2-hydroxybutyl]amino}methyl)phenyl]-2-methylpropanoate 3895 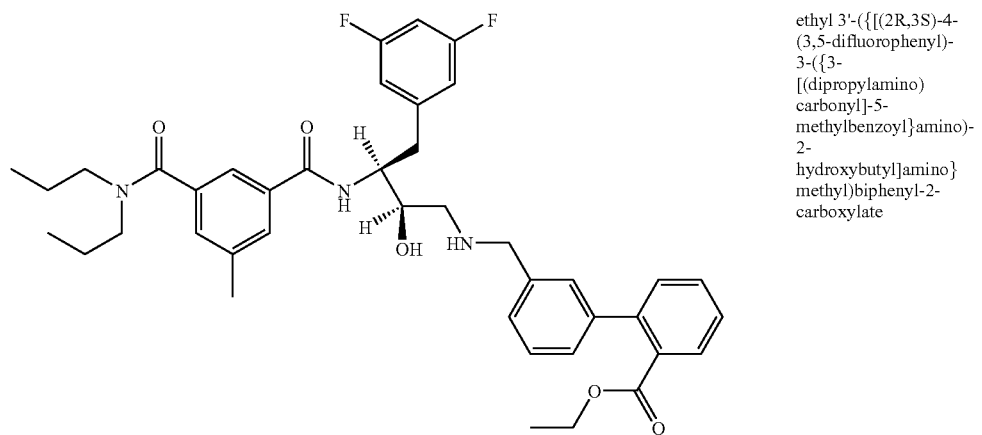 ethyl 3'-({[(2R,3S)-4-(3,5-difluorophenyl)-3-({3-[(dipropylamino)carbonyl]-5-methylbenzoyl}amino)-2-hydroxybutyl]amino}methyl)biphenyl-2-carboxylate

| | | | |
|---|---|---|---|
| 3896 | 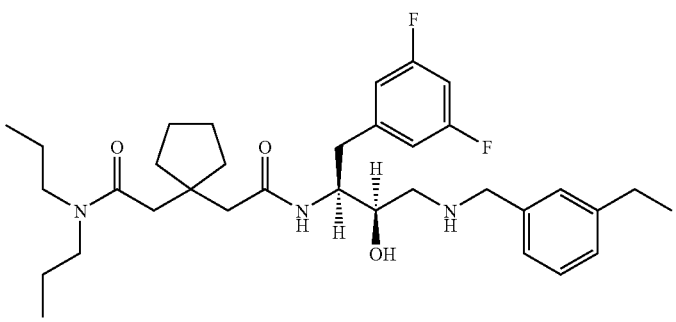 | 2-{1-(2-({(1S,2R)-1-(3,5-difluorobenzyl)-3-[(3-ethylbenzyl)amino]-2-hydroxypropyl}amino)-2-oxoethyl]cyclopentyl}-N,N-dipropylacetamide | |
| 3897 | 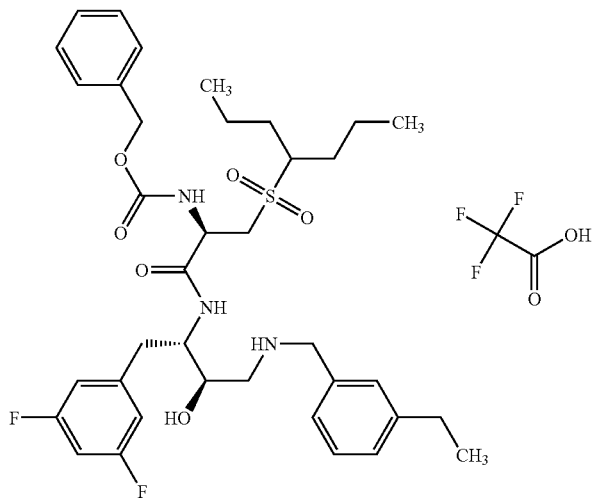 | $N^2$-[(benzyloxy)carbonyl]-$N^1$-{(1S,2R)-1-(3,5-difluorobenzyl)-3-[(3-ethylbenzyl)amino]-2-hydroxypropyl}-3-[(1-propylbutyl)sulfonyl]-D,L-alaninamide trifluoroacetate | 702 |
| 3898 | 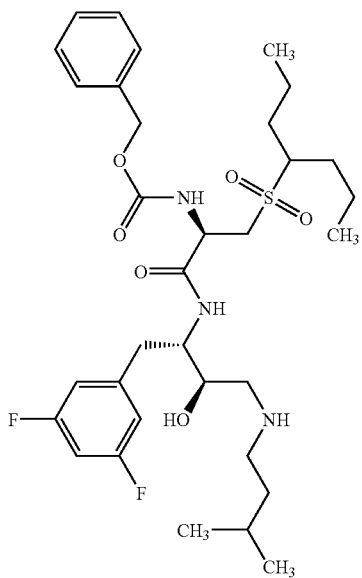 | $N^2$-[(benzyloxy)carbonyl]-$N^1$-{(1S,2R)-1-(3,5-difluorobenzyl)-3-[(3-methylbutyl)amino]-2-hydroxypropyl}-3-[(1-propylbutyl)sulfonyl]-D,L-alaninamide | 654 |

-continued

| | | | |
|---|---|---|---|
| 3899 | 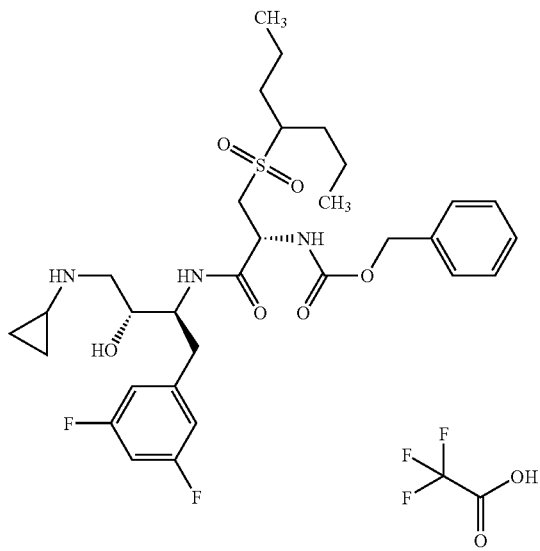 | $N^2$-[(benzyloxy)carbonyl]-$N^1$-{(1S,2R)-1-(3,5-difluorobenzyl)-3-(cyclopropylamino)-2-hydroxypropyl}3-[(1-propylbutyl)sulfonyl]-D,L-alaninamide trifluoroacetate | 624 |
| 3900 | 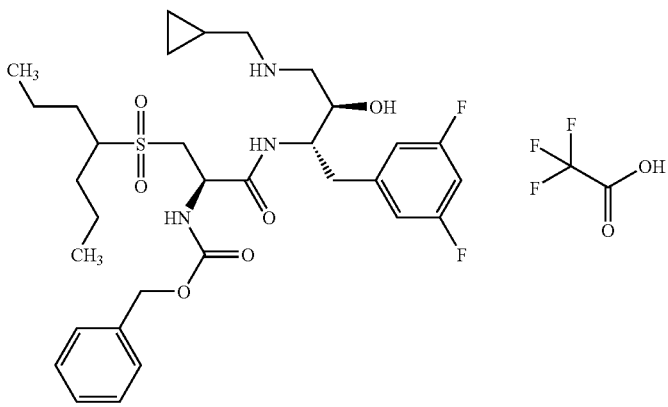 | $N^2$-[(benzyloxy)carbonyl]-$N^1$-{(1S,2R)-1-(3,5-difluorobenzyl)-3-[(cyclopropylmethyl)amino]-2-hydroxy-propyl}-3-[(1-propylbutyl)sulfonyl]-D,L-alaninamide trifluoroacetate | 638 |
| 3901 | 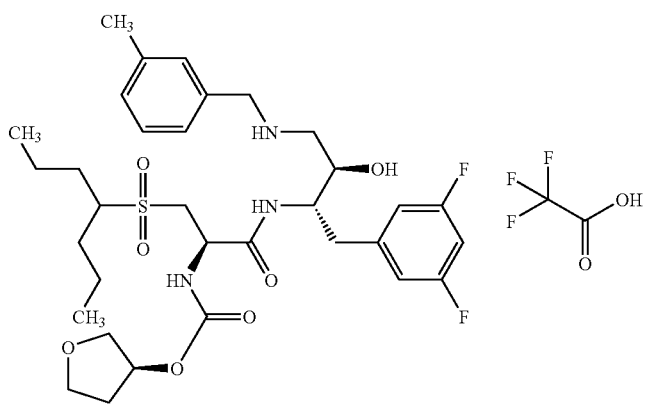 | $N^1$-{(1S,2R)-1-(3,5-difluorobenzyl)-3-[(3-ethylbenzyl)amino]-2-hydroxypropyl}-$N^2$-{[(3S)-tetrahydrofuran-3-yloxy]carbonyl}-3-[(1-propylbutyl)sulfonyl]-L-alaninamide trifluoroacetate | 682 |

-continued

| | | | |
|---|---|---|---|
| 3902 | 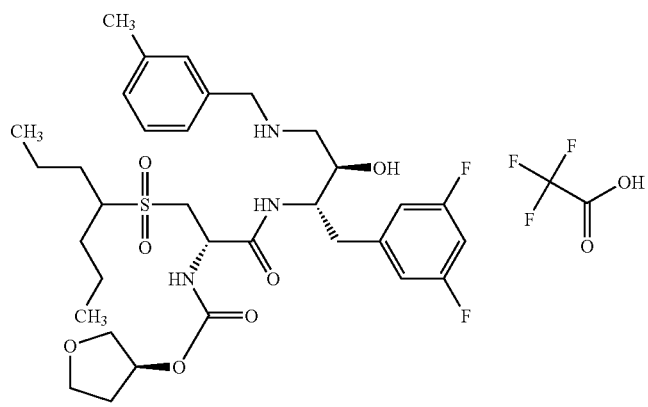 | N¹-{(1S,2R)-1-(3,5-difluorobenzyl)-3-[(3-ethylbenzyl)amino]-2-hydroxypropyl}-N²-{[(3S)-tetrahydrofuran-3-yloxy]carbonyl}-3-[(1-propylbutyl)sulfonyl]-D-alaninamide trifluoroacetate | 682 |
| 3903 | 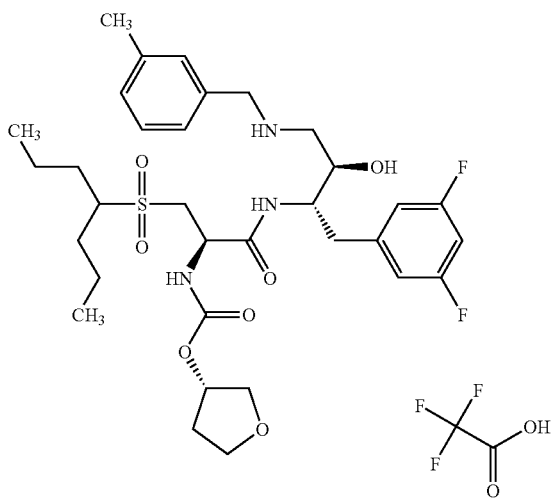 | N¹-{(1S,2R)-1-(3,5-difluorobenzyl)-3-[(3-ethylbenzyl)amino]-2-hydroxypropyl}-N²-{[(3S)-tetrahydrofuran-3-yloxy]carbonyl}-3-[(1-propylbutyl)sulfonyl]-D,L-alaninamide trifluoroacetate | 682 |
| 3904 | 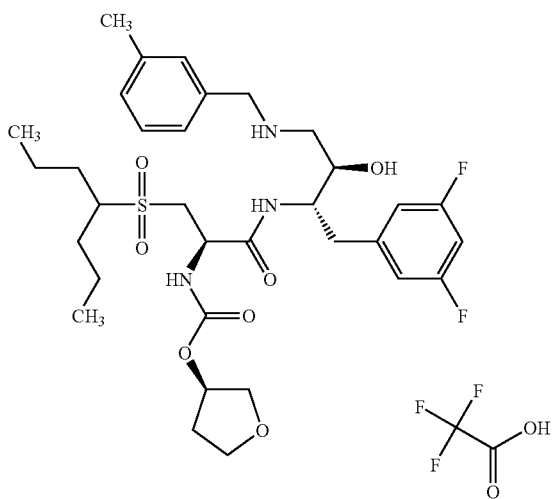 | N¹-{(1S,2R)-1-(3,5-difluorobenzyl)-3-[(3-ethylbenzyl)amino]-2-hydroxypropyl}-N²-{[(3R)-tetrahydrofuran-3-yloxy]carbonyl}-3-[(1-propylbutyl)sulfonyl]-D,L-alaninamide trifluoroacetate | 682 |

-continued

| | | | |
|---|---|---|---|
| 3905 | 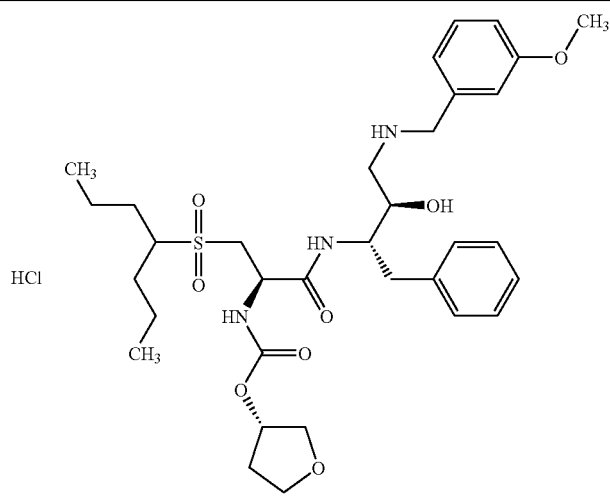 | N¹-{(1S,2R)-1-benzyl-3-[(3-methoxybenzyl)amino]-2-hydroxypropyl}-N²-{[(3S)-tetrahydrofuran-3-yloxy]carbonyl}-3-[(1-propylbutyl)sulfonyl]-D,L-alaninamide hydrochloride | 648 |
| 3906 | 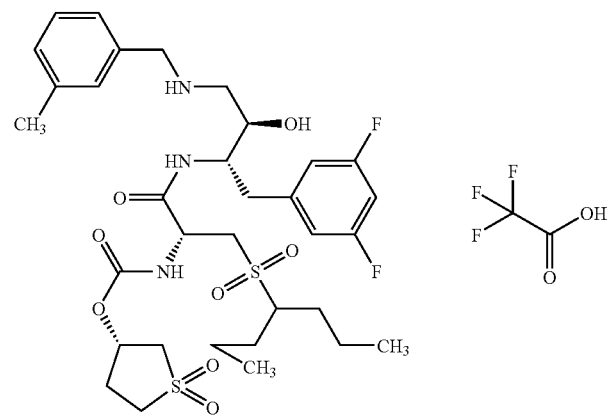 | N¹-{(1S,2R)-1-(3,5diflurobenzyl)-3-[(3-ethylbenzyl)amino]-2-hydroxypropyl}-N²-{[(3S)-1,1-dioxidotetrahydrothien-3-yloxy]carbonyl}-3-[(1-propylbutyl)sulfonyl]-D,L-alaninamide trifluoroacetate | 730 |
| 3907 | 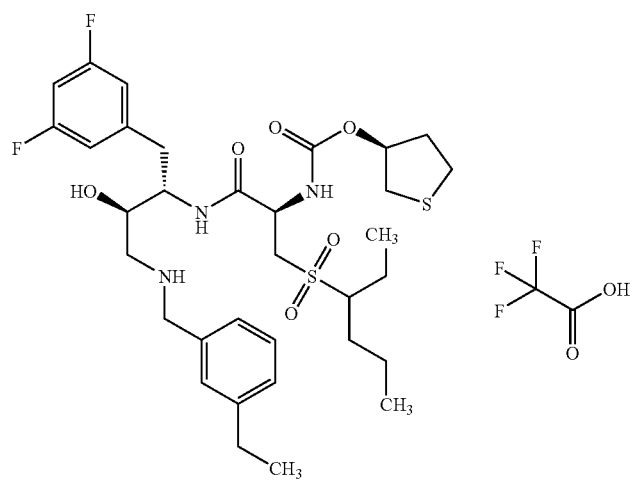 | N¹-{(1S,2R)-1-(3,5-difluorobenzyl)-3-[(3-ethylbenzyl)amino]-2-hydroxypropyl}-N²-{[(3S)-tetrahydrothiophen-3-yloxy]carbonyl}-3-[(1-propylbutyl)sulfonyl]-D,L-alaninamide trifluoroacetate | 698 |

-continued

| | | | |
|---|---|---|---|
| 3908 | 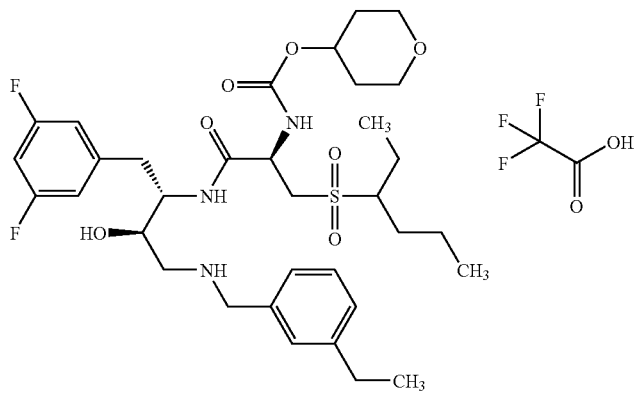 | | N$^1$-{(1S,2R)-1-(3,5-difluorobenzyl)-3-[(3-ethylbenzyl)amino]-2-hydroxypropyl}-N$^2$-}[tetrahydropyran-4-yloxy]carbonyl}-3-[(1-propylbutyl)sulfonyl]-D,L-alaninamide trifluoroacetate | 696 |
| 3909 | 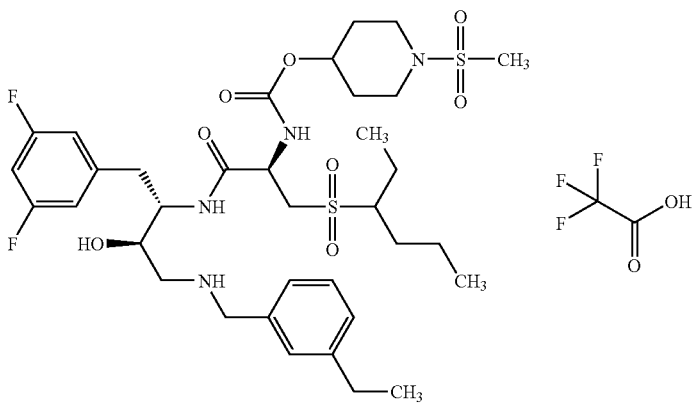 | | N$^1$-{(1S,2R)-1-(3,5-diflourobenzyl)-3-[(3-ethylbenzyl)amino]-2-hydroxypropyl}-N$^2$-{[1-(methylsulfonyl)piperidin-4-yloxy]carbonyl}-3-[(1-propylbutyl)sulfonyl]-D,L-alaninamide trifluoroacetate | 773 |
| 3910 | 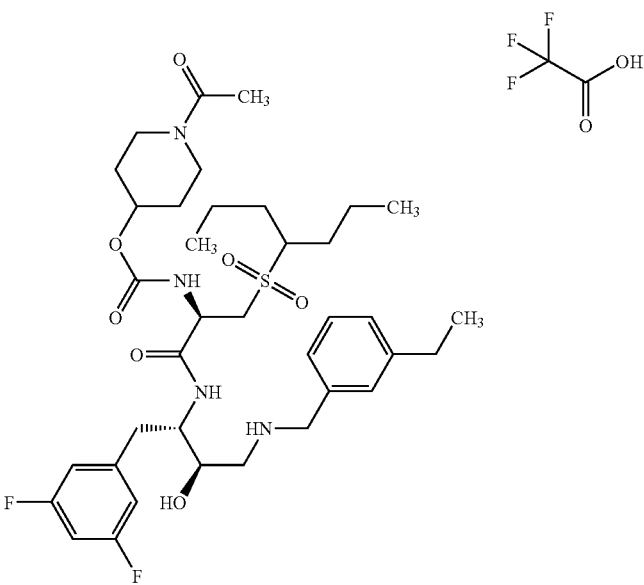 | | N$^2$-{(1-acetylpiperidin-4-yloxy]carbonyl}-N$^1$-{(1S,2R)-1-(3,5-difluorobenzyl)-3-[(3-ethylbenzyl)amino]-3-hydroxypropyl}-3-[(1-propylbutyl)sulfonyl]-D,L-alaninamide trifluoroacetate | 737 |

-continued

| | | | |
|---|---|---|---|
| 3911 | 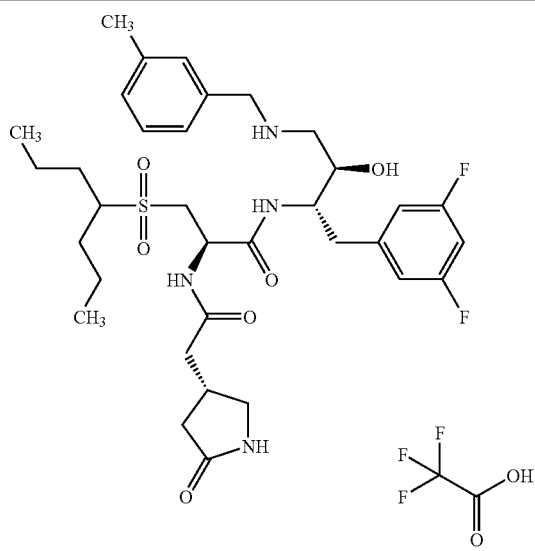 | N¹-{(1S,2R)-1-(3,5-difluorobenzyl)-3-[(3-ethylbenzyl)amino]-2-hydroxypropyl}-N²-{[[(3R)-5-oxopyrrolidin-3-yl]methyl]carbonyl}-3-[(1-propylbutyl)sulfonyl]-D,L-alaninamide trifluoroacetate | 709 |
| 3912 | 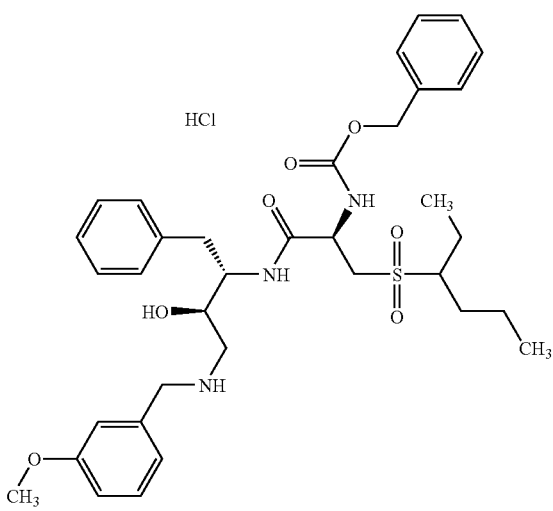 | N¹-{(1S,2R)-1-benzyl-3-[(3-methoxybenzyl)amino]-2-hydroxypropyl}-N²-[(benzyloxy)carbonyl]-3-[(1-propylbutyl)sulfonyl]-D,L-alaninamide hydrochloride | 668 |
| 3913 | 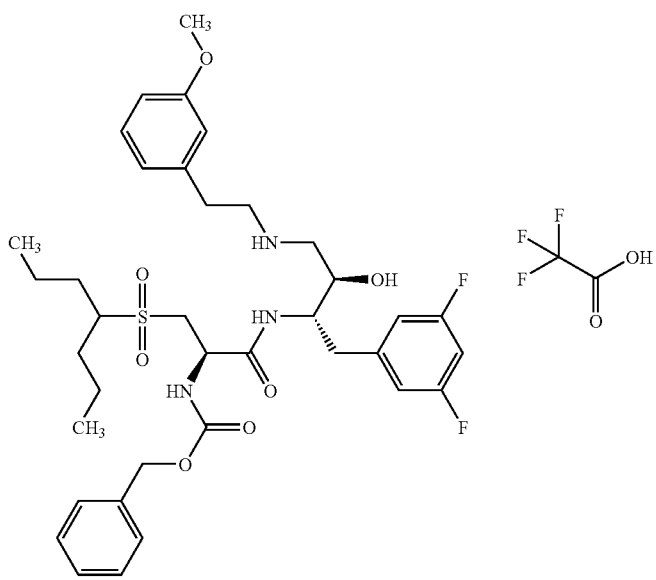 | N²-[(benzyloxy)carbonyl]-N¹-((1S,2R)-1-(3,5-difluorobenzyl)-2-hydroxy-3-{[2-(3-methoxyphenyl)ethyl]amino}propyl)-3-[(1-propylbutyl)sulfonyl]-D,L-alaninamide trifluoroacetate | 718 |

-continued
| | | | |
|---|---|---|---|
| 3914 | 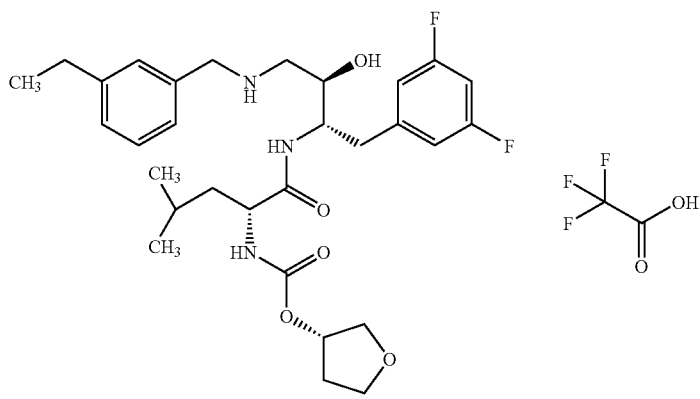 | N¹-{(1S,2R)-1-(3,5-difluorobenzyl)-3-[(3-ethylbenzyl)amino]-2-hydroxypropyl}-N²-{[(3S)-tetrahydrofuran-3-yloxy]carbonyl}-D-trifluoracetate | 562 |
| 3915 | 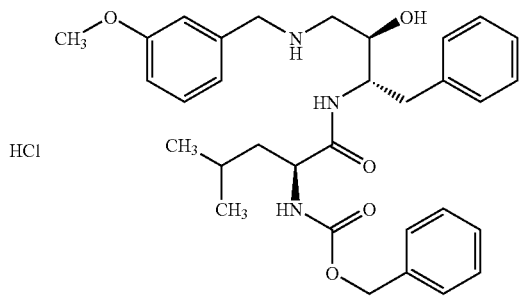 | N¹-{(1S,2R)-1-benzyl-2-hydroxy-3-[(3-methoxybenzyl)amino]propyl}-N²-[(benzyloxy)carbonyl]-L-leucinamide hydrochloride | 548 |
| 3916 | 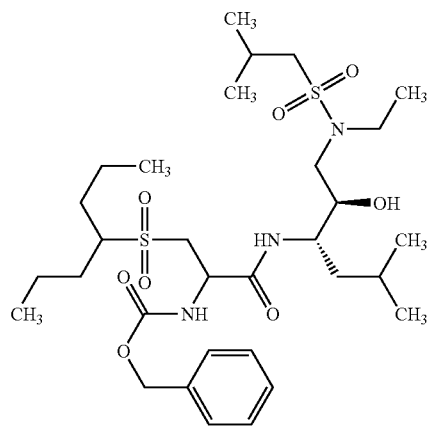 | N²-[(benzyloxy)carbonyl]-N¹-((1S)-1-{(1R)-2-[ethyl(isobutylsulfonyl)amino]-1-hydroxyethyl}-3-methylbutyl)-3-[(1-propylbutyl)sulfonyl]-D,L-alaninamide | 662 |

-continued

| | | | |
|---|---|---|---|
| 3917 | 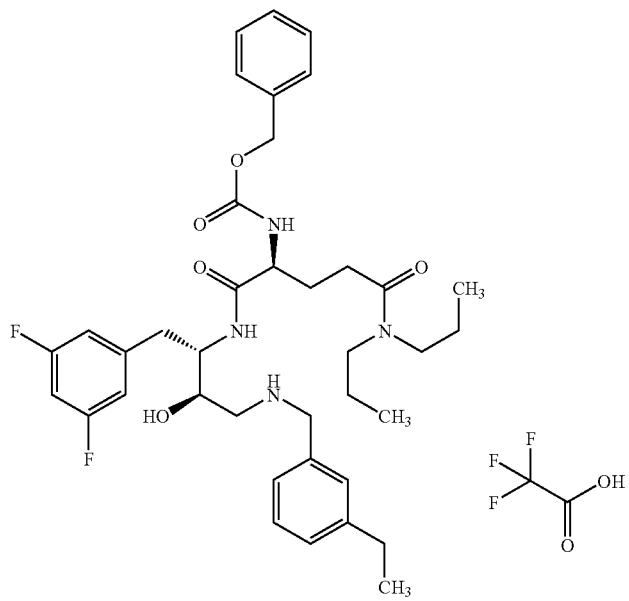 | $N^2$-[(benzyloxy)carbonyl]-$N^1$-{(1S,2R)-1-(3,5-difluorobenzyl)-3-[(3-ethylbenzyl)amino]2-hydroxypropyl}-$N^5$,$N^5$-dipropyl-L-glutamamide trifluoroacetate | 681 |
| 3918 | 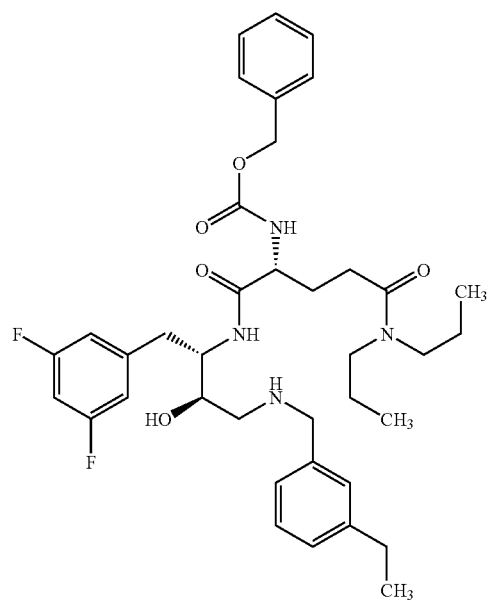 | $N^2$-[(benzyloxy)carbonyl]-$N^1$-{(1S,2R)-1-(3,5-difluorobenzyl)-3-[(3-ethylbenzyl)amino]2-hydroxypropyl}-$N^5$,$N^5$-dipropyl-D-glutamamide | 681 |
| 3919 | 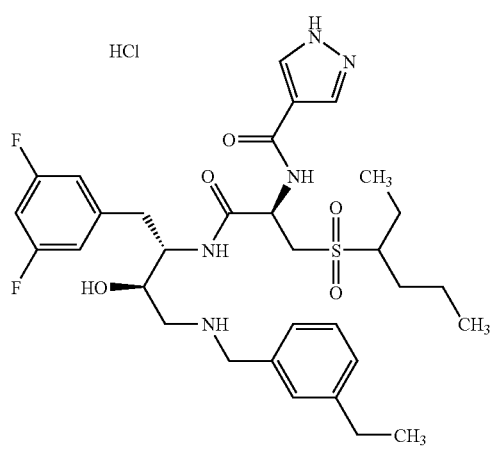 | $N^1$-{(1S,2R)-1-(3,5-difluorobenzyl)-)-3-[(3-ethylbenzyl)amino]-2-hydroxpropyl}-$N^2$-[(1H-pyrazol-4-yl)carbonyl]-3-[(1-propylbutyl)sulfonyl]-D,L-alaninamide hydrochloride | 662 |

-continued

| | | | |
|---|---|---|---|
| 3920 | 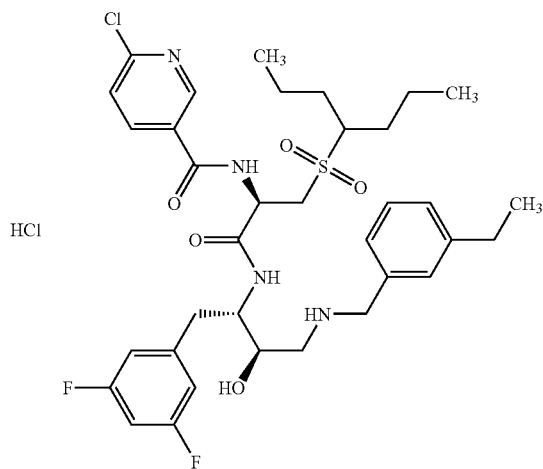 | N²-[(6-chloropyridin-3-yl)carbonyl]-N¹-{(1S,2R)-1-(3,5-difluorobenzyl)-3-[(3-ethylbenzyl)amino]-2-hydroxypropyl}-3-[(1-propylbutyl)sulfonyl]-D,L-alaninamide hydrochloride | 707 |
| 3921 | 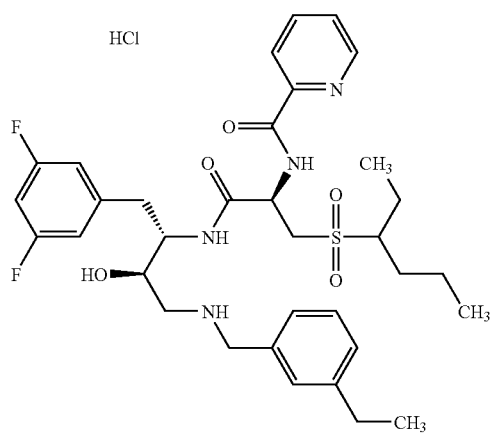 | N¹-{(1S,2R)-2-(3,5-difluorobenzyl)-3-[(3-ethylbenzyl)amino]-2-hydroxypropyl}-N²-[(pyridin-2-yl)carbonyl]-3-[(1-propylbutyl)sulfonyl]-D,L-alaninamide hydrochloride | 673 |
| 3922 | 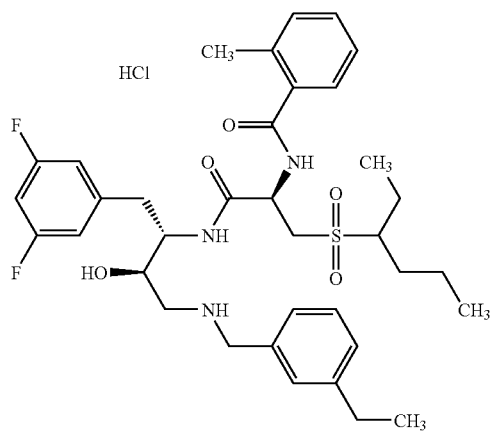 | N¹-{(1S,2R)-1-(3,5 difluorobenzyl)-3-[(3-ethylbenzyl)amino]-2-hydroxypropyl}-N²-(2-methylbenzoyl)-3-[(1-propylbutyl)sulfonyl]-D,L-alaninamide hydrochloride | 686 |

-continued

| | | | |
|---|---|---|---|
| 3923 | 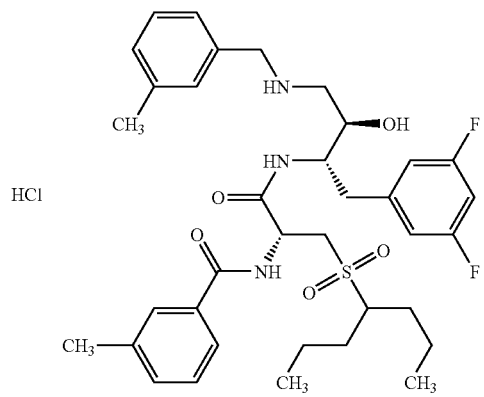 | N$^1$-{(1S,2R)-1-(3,5-difluorobenzyl)-3-[(3-ethylbenzyl)amino]-2-hydroxypropyl}-N$^2$-(3-methylbenzoyl)-3-[(1-propylbutyl)sulfonyl]-D,L-alaninamide hydrochloride | 686 |
| 3924 | 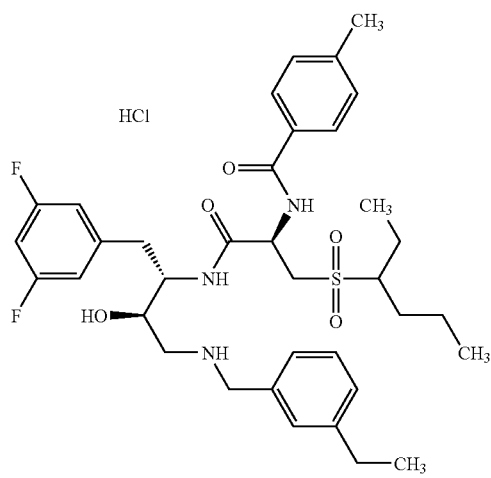 | N$^1$-{(1S,2R)-1-(3,5-difluorobenzyl)-3-[(3-ethylbenzyl)amino]-2-hydroxypropyl}-N$^2$-(4-methylbenzoyl)-3-[(1-propylbutyl)sulfonyl]-D,L-alaninamide hydrochloride | 686 |
| 3925 | 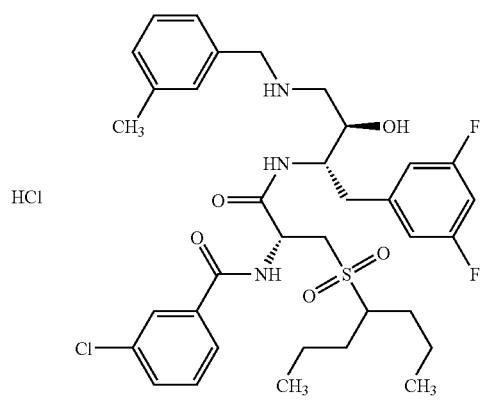 | N$^2$-(3-chlorobenzoyl)-N$^1$-{(1S,2R)-1-(3,5-difluorobenzyl)-3-[(3-ethylbenzyl)amino]-2-hydroxypropyl}-3-[(1-propylbutyl)sulfonyl]-D,L-alaninamide hydrochloride | 706 |

-continued

| | | | |
|---|---|---|---|
| 3926 | 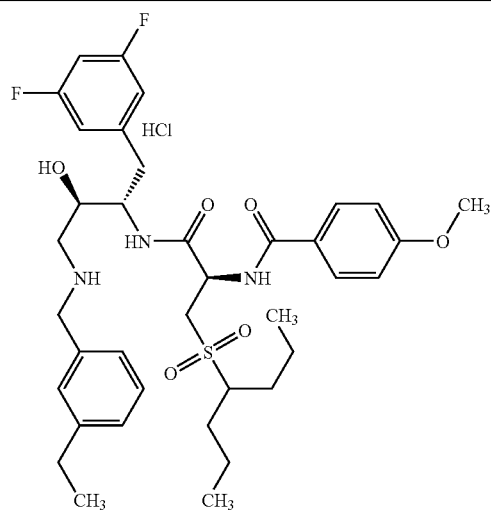 | N$^1$-{(1S,2R)-1-(3,5-difluorobenzyl)-3-[(3-ethylbenzyl)amino]-2-hydroxypropyl}-N$^2$-(4-methoxybenzoyl)-3-[(1-propylbutyl)sulfonyl]-D,L-alaninamide hydrochloride | 702 |
| 3927 | 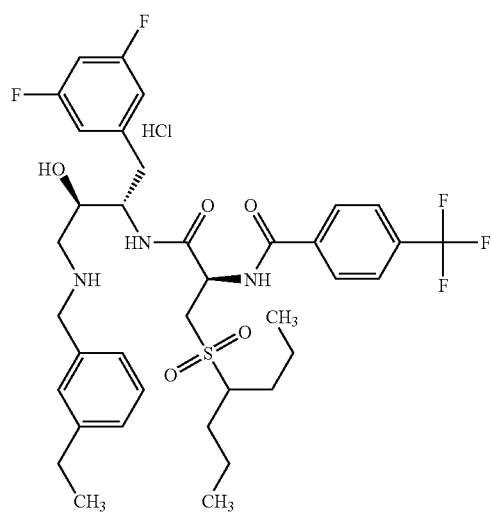 | N$^1$-{(1S,2R)-1-(3,5-difluorobenzyl)-3-[(3-ethylbenzyl)amino]-2-hydroxypropyl}-N$^2$-(4-trifluoromethylbenzoyl)-3-[(1-propylbutyl)sulfonyl]-D,L-alaninamide hydrochloride | 740 |
| 3928 | 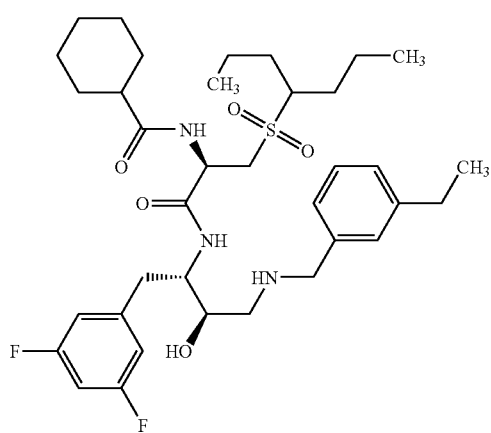 | N$^2$-(cyclohexylcarbonyl)-N$^1${(1S,2R)-1-(3,5-difluorobenzyl)-3-[(3-ethylbenzyl)amino]-2-hydroxypropyl}-3-[(1-propylbutyl)sulfonyl]-D,L-alaninamide hydrochloride | 678 |

-continued

| | | | |
|---|---|---|---|
| 3929 | 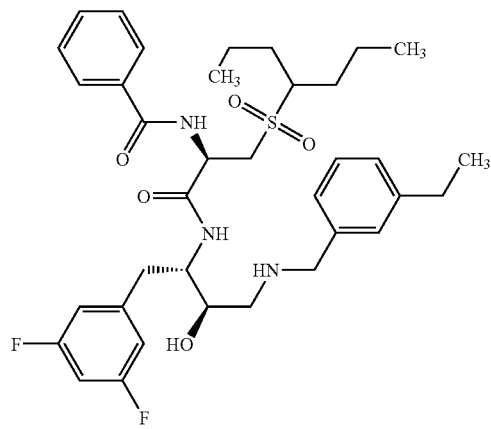 | $N^2$(benzoyl)-$N^1$-{(1S,2R)-1-(3,5-difluorobenzyl)-3-[(3-ethylbenzyl)amino]-2-hydroxypropyl}-3-[(1-propylbutyl)sulfonyl]-D,L-alaninamide | 672 |
| 3930 | 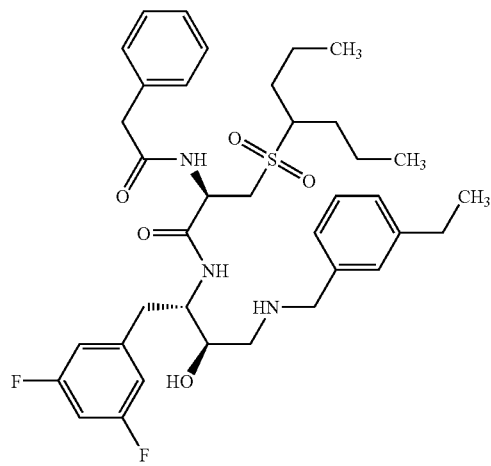 | $N^1$-{(1S,2R)-1-(3,5-difluorobenzyl)-3-[(3-ethylbenzyl)amino]-2-hydroxypropyl}-$N^2$-(phenylacetyl)-3-[(1-propylbutyl)sulfonyl]-D,L-alaninamide | 686 |
| 3931 | 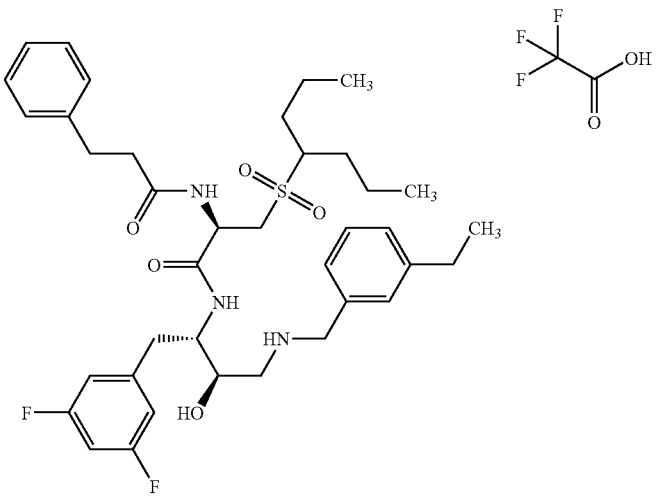 | $N^1$-{(1S,2R)-1-(3,5-difluorobenzyl)-3-[(3-ethylbenzyl)amino]-2-hydroxypropyl}-$N^2$-(3-phenylpropanoyl)-3-[(1-propylbutyl)sulfonyl]-D,L-alaninamide trifluoroacetate | 700 |

-continued

| | | | |
|---|---|---|---|
| 3932 | 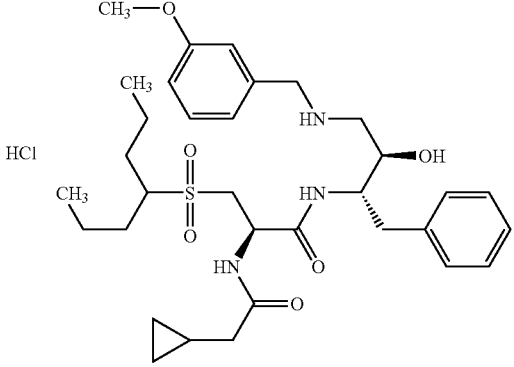 | N¹-{(1S,2R)-1-benzyl-2-hydroxy-3-[(3-methoxybenzyl)amino]propyl}-N²-(cyclopropylacetyl)-3-[(1-propylbutyl)sulfonyl]-D,L-alaninamide hydrochloride | 616 |
| 3933 | 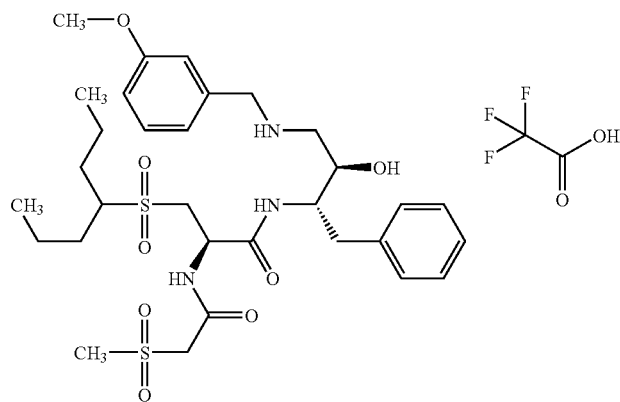 | N¹-{(1S,2R)-1-benzyl-2-hydroxy-3-[(3-methoxybenzyl)amino]propyl}-N²-[(methylsulfonyl)acetyl]-3-[(1-propylbutyl)sulfonyl]-D,L-alaninamide trifluoroacetate | 654 |
| 3934 | 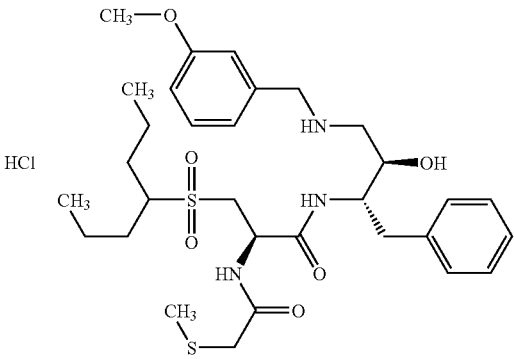 | N¹-{(1S,2R)-1-benzyl-2-hydroxy-3-[(3-methoxybenzyl)amino]propyl}-N²-[(methylthio)acetyl]-3-[(1-propylbutyl)sulfonyl]-D,L-alaninamide hydrochloride | 622 |
| 3935 | 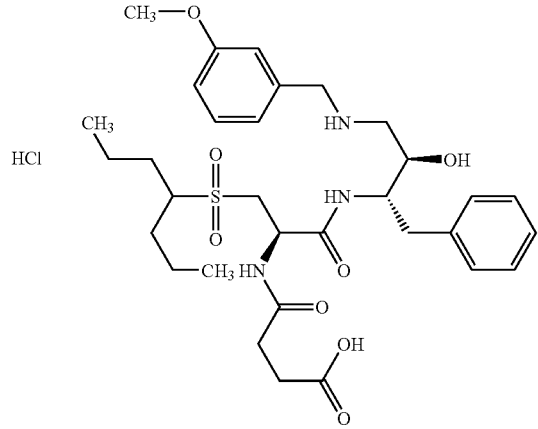 | N¹-{(1S,2R)-1-benzyl-2-hydroxy-3-[(3-methoxybenzyl)amino]propyl}-N²-(4-hydroxy-4-oxobutanoyl)-3-[(1-propylbutyl)sulfonyl]-D,L-alaninamide hydrochloride | 634 |

-continued

| | | | |
|---|---|---|---|
| 3936 | 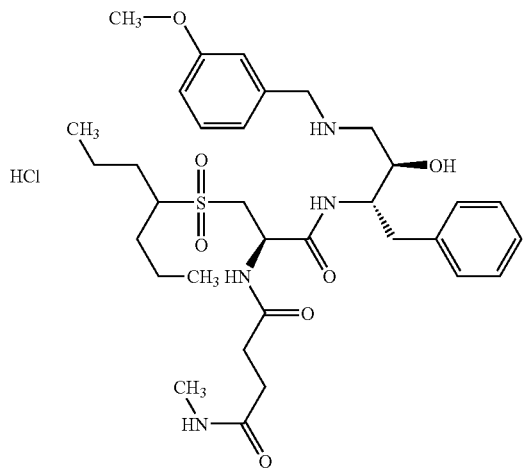 | N¹-{(1S,2R)-1-benzyl-2-hydroxy-3-[(3-methoxybenzyl)amino]propyl}-N²-[4-(methylamino)-4-oxobutanoyl]-3-[(1-propylbutyl)sulfonyl]-D,L-alaninamide hydrochloride | 647 |
| 3937 | 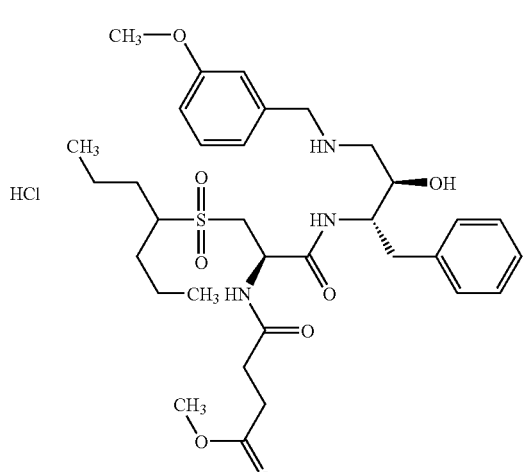 | N¹-{(1S,2R)-1-benzyl-2-hydroxy-3-[(3-methoxybenzyl)amino]propyl}-N²-(4-methoxy-4-oxobutanoyl)-3-[(1-propylbutyl)sulfonyl]-D,L-alaninamide hydrochloride | 648 |
| 3938 | 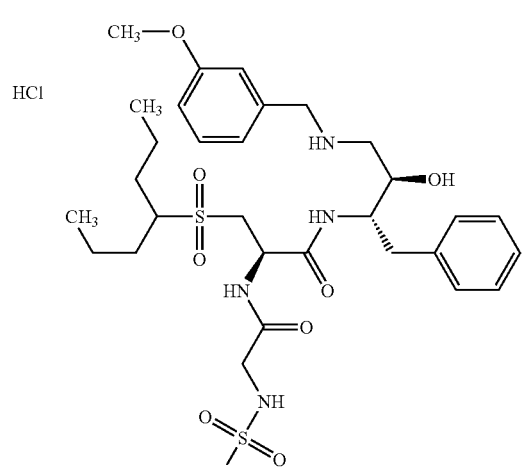 | N-(methylsulfonyl)glycyl-N¹-{(1S,2R)-1-benzyl-2-hydroxy-3-[(3-methoxybenzyl)amino]propyl}-3-[(1-propylbutyl)sulfonyl]-D,L-alaninamide hydrochloride | 669 |

| 3939 | 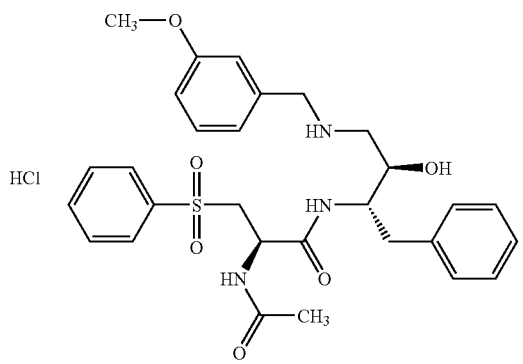 | N²-acetyl-N¹-{(1S,2R)-1-benzyl-2-hydroxy-3-[(3-methoxybenzyl)amino]propyl}-3-(phenylsulfonyl)-D,L-alaninamide hydrochloride | 554 |
| --- | --- | --- | --- |
| 3940 | 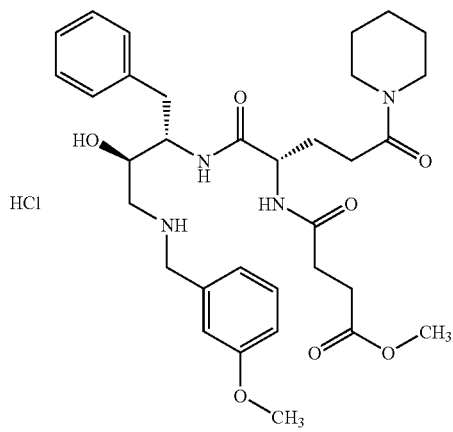 | (2S)-2-(4-methoxy-4-oxobutanoyl)amino-N-{(1S,2R)-1-benzyl-2-hydroxy-3-[(3-methoxybenzyl)amino]propyl}-5-oxo-5-piperidin-1-ylpentanamide hydrochloride | 611 |
| 3941 | 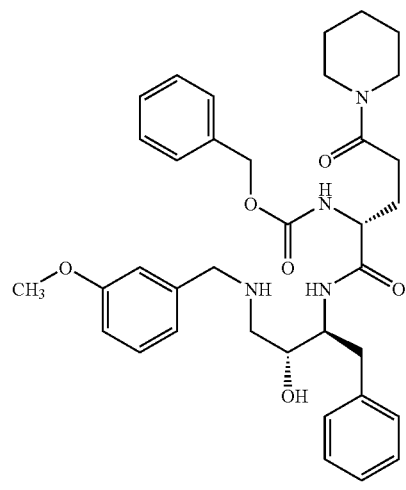 | (2R)-2-{[(benzyloxy)carbonyl]amino}-N-{(1S,2R)-1-benzyl-2-hydroxy-3-[(3-methoxybenzyl)amino]propyl}-5-oxo-5-piperidin-1-ylpentanamide hydrochloride | 631 |

-continued

| | | | |
|---|---|---|---|
| 3942 | 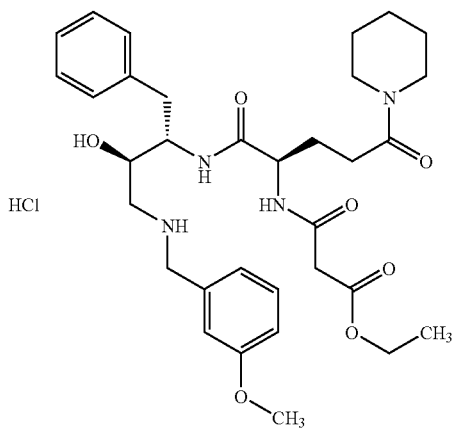 | (2R)-2-(3-ethoxy-3-oxopropanoyl)amino-N-{(1S,2R)-1-benzyl-2-hydroxy-3-[(3-methoxybenzyl)amino]propyl)-5-oxo-5-piperidin-1-ylpentanamide hydrochloride | 611 |
| 3943 | 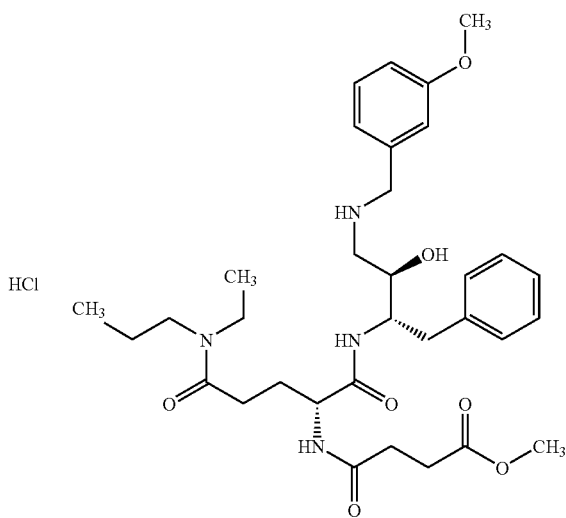 | $N^1$-{(1S,2R)-1-benzyl-3-[(3-methoxybenzyl)amino]-2-hydroxypropyl}-$N^2$-(4-methoxy-4-oxobutanoyl)-$N^5$,$N^5$-dipropyl-D-glutamamide hydrochloride | 627 |
| 3944 | 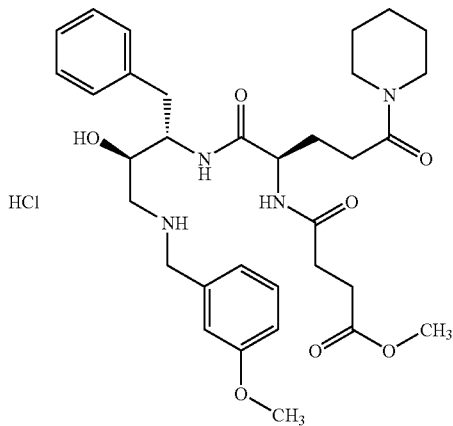 | (2R)-2-(4-methoxy-4-oxobutanoyl)amino-N-{(1S,2R)-1-benzyl-2-hydroxy-3-[(3-methoxybenzyl)amino]propyl}-5-oxo-5-piperidin-1-ylpentanamide hydrochloride | 611 |

-continued

| | | | |
|---|---|---|---|
| 3945 | 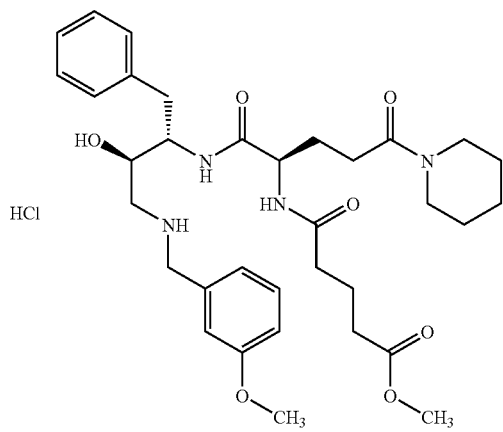 | (2R)-2-(5-methoxy-5-oxopentanoyl)amino-N-{(1S,2R)-1-benzyl-2-hydroxy-3-[3-methoxybenzyl)amino]propyl}-5-oxo-5-piperidin-1-ylpentanamide hydrochloride | 625 |
| 3946 | 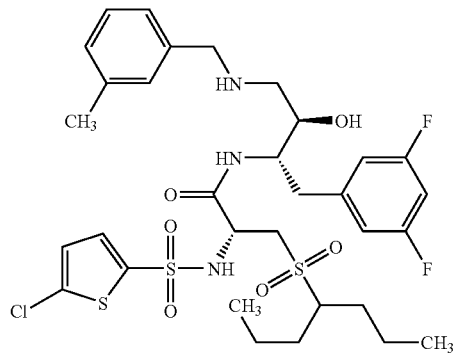 | N²-[(5-chlorothien-2-yl)sulfonyl]-N¹-{(1S,2R)-1-(3,5-difluorobenzyl)-3-[(3-ethylbenzyl)amino]-2-hydroxypropyl}-3-[(1-propylbutyl)sulfonyl]-D,L-alaninamide | 748 |
| 3947 | 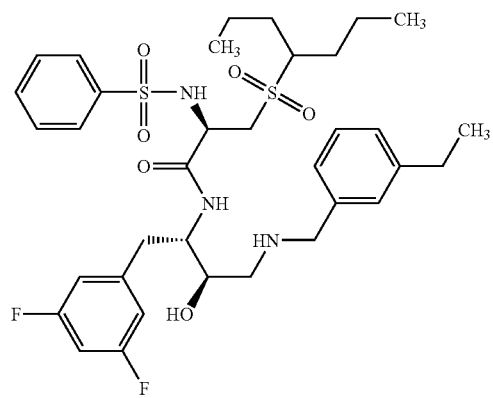 | N¹-{(1S,2R)-1-(3,5-difluorobenzyl)-3-[(3-ethylbenzyl)amino]-2-hydroxypropyl}-N²-(phenylsulfonyl)-3-[(1-propylbutyl)sulfonyl]-D,L-alaninamide | 708 |

-continued

| | | | |
|---|---|---|---|
| 3948 | 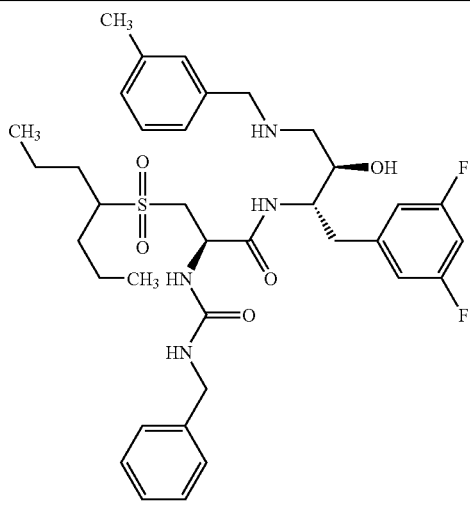 | N²-[(benzylamino)carbonyl]-N¹-{(1S,2R)-1-(3,5-difluorobenzyl)-3-[(3-ethylbenzyl)amino]-2-hydroxypropyl}-3-[(1-propylbutyl)sulfonyl]-D,L-alaninamide | 701 |
| 3949 | 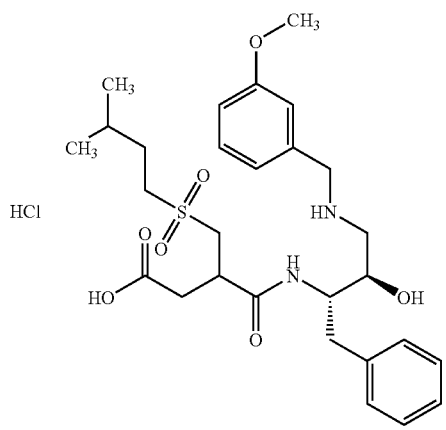 | 4-({(1S,2R)-1-benzyl-2-hydroxy-3-[(3-methoxybenzyl)amino]propyl}amino)-3-[(isopentylsulfonyl)methyl]-4-oxobutanoic acid hydrochloride | 549 |
| 3950 | 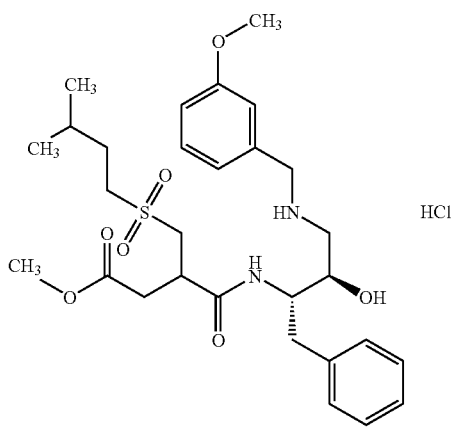 | methyl 4-({(1S,2R)-1-benzyl-2-hydroxy-3-[(3-methoxybenzyl)amino]propyl}amino)-3-[(isopentylsulfonyl)methyl]-4-oxobutanoate hydrochloride | 563 |

-continued
| | | | |
|---|---|---|---|
| 3951 | 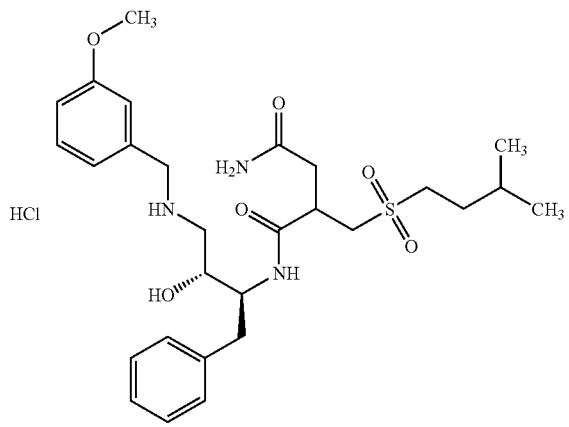 | N[1]-{(1S,2R)-1-benzyl)-2-hydroxy-3-[(3-methoxybenzyl)amino]propyl}-2-(isopentylsulfonyl)methyl]succinamide hydrochloride | 548 |
| 3952 | 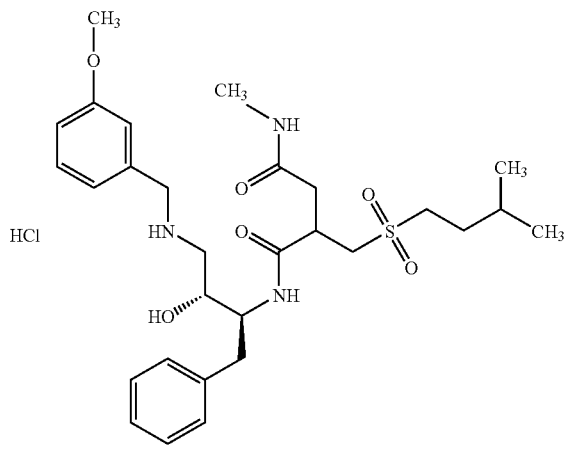 | N[1]-{(1S,2R)-1-benzyl-2-hydroxy-3-[(3-methoxybenzyl)amino]propyl}-2-[(isopentylsulfonyl)methyl]-N[4]-methylsuccinamide hydrochloride | 562 |
| 3953 | 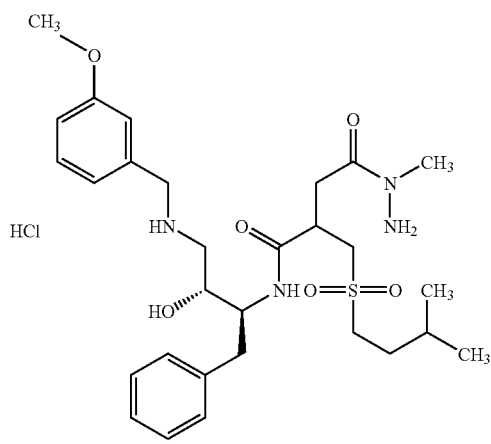 | N[1]-{(1S,2R)-1-benzyl-2-hydroxy-3-[(3-methoxybenzyl)amino]propyl}-2-[(isopentylsulfonyl)methyl]-N[4],N[4]-dimethylsuccinamide hydrochloride | 576 |

| | | |
|---|---|---|
| 3954 | 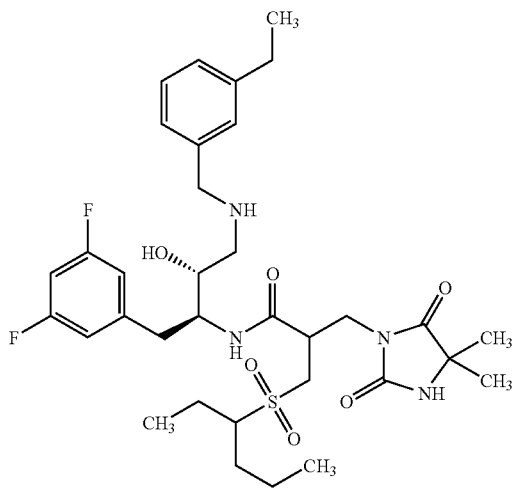 | N-{(1S,2R)-1-(3,5-difluorobenzyl)-3-[(3-ethylbenzyl)amino]-2-hydroxypropyl}-3-(4,4-dimethyl-2,5-dioxoimidazolidin-1-yl)-2-{[(1-propylbutyl)sulfonyl]methyl}propanamide   693 |
| 3955 | 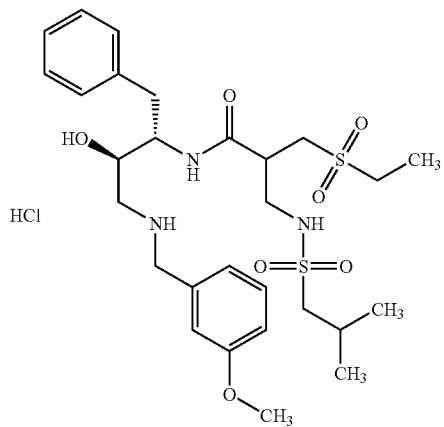 | N-{(1S,2R)-1-benzyl-2-hydroxy-3-[(3-methoxybenzyl)amino]propyl}-3-(ethylsulfonyl)-2-{[(isobutylsulfonyl)amino]methyl}propanamide hydrochloride   598 |
| 3956 | 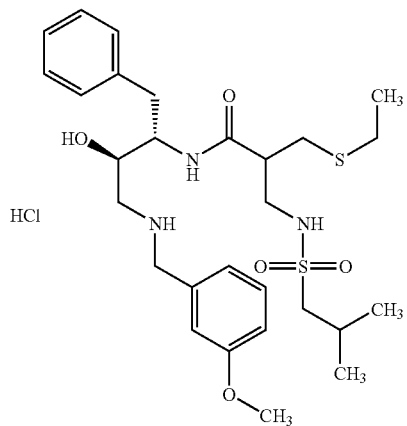 | N-{(1S,2R)-1-benzyl-2-hydroxy-3-[(3-methoxybenzyl)amino]propyl}-3-(ethylthio)-2-{[(isobutylsulfonyl)amino]methyl}propanamide hydrochloride   566 |

| | | | |
|---|---|---|---|
| 3957 | 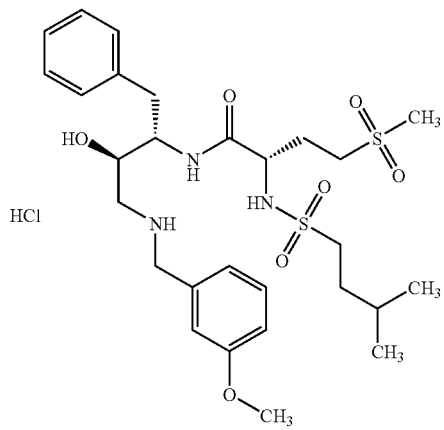 | (2S)-N-{(1S,2R)-1-benzyl-2-hydroxy-3-[(3-methoxybenzyl)amino]propyl}-2-[)isopentylsulfonyl)amino]-4-(methylsulfonyl)butanamide hydrochloride | 598 |
| 3958 | 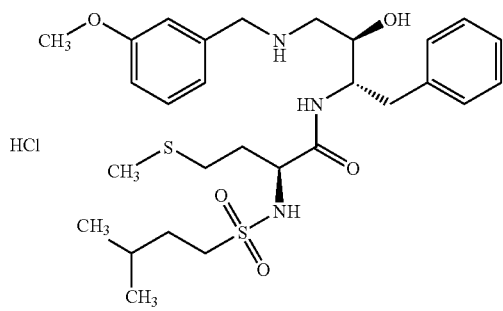 | N¹-{(1S,2R)-1-benzyl-2-hydroxy-3-[(3-methoxybenzyl)amino]propyl}-N²-(isopentylsulfonyl)-L-methioninamide hydrochloride | 566 |
| 3959 | 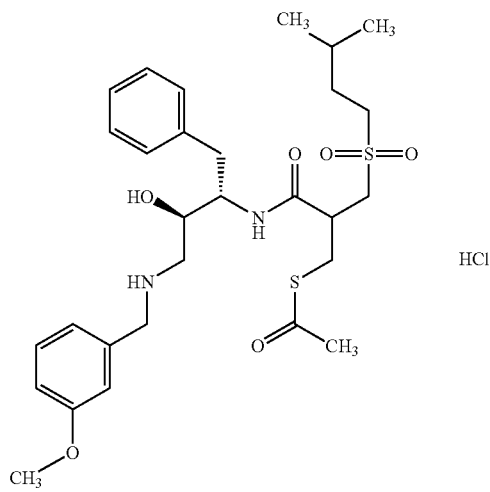 | S-{3-({(1S,2R)-1-benzyl-2-hydroxy-3-[(3-methoxybenzyl)amino]propyl}amino)-2-[(isopentylsulfonyl)methyl]-3-oxopropyl}ethanethioate hydrochloride | 579 |

-continued
| | | | |
|---|---|---|---|
| 3960 | 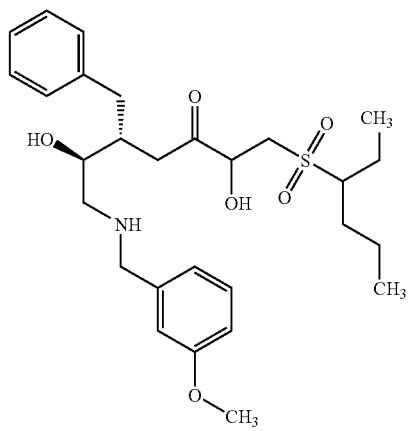 | N-{(1S,2R)-1-benzyl-2-hydroxy-3-[(3-methoxybenzyl)amino]propyl}-2-hydroxy-3-[(1-propylbutyl)sulfonyl]propanamide | 535 |
| 3961 | 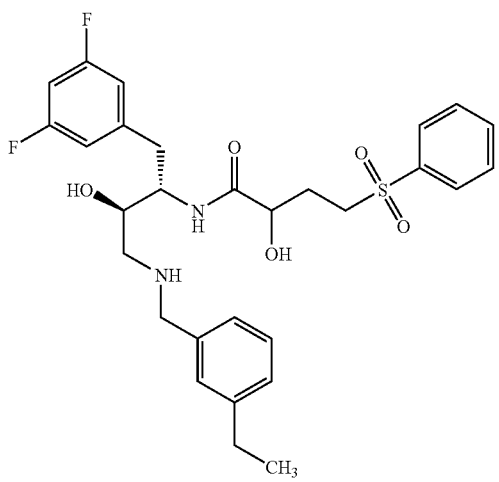 | N-{(1S,2R)-1-(3,5 difluorobenzyl)-3-[3-ethylbenzyl)amino]-2-hydroxypropyl}-2-hydroxy-4-(phenylsulfonyl)butanamide | 561 |
| 3962 | 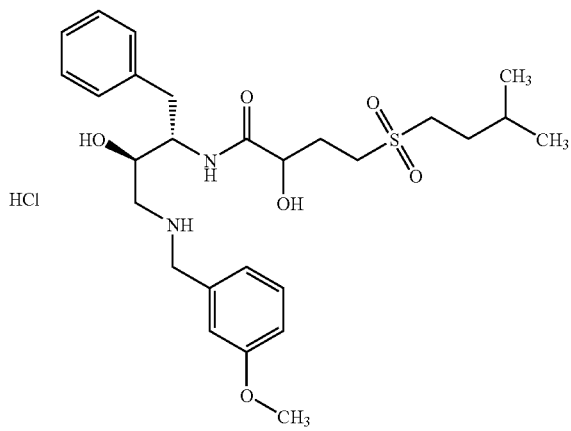 | N-{(1S,2R)-1-benzyl-2-hydroxy-3-[(3-methoxybenzyl)amino]propyl}-2-hydroxy-4-(isopentylsulfonyl)butanamide hydrochloride | 521 |

-continued
| | | | |
|---|---|---|---|
| 3963 | 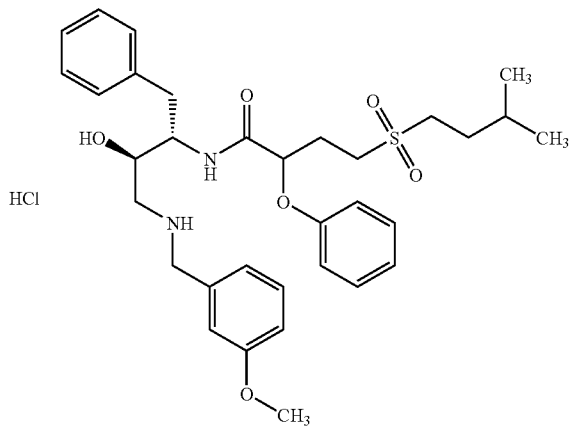 | N-{(1S,2R)-1-benzyl-2-hydroxy-3-[(3-methoxybenzyl)amino]propyl}-4-(isopentylsulfonyl)-2-phenoxybutanamide hydrochloride | 597 |
| 3964 | 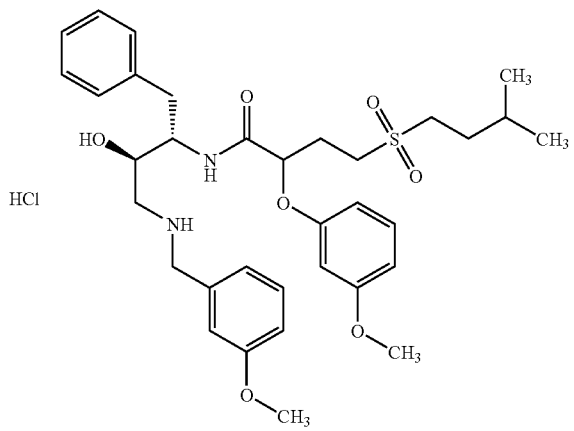 | N-{(1S,2R)-1-benzyl-2-hydroxy-3-[(3-methoxybenzyl)amino]propyl}-4-(isopentylsulfonyl)-2-(3-methoxyphenoxy)butanamide hydrochloride | 627 |
| 3965 | 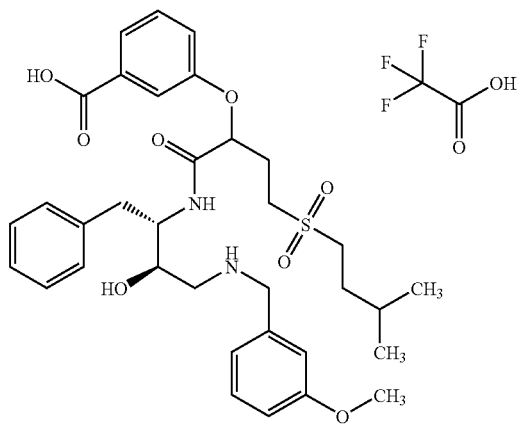 | 3-[1-[({(1S,2R)-1-benzyl-2-hydroxy-3-[(3-methoxybenzyl)amino]propyl}amino)carbonyl]-3-(isopentylsulfonyl)propoxy]benzoic acid trifluoroacetate | 641 |

| | | | |
|---|---|---|---|
| 3966 | 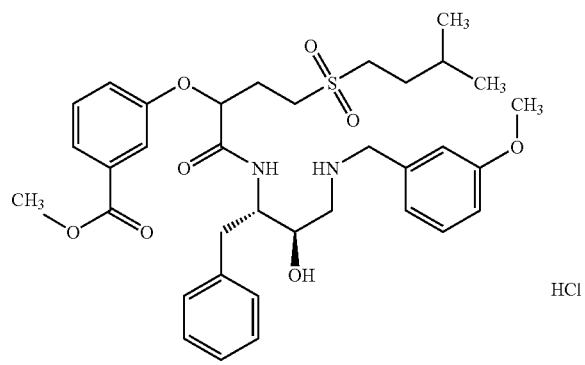 | methyl 3-[1-[({(1S,2R)-1-benzyl-2-hydroxy-3-[(3-methoxybenzyl)amino]propyl}amino)carbonyl]-3-(isopentylsulfonyl)propoxy)benzoate hydrochloride | 655 |
| 3967 | 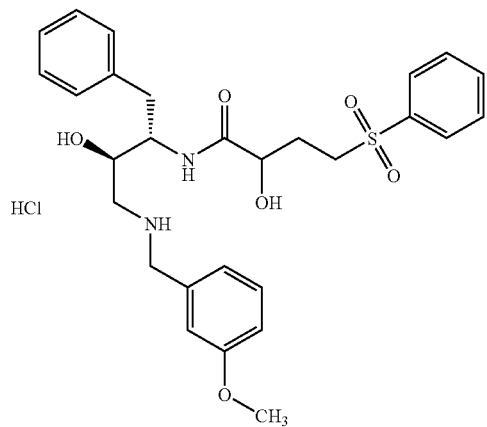 | N-{(1S,2R)-1-benzyl-2-hydroxy-3-[(3-methoxybenzyl)amino]propyl}-2-hydroxy-4-(phenylsulfonyl)butanamide hydrochloride | 527 |
| 3968 | 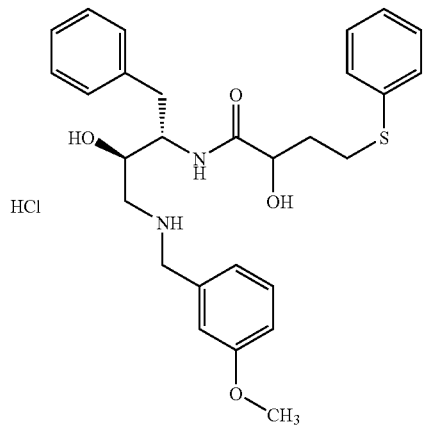 | N-{(1S,2R)-1-benzyl-2-hydroxy-3-[(3-methoxybenzyl)amino]propyl}-2-hydroxy-4-(phenylthio)butanamide hydrochloride | 495 |

-continued
| | | | |
|---|---|---|---|
| 3969 | 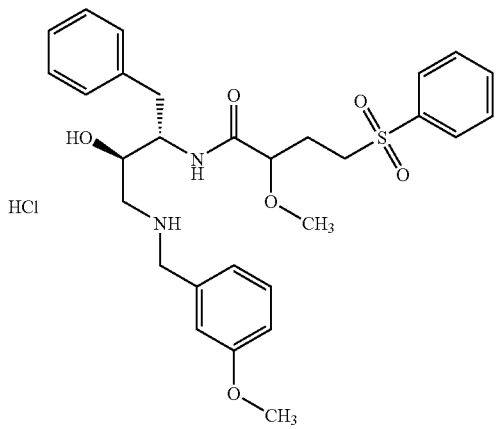 | N-{(1S,2R)-1-benzyl-2-hydroxy-3-[(3-methoxybenzyl)amino]propyl}-2-methoxy-4-(phenylsulfonyl)butanamide hydrochloride | 541 |
| 3970 | 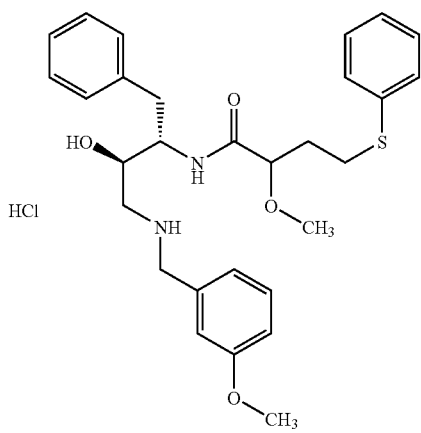 | N-{(1S,2R)-1-benzyl-2-hydroxy-3-[(3-methoxybenzyl)amino]propyl}-2-methoxy-4-(phenylthio)butanamide hydrochloride | 509 |
| 3971 | 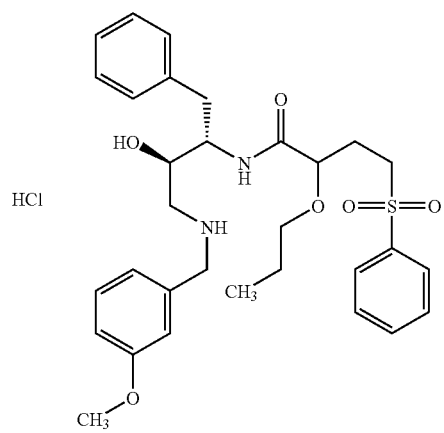 | N-{(1S,2R)-1-benzyl-2-hydroxy-3-[(3-methoxybenzyl)amino]propyl}-4-(phenylsulfonyl)-2-propoxybutanamide hydrochloride | 569 |

-continued
| | | | |
|---|---|---|---|
| 3972 | 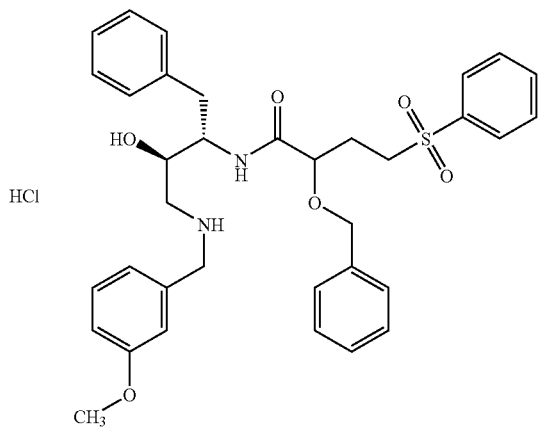 | N-{(1S,2R)-1-benzyl-2-hydroxy-3-[(3-methoxybenzyl)amino]propyl}-2-(benzyloxy)-4-(phenylsulfonyl)butanamide hydrochloride | 617 |
| 3973 | 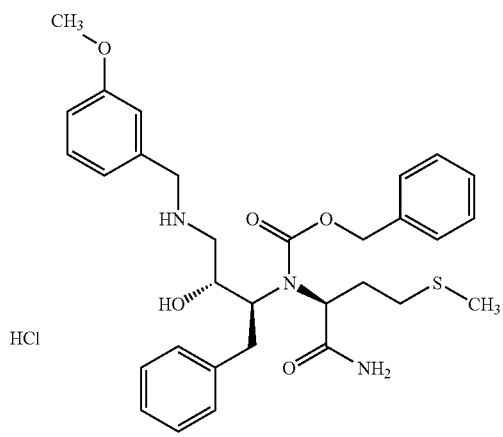 | N-{(1S,2R)-1-benzyl-2-hydroxy-3-[(3-methoxybenzyl)amino]propyl)-N²-[(benzyloxy)carbonyl]-D,L-methioninamide hydrochloride | 566 |
| 3974 | 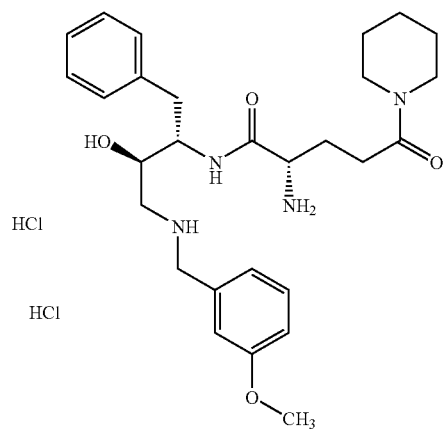 | (2S)-2-amino-N-{(1S,2R)-1-benzyl-2-hydroxy-3-[(3-methoxybenzyl)amino]propyl}-5-oxo-5-piperidin-1-ylpentanamide dihydrochloride | 497 |

-continued
| | | | |
|---|---|---|---|
| 3975 | 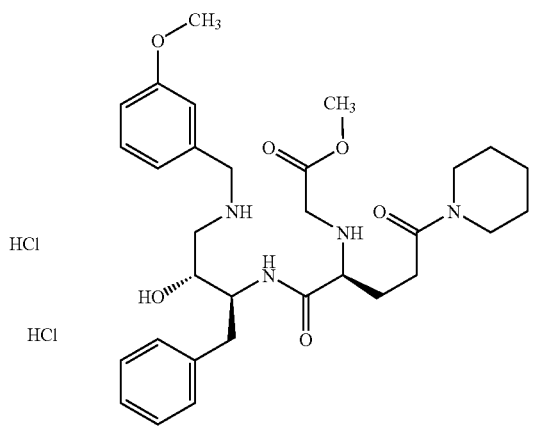 | (2S)-2-(2-ethoxy-2-oxoethanyl)amino-N-{(1S,2R)-1-benzyl-2-hydroxy-3-[(3-methoxybenzyl)amino]propyl}-5-oxo-5-piperidin-1-ylpentanamide dihydrochloride | 569 |
| 3976 | 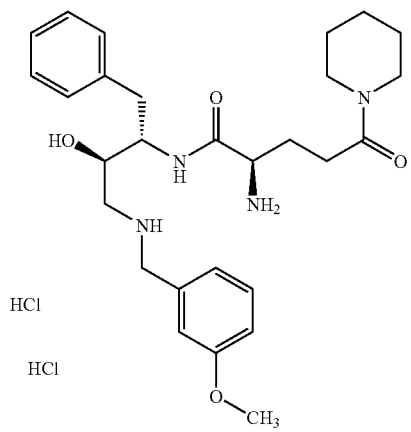 | (2R)-2-amino-N-{(1S,2R)-1-benzyl-2-hydroxy-3-[(3-methoxybenzyl)amino]propyl}-5-oxo-5-piperidin-1-ylpentanamide dihydrochloride | 497 |
| 3977 | 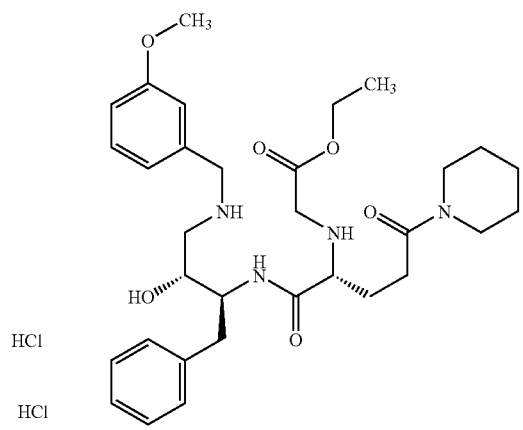 | (2R)-2-(2-ethoxy-2-oxoethanyl)amino-N-{(1S,2R)-1-benzyl-2-hydroxy-3-[(3-methoxybenzyl)amino]propyl}-5-oxo-5-piperidin-1-ylpentanamide dihydrochloride | 583 |

| | | |
|---|---|---|
| 3978 | 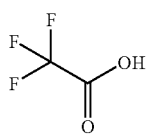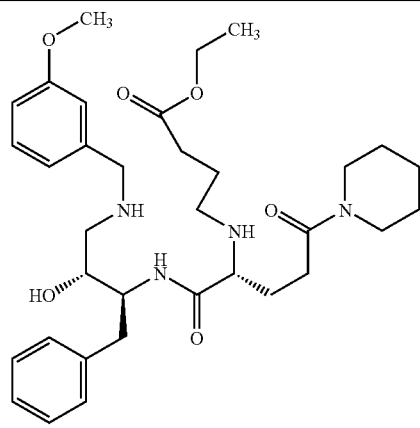 | (2R)-2-(4-ethoxy-4-oxobutanyl)amino-N-{(1S,2R)-1-benzyl-2-hydroxy-3-[(3-methoxybenzyl)amino]propyl}-5-oxo-5-piperidin-1-ylpentanamide ditrifluoroacetate    611 |
| 3979 | 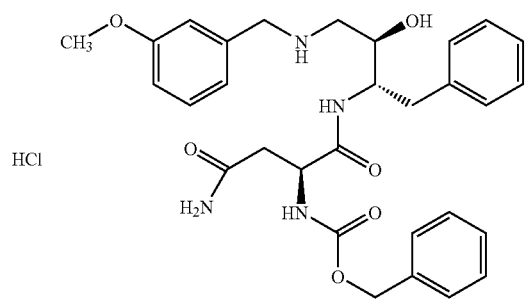 | N$^1$-{(1S,2R)-1-benzyl-2-hydroxy-3-[(3-methoxybenzyl)amino]propyl}-N$^2$-[(benzyloxy)carbonyl]-L-aspartamide hydrochloride    549 |
| 3980 | 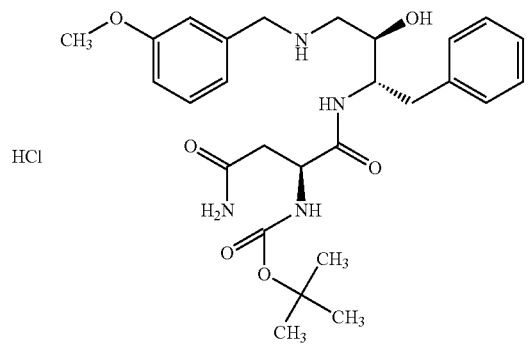 | N$^1$-{(1S,2R)-1-benzyl-2-hydroxy-3-[(3-methoxybenzyl)amino]propyl}-N$^2$-[(tertbutyloxy)carbonyl]-L-aspartamide hydrochloride    515 |

What is claimed is:

1. A compound of the formula

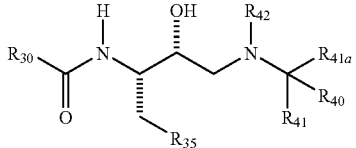

or a pharmaceutically acceptable salt thereof, wherein $R_{30}$ is selected from the group consisting of pyrazolopyrimidinyl, isoxazolyl, triazolopyridinyl, pyridyl, furyl, naphthothienyl, thiadiazolyl, oxazolidinyl, pyrazinyl mono N-oxide, benzofuranyl, pyrazolyl, benzimidazolyl, indolyl, isoquinolinyl, -thienyl-thienyl, benzothienyl, quinolinyl, thieno[2,3-b]thiophene, benzoxazole benzo[b]thiophene 1,1-dioxideisoindolyl, purinyl, oxazolyl, thiazolyl, pyridazinonyl, benzoindazolyl, imidazopyrazolyl, pyridyl N-oxide, pyrazolopyridinyl, thienopyrazolyl, indazolyl, thienopyridinyl, triazolopyrimidinyl, thienyl, benzooxadiazolyl, carbazolyl, chromeno[3,4-d]isoxazolyl, triazolopyridazinyl, -pyrrolyl-($C_1$-$C_6$ alkyl)-pyridyl, -pyrrolyl-cyclohexyl, benzooxadiazolyl mono N-oxide, thienoindolyl, thioxobenzothiazolyl,-imidazole-benzyl, thienoquinolinyl, pyrrolopyridinyl, 1-H-imidazo[1,2-b]pyrazolyl, and imidazobenzoxazinyl, wherein each of the above is unsubstituted or substituted with 1, 2, 3, 4, or 5 groups that are independently selected from the group consisting of $C_1$-$C_{10}$ alkyl optionally substituted with 1 phenyl or 1 CN; OH, hydroxy $C_1$-$C_{10}$ alkyl optionally substituted with phenyl or ($C_1$-$C_4$ alkyl)phenyl, $C_1$-$C_6$ alkoxy optionally substituted with 1 or 2 groups that are independently hydroxy or phenyl; haloalkyl, haloalkoxy, $(CH_2)_{0-4}C(O)NR_{31}R_{32}$, —$NR_{31}$—$SO_2$—($C_1$-$C_6$ alkyl) wherein the alkyl group is optionally substituted with 1, 2, or 3 groups that are independently halogen or $R_{33}$, —$SO_2$—NH($C_1$-$C_6$ alkyl) wherein the alkyl group is optionally substituted with 1 or 2 groups that are independently halogen, OH, alkoxy, or $R_{33}$; —($C_1$-$C_6$ alkyl)-$SO_2$—($C_1$-$C_6$ alkyl) wherein the alkyl group is optionally substituted with 1 or 2 groups that are independently halogen, OH, $C_1$-$C_4$ alkoxy, or $R_{33}$; —$SO_2$—($C_1$-$C_6$ alkyl) wherein the alkyl group is optionally substituted with 1 or 2 groups that are independently OH or $C_1$-$C_4$ alkoxy, —$SO_2$—N($C_1$-$C_6$ alkyl)($C_1$-$C_6$ alkyl) wherein each alkyl group is optionally substituted with 1 or 2 groups that are independently halogen, OH or $R_{33}$; —$SO_2$—NH($C_1$-$C_6$ alkyl)-phenyl wherein the phenyl is optionally substituted with 1 or 2 groups that are independently $C_1$-$C_4$ alkoxy or halogen, —($C_1$-$C_6$alkyl)-O-phenyl, —($C_1$-$C_6$ alkyl)-O—($C_1$-$C_6$ alkyl)-phenyl, triazolidine-3,5-dione, halogen, —NHC(O)NH$_2$, —NHC(O)NH($C_1$-$C_6$ alkyl), —NHC(O)N($C_1$-$C_6$alkyl)($C_1$-$C_6$ alkyl), —N($C_1$-$C_6$ alkyl)C(O)NH$_2$, —N($C_1$-$C_6$ alkyl)C(O)NH($C_1$-$C_6$alkyl), —N($C_1$-$C_6$ alkyl)C(O)N($C_1$-$C_6$ alkyl)($C_1$-$C_6$ alkyl), —($C_1$-$C_6$ alkyl)thienyl, —($C_1$-$C_6$ alkyl)furanyl, —S—($C_1$-$C_6$ alkyl)phenyl, —$SO_2NR_{31}R_{32}$, —C(O)—$NR_{31}R_{32}$, —$NR_{31}R_{32}$, dithiane, —NHC(S)NH$_2$, —NHC(S)NH($C_1$-$C_6$ alkyl), —NHC(S)N($C_1$-$C_6$alkyl)($C_1$-$C_6$ alkyl), —CO$_2$($C_1$-$C_6$ alkyl), tetrahydropyran, phenyl optionally substituted with 1 or 2 groups that are independently F, Cl or Br; pyridine, —$C_2$-$C_4$ alkynyl-phenyl, —O—$C_3$-$C_8$ cycloalkyl, —O—($C_1$-$C_6$ alkyl)-$R_{33}$; pyrrole optionally substituted with one or two methyl groups; 2,3-dihydrobenzofuran; benzo[1,2,5]oxadiazole, —C(O)—($C_1$-$C_{10}$ alkyl) wherein the alkyl group is optionally substituted with NH$_2$, N($C_1$-$C_6$ alkyl), or N($C_1$-$C_6$ alkyl)($C_1$-$C_6$ alkyl); —C(O)NH-phenyl, —C(O)N($C_1$-$C_6$ alkyl)-phenyl, 4,4-dimethyl-4,5-dihydro-oxazole, —($C_1$-$C_6$ alkyl)-S-pyridine, —($C_1$-$C_6$ alkyl)-$SO_2$-pyridine, —($C_1$-$C_6$ thioalkoxy)-pyridine, thiazole optionally substituted with 1 or 2 methyl groups, pyrazole, —S—($C_1$-$C_6$ alkyl) wherein the alkyl group is optionally substituted with 1 or 2 groups that are independently CN or OH; indole, ($C_1$-$C_6$ thioalkoxy)-($C_1$-$C_6$ alkyl), $C_2$-$C_8$ alkynyl, —$(CH_2)_{0-4}$—$SO_2$—($C_1$-$C_{10}$ alkyl) wherein the alkyl group is optionally substituted with OH; —NHC(O)NH($C_3$-$C_8$ cycloalkyl), —N($C_1$-$C_6$ alkyl)C(O)NH($C_3$-$C_8$ cycloalkyl), —N($C_1$-$C_6$ alkyl)C(O)N($C_1$-$C_6$ alkyl)($C_3$-$C_8$ cycloalkyl), —NHC(O)N($C_1$-$C_6$ alkyl)($C_3$-$C_8$ cycloalkyl), —($C_1$-$C_6$ alkoxy)-($C_1$-$C_6$ thioalkoxy); —CO$_2$—($C_1$-$C_6$ alkyl) wherein the alkyl group is optionally substituted with phenyl; —C(O)-furan; and imidazolyl;

wherein $R_{31}$ and $R_{32}$ at each occurrence are independently selected from the group consisting of hydrogen, $C_1$-$C_8$ alkyl, $C_2$-$C_8$ alkenyl, hydroxy $C_1$-$C_6$ alkyl, $C_1$-$C_6$ haloalkyl, $C_1$-$C_6$ alkoxy $C_1$-$C_6$ alkyl, —$(CH_2)_{0-4}$—$SO_2$—($C_1$-$C_6$ alkyl) wherein the alkyl is optionally substituted with 1, 2, 3 or 4 independently selected halogen atoms; —$(CH_2)_{0-4}$—$SO_2$-imidazolyl, —$(C_1-C_6$ alkyl)-$C(O)NH_2$, —$(C_1-C_6$ alkyl)-$C(O)NH(C_1-C_6$ alkyl), —$(C_1-C_6$ alkyl)-$C(O)N(C_1-C_6$ alkyl)$(C_1-C_6$ alkyl), —$(C_1-C_6$ alkyl)-$NH_2$, —$(C_1-C_6$ alkyl)-$NH(C_1-C_6$ alkyl), —$(C_1-C_6$ alkyl)-$N(C_1-C_6$ alkyl)$(C_1-C_6$ alkyl), —$(C_1-C_6$ alkyl)phenyl, —$(C_1-C_6$ alkyl)pyridyl, —C(O)furanyl, $(C_1-C_6$ alkyl)-tetrahydrofuran, cyclopropyl, cyclobutyl, cyclopentyl, cyclohexyl, —$CO_2$—$(C_1-C_6$ alkyl), —$(C_1-C_6$ alkyl)-furanyl, —$(CH_2)_{0-4}$—$SO_2$-thienyl, -pyrrolidinyl-benzyl, —$(C_1-C_6$ thioalkoxy)-$(C_1-C_6$ alkyl), —C(O)—$(C_1-C_6$ alkyl), $(C_1-C_6$ alkoxy), —$(C_2-C_6$ alkenyloxy), —$(C_1-C_6$ alkyl)-$CO_2$—$(C_1-C_6$ alkyl), and —C(O)-piperidinyl optionally substituted with $C_1-C_6$ alkyl; wherein the phenyl and pyridyl groups are unsubstituted or substituted with 1, 2, 3, 4, or 5 groups that are independently $C_1-C_4$ alkyl, hydroxy, $C_1-C_4$ alkoxy, halogen, or $R_{31}$, $R_{32}$ and the nitrogen to which they are attached form a 5, 6, or 7 membered heterocycloalkyl or a 6 membered heteroaryl ring, each of which is optionally fused to a benzene, pyridine or pyrimidine ring and each of which is optionally substituted with $C_1-C_6$ alkoxy, hydroxy, hydroxy $C_1-C_6$ alkyl, $C_1-C_4$ alkoxy $C_1-C_6$ alkyl, —$C(O)NH_2$, —C(O)NH—$(C_1-C_6$ alkyl)-phenyl;

$R_{33}$ at each occurrence is independently, H, $NH_2$, $NH(C_1-C_6$ alkyl), $N(C_1-C_6$ alkyl) $(C_1-C_6$ alkyl), $N(C_1-C_6$ alkyl)(phenyl), $N(C_1-C_6$ alkyl)(benzyl);

$R_{35}$ is phenyl, $C_3-C_8$ cycloalkyl, —S-phenyl, benzodioxole, thienyl, $C_1-C_6$ alkyl, furanyl, imidazolyl, each of which is unsubstituted or substituted with 1, 2, 3, 4, or 5 groups that are independently $C_1-C_4$ alkyl, $C_1-C_4$ alkoxy, OH, hydroxy $C_1-C_6$ alkyl, halogen, halo $C_1-C_6$ alkyl, halo $C_1-C_6$ alkoxy, —O—$(C_1-C_6$ alkyl)-phenyl, —$CO_2$—$(C_1-C_6$ alkyl), —$(C_1-C_4$ alkyl)-$(C_5-C_6$ cycloalkyl), or $(CH_2)_{0-4}CN$;

$R_{40}$ is phenyl, -phenyl-pyridyl, biphenyl, -phenyl-benzothienyl, -phenyl-thienyl, -phenyl-furanyl, -phenyl-pyrimidinyl, -phenyl-isoxazolyl, —C(O)-pyridyl, —$(C_1-C_4$ alkyl)-O—C(O)NH-phenyl wherein the phenyl is optionally substituted with 1, 2, or 3 halogen atoms; —$(C_1-C_4$ alkyl)-O—$C(O)N(C_1-C_6$ alkyl)-phenyl, —$(C_1-C_6$ alkyl)-phenyl, —$(C_1-C_4$ alkyl)-$SO_2NH_2$, —$(C_1-C_4$ alkyl)-$SO_2NH(C_1-C_6$ alkyl), —$(C_1-C_4$ alkyl)-$SO_2N(C_1-C_6$ alkyl)$(C_1-C_6$ alkyl), —$SO_2NH_2$, —$SO_2NH(C_1-C_6$ alkyl), —$SO_2N(C_1-C_6$ alkyl)$(C_1-C_6$ alkyl), CN, —$(CH_2)_{0-4}$-$(C_3-C_8$ cycloalkyl), —$(C_1-C_4$ alkyl)-C(O)O—$(C_1-C_4$ alkyl), —$(C_1-C_4$ alkyl)-$R_{33}$, $C_1-C_{10}$ alkyl, $C_2-C_8$ alkenyl, —$(C_1-C_4$ alkyl)-NHC(O)—$(C_1-C_4$ alkyl), —$(CH_2)_{0-4}$—$C(O)NH_2$, —$(CH_2)_{0-4}$—$C(0)NH(C_1-C_6$ alkyl), —$(CH_2)_{0-4}$—$C(O)N(C_1-C_6$ alkyl)$(C_1-C_6$ alkyl), naphthyl, tetrahydronaphthyl, dihydronaphthyl, —$(CH_2)_{0-4}$-imidazolyl, —$(CH_2)_{0-4}$-pyrrolidinyl, oxazolidinone 3,4-dihydrobenzo[e][1,2]oxathiine 2,2-dioxide, $R_{42}$ is H, $C_1-C_6$ alkyl optionally substituted with OH; benzyl; —NHC(O)—$(C_1-C_6$ alkyl);
—NHC(O)-phenyl wherein the phenyl is optionally substituted with 1 or 2 alkyl groups;
—$CO_2$—$(C_1-C_6$ alkyl); —$CO_2$-(benzyl); or —C(O)—$(C_1-C_6$ alkyl).

2. A compound according to claim 1 wherein
$R_{35}$ is phenyl, cyclohexyl, —S-phenyl, benzodioxole, thienyl, $C_3-C_6$ alkyl, furanyl, each of which is unsubstituted or substituted with 1, 2, 3, 4, or 5 groups that are independently $C_1-C_4$ alkyl, $C_1-C_4$ alkoxy, OH, hydroxy $C_1-C_6$ alkyl, halogen, halo $C_1-C_6$ alkyl, halo $C_1-C_6$ alkoxy, —O—$(C_1-C_6$ alkyl)-phenyl, —$CO_2$—$(C_1-C_6$ alkyl), —$(C_1-C_4$ alkyl)-$(C_5-C_6$ cycloalkyl);

$R_{40}$ is phenyl, -phenyl-pyridine, biphenyl, -phenyl-benzothienyl, -phenyl-thienyl, -phenyl-furanyl, -phenyl-pyrimidinyl, -phenyl-isooxazolyl, —C(O)-pyridyl, —$(C_1-C_4$ alkyl)-O—C(O)NH-phenyl, —$(C_1-C_4$ alkyl)-O—C(O)N$(C_1-C_6$ alkyl)-phenyl, —$(C_1-C_4$ alkyl)-phenyl, —$(C_1-C_4$ alkyl)-$SO_2NH_2$, —$(C_1-C_4$ alkyl)-$SO_2NH(C_1-C_6$ alkyl), —$(C_1-C_4$ alkyl)-$SO_2N(C_1-C_6$ alkyl)$(C_1-C_6$ alkyl), CN, —$(CH_2)_{0-4}$—$(C_3-C_8$ cycloalkyl), —$(C_1-C_4$ alkyl)-C(O)O—$(C_1-C_4$ alkyl), —$(C_1-C_4$ alkyl)-$R_{33}$, $C_1-C_8$ alkyl, —$(C_1-C_4$ alkyl)-NHC(O)—$(C_1-C_4$ alkyl), —$(CH_2)_{0-4}$—$C(O)NH_2$, —$(CH_2)_{0-4}$—$C(O)NH(C_1-C_6$ alkyl), —$(CH_2)_{0-4}$—$C(O)N(C_1-C_6$ alkyl)$(C_1-C_6$ alkyl), tetrahydronapthyl, dihydronaphthyl, wherein each of the above is unsubstituted or substituted with 1, 2, 3, 4, or 5 groups that are independently halogen, $C_1-C_4$ alkyl, $C_1-C_4$ alkoxy, halo$(C_1-C_4$ alkyl), —O—$(C_1-C_4$ alkyl)-phenyl wherein the phenyl is optionally substituted with 1 or 2 halogens, —CHO, $C_1-C_4$ thioalkoxy, —$NHSO_2$—$(C_1-C_4$ alkyl), —$N(C_1-C_4$ alkyl)$SO_2$—$(C_1-C_4$ alkyl) wherein the alkyl groups are optionally substituted with 1, 2, or 3 halogens; OH, $SO_2R_{33}$, $R_{33}$;

$R_{41}$ is H, cyclohexyl, phenyl, or $C_1-C_6$ alkyl optionally substituted with 1 or 2 groups that are phenyl, hydroxy, or $C_1-C_4$ thioalkoxy; and $R_{42}$ is hydrogen or —$CH_2CN$.

3. A compound of the formula:

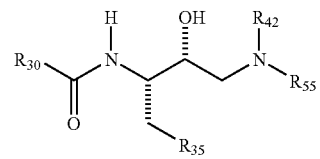

or a pharmaceutically acceptable salt thereof, wherein
$R_{30}$ is selected from the group consisting of pyrazolopyrimidinyl, isoxazolyl, triazolopyridinyl, pyridyl, furyl, naphthothienyl, thiadiazolyl, thienopyrimidinonyl, oxazolidinyl, purinyl, oxaxolyl, thiazolyl, pyridazinonyl, thiazolyl, benzoindazole, imidazopyrazolyl, pyridyl, pyrazolopyridinyl, thienopyrazolyl, oxazolyl, indazolyl, pyrrolidinyl, thienopyridinyl, dioxodihydrobenzoisothiazolonyl, triazolopyrimidinyl, thienyl, and benzooxadiazolyl, wherein each of the above is unsubstituted or substituted with 1, 2, 3, 4, or 5 groups that are independently selected from the group consisting of $C_1-C_{10}$ alkyl optionally substituted with phenyl, hydroxy, hydroxy $C_1-C_{10}$ alkyl optionally substituted with phenyl or $(C_1-C_4$ alkyl)phenyl, $C_1-C_6$ alkoxy optionally substituted with 1 or 2 hydroxy groups, —$C(O)NR_{31}R_{32}$, —$NR_{31}$—$SO_2$—$(C_1-C_6$ alkyl) wherein the alkyl group is optionally substituted with 1, 2, or 3 $R_{33}$ groups, —$SO_2$—$NH(C_1-C_6$ alkyl) wherein the alkyl group is optionally substituted with 1 or 2 $R_{33}$ groups, —$SO_2$—$N(C_1-C_6$ alkyl)$(C_1-C_6$ alkyl) wherein each alkyl group is optionally substituted with 1 or 2 $R_{33}$ groups, —$SO_2$—$NH(C_1-C_6$ alkyl)-phenyl wherein the phenyl is optionally substituted with 1 or 2 groups that are independently $C_1-C_4$ alkoxy or halogen, —O—($C_1$-$C_6$ alkyl)-phenyl, —($C_1$-$C_6$ alkyl)-O-phenyl, —($C_1$-$C_6$ alkyl)-O—($C_1$-$C_6$ alkyl)-phenyl, triazolidine-3,5-dione, halogen, —NHC(O)NH$_2$, —N($C_1$-$C_6$ alkyl)C(O)NH$_2$, —N($C_1$-$C_6$ alkyl)C(O)NH($C_1$-$C_6$ alkyl), —N($C_1$-$C_6$ alkyl)C(O)N($C_1$-$C_6$ alkyl) ($C_1$-$C_6$ alkyl), —($C_1$-$C_6$ alkyl)thienyl, —($C_1$-$C_6$ alkyl)furanyl, —S—($C_1$-$C_6$ alkyl) phenyl, —SO$_2$NR$_{31}$R$_{32}$, —C(O)—NR$_{31}$R$_{32}$, —NR$_{31}$R$_{32}$, dithiane, —NHC(S)NH$_2$, —NHC(S)NH ($C_1$-$C_6$ alkyl), —NHC(S)N($C_1$-$C_6$ alkyl)($C_1$-$C_6$ alkyl), —CO$_2$($C_1$-$C_6$ alkyl), tetrahydropyran, phenyl optionally substituted with 1 or 2 groups that are independently F, Cl or Br, pyridine, —$C_2$-$C_4$ alkynyl-phenyl, —O—$C_3$-$C_6$ cycloalkyl, —O—($C_1$-$C_6$ alkyl)-R$_{33}$, benzo[1,2,5]oxadiazole, —C(O)—($C_1$-$C_6$ alkyl) wherein the alkyl group is optionally substituted with NH$_2$, N($C_1$-$C_6$ alkyl), or N($C_1$-$C_6$ alkyl) ($C_1$-$C_6$ alkyl); —C(O)NH-phenyl, —C(O)N($C_1$-$C_6$ alkyl)-phenyl, 4,4-Dimethyl-4,5-dihydro-oxazole, —($C_1$-$C_6$ alkyl)-S-pyridine, —($C_1$-$C_6$ alkyl) —SO$_2$-pyridine, —($C_1$-$C_6$ thioalkoxy)-pyridine, wherein R$_{31}$ and R$_{32}$ at each occurrence are independently selected from the group consisting of hydrogen, $C_1$-$C_6$ alkyl, hydroxy $C_1$-$C_6$ alkyl, $C_1$-$C_6$ haloalkyl, —($C_1$-$C_6$ alkyl)-C(O)NH$_2$, —($C_1$-$C_6$ alkyl)-C(O)NH($C_1$-$C_6$ alkyl), —($C_1$-$C_6$ alkyl)—C(O)N($C_1$-$C_6$ alkyl)($C_1$-$C_6$ alkyl), —($C_1$-$C_6$ alkyl)-NH$_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), —($C_1$-$C_6$ alkyl)phenyl, —($C_1$-$C_6$ alkyl)pyridyl, —C(O) furanyl, ($C_1$-$C_6$ alkyl)-tetrahydrofuran, wherein the phenyl and pyridyl groups are unsubstituted or substituted with 1, 2, 3, 4, or 5 groups that are independently $C_1$-$C_4$ alkyl, hydroxy, $C_1$-$C_4$ alkoxy, halogen, or R$_{31}$, R$_{32}$ and the nitrogen to which they are attached form a 5, 6, or 7 membered heterocycloalkyl or a 6 membered heteroaryl ring, each of which is optionally fused to a benzene, pyridine or pyrimidine ring and each of which is optionally substituted with $C_1$-$C_6$ alkoxy, hydroxy, hydroxy $C_1$-$C_6$ alkyl, $C_1$-$C_4$ alkoxy $C_1$-$C_6$ alkyl, —C(O)NH$_2$, —C(O)NH—($C_1$-$C_6$ alkyl)-phenyl;

R$_{33}$ at each occurrence is independently, H, NH$_2$, NH($C_1$-$C_6$ alkyl), N($C_1$-$C_6$ alkyl) ($C_1$-$C_6$ alkyl), N($C_1$-$C_6$ alkyl)(phenyl);

R$_{35}$ is phenyl, $C_3$-$C_8$ cycloalkyl, —S-phenyl, benzodioxole, thienyl, $C_1$-$C_6$ alkyl, furanyl, each of which is unsubstituted or substituted with 1, 2, 3, 4, or 5 groups that are independently $C_1$-$C_4$ alkyl, $C_1$-$C_4$ alkoxy, OH, hydroxy $C_1$-$C_6$ alkyl, halogen, halo $C_1$-$C_6$ alkyl, halo $C_1$-$C_6$ alkoxy, —O—($C_1$-$C_6$ alkyl)-phenyl, —CO$_2$—($C_1$-$C_6$ alkyl), —($C_1$-$C_4$ alkyl)-($C_5$-$C_6$ cycloalkyl);

R$_{42}$ is H, $C_1$-$C_6$ alkyl, benzyl, —NHC(O)—($C_1$-$C_6$ alkyl), or —NHC(O)-phenyl wherein the phenyl is optionally substituted with 1 or 2 alkyl groups, R$_{55}$ is cyclohexyl; cyclopentyl; azepanone; phenyl; piperidinyl; —SO$_2$-phenyl; pyrrolidinyl; or 4,5,6,7-tetrahydro-thiazolo[5,4-c]pyridine; wherein each is optionally substituted with —C(O)NH$_2$; —C(O)NH ($C_1$-$C_6$ alkyl); —C(O)N($C_1$-$C_6$ alkyl)($C_1$-$C_6$ alkyl); $C_1$-$C_6$ alkoxycarbonyl; —O—($C_1$-$C_6$ alkyl)-C(O) NR$_{31}$R$_{32}$; —($C_1$-$C_6$ alkyl)-phenyl; 4,5-dihydro-2H-pyridazin-3-one; $C_5$-$C_6$ cycloalkyl which is optionally substituted with one CN group, phenyloxy wherein the phenyl group is optionally substituted with —NHC(O) $C_1$-$C_6$ alkyl, —N($C_1$-$C_6$ alkyl)-C(O)$C_1$-$C_6$ alkyl, wherein R$_{31}$, R$_{32}$ and the nitrogen to which they are attached form a pyrrolidine, piperidine, piperazine, morpholine, or thiamorpholine ring, wherein each ring is pyrimidinyl, 3,4-dihydro-2H-benzo[e][1,2]thiazine 1,1-dioxide, pyridyl, or pyrimidyl, alkoxyalkyl, -phenyl-benzothienyl, -phenyl-cyclohexyl, -phenyl-cyclopentyl, -phenyl-($C_1$-$C_6$ alkyl)-cyclopentyl, -phenyl-($C_1$-$C_6$ alkyl)-cyclohexyl, -phenyl-oxazolyl, furanyl, tetrahydrofuranyl, 7-oxa-bicyclo[2.2.1]heptyl; -dihydro-1-H-pyrazolidinone-phenyl; -phenyl-bicyclo[2.2.1]heptyl; imidazo[2,1-b][1,3]thiazolyl; azepanonyl; piperidinyl, —($C_1$-$C_6$ alkyl)-piperidinyl; bicyclo[2.2.1]heptyl; chromanonyl, —($C_1$-$C_6$ alkyl)-morpholinyl; -phenyl-C(O)-piperidinyl; tetrahydrothiazolopyridinyl, -pyrrolo-C(O)-pyrrolidinyl; -phenyl-C(O)-phenyl; -phenyl-O-phenyl; -phenyl-O-benzyl; -phenyl-tetrahydropyridazinonyl; and -phenyl-dihydropyridazinonyl;

wherein each of the above is unsubstituted or substituted with 1, 2, 3, 4, or 5 groups that are independently halogen, $C_1$-$C_8$ alkyl optionally substituted with 1 or two groups that are independently CN or OH; $C_1$-$C_6$ alkoxy, halo($C_1$-$C_8$ alkyl), halo($C_1$-$C_4$ alkoxy), —O—($C_1$-$C_4$ alkyl)-phenyl wherein the phenyl is optionally substituted with 1 or 2 halogens, CN, —CHO, $C_1$-$C_4$ thioalkoxy, —NHSO$_2$—($C_1$-$C_6$ alkyl), —N($C_1$-$C_4$ alkyl)SO$_2$—($C_1$-$C_4$ alkyl) wherein the alkyl groups are optionally substituted with 1, 2, or 3 halogens; OH; —SO$_2$R$_{33}$; R$_{33}$; $C_2$-$C_8$ alkynyl; $C_2$-$C_8$ alkenyl; thioalkoxyalkyl; —SO$_2$—($C_1$-$C_{10}$ alkyl); —NR$_{31}$R$_{32}$; —C(O)—NR$_{31}$R$_{32}$; —OC(O) R$_{33}$; $C_1$-$C_8$ alkanoyl; and —($C_1$-$C_6$ alkyl)-C(O)—($C_1$-$C_6$ alkoxy), —C(O)—($C_1$-$C_6$ alkoxy); —O—($C_1$-$C_6$ alkyl)-C(O)NR$_{31}$R$_{32}$; —CO$_2$—($C_1$-$C_6$ alkyl);

R$_{41a}$ and R$_{41}$ are independently H, cyclohexyl, phenyl, or $C_1$-$C_6$ alkyl optionally substituted with 1 or 2 groups that are phenyl, hydroxy, $C_1$-$C_4$ thioalkoxy, $C_1$-$C_4$ thioalkoxy $C_1$-$C_6$ alkyl; or —$C_1$-$C_6$ alkyl-SO$_2$—$C_1$-$C_6$ alkyl;

or R$_{40}$, R$_{41}$, and the atom to which they are attached form a $C_3$-$C_8$ cycloalkyl ring which is optionally substituted with $C_1$-$C_4$ alkyl, $C_1$-$C_4$ alkoxy, halogen, —CO$_2$NH$_2$, —CO$_2$NH($C_1$-$C_6$ alkyl), or —CO$_2$N($C_1$-$C_6$ alkyl)($C_1$-$C_6$ alkyl); a thiazolyl ring which is optionally substituted with $C_1$-$C_6$ alkyl; isoxazolyl ring which is optionally substituted with $C_1$-$C_6$ alkyl; phenyl which is optionally substituted with 1, 2, or 3 groups that are independently halogen or $C_1$-$C_6$ alkyl; -pyrrolidinyl-benzyl; piperidinyl optionally substituted with 1 or 2 groups that are independently —CO$_2$—($C_1$-$C_6$ alkyl) or —C(O)—($C_1$-$C_6$ alkyl);

and unsubstituted or substituted with 1, 2, or 3 groups that are independently OH, $C_1$-$C_6$ alkyl, $C_1$-$C_6$ alkoxy, —($C_1$-$C_6$ alkyl)-imidazole wherein the imidazole is optionally substituted with 1 or 2 $C_1$-$C_4$ alkyl groups, or hydroxy ($C_1$-$C_6$ alkyl) wherein the alkyl group is optionally substituted with 1 phenyl ring, or R$_{42}$, R$_{55}$ and the nitrogen to which they are attached form a tetrahydroisoquinolinyl, dihydroisoquinolinyl, or isoquinolinyl group which is optionally substituted by 1, 2, 3, or 4 groups that are independently halogen, $C_1$-$C_4$ alkyl, $C_1$-$C_4$ alkoxy, CN, OH, and phenyl, wherein the phenyl is optionally substituted with halogen, hydroxyl, $C_1$-$C_4$ alkoxy, and $C_1$-$C_4$ alkyl.

4. A compound according to claim 3 wherein $R_{30}$ is selected from the group consisting of pyridyl, furyl, and thienyl, wherein each of the above is unsubstituted or substituted with 1, 2, 3, 4, or 5 groups that are independently selected from the group consisting of $C_1$-$C_{10}$ alkyl, hydroxy, hydroxy $C_1$-$C_{10}$ alkyl $C_1$-$C_6$ alkoxy, —$NR_{31}$—$SO_2$—($C_1$-$C_6$ alkyl), —$SO_2$—NH($C_1$-$C_6$ alkyl), —$SO_2$—N($C_1$-$C_6$ alkyl)($C_1$-$C_6$ alkyl), halogen, —NHC(O)$NH_2$, —N($C_1$-$C_6$ alkyl)C(O)$NH_2$, —N($C_1$-$C_6$ alkyl)C(O)NH($C_1$-$C_6$ alkyl), —N($C_1$-$C_6$ alkyl)C(O)N($C_1$-$C_6$ alkyl)($C_1$-$C_6$ alkyl), —$SO_2NR_{31}R_{32}$, —C(O)—$NR_{31}R_{32}$, —$NR_{31}R_{32}$, —$C_2$-$C_4$ alkynyl-phenyl, —O—$C_3$-$C_6$ cycloalkyl, —O—($C_1$-$C_6$ alkyl)-$R_{33}$, benzo[1,2,5]oxadiazole, —C(O)—($C_1$-$C_6$ alkyl);

wherein $R_{31}$ and $R_{32}$ at each occurrence are independently selected from the group consisting of hydrogen, $C_1$-$C_6$ alkyl, hydroxy $C_1$-$C_6$ alkyl, $C_1$-$C_6$ haloalkyl, —($C_1$-$C_6$ alkyl)-C(O)$NH_2$, —($C_1$-$C_6$ alkyl)-C(O)NH($C_1$-$C_6$ alkyl), —($C_1$-$C_6$ alkyl)-C(O)N($C_1$-$C_6$ alkyl)($C_1$-$C_6$ alkyl), —($C_1$-$C_6$ alkyl)-$NH_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), benzyl, and —C(O)furanyl, wherein the phenyl and pyridyl groups are unsubstituted or substituted with 1, 2, or 3, groups that are independently $C_1$-$C_4$ alkyl, hydroxy, $C_1$-$C_4$ alkoxy, or halogen, or $R_{31}$, $R_{32}$ and the nitrogen to which they are attached form a 5, 6, or 7 membered heterocycloalkyl or a 6 membered heteroaryl ring, each of which is optionally substituted with $C_1$-$C_6$ alkoxy, hydroxy, hydroxy $C_1$-$C_6$ alkyl, $C_1$-$C_4$ alkoxy $C_1$-$C_6$ alkyl, or —C(O)$NH_2$;

$R_{35}$ is phenyl, $C_3$-$C_6$ cycloalkyl, or —S-phenyl, each of which is unsubstituted or substituted with 1, 2, or 3 groups that are independently $C_1$-$C_4$ alkyl, $C_1$-$C_4$ alkoxy, $CF_3$, $OCF_3$, halogen, —Obenzyl, —$CO_2$—($C_1$-$C_6$ alkyl), —($C_1$-$C_4$ alkyl)-($C_5$-$C_6$ cycloalkyl);

$R_{42}$ is H, $C_1$-$C_6$ alkyl, benzyl, —NHC(O)—($C_1$-$C_6$ alkyl), or —NHC(O)-phenyl wherein the phenyl is optionally substituted with 1 or 2 alkyl groups, $R_{55}$ is cyclohexyl; azepanone; phenyl; piperidinyl; —$SO_2$-phenyl; pyrrolidinyl; or 4,5,6,7-tetrahydro-thiazolo[5,4-c]pyridine; wherein each is optionally substituted with —C(O)$NH_2$; $C_1$-$C_6$ alkoxycarbonyl; —O—($C_1$-$C_6$ alkyl)-C(O)$NR_{31}R_{32}$; —($C_1$-$C_6$ alkyl)-phenyl; 4,5-dihydro-2H-pyridazin-3-one; cyclopentyl which is optionally substituted with one CN group, phenyloxy wherein the phenyl group is optionally substituted with —NHC(O)$C_1$-$C_6$ alkyl, wherein $R_{31}$, $R_{32}$ and the nitrogen to which they are attached form a pyrrolidine, piperidine, piperazine, or morpholine ring, wherein each ring is unsubstituted or substituted with 1, 2, or 3 groups that are independently OH, —($C_1$-$C_6$ alkyl)-imidazole wherein the imidazole is optionally substituted with 1 or 2 $C_1$-$C_4$ alkyl groups, or hydroxy ($C_1$-$C_6$ alkyl) wherein the alkyl group is optionally substituted with 1 phenyl ring, or $R_{42}$, $R_{55}$ and the nitrogen to which they are attached form a tetrahydroisoquinolinyl, group which is optionally substituted by 1, 2, 3, or 4 groups that are independently halogen, $C_1$-$C_4$ alkyl, $C_1$-$C_4$ alkoxy, CN, OH, and phenyl, wherein the phenyl is optionally substituted with halogen, hydroxyl, $C_1$-$C_4$ alkoxy, and $C_1$-$C_4$ alkyl.

5. A compound according to claim 3 wherein $R_{35}$ is phenyl; halophenyl, dihalophenyl; trihalophenyl; tetrahalophenyl; pentahalophenyl; phenyl substituted with one halogen and one benzyloxygroup; phenyl substituted with one halogen and one alkyl group; benzyloxyphenyl; cyclohexyl; ($C_1$-$C_4$ alkoxy)carbonylphenyl; ($C_1$-$C_4$ alkoxy)phenyl; —S-phenyl, or benzodioxole;

$R_{40}$ is phenyl, or —($C_1$-$C_4$ alkyl)-$SO_2NH_2$, wherein each of the above is unsubstituted or substituted with 1, 2, 3, 4, or 5 groups that are independently halogen, methyl, ethyl, methoxy, ethoxy, or —Obenzyl wherein the phenyl is optionally substituted with 1 or 2 halogens, $R_{42}$ is H.

6. A compound according to claim 1 wherein $R_{30}$ is pyridyl or pyrimidyl wherein each is unsubstituted or substituted with 1, 2, 3, 4, or 5 groups that are independently selected from the group consisting of $C_1$-$C_{10}$ alkyl optionally substituted with 1 phenyl or 1 CN; OH, hydroxy $C_1$-$C_{10}$ alkyl optionally substituted with phenyl or ($C_1$-$C_4$ alkyl)phenyl, $C_1$-$C_6$ alkoxy optionally substituted with 1 or 2 groups that are independently hydroxy or phenyl; haloalkyl, haloalkoxy, $(CH_2)_{0-4}C(O)NR_{31}R_{32}$, —$NR_{31}$—$SO_2$—($C_1$-$C_6$ alkyl) wherein the alkyl group is optionally substituted with 1, 2, or 3 groups that are independently halogen or $R_{33}$, —$SO_2$—NH($C_1$-$C_6$ alkyl) wherein the alkyl group is optionally substituted with 1 or 2 groups that are independently halogen, OH, alkoxy, or $R_{33}$; —($C_1$-$C_6$ alkyl)-$SO_2$—($C_1$-$C_6$ alkyl) wherein the alkyl group is optionally substituted with 1 or 2 groups that are independently halogen, OH, $C_1$-$C_4$ alkoxy, or $R_{33}$; —$SO_2$—($C_1$-$C_6$ alkyl) wherein the alkyl group is optionally substituted with 1 or 2 groups that are independently OH or $C_1$-$C_4$ alkoxy, —$SO_2$—N($C_1$-$C_6$ alkyl)($C_1$-$C_6$ alkyl) wherein each alkyl group is optionally substituted with 1 or 2 groups that are independently halogen, OH or $R_{33}$; —$SO_2$—NH($C_1$-$C_6$ alkyl)-phenyl wherein the phenyl is optionally substituted with 1 or 2 groups that are independently $C_1$-$C_4$ alkoxy or halogen, —($C_1$-$C_6$ alkyl)-O-phenyl, —($C_1$-$C_6$ alkyl)-O—($C_1$-$C_6$ alkyl)-phenyl, triazolidine-3,5-dione, halogen, —NHC(O)$NH_2$, —NHC(O)NH($C_1$-$C_6$ alkyl), —NHC(O)N($C_1$-$C_6$ alkyl)($C_1$-$C_6$ alkyl), —N($C_1$-$C_6$ alkyl)C(O)$NH_2$, —N($C_1$-$C_6$ alkyl)C(O)NH($C_1$-$C_6$ alkyl), —N($C_1$-$C_6$ alkyl)C(O)N($C_1$-$C_6$ alkyl)($C_1$-$C_6$ alkyl), —($C_1$-$C_6$ alkyl)thienyl, —($C_1$-$C_6$ alkyl)furanyl, —S—($C_1$-$C_6$ alkyl)phenyl, —$SO_2NR_{31}R_{32}$, —C(O)—$NR_{31}R_{32}$, —$NR_{31}R_{32}$, dithiane, —NHC(S)$NH_2$, —NHC(S)NH($C_1$-$C_6$ alkyl), —NHC(S)N($C_1$-$C_6$ alkyl)($C_1$-$C_6$ alkyl), —$CO_2$($C_1$-$C_6$ alkyl), tetrahydropyran, phenyl optionally substituted with 1 or 2 groups that are independently F, Cl or Br; pyridine, —$C_2$-$C_4$ alkynyl-phenyl, —O—$C_3$-$C_8$ cycloalkyl, —O—($C_1$-$C_6$ alkyl)-$R_{33}$; pyrrole optionally substituted with one or two methyl groups; 2,3-dihydro-benzofuran; benzo[1,2,5]oxadiazole, —C(O)—($C_1$-$C_{10}$ alkyl) wherein the alkyl group is optionally substituted with $NH_2$, N($C_1$-$C_6$ alkyl), or N($C_1$-$C_6$ alkyl)($C_1$-$C_6$ alkyl); —C(O)NH-phenyl, —C(O)N($C_1$-$C_6$ alkyl)-phenyl, 4,4-dimethyl-4,5-dihydro-oxazole, —($C_1$-$C_6$ alkyl)-S-pyridine, —($C_1$-$C_6$ alkyl)-$SO_2$-pyridine, —($C_1$-$C_6$ thioalkoxy)-pyridine, thiazole optionally substituted with 1 or 2 methyl groups, pyrazole, —S—($C_1$-$C_6$ alkyl) wherein the alkyl group is optionally substituted with 1 or 2 groups that are independently CN or OH; indole, ($C_1$-$C_6$ thioalkoxy)-($C_1$-$C_6$ alkyl), $C_2$-$C_8$ alkynyl, -$(CH_2)_{0-4}$—$SO_2$—($C_1$-$C_{10}$ alkyl) wherein the alkyl group is optionally substituted with OH; —NHC(O)NH($C_3$-$C_8$ cycloalkyl), —N($C_1$-$C_6$ alkyl) C(O)NH($C_3$-$C_8$ cycloalkyl), —N($C_1$-$C_6$ alkyl)C(O)N ($C_1$-$C_6$ alkyl)($C_3$-$C_8$ cycloalkyl), —NHC(O)N($C_1$-$C_6$ alkyl)($C_3$-$C_8$ cycloalkyl), —($C_1$-$C_6$ alkoxy)-($C_1$-$C_6$ thioalkoxy); —$CO_2$—($C_1$-$C_6$ alkyl) wherein the alkyl group is optionally substituted with phenyl; —C(O)-furan; and imidazolyl;

wherein $R_{31}$ and $R_{32}$ at each occurrence are independently selected from the group consisting of hydrogen, $C_1$-$C_8$ alkyl, $C_2$-$C_8$ alkenyl, hydroxy $C_1$-$C_6$ alkyl, $C_1$-$C_6$ haloalkyl, $C_1$-$C_6$ alkoxy $C_1$-$C_6$ alkyl, —$(CH_2)_{0-4}$—$SO_2$—($C_1$-$C_6$ alkyl) wherein the alkyl is optionally substituted with 1, 2, 3 or 4 independently selected halogen atoms; —$(CH_2)_{0-4}$—$SO_2$-imidazolyl, —($C_1$-$C_6$ alkyl)-C(O)$NH_2$, —($C_1$-$C_6$ alkyl)-C(O)NH($C_1$-$C_6$ alkyl), —($C_1$-$C_6$ alkyl)-C(O)N($C_1$-$C_6$ alkyl)($C_1$-$C_6$ alkyl), —($C_1$-$C_6$ alkyl)-$NH_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), —($C_1$-$C_6$ alkyl)phenyl, —($C_1$-$C_6$ alkyl)pyridyl, —C(O)furanyl, ($C_1$-$C_6$ alkyl)-tetrahydrofuran, cyclopropyl, cyclobutyl, cyclopentyl, cyclohexyl, —$CO_2$—($C_1$-$C_6$ alkyl), —($C_1$-$C_6$ alkyl)-furanyl, —$(CH_2)_{0-4}$—$SO_2$-thienyl, -pyrrolidinyl-benzyl, —($C_1$-$C_6$ thioalkoxy)-($C_1$-$C_6$ alkyl), —C(O)—(C$_1$-$C_6$ alkyl), ($C_1$-$C_6$ alkoxy), —($C_2$-$C_6$ alkenyloxy), —($C_1$-$C_6$ alkyl)-$CO_2$—($C_1$-$C_6$ alkyl), and —C(O)-piperidinyl optionally substituted with $C_1$-$C_6$ alkyl; wherein the phenyl and pyridyl groups are unsubstituted or substituted with 1, 2, 3, 4, or 5 groups that are independently $C_1$-$C_4$ alkyl, hydroxy, $C_1$-$C_4$ alkoxy, halogen, or $R_{31}$, $R_{32}$ and the nitrogen to which they are attached form a 5, 6, or 7 membered heterocycloalkyl or a 6 membered heteroaryl ring, each of which is optionally fused to a benzene, pyridine or pyrimidine ring and each of which is optionally substituted with $C_1$-$C_6$ alkoxy, hydroxy, hydroxy $C_1$-$C_6$ alkyl, $C_1$-$C_4$ alkoxy $C_1$-$C_6$ alkyl, —C(O)$NH_2$, —C(O)NH—($C_1$-$C_6$ alkyl)-phenyl;

$R_{33}$ at each occurrence is independently, H, $NH_2$, NH($C_1$-$C_6$ alkyl), N($C_1$-$C_6$ alkyl)($C_1$-$C_6$ alkyl), N($C_1$-$C_6$ alkyl)(phenyl), N($C_1$-$C_6$ alkyl)(benzyl);

$R_{35}$ is phenyl; halophenyl, dihalophenyl; trihalophenyl; tetrahalophenyl; pentahalophenyl; phenyl substituted with one halogen and one benzyloxy group; phenyl substituted with one halogen and one alkyl group; benzyloxyphenyl; cyclohexyl; ($C_1$-$C_4$ alkoxy)carbonylphenyl; ($C_1$-$C_4$ alkoxy)phenyl; —S-phenyl, or benzodioxole; and $R_{40}$ is phenyl, -phenyl-pyridine, biphenyl, -phenyl-benzothienyl, -phenyl-thienyl, -phenyl-furanyl, -phenyl-pyrimidinyl, -phenyl-isoxazolyl, —($C_1$-$C_4$ alkyl)-O—C(O)NH-phenyl, —($C_1$-$C_4$ alkyl)-O—C(O)N($C_1$-$C_6$ alkyl)-phenyl, —($C_1$-$C_4$ alkyl)-$SO_2NH_2$, CN, —($C_1$-$C_4$ alkyl)-($C_3$-$C_6$ cycloalkyl), —($C_1$-$C_4$ alkyl)-C(O)O—($C_1$-$C_4$ alkyl), —($C_1$-$C_4$ alkyl)-$R_{33}$, $C_1$-$C_8$ alkyl, pyridyl, or pyrimidyl, wherein each of the above is unsubstituted or substituted with 1, 2, or 3 groups that are independently halogen, $C_1$-$C_4$ alkyl, $C_1$-$C_4$ alkoxy, $CF_3$, —O—($C_1$-$C_4$ alkyl)-phenyl wherein the phenyl is optionally substituted with 1 or 2 halogens, —CHO, or —$NHSO_2$—($C_1$-$C_4$ alkyl).

7. A compound of the formula

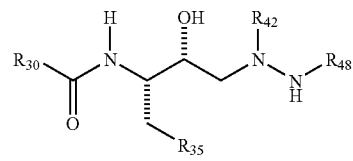

or a pharmaceutically acceptable salt thereof, wherein $R_{30}$ is selected from the group consisting of pyrazolopyrimidinyl, isoxazolyl, triazolopyridinyl, pyridyl, furyl, naphthothienyl, thiadiazolyl, thienopyrimidinonyl, oxazolidinyl, pyrazinyl mono N-oxide, benzofuranyl, pyrazolyl, -isoxazolyl-phenyl, benzimidazolyl, indolyl, isoquinolinyl, -thienyl-thienyl, benzothienyl, quinolinyl, thieno[2,3-b)]thiophene, benzoxazole; benzo[b] thiophene 1,1-dioxide; isoindolyl, purinyl, oxaxolyl, thiazolyl, pyridazinonyl, thiazolyl, benzoindazole, imidazopyrazolyl, pyridyl N-oxide, pyrazolopyridinyl, thienopyrazolyl, oxazolyl, indazolyl, thienopyridinyl, triazolopyrimidinyl, thienyl, and benzooxadiazolyl, wherein each of the above is unsubstituted or substituted with 1, 2, 3, 4, or 5 groups that are independently selected from the group consisting of $C_1$-$C_{10}$ alkyl optionally substituted with 1 phenyl or 1 CN; OH, hydroxy $C_1$-$C_{10}$ alkyl optionally substituted with phenyl or ($C_1$-$C_4$ alkyl)phenyl, $C_1$-$C_6$ alkoxy optionally substituted with 1 or 2 groups that are independently hydroxy or phenyl; haloalkyl, haloalkoxy, $(CH_2)_{0-4}C(O)NR_{31}R_{32}$, —$NR_{31}$—$SO_2$—($C_1$-$C_6$ alkyl) wherein the alkyl group is optionally substituted with 1, 2, or 3 groups that are independently halogen or $R_{33}$, —$SO_2$—NH($C_1$-$C_6$ alkyl) wherein the alkyl group is optionally substituted with 1 or 2 groups that are independently halogen, OH, alkoxy, or $R_{33}$; —($C_1$-$C_6$ alkyl)-$SO_2$—($C_1$-$C_6$ alkyl) wherein the alkyl group is optionally substituted with 1 or 2 groups that are independently halogen, OH, $C_1$-$C_4$ alkoxy, or $R_{33}$; —$SO_2$—($C_1$-$C_6$ alkyl) wherein the alkyl group is optionally substituted with 1 or 2 groups that are independently OH or $C_1$-$C_4$ alkoxy, —$SO_2$—N($C_1$-$C_6$ alkyl)($C_1$-$C_6$ alkyl) wherein each alkyl group is optionally substituted with 1 or 2 groups that are independently halogen, OH or $R_{33}$; —$SO_2$—NH($C_1$-$C_6$ alkyl)-phenyl wherein the phenyl is optionally substituted with 1 or 2 groups that are independently $C_1$-$C_4$ alkoxy or halogen, —O—($C_1$-$C_6$ alkyl)-phenyl, —($C_1$-$C_6$ alkyl)-O-phenyl, —($C_1$-$C_6$ alkyl)-O—($C_1$-$C_6$ alkyl)-phenyl, triazolidine-3,5-dione, halogen, —NHC(O)$NH_2$, —NHC(O)NH($C_1$-$C_6$ alkyl), —NHC(O)N($C_1$-$C_6$ alkyl)($C_1$-$C_6$ alkyl), —N($C_1$-$C_6$ alkyl)C(O)$NH_2$, —N($C_1$-$C_6$ alkyl)C(O)NH($C_1$-$C_6$ alkyl), —N($C_1$-$C_6$ alkyl)C(O)N($C_1$-$C_6$ alkyl)($C_1$-$C_6$ alkyl), —($C_1$-$C_6$ alkyl)thienyl, —($C_1$-$C_6$ alkyl)furanyl, —S—($C_1$-$C_6$ alkyl)phenyl, —$SO_2NR_{31}R_{32}$, —C(O)—$NR_{31}R_{32}$, —$NR_{31}R_{32}$, dithiane, —NHC(S)$NH_2$, —NHC(S)NH($C_1$-$C_6$ alkyl), —NHC(S)N($C_1$-$C_6$ alkyl)($C_1$-$C_6$ alkyl), —$CO_2$($C_1$-$C_6$ alkyl), tetrahydropyran, phenyl optionally substituted with 1 or 2 groups that are independently F, Cl or Br; pyridine, —$C_2$-$C_4$ alkynyl-phenyl, —O—$C_3$-$C_8$cycloalkyl, —O—($C_1$-$C_6$ alkyl)-$R_{33}$; pyrrole optionally substituted with one or two methyl groups; 2,3-dihydro-benzofuran; benzo[1,2,5]oxadiazole, —C(O)—($C_1$-$C_{10}$ alkyl) wherein the alkyl group is optionally substituted with $NH_2$, N($C_1$-$C_6$ alkyl), or N($C_1$-$C_6$ alkyl)($C_1$-$C_6$ alkyl); —C(O)NH-phenyl, —C(O)N($C_1$-$C_6$ alkyl)-phenyl, 4,4-dimethyl-4,5-dihydro-oxazole, —($C_1$-$C_6$ alkyl)-S-pyridine, —($C_1$-$C_6$ alkyl)-$SO_2$-pyridine, —($C_1$-$C_6$ thioalkoxy)-pyridine, thiazole optionally substituted with 1 or 2 methyl groups, pyrazole, S—($C_1$-$C_6$ alkyl), indole, ($C_1$-$C_6$ thioalkoxy)-($C_1$-$C_6$ alkyl), $C_2$-$C_8$ alkynyl, —$CO_2$—($C_1$-$C_6$ alkyl), $C_1$-$C_{10}$ alkanoyl; —($CH_2$)$_{0-4}$—$SO_2$—($C_1$-$C_{10}$ alkyl) wherein the alkyl group is optionally substituted with OH;

wherein $R_{31}$ and $R_{32}$ at each occurrence are independently selected from the group consisting of hydrogen, $C_1$-$C_8$ alkyl, $C_2$-$C_8$ alkenyl, hydroxy $C_1$-$C_6$ alkyl, $C_1$-$C_6$ haloalkyl, $C_1$-$C_6$ alkoxy $C_1$-$C_6$ alkyl, —($CH_2$)$_{0-4}$—$SO_2$—($C_1$-$C_6$ alkyl) wherein the alkyl is optionally substituted with 1, 2, 3 or 4 independently selected halogen atoms; —($CH_2$)$_{0-4}$—$SO_2$-imidazolyl, —($C_1$-$C_6$ alkyl)-C(O)$NH_2$, —($C_1$-$C_6$ alkyl)-C(O)NH($C_1$-$C_6$ alkyl), —($C_1$-$C_6$ alkyl)-C(O)N($C_1$-$C_6$ alkyl)($C_1$-$C_6$ alkyl), —($C_1$-$C_6$ alkyl)-$NH_2$, —($C_1$-$C_6$ alkyl)-NH($C_1$-$C_6$ alkyl), —($C_1$-$C_6$ alkyl)-N($C_1$-$C_6$ alkyl)($C_1$-$C_6$ alkyl), —($C_1$-$C_6$ alkyl)phenyl, —($C_1$-$C_6$ alkyl)pyridyl, —C(O)furanyl, ($C_1$-$C_6$ alkyl)-tetrahydrofuran, cyclopropyl, cyclobutyl, cyclopentyl, cyclohexyl, —$CO_2$—($C_1$-$C_6$ alkyl), —($C_1$-$C_6$ alkyl)-furanyl, —($CH_2$)$_{0-4}$—$SO_2$-thienyl, wherein the phenyl and pyridyl groups are unsubstituted or substituted with 1, 2, 3, 4, or 5 groups that are independently $C_1$-$C_4$ alkyl, hydroxy, $C_1$-$C_4$ alkoxy, halogen, or $R_{31}$, $R_{32}$ and the nitrogen to which they are attached form a 5, 6, or 7 membered heterocycloalkyl or a 6 membered heteroaryl ring, each of which is optionally fused to a benzene, pyridine or pyrimidine ring and each of which is optionally substituted with $C_1$-$C_6$ alkoxy, hydroxy, hydroxy $C_1$-$C_6$ alkyl, $C_1$-$C_4$ alkoxy $C_1$-$C_6$ alkyl, —C(O)$NH_2$, —C(O)NH—($C_1$-$C_6$ alkyl)-phenyl;

$R_{33}$ at each occurrence is independently, H, $NH_2$, NH($C_1$-$C_6$ alkyl), N($C_1$-$C_6$ alkyl)($C_1$-$C_6$ alkyl), N($C_1$-$C_6$ alkyl)(phenyl), N($C_1$-$C_6$ alkyl)(benzyl);

$R_{35}$ is phenyl, $C_3$-$C_8$ cycloalkyl, —S-phenyl, benzodioxole, thienyl, $C_1$-$C_6$ alkyl, furanyl, imidazolyl, each of which is unsubstituted or substituted with 1, 2, 3, 4, or 5 groups that are independently $C_1$-$C_4$ alkyl, $C_1$-$C_4$ alkoxy, OH, hydroxy $C_1$-$C_6$ alkyl, halogen, halo $C_1$-$C_6$ alkyl, halo $C_1$-$C_6$ alkoxy, —O—($C_1$-$C_6$ alkyl)-phenyl, —$CO_2$—($C_1$-$C_6$ alkyl), —($C_1$-$C_4$ alkyl)-( $C_5$-$C_6$ cycloalkyl), or ($CH_2$)$_{0-4}$CN;

$R_{42}$ is H, $C_1$-$C_6$ alkyl optionally substituted with OH; benzyl; —NHC(O)—($C_1$-$C_6$ alkyl); —NHC(O)-phenyl wherein the phenyl is optionally substituted with 1 or 2 alkyl groups; and $R_{48}$ is —C(O)$R_{49}$, wherein $R_{49}$ is phenyl, or $C_1$-$C_8$ alkyl, each of which is optionally substituted with halogen, $C_1$-$C_4$ alkoxy, $C_1$-$C_4$ alkyl, or $R_{33}$.

8. A compound of the formula

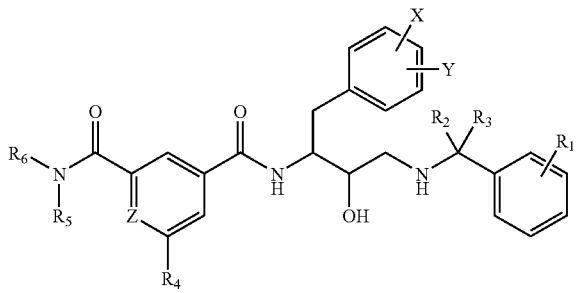

or a pharmaceutically acceptable salt thereof, wherein $R_1$ is $C_1$-$C_4$ alkyl, $C_2$-$C_4$ alkynyl, or $CF_3$;

$R_2$ and $R_3$ are both hydrogen; or $R_2$ and $R_3$ and the carbon to which they are attached form a cyclopropyl ring;

$R_4$ is oxazolyl optionally substituted with methyl, thiazolyl, $C_2$-$C_4$ alkynyl, or $C_1$-$C_4$ alkyl;

$R_5$ is $C_1$-$C_4$ alkyl;

$R_6$ is $C_1$-$C_4$ alkyl;

X and Y are independently halogen;

Z is N.

9. A compound of the formula

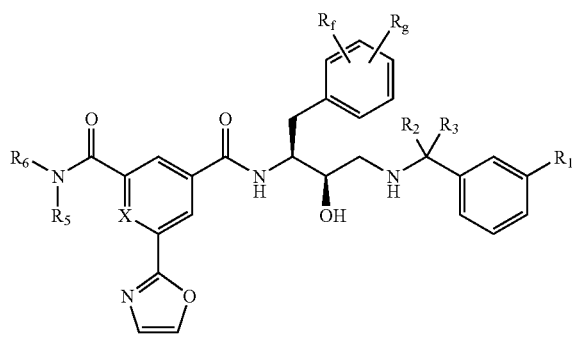

or a pharmaceutically acceptable salt thereof, wherein

X is nitrogen;

$R_1$ is $C_2$-$C_3$ alkyl, amino, mono($C_1$-$C_3$)alkylamino, di($C_1$-$C_3$)alkylamino, amino($C_1$-$C_3$)alkyl, mono($C_1$-$C_3$)alkylamino($C_1$-$C_2$)alkyl, or di($C_1$-$C_3$)alkylamino($C_1$-$C_2$)alkyl;

$R_2$ and $R_3$ are both hydrogen; or $R_f$ and $R_g$ are both hydrogen or independently halogen;

$R_5$ and $R_6$ are independently methyl or $C_2$-$C_3$-$C_4$ alkyl, where at least one of $R_5$ and $R_6$ is not methyl.

10. A compound of the formula

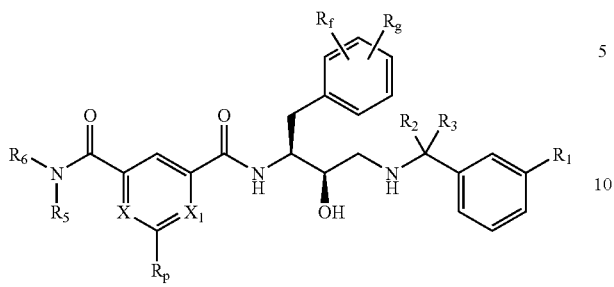

or a pharmaceutically acceptable salt thereof, wherein
one of X or $X_1$ is nitrogen or $N^+$—$O^-$ while the other is CH;
$R_1$ is $C_2$-$C_4$ alkynyl, cyano, or $C_1$-$C_3$ alkyl;
$R_2$ and $R_3$ are both hydrogen; or
$R_2$ and $R_3$ together form a 3-membered ring with the carbon atom to which they are attached;
$R_f$ and $R_g$ are independently halogen;
$R_p$ is hydrogen, $C_1$-$C_2$ alkyl, or oxazolyl; and
$R_5$ and $R_6$ are independently $C_3$-$C_4$ alkyl.

11. A compound according to claim 10, wherein X is nitrogen; $R_1$ is $C_2$-$C_3$ alkynyl; $R_2$ and $R_3$ together form a 3-membered ring with the carbon atom to which they are attached; and $R_p$ is $C_1$-$C_2$ alkyl.

12. A compound according to claim 10, wherein X is nitrogen; $R_1$ is $C_1$-$C_2$ alkyl; $R_2$ and $R_3$ are hydrogen; and $R_p$ is hydrogen, $C_1$-$C_2$ alkyl, cyano or oxazol-2-yl.

13. A compound according to claim 10, wherein X is nitrogen; $R_1$ is $C_2$-$C_3$ alkynyl; $R_2$ and $R_3$ together form a 3-membered ring with the carbon atom to which they are attached; and $R_p$ is $C_1$-$C_2$ alkyl.

14. A compound according to claim 11, wherein $R_f$ and $R_g$ are both chloro or fluoro; and $R_5$ and $R_6$ are independently propyl or butyl.

15. A compound according to claim 1 of the formula

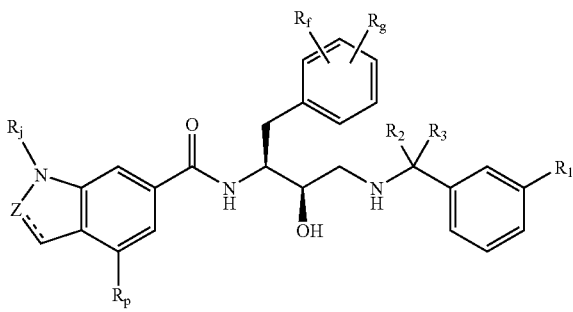

or a pharmaceutically acceptable salt thereof, wherein
Z is CH and the dashed line represents a double bond;
$R_1$ is $C_2$-$C_3$ alkyl;
$R_2$ and $R_3$ are both hydrogen;
$R_f$ and $R_g$ are independently halogen;
$R_p$ is hydrogen, cyano, $C_1$-$C_3$ alkyl, amino, —$(CH_2)_{0-4}$—N(—H or $R_{N-5}$)—$SO_2$—$R_{N-2}$, 2-oxazolyl, or 1-pyrrolyl optionally substituted in the 2 and 5 positions with $C_1$-$C_2$ alkyl;
$R_j$ is $C_1$-$C_5$ alkyl
$R_{N-2}$ is —$C_1$-$C_8$ alkyl optionally substituted with —NR'R";
$R_{N-5}$ is hydrogen or $(C_1$-$C_3)$alkyl; and R' and R" at each occurrence are the same or different and are —H, $C_1$-$C_4$ alkyl.

16. A compound of according to claim 1 the formula

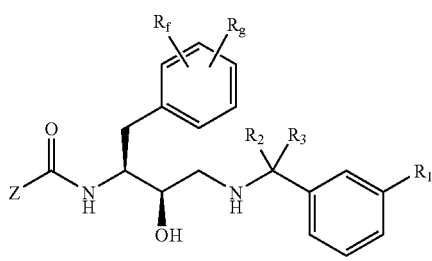

or a pharmaceutically acceptable salt thereof, wherein
Z is

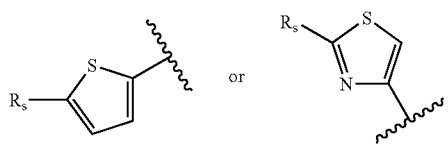

$R_1$ is $C_1$-$C_3$ alkyl or halogen;
$R_2$ and $R_3$ are both hydrogen;
$R_5$ is $C_1$-$C_3$ alkylsulfonyl, $C_1$-$C_3$ alkylsulfonyl$(C_1$-$C_3)$ alkyl, —$NHSO_2(C_1$-$C_2$ alkyl), or —$N(C_1$-$C_2$ alkyl)$SO_2$ $(C_1$-$C_2$ alkyl); and
$R_f$ and $R_g$ are independently halogen.

17. A compound of the formula

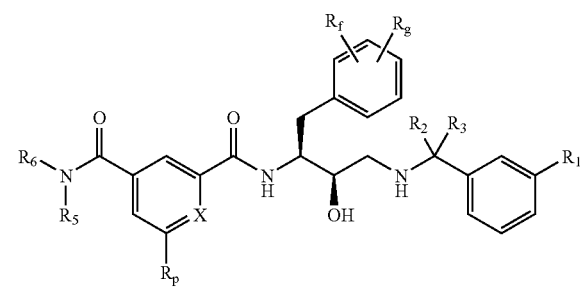

or a pharmaceutically acceptable salt thereof, wherein
X is nitrogen or $N^+$—$O^-$;
$R_1$ is $C_2$-$C_4$ alkynyl or $C_1$-$C_3$ alkyl;
$R_2$ and $R_3$ are both hydrogen; or
$R_2$ and $R_3$ together form a 3-membered ring with the carbon atom to which they are attached;
$R_f$ and $R_g$ are independently halogen;
$R_p$ is hydrogen or $C_1$-$C_2$ alkyl; and
$R_5$ and $R_6$ are independently $C_3$-$C_4$ alkyl.

18. A compound according to claim 17, wherein X is nitrogen; $R_p$ is $C_1$-$C_2$ alkyl; and $R_1$ is ethyl.

19. A compound of the formula

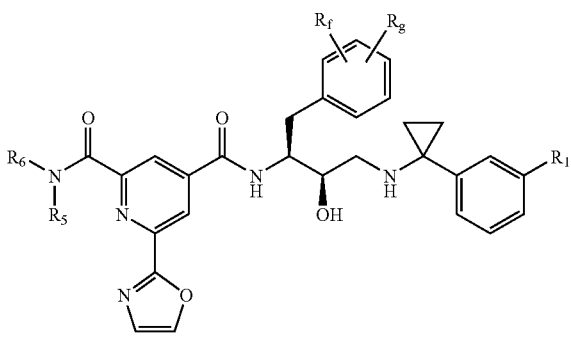

or a pharmaceutically acceptable salt thereof, wherein
$R_1$ is $C_2$-$C_3$ alkynyl or $C_1$-$C_3$ alkyl;
$R_f$ and $R_g$ are independently halogen;
$R_5$ and $R_6$ are independently $C_1$-$C_4$ alkyl.

20. A compound of the formula

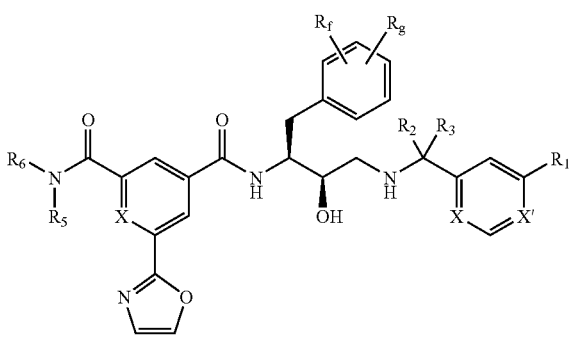

or a pharmaceutically acceptable salt thereof, wherein
one of X and X' is CH and the other is N;
$R_1$ is $C_2$-$C_4$ alkynyl; amino($C_1$-$C_3$)alkyl, mono($C_1$-$C_3$) alkylamino($C_1$-$C_2$)alkyl, or di($C_1$-$C_3$) alkylamino($C_1$-$C_2$)alkyl;
$R_2$ and $R_3$ are both hydrogen; or
$R_2$ and $R_3$ together form a 3-membered ring with the carbon atom to which they are attached;
$R_f$ and $R_g$ are independently halogen;
$R_5$ and $R_6$ are independently $C_1$-$C_3$-$C_4$ alkyl.

21. A compound according to claim 1 of the formula

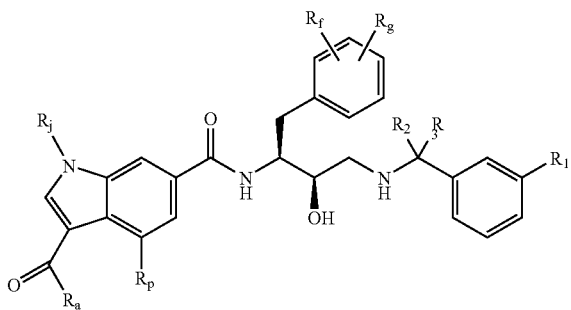

or a pharmaceutically acceptable salt thereof, wherein
$R_1$ is $C_2$-$C_3$ alkyl;
$R_2$ and $R_3$ are both hydrogen;
$R_f$ and $R_g$ are independently halogen;
$R_p$ is hydrogen, cyano, $C_1$-$C_3$ alkyl, amino, N—($C_1$-$C_3$ alkylsulfonyl)-N—(($C_1$-$C_3$)alkyl)amino, 2-oxazolyl, or 1-pyrrolyl optionally substituted in the 2 and 5 positions with $C_1$-$C_2$ alkyl;
$R_a$ is $C_1$-$C_3$ alkyl; and
$R_j$ is $C_1$-$C_5$ alkyl.

22. A compound according to claim 1 of the formula

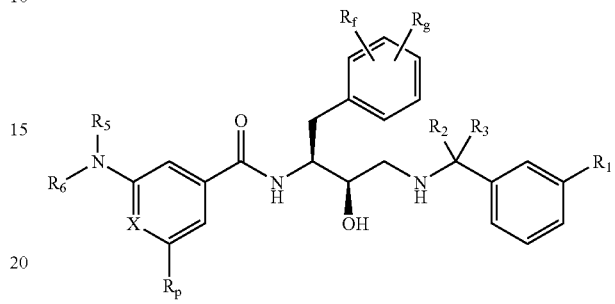

or a pharmaceutically acceptable salt thereof, wherein
X is nitrogen or $N^+$—$O^-$;
$R_1$ is $C_2$-$C_4$ alkynyl, cyano, $C_1$-$C_3$ alkyl, or $CF_3$;
$R_2$ and $R_3$ are both hydrogen; or
$R_2$ and $R_3$ together form a 3-membered ring with the carbon atom to which they are attached;
$R_f$ and $R_g$ are independently halogen;
$R_p$ is hydrogen, or $C_1$-$C_2$ alkyl; and
$R_5$ and $R_6$ are independently $C_1$-$C_4$ alkyl.

23. A compound according to claim 22, wherein X is N.

24. A compound according to claim 1 which is
$N^4$-((1S,2R)-1-(3,5-difluorobenzyl)-3-{[1-(3-ethylphenyl)cyclopropyl]amino}-2-hydroxypropyl)-6-methyl-$N^2$,$N^2$-dipropylpyridine-2,4-dicarboxamide;
2-(2,5-Dimethyl-pyrrol-1-yl)-thiophene-3-carboxylic acid [1-(3,5-difluoro-benzyl)-3-(3-ethyl-benzylamino)-2-hydroxy-propyl]-amide;
4-Phenyl-[1,2,3]thiadiazole-5-carboxylic acid [1-(3,5-difluoro-benzyl)-3-(3-ethyl-benzylamino)-2-hydroxy-propyl]-amide;
2-Methanesulfonylamino-oxazole-4-carboxylic acid {1-benzyl-3-[N-ethyl-N'-(3-ethyl-benzoyl)-hydrazino]-2-hydroxy-propyl}-amide;
2-Methanesulfonylamino-oxazole-4-carboxylic acid {1-benzyl-3-[N-ethyl-N'-(4-methyl-pentanoyl)-hydrazino]-2-hydroxy-propyl}-amide;
4-Acetylamino-1-methyl-1H-pyrrole-2-carboxylic acid [1-(3,5-difluoro-benzyl)-3-(3-ethyl-benzylamino)-2-hydroxy-propyl]-amide;
2-Ethyl-5-thiophen-2-yl-2H-pyrazole-3-carboxylic acid [1-(3,5-difluoro-benzyl)-3-(3-ethyl-benzylamino)-2-hydroxy-propyl]-amide;
2-Methanesulfonylamino-oxazole-4-carboxylic acid [3-(N'-acetyl-N-ethyl-hydrazino)-1-benzyl-2-hydroxy-propyl]-amide;
2-Methanesulfonylamino-oxazole-4-carboxylic acid [3-(N'-benzoyl-N-ethyl-hydrazino)-1-benzyl-2-hydroxy-propyl]-amide;
6-Methyl-4-oxo-1-phenyl-1,4-dihydro-pyridazine-3-carboxylic acid [1-(3,5-difluoro-benzyl)-3-(3-ethyl-benzylamino)-2-hydroxy-propyl]-amide;
2-Methanesulfonylamino-thiazole-4-carboxylic acid {1-benzyl-3-[N-ethyl-N'-(3-ethyl-benzoyl)-hydrazino]-2-hydroxy-propyl}-amide;

4-Methyl-2-phenyl-oxazole-5-carboxylic acid [1-(3,5-difluoro-benzyl)-3-(3-ethyl-benzylamino)-2-hydroxy-propyl]-amide;
2-Methanesulfonylamino-thiazole-4-carboxylic acid [3-(N'-acetyl-N-ethyl-hydrazino)-1-benzyl-2-hydroxy-propyl]-amide;
2-p-Tolyl-thiazole-4-carboxylic acid [1-(3,5-difluoro-benzyl)-3-(3-ethyl-benzylamino)-2-hydroxy-propyl]-amide;
2-Phenoxymethyl-thiazole-4-carboxylic acid [1-(3,5-difluoro-benzyl)-3-(3-ethyl-benzylamino)-2-hydroxy-propyl]-amide;
[1,2,5]Thiadiazole-3-carboxylic acid [1-(3,5-difluoro-benzyl)-3-(3-ethyl-benzylamino)-2-hydroxy-propyl]-amide;
2-m-Tolyl-thiazole-4-carboxylic acid [1-(3,5-difluoro-benzyl)-3-(3-ethyl-benzylamino)-2-hydroxy-propyl]-amide;
2-(2-Chloro-phenyl)-thiazole-4-carboxylic acid [1-(3,5-difluoro-benzyl)-3-(3-ethyl-benzylamino)-2-hydroxy-propyl]-amide;
2-Acetylamino-5-chloro-thiophene-3-carboxylic acid [1-(3,5-difluoro-benzyl)-3-(3-ethyl -benzylamino)-2-hydroxy-propyl]-amide;
4-(4-Methoxy-phenyl)-thiophene-2-carboxylic acid [1-(3,5-difluoro-benzyl)-3-(3-ethyl-benzylamino)-2-hydroxy-propyl]-amide;
1-(4-Fluoro-phenyl)-5-methyl-1H-[1,2,4]triazole-3-carboxylic acid [1-(3,5-difluoro-benzyl)-3-(3-ethyl-benzylamino)-2-hydroxy-propyl]-amide;
6-Chloro-4-trifluoromethyl-pyridine-2-carboxylic acid [1-(3,5-difluoro-benzyl)-3-(3-ethyl-benzylamino)-2-hydroxy-propyl]-amide;
4-Methoxy-thiophene-3-carboxylic acid [1-(3,5-difluoro-benzyl)-3-(3-ethyl-benzylamino)-2-hydroxy-propyl]-amide;
2,5-Dimethyl-1-pyridin-4-ylmethyl-1H-pyrrole-3-carboxylic acid [1-(3,5-difluoro-benzyl)-3-(3-ethyl-benzylamino)-2-hydroxy-propyl]-amide;
2-Methyl-5-thiophen-2-yl-furan-3-carboxylic acid [1-(3,5-difluoro-benzyl)-3-(3-ethyl-benzylamino)-2-hydroxy-propyl]-amide;
3-Chloro-5-phenyl-isothiazole-4-carboxylic acid [1-(3,5-difluoro-benzyl)-3-(3-ethyl-benzylamino)-2-hydroxy-propyl]-amide;
N-[1-(3,5-Difluoro-benzyl)-3-(3-ethyl-benzylamino)-2-hydroxy-propyl]-5-phenylethynyl-nicotinamide;
4,7-Dimethoxy-benzofuran-5-carboxylic acid [1-(3,5-difluoro-benzyl)-3-(3-ethyl-benzylamino)-2-hydroxy-propyl]-amide;
[1,6]Naphthyridine-2-carboxylic acid [1-(3,5-difluoro-benzyl)-3-(3-ethyl-benzylamino)-2-hydroxy-propyl]-amide;
8-Cyano-4-hydroxy-quinoline-3-carboxylic acid [1-(3,5-difluoro-benzyl)-3-(3-ethyl-benzylamino)-2-hydroxy-propyl]-amide;
2-Pyridin-3-yl-thiazole-4-carboxylic acid [1-(3,5-difluoro-benzyl)-3-(3-ethyl-benzylamino)-2-hydroxy-propyl]-amide;
5-Chloro-benzofuran-2-carboxylic acid [1-(3,5-difluoro-benzyl)-3-(3-ethyl-benzylamino)-2-hydroxy-propyl]-amide;
N-{[1-(3,5-Difluoro-benzyl)-3-(3-ethyl-benzylamino)-2-hydroxy-propylcarbamoyl]-methyl}-nicotinamide;
4-Chloro-6-methyl-quinoline-2-carboxylic acid [1-(3,5-difluoro-benzyl)-3-(3-ethyl-benzylamino)-2-hydroxy-propyl]-amide;
2-Methyl-pyrimidine-5-carboxylic acid [1-(3,5-difluoro-benzyl)-3-(3-ethyl-benzylamino)-2-hydroxy-propyl]-amide;
4-Methyl-oxazole-5-carboxylic acid [1-(3,5-difluoro-benzyl)-3-(3-ethyl-benzylamino)-2-hydroxy-propyl]-amide;
1H-Indole-5-carboxylic acid [1-(3,5-difluoro-benzyl)-3-(3-ethyl-benzylamino)-2-hydroxy-propyl]-amide;
6-Chloro-1H-indole-2-carboxylic acid [1-(3,5-difluoro-benzyl)-3-(3-ethyl-benzylamino)-2-hydroxy-propyl]-amide;
Thiophene-3-carboxylic acid [1-(3,5-difluoro-benzyl)-3-(3-ethyl-benzylamino)-2-hydroxy-propyl]-amide;
2-Methyl-oxazole-4-carboxylic acid [1-(3,5-difluoro-benzyl)-3-(3-ethyl-benzylamino)-2-hydroxy-propyl]-amide;
6-Hydroxy-2-methylsulfanyl-pyrimidine-4-carboxylic acid [1-(3,5-difluoro-benzyl)-3-(3-ethyl-benzylamino)-2-hydroxy-propyl]-amide;
2,5-Dimethyl-furan-3-carboxylic acid [1-(3,5-difluoro-benzyl)-3-(3-ethyl-benzylamino)-2-hydroxy-propyl]-amide;
N-[1-(3,5-Difluoro-benzyl)-3-(3-ethyl-benzylamino)-2-hydroxy-propyl]-nicotinamide;
Furan-2-carboxylic acid [1-(3,5-difluoro-benzyl)-3-(3-ethyl-benzylamino)-2-hydroxy-propyl]-amide;
1H-Indole-3-carboxylic acid [1-(3,5-difluoro-benzyl)-3-(3-ethyl-benzylamino)-2-hydroxy-propyl]-amide;
[2,3']Bithiophenyl-5-carboxylic acid [1-(3,5-difluoro-benzyl)-3-(3-ethyl-benzylamino)-2-hydroxy-propyl]-amide;
5-Methoxy-thiophene-2-carboxylic acid [1-(3,5-difluoro-benzyl)-3-(3-ethyl-benzylamino)-2-hydroxy-propyl]-amide;
4-Phenyl-thiophene-2-carboxylic acid [1-(3,5-difluoro-benzyl)-3-(3-ethyl-benzylamino)-2-hydroxy-propyl]-amide;
2-Oxo-2,3-dihydro-benzooxazole-6-carboxylic acid [1-(3,5-difluoro-benzyl)-3-(3-ethyl-benzylamino)-2-hydroxy-propyl]-amide;
Thieno[3,2-c]pyridine-2-carboxylic acid [1-(3,5-difluoro-benzyl)-3-(3-ethyl-benzylamino)-2-hydroxy-propyl]-amide;
1-Methyl-1H-indole-3-carboxylic acid [1-(3,5-difluoro-benzyl)-3-(3-ethyl-benzylamino)-2-hydroxy-propyl]-amide;
Benzo[b]thiophene-3-carboxylic acid [1-(3,5-difluoro-benzyl)-3-(3-ethyl-benzylamino)-2-hydroxy-propyl]-amide;
4-Oxy-3-propyl-pyrazine-2-carboxylic acid [1-(3,5-difluoro-benzyl)-3-(3-ethyl-benzylamino)-2-hydroxy-propyl]-amide;
1,1,3-Trioxo-2,3-dihydro-1H-1λ6-benzo[d]isothiazole-6-carboxylic acid [1-(3,5-difluoro-benzyl)-3-(3-ethyl-benzylamino)-2-hydroxy-propyl]-amide;
2-Hydroxy-6-methyl-quinoline-4-carboxylic acid [1-(3,5-difluoro-benzyl)-3-(3-ethyl-benzylamino)-2-hydroxy-propyl]-amide;
N-{(1S,2R)-1-(3,5-difluorobenzyl)-3-[(3-ethylbenzyl)amino]-2-hydroxypropyl}-2-[(methylsulfonyl)amino]-1,3-thiazole-4-carboxamide;
N-{(1S,2R)-1-(3,5-difluorobenzyl)-3-[(3-ethylbenzyl)amino]-2-hydroxypropyl}-3-hydroxyisoxazole-5-carboxamide;
N-{(1S,2R)-1-(3,5-difluorobenzyl)-3-[(3-ethylbenzyl)amino]-2-hydroxypropyl}-4-methyl-4H,6H-pyrrolo[1,2-a][4,1]benzoxazepine-4-carboxamide;

N-{(1S,2R)-1-(3,5-difluorobenzyl)-3-[(3-ethylbenzyl)amino]-2-hydroxypropyl}-2,8-dimethylquinoline-3-carboxamide;

3-(benzyloxy)-N-{(1S,2R)-1-(3,5-difluorobenzyl)-3-[(3-ethylbenzyl)amino]-2-hydroxypropyl}isoxazole-5-carboxamide;

4-[(butylthio)methyl]-N-{(1S,2R)-1-(3,5-difluorobenzyl)-3-[(3-ethylbenzyl)amino]-2-hydroxypropyl}-5-methyl-2-furamide;

N-{(1S,2R)-1-(3,5-difluorobenzyl)-3-[(3-ethylbenzyl)amino]-2-hydroxypropyl}-1,3,4,5-tetrahydrothiopyrano[4,3-b]indole-8-carboxamide;

N-{(1S,2R)-1-(3,5-difluorobenzyl)-3-[(3-ethylbenzyl)amino]-2-hydroxypropyl}-4,5-dimethyl-2-(1H-pyrrol-1-yl)thiophene-3-carboxamide;

N-{(1S,2R)-1-(3,5-difluorobenzyl)-3-[(3-ethylbenzyl)amino]-2-hydroxypropyl}-3-hydroxy-6-(1-hydroxy-2,2-dimethylpropyl)pyridine-2-carboxamide;

N-{(1S,2R)-1-(3,5-difluorobenzyl)-3-[(3-ethylbenzyl)amino]-2-hydroxypropyl}-2,2'-bithiophene-5-carboxamide;

3-chloro-N-{(1S,2R)-1-(3,5-difluorobenzyl)-3-[(3-ethylbenzyl)amino]-2-hydroxypropyl}-4-(methylsulfonyl)thiophene-2-carboxamide;

N-{(1S,2R)-1-(3,5-difluorobenzyl)-3-[(3-ethylbenzyl)amino])-2-hydroxypropyl}-5-methyl-7-(trifluoromethyl)pyrazolo[1,5-a]pyrimidine-2-carboxamide;

N-{(1S,2R)-1-(3,5-difluorobenzyl)-3-[(3-ethylbenzyl)amino]-2-hydroxypropyl}-4,5-dimethoxy-1-benzothoniophene-2-carboxamide;

5-(benzylthio)-N-{(1S,2R)-1-(3,5-difluorobenzyl)-3-[(3-ethylbenzyl)amino]-2-hydroxypropyl}nicotinamide;

N-{(1S,2R)-1-(3,5-difluorobenzyl)-3-[(3-ethylbenzyl)amino]-2-hydroxypropyl}-1H-pyrazole-5-carboxamide;

6-chloro-N-{(1S,2R)-1-(3,5-difluorobenzyl)-3-[(3-ethylbenzyl)amino]-2-hydroxypropyl}-3-methyl-2-oxo-2,3-dihydro-1,3-benzoxazole-5-carboxamide;

N-{(1S,2R)-1-(3,5-difluorobenzyl)-3-[(3-ethylbenzyl)amino]-2-hydroxypropyl}-1H-benzimidazole-2-carboxamide;

N-{(1S,2R)-1-(3,5-difluorobenzyl)-3-[(3-ethylbenzyl)amino]-2-hydroxypropyl}-6-hydroxy-4,7-dimethoxy-1-benzofuran-5-carboxamide;

N-{(1S,2R)-1-(3,5-difluorobenzyl)-3-[(3-ethylbenzyl)amino]-2-hydroxypropyl}[1,2,4]triazolo[4,3-a]pyridine-6-carboxamide;

N-{(1S,2R)-1-(3,5-difluorobenzyl)-3-[(3-ethylbenzyl)amino]-2-hydroxypropyl}-2-(2,3-dihydro-1-benzofuran-5-yl)-1,3-thiazole-4-carboxamide;

N-{(1S,2R)-1-(3,5-difluorobenzyl)-3-[(3-ethylbenzyl)amino]-2-hydroxypropyl}-5-hex-1-ynylnicotinamide;

N-{(1S,2R)-1-(3,5-difluorobenzyl)-3-[(3-ethylbenzyl)amino]-2-hydroxypropyl}-3-methoxyisoxazole-5-carboxamide;

N-{(1S,2R)-1-(3,5-difluorobenzyl)-3-[(3-ethylbenzyl)amino]-2-hydroxypropyl}-2,3-dimethyl-1H-indole-7-carboxamide;

N-{(1S,2R)-1-(3,5-difluorobenzyl)-3-[(3-ethylbenzyl)amino]-2-hydroxypropyl)}-5-methyl-3-phenylisoxazole-4-carboxamide;

N-{(1S,2R)-1-(3,5-difluorobenzyl)-3-[(3-ethylbenzyl)amino]-2-hydroxypropyl}-4-(2-fluorobenzoyl)-1H-pyrrole-2-carboxamide;

N-{(1S,2R)-1-(3,5-difluorobenzyl)-3-[(3-ethylbenzyl)amino]-2-hydroxypropyl}-5-(ethylthio)nicotinamide;

N-{(1S,2R)-1-(3,5-difluorobenzyl)-3-[(3-ethylbenzyl)amino]-2-hydroxypropyl}thieno[2,3-b]quinoline-2-carboxamide;

N-{2-[({(1S,2R)-1-(3,5-difluorobenzyl)-3-[(3-ethylbenzyl)amino]-2-hydroxypropyl}amino)carbonyl]phenyl}-N-methyl-2-furamide;

N-{(1S,2R)-1-(3,5-difluorobenzyl)-3-[(3-ethylbenzyl)amino]-2-hydroxypropyl}-5-hydroxy-1H-indole-2-carboxamide;

6-benzyl-N-{(1S,2R)-1-(3,5-difluorobenzyl)-3-[(3-ethylbenzyl)amino]-2-hydroxypropyl}pyrazine-2-carboxamide 4-oxide;

N-{(1S,2R)-1-(3,5-difluorobenzyl)-3-[(3-ethylbenzyl)amino]-2-hydroxypropyl}-3-methyl-4-oxo-3,4-dihydrophthalazine-1-carboxamide;

N-{(1S,2R)-1-(3,5-difluorobenzyl)-3-[(3-ethylbenzyl)amino]-2-hydroxypropyl}-5-methyl-4-oxo-3,4-dihydrothieno[2,3-d]pyrimidine-6-carboxamide;

N-{(1S,2R)-1-(3,5-difluorobenzyl)-3-[(3-ethylbenzyl)amino]-2-hydroxypropyl}-6-fluoro-2-hydroxyquinoline-4-carboxamide;

6-chloro-N-{(1S,2R)-1-(3,5-difluorobenzyl)-3-[(3-ethylbenzyl)amino]-2-hydroxypropyl}-4-hydroxyquinoline-2-carboxamide;

N-{(1S,2R)-1-(3,5-difluorobenzyl)-3-[(3-ethylbenzyl)amino]-2-hydroxypropyl}isoxazole-5-carboxamide;

N-{(1S,2R)-1-(3,5-difluorobenzyl)-3-[(3-ethylbenzyl)amino]-2-hydroxypropyl}-4,6-diethoxypyridine-2-carboxamide;

N-{(1S,2R)-1-(3,5-difluorobenzyl)-3-[(3-ethylbenzyl)amino]-2-hydroxypropyl}-2-(1,3-dithian-2-yl)-3-furamide;

N-{(1S,2R)-1-(3,5-difluorobenzyl)-3-[(3-ethylbenzyl)amino]-2-hydroxypropyl}-5-methylthiophene-2-carboxamide;

N-{(1S,2R)-1-(3,5-difluorobenzyl)-3-[(3-ethylbenzyl)amino]-2-hydroxypropyl}-1H-indole-7-carboxamide;

N-{(1S,2R)-1-(3,5-difluorobenzyl)-3-[(3-ethylbenzyl)amino]-2-hydroxypropyl}-1-methyl-1H-indole-2-carboxamide;

N-{(1S,2R)-1-(3,5-difluorobenzyl)-3-[(3-ethylbenzyl)amino]-2-hydroxypropyl}-7-fluoro-4H-imidazo[5,1-c][1,4]benzoxazine-3-carboxamide;

N-{(1S,2R)-1-(3,5-difluorobenzyl)-3-[(3-ethylbenzyl)amino]-2-hydroxypropyl}-1-benzofuran-3-carboxamide;

N-{(1S,2R)-1-(3,5-difluorobenzyl)-3-[(3-ethylbenzyl)amino]-2-hydroxypropyl}-2-methyl-4-oxo-4H-chromene-6-carboxamide;

N-[6-({(1S,2R)-1-(3,5-difluorobenzyl)-3-[(3-ethylbenzyl)amino]-2-hydroxypropyl}amino)-6-oxohexyl]-2-furamide;

N-{(1S,2R)-1-(3,5-difluorobenzyl)-3-[(3-ethylbenzyl)amino]-2-hydroxypropyl}indolizine-2-carboxamide;

N-{(1S,2R)-1-(3,5-difluorobenzyl)-3-[(3-ethylbenzyl)amino]-2-hydroxypropyl}nicotinamide 1-oxide;

N-{(1S,2R)-1-(3,5-difluorobenzyl)-3-[(3-ethylbenzyl)amino]-2-hydroxypropyl}-2,3-dihydro-1H-cyclopenta[b]quinoline-9-carboxamide;

N-{(1S,2R)-1-(3,5-difluorobenzyl)-3-[(3-ethylbenzyl)amino]-2-hydroxypropyl}-3-methyl-1H-pyrazole-5-carboxamide;

N-{(1S,2R)-1-(3,5-difluorobenzyl)-3-[(3-ethylbenzyl)amino]-2-hydroxypropyl}-5-pyridin-2-ylthiophene-2-carboxamide;

N-{(1S,2R)-1-(3,5-difluorobenzyl)-3-[(3-ethylbenzyl) amino]-2-hydroxypropyl}-2-isobutyl-1,3-dioxoisoindoline-5-carboxamide;

5-(acetylamino)-N-{(1S,2R)-1-(3,5-difluorobenzyl)-3-[(3-ethylbenzyl)amino]-2-hydroxypropyl}-2-furamide;

N-{(1S,2R)-1-(3,5-difluorobenzyl)-3-[(3-ethylbenzyl) amino]-2-hydroxypropyl}isoquinoline-4-carboxamide;

7-chloro-N-{(1S,2R)-1-(3,5-difluorobenzyl)-3-[(3-ethylbenzyl)amino]-2-hydroxypropyl}-1-benzofuran-2-carboxamide;

N-{(1S,2R)-1-(3,5-difluorobenzyl)-3-[(3-ethylbenzyl) amino]-2-hydroxypropyl}quinoline-6-carboxamide;

N-{(1S,2R)-1-(3,5-difluorobenzyl)-3-[(3-ethylbenzyl) amino]-2-hydroxypropyl}-3-(1H-indol-3-yl)-1H-pyrazole-5-carboxamide;

6-cholo-N—{(1S,2R)-1-(3,5-difluorobenzyl)-3-[(3-ethylbenzyl)amino]-2hydroxypropyl}nicotinamide;

3-(acetylamino)-N-{(1S,2R)-1-(3,5-difluorobenzyl)-3-[(3-ethylbenzyl)amino]-2-hydroxypropyl}-5-fluoro-1H-indole-2-carboxamide;

N-{(1S,2R)-1-(3,5-difluorobenzyl)-3-[(3-ethylbenzyl) amino]-2-hydroxypropyl}-4,5-dihydronaphtho[2,1-d] isoxazole-3-carboxamide;

N-{(1S,2R)-1-(3,5-difluorobenzyl)-3-[(3-ethylbenzyl) amino]-2-hydroxypropyl}-1-methyl-1H-benzo[g]indazole-3-carboxamide;

N-{(1S,2R)-1-(3,5-difluorobenzyl)-3-[(3-ethylbenzyl) amino]-2-hydroxypropyl}-2-methyl-1,3-thiazole-4-carboxamide;

N-{(1S,2R)-1-(3,5-difluorobenzyl)-3-[(3-ethylbenzyl) amino]-2-hydroxypropyl}-4-methoxy-1H-pyrrole-3-carboxamide;

N-{(1S,2R)-1-(3,5-difluorobenzyl)-3-[(3-ethylbenzyl) amino]-2-hydroxypropyl}-9-oxo-1,2,3,9-tetrahydrocyclopenta[b]chromene-7-carboxamide;

N-{(1S,2R)-1-(3,5-difluorobenzyl)-3-[(3-ethylbenzyl) amino]-2-hydroxypropyl}-6-methoxy-1-benzofuran-2-carboxamide;

N-{(1S,2R)-1-(3,5-difluorobenzyl)-3-[(3-ethylbenzyl) amino]-2-hydroxypropyl}-1H-imidazo[1,2-b]pyrazole-6-carboxamide;

N-{(1S,2R)-1-(3,5-difluorobenzyl)-3-[(3-ethylbenzyl) amino]-2-hydroxypropyl}-1H-benzimidazole-5-carboxamide;

7-(acetylamino)-N-{(1S,2R)-1-(3,5-difluorobenzyl)-3-[(3-ethylbenzyl)amino]-2-hydroxypropyl}-2-methylquinoline-5-carboxamide;

N-{(1S 2R)-1-(3,5-difluorobenzyl)-3-[(3-ethylbenzyl) amino]-2-hydroxypropyl}-1-methyl-5-phenyl-1H-pyrazole-3-carboxamide;

6-chloro-N-{(1S,2R)-1-(3,5-difluorobenzyl)-3-[(3-ethylbenzyl)amino]-2-hydroxypropyl}pyrazine-2-carboxamide 4-oxide;

N-{(1S,2R)-1-(3,5-difluorobenzyl)-3-[(3-ethylbenzyl) amino]-2-hydroxypropyl}-6-methoxypyrazine-2-carboxamide 4-oxide;

5-chloro-N-{(1S,2R)-1-(3,5-difluorobenzyl)-3-[(3-ethylbenzyl)amino]-2-hydroxypropyl}-2,3-dihydro-1-benzofuran-7-carboxamide;

N-{(1S,2R)-1-(3,5-difluorobenzyl)-3-[(3-ethylbenzyl) amino]-2-hydroxypropyl}-5-methyl-1-pyridin-4-yl-1H-1,2,3-triazole-4-carboxamide;

2-butyl-N-{(1S,2R)-1-(3,5-difluorobenzyl)-3-[(3-ethylbenzyl)amino]-2-hydroxypropyl}-4-oxo-3,4-dihydroquinazoline-6-carboxamide;

N-{(1S,2R)-1-(3,5-difluorobenzyl)-3-[(3-ethylbenzyl) amino]-2-hydroxypropyl}pyrazine-2-carboxamide 4-oxide;

7-chloro-N-{(1S,2R)-1-(3,5-difluorobenzyl)-3-[(3-ethylbenzyl)amino]-2-hydroxypropyl}quinoline-2-carboxamide;

5-(4-chlorophenyl)-N-{(1S,2R)-1-(3,5-difluorobenzyl)-3-[(3-ethylbenzyl)amino]-2-hydroxypropyl}-2-furamide;

4-cyano-N-{(1S,2R)-1-(3,5-difluorobenzyl)-3-[(3-ethylbenzyl)amino]-2-hydroxypropyl}-3-(1H-pyrrol-1-yl) thiophene-2-carboxamide;

N-{(1S,2R)-1-(3,5-difluorobenzyl)-3-[(3-ethylbenzyl) amino]-2-hydroxypropyl}-3,5-bis(methylthio)isothiazole-4-carboxamide;

4-chloro-N-{(1S,2R)-1-(3,5-difluorobenzyl)-3-[(3-ethylbenzyl)amino]-2-hydroxypropyl}-1,3-dimethyl-1H-pyrazolo[3,4-b]pyridine-5-carboxamide;

N-{2-[({(1S,2R)-1-(3,5-difluorobenzyl)-3-[(3-ethylbenzyl)amino]-2-hydroxypropyl}amino)carbonyl]phenyl}-5-methyl-2-furamide;

1-(cyanomethyl)-N-{(1S,2R)-1-(3,5-difluorobenzyl)-3-[(3-ethylbenzyl)amino]-2-hydroxypropyl}-1H-pyrrole-2-carboxamide;

N-{(1S,2R)-1-(3,5-difluorobenzyl)-3-[(3-ethylbenzyl) amino]-2-hydroxypropyl}-2,5-dimethyl-1-phenyl-1H-pyrrole-3-carboxamide;

N-{(1S,2R)-1-(3,5-difluorobenzyl)-3-[(3-ethylbenzyl) amino]-2-hydroxypropyl}-5-(piperidin-1-ylmethyl)-2-furamide;

N-{(1S,2R)-1-(3,5-difluorobenzyl)-3-[(3-ethylbenzyl) amino]-2-hydroxypropyl}-2-methyl-2,3-dihydro-1-benzothiophene-2-carboxamide 1,1-dioxide;

2-(2,1,3-benzoxadiazol-5-yl)-N-{(1S,2R)-1-(3,5-difluorobenzyl)-3-[(3-ethylbenzyl)amino]-2-hydroxypropyl}-1,3-thiazole-4-carboxamide;

N-{(1S,2R)-1-(3,5-difluorobenzyl)-3-[(3-ethylbenzyl) amino]-2-hydroxypropyl}-4,5-dihydrofuro[2,3-g][2,1] benzisoxazole-8-carboxamide;

N-{(1S,2R)-1-(3,5-difluorobenzyl)-3-[(3-ethylbenzyl) amino]-2-hydroxypropyl}-4-oxo-4,5,6,7-tetrahydro-1-benzofuran-3-carboxamide;

4,5-dichloro-N-{(1S,2R)-1-(3,5-difluorobenzyl)-3-[(3-ethylbenzyl)amino]-2-hydroxypropyl}isothiazole-3-carboxamide;

8-chloro-N-{(1S,2R)-1-(3,5-difluorobenzyl)-3-[(3-ethylbenzyl)amino]-2-hydroxypropyl}-4-hydroxycinnoline-3-carboxamide;

N-{(1S,2R)-1-(3,5-difluorobenzyl)-3-[(3-ethylbenzyl) amino]-2-hydroxypropyl}-2,6-dioxohexahydropyrimidine-4-carboxamide;

N-{(1S,2R)-1-(3,5-difluorobenzyl)-3-[(3-ethylbenzyl) amino]-2-hydroxypropyl}-2-phenylimidazo[1,2-a]pyridine-6-carboxamide;

N-{(1S,2R)-1-(3,5-difluorobenzyl)-3-[(3-ethylbenzyl) amino]-2-hydroxypropyl}-2-(4-methyl-1,2,3-thiadiazol-5-yl)-1,3-thiazole-4-carboxamide;

N-{(1S,2R)-1-(3,5-difluorobenzyl)-3-[(3-ethylbenzyl) amino]-2-hydroxypropyl}-5-methyl-2-phenyl-2H-1,2, 3-triazole-4-carboxamide;

N-{(1S,2R)-1-(3,5-difluorobenzyl)-3-[(3-ethylbenzyl) amino]-2-hydroxypropyl}-1, 3-dimethyl-1H-thieno[2, 3-c]pyrazole-5-carboxamide;

N-{(1S,2R)-1-(3,5-difluorobenzyl)-3-[(3-ethylbenzyl) amino]-2-hydroxypropyl}-3-methyl-5-(4-methyl-1,2, 3-thiadiazol-5-yl)isoxazole-4-carboxamide;

N-{(1S,2R)-1-(3,5-difluorobenzyl)-3-[(3-ethylbenzyl)amino]-2-hydroxypropyl}-1-phenyl-1,4,5,6-tetrahydrocyclopenta[c]pyrazole-3-carboxamide;

N-{(1S,2R)-1-(3,5-difluorobenzyl)-3-[(3-ethylbenzyl)amino]-2-hydroxypropyl}-2-phenyl-1,3-oxazole-4-carboxamide;

N-{(1S,2R)-1-(3,5-difluorobenzyl)-3-[(3-ethylbenzyl)amino]-2-hydroxypropyl}-4-hydroxy-7-methoxy-1-benzofuran-5-carboxamide;

N-{(1S,2R)-1-(3,5-difluorobenzyl)-3-[(3-ethylbenzyl)amino]-2-hydroxypropyl}-4-hydroxy-7-methoxy-1-benzothiophene-5-carboxamide;

N-{(1S,2R)-1-(3,5-difluorobenzyl)-3-[(3-ethylbenzyl)amino]-2-hydroxypropyl}-3,6,6-trimethyl-4-oxo-4,5,6,7-tetrahydro-1-benzofuran-2-carboxamide;

N-{(1S,2R)-1-(3,5-difluorobenzyl)-3-[(3-ethylbenzyl)amino]-2-hydroxypropyl}-5,6-dihydro-4H-cyclopenta[b]thiophene-2-carboxamide;

N-{(1S,2R)-1-(3,5-difluorobenzyl)-3-[(3-ethylbenzyl)amino]-2-hydroxypropyl}-1,3-thiazole-4-carboxamide;

N-{(1S,2R)-1-(3,5-difluorobenzyl)-3-[(3-ethylbenzyl)amino]-2-hydroxypropyl}-3-hydroxy-6-neopentylpyridine-2-carboxamide;

N-{(1S,2R)-1-(3,5-difluorobenzyl)-3-[(3-ethylbenzyl)amino]-2-hydroxypropyl}-1-(4-fluorophenyl)-1,4,5,6-tetrahydrocyclopenta[c]pyrazole-3-carboxamide;

N-{(1S,2R)-1-(3,5-difluorobenzyl)-3-[(3-ethylbenzyl)amino]-2-hydroxypropyl}-2-methyl-3-furamide;

N-{(1S,2R)-1-(3,5-difluorobenzyl)-3-[(3-ethylbenzyl)amino]-2-hydroxypropyl}-3-furamide;

N-{(1S,2R)-1-(3,5-difluorobenzyl)-3-[(3-ethylbenzyl)amino]-2-hydroxypropyl}thiophene-2-carboxamide;

N-{(1S,2R)-1-(3,5-difluorobenzyl)-3-[(3-ethylbenzyl)amino]-2-hydroxypropyl}-5-methyl-2-phenyl-1,3-oxazole-4-carboxamide;

N-{(1S,2R)-1-(3,5-difluorobenzyl)-3-[(3-ethylbenzyl)amino]-2-hydroxypropyl}-1H-indazole-3-carboxamide;

N-{(1S,2R)-1-(3,5-difluorobenzyl)-3-[(3-ethylbenzyl)amino]-2-hydroxypropyl}-3-hydroxyquinoxaline-2-carboxamide;

2-(acetylamino)-N-{(1S,2R)-1-(3,5-difluorobenzyl)-3-[(3-ethylbenzyl)amino]-2-hydroxypropyl}-4,5-dimethylthiophene-3-carboxamide;

N-{(1S,2R)-1-(3,5-difluorobenzyl)-3-[(3-ethylbenzyl)amino]-2-hydroxypropyl}-1-ethyl-1H-indole-2-carboxamide;

N-{(1S,2R)-1-(3,5-difluorobenzyl)-3-[(3-ethylbenzyl)amino]-2-hydroxypropyl}-1-benzofuran-2-carboxamide;

1-benzyl-N-{(1S,2R)-1-(3,5-difluorobenzyl)-3-[(3-ethylbenzyl)amino]-2-hydroxypropyl}-3,5-dimethyl-1H-pyrazole-4-carboxamide;

N-{(1S,2R)-1-(3,5-difluorobenzyl)-3-[(3-ethylbenzyl)amino]-2-hydroxypropyl}-4,8-dihydroxyquinoline-2-carboxamide;

methyl 5-[({(1S,2R)-1-(3,5-difluorobenzyl)-3-[(3-ethylbenzyl)amino]-2-hydroxypropyl}amino)carbonyl]-1H-benzimidazol-2-ylcarbamate;

N-{1S,2R)-1-(3,5-difluorobenzyl)-3-[(3-ethylbenzyl)amino]-2-hydroxypropyl}-2-[ethyl(methyl)amino]-4-hydroxypyrimidine-5-carboxamide;

2-(diethylamino)-N-{(1S,2R)-1-(3,5-difluorobenzyl)-3-[(3-ethylbenzyl)amino]-2-hydroxypropyl}-4-hydroxypyrimidine-5-carboxamide;

N-{(1S,2R)-1-(3,5-difluorobenzyl)-3-[(3-ethylbenzyl)amino]-2-hydroxypropyl}-5,6,7,8-tetrahydro-4H-cyclohepta[c]isoxazole-3-carboxamide;

N-{(1S,2R)-1-(3,5-difluorobenzyl)-3-[(3-ethylbenzyl)amino]-2-hydroxypropyl}-6-hydroxy-4-methylpyridine-2-carboxamide;

N-{(1S,2R)-1-(3,5-difluorobenzyl)-3-[(3-ethylbenzyl)amino]-2-hydroxyoropyl}-2-phenylimidazo[1,2-a]pyridine-7-carboxamide;

N-{(1S,2R)-1-(3,5-difluorobenzyl)-3-[(3-ethylbenzyl)amino]-2-hydroxypropyl}quinoline-4-carboxamide;

N-{(1S,2R)-1-(3,5-difluorobenzyl)-3-[(3-ethylbenzyl)amino]-2-hydroxypropyl}-5-methoxy-1H-indole-2-carboxamide;

N-{(1S,2R)-1-(3,5-difluorobenzyl)-3-[(3-ethylbenzyl)amino]-2-hydroxypropyl}-5-methylisoxazole-3-carboxamide;

N-{(1S,2R)-1-(3,5-difluorobenzyl)-3-[(3-ethylbenzyl)amino]-2-hydroxypropyl}-3-methylisoxazole-5-carboxamide;

N-{(1S,2R)-1-(3,5-difluorobenzyl)-3-[(3-ethylbenzyl)amino]-2-hydroxypropyl}-3-methyl-4-oxo-4,5,6,7-tetrahydro-1H-indole-2-carboxamide;

N-{(1S,2R)-1-(3,5-difluorobenzyl)-3-[(3-ethylbenzyl)amino]-2-hydroxypropyl}-1-benzothiophene-2-carboxamide;

N-{(1S,2R)-1-(3,5-difluorobenzyl)-3-[(3-ethylbenzyl)amino]-2-hydroxypropyl}-6-hydroxynicotinamide;

N-{(1S,2R)-1-(3,5-difluorobenzyl)-3-[(3-ethylbenzyl)amino]-2-hydroxypropyl}-2-hydroxyquinoline-4-carboxamide;

N-{(1S,2R)-1-(3,5-difluorobenzyl)-3-[(3-ethylbenzyl)amino]-2-hydroxypropyl}thieno[3,2-b]pyridine-6-carboxamide;

N-{(1S,2R)-1-(3,5-difluorobenzyl)-3-[(3-ethylbenzyl)amino]-2-hydroxypropyl}thieno[2,3-c]pyridine-2-carboxamide;

N-{(1S,2R)-1-(3,5-difluorobenzyl)-3-[(3-ethylbenzyl)amino]-2-hydroxypropyl}-5,6-dimethyl-4-oxo-3,4-dihydrothieno[2,3-d]pyrimidine-2-carboxamide;

N-{(1S,2R)-1-(3,5-difluorobenzyl)-3-[(3-ethylbenzyl)amino]-2-hydroxypropyl}-2-(4,4-dimethyl-4,5-dihydro-1,3-oxazol-2-yl)thiophene-3-carboxamide;

N-{(1S,2R)-1-(3,5-difluorobenzyl)-3-[(3-ethylbenzyl)amino]-2-hydroxypropyl}-5-(trifluoromethoxy)-1H-indole-2-carboxamide;

N-{(1S,2R)-1-(3,5-difluorobenzyl)-3-[(3-ethylbenzyl)amino]-2-hydroxypropyl}-1-phenyl-5-propyl-1H-pyrazole-4-carboxamide;

N-{(1S,2R)-1-(3,5-difluorobenzyl)-3-[(3-ethylbenzyl)amino]-2-hydroxypropyl}-5-[(pyridin-2-ylthio)methyl]-2-furamide;

5-chloro-N-{(1S,2R)-1-(3,5-difluorobenzyl)-3-[(3-ethylbenzyl)amino]-2-hydroxypropyl}-2-morpholin-4-ylpyrimidine-4-carboxamide;

5-chloro-N-{(1S,2R)-1-(3,5-difluorobenzyl)-3-[(3-ethylbenzyl)amino]-2-hydroxypropyl}-3-methyl-1-phenyl-1H-pyrazole-4-carboxamide;

N-{(1S,2R)-1-(3,5-difluorobenzyl)-3-[(3-ethylbenzyl)amino]-2-hydroxypropyl}-4-methyl-1,2,3-thiadiazole-5-carboxamide;

N-{(1S,2R)-1-(3,5-difluorobenzyl)-3-[(3-ethylbenzyl)amino]-2-hydroxypropyl}-2,1,3-benzoxadiazole-5-carboxamide;

2-(acetylamino)-N-{(1R,2R)-1-(3,5-difluorobenzyl)-2-hydroxy-3-[(3-iodobenzyl)amino]propyl}-1,3-oxazole-4-carboxamide;

N-{(1S,2R)-1-(3,5-difluorobenzyl)-3-[(3-ethylbenzyl)amino]-2-hydroxypropyl}-1-methyl-1,3-dihydro-2,1-benzisothiazole-5-carboxamide 2,2-dioxide;

N-{(1S,2R)-1-(3,5-difluorobenzyl)-3-[(3-ethylbenzyl)amino]-2-hydroxypropyl)}-2,2-dimethylchromane-6-carboxamide;

N-{(1S,2R)-1-(3,5-difluorobenzyl)-3-[(3-ethylbenzyl)amino]-2-hydroxypropyl}-6-[(2-methoxyethyl)(methylsulfonyl)amino]nicotinamide;

N-{(1S,2R)-1-(3,5-difluorobenzyl)-3-[(3-ethylbenzyl)amino]-2-hydroxypropyl}-2,2-dimethylchromane-7-carboxamide;

N-{(1S,2R)-1-(3,5-difluorobenzyl)-3-[(3-ethylbenzyl)amino]-2-hydroxypropyl}-6-[(3-hydroxypropyl)(methylsulfonyl)amino]nicotinamide;

N-{(1S,2R)-1-(3,5-difluorobenzyl)-3-[(3-ethylbenzyl)amino]-2-hydroxypropyl}-6-[(2-hydroxyethyl)(methylsulfonyl)amino]nicotinamide;

N-{(1S,2R)-1-(3,5-difluorobenzyl)-3-[(3-ethylbenzyl)amino]-2-hydroxypropyl}-6-[(2-methoxyethyl)(methylsulfonyl)amino]nicotinamide;

$N^1$-[(1S,2R)-3-(benzylamino)-2-hydroxy-1-(4-methoxybenzyl)propyl]-$N^3$ $N^3$-dipropylbenzene-1,3,5-tricarboxamide;

N-{(1S,2R)-1-(3,5-difluorobenzyl)-3-[(3-ethylbenzyl)amino]-2-hydroxypropyl}-2-[(2-methoxyethyl)(methylsulfonyl)amino]isonicotinamide;

N-{(1S,2R)-1-(3,5-difluorobenzyl)-3-[(3-ethylbenzyl)amino]-2-hydroxypropyl}-5-[(2-methoxyethyl)(methylsulfonyl)amino]nicotinamide;

N-{(1S,2R)-1-(3,5-difluorobenzyl)-3-[(3-ethylbenzyl)amino]-2-hydroxypropyl}-2-[(3-hydroxypropyl)(methylsulfonyl)amino]isonicotinamide;

N-{(1S,2R)-1-(3,5-difluorobenzyl)-3-[(3-ethylbenzyl)amino]-2-hydroxypropyl}-2-[(2-hydroxyethyl)(methylsulfonyl)amino]isonicotinamide;

N-{(1S,2R)-1-(3,5-difluorobenzyl)-3-[(3-ethylbenzyl)amino]-2-hydroxypropyl}-5-[(3-hydroxypropyl)(methylsulfonyl)amino]nicotinamide;

N-{(1S,2R)-1-(3,5-difluorobenzyl)-3-[(3-ethylbenzyl)amino]-2-hydroxypropyl}-5-[(3-hydroxypropyl)(methylsulfonyl)amino]nicotinamide;

N-{(1S,2R)-1-(3,5-difluorobenzyl)-3-[(3-ethylbenzyl)amino]-2-hydroxypropyl}-2-[(3-methoxypropyl)(methylsulfonyl)amino]isonicotinamide;

N-{(1S,2R)-1-(3,5-difluorobenzyl)-3-[(3-ethylbenzyl)amino]-2-hydroxypropyl}-5-[(3-methoxypropyl)(methylsulfonyl)amino]nicotinamide;

N-{(1S,2R)-1-(3,5-difluorobenzyl)-3-[(3-ethylbenzyl)amino]-2-hydroxypropyl}-1-(methylsulfonyl)-1H-indole-5-carboxamide;

N-{(1S,2R)-1-(3,5-difluorobenzyl)-3-[(3-ethylbenzyl)amino]-2-hydroxypropyl}-1-(methylsulfonyl)indoline-5-carboxamide;

N-{(1S,2R)-1-(3,5-difluorobenzyl)-3-[(3-ethylbenzyl)amino]-2-hydroxypropyl}-1-(methylsulfonyl)indoline-4-carboxamide;

N-{(1S,2R)-1-(3,5-difluorobenzyl)-3-[(3-ethylbenzyl)amino]-2-hydroxypropyl}-1-(methylsulfonyl)indoline-6-carboxamide;

N-{(1S,2R)-1-(3,5-difluorobenzyl)-3-[(3-ethylbenzyl)amino]-2-hydroxypropyl}-1-(methylsulfonyl)-1H-indole-4-carboxamide;

N-{(1S,2R)-1-(3,5-difluorobenzyl)-3-[(3-ethylbenzyl)amino]-2-hydroxypropyl}-2,3-dihydro-1-benzothiophene-5-carboxamide 1,1-dioxide;

N-{(1S,2R)-1-(3,5-difluorobenzyl)-3-[(3-ethylbenzyl)amino]-2-hydroxypropyl}-1-benzothiophene-5-carboxamide1,1-dioxide;

N-{(1S,2R)-1-(3,5-difluorobenzyl)-3-[(3-ethylbenzyl)amino]-2-hydroxypropyl}-2,3-dihydro-1-benzothiophene-3-carboxamide 1,1-dioxide;

N-{(1S,2R)-1-(3,5-difluorobenzyl)-3-[(3-ethylbenzyl)amino]-2-hydroxypropyl}-1-benzothiophene-6-carboxamide1,1-dioxide;

N-{(1S,2R)-1-(3,5-difluorobenzyl)-3-[(3-ethylbenzyl)amino]-2-hydroxypropyl}-2-methyl-2,3-dihydro-1,2-benzisothiazole-6-carboxamide 1,1-dioxide;

N-{(1S,2R)-1-(3,5-difluorobenzyl)-3-[(3-ethylbenzyl)amino]-2-hydroxypropyl}-2-methyl-2,3-dihydro-1,2-benzisothiazole-5-carboxamide 1,1-dioxide;

N-{(1S,2R)-1-(3,5-difluorobenzyl)-3-[(3-ethylbenzyl)amino]-2-hydroxypropyl}-2-methyl-1,3-dihydro-2,1-benzisothiazole-6-carboxamide 2,2-dioxide;

N-{(1S,2R)-1-(3,5-difluorobenzyl)-3-[(3-ethylbenzyl)amino]-2-hydroxypropyl}-2,3-dihydro-1H-cyclopenta[b]quinoline-9-carboxamide;

N-{(1S,2R)-1-(3,5-difluorobenzyl)-3-[(3-ethylbenzyl)amino]-2-hydroxypropyl}-4-hydroxy-6-oxo-1-phenyl-1,6-dihydropyridazine-3-carboxamide;

N-{(1S,2R)-1-(3,5-difluorobenzyl)-3-[(3-ethylbenzyl)amino]-2-hydroxypropyl}-1,3-dioxoisoindoline-5-carboxamide;

1-benzyl-N-{(1S,2R)-1-(3,5-difluorobenzyl)-3-[(3-ethylbenzyl)amino]-2-hydroxypropyl}-1H-imidazole-2-carboxamide;

N-{(1S,2R)-1-(3,5-difluorobenzyl)-3-[(3-ethylbenzyl)amino]-2-hydroxypropyl}-2-(4,4-dimethyl-4,5-dihydro-1,3-oxazol-2-yl)thiophene-3-carboxamide;

N-{(1S,2R)-1-(3,5-difluorobenzyl)-3-[(3-ethylbenzyl)amino]-2-hydroxypropyl}-2-isobutyl-1,3-dioxoisoindoline-5-carboxamide;

N-{(1S,2R)-1-(3,5-difluorobenzyl)-3-[(3-ethylbenzyl)amino]-2-hydroxypropyl}-5,6-dimethyl-4-oxo-3,4-dihydrothieno[2,3-d]pyrimidine-2-carboxamide;

N-{(1S,2R)-1-(3,5-difluorobenzyl)-3-[(3-ethylbenzyl)amino]-2-hydroxypropyl}thieno[2,3-c]pyridine-2-carboxamide;

N-{(1S,2R)-1-(3,5-difluorobenzyl)-3-[(3-ethylbenzyl)amino]-2-hydroxypropyl}thieno[3,2-b]pyridine-6-carboxamide;

N-{(1S,2R)-1-(3,5-difluorobenzyl)-3-[(3-ethylbenzyl)amino]-2-hydroxypropyl}-4-(2,3-dihydro-1H-indol-1-yl)-4-oxobutanamide;

N-{(1S,2R)-1-(3,5-difluorobenzyl)-3-[(3-ethylbenzyl)amino]-2-hydroxypropyl}-3-methyl-4-oxo-4,5,6,7-tetrahydro-1H-indole-2-carboxamide;

N-{(1S,2R)-1-(3,5-difluorobenzyl)-3-[(3-ethylbenzyl)amino]-2-hydroxypropyl}-5,6,7,8-tetrahydro-4H-cyclohepta[c]isoxazole-3-carboxamide;

N-{(1S,2R)-1-(3,5-difluorobenzyl)-3-[(3-ethylbenzyl)amino]-2-hydroxypropyl}-2-(1,3-dithian-2-yl)-3-furamide;

N-{(1S,2R)-1-(3,5-difluorobenzyl)-3-[(3-ethylbenzyl)amino]-2-hydroxypropyl})-2-methyl-5,6,7,8-tetrahydro-4H-pyrazolo[1,5-a]azepine-3-carboxamide;

N-{(1S,2R)-1-(3,5-difluorobenzyl)-3-[(3-ethylbenzyl)amino]-2-hydroxypropyl}-1-(4-fluorophenyl)-1,4,5,6-tetrahydrocyclopenta[a]pyrazole-3-carboxamide;

N-{(1S,2R)-1-(3,5-difluorobenzyl)-3-[(3-ethylbenzyl)amino]-2-hydroxypropyl)}-5,6-dihydro-4H-cyclopenta[b]thiophene-2-carboxamide;

N-{(1S,2R)-1-(3,5-difluorobenzyl)-3-[(3-ethylbenzyl)amino]-2-hydroxypropyl}-3,6,6-trimethyl-4-oxo-4,5,6,7-tetrahydro-1-benzofuran-2-carboxamide;

N-{(1S,2R)-1-(3,5-difluorobenzyl)-3-[(3-ethylbenzyl)amino]-2-hydroxypropyl}-2,3-dioxo-1,2,3,4-tetrahydroquinoxaline-6-carboxamide;

N-{(1S,2R)-1-(3,5-difluorobenzyl)-3-[(3-ethylbenzyl)amino]-2-hydroxypropyl}-4,5,6,7-tetrahydro-2H-indazole-3-carboxamide;

N-{(1S,2R)-1-(3,5-difluorobenzyl)-3-[(3-ethylbenzyl)amino]-2-hydroxypropyl}-5-methyl-4-oxo-3,4-dihydrothieno[2,3-d]pyrimidine-6-carboxamide;

N-{(1S,2R)-1-(3,5-difluorobenzyl)-3-[(3-ethylbenzyl)amino]-2-hydroxypropyl}-7-fluoro-4H-imidazo[5,1-c][1,4]benzoxazine-3-carboxamide;

N-{(1S,2R)-1-(3,5-difluorobenzyl)-3-[(3-ethylbenzyl)amino]-2-hydroxypropyl}[1,2,4]triazolo[4,3-a]pyridine-6-carboxamide;

N-{(1S,2R)-1-(3,5-difluorobenzyl)-3-[(3-ethylbenzyl)amino]-2-hydroxypropyl}-1-phenyl-1,4,5,6-tetrahydrocyclopenta[c]pyrazole-3-carboxamide;

N-{(1S,2R)-1-(3,5-difluorobenzyl)-3-[(3-ethylbenzyl)amino]-2-hydroxypropyl}-3-oxo-2,3-dihydro-1H-indazole-4-carboxamide;

N-{(1S,2R)-1-(3,5-difluorobenzyl)-3-[(3-ethylbenzyl)amino]-2-hydroxypropyl}-1,3-dimethyl-1H-thieno[2,3-c]pyrazole-5-carboxamide;

N-{(1S,2R)-1-(3,5-difluorobenzyl)-3-[(3-ethylbenzyl)amino]-2-hydroxypropyl}-2,6-dioxohexahydropyrimidine-4-carboxamide;

N-{(1S,2R)-1-(3,5-difluorobenzyl)-3-[(3-ethylbenzyl)amino]-2-hydroxypropyl}-5,7-dimethoxy-1-oxoindane-2-carboxamide;

N-{(1S,2R)-1-(3,5-difluorobenzyl)-3-[(3-ethylbenzyl)amino]-2-hydroxypropyl}-4-oxo-4,5,6,7-tetrahydro-1-benzofuran-3-carboxamide;

2-[(cyanomethyl)thio]-N-{(1S,2R)-1-(3,5-difluorobenzyl)-3-[(3-ethylbenzyl)amino]-2-hydroxypropyl}nicotinamide;

N-{(1S,2R)-1-(3,5-difluorobenzyl)-3-[(3-ethylbenzyl)amino]-2-hydroxypropyl}-4,5-dihydrofuro[2,3-g][2,1]benzisoxazole-8-carboxamide;

N-{(1S,2R)-1-(3,5-difluorobenzyl)-3-[(3-ethylbenzyl)amino]-2-hydroxypropyl}-1,3,4,5-tetrahydrothiopyrano[4,3-b]indole-8-carboxamide;

4-chloro-N-{(1S,2R)-1-(3,5-difluorobenzyl)-3-[(3-ethylbenzyl)amino]-2-hydroxypropyl}-1,3-dimethyl-1H-pyrazolo[3,4-b]pyridine-5-carboxamide;

N-{(1S,2R)-1-(3,5-difluorobenzyl)-3-[(3-ethylbenzyl)amino]-2-hydroxypropyl}-8H-thieno[2,3-b]indole-2-carboxamide;

N-{(1S,2R)-1-(3,5-difluorobenzyl)-3-[(3-ethylbenzyl)amino]-2-hydroxypropyl}-3,4-dihydro-2H-1,5-benzodioxepine-7-carboxamide;

N-{(1S,2R)-1-(3,5-difluorobenzyl)-3-[(3-ethylbenzyl)amino]-2-hydroxypropyl}-4H-chromeno[3,4-d]isoxazole-4-carboxamide;

4-(3,4-dichlorophenyl)-N-{(1S,2R)-1-(3,5-difluorobenzyl)-3-[(3-ethylbenzyl)amino]-2-hydroxypropyl}-4-oxobutanamide;

N-{(1S,2R)-1-(3,5-difluorobenzyl)-3-[(3-ethylbenzyl)amino]-2-hydroxypropyl}-3-oxoisoindoline-1-carboxamide;

N-{(1S,2R)-1-(3,5-difluorobenzyl)-3-[(3-ethylbenzyl)amino]-2-hydroxypropyl}-4H-chromeno[3,4-d]isoxazole-8-carboxamide;

N-{(1S,2R)-1-(3,5-difluorobenzyl)-3-[(3-ethylbenzyl)amino]-2-hydroxypropyl}-2-methyl-4-oxo-4H-chromene-6-carboxamide;

N-{(1S,2R)-1-(3,5-difluorobenzyl)-3-[(3-ethylbenzyl)amino]-2-hydroxypropyl}-2-ethyl-3-oxoisoindoline-1-carboxamide;

N-{(1S,2R)-1-(3,5-difluorobenzyl)-3-[(3-ethylbenzyl)amino]-2-hydroxypropyl}-1H-imidazo[1,2]pyrazole-6-carboxamide;

N-{(1S,2R)-1-(3,5-difluorobenzyl)-3-[(3-ethylbenzyl)amino]-2-hydroxypropyl}-9-oxo-1,2,3,9-tetrahydrocyclopenta[b]chromene-7-carboxamide;

N-{(1S,2R)-1-(3,5-difluorobenzyl)-3-[(3-ethylbenzyl)amino]-2-hydroxypropyl)}-1-methyl-1H-benzo[g]indazole-3-carboxamide;

N-{(1S,2R)-1-(3,5-difluorobenzyl)-3-[(3-ethylbenzyl)amino]-2-hydroxypropyl}-4,5-dihydronaphtho[2,1-d]isoxazole-3-carboxamide;

N-[(1S,2R)-3-(2-acetyl-1-ethylhydrazino)-1-benzyl-2-hydroxypropyl]-2-[(methylsulfonyl)amino]-1,3-thiazole-4-carboxamide;

N-{(1S,2R)-1-(3,5-difluorobenzyl)-2-hydroxy-3-[(3-iodobenzyl)amino]propyl}-2-[((methylsulfonyl)amino]-1,3-thiazole-4-carboxamide;

N-{(1S,2R)-1-(3,5-difluorobenzyl)-3-[(3-ethylbenzyl)amino]-2-hydroxypropyl}-2-[(methylsulfonyl)amino]-1,3-thiazole-4-carboxamide;

N-{(1S,2R)-1-(3,5-difluorobenzyl)-3-[(3-ethylbenzyl)amino]-2-hydroxypropyl}-2,8-dimethylquinoline-3-carboxamide;

N-{(1S,2R)-1-(3,5-difluorobenzyl)-3-[(3-ethylbenzyl)amino]-2-hydroxypropyl}-3-hydroxyisoxazole-5-carboxamide;

$N^4$-{(1S,2R)-1-(3,5-difluorobenzyl)-3-[(3-ethylbenzyl)amino]-2-hydroxypropyl}-6-methyl-$N^2$,$N^2$-dipropylpyridine-2,4-dicarboxammide;

$N^4$-{(1S,2R)-1-(3,5-difluorobenzyl)-2-hydroxy-3-[(3-isopropylbenzyl)amino]propyl}-6-methyl-$N^2$,$N^2$-dipropylpyridine-2,4-dicarboxammide;

$N^4$-{(1S,2R)-1-(3,5-difluorobenzyl)-3-[(3-ethynylbenzyl)amino]-2-hydroxypropyl}-6-methyl-$N^2$,$N^2$-dipropylpyridine-2,4-dicarboxammide;

$N^4$-((1S,2R)-1-(3,5-difluorobenzyl)-2-hydroxy-3-{[3-(trifluoromethyl)benzyl]amino}propyl)-6-methyl-$N^2$,$N^2$-dipropylpyridine-2,4-dicarboxammide;

$N^4$-((1S,2R)-1-(3,5-difluorobenzyl)-3-{[1-(3-ethylphenyl)cyclopropyl]amino}-2-hydroxypropyl)-6-methyl-$N^2$,$N^2$-dipropylpyridine-2,4-dicarboxammide;

2-[allyl(methylsulfonyl)amino]-N-{(1S,2R)-1-(3,5-difluorobenzyl)-3-[(3-ethylbenzyl)amino]-2-hydroxypropyl}-1,3-thiazole-5-carboxammide;

N-{(1S,2R)-1-(3,5-difluorobenzyl)-3-[(3-ethylbenzyl)amino]-2-hydroxypropyl}-3-hydroxy-6-(1-hydroxy-2,2-dimethylpropyl)pyridine-2-carboxammide;

1-(cyanomethyl)-N-{(1S,2R)-1-(3,5-difluorobenzyl)-3-[(3-ethylbenzyl)amino]-2-hydroxypropyl}-1H-pyrrole-2-carboxammide;

N-{(1S,2R)-1-(3,5-difluorobenzyl)-3-[(3-ethylbenzyl)amino]-2-hydroxypropyl}-1-(dipropylamino)isoquinoline-7-carboxammide;

N-{(1S,2R)-1-(3,5-difluorobenzyl)-3-[(3-ethylbenzyl)amino]-2-hydroxypropyl}-2-[methyl(methylsulfonyl)amino]-1,3-oxazole-4-carboxammide;

$N^2$-{(1S,2R)-1-(3,5-difluorobenzyl)-3-[(3-ethylbenzyl)amino]-2-hydroxypropyl}-3,4-dimethyl-$N^5$,$N^5$-dipropylthieno[2,3-b]thiophene-2,5-dicarboxammide;

N³-[(1S,2R)-1-(3,5-difluorobenzyl)-2-hydroxy-3-(1,2,3,4-tetrahydronaphthalen-1-ylamino)propyl]-N⁵,N⁵-diisopropylpyridine-3,5-dicarboxammide; or 2-[ally(methylsulfonyl)amino]-N-{(1S,2R)-1-(3,5-difluorobenzyl)-3-[(3-ethylbenzyl)amino]-2-hydroxypropyl}-1,3-oxazole-4-carboxammide;

or a pharmaceutically acceptable salt thereof.

25. A compound according to claim 1 of the formula:

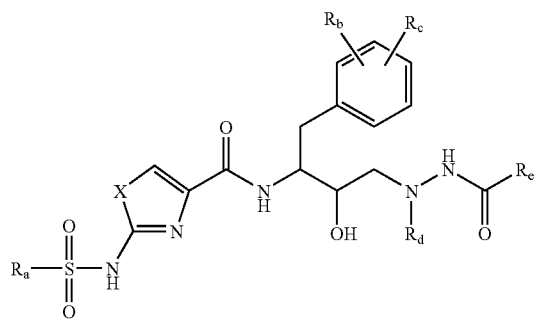

wherein $R_a$ and $R_d$ are independently $C_1$-$C_6$ alkyl;

X is O or S;

$R_b$ and $R_c$ are independently hydrogen or halogen;

$R_e$ is $C_1$-$C_6$ alkyl or an optionally substituted phenyl.

26. A compound which is:

N-{(1S,2R)-1-(3,5-difluorobenzyl)-3-[(3-ethylbenzyl)amino]-2-hydroxypropyl}-1-(dipropylamino)isoquinoline-7-carboxamide;

N-{(1S,2R)-1-(3,5-difluorobenzyl)-3-[(3-ethylbenzyl)amino]-2-hydroxypropyl}-2-[(methyl(methylsulfonyl)amino]-1,3-oxazole-4-carboxamide;

N²-{(1S,2R)-1-(3,5-difluorobenzyl)-3-[(3-ethylbenzyl)amino]-2-hydroxypropyl}-3,4-dimethyl-N⁵,N⁵-dipropylthieno[2,3-b]thiophene-2,5-dicarboxamide;

N-{(1S,2R)-1-(3,5-difluorobenzyl)-3-[(3-ethylbenzyl)amino]-2-hydroxypropyl}-2-propyl-1,3-benzoxazole-6-carboxamide;

N-{(1S,2R)-1-(3,5-difluorobenzyl)-3-[(3-ethylbenzyl)amino]-2-hydroxypropyl}-2-methyl-1,3-benzoxazole-6-carboxamide;

N⁴-((1S,2R)-1-(3,5-difluorobenzyl)-3-{[1-(3-ethylphenyl)cyclopropyl]amino}-2-hydroxypropyl)-6-methyl-N²,N²-dipropylpyridine-2,4-dicarboxamide;

N⁴-((1S,2R)-1-(3,5-difluorobenzyl)-3-{[1-(3-ethynylphenyl)cyclopropyl]amino}-2-hydroxypropyl)-6-methyl-N²,N²-dipropylpyridine-2,4-dicarboxamide;

N-{(1S,2R)-1-(3,5-difluorobenzyl)-3-[(3-ethylbenzyl)amino]-2-hydroxypropyl}-2-isopropyl-1,3-benzoxazole-6-carboxamide;

N-{(1S,2R)-1-(3,5-difluorobenzyl)-3-[(3-ethylbenzyl)amino]-2-hydroxypropyl}isonicotinamide;

N-{(1S,2R)-1-(3,5-difluorobenzyl)-3-[(3-ethylbenzyl)amino]-2-hydroxypropyl}-2-propyl-1,3-benzoxazole-5-carboxamide;

N-{(1S,2R)-1-(3,5-difluorobenzyl)-3-[(3-ethylbenzyl)amino]-2-hydroxypropyl}-2-isopropyl-1,3-benzoxazole-5-carboxamide;

N-{(1S,2R)-1-(3,5-difluorobenzyl)-3-[(3-ethylbenzyl)amino]-2-hydroxypropyl}-2-methyl-1,3-benzoxazole-7-carboxamide;

N-⁴-((1S,2R)-1-(3,5-difluorobenzyl)-3-{[1-(3-ethynylphenyl)cyclopropyl]amino}-2-hydroxypropyl)-6-methyl-N²,N²-dipropylpyridine-2,4-dicarboxamide;

N-{(1S,2R)-1-(3,5-difluorobenzyl)-3-[(3-ethylbenzyl)amino]-2-hydroxypropyl}-2,2-dimethylchromane-7-carboxamide;

N-{(1S,2R)-1-(3,5-difluorobenzyl)-3-[(3-ethylbenzyl)amino]-2-hydroxypropyl}-2,2-dimethylchromane-6-carboxamide;

N-{(1S,2R)-1-(3,5-difluorobenzyl)-3-[(3-ethylbenzyl)amino]-2-hydroxypropyl}-2-methyl-1,3-benzoxazole-4-carboxamide;

N-{(1S,2R)-1-(3,5-difluorobenzyl)-3-[(3-ethylbenzyl)amino]-2-hydroxypropyl}-2-propyl-1,3-benzoxazole-4-carboxamide;

1-butyl-N-{(1S,2R)-1-(3,5-difluorobenzyl)-3-[(3-ethylbenzyl)amino]-2-hydroxypropyl}-1H-indole-6-carboxamide;

N-{(1S,2R)-1-(3,5-difluorobenzyl)-3-[(3-ethylbenzyl)amino]-2-hydroxypropyl}-1-propyl-1H-indole-6-carboxamide;

1-butyl-N-{(1S,2R)-1-(3,5-difluorobenzyl)-3-[(3-ethylbenzyl)amino]-2-hydroxypropyl}-1H-indole-5-carboxamide;

1-butyl-N -{(1S,2 R)-1-(3,5-difluorobenzyl)-3-[(3-ethylbenzyl)amino]-2-hydroxypropyl}indoline-6-carboxamide;

N-{(1S,2R)-1-(3,5-difluorobenzyl)-3-[(3-ethylbenzyl)amino]-2-hydroxypropyl}-2,3-dihydro-1,4-benzodioxine-6-carboxamide;

1-butyl-N-{(1S,2R)-1-(3,5-difluorobenzyl)-3-[(3-ethylbenzyl)amino]-2-hydroxypropyl}-1H-indazole-6-carboxamide;

N-{(1S,2R)-1-(3,5-difluorobenzyl)-3-[(3-ethylbenzyl)amino]-2-hydroxypropyl}-2-thien-2-yl-1,3-thiazole-4-carboxamide;

5-(aminosulfonyl)-N-{(1S,2R)-1-(3,5-difluorobenzyl)-3-[(3-ethylbenzyl)amino]-2-hydroxypropyl}-1-methyl-1H-pyrrole-2-carboxamide;

N-{(1S,2R)-1-(3,5-difluorobenzyl)-3-[(3-ethylbenzyl)amino]-2-hydroxypropyl}-2-{[(2-furylmethyl)sulfonyl]methyl}-1,3-thiazole-4-carboxamide;

N-{(1S,2R)-1-(3,5-difluorobenzyl)-3-[(3-ethylbenzyl)amino]-2-hydroxypropyl}-2-{[(4-fluorobenzyl)sulfonyl]methyl}-1,3-thiazole-4-carboxamide;

1-butyl-N-{(1S,2R)-1-(3,5-difluorobenzyl)-3-[(3-ethylbenzyl)amino]-2-hydroxypropyl}-4-[methyl(methylsulfonyl)amino]-1H-indole-6-carboxamide;

N-{(1S,2R)-1-(3,5-difluorobenzyl)-3-[(3-ethylbenzyl)amino]-2-hydroxypropyl}isoquinoline-7-carboxamide;

N-{(1S,2R)-1-(3,5-difluorobenzyl)-3-[(3-ethylbenzyl)amino]-2-hydroxypropyl}-1-(propylamino)isoquinoline-7-carboxamide or N-{(1S,2R)-1-(3,5-difluorobenzyl)-3-[(3-ethylbenzyl)amino]-2-hydroxypropyl}-1-(propylamino)isoquinoline-7-carboxamide;

N-{(1S,2R)-1-(3,5-difluorobenzyl)-3-[(3-ethylbenzyl)amino]-2-hydroxypropyl}-1-(3-hydroxypropyl)-1H-indole-6-carboxamide;

N-{(1S,2R)-1-(3,5-difluorobenzyl)-3-[(3-ethylbenzyl)amino]-2-hydroxypropyl}-2-methyl-6-(pyrrolidin-1-ylcarbonyl)isonicotinamide;

N-{(1S,2R)-1-(3,5-difluorobenzyl)-3-[(3-ethylbenzyl)amino]-2-hydroxypropyl}-2-(dipropylamino)isonicotinamide;

N-{(1S,2R)-1-(3,5-difluorobenzyl)-3-[(3-ethylbenzyl)amino]-2-hydroxypropyl}-2-(dipropylamino)isonicotinamide;

N-{(1S,2R)-1-(3,5-difluorobenzyl)-3-[(3-ethylbenzyl)amino]-2-hydroxypropyl}-1-[methyl(propyl)amino]isoquinoline-7-carboxamide or N-{(1S,2R)-1-(3,5-difluorobenzyl)-3-[(3-ethylbenzyl)amino]-2-hydroxypropyl}-1-[methyl(propyl)amino]isoquinoline-7-carboxamide;

$N^5$-{(1S,2R)-1-(3,5-difluorobenzyl)-3-[(3-ethylbenzyl)amino]-2-hydroxypropyl}-$N^3$,$N^3$-dipropyl-1H-pyrazole-3,5-dicarboxamide;

N-{(1S,2R)-1-(3,5-difluorobenzyl)-3-[(3-ethylbenzyl)amino]-2-hydroxypropyl}-1-(2-methoxyethyl)-1H-indole-6-carboxamide;

N-{(1S,2R)-1-(3,5-difluorobenzyl)-3-[(3-ethylbenzyl)amino]-2-hydroxypropyl}-3,4-dihydro-2H-1,4-benzoxazine-6-carboxamide;

N-{(1S,2R)-1-(3,5-difluorobenzyl)-3-[(3-ethylbenzyl)amino]-2-hydroxypropyl}-4,8-diethoxyquinoline-2-carboxamide;

N-{(1S,2R)-1-(3,5-difluorobenzyl)-3-[(3-ethylbenzyl)amino]-2-hydroxypropyl}-2-(dipropylamino)-6-methylpyrimidine-4-carboxamide;

1-[butyl(methyl)amino]-N-{(1S,2R)-1-(3,5-difluorobenzyl)-3-[(3-ethylbenzyl)amino]-2-hydroxypropyl}isoquinoline-7-carboxamide or 1-[butyl(methyl)amino]-N-{(1S,2R)-1-(3,5-difluorobenzyl)-3-[(3-ethylbenzyl)amino]-2-hydroxypropyl}isoquinoline-7-carboxamide;

N-{(1S,2R)-1-(3,5-difluorobenzyl)-3-[(3-ethylbenzyl)amino]-2-hydroxypropyl}-1,3-dihydro-2-benzothiophene-5-carboxamide 2,2-dioxide;

N-{(1S,2R)-1-(3,5-difluorobenzyl)-3-[(3-ethylbenzyl)amino]-2-hydroxypropyl}-1-isobutyl-1H-indole-6-carboxamide;

1-butyl-N-{(1S,2R)-1-(3,5-difluorobenzyl)-3-[(3-ethylbenzyl)amino]-2-hydroxypropyl}-4-(2,5-dimethyl-1H-pyrrol-1-yl)-1H-indole-6-carboxamide;

1-butyl-N-{(1S,2R)-1-(3,5-difluorobenzyl)-3-[(3-ethylbenzyl)amino]-2-hydroxypropyl}-4-methyl-1H-indole-6-carboxamide;

N-{(1S,2R)-1-(3,5-difluorobenzyl)-3-[(3-ethylbenzyl)amino]-2-hydroxypropyl}-3-oxo-2-propyl-2,3-dihydro-1,2-benzisothiazole-6-carboxamide 1,1-dioxide;

1-butyl-N-{(1S,2R)-1-(3,5-difluorobenzyl)-3-[(3-ethylbenzyl)amino]-2-hydroxypropyl}-4-(1,3-oxazol-2-yl)-1H-indole-6-carboxamide;

N-{(1S,2R)-1-(3,5-difluorobenzyl)-3-[(3-ethylbenzyl)amino]-2-hydroxypropyl}-2-(dipropylamino)-6-methylisonicotinamide;

N-{(1S,2R)-1-(3,5-difluorobenzyl)-3-[(3-ethylbenzyl)amino]-2-hydroxypropyl}-2-[(methylsulfonyl)methyl]-1,3-thiazole-4-carboxamide;

4-amino-1-butyl-N-{(1S,2R)-1-(3,5-difluorobenzyl)-3-[(3-ethylbenzyl)amino]-2-hydroxypropyl}-1H-indole-6-carboxamide;

N-{(1S,2R)-1-(3,5-difluorobenzyl)-3-[(3-ethylbenzyl)amino]-2-hydroxypropyl}-2-ethyl-3-oxo-2,3-dihydro-1,2-benzisothiazole-6-carboxamide 1,1-dioxide;

4-butyl-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide;

methyl 2-[({(1S,2R)-1-(3,5-difluorobenzyl)-3-[(3-ethylbenzyl)amino]-2-hydroxypropyl}amino)carbonyl]-6-methylisonicotinate;

$N^4$-{(1S,2R)-1-(3,5-difluorobenzyl)-3-[(3-ethylbenzyl)amino]-2-hydroxypropyl}-6-methyl-$N^2$,$N^2$-dipropylpyridine-2,4-dicarboxamide 1-oxide;

1-butyl-4-cyano-N-{(1S,2R)-1-(3,5-difluorobenzyl)-3-[(3-ethylbenzyl)amino]-2-hydroxypropyl}-1H-indole-6-carboxamide;

1-butyl-4-cyano-N-{(1S,2R)-1-(3,5-difluorobenzyl)-3-[(3-ethylbenzyl)amino]-2-hydroxypropyl}-1H-indole-6-carboxamide;

N-{(1S,2R)-1-(3,5-difluorobenzyl)-3-[(3-ethylbenzyl)amino]-2-hydroxypropyl}-1-methyl-1,3-dihydro-2,1-benzisothiazole-5-carboxamide 2,2-dioxide;

2-chloro-N-{(1S,2R)-1-(3,5-difluorobenzyl)-3-[(3-ethylbenzyl)amino]-2-hydroxypropyl}-6-methylisonicotinamide;

N-{(1S,2R)-1-(3,5-difluorobenzyl)-3-[(3-ethylbenzyl)amino]-2-hydroxypropyl}-1-isopentyl-1H-indole-6-carboxamide;

N-{(1S,2R)-1-(3,5-difluorobenzyl)-3-[(3-ethylbenzyl)amino]-2-hydroxypropyl}-2-propyl-2,3-dihydro-1,2-benzisothiazole-6-carboxamide 1,1-dioxide;

N-{(1S,2R)-1-(3,5-difluorobenzyl)-3-[(3-ethylbenzyl)amino]-2-hydroxypropyl}-2-ethyl-2,3-dihydro-1,2-benzisothiazole-6-carboxamide 1,1-dioxide;

6-bromo-N-{(1S,2R)-1-(3,5-difluorobenzyl)-3-[(3-ethylbenzyl)amino]-2-hydroxypropyl}-2,2-dimethylchromane-8-carboxamide;

N-{(1S,2R)-1-(3,5-difluorobenzyl)-3-[(3-ethylbenzyl)amino]-2-hydroxypropyl}-5-[(methylsulfonyl)methyl]thiophene-2-carboxamide;

N-{(1S,2R)-1-(3,5-difluorobenzyl)-3-[(3-ethylbenzyl)amino]-2-hydroxypropyl}pyrazine-2-carboxamide;

N-{(1S,2R)-1-(3,5-difluorobenzyl)-3-[(3-ethylbenzyl)amino]-2-hydroxypropyl}-2-[(2S)-2-(methoxymethyl)pyrrolidin-1-yl]-6-methylisonicotinamide;

6-cyano-N-{(1S,2R)-1-(3,5-difluorobenzyl)-3-[(3-ethylbenzyl)amino]-2-hydroxypropyl}-2,2-dimethylchromane-8-carboxamide;

3-butyl-N-{(1S,2R)-1-(3,5-difluorobenzyl)-3-[(3-ethylbenzyl)amino]-2-hydroxypropyl}-1-methyl-1H-indole-5-carboxamide;

3-butyl-N-{(1S,2R)-1-(3,5-difluorobenzyl)-3-[(3-ethylbenzyl)amino]-2-hydroxypropyl}-1H-indole-5-carboxamide;

1-butyl-N-((1S,2R)-1-(3,5-difluorobenzyl)-3-{[1-(3-ethynylphenyl)cyclopropyl]amino}-2-hydroxypropyl)-1H-benzimidazole-6-carboxamide;

N-{(1S,2R)-1-(3,5-difluorobenzyl)-3-[(3-ethylbenzyl)amino]-2-hydroxypropyl}-5-[(methylsulfonyl)methyl]nicotinamide;

N-{(1S,2R)-1-(3,5-difluorobenzyl)-3-[(3-ethylbenzyl)amino]-2-hydroxypropyl}-2-(dipropylamino)-6-(1,3-oxazol-2-yl)isonicotinamide;

N-{(1S,2R)-1-(3,5-difluorobenzyl)-3-[(3-ethylbenzyl)amino]-2-hydroxypropyl}-2-methyl-6-(1,3-oxazol-2-yl)isonicotinamide;

1-butyl-N-((1S,2R)-1-(3,5-difluorobenzyl)-3-{[1-(3-ethynylphenyl)cyclopropyl]amino}-2-hydroxypropyl)-1H-benzimidazole-5-carboxamide;

N-{(1S,2R)-3-[(3-ethylbenzyl)amino]-1-[3-(hexyloxy)benzyl]-2-hydroxypropyl}-2-1(methylsulfonyl)amino-1,3-oxazole-4-carboxamide;

N-{(1S,2R)-1-(3,5-difluorobenzyl)-3-[(3-ethylbenzyl)amino]-2-hydroxypropyl}-6-[(methylsulfonyl)methyl]nicotinamide;

1-butyl-N-{(1S,2R)-1-(3,5-difluorobenzyl)-3-[(3-ethylbenzyl)amino]-2-hydroxypropyl}-5-methyl-1H-pyrrole-2-carboxamide;

N²-{(1S,2R)-1-(3,5-difluorobenzyl)-3-[(3-ethylbenzyl)amino]-2-hydroxypropyl}-6-methyl-N⁴,N⁴-dipropylpyridine-2,4-dicarboxamide;
N-{(1S,2R)-1-(3,5-difluorobenzyl)-3-[(3-ethylbenzyl)amino]-2-hydroxypropyl}-1,1-dipropyl-3,4-dihydro-1H-isochromene-7-carboxamide;
2-butyl-N-{(1S,2R)-1-(3,5-difluorobenzyl)-3-[(3-ethylbenzyl)amino]-2-hydroxypropyl}-1,2,3,4-tetrahydroisoquinoline-7-carboxamide;
1-butyl-N-((1S,2R)-1-(3,5-difluorobenzyl)-3-{[1-(3-ethynylphenyl)cyclopropyl]amino}-2-hydroxypropyl)-2-(2-methoxyethyl)-1H-benzimidazole-6-carboxamide;
N-((1S,2R)-1-(3,5-difluorobenzyl)-3-{[-(3-ethynylphenyl)cyclopropyl]amino}-2-hydroxypropyl)-2-(dipropylamino)-6-(1,3-oxazol-2-yl)isonicotinamide;
4-butyl-N-{(1S,2R)-1-(3,5-difluorobenzyl)-3-[(3-ethylbenzyl)amino]-2-hydroxypropyl}-1-(methylsulfonyl)-1,2,3,4-tetrahydroquinoxaline-6-carboxamide;
1-butyl-N-{(1S,2R)-1-(3,5-difluorobenzyl)-3-[(3-ethylbenzyl)amino]-2-hydroxypropyl}isoquinoline-7-carboxamide;
5-{[butyl(methyl)amino]methyl}-N-{(1S,2R)-1-(3,5-difluorobenzyl)-3-[(3-ethylbenzyl)amino]-2-hydroxypropyl}thiophene-2-carboxamide;
N-{(1S,2R)-1-(3,5-difluorobenzyl)-3-[(3-ethylbenzyl)amino]-2-hydroxypropyl}-2-(dipropylamino)-6-(1,3-thiazol-2-yl)isonicotinamide;
N-{(1S,2R)-1-(3-butoxybenzyl)-3-[(3-ethylbenzyl)amino]-2-hydroxypropyl}-2-[(methylsulfonyl)amino]-1,3-oxazole-4-carboxamide;
3-butyl-N-{(1S,2R)-1-(3,5-difluorobenzyl)-3-[(3-ethylbenzyl)amino]-2-hydroxypropyl}imidazo[1,2-a]pyridine-6-carboxamide;
2-[butyl(methyl)amino]-N-{(1S,2R)-1-(3,5-difluorobenzyl)-3-[(3-ethylbenzyl)amino]-2-hydroxypropyl}-6-(1,3-oxazol-2-yl)isonicotinamide;
N-{(1S,2R)-1-(3,5-difluorobenzyl)-3-[(3-ethylbenzyl)amino]-2-hydroxypropyl}-1,3-benzodioxole-5-carboxamide;
N-{(1S,2R)-1-(3,5-difluorobenzyl)-3-[(3-ethylbenzyl)amino]-2-hydroxypropyl}-2-[methyl(propyl)amino]-6-(1,3-oxazol-2-yl)isonicotinamide;
4-butyl-N-{(1S,2R)-1-(3,5-difluorobenzyl)-3-[(3-ethylbenzyl)amino]-2-hydroxypropyl}-3,4-dihydro-2H-1,4-benzothiazine-6-carboxamide;
4-butyl-N-{(1S,2R)-1-(3,5-difluorobenzyl)-3-[(3-ethylbenzyl)amino]-2-hydroxypropyl}-1,2,3,4-tetrahydroiuinoxaline-6-carboxamide;
N-((1S,2R)-1-(3,5-difluorobenzyl)-3-{[1-(3-ethynylphenyl)cyclopropyl]amino}-2-hydroxypropyl)-2-(dipropylamino)isonicotinamide;
N-{(1S,2R)-1-(3,5-difluorobenzyl)-3-[(3-ethylbenzyl)amino]-2-hydroxypropyl}-2-(dipropylamino)-4-methyl-1,3-thiazole-5-carboxamide;
N-{(1S,2R)-1-(3,5-difluorobenzyl)-3-[(3-ethylbenzyl)amino]-2-hydroxypropyl}-1-methyl-3-phenyl-1H-thieno[2,3-c]pyrazole-5-carboxamide;
1-butyl-N-((1S,2R)-1-(3,5-difluorobenzyl)-3-{[1-(3-ethynylphenyl)cyclopropyl]amino}-2-hydroxypropyl)-1H-indole-6-carboxamide;
1-butyl-N-{(1S,2R)-1-(3,5-difluorobenzyl)-3-[(3-ethylbenzyl)amino]-2-hydroxyproypyl}-1,2,3,4-tetrahydroisoquinoline-7-carboxamide;
4-butyl-N-{(1S,2R)-1-(3,5-difluorobenzyl)-3-[(3-ethylbenzyl)amino]-2-hydroxypropyl}-3,4-dihydro-2H-1,4-benzothiazine-6-carboxamide 1-oxide;
2-[butyl(methyl)amino]-6-chloro-N-{(1S,2R)-1-(3,5-difluorobenzyl)-3-[(3-ethylbenzyl)amino]-2-hydroxypropyl}isonicotinamide;
2-[butyl(methyl)amino]-6-cyano-N-{(1S,2R)-1-(3,5-difluorobenzyl)-3-[(3-ethylbenzyl)amino]-2-hydroxypropyl}isonicotinamide;
4-butyl-N-{(1S,2R)-1-(3,5-difluorobenzyl)-3-[(3-ethylbenzyl)amino]-2-hydroxypropyl}-8-(1,3-oxazol-2-yl)-3,4-dihydro-2H-1,4-benzoxazine-6-carboxamide or 4-butyl-N-{(1S,2R)-1-(3,5-difluorobenzyl)-3-[(3-ethylbenzyl)amino]-2-hydroxypropyl}-8-(1,3-oxazol-2-yl)-3,4-dihydro-2H-1,4-benzoxazine-6-carboxamide;
1-butyl-N-{(1S,2R)-1-(3,5-difluorobenzyl)-3-[(3-ethylbenzyl)amino]-2-hydroxypropyl}-1,2,3,4-tetrahydroquinoline-7-carboxamide or 1-butyl-N-{(1S,2R)-1-(3,5-difluorobenzyl)-3-[(3-ethylbenzyl)amino]-2-hydroxypropyl}-1,2,3,4-tetrahydroquinoline-7-carboxamide;
N-{(1S 2R)-1-(3,5-difluorobenzyl)-3-[(3-ethylbenzyl)amino]-2-hydroxypropyl}-3-propyl-1,2-benzisoxazole-5-carboxamide;
2-[allyl(methyl)amino]-N-{(1S,2R)-1-[3-(allyloxy)-5-fluorobenzyl]-3-[(3-ethylbenzyl)amino]-2-hydroxypropyl}isonicotinamide;
3-butyl-N-{(1S,2R)-1-(3,5-difluorobenzyl)-3-[(3-ethylbenzyl)amino]-2-hydroxypropyl}-1,2-benzisoxazole-5-carboxamide;
N-((1S,2R)-1-(3,5-difluorobenzyl)-3-{[1-(3-ethynylphenyl)cyclopropyl]amino}-2-hydroxypropyl)-5-pyrrolidin-1-ylpyrazine-2-carboxamide;
4-butoxy-N-{(1S,2R)-1-(3,5-difluorobenzyl)-3-[(3-ethybenzyl)amino]-2-hydroxypropyl}qouinoline-2-carboxamide;
2-cyano-N-{(1S,2R)-1-(3,5-difluorobenzyl)-3-[(3-ethylbenzyl)amino]-2-hydroxypropyl}-6-[methyl(propyl)amino]isonicotinamide;
3-acetyl-1-butyl-N-{(1S,2R)-1-(3,5-difluorobenzyl)-3-[(3-ethylbenzyl)amino]-2-hydroxypropyl}-1H-indole-6-carboxamide;
N-{(1S,2R)-1-(3,5-difluorobenzyl)-3-[(3-ethylbenzyl)amino]-2-hydroxypropyl}-3-isobutyl-1,2-benzisoxazole-5-carboxamide;
4,5-dibromo-N-{(1S,2R)-1-(3,5-difluorobenzyl)-3-[(3-ethylbenzyl)amino]-2-hydroxypropyl}thiophene-2-carboxamide;
N-((1S,2R)-1-(3,5-difluorobenzyl)-3-{[1-(3-ethynylphenyl)cyclopropyl]amino}-2-hydroxypropyl)-2,6-bis(dimethylamino)pyrimidine-4-carboxamide;
4-butyl-8-cyano-N-{(1S,2R)-1-(3,5-difluorobenzyl)-3-[(3-ethylbenzyl)amino]-2-hydroxypropyl}-3,4-dihydro-2H-1,4-benzoxazine-6-carboxamide;
1-butyl-N-{(1S,2R)-1-(3,5-difluorobenzyl)-3-[(3-ethylbenzyl)amino]-2-hydroxypropyl}-3-(trifluoroacetyl)-1H-indole-6-carboxamide;
N-((1S,2R)-1-(3,5-difluorobenzyl)-3-{[1-(3-ethynylphenyl)cyclopropyl]amino}-2-hydroxypropyl)-4-(dipropylamino)-1-methyl-1H-pyrrole-2-carboxamide;
2,6-dichloro-N-((1S,2R)-1-(3,5-difluorobenzyl)-3-{[1-(3-ethynylphenyl)cyclopropyl]amino}-2-hydroxypropyl)pyrimidine-4-carboxamide;
N-((1S,2R)-1-(3,5-difluorobenzyl)-3-{[1-(3-ethynylphenyl)cyclopropyl]amino}-2-hydroxypropyl)-2-morpholin-4-yl-4-(trifluoromethyl)-1,3-thiazole-5-carboxamide;
2-chloro-N-((1S,2R)-1-(3,5-difluorobenzyl)-3-{[1-(3-ethynylphenyl)cyclopropyl]amino}-2-hydroxypropyl)-6-morpholin-4-ylpyrimidine-4-carboxamide;

N-((1S,2R)-1-(3,5-difluorobenzyl)-3-{[1-(3-ethynylphenyl)cyclopropyl]amino}-2-hydroxypropyl)-2-(dipropylamino)-6-morpholin-4-ylpyrimidine-4-carboxamide;

N-((1S,2R)-1-(3,5-difluorobenzyl)-3-{[1-(3-ethynylphenyl)cyclopropyl]amino}-2-hydroxypropyl)-2,6-bis(dipropylamino)pyrimidine-4-carboxamide;

or pharmaceutically acceptable salts thereof.

27. A compound that is:

N'-{(1S,2R)-1-(3,5-difluorobenzyl)-2-hydroxy-3-[(3-isopropylbenzyl)amino]propyl}-N,N-dipropylpyridine-3,5-dicarboxamide;

N'-{(1S,2R)-1-(3,5-difluorobenzyl)-3-[(3-ethylbenzyl)amino]-2-hydroxypropyl}-N,N-dipropylpyridine-3,5-dicarboxamide 1-oxide;

$N^4$-{(1S,2R)-1-(3,5-difluorobenzyl)-2-hydroxy-3-[(3-isopropylbenzyl)amino]propyl}-6-methyl-$N^2,N^2$-dipropylpyridine-2,4-dicarboxamide;

N-{(1S 12R)-1-(3,5-difluorobenzyl)-3-[(3-ethylbenzyl)amino]-2-hydroxypropyl}-1-methyl-1H-imidazole-2-carboxamide;

tert-butyl 2-[({(1S,2R)-1-(3,5-difluorobenzyl)-3-[(3-ethylbenzyl)amino]-2-hydroxypropyl}amino)carbonyl]-1-methyl-1H-imidazol-4-ylcarbamate;

N-{(1S,2R)-1-(3,5-difluorobenzyl)-3-[(3-ethylbenzyl)amino]-2-hydroxypropyl}-2,1,3-benzoxadiazole-5-carboxamide;

N-{(1S,2R)-1-(3,5-difluorobenzyl)-3-[(3-ethylbenzyl)amino]-2-hydroxyoropyl}-4-methyl-1,2,3-thiadiazole-5-carboxamide;

N-{(1S,2R)-1-(3,5-difluorobenzyl)-3-[(3-ethylbenzyl)amino]-2-hydroxyoropyl}-5-[(pyridin-2-ylthio)methyl]-2-furamide;

N-{(1S,2R)-1-(3,5-difluorobenzyl)-3-[(3-ethylbenzyl)amino]-2-hydroxypropyl}-1-phenyl-5-propyl-1H-pyrazole-4-carboxamide;

N-{(1S,2R)-1-(3,5-difluorobenzyl)-3-[(3-ethylbenzyl)amino]-2-hydroxypropyl}-5-(trifluoromethoxy)-1H-indole-2-carboxamide;

N-{(1S,2R)-1-(3,5-difluorobenzyl)-3-[(3-ethylbenzyl)amino]-2-hydroxypropyl}-2,8-dimethylquinoline-3-carboxamide;

N-{(1S,2R)-1-(3,5-difluorobenzyl)-3-[(3-ethylbenzyl)amino]-2-hydroxypropyl}-2-hydroxy-6-methylquinoline-4-carboxamide;

N-{(1S,2R)-1-(3,5-difluorobenzyl)-3-[(3-ethylbenzyl)amino]-2-hydroxypropyl}-3-propylpyrazine-2-carboxamide 4-oxide;

N-{(1S,2R)-1-(3,5-difluorobenzyl)-3-[(3-ethylbenzyl)amino]-2-hydroxypropyl}-1-benzothiophene-3-carboxamide;

N-{(1S,2R)-1-(3,5-difluorobenzyl)-3-[(3-ethylbenzyl)amino]-2-hydroxypropyl}-1-methyl-1H-indole-3-carboxamide;

N-{(1S,2R)-1-(3,5-difluorobenzyl)-3-[(3-ethylbenzyl)amino]-2-hydroxypropyl}-6-methoxy-1,3-benzothiazole-2-carboxamide;

N-{(1S,2R)-1-(3,5-difluorobenzyl)-3-[(3-ethylbenzyl)amino]-2-hydroxypropyl}-4-phenylthiophene-2-carboxamide;

N-{(1S,2R)-1-(3,5-difluorobenzyl)-3-[(3-ethylbenzyl)amino]-2-hydroxypropyl}-5-methoxythiophene-2-carboxamide;

N-{(1S,2R)-1-(3,5-difluorobenzyl)-3-[(3-ethylbenzyl)amino]-2-hydroxypropyl}-2,3'-bithiophene-5-carboxamide;

N-{(1S,2R)-1-(3,5-difluorobenzyl)-3-[(3-ethylbenzyl)amino]-2-hydroxypropyl}-1H-indole-3-carboxamide;

N-{(1S,2R)-1-(3,5-difluorobenzyl)-3-[(3-ethylbenzyl)amino]-2-hydroxypropyl}-2-furamide;

N-{(1S,2R)-1-(3,5-difluorobenzyl)-3-[(3-ethylbenzyl)amino]-2-hydroxypropyl}nicotinamide;

N-{(1S,2R)-1-(3,5-difluorobenzyl)-3-[(3-ethylbenzyl)amino]-2-hydroxypropyl}-2-hydroxyquinoline-4-carboxamide;

N-{(1S,2R)-1-(3,5-difluorobenzyl)-3-[(3-ethylbenzyl)amino]-2-hydroxypropyl}-6-hydroxynicotinamide;

N-{(1S,2R)-1-(3,5-difluorobenzyl)-3-[(3-ethylbenzyl)amino]-2-hydroxypropyl}-1-benzothiophene-2-carboxamide;

7-chloro-N-{(1S,2R)-1-(3,5-difluorobenzyl)-3-[(3-ethylbenzyl)amino]-2-hydroxypropyl}-4-hydroxyquinoline-3-carboxamide;

N-{(1S,2R)-1-(3,5-difluorobenzyl)-3-[(3-ethylbenzyl)amino]-2-hydroxypropyl}-3-methylisoxazole-5-carboxamide;

N-{(1S,2R)-1-(3,5-difluorobenzyl)-3-[(3-ethylbenzyl)amino]-2-hydroxypropyl}-5-methylisoxazole-3-carboxamide;

N-{(1S,2R)-1-(3,5-difluorobenzyl)-3-[(3-ethylbenzyl)amino]-2-hydroxypropyl}-5-methoxy-1H-indole-2-carboxamide;

N-{(1S,2R)-1-(3,5-difluorobenzyl)-3-[(3-ethylbenzyl)amino]-2-hydroxypropyl}-2,5-dimethyl-3-furamide;

N-{(1S,2R)-1-(3,5-difluorobenzyl)-3-[(3-ethylbenzyl)amino]-2-hydroxypropyl}-6-hydroxy-2-(methylthio)pyrimidine-4-carboxamide;

N-{(1S,2R)-1-(3,5-difluorobenzyl)-3-[(3-ethylbenzyl)amino]-2-hydroxypropyl}-2-methyl-1,3-oxazole-4-carboxamide;

N-{(1S,2R)-1-(3,5-difluorobenzyl)-3-[(3-ethylbenzyl)amino]-2-hydroxypropyl}-3-methyl-1H-pyrazole-5-carboxamide;

N-{(1S,2R)-1-(3,5-difluorobenzyl)-3-[(3-ethylbenzyl)amino]-2-hydroxypropyl}thiophene-3-carboxamide;

6-chloro-N-{1S,2R)-1-(3,5-difluorobenzyl)-3-[(3-ethylbenzyl)amino]-2-hydroxypropyl}-1H-indole-2-carboxamide;

N-{(1S,2R)-1-(3,5-difluorobenzyl)-3-[(3-ethylbenzyl)amino]-2-hydroxypropyl}-1H-indole-5-carboxamide;

N-{(1S,2R)-1-(3,5-difluorobenzyl)-3-[(3-ethylbenzyl)amino]-2-hydroxypropyl}-4-methyl-1,3-oxazole-5-carboxamide;

N-{(1S,2R)-1-(3,5-difluorobenzyl)-3-[(3-ethylbenzyl)amino]-2-hydroxypropyl}-2-methylpyrimidine-5-carboxamide;

N-{(1S,2R)-1-(3,5-difluorobenzyl)-3-[(3-ethylbenzyl)amino]-2-hydroxypropyl}quinoline-4-carboxamide;

N-{(1S,2R)-1-(3,5-difluorobenzyl)-3-[(3-ethylbenzyl)amino]-2-hydroxypropyl}-2-phenylimidazo[1,2-a]pyridine-7-carboxamide;

N-{(1S,2R)-1-(3,5-difluorobenzyl)-3-[(3-ethylbenzyl)amino]-2-hydroxypropyl}-6-hydroxy-4-methylpyridine-2-carboxamide;

N-{(1S,2R)-1-(3,5-difluorobenzyl)-3-[(3-ethylbenzyl)amino]-2-hydroxypropyl}-2-[ethyl(methyl)amino]-4-hydroxypyrimidine-5-carboxamide;

N-{(1S,2R)-1-(3,5-difluorobenzyl)-3-[(3-ethylbenzyl)amino]-2-hydroxypropyl}-4,8-dihydroxyquinoline-2-carboxamide;

N-{(1S,2R)-1-(3,5-difluorobenzyl)-3-[(3-ethylbenzyl)amino]-2-hydroxypropyl}-1-benzofuran-2-carboxamide;

N-{(1S,2R)-1-(3,5-difluorobenzyl)-3-[(3-ethylbenzyl)amino]-2-hydroxypropyl}-1-ethyl-1H-indole-2-carboxamide;

2-(acetylamino)-N-{(1S,2R)-1-(3,5-difluorobenzyl)-3-[(3-ethylbenzyl)amino]-2-hydroxypropyl}-4,5-dimethylthiophene-3-carboxamide;

N-{(1S,2R)-1(3,5-difluorobenzyl)-3-[(3-ethylbenzyl)amino]-2-hydroxypropyl}-3-hydroxyquinoxaline-2-carboxamide;

N-{(1S,2R)-1-(3,5-difluorobenzyl)-3-[(3-ethylbenzyl)amino]-2-hydroxypropyl}-1H-indazole-3-carboxamide;

N-{(1S,2R)-1-(3,5-difluorobenzyl)-3-[(3-ethylbenzyl)amino]-2-hydroxypropyl}-5-methyl-2-phenyl-1,3-oxazole-4-carboxamide;

4-chloro-N-{(1S,2R)-1-(3,5-difluorobenzyl)-3-[(3-ethylbenzyl)amino]-2-hydroxypropyl}-6-methylquinoline-2-carboxamide;

N-{(1S,2R)-1-(3,5-difluorobenzyl)-3-[(3-ethylbenzyl)amino]-2-hydroxypropyl}thiophene-2-carboxamide;

N-{(1S,2R)-1-(3,5-difluorobenzyl)-3-[(3-ethylbenzyl)amino]-2-hydroxypropyl}-3-furamide;

N-{(1S,2R)-1(3,5-difluorobenzyl)-3-[(3-ethylbenzyl)amino]-2-hydroxypropyl}-2-methyl-3-furamide;

N-{(1S,2R)-1-(3,5-difluorobenzyl)-3-[(3-ethylbenzyl)amino]-2-hydroxypropyl}-3-hydroxy-6-neopentylpyridine-2-carboxamide;

N-{(1S,2R)-1-(3,5-difluorobenzyl)-3-[(3-ethylbenzyl)amino]-2-hydroxypropyl}-1,3-thiazole-4-carboxamide;

N-{(1S,2R)-1-(3,5-difluorobenzyl)-3-[(3-ethylbenzyl)amino]-2-hydroxypropyl}-4-hydroxy-7-methoxy-1-benzothiophene-5-carboxamide;

N-{(1S,2R)-1-(3,5-difluorobenzyl)-3-[(3-ethylbenzyl)amino]-2-hydroxypropyl}-4-hydroxy-7-methoxy-1-benzofuran-5-carboxamide;

N-{(1S,2R)-1-(3,5-difluorobenzyl)-3-[(3-ethylbenzyl)amino]-2-hydroxypropyl}-2-phenyl-1,3-oxazole-4-carboxamide;

N-{(1S,2R)-1-(3,5-difluorobenzyl)-3-[(3-ethylbenzyl)amino]-2-hydroxypropyl}-4-hydroxy-7-methoxyquinoline-3-carboxamide;

N-{(1S,2R)-1-(3,5-difluorobenzyl)-3-[(3-ethylbenzyl)amino]-2-hydroxypropyl}-3-methyl-5-(4-methyl-1,2,3-thiadiazol-5-yl)isoxazole-4-carboxamide;

N-{(1S,2R)-1-(3,5-difluorobenzyl)-3-[(3-ethylbenzyl)amino]-2-hydroxypropyl}-5-methyl-2-phenyl-2H-1,2,3-triazole-4-carboxamide;

N-{(1S,2R)-1-(3,5-difluorobenzyl)-3-[(3-ethylbenzyl)amino]-2-hydroxypropyl}-2-(4-methyl-1,2,3-thiadiazol-5-yl)-1,3-thiazole-4-carboxamide;

N-{(1S,2R)-1-(3,5-difluorobenzyl)-3-[(3-ethylbenzyl)amino]-2-hydroxypropyl}-2-phenylimidazo[1,2-a]pyridine-6-carboxamide;

N-{(1S,2R)-1-(3,5-difluorobenzyl)-3-[(3-ethylbenzyl)amino]-2-hydroxyoropyl}-5-(piperidin-1-ylmethyl)-2-furamide;

N-{(1S,2R)-1-(3,5-difluorobenzyl)-3-[(3-ethylbenzyl)amino]-2-hydroxypropyl}-2,5-dimethyl-1-phenyl-1H-pyrrole-3-carboxamide;

N-{(1S,2R)-1-(3,5-difluorobenzyl)-3-[(3-ethylbenzyl)amino]-2-hydroxypropyl}-5-methyl-1-phenyl-1H-pyrazole-3-carboxamide;

N-{(1S,2R)-1-(3,5-difluorobenzyl)-3-[(3-ethylbenzyl)amino]-2-hydroxypropyl}-3,5-bis(methylthio)isothiazole-4-carboxamide;

N-{(1S,2R)-1-(3,5-difluorobenzyl)-3-[(3-ethylbenzyl)amino]-2-hydroxypropyl}-3-methyl-5-(trifluoromethyl)isoxazole-4-carboxamide;

N-{(1S,2R)-1-(3,5-difluorobenzyl)-3-[(3-ethylbenzyl)amino]-2-hydroxypropyl}-1-phenyl-1H-pyrrole-2-carboxamide;

N-{(1S,2R)-1-(3,5-difluorobenzyl)-3-[(3-ethylbenzyl)amino]-2-hydroxypropyl}pyrazine-2-carboxamide 4-oxide;

N-{(1S,2R)-1-(3,5-difluorobenzyl)-3-[(3-ethylbenzyl)amino]-2-hydroxypropyl}-5-methyl-1-pyridin-4-yl-1H-1,2,3-triazole-4-carboxamide;

N-{(1S,2R)-1-(3,5-difluorobenzyl)-3-[(3-ethylbenzyl)amino]-2-hydroxypropyl}-6-methoxypyrazine-2-carboxamide 4-oxide;

N-{(1S,2R)-1-(3,5-difluorobenzyl)-3-[(3-ethylbenzyl)amino]-2-hydroxypropyl}-1-methyl-5-phenyl-1H-pyrazole-3-carboxamide;

N-{(1S,2R)-1-(3,5-difluorobenzyl)-3-[(3-ethylbenzyl)amino]-2-hydroxypropyl}-1H-benzimidazole-5-carboxamide;

5-chloro-N-{(1S,2R)-1-(3,5-difluorobenzyl)-3-[(3-ethylbenzyl)amino]-2-hydroxypropyl}-1-benzofuran-2-carboxamide;

N-{(1S,2R)-1-(3,5-difluorobenzyl)-3-[(3-ethylbenzyl)amino]-2-hydroxypropyl}-2-pyridin-3-yl-1,3-thiazole-4-carboxamide;

8-cyano-N-{(1S,2R)-1-(3,5-difluorobenzyl)-3-[(3-ethylbenzyl)amino]-2-hydroxypropyl}-4-hydroxyquinoline-3-carboxamide;

N-{(1S,2R)-1-(3,5-difluorobenzyl)-3-[(3-ethylbenzyl)amino]-2-hydroxypropyl}-1,6-naphthyridine-2-carboxamide;

N-{(1S,2R)-1-(3,5-difluorobenzyl)-3-[(3-ethylbenzyl)amino]-2-hydroxypropyl}-2,2-dimethyl-4-oxochromane-6-carboxamide;

N-{(1S,2R)-1-(3,5-difluorobenzyl)-3-[(3-ethylbenzyl)amino]-2-hydroxypropyl}-4,7-dimethoxy-1-benzofuran-5-carboxamide;

3-chloro-N-{(1S,2R)-1-(3,5-difluorobenzyl)-3-[(3-ethylbenzyl)amino]-2-hydroxypropyl}-5-phenylisothiazole-4-carboxamide;

N-{(1S,2R)-1-(3,5-difluorobenzyl)-3-[(3-ethylbenzyl)amino]-2-hydroxypropyl}-6-methoxy-1-benzofuran-2-carboxamide;

N-{(1S,2R)-1-(3,5-difluorobenzyl)-3-[(3-ethylbenzyl)amino]-2-hydroxypropyl}-4-methoxy-1H-pyrrole-3-carboxamide;

N-{(1S,2R)-1-(3,5-difluorobenzyl)-3-[(3-ethylbenzyl)amino]-2-hydroxypropyl}-2-methyl-1,3-thiazole-4-carboxamide;

N-{(1S,2R)-1-(3,5-difluorobenzyl)-3-[(3-ethylbenzyl)amino]-2-hydroxypropyl}-2-methyl-5-(2-thienyl)-3-furamide;

N-{(1S,2R)-1-(3,5-difluorobenzyl)-3-[(3-ethylbenzyl)amino]-2-hydroxypropyl}-4-methoxythiophene-3-carboxamide;

6-chloro-N-{(1S,2R)-1-(3,5-difluorobenzyl)-3-[(3-ethylbenzyl)amino]-2-hydroxypropyl}-4-(trifluoromethyl)pyridine-2-carboxamide;

N-{(1S,2R)-1-(3,5-difluorobenzyl)-3-[(3-ethylbenzyl)amino]-2-hydroxypropyl}-1-(4-fluorophenyl)-5-methyl-1H-1,2,4-triazole-3-carboxamide;

N-{(1S,2R)-1-(3,5-difluorobenzyl)-3-[(3-ethylbenzyl)amino]-2-hydroxypropyl}-4-(4-methoxyphenyl)thiophene-2-carboxamide;

2-(acetylamino)-5-chloro-N-{(1S,2R)-1-(3,5-difluorobenzyl)-3-[(3-ethylbenzyl)amino]-2-hydroxypropyl}thiophene-3-carboxamide;

4-chloro-N-{(1S,2R)-1-(3,5-difluorobenzyl)-3-[(3-ethylbenzyl)amino]-2-hydroxypropyl}-7,7-dimethyl-7,8-dihydro-5H-pyrano[4,3-b]pyridine-2-carboxamide;

2-(2-chlorophenyl)-N-{(1S,2R)-1-(3,5-difluorobenzyl)-3-[(3-ethylbenzyl)amino]-2-hydroxypropyl}-1,3-thiazole-4-carboxamide;

N-{(1S,2R)-1-(3,5-difluorobenzyl)-3-[(3-ethylbenzyl)amino]-2-hydroxypropyl}-2-(3-methylphenyl)-1,3-thiazole-4-carboxamide;

N-{(1S,2R)-1-(3,5-difluorobenzyl)-3-[(3-ethylbenzyl)amino]-2-hydroxypropyl}-1,2,5-thiadiazole-3-carboxamide;

N-{(1S,2R)-1-(3,5-difluorobenzyl)-3-[(3-ethylbenzyl)amino]-2-hydroxypropyl}-2-(phenoxymethyl)-1,3-thiazole-4-carboxamide;

N-{(1S,2R)-1-(3,5-difluorobenzyl)-3-[(3-ethylbenzyl)amino]-2-hydroxypropyl}-2-(4-methylphenyl)-1,3-thiazole-4-carboxamide;

N-{(1S,2R)-1-(3,5-difluorobenzyl)-3-[(3-ethylbenzyl)amino]-2-hydroxypropyl}-2-pyridin-3-ylbenzamide;

N-{(1S,2R)-1-(3,5-difluorobenzyl)-3-[(3-ethylbenzyl)amino]-2-hydroxypropyl}-4-methyl-2-phenyl-1,3-oxazole-5-carboxamide;

N-{(1S,2R)-1-(3,5-difluorobenzyl)-3-[(3-ethylbenzyl)amino]-2-hydroxypropyl}-1-ethyl-3-(2-thienyl)-1H-pyrazole-5-carboxamide;

4-(acetylamino)-N-{(1S,2R)-1-(3,5-difluorobenzyl)-3-[(3-ethylbenzyl)amino]-2-hydroxypropyl}-1-methyl-1H-pyrrole-2-carboxamide;

N-{(1S,2R)-1-(3,5-difluorobenzyl)-3-[(3-ethylbenzyl)amino]-2-hydroxypropyl}-4-phenyl-1,2,3-thiadiazole-5-carboxamide;

N-{(1S,2R)-1-(3,5-difluorobenzyl)-3-[(3-ethylbenzyl)amino]-2-hydroxypropyl}-2-(2,5-dimethyl-1H-pyrrol-1-yl)thiophene-3-carboxamide;

N-{(1S,2R)-1-benzyl-3-[1-ethyl-2-(4-methylpentanoyl)hydrazino]-2-hydroxypropyl}-2-[(methylsulfonyl)amino]-1,3-oxazole-4-carboxamide;

N-{(1S,2R)-1-(3,5-difluorobenzyl)-3-[(3-ethylbenzyl)amino]-2-hydroxypropyl}-1-methyl-1H-imidazole-2-carboxamide;

6-(4-benzylpiperazin-1-yl)-N-{(1S,2R)-1-(3,5-difluorobenzyl)-2-hydroxy-3-[(3-iodobenzyl)amino]propyl}nicotinamide N-{(1S,2R)-1-(3,5-difluorobenzyl)-3-[(3-ethylbenzyl)amino]-2-hydroxypropyl}-5-methyl-7-(trifluoromethyl)pyrazolo[1,5-a]pyrimidine-2-carboxamide N-{(1S,2R)-1-(3,5-difluorobenzyl)-3-[(3-ethylbenzyl)amino]-2-hydroxypropyl}thieno[2,3-b]quinoline-2-carboxamide N-{(1S,2R)-1-(3,5-difluorobenzyl)-3-[(3-ethylbenzyl)amino]-2-hydroxypropyl}-4-methyl-4H,6H-pyrrolo[1,2-a][4,1]benzoxazepine-4-carboxamide N-{(1S,2R)-1-(3,5-difluorobenzyl)-3-[(3-ethylbenzyl)amino]-2-hydroxypropyl}-3-oxo-2,3-dihydro-1,2-benzisothiazole-6-carboxamide 1,1-dioxide N-{(1S,2R)-1-(3,5-difluorobenzyl)-3-[(3-ethylbenzyl)amino]-2-hydroxypropyl}thieno[3,2-c]pyridine-2-carboxamide N-{(1S,2R)-1-(3,5-difluorobenzyl)-3-[(3-ethylbenzyl)amino]-2-hydroxypropyl}-2-oxo-2,3-dihydro-1,3-benzoxazole-6-carboxamide 6-chloro-N-{(1S,2R)-1-(3,5-difluorobenzyl)-3-[(3-ethylbenzyl)amino]-2-hydroxypropyl}-3-methyl-2-oxo-2,3-dihydro-1,3-benzoxazole-5-carboxamide N-{(1S,2R)-1-(3,5-difluorobenzyl)-3-[(3-ethylbenzyl)amino]-2-hydroxypropyl}-3-methyl-4-oxo-3,4-dihydrophthalazine-1-carboxamide N-{(1S,2R)-1-(3,5-difluorobenzyl)-3-[(3-ethylbenzyl)amino]-2-hydroxypropyl}indolizine-2-carboxamide N-{(1S,2R)-1-(3,5-difluorobenzyl)-3-[(3-ethylbenzyl)amino]-2-hydroxypropyl}-5-(phenylethynyl)nicotinamide N-{(1S,2R)-1-(3,5-difluorobenzyl)-3-[(3-ethylbenzyl)amino]-2-hydroxypropyl}-2,5-dimethyl-1-(pyridin-4-ylmethyl)-1H-pyrrole-3-carboxamide N-{(1S,2R)-1-(3,5-difluorobenzyl)-3-[(3-ethylbenzyl)amino]-2-hydroxypropyl}-3-(4-methylphenyl)-4,5-dihydro-1H-pyrazole-5-carboxamide N-{(1S,2R)-1-(3,5-difluorobenzyl)-3-[(3-ethylbenzyl)amino]-2-hydroxypropyl}-2,1,3-benzoxadiazole-5-carboxamide 1-oxide N-{(1S,2R)-1-(3,5-difluorobenzyl)-3-[(3-ethylbenzyl)amino]-2-hydroxypropyl}-4a,9a-dihydro-9H-carbazole-9-carboxamide N-{(1S,2R)-1-(3,5-difluorobenzyl)-3-[(3-ethylbenzyl)amino]-2-hydroxypropyl}-6-methyl-4-oxo-1-phenyl-1,4-dihydropyridazine-3-carboxamide or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 7,727,997 B2 | Page 1 of 1 |
| APPLICATION NO. | : 11/636903 | |
| DATED | : June 1, 2010 | |
| INVENTOR(S) | : John et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 494 days.

Signed and Sealed this
Fifteenth Day of February, 2011

David J. Kappos
*Director of the United States Patent and Trademark Office*